(12) United States Patent
Liu et al.

(10) Patent No.: US 12,359,218 B2
(45) Date of Patent: Jul. 15, 2025

(54) METHODS AND COMPOSITIONS FOR EVOLVING BASE EDITORS USING PHAGE-ASSISTED CONTINUOUS EVOLUTION (PACE)

(71) Applicants: President and Fellows of Harvard College, Cambridge, MA (US); The Broad Institute, Inc., Cambridge, MA (US)

(72) Inventors: David R. Liu, Cambridge, MA (US); Benjamin Thuronyi, Cambridge, MA (US); Christopher Gerard Wilson, Cambridge, MA (US)

(73) Assignees: President and Fellows of Harvard College, Cambridge, MA (US); The Broad Institute, Inc., Cambridge, MA (US)

(*) Notice: Subject to any disclaimer, the term of this patent is extended or adjusted under 35 U.S.C. 154(b) by 0 days.

(21) Appl. No.: 18/178,048

(22) Filed: Mar. 3, 2023

(65) Prior Publication Data
US 2023/0272425 A1 Aug. 31, 2023

Related U.S. Application Data

(63) Continuation of application No. 16/634,405, filed as application No. PCT/US2018/044242 on Jul. 27, 2018, now Pat. No. 11,732,274.

(60) Provisional application No. 62/538,380, filed on Jul. 28, 2017.

(51) Int. Cl.
| | | |
|---|---|---|
| C12N 15/86 | (2006.01) | |
| C07K 14/32 | (2006.01) | |
| C12N 9/22 | (2006.01) | |
| C12N 9/24 | (2006.01) | |
| C12N 9/78 | (2006.01) | |
| C12N 15/113 | (2010.01) | |

(52) U.S. Cl.
CPC .............. *C12N 15/86* (2013.01); *C12N 9/22* (2013.01); *C12N 15/113* (2013.01); *C07K 2319/80* (2013.01); *C12Y 305/04005* (2013.01)

(58) Field of Classification Search
None
See application file for complete search history.

(56) References Cited

U.S. PATENT DOCUMENTS

| | | |
|---|---|---|
| 4,182,449 A | 1/1980 | Kozlow |
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,663,290 A | 5/1987 | Weis et al. |
| 4,737,323 A | 4/1988 | Martin et al. |
| 4,774,085 A | 9/1988 | Fidler |
| 4,797,368 A | 1/1989 | Carter et al. |
| 4,837,028 A | 6/1989 | Allen |
| 4,873,316 A | 10/1989 | Meade et al. |
| 4,880,635 A | 11/1989 | Janoff et al. |
| 4,889,818 A | 12/1989 | Gelfand et al. |
| 4,897,355 A | 1/1990 | Eppstein et al. |
| 4,906,477 A | 3/1990 | Kurono et al. |
| 4,911,928 A | 3/1990 | Wallach |
| 4,917,951 A | 4/1990 | Wallach |
| 4,920,016 A | 4/1990 | Allen et al. |
| 4,921,757 A | 5/1990 | Wheatley et al. |
| 4,946,787 A | 8/1990 | Eppstein et al. |
| 4,965,185 A | 10/1990 | Grischenko et al. |
| 5,017,492 A | 5/1991 | Kotewicz et al. |
| 5,047,342 A | 9/1991 | Chatterjee |
| 5,049,386 A | 9/1991 | Eppstein et al. |
| 5,079,352 A | 1/1992 | Gelfand et al. |
| 5,139,941 A | 8/1992 | Muzyczka et al. |
| 5,173,414 A | 12/1992 | Lebkowski et al. |
| 5,223,409 A | 6/1993 | Ladner et al. |
| 5,244,797 A | 9/1993 | Kotewicz et al. |
| 5,270,179 A | 12/1993 | Chatterjee |
| 5,374,553 A | 12/1994 | Gelfand et al. |
| 5,405,776 A | 4/1995 | Kotewicz et al. |

(Continued)

FOREIGN PATENT DOCUMENTS

| | | |
|---|---|---|
| AU | 2012244264 A1 | 11/2012 |
| AU | 2015252023 A1 | 11/2015 |

(Continued)

OTHER PUBLICATIONS

U.S. Appl. No. 61/716,256, filed Oct. 19, 2012, Jinek et al.

(Continued)

*Primary Examiner* — Suzanne M Noakes
*Assistant Examiner* — Jae W Lee
(74) *Attorney, Agent, or Firm* — Wolf, Greenfield & Sacks, P.C.

(57) ABSTRACT

The instant specification provides for evolved base editors which overcome deficiencies of those in art (including increased efficiency and/or decreased requirement for specific sequence-context at an editing site) and which are obtained a result of a phage-assisted continuous evolution (PACE) system. In particular, the instant specification provides for evolved cytidine base editors (e.g., based on APOBEC1, CDA, or AID cytidine deaminase domains) which overcome deficiencies of those in art (including increased efficiency and/or decreased requirement for specific sequence-context at an editing site) and which are obtained a result of a phage-assisted continuous evolution (PACE) system.

9 Claims, 128 Drawing Sheets
Specification includes a Sequence Listing.

(56) References Cited

U.S. PATENT DOCUMENTS

| | | |
|---|---|---|
| 5,436,149 A | 7/1995 | Barnes |
| 5,449,639 A | 9/1995 | Wei et al. |
| 5,496,714 A | 3/1996 | Comb et al. |
| 5,512,462 A | 4/1996 | Cheng |
| 5,580,737 A | 12/1996 | Polisky et al. |
| 5,614,365 A | 3/1997 | Tabor et al. |
| 5,652,094 A | 7/1997 | Usman et al. |
| 5,658,727 A | 8/1997 | Barbas et al. |
| 5,668,005 A | 9/1997 | Kotewicz et al. |
| 5,677,152 A | 10/1997 | Birch et al. |
| 5,767,099 A | 6/1998 | Harris et al. |
| 5,780,053 A | 7/1998 | Ashley et al. |
| 5,830,430 A | 11/1998 | Unger et al. |
| 5,834,247 A | 11/1998 | Comb et al. |
| 5,835,699 A | 11/1998 | Kimura |
| 5,844,075 A | 12/1998 | Kawakami et al. |
| 5,849,548 A | 12/1998 | Haseloff et al. |
| 5,851,548 A | 12/1998 | Dattagupta et al. |
| 5,855,910 A | 1/1999 | Ashley et al. |
| 5,856,463 A | 1/1999 | Blankenborg et al. |
| 5,962,313 A | 10/1999 | Podsakoff et al. |
| 5,981,182 A | 11/1999 | Jacobs, Jr. et al. |
| 6,015,794 A | 1/2000 | Haseloff et al. |
| 6,057,153 A | 5/2000 | George et al. |
| 6,063,608 A | 5/2000 | Kotewicz et al. |
| 6,077,705 A | 6/2000 | Duan et al. |
| 6,099,857 A | 8/2000 | Gross |
| 6,156,509 A | 12/2000 | Schellenberger |
| 6,183,998 B1 | 2/2001 | Ivanov et al. |
| 6,355,415 B1 | 3/2002 | Wagner et al. |
| 6,416,997 B1 | 7/2002 | Mir-Shekari et al. |
| 6,429,298 B1 | 8/2002 | Ellington et al. |
| 6,453,242 B1 | 9/2002 | Eisenberg et al. |
| 6,479,264 B1 | 11/2002 | Louwrier |
| 6,503,717 B2 | 1/2003 | Case et al. |
| 6,534,261 B1 | 3/2003 | Cox, III et al. |
| 6,558,671 B1 | 5/2003 | Slingluff et al. |
| 6,589,768 B1 | 7/2003 | Kotewicz et al. |
| 6,599,692 B1 | 7/2003 | Case et al. |
| 6,607,882 B1 | 8/2003 | Cox, III et al. |
| 6,610,522 B1 | 8/2003 | Kotewicz et al. |
| 6,689,558 B2 | 2/2004 | Case et al. |
| 6,716,973 B2 | 4/2004 | Baskerville et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,045,337 B2 | 5/2006 | Schultz et al. |
| 7,067,650 B1 | 6/2006 | Tanaka |
| 7,070,928 B2 | 7/2006 | Liu et al. |
| 7,078,208 B2 | 7/2006 | Smith et al. |
| 7,083,970 B2 | 8/2006 | Schultz et al. |
| 7,163,824 B2 | 1/2007 | Cox, III et al. |
| 7,192,739 B2 | 3/2007 | Liu et al. |
| 7,223,545 B2 | 5/2007 | Liu et al. |
| 7,329,807 B2 | 2/2008 | Vadrucci et al. |
| 7,354,761 B2 | 4/2008 | Schultz et al. |
| 7,368,275 B2 | 5/2008 | Schultz et al. |
| 7,419,669 B2 | 9/2008 | Kosmatopoulos et al. |
| 7,442,160 B2 | 10/2008 | Liu et al. |
| 7,476,500 B1 | 1/2009 | Liu et al. |
| 7,476,734 B2 | 1/2009 | Liu |
| 7,479,573 B2 | 1/2009 | Chu et al. |
| 7,488,718 B2 | 2/2009 | Scheinberg et al. |
| 7,491,494 B2 | 2/2009 | Liu et al. |
| 7,510,706 B2 | 3/2009 | Yonemitsu et al. |
| 7,541,450 B2 | 6/2009 | Liu et al. |
| 7,556,940 B2 | 7/2009 | Galarza et al. |
| 7,557,068 B2 | 7/2009 | Liu et al. |
| 7,595,179 B2 | 9/2009 | Chen et al. |
| 7,638,300 B2 | 12/2009 | Schultz et al. |
| 7,670,807 B2 | 3/2010 | Lampson et al. |
| 7,678,554 B2 | 3/2010 | Liu et al. |
| 7,713,721 B2 | 5/2010 | Schultz et al. |
| 7,771,935 B2 | 8/2010 | Liu et al. |
| 7,794,931 B2 | 9/2010 | Breaker et al. |
| 7,807,408 B2 | 10/2010 | Liu et al. |
| 7,851,658 B2 | 12/2010 | Liu et al. |
| 7,915,025 B2 | 3/2011 | Schultz et al. |
| 7,919,277 B2 | 4/2011 | Russell et al. |
| 7,993,672 B2 | 8/2011 | Huang et al. |
| 7,998,904 B2 | 8/2011 | Liu et al. |
| 7,999,071 B2 | 8/2011 | Schlom et al. |
| 8,012,739 B2 | 9/2011 | Schultz et al. |
| 8,017,323 B2 | 9/2011 | Liu et al. |
| 8,017,755 B2 | 9/2011 | Liu et al. |
| 8,030,074 B2 | 10/2011 | Schultz et al. |
| 8,067,556 B2 | 11/2011 | Hogrefe et al. |
| 8,114,648 B2 | 2/2012 | Schultz et al. |
| 8,173,364 B2 | 5/2012 | Schultz et al. |
| 8,173,392 B2 | 5/2012 | Schultz et al. |
| 8,183,012 B2 | 5/2012 | Schultz et al. |
| 8,183,178 B2 | 5/2012 | Liu et al. |
| 8,206,914 B2 | 6/2012 | Liu et al. |
| 8,354,380 B2 | 1/2013 | Liu et al. |
| 8,361,725 B2 | 1/2013 | Russell et al. |
| 8,394,604 B2 | 3/2013 | Liu et al. |
| 8,420,104 B2 | 4/2013 | Charneau et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,492,082 B2 | 7/2013 | De Franciscis et al. |
| 8,546,553 B2 | 10/2013 | Terns et al. |
| 8,569,256 B2 | 10/2013 | Heyes et al. |
| 8,586,363 B2 | 11/2013 | Voytas et al. |
| 8,673,612 B2 | 3/2014 | Klatzmann et al. |
| 8,680,069 B2 | 3/2014 | de Fougerolles et al. |
| 8,691,729 B2 | 4/2014 | Liu et al. |
| 8,691,750 B2 | 4/2014 | Constien et al. |
| 8,697,359 B1 | 4/2014 | Zhang |
| 8,697,439 B2 | 4/2014 | Mangeot et al. |
| 8,697,853 B2 | 4/2014 | Voytas et al. |
| 8,709,466 B2 | 4/2014 | Coady et al. |
| 8,728,526 B2 | 5/2014 | Heller |
| 8,729,038 B2 | 5/2014 | Gruber et al. |
| 8,741,279 B2 | 6/2014 | Kasahara et al. |
| 8,748,667 B2 | 6/2014 | Budzik et al. |
| 8,758,810 B2 | 6/2014 | Okada et al. |
| 8,759,103 B2 | 6/2014 | Kim et al. |
| 8,759,104 B2 | 6/2014 | Unciti-Broceta et al. |
| 8,771,728 B2 | 7/2014 | Huang et al. |
| 8,790,664 B2 | 7/2014 | Pitard et al. |
| 8,795,965 B2 | 8/2014 | Zhang |
| 8,822,663 B2 | 9/2014 | Schrum et al. |
| 8,835,148 B2 | 9/2014 | Janulaitis et al. |
| 8,846,578 B2 | 9/2014 | McCray et al. |
| 8,871,445 B2 | 10/2014 | Cong et al. |
| 8,889,418 B2 | 11/2014 | Zhang et al. |
| 8,900,814 B2 | 12/2014 | Yasukawa et al. |
| 8,945,839 B2 | 2/2015 | Zhang |
| 8,975,232 B2 | 3/2015 | Liu et al. |
| 8,993,233 B2 | 3/2015 | Zhang et al. |
| 8,999,641 B2 | 4/2015 | Zhang et al. |
| 9,023,594 B2 | 5/2015 | Liu et al. |
| 9,023,649 B2 | 5/2015 | Mali et al. |
| 9,034,650 B2 | 5/2015 | Padidam |
| 9,068,179 B1 | 6/2015 | Liu et al. |
| 9,150,626 B2 | 10/2015 | Liu et al. |
| 9,163,271 B2 | 10/2015 | Schultz et al. |
| 9,163,284 B2 | 10/2015 | Liu et al. |
| 9,181,535 B2 | 11/2015 | Liu et al. |
| 9,200,045 B2 | 12/2015 | Liu et al. |
| 9,221,886 B2 | 12/2015 | Liu et al. |
| 9,228,207 B2 | 1/2016 | Liu et al. |
| 9,234,213 B2 | 1/2016 | Wu |
| 9,243,038 B2 | 1/2016 | Liu et al. |
| 9,267,127 B2 | 2/2016 | Liu et al. |
| 9,290,773 B2 | 3/2016 | Edgerton |
| 9,296,790 B2 | 3/2016 | Chatterjee et al. |
| 9,322,006 B2 | 4/2016 | Liu et al. |
| 9,322,037 B2 | 4/2016 | Liu et al. |
| 9,340,799 B2 | 5/2016 | Liu et al. |
| 9,340,800 B2 | 5/2016 | Liu et al. |
| 9,359,599 B2 | 6/2016 | Liu et al. |

(56) References Cited

U.S. PATENT DOCUMENTS

| | | |
|---|---|---|
| 9,388,430 B2 | 7/2016 | Liu et al. |
| 9,394,537 B2 | 7/2016 | Liu et al. |
| 9,434,774 B2 | 9/2016 | Liu et al. |
| 9,458,484 B2 | 10/2016 | Ma et al. |
| 9,512,446 B1 | 12/2016 | Joung et al. |
| 9,526,784 B2 | 12/2016 | Liu et al. |
| 9,534,210 B2 | 1/2017 | Park et al. |
| 9,580,698 B1 | 2/2017 | Xu et al. |
| 9,593,356 B2 | 3/2017 | Haugwitz et al. |
| 9,610,322 B2 | 4/2017 | Liu et al. |
| 9,637,739 B2 | 5/2017 | Siksnys et al. |
| 9,663,770 B2 | 5/2017 | Rogers et al. |
| 9,695,446 B2 | 7/2017 | Mangeot et al. |
| 9,737,604 B2 | 8/2017 | Jin et al. |
| 9,738,693 B2 | 8/2017 | Telford et al. |
| 9,753,340 B2 | 9/2017 | Saitou |
| 9,765,304 B2 | 9/2017 | Klatzmann et al. |
| 9,771,574 B2 | 9/2017 | Liu et al. |
| 9,777,043 B2 | 10/2017 | Anderson et al. |
| 9,783,791 B2 | 10/2017 | Hogrefe et al. |
| 9,816,093 B1 | 11/2017 | Donohoue et al. |
| 9,840,538 B2 | 12/2017 | Telford et al. |
| 9,840,690 B2 | 12/2017 | Karli et al. |
| 9,840,699 B2 | 12/2017 | Liu et al. |
| 9,840,702 B2 | 12/2017 | Collingwood et al. |
| 9,850,521 B2 | 12/2017 | Braman et al. |
| 9,873,907 B2 | 1/2018 | Zeiner et al. |
| 9,879,270 B2 | 1/2018 | Hittinger et al. |
| 9,914,939 B2 | 3/2018 | Church et al. |
| 9,932,567 B1 | 4/2018 | Xu et al. |
| 9,938,288 B1 | 4/2018 | Kishi et al. |
| 9,944,933 B2 | 4/2018 | Storici et al. |
| 9,982,279 B1 | 5/2018 | Gill et al. |
| 9,999,671 B2 | 6/2018 | Liu et al. |
| 10,011,868 B2 | 7/2018 | Liu et al. |
| 10,040,830 B2 | 8/2018 | Chatterjee et al. |
| 10,053,725 B2 | 8/2018 | Liu et al. |
| 10,059,940 B2 | 8/2018 | Zhong |
| 10,077,453 B2 | 9/2018 | Liu et al. |
| 10,113,163 B2 | 10/2018 | Liu et al. |
| 10,150,955 B2 | 12/2018 | Lambowitz et al. |
| 10,167,457 B2 | 1/2019 | Liu et al. |
| 10,179,911 B2 | 1/2019 | Liu et al. |
| 10,189,831 B2 | 1/2019 | Arrington et al. |
| 10,202,593 B2 | 2/2019 | Liu et al. |
| 10,202,658 B2 | 2/2019 | Parkin et al. |
| 10,227,581 B2 | 3/2019 | Liu et al. |
| 10,323,236 B2 | 6/2019 | Liu et al. |
| 10,336,997 B2 | 7/2019 | Liu et al. |
| 10,358,670 B2 | 7/2019 | Janulaitis et al. |
| 10,392,674 B2 | 8/2019 | Liu et al. |
| 10,407,474 B2 | 9/2019 | Liu et al. |
| 10,407,695 B2 | 9/2019 | Charneau et al. |
| 10,407,697 B2 | 9/2019 | Doudna et al. |
| 10,465,176 B2 | 11/2019 | Liu et al. |
| 10,508,298 B2 | 12/2019 | Liu et al. |
| 10,583,201 B2 | 3/2020 | Chen et al. |
| 10,597,679 B2 | 3/2020 | Liu et al. |
| 10,612,011 B2 | 4/2020 | Liu et al. |
| 10,640,767 B2 | 5/2020 | Maianti et al. |
| 10,682,410 B2 | 6/2020 | Liu et al. |
| 10,704,062 B2 | 7/2020 | Liu et al. |
| 10,745,677 B2 | 8/2020 | Maianti et al. |
| 10,858,639 B2 | 12/2020 | Liu et al. |
| 10,912,833 B2 | 2/2021 | Liu et al. |
| 10,930,367 B2 | 2/2021 | Zhang et al. |
| 10,947,530 B2 | 3/2021 | Liu et al. |
| 10,954,548 B2 | 3/2021 | Liu et al. |
| 11,046,948 B2 | 6/2021 | Liu et al. |
| 11,053,481 B2 | 7/2021 | Liu et al. |
| 11,124,782 B2 | 9/2021 | Liu et al. |
| 11,214,780 B2 | 1/2022 | Liu et al. |
| 11,268,082 B2 | 3/2022 | Liu et al. |
| 11,299,755 B2 | 4/2022 | Liu et al. |
| 11,306,324 B2 | 4/2022 | Liu et al. |
| 11,319,532 B2 | 5/2022 | Liu et al. |
| 11,447,770 B1 | 9/2022 | Liu et al. |
| 11,542,496 B2 | 1/2023 | Liu et al. |
| 11,542,509 B2 | 1/2023 | Maianti et al. |
| 11,560,566 B2 | 1/2023 | Liu et al. |
| 11,578,343 B2 | 2/2023 | Liu et al. |
| 11,643,652 B2 | 5/2023 | Liu et al. |
| 11,661,590 B2 | 5/2023 | Liu et al. |
| 11,702,651 B2 | 7/2023 | Liu et al. |
| 11,732,274 B2 | 8/2023 | Liu et al. |
| 11,795,443 B2 | 10/2023 | Liu et al. |
| 11,795,452 B2 | 10/2023 | Liu et al. |
| 11,820,969 B2 | 11/2023 | Maianti et al. |
| 11,898,179 B2 | 2/2024 | Maianti et al. |
| 11,912,985 B2 | 2/2024 | Liu et al. |
| 11,920,181 B2 | 3/2024 | Liu et al. |
| 11,932,884 B2 | 3/2024 | Liu et al. |
| 11,999,947 B2 | 6/2024 | Liu et al. |
| 12,006,520 B2 | 6/2024 | Liu et al. |
| 12,031,126 B2 | 7/2024 | Liu et al. |
| 12,043,852 B2 | 7/2024 | Liu et al. |
| 12,084,663 B2 | 9/2024 | Maianti et al. |
| 12,157,760 B2 | 12/2024 | Liu et al. |
| 2003/0082575 A1 | 5/2003 | Schultz et al. |
| 2003/0087817 A1 | 5/2003 | Cox et al. |
| 2003/0096337 A1 | 5/2003 | Hillman et al. |
| 2003/0108885 A1 | 6/2003 | Schultz et al. |
| 2003/0119764 A1 | 6/2003 | Loeb et al. |
| 2003/0167533 A1 | 9/2003 | Yadav et al. |
| 2003/0203480 A1 | 10/2003 | Kovesdi et al. |
| 2004/0003420 A1 | 1/2004 | Kuhn et al. |
| 2004/0028687 A1 | 2/2004 | Waelti |
| 2004/0115184 A1 | 6/2004 | Smith et al. |
| 2004/0156861 A1 | 8/2004 | Figdor et al. |
| 2004/0197892 A1 | 10/2004 | Moore et al. |
| 2004/0203109 A1 | 10/2004 | Lal et al. |
| 2005/0136429 A1 | 6/2005 | Guarente et al. |
| 2005/0222030 A1 | 10/2005 | Allison |
| 2005/0260626 A1 | 11/2005 | Lorens et al. |
| 2006/0088864 A1 | 4/2006 | Smolke et al. |
| 2006/0104984 A1 | 5/2006 | Littlefield et al. |
| 2006/0216702 A1 | 9/2006 | Compans et al. |
| 2006/0246568 A1 | 11/2006 | Honjo et al. |
| 2007/0015238 A1 | 1/2007 | Snyder et al. |
| 2007/0049533 A1 | 3/2007 | Liu et al. |
| 2007/0264692 A1 | 11/2007 | Liu et al. |
| 2007/0269817 A1 | 11/2007 | Shapero |
| 2007/0298118 A1 | 12/2007 | Lotvall et al. |
| 2008/0008697 A1 | 1/2008 | Mintier et al. |
| 2008/0051317 A1 | 2/2008 | Church et al. |
| 2008/0124725 A1 | 5/2008 | Barrangou et al. |
| 2008/0182254 A1 | 7/2008 | Hall et al. |
| 2008/0220502 A1 | 9/2008 | Schellenberger et al. |
| 2008/0241917 A1 | 10/2008 | Akita et al. |
| 2008/0268516 A1 | 10/2008 | Perreault et al. |
| 2009/0111119 A1 | 4/2009 | Doyon et al. |
| 2009/0130718 A1 | 5/2009 | Short |
| 2009/0202622 A1 | 8/2009 | Fleury et al. |
| 2009/0215878 A1 | 8/2009 | Tan et al. |
| 2009/0234109 A1 | 9/2009 | Han et al. |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0273857 A1 | 10/2010 | Thakker et al. |
| 2010/0305197 A1 | 12/2010 | Che |
| 2010/0316643 A1 | 12/2010 | Eckert et al. |
| 2011/0016540 A1 | 1/2011 | Weinstein et al. |
| 2011/0059160 A1 | 3/2011 | Essner et al. |
| 2011/0059502 A1 | 3/2011 | Chalasani |
| 2011/0104787 A1 | 5/2011 | Church et al. |
| 2011/0177495 A1 | 7/2011 | Liu et al. |
| 2011/0189775 A1 | 8/2011 | Ainley et al. |
| 2011/0189776 A1 | 8/2011 | Terns et al. |
| 2011/0206672 A1 | 8/2011 | Little |
| 2011/0217739 A1 | 9/2011 | Terns et al. |
| 2011/0301073 A1 | 12/2011 | Gregory et al. |
| 2012/0129759 A1 | 5/2012 | Liu et al. |
| 2012/0141523 A1 | 6/2012 | Castado et al. |
| 2012/0244601 A1 | 9/2012 | Bertozzi et al. |

(56) References Cited

U.S. PATENT DOCUMENTS

| | | |
|---|---|---|
| 2012/0270273 A1 | 10/2012 | Zhang et al. |
| 2012/0322861 A1 | 12/2012 | Byrne et al. |
| 2013/0022980 A1 | 1/2013 | Nelson et al. |
| 2013/0053426 A1 | 2/2013 | Seow et al. |
| 2013/0059931 A1 | 3/2013 | Petersen-Mahrt et al. |
| 2013/0108657 A1 | 5/2013 | Yee et al. |
| 2013/0117869 A1 | 5/2013 | Duchateau et al. |
| 2013/0130248 A1 | 5/2013 | Haurwitz et al. |
| 2013/0158245 A1 | 6/2013 | Russell et al. |
| 2013/0165389 A1 | 6/2013 | Schellenberger et al. |
| 2013/0212725 A1 | 8/2013 | Kuhn et al. |
| 2013/0309720 A1 | 11/2013 | Schultz et al. |
| 2013/0344117 A1 | 12/2013 | Mirosevich et al. |
| 2013/0345064 A1 | 12/2013 | Liu et al. |
| 2014/0004280 A1 | 1/2014 | Loomis |
| 2014/0005269 A1 | 1/2014 | Ngwuluka et al. |
| 2014/0017214 A1 | 1/2014 | Cost |
| 2014/0018404 A1 | 1/2014 | Chen et al. |
| 2014/0044793 A1 | 2/2014 | Goll et al. |
| 2014/0065711 A1 | 3/2014 | Liu et al. |
| 2014/0068797 A1 | 3/2014 | Doudna et al. |
| 2014/0127752 A1 | 5/2014 | Zhou et al. |
| 2014/0128449 A1 | 5/2014 | Liu et al. |
| 2014/0141094 A1 | 5/2014 | Smyth et al. |
| 2014/0141487 A1 | 5/2014 | Feldman et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0201858 A1 | 7/2014 | Ostertag et al. |
| 2014/0234289 A1 | 8/2014 | Liu et al. |
| 2014/0248702 A1 | 9/2014 | Zhang et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273234 A1 | 9/2014 | Zhang et al. |
| 2014/0283156 A1 | 9/2014 | Zador et al. |
| 2014/0295556 A1 | 10/2014 | Joung et al. |
| 2014/0295557 A1 | 10/2014 | Joung et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349400 A1 | 11/2014 | Jakimo et al. |
| 2014/0356867 A1 | 12/2014 | Peter et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357523 A1 | 12/2014 | Zeiner et al. |
| 2014/0377868 A1 | 12/2014 | Joung et al. |
| 2015/0010526 A1 | 1/2015 | Liu et al. |
| 2015/0031089 A1 | 1/2015 | Lindstrom |
| 2015/0031132 A1 | 1/2015 | Church et al. |
| 2015/0031133 A1 | 1/2015 | Church et al. |
| 2015/0044191 A1 | 2/2015 | Liu et al. |
| 2015/0044192 A1 | 2/2015 | Liu et al. |
| 2015/0044772 A1 | 2/2015 | Zhao |
| 2015/0050699 A1 | 2/2015 | Siksnys et al. |
| 2015/0056177 A1 | 2/2015 | Liu et al. |
| 2015/0056629 A1 | 2/2015 | Guthrie-Honea |
| 2015/0064138 A1 | 3/2015 | Lu et al. |
| 2015/0064789 A1 | 3/2015 | Paschon et al. |
| 2015/0071898 A1 | 3/2015 | Liu et al. |
| 2015/0071899 A1 | 3/2015 | Liu et al. |
| 2015/0071900 A1 | 3/2015 | Liu et al. |
| 2015/0071901 A1 | 3/2015 | Liu et al. |
| 2015/0071902 A1 | 3/2015 | Liu et al. |
| 2015/0071903 A1 | 3/2015 | Liu et al. |
| 2015/0071906 A1 | 3/2015 | Liu et al. |
| 2015/0079680 A1 | 3/2015 | Bradley et al. |
| 2015/0079681 A1 | 3/2015 | Zhang |
| 2015/0098954 A1 | 4/2015 | Hyde et al. |
| 2015/0118216 A1 | 4/2015 | Liu et al. |
| 2015/0128300 A1 | 5/2015 | Warming et al. |
| 2015/0132269 A1 | 5/2015 | Orkin et al. |
| 2015/0140664 A1 | 5/2015 | Byrne et al. |
| 2015/0159172 A1 | 6/2015 | Miller et al. |
| 2015/0165054 A1 | 6/2015 | Liu et al. |
| 2015/0166980 A1 | 6/2015 | Liu et al. |
| 2015/0166981 A1 | 6/2015 | Liu et al. |
| 2015/0166982 A1 | 6/2015 | Liu et al. |
| 2015/0166983 A1 | 6/2015 | Liu et al. |
| 2015/0166984 A1 | 6/2015 | Liu et al. |
| 2015/0166985 A1 | 6/2015 | Liu et al. |
| 2015/0191744 A1 | 7/2015 | Wolfe et al. |
| 2015/0197759 A1 | 7/2015 | Xu et al. |
| 2015/0211058 A1 | 7/2015 | Carstens |
| 2015/0218573 A1 | 8/2015 | Loque et al. |
| 2015/0225773 A1 | 8/2015 | Farmer et al. |
| 2015/0241440 A1 | 8/2015 | Fasan et al. |
| 2015/0252358 A1 | 9/2015 | Maeder et al. |
| 2015/0275202 A1 | 10/2015 | Liu et al. |
| 2015/0291965 A1 | 10/2015 | Zhang et al. |
| 2015/0307889 A1 | 10/2015 | Petolino et al. |
| 2015/0315252 A1 | 11/2015 | Haugwitz et al. |
| 2015/0344549 A1 | 12/2015 | Muir et al. |
| 2016/0017393 A1 | 1/2016 | Jacobson et al. |
| 2016/0017396 A1 | 1/2016 | Cann et al. |
| 2016/0032292 A1 | 2/2016 | Storici et al. |
| 2016/0032353 A1 | 2/2016 | Braman et al. |
| 2016/0040155 A1 | 2/2016 | Maizels et al. |
| 2016/0046952 A1 | 2/2016 | Hittinger et al. |
| 2016/0046961 A1 | 2/2016 | Jinek et al. |
| 2016/0046962 A1 | 2/2016 | May et al. |
| 2016/0053272 A1 | 2/2016 | Wurtzel et al. |
| 2016/0053304 A1 | 2/2016 | Wurtzel et al. |
| 2016/0074535 A1 | 3/2016 | Ranganathan et al. |
| 2016/0076093 A1 | 3/2016 | Shendure et al. |
| 2016/0090603 A1 | 3/2016 | Carnes et al. |
| 2016/0090622 A1 | 3/2016 | Liu et al. |
| 2016/0115488 A1 | 4/2016 | Zhang et al. |
| 2016/0137716 A1 | 5/2016 | El Andaloussi et al. |
| 2016/0138046 A1 | 5/2016 | Wu |
| 2016/0153003 A1 | 6/2016 | Joung et al. |
| 2016/0186214 A1 | 6/2016 | Brouns et al. |
| 2016/0200779 A1 | 7/2016 | Liu et al. |
| 2016/0201040 A1 | 7/2016 | Liu et al. |
| 2016/0201089 A1 | 7/2016 | Gersbach et al. |
| 2016/0206566 A1 | 7/2016 | Lu et al. |
| 2016/0208243 A1 | 7/2016 | Zhang et al. |
| 2016/0208288 A1 | 7/2016 | Liu et al. |
| 2016/0215275 A1 | 7/2016 | Zhong |
| 2016/0215276 A1 | 7/2016 | Liu et al. |
| 2016/0215300 A1 | 7/2016 | May et al. |
| 2016/0244784 A1 | 8/2016 | Jacobson et al. |
| 2016/0244829 A1 | 8/2016 | Bang et al. |
| 2016/0264934 A1 | 9/2016 | Giallourakis et al. |
| 2016/0272593 A1 | 9/2016 | Ritter et al. |
| 2016/0272965 A1 | 9/2016 | Zhang et al. |
| 2016/0281072 A1 | 9/2016 | Zhang |
| 2016/0298136 A1 | 10/2016 | Chen et al. |
| 2016/0304846 A1 | 10/2016 | Liu et al. |
| 2016/0304855 A1 | 10/2016 | Stark et al. |
| 2016/0312304 A1 | 10/2016 | Sorrentino et al. |
| 2016/0319262 A1 | 11/2016 | Doudna et al. |
| 2016/0333389 A1 | 11/2016 | Liu et al. |
| 2016/0340622 A1 | 11/2016 | Abdou |
| 2016/0340661 A1 | 11/2016 | Cong et al. |
| 2016/0340662 A1 | 11/2016 | Zhang et al. |
| 2016/0345578 A1 | 12/2016 | Barrangou et al. |
| 2016/0346360 A1 | 12/2016 | Quake et al. |
| 2016/0346361 A1 | 12/2016 | Quake et al. |
| 2016/0346362 A1 | 12/2016 | Quake et al. |
| 2016/0348074 A1 | 12/2016 | Quake et al. |
| 2016/0348096 A1 | 12/2016 | Liu et al. |
| 2016/0350476 A1 | 12/2016 | Quake et al. |
| 2016/0355796 A1 | 12/2016 | Davidson et al. |
| 2016/0369262 A1 | 12/2016 | Reik et al. |
| 2017/0009224 A1 | 1/2017 | Liu et al. |
| 2017/0009242 A1 | 1/2017 | McKinley et al. |
| 2017/0014449 A1 | 1/2017 | Bangera et al. |
| 2017/0020922 A1 | 1/2017 | Wagner et al. |
| 2017/0022251 A1 | 1/2017 | Rammensee et al. |
| 2017/0037432 A1 | 2/2017 | Donohoue et al. |
| 2017/0044520 A1 | 2/2017 | Liu et al. |

(56) References Cited

U.S. PATENT DOCUMENTS

| | | |
|---|---|---|
| 2017/0044592 A1 | 2/2017 | Peter et al. |
| 2017/0053729 A1 | 2/2017 | Kotani et al. |
| 2017/0058271 A1 | 3/2017 | Joung et al. |
| 2017/0058272 A1 | 3/2017 | Carter et al. |
| 2017/0058298 A1 | 3/2017 | Kennedy et al. |
| 2017/0073663 A1 | 3/2017 | Wang et al. |
| 2017/0073670 A1 | 3/2017 | Nishida et al. |
| 2017/0087224 A1 | 3/2017 | Quake |
| 2017/0087225 A1 | 3/2017 | Quake |
| 2017/0088587 A1 | 3/2017 | Quake |
| 2017/0088828 A1 | 3/2017 | Quake |
| 2017/0107536 A1 | 4/2017 | Zhang et al. |
| 2017/0107560 A1 | 4/2017 | Peter et al. |
| 2017/0112773 A1 | 4/2017 | Stachowiak et al. |
| 2017/0114367 A1 | 4/2017 | Hu et al. |
| 2017/0121693 A1 | 5/2017 | Liu et al. |
| 2017/0145394 A1 | 5/2017 | Yeo et al. |
| 2017/0145405 A1 | 5/2017 | Tang et al. |
| 2017/0145438 A1 | 5/2017 | Kantor |
| 2017/0152528 A1 | 6/2017 | Zhang |
| 2017/0152787 A1 | 6/2017 | Kubo et al. |
| 2017/0159033 A1 | 6/2017 | Kamtekar et al. |
| 2017/0166928 A1 | 6/2017 | Vyas et al. |
| 2017/0173113 A1 | 6/2017 | Besner et al. |
| 2017/0175086 A1 | 6/2017 | Schmitt et al. |
| 2017/0175104 A1 | 6/2017 | Doudna et al. |
| 2017/0175142 A1 | 6/2017 | Zhang et al. |
| 2017/0191047 A1 | 7/2017 | Terns et al. |
| 2017/0191078 A1 | 7/2017 | Zhang et al. |
| 2017/0198269 A1 | 7/2017 | Zhang et al. |
| 2017/0198277 A1 | 7/2017 | Kmiec et al. |
| 2017/0198302 A1 | 7/2017 | Feng et al. |
| 2017/0211061 A1 | 7/2017 | Weiss et al. |
| 2017/0224843 A1 | 8/2017 | Deglon et al. |
| 2017/0226522 A1 | 8/2017 | Hu et al. |
| 2017/0233703 A1 | 8/2017 | Xie et al. |
| 2017/0233708 A1 | 8/2017 | Liu et al. |
| 2017/0233756 A1 | 8/2017 | Begemann et al. |
| 2017/0247671 A1 | 8/2017 | Yung et al. |
| 2017/0247703 A1 | 8/2017 | Sloan et al. |
| 2017/0268022 A1 | 9/2017 | Liu et al. |
| 2017/0275648 A1 | 9/2017 | Barrangou et al. |
| 2017/0275665 A1 | 9/2017 | Silas et al. |
| 2017/0283797 A1 | 10/2017 | Robb et al. |
| 2017/0283831 A1 | 10/2017 | Zhang et al. |
| 2017/0306306 A1 | 10/2017 | Potter et al. |
| 2017/0314016 A1 | 11/2017 | Kim et al. |
| 2017/0362635 A1 | 12/2017 | Chamberlain et al. |
| 2018/0023062 A1 | 1/2018 | Lamb et al. |
| 2018/0037877 A1 | 2/2018 | Gao et al. |
| 2018/0064077 A1 | 3/2018 | Dunham et al. |
| 2018/0066258 A1 | 3/2018 | Powell |
| 2018/0068062 A1 | 3/2018 | Zhang et al. |
| 2018/0073012 A1 | 3/2018 | Liu et al. |
| 2018/0080051 A1 | 3/2018 | Sheikh et al. |
| 2018/0087046 A1 | 3/2018 | Badran et al. |
| 2018/0100147 A1 | 4/2018 | Yates et al. |
| 2018/0105867 A1 | 4/2018 | Xiao et al. |
| 2018/0119118 A1 | 5/2018 | Lu et al. |
| 2018/0127759 A1 | 5/2018 | Lu et al. |
| 2018/0127780 A1 | 5/2018 | Liu et al. |
| 2018/0155708 A1 | 6/2018 | Church et al. |
| 2018/0155720 A1 | 6/2018 | Donohoue et al. |
| 2018/0163213 A1 | 6/2018 | Aneja et al. |
| 2018/0170984 A1 | 6/2018 | Harris et al. |
| 2018/0177727 A1 | 6/2018 | Kalluri et al. |
| 2018/0179503 A1 | 6/2018 | Maianti et al. |
| 2018/0179547 A1 | 6/2018 | Zhang et al. |
| 2018/0201921 A1 | 7/2018 | Malcolm |
| 2018/0230464 A1 | 8/2018 | Zhong |
| 2018/0230471 A1 | 8/2018 | Storici et al. |
| 2018/0236081 A1 | 8/2018 | Liu et al. |
| 2018/0237787 A1 | 8/2018 | Maianti et al. |
| 2018/0245066 A1 | 8/2018 | Yao et al. |
| 2018/0245075 A1 | 8/2018 | Khalil et al. |
| 2018/0258418 A1 | 9/2018 | Kim |
| 2018/0265864 A1 | 9/2018 | Li et al. |
| 2018/0273935 A1 | 9/2018 | Lane et al. |
| 2018/0273939 A1 | 9/2018 | Yu et al. |
| 2018/0273976 A1 | 9/2018 | Ümit et al. |
| 2018/0282722 A1 | 10/2018 | Jakimo et al. |
| 2018/0298391 A1 | 10/2018 | Jakimo et al. |
| 2018/0305688 A1 | 10/2018 | Zhong |
| 2018/0305704 A1 | 10/2018 | Zhang |
| 2018/0312822 A1 | 11/2018 | Lee et al. |
| 2018/0312825 A1 | 11/2018 | Liu et al. |
| 2018/0312828 A1 | 11/2018 | Liu et al. |
| 2018/0312835 A1 | 11/2018 | Yao et al. |
| 2018/0327756 A1 | 11/2018 | Zhang et al. |
| 2018/0346927 A1 | 12/2018 | Doudna et al. |
| 2018/0371497 A1 | 12/2018 | Gill et al. |
| 2019/0010481 A1 | 1/2019 | Joung et al. |
| 2019/0032053 A1 | 1/2019 | Ji et al. |
| 2019/0055543 A1 | 2/2019 | Tran et al. |
| 2019/0055549 A1 | 2/2019 | Capurso et al. |
| 2019/0062734 A1 | 2/2019 | Cotta-Ramusino et al. |
| 2019/0093099 A1 | 3/2019 | Liu et al. |
| 2019/0135869 A1 | 5/2019 | Chatterjee et al. |
| 2019/0167810 A1 | 6/2019 | Hean et al. |
| 2019/0185883 A1 | 6/2019 | Liu et al. |
| 2019/0203228 A1 | 7/2019 | Bouille et al. |
| 2019/0218547 A1 | 7/2019 | Lee et al. |
| 2019/0224331 A1 | 7/2019 | Wiklander |
| 2019/0225955 A1 | 7/2019 | Liu et al. |
| 2019/0233847 A1 | 8/2019 | Savage et al. |
| 2019/0241633 A1 | 8/2019 | Fotin-Mleczek et al. |
| 2019/0256842 A1 | 8/2019 | Liu et al. |
| 2019/0264202 A1 | 8/2019 | Church et al. |
| 2019/0276816 A1 | 9/2019 | Liu et al. |
| 2019/0309290 A1 | 10/2019 | Neuteboom et al. |
| 2019/0322992 A1 | 10/2019 | Liu et al. |
| 2019/0330619 A1 | 10/2019 | Smith et al. |
| 2019/0352632 A1 | 11/2019 | Liu et al. |
| 2019/0367891 A1 | 12/2019 | Liu et al. |
| 2019/0388347 A1 | 12/2019 | Wiklander et al. |
| 2020/0010818 A1 | 1/2020 | Liu et al. |
| 2020/0010835 A1 | 1/2020 | Maianti et al. |
| 2020/0023012 A1 | 1/2020 | Joseph et al. |
| 2020/0056206 A1 | 2/2020 | Tremblay et al. |
| 2020/0060980 A1 | 2/2020 | Von Maltzahn et al. |
| 2020/0062813 A1 | 2/2020 | Nordin et al. |
| 2020/0063127 A1 | 2/2020 | Lu et al. |
| 2020/0071722 A1 | 3/2020 | Liu et al. |
| 2020/0109398 A1 | 4/2020 | Rubens et al. |
| 2020/0157570 A1 | 5/2020 | Loiler |
| 2020/0172931 A1 | 6/2020 | Liu et al. |
| 2020/0181619 A1 | 6/2020 | Tang et al. |
| 2020/0190493 A1 | 6/2020 | Liu et al. |
| 2020/0206360 A1 | 7/2020 | Choi et al. |
| 2020/0216833 A1 | 7/2020 | Liu et al. |
| 2020/0255868 A1 | 8/2020 | Liu et al. |
| 2020/0277587 A1 | 9/2020 | Liu et al. |
| 2020/0323984 A1 | 10/2020 | Liu et al. |
| 2020/0399619 A1 | 12/2020 | Maianti et al. |
| 2020/0399626 A1 | 12/2020 | Liu et al. |
| 2021/0054416 A1 | 2/2021 | Liu et al. |
| 2021/0115428 A1 | 4/2021 | Maianti et al. |
| 2021/0196809 A1 | 7/2021 | Maianti et al. |
| 2021/0198330 A1 | 7/2021 | Liu et al. |
| 2021/0214698 A1 | 7/2021 | Liu et al. |
| 2021/0230577 A1 | 7/2021 | Liu et al. |
| 2021/0254127 A1 | 8/2021 | Liu et al. |
| 2021/0315994 A1 | 10/2021 | Liu et al. |
| 2021/0317440 A1 | 10/2021 | Liu et al. |
| 2022/0033785 A1 | 2/2022 | Liu et al. |
| 2022/0119785 A1 | 4/2022 | Liu et al. |
| 2022/0170013 A1 | 6/2022 | Liu et al. |
| 2022/0177877 A1 | 6/2022 | Church et al. |
| 2022/0204975 A1 | 6/2022 | Liu et al. |
| 2022/0213507 A1 | 7/2022 | Liu et al. |
| 2022/0220462 A1 | 7/2022 | Liu et al. |
| 2022/0238182 A1 | 7/2022 | Shen et al. |
| 2022/0249697 A1 | 8/2022 | Liu et al. |
| 2022/0282275 A1 | 9/2022 | Liu et al. |

(56) References Cited

U.S. PATENT DOCUMENTS

| | | |
|---|---|---|
| 2022/0290115 A1 | 9/2022 | Liu et al. |
| 2022/0307001 A1 | 9/2022 | Liu et al. |
| 2022/0307003 A1 | 9/2022 | Liu et al. |
| 2022/0315906 A1 | 10/2022 | Liu et al. |
| 2022/0356469 A1 | 11/2022 | Liu et al. |
| 2022/0380740 A1 | 12/2022 | Liu et al. |
| 2022/0389395 A1 | 12/2022 | Liu et al. |
| 2023/0002745 A1 | 1/2023 | Liu et al. |
| 2023/0021641 A1 | 1/2023 | Liu et al. |
| 2023/0056852 A1 | 2/2023 | Liu et al. |
| 2023/0058176 A1 | 2/2023 | Liu et al. |
| 2023/0078265 A1 | 3/2023 | Liu et al. |
| 2023/0086199 A1 | 3/2023 | Liu et al. |
| 2023/0090221 A1 | 3/2023 | Liu et al. |
| 2023/0108687 A1 | 4/2023 | Liu et al. |
| 2023/0123669 A1 | 4/2023 | Liu et al. |
| 2023/0127008 A1 | 4/2023 | Liu et al. |
| 2023/0159913 A1 | 5/2023 | Liu et al. |
| 2023/0193295 A1 | 6/2023 | Maianti et al. |
| 2023/0220374 A1 | 7/2023 | Liu et al. |
| 2023/0272425 A1 | 8/2023 | Liu et al. |
| 2023/0332144 A1 | 10/2023 | Liu et al. |
| 2023/0340465 A1 | 10/2023 | Liu et al. |
| 2023/0340466 A1 | 10/2023 | Liu et al. |
| 2023/0340467 A1 | 10/2023 | Liu et al. |
| 2023/0348883 A1 | 11/2023 | Liu et al. |
| 2023/0357766 A1 | 11/2023 | Liu et al. |
| 2023/0383289 A1 | 11/2023 | Liu et al. |
| 2024/0035017 A1 | 2/2024 | Liu et al. |
| 2024/0076652 A1 | 3/2024 | Liu et al. |
| 2024/0110166 A1 | 4/2024 | Maianti et al. |
| 2024/0124866 A1 | 4/2024 | Liu et al. |
| 2024/0173430 A1 | 5/2024 | Liu et al. |
| 2024/0209329 A1 | 6/2024 | Liu et al. |
| 2024/0229077 A1 | 7/2024 | Liu et al. |
| 2024/0271116 A1 | 8/2024 | Maianti et al. |
| 2024/0287487 A1 | 8/2024 | Liu et al. |
| 2024/0327872 A1 | 10/2024 | Liu et al. |

FOREIGN PATENT DOCUMENTS

| | | |
|---|---|---|
| AU | 2015101792 A4 | 1/2016 |
| AU | 2012354062 B2 | 9/2017 |
| BR | 112015013786 A2 | 7/2017 |
| CA | 2480696 A1 | 10/2003 |
| CA | 2894668 A1 | 6/2014 |
| CA | 2894681 A1 | 6/2014 |
| CA | 2894684 A1 | 6/2014 |
| CA | 2852593 A1 | 11/2015 |
| CN | 1069962 A | 3/1993 |
| CN | 101460619 A | 6/2009 |
| CN | 101873862 A | 10/2010 |
| CN | 102057039 A | 5/2011 |
| CN | 102892777 A | 1/2013 |
| CN | 103224947 A | 7/2013 |
| CN | 103233028 A | 8/2013 |
| CN | 103388006 A | 11/2013 |
| CN | 103614415 A | 3/2014 |
| CN | 103642836 A | 3/2014 |
| CN | 103668472 A | 3/2014 |
| CN | 103820441 A | 5/2014 |
| CN | 103820454 A | 5/2014 |
| CN | 103911376 A | 7/2014 |
| CN | 103923911 A | 7/2014 |
| CN | 103981211 A | 8/2014 |
| CN | 103981212 A | 8/2014 |
| CN | 104004778 A | 8/2014 |
| CN | 104004782 A | 8/2014 |
| CN | 104017821 A | 8/2014 |
| CN | 104109687 A | 10/2014 |
| CN | 104178461 A | 12/2014 |
| CN | 104342457 A | 2/2015 |
| CN | 104404036 A | 3/2015 |
| CN | 104450774 A | 3/2015 |
| CN | 104480144 A | 4/2015 |
| CN | 104498493 A | 4/2015 |
| CN | 104504304 A | 4/2015 |
| CN | 104531704 A | 4/2015 |
| CN | 104531705 A | 4/2015 |
| CN | 104560864 A | 4/2015 |
| CN | 104561095 A | 4/2015 |
| CN | 104593418 A | 5/2015 |
| CN | 104593422 A | 5/2015 |
| CN | 104611370 A | 5/2015 |
| CN | 104651392 A | 5/2015 |
| CN | 104651398 A | 5/2015 |
| CN | 104651399 A | 5/2015 |
| CN | 104651401 A | 5/2015 |
| CN | 104673816 A | 6/2015 |
| CN | 104725626 A | 6/2015 |
| CN | 104726449 A | 6/2015 |
| CN | 104726494 A | 6/2015 |
| CN | 104745626 A | 7/2015 |
| CN | 104762321 A | 7/2015 |
| CN | 104805078 A | 7/2015 |
| CN | 104805099 A | 7/2015 |
| CN | 104805118 A | 7/2015 |
| CN | 104846010 A | 8/2015 |
| CN | 104894068 A | 9/2015 |
| CN | 104894075 A | 9/2015 |
| CN | 104928321 A | 9/2015 |
| CN | 105039339 A | 11/2015 |
| CN | 105039399 A | 11/2015 |
| CN | 105063061 A | 11/2015 |
| CN | 105087620 A | 11/2015 |
| CN | 105112422 A | 12/2015 |
| CN | 105112445 A | 12/2015 |
| CN | 105112519 A | 12/2015 |
| CN | 105121648 A | 12/2015 |
| CN | 105132427 A | 12/2015 |
| CN | 105132451 A | 12/2015 |
| CN | 105177038 A | 12/2015 |
| CN | 105177126 A | 12/2015 |
| CN | 105210981 A | 1/2016 |
| CN | 105219799 A | 1/2016 |
| CN | 105238806 A | 1/2016 |
| CN | 105255937 A | 1/2016 |
| CN | 105274144 A | 1/2016 |
| CN | 105296518 A | 2/2016 |
| CN | 105296537 A | 2/2016 |
| CN | 105316324 A | 2/2016 |
| CN | 105316327 A | 2/2016 |
| CN | 105316337 A | 2/2016 |
| CN | 105331607 A | 2/2016 |
| CN | 105331608 A | 2/2016 |
| CN | 105331609 A | 2/2016 |
| CN | 105331627 A | 2/2016 |
| CN | 105400773 A | 3/2016 |
| CN | 105400779 A | 3/2016 |
| CN | 105400810 A | 3/2016 |
| CN | 105441451 A | 3/2016 |
| CN | 105462968 A | 4/2016 |
| CN | 105463003 A | 4/2016 |
| CN | 105463027 A | 4/2016 |
| CN | 105492608 A | 4/2016 |
| CN | 105492609 A | 4/2016 |
| CN | 105505976 A | 4/2016 |
| CN | 105505979 A | 4/2016 |
| CN | 105518134 A | 4/2016 |
| CN | 105518135 A | 4/2016 |
| CN | 105518137 A | 4/2016 |
| CN | 105518138 A | 4/2016 |
| CN | 105518139 A | 4/2016 |
| CN | 105518140 A | 4/2016 |
| CN | 105543228 A | 5/2016 |
| CN | 105543266 A | 5/2016 |
| CN | 105543270 A | 5/2016 |
| CN | 105567688 A | 5/2016 |
| CN | 105567689 A | 5/2016 |
| CN | 105567734 A | 5/2016 |
| CN | 105567735 A | 5/2016 |
| CN | 105567738 A | 5/2016 |
| CN | 105593367 A | 5/2016 |
| CN | 105594664 A | 5/2016 |

(56) References Cited

FOREIGN PATENT DOCUMENTS

| | | | |
|---|---|---|---|
| CN | 105602987 A | 5/2016 |
| CN | 105624146 A | 6/2016 |
| CN | 105624187 A | 6/2016 |
| CN | 105646719 A | 6/2016 |
| CN | 105647922 A | 6/2016 |
| CN | 105647962 A | 6/2016 |
| CN | 105647968 A | 6/2016 |
| CN | 105647969 A | 6/2016 |
| CN | 105671070 A | 6/2016 |
| CN | 105671083 A | 6/2016 |
| CN | 105695485 A | 6/2016 |
| CN | 105779448 A | 7/2016 |
| CN | 105779449 A | 7/2016 |
| CN | 105802980 A | 7/2016 |
| CN | 105821039 A | 8/2016 |
| CN | 105821040 A | 8/2016 |
| CN | 105821049 A | 8/2016 |
| CN | 105821072 A | 8/2016 |
| CN | 105821075 A | 8/2016 |
| CN | 105821116 A | 8/2016 |
| CN | 105838733 A | 8/2016 |
| CN | 105861547 A | 8/2016 |
| CN | 105861552 A | 8/2016 |
| CN | 105861554 A | 8/2016 |
| CN | 105886498 A | 8/2016 |
| CN | 105886534 A | 8/2016 |
| CN | 105886616 A | 8/2016 |
| CN | 105907758 A | 8/2016 |
| CN | 105907785 A | 8/2016 |
| CN | 105925608 A | 9/2016 |
| CN | 105934516 A | 9/2016 |
| CN | 105950560 A | 9/2016 |
| CN | 105950626 A | 9/2016 |
| CN | 105950633 A | 9/2016 |
| CN | 105950639 A | 9/2016 |
| CN | 105985985 A | 10/2016 |
| CN | 106011104 A | 10/2016 |
| CN | 106011150 A | 10/2016 |
| CN | 106011167 A | 10/2016 |
| CN | 106011171 A | 10/2016 |
| CN | 106032540 A | 10/2016 |
| CN | 106047803 A | 10/2016 |
| CN | 106047877 A | 10/2016 |
| CN | 106047930 A | 10/2016 |
| CN | 106086008 A | 11/2016 |
| CN | 106086028 A | 11/2016 |
| CN | 106086061 A | 11/2016 |
| CN | 106086062 A | 11/2016 |
| CN | 106103475 A | 11/2016 |
| CN | 106109417 A | 11/2016 |
| CN | 106119275 A | 11/2016 |
| CN | 106119283 A | 11/2016 |
| CN | 106148286 A | 11/2016 |
| CN | 106148370 A | 11/2016 |
| CN | 106148416 A | 11/2016 |
| CN | 106167525 A | 11/2016 |
| CN | 106167808 A | 11/2016 |
| CN | 106167810 A | 11/2016 |
| CN | 106167821 A | 11/2016 |
| CN | 106172238 A | 12/2016 |
| CN | 106190903 A | 12/2016 |
| CN | 106191057 A | 12/2016 |
| CN | 106191061 A | 12/2016 |
| CN | 106191062 A | 12/2016 |
| CN | 106191064 A | 12/2016 |
| CN | 106191071 A | 12/2016 |
| CN | 106191099 A | 12/2016 |
| CN | 106191107 A | 12/2016 |
| CN | 106191113 A | 12/2016 |
| CN | 106191114 A | 12/2016 |
| CN | 106191116 A | 12/2016 |
| CN | 106191124 A | 12/2016 |
| CN | 106222177 A | 12/2016 |
| CN | 106222193 A | 12/2016 |
| CN | 106222203 A | 12/2016 |
| CN | 106232823 A | 12/2016 |
| CN | 106244555 A | 12/2016 |
| CN | 106244557 A | 12/2016 |
| CN | 106244591 A | 12/2016 |
| CN | 106244609 A | 12/2016 |
| CN | 106282241 A | 1/2017 |
| CN | 106318934 A | 1/2017 |
| CN | 106318973 A | 1/2017 |
| CN | 106350540 A | 1/2017 |
| CN | 106367435 A | 2/2017 |
| CN | 106399306 A | 2/2017 |
| CN | 106399311 A | 2/2017 |
| CN | 106399360 A | 2/2017 |
| CN | 106399367 A | 2/2017 |
| CN | 106399375 A | 2/2017 |
| CN | 106399377 A | 2/2017 |
| CN | 106434651 A | 2/2017 |
| CN | 106434663 A | 2/2017 |
| CN | 106434688 A | 2/2017 |
| CN | 106434737 A | 2/2017 |
| CN | 106434748 A | 2/2017 |
| CN | 106434752 A | 2/2017 |
| CN | 106434782 A | 2/2017 |
| CN | 106446600 A | 2/2017 |
| CN | 106479985 A | 3/2017 |
| CN | 106480027 A | 3/2017 |
| CN | 106480036 A | 3/2017 |
| CN | 106480067 A | 3/2017 |
| CN | 106480080 A | 3/2017 |
| CN | 106480083 A | 3/2017 |
| CN | 106480097 A | 3/2017 |
| CN | 106544351 A | 3/2017 |
| CN | 106544353 A | 3/2017 |
| CN | 106544357 A | 3/2017 |
| CN | 106554969 A | 4/2017 |
| CN | 106566838 A | 4/2017 |
| CN | 106701763 A | 5/2017 |
| CN | 106701808 A | 5/2017 |
| CN | 106701818 A | 5/2017 |
| CN | 106701823 A | 5/2017 |
| CN | 106701830 A | 5/2017 |
| CN | 106754912 A | 5/2017 |
| CN | 106755026 A | 5/2017 |
| CN | 106755077 A | 5/2017 |
| CN | 106755088 A | 5/2017 |
| CN | 106755091 A | 5/2017 |
| CN | 106755097 A | 5/2017 |
| CN | 106755424 A | 5/2017 |
| CN | 106801056 A | 6/2017 |
| CN | 106834323 A | 6/2017 |
| CN | 106834341 A | 6/2017 |
| CN | 106834347 A | 6/2017 |
| CN | 106845151 A | 6/2017 |
| CN | 106868008 A | 6/2017 |
| CN | 106868031 A | 6/2017 |
| CN | 106906240 A | 6/2017 |
| CN | 106906242 A | 6/2017 |
| CN | 106916820 A | 7/2017 |
| CN | 106916852 A | 7/2017 |
| CN | 106939303 A | 7/2017 |
| CN | 106947750 A | 7/2017 |
| CN | 106947780 A | 7/2017 |
| CN | 106957830 A | 7/2017 |
| CN | 106957831 A | 7/2017 |
| CN | 106957844 A | 7/2017 |
| CN | 106957855 A | 7/2017 |
| CN | 106957858 A | 7/2017 |
| CN | 106967697 A | 7/2017 |
| CN | 106967726 A | 7/2017 |
| CN | 106978428 A | 7/2017 |
| CN | 106987570 A | 7/2017 |
| CN | 106987757 A | 7/2017 |
| CN | 107012164 A | 8/2017 |
| CN | 107012174 A | 8/2017 |
| CN | 107012213 A | 8/2017 |
| CN | 107012250 A | 8/2017 |
| CN | 107022562 A | 8/2017 |
| CN | 107034188 A | 8/2017 |
| CN | 107034218 A | 8/2017 |

(56) References Cited

FOREIGN PATENT DOCUMENTS

| | | |
|---|---|---|
| CN | 107034229 A | 8/2017 |
| CN | 107043775 A | 8/2017 |
| CN | 107043779 A | 8/2017 |
| CN | 107043787 A | 8/2017 |
| CN | 107058320 A | 8/2017 |
| CN | 107058328 A | 8/2017 |
| CN | 107058358 A | 8/2017 |
| CN | 107058372 A | 8/2017 |
| CN | 107083392 A | 8/2017 |
| CN | 107099533 A | 8/2017 |
| CN | 107099850 A | 8/2017 |
| CN | 107119053 A | 9/2017 |
| CN | 107119071 A | 9/2017 |
| CN | 107129999 A | 9/2017 |
| CN | 107130000 A | 9/2017 |
| CN | 107142272 A | 9/2017 |
| CN | 107142282 A | 9/2017 |
| CN | 107177591 A | 9/2017 |
| CN | 107177595 A | 9/2017 |
| CN | 107177625 A | 9/2017 |
| CN | 107177631 A | 9/2017 |
| CN | 107190006 A | 9/2017 |
| CN | 107190008 A | 9/2017 |
| CN | 107217042 A | 9/2017 |
| CN | 107217075 A | 9/2017 |
| CN | 107227307 A | 10/2017 |
| CN | 107227352 A | 10/2017 |
| CN | 107236737 A | 10/2017 |
| CN | 107236739 A | 10/2017 |
| CN | 107236741 A | 10/2017 |
| CN | 107245502 A | 10/2017 |
| CN | 107254485 A | 10/2017 |
| CN | 107266541 A | 10/2017 |
| CN | 107267515 A | 10/2017 |
| CN | 107287245 A | 10/2017 |
| CN | 107298701 A | 10/2017 |
| CN | 107299114 A | 10/2017 |
| CN | 107304435 A | 10/2017 |
| CN | 107312785 A | 11/2017 |
| CN | 107312793 A | 11/2017 |
| CN | 107312795 A | 11/2017 |
| CN | 107312798 A | 11/2017 |
| CN | 107326042 A | 11/2017 |
| CN | 107326046 A | 11/2017 |
| CN | 107354156 A | 11/2017 |
| CN | 107354173 A | 11/2017 |
| CN | 107356793 A | 11/2017 |
| CN | 107362372 A | 11/2017 |
| CN | 107365786 A | 11/2017 |
| CN | 107365804 A | 11/2017 |
| CN | 107384894 A | 11/2017 |
| CN | 107384922 A | 11/2017 |
| CN | 107384926 A | 11/2017 |
| CN | 107400677 A | 11/2017 |
| CN | 107418974 A | 12/2017 |
| CN | 107435051 A | 12/2017 |
| CN | 107435069 A | 12/2017 |
| CN | 107446922 A | 12/2017 |
| CN | 107446923 A | 12/2017 |
| CN | 107446924 A | 12/2017 |
| CN | 107446932 A | 12/2017 |
| CN | 107446951 A | 12/2017 |
| CN | 107446954 A | 12/2017 |
| CN | 107460196 A | 12/2017 |
| CN | 107474129 A | 12/2017 |
| CN | 107475300 A | 12/2017 |
| CN | 107488649 A | 12/2017 |
| CN | 107502608 A | 12/2017 |
| CN | 107502618 A | 12/2017 |
| CN | 107513531 A | 12/2017 |
| CN | 107519492 A | 12/2017 |
| CN | 107523567 A | 12/2017 |
| CN | 107523583 A | 12/2017 |
| CN | 107541525 A | 1/2018 |
| CN | 107557373 A | 1/2018 |
| CN | 107557378 A | 1/2018 |
| CN | 107557381 A | 1/2018 |
| CN | 107557390 A | 1/2018 |
| CN | 107557393 A | 1/2018 |
| CN | 107557394 A | 1/2018 |
| CN | 107557455 A | 1/2018 |
| CN | 107574179 A | 1/2018 |
| CN | 107586777 A | 1/2018 |
| CN | 107586779 A | 1/2018 |
| CN | 107604003 A | 1/2018 |
| CN | 107619829 A | 1/2018 |
| CN | 107619837 A | 1/2018 |
| CN | 107630006 A | 1/2018 |
| CN | 107630041 A | 1/2018 |
| CN | 107630042 A | 1/2018 |
| CN | 107630043 A | 1/2018 |
| CN | 107641631 A | 1/2018 |
| CN | 107653256 A | 2/2018 |
| CN | 107686848 A | 2/2018 |
| CN | 206970581 A | 2/2018 |
| CN | 107760652 A | 3/2018 |
| CN | 107760663 A | 3/2018 |
| CN | 107760684 A | 3/2018 |
| CN | 107760715 A | 3/2018 |
| CN | 107784200 A | 3/2018 |
| CN | 107794272 A | 3/2018 |
| CN | 107794276 A | 3/2018 |
| CN | 107815463 A | 3/2018 |
| CN | 107828738 A | 3/2018 |
| CN | 107828794 A | 3/2018 |
| CN | 107828826 A | 3/2018 |
| CN | 107828874 A | 3/2018 |
| CN | 107858346 A | 3/2018 |
| CN | 107858373 A | 3/2018 |
| CN | 107880132 A | 4/2018 |
| CN | 107881184 A | 4/2018 |
| CN | 107893074 A | 4/2018 |
| CN | 107893075 A | 4/2018 |
| CN | 107893076 A | 4/2018 |
| CN | 107893080 A | 4/2018 |
| CN | 107893086 A | 4/2018 |
| CN | 107904261 A | 4/2018 |
| CN | 107937427 A | 4/2018 |
| CN | 107937432 A | 4/2018 |
| CN | 107937501 A | 4/2018 |
| CN | 107974466 A | 5/2018 |
| CN | 107988229 A | 5/2018 |
| CN | 107988246 A | 5/2018 |
| CN | 107988256 A | 5/2018 |
| CN | 107988268 A | 5/2018 |
| CN | 108018316 A | 5/2018 |
| CN | 108034656 A | 5/2018 |
| CN | 108048466 A | 5/2018 |
| CN | 108102940 A | 6/2018 |
| CN | 108103090 A | 6/2018 |
| CN | 108103092 A | 6/2018 |
| CN | 108103098 A | 6/2018 |
| CN | 108103586 A | 6/2018 |
| CN | 108148835 A | 6/2018 |
| CN | 108148837 A | 6/2018 |
| CN | 108148873 A | 6/2018 |
| CN | 108192956 A | 6/2018 |
| CN | 108243575 A | 7/2018 |
| CN | 108251423 A | 7/2018 |
| CN | 108251451 A | 7/2018 |
| CN | 108251452 A | 7/2018 |
| CN | 108342480 A | 7/2018 |
| CN | 108359691 A | 8/2018 |
| CN | 108359712 A | 8/2018 |
| CN | 108384784 A | 8/2018 |
| CN | 108396027 A | 8/2018 |
| CN | 108410877 A | 8/2018 |
| CN | 108410906 A | 8/2018 |
| CN | 108410907 A | 8/2018 |
| CN | 108410911 A | 8/2018 |
| CN | 108424931 A | 8/2018 |
| CN | 108441519 A | 8/2018 |
| CN | 108441520 A | 8/2018 |
| CN | 108472314 A | 8/2018 |

(56) References Cited

FOREIGN PATENT DOCUMENTS

| | | |
|---|---|---|
| CN | 108486108 A | 9/2018 |
| CN | 108486111 A | 9/2018 |
| CN | 108486145 A | 9/2018 |
| CN | 108486146 A | 9/2018 |
| CN | 108486154 A | 9/2018 |
| CN | 108486159 A | 9/2018 |
| CN | 108486234 A | 9/2018 |
| CN | 108504657 A | 9/2018 |
| CN | 108504685 A | 9/2018 |
| CN | 108504693 A | 9/2018 |
| CN | 108513575 A | 9/2018 |
| CN | 108546712 A | 9/2018 |
| CN | 108546717 A | 9/2018 |
| CN | 108546718 A | 9/2018 |
| CN | 108559730 A | 9/2018 |
| CN | 108559732 A | 9/2018 |
| CN | 108559745 A | 9/2018 |
| CN | 108559760 A | 9/2018 |
| CN | 108570479 A | 9/2018 |
| CN | 108588071 A | 9/2018 |
| CN | 108588123 A | 9/2018 |
| CN | 108588128 A | 9/2018 |
| CN | 108588182 A | 9/2018 |
| CN | 108610399 A | 10/2018 |
| CN | 108611364 A | 10/2018 |
| CN | 108624622 A | 10/2018 |
| CN | 108642053 A | 10/2018 |
| CN | 108642055 A | 10/2018 |
| CN | 108642077 A | 10/2018 |
| CN | 108642078 A | 10/2018 |
| CN | 108642090 A | 10/2018 |
| CN | 108690844 A | 10/2018 |
| CN | 108699542 A | 10/2018 |
| CN | 108707604 A | 10/2018 |
| CN | 108707620 A | 10/2018 |
| CN | 108707621 A | 10/2018 |
| CN | 108707628 A | 10/2018 |
| CN | 108707629 A | 10/2018 |
| CN | 108715850 A | 10/2018 |
| CN | 108728476 A | 11/2018 |
| CN | 108728486 A | 11/2018 |
| CN | 108753772 A | 11/2018 |
| CN | 108753783 A | 11/2018 |
| CN | 108753813 A | 11/2018 |
| CN | 108753817 A | 11/2018 |
| CN | 108753832 A | 11/2018 |
| CN | 108753835 A | 11/2018 |
| CN | 108753836 A | 11/2018 |
| CN | 108795902 A | 11/2018 |
| CN | 108822217 A | 11/2018 |
| CN | 108823248 A | 11/2018 |
| CN | 108823249 A | 11/2018 |
| CN | 108823291 A | 11/2018 |
| CN | 108841845 A | 11/2018 |
| CN | 108853133 A | 11/2018 |
| CN | 108866093 A | 11/2018 |
| CN | 108893529 A | 11/2018 |
| CN | 108913664 A | 11/2018 |
| CN | 108913691 A | 11/2018 |
| CN | 108913714 A | 11/2018 |
| CN | 108913717 A | 11/2018 |
| CN | 208034188 U | 11/2018 |
| CN | 109517841 A | 3/2019 |
| EP | 0264166 A1 | 4/1988 |
| EP | 321201 B2 | 6/1989 |
| EP | 519463 A1 | 12/1992 |
| EP | 1085892 A2 | 3/2001 |
| EP | 1092770 A2 | 4/2001 |
| EP | 2350295 B1 | 5/2013 |
| EP | 2604255 A1 | 6/2013 |
| EP | 2840140 A1 | 2/2015 |
| EP | 2877490 A2 | 6/2015 |
| EP | 2966170 A1 | 1/2016 |
| EP | 3009511 A2 | 4/2016 |
| EP | 3031921 A1 | 6/2016 |
| EP | 3045537 A1 | 7/2016 |
| EP | 3115457 A1 | 1/2017 |
| EP | 3144390 A1 | 3/2017 |
| EP | 2583974 B1 | 4/2017 |
| EP | 3199632 A1 | 8/2017 |
| EP | 3216867 A1 | 9/2017 |
| EP | 3235828 A1 | 10/2017 |
| EP | 3252160 A1 | 12/2017 |
| EP | 2498823 B1 | 8/2018 |
| EP | 3365437 A1 | 8/2018 |
| EP | 3454889 A2 | 3/2019 |
| EP | 3008192 B1 | 7/2019 |
| EP | 3079725 B1 | 10/2019 |
| EP | 3450553 B1 | 12/2019 |
| EP | 3622079 A1 | 3/2020 |
| ES | 2740248 T3 | 2/2020 |
| GB | 2528177 A | 1/2016 |
| GB | 2531454 A1 | 4/2016 |
| GB | 2542653 A | 3/2017 |
| HK | 1208045 A1 | 2/2016 |
| JP | 2007-501626 A | 2/2007 |
| JP | 2008-515405 A | 5/2008 |
| JP | 2010-033344 A | 2/2010 |
| JP | 2010-535744 A | 11/2010 |
| JP | 2010-539929 A | 12/2010 |
| JP | 2011-081011 A | 4/2011 |
| JP | 2011-523353 A | 8/2011 |
| JP | 2012-525146 A | 10/2012 |
| JP | 2012-210172 A | 11/2012 |
| JP | 2012-531909 A | 12/2012 |
| JP | 2015-523856 A | 8/2015 |
| JP | 2015-532654 A | 11/2015 |
| JP | 2016-525888 A | 9/2016 |
| JP | 2016-534132 A | 11/2016 |
| JP | 2017-500035 A | 1/2017 |
| JP | 2018-521045 A | 8/2018 |
| JP | 2019-506123 A | 2/2019 |
| JP | 6629734 B2 | 1/2020 |
| JP | 6633524 B2 | 1/2020 |
| JP | 6830517 B2 | 2/2021 |
| JP | 7324523 B2 | 8/2023 |
| KR | 101584933 B1 | 1/2016 |
| KR | 2016-0050069 A | 5/2016 |
| KR | 20160133380 A | 11/2016 |
| KR | 20170037025 A | 4/2017 |
| KR | 20170037028 A | 4/2017 |
| KR | 101748575 B1 | 6/2017 |
| KR | 20170128137 A | 11/2017 |
| KR | 2018-0022465 A | 3/2018 |
| RU | 2016104674 A | 8/2017 |
| RU | 2634395 C1 | 10/2017 |
| RU | 2652899 C1 | 5/2018 |
| RU | 2015128057 A | 3/2019 |
| RU | 2015128098 A | 3/2019 |
| RU | 2687451 C1 | 5/2019 |
| RU | 2019112514 A | 6/2019 |
| RU | 2019127300 A | 9/2019 |
| RU | 2701850 C2 | 10/2019 |
| SG | 10201707569 | 10/2017 |
| SG | 10201707569 Y | 10/2017 |
| SG | 10201710486 | 1/2018 |
| SG | 10201710486X | 1/2018 |
| SG | 10201710487 | 1/2018 |
| SG | 10201710488 | 1/2018 |
| SG | 10201710488 T | 1/2018 |
| TW | I608100 B | 12/2017 |
| TW | 201809272 A | 3/2018 |
| TW | 2018-29773 A | 8/2018 |
| WO | WO 1990/002809 A1 | 3/1990 |
| WO | WO 1991/003162 A1 | 3/1991 |
| WO | WO 1991/016024 A1 | 10/1991 |
| WO | WO 1991/017271 A1 | 11/1991 |
| WO | WO 1991/017424 A1 | 11/1991 |
| WO | WO 1992/006188 A2 | 4/1992 |
| WO | WO 1992/006200 A1 | 4/1992 |
| WO | WO 1992/007065 A1 | 4/1992 |
| WO | WO 1993/015187 A1 | 8/1993 |
| WO | WO 1993/024641 A2 | 12/1993 |
| WO | WO 1994/018316 A2 | 8/1994 |

(56) References Cited

FOREIGN PATENT DOCUMENTS

| | | |
|---|---|---|
| WO | WO 1994/026877 A1 | 11/1994 |
| WO | WO 1996/004403 A1 | 2/1996 |
| WO | WO 1996/010640 A1 | 4/1996 |
| WO | WO 1997/025416 A2 | 7/1997 |
| WO | WO 1998/032845 A1 | 7/1998 |
| WO | WO 1998/050538 A1 | 11/1998 |
| WO | WO 2001/036452 A2 | 5/2001 |
| WO | WO 2001/038547 A2 | 5/2001 |
| WO | WO 2002/059296 A2 | 8/2002 |
| WO | WO 2002/068676 A2 | 9/2002 |
| WO | WO 2002/103028 A2 | 12/2002 |
| WO | WO 2003/004608 A2 | 1/2003 |
| WO | WO 2004/007684 A2 | 1/2004 |
| WO | WO 2005/014791 A2 | 2/2005 |
| WO | WO 2005/019415 A2 | 3/2005 |
| WO | WO 2006/002547 A1 | 1/2006 |
| WO | WO 2006/042112 A2 | 4/2006 |
| WO | WO 2007/025097 A2 | 3/2007 |
| WO | WO 2007/037444 A1 | 4/2007 |
| WO | WO 2007/066923 A1 | 6/2007 |
| WO | WO 2007/136815 A2 | 11/2007 |
| WO | WO 2007/143574 A1 | 12/2007 |
| WO | WO 2008/005529 A2 | 1/2008 |
| WO | WO 2008/108989 A2 | 9/2008 |
| WO | WO 2009/002418 A2 | 12/2008 |
| WO | WO 2009/019317 A1 | 2/2009 |
| WO | WO 2009/098290 A1 | 8/2009 |
| WO | WO 2009/134808 A2 | 11/2009 |
| WO | WO 2010/011961 A2 | 1/2010 |
| WO | WO 2010/012902 A1 | 2/2010 |
| WO | WO 2010/028347 A2 | 3/2010 |
| WO | WO 2010/054108 A2 | 5/2010 |
| WO | WO 2010/054154 A2 | 5/2010 |
| WO | WO 2010/068289 A2 | 6/2010 |
| WO | WO 2010/075424 A2 | 7/2010 |
| WO | WO 2010/091122 A1 | 8/2010 |
| WO | WO 2010/102257 A2 | 9/2010 |
| WO | WO 2010/104749 A2 | 9/2010 |
| WO | WO 2010/129019 A2 | 11/2010 |
| WO | WO 2010/129023 A2 | 11/2010 |
| WO | WO 2010/132092 A2 | 11/2010 |
| WO | WO 2010/144150 A2 | 12/2010 |
| WO | WO 2011/002503 A1 | 1/2011 |
| WO | WO 2011/017293 A2 | 2/2011 |
| WO | WO 2017/062983 A1 | 4/2011 |
| WO | WO 2011/053868 A1 | 5/2011 |
| WO | WO 2011/053982 A2 | 5/2011 |
| WO | WO 2011/068810 A1 | 6/2011 |
| WO | WO 2011/075627 A1 | 6/2011 |
| WO | WO 2011/091311 A2 | 7/2011 |
| WO | WO 2011/091396 A1 | 7/2011 |
| WO | WO 2011/109031 A1 | 9/2011 |
| WO | WO 2011/143124 A2 | 11/2011 |
| WO | WO 2011/147590 A2 | 12/2011 |
| WO | WO 2011/159369 A1 | 12/2011 |
| WO | WO 2012/054726 A1 | 4/2012 |
| WO | WO 2012/061815 A2 | 5/2012 |
| WO | WO 2012/065043 A2 | 5/2012 |
| WO | WO 2012/088381 A2 | 6/2012 |
| WO | WO 2012/125445 A2 | 9/2012 |
| WO | WO 2012/138927 A2 | 10/2012 |
| WO | WO 2012/149470 A1 | 11/2012 |
| WO | WO 2012/158985 A2 | 11/2012 |
| WO | WO 2012/158986 A2 | 11/2012 |
| WO | WO 2012/164565 A1 | 12/2012 |
| WO | WO 2012/170930 A1 | 12/2012 |
| WO | WO 2013/012674 A1 | 1/2013 |
| WO | WO 2013/013105 A2 | 1/2013 |
| WO | WO 2013/039857 A1 | 3/2013 |
| WO | WO 2013/039861 A2 | 3/2013 |
| WO | WO 2013/040093 A2 | 3/2013 |
| WO | WO 2013/045632 A1 | 4/2013 |
| WO | WO 2013/047844 A1 | 4/2013 |
| WO | WO 2013/066438 A2 | 5/2013 |
| WO | WO 2013/086441 A2 | 6/2013 |
| WO | WO 2013/086444 A2 | 6/2013 |
| WO | WO 2013/098244 A1 | 7/2013 |
| WO | WO 2013/119602 A1 | 8/2013 |
| WO | WO 2013/120022 A2 | 8/2013 |
| WO | WO 2013/122617 A1 | 8/2013 |
| WO | WO 2013/126794 A1 | 8/2013 |
| WO | WO 2013/130683 A2 | 9/2013 |
| WO | WO 2013/130824 A1 | 9/2013 |
| WO | WO 2013/141680 A1 | 9/2013 |
| WO | WO 2013/142578 A2 | 9/2013 |
| WO | WO 2013/152359 A1 | 10/2013 |
| WO | WO 2013/160230 A1 | 10/2013 |
| WO | WO 2013/166315 A1 | 11/2013 |
| WO | WO 2013/169398 A2 | 11/2013 |
| WO | WO 2013/169802 A1 | 11/2013 |
| WO | WO 2013/176772 A2 | 11/2013 |
| WO | WO 2013/176915 A1 | 11/2013 |
| WO | WO 2013/176916 A1 | 11/2013 |
| WO | WO 2013/181440 A1 | 12/2013 |
| WO | WO 2013/186754 A2 | 12/2013 |
| WO | WO 2013/188037 A2 | 12/2013 |
| WO | WO 2013/188522 A2 | 12/2013 |
| WO | WO 2013/188638 A2 | 12/2013 |
| WO | WO 2013/192278 A1 | 12/2013 |
| WO | WO 2013/142378 A9 | 1/2014 |
| WO | WO 2014/004336 A1 | 1/2014 |
| WO | WO 2014/005042 A2 | 1/2014 |
| WO | WO 2014/011237 A1 | 1/2014 |
| WO | WO 2014/011901 A2 | 1/2014 |
| WO | WO 2014/018423 A2 | 1/2014 |
| WO | WO 2014/020608 A1 | 2/2014 |
| WO | WO 2014/022120 A1 | 2/2014 |
| WO | WO 2014/022702 A2 | 2/2014 |
| WO | WO 2014/036219 A2 | 3/2014 |
| WO | WO 2014/039513 A2 | 3/2014 |
| WO | WO 2014/039523 A1 | 3/2014 |
| WO | WO 2014/039585 A2 | 3/2014 |
| WO | WO 2014/039684 A1 | 3/2014 |
| WO | WO 2014/039692 A2 | 3/2014 |
| WO | WO 2014/039702 A2 | 3/2014 |
| WO | WO 2014/039872 A1 | 3/2014 |
| WO | WO 2014/039970 A1 | 3/2014 |
| WO | WO 2014/041327 A1 | 3/2014 |
| WO | WO 2014/043143 A1 | 3/2014 |
| WO | WO 2014/047103 A2 | 3/2014 |
| WO | WO 2014/055782 A1 | 4/2014 |
| WO | WO 2014/059173 A2 | 4/2014 |
| WO | WO 2014/059255 A1 | 4/2014 |
| WO | WO 2014/065596 A1 | 5/2014 |
| WO | WO 2014/066505 A1 | 5/2014 |
| WO | WO 2014/068346 A2 | 5/2014 |
| WO | WO 2014/070887 A1 | 5/2014 |
| WO | WO 2014/071006 A1 | 5/2014 |
| WO | WO 2014/071219 A1 | 5/2014 |
| WO | WO 2014/071235 A1 | 5/2014 |
| WO | WO 2014/072941 A1 | 5/2014 |
| WO | WO 2014/081729 A1 | 5/2014 |
| WO | WO 2014/081730 A1 | 5/2014 |
| WO | WO 2014/081855 A1 | 5/2014 |
| WO | WO 2014/082644 A1 | 6/2014 |
| WO | WO 2014/085261 A1 | 6/2014 |
| WO | WO 2014/085593 A1 | 6/2014 |
| WO | WO 2014/085830 A2 | 6/2014 |
| WO | WO 2014/089212 A1 | 6/2014 |
| WO | WO 2014/089290 A1 | 6/2014 |
| WO | WO 2014/089348 A1 | 6/2014 |
| WO | WO 2014/089513 A1 | 6/2014 |
| WO | WO 2014/089533 A2 | 6/2014 |
| WO | WO 2014/089541 A2 | 6/2014 |
| WO | WO 2014/093479 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093709 A1 | 6/2014 |
| WO | WO 2014/093712 A1 | 6/2014 |

(56) References Cited

FOREIGN PATENT DOCUMENTS

| | | |
|---|---|---|
| WO | WO 2014/093718 A1 | 6/2014 |
| WO | WO 2014/093736 A1 | 6/2014 |
| WO | WO 2014/093768 A1 | 6/2014 |
| WO | WO 2014/093852 A1 | 6/2014 |
| WO | WO 2014/096972 A2 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2014/110006 A1 | 7/2014 |
| WO | WO 2014/110552 A1 | 7/2014 |
| WO | WO 2014/113493 A1 | 7/2014 |
| WO | WO 2014/123967 A2 | 8/2014 |
| WO | WO 2014/124226 A1 | 8/2014 |
| WO | WO 2014/125668 A1 | 8/2014 |
| WO | WO 2014/127287 A1 | 8/2014 |
| WO | WO 2014/128324 A1 | 8/2014 |
| WO | WO 2014/128659 A1 | 8/2014 |
| WO | WO 2014/130706 A1 | 8/2014 |
| WO | WO 2014/130955 A1 | 8/2014 |
| WO | WO 2014/131833 A1 | 9/2014 |
| WO | WO 2014/138379 A1 | 9/2014 |
| WO | WO 2014/143381 A1 | 9/2014 |
| WO | WO 2014/144094 A1 | 9/2014 |
| WO | WO 2014/144155 A1 | 9/2014 |
| WO | WO 2014/144288 A1 | 9/2014 |
| WO | WO 2014/144592 A2 | 9/2014 |
| WO | WO 2014/144761 A2 | 9/2014 |
| WO | WO 2014/144951 A1 | 9/2014 |
| WO | WO 2014/145599 A2 | 9/2014 |
| WO | WO 2014/145736 A2 | 9/2014 |
| WO | WO 2014/150624 A1 | 9/2014 |
| WO | WO 2014/152432 A2 | 9/2014 |
| WO | WO 2014/152940 A1 | 9/2014 |
| WO | WO 2014/153118 A1 | 9/2014 |
| WO | WO 2014/153470 A2 | 9/2014 |
| WO | WO 2014/158593 A1 | 10/2014 |
| WO | WO 2014/161821 A1 | 10/2014 |
| WO | WO 2014/164466 A1 | 10/2014 |
| WO | WO 2014/165177 A1 | 10/2014 |
| WO | WO 2014/165349 A1 | 10/2014 |
| WO | WO 2014/165612 A2 | 10/2014 |
| WO | WO 2014/165707 A2 | 10/2014 |
| WO | WO 2014/165825 A2 | 10/2014 |
| WO | WO 2014/172458 A1 | 10/2014 |
| WO | WO 2014/172470 A2 | 10/2014 |
| WO | WO 2014/172489 A2 | 10/2014 |
| WO | WO 2014/173955 A1 | 10/2014 |
| WO | WO 2014/182700 A1 | 11/2014 |
| WO | WO 2014/183071 A2 | 11/2014 |
| WO | WO 2014/184143 A1 | 11/2014 |
| WO | WO 2014/184741 A1 | 11/2014 |
| WO | WO 2014/184744 A1 | 11/2014 |
| WO | WO 2014/186585 A2 | 11/2014 |
| WO | WO 2014/186686 A2 | 11/2014 |
| WO | WO 2014/190181 A1 | 11/2014 |
| WO | WO 2014/191128 A1 | 12/2014 |
| WO | WO 2014/191518 A1 | 12/2014 |
| WO | WO 2014/191521 A2 | 12/2014 |
| WO | WO 2014/191525 A1 | 12/2014 |
| WO | WO 2014/191527 A1 | 12/2014 |
| WO | WO 2014/193583 A2 | 12/2014 |
| WO | WO 2014/194190 A1 | 12/2014 |
| WO | WO 2014/197568 A2 | 12/2014 |
| WO | WO 2014/197748 A2 | 12/2014 |
| WO | WO 2014/199358 A1 | 12/2014 |
| WO | WO 2014/200659 A1 | 12/2014 |
| WO | WO 2014/201015 A2 | 12/2014 |
| WO | WO 2014/204578 A1 | 12/2014 |
| WO | WO 2014/204723 A1 | 12/2014 |
| WO | WO 2014/204724 A1 | 12/2014 |
| WO | WO 2014/204725 A1 | 12/2014 |
| WO | WO 2014/204726 A1 | 12/2014 |
| WO | WO 2014/204727 A1 | 12/2014 |
| WO | WO 2014/204728 A1 | 12/2014 |
| WO | WO 2014/204729 A1 | 12/2014 |
| WO | WO 2014/205192 A2 | 12/2014 |
| WO | WO 2014/207043 A1 | 12/2014 |
| WO | WO 2015/002780 A1 | 1/2015 |
| WO | WO 2015/004241 A2 | 1/2015 |
| WO | WO 2015/006290 A1 | 1/2015 |
| WO | WO 2015/006294 A2 | 1/2015 |
| WO | WO 2015/006437 A1 | 1/2015 |
| WO | WO 2015/006498 A2 | 1/2015 |
| WO | WO 2015/006747 A2 | 1/2015 |
| WO | WO 2015/007194 A1 | 1/2015 |
| WO | WO 2015/010114 A1 | 1/2015 |
| WO | WO 2015/011483 A1 | 1/2015 |
| WO | WO 2015/013583 A2 | 1/2015 |
| WO | WO 2015/017866 A1 | 2/2015 |
| WO | WO 2015/018503 A1 | 2/2015 |
| WO | WO 2015/021353 A2 | 2/2015 |
| WO | WO 2015/021426 A1 | 2/2015 |
| WO | WO 2015/021990 A1 | 2/2015 |
| WO | WO 2015/024017 A2 | 2/2015 |
| WO | WO 2015/024986 A1 | 2/2015 |
| WO | WO 2015/026883 A1 | 2/2015 |
| WO | WO 2015/026885 A1 | 2/2015 |
| WO | WO 2015/026886 A1 | 2/2015 |
| WO | WO 2015/026887 A1 | 2/2015 |
| WO | WO 2015/027134 A1 | 2/2015 |
| WO | WO 2015/028969 A2 | 3/2015 |
| WO | WO 2015/030881 A1 | 3/2015 |
| WO | WO 2015/031619 A1 | 3/2015 |
| WO | WO 2015/031775 A1 | 3/2015 |
| WO | WO 2015/032494 A2 | 3/2015 |
| WO | WO 2015/033293 A1 | 3/2015 |
| WO | WO 2015/034872 A2 | 3/2015 |
| WO | WO 2015/034885 A1 | 3/2015 |
| WO | WO 2015/035136 A2 | 3/2015 |
| WO | WO 2015/035139 A2 | 3/2015 |
| WO | WO 2015/035162 A2 | 3/2015 |
| WO | WO 2015/040075 A1 | 3/2015 |
| WO | WO 2015/040402 A1 | 3/2015 |
| WO | WO 2015/042393 A2 | 3/2015 |
| WO | WO 2015/042585 A1 | 3/2015 |
| WO | WO 2015/048577 A2 | 4/2015 |
| WO | WO 2015/048690 A1 | 4/2015 |
| WO | WO 2015/048707 A2 | 4/2015 |
| WO | WO 2015/048801 A2 | 4/2015 |
| WO | WO 2015/049897 A1 | 4/2015 |
| WO | WO 2015/051191 A1 | 4/2015 |
| WO | WO 2015/052133 A1 | 4/2015 |
| WO | WO 2015/052231 A2 | 4/2015 |
| WO | WO 2015/052335 A1 | 4/2015 |
| WO | WO 2015/053995 A1 | 4/2015 |
| WO | WO 2015/054253 A1 | 4/2015 |
| WO | WO 2015/054315 A1 | 4/2015 |
| WO | WO 2015/057671 A1 | 4/2015 |
| WO | WO 2015/057834 A1 | 4/2015 |
| WO | WO 2015/057852 A1 | 4/2015 |
| WO | WO 2015/057976 A1 | 4/2015 |
| WO | WO 2015/057980 A1 | 4/2015 |
| WO | WO 2015/059265 A1 | 4/2015 |
| WO | WO 2015/065964 A1 | 5/2015 |
| WO | WO 2015/066119 A1 | 5/2015 |
| WO | WO 2015/066634 A2 | 5/2015 |
| WO | WO 2015/066636 A2 | 5/2015 |
| WO | WO 2015/066637 A1 | 5/2015 |
| WO | WO 2015/066638 A2 | 5/2015 |
| WO | WO 2015/066643 A1 | 5/2015 |
| WO | WO 2015/069682 A2 | 5/2015 |
| WO | WO 2015/070083 A1 | 5/2015 |
| WO | WO 2015/070193 A1 | 5/2015 |
| WO | WO 2015/070212 A1 | 5/2015 |
| WO | WO 2015/071474 A2 | 5/2015 |
| WO | WO 2015/073683 A2 | 5/2015 |
| WO | WO 2015/073867 A2 | 5/2015 |
| WO | WO 2015/073990 A1 | 5/2015 |
| WO | WO 2015/075056 A1 | 5/2015 |
| WO | WO 2015/075154 A2 | 5/2015 |
| WO | WO 2015/075175 A1 | 5/2015 |
| WO | WO 2015/075195 A1 | 5/2015 |
| WO | WO 2015/075557 A2 | 5/2015 |
| WO | WO 2015/077058 A2 | 5/2015 |

(56) References Cited

FOREIGN PATENT DOCUMENTS

| | | |
|---|---|---|
| WO | WO 2015/077290 A2 | 5/2015 |
| WO | WO 2015/077318 A1 | 5/2015 |
| WO | WO 2015/079056 A1 | 6/2015 |
| WO | WO 2015/079057 A2 | 6/2015 |
| WO | WO 2015/086795 A1 | 6/2015 |
| WO | WO 2015/086798 A2 | 6/2015 |
| WO | WO 2015/088643 A1 | 6/2015 |
| WO | WO 2015/089046 A1 | 6/2015 |
| WO | WO 2015/089077 A2 | 6/2015 |
| WO | WO 2015/089277 A1 | 6/2015 |
| WO | WO 2015/089351 A1 | 6/2015 |
| WO | WO 2015/089354 A1 | 6/2015 |
| WO | WO 2015/089364 A1 | 6/2015 |
| WO | WO 2015/089406 A1 | 6/2015 |
| WO | WO 2015/089419 A2 | 6/2015 |
| WO | WO 2015/089427 A1 | 6/2015 |
| WO | WO 2015/089462 A1 | 6/2015 |
| WO | WO 2015/089465 A1 | 6/2015 |
| WO | WO 2015/089473 A1 | 6/2015 |
| WO | WO 2015/089486 A2 | 6/2015 |
| WO | WO 2015/095804 A1 | 6/2015 |
| WO | WO 2015/099850 A1 | 7/2015 |
| WO | WO 2015/100929 A1 | 7/2015 |
| WO | WO 2015/103057 A1 | 7/2015 |
| WO | WO 2015/103153 A1 | 7/2015 |
| WO | WO 2015/105928 A1 | 7/2015 |
| WO | WO 2015/108993 A1 | 7/2015 |
| WO | WO 2015/109752 A1 | 7/2015 |
| WO | WO 2015/110474 A1 | 7/2015 |
| WO | WO 2015/112790 A2 | 7/2015 |
| WO | WO 2015/112896 A2 | 7/2015 |
| WO | WO 2015/113063 A1 | 7/2015 |
| WO | WO 2015/114365 A1 | 8/2015 |
| WO | WO 2015/115903 A1 | 8/2015 |
| WO | WO 2015/116686 A1 | 8/2015 |
| WO | WO 2015/116969 A2 | 8/2015 |
| WO | WO 2015/117021 A1 | 8/2015 |
| WO | WO 2015/117041 A1 | 8/2015 |
| WO | WO 2015/117081 A2 | 8/2015 |
| WO | WO 2015/118156 A1 | 8/2015 |
| WO | WO 2015/119941 A2 | 8/2015 |
| WO | WO 2015/121454 A1 | 8/2015 |
| WO | WO 2015/122967 A1 | 8/2015 |
| WO | WO 2015/123339 A1 | 8/2015 |
| WO | WO 2015/124715 A1 | 8/2015 |
| WO | WO 2015/124718 A1 | 8/2015 |
| WO | WO 2015/126927 A2 | 8/2015 |
| WO | WO 2015/127428 A1 | 8/2015 |
| WO | WO 2015/127439 A1 | 8/2015 |
| WO | WO 2015/129686 A1 | 9/2015 |
| WO | WO 2015/131101 A1 | 9/2015 |
| WO | WO 2015/133554 A1 | 9/2015 |
| WO | WO 2015/134121 A2 | 9/2015 |
| WO | WO 2015/134812 A1 | 9/2015 |
| WO | WO 2015/136001 A1 | 9/2015 |
| WO | WO 2015/138510 A1 | 9/2015 |
| WO | WO 2015/138739 A2 | 9/2015 |
| WO | WO 2015/138855 A1 | 9/2015 |
| WO | WO 2015/138870 A2 | 9/2015 |
| WO | WO 2015/139008 A1 | 9/2015 |
| WO | WO 2015/139139 A1 | 9/2015 |
| WO | WO 2015/143046 A2 | 9/2015 |
| WO | WO 2015/143177 A1 | 9/2015 |
| WO | WO 2015/145417 A1 | 10/2015 |
| WO | WO 2015/148431 A1 | 10/2015 |
| WO | WO 2015/148670 A1 | 10/2015 |
| WO | WO 2015/148680 A1 | 10/2015 |
| WO | WO 2015/148760 A1 | 10/2015 |
| WO | WO 2015/148761 A1 | 10/2015 |
| WO | WO 2015/148860 A1 | 10/2015 |
| WO | WO 2015/148863 A2 | 10/2015 |
| WO | WO 2015/153760 A2 | 10/2015 |
| WO | WO 2015/153780 A1 | 10/2015 |
| WO | WO 2015/153789 A1 | 10/2015 |
| WO | WO 2015/153791 A1 | 10/2015 |
| WO | WO 2015/153889 A2 | 10/2015 |
| WO | WO 2015/153940 A1 | 10/2015 |
| WO | WO 2015/155341 A1 | 10/2015 |
| WO | WO 2015/155686 A2 | 10/2015 |
| WO | WO 2015/157070 A2 | 10/2015 |
| WO | WO 2015/157534 A1 | 10/2015 |
| WO | WO 2015/159068 A1 | 10/2015 |
| WO | WO 2015/159086 A1 | 10/2015 |
| WO | WO 2015/159087 A1 | 10/2015 |
| WO | WO 2015/160683 A1 | 10/2015 |
| WO | WO 2015/161276 A2 | 10/2015 |
| WO | WO 2015/163733 A1 | 10/2015 |
| WO | WO 2015/164740 A1 | 10/2015 |
| WO | WO 2015/164748 A1 | 10/2015 |
| WO | WO 2015/165274 A1 | 11/2015 |
| WO | WO 2015/165275 A1 | 11/2015 |
| WO | WO 2015/165276 A1 | 11/2015 |
| WO | WO 2015/166272 A2 | 11/2015 |
| WO | WO 2015/167766 A1 | 11/2015 |
| WO | WO 2015/167956 A1 | 11/2015 |
| WO | WO 2015/168125 A1 | 11/2015 |
| WO | WO 2015/168158 A1 | 11/2015 |
| WO | WO 2015/168404 A1 | 11/2015 |
| WO | WO 2015/168547 A2 | 11/2015 |
| WO | WO 2015/168800 A1 | 11/2015 |
| WO | WO 2015/171603 A1 | 11/2015 |
| WO | WO 2015/171894 A1 | 11/2015 |
| WO | WO 2015/171932 A1 | 11/2015 |
| WO | WO 2015/172128 A1 | 11/2015 |
| WO | WO 2015/173436 A1 | 11/2015 |
| WO | WO 2015/175642 A2 | 11/2015 |
| WO | WO 2015/179540 A1 | 11/2015 |
| WO | WO 2015/183025 A1 | 12/2015 |
| WO | WO 2015/183026 A1 | 12/2015 |
| WO | WO 2015/183885 A1 | 12/2015 |
| WO | WO 2015/184259 A1 | 12/2015 |
| WO | WO 2015/184262 A1 | 12/2015 |
| WO | WO 2015/184268 A1 | 12/2015 |
| WO | WO 2015/188056 A1 | 12/2015 |
| WO | WO 2015/188065 A1 | 12/2015 |
| WO | WO 2015/188094 A1 | 12/2015 |
| WO | WO 2015/188109 A1 | 12/2015 |
| WO | WO 2015/188132 A1 | 12/2015 |
| WO | WO 2015/188135 A1 | 12/2015 |
| WO | WO 2015/188191 A1 | 12/2015 |
| WO | WO 2015/189693 A1 | 12/2015 |
| WO | WO 2015/191693 A2 | 12/2015 |
| WO | WO 2015/191899 A1 | 12/2015 |
| WO | WO 2015/191911 A2 | 12/2015 |
| WO | WO 2015/193858 A1 | 12/2015 |
| WO | WO 2015/195547 A1 | 12/2015 |
| WO | WO 2015/195621 A1 | 12/2015 |
| WO | WO 2015/195798 A1 | 12/2015 |
| WO | WO 2015/198020 A1 | 12/2015 |
| WO | WO 2015/200334 A1 | 12/2015 |
| WO | WO 2015/200378 A1 | 12/2015 |
| WO | WO 2015/200555 A2 | 12/2015 |
| WO | WO 2015/200805 A2 | 12/2015 |
| WO | WO 2016/001978 A1 | 1/2016 |
| WO | WO 2016/004010 A1 | 1/2016 |
| WO | WO 2016/004318 A1 | 1/2016 |
| WO | WO 2016/007347 A1 | 1/2016 |
| WO | WO 2016/007604 A1 | 1/2016 |
| WO | WO 2016/007948 A1 | 1/2016 |
| WO | WO 2016/011080 A2 | 1/2016 |
| WO | WO 2016/011210 A2 | 1/2016 |
| WO | WO 2016/011428 A1 | 1/2016 |
| WO | WO 2016/012544 A2 | 1/2016 |
| WO | WO 2016/012552 A1 | 1/2016 |
| WO | WO 2016/014409 A1 | 1/2016 |
| WO | WO 2016/014565 A2 | 1/2016 |
| WO | WO 2016/014794 A1 | 1/2016 |
| WO | WO 2016/014837 A1 | 1/2016 |
| WO | WO 2016/016119 A1 | 2/2016 |
| WO | WO 2016/016358 A1 | 2/2016 |
| WO | WO 2016/019144 A2 | 2/2016 |
| WO | WO 2016/020399 A1 | 2/2016 |
| WO | WO 2016/021972 A1 | 2/2016 |
| WO | WO 2016/021973 A1 | 2/2016 |

(56) References Cited

FOREIGN PATENT DOCUMENTS

| | | |
|---|---|---|
| WO | WO 2016/022363 A2 | 2/2016 |
| WO | WO 2016/022866 A1 | 2/2016 |
| WO | WO 2016/022931 A1 | 2/2016 |
| WO | WO 2016/025131 A1 | 2/2016 |
| WO | WO 2016/025469 A1 | 2/2016 |
| WO | WO 2016/025759 A1 | 2/2016 |
| WO | WO 2016/026444 A1 | 2/2016 |
| WO | WO 2016/028682 A1 | 2/2016 |
| WO | WO 2016/028843 A2 | 2/2016 |
| WO | WO 2016/028887 A1 | 2/2016 |
| WO | WO 2016/033088 A1 | 3/2016 |
| WO | WO 2016/033230 A1 | 3/2016 |
| WO | WO 2016/033246 A1 | 3/2016 |
| WO | WO 2016/033298 A1 | 3/2016 |
| WO | WO 2016/035044 A1 | 3/2016 |
| WO | WO 2016/035918 A1 | 3/2016 |
| WO | WO 2016/036754 A1 | 3/2016 |
| WO | WO 2016/037157 A2 | 3/2016 |
| WO | WO 2016/040030 A1 | 3/2016 |
| WO | WO 2016/040594 A1 | 3/2016 |
| WO | WO 2016/044182 A1 | 3/2016 |
| WO | WO 2016/044416 A1 | 3/2016 |
| WO | WO 2016/046635 A1 | 3/2016 |
| WO | WO 2016/049024 A2 | 3/2016 |
| WO | WO 2016/049163 A2 | 3/2016 |
| WO | WO 2016/049230 A1 | 3/2016 |
| WO | WO 2016/049251 A1 | 3/2016 |
| WO | WO 2016/049258 A2 | 3/2016 |
| WO | WO 2016/053397 A2 | 4/2016 |
| WO | WO 2016/054326 A1 | 4/2016 |
| WO | WO 2016/057061 A2 | 4/2016 |
| WO | WO 2016/057821 A2 | 4/2016 |
| WO | WO 2016/057835 A2 | 4/2016 |
| WO | WO 2016/057850 A1 | 4/2016 |
| WO | WO 2016/057951 A2 | 4/2016 |
| WO | WO 2016/057961 A1 | 4/2016 |
| WO | WO 2016/061073 A1 | 4/2016 |
| WO | WO 2016/061374 A1 | 4/2016 |
| WO | WO 2016/061481 A1 | 4/2016 |
| WO | WO 2016/061523 A1 | 4/2016 |
| WO | WO 2016/064894 A2 | 4/2016 |
| WO | WO 2016/065364 A1 | 4/2016 |
| WO | WO 2016/069282 A1 | 5/2016 |
| WO | WO 2016/069283 A1 | 5/2016 |
| WO | WO 2016/069591 A2 | 5/2016 |
| WO | WO 2016/069774 A1 | 5/2016 |
| WO | WO 2016/069910 A1 | 5/2016 |
| WO | WO 2016/069912 A1 | 5/2016 |
| WO | WO 2016/070037 A2 | 5/2016 |
| WO | WO 2016/070070 A1 | 5/2016 |
| WO | WO 2016/070129 A1 | 5/2016 |
| WO | WO 2016/072399 A1 | 5/2016 |
| WO | WO 2016/072936 A1 | 5/2016 |
| WO | WO 2016/073433 A1 | 5/2016 |
| WO | WO 2016/073559 A1 | 5/2016 |
| WO | WO 2016/073990 A2 | 5/2016 |
| WO | WO 2016/075662 A2 | 5/2016 |
| WO | WO 2016/076672 A1 | 5/2016 |
| WO | WO 2016/077273 A1 | 5/2016 |
| WO | WO 2016/077350 A1 | 5/2016 |
| WO | WO 2016/080097 A1 | 5/2016 |
| WO | WO 2016/080795 A1 | 5/2016 |
| WO | WO 2016/081923 A2 | 5/2016 |
| WO | WO 2016/081924 A1 | 5/2016 |
| WO | WO 2016/082135 A1 | 6/2016 |
| WO | WO 2016/083811 A1 | 6/2016 |
| WO | WO 2016/084084 A1 | 6/2016 |
| WO | WO 2016/084088 A1 | 6/2016 |
| WO | WO 2016/086177 A2 | 6/2016 |
| WO | WO 2016/089433 A1 | 6/2016 |
| WO | WO 2016/089866 A1 | 6/2016 |
| WO | WO 2016/089883 A1 | 6/2016 |
| WO | WO 2016/090385 A1 | 6/2016 |
| WO | WO 2016/094679 A1 | 6/2016 |
| WO | WO 2016/094845 A2 | 6/2016 |
| WO | WO 2016/094867 A1 | 6/2016 |
| WO | WO 2016/094872 A1 | 6/2016 |
| WO | WO 2016/094874 A1 | 6/2016 |
| WO | WO 2016/094880 A1 | 6/2016 |
| WO | WO 2016/094888 A1 | 6/2016 |
| WO | WO 2016/097212 A1 | 6/2016 |
| WO | WO 2016/097231 A2 | 6/2016 |
| WO | WO 2016/097751 A1 | 6/2016 |
| WO | WO 2016/099887 A1 | 6/2016 |
| WO | WO 2016/100272 A1 | 6/2016 |
| WO | WO 2016/100389 A1 | 6/2016 |
| WO | WO 2016/100568 A1 | 6/2016 |
| WO | WO 2016/100571 A1 | 6/2016 |
| WO | WO 2016/100951 A2 | 6/2016 |
| WO | WO 2016/100955 A2 | 6/2016 |
| WO | WO 2016/100974 A1 | 6/2016 |
| WO | WO 2016/103233 A2 | 6/2016 |
| WO | WO 2016/104716 A1 | 6/2016 |
| WO | WO 2016/106236 A1 | 6/2016 |
| WO | WO 2016/106239 A1 | 6/2016 |
| WO | WO 2016/106244 A1 | 6/2016 |
| WO | WO 2016/106338 A2 | 6/2016 |
| WO | WO 2016/108926 A1 | 7/2016 |
| WO | WO 2016/109255 A1 | 7/2016 |
| WO | WO 2016/109840 A2 | 7/2016 |
| WO | WO 2016/110214 A1 | 7/2016 |
| WO | WO 2016/110453 A1 | 7/2016 |
| WO | WO 2016/110511 A1 | 7/2016 |
| WO | WO 2016/110512 A1 | 7/2016 |
| WO | WO 2016/111546 A2 | 7/2016 |
| WO | WO 2016/112242 A1 | 7/2016 |
| WO | WO 2016/112351 A1 | 7/2016 |
| WO | WO 2016/112963 A1 | 7/2016 |
| WO | WO 2016/113357 A1 | 7/2016 |
| WO | WO 2016/114972 A1 | 7/2016 |
| WO | WO 2016/115179 A1 | 7/2016 |
| WO | WO 2016/115326 A1 | 7/2016 |
| WO | WO 2016/115355 A1 | 7/2016 |
| WO | WO 2016/116032 A1 | 7/2016 |
| WO | WO 2016/120480 A1 | 8/2016 |
| WO | WO 2016/123071 A1 | 8/2016 |
| WO | WO 2016/123230 A1 | 8/2016 |
| WO | WO 2016/123243 A1 | 8/2016 |
| WO | WO 2016/123578 A1 | 8/2016 |
| WO | WO 2016/126747 A1 | 8/2016 |
| WO | WO 2016/130600 A2 | 8/2016 |
| WO | WO 2016/130697 A1 | 8/2016 |
| WO | WO 2016/131009 A1 | 8/2016 |
| WO | WO 2016/132122 A1 | 8/2016 |
| WO | WO 2016/133165 A1 | 8/2016 |
| WO | WO 2016/135507 A1 | 9/2016 |
| WO | WO 2016/135557 A2 | 9/2016 |
| WO | WO 2016/135558 A2 | 9/2016 |
| WO | WO 2016/135559 A2 | 9/2016 |
| WO | WO 2016/137774 A1 | 9/2016 |
| WO | WO 2016/137949 A1 | 9/2016 |
| WO | WO 2016/141224 A1 | 9/2016 |
| WO | WO 2016/141893 A1 | 9/2016 |
| WO | WO 2016/142719 A1 | 9/2016 |
| WO | WO 2016/145150 A2 | 9/2016 |
| WO | WO 2016/148994 A1 | 9/2016 |
| WO | WO 2016/149484 A2 | 9/2016 |
| WO | WO 2016/149547 A1 | 9/2016 |
| WO | WO 2016/150336 A1 | 9/2016 |
| WO | WO 2016/150855 A1 | 9/2016 |
| WO | WO 2016/154016 A2 | 9/2016 |
| WO | WO 2016/154579 A2 | 9/2016 |
| WO | WO 2016/154596 A1 | 9/2016 |
| WO | WO 2016/155482 A1 | 10/2016 |
| WO | WO 2016/161004 A1 | 10/2016 |
| WO | WO 2016/161207 A1 | 10/2016 |
| WO | WO 2016/161260 A1 | 10/2016 |
| WO | WO 2016/161380 A1 | 10/2016 |
| WO | WO 2016/161446 A1 | 10/2016 |
| WO | WO 2016/164305 A1 | 10/2016 |
| WO | WO 2016/164356 A1 | 10/2016 |
| WO | WO 2016/164797 A1 | 10/2016 |
| WO | WO 2016/166340 A1 | 10/2016 |
| WO | WO 2016/167300 A1 | 10/2016 |

(56) References Cited

FOREIGN PATENT DOCUMENTS

| | | |
|---|---|---|
| WO | WO 2016/168631 A1 | 10/2016 |
| WO | WO 2016/170484 A1 | 10/2016 |
| WO | WO 2016/172359 A2 | 10/2016 |
| WO | WO 2016/172727 A1 | 10/2016 |
| WO | WO 2016/174056 A1 | 11/2016 |
| WO | WO 2016/174151 A1 | 11/2016 |
| WO | WO 2016/174250 A1 | 11/2016 |
| WO | WO 2016/176191 A1 | 11/2016 |
| WO | WO 2016/176404 A1 | 11/2016 |
| WO | WO 2016/176690 A2 | 11/2016 |
| WO | WO 2016/177682 A1 | 11/2016 |
| WO | WO 2016/178207 A1 | 11/2016 |
| WO | WO 2016/179038 A1 | 11/2016 |
| WO | WO 2016/179112 A1 | 11/2016 |
| WO | WO 2016/181357 A1 | 11/2016 |
| WO | WO 2016/182893 A1 | 11/2016 |
| WO | WO 2016/182917 A1 | 11/2016 |
| WO | WO 2016/182959 A1 | 11/2016 |
| WO | WO 2016/183236 A1 | 11/2016 |
| WO | WO 2016/183298 A2 | 11/2016 |
| WO | WO 2016/183345 A1 | 11/2016 |
| WO | WO 2016/183402 A2 | 11/2016 |
| WO | WO 2016/183438 A1 | 11/2016 |
| WO | WO 2016/183448 A1 | 11/2016 |
| WO | WO 2016/184955 A2 | 11/2016 |
| WO | WO 2016/184989 A1 | 11/2016 |
| WO | WO 2016/185411 A1 | 11/2016 |
| WO | WO 2016/186745 A1 | 11/2016 |
| WO | WO 2016/186772 A2 | 11/2016 |
| WO | WO 2016/186946 A1 | 11/2016 |
| WO | WO 2016/186953 A1 | 11/2016 |
| WO | WO 2016/187717 A1 | 12/2016 |
| WO | WO 2016/187904 A1 | 12/2016 |
| WO | WO 2016/191684 A1 | 12/2016 |
| WO | WO 2016/191869 A1 | 12/2016 |
| WO | WO 2016/196273 A1 | 12/2016 |
| WO | WO 2016/196282 A1 | 12/2016 |
| WO | WO 2016/196308 A1 | 12/2016 |
| WO | WO 2016/196361 A1 | 12/2016 |
| WO | WO 2016/196499 A1 | 12/2016 |
| WO | WO 2016/196539 A2 | 12/2016 |
| WO | WO 2016/196655 A1 | 12/2016 |
| WO | WO 2016/196805 A1 | 12/2016 |
| WO | WO 2016/196887 A1 | 12/2016 |
| WO | WO 2016/197132 A1 | 12/2016 |
| WO | WO 2016/197133 A1 | 12/2016 |
| WO | WO 2016/197354 A1 | 12/2016 |
| WO | WO 2016/197355 A1 | 12/2016 |
| WO | WO 2016/197356 A1 | 12/2016 |
| WO | WO 2016/197357 A1 | 12/2016 |
| WO | WO 2016/197358 A1 | 12/2016 |
| WO | WO 2016/197359 A1 | 12/2016 |
| WO | WO 2016/197360 A1 | 12/2016 |
| WO | WO 2016/197361 A1 | 12/2016 |
| WO | WO 2016/197362 A1 | 12/2016 |
| WO | WO 2016/198361 A1 | 12/2016 |
| WO | WO 2016/198500 A1 | 12/2016 |
| WO | WO 2016/200263 A1 | 12/2016 |
| WO | WO 2016/201047 A1 | 12/2016 |
| WO | WO 2016/201138 A1 | 12/2016 |
| WO | WO 2016/201152 A1 | 12/2016 |
| WO | WO 2016/201153 A1 | 12/2016 |
| WO | WO 2016/201155 A1 | 12/2016 |
| WO | WO 2016/205276 A1 | 12/2016 |
| WO | WO 2016/205613 A1 | 12/2016 |
| WO | WO 2016/205623 A1 | 12/2016 |
| WO | WO 2016/205680 A1 | 12/2016 |
| WO | WO 2016/205688 A2 | 12/2016 |
| WO | WO 2016/205703 A1 | 12/2016 |
| WO | WO 2016/205711 A1 | 12/2016 |
| WO | WO 2016/205728 A1 | 12/2016 |
| WO | WO 2016/205745 A2 | 12/2016 |
| WO | WO 2016/205749 A1 | 12/2016 |
| WO | WO 2016/205759 A1 | 12/2016 |
| WO | WO 2016/205764 A1 | 12/2016 |
| WO | WO 2017/001572 A1 | 1/2017 |
| WO | WO 2017/001988 A1 | 1/2017 |
| WO | WO 2017/004261 A1 | 1/2017 |
| WO | WO 2017/004279 A2 | 1/2017 |
| WO | WO 2017/004616 A1 | 1/2017 |
| WO | WO 2017/005807 A1 | 1/2017 |
| WO | WO 2017/009399 A1 | 1/2017 |
| WO | WO 2017/010556 A1 | 1/2017 |
| WO | WO 2017/011519 A1 | 1/2017 |
| WO | WO 2017/011721 A1 | 1/2017 |
| WO | WO 2017/011804 A1 | 1/2017 |
| WO | WO 2017/015015 A1 | 1/2017 |
| WO | WO 2017/015101 A1 | 1/2017 |
| WO | WO 2017/015545 A1 | 1/2017 |
| WO | WO 2017/015567 A1 | 1/2017 |
| WO | WO 2017/015637 A1 | 1/2017 |
| WO | WO 2017/017016 A1 | 2/2017 |
| WO | WO 2017/019867 A1 | 2/2017 |
| WO | WO 2017/019895 A1 | 2/2017 |
| WO | WO 2017/023803 A1 | 2/2017 |
| WO | WO 2017/023974 A1 | 2/2017 |
| WO | WO 2017/024047 A1 | 2/2017 |
| WO | WO 2017/024319 A1 | 2/2017 |
| WO | WO 2017/024343 A1 | 2/2017 |
| WO | WO 2017/024602 A1 | 2/2017 |
| WO | WO 2017/025323 A1 | 2/2017 |
| WO | WO 2017/027423 A1 | 2/2017 |
| WO | WO 2017/028768 A1 | 2/2017 |
| WO | WO 2017/029664 A1 | 2/2017 |
| WO | WO 2017/031360 A1 | 2/2017 |
| WO | WO 2017/031483 A1 | 2/2017 |
| WO | WO 2017/035416 A2 | 3/2017 |
| WO | WO 2017/040348 A1 | 3/2017 |
| WO | WO 2017/040511 A1 | 3/2017 |
| WO | WO 2017/040709 A1 | 3/2017 |
| WO | WO 2017/040786 A1 | 3/2017 |
| WO | WO 2017/040793 A1 | 3/2017 |
| WO | WO 2017/040813 A2 | 3/2017 |
| WO | WO 2017/043573 A1 | 3/2017 |
| WO | WO 2017/043656 A1 | 3/2017 |
| WO | WO 2017/044419 A1 | 3/2017 |
| WO | WO 2017/044776 A1 | 3/2017 |
| WO | WO 2017/044857 A2 | 3/2017 |
| WO | WO 2017/048390 A1 | 3/2017 |
| WO | WO 2017/049129 A2 | 3/2017 |
| WO | WO 2017/050963 A1 | 3/2017 |
| WO | WO 2017/053312 A1 | 3/2017 |
| WO | WO 2017/053431 A2 | 3/2017 |
| WO | WO 2017/053713 A1 | 3/2017 |
| WO | WO 2017/053729 A1 | 3/2017 |
| WO | WO 2017/053753 A1 | 3/2017 |
| WO | WO 2017/053762 A1 | 3/2017 |
| WO | WO 2017/053879 A1 | 3/2017 |
| WO | WO 2017/054721 A1 | 4/2017 |
| WO | WO 2017/058658 A2 | 4/2017 |
| WO | WO 2017/059241 A1 | 4/2017 |
| WO | WO 2017/062605 A1 | 4/2017 |
| WO | WO 2017/062723 A1 | 4/2017 |
| WO | WO 2017/062754 A1 | 4/2017 |
| WO | WO 2017/062855 A1 | 4/2017 |
| WO | WO 2017/062886 A1 | 4/2017 |
| WO | WO 2017/064439 A1 | 4/2017 |
| WO | WO 2017/064546 A1 | 4/2017 |
| WO | WO 2017/064566 A2 | 4/2017 |
| WO | WO 2017/066175 A1 | 4/2017 |
| WO | WO 2017/066497 A2 | 4/2017 |
| WO | WO 2017/066588 A2 | 4/2017 |
| WO | WO 2017/066707 A1 | 4/2017 |
| WO | WO 2017/066781 A1 | 4/2017 |
| WO | WO 2017/068077 A1 | 4/2017 |
| WO | WO 2017/068377 A1 | 4/2017 |
| WO | WO 2017/069829 A2 | 4/2017 |
| WO | WO 2017/070029 A1 | 4/2017 |
| WO | WO 2017/070032 A1 | 4/2017 |
| WO | WO 2017/070169 A1 | 4/2017 |
| WO | WO 2017/070284 A1 | 4/2017 |
| WO | WO 2017/070598 A1 | 4/2017 |
| WO | WO 2017/070605 A1 | 4/2017 |
| WO | WO 2017/070632 A2 | 4/2017 |

(56) References Cited

FOREIGN PATENT DOCUMENTS

| | | |
|---|---|---|
| WO | WO 2017/070633 A2 | 4/2017 |
| WO | WO 2017/072590 A1 | 5/2017 |
| WO | WO 2017/074526 A1 | 5/2017 |
| WO | WO 2017/074962 A1 | 5/2017 |
| WO | WO 2017/075261 A1 | 5/2017 |
| WO | WO 2017/075335 A1 | 5/2017 |
| WO | WO 2017/075475 A1 | 5/2017 |
| WO | WO 2017/077135 A1 | 5/2017 |
| WO | WO 2017/077329 A2 | 5/2017 |
| WO | WO 2017/078751 A1 | 5/2017 |
| WO | WO 2017/079400 A1 | 5/2017 |
| WO | WO 2017/079428 A1 | 5/2017 |
| WO | WO 2017/079673 A1 | 5/2017 |
| WO | WO 2017/079724 A1 | 5/2017 |
| WO | WO 2017/081097 A1 | 5/2017 |
| WO | WO 2017/081288 A1 | 5/2017 |
| WO | WO 2017/083368 A1 | 5/2017 |
| WO | WO 2017/083722 A1 | 5/2017 |
| WO | WO 2017/083766 A1 | 5/2017 |
| WO | WO 2017/087395 A1 | 5/2017 |
| WO | WO 2017/090724 A1 | 6/2017 |
| WO | WO 2017/091510 A1 | 6/2017 |
| WO | WO 2017/091630 A1 | 6/2017 |
| WO | WO 2017/092201 A1 | 6/2017 |
| WO | WO 2017/093370 A1 | 6/2017 |
| WO | WO 2017/093969 A1 | 6/2017 |
| WO | WO 2017/095111 A1 | 6/2017 |
| WO | WO 2017/096041 A1 | 6/2017 |
| WO | WO 2017/096237 A1 | 6/2017 |
| WO | WO 2017/100158 A1 | 6/2017 |
| WO | WO 2017/100431 A2 | 6/2017 |
| WO | WO 2017/104404 A1 | 6/2017 |
| WO | WO 2017/105251 A1 | 6/2017 |
| WO | WO 2017/105350 A1 | 6/2017 |
| WO | WO 2017/105991 A1 | 6/2017 |
| WO | WO 2017/106414 A1 | 6/2017 |
| WO | WO 2017/106528 A2 | 6/2017 |
| WO | WO 2017/106537 A2 | 6/2017 |
| WO | WO 2017/106569 A1 | 6/2017 |
| WO | WO 2017/106616 A1 | 6/2017 |
| WO | WO 2017/106657 A1 | 6/2017 |
| WO | WO 2017/106767 A1 | 6/2017 |
| WO | WO 2017/109134 A1 | 6/2017 |
| WO | WO 2017/109757 A1 | 6/2017 |
| WO | WO 2017/112620 A1 | 6/2017 |
| WO | WO 2017/115268 A1 | 7/2017 |
| WO | WO 2017/117395 A1 | 7/2017 |
| WO | WO 2017/118598 A1 | 7/2017 |
| WO | WO 2017/118720 A1 | 7/2017 |
| WO | WO 2017/123609 A1 | 7/2017 |
| WO | WO 2017/123910 A1 | 7/2017 |
| WO | WO 2017/124086 A1 | 7/2017 |
| WO | WO 2017/124100 A1 | 7/2017 |
| WO | WO 2017/124652 A1 | 7/2017 |
| WO | WO 2017/126987 A1 | 7/2017 |
| WO | WO 2017/127807 A1 | 7/2017 |
| WO | WO 2017/131237 A1 | 8/2017 |
| WO | WO 2017/132112 A1 | 8/2017 |
| WO | WO 2017/132580 A2 | 8/2017 |
| WO | WO 2017/136520 A1 | 8/2017 |
| WO | WO 2017/136629 A1 | 8/2017 |
| WO | WO 2017/136794 A1 | 8/2017 |
| WO | WO 2017/139264 A1 | 8/2017 |
| WO | WO 2017/139505 A2 | 8/2017 |
| WO | WO 2017/141173 A2 | 8/2017 |
| WO | WO 2017/142835 A1 | 8/2017 |
| WO | WO 2017/142923 A1 | 8/2017 |
| WO | WO 2017/142999 A2 | 8/2017 |
| WO | WO 2017/143042 A2 | 8/2017 |
| WO | WO 2017/147056 A1 | 8/2017 |
| WO | WO 2017/147278 A1 | 8/2017 |
| WO | WO 2017/147432 A1 | 8/2017 |
| WO | WO 2017/147446 A1 | 8/2017 |
| WO | WO 2017/147555 A1 | 8/2017 |
| WO | WO 2017/151444 A1 | 9/2017 |
| WO | WO 2017/151719 A1 | 9/2017 |
| WO | WO 2017/152015 A1 | 9/2017 |
| WO | WO 2017/155717 A1 | 9/2017 |
| WO | WO 2017/157422 A1 | 9/2017 |
| WO | WO 2017/158153 A1 | 9/2017 |
| WO | WO 2017/160689 A1 | 9/2017 |
| WO | WO 2017/160752 A1 | 9/2017 |
| WO | WO 2017/160890 A1 | 9/2017 |
| WO | WO 2017/161068 A1 | 9/2017 |
| WO | WO 2017/165741 A1 | 9/2017 |
| WO | WO 2017/165826 A1 | 9/2017 |
| WO | WO 2017/165862 A1 | 9/2017 |
| WO | WO 2017/167712 A1 | 10/2017 |
| WO | WO 2017/172644 A2 | 10/2017 |
| WO | WO 2017/172645 A2 | 10/2017 |
| WO | WO 2017/172860 A1 | 10/2017 |
| WO | WO 2017/173004 A1 | 10/2017 |
| WO | WO 2017/173054 A1 | 10/2017 |
| WO | WO 2017/173092 A1 | 10/2017 |
| WO | WO 2017/174329 A1 | 10/2017 |
| WO | WO 2017/176529 A1 | 10/2017 |
| WO | WO 2017/176806 A1 | 10/2017 |
| WO | WO 2017/178590 A1 | 10/2017 |
| WO | WO 2017/180694 A1 | 10/2017 |
| WO | WO 2017/180711 A1 | 10/2017 |
| WO | WO 2017/180915 A2 | 10/2017 |
| WO | WO 2017/180926 A1 | 10/2017 |
| WO | WO 2017/181107 A2 | 10/2017 |
| WO | WO 2017/181735 A2 | 10/2017 |
| WO | WO 2017/182468 A1 | 10/2017 |
| WO | WO 2017/182585 A1 | 10/2017 |
| WO | WO 2017/182607 A1 | 10/2017 |
| WO | WO 2017/184334 A1 | 10/2017 |
| WO | WO 2017/184768 A1 | 10/2017 |
| WO | WO 2017/184786 A1 | 10/2017 |
| WO | WO 2017/186550 A1 | 11/2017 |
| WO | WO 2017/189308 A1 | 11/2017 |
| WO | WO 2017/189336 A1 | 11/2017 |
| WO | WO 2017/190041 A1 | 11/2017 |
| WO | WO 2017/190257 A1 | 11/2017 |
| WO | WO 2017/190664 A1 | 11/2017 |
| WO | WO 2017/191210 A1 | 11/2017 |
| WO | WO 2017/191274 A2 | 11/2017 |
| WO | WO 2017/192172 A1 | 11/2017 |
| WO | WO 2017/192512 A2 | 11/2017 |
| WO | WO 2017/192544 A1 | 11/2017 |
| WO | WO 2017/192573 A1 | 11/2017 |
| WO | WO 2017/193029 A2 | 11/2017 |
| WO | WO 2017/193053 A1 | 11/2017 |
| WO | WO 2017/196768 A1 | 11/2017 |
| WO | WO 2017/197038 A1 | 11/2017 |
| WO | WO 2017/197238 A1 | 11/2017 |
| WO | WO 2017/197301 A1 | 11/2017 |
| WO | WO 2017/201476 A1 | 11/2017 |
| WO | WO 2017/205290 A1 | 11/2017 |
| WO | WO 2017/205423 A1 | 11/2017 |
| WO | WO 2017/207589 A1 | 12/2017 |
| WO | WO 2017/208247 A1 | 12/2017 |
| WO | WO 2017/209809 A1 | 12/2017 |
| WO | WO 2017/213896 A1 | 12/2017 |
| WO | WO 2017/213898 A2 | 12/2017 |
| WO | WO 2017/214460 A1 | 12/2017 |
| WO | WO 2017/216392 A1 | 12/2017 |
| WO | WO 2017/216771 A2 | 12/2017 |
| WO | WO 2017/218185 A1 | 12/2017 |
| WO | WO 2017/219027 A1 | 12/2017 |
| WO | WO 2017/219033 A1 | 12/2017 |
| WO | WO 2017/220751 A1 | 12/2017 |
| WO | WO 2017/222370 A1 | 12/2017 |
| WO | WO 2017/222773 A1 | 12/2017 |
| WO | WO 2017/222834 A1 | 12/2017 |
| WO | WO 2017/223107 A1 | 12/2017 |
| WO | WO 2017/223330 A1 | 12/2017 |
| WO | WO 2018/000657 A1 | 1/2018 |
| WO | WO 2018/002719 A1 | 1/2018 |
| WO | WO 2018/005117 A1 | 1/2018 |
| WO | WO 2018/005289 A2 | 1/2018 |
| WO | WO 2018/005691 A1 | 1/2018 |
| WO | WO 2018/005782 A1 | 1/2018 |

(56) References Cited

FOREIGN PATENT DOCUMENTS

| | | |
|---|---|---|
| WO | WO 2018/005873 A1 | 1/2018 |
| WO | WO 2018/06693 A1 | 1/2018 |
| WO | WO 2018/009520 A1 | 1/2018 |
| WO | WO 2018/009562 A1 | 1/2018 |
| WO | WO 2018/009822 A1 | 1/2018 |
| WO | WO 2018/013821 A1 | 1/2018 |
| WO | WO 2018/013932 A1 | 1/2018 |
| WO | WO 2018/013990 A1 | 1/2018 |
| WO | WO 2018/014384 A1 | 1/2018 |
| WO | WO 2018/015444 A1 | 1/2018 |
| WO | WO 2018/015936 A2 | 1/2018 |
| WO | WO 2018/017754 A1 | 1/2018 |
| WO | WO 2018/018979 A1 | 2/2018 |
| WO | WO 2018/020248 A1 | 2/2018 |
| WO | WO 2018/021878 A1 | 2/2018 |
| WO | WO 2018/022480 A1 | 2/2018 |
| WO | WO 2018/022634 A1 | 2/2018 |
| WO | WO 2018/025206 A1 | 2/2018 |
| WO | WO 2018/026723 A1 | 2/2018 |
| WO | WO 2018/026976 A1 | 2/2018 |
| WO | WO 2018/027078 A1 | 2/2018 |
| WO | WO 2018/030608 A1 | 2/2018 |
| WO | WO 2018/031683 A1 | 2/2018 |
| WO | WO 2018/035250 A1 | 2/2018 |
| WO | WO 2018/035300 A1 | 2/2018 |
| WO | WO 2018/035423 A1 | 2/2018 |
| WO | WO 2018/035503 A1 | 2/2018 |
| WO | WO 2018/039145 A1 | 3/2018 |
| WO | WO 2018/039438 A1 | 3/2018 |
| WO | WO 2018/039440 A1 | 3/2018 |
| WO | WO 2018/039448 A1 | 3/2018 |
| WO | WO 2018/045630 A1 | 3/2018 |
| WO | WO 2018/048827 A1 | 3/2018 |
| WO | WO 2018/049073 A1 | 3/2018 |
| WO | WO 2018/049168 A1 | 3/2018 |
| WO | WO 2018/051347 A1 | 3/2018 |
| WO | WO 2018/058064 A1 | 3/2018 |
| WO | WO 2018/062866 A2 | 4/2018 |
| WO | WO 2018/064352 A1 | 4/2018 |
| WO | WO 2018/064371 A1 | 4/2018 |
| WO | WO 2018/064516 A1 | 4/2018 |
| WO | WO 2018/067546 A1 | 4/2018 |
| WO | WO 2018/067846 A1 | 4/2018 |
| WO | WO 2018/068053 A2 | 4/2018 |
| WO | WO 2018/069474 A1 | 4/2018 |
| WO | WO 2018/071623 A2 | 4/2018 |
| WO | WO 2018/071663 A1 | 4/2018 |
| WO | WO 2018/071868 A1 | 4/2018 |
| WO | WO 2018/071892 A1 | 4/2018 |
| WO | WO 2018/074979 A1 | 4/2018 |
| WO | WO 2018/079134 A1 | 5/2018 |
| WO | WO 2018/080573 A1 | 5/2018 |
| WO | WO 2018/081504 A1 | 5/2018 |
| WO | WO 2018/081535 A2 | 5/2018 |
| WO | WO 2018/081728 A1 | 5/2018 |
| WO | WO 2018/083128 A2 | 5/2018 |
| WO | WO 2018/083606 A1 | 5/2018 |
| WO | WO 2018/085288 A1 | 5/2018 |
| WO | WO 2018/085414 A1 | 5/2018 |
| WO | WO 2018/085842 A1 | 5/2018 |
| WO | WO 2018/086623 A1 | 5/2018 |
| WO | WO 2018/089664 A1 | 5/2018 |
| WO | WO 2018/093990 A1 | 5/2018 |
| WO | WO 2018/098383 A1 | 5/2018 |
| WO | WO 2018/098480 A1 | 5/2018 |
| WO | WO 2018/098587 A1 | 6/2018 |
| WO | WO 2018/099256 A1 | 6/2018 |
| WO | WO 2018/103686 A1 | 6/2018 |
| WO | WO 2018/106268 A1 | 6/2018 |
| WO | WO 2018/107028 A1 | 6/2018 |
| WO | WO 2018/107103 A1 | 6/2018 |
| WO | WO 2018/107129 A1 | 6/2018 |
| WO | WO 2018/108272 A1 | 6/2018 |
| WO | WO 2018/109101 A1 | 6/2018 |
| WO | WO 2018/111946 A1 | 6/2018 |
| WO | WO 2018/111947 A1 | 6/2018 |
| WO | WO 2018/112336 A1 | 6/2018 |
| WO | WO 2018/112446 A2 | 6/2018 |
| WO | WO 2018/119354 A1 | 6/2018 |
| WO | WO 2018/119359 A1 | 6/2018 |
| WO | WO 2018/120283 A1 | 7/2018 |
| WO | WO 2018/130830 A1 | 7/2018 |
| WO | WO 2018/135838 A2 | 7/2018 |
| WO | WO 2018/136396 A2 | 7/2018 |
| WO | WO 2018/138385 A1 | 8/2018 |
| WO | WO 2018/142364 A1 | 8/2018 |
| WO | WO 2018/148246 A1 | 8/2018 |
| WO | WO 2018/148256 A1 | 8/2018 |
| WO | WO 2018/148647 A2 | 8/2018 |
| WO | WO 2018/149418 A1 | 8/2018 |
| WO | WO 2018/149888 A1 | 8/2018 |
| WO | WO 2018/149915 A1 | 8/2018 |
| WO | WO 2018/152197 A1 | 8/2018 |
| WO | WO 2018/152418 A1 | 8/2018 |
| WO | WO 2018/154380 A1 | 8/2018 |
| WO | WO 2018/154387 A1 | 8/2018 |
| WO | WO 2018/154412 A1 | 8/2018 |
| WO | WO 2018/154413 A1 | 8/2018 |
| WO | WO 2018/154418 A1 | 8/2018 |
| WO | WO 2018/154439 A1 | 8/2018 |
| WO | WO 2018/154459 A1 | 8/2018 |
| WO | WO 2018/154462 A2 | 8/2018 |
| WO | WO 2018/156372 A1 | 8/2018 |
| WO | WO 2018/156824 A1 | 8/2018 |
| WO | WO 2018/161009 A1 | 9/2018 |
| WO | WO 2018/161032 A1 | 9/2018 |
| WO | WO 2018/165504 A1 | 9/2018 |
| WO | WO 2018/165629 A1 | 9/2018 |
| WO | WO 2018/170015 A1 | 9/2018 |
| WO | WO 2018/170340 A1 | 9/2018 |
| WO | WO 2018/175502 A2 | 9/2018 |
| WO | WO 2018/176009 A1 | 9/2018 |
| WO | WO 2018/177351 A1 | 10/2018 |
| WO | WO 2018/179578 A1 | 10/2018 |
| WO | WO 2018/183403 A1 | 10/2018 |
| WO | WO 2018/189184 A1 | 10/2018 |
| WO | WO 2018/191388 A1 | 10/2018 |
| WO | WO 2018/195402 A1 | 10/2018 |
| WO | WO 2018/195545 A2 | 10/2018 |
| WO | WO 2018/195555 A1 | 10/2018 |
| WO | WO 2018/197020 A1 | 11/2018 |
| WO | WO 2018/197495 A1 | 11/2018 |
| WO | WO 2018/202800 A1 | 11/2018 |
| WO | WO 2018/204493 A1 | 11/2018 |
| WO | WO 2018/208755 A1 | 11/2018 |
| WO | WO 2018/208998 A1 | 11/2018 |
| WO | WO 2018/209158 A2 | 11/2018 |
| WO | WO 2018/209320 A1 | 11/2018 |
| WO | WO 2018/213351 A1 | 11/2018 |
| WO | WO 2018/213708 A1 | 11/2018 |
| WO | WO 2018/213726 A1 | 11/2018 |
| WO | WO 2018/213771 A1 | 11/2018 |
| WO | WO 2018/213791 A1 | 11/2018 |
| WO | WO 2018/217852 A1 | 11/2018 |
| WO | WO 2018/217981 A1 | 11/2018 |
| WO | WO 2018/218166 A1 | 11/2018 |
| WO | WO 2018/218188 A2 | 11/2018 |
| WO | WO 2018/218206 A1 | 11/2018 |
| WO | WO 2018/226855 A1 | 12/2018 |
| WO | WO 2019/005884 A1 | 1/2019 |
| WO | WO 2019/005886 A1 | 1/2019 |
| WO | WO 2019/010384 A1 | 1/2019 |
| WO | WO 2019/023680 A1 | 1/2019 |
| WO | WO 2019/042284 A1 | 3/2019 |
| WO | WO 2019/051097 A1 | 3/2019 |
| WO | WO 2019/067992 A1 | 4/2019 |
| WO | WO 2019/075357 A1 | 4/2019 |
| WO | WO 2019/079347 A1 | 4/2019 |
| WO | WO 2019/084062 A1 | 5/2019 |
| WO | WO 2019/090169 A1 | 5/2019 |
| WO | WO 2019/090367 A1 | 5/2019 |
| WO | WO 2019/092042 A1 | 5/2019 |
| WO | WO 2019/118497 A1 | 6/2019 |
| WO | WO 2019/118935 A1 | 6/2019 |

(56) References Cited

FOREIGN PATENT DOCUMENTS

| | | |
|---|---|---|
| WO | WO 2019/118949 A1 | 6/2019 |
| WO | WO 2019/123430 A1 | 6/2019 |
| WO | WO 2019/126709 A1 | 6/2019 |
| WO | WO 2019/139645 A2 | 7/2019 |
| WO | WO 2019/139951 A1 | 7/2019 |
| WO | WO 2019/147014 A1 | 8/2019 |
| WO | WO 2019/161251 A1 | 8/2019 |
| WO | WO 2019/168953 A1 | 9/2019 |
| WO | WO 2019/183641 A1 | 9/2019 |
| WO | WO 2019/204369 A1 | 10/2019 |
| WO | WO 2019/213257 A1 | 11/2019 |
| WO | WO 2019/217942 A1 | 11/2019 |
| WO | WO 2019/226593 A1 | 11/2019 |
| WO | WO 2019/226953 A1 | 11/2019 |
| WO | WO 2019/236566 A1 | 12/2019 |
| WO | WO 2019/241649 A1 | 12/2019 |
| WO | WO 2020/014261 A1 | 1/2020 |
| WO | WO 2020/028555 A2 | 2/2020 |
| WO | WO 2020/028823 A1 | 2/2020 |
| WO | WO 2020/041751 A1 | 2/2020 |
| WO | WO 2020/047124 A1 | 3/2020 |
| WO | WO 2020/051360 A1 | 3/2020 |
| WO | WO 2020/081568 A1 | 4/2020 |
| WO | WO 2020/086908 A1 | 4/2020 |
| WO | WO 2020/092453 A1 | 5/2020 |
| WO | WO 2020/102659 A1 | 5/2020 |
| WO | WO 2020/102709 A1 | 5/2020 |
| WO | WO 2020/154500 A1 | 7/2020 |
| WO | WO 2020/180975 A1 | 9/2020 |
| WO | WO 2020/181178 A1 | 9/2020 |
| WO | WO 2020/181180 A1 | 9/2020 |
| WO | WO 2020/181193 A1 | 9/2020 |
| WO | WO 2020/181195 A1 | 9/2020 |
| WO | WO 2020/181202 A1 | 9/2020 |
| WO | WO 2020/191153 A2 | 9/2020 |
| WO | WO 2020/191171 A1 | 9/2020 |
| WO | WO 2020/191233 A1 | 9/2020 |
| WO | WO 2020/191234 A1 | 9/2020 |
| WO | WO 2020/191239 A1 | 9/2020 |
| WO | WO 2020/191241 A1 | 9/2020 |
| WO | WO 2020/191242 A1 | 9/2020 |
| WO | WO 2020/191243 A1 | 9/2020 |
| WO | WO 2020/191245 A1 | 9/2020 |
| WO | WO 2020/191246 A1 | 9/2020 |
| WO | WO 2020/191248 A1 | 9/2020 |
| WO | WO 2020/191249 A1 | 9/2020 |
| WO | WO 2020/210751 A1 | 10/2020 |
| WO | WO 2020/214842 A1 | 10/2020 |
| WO | WO 2020/236982 A1 | 11/2020 |
| WO | WO 2021/025750 A1 | 2/2021 |
| WO | WO 2021/030666 A1 | 2/2021 |
| WO | WO 2021/072328 A1 | 4/2021 |
| WO | WO 2021/108717 A2 | 6/2021 |
| WO | WO 2021/138469 A1 | 7/2021 |
| WO | WO 2021/155065 A1 | 8/2021 |
| WO | WO 2021/158921 A2 | 8/2021 |
| WO | WO 2021/158995 A1 | 8/2021 |
| WO | WO 2021/158999 A1 | 8/2021 |
| WO | WO 2021/222318 A1 | 11/2021 |
| WO | WO 2021/226558 A1 | 11/2021 |
| WO | WO 2022/067130 A2 | 3/2022 |
| WO | WO 2022/150790 A2 | 7/2022 |
| WO | WO 2023/015309 A2 | 2/2023 |

OTHER PUBLICATIONS

U.S. Appl. No. 61/717,324, filed Oct. 23, 2012, Cho et al.
U.S. Appl. No. 61/734,256, filed Dec. 6, 2012, Chen et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/794,422, filed Mar. 15, 2013, Knight et al.
U.S. Appl. No. 61/803,599, filed Mar. 20, 2013, Kim et al.
U.S. Appl. No. 61/837,481, filed Jun. 20, 2013, Cho et al.
U.S. Appl. No. 61/838,178, filed Jun. 21, 2013, Joung et al.
U.S. Appl. No. 61/874,682, filed Sep. 6, 2013, Liu et al.
U.S. Appl. No. 61/874,746, filed Sep. 6, 2013, Liu et al.
U.S. Appl. No. 62/288,661, filed Jan. 29, 2016, Muir et al.
U.S. Appl. No. 62/357,332, filed Jun. 30, 2016, Liu et al.
International Search Report and Written Opinion for PCT/US2018/044242, mailed Nov. 21, 2019.
International Preliminary Report on Patentability for PCT/US2018/044242, mailed Feb. 6, 2020.
[No Author Listed] HyPhy - Hypothesis testing using Phylogenies. Last modified Apr. 21, 2017. Accessed online via http://hyphy.org/w/index.php/Main_Page on Apr. 28, 2021.
[No Author Listed] NCBI Accession No. XP_015843220.1. C →U editing enzyme APOBEC-1 [Peromyscus maniculatus bairdii], XP002793540. Mar. 21, 2016.
[No Author Listed] NCBI Accession No. XP_021505673.1. C →U editing enzyme APOBEC-1 [Meriones unguiculatus], XP002793541. Jun. 27, 2017.
[No Author Listed] NCBI Reference Sequence: WP_087959824.1. Oct. 9, 2019. 2 pages.
[No Author Listed] Score result for SEQ 355 to WO2017032580. Muir et al. 2016.
[No Author Listed], "Human genome." Encyclopedia Britannica. Encyclopedia Brittanica, Inc. Published Feb. 15, 2019. Last accessed online via https://www.britannica.com/science/human-genome on Mar. 19, 2021. 2 pages.
[No Author Listed], "Lambda DNA" from Catalog & Technical Reference. New England Biolabs Inc. 2002/2003. pp. 133 and 270-273.
[No Author Listed], EMBL Accession No. Q99ZW2. Nov. 2012. 2 pages.
[No Author Listed], Gag-Pol polyprotein. UniProtKB/Swiss-Prot No. P03355.5. Sep. 18, 2019. 18 pages.
[No Author Listed], *Homo sapiens* signal transducer and activator of transcription 3 (STAT3), transcript variant 1, mRNA. NCBI Ref Seq No. NM_139276.2. Retrived from https://www.ncbi.nlm.nih.gov/nuccore/nm_139276.2. Feb. 26, 2020. 8 pages.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.
[No Author Listed], *Mus musculus* (Mouse). UniProtKB Accession No. P51908 (ABEC1_MOUSE). Oct. 1, 1996. 10 pages.
[No Author Listed], Thermo Fisher Scientific—How Cationic Lipid Mediated Transfection Works, retrieved from the internet Aug. 27, 2015. 2 pages.
Abremski et al., Bacteriophage P1 site-specific recombination. Purification and properties of the Cre recombinase protein. J Biol Chem. Feb. 10, 1984;259(3):1509-14.
Abudayyeh et al., A cytosine deaminase for programmable single-base RNA editing. Science. Jul. 26, 2019;365(6451):382-386. doi: 10.1126/science.aax7063. Epub Jul. 11, 2019.
Abudayyeh et al., C2c2 is a single-component programmable RNA-guided RNA-targeting CRISPR effector. Science Aug. 2016;353(6299):aaf5573. DOI: 10.1126/science.aaf5573.
Abudayyeh et al., RNA targeting with CRISPR-Cas13. Nature. Oct. 12, 2017;550(7675):280-284. doi: 10.1038/nature24049. Epub Oct. 4, 2017.
Ada et al., Carbohydrate-protein conjugate vaccines. Clin Microbiol Infect. Feb. 2003;9(2):79- 85. doi: 10.1046/j.1469-0691.2003.00530.x.
Adamala et al., Programmable RNA-binding protein composed of repeats of a single modular unit. Proc Natl Acad Sci U S A. May 10, 2016;113(19):E2579-88. doi: 10.1073/pnas.1519368113. Epub Apr. 26, 2016.
Adams et al., New biarsenical ligands and tetracysteine motifs for protein labeling in vitro and in vivo: synthesis and biological applications. J Am Chem Soc. May 29, 2002;124(21):6063-76. doi: 10.1021/ja017687n.
Addgene Plasmid # 44246. pdCas9-humanized, 2017, Stanley Qi.
Addgene Plasmid # 73021. PCMV-BE3, 2017, David Liu.

(56) References Cited

OTHER PUBLICATIONS

Addgene Plasmid # 79620. pcDNA3.1_pCMV-nCas-PmCDA1-ugi pH1-gRNA(HPRT), 2017, Akihiko Kondo.
Adli, The CRISPR tool kit for genome editing and beyond. Nat Commun. May 15, 2018;9(1):1911. doi: 10.1038/s41467-018-04252-2.
Aguilo et al., Coordination of m(6)A mRNA Methylation and Gene Transcription by ZFP217 Regulates Pluripotency and Reprogramming. Cell Stem Cell. Dec. 3, 2015;17(6):689-704. doi: 10.1016/j.stem.2015.09.005. Epub Oct. 29, 2015.
Ahmad et al., Antibody-mediated specific binding and cytotoxicity of liposome-entrapped doxorubicin to lung cancer cells in vitro. Cancer Res. Sep. 1, 1992;52(17):4817-20.
Ai et al., C-terminal Loop Mutations Determine Folding and Secretion Properties of PCSK9. iMedPub J: Biochem Mol Biol J. Nov. 5, 2016;2(3):17. doi: 10.21767/2471-8084.100026. 12 pages.
Aihara et al., A conformational switch controls the DNA cleavage activity of lambda integrase. Mol Cell. Jul. 2003;12(1):187-98.
Aik et al., Structure of human RNA $N^6$-methyladenine demethylase ALKBH5 provides insights into its mechanisms of nucleic acid recognition and demethylation. Nucleic Acids Res. Apr. 2014;42(7):4741-54. doi: 10.1093/nar/gku085. Epub Jan. 30, 2014.
Aird et al., Increasing Cas9-mediated homology-directed repair efficiency through covalent tethering of DNA repair template. Commun Biol. May 31, 2018;1:54. doi: 10.1038/s42003-018-0054-2.
Akcakaya et al., In vivo CRISPR editing with no detectable genome-wide off-target mutations. Nature. Sep. 2018;561(7723):416-419. doi: 10.1038/s41586-018-0500-9. Epub Sep. 12, 2018. PMID: 30209390; PMCID: PMC6194229.
Akins et al., Mitochondrial plasmids of Neurospora: integration into mitochondrial DNA and evidence for reverse transcription in mitochondria. Cell. Nov. 21, 1986;47(4):505-16. doi: 10.1016/0092-8674(86)90615-x.
Akinsheye et al., Fetal hemoglobin in sickle cell anemia. Blood. Jul. 7, 2011;118(1):19-27. doi: 10.1182/blood-2011-03-325258. Epub Apr. 13, 2011.
Akopian et al., Chimeric recombinases with designed DNA sequence recognition. Proc Natl Acad Sci U S A. Jul. 22, 2003;100(15):8688-91. Epub Jul. 1, 2003.
Alarcón et al., HNRNPA2B1 Is a Mediator of m(6)A-Dependent Nuclear RNA Processing Events. Cell. Sep. 10, 2015;162(6):1299-308. doi: 10.1016/j.cell.2015.08.011. Epub Aug. 27, 2015.
Alarcón et al., N6-methyladenosine marks primary microRNAs for processing. Nature. Mar. 26, 2015;519(7544):482-5. doi: 10.1038/nature14281. Epub Mar. 18, 2015.
Alexander, HFE-associated hereditary hemochromatosis. Genet Med. May 2009;11(5):307-13. doi: 10.1097/GIM.0b013e31819d30f2.
Alexandrov et al., Signatures of mutational processes in human cancer. Nature. Aug. 22, 2013;500(7463):415-21. doi: 10.1038/nature12477. Epub Aug. 14, 2013.
Ali et al., Novel genetic abnormalities in Bernard-Soulier syndrome in India. Ann Hematol. Mar. 2014;93(3):381-4. doi: 10.1007/s00277-013-1895-x. Epub Sep. 1, 2013.
Altschul et al., Basic local alignment search tool. J Mol Biol. Oct. 5, 1990;215(3):403-10. doi: 10.1016/S0022-2836(05)80360-2.
Amato et al., Interpreting elevated fetal hemoglobin in pathology and health at the basic laboratory level: new and known γ-gene mutations associated with hereditary persistence of fetal hemoglobin. Int J Lab Hematol. Feb. 2014;36(1):13-9. doi: 10.1111/ijlh.12094. Epub Apr. 29, 2013.
Ames et al., A eubacterial riboswitch class that senses the coenzyme tetrahydrofolate. Chem Biol. Jul. 30, 2010;17(7):681-5. doi: 10.1016/j.chembiol.2010.05.020.
Amrann et al., Tightly regulated tac promoter vectors useful for the expression of unfused and fused proteins in *Escherichia coli*. Gene. Sep. 30, 1988;69(2):301-15.
Anders et al., Chapter One: In Vitro Enzymology of Cas9. in Methods in Enzymology, eds Doudna et al. 2014: 546:1-20.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.
Anderson, Human gene therapy. Science. May 8, 1992;256(5058):808-13. doi: 10.1126/science.1589762.
André et al., Axotomy-induced expression of calcium-activated chloride current in subpopulations of mouse dorsal root ganglion neurons. J Neurophysiol. Dec. 2003;90(6):3764-73. doi: 10.1152/jn.00449.2003. Epub Aug. 27, 2003.
Anzalone et al., Genome editing with CRISPR-Cas nucleases, base editors, transposases and prime editors. Nat Biotechnol. Jul. 2020;38(7):824-844. doi: 10.1038/s41587-020-0561-9. Epub Jun. 22, 2020.
Anzalone et al., Reprogramming eukaryotic translation with ligand-responsive synthetic RNA switches. Nat Methods. May 2016;13(5):453-8. doi: 10.1038/nmeth.3807. Epub Mar. 21, 2016.
Anzalone et al., Search-and-replace genome editing without double-strand breaks or donor DNA. Nature. Dec. 2019;576(7785):149-157 and Suppl Info. doi: 10.1038/s41586-019-1711-4. Epub Oct. 21, 2019. 72 pages.
Anzalone et al., Search-and-replace genome editing without double-strand breaks or donor DNA. Nature. Dec. 2019;576(7785):149-157. doi: 10.1038/s41586-019-1711-4. Epub Oct. 21, 2019.
Aplan, Causes of oncogenic chromosomal translocation. Trends Genet. Jan. 2006;22(1):46-55. doi: 10.1016/j.tig.2005.10.002. Epub Oct. 28, 2005.
Arakawa et al., A method to convert mRNA into a gRNA library for CRISPR/Cas9 editing of any organism. Sci Adv. Aug. 24, 2016;2(8):e1600699. doi: 10.1126/sciadv.1600699.
Araki et al., Comparative analysis of right element mutant lox sites on recombination efficiency in embryonic stem cells. BMC Biotechnol. Mar. 31, 2010;10:29. doi: 10.1186/1472-6750-10-29.
Araki et al., Site-specific recombinase, R, encoded by yeast plasmid pSR1. J Mol Biol. May 5, 1992;225(1):25-37. doi: 10.1016/0022-2836(92)91023-i.
Araki et al., Targeted integration of DNA using mutant lox sites in embryonic stem cells. Nucleic Acids Res. Feb. 15, 1997;25(4):868-72. doi: 10.1093/nar/25.4.868.
Arambula et al., Surface display of a massively variable lipoprotein by a Legionella diversity-generating retroelement. Proc Natl Acad Sci U S A. May 14, 2013;110(20):8212-7. doi: 10.1073/pnas.1301366110. Epub Apr. 30, 2013.
Arazoe et al., Targeted Nucleotide Editing Technologies for Microbial Metabolic Engineering. Biotechnol J. Sep. 2018;13(9):e1700596. doi: 10.1002/biot.201700596. Epub Jun. 19, 2018.
Arbab et al., Cloning-free CRISPR. Stem Cell Reports. Nov. 10, 2015;5(5):908-917. doi: 10.1016/j.stemcr.2015.09.022. Epub Oct. 29, 2015.
Arbab et al., Determinants of Base Editing Outcomes from Target Library Analysis and Machine Learning. Cell. Jul. 23, 2020;182(2):463-480.e30. doi: 10.1016/j.cell.2020.05.037. Epub Jun. 12, 2020.
Arezi et al., Novel mutations in Moloney Murine Leukemia Virus reverse transcriptase increase thermostability through tighter binding to template-primer. Nucleic Acids Res. Feb. 2009;37(2):473-81. doi: 10.1093/nar/gkn952. Epub Dec. 4, 2008.
Arnold et al., Mutants of Tn3 resolvase which do not require accessory binding sites for recombination activity. EMBO J. Mar. 1, 1999;18(5):1407-14.
Asante et al., A naturally occurring variant of the human prion protein completely prevents prion disease. Nature. Jun. 25, 2015;522(7557):478-81. doi: 10.1038/nature14510. Epub Jun. 10, 2015.
Asokan et al., The AAV vector toolkit: poised at the clinical crossroads. Mol Ther. Apr. 2012;20(4):699-708. doi: 10.1038/mt.2011.287. Epub Jan. 24, 2012.
Atkins et al., Ribosomal frameshifting and transcriptional slippage: From genetic steganography and cryptography to adventitious use. Nucleic Acids Res. Sep. 6, 2016;44(15):7007-78. doi: 10.1093/nar/gkw530. Epub Jul. 19, 2016.
Auer et al., Highly efficient CRISPR/Cas9-mediated knock-in in zebrafish by homology-independent DNA repair. Genome Res. Jan. 2014;24(1):142-53. doi: 10.1101/gr.161638.113. Epub Oct. 31, 2013.

(56) References Cited

OTHER PUBLICATIONS

Auricchio et al., Exchange of surface proteins impacts on viral vector cellular specificity and transduction characteristics: the retina as a model. Hum Mol Genet. Dec. 15, 2001;10(26):3075-81. doi: 10.1093/hmg/10.26.3075.

Autieri et al., IRT-1, a novel interferon-gamma-responsive transcript encoding a growth-suppressing basic leucine zipper protein. J Biol Chem. Jun. 12, 1998;273(24):14731-7. doi: 10.1074/jbc.273.24.14731.

Avidan et al., The processivity and fidelity of DNA synthesis exhibited by the reverse transcriptase of bovine leukemia virus. Eur J Biochem. Feb. 2002;269(3):859-67. doi: 10.1046/j.0014-2956.2001.02719.x.

Baba et al., Construction of *Escherichia coli* K-12 in-frame, single-gene knockout mutants: the Keio collection. Mol Syst Biol. 2006;2:2006. 0008. doi: 10.1038/msb4100050. Epub Feb. 21, 2006.

Babacic et al., CRISPR-cas gene-editing as plausible treatment of neuromuscular and nucleotide-repeat-expansion diseases: A systematic review. PLoS One. Feb. 22, 2019;14(2):e0212198. doi: 10.1371/journal.pone.0212198.

Bacman et al., Specific elimination of mutant mitochondrial genomes in patient-derived cells by mitoTALENs. Nat Med. Sep. 2013;19(9):1111-3. doi: 10.1038/nm.3261. Epub Aug. 4, 2013.

Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. Feb. 2015;24:1-10. doi: 10.1016/j.cbpa.2014.09.040. Epub Nov. 7, 2014.
Bae et al., Cas-OFFinder: a fast and versatile algorithm that searches for potential off-target sites of Cas9 RNA-guided endonucleases. Bioinformatics. May 15, 2014;30(10):1473-5. doi: 10.1093/bioinformatics/btu048. Epub Jan. 24, 2014.
Bae et al., Microhomology-based choice of Cas9 nuclease target sites. Nat Methods. Jul. 2014;11(7):705-6. doi: 10.1038/nmeth.3015.
Bagal et al., Recent progress in sodium channel modulators for pain. Bioorg Med Chem Lett. Aug. 15, 2014;24(16):3690-9. doi: 10.1016/j.bmcl.2014.06.038. Epub Jun. 21, 2014.
Bagyinszky et al., Characterization of mutations in PRNP (prion) gene and their possible roles in neurodegenerative diseases. Neuropsychiatr Dis Treat. Aug. 14, 2018;14:2067-2085. doi: 10.2147/NDT.S165445.
Balakrishnan et al., Flap endonuclease 1. Annu Rev Biochem. 2013;82:119-38. doi: 10.1146/annurev-biochem-072511-122603. Epub Feb. 28, 2013.
Baldari et al., A novel leader peptide which allows efficient secretion of a fragment of human interleukin 1 beta in *Saccharomyces cerevisiae*. EMBO J. Jan. 1987;6(1):229-34.
Banerjee et al., Cadmium inhibits mismatch repair by blocking the ATPase activity of the MSH2-MSH6 complex [published correction appears in Nucleic Acids Res. 2005;33(5):1738]. Nucleic Acids Res. 2005;33(4):1410-1419. Published Mar. 3, 2005. doi: 10.1093/nar/gki291.
Banerji et al., A lymphocyte-specific cellular enhancer is located downstream of the joining region in immunoglobulin heavy chain genes. Cell. Jul. 1983;33(3):729-40. doi: 10.1016/0092-8674(83)90015-6.
Bannert et al., Retroelements and the human genome: new perspectives on an old relation. Proc Natl Acad Sci U S A. Oct. 5, 2004;101 Suppl 2(Suppl 2):14572-9. doi: 10.1073/pnas.0404838101. Epub Aug. 13, 2004.
Banno et al., Deaminase-mediated multiplex genome editing in *Escherichia coli*. Nat Microbiol. Apr. 2018;3(4):423-429. doi: 10.1038/s41564-017-0102-6. Epub Feb. 5, 2018.
Baranauskas et al., Generation and characterization of new highly thermostable and processive M-MuLV reverse transcriptase variants. Protein Eng Des Sel. Oct. 2012;25(10):657-68. doi: 10.1093/protein/gzs034. Epub Jun. 12, 2012.
Barmania et al., C—C chemokine receptor type five (CCR5): An emerging target for the control of HIV infection. Appl Transl Genom. May 26, 2013;2:3-16. doi: 10.1016/j.atg.2013.05.004.
Barnes et al., Repair and genetic consequences of endogenous DNA base damage in mammalian cells. Annu Rev Genet. 2004;38:445-76.
Barnes et al., The fidelity of Taq polymerase catalyzing PCR is improved by an N-terminal deletion. Gene. Mar. 1, 1992;112(1):29-35. doi: 10.1016/0378-1119(92)90299-5.
Barrangou et al., CRISPR provides acquired resistance against viruses in prokaryotes. Science. Mar. 23, 2007;315(5819):1709-12.
Barrangou, RNA-mediated programmable DNA cleavage. Nat Biotechnol. Sep. 2012;30(9):836-8. doi: 10.1038/nbt.2357.
Bartlett et al., Efficient expression of protein coding genes from the murine U1 small nuclear RNA promoters. Proc Natl Acad Sci U S A. Aug. 20, 1996;93(17):8852-7. doi: 10.1073/pnas.93.17.8852.
Bartosovic et al., N6-methyladenosine demethylase FTO targets pre-mRNAs and regulates alternative splicing and 3'-end processing. Nucleic Acids Res. Nov. 2, 2017;45(19):11356-11370. doi: 10.1093/nar/gkx778.
Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.
Basila et al., Minimal 2'-O-methyl phosphorothioate linkage modification pattern of synthetic guide RNAs for increased stability and efficient CRISPR-Cas9 gene editing avoiding cellular toxicity. PLoS One. Nov. 27, 2017;12(11):e0188593. doi: 10.1371/journal.pone.0188593.
Bass, B.L., RNA editing by adenosine deaminases that act on RNA. Annu Rev Biochem. 2002;71:817-46. doi: 10.1146/annurev.biochem.71.110601.135501. Epub Nov. 9, 2001.
Basturea et al., Substrate specificity and properties of the *Escherichia coli* 16S rRNA methyltransferase, RsmE. RNA. Nov. 2007;13(11):1969-76. doi: 10.1261/rna.700507. Epub Sep. 13, 2007.
Batey et al., Structure of a natural guanine-responsive riboswitch complexed with the metabolite hypoxanthine. Nature. Nov. 18, 2004;432(7015):411-5.
Beale et al., Comparison of the differential context-dependence of DNA deamination by APOBEC enzymes: correlation with mutation spectra in vivo. J Mol Biol. Mar. 26, 2004;337(3):585-96.
Beaudry et al., Directed evolution of an RNA enzyme. Science. Jul. 31, 1992;257(5070):635-41. doi: 10.1126/science.1496376.
Bebenek et al., Error-prone polymerization by HIV-1 reverse transcriptase. Contribution of template-primer misalignment, miscoding, and termination probability to mutational hot spots. J Biol Chem. May 15, 1993;268(14):10324-34.
Bedell et al., In vivo genome editing using a high-efficiency TALEN system. Nature. Nov. 1, 2012;491(7422):114-8. Doi: 10.1038/nature11537. Epub Sep. 23, 2012.
Begley, Scientists unveil the 'most clever CRISPR gadget' so far. STAT, Apr. 20, 2016. https://www.statnews.com/2016/04/20/clever-crispr-advance-unveiled/.
Behr, Gene transfer with synthetic cationic amphiphiles: prospects for gene therapy. Bioconjug Chem. Sep.-Oct. 1994;5(5):382-9. doi: 10.1021/bc00029a002.
Bell et al., Ribozyme-catalyzed excision of targeted sequences from within RNAs. Biochemistry. Dec. 24, 2002;41(51):15327-33. doi: 10.1021/bi0267386.
Belshaw et al., Controlling programmed cell death with a cyclophilin-cyclosporin-based chemical inducer of dimerization. Chem Biol. Sep. 1996;3(9):731-8. doi: 10.1016/s1074-5521(96)90249-5.
Belshaw et al., Controlling protein association and subcellular localization with a synthetic ligand that induces heterodimerization of proteins. Proc Natl Acad Sci U S A. May 14, 1996;93(10):4604-7. doi: 10.1073/pnas.93.10.4604.
Benarroch, HCN channels: function and clinical implications. Neurology. Jan. 15, 2013;80(3):304-10. doi: 10.1212/WNL.0b013e31827dec42.

(56) References Cited

OTHER PUBLICATIONS

Bennett et al., Painful and painless channelopathies. Lancet Neurol. Jun. 2014;13(6):587-99. doi: 10.1016/S1474-4422(14)70024-9. Epub May 6, 2014.
Bentin, T., A ribozyme transcribed by a ribozyme. Artif DNA PNA XNA. Apr. 2011;2(2):40-42. doi: 10.4161/adna.2.2.16852.
Berger et al., Reverse transcriptase and its associated ribonuclease H: interplay of two enzyme activities controls the yield of single-stranded complementary deoxyribonucleic acid. Biochemistry. May 10, 1983;22(10):2365-72. doi: 10.1021/bi00279a010.
Berges et al., Transduction of brain by herpes simplex virus vectors. Mol Ther. Jan. 2007;15(1):20-9. doi: 10.1038/sj.mt.6300018.
Berkhout et al., Identification of an active reverse transcriptase enzyme encoded by a human endogenous HERV-K retrovirus. J Virol. Mar. 1999;73(3):2365-75. doi: 10.1128/JVI.73.3.2365-2375.1999.
Bernhart et al., Local RNA base pairing probabilities in large sequences. Bioinformatics. Mar. 1, 2006;22(5):614-5. doi: 10.1093/bioinformatics/btk014. Epub Dec. 20, 2005.
Bernstein et al., Role for a bidentate ribonuclease in the initiation step of RNA interference. Nature. Jan. 18, 2001;409(6818):363-6. doi: 10.1038/35053110.
Bershtein et al., Advances in laboratory evolution of enzymes. Curr Opin; Chem Biol. Apr. 2008;12(2):151-8. doi: 10.1016/j.cbpa.2008.01.027. Epub Mar. 7, 2008. Review.
Bertolotti et al., Toward genosafe endonuclease-boosted gene targeting using breakthrough CRISP/Cas9 for next generation stem cell gene therapy culminating in efficient ex VIVO in VIVO gene repair/genomic editing. Molecular Therapy. May 2015;23(Suppl1):S139. Abstract 350. 18th Ann Meeting of the American Society of Gene and Cell Therapy. ASGCT 2015. New Orleans, LA. May 13, 2015-May 16, 2015.
Bertrand et al., Localization of ASH1 mRNA particles in living yeast. Mol Cell. Oct. 1998;2(4):437-45. doi: 10.1016/s1097-2765(00)80143-4.
Bertsimas et al., Simulated annealing. Statistical Science. Feb. 1993;8(1):10-15. doi: 10.1214/ss/1177011077.
Bessen et al., High-resolution specificity profiling and off-target prediction for site-specific DNA recombinases. Nat Commun. Apr. 2, 20196;10(1):1937. doi: 10.1038/s41467-019-09987-0.
Beumer et al., Efficient gene targeting in *Drosophila* with zinc-finger nucleases. Genetics. Apr. 2006; 172(4):2391-403. Epub Feb. 1, 2006.
Bhagwat, DNA-cytosine deaminases: from antibody maturation to antiviral defense. DNA Repair (Amst). Jan. 5, 2004;3(1):85-9.
Bi et al., Pseudo attP sites in favor of transgene integration and expression in cultured porcine cells identified by Streptomyces phage phiC31 integrase. BMC Mol Biol. Sep. 8, 2013;14:20. doi: 10.1186/1471-2199-14-20.
Bibb et al., Integration and excision by the large serine recombinase phiRv1 integrase. Mol Microbiol. Mar. 2005;55(6):1896-910. doi: 10.1111/j.1365-2958.2005.04517.x.
Bibikova et al., Targeted chromosomal cleavage and mutagenesis in *Drosophila* using zinc-finger nucleases. Genetics. Jul. 2002;161(3):1169-75. doi: 10.1093/genetics/161.3.1169.
Biehs et al., DNA Double-Strand Break Resection Occurs during Non-homologous End Joining in G1 but Is Distinct from Resection during Homologous Recombination. Mol Cell. Feb. 16, 2017;65(4):671-684.e5. doi: 10.1016/j.molcel.2016.12.016. Epub Jan. 26, 2017.
Billon et al., CRISPR-Mediated Base Editing Enables Efficient Disruption of Eukaryotic Genes through Induction of STOP Codons. Mol Cell. Sep. 21, 2017;67(6):1068-1079.e4. doi: 10.1016/j.molcel.2017.08.008. Epub Sep. 7, 2017.
Birling et al., Site-specific recombinases for manipulation of the mouse genome. Methods Mol Biol. 2009;561:245-63. doi: 10.1007/978-1-60327-019-9_16.
Biswas et al., A structural basis for allosteric control of DNA recombination by lambda integrase. Nature. Jun. 23, 2005;435(7045):1059-66. doi: 10.1038/nature03657.
Bitinaite et al., FokI dimerization is required for DNA cleavage. Proc Natl Acad Sci U S A. Sep. 1, 1998;95(18):10570-5.
Blaese et al., Vectors in cancer therapy: how will they deliver? Cancer Gene Ther. Dec. 1995;2(4):291-7.
Blain et al., Nuclease activities of Moloney murine leukemia virus reverse transcriptase. Mutants with altered substrate specificities. J Biol Chem. Nov. 5, 1993;268(31):23585-92.
Blaisonneau et al., A circular plasmid from the yeast Torulaspora delbrueckii. Plasmid. 1997;38(3):202-9. doi: 10.1006/plas.1997.1315.
Blau et al., A proliferation switch for genetically modified cells. PNAS Apr. 1, 1997 94 (7) 3076-3081; https://doi.org/10.1073/pnas.94.7.3076.
Blauw et al., SMN1 gene duplications are associated with sporadic ALS. Neurology. Mar. 13, 2012;78(11):776-80. doi: 10.1212/WNL.0b013e318249f697. Epub Feb. 8, 2012.
Bloom et al., Evolving strategies for enzyme engineering. Curr Opin Struct Biol. Aug. 2005;15(4):447-52.
Boch, TALEs of genome targeting. Nat Biotechnol. Feb. 2011;29(2):135-6. Doi: 10.1038/nbt.1767.
Bodi et al., Yeast m6A Methylated mRNAs Are Enriched on Translating Ribosomes during Meiosis, and under Rapamycin Treatment. PLoS One. Jul. 17, 2015;10(7):e0132090. doi: 10.1371/journal.pone.0132090.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Boersma et al., Selection strategies for improved biocatalysts. FEBS J. May 2007;274(9):2181-95.
Bogdanove et al., Engineering altered protein-DNA recognition specificity. Nucleic Acids Res. Jun. 1, 2018;46(10):4845-4871. doi: 10.1093/nar/gky289.
Bogdanove et al., TAL effectors: customizable proteins for DNA targeting. Science. Sep. 30, 2011;333(6051):1843-6. doi: 10.1126/science.1204094.
Bohlke et al., Sense codon emancipation for proteome-wide incorporation of noncanonical amino acids: rare isoleucine codon AUA as a target for genetic code expansion. FEMS Microbiol Lett. Feb. 2014;351(2):133-44. doi: 10.1111/1574-6968.12371. Epub Jan. 27, 2014.
Bolotin et al., Clustered regularly interspaced short palindrome repeats (CRISPRs) have spacers of extrachromosomal origin. Microbiology. Aug. 2005;151(Pt 8):2551-61.
Bolusani et al., Evolution of variants of yeast site-specific recombinase Flp that utilize native genomic sequences as recombination target sites. Nucleic Acids Res. 2006;34(18):5259-69. Epub Sep. 26, 2006.
Bondeson et al., Inversion of the IDS gene resulting from recombination with IDS-related sequences is a common cause of the Hunter syndrome. Hum Mol Genet. Apr. 1995;4(4):615-21. doi: 10.1093/hmg/4.4.615.
Borchardt et al., Controlling mRNA stability and translation with the CRISPR endoribonuclease Csy4. RNA. Nov. 2015;21(11):1921-30. doi: 10.1261/rna.051227.115. Epub Sep. 9, 2015.
Borman, Improved route to single-base genome editing. Chemical & Engineering News, Apr. 25, 2016;94(17)p5. http://cen.acs.org/articles/94/i17/Improved-route-single-base-genome.html.
Bothmer et al., Characterization of the interplay between DNA repair and CRISPR/Cas9-induced DNA lesions at an endogenous locus. Nat Commun. Jan. 9, 2017;8:13905. doi: 10.1038/ncomms13905.
Bourinet et al., Silencing of the Cav3.2 T-type calcium channel gene in sensory neurons demonstrates its major role in nociception. EMBO J. Jan. 26, 2005;24(2):315-24. doi: 10.1038/sj.emboj.7600515. Epub Dec. 16, 2004.
Boutabout et al., DNA synthesis fidelity by the reverse transcriptase of the yeast retrotransposon Ty1. Nucleic Acids Res. Jun. 1, 2001;29(11):2217-22. doi: 10.1093/nar/29.11.2217.
Box et al., A multi-domain protein system based on the HC fragment of tetanus toxin for targeting DNA to neuronal cells. J Drug Target. Jul. 2003;11(6):333-43. doi: 10.1080/10611863100016346674667.
Branden and Tooze, Introduction to Protein Structure. 1999; 2nd edition. Garland Science Publisher: 3-12.

(56) References Cited

OTHER PUBLICATIONS

Braun et al., Immunogenic duplex nucleic acids are nuclease resistant. J Immunol. Sep. 15, 1988;141(6):2084-9.
Brierley et al., Viral RNA pseudoknots: versatile motifs in gene expression and replication. Nat Rev Microbiol. Aug. 2007;5(8):598-610. doi: 10.1038/nrmicro1704.
Briner et al., Guide RNA functional modules direct Cas9 activity and orthogonality. Mol Cell. Oct. 23, 2014;56(2):333-339. doi: 10.1016/j.molcel.2014.09.019.
Britt et al., Re-engineering plant gene targeting. Trends Plant Sci. Feb. 2003;8(2):90-5.
Brouns et al., Small CRISPR RNAs guide antiviral defense in prokaryotes. Science. Aug. 15, 2008;321(5891):960-4. doi: 10.1126/science.1159689.
Brown et al., A mammalian protein targeted by G1-arresting rapamycin-receptor complex. Nature. Jun. 30, 1994;369(6483):756-8. doi: 10.1038/369756a0.
Brown et al., Characterization of the genetic elements required for site-specific integration of plasmid pSE211 in Saccharopolyspora erythraea. J Bacteriol. Apr. 1990;172(4):1877-88. doi: 10.1128/jb.172.4.1877-1888.1990.
Brown et al., Serine recombinases as tools for genome engineering. Methods. Apr. 2011;53(4):372-9. doi: 10.1016/j.ymeth.2010.12.031. Epub Dec. 30, 2010.
Brown et al., Structural insights into the stabilization of MALAT1 noncoding RNA by a bipartite triple helix. Nat Struct Mol Biol. Jul. 2014;21(7):633-40. doi: 10.1038/nsmb.2844. Epub Jun. 22, 2014.
Brusse et al., Spinocerebellar ataxia associated with a mutation in the fibroblast growth factor 14 gene (SCA27): A new phenotype. Mov Disord. Mar. 2006;21(3):396-401.
Brutlag et al., Improved sensitivity of biological sequence database searches. Comput Appl Biosci. Jul. 1990;6(3):237-45. doi: 10.1093/bioinformatics/6.3.237.
Brzezicha et al., Identification of human tRNA:m5C methyltransferase catalysing intron-dependent m5C formation in the first position of the anticodon of the pre-tRNA Leu (CAA). Nucleic Acids Res. 2006;34(20):6034-43. doi: 10.1093/nar/gkl765. Epub Oct. 27, 2006.
Buchholz et al., Alteration of Cre recombinase site specificity by substrate-linked protein evolution. Nat Biotechnol. Nov. 2001;19(11):1047-52.
Buchschacher et al., Human immunodeficiency virus vectors for inducible expression of foreign genes. J Virol. May 1992;66(5):2731-9. doi: 10.1128/JVI.66.5.2731-2739.1992.
Buchwald et al., Long-term, continuous intravenous heparin administration by an implantable infusion pump in ambulatory patients with recurrent venous thrombosis. Surgery. Oct. 1980;88(4):507-16.
Buckley et al., Targeting the von Hippel-Lindau E3 ubiquitin ligase using small molecules to disrupt the VHL/HIF-1 a interaction. J Am Chem Soc. Mar. 14, 2012;134(10):4465-8. doi: 10.1021/ja209924v. Epub Feb. 27, 2012.
Budisa et al., Residue-specific bioincorporation of non-natural, biologically active amino acids into proteins as possible drug carriers: structure and stability of the per-thiaproline mutant of annexin V. Proc Natl Acad Sci U S A. Jan. 20, 1998;95(2):455-9.
Budker et al., Protein/amphipathic polyamine complexes enable highly efficient transfection with minimal toxicity. Biotechniques. Jul. 1997;23(1):139, 142-7. doi: 10.2144/97231rr02.
Budworth et al., A brief history of triplet repeat diseases. Methods Mol Biol. 2013; 1010:3-17. doi: 10.1007/978-1-62703-411-1_1.
Bulow et al., Multienzyme systems obtained by gene fusion. Trends Biotechnol. Jul. 1991;9(7):226-31.
Burke et al., Activating mutations of Tn3 resolvase marking interfaces important in recombination catalysis and its regulation. Mol Microbiol. Feb. 2004;51(4):937-48.
Burke et al., RNA Aptamers to the Adenosine Moiety of S-adenosyl Methionine: Structural Inferences From Variations on a Theme and the Reproducibility of SELEX. Nucleic Acids Res. May 15, 1997;25(10):2020-4. doi: 10.1093/nar/25.10.2020.
Burstein et al., New CRISPR-Cas systems from uncultivated microbes. Nature Feb. 2017;542(7640):237-240.
Burton et al., Gene delivery using herpes simplex virus vectors. DNA Cell Biol. Dec. 2002;21(12):915-36. doi: 10.1089/104454902762053864.
Buskirk et al., Directed evolution of ligand dependence: small-molecule-activated protein splicing. Proc Natl Acad Sci U S A. Jul. 20, 2004;101(29):10505-10. Epub Jul. 9, 2004.
Buskirk et al., In vivo evolution of an RNA-based transcriptional activator. Chem Biol. Jun. 2003;10(6):533-40. doi: 10.1016/s1074-5521(03)00109-1.
Butt et al., Efficient CRISPR/Cas9-Mediated Genome Editing Using a Chimeric Single-Guide RNA Molecule. Front Plant Sci. Aug. 24, 2017;8:1441(1-8). doi: 10.3389/fpls.2017.01441.
Byrne et al., Multiplex gene regulation: a two-tiered approach to transgene regulation in transgenic mice. Proc Natl Acad Sci U S A. Jul. 1989;86(14):5473-7. doi: 10.1073/pnas.86.14.5473.
Böck et al., Selenocysteine: the 21st amino acid. Mol Microbiol. Mar. 1991;5(3):515-20.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Cadwell et al., Randomization of genes by PCR mutagenesis. PCR Methods Appl. Aug. 1992;2(1):28-33. doi: 10.1101/gr.2.1.28.
Cai et al., Reconstruction of ancestral protein sequences and its applications. BMC Evol Biol. Sep. 17, 2004;4:33. doi: 10.1186/1471-2148-4-33.
Calame et al., Transcriptional controlling elements in the immunoglobulin and T cell receptor loci. Adv Immunol. 1988;43:235-75. doi: 10.1016/s0065-2776(08)60367-3.
Caldecott et al., Single-strand break repair and genetic disease. Nat Rev Genet. Aug. 2008;9(8):619-31. doi: 10.1038/nrg2380.
Camarero et al., Biosynthesis of a Head-to-Tail Cyclized Protein with Improved Biological Activity. J. Am. Chem. Soc. May 29, 1999; 121(23):5597-5598. https://doi.org/10.1021/ja990929n.
Cameron, Recent advances in transgenic technology. Mol Biotechnol. Jun. 1997;7(3):253-65.
Camper et al., Postnatal repression of the alpha-fetoprotein gene is enhancer independent. Genes Dev. Apr. 1989;3(4):537-46. doi: 10.1101/gad.3.4.537.
Camps et al., Targeted gene evolution in *Escherichia coli* using a highly error-prone DNA polymerase I. Proc Natl Acad Sci U S A. Aug. 1, 20039;100(17):9727-32. Epub Aug. 8, 2003.
Canchaya et al., Genome analysis of an inducible prophage and prophage remnants integrated in the *Streptococcus pyogenes* strain SF370. Virology. Oct. 25, 2002;302(2):245-58. doi: 10.1006/viro.2002.1570.
Canny et al., Inhibition of 53BP1 Favors Homology-Dependent DNA Repair and Increases CRISPR-Cas9 Genome-Editing Efficiency. Nat Biotechnol. Jan. 2018;36(1):95-102. doi: 10.1038/nbt.4021. Epub Nov. 27, 2017.
Canver et al., Customizing the genome as therapy for the β-hemoglobinopathies. Blood. May 26, 2016;127(21):2536-45. doi: 10.1182/blood-2016-01-678128. Epub Apr. 6, 2016.
Cao et al., Rapamycin reverses cellular phenotypes and enhances mutant protein clearance in Hutchinson-Gilford progeria syndrome cells. Sci Transl Med. Jun. 29, 2011;3(89):89ra58. doi: 10.1126/scitranslmed.3002346.
Cargill et al., Characterization of single-nucleotide polymorphisms in coding regions of human genes. Nat Genet. Jul. 1999;22(3):231-8.
Carlier et al., Burkholderia cenocepacia H111 Rhy-family protein. Apr. 16, 2015. Retrieved from the Internet via https://www.ebi.ac.uk/ena/browser/api/embl/CDN65395.1?lineLimit=1000. Last retrieved Apr. 26, 2021.
Carlier et al., Genome Sequence of Burkholderia cenocepacia H111, a Cystic Fibrosis Airway Isolate. Genome Announc. Apr. 10, 2014;2(2):e00298-14. doi: 10.1128/genomeA.00298-14.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Caron et al., Intracellular delivery of a Tat-eGFP fusion protein into muscle cells. Mol Ther. Mar. 2001;3(3):310-8.

(56) References Cited

OTHER PUBLICATIONS

Carr et al., Genome engineering. Nat Biotechnol. Dec. 2009;27(12):1151-62. doi: 10.1038/nbt.1590.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Carroll, A CRISPR approach to gene targeting. Mol Ther. Sep. 2012;20(9):1658-60. doi: 10.1038/mt.2012.171.
Carroll, Genome engineering with zinc-finger nucleases. Genetics. Aug. 2011;188(4):773-82. doi: 10.1534/genetics.111.131433. Review.
Cartegni et al., Determinants of exon 7 splicing in the spinal muscular atrophy genes, SMN1 and SMN2. Am J Hum Genet. Jan. 2006;78(1):63-77. doi: 10.1086/498853. Epub Nov. 16, 2005.
Carvalho et al., Evolution in health and medicine Sackler colloquium: Genomic disorders: a window into human gene and genome evolution. Proc Natl Acad Sci U S A. Jan. 26, 2010;107 Suppl 1(Suppl 1):1765-71. doi: 10.1073/pnas.0906222107. Epub Jan. 13, 2010.
Caspi et al., Distribution of split DnaE inteins in cyanobacteria. Mol Microbiol. Dec. 2003;50(5):1569-77. doi: 10.1046/j.1365-2958.2003.03825.x.
Cattaneo et al., SEL1L affects human pancreatic cancer cell cycle and invasiveness through modulation of PTEN and genes related to cell-matrix interactions. Neoplasia. 2005;7(11):1030-1038.
Ceccaldi et al., Repair Pathway Choices and Consequences at the Double-Strand Break. Trends Cell Biol. Jan. 2016;26(1):52-64. doi: 10.1016/j.tcb.2015.07.009. Epub Oct. 1, 2015.
Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.
Chadalavada et al., Wild-type is the optimal sequence of the HDV ribozyme under cotranscriptional conditions. RNA. Dec. 2007;13(12):2189-201. doi: 10.1261/rna.778107. Epub Oct. 23, 2007.
Chadwick et al., In Vivo Base Editing of PCSK9 (Proprotein Convertase Subtilisin/Kexin Type 9) as a Therapeutic Alternative to Genome Editing. Arterioscler Thromb Vasc Biol. Sep. 2017;37(9):1741-1747. doi: 10.1161/ATVBAHA.117.309881. Epub Jul. 27, 2017.
Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.
Chalberg et al., Integration specificity of phage phiC31 integrase in the human genome. J Mol Biol. Mar. 17, 2006;357(1):28-48. doi: 10.1016/j.jmb.2005.11.098. Epub Dec. 22, 2005.
Chalberg et al., phiC31 integrase confers genomic integration and long-term transgene expression in rat retina. Invest Ophthalmol Vis Sci. Jun. 2005;46(6):2140-6. doi: 10.1167/iovs.04-1252.
Chan et al., Molecular recording of mammalian embryogenesis. Nature. Jun. 2019;570(7759):77-82. doi: 10.1038/s41586-019-1184-5. Epub May 13, 2019.
Chan et al., Novel selection methods for DNA-encoded chemical libraries. Curr Opin Chem Biol. 2015;26:55-61. doi:10.1016/j.cbpa.2015.02.010.
Chan et al., The choice of nucleotide inserted opposite abasic sites formed within chromosomal DNA reveals the polymerase activities participating in translesion DNA synthesis. DNA Repair (Amst). Nov. 2013;12(11):878-89. doi: 10.1016/j.dnarep.2013.07.008. Epub Aug. 26, 2013.
Chang et al., Degradation of survival motor neuron (SMN) protein is mediated via the ubiquitin/proteasome pathway. Neurochem Int. Dec. 2004;45(7):1107-12. doi: 10.1016/j.neuint.2004.04.005.
Chapman et al., Playing the end game: DNA double-strand break repair pathway choice. Mol Cell. Aug. 24, 2012;47(4):497-510. doi: 10.1016/j.molcel.2012.07.029.
Chari et al., Unraveling CRISPR-Cas9 genome engineering parameters via a library-on-library approach. Nat Methods. Sep. 2015;12(9):823-6. doi: 10.1038/nmeth.3473. Epub Jul. 13, 2015.
Charpentier et al., Biotechnology: Rewriting a genome. Nature. Mar. 7, 2013;495(7439):50-1. doi: 10.1038/495050a.
Chatterjee et al., A Cas9 with PAM recognition for adenine dinucleotides. Nat Commun. May 1, 20208;11(1):2474. doi: 10.1038/s41467-020-16117-8.
Chatterjee et al., Robust Genome Editing of Single-Base PAM Targets; with Engineered ScCas9 Variants. bioRxiv. doi: 10.1101/620351. Posted Apr. 26, 2019.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Chavez et al., Highly efficient Cas9-mediated transcriptional programming. Nat Methods. Apr. 2015;12(4):326-8. doi: 10.1038/nmeth.3312. Epub Mar. 2, 2015.
Chavez et al., Precise Cas9 targeting enables genomic mutation prevention. bioRxiv. Jun. 14, 2016; http://dx/doi.oreg/10.1101/058974. 6 pages. bioRxiv preprint first posted online Jun. 14, 2016.
Chavez et al., Therapeutic applications of the ΦC31 integrase system. Curr Gene Ther. Oct. 2011; 11(5):375-81. Review.
Chavez et al., Therapeutic applications of the PhiC31 integrase system. Curr Gene Ther. Oct. 2011;11(5):375-81. Review.
Chawla et al., An atlas of RNA base pairs involving modified nucleobases with optimal geometries and accurate energies. Nucleic Acids Res. Aug. 18, 2015;43(14):6714-29. doi: 10.1093/nar/gkv606. Epub Jun. 27, 2015.
Chelico et al., Biochemical basis of immunological and retroviral responses to DNA-targeted cytosine deamination by activation-induced cytidine deaminase and APOBEC3G. J Biol Chem. Oct. 9, 2009;284(41):27761-5. doi: 10.1074/jbc.R109.052449. Epub Aug. 13, 2009.
Chelico et al., Stochastic properties of processive cytidine DNA deaminases AID and APOBEC3G. Philos Trans R Soc Lond B Biol Sci. Mar. 12, 2009;364(1517):583-93. doi: 10.1098/rstb.2008.0195.
Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.
Chen et al., Alterations in PMS2, MSH2 and MLH1 expression in human prostate cancer. Int J Oncol. May 2003;22(5):1033-43.
Chen et al., Dynamic imaging of genomic loci in living human cells by an optimized CRISPR/Cas system. Cell. Dec. 1, 20139;155(7):1479-91. doi: 10.1016/j.cell.2013.12.001. Erratum in: Cell. Jan. 16, 2014;156(1-2):373.
Chen et al., Enhanced prime editing systems by manipulating cellular determinants of editing outcomes. Cell. Oct. 28, 2021;184(22):5635-5652.e29. doi: 10.1016/j.cell.2021.09.018. Epub Oct. 14, 2021.
Chen et al., Enhanced proofreading governs CRISPR-Cas9 targeting accuracy. Nature. Oct. 19, 2017;550(7676):407-410. doi: 10.1038/nature24268. Epub Sep. 20, 2017.
Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.
Chen et al., Genome-wide CRISPR screen in a mouse model of tumor growth and metastasis. Cell. Mar. 12, 2015;160(6):1246-60. doi: 10.1016/j.cell.2015.02.038. Epub Mar. 5, 2015.
Chen et al., Highly Efficient Mouse Genome Editing by CRISPR Ribonucleoprotein Electroporation of Zygotes. J Biol Chem. Jul. 8, 2016;291(28):14457-67. doi: 10.1074/jbc.M116.733154. Epub May 5, 2016.
Chen et al., m(6)A RNA methylation is regulated by microRNAs and promotes reprogramming to pluripotency. Cell Stem Cell. Mar. 5, 2015;16(3):289-301. doi: 10.1016/j.stem.2015.01.016. Epub Feb. 12, 2015.
Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.

(56) References Cited

OTHER PUBLICATIONS

Chen et al., Targeting genomic rearrangements in tumor cells through Cas9-mediated insertion of a suicide gene. Nat Biotechnol. Jun. 2017;35(6):543-550. doi: 10.1038/nbt.3843. Epub May 1, 2017.

Cheng et al., [Cloning,expression and activity identification of human innate immune protein apolipoprotein B mRNA editing enzyme catalytic subunit 3A(APOBEC3A)]. Xi Bao Yu Fen Zi Mian Yi Xue Za Zhi. Chinese Journal of Cellular and Molecular Immunology, Feb. 2017;33(2):179-84. Chinese.

Cheng et al., Multiplexed activation of endogenous genes by CRISPR-on, an RNA-guided transcriptional activator system. Cell Res. Oct. 2013;23(10):1163-71. doi: 10.1038/cr.2013.122. Epub Aug. 27, 2013.

Chesnoy et al., Structure and function of lipid-DNA complexes for gene delivery. Annu Rev Biophys Biomol Struct. 2000;29:27-47.

Chester et al., The apolipoprotein B mRNA editing complex performs a multifunctional cycle and suppresses nonsense-mediated decay. EMBO J. Aug. 1, 2003;22(15):3971-82. doi: 10.1093/emboj/cdg369.

Chew et al., A multifunctional AAV-CRISPR-Cas9 and its host response. Nat Methods. Oct. 2016; 13(10):868-74. doi: 10.1038/nmeth.3993. Epub Sep. 5, 2016.

Chew et al., A multifunctional AAV-CRISPR-Cas9 and its host response. Nat Methods. Oct. 2016; 13(10):868-74. doi: 10.1038/nmeth.3993. Epub Sep. 5, 2016. Supplementary Information.

Chichili et al., Linkers in the structural biology of protein-protein interactions. Protein Science. 2013;22:153-67.

Chin, Expanding and reprogramming the genetic code of cells and animals. Annu Rev Biochem. 2014;83:379-408. doi: 10.1146/annurev-biochem-060713-035737. Epub Feb. 10, 2014.

Chipev et al., A leucine—proline mutation in the H1 subdomain of keratin 1 causes epidermolytic hyperkeratosis. Cell. Sep. 4, 1992;70(5):821-8.

Cho et al., A degron created by SMN2 exon 7 skipping is a principal contributor to spinal muscular atrophy severity. Genes Dev. Mar. 1, 2010;24(5):438-42. doi: 10.1101/gad.1884910.

Cho et al., Analysis of off-target effects of CRISPR/Cas-derived RNA-guided endonucleases and nickases. Genome Res. Jan. 2014;24(1):132-41. doi: 10.1101/gr.162339.113. Epub Nov. 19, 2013.

Cho et al., Site-specific recombination of bacteriophage P22 does not require integration host factor. J Bacteriol. Jul. 1999;181(14):4245-9. doi: 10.1128/JB.181.14.4245-4249.1999.

Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.

Cho et al., The calcium-activated chloride channel anoctamin 1 acts as a heat sensor in nociceptive neurons. Nat Neurosci. May 27, 2012;15(7):1015-21. doi: 10.1038/nn.3111.

Choe et al., Forging Ahead through Darkness: PCNA, Still the Principal Conductor at the Replication Fork. Mol Cell. Feb. 2, 2017;65(3):380-392. doi: 10.1016/j.molcel.2016.12.020.

Choi et al., N(6)-methyladenosine in mRNA disrupts tRNA selection and translation-elongation dynamics. Nat Struct Mol Biol. Feb. 2016;23(2):110-5. doi: 10.1038/nsmb.3148. Epub Jan. 11, 2016.

Choi et al., Protein trans-splicing and characterization of a split family B-type DNA polymerase from the hyperthermophilic archaeal parasite Nanoarchaeum equitans. J Mol Biol. Mar. 10, 2006;356(5):1093-106. doi: 10.1016/j.jmb.2005.12.036. Epub Dec. 27, 2005.

Choi et al., Translesion synthesis across abasic lesions by human B-family and Y-family DNA polymerases α, δ, η, ι, κ, and REV1. J Mol Biol. Nov. 19, 2010;404(1):34-44. doi: 10.1016/j.jmb.2010.09.015. Epub Oct. 1, 2010.

Chong et al., Utilizing the C-terminal cleavage activity of a protein splicing element to purify recombinant proteins in a single chromatographic step. Nucleic Acids Res. Nov. 15, 1998;26(22):5109-15. doi: 10.1093/nar/26.22.5109.

Chong et al., Modulation of protein splicing of the *Saccharomyces cerevisiae* vacuolar membrane ATPase intein. J Biol Chem. Apr. 24, 1998;273(17):10567-77. doi: 10.1074/jbc.273.17.10567.

Chong et al., Protein splicing involving the Saccharomyces cerevisiae VMA intein. The steps in the splicing pathway, side reactions leading to protein cleavage, and establishment of an in vitro splicing system. J Biol Chem. Sep. 6, 1996;271(36):22159-68. doi: 10.1074/jbc.271.36.22159.

Chong et al., Protein splicing of the *Saccharomyces cerevisiae* VMA intein without the endonuclease motifs. J Biol Chem. Jun. 20, 1997;272(25):15587-90. doi: 10.1074/jbc.272.25.15587.

Chong et al., Single-column purification of free recombinant proteins using a self-cleavable affinity tag derived from a protein splicing element. Gene. Jun. 19, 1997;192(2):271-81. doi: 10.1016/s0378-1119(97)00105-4.

Choudhury et al., CRISPR-dCas9 mediated TET1 targeting for selective DNA demethylation at BRCA1 promoter. Oncotarget. Jul. 19, 2016;7(29):46545-46556. doi: 10.18632/oncotarget.10234.

Choudhury et al., CRISPR/Cas9 recombineering-mediated deep mutational scanning of essential genes in *Escherichia coli*. Mol Syst Biol. Mar. 2020; 16(3):e9265. doi: 10.15252/msb.20199265.

Choudhury et al., Engineering RNA endonucleases with customized sequence specificities. Nat Commun. 2012;3:1147. doi: 10.1038/ncomms2154.

Choulika et al., Induction of homologous recombination in mammalian chromosomes by using the I-ScI system of *Saccharomyces cerevisiae*. Mol Cell Biol. Apr. 1995;15(4):1968-73. doi: 10.1128/MCB.15.4.1968.

Christian et al., Targeting G with TAL effectors: a comparison of activities of TALENs constructed with NN and NK repeat variable di-residues. PLoS One. 2012;7(9):e45383. doi: 10.1371/journal.pone.0045383. Epub Sep. 24, 2012.

Christian et al., Targeting DNA double-strand breaks with TAL effector nucleases. Genetics. Oct. 2010;186(2):757-61. doi: 10.1534/genetics.110.120717. Epub Jul. 26, 2010.

Christiansen et al., Characterization of the lactococcal temperate phage TP901-1 and its site-specific integration. J Bacteriol. Feb. 1994; 176(4):1069-76. doi: 10.1128/jb.176.4.1069-1076.1994.

Chu et al., Increasing the efficiency of homology-directed repair for CRISPR-Cas9-induced precise gene editing in mammalian cells. Nat Biotech. Feb. 13, 2015;33:543-8. doi: 10.1038/nbt.3198. Epub Mar. 24, 2015.

Chuai et al., DeepCRISPR: optimized CRISPR guide RNA design by deep learning. Genome Biol. Jun. 26, 2018;19(1):80. doi: 10.1186/s13059-018-1459-4.

Chuai et al., In Silico Meets In Vivo: Towards Computational CRISPR-Based sgRNA Design. Trends Biotechnol. Jan. 2017;35(1):12-21. doi: 10.1016/j.tibtech.2016.06.008. Epub Jul. 11, 2016.

Chuang et al., Novel Heterotypic Rox Sites for Combinatorial Dre Recombination Strategies. G3 (Bethesda). Dec. 29, 2015;6(3):559-71. doi: 10.1534/g3.115.025841.

Chujo et al., Trmt61B is a methyltransferase responsible for 1-methyladenosine at position 58 of human mitochondrial tRNAs. RNA. Dec. 2012;18(12):2269-76. doi: 10.1261/rna.035600.112. Epub Oct. 24, 2012.

Chung-Il et al., Artificial control of gene expression in mammalian cells by modulating RNA interference through aptamer-small molecule interaction. RNA. May 2006;12(5):710-6. Epub Apr. 10, 2006.

Chylinski et al., The tracrRNA and Cas9 families of type II CRISPR-Cas immunity systems. RNA Biol. May 2013;10(5):726-37. doi: 10.4161/rna.24321. Epub Apr. 5, 2013.

Clackson et al., Redesigning an FKBP-ligand interface to generate chemical dimerizers with novel specificity. Proc Natl Acad Sci U S A. Sep. 1, 1998;95(18):10437-42. doi: 10.1073/pnas.95.18.10437.

Clement et al., CRISPResso2 provides accurate and rapid genome editing sequence analysis. Nat Biotechnol. Mar. 2019;37(3):224-226. doi: 10.1038/s41587-019-0032-3.

Cobb et al., Directed evolution as a powerful synthetic biology tool. Methods. Mar. 15, 2013;60(1):81-90. doi: 10.1016/j.ymeth.2012.03.009. Epub Mar. 23, 2012.

Coffey et al., The Economic Impact of BSE on the U.S. Beef Industry: Product Value Losses, Regulatory Costs, and Consumer

(56) References Cited

OTHER PUBLICATIONS

Reactions. Kansas State University Agricultural Experiment Station and Cooperative Extension Service. MF-2678. May 2005. 68 pages. Accessed via https://bookstore.ksre.ksu.edu/pubs/MF2678.pdf.
Coffin et al., Retroviruses. 1997. Cold Spring Harbor Laboratory Press, New York, NY. Accessible at https://www.ncbi.nlm.nih.gov/books/NBK19376/.
Cokol et al., Finding nuclear localization signals. EMBO Rep. Nov. 2000;1(5):411-5. doi: 10.1093/embo-reports/kvd092.
Cole et al., Reconstructing evolutionary adaptive paths for protein engineering. Methods Mol Biol. 2013;978:115-25. doi: 10.1007/978-1-62703-293-3_8.
Cole-Strauss et al., Correction of the mutation responsible for sickle cell anemia by an RNA-DNA oligonucleotide. Science. Sep. 6, 1996;273(5280):1386-9.
Collinge, Prion diseases of humans and animals: their causes and molecular basis. Annu Rev Neurosci. 2001;24:519-50. doi: 10.1146/annurev.neuro.24.1.519.
Cong et al., Multiplex genome engineering using CRISPR/Cas systems. Science. Feb. 15, 2013;339(6121):819-23. doi: 10.1126/science.1231143. Epub Jan. 3, 2013.
Conrad et al., A Kaposi's sarcoma virus RNA element that increases the nuclear abundance of intronless transcripts. EMBO J. May 18, 2005;24(10):1831-41. doi: 10.1038/sj.emboj.7600662. Epub Apr. 28, 2005.
Conticello, The AID/APOBEC family of nucleic acid mutators. Genome Biol. 2008;9(6):229. doi: 10.1186/GB-2008-9-6-229. Epub Jun. 17, 2008.
Corcia et al., The importance of the SMN genes in the genetics of sporadic ALS. Amyotroph Lateral Scler. Oct.-Dec. 2009;10(5-6):436-40. doi: 10.3109/17482960902759162.
Cornu et al., Refining strategies to translate genome editing to the clinic. Nat Med. Apr. 3, 2017;23(4):415-423. doi: 10.1038/nm.4313.
Corti et al., Genetic correction of human induced pluripotent stem cells from patients with spinal muscular atrophy. Sci Transl Med. Dec. 19, 2012;4(165):165ra162. doi: 10.1126/scitranslmed.3004108.
Costa et al., Frequent use of the same tertiary motif by self-folding RNAs. EMBO J. Mar. 15, 1995;14(6):1276-85.
Cotton et al., Insertion of a Synthetic Peptide into a Recombinant Protein Framework: A Protein Biosensor. J. Am. Chem. Soc. Jan. 22, 1999; 121(5):1100-1. https://doi.org/10.1021/ja983804b.
Covino et al., The CCL2/CCR2 Axis in the Pathogenesis of HIV-1 Infection: A New Cellular Target for Therapy? Current Drug Targets Dec. 2016;17(1):76-110. DOI : 10.2174/1389450117011511217110917.
Cox et al., An SCN9A channelopathy causes congenital inability to experience pain. Nature. Dec. 14, 2006;444(7121):894-8. doi: 10.1038/nature05413.
Cox et al., Conditional gene expression in the mouse inner ear using Cre-loxP. J Assoc Res Otolaryngol. Jun. 2012;13(3):295-322. doi: 10.1007/s10162-012-0324-5. Epub Apr. 24, 2012.
Cox et al., Congenital insensitivity to pain: novel SCN9A missense and in-frame deletion mutations. Hum Mutat. Sep. 2010;31(9):E1670-86. doi: 10.1002/humu.21325.
Cox et al., RNA editing with CRISPR-Cas13. Science. Nov. 24, 2017;358(6366):1019-1027. doi: 10.1126/science.aaq0180. Epub Oct. 25, 2017.
Cox et al., Therapeutic genome editing: prospects and challenges. Nat Med. Feb. 2015;21(2):121-31. doi: 10.1038/nm.3793.
Cox, Proteins pinpoint double strand breaks. Elife. Oct. 29, 2013;2:e01561. doi: 10.7554/eLife.01561.
Crabtree et al., Three-part inventions: intracellular signaling and induced proximity. Trends Biochem Sci. Nov. 1996;21(11):418-22. doi: 10.1016/s0968-0004(96)20027-1.
Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.
Cradick et al., ZFN-site searches genomes for zinc finger nuclease target sites and off-target sites. BMC Bioinformatics. May 13, 2011;12:152. doi: 10.1186/1471-2105-12-152.
Cradick et al., Zinc-finger nucleases as a novel therapeutic strategy for targeting hepatitis B virus DNAs. Mol Ther. May 2010;18(5):947-54. DOI: 10.1038/mt.2010.20. Epub Feb. 16, 2010.
Crick, On protein synthesis. Symp Soc Exp Biol. 1958;12:138-63.
Cronican et al., A class of human proteins that deliver functional proteins into mammalian cells in vitro and in vivo. Chem Biol. Jul. 29, 2011;18(7):833-8. doi: 10.1016/j.chembiol.2011.07.003.
Cronican et al., Potent delivery of functional proteins into Mammalian cells in vitro and in vivo using a supercharged protein. ACS Chem Biol. Aug. 20, 2010;5(8):747-52. doi:10.1021/cb1001153.
Crystal, Transfer of genes to humans: early lessons and obstacles to success. Science. Oct. 20, 1995;270(5235):404-10. doi: 10.1126/science.270.5235.404.
Cucchiarini et al., Enhanced expression of the central survival of motor neuron (SMN) protein during the pathogenesis of osteoarthritis. J Cell Mol Med. Jan. 2014;18(1):115-24. doi: 10.1111/jcmm.12170. Epub Nov. 17, 2013.
Cui et al., Consequences of Cas9 cleavage in the chromosome of *Escherichia coli*. Nucleic Acids Res. May 19, 2016;44(9):4243-51. doi: 10.1093/nar/gkw223. Epub Apr. 8, 2016.
Cui et al., m6A RNA Methylation Regulates the Self-Renewal and Tumorigenesis of Glioblastoma Stem Cells. Cell Rep. Mar. 14, 2017;18(11):2622-2634. doi: 10.1016/j.celrep.2017.02.059.
Cui et al., Review of CRISPR/Cas9 sgRNA Design Tools. Interdiscip Sci. Jun. 2018;10(2):455- 465. doi: 10.1007/s12539-018-0298-z. Epub Apr. 11, 2018.
Cui et al., Targeted integration in rat and mouse embryos with zinc-finger nucleases. Nat Biotechnol. Jan. 2011;29(1):64-7. DOI: 10.1038/nbt.1731. Epub Dec. 12, 2010.
Cunningham et al., Ensembl 2015. Nucleic Acids Res. Jan. 2015;43(Database issue):D662-9. doi: 10.1093/nar/gku1010. Epub Oct. 28, 2014.
Cupples et al., A set of lacZ mutations in *Escherichia coli* that allow rapid detection of each of the six base substitutions. Proc Natl Acad Sci U S A. Jul. 1989;86(14):5345-9.
D'Adda di Fagagna et al., The Gam protein of bacteriophage Mu is an orthologue of eukaryotic Ku. EMBO Rep. Jan. 2003;4(1):47-52.
D'Ydewalle et al., The Antisense Transcript SMN-AS1 Regulates SMN Expression and Is a Novel Therapeutic Target for Spinal Muscular Atrophy. Neuron. Jan. 4, 2017;93(1):66-79 and Supplemental Information. doi: 10.1016/j.neuron.2016.11.033. Epub Dec. 22, 2016.
Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.
Dahlgren et al., A novel mutation in ribosomal protein S4 that affects the function of a mutated RF1. Biochimie. Aug. 2000;82(8):683-91.
Dahlman et al., Orthogonal gene knockout and activation with a catalytically active Cas9 nuclease. Nat Biotechnol. Nov. 2015;33(11):1159-61. doi: 10.1038/nbt.3390.
Dandage et al., beditor: A Computational Workflow for Designing Libraries of Guide RNAs for CRISPR-Mediated Base Editing. Genetics. Jun. 2019;212(2):377-385. doi: 10.1534/genetics.119.302089. Epub Apr. 1, 2019.
Dang et al., Optimizing sgRNA structure to improve CRISPR-Cas9 knockout efficiency. Genome Biol. Dec. 15, 2015;16:280. doi: 10.1186/s13059-015-0846-3.
Das et al., The crystal structure of the monomeric reverse transcriptase from Moloney murine leukemia virus. Structure. May 2004;12(5):819-29. doi: 10.1016/j.str.2004.02.032.
Dassa et al., Fractured genes: a novel genomic arrangement involving new split inteins and a new homing endonuclease family. Nucleic Acids Res. May 2009;37(8):2560-73. doi: 10.1093/nar/gkp095. Epub Mar. 5, 2009.
Dassa et al., Trans protein splicing of cyanobacterial split inteins in endogenous and exogenous combinations. Biochemistry. Jan. 9, 2007;46(1):322-30. doi: 10.1021/bi0611762.
Database EBI Accession No. ADE34233 Jan. 29, 2004.

(56) References Cited

OTHER PUBLICATIONS

Database EBI Accession No. BFF09785. May 31, 2018. 2 pages.
Database EBI Accession No. BGE38086. Jul. 25, 2019. 2 pages.
Database UniProt Accession No. G8I3E0. Jan. 14, 2012.
Datsenko et al., One-step inactivation of chromosomal genes in *Escherichia coli* K-12 using PCR products. Proc Natl Acad Sci U S A. Jun. 6, 2000;97(12):6640-5.
Davidson et al., Viral vectors for gene delivery to the nervous system. Nat Rev Neurosci. May 2003;4(5):353-64. doi: 10.1038/nrn1104.
Davis et al., Assaying Repair at DNA Nicks. Methods Enzymol. 2018;601:71-89. doi: 10.1016/bs.mie.2017.12.001. Epub Feb. 1, 2018.
Davis et al., DNA double strand break repair via non-homologous end-joining. Transl Cancer Res. Jun. 2013;2(3):130-143.
Davis et al., Homology-directed repair of DNA nicks via pathways distinct from canonical double-strand break repair. Proc Natl Acad Sci U S A. Mar. 11, 2014;111(10):E924-32. doi: 10.1073/pnas.1400236111. Epub Feb. 20, 2014.
Davis et al., Small molecule-triggered Cas9 protein with improved genome-editing specificity. Nat Chem Biol. May 2015;11(5):316-8. doi: 10.1038/nchembio.1793. Epub Apr. 6, 2015.
Davis et al., Two Distinct Pathways Support Gene Correction by Single-Stranded Donors at DNA Nicks. Cell Rep. Nov. 8, 2016;17(7):1872-1881. doi: 10.1016/j.celrep.2016.10.049.
De Felipe et al., Co-translational, intraribosomal cleavage of polypeptides by the foot-and-mouth disease virus 2A peptide. J Biol Chem. Mar. 28, 2003;278(13):11441-8. doi: 10.1074/jbc.M211644200. Epub Jan. 8, 2003.
De La Peña et al., The Hammerhead Ribozyme: A Long History for a Short RNA. Molecules. Jan. 4, 2017;22(1):78. doi: 10.3390/molecules22010078.
De Sandre-Giovannoli et al., Lamin a truncation in Hutchinson-Gilford progeria. Science. Jun. 27, 2003;300(5628):2055. doi: 10.1126/science.1084125. Epub Apr. 17, 2003.
De Souza, Primer: genome editing with engineered nucleases. Nat Methods. Jan. 2012;9(1):27.
De Wit et al., The Human CD4+ T Cell Response against Mumps Virus Targets a Broadly Recognized Nucleoprotein Epitope. J Virol. Mar. 5, 2019;93(6):e01883-18. doi: 10.1128/JVI.01883-18.
Dean et al., Genetic restriction of HIV-1 infection and progression to AIDS by a deletion allele of the CKR5 structural gene. Hemophilia Growth and Development Study, Multicenter AIDS Cohort Study, Multicenter Hemophilia Cohort Study, San Francisco City Cohort, ALIVE Study. Science. Sep. 27, 1996;273(5283):1856-62. doi: 10.1126/science.273.5283.1856.
Dekosky et al., Large-scale sequence and structural comparisons of human naive and antigen-experienced antibody repertoires. Proc Natl Acad Sci U S A. May 10, 2016;113(19):E2636-45. doi: 10.1073/pnas.1525510113. Epub Apr. 25, 2016.
Delebecque et al., Organization of intracellular reactions with rationally designed RNA assemblies. Science. Jul. 22, 2011;333(6041):470-4. doi: 10.1126/science.1206938. Epub Jun. 23, 2011.
Deltcheva et al., CRISPR RNA maturation by trans-encoded small RNA and host factor RNase III. Nature. Mar. 31, 2011;471(7340):602-7. doi: 10.1038/nature09886.
Deng et al., Widespread occurrence of N6-methyladenosine in bacterial mRNA. Nucleic Acids Res. Jul. 27, 2015;43(13):6557-67. doi: 10.1093/nar/gkv596. Epub Jun. 11, 2015.
Denizio et al., Harnessing natural DNA modifying activities for editing of the genome and epigenome. Curr Opin Chem Biol. Aug. 2018;45:10-17. doi: 10.1016/j.cbpa.2018.01.016. Epub Feb. 13, 2018.
Deriano et al., Modernizing the nonhomologous end-joining repertoire: alternative and classical NHEJ share the stage. Annu Rev Genet. 2013;47:433-55. doi: 10.1146/annurev-genet-110711-155540. Epub Sep. 11, 2013.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Dever et al., CRISPR/Cas9 β-globin gene targeting in human haematopoietic stem cells. Nature. Nov. 17, 2016;539(7629):384-389. doi: 10.1038/nature20134. Epub Nov. 7, 2016.
Deverman et al., Cre-dependent selection yields AAV variants for widespread gene transfer to the adult brain. Nat Biotechnol. Feb. 2016;34(2):204-9. doi: 10.1038/nbt.3440. Epub Feb. 1, 2016.
Devigili et al., Paroxysmal itch caused by gain-of-function Nav1.7 mutation. Pain. Sep. 2014;155(9):1702-1707. doi: 10.1016/j.pain.2014.05.006. Epub May 10, 2014.
Dianov et al., Mammalian base excision repair: the forgotten archangel. Nucleic Acids Res. Apr. 1, 2013;41(6):3483-90. doi: 10.1093/nar/gkt076. Epub Feb. 13, 2013.
Dicarlo et al., Genome engineering in *Saccharomyces cerevisiae* using CRISPR-Cas systems. Nucleic Acids Research Apr. 2013;41(7):4336-43.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Dicarlo et al., Safeguarding CRISPR-Cas9 gene drives in yeast. Nat Biotechnol. Dec. 2015;33(12):1250-1255. doi: 10.1038/nbt.3412. Epub Nov. 16, 2015.
Dickey et al., Single-stranded DNA-binding proteins: multiple domains for multiple functions. Structure. Jul. 2, 2013;21(7):1074-84. doi: 10.1016/j.str.2013.05.013.
Dickinson et al., A system for the continuous directed evolution of proteases rapidly reveals drug-resistance mutations. Nat Commun. Oct. 30, 2014;5:5352. doi: 10.1038/ncomms6352.
Dickinson et al., Experimental interrogation of the path dependence and stochasticity of protein evolution using phage-assisted continuous evolution. Proc Natl Acad Sci USA. May 2013;110(22):9007-12.
Dillon, Regulating gene expression in gene therapy. Trends Biotechnol. May 1993;11(5):167-73. doi: 10.1016/0167-7799(93)90109-M.
Ding et al., A TALEN genome-editing system for generating human stem cell-based disease models. Cell Stem Cell. Feb. 7, 2013;12(2):238-51. Doi: 10.1016/j.stem.2012.11.011. Epub Dec. 13, 2012.
Ding et al., Permanent alteration of PCSK9 with in vivo CRISPR-Cas9 genome editing. Circ Res. Aug. 15, 2014;115(5):488-92. doi: 10.1161/CIRCRESAHA.115.304351. Epub Jun. 10, 2014.
Dingwall et al., Nuclear targeting sequences—a consensus? Trends Biochem Sci. Dec. 1991;16(12):478-81. doi: 10.1016/0968-0004(91)90184-w.
Diver et al., Single-Step Synthesis of Cell-Permeable Protein Dimerizers That Activate Signal Transduction and Gene Expression. J. Am. Chem. Soc. Jun. 4, 1997;119(22):5106-5109. https://doi.org/10.1021/ja963891c.
Dixon et al., Reengineering orthogonally selective riboswitches. Proc Natl Acad Sci U S A. Feb. 16, 2010;107(7):2830-5. doi: 10.1073/pnas.0911209107. Epub Jan. 26, 2010.
Doench et al., Optimized sgRNA design to maximize activity and minimize off-target effects of CRISPR-Cas9. Nat Biotechnol. Feb. 2016;34(2):184-191. doi: 10.1038/nbt.3437.
Doench et al., Rational design of highly active sgRNAs for CRISPR-Cas9-mediated gene inactivation. Nat Biotechnol. Dec. 2014;32(12):1262-7. doi: 10.1038/nbt.3026. Epub Sep. 3, 2014.
Dolan et al., Trans-splicing with the group I intron ribozyme from Azoarcus. RNA. Feb. 2014;20(2):202-13. doi: 10.1261/rna.041012.113. Epub Dec. 16, 2013.
Doman et al., Evaluation and minimization of Cas9-independent off-target DNA editing by cytosine base editors. Nat Biotechnol. May 2020;38(5):620-628. doi: 10.1038/s41587-020-0414- 6. Epub Feb. 10, 2020.
Dominissini et al., Topology of the human and mouse m6A RNA methylomes revealed by m6A-seq. Nature. Apr. 29, 2012;485(7397):201-6. doi: 10.1038/nature11112.
Dorgan et al., An enzyme-coupled continuous spectrophotometric assay for S-adenosylmethionine-dependent methyltransferases. Anal Biochem. Mar. 15, 2006;350(2):249-55. doi: 10.1016/j.ab.2006.01.004. Epub Feb. 7, 2006.

(56) References Cited

OTHER PUBLICATIONS

Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.

Dorr et al., Reprogramming the specificity of sortase enzymes. Proc Natl Acad Sci U S A. Sep. 16, 2014;111(37):13343-8. doi: 10.1073/pnas.1411179111. Epub Sep. 3, 2014.

Doudna et al., Genome editing. The new frontier of genome engineering with CRISPR-Cas9. Science. Nov. 28, 2014;346(6213):1258096. doi: 10.1126/science.1258096.

Doudna, The promise and challenge of therapeutic genome editing. Nature. Feb. 2020;578(7794):229-236. doi: 10.1038/s41586-020-1978-5. Epub Feb. 12, 2020.

Dove et al., Conversion of the omega subunit of Escherichia coli RNA polymerase into a transcriptional activator or an activation target. Genes Dev. Mar. 1, 1998;12(5):745-54.

Doyon et al., Directed evolution and substrate specificity profile of homing endonuclease I-SceI. J Am Chem Soc. Feb. 22, 2006;128(7):2477-84.

Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.

Drake, A constant rate of spontaneous mutation in DNA-based microbes. Proc Natl Acad Sci USA. Aug. 15, 1991;88(16):7160-4.

Drenth et al., Mutations in sodium-channel gene SCN9A cause a spectrum of human genetic pain disorders. J Clin Invest. Dec. 2007;117(12):3603-9. doi: 10.1172/JCI33297.

Drost et al., Inactivation of DNA mismatch repair by variants of uncertain significance in the PMS2 gene. Hum Mutat. Nov. 2013;34(11):1477-80. doi: 10.1002/humu.22426. Epub Sep. 11, 2013.

Duan et al., Enhancement of muscle gene delivery with pseudotyped adeno-associated virus type 5 correlates with myoblast differentiation. J Virol. Aug. 2001;75(16):7662-71. doi: 10.1128/JVI.75.16.7662-7671.2001.

Dubois et al., Retroviral RNA Dimerization: From Structure to Functions. Front Microbiol. Mar. 22, 2018;9:527. doi: 10.3389/fmicb.2018.00527.

Dugar et al., CRISPR RNA-Dependent Binding and Cleavage of Endogenous RNAs by the Campylobacter jejuni Cas9. Mol Cell. Mar. 1, 2018;69(5):893-905.e7. doi: 10.1016/j.molcel.2018.01.032.

Dumas et al., Designing logical codon reassignment—Expanding the chemistry in biology. Chem Sci. Jan. 1, 2015;6(1):50-69. doi: 10.1039/c4sc01534g. Epub Jul. 14, 2014. Review.

Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.

Dunbar et al., Gene therapy comes of age. Science. Jan. 12, 2018;359(6372):eaan4672. doi: 10.1126/science.aan4672.

Dupuy et al., Le syndrome de De La Chapelle [De La Chapelle syndrome]. Presse Med. Mar. 3, 2001;30(8):369-72. French.

Durai et al., A bacterial one-hybrid selection system for interrogating zinc finger-DNA interactions. Comb Chem High Throughput Screen. May 2006;9(4):301-11.

Durai et al., Zinc finger nucleases: custom-designed molecular scissors for genome engineering of plant and mammalian cells. Nucleic Acids Res. Oct. 26, 2005;33(18):5978-90. doi: 10.1093/nar/gki912.

During et al., Controlled release of dopamine from a polymeric brain implant: in vivo characterization. Ann Neurol. Apr. 1989;25(4):351-6.

East-Seletsky et al., Two distinct RNase activities of CRISPR-C2c2 enable guide-RNA processing and RNA detection. Nature Oct. 2016;538(7624):270-3.

Edlund et al., Cell-specific expression of the rat insulin gene: evidence for role of two distinct 5' flanking elements. Science. Nov. 22, 1985;230(4728):912-6. doi: 10.1126/science.3904002.

Edwards et al., An Escherichia coli tyrosine transfer RNA is a leucine-specific transfer RNA in the yeast Saccharomyces cerevisiae. Proc Natl Acad Sci U S A. Feb. 15, 1991;88(4):1153-6.

Edwards et al., Crystal structures of the thi-box riboswitch bound to thiamine pyrophosphate analogs reveal adaptive RNA-small molecule recognition. Structure. Sep. 2006;14(9):1459-68.

Eick et al., Robustness of Reconstructed Ancestral Protein Functions to Statistical Uncertainty. Mol Biol Evol. Feb. 1, 2017;34(2):247-261. doi: 10.1093/molbev/msw223.

Eiler et al., Structural Basis for the Fast Self-Cleavage Reaction Catalyzed by the Twister Ribozyme. Proc Natl Acad Sci U S A. Sep. 9, 2014;111(36):13028-33. doi: 10.1073/pnas.1414571111. Epub Aug. 25, 2014.

Eisenberg et al., A-to-I RNA editing—immune protector and transcriptome diversifier. Nat Rev Genet. Aug. 2018;19(8):473-490. doi: 10.1038/s41576-018-0006-1.

Ekstrand et al., Frequent alterations of the PI3K/AKT/mTOR pathways in hereditary nonpolyposis colorectal cancer. Fam Cancer. Jun. 2010;9(2):125-9. doi: 10.1007/s10689-009-9293-1.

Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.

Emery et al., HCN2 ion channels play a central role in inflammatory and neuropathic pain. Science. Sep. 9, 2011;333(6048):1462-6. doi: 10.1126/science.1206243.

Endo et al., Toward establishing an efficient and versatile gene targeting system in higher plants. Biocatalysis and Agricultural Biotechnology 2014;3,(1):2-6.

Engel et al., The emerging role of mRNA methylation in normal and pathological behavior. Genes Brain Behav. Mar. 2018;17(3):e12428. doi: 10.1111/gbb.12428. Epub Nov. 17, 2017.

Engelward et al., Base excision repair deficient mice lacking the Aag alkyladenine DNA glycosylase. Proc Natl Acad Sci U S A. Nov. 25, 1997;94(24):13087-92.

England, Unnatural amino acid mutagenesis: a precise tool for probing protein structure and function. Biochemistry. Sep. 21, 2004;43(37):11623-9.

Entin-Meer et al., The role of phenylalanine-119 of the reverse transcriptase of mouse mammary tumour virus in DNA synthesis, ribose selection and drug resistance. Biochem J. Oct. 15, 2002;367(Pt 2):381-91. doi: 10.1042/BJ20020712.

Enyeart et al., Biotechnological applications of mobile group II introns and their reverse transcriptases: gene targeting, RNA-seq, and non-coding RNA analysis. Mobile DNA 5, 2 (2014). https://doi.org/10.1186/1759-8753-5-2. https://doi.org/10.1186/1759-8753-5-2.

Epstein, HSV-1-based amplicon vectors: design and applications. Gene Ther. Oct. 2005;12 Suppl 1:S154-8. doi: 10.1038/sj.gt.3302617.

Eriksson et al., Recurrent de novo point mutations in lamin A cause Hutchinson-Gilford progeria syndrome. Nature. May 15, 2003;423(6937):293-8. doi: 10.1038/nature01629. Epub Apr. 25, 2003. PMID: 12714972.

Estacion et al., A sodium channel gene SCN9A polymorphism that increases nociceptor excitability. Ann Neurol. Dec. 2009;66(6):862-6. doi: 10.1002/ana.21895.

Esvelt et al., A system for the continuous directed evolution of biomolecules. Nature. Apr. 28, 2011;472(7344):499-503. doi: 10.1038/nature09929. Epub Apr. 10, 2011.

Esvelt et al., Genome-scale engineering for systems and synthetic biology. Mol Syst Biol. 2013;9:641. doi: 10.1038/msb.2012.66.

Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.

Evans et al., Protein trans-splicing and cyclization by a naturally split intein from the dnaE gene of Synechocystis species PCC6803. J Biol Chem. Mar. 31, 2000;275(13):9091-4. doi: 10.1074/jbc.275.13.9091.

Evans et al., Semisynthesis of cytotoxic proteins using a modified protein splicing element. Protein Sci. Nov. 1998;7(11):2256-64. doi: 10.1002/pro.5560071103.

(56) References Cited

OTHER PUBLICATIONS

Evans et al., The cyclization and polymerization of bacterially expressed proteins using modified self-splicing inteins. J Biol Chem. Jun. 25, 1999;274(26):18359-63. doi: 10.1074/jbc.274.26.18359.
Evans et al., The in vitro ligation of bacterially expressed proteins using an intein from Methanobacterium thermoautotrophicum. J Biol Chem. Feb. 12, 1999;274(7):3923-6. doi: 10.1074/jbc.274.7.3923.
Evers et al., CRISPR knockout screening outperforms shRNA and CRISPRi in identifying essential genes. Nat Biotechnol. Jun. 2016;34(6):631-3. doi: 10.1038/nbt.3536. Epub Apr. 25, 2016.
Fagerlund et al., The Cpf1 CRISPR-Cas protein expands genome-editing tools. Genome Biology Nov. 17, 2015;16:251. https://doi.org/10.1186/s13059-015-0824-9.
Falnes et al., DNA repair by bacterial AlkB proteins. Res Microbiol. Oct. 2003;154(8):531-8. doi: 10.1016/S0923-2508(03)00150-5.
Falnes et al., Repair of methyl lesions in DNA and RNA by oxidative demethylation. Neuroscience. Apr. 14, 2007;145(4):1222-32. doi: 10.1016/j.neuroscience.2006.11.018. Epub Dec. 18, 2006.
Fang et al., Synthetic Studies Towards Halichondrins: Synthesis of the Left Halves of Norhalichondrins and Homohalichondrins. Tetrahedron Letters 1992;33(12):1557-1560.
Fang et al., The Menu of Features that Define Primary MicroRNAs and Enable De Novo Design of MicroRNA Genes. Mol Cell. Oct. 1, 2015;60(1):131-45. doi: 10.1016/j.molcel.2015.08.015. Epub Sep. 24, 2015.
Farboud et al., Dramatic enhancement of genome editing by CRISPR/Cas9 through improved guide RNA design. Genetics. Apr. 2015;199(4):959-71. doi: 10.1534/genetics.115.175166. Epub Feb. 18, 2015.
Farhood et al., Codelivery to mammalian cells of a transcriptional factor with cis-acting element using cationic liposomes. Anal Biochem. Feb. 10, 1995;225(1):89-93.
Fawcett et al., Transposable elements controlling I-R hybrid dysgenesis in *D. melanogaster* are similar to mammalian LINEs. Cell. Dec. 26, 1986;47(6):1007-15. doi: 10.1016/0092-8674(86)90815-9.
Feldstein et al., Two sequences participating in the autolytic processing of satellite tobacco ringspot virus complementary RNA. Gene. Oct. 15, 1989;82(1):53-61. doi: 10.1016/0378-1119(89)90029-2.
Felletti et al., Twister Ribozymes as Highly Versatile Expression Platforms for Artificial Riboswitches. Nat Commun. Sep. 27, 2016;7:12834. doi: 10.1038/ncomms12834.
Feng et al., Crystal structures of the human RNA demethylase Alkbh5 reveal basis for substrate recognition. J Biol Chem. Apr. 25, 2014;289(17):11571-11583. doi: 10.1074/jbc.M113.546168. Epub Mar. 10, 2014.
Feng et al., Human L1 retrotransposon encodes a conserved endonuclease required for retrotransposition. Cell. Nov. 29, 1996;87(5):905-16. doi: 10.1016/s0092-8674(00)81997-2.
Ferreira Da Silva et al., Prime editing efficiency and fidelity are enhanced in the absence of mismatch repair. Nat Commun. Feb. 9, 2022;13(1):760. doi: 10.1038/s41467-022-28442-1.
Ferretti et al., Complete genome sequence of an M1 strain of *Streptococcus pyogenes*. Proc Natl Acad Sci U S A. Apr. 10, 2001;98(8):4658-63.
Ferry et al., Rational design of inducible CRISPR guide RNAs for de novo assembly of transcriptional programs. Nat Commun. Mar. 3, 2017;8:14633. doi: 10.1038/ncomms14633.
Feuk, Inversion variants in the human genome: role in disease and genome architecture. Genome Med. Feb. 12, 2010;2(2):11. doi: 10.1186/gm132.
Filippov et al., A novel type of RNase III family proteins in eukaryotes. Gene. Mar. 7, 2000;245(1):213-21. doi: 10.1016/s0378-1119(99)00571-5.
Filippova et al., Guide RNA modification as a way to improve CRISPR/Cas9-based genome-editing systems. Biochimie. Dec. 2019;167:49-60. doi: 10.1016/j.biochi.2019.09.003. Epub Sep. 4, 2019.

Fine et al., Trans-spliced Cas9 allows cleavage of HBB and CCR5 genes in human cells using compact expression cassettes. Scientific Reports 2015;5(1):Article No. 10777. doi:10.1038/srep10777. With Supplementary Information.
Fire et al., Potent and specific genetic interference by double-stranded RNA in Caenorhabditis elegans. Nature. Feb. 19, 1998;391(6669):806-11. doi: 10.1038/35888.
Fischbach et al., Directed evolution can rapidly improve the activity of chimeric assembly-line enzymes. Proc Natl Acad Sci U S A. Jul. 17, 2007;104(29):11951-6. doi: 10.1073/pnas.0705348104. Epub Jul. 9, 2007.
Fischer et al., Cryptic epitopes induce high-titer humoral immune response in patients with cancer. J Immunol. Sep. 1, 2010;185(5):3095-102. doi: 10.4049/jimmunol.0902166. Epub Jul. 26, 2010.
Fitzjohn, Diversitree: comparative phylogenetic analyses of diversification in R. Methods in Evology and Evolution. Dec. 2012;3(6):1084-92 .doi: 10.1111/j.2041-210X.2012.00234.x.
Flajolet et al., Woodchuck hepatitis virus enhancer I and enhancer II are both involved in N-myc2 activation in woodchuck liver tumors. J Virol. Jul. 1998;72(7):6175-80. doi: 10.1128/JVI.72.7.6175-6180.1998.
Flaman et al., A rapid PCR fidelity assay. Nucleic Acids Res. Aug. 11, 1994;22(15):3259-60. doi: 10.1093/nar/22.15.3259.
Flynn et al., CRISPR-mediated genotypic and phenotypic correction of a chronic granulomatous disease mutation in human iPS cells. Exp Hematol. Oct. 2015;43(10):838-848.e3. doi: 10.1016/j.exphem.2015.06.002. Epub Jun. 19, 2015. Including supplementary figures and data.
Fogg et al., Genome Integration and Excision by a New Streptomyces Bacteriophage, φJoe. Appl Environ Microbiol. Feb. 15, 2017;83(5):e02767-16. doi: 10.1128/AEM.02767-16.
Fogg et al., New applications for phage integrases. J Mol Biol. Jul. 29, 2014;426(15):2703-16. doi: 10.1016/j.jmb.2014.05.014. Epub May 22, 2014.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013. Including Supplementary Information.
Forster et al., Self-cleavage of virusoid RNA is performed by the proposed 55-nucleotide active site. Cell. Jul. 3, 1987;50(1):9-16. doi: 10.1016/0092-8674(87)90657-x.
Fortini et al., Different DNA polymerases are involved in the short- and long-patch base excision repair in mammalian cells. Biochemistry. Mar. 17, 1998;37(11):3575-80. doi: 10.1021/bi972999h.
Fouts et al., Sequencing Bacillus anthracis typing phages gamma and cherry reveals a common ancestry. J Bacteriol. May 2006;188(9):3402-8. doi: 10.1128/JB.188.9.3402-3408.2006.
Freitas et al., Mechanisms and signals for the nuclear import of proteins. Curr Genomics. Dec. 2009;10(8):550-7. doi: 10.2174/138920209789503941.
Freshney, Culture of Animal Cells. A Manual of Basic Technique. Alan R. Liss, Inc. New York. 1983;4.
Friedman, J. H., Greedy function approximation: A gradient boosting machine. Ann. Statist. Oct. 2001;29(5):1189-232. doi: 10.1214/aos/1013203451.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., Promises and Pitfalls of Intracellular Delivery of Proteins. Bioconjugate Chemistry. Aug. 2014;25:1602-8.
Fuchs et al., Polyarginine as a multifunctional fusion tag. Protein Sci. Jun. 2005;14(6):1538-44.
Fujisawa et al., Disease-associated mutations in CIAS1 induce cathepsin B-dependent rapid cell death of human THP-1 monocytic cells. Blood. Apr. 1, 2007;109(7):2903-11.
Fukui et al., DNA Mismatch Repair in Eukaryotes and Bacteria. J Nucleic Acids. Jul. 27, 2010;2010. pii: 260512. doi: 10.4061/2010/260512.

(56) References Cited

OTHER PUBLICATIONS

Fung et al., Repair at single targeted DNA double-strand breaks in pluripotent and differentiated human cells. PLoS One. 2011;6(5):e20514. doi: 10.1371/journal.pone.0020514. Epub May 25, 2011.
Furukawa et al., In vitro selection of allosteric ribozymes that sense the bacterial second messenger c-di-GMP. Methods Mol Biol. 2014;1111:209-20. doi: 10.1007/978-1-62703-755-6_15.
Fusi et al., In Silico Predictive Modeling of CRISPR/Cas9 guide efficiency. Jun. 26, 2015; bioRxiv. http://dx.doi.org/10.1101/021568.
Gaj et al., 3rd. Genome engineering with custom recombinases. Methods Enzymol. 2014;546:79-91. doi: 10.1016/B978-0-12-801185-0.00004-0.
Gaj et al., A comprehensive approach to zinc-finger recombinase customization enables genomic targeting in human cells. Nucleic Acids Res. Feb. 6, 2013;41(6):3937-46.
Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Gaj et al., Structure-guided reprogramming of serine recombinase DNA sequence specificity. Proc Natl Acad Sci U S A. Jan. 11, 2011;108(2):498-503. doi: 10.1073/pnas.1014214108. Epub Dec. 27, 2010.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gajula, Designing an Elusive C•G→G•C CRISPR Base Editor. Trends Biochem Sci. Feb. 2019;44(2):91-94. doi: 10.1016/j.tibs.2018.10.004. Epub Nov. 13, 2018.
Gallo et al., A novel pathogenic PSEN1 mutation in a family with Alzheimer's disease: phenotypical and neuropathological features. J Alzheimers Dis. 2011;25(3):425-31. doi: 10.3233/JAD-2011-110185.
Gangopadhyay et al., Precision Control of CRISPR-Cas9 Using Small Molecules and Light. Biochemistry. Jan. 29, 2019;58(4):234-244. doi: 10.1021/acs.biochem.8b01202. Epub Jan. 22, 2019.
Gao et al., Cationic liposome-mediated gene transfer. Gene Ther. Dec. 1995;2(10):710-22.
Gao et al., DNA-guided genome editing using the Natronobacterium gregoryi Argonaute. Nat Biotechnol. Jul. 2016;34(7):768-73. doi: 10.1038/nbt.3547. Epub May 2, 2016.
Gao et al., Self-processing of ribozyme-flanked RNAs into guide RNAs in vitro and in vivo for CRISPR-mediated genome editing. J Integr Plant Biol. Apr. 2014;56(4):343-9. doi: 10.1111/jipb.12152. Epub Mar. 6, 2014.
Gao et al., Treatment of autosomal dominant hearing loss by in vivo delivery of genome editing agents. Nature. Jan. 11, 2018;553(7687):217-221. doi: 10.1038/nature25164. Epub Dec. 20, 2017.
Gapinske et al., CRISPR-SKIP: programmable gene splicing with single base editors. Genome Biol. Aug. 15, 2018;19(1):107. doi: 10.1186/s13059-018-1482-5.
Garcia et al., Transglycosylation: a mechanism for RNA modification (and editing?). Bioorg Chem. Jun. 2005;33(3):229-51. doi: 10.1016/j.bioorg.2005.01.001. Epub Feb. 23, 2005.
Gardlik et al., Vectors and delivery systems in gene therapy. Med Sci Monit. Apr. 2005;11(4):RA110-21. Epub Mar. 24, 2005.
Garibyan et al., Use of the rpoB gene to determine the specificity of base substitution mutations on the *Escherichia coli* chromosome. DNA Repair (Amst). May 13, 2003;2(5):593-608.
Garneau et al., The CRISPR/Cas bacterial immune system cleaves bacteriophage and plasmid DNA. Nature. Nov. 4, 2010;468(7320):67-71. doi: 10.1038/nature09523.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Gaudelli et al., Directed evolution of adenine base editors with increased activity and therapeutic application. Nat Biotechnol. Jul. 2020;38(7):892-900. doi: 10.1038/s41587-020-0491-6. Epub Apr. 13, 2020.
Gaudelli et al., Programmable base editing of A•T to G•C in genomic DNA without DNA cleavage. Nature. Nov. 23, 2017;551(7681):464-471. doi: 10.1038/nature24644. Epub Oct. 25, 2017. Erratum in: Nature. May 2, 2018.
Gearing, Addgene blog. CRISPR 101: Cas9 nickase design and homology directed repair. 2018. pp. 1-12. https://blog.addgene.org/crispr-101-cas9-nickase-design-and-homlogy-directed-repair. Last retrieved online Jun. 25, 2021.
Gehrke et al., An APOBEC3A-Cas9 base editor with minimized bystander and off-target activities. Nat Biotechnol. Nov. 2018;36(10):977-982. doi: 10.1038/nbt.4199. Epub Jul. 30, 2018.
Geisberg et al., Global analysis of mRNA isoform half-lives reveals stabilizing and destabilizing elements in yeast. Cell. Feb. 13, 2014;156(4):812-24. doi: 10.1016/j.cell.2013.12.026.
GenBank Accession No. J01600.1. Brooks et al., *E.coli* dam gene coding for DNA adenine methylase. Apr. 26, 1993.
GenBank Accession No. U07651.1. Lu, *Escherichia coli* K12 negative regulator of replication initiation (seqA) gene, complete cds. Jul. 19, 1994.
GenBank Submission; NIH/NCBI Accession No. 4UN5_B. Anders et al., Jul. 23, 2014. 5 pages.
GenBank Submission; NIH/NCBI, Accession No. AAA66622.1. Martinelli et al., May 18, 1995. 2 pages.
GenBank Submission; NIH/NCBI, Accession No. AGT42196. Farzadfar et al., Nov. 2, 2013. 2 pages.
GenBank Submission; NIH/NCBI, Accession No. AIT42264.1. Hyun et al., Oct. 15, 2014. 2 pages.
GenBank Submission; NIH/NCBI, Accession No. AKA60242.1. Tong et al., Apr. 5, 2015. 1 page.
GenBank Submission; NIH/NCBI, Accession No. AKQ21048.1. Gilles et al., Jul. 19, 2015. 1 page.
GenBank Submission; NIH/NCBI, Accession No. AKS40380.1. Nodvig et al., Aug. 2, 2015. 1 page.
GenBank Submission; NIH/NCBI, Accession No. APG80656.1. Burstein et al., Dec. 10, 2016. 1 pages.
GenBank Submission; NIH/NCBI, Accession No. AYD60528.1. Ram et al., Oct. 2, 2018. 1 page.
GenBank Submission; NIH/NCBI, Accession No. BDB43378. Zhang et al., Aug. 11, 2016. 2 pages.
GenBank Submission; NIH/NCBI, Accession No. J04623. Kita et al., Apr. 26, 1993. 2 pages.
GenBank Submission; NIH/NCBI, Accession No. KR710351.1. Sahni et al., Jun. 1, 2015. 2 pages.
GenBank Submission; NIH/NCBI, Accession No. NC_000001.11. Gregory et al., Jun. 6, 2016. 3 pages.
GenBank Submission; NIH/NCBI, Accession No. NC_002737.1. Ferretti et al., Jun. 27, 2013. 1 page.
GenBank Submission; NIH/NCBI, Accession No. NC_015683.1. Trost et al., Jul. 6, 2013. 1 page.
GenBank Submission; NIH/NCBI, Accession No. NC_016782.1. Trost et al., Jun. 11, 2013. 1 page.
GenBank Submission; NIH/NCBI, Accession No. NC_016786.1. Trost et al., Aug. 28, 2013. 1 page.
GenBank Submission; NIH/NCBI, Accession No. NC_017053.1. Fittipaldi et al., Jul. 6, 2013. 1 page.
GenBank Submission; NIH/NCBI, Accession No. NC_017317.1. Trost et al., Jun. 11, 2013. 1 page.
GenBank Submission; NIH/NCBI, Accession No. NC_017861.1. Heidelberg et al., Jun. 11, 2013. 1 page.
GenBank Submission; NIH/NCBI, Accession No. NC_018010.1. Lucas et al., Jun. 11, 2013. 2 pages.
GenBank Submission; NIH/NCBI, Accession No. NC_018721.1. Feng et al., Jun. 11, 2013. 1 pages.
GenBank Submission; NIH/NCBI, Accession No. NC_021284.1. Ku et al., Jul. 12, 2013. 1 page.

(56) References Cited

OTHER PUBLICATIONS

GenBank Submission; NIH/NCBI, Accession No. NC_021314.1. Zhang et al., Jul. 15, 2013. 1 page.
GenBank Submission; NIH/NCBI, Accession No. NC_021846.1. Lo et al., Jul. 22, 2013. 1 page.
GenBank Submission; NIH/NCBI, Accession No. NG_008692.2. McClintock et al., Aug. 27, 2018. 33 pages.
GenBank Submission; NIH/NCBI, Accession No. NM_002945.3. Weiser et al., Sep. 3, 2017. 5 pages.
GenBank Submission; NIH/NCBI, Accession No. NM_002947.4. Xiao et al., May 1, 2019. 4 pages.
GenBank Submission; NIH/NCBI, Accession No. NM_174936. Guo et al., Oct. 28, 2015. 6 pages.
GenBank Submission; NIH/NCBI, Accession No. NM_206933.2. Khalaileh et al., Sep. 16, 2018. 12 pages.
GenBank Submission; NIH/NCBI, Accession No. NP_001075493.1. Schiaffella et al., Jun. 24, 2018. 2 pages.
GenBank Submission; NIH/NCBI, Accession No. NP_001157741.1. Zeng et al., Sep. 17, 2018. 3 pages.
GenBank Submission; NIH/NCBI, Accession No. NP_001157742.1. Zeng et al., Oct. 21, 2018. 3 pages.
GenBank Submission; NIH/NCBI, Accession No. NP_033040.2. Liu et al., Jun. 23, 2018. 2 pages.
GenBank Submission; NIH/NCBI, Accession No. NP_358988.1. Hoskins et al., Jan. 11, 2017. 2 pages.
GenBank Submission; NIH/NCBI, Accession No. NP_472073.1. Glaser et al., Jun. 27, 2013. 2 pages.
GenBank Submission; NIH/NCBI, Accession No. NP_628093.1. Hsiao et al., Aug. 3, 2016. 2 pages.
GenBank Submission; NIH/NCBI, Accession No. NP_955579.1. Chen et al., Aug. 13, 2018. 5 pages.
GenBank Submission; NIH/NCBI, Accession No. NP_996816.2. Fu et al., Sep. 22, 2019. 9 pages.
GenBank Submission; NIH/NCBI, Accession No. P42212. Prasher et al., Mar. 19, 2014. 7 pages.
GenBank Submission; NIH/NCBI, Accession No. RFF81513.1. Zhou et al., Aug. 21, 2018. 2 pages.
GenBank Submission; NIH/NCBI, Accession No. SNX31424.1. Weckx, S., Feb. 16, 2018. 2 pages.
GenBank Submission; NIH/NCBI, Accession No. TGH57013. Xu et al., Apr. 9, 2019. 2 pages.
GenBank Submission; NIH/NCBI, Accession No. WP_002989955.1. No Author Listed, May 6, 2013. 1 page.
GenBank Submission; NIH/NCBI, Accession No. WP_010922251.1. No Author Listed, May 15, 2013. 1 page.
GenBank Submission; NIH/NCBI, Accession No. WP_011054416.1. No Author Listed, May 15, 2013. 1 page.
GenBank Submission; NIH/NCBI, Accession No. WP_011284745.1. No Author Listed, May 16, 2013. 1 page.
GenBank Submission; NIH/NCBI, Accession No. WP_011285506.1. No Author Listed, May 16, 2013. 1 page.
GenBank Submission; NIH/NCBI, Accession No. WP_011527619.1. No Author Listed, May 16, 2013. 1 page.
GenBank Submission; NIH/NCBI, Accession No. WP_012560673.1. No Author Listed, May 17, 2013. 1 page.
GenBank Submission; NIH/NCBI, Accession No. WP_014407541.1. No Author Listed, May 18, 2013. 1 page.
GenBank Submission; NIH/NCBI, Accession No. WP_020905136.1. No Author Listed, Jul. 25, 2013. 1 page.
GenBank Submission; NIH/NCBI, Accession No. WP_023080005.1. No Author Listed, Oct. 27, 2013. 1 page.
GenBank Submission; NIH/NCBI, Accession No. WP_023610282.1. No Author Listed, Nov. 27, 2013. 1 page.
GenBank Submission; NIH/NCBI, Accession No. WP_030125963.1. No Author Listed, Jul. 9, 2014. 1 page.
GenBank Submission; NIH/NCBI, Accession No. WP_030126706.1. No Author Listed, Jul. 9, 2014. 1 page.
GenBank Submission; NIH/NCBI, Accession No. WP_031386437.1. No Author Listed., Sep. 23, 2019. 1 page.
GenBank Submission; NIH/NCBI, Accession No. WP_031488318.1. No Author Listed., Aug. 5, 2014. 1 page.
GenBank Submission; NIH/NCBI, Accession No. WP_031589969.1. Haft et al., Oct. 9, 2019. 2 pages.
GenBank Submission; NIH/NCBI, Accession No. WP_032460140.1. No Author Listed, Oct. 4, 2014. 1 page.
GenBank Submission; NIH/NCBI, Accession No. WP_032461047.1. No Author Listed, Oct. 4, 2014. 1 page.
GenBank Submission; NIH/NCBI, Accession No. WP_032462016.1. Haft et al., Oct. 4, 2014. 1 page.
GenBank Submission; NIH/NCBI, Accession No. WP_032462936.1. No Author Listed, Oct. 4, 2014. 1 page.
GenBank Submission; NIH/NCBI, Accession No. WP_032464890.1. No Author Listed, Oct. 4, 2014. 1 page.
GenBank Submission; NIH/NCBI, Accession No. WP_038431314.1. No Author Listed, Dec. 26, 2014. 1 page.
GenBank Submission; NIH/NCBI, Accession No. WP_038432938.1. No Author Listed, Dec. 26, 2014. 1 page.
GenBank Submission; NIH/NCBI, Accession No. WP_038434062.1. No Author Listed, Dec. 26, 2014. 1 page.
GenBank Submission; NIH/NCBI, Accession No. WP_044924278.1. Haft et al., Oct. 9, 2019. 2 pages.
GenBank Submission; NIH/NCBI, Accession No. WP_047338501.1. Haft et al., Oct. 9, 2019. 2 pages.
GenBank Submission; NIH/NCBI, Accession No. WP_048327215.1. No Author Listed, Jun. 26, 2015. 1 page.
GenBank Submission; NIH/NCBI, Accession No. WP_049519324.1. No Author Listed, Jul. 20, 2015. 1 page.
GenBank Submission; NIH/NCBI, Accession No. WP_060798984.1. Haft et al., Oct. 9, 2019. 2 pages.
GenBank Submission; NIH/NCBI, Accession No. WP_062913273.1. Haft et al., Oct. 9, 2019, 2 pages.
GenBank Submission; NIH/NCBI, Accession No. WP_072754838. No Author Listed., Sep. 23, 2019. 1 page.
GenBank Submission; NIH/NCBI, Accession No. WP_095142515.1. No Author Listed., Sep. 23, 2019. 1 page.
GenBank Submission; NIH/NCBI, Accession No. WP_118538418.1. No Author Listed., Oct. 13, 2019. 1 page.
GenBank Submission; NIH/NCBI, Accession No. WP_119223642.1. No Author Listed., Oct. 13, 2019. 1 page.
GenBank Submission; NIH/NCBI, Accession No. WP_119227726.1. No Author Listed., Oct. 13, 2019. 1 page.
GenBank Submission; NIH/NCBI, Accession No. WP_119623382.1. No Author Listed., Oct. 13, 2019. 1 page.
GenBank Submission; NIH/NCBI, Accession No. WP_132221894.1. No Author Listed., Sep. 23, 2019. 1 page.
GenBank Submission; NIH/NCBI, Accession No. WP_133478044.1. Haft et al., Oct. 9, 2019. 2 pages.
GenBank Submission; NIH/NCBI, Accession No. XP_003314669.1. No Author Listed, Mar. 20, 2018. 2 pages.
GenBank Submission; NIH/NCBI, Accession No. XP_026671085.1. No Author Listed, Oct. 17, 2018. 1 page.
GenBank Submission; NIH/NCBI, Accession No. YP_002342100.1. Bernardini et al., Jun. 10, 2013. 2 pages.
GenBank Submission; NIH/NCBI, Accession No. YP_002344900.1. Gundogdu et al., Mar. 19, 2014. 2 pages.
GenBank Submission; NIH/NCBI, Accession No. YP_009137104.1. Davison, Aug. 13, 2018. 2 pages.
GenBank Submission; NIH/NCBI, Accession No. YP_009283008.1. Bernardini et al., Sep. 23, 2016. 2 pages.
GenBank Submission; NIH/NCBI, Accession No. YP_820832.1. Makarova et al., Aug. 27, 2013. 2 pages.
George et al., Adenosine deaminases acting on RNA, RNA editing, and interferon action. J Interferon Cytokine Res. Jan. 2011;31(1):99-117. doi: 10.1089/jir.2010.0097. Epub Dec. 23, 2010. PMID: 21182352; PMCID: PMC3034097.
Gerard et al., Influence on stability in *Escherichia coli* of the carboxy-terminal structure of cloned Moloney murine leukemia virus reverse transcriptase. DNA. Aug. 1986;5(4):271-9. doi: 10.1089/dna.1986.5.271.

(56) References Cited

OTHER PUBLICATIONS

Gerard et al., Purification and characterization of the DNA polymerase and RNase H activities in Moloney murine sarcoma-leukemia virus. J Virol. Apr. 1975;15(4):785-97. doi: 10.1128/JVI.15.4.785-797.1975.

Gerard et al., The role of template-primer in protection of reverse transcriptase from thermal inactivation. Nucleic Acids Res. Jul. 15, 2002;30(14):3118-29. doi: 10.1093/nar/gkf417.

Gerber et al., An adenosine deaminase that generates inosine at the wobble position of tRNAs. Science. Nov. 5, 1999;286(5442):1146-9. doi: 10.1126/science.286.5442.1146.

Gerber et al., RNA editing by base deamination: more enzymes, more targets, new mysteries. Trends Biochem Sci. Jun. 2001;26(6):376-84.

Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.

Gersbach et al., Targeted plasmid integration into the human genome by an engineered zinc-finger recombinase. Nucleic Acids Res. Sep. 1, 2011;39(17):7868-78. doi: 10.1093/nar/gkr421. Epub Jun. 7, 2011.

Ghahfarokhi et al., Blastocyst Formation Rate and Transgene Expression are Associated with Gene Insertion into Safe and Non-Safe Harbors in the Cattle Genome. Sci Rep. Nov. 13, 2017;7(1):15432. doi: 10.1038/s41598-017-15648-3.

Gibson et al., Enzymatic assembly of DNA molecules up to several hundred kilobases. Nat Methods. May 2009;6(5):343-5. doi: 10.1038/nmeth.1318. Epub Apr. 12, 2009.

Gil, Position-dependent sequence elements downstream of AAUAAA are required for efficient rabbit beta-globin mRNA 3' end formation. Cell. May 8, 1987;49(3):399-406. doi: 10.1016/0092-8674(87)90292-3.

Gilbert et al., CRISPR-mediated modular RNA-guided regulation of transcription in eukaryotes. Cell. 2013 154(2):442-51.

Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.

Glasgow et al.,DNA-binding properties of the Hin recombinase. J Biol Chem. Jun. 15, 1989;264(17):10072-82.

Glassner et al., Generation of a strong mutator phenotype in yeast by imbalanced base excision repair. Proc Natl Acad Sci U S A. Aug. 18, 1998;95(17):9997-10002.

Goldberg et al., Epigenetics: a landscape takes shape. Cell. Feb. 23, 2007;128(4):635-8. doi: 10.1016/j.cell.2007.02.006.

Goldberg et al., Loss-of-function mutations in the Nav1.7 gene underlie congenital indifference to pain in multiple human populations. Clin Genet. Apr. 2007;71(4):311-9. doi: 10.1111/j.1399-0004.2007.00790.x.

Gong et al., Active DNA demethylation by oxidation and repair. Cell Res. Dec. 2011;21(12):1649-51. doi: 10.1038/cr.2011.140. Epub Aug. 23, 2011.

Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.

Goodnough et al., Development of a delivery vehicle for intracellular transport of botulinum neurotoxin antagonists. FEBS Lett. Feb. 27, 2002;513(2-3):163-8.
Gordley et al., Evolution of programmable zinc finger-recombinases with activity in human cells. J Mol Biol. Mar. 30, 2007;367(3):802-13. Epub Jan. 12, 2007.
Gordley et al., Synthesis of programmable integrases. Proc Natl Acad Sci U S A. Mar. 31, 2009;106(13):5053-8. doi: 10.1073/pnas.0812502106. Epub Mar. 12, 2009.
Gou et al., Designing single guide RNA for CIRSPR-Cas9 base editor by deep learning. Peer reviewed Thesis/Dissertation. UCLA Electronic Theses and Dissertations. Jan. 1, 2019. Retrieved from the Internet via https://escholarship.org/uc/item/7vf9z54t. Last accessed on Apr. 29, 2021.
Grainge et al., The integrase family of recombinase: organization and function of the active site. Mol Microbiol. Aug. 1999;33(3):449-56.
Grati et al., Localization of PDZD7 to the stereocilia ankle-link associates this scaffolding protein with the Usher syndrome protein network. J Neurosci. Oct. 10, 2012;32(41):14288-93. doi: 10.1523/JNEUROSCI.3071-12.2012.
Green et al., Characterization of the mechanical unfolding of RNA pseudoknots. J Mol Biol. Jan. 11, 2008;375(2):511-28. doi: 10.1016/j.jmb.2007.05.058. Epub May 26, 2007.
Gregory et al., Integration site for Streptomyces phage phiBT1 and development of site-specific integrating vectors. J Bacteriol. Sep. 2003;185(17):5320-3. doi: 10.1128/jb.185.17.5320-5323.2003.
Griffiths, Endogenous retroviruses in the human genome sequence. Genome Biol. 2001;2(6):Reviews1017. doi: 10.1186/GB-2001-2-6-reviews1017. Epub Jun. 5, 2001.
Grindley et al., Mechanisms of site-specific recombination. Annu Rev Biochem. 2006;75:567-605. doi: 10.1146/annurev.biochem.73.011303.073908.
Grishok et al., Genes and Mechanisms Related to RNA Interference Regulate Expression of the Small Temporal RNAs that Control C. elegans Developmental Timing. Jul. 13, 2001:106(1):P23-4.
Groher et al., Synthetic riboswitches—A tool comes of age. Biochim Biophys Acta. Oct. 2014;1839(10):964-973. doi: 10.1016/j.bbagrm.2014.05.005. Epub May 17, 2014.
Groth et al., Construction of transgenic *Drosophila* by using the site-specific integrase from phage phiC31. Genetics. Apr. 2004;166(4):1775-82. doi: 10.1534/genetics.166.4.1775.
Groth et al., Phage integrases: biology and applications. J Mol Biol. Jan. 16, 2004;335(3):667-78.
Gruber et al., Strategies for measuring evolutionary conservation of RNA secondary structures. BMC Bioinformatics. Feb. 26, 2008;9:122. doi: 10.1186/1471-2105-9-122.
Gruber et al., The Vienna RNA websuite. Nucleic Acids Res. Jul. 1, 2008;36(Web Server issue):W70-4. doi: 10.1093/nar/gkn188. Epub Apr. 19, 2008.
Grunebaum et al., Recent advances in understanding and managing adenosine deaminase and purine nucleoside phosphorylase deficiencies. Curr Opin Allergy Clin Immunol. Dec. 2013;13(6):630-8. doi: 10.1097/ACI.0000000000000006.
Grünewald et al., Transcriptome-wide off-target RNA editing induced by CRISPR-guided DNA base editors. Nature. May 2019;569(7756):433-437. doi: 10.1038/s41586-019-1161-z. Epub Apr. 17, 2019.
Guedon et al., Current gene therapy using viral vectors for chronic pain. Mol Pain. May 13, 2015;11:27. doi: 10.1186/s12990-015-0018-1.
Guilinger et al., Broad specificity profiling of TALENs results in engineered nucleases with improved DNA-cleavage specificity. Nat Methods. Apr. 2014; 11(4):429-35. doi: 10.1038/nmeth.2845. Epub Feb. 16, 2014.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Gumulya et al., Exploring the past and the future of protein evolution with ancestral sequence reconstruction: the 'retro' approach to protein engineering. Biochem J. Jan. 1, 2017;474(1):1-19. doi: 10.1042/BCJ20160507.
Guo et al., Evolution of Tetrahymena ribozyme mutants with increased structural stability. Nat Struct Biol. Nov. 2002;9(11):855-61. doi: 10.1038/nsb850.
Guo et al., Facile functionalization of FK506 for biological studies by the thiol-ene 'click' reaction. RSC Advances. 2014;22:11400-3.
Guo et al., Protein tolerance to random amino acid change. Proc Natl Acad Sci U S A. Jun. 22, 2004;101(25):9205-10. Epub Jun. 14, 2004.
Guo et al., Structure of Cre recombinase complexed with DNA in a site-specific recombination synapse. Nature. Sep. 4, 1997;389(6646):40-6.
Gupta et al., Cross-talk between cognate and noncognate RpoE sigma factors and Zn(2+)-binding anti-sigma factors regulates

(56) References Cited

OTHER PUBLICATIONS photooxidative stress response in Azospirillum brasilense. Antioxid Redox Signal. Jan. 1, 2014;20(1):42-59. doi: 10.1089/ars.2013.5314. Epub Jul. 19, 2013.

Gupta et al., Sequences in attB that affect the ability of phiC31 integrase to synapse and to activate DNA cleavage. Nucleic Acids Res. 2007;35(10):3407-19. doi: 10.1093/nar/gkm206. Epub May 3, 2007.

Gutschner et al., Post-translational Regulation of Cas9 during G1 Enhances Homology-Directed Repair. Cell Rep. Feb. 16, 2016;14(6):1555-1566. doi: 10.1016/j.celrep.2016.01.019. Epub Feb. 4, 2016.

Guzman et al., Tight regulation, modulation, and high-level expression by vectors containing the arabinose PBAD promoter. J Bacteriol. 1995;177(14):4121-4130.

Haapaniemi et al., CRISPR-Cas9 genome editing induces a p53-mediated DNA damage response. Nat Med. Jul. 2018;24(7):927-930. doi: 10.1038/s41591-018-0049-z. Epub Jun. 11, 2018.

Haddada et al., Gene therapy using adenovirus vectors. Curr Top Microbiol Immunol. 1995;199 ( Pt 3):297-306. doi: 10.1007/978-3-642-79586-2_14.

Haeussler et al., Evaluation of off-target and on-target scoring algorithms and integration into the guide RNA selection tool CRISPOR. Genome Biol. Jul. 5, 2016;17(1):148. doi: 10.1186/s13059-016-1012-2.

Hagen et al., A high rate of polymerization during synthesis of mouse mammary tumor virus DNA alleviates hypermutation by APOBEC3 proteins. PLoS Pathog. Feb. 15, 2019;15(2):e1007533. doi: 10.1371/journal.ppat.1007533.

Halbert et al., Repeat transduction in the mouse lung by using adeno-associated virus vectors with different serotypes. J Virol. Feb. 2000;74(3):1524-32. doi: 10.1128/jvi.74.3.1524-1532.2000.

Hale et al., RNA-guided RNA cleavage by a CRISPR RNA-Cas protein complex. Cell. Nov. 25, 2009;139(5):945-56. doi: 10.1016/j.cell.2009.07.040.

Halmai et al., Targeted CRIPSR/dCas9-mediated reactivation of epigenetically silenced genes suggests limited escape from the inactive X chromosome. 2nd Intl Conf on Epigenetics and Bioengineering. Oct. 4, 2018; Retrieved from the Internet: https://aiche.confex.com/aiche/epibiol8/webprogram/paper544785.html. Retrieved Jun. 29, 2020.

Halperin et al., CRISPR-guided DNA polymerases enable diversification of all nucleotides in a tunable window. Nature. Aug. 2018;560(7717):248-252. doi: 10.1038/s41586-018-0384-8. Epub Aug. 1, 2018.

Halvas et al., Role of murine leukemia virus reverse transcriptase deoxyribonucleoside triphosphate-binding site in retroviral replication and in vivo fidelity. J Virol. Nov. 2000;74(22):10349-58. doi: 10.1128/jvi.74.22.10349-10358.2000.

Hamano-Takaku et al., A mutant *Escherichia coli* tyrosyl-tRNA synthetase utilizes the unnatural amino acid azatyrosine more efficiently than tyrosine. J Biol Chem. Dec. 22, 2000;275(51):40324-8.

Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.

Handa et al., Template-assisted synthesis of adenine-mutagenized cDNA by a retroelement protein complex. Nucleic Acids Res. Oct. 12, 2018;46(18):9711-9725. doi: 10.1093/nar/gky620.

Hanson et al., Codon optimality, bias and usage in translation and mRNA decay. Nat Rev Mol Cell Biol. Jan. 2018;19(1):20-30. doi: 10.1038/nrm.2017.91. Epub Oct. 11, 2017.

Hardt et al.,Missense variants in hMLH1 identified in patients from the German HNPCC consortium and functional studies. Fam Cancer. Jun. 2011;10(2):273-84. doi: 10.1007/s10689-011-9431-4.

Harms et al., Evolutionary biochemistry: revealing the historical and physical causes of protein properties. Nat Rev Genet. Aug. 2013;14(8):559-71. doi: 10.1038/nrg3540.

Harmsen et al., DNA mismatch repair and oligonucleotide end-protection promote base-pair substitution distal from a CRISPR/Cas9-induced DNA break. Nucleic Acids Res. Apr. 6, 2018;46(6):2945-2955. doi: 10.1093/nar/gky076.

Harrington et al., A thermostable Cas9 with increased lifetime in human plasma. Nat Commun. Nov. 10, 2017;8(1):1424. doi: 10.1038/s41467-017-01408-4. Posted May 16, 2017 as bioRxiv preprint. Doi.org/10.1101/138867.

Harrington et al., Programmed DNA destruction by miniature CRISPR-Cas14 enzymes. Science. Nov. 16, 2018;362(6416):839-842. doi: 10.1126/science.aav4294. Epub Oct. 18, 2018.

Harris et al., RNA Editing Enzyme APOBEC1 and Some of Its Homologs Can Act as DNA Mutators. Mol Cell. Nov. 2002;10(5):1247-53.

Hart et al., High-Resolution CRISPR Screens Reveal Fitness Genes and Genotype-Specific Cancer Liabilities. Cell. Dec. 3, 2015;163(6):1515-26. doi: 10.1016/j.cell.2015.11.015. Epub Nov. 25, 2015.

Hartung et al., Correction of metabolic, craniofacial, and neurologic abnormalities in MPS I mice treated at birth with adeno-associated virus vector transducing the human alpha-L-iduronidase gene. Mol Ther. Jun. 2004;9(6):866-75.

Hartung et al., Cre mutants with altered DNA binding properties. J Biol Chem. Sep. 4, 1998;273(36):22884-91.

Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.

Hasegawa et al., Spontaneous mutagenesis associated with nucleotide excision repair in *Escherichia coli*. Genes Cells. May 2008;13(5):459-69. doi: 10.1111/j.1365-2443.2008.01185.x.

Hawley-Nelson et al., Transfection of Cultured Eukaryotic Cells Using Cationic Lipid Reagents. Curr Prot Mol Biol. Jan. 2008;9.4.1-9.4.17. doi: 10.102/0471142727.mb0904s81. 17 pages.

Hayes et al., Stop codons preceded by rare arginine codons are efficient determinants of SsrA tagging in *Escherichia coli*. Proc Natl Acad Sci U S A. Mar. 19, 2002;99(6):3440-5. Epub Mar. 12, 2002.

Hector et al., CDKL5 variants: Improving our understanding of a rare neurologic disorder. Neurol Genet. Dec. 15, 2017;3(6):e200. doi: 10.1212/NXG.0000000000000200.

Heidenreich et al., Non-homologous end joining as an important mutagenic process in cell cycle-arrested cells. EMBO J. May 1, 2003;22(9):2274-83. doi: 10.1093/emboj/cdg203.

Held et al., In vivo correction of murine hereditary tyrosinemia type I by phiC31 integrase-mediated gene delivery. Mol Ther. Mar. 2005;11(3):399-408. doi: 10.1016/j.ymthe.2004.11.001.

Heller et al., Replisome assembly and the direct restart of stalled replication forks. Nat Rev Mol Cell Biol. Dec. 2006;7(12):932-43. Epub Nov. 8, 2006.

Hendel et al., Chemically modified guide RNAs enhance CRISPR-Cas genome editing in human primary cells. Nat Biotechnol. Sep. 2015;33(9):985-989. doi: 10.1038/nbt.3290. Epub Jun. 29, 2015. Author Manuscript. 14 pages.

Hendricks et al., The *S. cerevisiae* Mag1 3-methyladenine DNA glycosylase modulates susceptibility to homologous recombination. DNA Repair (Amst). 2002;1(8):645-659.

Hermonat et al., Use of adeno-associated virus as a mammalian DNA cloning vector: transduction of neomycin resistance into mammalian tissue culture cells. Proc Natl Acad Sci U S A. Oct. 1984;81(20):6466-70. doi: 10.1073/pnas.81.20.6466.

Herschhorn et al., Retroviral reverse transcriptases. Cell Mol Life Sci. Aug. 2010;67(16):2717-47. doi: 10.1007/s00018-010-0346-2. Epub Apr. 1, 2010.

Herzig et al., A Novel Leu92 Mutant of HIV-1 Reverse Transcriptase with a Selective Deficiency in Strand Transfer Causes a Loss of Viral Replication. J Virol. Aug. 2015;89(16):8119-29. doi: 10.1128/JVI.00809-15. Epub May 20, 2015.

Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.

Heyer et al., Regulation of homologous recombination in eukaryotes. Annu Rev Genet. 2010;44:113-39. doi: 10.1146/annurev-genet-051710-150955. Author Manuscript. 33 pages.

(56) References Cited

OTHER PUBLICATIONS

Hickford et al., Antitumour polyether macrolides: four new halichondrins from the New Zealand deep-water marine sponge Lissodendoryx sp. Bioorg Med Chem. Mar. 15, 2009;17(6):2199-203. doi: 10.1016/j.bmc.2008.10.093. Epub Nov. 19, 2008.

Hida et al., Directed evolution for drug and nucleic acid; delivery. Adv Drug Deliv Rev. Dec. 22, 2007;59(15):1562-78. Epub Aug. 28, 2007.; Review.

Higgs et al., Genetic complexity in sickle cell disease. Proc Natl Acad Sci U S A. Aug. 19, 2008;105(33):11595-6. doi: 10.1073/pnas.0806633105. Epub Aug. 11, 2008.

Hilbers et al., New developments in structure determination of pseudoknots. Biopolymers. 1998;48(2-3):137-53. doi: 10.1002/(SICI)1097-0282(1998)48:2<137::AID-BIP4>3.0.CO;2-H.

Hill et al., Functional analysis of conserved histidines in ADP-glucose pyrophosphorylase from Escherichia coli.Biochem Biophys Res Commun. Mar. 17, 1998;244(2):573-7.

Hille et al., The Biology of CRISPR-Cas: Backward and Forward. Cell. Mar. 8, 2018;172(6):1239-1259. doi: 10.1016/j.cell.2017.11.032.

Hilton et al., Enabling functional genomics with genome engineering. Genome Res. Oct. 2015;25(10):1442-55. doi: 10.1101/gr.190124.115.

Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011. Review.

Hirano et al., Structural Basis for the Altered PAM Specificities of Engineered CRISPR-Cas9. Mol Cell. Mar. 17, 2016;61(6):886-94. doi: 10.1016/j.molcel.2016.02.018.

Hoang et al., UFBoot2: Improving the Ultrafast Bootstrap Approximation. Mol Biol Evol. Feb. 1, 2018;35(2):518-522. doi: 10.1093/molbev/msx281.

Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.

Hockemeyer et al., Genetic engineering of human pluripotent cells using TALE nucleases. Nat Biotechnol. Jul. 7, 2011;29(8):731-4. doi: 10.1038/nbt.1927.

Hoernes et al., Translating the epitranscriptome. Wiley Interdiscip Rev RNA. Jan. 2017;8(1):e1375. doi: 10.1002/wrna.1375. Epub Jun. 27, 2016.

Hoess et al., DNA specificity of the Cre recombinase resides in the 25 kDa carboxyl domain of the protein. J Mol Biol. Dec. 20, 1990;216(4):873-82. doi: 10.1016/S0022-2836(99)80007-2.

Holden et al., Crystal structure of the anti-viral APOBEC3G catalytic domain and functional implications. Nature. Nov. 6, 2008;456(7218):121-4. doi: 10.1038/nature07357. Epub Oct. 12, 2008.

Hollis et al., Phage integrases for the construction and manipulation of transgenic mammals. Reprod Biol Endocrinol. Nov. 7, 2003;1:79. doi: 10.1186/1477-7827-1-79.

Holsinger et al., Signal transduction in T lymphocytes using a conditional allele of Sos. Proc Natl Acad Sci U S A. Oct. 10, 1995;92(21):9810-4. doi: 10.1073/pnas.92.21.9810.

Holt et al., Human hematopoietic stem/progenitor cells modified by zinc-finger nucleases targeted to CCR5 control HIV-1 in vivo. Nat Biotechnol. Aug. 2010;28(8):839-47. doi: 10.1038/nbt.1663. Epub Jul. 2, 2010.

Hondares et al., Peroxisome Proliferator-activated Receptor a (PPARα) Induces PPARγ Coactivator 1α (PGC-1α) Gene Expression and Contributes to Thermogenic Activation of Brown Fat. J Biol. Chem Oct. 2011; 286(50):43112-22. doi: 10.1074/jbc.M111.252775.

Hoogenboom et al., Natural and designer binding sites made by phage display technology. Immunol Today. Aug. 2000;21(8):371-8.

Horvath et al., CRISPR/Cas, the immune system of bacteria and archaea. Science. Jan. 8, 2010;327(5962):167-70. doi: 10.1126/science.1179555.

Horvath et al., Diversity, Activity, and Evolution of CRISPR Loci in Streptococcus thermophilus. J Bacteriol. Feb. 2008;190(4):1401-12. doi: 10.1128/JB.01415-07. Epub Dec. 7, 2007.

Hotta et al., [Neurotropic viruses—classification, structure and characteristics]. Nihon Rinsho. Apr. 1997;55(4):777-82. Japanese.

Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.

Houck-Loomis et al., An equilibrium-dependent retroviral mRNA switch regulates translational recoding. Nature. Nov. 27, 2011;480(7378):561-4. doi: 10.1038/nature10657.

Houdebine, The methods to generate transgenic animals and to control transgene expression. J Biotechnol. Sep. 25, 2002;98(2-3):145-60.

Housden et al., Identification of potential drug targets for tuberous sclerosis complex by synthetic screens combining CRISPR-based knockouts with RNAi. Sci Signal. Sep. 8, 2015;8(393):rs9. doi: 10.1126/scisignal.aab3729.

Houseley et al., The many pathways of RNA degradation. Cell. Feb. 20, 2009;136(4):763-76. doi: 10.1016/j.cell.2009.01.019.

Howard et al., Intracerebral drug delivery in rats with lesion-induced memory deficits. J Neurosurg. Jul. 1989;71(1):105-12.

Hower et al., Shape-based peak identification for ChIP-Seq. BMC Bioinformatics. Jan. 12, 2011;12:15. doi: 10.1186/1471-2105-12-15.

Hsu et al., DNA targeting specificity of RNA-guided Cas9 nucleases. Nat Biotechnol. Sep. 2013;31(9):827-32. doi: 10.1038/nbt.2647. Epub Jul. 21, 2013.

Hsu et al., DNA targeting specificity of RNA-guided Cas9 nucleases. Nat Biotechnol. Sep. 2013;31(9):827-32. doi: 10.1038/nbt.2647. Epub Jul. 21, 2013. Supplementary Information. 27 pages.

Hu et al., Chemical Biology Approaches to Genome Editing: Understanding, Controlling, and Delivering Programmable Nucleases. Cell Chem Biol. Jan. 21, 2016;23(1):57-73. doi: 10.1016/j.chembiol.2015.12.009.

Hu et al., Evolved Cas9 variants with broad PAM compatibility and high DNA specificity. Nature. Apr. 5, 2018;556(7699):57-63 and Extended/Supplementary Data. doi: 10.1038/nature26155. Epub Feb. 28, 2018. 21 pages.

Hu et al., Evolved Cas9 variants with broad PAM compatibility and high DNA specificity. Nature. Apr. 5, 2018;556(7699):57-63. doi: 10.1038/nature26155. Epub Feb. 28, 2018.

Hua et al., Expanding the base editing scope in rice by using Cas9 variants. Plant Biotechnol J. Feb. 2019;17(2):499-504. doi: 10.1111/pbi.12993. Epub Oct. 5, 2018.

Hua et al., Precise A•T to G•C Base Editing in the Rice Genome. Mol Plant. Apr. 2, 2018;11(4):627-630. doi: 10.1016/j.molp.2018.02.007. Epub Feb. 21, 2018.

Huang et al., Circularly permuted and PAM-modified Cas9 variants broaden the targeting scope of base editors. Nat Biotechnol. Jun. 2019;37(6):626-631. doi: 10.1038/s41587-019-0134-y. Epub May 20, 2019. Including Supplementary Information.

Huang et al., Gain-of-function mutations in sodium channel Na(v)1.9 in painful neuropathy. Brain. Jun. 2014;137(Pt 6):1627-42. doi: 10.1093/brain/awu079. Epub Apr. 27, 2014.

Huang et al., Heritable gene targeting in zebrafish using customized TALENs. Nat Biotechnol. Aug. 5, 2011;29(8):699-700. doi: 10.1038/nbt.1939.

Huggins et al., Flap endonuclease 1 efficiently cleaves base excision repair and DNA replication intermediates assembled into nucleosomes. Mol Cell. Nov. 2002;10(5):1201-11. doi: 10.1016/s1097-2765(02)00736-0.

Humbert et al., Targeted gene therapies: tools, applications, optimization. Crit Rev Biochem Mol Biol. May-Jun. 2012;47(3):264-81. doi: 10.3109/10409238.2012.658112.

Hung et al., Protein localization in disease and therapy. J Cell Sci. Oct. 15, 2011;124(Pt 20):3381-92. doi: 10.1242/jcs.089110.

Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.

Husimi, Selection and evolution of bacteriophages in cellstat. Adv Biophys. ; 1989;25:1-43. Review.

Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.

(56) References Cited

OTHER PUBLICATIONS

Hwang et al., Efficient In Vivo Genome Editing Using RNA-Guided Nucleases. Nat Biotechnol. Mar. 2013;31(3):227-229. doi: 10.1038/nbt.2501. Epub Jan. 29, 2013.

Hwang et al., Web-based design and analysis tools for CRISPR base editing. BMC Bioinformatics. Dec. 27, 2018;19(1):542. doi: 10.1186/s12859-018-2585-4.

Hänsel-Hertsch et al., DNA G-quadruplexes in the human genome: detection, functions and therapeutic potential. Nat Rev Mol Cell Biol. May 2017;18(5):279-284. doi: 10.1038/nrm.2017.3. Epub Feb. 22, 2017.

Ibba et al., Relaxing the substrate specificity of an aminoacyl-tRNA synthetase allows in vitro and in vivo synthesis of proteins containing unnatural amino acids. FEBS Lett. May 15, 1995;364(3):272-5.

Ibba et al., Substrate specificity is determined by amino acid binding pocket size in *Escherichia coli* phenylalanyl-tRNA synthetase. Biochemistry. Jun. 14, 1994;33(23):7107-12.

Ibrahim et al., RNA recognition by 3'-to-5' exonucleases: the substrate perspective. Biochim Biophys Acta. Apr. 2008;1779(4):256-65. doi: 10.1016/j.bbagrm.2007.11.004. Epub Dec. 3, 2007.

Ihry et al., p53 inhibits CRISPR-Cas9 engineering in human pluripotent stem cells. Nat Med. Jul. 2018;24(7):939-946. doi: 10.1038/s41591-018-0050-6. Epub Jun. 11, 2018.

Iida et al., A site-specific, conservative recombination system carried by bacteriophage P1. Mapping the recombinase gene cin and the cross-over sites cix for the inversion of the C segment. EMBO J. 1982;1(11):1445-53.

Iida et al., The Min DNA inversion enzyme of plasmid p15B of *Escherichia coli* 15T-: a new member of the Din family of site-specific recombinases. Mol Microbiol. Jun. 1990;4(6):991-7. doi: 10.1111/j.1365-2958.1990.tb00671.x.

Ikediobi et al., Mutation analysis of 24 known cancer genes in the NCI-60 cell line set. Mol Cancer Ther. Nov. 2006;5(11):2606-12. Epub Nov. 6, 2006.

Imanishi et al., Detection of N6-methyladenosine based on the methyl-sensitivity of MazF RNA endonuclease. Chem Commun (Camb). Nov. 30, 2017;53(96):12930-12933. doi: 10.1039/c7cc07699a.

Imburgio et al., Studies of promoter recognition and start site selection by T7 RNA polymerase using a comprehensive collection of promoter variants. Biochemistry. Aug. 29, 2000;39(34):10419-30.

Ingram, A specific chemical difference between the globins of normal human and sickle-cell anaemia haemoglobin. Nature. Oct. 13, 1956;178(4537):792-4. doi: 10.1038/178792a0.

Irion et al., Identification and targeting of the ROSA26 locus in human embryonic stem cells. Nat Biotechnol. Dec. 2007;25(12):1477-82. doi: 10.1038/nbt1362. Epub Nov. 25, 2007.

Irrthum et al., Congenital hereditary lymphedema caused by a mutation that inactivates VEGFR3 tyrosine kinase. Am J Hum Genet. Aug. 2000;67(2):295-301. Epub Jun. 9, 2000.

Isaacs et al., Engineered riboregulators enable post-transcriptional control of gene expression. Nat Biotechnol. Jul. 2004;22(7):841-7. doi: 10.1038/nbt986. Epub Jun. 20, 2004.

Ishino et al., Nucleotide sequence of the iap gene, responsible for alkaline phosphatase isozyme conversion in *Escherichia coli*, and identification of the gene product. J Bacteriol. Dec. 1987;169(12):5429-33.

Ishizuka et al., Loss of ADAR1 in tumours overcomes resistance to immune checkpoint blockade. Nature. Jan. 2019;565(7737):43-48. doi: 10.1038/s41586-018-0768-9. Epub Dec. 17, 2018.

Iwai et al., Circular beta-lactamase: stability enhancement by cyclizing the backbone. FEBS Lett. Oct. 8, 1999;459(2):166-72. doi: 10.1016/s0014-5793(99)01220-x.

Iwai et al., Highly efficient protein trans-splicing by a naturally split DnaE intein from Nostoc punctiforme. FEBS Lett. Mar. 20, 2006;580(7):1853-8. doi: 10.1016/j.febslet.2006.02.045. Epub Feb. 24, 2006.

Iyama et al., DNA repair mechanisms in dividing and non-dividing cells. DNA Repair (Amst). Aug. 2013;12(8):620-36. doi: 10.1016/j.dnarep.2013.04.015. Epub May 16, 2013.

Jaffrey et al., Emerging links between m6A and misregulated mRNA methylation in cancer. Genome Med. Jan. 12, 2017;9(1):2. doi: 10.1186/s13073-016-0395-8.

Jakimo et al., A Cas9 with Complete PAM Recognition for Adenine Dinucleotides. bioRxiv preprint. Sep. 27, 2018. doi.org/10.1101/429654. 29 pages.

Jamieson et al., Drug discovery with engineered zinc-finger proteins. Nat Rev Drug Discov. May 2003;2(5):361-8.

Jansen et al., Backbone and nucleobase contacts to glucosamine-6-phosphate in the glmS ribozyme. Nat Struct Mol Biol. Jun. 2006;13(6):517-23. Epub May 14, 2006.

Jansen et al., Identification of genes that are associated with DNA repeats in prokaryotes. Mol Microbiol. Mar. 2002;43(6):1565-75.

Jardine et al., HIV-1 Vaccines. Priming a broadly neutralizing antibody response to HIV-1 using a germline-targeting immunogen. Science. Jul. 10, 2015;349(6244):156-61. doi: 10.1126/science.aac5894. Epub Jun. 18, 2015.

Jasin et al., Repair of strand breaks by homologous recombination. Cold Spring Harb Perspect Biol. Nov. 1, 2013;5(11):a012740. doi: 10.1101/cshperspect.a012740.

Jeggo, DNA breakage and repair. Adv Genet. 1998;38:185-218. doi: 10.1016/s0065-2660(08)60144-3.

Jemielity et al., Novel "anti-reverse" cap analogs with superior translational properties. RNA. Sep. 2003;9(9):1108-22. doi: 10.1261/rna.5430403.

Jenkins et al., Comparison of a preQ1 riboswitch aptamer in metabolite-bound and free states with implications for gene regulation. J Biol Chem. Jul. 15, 2011;286(28):24626-37. doi: 10.1074/jbc.M111.230375. Epub May 18, 2011.

Jeong et al., Measurement of deoxyinosine adduct: Can it be a reliable tool to assess oxidative or nitrosative DNA damage? Toxicol Lett. Oct. 17, 2012;214(2):226-33. doi: 10.1016/j.toxlet.2012.08.013. Epub Aug. 23, 2012.

Jia et al., The MLH1 ATPase domain is needed for suppressing aberrant formation of interstitial telomeric sequences. DNA Repair (Amst). May 2018;65:20-25. doi: 10.1016/j.dnarep.2018.03.002. Epub Mar. 7, 2018.

Jiang et al., Chemical modifications of adenine base editor mRNA and guide RNA expand its application scope. Nat Commun. Apr. 24, 2020;11(1):1979. doi: 10.1038/s41467-020-15892-8.

Jiang et al., CRISPR-Cas9 Structures and Mechanisms. Annu Rev Biophys. May 22, 2017;46:505-529. doi: 10.1146/annurev-biophys-062215-010822. Epub Mar. 30, 2017.

Jiang et al., Prime editing efficiently generates W542L and S621I double mutations in two ALS genes of maize. bioRxiv preprint. Jul. 6, 2020. Retrieved from www.biorxiv.org. doi: 10.1101/2020.07.06.188896. 15 pages.

Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.

Jiang et al., Structural Biology. A Cas9-guide RNA Complex Preorganized for Target DNA Recognition. Science. Jun. 26, 2015;348(6242):1477-81. doi: 10.1126/science.aab1452.

Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.

Jin et al., Cytosine, but not adenine, base editors induce genome-wide off-target mutations in rice. Science. Apr. 19, 2019;364(6437):292-295. doi: 10.1126/science.aaw7166. Epub Feb. 28, 2019.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Jinek et al., RNA-programmed genome editing in human cells. Elife. Jan. 29, 2013;2:e00471. doi: 10.7554/eLife.00471.

Jinek et al., Structures of Cas9 endonucleases reveal RNA-mediated conformational activation. Science. Mar. 14, 2014;343(6176):1247997. doi: 10.1126/science.1247997. Epub Feb. 6, 2014.

Jiricny, The multifaceted mismatch-repair system. Nat Rev Mol Cell Biol. May 2006;7(5):335-46. doi: 10.1038/nrm1907.

(56) References Cited

OTHER PUBLICATIONS

Johann et al., GLVR1, a receptor for gibbon ape leukemia virus, is homologous to a phosphate permease of Neurospora crassa and is expressed at high levels in the brain and thymus. J Virol. Mar. 1992;66(3):1635-40. doi: 10.1128/JVI.66.3.1635-1640.1992.
Johansson et al., RNA Recognition by the MS2 Phage Coat Protein. Seminars in Virology. 1997;8(3):176-85. https://doi.org/10.1006/smvy.1997.0120.
Johansson et al., Selenocysteine in proteins-properties and biotechnological use. Biochim Biophys Acta. Oct. 30, 2005;1726(1):1-13. Epub Jun. 1, 2005.
Johns et al., The promise and peril of continuous in vitro evolution. J Mol Evol. Aug. 2005;61(2):253-63. Epub Jun. 27, 2005.
Johnson et al., Trans insertion-splicing: ribozyme-catalyzed insertion of targeted sequences into RNAs. Biochemistry. Aug. 9, 2005;44(31):10702-10. doi: 10.1021/bi0504815.
Joho et al., Identification of a region of the bacteriophage T3 and T7 RNA polymerases that determines promoter specificity. J Mol Biol. Sep. 5, 1990;215(1):31-9.
Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.
Jost et al., Titrating gene expression using libraries of systematically attenuated CRISPR guide RNAs. Nat Biotechnol. Mar. 2020;38(3):355-364. doi: 10.1038/s41587-019-0387-5. Epub Jan. 13, 2020.
Joung et al., TALENs: a widely applicable technology for targeted genome editing. Nat Rev Mol Cell Biol. Jan. 2013;14(1):49-55. doi: 10.1038/nrm3486. Epub Nov. 21, 2012.
Joyce et al., Amplification, mutation and selection of catalytic RNA. Gene. Oct. 15, 1989;82(1):83-7. doi: 10.1016/0378-1119(89)90033-4.
Jusiak et al., Comparison of Integrases Identifies Bxb1-GA Mutant as the Most Efficient Site-Specific Integrase System in Mammalian Cells. ACS Synth Biol. Jan. 18, 2019;8(1):16-24. doi: 10.1021/acssynbio.8b00089. Epub Jan. 9, 2019.
Jyothy et al., Translocation Down syndrome. Indian J Med Sci. Mar. 2002;56(3):122-6.
Kacian et al., Purification of the DNA polymerase of avian myeloblastosis virus. Biochim Biophys Acta. Sep. 24, 1971;246(3):365-83. doi: 10.1016/0005-2787(71)90773-8.
Kaczmarczyk et al., Manipulating the Prion Protein Gene Sequence and Expression Levels with CRISPR/Cas9. PLoS One. Apr. 29, 2016;11(4):e0154604. doi: 10.1371/journal.pone.0154604.
Kadoch et al., Reversible disruption of mSWI/SNF (BAF) complexes by the SS18-SSX oncogenic fusion in synovial sarcoma. Cell. Mar. 28, 2013;153(1):71-85. doi: 10.1016/j.cell.2013.02.036.
Kahmann et al., G inversion in bacteriophage Mu DNA is stimulated by a site within the invertase gene and a host factor. Cell. Jul. 1985;41(3):771-80. doi: 10.1016/s0092-8674(85)80058-1.
Kaiser et al., Gene therapy. Putting the fingers on gene repair. Science. Dec. 23, 2005;310(5756):1894-6.
Kakiyama et al., A peptide release system using a photo-cleavable linker in a cell array format for cell-toxicity analysis. Polymer J. Feb. 27, 2013;45:535-9.
Kalyaanamoorthy et al., ModelFinder: fast model selection for accurate phylogenetic estimates. Nat Methods. Jun. 2017;14(6):587-589. doi: 10.1038/nmeth.4285. Epub May 8, 2017.
Kan et al., Mechanisms of precise genome editing using oligonucleotide donors. Genome Res. Jul. 2017;27(7):1099-1111. doi: 10.1101/gr.214775.116. Epub Mar. 29, 2017.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Kang et al., Structural Insights into riboswitch control of the biosynthesis of queuosine, a modified nucleotide found in the anticodon of tRNA. Mol Cell. Mar. 27, 2009;33(6):784-90. doi: 10.1016/j.molcel.2009.02.019. Epub Mar. 12, 2009.

Kang et al., Precision genome engineering through adenine base editing in plants. Nat Plants. Jul. 2018;4(7):427-431. doi: 10.1038/s41477-018-0178-x. Epub Jun. 4, 2018. Erratum in: Nat Plants. Sep. 2018;4(9):730.
Kao et al., Cleavage specificity of *Saccharomyces cerevisiae* flap endonuclease 1 suggests a double-flap structure as the cellular substrate. J Biol Chem. Apr. 26, 2002;277(17):14379-89. doi: 10.1074/jbc.M110662200. Epub Feb. 1, 2002.
Kappel et al., Regulating gene expression in transgenic animals. Curr Opin Biotechnol. Oct. 1992;3(5):548-53.
Karimova et al., Discovery of Nigri/nox and Panto/pox site-specific recombinase systems facilitates advanced genome engineering. Sci Rep. Jul. 22, 2016;6:30130. doi: 10.1038/srep30130.
Karimova et al., Vika/vox, a novel efficient and specific Cre/loxP-like site-specific recombination system. Nucleic Acids Res. Jan. 2013;41(2):e37. doi: 10.1093/nar/gks1037. Epub Nov. 9, 2012.
Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012. Review.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Katafuchi et al., DNA polymerases involved in the incorporation of oxidized nucleotides into DNA: their efficiency and template base preference. Mutat Res. Nov. 28, 2010;703(1):24-31. doi: 10.1016/j.mrgentox.2010.06.004. Epub Jun. 11, 2010.
Kato et al., Improved purification and enzymatic properties of three forms of reverse transcriptase from avian myeloblastosis virus. J Virol Methods. Dec. 1984;9(4):325-39. doi: 10.1016/0166-0934(84)90058-2.
Katoh et al., MAFFT multiple sequence alignment software version 7: improvements in performance and usability. Mol Biol Evol. Apr. 2013;30(4):772-80. doi: 10.1093/molbev/mst010. Epub Jan. 16, 2013.
Kaufman et al., Translational efficiency of polycistronic mRNAs and their utilization to express heterologous genes in mammalian cells. EMBO J. Jan. 1987;6(1):187-93.
Kavli et al., Excision of cytosine and thymine from DNA by mutants of human uracil-DNA glycosylase. EMBO J. Jul. 1, 1996;15(13):3442-7.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Kay et al., Viral vectors for gene therapy: the art of turning infectious agents into vehicles of therapeutics. Nat Med. Jan. 2001;7(1):33-40.
Kaya et al., A bacterial Argonaute with noncanonical guide RNA specificity. Proc. Natl. Acad. Sci. USA Apr. 2016;113(15):4057-62.
Keijzers et al., Human exonuclease 1 (EXO1) activity characterization and its function on flap structures. Biosci Rep. Apr. 25, 2015;35(3):e00206. doi: 10.1042/BSR20150058.
Kellendonk et al., Regulation of Cre recombinase activity by the synthetic steroid RU 486. Nucleic Acids Res. Apr. 15, 1996;24(8):1404-11.
Kelman, PCNA: structure, functions and interactions. Oncogene. Feb. 13, 1997;14(6):629-40. doi: 10.1038/sj.onc.1200886.
Keravala et al., A diversity of serine phage integrases mediate site-specific recombination in mammalian cells. Mol Genet Genomics. Aug. 2006;276(2):135-46. doi: 10.1007/s00438-006-0129-5. Epub May 13, 2006.
Kessel et al., Murine developmental control genes. Science. Jul. 27, 1990;249(4967):374-9. doi: 10.1126/science.1974085.
Kessler et al., Gene delivery to skeletal muscle results in sustained expression and systemic delivery of a therapeutic protein. Proc Natl Acad Sci U S A. Nov. 26, 1996;93(24):14082-7. doi: 10.1073/pnas.93.24.14082.
Ketha et al., Application of bioinformatics-coupled experimental analysis reveals a new transport-competent nuclear localization signal in the nucleoprotein of Influenza A virus strain. BMC Cell Biol. Apr. 28, 2008; 9:22. https://doi.org/10.1186/1471-2121-9-22.

(56) References Cited

OTHER PUBLICATIONS

Kiga et al., An engineered *Escherichia coli* tyrosyl-tRNA synthetase for site-specific incorporation of an unnatural amino acid into proteins in eukaryotic translation and its application in a wheat germ cell-free system. Proc Natl Acad Sci U S A. Jul. 23, 2002;99(15):9715-20. Epub Jul. 3, 2002.

Kilbride et al., Determinants of product topology in a hybrid Cre-Tn3 resolvase site-specific recombination system. J Mol Biol. Jan. 13, 2006;355(2):185-95. Epub Nov. 9, 2005.

Kilcher et al., Brochothrix thermosphacta bacteriophages feature heterogeneous and highly mosaic genomes and utilize unique prophage insertion sites. J Bacteriol. Oct. 2010;192(20):5441-53. doi: 10.1128/JB.00709-10. Epub Aug. 13, 2010.

Kim et al., DJ-1, a novel regulator of the tumor suppressor PTEN. Cancer Cell. 2005;7(3):263-273.

Kim et al., Genome-wide target specificity of CRISPR RNA-guided adenine base editors. Nat Biotechnol. Apr. 2019;37(4):430-435. doi: 10.1038/s41587-019-0050-1. Epub Mar. 4, 2019.

Kim et al., A library of TAL effector nucleases spanning the human genome. Nat Biotechnol. Mar. 2013;31(3):251-8. Doi: 10.1038/nbt. 2517. Epub Feb. 17, 2013.

Kim et al., Adenine base editors catalyze cytosine conversions in human cells. Nat Biotechnol. Oct. 2019;37(10):1145-1148. doi: 10.1038/s41587-019-0254-4. Epub Sep. 23, 2019.

Kim et al., An anionic human protein mediates cationic liposome delivery of genome editing proteins into mammalian cells. Nat Commun. Jul. 2, 2019;10(1):2905. doi: 10.1038/s41467-019-10828-3.

Kim et al., Evaluating and Enhancing Target Specificity of Gene-Editing Nucleases and Deaminases. Annu Rev Biochem. Jun. 20, 2019;88:191-220. doi: 10.1146/annurev-biochem-013118-111730. Epub Mar. 18, 2019.

Kim et al., Genome-wide target specificities of CRISPR RNA-guided programmable deaminases. Nat Biotechnol. May 2017;35(5):475-480. doi: 10.1038/nbt.3852. Epub Apr. 10, 2017.

Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.

Kim et al., High-throughput analysis of the activities of xCas9, SpCas9-NG and SpCas9 at matched and mismatched target sequences in human cells. Nat Biomed Eng. Jan. 2020;4(1):111-124. doi: 10.1038/s41551-019-0505-1. Epub Jan. 14, 2020.

Kim et al., Highly efficient RNA-guided base editing in mouse embryos. Nat Biotechnol. May 2017;35(5):435-437. doi: 10.1038/nbt.3816. Epub Feb. 27, 2017.

Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.

Kim et al., In vivo genome editing with a small Cas9 orthologue derived from Campylobacter jejuni. Nat Commun. Feb. 21, 2017;8:14500. doi: 10.1038/ncomms14500. PMID: 28220790; PMCID: PMC5473640.

Kim et al., In vivo high-throughput profiling of CRISPR-Cpf1 activity. Nat Methods. Feb. 2017;14(2):153-159. doi: 10.1038/nmeth. 4104. Epub Dec. 19, 2016.

Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.

Kim et al., Mycobacteriophage Bxb1 integrates into the *Mycobacterium smegmatis* groEL1 gene. Mol Microbiol. Oct. 2003;50(2):463-73. doi: 10.1046/j.1365-2958.2003.03723.x.

Kim et al., Predicting the efficiency of prime editing guide RNAs in human cells. Nat Biotechnol. Feb. 2021;39(2):198-206. doi: 10.1038/s41587-020-0677-y. Epub Sep. 21, 2020.

Kim et al., RAD51 mutants cause replication defects and chromosomal instability. Mol Cell Biol. Sep. 2012;32(18):3663-80. doi: 10.1128/MCB.00406-12. Epub Jul. 9, 2012.

Kim et al., Rescue of high-specificity Cas9 variants using sgRNAs with matched 5' nucleotides. Genome Biol. Nov. 15, 2017;18(1):218. doi: 10.1186/s13059-017-1355-3.

Kim et al., Structural and kinetic characterization of *Escherichia coli* TadA, the wobble-specific tRNA deaminase. Biochemistry. May 23, 2006;45(20):6407-16. doi: 10.1021/bi0522394. PMID: 16700551.

Kim et al., TALENs and ZFNs are associated with different mutation signatures. Nat Methods. Mar. 2013;10(3):185. doi: 10.1038/nmeth.2364. Epub Feb. 10, 2013.

Kim et al., Targeted genome editing in human cells with zinc finger nucleases constructed via modular assembly. Genome Res. Jul. 2009; 19(7):1279-88. doi: 10.1101/gr.089417.108. Epub May 21, 2009.

Kim et al., The role of apolipoprotein E in Alzheimer's disease. Neuron. Aug. 13, 2009;63(3):287-303. doi: 10.1016/j.neuron.2009. 06.026.

Kim et al., Transcriptional repression by zinc finger peptides. Exploring the potential for applications in gene therapy. J Biol Chem. Nov. 21, 1997;272(47):29795-800.

King et al., No gain, no pain: NaV1.7 as an analgesic target. ACS Chem Neurosci. Sep. 17, 2014;5(9):749-51. doi: 10.1021/cn500171p. Epub Aug. 11, 2014.

Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat. 1003361. Epub May 16, 2013.

Klapacz et al., Frameshift mutagenesis and microsatellite instability induced by human alkyladenine DNA glycosylase. Mol Cell. Mar. 26, 2010;37(6):843-53. doi: 10.1016/j.molcel.2010.01.038.

Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.

Klein et al., Cocrystal structure of a class I preQ1 riboswitch reveals a pseudoknot recognizing an essential hypermodified nucleobase. Nat Struct Mol Biol. Mar. 2009;16(3):343-4. doi: 10.1038/nsmb. 1563.Epub Feb. 22, 2009.

Kleiner et al., In vitro selection of a DNA-templated small-molecule library reveals a class of macrocyclic kinase inhibitors. J Am Chem Soc. Aug. 25, 2010;132(33):11779-91. doi: 10.1021/ja104903x.

Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.

Kleinstiver et al., Engineered CRISPR-Cas9 nucleases with altered PAM specificities. Nature. Jul. 23, 2015;523(7561):481-5 and Supplementary Materials. doi: 10.1038/nature14592. Epub Jun. 22, 2015. 27 pages.

Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.

Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.

Kleinstiver et al., Monomeric site-specific nucleases for genome editing. Proc Natl Acad Sci U S A. May 22, 2012;109(21):8061-6. doi: 10.1073/pnas.1117984109. Epub May 7, 2012.

Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.

Klippel et al., Isolation and characterization of unusual gin mutants. EMBO J. Dec. 1, 1988;7(12):3983-9.

Klippel et al., The DNA invertase Gin of phage Mu: formation of a covalent complex with DNA via a phosphoserine at amino acid position 9. EMBO J. Apr. 1988;7(4):1229-37.

Klompe et al., Transposon-encoded CRISPR-Cas systems direct RNA-guided DNA integration. Nature. Jul. 2019;571(7764):219-225. doi: 10.1038/s41586-019-1323-z. Epub Jun. 12, 2019.

(56) References Cited

OTHER PUBLICATIONS

Knott et al., CRISPR-Cas guides the future of genetic engineering. Science. Aug. 31, 2018;361(6405):866-869. doi: 10.1126/science.aat5011.

Knott et al., Guide-bound structures of an RNA-targeting A-cleaving CRISPR-Cas13a enzyme. Nat Struct Mol Biol. Oct. 2017;24(10):825-833. doi: 10.1038/nsmb.3466. Epub Sep. 11, 2017.

Koblan et al., Improving cytidine and adenine base editors by expression optimization and ancestral reconstruction. Nat Biotechnol. Oct. 2018;36(9):843-846. doi: 10.1038/nbt.4172. Epub May 29, 2018.

Kobori et al., Deep Sequencing Analysis of Aptazyme Variants Based on a Pistol Ribozyme. ACS Synth Biol. Jul. 21, 2017;6(7):1283-1288. doi: 10.1021/acssynbio.7b00057. Epub Apr. 14, 2017.

Kohli et al., A portable hot spot recognition loop transfers sequence preferences from APOBEC family members to activation-induced cytidine deaminase. J Biol Chem. Aug. 21, 2009;284(34):22898-904. doi: 10.1074/jbc.M109.025536. Epub Jun. 26, 2009.

Kohli et al., Local sequence targeting in the AID/APOBEC family differentially impacts retroviral restriction and antibody diversification. J Biol Chem. Dec. 24, 2010;285(52):40956-64. doi: 10.1074/jbc.M110.177402. Epub Oct. 6, 2010.

Koike-Yusa et al., Genome-wide recessive genetic screening in mammalian cells with a lentiviral CRISPR-guide RNA library. Nat Biotechnol. Mar. 2014;32(3):267-73. doi: 10.1038/nbt.2800. Epub Dec. 23, 2013.

Kolot et al., Site promiscuity of coliphage HK022 integrase as a tool for gene therapy. Gene Ther. Jul. 2015;22(7):521-7. doi: 10.1038/gt.2015.9. Epub Mar. 12, 2015.

Kolot et al., Site-specific recombination in mammalian cells expressing the Int recombinase of bacteriophage HK022. Mol Biol Rep. Aug. 1999;26(3):207-13. doi: 10.1023/a:1007096701720.

Komor et al., CRISPR-Based Technologies for the Manipulation of Eukaryotic Genomes. Cell. Jan. 12, 2017;168(1-2):20-36. doi: 10.1016/j.cell.2016.10.044.

Komor et al., Improved base excision repair inhibition and bacteriophage Mu Gam protein yields C:G-to-T:A base editors with higher efficiency and product purity. Sci Adv. Aug. 30, 2017;3(8):eaao4774. doi: 10.1126/sciadv.aao4774. eCollection Aug. 2017.

Komor et al., Programmable editing of a target base in genomic DNA without double-stranded DNA cleavage. Nature. Apr. 20, 2016;533(7603):420-4. doi: 10.1038/nature17946.

Komor, Editing the Genome Without Double-Stranded DNA Breaks. ACS Chem Biol. Feb. 16, 2018;13(2):383-388. doi: 10.1021/acschembio.7b00710. Epub Oct. 9, 2017.

Konermann et al., Genome-scale transcriptional activation by an engineered CRISPR-Cas9 complex. Nature. Jan. 29, 2015;517(7536):583-8. doi: 10.1038/nature14136. Epub Dec. 10, 2014.

Konishi et al., Amino acid substitutions away from the RNase H catalytic site increase the thermal stability of Moloney murine leukemia virus reverse transcriptase through RNase H inactivation. Biochem Biophys Res Commun. Nov. 14, 2014;454(2):269-74. doi: 10.1016/j.bbrc.2014.10.044. Epub Oct. 17, 2014.

Koonin et al., Diversity, classification and evolution of CRISPR-Cas systems. Curr Opin Microbiol. 2017;37:67-78. doi:10.1016/j.mib.2017.05.008.

Kosicki et al., Repair of double-strand breaks induced by CRISPR-Cas9 leads to large deletions and complex rearrangements. Nat Biotechnol. Sep. 2018;36(8):765-771. doi: 10.1038/nbt.4192. Epub Jul. 16, 2018.

Kotewicz et al., Cloning and overexpression of Moloney murine leukemia virus reverse transcriptase in *Escherichia coli*. Gene. 1985;35(3):249-58. doi: 10.1016/0378-1119(85)90003-4.

Kotewicz et al., Isolation of cloned Moloney murine leukemia virus reverse transcriptase lacking ribonuclease H activity. Nucleic Acids Res. Jan. 11, 1988;16(1):265-77. doi: 10.1093/nar/16.1.265.

Kotin, Prospects for the use of adeno-associated virus as a vector for human gene therapy. Hum Gene Ther. Jul. 1994;5(7):793-801. doi: 10.1089/hum.1994.5.7-793.

Kouzminova et al., Patterns of chromosomal fragmentation due to uracil-DNA incorporation reveal a novel mechanism of replication-dependent double-stranded breaks. Mol Microbiol. Apr. 2008;68(1):202-15. doi: 10.1111/j.1365-2958.2008.06149.x.

Kowal et al., Exploiting unassigned codons in Micrococcus luteus for tRNA-based amino acid mutagenesis. Nucleic Acids Res. Nov. 15, 1997;25(22):4685-9.

Kowalski et al., Delivering the Messenger: Advances in Technologies for Therapeutic mRNA Delivery. Mol Ther. Apr. 10, 2019;27(4):710-728. doi: 10.1016/j.ymthe.2019.02.012. Epub Feb. 19, 2019.

Kozak, An analysis of 5'-noncoding sequences from 699 vertebrate messenger RNAs. Nucleic Acids Res. Oct. 26, 1987;15(20):8125-48. doi: 10.1093/nar/15.20.8125.

Kraft et al., Deletions, Inversions, Duplications: Engineering of Structural Variants using CRISPR/Cas in Mice. Cell Rep. Feb. 10, 2015;10(5):833-839. doi: 10.1016/j.celrep.2015.01.016. Epub Feb. 7, 2015.

Kremer et al., Adenovirus and adeno-associated virus mediated gene transfer. Br Med Bull. Jan. 1995;51(1):31-44. doi: 10.1093/oxfordjournals.bmb.a072951.

Krokan et al., Uracil in DNA—occurrence, consequences and repair. Oncogene. Dec. 16, 2002;21(58):8935-48. doi: 10.1038/sj.onc.1205996.

Krokan et al., Base excision repair. Cold Spring Harb Perspect Biol. Apr. 1, 2013;5(4):a012583. doi: 10.1101/cshperspect.a012583.

Krzywkowski et al., Limited reverse transcriptase activity of phi29 DNA polymerase. Nucleic Acids Res. Apr. 20, 2018;46(7):3625-3632. doi: 10.1093/nar/gky190.

Ku et al., Nucleic Acid Aptamers: An Emerging Tool for Biotechnology and Biomedical Sensing. Sensors (Basel). Jul. 6, 2015;15(7):16281-313. doi: 10.3390/s150716281.

Kuan et al., A systematic evaluation of nucleotide properties for CRISPR sgRNA design. BMC Bioinformatics. Jun. 6, 2017;18(1):297. doi: 10.1186/s12859-017-1697-6.

Kumar et al., Gene therapy for chronic neuropathic pain: how does it work and where do we stand today? Pain Med. May 2011;12(5):808-22. doi: 10.1111/j.1526-4637.2011.01120.x.

Kumar et al., Structural and functional consequences of the mutation of a conserved arginine residue in alphaA and alphaB crystallins. J Biol Chem. Aug. 20, 1999;274(34):24137-41.

Kundu et al., Leucine to proline substitution by SNP at position 197 in Caspase-9 gene expression leads to neuroblastoma: a bioinformatics analysis. 3 Biotech. 2013; 3:225-34.

Kunkel et al., Eukaryotic Mismatch Repair in Relation to DNA Replication. Annu Rev Genet. 2015;49:291-313. doi: 10.1146/annurev-genet-112414-054722.

Kunz et al., DNA Repair in mammalian cells: Mismatched repair: variations on a theme. Cell Mol Life Sci. Mar. 2009;66(6):1021-38. doi: 10.1007/s00018-009-8739-9.

Kurjan et al., Structure of a yeast pheromone gene (MF alpha): a putative alpha-factor precursor contains four tandem copies of mature alpha-factor. Cell. Oct. 1982;30(3):933-43. doi: 10.1016/0092-8674(82)90298-7.

Kury et al., De Novo Disruption of the Proteasome Regulatory Subunit PSMD12 Causes a Syndromic Neurodevelopmental Disorder. Am J Hum Genet. Feb. 2, 2017;100(2):352-363. doi: 10.1016/j.ajhg.2017.01.003. Epub Jan. 26, 2017.

Kuscu et al., CRISPR-Cas9-AID base editor is a powerful gain-of-function screening tool. Nat Methods. Nov. 29, 2016;13(12):983-984. doi: 10.1038/nmeth.4076.

Kuscu et al., CRISPR-STOP: gene silencing through base-editing-induced nonsense mutations. Nat Methods. Jul. 2017;14(7):710-712. doi: 10.1038/nmeth.4327. Epub Jun. 5, 2017.

Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.

Kwart et al., Precise and efficient scarless genome editing in stem cells using CORRECT. Nat Protoc. Feb. 2017;12(2):329-354. doi: 10.1038/nprot.2016.171. Epub Jan. 19, 2017.

(56) References Cited

OTHER PUBLICATIONS

Kweon et al., A CRISPR-based base-editing screen for the functional assessment of BRCA1 variants. Oncogene. Jan. 2020;39(1):30-35. doi: 10.1038/s41388-019-0968-2. Epub Aug. 29, 2019.
Kweon et al., Fusion guide RNAs for orthogonal gene manipulation with Cas9 and Cpf1. Nat Commun. Nov. 23, 2017;8(1):1723. doi: 10.1038/s41467-017-01650-w. Erratum in: Nat Commun. Jan. 16, 2018;9(1):303.
Kwok et al., G-Quadruplexes: Prediction, Characterization, and Biological Application. Trends Biotechnol. Oct. 2017;35(10):997-1013. doi: 10.1016/j.tibtech.2017.06.012. Epub Jul. 26, 2017.
Kwon et al., Chemical basis of glycine riboswitch cooperativity. RNA. Jan. 2008;14(1):25-34. Epub Nov. 27, 2007.
Köhrer et al., A possible approach to site-specific insertion of two different unnatural amino acids into proteins in mammalian cells via nonsense suppression. Chem Biol. Nov. 2003;10(11):1095-102.
Köhrer et al., Complete set of orthogonal 21st aminoacyl-tRNA synthetase-amber, ochre and opal suppressor tRNA pairs: concomitant suppression of three different termination codons in an mRNA in mammalian cells. Nucleic Acids Res. Dec. 1, 2004;32(21):6200-11. Print 2004.
Kügler et al., Human synapsin 1 gene promoter confers highly neuron-specific long-term transgene expression from an adenoviral vector in the adult rat brain depending on the transduced area. Gene Ther. Feb. 2003; 10(4):337-47. doi: 10.1038/sj.gt.3301905.
Lada et al., Mutator effects and mutation signatures of editing deaminases produced in bacteria and yeast. Biochemistry (Mosc). Jan. 2011;76(1):131-46.
Lakich et al., Inversions disrupting the factor VIII gene are a common cause of severe haemophilia A. Nat Genet. Nov. 1993;5(3):236-41. doi: 10.1038/ng1193-236.
Lancaster et al., Limited trafficking of a neurotropic virus through inefficient retrograde axonal transport and the type I interferon response. PLoS Pathog. Mar. 5, 2010;6(3):e1000791. doi: 10.1371/journal.ppat.1000791.
Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.
Landrum et al., ClinVar: public archive of relationships among sequence variation and human phenotype. Nucleic Acids Res. Jan. 2014;42(Database issue):D980-5. doi: 10.1093/nar/gkt1113. Epub Nov. 14, 2013.
Langer et al., Chemical and Physical Structure of Polymers as Carriers for Controlled Release of Bioactive Agents: A Review. J Macromol Sci, Part C, 1983;23(1):61-126. doi: 10.1080/07366578308079439.
Langer et al., Chemical and Physical Structure of Polymers as Carriers for Controlled Release of Bioactive Agents: A Review. Journal of Macromolecular Science, 2006;23(1):61-126. DOI: 10.1080/07366578308079439.
Langer et al., New methods of drug delivery. Science. Sep. 28, 1990;249(4976):1527-33.
Lapinaite et al., DNA capture by a CRISPR-Cas9-guided adenine base editor. Science. Jul. 31, 2020;369(6503):566-571. doi: 10.1126/science.abb1390.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lau et al., Molecular basis for discriminating between normal and damaged bases by the human alkyladenine glycosylase, AAG. Proc Natl Acad Sci U S A. Dec. 5, 2000;97(25):13573-8.
Lauer et al., Construction, characterization, and use of two Listeria monocytogenes site-specific phage integration vectors. J Bacteriol. Aug. 2002; 184(15):4177-86. doi: 10.1128/jb.184.15.4177-4186.2002.
Lavergne et al., Defects in type IIA von Willebrand disease: a cysteine 509 to arginine substitution in the mature von Willebrand factor disrupts a disulphide loop involved in the interaction with platelet glycoprotein Ib-IX. Br J Haematol. Sep. 1992;82(1):66-72.

Lawrence et al., Supercharging proteins can impart unusual resilience. J Am Chem Soc. Aug. 22, 2007;129(33): 10110-2. Epub Aug. 1, 2007.
Lawyer et al., High-level expression, purification, and enzymatic characterization of full-length Thermus aquaticus DNA polymerase and a truncated form deficient in 5' to 3' exonuclease activity. PCR Methods Appl. May 1993;2(4):275-87. doi: 10.1101/gr.2.4.275.
Lazar et al., Transforming growth factor alpha: mutation of aspartic acid 47 and leucine 48 results in different biological activities. Mol Cell Biol. Mar. 1988;8(3):1247-52.
Lazarevic et al., Nucleotide sequence of the Bacillus subtilis temperate bacteriophage SPbetac2. Microbiology (Reading). May 1999;145 ( Pt 5): 1055-1067. doi: 10.1099/13500872-145-5-1055.
Le et al., SMNDelta7, the major product of the centromeric survival motor neuron (SMN2) gene, extends survival in mice with spinal muscular atrophy and associates with full-length SMN. Hum Mol Genet. Mar. 15, 2005;14(6):845-57. doi: 10.1093/hmg/ddi078. Epub Feb. 9, 2005.
Le Grice et al., Purification and characterization of recombinant equine infectious anemia virus reverse transcriptase. J Virol. Dec. 1991;65(12):7004-7. doi: 10.1128/JVI.65.12.7004-7007.1991.
Leaver-Fay et al., ROSETTA3: an object-oriented software suite for the simulation and design of macromolecules. Methods Enzymol. 2011;487:545-74. doi: 10.1016/B978-0-12-381270-4.00019-6.
Leconte et al., A population-based experimental model for protein evolution: effects of mutation rate and selection stringency on evolutionary outcomes. Biochemistry. Feb. 26, 2013;52(8):1490-9. doi: 10.1021/bi3016185. Epub Feb. 14, 2013.
Ledford, Gene-editing hack yields pinpoint precision. Nature, Apr. 20, 2016. http://www.nature.com/news/gene-editing-hack-yields-pinpoint-precision-1.19773.
Lee et al., A chimeric thyroid hormone receptor constitutively bound to DNA requires retinoid X receptor for hormone-dependent transcriptional activation in yeast. Mol Endocrinol. Sep. 1994;8(9):1245-52.
Lee et al., A monoclonal antibody that targets a NaV1.7 channel voltage sensor for pain and itch relief. Cell. Jun. 5, 2014;157(6):1393-1404. doi: 10.1016/j.cell.2014.03.064. Epub May 22, 2014. Retraction in: Cell. Jun. 25, 2020;181(7):1695.
Lee et al., An allosteric self-splicing ribozyme triggered by a bacterial second messenger. Science. Aug. 13, 2010;329(5993):845-8. doi: 10.1126/science.1190713.
Lee et al., Failure to detect DNA-guided genome editing using Natronobacterium gregoryi Argonaute. Nat Biotechnol. Nov. 28, 2016;35(1):17-18. doi: 10.1038/nbt.3753.
Lee et al., Group I Intron-Based Therapeutics Through Trans-Splicing Reaction. Prog Mol Biol Transl Sci. 2018;159:79-100. doi: 10.1016/bs.pmbts.2018.07.001. Epub Aug. 9, 2018.
Lee et al., PIK3CA gene is frequently mutated in breast carcinomas and hepatocellular carcinomas. Oncogene. Feb. 17, 2005;24(8):1477-80.
Lee et al., Recognition of liposomes by cells: in vitro binding and endocytosis mediated by specific lipid headgroups and surface charge density. Biochim Biophys Acta. Jan. 31, 1992;1103(2):185-97.
Lee et al., Ribozyme Mediated gRNA Generation for In Vitro and In Vivo CRISPR/Cas9 Mutagenesis. PLoS One. Nov. 10, 2016;11(11):e0166020. doi: 10.1371/journal.pone.0166020. eCollection 2016.
Lee et al., Simultaneous targeting of linked loci in mouse embryos using base editing. Sci Rep. Feb. 7, 2019;9(1):1662. doi: 10.1038/s41598-018-33533-5.
Lee et al., Single C-to-T substitution using engineered APOBEC3G-nCas9 base editors with minimum genome- and transcriptome-wide off-target effects. Sci Adv. Jul. 15, 2020;6(29):eaba1773. doi: 10.1126/sciadv.aba1773.
Lee et al., Single C-to-T substitution using engineered APOBEC3G-nCas9 base editors with minimum genome- and transcriptome-wide off-target effects. Sci Adv. Jul. 15, 2020;6(29):eaba1773. doi: 10.1126/sciadv.aba1773. 13 pages.
Lee et al., Site-specific integration of mycobacteriophage L5: integration-proficient vectors for *Mycobacterium smegmatis, Mycobacterium*

(56) References Cited

OTHER PUBLICATIONS

*tuberculosis*, and bacille Calmette-Guérin. Proc Natl Acad Sci U S A. Apr. 15, 1991;88(8):3111-5. doi: 10.1073/pnas.88.8.3111.
Lee et al., Synthetically modified guide RNA and donor DNA are a versatile platform for CRISPR-Cas9 engineering. Elife. May 2, 2017;6:e25312. doi: 10.7554/eLife.25312.
Lee et al., Targeted chromosomal deletions in human cells using zinc finger nucleases. Genome Res. Jan. 2010 20: 81-89; Published in Advance Dec. 1, 2009, doi:10.1101/gr.099747.109.
Lee et al., Targeting fidelity of adenine and cytosine base editors in mouse embryos. Nat Commun. Nov. 15, 2018;9(1):4804. doi: 10.1038/s41467-018-07322-7.
Lee et al., Transcriptional regulation and its misregulation in disease. Cell. Mar. 14, 2013;152(6):1237-51. doi: 10.1016/j.cell. 2013.02.014.
Lefebvre et al., Identification and characterization of a spinal muscular atrophy-determining gene. Cell. Jan. 13, 1995;80(1):155-65. doi: 10.1016/0092-8674(95)90460-3.
Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.
Lei et al., Site-specificity of serine integrase demonstrated by the attB sequence preference of QBT1 integrase. FEBS Lett. Apr. 2018;592(8):1389-1399. doi: 10.1002/1873-3468.13023. Epub Mar. 25, 2018.
Leipold et al., A de novo gain-of-function mutation in SCN11A causes loss of pain perception. Nat Genet. Nov. 2013;45(11):1399-404. doi: 10.1038/ng.2767. Epub Sep. 15, 2013.
Lemos et al., CRISPR/Cas9 cleavages in budding yeast reveal templated insertions and strand-specific insertion/deletion profiles. Proc Natl Acad Sci U S A. Feb. 27, 2018;115(9):E2040-E2047. doi: 10.1073/pnas.1716855115. Epub Feb. 13, 2018.
Lenk et al., Pathogenic mechanism of the FIG4 mutation responsible for Charcot-Marie-Tooth disease CMT4J. PLoS Genet. Jun. 2011;7(6):e1002104. doi: 10.1371/journal.pgen.1002104. Epub Jun. 2, 2011.
Lesinski et al., The potential for targeting the STAT3 pathway as a novel therapy for melanoma. Future Oncol. Jul. 2013;9(7):925-7. doi: 10.2217/fon.13.83. Author Manuscript. 4 pages.
Levy et al., Cytosine and adenine base editing of the brain, liver, retina, heart and skeletal muscle of mice via adeno-associated viruses. Nat Biomed Eng. 2020;4(1):97-110. doi:10.1038/s41551-019-0501-5.
Levy et al., Inhibition of calcification of bioprosthetic heart valves by local controlled-release diphosphonate. Science. Apr. 12, 1985;228(4696):190-2.
Levy et al., Membrane-associated guanylate kinase dynamics reveal regional and developmental specificity of synapse stability. J Physiol. Mar. 1, 2017;595(5):1699-1709. doi: 10.1113/JP273147. Epub Jan. 18, 2017.
Lew et al., Protein splicing in vitro with a semisynthetic two-component minimal intein. J Biol Chem. Jun. 26, 1998;273(26):15887-90. doi: 10.1074/jbc.273.26.15887.
Lewis et al., A serum-resistant cytofectin for cellular delivery of antisense oligodeoxynucleotides and plasmid DNA. Proc Natl Acad Sci U S A. Apr. 16, 1996;93(8):3176-81.
Lewis et al., Building the Class 2 CRISPR-Cas Arsenal. Mol Cell 2017;65(3);377-379.
Lewis et al., Codon 129 polymorphism of the human prion protein influences the kinetics of amyloid formation. J Gen Virol. Aug. 2006;87(Pt 8):2443-9.
Lewis et al., Cytosine deamination and the precipitous decline of spontaneous mutation during Earth's history. Proc Natl Acad Sci U S A. Jul. 19, 2016;113(29):8194-9. doi: 10.1073/pnas.1607580113. Epub Jul. 5, 2016.
Lewis et al., RNA modifications and structures cooperate to guide RNA-protein interactions. Nat Rev Mol Cell Biol. Mar. 2017;18(3):202-210. doi: 10.1038/nrm.2016.163. Epub Feb. 1, 2017.

Li et al., A Radioactivity-Based Assay for Screening Human m6A-RNA Methyltransferase, METTL3-METTL14 Complex, and Demethylase ALKBH5. J Biomol Screen. Mar. 2016;21(3):290-7. doi: 10.1177/1087057115623264. Epub Dec. 23, 2015.
Li et al., Base editing with a Cpf1-cytidine deaminase fusion. Nat Biotechnol. Apr. 2018;36(4):324-327. doi: 10.1038/nbt.4102. Epub Mar. 19, 2018.
Li et al., Current approaches for engineering proteins with diverse biological properties. Adv Exp Med Biol. 2007;620:18-33.
Li et al., Disruption of splicing-regulatory elements using CRISPR/Cas9 to rescue spinal muscular atrophy in human iPSCs and mice. National Science Review. Jan. 1, 2020:92-101. DOI: 10.1093/nsr/nwz131. Retrieved from the Internet via https://academic.oup.com/nsr/article-pdf/7/1/92/33321439/nwz131.pdf. Last accessed Apr. 28, 2021.
Li et al., Fast and accurate short read alignment with Burrows-Wheeler transform. Bioinformatics. Jul. 15, 2009;25(14):1754-60. doi: 10.1093/bioinformatics/btp324. Epub May 18, 2009.
Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.
Li et al., Highly efficient and precise base editing in discarded human tripronuclear embryos. Protein Cell. Aug. 19, 2017. doi: 10.1007/s13238-017-0458-7. [Epub ahead of print].
Li et al., Lagging strand DNA synthesis at the eukaryotic replication fork involves binding and stimulation of FEN-1 by proliferating cell nuclear antigen. J Biol Chem. Sep. 22, 1995;270(38):22109-12. doi: 10.1074/jbc.270.38.22109.
Li et al., Loss of post-translational modification sites in disease. Pac Symp Biocomput. 2010:337-47. doi: 10.1142/9789814295291_0036.
Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.
Li et al., Multiplex and homologous recombination-mediated genome editing in *Arabidopsis* and Nicotiana benthamiana using guide RNA and Cas9. Nat Biotechnol. Aug. 2013;31(8):688-91. doi: 10.1038/nbt.2654.
Li et al., Precise Modifications of Both Exogenous and Endogenous Genes in Rice by Prime Editing. Mol Plant. May 4, 2020;13(5):671-674. doi: 10.1016/j.molp.2020.03.011. Epub Mar. 25, 2020.
Li et al., Programmable Single and Multiplex Base-Editing in Bombyx mori Using RNA-Guided Cytidine Deaminases. G3 (Bethesda). May 4, 2018;8(5):1701-1709. doi: 10.1534/g3.118.200134.
Li et al., Protein trans-splicing as a means for viral vector-mediated in vivo gene therapy. Hum Gene Ther. Sep. 2008;19(9):958-64. doi: 10.1089/hum.2008.009.
Li et al., RSEM: accurate transcript quantification from RNA-Seq data with or without a reference genome. BMC Bioinformatics. Aug. 4, 2011;12:323. doi: 10.1186/1471-2105-12-323.
Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.
Li, Mechanisms and functions of DNA mismatch repair. Cell Res. Jan. 2008;18(1):85-98. doi: 10.1038/cr.2007.115.
Liang et al., Correction of β-thalassemia mutant by base editor in human embryos. Protein Cell. Nov. 2017;8(11):811-822. doi: 10.1007/s13238-017-0475-6. Epub Sep. 23, 2017.
Liang et al., Homology-directed repair is a major double-strand break repair pathway in mammalian cells. Proc Natl Acad Sci U S A. Apr. 28, 1998;95(9):5172-7. doi: 10.1073/pnas.95.9.5172.
Liang et al., Rapid and highly efficient mammalian cell engineering via Cas9 protein transfection. Send to; J Biotechnol. Aug. 20, 2015;208:44-53. doi: 10.1016/j.jbiotec.2015.04.024.
Liao et al., One-step assembly of large CRISPR arrays enables multi-functional targeting and reveals constraints on array design. bioRxiv. May 2, 2018. doi: 10.1101/312421. 45 pages.
Lieber et al., Mechanism and regulation of human non-homologous DNA end-joining. Nat Rev Mol Cell Biol. Sep. 2003;4(9):712-20.
Liefke et al., The oxidative demethylase ALKBH3 marks hyperactive gene promoters in human cancer cells. Genome Med. Jun. 30, 2015;7(1):66. doi: 10.1186/s13073-015-0180-0.

(56) References Cited

OTHER PUBLICATIONS

Lienert et al., Two- and three-input TALE-based AND logic computation in embryonic stem cells. Nucleic Acids Res. Nov. 2013;41(21):9967-75. doi: 10.1093/nar/gkt758. Epub Aug. 27, 2013.
Lilley, D.M. The Varkud Satellite Ribozyme. RNA. Feb. 2004;10(2):151-8.doi: 10.1261/rna.5217104.
Lim et al., Crystal structure of the moloney murine leukemia virus RNase H domain. J Virol. Sep. 2006;80(17):8379-89. doi: 10.1128/JVI.00750-06.
Lim et al., Viral vectors for neurotrophic factor delivery: a gene therapy approach for neurodegenerative diseases of the CNS. Pharmacol Res. Jan. 2010;61(1):14-26. doi: 10.1016/j.phrs.2009.10.002. Epub Oct. 17, 2009.
Lin et al., [Construction and evaluation of DnaB split intein high expression vector and a six amino acids cyclic peptide library]. Sheng Wu Gong Cheng Xue Bao. Nov. 2008;24(11):1924-30. Chinese.
Lin et al., Base editing-mediated splicing correction therapy for spinal muscular atrophy. Cell Res. Jun. 2020;30(6):548-550. doi: 10.1038/s41422-020-0304-y. Epub Mar. 24, 2020.
Lin et al., Enhanced homology-directed human genome engineering by controlled timing of CRISPR/Cas9 delivery. Elife. Dec. 15, 2014;3:e04766. doi: 10.7554/eLife.04766.
Lin et al., Prime genome editing in rice and wheat. Nat Biotechnol. May 2020;38(5):582-585 and Supplemental Info. doi: 10.1038/s41587-020-0455-x. Epub Mar. 16, 2020. 8 pages.
Lin et al., Prime genome editing in rice and wheat. Nat Biotechnol. May 2020;38(5):582-585. doi: 10.1038/s41587-020-0455-x. Epub Mar. 16, 2020.
Lin et al., The human REV1 gene codes for a DNA template-dependent dCMP transferase. Nucleic Acids Res. Nov. 15, 1999;27(22):4468-75. doi: 10.1093/nar/27.22.4468.
Lindahl, T., Instability and decay of the primary structure of DNA. Nature. Apr. 22, 1993;362(6422):709-15. doi: 10.1038/362709a0.
Link et al., Engineering ligand-responsive gene-control elements: lessons learned from natural riboswitches. Gene Ther. Oct. 2009; 16(10):1189-201. doi: 10.1038/gt.2009.81. Epub Jul. 9, 2009. Review.
Liu et al., C2c1-sgRNA Complex Structure Reveals RNA-Guided DNA Cleavage Mechanism. Molecular Cell Jan. 2017;65(2):310-22.
Liu et al., Split dnaE genes encoding multiple novel inteins in Trichodesmium erythraeum. J Biol Chem. Jul. 18, 2003;278(29):26315-8. doi: 10.1074/jbc.C300202200. Epub May 24, 2003.
Liu et al., A METTL3-METTL14 complex mediates mammalian nuclear RNA N6-adenosine methylation. Nat Chem Biol. Feb. 2014;10(2):93-5. doi: 10.1038/nchembio.1432. Epub Dec. 6, 2013.
Liu et al., Adding new chemistries to the genetic code. Annu Rev Biochem. 2010;79:413-44. doi: 10.1146/annurev.biochem.052308. 105824.
Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.
Liu et al., Balancing AID and DNA repair during somatic hypermutation. Trends Immunol. Apr. 2009;30(4):173-81. doi: 10.1016/j.it. 2009.01.007.
Liu et al., Calcineurin is a common target of cyclophilin-cyclosporin A and FKBP-FK506 complexes. Cell. Aug. 23, 1991;66(4):807-15. doi: 10.1016/0092-8674(91)90124-h.
Liu et al., CasX enzymes comprise a distinct family of RNA-guided genome editors. Nature. Feb. 2019;566(7743):218-223. doi: 10.1038/s41586-019-0908-x. Epub Feb. 4, 2019. Author manuscript entitled CRISPR-CasX is an RNA-dominated enzyme active for human genome editing.
Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.
Liu et al., Computational approaches for effective CRISPR guide RNA design and evaluation. Comput Struct Biotechnol J. Nov. 29, 2019;18:35-44. doi: 10.1016/j.csbj.2019.11.006.

Liu et al., Design of polydactyl zinc-finger proteins for unique addressing within complex genomes. Proc Natl Acad Sci U S A. May 27, 1997;94(11):5525-30.
Liu et al., Direct Promoter Repression by BCL11A Controls the Fetal to Adult Hemoglobin Switch. Cell. Apr. 5, 2018;173(2):430-442.e17. doi: 10.1016/j.cell.2018.03.016. Epub Mar. 29, 2018.
Liu et al., Distance determination by GIY-YIG intron endonucleases: discrimination between repression and cleavage functions. Nucleic Acids Res. Mar. 31, 2006;34(6):1755-64. Print 2006.
Liu et al., Editing DNA Methylation in the Mammalian Genome. Cell. Sep. 22, 2016;167(1):233- 247.e17. doi: 10.1016/j.cell.2016. 08.056.
Liu et al., Engineering a tRNA and aminoacyl-tRNA synthetase for the site-specific incorporation of unnatural amino acids into proteins in vivo. Proc Natl Acad Sci U S A. Sep. 16, 1997;94(19):10092-7.
Liu et al., Fast Colorimetric Sensing of Adenosine and Cocaine Based on a General Sensor Design Involving Aptamers and Nanoparticles. Angew Chem. Dec. 16, 2006;45(1):90-4. DOI: 10.1002/anie.200502589.
Liu et al., Fast Colorimetric Sensing of Adenosine and Cocaine Based on a General Sensor Design Involving Aptamers and Nanoparticles. Angew Chem. 2006;118(1):96-100.
Liu et al., Flap endonuclease 1: a central component of DNA metabolism. Annu Rev Biochem. 2004;73:589-615. doi:10.1146/annurev.biochem.73.012803.092453.
Liu et al., Functional Nucleic Acid Sensors. Chem Rev. May 2009;109(5):1948-98. doi: 10.1021/cr030183i.
Liu et al., Genetic incorporation of unnatural amino acids into proteins in mammalian cells. Nat Methods. Mar. 2007;4(3):239-44. Epub Feb. 25, 2007.
Liu et al., Highly efficient RNA-guided base editing in rabbit. Nat Commun. Jul. 13, 2018;9(1):2717. doi: 10.1038/s41467-018-05232-2.
Liu et al., Human BRCA2 protein promotes RAD51 filament formation on RPA-covered single-stranded DNA. Nat Struct Mol Biol. Oct. 2010; 17(10):1260-2. doi: 10.1038/nsmb.1904. Epub Aug. 22, 2010.
Liu et al., Improving Editing Efficiency for the Sequences with NGH PAM Using xCas9-Derived Base Editors. Mol Ther Nucleic Acids. Sep. 6, 2019;17:626-635. doi: 10.1016/j.omtn.2019.06.024. Epub Jul. 12, 2019.
Liu et al., Intrinsic Nucleotide Preference of Diversifying Base Editors Guides Antibody Ex Vivo Affinity Maturation. Cell Rep. Oct. 23, 2018;25(4):884-892.e3. doi: 10.1016/j.celrep.2018.09.090.
Liu et al., N(6)-methyladenosine-dependent RNA structural switches regulate RNA-protein interactions. Nature. Feb. 26, 2015;518(7540):560-4. doi: 10.1038/nature14234.
Liu et al., Probing N6-methyladenosine RNA modification status at single nucleotide resolution in mRNA and long noncoding RNA. RNA. Dec. 2013;19(12):1848-56. doi: 10.1261/rna.041178.113. Epub Oct. 18, 2013.
Liu et al., Reverse transcriptase of foamy virus. Purification of the enzymes and immunological identification. Arch Virol. 1977;55(3):187-200. doi: 10.1007/BF01319905.
Liu et al., Reverse transcriptase-mediated tropism switching in Bordetella bacteriophage. Science. Mar. 15, 2002;295(5562):2091-4. doi: 10.1126/science.1067467.
Liu et al., *Saccharomyces cerevisiae* flap endonuclease 1 uses flap equilibration to maintain triplet repeat stability. Mol Cell Biol. May 2004;24(9):4049-64. doi: 10.1128/MCB.24.9.4049-4064.2004.
Liu et al., The Molecular Architecture for RNA-Guided RNA Cleavage by Cas13a. Cell. Aug. 10, 2017;170(4):714-726.e10. doi: 10.1016/j.cell.2017.06.050. Epub Jul. 27, 2017.
Liu et al., Usherin is required for maintenance of retinal photoreceptors and normal development of cochlear hair cells. Proc Natl Acad Sci U S A. Mar. 13, 2007;104(11):4413-8. doi: 10.1073/pnas. 0610950104. Epub Mar. 5, 2007.
Loessner et al., Complete nucleotide sequence, molecular analysis and genome structure of bacteriophage A118 of Listeria monocytogenes: implications for phage evolution. Mol Microbiol. Jan. 2000;35(2):324-40. doi: 10.1046/j.1365-2958.2000.01720.x.

(56) References Cited

OTHER PUBLICATIONS

Lombardo et al., Gene editing in human stem cells using zinc finger nucleases and integrase-defective lentiviral vector delivery. Nat Biotechnol. Nov. 2007;25(11):1298-306. Epub Oct. 28, 2007.
Long et al., Postnatal genome editing partially restores dystrophin expression in a mouse model of muscular dystrophy. Science. Jan. 22, 2016;351(6271):400-3. doi: 10.1126/science.aad5725. Epub Dec. 31, 2015.
Lopez-Girona et al., Cereblon is a direct protein target for immunomodulatory and antiproliferative activities of lenalidomide and pomalidomide. Leukemia. Nov. 2012;26(11):2326-35. doi: 10.1038/leu.2012.119. Epub May 3, 2012.
Lorenz et al., ViennaRNA Package 2.0. Algorithms Mol Biol. Nov. 24, 2011;6:26. doi: 10.1186/1748-7188-6-26.
Lorson et al., A single nucleotide in the SMN gene regulates splicing and is responsible for spinal muscular atrophy. Proc Natl Acad Sci U S A. May 25, 1999;96(11):6307-11. doi: 10.1073/pnas.96.11.6307.
Losey et al., Crystal structure of *Staphylococcus sureus* tRNA adenosine deaminase tadA in complex with RNA. Nature Struct. Mol. Biol. Feb. 2006;13(2):153-9.
Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.
Luan et al., Reverse transcription of R2Bm RNA is primed by a nick at the chromosomal target site: a mechanism for non-LTR retrotransposition. Cell. Feb. 26, 1993;72(4):595-605. doi: 10.1016/0092-8674(93)90078-5.
Luckow et al., High level expression of nonfused foreign genes with Autographa californica nuclear polyhedrosis virus expression vectors. Virology. May 1989;170(1):31-9. doi: 10.1016/0042-6822(89)90348-6.
Lukacsovich et al., Repair of a specific double-strand break generated within a mammalian chromosome by yeast endonuclease I-SceI. Nucleic Acids Res. Dec. 25, 1994;22(25):5649-57. doi: 10.1093/nar/22.25.5649.
Lundberg et al., Delivery of short interfering RNA using endosomolytic cell-penetrating peptides. FASEB J. Sep. 2007;21(11):2664-71. Epub Apr. 26, 2007.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.
Lutz et al., Postsymptomatic restoration of SMN rescues the disease phenotype in a mouse model of severe spinal muscular atrophy. J Clin Invest. Aug. 2011;121(8):3029-41. doi: 10.1172/JCI57291. Epub Jul. 25, 2011.
Lynch, Evolution of the mutation rate. Trends Genet. Aug. 2010;26(8):345-52. doi: 10.1016/j.tig.2010.05.003. Epub Jun. 30, 2010.
Lyons et al., Efficient Recognition of an Unpaired Lesion by a DNA Repair Glycosylase. J. Am. Chem. Soc., 2009;131(49):17742-3. DOI: 10.1021/ja908378y.
Luke et al., Partial purification and characterization of the reverse transcriptase of the simian immunodeficiency virus TYO-7 isolated from an African green monkey. Biochemistry. Feb. 20, 1990;29(7):1764-9. doi: 10.1021/bi00459a015.
Ma et al., Human RAD52 interactions with replication protein A and the RAD51 presynaptic complex. J Biol Chem. Jul. 14, 2017;292(28):11702-11713. doi: 10.1074/jbc.M117.794545. Epub May 27, 2017.
Ma et al., Identification of pseudo attP sites for phage phiC31 integrase in bovine genome. Biochem Biophys Res Commun. Jul. 7, 2006;345(3):984-8. doi: 10.1016/j.bbrc.2006.04.145. Epub May 3, 2006.
Ma et al., In vitro protein engineering using synthetic tRNA(Ala) with different anticodons. Biochemistry. Aug. 10, 1993;32(31):7939-45.

Ma et al., PhiC31 integrase induces efficient site-specific recombination in the Capra hircus genome. DNA Cell Biol. Aug. 2014;33(8):484-91. doi: 10.1089/dna.2013.2124. Epub Apr. 22, 2014.
Ma et al., Single-Stranded DNA Cleavage by Divergent CRISPR-Cas9 Enzymes. Mol Cell. Nov. 5, 2015;60(3):398-407. doi: 10.1016/j.molcel.2015.10.030.
Ma et al., Targeted AID-mediated mutagenesis (TAM) enables efficient genomic diversification in mammalian cells. Nature Methods. Oct. 2016; 13:1029-35. doi:10.1038/nmeth.4027.
Maas et al., Identification and characterization of a human tRNA-specific adenosine deaminase related to the ADAR family of pre-mRNA editing enzymes. Proc Natl Acad Sci U S A. Aug. 3, 1999;96(16):8895-900. doi: 10.1073/pnas.96.16.8895.
MacBeth et al., Inositol hexakisphosphate is bound in the ADAR2 core and required for RNA editing. Science. Sep. 2, 2005;309(5740):1534-9. doi: 10.1126/science.1113150.
MacFadden et al., Mechanism and structural diversity of exoribonuclease-resistant RNA structures in flaviviral RNAs. Nat Commun. Jan. 9, 2018;9(1):119. doi: 10.1038/s41467-017-02604-y.
MacRae et al., Ribonuclease revisited: structural insights into ribonuclease III family enzymes. Curr Opin Struct Biol. Feb. 2007;17(1):138-45. doi: 10.1016/j.sbi.2006.12.002. Epub Dec. 27, 2006.
Madura et al., Structural basis for ineffective T-cell responses to MHC anchor residue-improved "heteroclitic" peptides. Eur J Immunol. Feb. 2015;45(2):584-91. doi: 10.1002/eji.201445114. Epub Dec. 28, 2014.
Maeder et al., CRISPR RNA-guided activation of endogenous human genes. Nat Methods. Oct. 2013;10(10):977-9. doi: 10.1038/nmeth.2598. Epub Jul. 25, 2013.
Maeder et al., Rapid "open-source" engineering of customized zinc-finger nucleases for highly efficient gene modification. Mol Cell. Jul. 25, 2008;31(2):294-301. doi:10.1016/j.molcel.2008.06.016.
Maeder et al., Robust, synergistic regulation of human gene expression using TALE activators. Nat Methods. Mar. 2013;10(3):243-5. doi: 10.1038/nmeth.2366. Epub Feb. 10, 2013.
Maerker et al., A novel Usher protein network at the periciliary reloading point between molecular transport machineries in vertebrate photoreceptor cells. Hum Mol Genet. Jan. 1, 2008;17(1):71-86. doi: 10.1093/hmg/ddm285. Epub Sep. 28, 2007.
Magin et al., Corf, the Rev/Rex homologue of HTDV/HERV-K, encodes an arginine-rich nuclear localization signal that exerts a trans-dominant phenotype when mutated. Virology. Aug. 15, 2000;274(1):11-6. doi: 10.1006/viro.2000.0438.
Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.
Maizels et al., Initiation of homologous recombination at DNA nicks. Nucleic Acids Res. Aug. 21, 2018;46(14):6962-6973. doi: 10.1093/nar/gky588.
Maji et al., A High-Throughput Platform to Identify Small-Molecule Inhibitors of CRISPR-Cas9. Cell. May 2, 2019;177(4): 1067-1079. e19. doi: 10.1016/j.cell.2019.04.009.
Makarova et al., An updated evolutionary classification of CRISPR-Cas systems. Nat Rev Microbiol. Nov. 2015;13(11):722-36. doi: 10.1038/nrmicro3569. Epub Sep. 28, 2015.
Makarova et al., Classification and Nomenclature of CRISPR-Cas Systems: Where from Here? CRISPR J. Oct. 2018;1(5):325-336. doi: 10.1089/crispr.2018.0033.
Makarova et al., Evolution and classification of the CRISPR-Cas systems. Nat Rev Microbiol. Jun. 2011;9(6):467-77. doi: 10.1038/nrmicro2577. Epub May 9, 2011.
Makarova et al., Prokaryotic homologs of Argonaute proteins are predicted to function as key components of a novel system of defense against mobile genetic elements. Biology Direct 2009;4:29. doi: 10.1186/1745-6150-4-29.
Makeyev et al., Evolutionary potential of an RNA virus. J Virol. Feb. 2004;78(4):2114-20.

(56) References Cited

OTHER PUBLICATIONS

Malashkevich et al., Crystal structure of tRNA adenosine deaminase TadA from *Escherichia coli*. Deposited: Mar. 10, 2005 Released: Feb. 21, 2006 doi:10.2210/pdb1z3a/pdb (2006).
Mali et al., Cas9 as a versatile tool for engineeringbiology. Nat Methods. Oct. 2013;10(10):957-63. doi: 10.1038/nmeth.2649.
Mali et al., CAS9 transcriptional activators for target specificity screening and paired nickases for cooperative genome engineering. Nat Biotechnol. Sep. 2013;31(9):833-8, Supplemental Info. doi: 10.1038/nbt.2675. Epub Aug. 1, 2013.
Mali et al., RNA-guided human genome engineering via Cas9. Science. Feb. 15, 2013;339(6121):823-6. doi: 10.1126/science. 1232033. Epub Jan. 3, 2013.
Malito et al., Structural basis for lack of toxicity of the diphtheria toxin mutant CRM197. Proc Natl Acad Sci U S A. Apr. 3, 2012;109(14):5229-34. doi: 10.1073/pnas. 1201964109. Epub Mar. 19, 2012.
Mandal et al., Efficient ablation of genes in human hematopoietic stem and effector cells using CRISPR/Cas9. Cell Stem Cell. Nov. 6, 2014;15(5):643-52. doi: 10.1016/j.stem.2014.10.004. Epub Nov. 6, 2014.
Mandal et al., Riboswitches Control Fundamental Biochemical Pathways in Bacillus Subtilis and Other Bacteria. Cell. May 30, 2003;113(5):577-86. doi: 10.1016/s0092-8674(03)00391-x.
Mangeot et al., Genome editing in primary cells and in vivo using viral-derived Nanoblades loaded with Cas9-sgRNA ribonucleoproteins. Nat Commun. Jan. 3, 2019;10(1):45. doi: 10.1038/s41467-018-07845-z.
Mani et al., Design, engineering, and characterization of zinc finger nucleases. Biochem Biophys Res Commun. Sep. 23, 2005;335(2):447-57.
Marceau, Functions of single-strand DNA-binding proteins in DNA replication, recombination, and repair. Methods Mol Biol. 2012;922:1-21. doi: 10.1007/978-1-62703-032-8_1.
Marcovitz et al., Frustration in protein-DNA binding influences conformational switching and target search kinetics. Proc Natl Acad Sci U S A. Nov. 1, 2011;108(44):17957-62. doi: 10.1073/pnas. 1109594108. Epub Oct. 14, 2011.
Maresca et al., Obligate ligation-gated recombination (ObLiGaRe): custom-designed nuclease-mediated targeted integration through nonhomologous end joining. Genome Res. Mar. 2013;23(3):539-46. Doi: 10.1101/gr.145441.112. Epub Nov. 14, 2012.
Marioni et al., DNA methylation age of blood predicts all-cause mortality in later life. Genome Biol. Jan. 30, 2015;16:25. doi: 10.1186/s13059-015-0584-6.
Marquart et al., Predicting base editing outcomes with an attention-based deep learning algorithm trained on high-throughput target library screeen. bioRxiv. Jul. 5, 2020. DOI:10.1101/2020.07.05. 186544. Retrieved from the Internet via https://www.biorxiv.org/content/10.1101/2020.07.05.186544v1.full.pdf lased accessed on Apr. 28, 2021.
Marraffini et al., CRISPR interference limits horizontal gene transfer in staphylococci by targeting DNA. Science. Dec. 19, 2008;322(5909):1843-5. doi: 10.1126/science.1165771.
Marsden et al., The Tumor-Associated Variant RAD51 G151D Induces a Hyper- Recombination Phenotype. PLoS Genet. Aug. 11, 2016;12(8):e1006208. doi: 10.1371/journal.pgen.1006208.
Martinez et al., Hypermutagenesis of RNA using human immunodeficiency virus type 1 reverse transcriptase and biased dNTP concentrations. Proc Natl Acad Sci U S A. Dec. 6, 1994;91(25):11787-91. doi: 10.1073/pnas.91.25.11787.
Martsolf et al., Complete trisomy 17p a relatively new syndrome. Ann Genet. 1988;31(3):172-4.
Martz, L., Nav-i-gating antibodies for pain. Science-Business eXchange. Jun. 12, 2014;7(662):1-2. doi: 10.1038/scibx.2014.662.
Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.
Marzec et al., Prime Editing: A New Way for Genome Editing. Trends Cell Biol. Apr. 2020;30(4):257-259. doi: 10.1016/j.tcb.2020. 01.004. Epub Jan. 27, 2020.
Mascola et al., HIV-1 neutralizing antibodies: understanding nature's pathways. Immunol Rev. Jul. 2013;254(1):225-44. doi: 10.1111/imr. 12075.
Mason et al., Non-enzymatic roles of human RAD51 at stalled replication forks. bioRxiv. Jul. 31, 2019; doi.org/10.1101/359380. 36 pages. bioRxiv preprint first posted online Jul. 31, 2019.
Mathys et al., Characterization of a self-splicing mini-intein and its conversion into autocatalytic N- and C-terminal cleavage elements: facile production of protein building blocks for protein ligation. Gene. Apr. 29, 1999;231(1-2):1-13. doi: 10.1016/s0378-1119(99)00103-1.
Matsuura et al., A gene essential for the site-specific excision of actinophage r4 prophage genome from the chromosome of a lysogen. J Gen Appl Microbiol. 1995;41(1):53-61.
Matthews, Structures of human ADAR2 bound to dsRNA reveal base-flipping mechanism and basis for site selectivity. Nat Struct Mol Biol. May 2016;23(5):426-33. doi: 10.1038/nsmb.3203. Epub Apr. 11, 2016.
May et al., Emergent lineages of mumps virus suggest the need for a polyvalent vaccine. Int J Infect Dis. Jan. 2018;66:1-4. doi: 10.1016/j.ijid.2017.09.024. Epub Oct. 4, 2017.
McCarroll et al., Copy-number variation and association studies of human disease. Nat Genet. Jul. 2007;39(7 Suppl):S37-42. doi: 10.1038/ng2080.
McDonald et al., Characterization of mutations at the mouse phenylalanine hydroxylase locus. Genomics. Feb. 1, 1997;39(3):402-5. doi: 10.1006/geno.1996.4508.
McInerney et al., Error Rate Comparison during Polymerase Chain Reaction by DNA Polymerase. Mol Biol Int. 2014;2014:287430. doi: 10.1155/2014/287430. Epub Aug. 17, 2014.
McKenna et al., Recording development with single cell dynamic lineage tracing. Development. Jun. 27, 2019;146(12):dev169730. doi: 10.1242/dev.169730.
McKenna et al., Whole-organism lineage tracing by combinatorial and cumulative genome editing. Science. Jul. 29, 2016;353(6298):aaf7907. doi: 10.1126/science.aaf7907. Epub May 26, 2016.
McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas. 0807883106. Epub Mar. 23, 2009.
McVey et al., MMEJ repair of double-strand breaks (director's cut): deleted sequences and alternative endings. Trends Genet. Nov. 2008;24(11):529-38. doi: 10.1016/j.tig.2008.08.007. Epub Sep. 21, 2008.
Mead et al., A novel protective prion protein variant that colocalizes with kuru exposure. N Engl J Med. Nov. 19, 2009;361(21):2056-65. doi: 10.1056/NEJMoa0809716.
Mei et al., Recent Progress in CRISPR/Cas9 Technology. J Genet Genomics. Feb. 20, 2016;43(2):63-75. doi: 10.1016/j.jgg.2016.01. 001. Epub Jan. 18, 2016.
Meinke et al., Cre Recombinase and Other Tyrosine Recombinases. Chem Rev. Oct. 26, 2016;116(20):12785-12820. doi: 10.1021/acs. chemrev.6b00077. Epub May 10, 2016.
Mendell et al., Single-Dose Gene-Replacement Therapy for Spinal Muscular Atrophy. N Engl J Med. Nov. 2, 2017;377(18):1713-1722. doi: 10.1056/NEJMoa1706198.
Meng et al., Targeted gene inactivation in zebrafish using engineered zinc-finger nucleases. Nat Biotechnol. Jun. 2008;26(6):695-701. doi: 10.1038/nbt1398. Epub May 25, 2008.
Menéndez-Arias, Mutation rates and intrinsic fidelity of retroviral reverse transcriptases. Viruses. Dec. 2009;1(3):1137-65. doi: 10.3390/v1031137. Epub Dec. 4, 2009.
Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.
Mertens et al., Site-specific recombination in bacteriophage Mu: characterization of binding sites for the DNA invertase Gin. EMBO J. Apr. 1988;7(4):1219-27.

(56) References Cited

OTHER PUBLICATIONS

Meyer et al., Breathing life into polycations: functionalization with pH-responsive endosomolytic peptides and polyethylene glycol enables siRNA delivery. J Am Chem Soc. Mar. 19, 2008;130(11):3272-3. doi: 10.1021/ja710344v. Epub Feb. 21, 2008.
Meyer et al., Comprehensive analysis of mRNA methylation reveals enrichment in 3' UTRs and near stop codons. Cell. Jun. 22, 2012;149(7):1635-46. doi: 10.1016/j.cell.2012.05.003. Epub May 17, 2012.
Meyer et al., Confirmation of a second natural preQ1 aptamer class in Streptococcaceae bacteria. RNA. Apr. 2008;14(4):685-95. doi: 10.1261/rna.937308. Epub Feb. 27, 2008.
Meyer et al., Library generation by gene shuffling. Curr Protoc Mol Biol. Jan. 6, 2014;105:Unit 15.12.. doi: 10.1002/0471142727. mb1512s105.
Meyer et al., Ribosome biogenesis factor Tsr3 is the aminocarboxypropyl transferase responsible for 18S rRNA hypermodification in yeast and humans. Nucleic Acids Res. May 19, 2016;44(9):4304-16. doi: 10.1093/nar/gkw244. Epub Apr. 15, 2016.
Meyer et al., The dynamic epitranscriptome: N6-methyladenosine and gene expression control. Nat Rev Mol Cell Biol. May 2014; 15(5):313-26. doi: 10.1038/nrm3785. Epub Apr. 9, 2014.
Michel et al., Mitochondrial class II introns encode proteins related to the reverse transcriptases of retroviruses. Nature. Aug. 15-21, 1985;316(6029):641-3. doi: 10.1038/316641a0.
Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.1476-5381.2009.00288.x.
Mihai et al., PTEN inhibition improves wound healing in lung epithelia through changes in cellular mechanics that enhance migration. Am J Physiol Lung Cell Mol Physiol. 2012;302(3):L287-L299.
Mijakovic et al., Bacterial single-stranded DNA-binding proteins are phosphorylated on tyrosine. Nucleic Acids Res. Mar. 20, 2006;34(5):1588-96. doi: 10.1093/nar/gkj514.
Miller et al., A TALE nuclease architecture for efficient genome editing. Nat Biotechnol. Feb. 2011;29(2):143-8. doi:10.1038/nbt.1755. Epub Dec. 22, 2010.
Miller et al., An improved zinc-finger nuclease architecture for highly specific genome editing. Nat Biotechnol. Jul. 2007;25(7):778-85. Epub Jul. 1, 2007.
Miller et al., Construction and properties of retrovirus packaging cells based on gibbon ape leukemia virus. J Virol. May 1991;65(5):2220-4. doi: 10.1128/JVI.65.5.2220-2224.1991.
Miller et al., Continuous evolution of SpCas9 variants compatible with non-G PAMs. Nat Biotechnol. Apr. 2020;38(4):471-481. doi: 10.1038/s41587-020-0412-8. Epub Feb. 10, 2020.
Miller, Human gene therapy comes of age. Nature. Jun. 11, 1992;357(6378):455-60. doi: 10.1038/357455a0.
Millevoi et al., G-quadruplexes in RNA biology. Wiley Interdiscip Rev RNA. Jul.-Aug. 2012;3(4):495-507. doi: 10.1002/wrna.1113. Epub Apr. 4, 2012.
Mills et al., Protein splicing in trans by purified N- and C-terminal fragments of the Mycobacterium tuberculosis RecA intein. Proc Natl Acad Sci U S A. Mar. 31, 1998;95(7):3543-8. doi: 10.1073/pnas.95.7.3543.
Min et al., Deep learning in bioinformatics. Brief Bioinform. Sep. 1, 2017;18(5):851-869. doi: 10.1093/bib/bbw068.
Minoche et al., Evaluation of genomic high-throughput sequencing data generated on Illumina HiSeq and genome analyzer systems. Genome Biol. Nov. 8, 2011;12(11):R112. doi: 10.1186/GB-2011-12-11-r112.
Minoretti et al., A W148R mutation in the human FOXD4 gene segregating with dilated cardiomyopathy, obsessive-compulsive disorder, and suicidality. Int J Mol Med. Mar. 2007;19(3):369-72.
Mir et al., Two Active Site Divalent Ions in the Crystal Structure of the Hammerhead Ribozyme Bound to a Transition State Analogue. Biochemistry. . Feb. 2, 2016;55(4):633-6. doi: 10.1021/acs.biochem.5b01139. Epub Jan. 19, 2016.
Mir et al., Type II-C CRISPR-Cas9 Biology, Mechanism, and Application. ACS Chem Biol. Feb. 16, 2018;13(2):357-365. doi: 10.1021/acschembio.7b00855. Epub Dec. 20, 2017.
Mishina et al., Conditional gene targeting on the pure C57BL/6 genetic background. Neurosci Res. Jun. 2007;58(2):105-12. doi: 10.1016/j.neures.2007.01.004. Epub Jan. 18, 2007.
Mitani et al., Delivering therapeutic genes—matching approach and application. Trends Biotechnol. May 1993;11(5):162-6. doi: 10.1016/0167-7799(93)90108-L.
Mitton-Fry et al., Poly(A) tail recognition by a viral RNA element through assembly of a triple helix. Science. Nov. 26, 2010;330(6008):1244-7. doi: 10.1126/science.1195858.
Miyaoka et al., Systematic quantification of HDR and NHEJ reveals effects of locus, nuclease, and cell type on genome-editing. Sci Rep. Mar. 31, 2016;6:23549. doi: 10.1038/srep23549.
Moede et al., Identification of a nuclear localization signal, RRMKWKK, in the homeodomain transcription factor PDX-1. Febs Lett. Nov. 19, 1999;461(3):229-34. doi: 10.1016/s0014-5793(99)01446-5.
Mohr et al., A Reverse Transcriptase-Cas1 Fusion Protein Contains a Cas6 Domain Required for Both Crispr RNA Biogenesis and RNA Spacer Acquisition. Mol Cell. Nov. 15, 2018;72(4):700-714.e8. doi: 10.1016/j.molcel.2018.09.013. Epub Oct. 18, 2018. Including Supplemental Information.
Mohr et al., Thermostable group II intron reverse transcriptase fusion proteins and their use in cDNA synthesis and next-generation RNA sequencing. RNA. Jul. 2013;19(7):958-70. doi: 10.1261/rna.039743.113. Epub May 22, 2013.
Mojica et al., Intervening sequences of regularly spaced prokaryotic repeats derive from foreign genetic elements. J Mol Evol. Feb. 2005;60(2):174-82.
Mok et al., A bacterial cytidine deaminase toxin enables CRISPR-free mitochondrial base editing. Nature. Jul. 2020;583(7817):631-637. doi: 10.1038/s41586-020-2477-4. Epub Jul. 8, 2020.
Mol et al., Crystal structure and mutational analysis of human uracil-DNA glycosylase: structural basis for specificity and catalysis. Cell. Mar. 24, 1995;80(6):869-78. doi: 10.1016/0092-8674(95)90290-2.
Mol et al., Crystal structure of human uracil-DNA glycosylase in complex with a protein inhibitor: protein mimicry of DNA. Cell. Sep. 8, 1995;82(5):701-8.
Molla et al., CRISPR/Cas-Mediated Base Editing: Technical Considerations and Practical Applications. Trends Biotechnol. Oct. 2019;37(10):1121-1142. doi: 10.1016/j.tibtech.2019.03.008. Epub Apr. 14, 2019.
Monahan et al., Site-specific incorporation of unnatural amino acids into receptors expressed in Mammalian cells. Chem Biol. Jun. 2003;10(6):573-80.
Monani et al., A single nucleotide difference that alters splicing patterns distinguishes the SMA gene SMN1 from the copy gene SMN2. Hum Mol Genet. Jul. 1999;8(7):1177-83. doi: 10.1093/hmg/8.7.1177.
Monot et al., The specificity and flexibility of l1 reverse transcription priming at imperfect T-tracts. PLoS Genet. May 2013;9(5):e1003499. doi: 10.1371/journal.pgen.1003499. Epub May 9, 2013.
Montange et al., Structure of the S-adenosylmethionine riboswitch regulatory mRNA element. Nature. Jun. 29, 2006;441(7097):1172-5.
Moore et al., Improved somatic mutagenesis in zebrafish using transcription activator-like effector nucleases (TALENs). PLoS One. 2012;7(5):e37877. Doi: 10.1371/journal.pone.0037877. Epub May 24, 2012.
Mootz et al., Conditional protein splicing: a new tool to control protein structure and function in vitro and in vivo. J Am Chem Soc. Sep. 3, 2003;125(35):10561-9.
Mootz et al., Protein splicing triggered by a small molecule. J Am Chem Soc. Aug. 7, 2002;124(31):9044-5 and Supporting Information. doi: 10.1021/ja0267690. 4 pages.
Mootz et al., Protein splicing triggered by a small molecule. J Am Chem Soc. Aug. 7, 2002;124(31):9044-5.
Morbitzer et al., Assembly of custom TALE-type DNA binding domains by modular cloning. Nucleic Acids Res. Jul. 2011;39(13):5790-9. doi: 10.1093/nar/gkr151. Epub Mar. 18, 2011.

(56) References Cited

OTHER PUBLICATIONS

Moreno-Mateos et al., CRISPRscan: designing highly efficient sgRNAs for CRISPR-Cas9 targeting in vivo. Nat Methods. Oct. 2015;12(10):982-8. doi: 10.1038/nmeth.3543. Epub Aug. 31, 2015.
Morita et al., The site-specific recombination system of actinophage TG1. FEMS Microbiol Lett. Aug. 2009;297(2):234-40. doi: 10.1111/j.1574-6968.2009.01683.x.
Morris et al., A peptide carrier for the delivery of biologically active proteins into mammalian cells. Nat Biotechnol. Dec. 2001;19(12):1173-6.
Moscou et al., A simple cipher governs DNA recognition by TAL effectors. Science. Dec. 11, 2009;326(5959):1501. doi: 10.1126/science.1178817.
Mougiakos et al., Characterizing a thermostable Cas9 for bacterial genome editing and silencing. Nat Commun. Nov. 21, 2017;8(1):1647. doi: 10.1038/s41467-017-01591-4.
Muir et al., Expressed protein ligation: a general method for protein engineering. Proc Natl Acad Sci U S A. Jun. 9, 1998;95(12):6705-10. doi: 10.1073/pnas.95.12.6705.
Muller et al., Nucleotide exchange and excision technology (NExT) DNA shuffling: a robust method for DNA fragmentation and directed evolution. Nucleic Acids Res. Aug. 1, 2005;33(13):e117. doi: 10.1093/nar/gni116. PMID: 16061932; PMCID: PMC1182171.
Muller, U.F., Design and Experimental Evolution of trans-Splicing Group I Intron Ribozymes. Molecules. Jan. 2, 2017;22(1):75. doi: 10.3390/molecules22010075.
Mullins et al., Transgenesis in nonmurine species. Hypertension. Oct. 1993;22(4):630-3.
Mumtsidu et al., Structural features of the single-stranded DNA-binding protein of Epstein-Barr virus. J Struct Biol. Feb. 2008;161(2):172-87. doi: 10.1016/j.jsb.2007.10.014. Epub Nov. 1, 2007.
Murphy, Phage recombinases and their applications. Adv Virus Res. 2012;83:367-414. doi: 10.1016/B978-0-12-394438-2.00008-6. Review.
Murray et al., Selective vulnerability of motor neurons and dissociation of pre- and post-synaptic pathology at the neuromuscular junction in mouse models of spinal muscular atrophy. Hum Mol Genet. Apr. 1, 2008;17(7):949-62. doi: 10.1093/hmg/ddm367. Epub Dec. 8, 2007.
Murugan et al., The Revolution Continues: Newly Discovered Systems Expand the CRISPR-Cas Toolkit. Mol Cell. Oct. 5, 2017;68(1):15-25. doi: 10.1016/j.molcel.2017.09.007.
Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Muzyczka et al., Adeno-associated virus (AAV) vectors: will they work? J Clin Invest. Oct. 1994;94(4):1351. doi: 10.1172/JCI117468.
Myerowitz et al., The major defect in Ashkenazi Jews with Tay-Sachs disease is an insertion in the gene for the alpha-chain of beta-hexosaminidase. J Biol Chem. Dec. 15, 1988;263(35):18587-9.
Myers et al., Insulin signal transduction and the IRS proteins. Annu Rev Pharmacol Toxicol. 1996;36:615-58. doi: 10.1146/annurev.pa.36.040196.003151.
Nabel et al., Direct gene transfer for immunotherapy and immunization. Trends Biotechnol. May 1993;11(5):211-5. doi: 10.1016/0167-7799(93)90117-R.
Nahar et al., A G-quadruplex motif at the 3' end of sgRNAs improves CRISPR-Cas9 based genome editing efficiency. Chem Commun (Camb). Mar. 7, 2018;54(19):2377-2380. doi: 10.1039/c7cc08893k. Epub Feb. 16, 2018.
Nahvi et al., Coenzyme B12 riboswitches are widespread genetic control elements in prokaryotes. Nucleic Acids Res. Jan. 2, 2004;32(1):143-50.
Nakade et al., Microhomology-mediated end-joining-dependent integration of donor DNA in cells and animals using TALENs and CRISPR/Cas9. Nat Commun. Nov. 20, 2014;5:5560. doi: 10.1038/ncomms6560.
Nakamura et al., Codon usage tabulated from international DNA sequence databases: status for the year 2000. Nucleic Acids Res. Jan. 1, 2000;28(1):292. doi: 10.1093/nar/28.1.292.
Naorem et al., DGR mutagenic transposition occurs via hypermutagenic reverse transcription primed by nicked template RNA. Proc Natl Acad Sci U S A. Nov. 21, 2017;114(47):E10187-E10195. doi: 10.1073/pnas.1715952114. Epub Nov. 6, 2017.
Narayanan et al., Clamping down on weak terminal base pairs: oligonucleotides with molecular caps as fidelity-enhancing elements at the 5'- and 3'-terminal residues. Nucleic Acids Res. May 2, 20040;32(9):2901-11. Print 2004.
Navaratnam et al., An overview of cytidine deaminases. Int J Hematol. Apr. 2006;83(3):195-200.
NCBI Reference Sequence: NM_002427.3. Wu et al., May 3, 2014. 5 pages.
Neel et al., Riboswitches: Classification, function and in silico approach, International Journal of Pharma Sciences and Research. 2010;1(9):409-420.
Nelson et al., Filamentous phage DNA cloning vectors: a noninfective mutant with a nonpolar deletion in gene III. Virology. 1981;108(2): 338-50.
Nelson et al., In vivo genome editing improves muscle function in a mouse model of Duchenne muscular dystrophy. Science. Jan. 22, 2016;351(6271):403-7. doi: 10.1126/science.aad5143. Epub Dec. 31, 2015.
Nelson et al., The unstable repeats—three evolving faces of neurological disease. Neuron. Mar. 6, 2013;77(5):825-43. doi: 10.1016/j.neuron.2013.02.022.
Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.
Nguyen et al., Evolutionary drivers of thermoadaptation in enzyme catalysis. Science. Jan. 20, 2017;355(6322):289-294. doi: 10.1126/science.aah3717. Epub Dec. 22, 2016.
Nguyen et al., IQ-TREE: a fast and effective stochastic algorithm for estimating maximum-likelihood phylogenies. Mol Biol Evol. Jan. 2015;32(1):268-74. doi: 10.1093/molbev/msu300. Epub Nov. 3, 2014.
Ni et al., A PCSK9-binding antibody that structurally mimics the EGF(A) domain of LDL-receptor reduces LDL cholesterol in vivo. J Lipid Res. 2011;52:76-86.
Ni et al., Nucleic acid aptamers: clinical applications and promising new horizons. Curr Med Chem. 2011;18(27):4206-14. Review.
Nishida et al., Targeted nucleotide editing using hybrid prokaryotic and vertebrate adaptive immune systems. Science. Sep. 16, 2016;353(6305):1248. pii: aaf8729. doi: 10.1126/science.aaf8729. Epub Aug. 4, 2016.
Nishikura, Functions and regulation of RNA editing by ADAR deaminases. Annu Rev Biochem. 2010;79:321-349. doi:10.1146/annurev-biochem-060208-105251.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
Nishimasu et al., Crystal Structure of *Staphylococcus aureus* Cas9. Cell. Aug. 27, 2015;162(5): 1113-26. doi: 10.1016/j.cell.2015.08.007.
Nishimasu et al., Engineered CRISPR-Cas9 nuclease with expanded targeting space. Science. Sep. 21, 2018;361(6408):1259-1262. doi: 10.1126/science.aas9129. Epub Aug. 30, 2018.
Noack et al., Epitranscriptomics: A New Regulatory Mechanism of Brain Development and Function. Front Neurosci. Feb. 20, 2018;12:85. doi: 10.3389/fnins.2018.00085. 9 pages.
Nomura et al., Controlling Mammalian Gene Expression by Allosteric Hepatitis Delta Virus Ribozymes. ACS Synth Biol. Dec. 20, 2013;2(12):684-9. doi: 10.1021/sb400037a. Epub May 22, 2013.
Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.

(56) References Cited

OTHER PUBLICATIONS

Noris et al., A phenylalanine-55 to serine amino-acid substitution in the human glycoprotein IX leucine-rich repeat is associated with Bernard-Soulier syndrome. Br J Haematol. May 1997;97(2):312-20.
Nottingham et al., RNA-seq of human reference RNA samples using a thermostable group II intron reverse transcriptase. RNA. Apr. 2016;22(4):597-613. doi: 10.1261/rna.055558.115. Epub Jan. 29, 2016.
Nowak et al., Characterization of single-stranded DNA-binding proteins from the psychrophilic bacteria Desulfotalea psychrophila, Flavobacterium psychrophilum, Psychrobacter arcticus, Psychrobacter cryohalolentis, Psychromonas ingrahamii, Psychroflexus torquis, and Photobacterium profundum. BMC Microbiol. Apr. 14, 2014;14:91. doi: 10.1186/1471-2180-14-91.
Nowak et al., Guide RNA Engineering for Versatile Cas9 Functionality. Nucleic Acids Res. Nov. 16, 2016;44(20):9555-9564. doi: 10.1093/nar/gkw908. Epub Oct. 12, 2016.
Nowak et al., Structural analysis of monomeric retroviral reverse transcriptase in complex with an RNA/DNA hybrid. Nucleic Acids Res. Apr. 1, 2013;41(6):3874-87. doi: 10.1093/nar/gkt053. Epub Feb. 4, 2013.
Numrych et al., A comparison of the effects of single-base and triple-base changes in the integrase arm-type binding sites on the site-specific recombination of bacteriophage lambda. Nucleic Acids Res. Jul. 11, 1990;18(13):3953-9. doi: 10.1093/nar/18.13.3953.
Nyerges et al., A highly precise and portable genome engineering method allows comparison of mutational effects across bacterial species. Proc Natl Acad Sci U S A. Mar. 1, 2016;113(9):2502-7. doi: 10.1073/pnas.1520040113. Epub Feb. 16, 2016.
O'Connell et al., Programmable RNA recognition and cleavage by CRISPR/Cas9. Nature. Dec. 11, 2014;516(7530):263-6. doi: 10.1038/nature13769. Epub Sep. 28, 2014.
O'Maille et al., Structure-based combinatorial protein engineering (Scope). J Mol Biol. Aug. 23, 2002;321(4):677-91.
Oakes et al., CRISPR-Cas9 Circular Permutants as Programmable Scaffolds for Genome Modification. Cell. Jan. 10, 2019;176(1-2):254-267.e16. doi: 10.1016/j.cell.2018.11.052.
Oakes et al., Profiling of engineering hotspots identifies an allosteric CRISPR-Cas9 switch. Nat Biotechnol. Jun. 2016;34(6):646-51. doi: 10.1038/nbt.3528. Epub May 2, 2016.
Oakes et al., Protein engineering of Cas9 for enhanced function. Methods Enzymol. 2014;546:491-511.
Odsbu et al., Specific N-terminal interactions of the *Escherichia coli* SeqA protein are required to form multimers that restrain negative supercoils and form foci. Genes Cells. Nov. 2005;10(11):1039-49.
Oeemig et al., Solution structure of DnaE intein from Nostoc punctiforme: structural basis for the design of a new split intein suitable for site-specific chemical modification. FEBS Lett. May 6, 2009;583(9):1451-6.
Offord, Advances in Genome Editing. The Scientist, Apr. 20, 2016. http://www.the-scientist.com/?articles.view/articleNo/45903/title/Advances-in-Genome-Editing/.
Oh et al., Positional cloning of a gene for Hermansky-Pudlak syndrome, a disorder of cytoplasmic organelles. Nat Genet. Nov. 1996;14(3):300-6. doi: 10.1038/ng1196-300.
Ohe et al., Purification and properties of xanthine dehydrogenase from Streptomyces cyanogenus. J Biochem. Jul. 1979;86(1):45-53.
Olivares et al., Site-specific genomic integration produces therapeutic Factor IX levels in mice. Nat Biotechnol. Nov. 2002;20(11):1124-8. doi: 10.1038/nbt753. Epub Oct. 15, 2002.
Olorunniji et al., Purification and In Vitro Characterization of Zinc Finger Recombinases. Methods Mol Biol. 2017;1642:229-245. doi: 10.1007/978-1-4939-7169-5_15.
Olorunniji et al., Site-specific recombinases: molecular machines for the Genetic Revolution. Biochem J. Mar. 15, 2016;473(6):673-84. doi: 10.1042/BJ20151112.
Olorunniji et al., Synapsis and catalysis by activated Tn3 resolvase mutants. Nucleic Acids Res. Dec. 2008;36(22):7181-91. doi: 10.1093/nar/gkn885. Epub Nov. 10, 2008.
Orlando et al., Zinc-finger nuclease-driven targeted integration into mammalian genomes using donors with limited chromosomal homology. Nucleic Acids Res. Aug. 2010;38(15):e152. doi: 10.1093/nar/gkq512. Epub Jun. 8, 2010.
Orthwein et al., A mechanism for the suppression of homologous recombination in G1 cells. Nature. Dec. 17, 2015;528(7582):422-6. doi: 10.1038/nature16142. Epub Dec. 9, 2015.
Ortiz-Urda et al., Stable nonviral genetic correction of inherited human skin disease. Nat Med. Oct. 2002;8(10):1166-70. doi: 10.1038/nm766. Epub Sep. 16, 2002. Erratum in: Nat Med. Feb. 2003;9(2):237.
Osborn et al., Base Editor Correction of COL7A1 in Recessive Dystrophic Epidermolysis Bullosa Patient-Derived Fibroblasts and iPSCs. J Invest Dermatol. Feb. 2020; 140(2):338-347.e5. doi: 10.1016/j.jid.2019.07.701. Epub Aug. 19, 2019.
Osborn et al., TALEN-based gene correction for epidermolysis bullosa. Mol Ther. Jun. 2013;21(6):1151-9. doi: 10.1038/mt.2013.56. Epub Apr. 2, 2013.
Ostermeier et al., A combinatorial approach to hybrid enzymes independent of DNA homology. Nat Biotechnol. Dec. 1999;17(12):1205-9.
Ostertag et al., Biology of mammalian L1 retrotransposons. Annu Rev Genet. 2001;35:501-38. doi: 10.1146/annurev.genet.35.102401.091032.
Otomo et al., Improved segmental isotope labeling of proteins and application to a larger protein. J Biomol NMR. Jun. 1999;14(2):105-14. doi: 10.1023/a:1008308128050.
Otomo et al., NMR observation of selected segments in a larger protein: central-segment isotope labeling through intein-mediated ligation. Biochemistry. Dec. 7, 1999;38(49):16040-4. doi: 10.1021/bi991902j.
Ottesen, ISS-N1 makes the First FDA-approved Drug for Spinal Muscular Atrophy. Transl Neurosci. Jan. 26, 2017;8:1-6. doi: 10.1515/tnsci-2017-0001.
Otto et al., The probability of fixation in populations of changing size. Genetics. Jun. 1997; 146(2):723-33.
Ousterout et al., Multiplex CRISPR/Cas9-based genome editing for correction of dystrophin mutations that cause Duchenne muscular dystrophy. Nat Commun. Feb. 18, 2015;6:6244. doi: 10.1038/ncomms7244.
Packer et al., Methods for the directed evolution of proteins. Nat Rev Genet. Jul. 2015;16(7):379-94. doi: 10.1038/nrg3927. Epub Jun. 9, 2015.
Packer et al., Phage-assisted continuous evolution of proteases with altered substrate specificity. Nat Commun. Oct. 16, 2017;8(1):956. doi: 10.1038/s41467-017-01055-9.
Paige et al., RNA mimics of green fluorescent protein. Science. Jul. 29, 2011;333(6042):642-6. doi:10.1126/science.1207339.
Paiva et al., Targeted protein degradation: elements of PROTAC design. Curr Opin Chem Biol. Jun. 2019;50:111-119. doi: 10.1016/j.cbpa.2019.02.022. Epub Apr. 17, 2019.
Pan et al., Biological and biomedical applications of engineered nucleases. Mol Biotechnol. Sep. 2013;55(1):54-62. doi: 10.1007/s12033-012-9613-9.
Pandey et al., Effect of loops and G-quartets on the stability of RNA G-quadruplexes. J Phys Chem B. Jun. 13, 2013;117(23):6896-905. doi: 10.1021/jp401739m. Epub May 29, 2013. Supplementary Information, 21 pages.
Paquet et al., Efficient introduction of specific homozygous and heterozygous mutations using CRISPR/Cas9. Nature. May 5, 2016;533(7601):125-9. doi: 10.1038/nature17664. Epub Apr. 27, 2016.
Parente et al., Advances in spinal muscular atrophy therapeutics. Ther Adv Neurol Disord. Feb. 5, 2018;11:1756285618754501. doi: 10.1177/1756285618754501. 13 pages.
Park et al., Digenome-seq web tool for profiling CRISPR specificity. Nat Methods. May 30, 2017;14(6):548-549. doi: 10.1038/nmeth.4262.
Park et al., Highly efficient editing of the β-globin gene in patient-derived hematopoietic stem and progenitor cells to treat sickle cell disease. Nucleic Acids Res. Sep. 5, 2019;47(15):7955-7972. doi: 10.1093/nar/gkz475.

(56) References Cited

OTHER PUBLICATIONS

Park et al., Sendai virus, an RNA virus with no risk of genomic integration, delivers CRISPR/Cas9 for efficient gene editing. Mol Ther Methods Clin Dev. Aug. 24, 2016;3:16057. doi: 10.1038/mtm.2016.57.

Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.

Passini et al., Antisense oligonucleotides delivered to the mouse CNS ameliorate symptoms of severe spinal muscular atrophy. Sci Transl Med. Mar. 2, 2011;3(72):72ra18. doi: 10.1126/scitranslmed.3001777.

Patel et al., Flap endonucleases pass 5'-flaps through a flexible arch using a disorder-thread-order mechanism to confer specificity for free 5'-ends. Nucleic Acids Res. May 2012;40(10):4507-19. doi: 10.1093/nar/gks051. Epub Feb. 8, 2012.

Pattanayak et al., Determining the specificities of TALENs, Cas9, and other genome-editing enzymes. Methods Enzymol. 2014;546:47-78. doi: 10.1016/B978-0-12-801185-0.00003-9.

Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.

Pattanayak et al., Revealing off-target cleavage specificities of zinc-finger nucleases by in vitro selection. Nat Methods. Aug. 7, 2011;8(9):765-70. doi: 10.1038/nmeth.1670.

Pavletich et al., Zinc finger-DNA recognition: crystal structure of a Zif268-DNA complex at 2.1 A. Science. May 10, 1991;252(5007):809-17.

Pawson et al., Protein phosphorylation in signaling—50 years and counting. Trends Biochem Sci. Jun. 2005;30(6):286-90. doi: 10.1016/j.tibs.2005.04.013.

Pearl, Structure and function in the uracil-DNA glycosylase superfamily. Mutat Res. Aug. 30, 2000;460(3-4):165-81.

Peck et al., Directed evolution of a small-molecule-triggered intein with improved splicing properties in mammalian cells. Chem Biol. May 27, 2011;18(5):619-30. doi: 10.1016/j.chembiol.2011.02.014.

Pellegrini et al., Insights into DNA recombination from the structure of a RAD51-BRCA2 complex. Nature. Nov. 21, 2002;420(6913):287-93. doi: 10.1038/nature01230. Epub Nov. 10, 2002.

Pellenz et al., New human chromosomal safe harbor sites for genome engineering with CRISPR/Cas9, TAL effector and homing endonucleases. Aug. 20, 2018. bioRxiv doi: https://doi.org/10.1101/396390.

Pelletier, CRISPR-Cas systems for the study of the immune function. Nov. 15, 2016. https://doi.org/10.1002/9780470015902.a0026896.

Pendse et al., Exon 13-skipped USH2A protein retains functional integrity in mice, suggesting an exo-skipping therapeutic approach to treat USH2A-associated disease. bioRxiv preprint. Feb. 4, 2020. Retrieved from www.biorxiv.org. doi: 10.1101/2020.02.04.934240. 34 pages.

Pendse et al., In Vivo Assessment of Potential Therapeutic Approaches for USH2A-Associated Diseases. Adv Exp Med Biol. 2019;1185:91-96. doi: 10.1007/978-3-030-27378-1_15.

Pennisi et al., The CRISPR craze. Science. Aug. 23, 2013;341(6148):833-6. doi: 10.1126/science.341.6148.833.

Pennisi et al., The tale of the TALEs. Science. Dec. 14, 2012;338(6113):1408-11. doi: 10.1126/science.338.6113.1408.

Perach et al., Catalytic features of the recombinant reverse transcriptase of bovine leukemia virus expressed in bacteria. Virology. Jun. 20, 1999;259(1):176-89. doi: 10.1006/viro.1999.9761.

Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.

Perez-Palma et al., Simple ClinVar: an interactive web server to explore and retrieve gene and disease variants aggregated in ClinVar database. Nucleic Acids Res. Jul. 2, 2019;47(W1):W99-W105. doi: 10.1093/nar/gkz411.

Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.

Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.

Perler et al., Protein splicing and autoproteolysis mechanisms. Curr Opin Chem Biol. Oct. 1997;1(3):292-9. doi: 10.1016/s1367-5931(97)80065-8.

Perler et al., Protein splicing elements: inteins and exteins—a definition of terms and recommended nomenclature. Nucleic Acids Res. Apr. 11, 1994;22(7):1125-7. doi: 10.1093/nar/22.7.1125.

Perler, InBase, the New England Biolabs Intein Database. Nucleic Acids Res. Jan. 1, 1999;27(1):346-7. doi: 10.1093/nar/27.1.346.

Perler, Protein splicing of inteins and hedgehog autoproteolysis: structure, function, and evolution. Cell. Jan. 9, 1998;92(1):1-4. doi: 10.1016/s0092-8674(00)80892-2.

Perreault et al., Mixed deoxyribo- and ribo-oligonucleotides with catalytic activity. Nature. Apr. 5, 1990;344(6266):565-7. doi: 10.1038/344565a0.

Petek et al., Frequent endonuclease cleavage at off-target locations in vivo. Mol Ther. May 2010;18(5):983-6. Doi: 10.1038/mt.2010.35. Epub Mar. 9, 2010.

Petersen-Mahrt et al., AID mutates *E. coli* suggesting a DNA deamination mechanism for antibody diversification. Nature. Jul. 4, 2002;418(6893):99-103.

Petolino et al., Editing Plant Genomes: a new era of crop improvement. Plant Biotechnol J. Feb. 2016;14(2):435-6. doi: 10.1111/pbi.12542.

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.

Pfeiffer et al., Mechanisms of DNA double-strand break repair and their potential to induce chromosomal aberrations. Mutagenesis. Jul. 2000;15(4):289-302. doi: 10.1093/mutage/15.4.289.

Phillips, The challenge of gene therapy and DNA delivery. J Pharm Pharmacol. Sep. 2001;53(9):1169-74.

Pickart et al., Ubiquitin: structures, functions, mechanisms. Biochim Biophys Acta. Nov. 29, 2004;1695(1-3):55-72. doi: 10.1016/j.bbamcr.2004.09.019.

Pieken et al., Kinetic characterization of ribonuclease-resistant 2'-modified hammerhead ribozymes. Science. Jul. 19, 1991;253(5017):314-7. doi: 10.1126/science.1857967.

Pijlman et al., A highly structured, nuclease-resistant, noncoding RNA produced by flaviviruses is required for pathogenicity. Cell Host Microbe. Dec. 11, 2008;4(6):579-91. doi: 10.1016/j.chom.2008.10.007.

Pinkert et al., An albumin enhancer located 10 kb upstream functions along with its promoter to direct efficient, liver-specific expression in transgenic mice. Genes Dev. May 1987;1(3):268-76. doi: 10.1101/gad.1.3.268.

Piotukh et al., Directed evolution of sortase A mutants with altered substrate selectivity profiles. J Am Chem Soc. Nov. 9, 2011;133(44):17536-9. doi: 10.1021/ja205630g. Epub Oct. 13, 2011.

Pirakitikulr et al., PCRless library mutagenesis via oligonucleotide recombination in yeast. Protein Sci. Dec. 2010;19(12):2336-46. doi: 10.1002/pro.513.

Plasterk et al., DNA inversions in the chromosome of *Escherichia coli* and in bacteriophage Mu: relationship to other site-specific recombination systems. Proc Natl Acad Sci U S A. Sep. 1983;80(17):5355-8.

Plosky et al., CRISPR-Mediated Base Editing without DNA Double-Strand Breaks. Mol Cell. May 19, 2016;62(4):477-8. doi: 10.1016/j.molcel.2016.05.006.

Pluciennik et al., PCNA function in the activation and strand direction of MutLα endonuclease in mismatch repair. Proc Natl Acad Sci U S A. Sep. 14, 2010;107(37):16066-71. doi: 10.1073/pnas.1010662107. Epub Aug. 16, 2010.

Poller et al., A leucine-to-proline substitution causes a defective alpha 1-antichymotrypsin allele associated with familial obstructive lung disease. Genomics. Sep. 1993;17(3):740-3.

(56) References Cited

OTHER PUBLICATIONS

Popp et al., Sortagging: a versatile method for protein labeling. Nat Chem Biol. Nov. 2007;3(11):707-8. doi: 10.1038/nchembio.2007.31. Epub Sep. 23, 2007.
Porensky et al., A single administration of morpholino antisense oligomer rescues spinal muscular atrophy in mouse. Hum Mol Genet. Apr. 1, 2012;21(7):1625-38. doi: 10.1093/hmg/ddr600. Epub Dec. 20, 2011.
Porteus, Design and testing of zinc finger nucleases for use in mammalian cells. Methods Mol Biol. 2008;435:47-61. doi: 10.1007/978-1-59745-232-8_4.
Posnick et al., Imbalanced base excision repair increases spontaneous mutation and alkylation sensitivity in *Escherichia coli*. J Bacteriol. Nov. 1999;181(21):6763-71.
Pospíšilová et al., Hydrolytic cleavage of N6-substituted adenine derivatives by eukaryotic adenine and adenosine deaminases. Biosci Rep. 2008;28(6):335-347. doi:10.1042/BSR20080081.
Pourcel et al., CRISPR elements in Yersinia pestis acquire new repeats by preferential uptake of bacteriophage DNA, and provide additional tools for evolutionary studies. Microbiology. Mar. 2005;151(Pt 3):653-63.
Prasad et al., Rev1 is a base excision repair enzyme with 5'-deoxyribose phosphate lyase activity. Nucleic Acids Res. Dec. 15, 2016;44(22):10824-10833. doi: 10.1093/nar/gkw869. Epub Sep. 28, 2016.
Prasad et al., Visualizing the assembly of human Rad51 filaments on double-stranded DNA. J Mol Biol. Oct. 27, 2006;363(3):713-28. doi: 10.1016/j.jmb.2006.08.046. Epub Aug. 22, 2006.
Prashant et al., CAS9 transcriptional activators for target specificity screening and paired nickases for cooperative genome engineering. Nature Biotechnology 2013;31(9):833-8.
Prorocic et al., Zinc-finger recombinase activities in vitro. Nucleic Acids Res. Nov. 2011;39(21):9316-28. doi: 10.1093/nar/gkr652. Epub Aug. 17, 2011.
Proudfoot et al., Zinc finger recombinases with adaptable DNA sequence specificity. PLoS One. Apr. 29, 2011;6(4):e19537. doi: 10.1371/journal.pone.0019537.
Pruschy et al., Mechanistic studies of a signaling pathway activated by the organic dimerizer FK1012. Chem Biol. Nov. 1994;1(3):163-72. doi: 10.1016/1074-5521(94)90006-x.
Prykhozhij et al., CRISPR multitargeter: a web tool to find common and unique CRISPR single guide RNA targets in a set of similar sequences. PLoS One. Mar. 5, 2015;10(3):e0119372. doi: 10.1371/journal.pone.0119372. eCollection 2015.
Pu et al., Evolution of a split RNA polymerase as a versatile biosensor platform. Nat Chem Biol. Apr. 2017;13(4):432-438. doi: 10.1038/nchembio.2299. Epub Feb. 13, 2017.
Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46.
Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.
Qi et al., Repurposing CRISPR as an RNA-guided platform for sequence-specific control of gene expression. Cell. Feb. 28, 2013;152(5):1173-83. doi: 10.1016/j.cell.2013.02.022.
Qu et al., Global mapping of binding sites for phic31 integrase in transgenic maden-darby bovine kidney cells using ChIP-seq. Hereditas. Jan. 14, 2019;156:3. doi: 10.1186/s41065-018-0079-z.
Queen et al., Immunoglobulin gene transcription is activated by downstream sequence elements. Cell. Jul. 1983;33(3):741-8. doi: 10.1016/0092-8674(83)90016-8.
Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.
Raghavan et al., Abstract 27: Therapeutic Targeting of Human Lipid Genes with in vivo CRISPR-Cas9 Genome Editing. Oral Abstract Presentations: Lipoprotein Metabolism and Therapeutic Targets. Arterioscler THromb Vasc Biol. 2015;35(Suppl. 1):Abstract 27. 5 pages.
Raillard et al., Targeting sites within HIV-1 cDNA with a DNA-cleaving ribozyme. Biochemistry. Sep. 10, 1996;35(36):11693-701. doi: 10.1021/bi960845g.
Raina et al., PROTAC-induced BET protein degradation as a therapy for castration-resistant prostate cancer. Proc Natl Acad Sci U S A. Jun. 28, 2016;113(26):7124-9. doi: 10.1073/pnas.1521738113. Epub Jun. 6, 2016.
Rajagopal et al., High-throughput mapping of regulatory DNA. Nat Biotechnol. Feb. 2016;34(2):167-74. doi: 10.1038/nbt.3468. Epub Jan. 25, 2016.
Rakonjac et al., Roles of PIII in filamentous phage assembly. J Mol Biol. 1998; 282(1)25-41.
Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.
Ramamurthy et al., Identification of immunogenic B-cell epitope peptides of rubella virus E1 glycoprotein towards development of highly specific immunoassays and/or vaccine. Conference Abstract. 2019.
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Ramirez et al., Unexpected failure rates for modular assembly of engineered zinc fingers. Nat Methods. May 2008;5(5):374-5. Doi: 10.1038/nmeth0508-374.
Ramos et al., Age-dependent SMN expression in disease-relevant tissue and implications for SMA treatment. J Clin Invest. Nov. 1, 2019;129(11):4817-4831. doi: 10.1172/JCI124120.
Ran et al., Double Nicking by RNA-guided CRISPR Cas9 for Enhanced Genome Editing Specificity. Cell. Sep. 12, 2013;154(6):1380-9. doi: 10.1016/j.cell.2013.08.021. Epub Aug. 29, 2013.
Ran et al., Genome engineering using the CRISPR-Cas9 system. Nat Protoc. Nov. 2013;8(11):2281-308. doi: 10.1038/nprot.2013.143. Epub Oct. 24, 2013.
Ran et al., In vivo genome editing using *Staphylococcus aureus* Cas9. Nature. Apr. 9, 2015;520(7546):186-91. doi: 10.1038/nature14299. Epub Apr. 1, 2015.
Ranzau et al., Genome, Epigenome, and Transcriptome Editing via Chemical Modification of Nucleobases in Living Cells. Biochemistry. Feb. 5, 2019;58(5):330-335. doi: 10.1021/acs.biochem.8b00958. Epub Dec. 12, 2018.
Rashel et al., A novel site-specific recombination system derived from bacteriophage phiMR11. Biochem Biophys Res Commun. Apr. 4, 2008;368(2):192-8. doi: 10.1016/j.bbrc.2008.01.045. Epub Jan. 22, 2008.
Rasila et al., Critical evaluation of random mutagenesis by error-prone polymerase chain reaction protocols, *Escherichia coli* mutator strain, and hydroxylamine treatment. Anal Biochem. May 1, 2009;388(1):71-80. doi: 10.1016/j.ab.2009.02.008. Epub Feb. 10, 2009.
Raskin et al., Substitution of a single bacteriophage T3 residue in bacteriophage T7 RNA polymerase at position 748 results in a switch in promoter specificity. J Mol Biol. Nov. 20, 1992;228(2):506-15.
Raskin et al., T7 RNA polymerase mutants with altered promoter specificities. Proc Natl Acad Sci U S A. Apr. 15, 1993;90(8):3147-51.
Rath et al., Fidelity of end joining in mammalian episomes and the impact of Metnase on joint processing. BMC Mol Biol. Mar. 22, 2014;15:6. doi: 10.1186/1471-2199-15-6.
Rauch et al., Programmable RNA Binding Proteins for Imaging and Therapeutics. Biochemistry. Jan. 30, 2018;57(4):363-364. doi: 10.1021/acs.biochem.7b01101. Epub Nov. 17, 2017.
Ravishankar et al., X-ray analysis of a complex of *Escherichia coli* uracil DNA glycosylase (EcUDG) with a proteinaceous inhibitor. The structure elucidation of a prokaryotic UDG. Nuclei Acids Res. 26 (21): 4880-4887 (1998).

(56) References Cited

OTHER PUBLICATIONS

Ray et al., A compendium of RNA-binding motifs for decoding gene regulation. Nature. Jul. 11, 2013;499(7457):172-7. doi: 10.1038/nature12311.
Ray et al., Homologous recombination: ends as the means. Trends Plant Sci. Oct. 2002;7(10):435-40.
Rebar et al., Phage display methods for selecting zinc finger proteins with novel DNA-binding specificities. Methods Enzymol. 1996;267:129-49.
Rebuzzini et al., New mammalian cellular systems to study mutations introduced at the break site by non-homologous end-joining. DNA Repair (Amst). May 2, 2005;4(5):546-55.
Rees et al., Analysis and minimization of cellular RNA editing by DNA adenine base editors. Sci Adv. May 8, 2019;5(5):eaax5717. doi: 10.1126/sciadv.aax5717.
Rees et al., Base editing: precision chemistry on the genome and transcriptome of living cells. Nat Rev Genet. Dec. 2018; 19(12):770-788. doi: 10.1038/s41576-018-0059-1.
Rees et al., Development of hRad51-Cas9 nickase fusions that mediate HDR without double-stranded breaks. Nat Commun. May 17, 2019;10(1):2212. doi: 10.1038/s41467-019-09983-4.
Rees et al., Improving the DNA specificity and applicability of base editing through protein engineering and protein delivery. Nat Commun. Jun. 6, 2017;8:15790. doi: 10.1038/ncomms15790.
Reiners et al., Scaffold protein harmonin (USH1C) provides molecular links between Usher syndrome type 1 and type 2. Hum Mol Genet. Dec. 15, 2005;14(24):3933-43. doi: 10.1093/hmg/ddi417. Epub Nov. 21, 2005.
Relph et al., Recent developments and current status of gene therapy using viral vectors in the United Kingdom. BMJ. 2004;329(7470):839-842. doi:10.1136/bmj.329.7470.839.
Remy et al., Gene transfer with a series of lipophilic DNA-binding molecules. Bioconjug Chem. Nov.-Dec. 1994;5(6):647-54. doi: 10.1021/bc00030a021.
Ren et al., In-line Alignment and $Mg^{2+}$ Coordination at the Cleavage Site of the env22 Twister Ribozyme. Nat Commun. Nov. 2, 20140;5:5534. doi: 10.1038/ncomms6534.
Ren et al., Pistol Ribozyme Adopts a Pseudoknot Fold Facilitating Site-Specific In-Line Cleavage. Nat Chem Biol. Sep. 2016;12(9):702-8. doi: 10.1038/nchembio.2125. Epub Jul. 11, 2016.
Reynaud et al., What role for AID: mutator, or assembler of the immunoglobulin mutasome? Nat Immunol. Jul. 2003;4(7):631-8.
Reyon et al., FLASH assembly of TALENs for high-throughput genome editing. Nat Biotechnol. May 2012;30(5):460-5. doi: 10.1038/nbt.2170.
Ribeiro et al., Protein Engineering Strategies to Expand CRISPR-Cas9 Applications. Int J Genomics. Aug. 2, 2018;2018:1652567. doi: 10.1155/2018/1652567.
Richardson et al., CRISPR-Cas9 genome editing in human cells occurs via the Fanconi anemia pathway. Nat Genet. Aug. 2018;50(8):1132-1139. doi: 10.1038/s41588-018-0174-0. Epub Jul. 27, 2018.
Richardson et al., Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016.
Richardson et al., Frequent chromosomal translocations induced by DNA double-strand breaks. Nature. Jun. 8, 2000;405(6787):697-700. doi: 10.1038/35015097.
Richter et al., Function and regulation of clustered regularly interspaced short palindromic repeats (CRISPR) / CRISPR associated (Cas) systems. Viruses. Oct. 19, 2012;4(10):2291-311. doi: 10.3390/v4102291.
Richter et al., Phage-assisted evolution of an adenine base editor with improved Cas domain compatibility and activity. Nat Biotechnol. Jul. 2020;38(7):883-891. doi: 10.1038/s41587-020-0453-z. Epub Mar. 16, 2020.
Riechmann et al., The C-terminal domain of TolA is the coreceptor for filamentous phage infection of *E. coli*. Cell. 1997; 90(2):351-60. PMID:9244308.
Ringrose et al., The Kw recombinase, an integrase from Kluyveromyces waltii. Eur J Biochem. Sep. 15, 1997;248(3):903-12. doi: 10.1111/j.1432-1033.1997.00903.x.
Risso et al., Hyperstability and substrate promiscuity in laboratory resurrections of Precambrian B-lactamases. J Am Chem Soc. Feb. 27, 2013;135(8):2899-902. doi: 10.1021/ja311630a. Epub Feb. 14, 2013.
Ritchie et al., limma powers differential expression analyses for RNA-sequencing and microarray studies. Nucleic Acids Res. Apr. 20, 2015;43(7):e47. doi: 10.1093/nar/gkv007. Epub Jan. 20, 2015.
Robert et al., Virus-Like Particles Derived from HIV-1 for Delivery of Nuclear Proteins: Improvement of Production and Activity by Protein Engineering. Mol Biotechnol. Jan. 2017;59(1):9-23. doi: 10.1007/s12033-016-9987-1.
Robertson et al., DNA repair in mammalian cells: Base excision repair: the long and short of it. Cell Mol Life Sci. Mar. 2009;66(6):981-93. doi: 10.1007/s00018-009-8736-z.
Robertson et al., Selection in vitro of an RNA enzyme that specifically cleaves single-stranded DNA. Nature. Mar. 29, 1990;344(6265):467-8. doi: 10.1038/344467a0.
Robinson et al., The protein tyrosine kinase family of the human genome. Oncogene. Nov. 20, 2000;19(49):5548-57. doi: 10.1038/sj.onc.1203957.
Rodriguez-Muela et al., Single-Cell Analysis of SMN Reveals Its Broader Role in Neuromuscular Disease. Cell Rep. Feb. 7, 2017;18(6):1484-1498 and Supplemental Information. doi: 10.1016/j.celrep.2017.01.035.
Rogozin et al., Evolution and diversification of lamprey antigen receptors: evidence for involvement of an AID-APOBEC family cytosine deaminase. Nat Immunol. Jun. 2007;8(6):647-56. doi: 10.1038/ni1463. Epub Apr. 29, 2007.
Rong et al., Homologous recombination in human embryonic stem cells using CRISPR/Cas9 nickase and a long DNA donor template. Protein Cell. Apr. 2014;5(4):258-60. doi: 10.1007/s13238-014-0032-5.
Rongrong et al., Effect of deletion mutation on the recombination activity of Cre recombinase. Acta Biochim Pol. 2005;52(2):541-4. Epub May 15, 2005.
Roth et al., A widespread self-cleaving ribozyme class is revealed by bioinformatics. Nat Chem Biol. Jan. 2014;10(1):56-60. doi: 10.1038/nchembio.1386. Epub Nov. 17, 2013.
Roth et al., Purification and characterization of murine retroviral reverse transcriptase expressed in *Escherichia coli*. J Biol Chem. Aug. 5, 1985;260(16):9326-35.
Rouet et al., Expression of a site-specific endonuclease stimulates homologous recombination in mammalian cells. Proc Natl Acad Sci U S A. Jun. 21, 1994;91(13):6064-8. doi: 10.1073/pnas.91.13.6064.
Rouet et al., Introduction of double-strand breaks into the genome of mouse cells by expression of a rare-cutting endonuclease. Mol Cell Biol. Dec. 1994;14(12):8096-106. doi: 10.1128/mcb.14.12.8096.
Rouet et al., Receptor-Mediated Delivery of CRISPR-Cas9 Endonuclease for Cell-Type-Specific Gene Editing. J Am Chem Soc. May 30, 2018;140(21):6596-6603. doi: 10.1021/jacs.8b01551. Epub May 18, 2018.
Roundtree et al., YTHDC1 mediates nuclear export of N6-methyladenosine methylated mRNAs. Elife. Oct. 6, 2017;6:e31311. doi: 10.7554/eLife.31311.
Rowland et al., Regulatory mutations in Sin recombinase support a structure-based model of the synaptosome. Mol Microbiol. Oct. 2009;74(2):282-98. doi: 10.1111/j.1365-2958.2009.06756.x. Epub Jun. 8, 2009.
Rowland et al., Sin recombinase from *Staphylococcus aureus*: synaptic complex architecture and transposon targeting. Mol Microbiol. May 2002;44(3):607-19. doi: 10.1046/j.1365-2958.2002.02897.x.
Rowley, Chromosome translocations: dangerous liaisons revisited. Nat Rev Cancer. Dec. 2001;1(3):245-50. doi: 10.1038/35106108.
Rubio et al., An adenosine-to-inosine tRNA-editing enzyme that can perform C-to-U deamination of DNA. Proc Natl Acad Sci U S A. May 8, 2007;104(19):7821-6. doi: 10.1073/pnas.0702394104. Epub May 1, 2007. PMID: 17483465; PMCID: PMC1876531.

(56) References Cited

OTHER PUBLICATIONS

Rubio et al., Transfer RNA travels from the cytoplasm to organelles. Wiley Interdiscip Rev RNA. Nov.-Dec. 2011;2(6):802-17. doi: 10.1002/wrna.93. Epub Jul. 11, 2011.
Rudolph et al., Synthetic riboswitches for the conditional control of gene expression in Streptomyces coelicolor. Microbiology. Jul. 2013;159(Pt 7):1416-22. doi: 10.1099/mic.0.067322-0. Epub May 15, 2013.
Rutherford et al., Attachment site recognition and regulation of directionality by the serine integrases. Nucleic Acids Res. Sep. 2013;41(17):8341-56. doi: 10.1093/nar/gkt580. Epub Jul. 2, 2013.
Ryu et al., Adenine base editing in mouse embryos and an adult mouse model of Duchenne muscular dystrophy. Nat Biotechnol. Jul. 2018;36(6):536-539. doi: 10.1038/nbt.4148. Epub Apr. 27, 2018.
Rüfer et al., Non-contact positions impose site selectivity on Cre recombinase. Nucleic Acids Res. Jul. 1, 2002;30(13):2764-71. doi: 10.1093/nar/gkf399.
Saayman et al., The therapeutic application of CRISPR/Cas9 technologies for HIV. Expert Opin Biol Ther. Jun. 2015;15(6):819-30. doi: 10.1517/14712598.2015.1036736. Epub Apr. 12, 2015.
Sadelain et al., Safe harbours for the integration of new DNA in the human genome. Nat Rev Cancer. Dec. 1, 2011;12(1):51-8. doi: 10.1038/nrc3179.
Sadowski, The Flp recombinase of the 2-microns plasmid of *Saccharomyces cerevisiae*. Prog Nucleic Acid Res Mol Biol. 1995;51:53-91.
Safari et al., CRISPR Cpf1 proteins: structure, function and implications for genome editing. Cell Biosci. May 9, 2019;9:36. doi: 10.1186/s13578-019-0298-7.
Sage et al., Proliferation of functional hair cells in vivo in the absence of the retinoblastoma protein. Science. Feb. 18, 2005;307(5712):1114-8. Epub Jan. 13, 2005.
Sakuma et al., MMEJ-assisted gene knock-in using TALENs and CRISPR-Cas9 with the PITCh systems. Nat Protoc. Jan. 2016;11(1):118-33. doi: 10.1038/nprot.2015.140. Epub Dec. 17, 2015.
Sale et al., Y-family DNA polymerases and their role in tolerance of cellular DNA damage. Nat Rev Mol Cell Biol. Feb. 23, 2012;13(3):141-52. doi: 10.1038/nrm3289.
Saleh-Gohari et al., Conservative homologous recombination preferentially repairs DNA double-strand breaks in the S phase of the cell cycle in human cells. Nucleic Acids Res. Jul. 13, 2004;32(12):3683-8. Print 2004.
Samal et al., Cationic polymers and their therapeutic potential. Chem Soc Rev. Nov. 7, 2012;41(21):7147-94. doi: 10.1039/c2cs35094g. Epub Aug. 10, 2012.
Samanta et al., A reverse transcriptase ribozyme. Elife. Sep. 26, 2017;6:e31153. doi: 10.7554/eLife.31153.
Samulski et al., Helper-free stocks of recombinant adeno-associated viruses: normal integration does not require viral gene expression. J Virol. Sep. 1989;63(9):3822-8. doi: 10.1128/JVI.63.9.3822-3828.1989.
San Filippo et al., Mechanism of eukaryotic homologous recombination. Annu Rev Biochem. 2008;77:229-57. doi: 10.1146/annurev.biochem.77.061306.125255.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sander et al., In silico abstraction of zinc finger nuclease cleavage profiles reveals an expanded landscape of off-target sites. Nucleic Acids Res. Oct. 2013;41(19):e181. doi: 10.1093/nar/gkt716. Epub Aug. 14, 2013.
Sander et al., Targeted gene disruption in somatic zebrafish cells using engineered TALENs. Nat Biotechnol. Aug. 5, 2011;29(8):697-8. doi: 10.1038/nbt.1934.
Sang et al., A unique uracil-DNA binding protein of the uracil DNA glycosylase superfamily. Nucleic Acids Res. Sep. 30, 2015;43(17):8452-63. doi: 10.1093/nar/gkv854. Epub Aug. 24, 2015.
Sang, Prospects for transgenesis in the chick. Mech Dev. Sep. 2004;121(9):1179-86.
Sanjana et al., A transcription activator-like effector toolbox for genome engineering. Nat Protoc. Jan. 5, 2012;7(1):171-92. doi: 10.1038/nprot.2011.431.
Sanjurjo-Soriano et al., Genome Editing in Patient iPSCs Corrects the Most Prevalent USH2A Mutations and Reveals Intriguing Mutant mRNA Expression Profiles. Mol Ther Methods Clin Dev. Nov. 27, 2019;17:156-173. doi: 10.1016/j.omtm.2019.11.016.
Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.
Santoro et al., Directed evolution of the site specificity of Cre recombinase. Proc Natl Acad Sci U S A. Apr. 2, 2002;99(7):4185-90. Epub Mar. 19, 2002.
Saparbaev et al., Excision of hypoxanthine from DNA containing dIMP residues by the *Escherichia coli*, yeast, rat, and human alkylpurine DNA glycosylases. Proc Natl Acad Sci U S A. Jun. 21, 1994;91(13):5873-7. doi: 10.1073/pnas.91.13.5873.
Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.
Sapunar et al., Dorsal root ganglion—a potential new therapeutic target for neuropathic pain. J Pain Res. 2012;5:31-8. doi: 10.2147/JPR.S26603. Epub Feb. 16, 2012.
Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.
Sarkar et al., HIV-1 proviral DNA excision using an evolved recombinase. Science. Jun. 29, 2007;316(5833):1912-5. doi: 10.1126/science.1141453.
Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.
Sasidharan et al., The selection of acceptable protein mutations. PNAS; Jun. 12, 2007;104(24):10080-5. www.pnas.org/cgi/doi/10.1073.pnas.0703737104.
Satomura et al., Precise genome-wide base editing by the CRISPR Nickase system in yeast. Sci Rep. May 18, 2017;7(1):2095. doi: 10.1038/s41598-017-02013-7.
Saudek et al., A preliminary trial of the programmable implantable medication system for insulin delivery. N Engl J Med. Aug. 31, 1989;321(9):574-9.
Sauer et al., DNA recombination with a heterospecific Cre homolog identified from comparison of the pac-c1 regions of P1-related phages. Nucleic Acids Res. Nov. 18, 2004;32(20):6086-95. doi: 10.1093/nar/gkh941.
Savic et al., Covalent linkage of the DNA repair template to the CRISPR-Cas9 nuclease enhances homology-directed repair. Elife. May 29, 2018;7:e33761. doi: 10.7554/eLife.33761.
Saville et al., A site-specific self-cleavage reaction performed by a novel RNA in Neurospora mitochondria. Cell. May 18, 1990;61(4):685-96. doi: 10.1016/0092-8674(90)90480-3.
Savva et al., The structural basis of specific base-excision repair by uracil-DNA glycosylase. Nature. Feb. 9, 1995;373(6514):487-93. doi: 10.1038/373487a0.
Schaaper et al., Base selection, proofreading, and mismatch repair during DNA replication in *Escherichia coli*. J Biol Chem. Nov. 15, 1993;268(32):23762-5.
Schaaper et al., Spectra of spontaneous mutations in *Escherichia coli* strains defective in mismatch correction: the nature of in vivo DNA replication errors. Proc Natl Acad Sci U S A. Sep. 1987;84(17):6220-4.
Schaefer et al., Understanding RNA modifications: the promises and technological bottlenecks of the 'epitranscriptome'. Open Biol. May 2017;7(5):170077. doi: 10.1098/rsob.170077.
Schechner et al., Multiplexable, locus-specific targeting of long RNAs with CRISPR-Display. Nat Methods. Jul. 2015;12(7):664-70. doi: 10.1038/nmeth.3433. Epub Jun. 1, 2015. Author manuscript entitled CRISPR Display: A modular method for locus-specific targeting of long noncoding RNAs and synthetic RNA devices in vivo.

(56) References Cited

OTHER PUBLICATIONS

Schek et al., Definition of the upstream efficiency element of the simian virus 40 late polyadenylation signal by using in vitro analyses. Mol Cell Biol. Dec. 1992;12(12):5386-93. doi: 10.1128/mcb.12.12.5386.
Schenk et al., MPDU1 mutations underlie a novel human congenital disorder of glycosylation, designated type If. J Clin Invest. Dec. 2001;108(11):1687-95. doi: 10.1172/JCI13419.
Schlacher et al., Double-strand break repair-independent role for BRCA2 in blocking stalled replication fork degradation by MRE11. Cell. May 13, 2011;145(4):529-42. doi: 10.1016/j.cell.2011.03.041. Erratum in: Cell. Jun. 10, 2011;145(6):993.
Schmitz et al., Behavioral abnormalities in prion protein knockout mice and the potential relevance of PrP(C) for the cytoskeleton. Prion. 2014;8(6):381-6. doi: 10.4161/19336896.2014.983746.
Schrank et al., Inactivation of the survival motor neuron gene, a candidate gene for human spinal muscular atrophy, leads to massive cell death in early mouse embryos. Proc Natl Acad Sci USA. Sep. 2, 1997;94(18):9920-5. doi: 10.1073/pnas.94.18.9920.
Schriefer et al., Low pressure DNA shearing: a method for random DNA sequence analysis. Nucleic Acids Res. Dec. 25, 1990;18(24):7455-6.
Schultz et al., Expression and secretion in yeast of a 400-kDa envelope glycoprotein derived from Epstein-Barr virus. Gene. 1987;54(1):113-23. doi: 10.1016/0378-1119(87)90353-2.
Schultz et al., Oligo-2'-fluoro-2'-deoxynucleotide N3'→P5' phosphoramidates: synthesis and properties. Nucleic Acids Res. Aug. 1, 1996;24(15):2966-73.
Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.
Schwartz et al., Post-translational enzyme activation in an animal via optimized conditional protein splicing. Nat Chem Biol. Jan. 2007;3(1):50-4. Epub Nov. 26, 2006.
Schwarze et al., In vivo protein transduction: delivery of a biologically active protein into the mouse. Science. Sep. 3, 1999;285(5433):1569-72.
Schöller et al., Interactions, localization, and phosphorylation of the m6A generating METTL3-METTL14-WTAP complex. RNA. Apr. 2018;24(4):499-512. doi: 10.1261/rna.064063.117. Epub Jan. 18, 2018.
Sclimenti et al., Directed evolution of a recombinase for improved genomic integration at a native human sequence. Nucleic Acids Res. Dec. 15, 2001;29(24):5044-51.
SCORE Results for Luetticken et al., Complete genome sequence of a *Streptococcus dysgalactiae* subsp. RT equisimilis strain possessing Lancefield's group A antigen. RL Submitted to the EMBL/GenBank/DDBJ databases. May 2012. 3 pages.
SCORE Results for Okumura et al., Evolutionary paths of streptococcal and staphylococcal superantigens. RL BMC Genomics. 2012; 13:404-404. 3 pages.
SCORE Results for Shimomura et al., Complete Genome Sequencing and Analysis of a Lancefield Group G Rt *Streptococcus dysagalactiae* Subsp. *Equisimilis* Strain Causing Streptococcal RT Toxic Shock Syndrome (STSS). RL BMC Genomics. 2011;12:17-17. 3 pages.
Scott et al., Production of cyclic peptides and proteins in vivo. Proc Natl Acad Sci U S A. Nov. 23, 1999;96(24):13638-43. doi: 10.1073/pnas.96.24.13638.
Sebastían-Martín et al., Transcriptional inaccuracy threshold attenuates differences in RNA-dependent DNA synthesis fidelity between retroviral reverse transcriptases. Sci Rep. Jan. 12, 2018;8(1):627. doi: 10.1038/s41598-017-18974-8.
Seed, An LFA-3 cDNA encodes a phospholipid-linked membrane protein homologous to its receptor CD2. Nature. Oct. 29-Nov. 4, 1987;329(6142):840-2. doi: 10.1038/329840a0.
Sefton et al., Implantable pumps. Crit Rev Biomed Eng. 1987;14(3):201-40.

Segal et al., Toward controlling gene expression at will: selection and design of zinc finger domains recognizing each of the 5'-GNN-3' DNA target sequences. Proc Natl Acad Sci U S A. Mar. 16, 1999;96(6):2758-63.
Sells et al., Delivery of protein into cells using polycationic liposomes. Biotechniques. Jul. 1995;19(1):72-6, 78.
Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.
Semple et al., Rational design of cationic lipids for siRNA delivery. Nat Biotechnol. Feb. 2010;28(2):172-6. doi: 10.1038/nbt.1602. Epub Jan. 17, 2010.
Serganov et al., Coenzyme recognition and gene regulation by a flavin mononucleotide riboswitch. Nature. Mar. 12, 2009;458(7235):233-7. doi: 10.1038/nature07642. Epub Jan. 25, 2009.
Serganov et al., Structural basis for discriminative regulation of gene expression by adenine- and guanine-sensing mRNAs. Chem Biol. Dec. 2004;11(12):1729-41.
Serganov et al., Structural basis for gene regulation by a thiamine pyrophosphate-sensing riboswitch. Nature. Jun. 29, 2006;441(7097):1167-71. Epub May 21, 2006.
Seripa et al., The missing ApoE allele. Ann Hum Genet. Jul. 2007;71(Pt 4):496-500. Epub Jan. 22, 2007.
Serrano-Heras et al., Protein p56 from the Bacillus subtilis phage phi29 inhibits DNA-binding ability of uracil-DNA glycosylase. Nucleic Acids Res. 2007;35(16):5393-401. Epub Aug. 13, 2007.
Setten et al., The current state and future directions of RNAi-based therapeutics. Nat Rev Drug Discov. Jun. 2019; 18(6):421-446. doi: 10.1038/s41573-019-0017-4.
Severinov et al., Expressed protein ligation, a novel method for studying protein-protein interactions in transcription. J Biol Chem. Jun. 26, 1998;273(26):16205-9. doi: 10.1074/jbc.273.26.16205.
Sha et al., Monobodies and other synthetic binding proteins for expanding protein science. Protein Sci. May 2017;26(5):910-924. doi: 10.1002/pro.3148. Epub Mar. 24, 2017.
Shah et al., Inteins: nature's gift to protein chemists. Chem Sci. 2014;5(1):446-461.
Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.
Shah et al., Protospacer recognition motifs: mixed identities and functional diversity. RNA Biol. May 2013;10(5):891-9. doi: 10.4161/rna.23764. Epub Feb. 12, 2013.
Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.
Shaikh et al., Chimeras of the Flp and Cre recombinases: tests of the mode of cleavage by Flp and Cre. J Mol Biol. Sep. 8, 2000;302(1):27-48.
Shalem et al., Genome-scale CRISPR-Cas9 knockout screening in human cells. Science. Jan. 3, 2014;343(6166):84-7. doi: 10.1126/science.1247005. Epub Dec. 12, 2013.
Shalem et al., High-throughput functional genomics using CRISPR-Cas9. Nat Rev Genet. May 2015;16(5):299-311. doi: 10.1038/nrg3899. Epub Apr. 9, 2015.
Sharbeen et al., Ectopic restriction of DNA repair reveals that UNG2 excises AID-induced uracils predominantly or exclusively during G1 phase. J Exp Med. May 7, 2012;209(5):965-74. doi: 10.1084/jem.20112379. Epub Apr. 23, 2012.
Sharer et al., The ARF-like 2 (ARL2)-binding protein, BART. Purification, cloning, and initial characterization. J Biol Chem. Sep. 24, 1999;274(39):27553-61. doi: 10.1074/jbc.274.39.27553.
Sharma et al., Efficient introduction of aryl bromide functionality into proteins in vivo. FEBS Lett. Feb. 4, 2000;467(1):37-40.
Sharma et al., Identification of novel methyltransferases, Bmt5 and Bmt6, responsible for the m3U methylations of 25S rRNA in *Saccharomyces cerevisiae*. Nucleic Acids Res. Mar. 2014;42(5):3246-60. doi: 10.1093/nar/gkt1281. Epub Dec. 11, 2013.
Sharon et al., Functional Genetic Variants Revealed by Massively Parallel Precise Genome Editing. Cell. Oct. 4, 2018;175(2):544-557.e16. doi: 10.1016/j.cell.2018.08.057. Epub Sep. 20, 2018.

(56) References Cited

OTHER PUBLICATIONS

Shaw et al., Implications of human genome architecture for rearrangement-based disorders: the genomic basis of disease. Hum Mol Genet. Apr. 1, 2004;13 Spec No. 1:R57-64. doi: 10.1093/hmg/ddh073. Epub Feb. 5, 2004.
Shcherbakova et al., Near-infrared fluorescent proteins for multicolor in vivo imaging. Nat Methods. Aug. 2013;10(8):751-4. doi: 10.1038/nmeth.2521. Epub Jun. 16, 2013.
Shechner et al., Multiplexable, locus-specific targeting of long RNAs with CRISPR-Display. Nat Methods. Jul. 2015;12(7):664-70. doi: 10.1038/nmeth.3433. Epub Jun. 1, 2015.
Shee et al., Engineered proteins detect spontaneous DNA breakage in human and bacterial cells. Elife. Oct. 29, 2013;2:e01222. doi: 10.7554/eLife.01222.
Shen et al., Efficient genome modification by CRISPR-Cas9 nickase with minimal off-target effects. Nat Methods. Apr. 2014; 11(4):399-402. doi: 10.1038/nmeth.2857. Epub Mar. 2, 2014.
Shen et al., Herpes simplex virus 1 (HSV-1) for cancer treatment. Cancer Gene Ther. Nov. 2006;13(11):975-92. doi: 10.1038/sj.cgt.7700946. Epub Apr. 7, 2006.
Shen et al., Predictable and precise template-free CRISPR editing of pathogenic variants. Nature. Nov. 2018;563(7733):646-651. doi: 10.1038/s41586-018-0686-x. Epub Nov. 7, 2018.
Shen, Data processing, Modeling and Analysis scripts for CRISPR-inDelphi. GitHub—maxwshen/indelphi-dataprocessinganalysis at 6b68e3cec73c9358fef6e5f178a935f3c2a4118f. Apr. 10, 2018. Retrieved online via https://github.com/maxwshen/indelphi-sataprocessinganalysis/tree/6b68e3cec73c9358fef6e5f178a935f3c2a4118f Last retrieved on Jul. 26, 2021. 2 pages.
Sheridan, First CRISPR-Cas patent opens race to stake out intellectual property. Nat Biotechnol. 2014;32(7):599-601.
Sheridan, Gene therapy finds its niche. Nat Biotechnol. Feb. 2011;29(2):121-8. doi: 10.1038/nbt.1769.
Sherwood et al., Discovery of directional and nondirectional pioneer transcription factors by modeling DNase profile magnitude and shape. Nat Biotechnol. Feb. 2014;32(2):171-178. doi: 10.1038/nbt.2798. Epub Jan. 19, 2014.
Shi et al., Structural basis for targeted DNA cytosine deamination and mutagenesis by APOBEC3A and APOBEC3B. Nat Struct Mol Biol. Feb. 2017;24(2):131-139. doi: 10.1038/nsmb.3344. Epub Dec. 19, 2016.
Shi et al., YTHDF3 facilitates translation and decay of N6-methyladenosine-modified RNA. Cell Res. Mar. 2017;27(3):315-328. doi: 10.1038/cr.2017.15. Epub Jan. 20, 2017.
Shimantani et al., Targeted base editing in rice and tomato using a CRISPR-Cas9 cytidine deaminase fusion. Nat Biotechnol. May 2017;35(5):441-443. doi: 10.1038/nbt.3833. Epub Mar. 27, 2017.
Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi: 10.1016/j.braindev.2011.04.014. Epub May 19, 2011.
Shin et al., CRISPR/Cas9 targeting events cause complex deletions and insertions at 17 sites in the mouse genome. Nat Commun. May 31, 2017;8:15464. doi: 10.1038/ncomms15464.
Shindo et al., A Comparison of Two Single-Stranded DNA Binding Models by Mutational Analysis of APOBEC3G. Biology (Basel). Aug. 2, 2012;1(2):260-76. doi: 10.3390/biology1020260.
Shingledecker et al., Molecular dissection of the *Mycobacterium tuberculosis* RecA intein: design of a minimal intein and of a trans-splicing system involving two intein fragments. Gene. Jan. 30, 1998;207(2):187-95. doi: 10.1016/s0378-1119(97)00624-0.
Shmakov et al., Discovery and Functional Characterization of Diverse Class 2 CRISPR Cas Systems. Molecular Cell Nov. 2015;60(3):385-97.
Shmakov et al., Diversity and evolution of class 2 CRISPR-Cas systems. Nat Rev Microbiol. Mar. 2017;15(3):169-182. doi: 10.1038/nrmicro.2016.184. Epub Jan. 23, 2017.

Shultz et al., A genome-wide analysis of FRT-like sequences in the human genome. PLoS One. Mar. 23, 2011;6(3):e18077. doi: 10.1371/journal.pone.0018077.
Siebert et al., An improved PCR method for walking in uncloned genomic DNA. Nucleic Acids Res. Mar. 25, 1995;23(6):1087-8.
Silas et al., Direct CRISPR spacer acquisition from RNA by a natural reverse transcriptase-Cas1 fusion protein. Science. Feb. 26, 2016;351(6276):aad4234. doi: 10.1126/science.aad4234.
Silva et al., Selective disruption of the DNA polymerase III $\alpha$-$\beta$ complex by the umuD gene products. Nucleic Acids Res. Jul. 2012;40(12):5511-22. doi: 10.1093/nar/gks229. Epub Mar. 9, 2012.
Simonelli et al., Base excision repair intermediates are mutagenic in mammalian cells. Nucleic Acids Res. Aug. 2, 2005;33(14):4404-11. Print 2005.
Singh et al., Cross-talk between diverse serine integrases. J Mol Biol. Jan. 23, 2014;426(2):318-31. doi: 10.1016/j.jmb.2013.10.013. Epub Oct. 22, 2013.
Singh et al., Real-time observation of DNA recognition and rejection by the RNA-guided endonuclease Cas9. Nat Commun. Sep. 14, 2016;7:12778. doi: 10.1038/ncomms12778.
Singh et al., Real-time observation of DNA target interrogation and product release by the RNA-guided endonuclease CRISPR Cpf1 (Cas12a). Proc Natl Acad Sci U S A. May 22, 2018;115(21):5444-5449. doi: 10.1073/pnas.1718686115. Epub May 7, 2018.
Singh et al., Splicing of a critical exon of human Survival Motor Neuron is regulated by a unique silencer element located in the last intron. Mol Cell Biol. Feb. 2006;26(4):1333-46. doi: 10.1128/MCB.26.4.1333-1346.2006.
Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.
Siu et al., Riboregulated toehold-gated gRNA for programmable CRISPR-Cas9 function. Nat Chem Biol. Mar. 2019;15(3):217-220. doi: 10.1038/s41589-018-0186-1. Epub Dec. 10, 2018.
Sivalingam et al., Biosafety assessment of site-directed transgene integration in human umbilical cord-lining cells. Mol Ther. Jul. 2010;18(7):1346-56. doi: 10.1038/mt.2010.61. Epub Apr. 27, 2010.
Sjoblom et al., The consensus coding sequences of human breast and colorectal cancers. Science. Oct. 13, 2006;314(5797):268-74. Epub Sep. 7, 2006.
Skretas et al., Regulation of protein activity with small-molecule-controlled inteins. Protein Sci. Feb. 2005;14(2):523-32. Epub Jan. 4, 2005.
Slaymaker et al., Rationally engineered Cas9 nucleases with improved specificity. Science. Jan. 1, 2016;351(6268):84-8. doi: 10.1126/science.aad5227. Epub Dec. 1, 2015.
Sledz et al., Structural insights into the molecular mechanism of the m(6)A writer complex. Elife. Sep. 14, 2016;5:e18434. doi: 10.7554/eLife.18434.
Slupphaug et al., A nucleotide-flipping mechanism from the structure of human uracil-DNA glycosylase bound to DNA. Nature. Nov. 7, 1996;384(6604):87-92. doi: 10.1038/384087a0.
Smargon et al., Cas13b Is a Type VI-B CRISPR-Associated RNA-Guided RNase Differentially Regulated by Accessory Proteins Csx27 and Csx28. Mol Cell. Feb. 16, 2017;65(4):618-630.e7. doi: 10.1016/j.molcel.2016.12.023. Epub Jan. 5, 2017.
Smith et al., Diversity in the serine recombinases. Mol Microbiol. Apr. 2002;44(2):299-307. Review.
Smith et al., Expression of a dominant negative retinoic acid receptor $\gamma$ in Xenopus embryos leads to partial resistance to retinoic acid. Roux Arch Dev Biol. Mar. 1994;203(5):254-265. doi: 10.1007/BF00360521.
Smith et al., Herpesvirus transport to the nervous system and back again. Annu Rev Microbiol. 2012;66:153-76. doi: 10.1146/annurev-micro-092611-150051. Epub Jun. 15, 2012.
Smith et al., Production of human beta interferon in insect cells infected with a baculovirus expression vector. Mol Cell Biol. Dec. 1983;3(12):2156-65. doi: 10.1128/mcb.3.12.2156.
Smith et al., Single-step purification of polypeptides expressed in *Escherichia coli* as fusions with glutathione S-transferase. Gene. Jul. 15, 1988;67(1):31-40. doi: 10.1016/0378-1119(88)90005-4.

(56) References Cited

OTHER PUBLICATIONS

Smith, Filamentous fusion phage: novel expression vectors that display cloned antigens on the virion surface. Science. Jun. 14, 1985;228(4705):1315-7.
Smith, Phage-encoded Serine Integrases and Other Large Serine Recombinases. Microbiol Spectr. Aug. 2015;3(4). doi: 10.1128/microbiolspec.MDNA3-0059-2014.
Somanathan et al., AAV vectors expressing LDLR gain-of-function variants demonstrate increased efficacy in mouse models of familial hypercholesterolemia. Circ Res. Aug. 29, 2014;115(6):591-9. doi: 10.1161/CIRCRESAHA.115.304008. Epub Jul. 14, 2014.
Sommerfelt et al., Receptor interference groups of 20 retroviruses plating on human cells. Virology. May 1990;176(1):58-69. doi: 10.1016/0042-6822(90)90230-0.
Song et al., Adenine base editing in an adult mouse model of tyrosinaemia. Nat Biomed Eng. Jan. 2020;4(1):125-130. doi: 10.1038/s41551-019-0357-8. Epub Feb. 25, 2019.
Song et al., Delivery of CRISPR/Cas systems for cancer gene therapy and immunotherapy. Adv Drug Deliv Rev. Jan. 2021;168:158-180. doi: 10.1016/j.addr.2020.04.010. Epub May 1, 2020.
Song et al., RS-1 enhances CRISPR/Cas9- and TALEN-mediated knock-in efficiency. Nat Commun. Jan. 28, 2016;7:10548. doi: 10.1038/ncomms10548.
Sorusch et al., Characterization of the ternary Usher syndrome SANS/ush2a/whirlin protein complex. Hum Mol Genet. Mar. 15, 2017;26(6):1157-1172. doi: 10.1093/hmg/ddx027.
Southworth et al., Control of protein splicing by intein fragment reassembly. EMBO J. Feb. 16, 1998;17(4):918-26. doi: 10.1093/emboj/17.4.918.
Southworth et al., Purification of proteins fused to either the amino or carboxy terminus of the *Mycobacterium xenopi* gyrase A intein. Biotechniques. Jul. 1999;27(1):110-4, 116, 118-20. doi: 10.2144/99271st04.
Spencer et al., A general strategy for producing conditional alleles of Src-like tyrosine kinases. Proc Natl Acad Sci U S A. Oct. 10, 1995;92(21):9805-9. doi: 10.1073/pnas.92.21.9805.
Spencer et al., Controlling signal transduction with synthetic ligands. Science. Nov. 12, 1993;262(5136):1019-24. doi: 10.1126/science.7694365.
Spencer et al., Functional analysis of Fas signaling in vivo using synthetic inducers of dimerization. Curr Biol. Jul. 1, 1996;6(7):839-47. doi: 10.1016/s0960-9822(02)00607-3.
Srivastava et al., An inhibitor of nonhomologous end-joining abrogates double-strand break repair and impedes cancer progression. Cell. Dec. 21, 2012;151(7):1474-87. doi: 10.1016/j.cell.2012.11.054.
Stadtman, Selenocysteine. Annu Rev Biochem. 1996;65:83-100.
Stamos et al., Structure of a Thermostable Group II Intron Reverse Transcriptase with Template-Primer and Its Functional and Evolutionary Implications. Mol Cell. Dec. 7, 2017;68(5):926-939.e4. doi: 10.1016/j.molcel.2017.10.024. Epub Nov. 16, 2017.
Stark et al., ATP hydrolysis by mammalian RAD51 has a key role during homology-directed DNA repair. J Biol Chem. Jun. 7, 2002;277(23):20185-94. doi: 10.1074/jbc.M112132200. Epub Mar. 28, 2002.
Steckelberg et al., A folded viral noncoding RNA blocks host cell exoribonucleases through a conformationally dynamic RNA structure. Proc Natl Acad Sci U S A. Jun. 19, 2018;115(25):6404-6409. doi: 10.1073/pnas.1802429115. Epub Jun. 4, 2018.
Steele et al., The prion protein knockout mouse: a phenotype under challenge. Prion. Apr.-Jun. 2007;1(2):83-93. doi: 10.4161/pri.1.2.4346. Epub Apr. 25, 2007.
Steiner et al., The neurotropic herpes viruses: herpes simplex and varicella-zoster. Lancet Neurol. Nov. 2007;6(11):1015-28. doi: 10.1016/S1474-4422(07)70267-3.
Stella et al., Structure of the Cpf1 endonuclease R-loop complex after target DNA cleavage. Nature. Jun. 22, 2017;546(7659):559-563. doi: 10.1038/nature22398. Epub May 31, 2017.
Stenglein et al., APOBEC3 proteins mediate the clearance of foreign DNA from human cells. Nat Struct Mol Biol. Feb. 2010;17(2):222-9. doi: 10.1038/nsmb.1744. Epub Jan. 10, 2010.
Stenson et al., The Human Gene Mutation Database: towards a comprehensive repository of inherited mutation data for medical research, genetic diagnosis and next-generation sequencing studies. Hum Genet. Jun. 2017;136(6):665-677. doi: 10.1007/s00439-017-1779-6. Epub Mar. 27, 2017.
Stephens et al., The landscape of cancer genes and mutational processes in breast cancer. Nature Jun. 2012;486:400-404. doi: 10.1038/nature11017.
Sternberg et al., Conformational control of DNA target cleavage by CRISPR-Cas9. Nature. Nov. 5, 2015;527(7576):110-3. doi: 10.1038/nature15544. Epub Oct. 28, 2015.
Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.
Sterne-Weiler et al., Exon identity crisis: disease-causing mutations that disrupt the splicing code. Genome Biol. Jan. 23, 2014;15(1):201. doi: 10.1186/gb4150.
Stevens et al., A promiscuous split intein with expanded protein engineering applications. Proc Natl Acad Sci U S A. Aug. 8, 2017;114(32):8538-8543. doi: 10.1073/pnas.1701083114. Epub Jul. 24, 2017.
Stevens et al., Design of a Split Intein with Exceptional Protein-Splicing Activity. J Am Chem Soc. Feb. 24, 2016;138(7):2162-5. doi: 10.1021/jacs.5b13528. Epub Feb. 8, 2016.
Stockwell et al., Probing the role of homomeric and heteromeric receptor interactions in TGF-beta signaling using small molecule dimerizers. Curr Biol. Jun. 18, 1998;8(13):761-70. doi: 10.1016/s0960-9822(98)70299-4.
Strecker et al., Engineering of CRISPR-Cas12b for human genome editing. Nat Commun. Jan. 22, 2019;10(1):212. doi: 10.1038/s41467-018-08224-4.
Strecker et al., RNA-guided DNA insertion with CRISPR-associated transposases. Science. Jul. 5, 2019;365(6448):48-53. doi: 10.1126/science.aax9181. Epub Jun. 6, 2019.
Strutt et al., RNA-dependent RNA targeting by CRISPR-Cas9. Elife. Jan. 5, 2018;7:e32724. doi: 10.7554/eLife.32724.
Su et al., Human DNA polymerase n has reverse transcriptase activity in cellular environments. J Biol Chem. Apr. 12, 2019;294(15):6073-6081. doi: 10.1074/jbc.RA119.007925. Epub Mar. 6, 2019.
Sudarsan et al., An mRNA structure in bacteria that controls gene expression by binding lysine. Genes Dev. Nov. 1, 2003;17(21):2688-97.
Sudarsan et al., Riboswitches in eubacteria sense the second messenger cyclic di-GMP. Science. Jul. 18, 2008;321(5887):411-3. doi: 10.1126/science.1159519.
Suess et al., A theophylline responsive riboswitch based on helix slipping controls gene expression in vivo. Nucleic Acids Res. Mar. 5, 2004;32(4):1610-4.
Sullenger et al., Ribozyme-mediated repair of defective mRNA by targeted, trans-splicing. Nature. Oct. 13, 1994;371(6498):619-22. doi: 10.1038/371619a0.
Sumner et al., Two breakthrough gene-targeted treatments for spinal muscular atrophy: challenges remain. J Clin Invest. Aug. 1, 2018;128(8):3219-3227. doi: 10.1172/JCI121658. Epub Jul. 9, 2018.
Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.
Sun et al., The CRISPR/Cas9 system for gene editing and its potential application in pain research. Transl Periop & Pain Med. Aug. 3, 2016;1(3):22-33.
Surun et al., High Efficiency Gene Correction in Hematopoietic Cells by Donor-Template-Free CRISPR/Cas9 Genome Editing. Mol Ther Nucleic Acids. Mar. 2, 2018;10:1-8. doi: 10.1016/j.omtn.2017.11.001. Epub Nov. 10, 2017.
Suzuki et al., Crystal structures reveal an elusive functional domain of pyrrolysyl-tRNA synthetase. Nat Chem Biol. Dec. 2017;13(12):1261-1266. doi: 10.1038/nchembio.2497. Epub Oct. 16, 2017.

(56) References Cited

OTHER PUBLICATIONS

Suzuki et al., In vivo genome editing via CRISPR/Cas9 mediated homology-independent targeted integration. Nature. Dec. 1, 2016;540(7631):144-149. doi: 10.1038/nature20565. Epub Nov. 16, 2016.
Suzuki et al., VCre/VloxP and SCre/SloxP: new site-specific recombination systems for genome engineering. Nucleic Acids Res. Apr. 2011;39(8):e49. doi: 10.1093/nar/gkq1280. Epub Feb. 1, 2011.
Swarts et al., Argonaute of the archaeon Pyrococcus furiosus is a DNA-guided nuclease that targets cognate DNA. Nucleic Acids Res. May 26, 20156;43(10):5120-9. doi: 10.1093/nar/gkv415. Epub Apr. 29, 2015.
Swarts et al., DNA-guided DNA interference by a prokaryotic Argonaute. Nature. Mar. 13, 2014;507(7491):258-61. doi: 10.1038/nature12971. Epub Feb. 16, 2014.
Swarts et al., The evolutionary journey of Argonaute proteins. Nat Struct Mol Biol. Sep. 2014;21(9):743-53. doi: 10.1038/nsmb.2879.
Szczepek et al., Structure-based redesign of the dimerization interface reduces the toxicity of zinc-finger nucleases. Nat Biotechnol. Jul. 2007;25(7):786-93. Epub Jul. 1, 2007.
Tabebordbar et al., In vivo gene editing in dystrophic mouse muscle and muscle stem cells. Science. Jan. 22, 2016;351(6271):407-411. doi: 10.1126/science.aad5177. Epub Dec. 31, 2015.
Tagalakis et al., Lack of RNA-DNA oligonucleotide (chimeraplast) mutagenic activity in mouse embryos. Mol Reprod Dev. Jun. 2005;71(2):140-4.
Tahara et al., Potent and Selective Inhibitors of 8-Oxoguanine DNA Glycosylase. J Am Chem Soc. Feb. 14, 2018;140(6):2105-2114. doi: 10.1021/jacs.7b09316. Epub Feb. 5, 2018.
Tajiri et al., Functional cooperation of MutT, MutM and MutY proteins in preventing mutations caused by spontaneous oxidation of guanine nucleotide in *Escherichia coli*. Mutat Res. May 1995;336(3):257-67. doi: 10.1016/0921-8777(94)00062-b.
Takimoto et al., Stereochemical basis for engineered pyrrolysyl-tRNA synthetase and the efficient in vivo incorporation of structurally divergent non-native amino acids. ACS Chem Biol. Jul. 15, 2011;6(7):733-43. doi: 10.1021/cb200057a. Epub May 5, 2011.
Talbot et al., Spinal muscular atrophy. Semin Neurol. Jun. 2001;21(2):189-97. doi: 10.1055/s-2001-15264.
Tambunan et al., Vaccine Design for H5N1 Based on B- and T-cell Epitope Predictions. Bioinform Biol Insights. Apr. 28, 2016;10:27-35. doi: 10.4137/BBI.S38378.
Tan et al., Engineering of high-precision base editors for site-specific single nucleotide replacement. Nat Commun. Jan. 25, 2019;10(1):439. doi: 10.1038/s41467-018-08034-8. Erratum in: Nat Commun. May 1, 2019;10(1):2019.
Tanenbaum et al., A protein-tagging system for signal amplification in gene expression and fluorescence imaging. Cell. Oct. 23, 2014;159(3):635-46. doi: 10.1016/j.cell.2014.09.039. Epub Oct. 9, 2014.
Tanese et al., Expression of enzymatically active reverse transcriptase in *Escherichia coli*. Proc Natl Acad Sci U S A. Aug. 1985;82(15):4944-8. doi: 10.1073/pnas.82.15.4944.
Tang et al., Aptazyme-embedded guide RNAs enable ligand-responsive genome editing and transcriptional activation. Nat Commun. Jun. 2, 20178;8:15939. doi: 10.1038/ncomms15939.
Tang et al., Evaluation of Bioinformatic Programmes for the Analysis of Variants within Splice Site Consensus Regions. Adv Bioinformatics. 2016;2016:5614058. doi: 10.1155/2016/5614058. Epub May 24, 2016.
Tang et al., Rewritable multi-event analog recording in bacterial and mammalian cells. Science. Apr. 13, 2018;360(6385):eaap8992. doi: 10.1126/science.aap8992. Epub Feb. 15, 2018.
Tassabehji, Williams-Beuren syndrome: a challenge for genotype-phenotype correlations. Hum Mol Genet. Oct. 15, 2003;12 Spec No. 2:R229-37. doi: 10.1093/hmg/ddg299. Epub Sep. 2, 2003.
Taube et al., Reverse transcriptase of mouse mammary tumour virus: expression in bacteria, purification and biochemical characterization. Biochem J. Feb. 1, 1998;329 ( Pt 3)(Pt 3):579-87. doi: 10.1042/bj3290579. Erratum in: Biochem J Jun. 15, 1998;332(Pt 3):808.
Tebas et al., Gene editing of CCR5 in autologous CD4 T cells of persons infected with HIV. N Engl J Med. Mar. 6, 2014;370(10):901-10. doi: 10.1056/NEJMoa1300662.
Tee et al., Polishing the craft of genetic diversity creation in directed evolution. Biotechnol Adv. Dec. 2013;31(8):1707-21. doi: 10.1016/j.biotechadv.2013.08.021. Epub Sep. 6, 2013.
Telenti et al., The *Mycobacterium xenopi* GyrA protein splicing element: characterization of a minimal intein. J Bacteriol. Oct. 1997;179(20):6378-82. doi: 10.1128/jb.179.20.6378-6382.1997.
Telesnitsky et al., RNase H domain mutations affect the interaction between Moloney murine leukemia virus reverse transcriptase and its primer-template. Proc Natl Acad Sci U S A. Feb. 15, 1993;90(4):1276-80. doi: 10.1073/pnas.90.4.1276.
Teng et al., Mutational analysis of apolipoprotein B mRNA editing enzyme (APOBEC1). structure-function relationships of RNA editing and dimerization. J Lipid Res. Apr. 1999;40(4):623-35.
Tessarollo et al., Targeted mutation in the neurotrophin-3 gene results in loss of muscle sensory neurons. Proc Natl Acad Sci U S A. Dec. 6, 1994;91(25):11844-8.
Tesson et al., Knockout rats generated by embryo microinjection of TALENs. Nat Biotechnol. Aug. 5, 2011;29(8):695-6. doi: 10.1038/nbt.1940.
Thompson et al., Cellular uptake mechanisms and endosomal trafficking of supercharged proteins. Chem Biol. Jul. 27, 2012;19(7):831-43. doi: 10.1016/j.chembiol.2012.06.014.
Thompson et al., Engineering and identifying supercharged proteins for macromolecule delivery into mammalian cells. Methods Enzymol. 2012;503:293-319. doi: 10.1016/B978-0-12396962-0.00012-4.
Thompson et al., The Future of Multiplexed Eukaryotic Genome Engineering. ACS Chem Biol. Feb. 16, 2018;13(2):313-325. doi: 10.1021/acschembio.7b00842. Epub Dec. 28, 2017.
Thomson et al., Mutational analysis of loxP sites for efficient Cre-mediated insertion into genomic DNA. Genesis. Jul. 2003;36(3):162-7. doi: 10.1002/gene.10211.
Thorpe et al., Functional correction of episomal mutations with short DNA fragments and RNA-DNA oligonucleotides. J Gene Med. Mar.-Apr. 2002;4(2):195-204.
Thuronyi et al., Continuous evolution of base editors with expanded target compatibility and improved activity. Nat Biotechnol. Sep. 2019;37(9):1070-1079. doi: 10.1038/s41587-019-0193-0. Epub Jul. 22, 2019.
Thyagarajan et al., Creation of engineered human embryonic stem cell lines using phiC31 integrase. Stem Cells. Jan. 2008;26(1):119-26. doi: 10.1634/stemcells.2007-0283. Epub Oct. 25, 2007.
Thyagarajan et al., Mammalian genomes contain active recombinase recognition sites. Gene. Feb. 22, 2000;244(1-2):47-54.
Thyagarajan et al., Site-specific genomic integration in mammalian cells mediated by phage phiC31 integrase. Mol Cell Biol. Jun. 2001;21(12):3926-34.
Tinland et al., The T-DNA-linked VirD2 protein contains two distinct functional nuclear localization signals. Proc Natl Acad Sci U S A. Aug. 15, 1992;89(16):7442-6. doi: 10.1073/pnas.89.16.7442.
Tirumalai et al., Recognition of core-type DNA sites by lambda integrase. J Mol Biol. Jun. 12, 1998;279(3):513-27.
Tom et al., Mechanism whereby proliferating cell nuclear antigen stimulates flap endonuclease 1. J Biol Chem. Apr. 7, 2000;275(14):10498-505. doi: 10.1074/jbc.275.14.10498.
Tone et al., Single-stranded DNA binding protein Gp5 of Bacillus subtilis phage Φ29 is required for viral DNA replication in growth-temperature dependent fashion. Biosci Biotechnol Biochem. 2012;76(12):2351-3. doi: 10.1271/bbb.120587. Epub Dec. 7, 2012.
Toor et al., Crystal structure of a self-spliced group II intron. Science. Apr. 4, 2008;320(5872):77-82. doi: 10.1126/science.1153803.
Toro et al., On the Origin and Evolutionary Relationships of the Reverse Transcriptases Associated With Type III CRISPR-Cas Systems. Front Microbiol. Jun. 15, 2018;9:1317. doi: 10.3389/fmicb.2018.01317.

(56) References Cited

OTHER PUBLICATIONS

Toro et al., The Reverse Transcriptases Associated with CRISPR-Cas Systems. Sci Rep. Aug. 2, 2017;7(1):7089. doi: 10.1038/s41598-017-07828-y.

Torres et al., Non-integrative lentivirus drives high-frequency cre-mediated cassette exchange in human cells. PLoS One. 2011;6(5):e19794. doi: 10.1371/journal.pone.0019794. Epub May 23, 2011.

Tourdot et al., A general strategy to enhance immunogenicity of low-affinity HLA-A2. 1-associated peptides: implication in the identification of cryptic tumor epitopes. Eur J Immunol. Dec. 2000;30(12):3411-21.

Townsend et al., Role of HFE in iron metabolism, hereditary haemochromatosis, anaemia of chronic disease, and secondary iron overload. Lancet. Mar. 2, 2002;359(9308):786-90. doi: 10.1016/S0140-6736(02)07885-6.

Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.

Tratschin et al., A human parvovirus, adeno-associated virus, as a eucaryotic vector: transient expression and encapsidation of the procaryotic gene for chloramphenicol acetyltransferase. Mol Cell Biol. Oct. 1984;4(10):2072-81. doi: 10.1128/mcb.4.10.2072.

Tratschin et al., Adeno-associated virus vector for high-frequency integration, expression, and rescue of genes in mammalian cells. Mol Cell Biol. Nov. 1985;5(11):3251-60. doi: 10.1128/mcb.5.11.3251.

Trausch et al., The structure of a tetrahydrofolate-sensing riboswitch reveals two ligand binding sites in a single aptamer. Structure. Oct. 1, 20112;19(10):1413-23. doi: 10.1016/j.str.2011.06.019. Epub Sep. 8, 2011.

Traxler et al., A genome-editing strategy to treat β-hemoglobinopathies that recapitulates a mutation associated with a benign genetic condition. Nat Med. Sep. 2016;22(9):987-90. doi: 10.1038/nm.4170. Epub Aug. 15, 2016.

Trojan et al., Functional analysis of hMLH1 variants and HNPCC-related mutations using a human expression system. Gastroenterology. Jan. 2002;122(1):211-9. doi: 10.1053/gast.2002.30296.

Trudeau et al., On the Potential Origins of the High Stability of Reconstructed Ancestral Proteins. Mol Biol Evol. Oct. 2016;33(10):2633-41. doi: 10.1093/molbev/msw138. Epub Jul. 12, 2016.

Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015. With Supplementary Data.

Tsai et al., GUIDE-seq enables genome-wide profiling of off-target cleavage by CRISPR-Cas nucleases. Nat Biotechnol. Feb. 2015;33(2):187-197. doi: 10.1038/nbt.3117. Epub Dec. 16, 2014.

Tsai et al., CIRCLE-seq: a highly sensitive in vitro screen for genome-wide CRISPR-Cas9 nuclease off-targets. Nat Methods. Jun. 2017; 14(6):607-614. doi: 10.1038/nmeth.4278. Epub May 1, 2017.

Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.

Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.

Tsang et al., Specialization of the DNA-cleaving activity of a group I ribozyme through in vitro evolution. J Mol Biol. Sep. 13, 1996;262(1):31-42. doi: 10.1006/jmbi.1996.0496.

Tsutakawa et al., Human flap endonuclease structures, DNA double-base flipping, and a unified understanding of the FEN1 superfamily. Cell. Apr. 15, 2011;145(2):198-211. doi: 10.1016/j.cell.2011.03.004.

Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.11.016. Epub Nov. 29, 2012.

Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.

Turan et al., Site-specific recombinases: from tag-and-target- to tag-and-exchange-based genomic modifications. FASEB J. Dec. 2011;25(12):4088-107. doi: 10.1096/fj.11-186940. Epub Sep. 2, 2011. Review.

Tycko et al., Pairwise library screen systematically interrogates *Staphylococcus aureus* Cas9 specificity in human cells. bioRxiv. doi: https://doi.org/10.1101/269399 Posted Feb. 22, 2018.

UniProt Consortium, UniProt: the universal protein knowledgebase. Nucleic Acids Res. Mar. 16, 2018;46(5):2699. doi: 10.1093/nar/gky092. Erratum for: Nucleic Acids Res. Jan. 4, 2017;45(D1):D158-D169.

UniProt Submission; UniProt, Accession No. P01011. Last modified Jun. 11, 2014, version 2. 15 pages.

UniProt Submission; UniProt, Accession No. P01011. Last modified Sep. 18, 2013, version 2. 15 pages.

UniProt Submission; UniProt, Accession No. P04264. Last modified Jun. 11, 2014, version 6. 15 pages.

UniProt Submission; UniProt, Accession No. P04275. Last modified Jul. 9, 2014, version 107. 29 pages.

UniProtein A0A1V6. Dec. 11, 2019.

UniProtKB Submission; Accession No. F0NH53. May 3, 2011. 4 pages.

UniProtKB Submission; Accession No. F0NN87. May 3, 2011. 4 pages.

UniProtKB Submission; Accession No. P0DOC6. No Author Listed., Oct. 5, 2016. 5 pages.

UniProtKB Submission; Accession No. T0D7A2. Oct. 16, 2013. 10 pages.

Urasaki et al., Functional dissection of the Tol2 transposable element identified the minimal cis-sequence and a highly repetitive sequence in the subterminal region essential for transposition. Genetics. Oct. 2006;174(2):639-49. doi: 10.1534/genetics.106.060244. Epub Sep. 7, 2006.

Urnov et al., Genome editing with engineered zinc finger nucleases. Nat Rev Genet. Sep. 2010;11(9):636-46. doi: 10.1038/nrg2842.

Urnov et al., Highly efficient endogenous human gene correction using designed zinc-finger nucleases. Nature. Jun. 2, 2005;435(7042):646-51. Epub Apr. 3, 2005.

Usman et al., Exploiting the chemical synthesis of RNA. Trends Biochem Sci. Sep. 1992;17(9):334-9. doi: 10.1016/0968-0004(92)90306-t.

Vagner et al., Efficiency of homologous DNA recombination varies along the Bacillus subtilis chromosome. J Bacteriol. Sep. 1988;170(9):3978-82.

Vakulskas et al., A high-fidelity Cas9 mutant delivered as a ribonucleoprotein complex enables efficient gene editing in human hematopoietic stem and progenitor cells. Nat Med. Aug. 2018;24(8):1216-1224. doi: 10.1038/s41591-018-0137-0. Epub Aug. 6, 2018.

Van Brunt et al., Genetically Encoded Azide Containing Amino Acid in Mammalian Cells Enables Site-Specific Antibody-Drug Conjugates Using Click Cycloaddition Chemistry. Bioconjug Chem. Nov. 18, 2015;26(11):2249-60. doi: 10.1021/acs.bioconjchem.5b00359. Epub Sep. 11, 2015.

Van Brunt et al., Molecular Farming: Transgenic Animals as Bioreactors. Biotechnology (NY). 1988;6(10):1149-1154. doi: 10.1038/nbt1088-1149.

Van Den Oord et al., Pixel Recurrent Neural Networks. Proceedings of the 33rd International Conference on Machine Learning. Journal of Machine Learning Research. Aug. 19, 2016. vol. 48. 11 pages.

Van Duyne et al., Teaching Cre to follow directions. Proc Natl Acad Sci U S A. Jan. 6, 2009;106(1):4-5. doi: 10.1073/pnas.0811624106. Epub Dec. 31, 2008.

Van Overbeek et al., DNA Repair Profiling Reveals Nonrandom Outcomes at Cas9-Mediated Breaks. Mol Cell. Aug. 18, 2016;63(4):633-646. doi: 10.1016/j.molcel.2016.06.037. Epub Aug. 4, 2016.

(56) References Cited

OTHER PUBLICATIONS

Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.

Van Wijk et al., Identification of 51 novel exons of the Usher syndrome type 2A (USH2A) gene that encode multiple conserved functional domains and that are mutated in patients with Usher syndrome type II. Am J Hum Genet. Apr. 2004;74(4):738-44. doi: 10.1086/383096. Epub Mar. 10, 2004.

Vanamee et al., FokI requires two specific DNA sites for cleavage. J Mol Biol. May 25, 2001;309(1):69-78.

Varga et al., Progressive vascular smooth muscle cell defects in a mouse model of Hutchinson-Gilford progeria syndrome. Proc Natl Acad Sci U S A. Feb. 28, 2006;103(9):3250-5. doi: 10.1073/pnas. 0600012103. Epub Feb. 21, 2006.

Varshney et al., The regulation and functions of DNA and RNA G-quadruplexes. Nat Rev Mol Cell Biol. Aug. 2020;21(8):459-474. doi: 10.1038/s41580-020-0236-x. Epub Apr. 20, 2020.

Vellore et al., A group II intron-type open reading frame from the thermophile Bacillus (Geobacillus) stearothermophilus encodes a heat-stable reverse transcriptase. Appl Environ Microbiol. Dec. 2004;70(12):7140-7. doi: 10.1128/AEM.70.12.7140-7147.2004.

Venken et al., Genome-wide manipulations of *Drosophila melanogaster* with transposons, Flp recombinase, and ΦC31 integrase. Methods Mol Biol. 2012;859:203-28. doi: 10.1007/978-1- 61779-603-6_12.

Verma, The reverse transcriptase. Biochim Biophys Acta. Mar. 21, 1977;473(1):1-38. doi: 10.1016/0304-419x(77)90005-1.

Vidal et al., Yeast forward and reverse 'n'-hybrid systems. Nucleic Acids Res. Feb. 15, 1999;27(4):919-29. doi: 10.1093/nar/27.4.919.

Vigne et al., Third-generation adenovectors for gene therapy. Restor Neurol Neurosci. Jan. 1, 1995;8(1):35-6. doi: 10.3233/RNN-1995-81208.

Vik et al., Endonuclease V cleaves at inosines in RNA. Nat Commun. 2013;4:2271. doi: 10.1038/ncomms3271.

Vilenchik et al., Endogenous DNA double-strand breaks: production, fidelity of repair, and induction of cancer. Proc Natl Acad Sci U S A. Oct. 28, 2003;100(22):12871-6. doi: 10.1073/pnas. 2135498100. Epub Oct. 17, 2003.

Villiger et al., Treatment of a metabolic liver disease by in vivo genome base editing in adult mice. Nat Med. Oct. 2018;24(10):1519-1525. doi: 10.1038/s41591-018-0209-1. Epub Oct. 8, 2018.

Vitreschak et al., Regulation of the vitamin B12 metabolism and transport in bacteria by a conserved RNA structural element. RNA. Sep. 2003;9(9):1084-97.

Voigt et al., Rational evolutionary design: the theory of in vitro protein evolution. Adv Protein Chem. 2000;55:79-160.

Vriend et al., Nick-initiated homologous recombination: Protecting the genome, one strand at a time. DNA Repair (Amst). Feb. 2017;50:1-13. doi: 10.1016/j.dnarep.2016.12.005. Epub Dec. 29, 2016.

Wacey et al., Disentangling the perturbational effects of amino acid substitutions in the DNA-binding domain of p53. Hum Genet. Jan. 1999; 104(1):15-22.

Wadia et al., Modulation of cellular function by TAT mediated transduction of full length proteins. Curr Protein Pept Sci. Apr. 2003;4(2):97-104.

Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.

Wah et al., Structure of FokI has implications for DNA cleavage. Proc Natl Acad Sci U S A. Sep. 1, 1998;95(18):10564-9.

Wals et al., Unnatural amino acid incorporation in *E. coli:* current and future applications in the design of therapeutic proteins. Front Chem. Apr. 1, 2014;2:15. doi: 10.3389/fchem.2014.00015. eCollection 2014.

Walton et al., Unconstrained genome targeting with near-PAMless engineered CRISPR-Cas9 variants. Science. Apr. 17, 2020;368(6488):290-296. doi: 10.1126/science.aba8853. Epub Mar. 26, 2020.

Wan et al., Material solutions for delivery of CRISPR/Cas-based genome editing tools: Current status and future outlook. Materials Today. Jun. 2019;26:40-66. doi: 10.1016/j.mattod.2018.12.003.

Wang et al. CRISPR-Cas9 and CRISPR-Assisted Cytidine Deaminase Enable Precise and Efficient Genome Editing in Klebsiella pneumoniae. Appl Environ Microbiol. 2018;84(23):e01834-18. Published Nov. 15, 2018. doi:10.1128/AEM.01834-18.

Wang et al., AID upmutants isolated using a high-throughput screen highlight the immunity/cancer balance limiting DNA deaminase activity. Nat Struct Mol Biol. Jul. 2009;16(7):769-76. doi: 10.1038/nsmb.1623. Epub Jun. 21, 2009.

Wang et al., Continuous directed evolutions of proteins with improved soluble expression. Nature Chemical Biology. Nat Publishing Group. Aug. 20, 2018; 14(10):972-980.

Wang et al., CRISPR-Cas9 Targeting of PCSK9 in Human Hepatocytes In Vivo-Brief Report. Arterioscler Thromb Vasc Biol. May 2016;36(5):783-6. doi: 10.1161/ATVBAHA.116.307227. Epub Mar. 3, 2016.

Wang et al., Efficient delivery of genome-editing proteins using bioreducible lipid nanoparticles. Proc Natl Acad Sci U S A. Feb. 29, 2016. pii: 201520244. [Epub ahead of print].

Wang et al., Enhanced base editing by co-expression of free uracil DNA glycosylase inhibitor. Cell Res. Oct. 2017;27(1):1289-92. doi: 10.1038/cr.2017.111. Epub Aug. 29, 2017.

Wang et al., Evolution of new nonantibody proteins via iterative somatic hypermutation. Proc Natl Acad Sci U S A. Nov. 30, 2004;101(48):16745-9. Epub Nov. 19, 2004.

Wang et al., Expanding the genetic code. Annu Rev Biophys Biomol Struct. 2006;35:225-49. Review.

Wang et al., Genetic screens in human cells using the CRISPR-Cas9 system. Science. Jan. 3, 2014;343(6166):80-4. doi: 10.1126/science. 1246981. Epub Dec. 12, 2013.

Wang et al., Highly efficient CRISPR/HDR-mediated knock-in for mouse embryonic stem cells and zygotes. Biotechniques. 2015:59,201-2;204:206-8.

Wang et al., N(6)-methyladenosine Modulates Messenger RNA Translation Efficiency. Cell. Jun. 4, 2015;161(6):1388-99. doi: 10.1016/j.cell.2015.05.014.

Wang et al., N6-methyladenosine-dependent regulation of messenger RNA stability. Nature. Jan. 2, 2014;505(7481): 117-20. doi: 10.1038/nature12730. Epub Nov. 27, 2013.

Wang et al., Nucleation, propagation and cleavage of target RNAs in Ago silencing complexes. Nature. Oct. 8, 2009;461(7265):754-61. doi: 10.1038/nature08434.

Wang et al., One-step generation of mice carrying mutations in multiple genes by CRISPR/Cas-mediated genome engineering. Cell. May 9, 2013;153(4):910-8. doi: 10.1016/j.cell.2013.04.025. Epub May 2, 2013.

Wang et al., Optimized paired-sgRNA/Cas9 cloning and expression cassette triggers high-efficiency multiplex genome editing in kiwifruit. Plant Biotechnol J. Aug. 2018;16(8):1424-1433. doi: 10.1111/pbi.12884. Epub Feb. 6, 2018.

Wang et al., Programming cells by multiplex genome engineering and accelerated evolution. Nature. Aug. 13, 2009;460(7257):894-8. Epub Jul. 26, 2009.

Wang et al., Reading RNA methylation codes through methyl-specific binding proteins. RNA Biol. 2014;11(6):669-72. doi: 10.4161/rna.28829. Epub Apr. 24, 2014.

Wang et al., Recombinase technology: applications and possibilities. Plant Cell Rep. Mar. 2011;30(3):267-85. doi: 10.1007/s00299-010-0938-1. Epub Oct. 24, 2010.

Wang et al., Riboswitches that sense S-adenosylhomocysteine and activate genes involved in coenzyme recycling. Mol Cell. Mar. 28, 2008;29(6):691-702. doi: 10.1016/j.molcel.2008.01.012.

Wang et al., *Staphylococcus aureus* protein SAUGI acts as a uracil-DNA glycosylase inhibitor. Nucleic Acids Res. Jan. 2014;42(2):1354-64. doi: 10.1093/nar/gkt964. Epub Oct. 22, 2013.

Wang et al., Structural basis of N(6)-adenosine methylation by the METTL3-METTL14 complex. Nature. Jun. 23, 2016;534(7608):575-8. doi: 10.1038/nature18298. Epub May 25, 2016.

(56) References Cited

OTHER PUBLICATIONS

Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Wang et al., Uracil-DNA glycosylase inhibitor gene of bacteriophage PBS2 encodes a binding protein specific for uracil-DNA glycosylase. J Biol Chem. Jan. 15, 1989;264(2):1163-71.
Warren et al., A chimeric Cre recombinase with regulated directionality. Proc Natl Acad Sci USA. Nov. 25, 2008;105(47):18278-83. doi: 10.1073/pnas.0809949105. Epub Nov. 14, 2008.
Warren et al., Mutations in the amino-terminal domain of lambda-integrase have differential effects on integrative and excisive recombination. Mol Microbiol. Feb. 2005;55(4):1104-12.
Watowich, The erythropoietin receptor: molecular structure and hematopoietic signaling pathways. J Investig Med. Oct. 2011;59(7):1067-72. doi: 10.2310/JIM.0b013e31820fb28c.
Waxman et al., Regulating excitability of peripheral afferents: emerging ion channel targets. Nat Neurosci. Feb. 2014;17(2):153-63. doi: 10.1038/nn.3602. Epub Jan. 28, 2014.
Weber et al., Assembly of designer TAL effectors by Golden Gate cloning. PLoS One. 2011;6(5):e19722. doi: 10.1371/journal.pone. 0019722. Epub May 19, 2011.
Weill et al., DNA polymerases in adaptive immunity. Nat Rev Immunol. Apr. 2008;8(4):302-12. doi: 10.1038/nri2281. Epub Mar. 14, 2008.
Weinberg et al., New Classes of Self-Cleaving Ribozymes Revealed by Comparative Genomics Analysis. Nat Chem Biol. Aug. 2015;11(8):606-10. doi: 10.1038/nchembio.1846. Epub Jul. 13, 2015.
Weinberg et al., The aptamer core of SAM-IV riboswitches mimics the ligand-binding site of SAM-I riboswitches. RNA. May 2008;14(5):822-8. doi: 10.1261/rna.988608. Epub Mar. 27, 2008.
Weinberger et al., Disease-causing mutations C277R and C277Y modify gating of human ClC-1 chloride channels in myotonia congenita. J Physiol. Aug. 1, 2012;590(Pt 15):3449-64. doi: 0.1113/jphysiol.2012.232785. Epub May 28, 2012.
Weinert et al., Unbiased detection of CRISPR off-targets in vivo using DISCOVER-Seq. Science. Apr. 19, 2019;364(6437):286-289. doi: 10.1126/science.aav9023. Epub Apr. 18, 2019.
Weiss et al., Loss-of-function mutations in sodium channel Nav1.7 cause anosmia. Nature. Apr. 14, 2011;472(7342):186-90. doi: 10.1038/nature09975. Epub Mar. 23, 2011.
Wen et al., Inclusion of a universal tetanus toxoid CD4(+) T cell epitope P2 significantly enhanced the immunogenicity of recombinant rotavirus ΔVP8* subunit parenteral vaccines. Vaccine. Jul. 3, 20141;32(35):4420-4427. doi: 10.1016/j.vaccine.2014.06.060. Epub Jun. 21, 2014.
West et al., Gene expression in adeno-associated virus vectors: the effects of chimeric mRNA structure, helper virus, and adenovirus VA1 Rna. Virology. Sep. 1987;160(1):38-47. doi: 10.1016/0042-6822(87)90041-9.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wheeler et al., The thermostability and specificity of ancient proteins. Curr Opin Struct Biol. Jun. 2016;38:37-43. doi: 10.1016/j.sbi.2016.05.015. Epub Jun. 9, 2016.
Wiedenheft et al., RNA-guided genetic silencing systems in bacteria and archaea. Nature. Feb. 15, 2012;482(7385):331-8. doi: 10.1038/nature10886. Review.
Wienert et al., KLF1 drives the expression of fetal hemoglobin in British HPFH. Blood. Aug. 10, 2017;130(6):803-807. doi: 10.1182/blood-2017-02-767400. Epub Jun. 28, 2017.

Wijesinghe et al., Efficient deamination of 5-methylcytosines in DNA by human APOBEC3A, but not by AID or APOBEC3G. Nucleic Acids Res. Oct. 2012;40(18):9206-17. doi: 10.1093/nar/gks685. Epub Jul. 13, 2012.
Wijnker et al., Managing meiotic recombination in plant breeding. Trends Plant Sci. Dec. 2008;13(12):640-6. doi: 10.1016/j.tplants. 2008.09.004. Epub Oct. 22, 2008.
Williams et al., Assessing the accuracy of ancestral protein reconstruction methods. PLoS Comput Biol. Jun. 23, 2006;2(6):e69. doi: 10.1371/journal.pcbi.0020069. Epub Jun. 23, 2006.
Wills et al., Pseudoknot-dependent read-through of retroviral gag termination codons: importance of sequences in the spacer and loop 2. EMBO J. Sep. 1, 1994;13(17):4137-44. doi: 10.1002/j.1460-2075. 1994.tb06731.x.
Wilson et al., Assessing annotation transfer for genomics: quantifying the relations between protein sequence, structure and function through traditional and probabilistic scores. J Mol Biol 2000;297:233-49.
Wilson et al., Formation of infectious hybrid virions with gibbon ape leukemia virus and human T-cell leukemia virus retroviral envelope glycoproteins and the gag and pol proteins of Moloney murine leukemia virus. J Virol. May 1989;63(5):2374-8. doi: 10.1128/JVI.63.5.2374-2378.1989.
Wilson et al., In Vitro Selection of Functional Nucleic Acids. Annu Rev Biochem. 1999;68:611-47. doi: 10.1146/annurev.biochem.68. 1.611.
Wilson et al., Kinase dynamics. Using ancient protein kinases to unravel a modern cancer drug's mechanism. Science. Feb. 20, 2015;347(6224):882-6. doi: 10.1126/science.aaa1823.
Wilson et al., Programmable m6A modification of cellular RNAs with a Cas13-directed methyltransferase. Nat Biotechnol. Dec. 2020;38(12):1431-1440. doi: 10.1038/s41587-020-0572- 6. Epub Jun. 29, 2020.
Winkler et al., An mRNA structure that controls gene expression by binding FMN. Proc Natl Acad Sci U S A. Dec. 10, 2002;99(25):15908-13. Epub Nov. 27, 2002.
Winkler et al., Control of gene expression by a natural metabolite-responsive ribozyme. Nature. Mar. 18, 2004;428(6980):281-6.
Winkler et al., Thiamine derivatives bind messenger RNAs directly to regulate bacterial gene expression. Nature. Oct. 31, 2002;419(6910):952-6. Epub Oct. 16, 2002.
Winoto et al., A novel, inducible and T cell-specific enhancer located at the 3' end of the T cell receptor alpha locus. EMBO J. Mar. 1989;8(3):729-33.
Winter et al., Drug Development. Phthalimide conjugation as a strategy for in vivo target protein degradation. Science. Jun. 19, 2015;348(6241):1376-81. doi:; 10.1126/science.aab1433. Epub May 21, 2015.
Winter et al., Targeted exon skipping with AAV-mediated split adenine base editors. Cell Discov. Aug. 20, 2019;5:41. doi: 10.1038/s41421-019-0109-7.
Wirth et al., Mildly affected patients with spinal muscular atrophy are partially protected by an increased SMN2 copy number. Hum Genet. May 2006;119(4):422-8. doi: 10.1007/s00439-006-0156-7. Epub Mar. 1, 2006.
Wold, Replication protein A: a heterotrimeric, single-stranded DNA-binding protein required for eukaryotic DNA metabolism. Annu Rev Biochem. 1997;66:61-92. doi: 10.1146/annurev.biochem.66.1. 61.
Wolf et al., tadA, an essential tRNA-specific adenosine deaminase from *Escherichia coli*. EMBO J. Jul. 15, 2002;21(14):3841-51.
Wolfe et al., Analysis of zinc fingers optimized via phage display: evaluating the utility of a recognition code. J Mol Biol. Feb. 5, 1999;285(5):1917-34.
Wong et al., A statistical analysis of random mutagenesis methods used for directed protein evolution. J Mol Biol. Jan. 27, 2006;355(4):858-71. Epub Nov. 17, 2005.
Wong et al., The Diversity Challenge in Directed Protein Evolution. Comb Chem High Throughput Screen. May 2006;9(4):271-88.
Woo et al., Gene activation of SMN by selective disruption of lncRNA-mediated recruitment of PRC2 for the treatment of spinal

(56) References Cited

OTHER PUBLICATIONS muscular atrophy. Proc Natl Acad Sci U S A. Feb. 21, 2017;114(8):E1509-E1518. doi:10.1073/pnas.1616521114. Epub Feb. 13, 2017.
Wood et al., A genetic system yields self-cleaving inteins for bioseparations. Nat Biotechnol. Sep. 1999;17(9):889-92. doi: 10.1038/12879.
Wood et al., Targeted genome editing across species using ZFNs and TALENs. Science. Jul. 15, 2011;333(6040):307. doi: 10.1126/science.1207773. Epub Jun. 23, 2011.
Woods et al., The phenotype of congenital insensitivity to pain due to the NaV1.9 variant p.L811P. Eur J Hum Genet. May 2015;23(5):561-3. doi: 10.1038/ejhg.2014.166. Epub Aug. 13, 2014.
Wright et al., Continuous in vitro evolution of catalytic function. Science. Apr. 25, 1997;276(5312):614-7.
Wright et al., Rational design of a split-Cas9 enzyme complex. Proc Natl Acad Sci U S A. Mar. 10, 2015;112(10):2984-9. doi: 10.1073/pnas.1501698112. Epub Feb. 23, 2015.
Wu et al., A novel SCN9A mutation responsible for primary erythromelalgia and is resistant to the treatment of sodium channel blockers. PLoS One. 2013;8(1):e55212. doi: 10.1371/journal.pone.0055212. Epub Jan. 31, 2013. 15 pages.
Wu et al., Correction of a genetic disease in mouse via use of CRISPR-Cas9. Cell Stem Cell. Dec. 5, 2013;13(6):659-62. doi: 10.1016/j.stem.2013.10.016.
Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.
Wu et al., Human single-stranded DNA binding proteins: guardians of genome stability. Acta Biochim Biophys Sin (Shanghai). Jul. 2016;48(7):671-7. doi: 10.1093/abbs/gmw044. Epub May 23, 2016.
Wu et al., MLV based viral-like-particles for delivery of toxic proteins and nuclear transcription factors. Biomaterials. Sep. 2014;35(29):8416-26. doi: 10.1016/j.biomaterials.2014.06.006. Epub Jul. 3, 2014.
Wu et al., Protein trans-splicing and functional mini-inteins of a cyanobacterial dnaB intein. Biochim Biophys Acta. Sep. 8, 1998;1387(1-2):422-32. doi: 10.1016/s0167-4838(98)00157-5.
Wu et al., Protein trans-splicing by a split intein encoded in a split DnaE gene of *Synechocystis* sp. PCC6803. Proc Natl Acad Sci U S A. Aug. 4, 1998;95(16):9226-31. doi: 10.1073/pnas.95.16.9226.
Wu et al., Readers, writers and erasers of N6-methylated adenosine modification. Curr Opin Struct Biol. Dec. 2017;47:67-76. doi: 10.1016/j.sbi.2017.05.011. Epub Jun. 16, 2017.
Wu et al., Widespread Influence of 3'-End Structures on Mammalian mRNA Processing and Stability. Cell. May 18, 2017;169(5):905-917.e11. doi: 10.1016/j.cell.2017.04.036.
Xiang et al., RNA m6A methylation regulates the ultraviolet-induced DNA damage response. Nature. Mar. 23, 2017;543(7646):573-576. doi: 10.1038/nature21671. Epub Mar. 15, 2017.
Xiao et al., Genetic incorporation of multiple unnatural amino acids into proteins in mammalian cells. Angew Chem Int Ed Engl. Dec. 23, 2013;52(52):14080-3. doi: 10.1002/anie.201308137. Epub Nov. 8, 2013.
Xiao et al., Nuclear m(6)A Reader YTHDC1 Regulates mRNA Splicing. Mol Cell. Feb. 18, 2016;61(4):507-519. doi: 10.1016/j.molcel.2016.01.012. Epub Feb. 11, 2016.
Xie et al., Adjusting the attB site in donor plasmid improves the efficiency of ΦC31 integrase system. DNA Cell Biol. Jul. 2012;31(7):1335-40. doi: 10.1089/dna.2011.1590. Epub Apr. 10, 2012.
Xiong et al., Origin and evolution of retroelements based upon their reverse transcriptase sequences. EMBO J. Oct. 1990;9(10):3353-62.
Xu et al., Accuracy and efficiency define Bxb1 integrase as the best of fifteen candidate serine recombinases for the integration of DNA into the human genome. BMC Biotechnol. Oct. 20, 2013;13:87. doi: 10.1186/1472-6750-13-87.

Xu et al., Chemical ligation of folded recombinant proteins: segmental isotopic labeling of domains for NMR studies. Proc Natl Acad Sci U S A. Jan. 19, 1999;96(2):388-93. doi: 10.1073/pnas.96.2.388.
Xu et al., Multiplex nucleotide editing by high-fidelity Cas9 variants with improved efficiency in rice. BMC Plant Biol. 2019;19(1):511. Published Nov. 21, 2019. doi:10.1186/s12870-019-2131-1. Includes supplementary data and materials.
Xu et al., Protein splicing: an analysis of the branched intermediate and its resolution by succinimide formation. EMBO J. Dec. 1, 1994;13(23):5517-22.
Xu et al., PTMD: A Database of Human Disease-associated Post-translational Modifications. Genomics Proteomics Bioinformatics. Aug. 2018; 16(4):244-251. doi: 10.1016/j.gpb.2018.06.004. Epub Sep. 21, 2018.
Xu et al., Sequence determinants of improved CRISPR sgRNA design. Genome Res. Aug. 2015;25(8):1147-57. doi: 10.1101/gr.191452.115. Epub Jun. 10, 2015.
Xu et al., Structures of human ALKBH5 demethylase reveal a unique binding mode for specific single-stranded N6-methyladenosine RNA demethylation. J Biol Chem. Jun. 20, 2014;289(25):17299-311. doi: 10.1074/jbc.M114.550350. Epub Apr. 28, 2014.
Xu et al., The mechanism of protein splicing and its modulation by mutation. EMBO J. Oct. 1, 1996;15(19):5146-53.
Yahata et al., Unified, Efficient, and Scalable Synthesis of Halichondrins: Zirconium/Nickel-Mediated One-Pot Ketone Synthesis as the Final Coupling Reaction. Angew Chem Int Ed Engl. Aug. 28, 2017;56(36):10796-10800. doi: 10.1002/anie.201705523. Epub Jul. 28, 2017.
Yamada et al., Crystal Structure of the Minimal Cas9 from Campylobacter jejuni Reveals the Molecular Diversity in the CRISPR-Cas9 Systems. Mol Cell. Mar. 16, 2017;65(6):P1109-1121./doi.org/10.1016/j.molcel.2017.02.007.
Yamamoto et al., The ons and offs of inducible transgenic technology: a review. Neurobiol Dis. Dec. 2001;8(6):923-32.
Yamamoto et al., Virological and immunological bases for HIV-1 vaccine design. Uirusu 2007;57(2):133-139. https://doi.org/10.2222/jsv.57.133.
Yamane et al., Deep-sequencing identification of the genomic targets of the cytidine deaminase AID and its cofactor RPA in B lymphocytes. Nat Immunol. Jan. 2011;12(1):62-9. doi: 10.1038/ni.1964. Epub Nov. 28, 2010.
Yamano et al., Crystal Structure of Cpf1 in Complex with Guide RNA and Target DNA. Cell. May 5, 2016;165(4):949-62 and Supplemental Info. doi: 10.1016/j.cell.2016.04.003. Epub Apr. 21, 2016.
Yamano et al., Crystal Structure of Cpf1 in Complex with Guide RNA and Target DNA. Cell. May 5, 2016;165(4):949-62. doi: 10.1016/j.cell.2016.04.003. Epub Apr. 21, 2016.
Yamazaki et al., Segmental Isotope Labeling for Protein NMR Using Peptide Splicing. J. Am. Chem. Soc. May 22, 1998; 120(22):5591-2. https://doi.org/10.1021/ja9807760.
Yan et al., Cas13d Is a Compact RNA-Targeting Type VI CRISPR Effector Positively Modulated by a WYL-Domain-Containing Accessory Protein. Mol Cell. Apr. 19, 2018;70(2):327- 339.e5. doi: 10.1016/j.molcel.2018.02.028. Epub Mar. 15, 2018.
Yan et al., Functionally diverse type V CRISPR-Cas systems. Science. Jan. 4, 2019;363(6422):88-91. doi: 10.1126/science.aav7271. Epub Dec. 6, 2018.
Yan et al., Highly Efficient A•T to G•C Base Editing by Cas9n-Guided tRNA Adenosine Deaminase in Rice. Mol Plant. Apr. 2, 2018;11(4):631-634. doi: 10.1016/j.molp.2018.02.008. Epub Feb. 22, 2018.
Yang et al., A Tale of Two Moieties: Rapidly Evolving CRISPR/Cas-Based Genome Editing. Trends Biochem Sci. Oct. 2020;45(10):874-888. doi: 10.1016/j.tibs.2020.06.003. Epub Jun. 30, 2020.
Yang et al., APOBEC: From mutator to editor. J Genet Genomics. Sep. 20, 2017;44(9):423-437. doi: 10.1016/j.jgg.2017.04.009. Epub Aug. 7, 2017.
Yang et al., BRCA2 function in DNA binding and recombination from a BRCA2-DSS1-ssDNA structure. Science. Sep. 13, 2002;297(5588):1837-48. doi: 10.1126/science.297.5588.1837.

(56) References Cited

OTHER PUBLICATIONS

Yang et al., Construction of an integration-proficient vector based on the site-specific recombination mechanism of enterococcal temperate phage phiFC1. J Bacteriol. Apr. 2002; 184(7):1859-64. doi: 10.1128/jb.184.7.1859-1864.2002.

Yang et al., Engineering and optimising deaminase fusions for genome editing. Nat Commun. Nov. 2, 2016;7:13330. doi: 10.1038/ncomms13330.

Yang et al., Genome editing with targeted deaminases. BioRxiv. Preprint. First posted online Jul. 28, 2016.

Yang et al., Genome-wide inactivation of porcine endogenous retroviruses (PERVs). Science. Nov. 27, 2015;350(6264):1101-4. doi: 10.1126/science.aad1191. Epub Oct. 11, 2015.

Yang et al., Increasing targeting scope of adenosine base editors in mouse and rat embryos through fusion of TadA deaminase with Cas9 variants. Protein Cell. Sep. 2018;9(9):814-819. doi: 10.1007/s13238-018-0568-x.

Yang et al., Mutations in SCN9A, encoding a sodium channel alpha subunit, in patients with primary erythermalgia. J Med Genet. Mar. 2004;41(3):171-4. doi: 10.1136/jmg.2003.012153.

Yang et al., New CRISPR-Cas systems discovered. Cell Res. Mar. 2017;27(3):313-314. doi: 10.1038/cr.2017.21. Epub Feb. 21, 2017.

Yang et al., One Prime for All Editing. Cell. Dec. 12, 2019;179(7):1448-1450. doi: 10.1016/j.cell.2019.11.030.

Yang et al., One-step generation of mice carrying reporter and conditional alleles by CRISPR/Cas-mediated genome engineering. Cell. Sep. 12, 2013;154(6):1370-9. doi: 10.1016/j.cell.2013.08.022. Epub Aug. 29, 2013.

Yang et al., PAM-dependent Target DNA Recognition and Cleavage by C2C1 CRISPR-Cas endonuclease. Cell Dec. 2016;167(7):1814-28.

Yang et al., Permanent genetic memory with >1-byte capacity. Nat Methods. Dec. 2014;11(12):1261-6. doi: 10.1038/nmeth.3147. Epub Oct. 26, 2014.

Yang et al., Preparation of RNA-directed DNA polymerase from spleens of Balb-c mice infected with Rauscher leukemia virus. Biochem Biophys Res Commun. Apr. 28, 1972;47(2):505-11. doi: 10.1016/0006-291x(72)90743-7.

Yang et al., Small-molecule control of insulin and PDGF receptor signaling and the role of membrane attachment. Curr Biol. Jan. 1, 1998;8(1):11-8. doi: 10.1016/s0960-9822(98)70015-6.

Yang et al., The BRCA2 homologue Brh2 nucleates RAD51 filament formation at a dsDNA-ssDNA junction. Nature. Feb. 10, 2005;433(7026):653-7. doi: 10.1038/nature03234.

Yang, Development of Human Genome Editing Tools for the Study of Genetic Variations and Gene Therapies. Doctoral Dissertation. Harvard University. 2013. Accessible via nrs.harvard.edu/urn-3:HUL.InstRepos:11181072. 277 pages.

Yang, Nucleases: diversity of structure, function and mechanism. Q Rev Biophys. Feb. 2011;44(1):1-93. doi: 10.1017/S0033583510000181. Epub Sep. 21, 2010.

Yang, PAML 4: phylogenetic analysis by maximum likelihood. Mol Biol Evol. Aug. 2007;24(8):1586-91. doi: 10.1093/molbev/msm088. Epub May 4, 2007.

Yanover et al., Extensive protein and DNA backbone sampling improves structure-based specificity prediction for C2H2 zinc fingers. Nucleic Acids Res. Jun. 2011;39(11):4564-76. doi: 10.1093/nar/gkr048. Epub Feb. 22, 2011.

Yasui et al., Miscoding Properties of 2'-Deoxyinosine, a Nitric Oxide-Derived DNA Adduct, during Translesion Synthesis Catalyzed by Human DNA Polymerases. J Molec Biol. Apr. 4, 2008;377(4):1015-23.

Yasui, Alternative excision repair pathways. Cold Spring Harb Perspect Biol. Jun. 1, 2013;5(6):a012617. doi: 10.1101/cshperspect.a012617.

Yasukawa et al., Characterization of Moloney murine leukaemia virus/avian myeloblastosis virus chimeric reverse transcriptases. J Biochem. Mar. 2009;145(3):315-24. doi: 10.1093/jb/mvn166. Epub Dec. 6, 2008.

Yazaki et al., Hereditary systemic amyloidosis associated with a new apolipoprotein AII stop codon mutation Stop78Arg. Kidney Int. Jul. 2003;64(1):11-6.

Yeh et al., In vivo base editing of post-mitotic sensory cells. Nat Commun. Jun. 5, 2018;9(1):2184. doi: 10.1038/s41467-018-04580-3.

Yeh et al., In vivo base editing restores sensory transduction and transiently improves auditory function in a mouse model of recessive deafness. Sci Transl Med. Jun. 3, 2020;12(546):eaay9101. doi: 10.1126/scitranslmed.aay9101.

Yi et al., Engineering of TEV protease variants by yeast ER sequestration screening (YESS) of combinatorial libraries. Proc Natl Acad Sci U S A. Apr. 30, 2013;110(18):7229-34. doi: 10.1073/pnas.1215994110. Epub Apr. 15, 2013.

Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.

Yokoe et al., Spatial dynamics of GFP-tagged proteins investigated by local fluorescence enhancement. Nat Biotechnol. Oct. 1996;14(10):1252-6. doi: 10.1038/nbt1096-1252.

Young et al., Beyond the canonical 20 amino acids: expanding the genetic lexicon. J Biol Chem. Apr. 9, 2010;285(15):11039-44. doi: 10.1074/jbc.R109.091306. Epub Feb. 10, 2010.

Yu et al., Circular permutation: a different way to engineer enzyme structure and function. Trends Biotechnol. Jan. 2011;29(1):18-25. doi: 10.1016/j.tibtech.2010.10.004. Epub Nov. 17, 2010.

Yu et al., Cytosine base editors with minimized unguided DNA and RNA off-target events and high on-target activity. Nat Commun. Apr. 28, 2020;11(1):2052. doi: 10.1038/s41467-020-15887-5.

Yu et al., Dynamic control of Rad51 recombinase by self-association and interaction with BRCA2. Mol Cell. Oct. 2003;12(4):1029-41. doi: 10.1016/s1097-2765(03)00394-0.

Yu et al., Liposome-mediated in vivo E1A gene transfer suppressed dissemination of ovarian cancer cells that overexpress HER-2/neu. Oncogene. Oct. 5, 1995;11(7):1383-8.

Yu et al., Progress towards gene therapy for HIV infection. Gene Ther. Jan. 1994;1(1):13-26.

Yu et al., Small molecules enhance CRISPR genome editing in pluripotent stem cells. Cell Stem Cell. Feb. 5, 2015;16(2):142-7. doi: 10.1016/j.stem.2015.01.003.

Yu et al., Synthesis-dependent microhomology-mediated end joining accounts for multiple types of repair junctions. Nucleic Acids Res. Sep. 2010;38(17):5706-17. doi: 10.1093/nar/gkq379. Epub May 11, 2010.

Yuan et al., Laboratory-directed protein evolution. Microbiol Mol Biol Rev. 2005; 69(3):373-92. PMID: 16148303.

Yuan et al., Tetrameric structure of a serine integrase catalytic domain. Structure. Aug. 6, 2008;16(8):1275-86. doi: 10.1016/j.str.2008.04.018.

Yuen et al., Control of transcription factor activity and osteoblast differentiation in mammalian cells using an evolved small-molecule-dependent intein. J Am Chem Soc. Jul. 12, 2006;128(27):8939-46.

Zakas et al., Enhancing the pharmaceutical properties of protein drugs by ancestral sequence reconstruction. Nat Biotechnol. Jan. 2017;35(1):35-37. doi: 10.1038/nbt.3677. Epub Sep. 26, 2016.

Zalatan et al., Engineering complex synthetic transcriptional programs with Crispr Rna scaffolds. Cell. Jan. 15, 2015;160(1-2):339-50. doi: 10.1016/j.cell.2014.11.052. Epub Dec. 17, 2014.

Zelphati et al., Intracellular delivery of proteins with a new lipid-mediated delivery system. J Biol Chem. Sep. 14, 2001;276(37):35103-10. Epub Jul. 10, 2001.

Zeng et al., Correction of the Marfan Syndrome Pathogenic FBN1 Mutation by Base Editing in Human Cells and Heterozygous Embryos. Mol Ther. Nov. 7, 2018;26(11):2631-2637. doi: 10.1016/j.ymthe.2018.08.007. Epub Aug. 14, 2018.

Zetsche et al., A split-Cas9 architecture for inducible genome editing and transcription modulation. Nat Biotechnol. Feb. 2015;33(2):139-42. doi: 10.1038/nbt.3149.

Zetsche et al., Cpf1 is a single RNA-guided endonuclease of a class 2 CRISPR-Cas system. Cell. Oct. 22, 2015;163(3):759-71 and Supplemental Info. doi: 10.1016/j.cell.2015.09.038. Epub Sep. 25, 2015.

(56) References Cited

OTHER PUBLICATIONS

Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.

Zettler et al., The naturally split Npu DnaE intein exhibits an extraordinarily high rate in the protein trans-splicing reaction. FEBS Lett. Mar. 4, 2009;583(5):909-14. doi: 10.1016/j.febslet.2009.02. 003. Epub Feb. 10, 2009.

Zhang et al., Π-Clamp-mediated cysteine conjugation. Nat Chem. Feb. 2016;8(2):120-8. doi: 10.1038/nchem.2413. Epub Dec. 21, 2015.

Zhang et al., A new strategy for the site-specific modification of proteins in vivo. Biochemistry. Jun. 10, 2003;42(22):6735-46.

Zhang et al., Circular intronic long noncoding RNAs. Mol Cell. Sep. 26, 2013;51(6):792-806. doi: 10.1016/j.molcel.2013.08.017. Epub Sep. 12, 2013.

Zhang et al., Comparison of non-canonical PAMs for CRISPR/Cas9-mediated DNA cleavage in human cells. Sci Rep. Jun. 2014;4:5405.

Zhang et al., Conditional gene manipulation: Cre-ating a new biological era. J Zhejiang Univ Sci B. Jul. 2012;13(7):511-24. doi: 10.1631/jzus.B1200042. Review.

Zhang et al., Copy number variation in human health, disease, and evolution. Annu Rev Genomics Hum Genet. 2009;10:451-81. doi: 10.1146/annurev.genom.9.081307.164217.

Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.

Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.

Zhang et al., Efficient precise knockin with a double cut HDR donor after CRISPR/Cas9- mediated double-stranded DNA cleavage. Genome Biol. Feb. 20, 2017;18(1):35. doi: 10.1186/s13059-017-1164-8.

Zhang et al., Global analysis of small RNA and mRNA targets of Hfq. Mol Microbiol. Nov. 2003;50(4):1111-24. doi: 10.1046/j.1365-2958.2003.03734.x.

Zhang et al., Large genomic fragment deletions and insertions in mouse using CRISPR/Cas9. PLoS One. Mar. 24, 2015;10(3):e0120396. doi: 10.1371/journal.pone.0120396. 14 pages.

Zhang et al., Myoediting: Toward Prevention of Muscular Dystrophy by Therapeutic Genome Editing. Physiol Rev. Jul. 1, 2018;98(3):1205-1240. doi: 10.1152/physrev.00046.2017.

Zhang et al., Programmable base editing of zebrafish genome using a modified CRISPR-Cas9 system. Nat Commun. Jul. 25, 2017;8(1):118. doi: 10.1038/s41467-017-00175-6.

Zhang et al., Reversible RNA Modification N1-methyladenosine (m1A) in mRNA and tRNA. Genomics Proteomics Bioinformatics. Jun. 2018; 16(3):155-161. doi: 10.1016/j.gpb.2018.03.003. Epub Jun. 14, 2018.

Zhang et al., Ribozymes and Riboswitches: Modulation of RNA Function by Small Molecules. Biochemistry. Nov. 2, 2010;49(43):9123-31. doi: 10.1021/bi1012645.

Zhang et al., Stabilized plasmid-lipid particles for regional gene therapy: formulation and transfection properties. Gene Ther. Aug. 1999;6(8):1438-47.

Zhao et al., An ultraprocessive, accurate reverse transcriptase encoded by a metazoan group II intron. RNA. Feb. 2018;24(2):183-195. doi: 10.1261/rna.063479.117. Epub Nov. 6, 2017.

Zhao et al., Crystal structures of a group II intron maturase reveal a missing link in spliceosome evolution. Nat Struct Mol Biol. Jun. 2016;23(6):558-65. doi: 10.1038/nsmb.3224. Epub May 2, 2016.

Zhao et al., Post-transcriptional gene regulation by mRNA modifications. Nat Rev Mol Cell Biol. Jan. 2017;18(1):31-42. doi: 10.1038/nrm. 2016.132. Epub Nov. 3, 2016.

Zheng et al., ALKBH5 is a mammalian RNA demethylase that impacts RNA metabolism and mouse fertility. Mol Cell. Jan. 10, 2013;49(1):18-29. doi: 10.1016/j.molcel.2012.10.015. Epub Nov. 21, 2012.

Zheng et al., DNA editing in DNA/RNA hybrids by adenosine deaminases that act on RNA. Nucleic Acids Res. Apr. 7, 2017;45(6):3369-3377. doi: 10.1093/nar/gkx050.

Zheng et al., Highly efficient base editing in bacteria using a Cas9-cytidine deaminase fusion. Commun Biol. Apr. 19, 2018;1:32. doi: 10.1038/s42003-018-0035-5.

Zheng et al., Structural basis for the complete resistance of the human prion protein mutant G127V to prion disease. Sci Rep. Sep. 4, 2018;8(1):13211. doi: 10.1038/s41598-018-31394-6.

Zhong et al., Rational Design of Aptazyme Riboswitches for Efficient Control of Gene Expression in Mammalian Cells. Elife. Nov. 2, 2016;5:e18858. doi: 10.7554/eLife.18858.

Zhou et al., Dynamic m(6)A mRNA methylation directs translational control of heat shock response. Nature. Oct. 22, 2015;526(7574):591-4. doi: 10.1038/nature15377. Epub Oct. 12, 2015.

Zhou et al., GISSD: Group I Intron Sequence and Structure Database. Nucleic Acids Res. Jan. 2008;36(Database issue):D31-7. doi: 10.1093/nar/gkm766. Epub Oct. 16, 2007.

Zhou et al., Off-target RNA mutation induced by DNA base editing and its elimination by mutagenesis. Nature. Jul. 2019;571(7764):275-278. doi: 10.1038/s41586-019-1314-0. Epub Jun. 10, 2019.

Zhou et al., Protective V127 prion variant prevents prion disease by interrupting the formation of dimer and fibril from molecular dynamics simulations. Sci Rep. Feb. 24, 2016;6:21804. doi: 10.1038/srep21804.

Zhou et al., Seamless Genetic Conversion of SMN2 to SMN1 via CRISPR/Cpf1 and Single-Stranded Oligodeoxynucleotides in Spinal Muscular Atrophy Patient-Specific Induced Pluripotent Stem Cells. Hum Gene Ther. Nov. 2018;29(11):1252-1263. doi: 10.1089/hum.2017.255. Epub May 9, 2018.

Zhu et al., Novel Thrombotic Function of a Human SNP in STXBP5 Revealed by CRISPR/Cas9 Gene Editing in Mice. Arterioscler Thromb Vasc Biol. Feb. 2017;37(2):264-270. doi: 10.1161/ATVBAHA. 116.308614. Epub Dec. 29, 2016.

Zielenski, Genotype and phenotype in cystic fibrosis. Respiration. 2000;67(2):117-33. doi: 10.1159/000029497.

Zimmerly et al., An Unexplored Diversity of Reverse Transcriptases in Bacteria. Microbiol Spectr. Apr. 2015;3(2):MDNA3-0058-2014. doi: 10.1128/microbiolspec.MDNA3-0058-2014.

Zimmerly et al., Group II intron mobility occurs by target DNA-primed reverse transcription. Cell. Aug. 25, 1995;82(4):545-54. doi: 10.1016/0092-8674(95)90027-6.

Zimmermann et al., Molecular interactions and metal binding in the theophylline-binding core of an RNA aptamer. RNA. May 2000;6(5):659-67.

Zolotukhin et al., Production and purification of serotype 1, 2, and 5 recombinant adeno-associated viral vectors. Methods. Oct. 2002;28(2):158-67. doi: 10.1016/s1046-2023(02)00220-7.

Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.

Zorko et al., Cell-penetrating peptides: mechanism and kinetics of cargo delivery. Adv Drug Deliv Rev. Feb. 28, 2005;57(4):529-45. Epub Jan. 22, 2005.

Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.

Zufferey et al., Woodchuck hepatitis virus posttranscriptional regulatory element enhances expression of transgenes delivered by retroviral vectors. J Virol. Apr. 1999;73(4):2886-92. doi: 10.1128/JVI.73.4.2886-2892.1999.

Zuker et al., Optimal computer folding of large RNA sequences using thermodynamics and auxiliary information. Nucleic Acids Res. Jan. 10, 1981;9(1):133-48. doi: 10.1093/nar/9.1.133.

Zuo et al., Cytosine base editor generates substantial off-target single-nucleotide variants in mouse embryos. Science. Apr. 19, 2019;364(6437):289-292. doi: 10.1126/science.aav9973. Epub Feb. 28, 2019.

Zuris et al., Cationic lipid-mediated delivery of proteins enables efficient protein-based genome editing in vitro and in vivo. Nat Biotechnol. 2015;33:73-80.

(56) References Cited

OTHER PUBLICATIONS

[No Author Listed], CMP/dCMP-type deaminase domain-containing protein. Uniprot Accession No. A0A2Z6RZE9. Oct. 10, 2018. Accessible at https://www.uniprot.org/uniprotkb/A0A2Z6RZE9/entry. 8 pages.
[No Author Listed], dCas9-5xPlat2AfID-P2A-scFvGCN4sfGFPTET1CD [Cloning vector pPlatTET-gRNA2]. GenBank No. BAV54124. Apr. 18, 20178. 5 pages.
[No Author Listed], MutL homolog 1. UniProtKB Acc. No. F1MPG0. May 3, 2011. Accessible at https://rest.uniprot.org/unisave/F1MPG0?format=txt&versions=1. 1 page.
[No Author Listed], NCBI Reference Sequence: WP_032188360.1. Apr. 6, 2015. 1 page.
[No Author Listed], tRNA-specific adenosine deaminase [Candidatus Moranella endobia PCVAL]. GenBank Acc. No. AGJ61179.1. Accessible at https://www.ncbi.nlm.nih.gov/protein/AGJ61179. Jan. 3, 20140. 3 pages.
[No Author Listed], tRNA-specific adenosine deaminase [*Escherichia coli*]. GenBank Acc. No. CTS26096.1. Accessible at https://www.ncbi.nlm.nih.gov/protein/CTS26096.1. Aug. 22, 2015. 1 page.
[No Author Listed], tRNA-specific adenosine deaminase 2 [Terrapene triunguis]. GenBank Acc. No. XP_024075810.1. Accessible at https://www.ncbi.nlm.nih.gov/protein/XP_024075810. Jul. 15, 2019. 2 pages.
[No Author Listed], tRNA-specific adenosine deaminase TAD2 isoform X1 [*Oryza sativa* Japonica Group]. GenBank Acc. No. XP_15631651.1. Accessible at https://www.ncbi.nlm.nih.gov/protein/1002254769?sat=58&satkey=133677684. Aug. 7, 2018. 2 pages.
[No Author Listed], tRNA-specific adenosine deaminase TAD2 isoform X2 [Panicum hallii]. GenBank Acc. No. XP_025793740.1. Accessible at https://www.ncbi.nlm.nih.gov/protein/025793740. Jul. 27, 2018. 1 page.
[No Author Listed], tRNA-specific adenosine deaminase. Uniprot Accession No. A0A1U7M801. May 10, 2017. Accessible at https://www.uniprot.org/uniprotkb/A0A1U7M801/history. 3 pages.
[No Author Listed], tRNA-specific adenosine deaminase. Uniprot Accession No. A0A1Z4VPW4. Sep. 27, 2017. Accessible at https://www.uniprot.org/uniprotkb/A0A1Z4VPW4/history. 3 pages.
[No Author Listed], tRNA-specific adenosine deaminase. Uniprot Accession No. A0A1Z9LY19. Oct. 25, 2017. Accessible at https://www.uniprot.org/uniprotkb/A0A1Z9LY19/entry. 12 pages.
[No Author Listed], tRNA-specific adenosine deaminase. Uniprot Accession No. A0A2P5TOZ9. May 23, 2018. Accessible at https://www.uniprot.org/uniprotkb/A0A2P5T0Z9/entry. 10 pages.
[No Author Listed], tRNA-specific adenosine deaminase. Uniprot Accession No. A0A4P6PH16. Jul. 31, 2019. Accessible at https://www.uniprot.org/uniprotkb/A0A4P6PH16/entry. 12 pages.
[No Author Listed], tRNA-specific adenosine deaminase. Uniprot Accession No. A0A520SVM3. Oct. 16, 2019. Accessible at https://www.uniprot.org/uniprotkb/A0A520SVM3/entry. 10 pages.
[No Author Listed], tRNA-specific adenosine deaminase. Uniprot Accession No. U2JUU0. Nov. 13, 2013. Accessible at https://www.uniprot.org/uniprotkb/U2JUU0/entry. 11 pages.
Abed et al., The Gag protein PEG10 binds to RNA and regulates trophoblast stem cell lineage specification. PLoS One. Apr. 5, 2019;14(4):e0214110. doi: 10.1371/journal.pone.0214110.
Acharya et al., hMSH2 forms specific mispair-binding complexes with hMSH3 and hMSH6. Proc Natl Acad Sci U S A. Nov. 26, 1996;93(24):13629-34. doi: 10.1073/pnas.93.24.13629.
Alizadeh et al., HR9: An Important Cell Penetrating Peptide for Delivery of Hcv NS3 DNA into HEK-293T Cells. Avicenna J Med Biotechnol. Jan.-Mar. 2020;12(1):44-51.
Alves et al., Immunogenicity of the carcinoembryonic antigen derived peptide 694 in HLA-A2 healthy donors and colorectal carcinoma patients. Cancer Immunol Immunother. Nov. 2007;56(11):1795-805. doi: 10.1007/s00262-007-0323-2. Epub Apr. 20, 2007.
Asemissen et al., Identification of a highly immunogenic HLA-A*01-binding T cell epitope of WT1. Clin Cancer Res. Dec. 15, 2006;12(24):7476-82. doi: 10.1158/1078-0432.CCR-06-1337.

Ashley et al., Retrovirus-like Gag Protein Arc1 Binds RNA and Traffics across Synaptic Boutons. Cell. Jan. 11, 2018;172(1-2):262-274.e11. doi: 10.1016/j.cell.2017.12.022.
Attia et al., Autoimmunity correlates with tumor regression in patients with metastatic melanoma treated with anti-cytotoxic T-lymphocyte antigen-4. J Clin Oncol. Sep. 1, 2005;23(25):6043-53. doi: 10.1200/JCO.2005.06.205. Epub Aug. 8, 2005.
Aurisicchio et al., A novel minigene scaffold for therapeutic cancer vaccines. Oncoimmunology. Jan. 1, 2014;3(1):e27529. doi: 10.4161/onci.27529. Epub Jan. 16, 2014.
Avidan et al., Expression and characterization of a recombinant novel reverse transcriptase of a porcine endogenous retrovirus. Virology. Mar. 15, 2003;307(2):341-57. doi: 10.1016/s0042-6822(02)00131-9.
Bae et al., Heteroclitic CD33 peptide with enhanced anti-acute myeloid leukemic immunogenicity. Clin Cancer Res. Oct. 15, 2004;10(20):7043-52. doi: 10.1158/1078-0432.CCR-04-0322.
Bae et al., Identification of novel CD33 antigen-specific peptides for the generation of cytotoxic T lymphocytes against acute myeloid leukemia. Cell Immunol. Jan. 2004;227(1):38-50. doi: 10.1016/j.cellimm.2004.01.002.
Bakker et al., Analogues of CTL epitopes with improved MHC class-I binding capacity elicit anti-melanoma CTL recognizing the wild-type epitope. Int J Cancer. Jan. 27, 1997;70(3):302-9. doi: 10.1002/(sici)1097-0215(19970127)70:3<302::aid-ijc10>3.0.co;2-h.
Banerjee et al., Viral glycoproteins: biological role and application in diagnosis. Virusdisease. Mar. 2016;27(1):1-11. doi: 10.1007/s13337-015-0293-5. Epub Jan. 18, 2016.
Baños-Sanz et al., Crystal structure and functional insights into uracil-DNA glycosylase inhibition by phage Φ29 DNA mimic protein p56. Nucleic Acids Res. Jul. 2013;41(13):6761-73. doi: 10.1093/nar/gkt395. Epub May 13, 2013.
Barve et al., Induction of immune responses and clinical efficacy in a phase II trial of IDM-2101, a 10-epitope cytotoxic T-lymphocyte vaccine, in metastatic non-small-cell lung cancer. J Clin Oncol. Sep. 20, 2008;26(27):4418-25. doi: 10.1200/JCO.2008.16.6462.
Bender et al., Receptor-Targeted Nipah Virus Glycoproteins Improve Cell-Type Selective Gene Delivery and Reveal a Preference for Membrane-Proximal Cell Attachment. PLoS Pathog. Jun. 9, 2016;12(6):e1005641. doi: 10.1371/journal.ppat.1005641.
Benlalam et al., Identification of five new HLA-B*3501-restricted epitopes derived from common melanoma-associated antigens, spontaneously recognized by tumor-infiltrating lymphocytes. J Immunol. Dec. 1, 2003;171(11):6283-9. doi: 10.4049/jimmunol.171.11.6283.
Bernatchez et al., Altered decamer and nonamer from an HLA-A0201-restricted epitope of Survivin differentially stimulate T-cell responses in different individuals. Vaccine. Apr. 5, 2011;29(16):3021-30. doi: 10.1016/j.vaccine.2011.01.115. Epub Feb. 12, 2011.
Bikard et al., Programmable repression and activation of bacterial gene expression using an engineered CRISPR-Cas system. Nucleic Acids Res. Aug. 2013;41(15):7429-37. doi: 10.1093/nar/gkt520. Epub Jun. 12, 2013.
Bioley et al., Melan-A/MART-1-specific CD4 T cells in melanoma patients: identification of new epitopes and ex vivo visualization of specific T cells by MHC class II tetramers. J Immunol. Nov. 15, 2006;177(10):6769-79. doi: 10.4049/jimmunol.177.10.6769.
Blanchet et al., A new generation of Melan-A/MART-1 peptides that fulfill both increased immunogenicity and high resistance to biodegradation: implication for molecular anti-melanoma immunotherapy. J Immunol. Nov. 1, 20015;167(10):5852-61. doi: 10.4049/jimmunol.167.10.5852.
Bolukbasi et al., DNA-binding-domain fusions enhance the targeting range and precision of Cas9. Nat Methods. Dec. 2015;12(12):1150-6. doi: 10.1038/nmeth.3624. Epub Oct. 19, 2015.
Borbulevych et al., Increased immunogenicity of an anchor-modified tumor-associated antigen is due to the enhanced stability of the peptide/MHC complex: implications for vaccine design. J Immunol. Apr. 15, 2005;174(8):4812-20. doi: 10.4049/jimmunol.174.8.4812.

(56) References Cited

OTHER PUBLICATIONS

Brichard et al., A tyrosinase nonapeptide presented by HLA-B44 is recognized on a human melanoma by autologous cytolytic T lymphocytes. Eur J Immunol. Jan. 1996;26(1):224-30. doi: 10.1002/eji.1830260135.

Cacabelos et al., Chapter 1—The Epigenetic Machinery in the Life Cycle and Pharmacoepigenetics. Pharmacoepigenetics. vol. 10 in Translational Epigenetics. 2019:1-100. doi: https://doi.org/10.1016/B978-0-12-813939-4.00001-2. 7 pages.

Cai et al. Targeted genome editing by lentiviral protein transduction of zinc-finger and TAL- effector nucleases. Elife. Apr. 24, 2014;3:e01911. doi: 10.7554/eLife.01911.

Cai et al., Abstract OR021: Targeted Genome Editing by Lentiviral Protein Transduction of ZFN and Cas9 Proteins Abstract, Presented at Proceedings of the ESGCT and NVGCT Collaborative Congress: The Hague. Human Gene Therapy. 2014. 15 pages.

Cai, Protein Transduction Using Lentiviral Vectors for Transposition and Site-directed Gene Editing. Thesis for the degree of Doctor of Philosophy, Aarhus University, Department of Biomedicine. 2014. 74 pages.

Campbell et al., Gesicle-Mediated Delivery of CRISPR/Cas9 Ribonucleoprotein Complex for Inactivating the HIV Provirus. Mol Ther. Jan. 2, 2019;27(1):151-163. doi: 10.1016/j.ymthe.2018.10.002. Epub Oct. 11, 2018.

Campi et al., CD4(+) T cells from healthy subjects and colon cancer patients recognize a carcinoembryonic antigen-specific immunodominant epitope. Cancer Res. Dec. 1, 2003;63(23):8481-6.

Casnici et al., Immunologic evaluation of peptides derived from BCR/ABL-out-of-frame fusion protein in HLA A2.1 transgenic mice. J Immunother. May 2012;35(4):321-8. doi: 10.1097/CJI.0b013e3182562d37.

Casnici et al., Out of frame peptides from BCR/ABL alternative splicing are immunogenic in HLA A2.1 transgenic mice. Cancer Lett. Apr. 8, 2009;276(1):61-7. doi: 10.1016/j.canlet.2008.10.032. Epub Dec. 4, 2008.

Castelli et al., Mass spectrometric identification of a naturally processed melanoma peptide recognized by CD8+ cytotoxic T lymphocytes. J Exp Med. Jan. 1, 1995;181(1):363-8. doi: 10.1084/jem.181.1.363.

Castelli et al., Novel HLA-Cw8-restricted T cell epitopes derived from tyrosinase-related protein-2 and gp100 melanoma antigens. J Immunol. Feb. 1, 1999;162(3):1739-48.

Castle et al., Exploiting the mutanome for tumor vaccination. Cancer Res. Mar. 1, 2012;72(5): 1081-91. doi: 10.1158/0008-5472.CAN-11-3722. Epub Jan. 11, 2012.

Cervera et al., Generation of HIV-1 Gag VLPs by transient transfection of HEK 293 suspension cell cultures using an optimized animal-derived component free medium. J Biotechnol. Jul. 20, 2013;166(4):152-65. doi: 10.1016/j.jbiotec.2013.05.001. Epub May 17, 2013.

Chang et al., Functional characterization of the placental fusogenic membrane protein syncytin. Biol Reprod. Dec. 2004;71(6):1956-62. doi: 10.1095/biolreprod.104.033340. Epub Jul. 21, 2004.

Chen et al., DNA methylation and demethylation in mammals. J Biol Chem. May 27, 2011;286(21):18347-53. doi: 10.1074/jbc.R110.205286. Epub Mar. 24, 2011.

Chen et al., Identification of NY-ESO-1 peptide analogues capable of improved stimulation of tumor-reactive CTL. J Immunol. Jul. 15, 2000;165(2):948-55. doi: 10.4049/jimmunol.165.2.948.

Cheriyan et al., Faster protein splicing with the Nostoc punctiforme DnaE intein using non-native extein residues. J Biol Chem. Mar. 1, 2013;288(9):6202-11. doi: 10.1074/jbc.M112.433094. Epub Jan. 10, 2013.

Cho et al., Heritable gene knockout in Caenorhabditis elegans by direct injection of Cas9-sgRNA ribonucleoproteins. Genetics. Nov. 2013;195(3):1177-80. doi: 10.1534/genetics.113.155853. Epub Aug. 26, 2013.

Cho et al., Optimized peptide vaccines eliciting extensive CD8 T-cell responses with therapeutic antitumor effects. Cancer Res. Dec. 1, 2009;69(23):9012-9. doi: 10.1158/0008-5472.CAN-09-2019. Epub Nov. 10, 2009.

Choi et al., Lentivirus pre-packed with Cas9 protein for safer gene editing. Gene Ther. Jul. 2016;23(7):627-33. doi: 10.1038/gt.2016.27. Epub Apr. 7, 2016.

Choi et al., Optimization of AAV expression cassettes to improve packaging capacity and transgene expression in neurons. Mol Brain. Mar. 11, 2014;7:17. doi: 10.1186/1756-6606-7-17.

Christensen et al., Melan-A/MART1 analog peptide triggers antimyeloma T-cells through crossreactivity with HM1.24. J Immunother. Jul.-Aug. 2009;32(6):613-21. doi: 10.1097/CJI.0b013e3181a95198.

Chylinski et al., The tracrRNA and Cas9 families of type II CRISPR-Cas immunity systems. RNA Biol. May 2013;10(5):Supplementary Material. doi: 10.4161/rna.24321. Epub Apr. 5, 2013. 12 pages.

Coey, Sumoylation of thymine DNA glycosylase occurs efficiently and weakens DNA binding but does not regulate enzymatic turnover. Dissertation. 2017. 178 pages.

Contreras-Galindo et al., Human Endogenous Retrovirus Type K (HERV-K) Particles Package and Transmit HERV-K-Related Sequences. J Virol. Jul. 2015;89(14):7187-201. doi: 10.1128/JVI.00544-15. Epub Apr. 29, 2015.

Coquin, Characterization of lentiviral vectors pseudotyped with murine syncytins and their cellular targets in vitro and in vivo. Thesis. University of Évry Val d'Essonne. Defense on Dec. 10, 2019. 238 pages.

Correale et al., In vitro generation of human cytotoxic T lymphocytes specific for peptides derived from prostate-specific antigen. J Natl Cancer Inst. Feb. 19, 1997;89(4):293-300. doi: 10.1093/jnci/89.4.293.

Courtney et al., CRISPR/Cas9 DNA cleavage at SNP-derived PAM enables both in vitro and in vivo KRT12 mutation-specific targeting. Gene Ther. Jan. 2016;23(1):108-12. doi: 10.1038/gt.2015.82. Epub Aug. 20, 2015.

Cox et al., Identification of a peptide recognized by five melanoma-specific human cytotoxic T cell lines. Science. Apr. 29, 1994;264(5159):716-9. doi: 10.1126/science.7513441.

Cronin et al., Altering the tropism of lentiviral vectors through pseudotyping. Curr Gene Ther. Aug. 2005;5(4):387-98. doi: 10.2174/1566523054546224. Erratum in: Curr Gene Ther. Oct. 2005;5(5):531. Author Manuscript, 19 pages.

Crosti et al., Identification of novel subdominant epitopes on the carcinoembryonic antigen recognized by CD4+ T cells of lung cancer patients. J Immunol. Apr. 15, 2006;176(8):5093-9. doi: 10.4049/jimmunol.176.8.5093.

Dalet et al., An antigenic peptide produced by reverse splicing and double asparagine deamidation. Proc Natl Acad Sci U S A. Jul. 19, 2011;108(29):E323-31. doi: 10.1073/pnas.1101892108. Epub Jun. 13, 2011.

Damdindorj et al., A comparative analysis of constitutive promoters located in adeno-associated viral vectors. PLoS One. Aug. 29, 2014;9(8):e106472. doi: 10.1371/journal.pone.0106472.

David et al., Viral Vectors: The Road to Reducing Genotoxicity. Toxicol Sci. Feb. 2017;155(2):315-325. doi: 10.1093/toxsci/kfw220. Epub Nov. 1, 2016.

Depontieu et al., Identification of tumor-associated, MHC class II-restricted phosphopeptides as targets for immunotherapy. Proc Natl Acad Sci U S A. Jul. 21, 2009;106(29):12073-8. doi: 10.1073/pnas.0903852106. Epub Jul. 6, 2009.

Di Stasi et al., Review of the Results of WT1 Peptide Vaccination Strategies for Myelodysplastic Syndromes and Acute Myeloid Leukemia from Nine Different Studies. Front Immunol. Feb. 4, 2015;6:36. doi: 10.3389/fimmu.2015.00036.

Ding et al., Gene therapy for cardiovascular disease. Journal of Shanghai University (Natural Science Edition) . 2016;3:270-9 . DOI: 10.3969/j.issn.1007-2861.2016.03.013.

Duan et al., Immune rejection of mouse tumors expressing mutated self. Cancer Res. Apr. 15, 2009;69(8):3545-53. doi: 10.1158/0008-5472.CAN-08-2779. Epub Apr. 7, 2009. Author Manuscript. 18 pages.

(56) References Cited

OTHER PUBLICATIONS

Duportet et al., A platform for rapid prototyping of synthetic gene networks in mammalian cells. Nucleic Acids Res. Dec. 1, 2014;42(21):13440-51. doi: 10.1093/nar/gku1082. Epub Nov. 5, 2014.
Edraki et al., A Compact, High-Accuracy Cas9 with a Dinucleotide PAM for In Vivo Genome Editing. Mol Cell. Feb. 21, 2019;73(4):714-726.e4 and Supplemental Info. doi: 10.1016/j.molcel.2018.12.003. Epub Dec. 20, 2018.
Ekman et al., CRISPR-Cas9-Mediated Genome Editing Increases Lifespan and Improves Motor Deficits in a Huntington's Disease Mouse Model. Mol Ther Nucleic Acids. Sep. 6, 2019;17:829-839. doi: 10.1016/j.omtn.2019.07.009. Epub Jul. 26, 2019.
Eriksen et al., Occlusion of the Ribosome Binding Site Connects the Translational Initiation Frequency, mRNA Stability and Premature Transcription Termination. Front Microbiol. Mar. 14, 2017;8:362. doi: 10.3389/fmicb.2017.00362.
Fang et al., Human strand-specific mismatch repair occurs by a bidirectional mechanism similar to that of the bacterial reaction. J Biol Chem. Jun. 5, 1993;268(16):11838-44.
Feng et al., Efficient genome editing in plants using a CRISPR/Cas system. Cell Res. Oct. 2013;23(10):1229-32. doi: 10.1038/cr.2013.114. Epub Aug. 20, 2013.
Fikes et al., Design of multi-epitope, analogue-based cancer vaccines. Expert Opin Biol Ther. Sep. 2003;3(6):985-93. doi: 10.1517/14712598.3.6.985.
Fishel et al., The human mutator gene homolog MSH2 and its association with hereditary nonpolyposis colon cancer. Cell. Dec. 3, 1993;75(5):1027-38. doi: 10.1016/0092-8674(93)90546-3. Erratum in: Cell. Apr. 8, 1994;77(1):1 p following 166.
Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013. Supplementary Information. 67 pages.
Fontana et al., Rabies virus-like particles expressed in HEK293 cells. Vaccine. May 19, 2014;32(24):2799-804. doi: 10.1016/j.vaccine.2014.02.031. Epub Mar. 12, 2014.
Fonteneau et al., The Tumor Antigen NY-ESO-1 Mediates Direct Recognition of Melanoma Cells by CD4+ T Cells after Intercellular Antigen Transfer. J Immunol. Jan. 1, 2016;196(1):64- 71. doi: 10.4049/jimmunol. 1402664. Epub Nov. 25, 2015.
Fourcade et al., PD-1 and Tim-3 regulate the expansion of tumor antigen-specific CD8+ T cells induced by melanoma vaccines. Cancer Res. Feb. 15, 2014;74(4):1045-55. doi: 10.1158/0008-5472.CAN-13-2908. Epub Dec. 16, 2013.
Fridman et al., An efficient T-cell epitope discovery strategy using in silico prediction and the iTopia assay platform. Oncoimmunology. Nov. 1, 2012;1(8):1258-1270. doi: 10.4161/onci.21355.
Fu et al., Targeted genome editing in human cells using CRISPR/Cas nucleases and truncated guide RNAs. Methods Enzymol. 2014;546:21-45. doi: 10.1016/B978-0-12-801185-0.00002-7.
Fujiki et al., Identification and characterization of a WT1 (Wilms Tumor Gene) protein-derived HLA-DRB1*0405-restricted 16-mer helper peptide that promotes the induction and activation of WT1-specific cytotoxic T lymphocytes. J Immunother. Apr. 2007;30(3):282-93. doi: 10.1097/01.cji.0000211337.91513.94.
Gaidukov et al., A multi-landing pad DNA integration platform for mammalian cell engineering. Nucleic Acids Res. May 4, 2018;46(8):4072-4086. doi: 10.1093/nar/gky216.
Gee et al., Extracellular nanovesicles for packaging of CRISPR-Cas9 protein and sgRNA to induce therapeutic exon skipping. Nat Commun. Mar. 13, 2020;11(1):1334. doi: 10.1038/s41467-020-14957-y.
GenBank Access No. BAP64357. Aug. 1, 2013. 1 page.
GenBank Accession No. AAH57574.1 2009. 2 pages.
GenBank Submission; NIH/NCBI, Accession No. NP_060228.2. Bi et al., Dec. 21, 2005. 1 page.
GenBank Submission; NIH/NCBI, Accession No. NP_062826.2. Bokar et al., Sep. 18, 2004. 2 pages.
GenBank Submission; NIH/NCBI, Accession No. NP_066012.1. Ota et al., Apr. 3, 2005. 2 pages.
GenBank Submission; NIH/NCBI, Accession No. WP_042518169.1. No Author, Feb. 10, 2015. 1 page.
Geng et al., In vitro studies of DNA mismatch repair proteins. Anal Biochem. Jun. 15, 2011;413(2):179-84. doi: 10.1016/j.ab.2011.02.017. Epub Feb. 15, 2011.
Genschel et al., Human exonuclease I is required for 5' and 3' mismatch repair. J Biol Chem. Apr. 12, 2002;277(15):13302-11. doi: 10.1074/jbc.M111854200. Epub Jan. 24, 2002.
Genschel et al., Isolation of MutSbeta from human cells and comparison of the mismatch repair specificities of MutSbeta and MutSalpha. J Biol Chem. Jul. 31, 1998;273(31):19895-901. doi: 10.1074/jbc.273.31.19895. Erratum in: J Biol Chem Oct. 9, 1998;273(41):27034.
Geynisman et al., A randomized pilot phase I study of modified carcinoembryonic antigen (CEA) peptide (CAP1-6D)/montanide/GM-CSF-vaccine in patients with pancreatic adenocarcinoma. J Immunother Cancer. Jun. 27, 2013;1:8. doi: 10.1186/2051-1426-1-8.
Ghosh et al., Synapsis in phage Bxb1 integration: selection mechanism for the correct pair of recombination sites. J Mol Biol. Jun. 3, 2005;349(2):331-48. doi: 10.1016/j.jmb.2005.03.043. Epub Apr. 7, 2005.
Girard-Gagnepain et al., Baboon envelope pseudotyped LVs outperform VSV-G-LVs for gene transfer into early-cytokine-stimulated and resting HSCs. Blood. Aug. 21, 2014;124(8):1221-31. doi: 10.1182/blood-2014-02-558163. Epub Jun. 20, 2014.
Godefroy et al., Identification of two Melan-A CD4+ T cell epitopes presented by frequently expressed MHC class II alleles. Clin Immunol. Oct. 2006; 121(1):54-62. doi: 10.1016/j.clim.2006.05.007. Epub Jun. 30, 2006.
Graff-Dubois et al., Generation of CTL recognizing an HLA-A*0201-restricted epitope shared by MAGE-A1, -A2, -A3, -A4, -A6, -A10, and -A12 tumor antigens: implication in a broad-spectrum tumor immunotherapy. J Immunol. Jul. 1, 2002;169(1):575-80. doi: 10.4049/jimmunol.169.1.575.
Gross et al., High vaccination efficiency of low-affinity epitopes in antitumor immunotherapy. J Clin Invest. Feb. 2004;113(3):425-33. doi: 10.1172/JCI19418.
Gueneau et al., Structure of the MutLα C-terminal domain reveals how Mlh1 contributes to Pms1 endonuclease site. Nat Struct Mol Biol. Apr. 2013;20(4):461-8. doi: 10.1038/nsmb.2511. Epub Feb. 24, 2013.
Guerrette et al., The interaction of the human MutL homologues in hereditary nonpolyposis colon cancer. J Biol Chem. Mar. 5, 1999;274(10):6336-41. doi: 10.1074/jbc.274.10.6336.
Guevara-Patiño et al., Optimization of a self antigen for presentation of multiple epitopes in cancer immunity. J Clin Invest. May 2006;116(5): 1382-90. doi: 10.1172/JCI25591. Epub Apr. 13, 2006.
Guibinga et al., Cell surface heparan sulfate is a receptor for attachment of envelope protein-free retrovirus-like particles and VSV-G pseudotyped MLV-derived retrovirus vectors to target cells. Mol Ther. May 2002;5(5 Pt 1):538-46. doi: 10.1006/mthe.2002.0578.
Gulley et al., Combining a Recombinant Cancer Vaccine with Standard Definitive Radiotherapy in Patients with Localized Prostate Cancer. Clin Cancer Res. May 2, 2005;11(9):3353-62. doi: 10.1158/1078-0432.CCR-04-2062.
Guo et al., Direct recognition and lysis of leukemia cells by WT1-specific CD4+ T lymphocytes in an HLA class II-restricted manner. Blood. Aug. 15, 2005;106(4):1415-8. doi: 10.1182/blood-2005-01-0413. Epub Apr. 21, 2005.
Gupta et al., Mechanism of mismatch recognition revealed by human MutSβ bound to unpaired DNA loops. Nat Struct Mol Biol. Dec. 18, 2011;19(1):72-8. doi: 10.1038/nsmb.2175.
Haeussler et al., Genome Editing with CRISPR-Cas9: Can It Get Any Better? J Genet Genomics. May 20, 2016;43(5):239-50. doi: 10.1016/j.jgg.2016.04.008. Epub Apr. 24, 2016. Author Manuscript. 22 pages.
Hamilton et al., Knocking out barriers to engineered cell activity. Science. Feb. 28, 2020;367(6481):976-977. doi: 10.1126/science.aba9844. Epub Feb. 6, 2020.

(56) References Cited

OTHER PUBLICATIONS

Heins et al., Designing Automated, High-throughput, Continuous Cell Growth Experiments Using eVOLVER. J Vis Exp. May 19, 2019;(147):10.3791/59652. doi: 10.3791/59652.
Heintze et al., A CRISPR CASe for high-throughput silencing. Front Genet. Oct. 7, 2013;4:193. doi: 10.3389/fgene.2013.00193.
Herbst-Kralovetz et al., Norwalk virus-like particles as vaccines. Expert Rev Vaccines. Mar. 2010;9(3):299-307. doi: 10.1586/erv.09.163. Author Manuscript, 16 pages.
Hirohashi et al., An HLA-A24-restricted cytotoxic T lymphocyte epitope of a tumor-associated protein, survivin. Clin Cancer Res. Jun. 2002;8(6):1731-9.
Hizi et al., Retroviral reverse transcriptases (other than those of HIV-1 and murine leukemia virus): a comparison of their molecular and biochemical properties. Virus Res. Jun. 2008;134(1-2):203-20. doi: 10.1016/j.virusres.2007.12.008. Epub Mar. 3, 2008.
Hong et al., Novel recombinant hepatitis B virus vectors efficiently deliver protein and RNA encoding genes into primary hepatocytes. J Virol. Jun. 2013;87(12):6615-24. doi: 10.1128/JVI.03328-12. Epub Apr. 3, 2013.
Houghton et al., Immunological validation of the EpitOptimizer program for streamlined design of heteroclitic epitopes. Vaccine. Jul. 20, 2007;25(29):5330-42. doi: 10.1016/j.vaccine.2007.05.008. Epub Jun. 4, 2007.
Hwang et al., Heritable and precise zebrafish genome editing using a CRISPR-Cas system. PLoS One. Jul. 9, 2013;8(7):e68708. doi: 10.1371/journal.pone.0068708.
Iaccarino et al., hMSH2 and hMSH6 play distinct roles in mismatch binding and contribute differently to the ATPase activity of hMutSalpha. Embo J. May 1, 1998;17(9):2677-86. doi: 10.1093/emboj/17.9.2677.
Iyer et al., DNA mismatch repair: functions and mechanisms. Chem Rev. Feb. 2006;106(2):302-23. doi: 10.1021/cr0404794.
Jacobs et al., DNA glycosylases: in DNA repair and beyond. Chromosoma. Feb. 2012;121(1):1-20. doi: 10.1007/s00412-011-0347-4. Epub Nov. 3, 2011. 20 pages.
Jalaguier et al., Efficient production of HIV-1 virus-like particles from a mammalian expression vector requires the N-terminal capsid domain. PLoS One. 2011;6(11):e28314. doi: 10.1371/journal.pone.0028314. Epub Nov. 30, 2011.
Jaramillo et al., Identification of HLA-A3-restricted CD8+ T cell epitopes derived from mammaglobin-A, a tumor-associated antigen of human breast cancer. Int J Cancer. Dec. 10, 2002;102(5):499-506. doi: 10.1002/ijc.10736.
Jeong et al., Current Status and Challenges of DNA Base Editing Tools. Mol Ther. Sep. 2, 2020;28(9):1938-1952. doi: 10.1016/j.ymthe.2020.07.021. Epub Jul. 23, 2020.
Jinek et al., A programmable dual-RNA-guided DNA endonuclease in adaptive bacterial immunity. Science. Aug. 17, 2012;337(6096):Supplementary Material. doi: 10.1126/science.1225829. Epub Jun. 28, 2012. 37 pages.
Joglekar et al., Pseudotyped Lentiviral Vectors: One Vector, Many Guises. Hum Gene Ther Methods. Dec. 2017;28(6):291-301. doi: 10.1089/hgtb.2017.084. Epub Sep. 4, 2017.
Johnson, Origins and evolutionary consequences of ancient endogenous retroviruses. Nat Rev Microbiol. Jun. 2019;17(6):355-370. doi: 10.1038/s41579-019-0189-2.
Kaczmarczyk et al., Protein delivery using engineered virus-like particles. Proc Natl Acad Sci US A. Oct. 11, 2011;108(41):16998-7003. doi: 10.1073/pnas.1101874108. Epub Sep. 26, 2011.
Kadyrov et al., Endonucleolytic function of MutLalpha in human mismatch repair. Cell. Jul. 28, 2006;126(2):297-308. doi: 10.1016/j.cell.2006.05.039.
Kang et al., Chimeric rabies virus-like particles containing membrane-anchored GM-CSF enhances the immune response against rabies virus. Viruses. Mar. 11, 2015;7(3):1134-52. doi: 10.3390/v7031134.
Kang et al., Identification of a tyrosinase epitope recognized by HLA-A24-restricted, tumor-infiltrating lymphocytes. J Immunol. Aug. 1, 1995;155(3):1343-8.

Karbach et al., Long-term complete remission following radiosurgery and immunotherapy in a melanoma patient with brain metastasis: immunologic correlates. Cancer Immunol Res. May 2014;2(5):404-9. doi: 10.1158/2326-6066.CIR-13-0200. Epub Feb. 5, 2014.
Kato et al., A lentiviral strategy for highly efficient retrograde gene transfer by pseudotyping with fusion envelope glycoprotein. Hum Gene Ther. Feb. 2011;22(2):197-206. doi: 10.1089/hum.2009.179. Epub Jan. 27, 2011.
Kato et al., Selective neural pathway targeting reveals key roles of thalamostriatal projection in the control of visual discrimination. J Neurosci. Nov. 23, 2011;31(47): 17169-79. doi: 10.1523/JNEUROSCI.4005-11.2011.
Katoh et al., Exploitation of the interaction of measles virus fusogenic envelope proteins with the surface receptor CD46 on human cells for microcell-mediated chromosome transfer. BMC Biotechnol. May 6, 2010;10:37. doi: 10.1186/1472-6750-10-37.
Kawakami et al., Identification of a human melanoma antigen recognized by tumor- infiltrating lymphocytes associated with in vivo tumor rejection. Proc Natl Acad Sci U S A. Jul. 5, 1994;91(14):6458-62. doi: 10.1073/pnas.91.14.6458.
Kawakami et al., Identification of new melanoma epitopes on melanosomal proteins recognized by tumor infiltrating T lymphocytes restricted by HLA-A1, -A2, and -A3 alleles. J Immunol. Dec. 1, 19985;161(12):6985-92.
Kawakami et al., Identification of the immunodominant peptides of the MART-1 human melanoma antigen recognized by the majority of HLA-A2-restricted tumor infiltrating lymphocytes. J Exp Med. Jul. 1, 1994;180(1):347-52. doi: 10.1084/jem.180.1.347.
Kawakami et al., Recognition of multiple epitopes in the human melanoma antigen gp100 by tumor-infiltrating T lymphocytes associated with in vivo tumor regression. J Immunol. Apr. 1, 19955;154(8):3961-8.
Kawashima et al., Identification of gp100-derived, melanoma-specific cytotoxic T- lymphocyte epitopes restricted by HLA-A3 supertype molecules by primary in vitro immunization with peptide-pulsed dendritic cells. Int J Cancer. Nov. 9, 1998;78(4):518-24. doi: 10.1002/(sici)1097-0215(19981109)78:4<518 :: aid-ijc20>3.0.co;2-0.
Kawashima et al., Identification of HLA-A3-restricted cytotoxic T lymphocyte epitopes from carcinoembryonic antigen and HER-2/neu by primary in vitro immunization with peptide- pulsed dendritic cells. Cancer Res. Jan. 1, 19995;59(2):431-5.
Kawashima et al., The multi-epitope approach for immunotherapy for cancer: identification of several CTL epitopes from various tumor-associated antigens expressed on solid epithelial tumors. Hum Immunol. Jan. 1998;59(1):1-14. doi: 10.1016/s0198-8859(97)00255-3.
Kemmler et al., Elevated tumor-associated antigen expression suppresses variant peptide vaccine responses. J Immunol. Nov. 1, 2011;187(9):4431-9. doi: 10.4049/jimmunol.1101555. Epub Sep. 2, 20111.
Kirshenboim et al., Expression and characterization of a novel reverse transcriptase of the LTR retrotransposon Tf1. Virology. Sep. 3, 20070;366(2):263-76. doi: 10.1016/j.virol.2007.04.002. Epub May 2, 20073.
Kittlesen et al., Human melanoma patients recognize an HLA-A1-restricted CTL epitope from tyrosinase containing two cysteine residues: implications for tumor vaccine development. J Immunol. Mar. 1, 1998;160(5):2099-106. Erratum in: J Immunol Mar. 1, 1999;162(5):3106. Shabanowitz JA [corrected to Shabanowitz J].
Kizer et al., Application of functional genomics to pathway optimization for increased isoprenoid production. Appl Environ Microbiol. May 2008;74(10):3229-41. doi: 10.1128/AEM.02750-07. Epub Mar. 1, 20084.
Kleinstiver et al., Broadening the targeting range of Staphylococcus aureus CRISPR-Cas9 by modifying PAM recognition. Nat Biotechnol. Dec. 2015;33(12):1293-1298. doi: 10.1038/nbt.3404. Epub Nov. 2, 2015. Author Manuscript, 14 pages.
Kneissl et al., Measles virus glycoprotein-based lentiviral targeting vectors that avoid neutralizing antibodies. PLoS One. 2012;7(10):e46667. doi: 10.1371/journal.pone.0046667. Epub Oct. 10, 2012.

(56) References Cited

OTHER PUBLICATIONS

Kobayashi et al., CD4+ T cells from peripheral blood of a melanoma patient recognize peptides derived from nonmutated tyrosinase. Cancer Res. Jan. 15, 1998;58(2):296-301.
Kobayashi et al., Identification of an antigenic epitope for helper T lymphocytes from carcinoembryonic antigen. Clin Cancer Res. Oct. 2002;8(10):3219-25.
Kobayashi et al., Identification of helper T-cell epitopes that encompass or lie proximal to cytotoxic T-cell epitopes in the gp100 melanoma tumor antigen. Cancer Res. Oct. 15, 2001;61(20):7577-84.
Kotterman et al., Engineering adeno-associated viruses for clinical gene therapy. Nat Rev Genet. Jul. 2014; 15(7):445-51. doi: 10.1038/nrg3742. Epub May 20, 2014.
Kueh et al., The new editor-targeted genome engineering in the absence of homology-directed repair. Cell Death Discov. Jun. 13, 2016;2:16042. doi: 10.1038/cddiscovery.2016.42.
Kunkel et al., DNA mismatch repair. Annu Rev Biochem. 2005;74:681-710. doi: 10.1146/annurev.biochem.74.082803.133243.
Kurt et al., CRISPR C-to-G base editors for inducing targeted DNA transversions in human cells. Nat Biotechnol. Jan. 2021;39(1):41-46. doi: 10.1038/s41587-020-0609-x. Epub Jul. 20, 2020.
Kushnir et al., Virus-like particles as a highly efficient vaccine platform: diversity of targets and production systems and advances in clinical development. Vaccine. Dec. 17, 2012;31(1):58- 83. doi: 10.1016/j.vaccine.2012.10.083. Epub Nov. 6, 2012.
Lahue et al., DNA mismatch correction in a defined system. Science. Jul. 14, 1989;245(4914):160-4. doi: 10.1126/science.2665076.
Lally et al., Unmasking cryptic epitopes after loss of immunodominant tumor antigen expression through epitope spreading. Int J Cancer. Sep. 2001;93(6):841-7. doi: 10.1002/ijc.1420.
Lapointe et al., Retrovirally transduced human dendritic cells can generate T cells recognizing multiple MHC class I and class II epitopes from the melanoma antigen glycoprotein 100. J Immunol. Oct. 15, 2001;167(8):4758-64. doi: 10.4049/jimmunol.167.8.4758.
Larrieu et al., A HLA-Cw*0701 restricted Melan-A/MART1 epitope presented by melanoma tumor cells to CD8+ tumor infiltrating lymphocytes. Cancer Immunol Immunother. May 2008;57(5):745-52. doi: 10.1007/s00262-007-0436-7. Epub Dec. 21, 2007.
Latham et al., Formation of wild-type and chimeric influenza virus-like particles following simultaneous expression of only four structural proteins. J Virol. Jul. 2001;75(13):6154-65. doi: 10.1128/JVI.75.13.6154-6165.2001.
Leach et al., Mutations of a mutS homolog in hereditary nonpolyposis colorectal cancer. Cell. Dec. 17, 1993;75(6):1215-25. doi: 10.1016/0092-8674(93)90330-s.
Lee et al., Reconstitution of an infectious human endogenous retrovirus. PLoS Pathog. Jan. 2007;3(1):e10. doi: 10.1371/journal.ppat.0030010.
Leenay et al., Identifying and Visualizing Functional PAM Diversity across CRISPR-Cas Systems. Mol Cell. Apr. 7, 2016;62(1):137-47. doi: 10.1016/j.molcel.2016.02.031. Epub Mar. 31, 2016.
Lennerz et al., The response of autologous T cells to a human melanoma is dominated by mutated neoantigens. Proc Natl Acad Sci U S A. Nov. 1, 2005;102(44):16013-8. doi: 10.1073/pnas.0500090102. Epub Oct. 24, 2005.
Li et al., A dominant-negative form of mouse SOX2 induces trophectoderm differentiation and progressive polyploidy in mouse embryonic stem cells. J Biol Chem. Jul. 6, 2007;282(27):19481- 92. doi: 10.1074/jbc.M702056200. Epub May 15, 2007.
Li et al., Base-Resolution Mapping Reveals Distinct m1A Methylome in Nuclear- and Mitochondrial-Encoded Transcripts. Mol Cell. Dec. 7, 2017;68(5):993-1005.e9. doi: 10.1016/j.molcel.2017.10.019. Epub Nov. 5, 2017.
Li et al., Expression and self-assembly of empty virus-like particles of hepatitis E virus. J Virol. Oct. 1997;71(10):7207-13. doi: 10.1128/JVI.71.10.7207-7213.1997.
Lin et al., HLA-DPB1*05: 01-restricted WT1332-specific TCR-transduced CD4+ T lymphocytes display a helper activity for WT1-specific CTL induction and a cytotoxicity against leukemia cells. J Immunother. Apr. 2013;36(3):159-70. doi: 10.1097/CJI.0b013e3182873581.
Liu et al., Delivery methods for site-specific nucleases: Achieving the full potential of therapeutic gene editing. J Control Release. Dec. 28, 2016;244(Pt A):83-97. doi: 10.1016/j.jconrel.2016.11.014. Epub Nov. 16, 2016.
Longsworth, Expanding the Enzymatic Activity of the Programmable Endonuclease Cas9 in Zebrafish. Thesis. Rice University. Houston, TX. May 17, 2019. 41 pages.
Lu, Periodic Chart of Amino Acid PDF. Accessed on the internet at https://figshare.com/articles/figure/periodic_chart_of_amino_acid_pdf/3445001/1. Posted Jun. 21, 2016. www.bachem.com. 1 page.
Ludwig et al., Virus-like particles-universal molecular toolboxes. Curr Opin Biotechnol. Dec. 2007;18(6):537-45. doi: 10.1016/j.copbio.2007.10.013.
Lueck et al., Engineered transfer RNAs for suppression of premature termination codons. Nat Commun. Feb. 18, 2019;10(1):822. doi: 10.1038/s41467-019-08329-4.
Lujan et al., Heterogeneous polymerase fidelity and mismatch repair bias genome variation and composition. Genome Res. Nov. 2014;24(11):1751-64. doi: 10.1101/gr.178335.114. Epub Sep. 12, 2014.
Lupetti et al., Translation of a retained intron in tyrosinase-related protein (TRP) 2 mRNA generates a new cytotoxic T lymphocyte (CTL)-defined and shared human melanoma antigen not expressed in normal cells of the melanocytic lineage. J Exp Med. Sep. 21, 1998;188(6):1005-16. doi: 10.1084/jem.188.6.1005.
Lyu et al., Delivering Cas9/sgRNA ribonucleoprotein (RNP) by lentiviral capsid-based bionanoparticles for efficient 'hit-and-run' genome editing. Nucleic Acids Res. Sep. 26, 2019;47(17):e99. doi: 10.1093/nar/gkz605.
Maetzig et al., Retroviral protein transfer: falling apart to make an impact. Curr Gene Ther. Oct. 2012;12(5):389-409. doi: 10.2174/156652312802762581.
Mahoney et al., The Next Immune-Checkpoint Inhibitors: PD-1/PD-L1 Blockade in Melanoma. Clin Ther. Apr. 1, 2015;37(4):764-82. doi: 10.1016/j.clinthera.2015.02.018. Epub Mar. 29, 2015.
Mandic et al., The alternative open reading frame of LAGE-1 gives rise to multiple promiscuous HLA-DR-restricted epitopes recognized by T-helper 1-type tumor-reactive CD4+ T cells. Cancer Res. Oct. 1, 2003;63(19):6506-15.
Mangeot et al., A universal transgene silencing method based on RNA interference. Nucleic Acids Res. Jul. 12, 2004;32(12):e102. doi: 10.1093/nar/gnh105.
Mangeot et al., Development of minimal lentivirus vectors derived from simian immunodeficiency virus (SIVmac251) and their use for gene transfer into human dendritic cells. J Virol. Sep. 2000;74(18):8307-15. doi: 10.1128/jvi.74.18.8307-8315.2000.
Mangeot et al., Protein transfer into human cells by VSV-G-induced nanovesicles. Mol Ther. Sep. 2011;19(9):1656-66. doi: 10.1038/mt.2011.138. Epub Jul. 12, 2011.
Mariani et al., Species-specific exclusion of APOBEC3G from HIV-1 virions by Vif. Cell. Jul. 11, 2003;114(1):21-31. doi: 10.1016/s0092-8674(03)00515-4.
Martín et al., Envelope-targeted retrovirus vectors transduce melanoma xenografts but not spleen or liver. Mol Ther. Mar. 2002;5(3):269-74. doi: 10.1006/mthe.2002.0550.
Meng et al., Identification of an HLA-DPB1*0501 restricted Melan-A/MART-1 epitope recognized by CD4+ T lymphocytes: prevalence for immunotherapy in Asian populations. J Immunother. Sep. 2011;34(7):525-34. doi: 10.1097/CJI.0b013e318226bd45. Author Manuscript. 16 pages.
Michaux et al., A spliced antigenic peptide comprising a single spliced amino acid is produced in the proteasome by reverse splicing of a longer peptide fragment followed by trimming. J Immunol. Feb. 15, 2014;192(4):1962-71. doi: 10.4049/jimmunol.1302032. Epub Jan. 22, 2014.
Micozzi et al., Human cytidine deaminase: a biochemical characterization of its naturally occurring variants. Int J Biol Macromol. Feb. 2014;63:64-74. doi: 10.1016/j.ijbiomac.2013.10.029. Epub Oct. 29, 2013. Erratum in: Int J Biol Macromol. Feb. 2014;63:262.

(56) References Cited

OTHER PUBLICATIONS

Milone et al., Clinical use of lentiviral vectors. Leukemia. Jul. 2018;32(7):1529-1541. doi: 10.1038/s41375-018-0106-0. Epub Mar. 22, 2018.
Misra et al., An enzymatically active chimeric HIV-1 reverse transcriptase (RT) with the RNase-H domain of murine leukemia virus RT exists as a monomer. J Biol Chem. Apr. 17, 1998;273(16):9785-9. doi: 10.1074/jbc.273.16.9785.
Momose et al., Diving into marine genomics with CRISPR/Cas9 systems. Mar Genomics. Dec. 2016;30:55-65. doi: 10.1016/j.margen.2016.10.003. Epub Oct. 12, 2016.
Morel et al., A tyrosinase peptide presented by HLA-B35 is recognized on a human melanoma by autologous cytotoxic T lymphocytes. Int J Cancer. Dec. 10, 1999;83(6):755-9. doi: 10.1002/(sici)1097-0215(19991210)83:6<755::aid-ijc10>3.0.co;2-s.
Morrison et al., The developing toolkit of continuous directed evolution. Nat Chem Biol. Jun. 2020; 16(6):610-619. doi: 10.1038/s41589-020-0532-y. Epub May 22, 2020.
Mselli-Lakhal et al., Gene transfer system derived from the caprine arthritis-encephalitis lentivirus. J Virol Methods. Sep. 2006;136(1-2):177-84. doi: 10.1016/j.jviromet.2006.05.006. Epub Jun. 21, 2006.
Murawski et al., Newcastle disease virus-like particles containing respiratory syncytial virus G protein induced protection in BALB/c mice, with no evidence of immunopathology. J Virol. Jan. 2010;84(2):1110-23. doi: 10.1128/JVI.01709-09. Epub Nov. 4, 2009.
Naskalska et al., Virus Like Particles as Immunogens and Universal Nanocarriers. Pol J Microbiol. 2015;64(1):3-13.
Nawaz et al., Extracellular Vesicles, Tunneling Nanotubes, and Cellular Interplay: Synergies and Missing Links. Front Mol Biosci. Jul. 18, 2017;4:50. doi: 10.3389/fmolb.2017.00050.
Negre et al., Characterization of novel safe lentiviral vectors derived from simian immunodeficiency virus (SIVmac251) that efficiently transduce mature human dendritic cells. Gene Ther. Oct. 2000;7(19):1613-23. doi: 10.1038/sj.gt.3301292.
Nesbitt, Targeted Intracellular Therapeutic Delivery Using Liposomes Formulated with Multifunctional FAST proteins. Electronic Thesis and Dissertation Repository. The University of Western Ontario. 2012. 126 pages.
Niemeyer, C.M., Semisynthetic DNA-protein conjugates for biosensing and nanofabrication. Angew Chem Int Ed Engl. Feb. 8, 2010;49(7):1200-16. doi: 10.1002/anie.200904930.
Noppen et al., Naturally processed and concealed HLA-A2.1-restricted epitopes from tumor-associated antigen tyrosinase-related protein-2. Int J Cancer. Jul. 15, 2000;87(2):241-6.
Nowak et al., Ty3 reverse transcriptase complexed with an RNA-DNA hybrid shows structural and functional asymmetry. Nat Struct Mol Biol. Apr. 2014;21(4):389-96. doi: 10.1038/nsmb.2785. Epub Mar. 9, 2014. Author Manuscript, 22 pages.
Nukaya et al., Identification of HLA-A24 epitope peptides of carcinoembryonic antigen which induce tumor-reactive cytotoxic T lymphocyte. Int J Cancer. Jan. 5, 1999;80(1):92-7. doi: 10.1002/(sici)1097-0215(19990105)80:1<92::aid-ijc18>3.0.co;2-m.
Ogasawara et al., Recombinant viral-like particles of parvovirus B19 as antigen carriers of anthrax protective antigen. In Vivo. May-Jun. 2006;20(3):319-24.
Ohminami et al., HLA class I-restricted lysis of leukemia cells by a CD8(+) cytotoxic T-lymphocyte clone specific for WT1 peptide. Blood. Jan. 1, 2000;95(1):286-93.

Oka et al., WT1 peptide vaccine for the treatment of cancer. Curr Opin Immunol. Apr. 2008;20(2):211-20. doi: 10.1016/j.coi.2008.04.009. Epub May 24, 2008.

Olsen, J.C., Gene transfer vectors derived from equine infectious anemia virus. Gene Ther. Nov. 1998;5(11):1481-7. doi: 10.1038/sj.gt.3300768.

Olson et al., HLA-A2-restricted T-cell epitopes specific for prostatic acid phosphatase. Cancer Immunol Immunother. Jun. 2010;59(6):943-53. doi: 10.1007/s00262-010-0820-6. Epub Feb. 6, 2010.

Osen et al., Screening of human tumor antigens for CD4 T cell epitopes by combination of HLA-transgenic mice, recombinant adenovirus and antigen peptide libraries. PLoS One. Nov. 30, 2010;5(11):e14137. doi: 10.1371/journal.pone.0014137.

Pan et al., Biodistribution and toxicity studies of VSVG-pseudotyped lentiviral vector after intravenous administration in mice with the observation of in vivo transduction of bone marrow. Mol Ther. Jul. 2002;6(1):19-29. doi: 10.1006/mthe.2002.0630.

Pan et al., Identification of a nuclear localization signal in OCT4 and generation of a dominant negative mutant by its ablation. J Biol Chem. Aug. 27, 2004;279(35):37013-20. doi: 10.1074/jbc.M405117200. Epub Jun. 24, 2004.

Parkhurst et al., Identification of a shared HLA-A*0201-restricted T-cell epitope from the melanoma antigen tyrosinase-related protein 2 (TRP2). Cancer Res. Nov. 1, 1998;58(21):4895-901.

Parkhurst et al., Induction of CD4+ Th1 lymphocytes that recognize known and novel class II MHC restricted epitopes from the melanoma antigen gp100 by stimulation with recombinant protein. J Immunother. Mar.-Apr. 2004;27(2):79-91. doi: 10.1097/00002371-200403000-00001. Author Manuscript. 22 pages.

Parr-Brownlie et al., Lentiviral vectors as tools to understand central nervous system biology in mammalian model organisms. Front Mol Neurosci. May 18, 2015;8:14. doi: 10.3389/fnmol.2015.00014.

Parsons et al., Hypermutability and mismatch repair deficiency in RER+ tumor cells. Cell. Dec. 17, 1993;75(6):1227-36. doi: 10.1016/0092-8674(93)90331-j.

Paschen et al., Detection of spontaneous CD4+ T-cell responses in melanoma patients against a tyrosinase-related protein-2-derived epitope identified in HLA-DRB1*0301 transgenic mice. Clin Cancer Res. Jul. 15, 2005;11(14):5241-7. doi: 10.1158/1078-0432.CCR-05-0170.

Pastuzyn et al., The Neuronal Gene Arc Encodes a Repurposed Retrotransposon Gag Protein that Mediates Intercellular RNA Transfer. Cell. Jan. 11, 2018;172(1-2):275-288.e18. doi: 10.1016/j.cell.2017.12.024. Erratum in: Cell. Mar. 22, 2018;173(1):275. doi: 10.1016/j.cell.2018.03.024.

Pavlov et al., Roles of DNA polymerases in replication, repair, and recombination in eukaryotes. Int Rev Cytol. 2006;255:41-132. doi: 10.1016/S0074-7696(06)55002-8.

Pinilla et al., Combinatorial peptide libraries as an alternative approach to the identification of ligands for tumor-reactive cytolytic T lymphocytes. Cancer Res. Jul. 1, 2001;61(13):5153-60.

Pinilla-Ibarz et al., Improved human T-cell responses against synthetic HLA-0201 analog peptides derived from the WT1 oncoprotein. Leukemia. Nov. 2006;20(11):2025-33. doi: 10.1038/sj.leu.2404380. Epub Aug. 31, 2006.

Plotz et al., N-terminus of hMLH1 confers interaction of hMutLalpha and hMutLbeta with hMutSalpha. Nucleic Acids Res. Jun. 15, 2003;31(12):3217-26. doi: 10.1093/nar/gkg420.

Podbilewicz, Virus and cell fusion mechanisms. Annu Rev Cell Dev Biol. 2014;30:111-39. doi: 10.1146/annurev-cellbio-101512-122422. Epub Jun. 27, 2014.

Prather et al., De novo biosynthetic pathways: rational design of microbial chemical factories. Curr Opin Biotechnol. Oct. 2008; 19(5):468-74. doi: 10.1016/j.copbio.2008.07.009. Epub Sep. 5, 2008.

Puppo et al., Retinal transduction profiles by high-capacity viral vectors. Gene Ther. Oct. 2014;21(10):855-65. doi: 10.1038/gt.2014.57. Epub Jul. 3, 2014.

Qi et al., Repurposing CRISPR as an RNA-guided platform for sequence-specific control of gene expression. Cell. Feb. 28, 2013;152(5):Supplementary Material. doi: 10.1016/j.cell.2013.02.022. 4 pages.

Quan et al., Influenza M1 VLPs containing neuraminidase induce heterosubtypic cross-protection. Virology. Sep. 1, 2012;430(2):127-35. doi: 10.1016/j.virol.2012.05.006. Epub Jun. 2, 2012.

Raaijmakers et al., CRISPR/Cas Applications in Myotonic Dystrophy: Expanding Opportunities. Int J Mol Sci. Jul. 27, 2019;20(15):3689. doi: 10.3390/ijms20153689.

Ramiro et al., Transcription enhances AID-mediated cytidine deamination by exposing single- stranded DNA on the nontemplate strand. Nat Immunol. May 2003;4(5):452-6. doi: 10.1038/ni920.

Räschle et al., Mutations within the hMLH1 and hPMS2 subunits of the human MutLalpha mismatch repair factor affect its ATPase

(56) References Cited

OTHER PUBLICATIONS activity, but not its ability to interact with hMutSalpha. J Biol Chem. Jun. 14, 2002;277(24):21810-20. doi: 10.1074/jbc.M108787200. Epub Apr. 10, 2002.

Rasmussen et al., Characterization of virus-like particles produced by a recombinant baculovirus containing the gag gene of the bovine immunodeficiency-like virus. Virology. Oct. 1990; 178(2):435-51. doi: 10.1016/0042-6822(90)90341-n.

Remington et al., Complete nucleotide sequence of a neuropathogenic variant of Friend murine leukemia virus PVC-211. Nucleic Acids Res. Jun. 25, 1992;20(12):3249. doi: 10.1093/nar/20.12.3249.

Renner et al., Intact Viral Particle Counts Measured by Flow Virometry Provide Insight into the Infectivity and Genome Packaging Efficiency of Moloney Murine Leukemia Virus. J Virol. Jan. 6, 2020;94(2):e01600-19. doi: 10.1128/JVI.01600-19.

Richter et al., Phage-assisted evolution of an adenine base editor with improved Cas domain compatibility and activity. Nat Biotechnol. Jul. 2020;38(7):883-891. doi: 10.1038/s41587-020-0453-z. Epub Mar. 16, 2020. Author Manuscript, 30 pages.

Riddle et al., Frameshift suppression: a nucleotide addition in the anticodon of a glycine transfer RNA. Nat New Biol. Apr. 25, 1973;242(121):230-4. doi: 10.1038/newbio242230a0.

Riddle et al., Frameshift suppressors. II. Genetic mapping and dominance studies. J Mol Biol. May 28, 1972;66(3):483-93. doi: 10.1016/0022-2836(72)90428-7.

Riddle et al., Suppressors of frameshift mutations in Salmonella typhimurium. J Mol Biol. Nov. 28, 1970;54(1):131-44. doi: 10.1016/0022-2836(70)90451-1.

Riley et al., Identification of a new shared HLA-A2.1 restricted epitope from the melanoma antigen tyrosinase. J Immunother. May-Jun. 2001;24(3):212-20.

Rimoldi et al., Efficient simultaneous presentation of NY-ESO-1/LAGE-1 primary and nonprimary open reading frame-derived CTL epitopes in melanoma. J Immunol. Dec. 15, 2000;165(12):7253-61. doi: 10.4049/jimmunol.165.12.7253.

Robbins et al., Multiple HLA class II-restricted melanocyte differentiation antigens are recognized by tumor-infiltrating lymphocytes from a patient with melanoma. J Immunol. Nov. 15, 2002;169(10):6036-47. doi: 10.4049/jimmunol.169.10.6036.

Robbins et al., The intronic region of an incompletely spliced gp100 gene transcript encodes an epitope recognized by melanoma-reactive tumor-infiltrating lymphocytes. J Immunol. Jul. 1, 1997;159(1):303-8.

Rohovie et al., Virus-like particles: Next-generation nanoparticles for targeted therapeutic delivery. Bioeng Transl Med. Jan. 19, 2017;2(1):43-57. doi: 10.1002/btm2.10049.

Romero et al., Exploring protein fitness landscapes by directed evolution. Nat Rev Mol Cell Biol. Dec. 2009; 10(12):866-76. doi: 10.1038/nrm2805.

Rosenberg et al., Immunologic and therapeutic evaluation of a synthetic peptide vaccine for the treatment of patients with metastatic melanoma. Nat Med. Mar. 1998;4(3):321-7. doi: 10.1038/nm0398-321.

Rubio-Godoy et al., Toward synthetic combinatorial peptide libraries in positional scanning format (PS-SCL)-based identification of CD8+ Tumor-reactive T-Cell Ligands: a comparative analysis of PS-SCL recognition by a single tumor-reactive CD8+ cytolytic T-lymphocyte clone. Cancer Res. Apr. 1, 2002;62(7):2058-63.

Ruiz et al., Identification and characterization of a T-helper peptide from carcinoembryonic antigen. Clin Cancer Res. Apr. 15, 2004;10(8):2860-7. doi: 10.1158/1078-0432.ccr-03-0476.

Rusk, Cas9 and the importance of asymmetry. Nat Methods. Apr. 2016;13(4):286-7. doi: 10.1038/nmeth.3826.

Sadowski et al., The sequence-structure relationship and protein function prediction. Curr Opin Struct Biol. Jun. 2009;19(3):357-62. doi: 10.1016/j.sbi.2009.03.008. Epub May 4, 2009.

Saenger et al., Improved tumor immunity using anti-tyrosinase related protein-1 monoclonal antibody combined with DNA vaccines in murine melanoma. Cancer Res. Dec. 1, 2008;68(23):9884-91. doi: 10.1158/0008-5472.CAN-08-2233. Author Manuscript. 19 pages.

Saenz et al., Feline immunodeficiency virus-based lentiviral vectors. Cold Spring Harb Protoc. Jan. 1, 2012;2012(1):71-6. doi: 10.1101/pdb.ip067579.

Saenz et al., Production, harvest, and concentration of feline immunodeficiency virus-based lentiviral vector from cells grown in CF10 or CF2 devices. Cold Spring Harb Protoc. Jan. 1, 2012;2012(1):118-23. doi: 10.1101/pdb.prot067546.

Sakuma et al., Multiplex genome engineering in human cells using all-in-one CRISPR/Cas9 vector system. Sci Rep. Jun. 23, 2014;4:5400. doi: 10.1038/srep05400.

Sanjana et al., Improved vectors and genome-wide libraries for CRISPR screening. Nat Methods. Aug. 2014;11(8):783-784. doi: 10.1038/nmeth.3047.

Sapir et al., Viral and developmental cell fusion mechanisms: conservation and divergence. Dev Cell. Jan. 2008;14(1):11-21. doi: 10.1016/j.devcel.2007.12.008.

Schneider et al., MuLV IN mutants responsive to HDAC inhibitors enhance transcription from unintegrated retroviral DNA. Virology. May 10, 2012;426(2):188-96. doi: 10.1016/j.virol.2012.01.034. Epub Feb. 23, 2012.

Schneider et al., Overlapping peptides of melanocyte differentiation antigen Melan-A/MART-1 recognized by autologous cytolytic T lymphocytes in association with HLA-B45.1 and HLA-A2.1. Int J Cancer. Jan. 30, 1998;75(3):451-8. doi: 10.1002/(sici)1097-0215(19980130)75:3<451::aid-ijc20>3.0.co;2-a.

SCORE Results for US 2014-0186919 A1 to Zhang et al. Aug. 28, 2014. 3 pages.

Seffernick et al., Melamine deaminase and atrazine chlorohydrolase: 98 percent identical but functionally different. J Bacteriol. Apr. 2001;183(8):2405-10. doi: 10.1128/JB.183.8.2405-2410.2001.

Sensi et al., Identification of a novel gp100/pMel17 peptide presented by HLA-A*6801 and recognized on human melanoma by cytolytic T cell clones. Tissue Antigens. Apr. 2002;59(4):273-9. doi: 10.1034/j.1399-0039.2002.590404.x.

Shang et al., The spontaneous CD8+ T-cell response to HLA-A2-restricted NY-ESO-1b peptide in hepatocellular carcinoma patients. Clin Cancer Res. Oct. 15, 2004;10(20):6946-55. doi: 10.1158/1078-0432.CCR-04-0502.

Sharma et al., Noninfectious virus-like particles produced by Moloney murine leukemia virus-based retrovirus packaging cells deficient in viral envelope become infectious in the presence of lipofection reagents. Proc Natl Acad Sci U S A. Sep. 30, 1997;94(20):10803-8. doi: 10.1073/pnas.94.20.10803.

Shcherbakova et al., Mutator phenotypes conferred by MLH1 overexpression and by heterozygosity for mlh1 mutations. Mol Cell Biol. Apr. 1999;19(4):3177-83. doi: 10.1128/MCB.19.4.3177.

Shellenberger et al., A recombinant polypeptide extends the in vivo half-life of peptides and proteins in a tunable manner. Nat Biotechnol. Dec. 2009;27(12):1186-90. doi: 10.1038/nbt.1588.

Shen et al., Activation-induced cytidine deaminase (AID) can target both DNA strands when the DNA is supercoiled. Proc Natl Acad Sci U S A. Aug. 31, 2004;101(35):12997-3002. doi: 10.1073/pnas.0404974101. Epub Aug. 24, 2004.

Shen et al., Identification of a MHC class-II restricted epitope in carcinoembryonic antigen. Cancer Immunol Immunother. May 2004;53(5):391-403. doi: 10.1007/s00262-003-0455-y. Epub Nov. 18, 2003.

Shim et al., Nonviral Delivery Systems for Cancer Gene Therapy: Strategies and Challenges. Curr Gene Ther. 2018;18(1):3-20. doi: 10.2174/1566523218666180119121949.

Simon et al., Retrons and their applications in genome engineering. Nucleic Acids Res. Dec. 2, 2019;47(21):11007-11019. doi: 10.1093/nar/gkz865.

Singh et al., Protein Engineering Approaches in the Post-Genomic Era. Curr Protein Pept Sci. 2018;19(1):5-15. doi: 10.2174/1389203718666161117114243.

Skipper et al., An HLA-A2-restricted tyrosinase antigen on melanoma cells results from posttranslational modification and suggests a novel pathway for processing of membrane proteins. J Exp Med. Feb. 1, 1996;183(2):527-34. doi: 10.1084/jem.183.2.527.

(56) References Cited

OTHER PUBLICATIONS

Skipper et al., Delivering the Goods for Genome Engineering and Editing. Hum Gene Ther. Aug. 2015;26(8):486-97. doi: 10.1089/hum.2015.063.
Skipper et al., Shared epitopes for HLA-A3-restricted melanoma-reactive human CTL include a naturally processed epitope from Pmel-17/gp100. J Immunol. Dec. 1, 1996;157(11):5027-33.
Slansky et al., Enhanced antigen-specific antitumor immunity with altered peptide ligands that stabilize the MHC-peptide-TCR complex. Immunity. Oct. 2000;13(4):529-38. doi: 10.1016/s1074-7613(00)00052-2.
Slingluff et al., Clinical and immunologic results of a randomized phase II trial of vaccination using four melanoma peptides either administered in granulocyte-macrophage colony-stimulating factor in adjuvant or pulsed on dendritic cells. J Clin Oncol. Nov. 1, 2003;21(21):4016-26. doi: 10.1200/JCO.2003.10.005.
Slingluff et al., Immunologic and clinical outcomes of vaccination with a multiepitope melanoma peptide vaccine plus low-dose interleukin-2 administered either concurrently or on a delayed schedule. J Clin Oncol. Nov. 15, 2004;22(22):4474-85. doi: 10.1200/JCO.2004.10.212.
Stevens et al., Design of a Split Intein with Exceptional Protein Splicing Activity. J Am Chem Soc. Feb. 24, 2016;138(7):2162-5. doi: 10.1021/jacs.5b13528. Epub Feb. 8, 2016. Abstract Only. 1 page.
Strand et al., Destabilization of tracts of simple repetitive DNA in yeast by mutations affecting DNA mismatch repair. Nature. Sep. 16, 1993;365(6443):274-6. doi: 10.1038/365274a0. Erratum in: Nature Apr. 7, 1994;368(6471);569.
Studebaker et al., Depletion of uracil-DNA glycosylase activity is associated with decreased cell proliferation. Biochem Biophys Res Commun. Aug. 26, 2005;334(2):509-15. doi: 10.1016/j.bbrc.2005.06.118.
Su et al., Mispair specificity of methyl-directed DNA mismatch correction in vitro. J Biol Chem. May 15, 1988;263(14):6829-35. Erratum in: J Biol Chem Aug. 5, 1988;263(22):11015.
Sugawara et al., Heteroduplex rejection during single-strand annealing requires Sgs1 helicase and mismatch repair proteins Msh2 and Msh6 but not Pms1. Proc Natl Acad Sci U S A. Jun. 22, 2004;101(25):9315-20. doi: 10.1073/pnas.0305749101. Epub Jun. 15, 2004.
Supek et al., Differential DNA mismatch repair underlies mutation rate variation across the human genome. Nature. May 7, 2015;521(7550):81-4. doi: 10.1038/nature14173. Epub Feb. 23, 2015.
Svitashev et al., Targeted Mutagenesis, Precise Gene Editing, and Site-Specific Gene Insertion in Maize Using Cas9 and Guide RNA. Plant Physiol. Oct. 2015; 169(2):931-45. doi: 10.1104/p. 15.00793. Epub Aug. 12, 2015.
Tang et al., Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318.
Tang et al., The *Arabidopsis* TRM61/TRM6 complex is a bona fide tRNA N1-methyladenosine methyltransferase. J Exp Bot. May 30, 2020;71(10):3024-3036. doi: 10.1093/jxb/eraa100.
Tangri et al., Structural features of peptide analogs of human histocompatibility leukocyte antigen class I epitopes that are more potent and immunogenic than wild-type peptide. J Exp Med. Sep. 17, 2001;194(6):833-46. doi: 10.1084/jem.194.6.833.
Thakore et al., Highly specific epigenome editing by CRISPR-Cas9 repressors for silencing of distal regulatory elements. Nat Methods. Dec. 2015;12(12):1143-9. doi: 10.1038/nmeth.3630. Epub Oct. 26, 2015.
Thomas et al., Heteroduplex repair in extracts of human HeLa cells. J Biol Chem. Feb. 25, 1991;266(6):3744-51.
Tomé-Amat et al., Secreted production of assembled Norovirus virus-like particles from Pichia pastoris. Microb Cell Fact. Sep. 10, 2014;13:134. doi: 10.1186/s12934-014-0134-z.

Tomer et al., Contribution of human mlh1 and pms2 ATPase activities to DNA mismatch repair. J Biol Chem. Jun. 14, 2002;277(24):21801-9. doi: 10.1074/jbc.M111342200. Epub Mar. 15, 2002.
Topalian et al., Melanoma-specific CD4+ T cells recognize nonmutated HLA-DR-restricted tyrosinase epitopes. J Exp Med. May 1, 1996;183(5):1965-71. doi: 10.1084/jem.183.5.1965.
Toro et al., Comprehensive phylogenetic analysis of bacterial reverse transcriptases. PLoS One. Nov. 25, 2014;9(11):e114083. doi: 10.1371/journal.pone.0114083.
Touloukian et al., Expression of a "self-"antigen by human tumor cells enhances tumor antigen-specific CD4(+) T-cell function. Cancer Res. Sep. 15, 2002;62(18):5144-7. Author Manuscript. 11 pages.
Touloukian et al., Identification of a MHC class II-restricted human gp100 epitope using DR4-IE transgenic mice. J Immunol. Apr. 1, 2000;164(7):3535-42. doi: 10.4049/jimmunol.164.7.3535.
Touloukian et al., Normal tissue depresses while tumor tissue enhances human T cell responses in vivo to a novel self/tumor melanoma antigen, OA1. J Immunol. Feb. 1, 2003;170(3):1579-85. doi: 10.4049/jimmunol.170.3.1579.
Tran et al., Hypermutability of homonucleotide runs in mismatch repair and DNA polymerase proofreading yeast mutants. Mol Cell Biol. May 1997;17(5):2859-65. doi: 10.1128/MCB.17.5.2859.
Trojan et al., Generation of cytotoxic T lymphocytes against native and altered peptides of human leukocyte antigen-A*0201 restricted epitopes from the human epithelial cell adhesion molecule. Cancer Res. Jun. 15, 2001;61(12):4761-5.
Tsai et al., Identification of subdominant CTL epitopes of the GP100 melanoma-associated tumor antigen by primary in vitro immunization with peptide-pulsed dendritic cells. J Immunol. Feb. 15, 1997;158(4):1796-802.
Tsang et al., A human cytotoxic T-lymphocyte epitope and its agonist epitope from the nonvariable number of tandem repeat sequence of MUC-1. Clin Cancer Res. Mar. 15, 2004;10(6):2139-49. doi: 10.1158/1078-0432.ccr-1011-03.
Tsang et al., Generation of human cytotoxic T cells specific for human carcinoembryonic antigen epitopes from patients immunized with recombinant vaccinia-CEA vaccine. J Natl Cancer Inst. Jul. 5, 1995;87(13):982-90. doi: 10.1093/jnci/87.13.982.
Tsuboi et al., Enhanced induction of human WT1-specific cytotoxic T lymphocytes with a 9-mer WT1 peptide modified at HLA-A*2402-binding residues. Cancer Immunol Immunother. Dec. 2002;51(11-12):614-20. doi: 10.1007/s00262-002-0328-9. Epub Oct. 18, 2002.
Tuorto et al., Genome recoding by tRNA modifications. Open Biol. Dec. 2016;6(12):160287. doi: 10.1098/rsob.160287.
Tycko et al., Methods for Optimizing CRISPR-Cas9 Genome Editing Specificity. Mol Cell. Aug. 4, 2016;63(3):355-70. doi: 10.1016/j.molcel.2016.07.004.
Umar et al., DNA loop repair by human cell extracts. Science. Nov. 4, 1994;266(5186):814-6. doi: 10.1126/science.7973637.
Urano et al., Substitution of the myristoylation signal of human immunodeficiency virus type 1 Pr55Gag with the phospholipase C-delta1 pleckstrin homology domain results in infectious pseudovirion production. J Gen Virol. Dec. 2008;89(Pt 12):3144-3149. doi: 10.1099/vir.0.2008/004820-0.
Valmori et al., Analysis of the cytolytic T lymphocyte response of melanoma patients to the naturally HLA-A*0201-associated tyrosinase peptide 368-376. Cancer Res. Aug. 15, 1999;59(16):4050-5.
Valmori et al., Enhanced generation of specific tumor-reactive CTL in vitro by selected Melan-A/MART-1 immunodominant peptide analogues. J Immunol. Feb. 15, 1998;160(4):1750-8.
Valmori et al., Naturally occurring human lymphocyte antigen-A2 restricted CD8+ T-cell response to the cancer testis antigen NY-ESO-1 in melanoma patients. Cancer Res. Aug. 15, 2000;60(16):4499-506.
Vigneron et al., A peptide derived from melanocytic protein gp100 and presented by HLA-B35 is recognized by autologous cytolytic T lymphocytes on melanoma cells. Tissue Antigens. Feb. 2005;65(2):156-62. doi: 10.1111/j.1399-0039.2005.00365.x.
Vigneron et al., An antigenic peptide produced by peptide splicing in the proteasome. Science. Apr. 23, 2004;304(5670):587-90. doi: 10.1126/science.1095522.

(56) References Cited

OTHER PUBLICATIONS

Visseren et al., Affinity, specificity and T-cell-receptor diversity of melanoma-specific CTL generated in vitro against a single tyrosinase epitope. Int J Cancer. Sep. 17, 1997;72(6):1122-8. doi: 10.1002/(sici)1097-0215(19970917)72:6<1122::aid-ijc30>3.0.co;2-3.
Voelkel et al., Protein transduction from retroviral Gag precursors. Proc Natl Acad Sci U S A. Apr. 27, 2010;107(17):7805-10. doi: 10.1073/pnas.0914517107. Epub Apr. 12, 2010.
Voisset et al., Phylogeny of a novel family of human endogenous retrovirus sequences, HERV-W, in humans and other primates. AIDS Res Hum Retroviruses. Nov. 20, 1999;15(17):1529-33. doi: 10.1089/088922299309810.
Volpe et al., Alternative BCR/ABL splice variants in Philadelphia chromosome-positive leukemias result in novel tumor-specific fusion proteins that may represent potential targets for immunotherapy approaches. Cancer Res. Jun. 1, 2007;67(11):5300-7. doi: 10.1158/0008-5472.CAN-06-3737.
Voutev et al., Bxb1 phage recombinase assists genome engineering in *Drosophila melanogaster*. Biotechniques. Jan. 1, 2017;62(1):37-38. doi: 10.2144/000114494.
Walpita et al., Mammalian Cell-Derived Respiratory Syncytial Virus-Like Particles Protect the Lower as well as the Upper Respiratory Tract. PLoS One. Jul. 1, 20154;10(7):e0130755. doi: 10.1371/journal.pone.0130755.
Walton et al., Spontaneous CD8 T cell responses against the melanocyte differentiation antigen RAB38/NY-MEL-1 in melanoma patients. J Immunol. Dec. 1, 2006;177(11):8212-8. doi: 10.4049/jimmunol.177.11.8212.
Wang et al., CRISPR/Cas9 in Genome Editing and Beyond. Annu Rev Biochem. Jun. 2, 2016;85:227-64. doi: 10.1146/annurev-biochem-060815-014607. Epub Apr. 25, 2016.
Wang et al., CRISPR-Based Therapeutic Genome Editing: Strategies and In Vivo Delivery by AAV Vectors. Cell. Apr. 2, 2020;181(1):136-150. doi: 10.1016/j.cell.2020.03.023.
Wang et al., Influence of the polyanion on the physico-chemical properties and biological activities of polyanion/DNA/polycation ternary polyplexes. Acta Biomater. Aug. 2012;8(8):3014-26. doi: 10.1016/j.actbio.2012.04.034. Epub Apr. 27, 2012.
Wang et al., Recognition of an antigenic peptide derived from tyrosinase-related protein-2 by CTL in the context of HLA-A31 and -A33. J Immunol. Jan. 15, 1998;160(2):890-7.
Wang et al., Recognition of breast cancer cells by CD8+ cytotoxic T-cell clones specific for NY-BR-1. Cancer Res. Jul. 1, 2006;66(13):6826-33. doi: 10.1158/0008-5472.CAN-05-3529.
Wang et al., Utilization of an alternative open reading frame of a normal gene in generating a novel human cancer antigen. J Exp Med. Mar. 1, 1996;183(3):1131-40. doi: 10.1084/jem.183.3.1131.
Wang et al., Virus-like particles for the prevention of human papillomavirus-associated malignancies. Expert Rev Vaccines. Feb. 2013;12(2):129-41. doi: 10.1586/erv.12.151. Author Manuscript, 22 pages.
Warren et al., Structure of the human MutSalpha DNA lesion recognition complex. Mol Cell. May 25, 2007;26(4):579-92. doi: 10.1016/j.molcel.2007.04.018.
Wei et al., Systemic nanoparticle delivery of CRISPR-Cas9 ribonucleoproteins for effective tissue specific genome editing. Nat Commun. Jun. 26, 2020;11(1):3232. doi: 10.1038/s41467-020-17029-3.
Witkowski et al., Conversion of a beta-ketoacyl synthase to a malonyl decarboxylase by replacement of the active-site cysteine with glutamine. Biochemistry. Sep. 7, 1999;38(36):11643-50. doi: 10.1021/bi990993h.
Wölfel et al., Two tyrosinase nonapeptides recognized on HLA-A2 melanomas by autologous cytolytic T lymphocytes. Eur J Immunol. Mar. 1994;24(3):759-64. doi: 10.1002/eji.1830240340.
Xi et al., C-terminal Loop Mutations Determine Folding and Secretion Properties of PCSK9. Biochem Mol Biol J. 2016;2(3):17. doi: 10.21767/2471-8084.100026. 12 pages.
Xu et al., Cas9-based tools for targeted genome editing and transcriptional control. Appl Environ Microbiol. Mar. 2014;80(5):1544-52. doi: 10.1128/AEM.03786-13. Epub Jan. 3, 2014.
Xu et al., Sequence and structural analyses of nuclear export signals in the NESdb database. Mol Biol Cell. Sep. 2012;23(18):3677-93. doi: 10.1091/mbc.E12-01-0046. Epub Jul. 25, 2012.
Yang et al., HIV-1 virus-like particles produced by stably transfected *Drosophila* S2 cells: a desirable vaccine component. J Virol. Jul. 2012;86(14):7662-76. doi: 10.1128/JVI.07164-11. Epub May 2, 2012.
Yee et al., A general method for the generation of high-titer, pantropic retroviral vectors: highly efficient infection of primary hepatocytes. Proc Natl Acad Sci U S A. Sep. 27, 1994;91(20):9564-8. doi: 10.1073/pnas.91.20.9564.
Yin et al., Optimizing genome editing strategy by primer-extension-mediated sequencing. Cell Discov. Mar. 26, 2019;5:18. doi: 10.1038/s41421-019-0088-8.
Yu et al., Poor immunogenicity of a self/tumor antigen derives from peptide-MHC-I instability and is independent of tolerance. J Clin Invest. Aug. 2004; 114(4):551-9. doi: 10.1172/JCI21695.
Zarour et al., Melan-A/MART-1(51-73) represents an immunogenic HLA-DR4-restricted epitope recognized by melanoma-reactive CD4(+) T cells. Proc Natl Acad Sci U S A. Jan. 4, 2000;97(1):400-5. doi: 10.1073/pnas.97.1.400.
Zeltins, A., Construction and characterization of virus-like particles: a review. Mol Biotechnol. Jan. 2013;53(1):92-107. doi: 10.1007/s12033-012-9598-4.
Zhang et al., Cell-specific targeting of lentiviral vectors mediated by fusion proteins derived from Sindbis virus, vesicular stomatitis virus, or avian sarcoma/leukosis virus. Retrovirology. Jan. 25, 2010;7:3. doi: 10.1186/1742-4690-7-3.
Zhang et al., CRISPR-Cpf1 correction of muscular dystrophy mutations in human cardiomyocytes and mice. Sci Adv. Apr. 12, 2017;3(4):e1602814. doi: 10.1126/sciadv.1602814.
Zhang et al., Propagated Perturbations from a Peripheral Mutation Show Interactions Supporting WW Domain Thermostability. Structure. Nov. 6, 2018;26(11):1474-1485.e5. doi: 10.1016/j.str.2018.07.014. Epub Sep. 6, 2018.
Zhang et al., Reconstitution of 5'-directed human mismatch repair in a purified system. Cell. Sep. 9, 2005;122(5):693-705. doi: 10.1016/j.cell.2005.06.027.
Zhao et al., Glycosylase base editors enable C-to-A and C-to-G base changes. Nat Biotechnol. Jan. 2021;39(1):35-40. doi: 10.1038/s41587-020-0592-2. Epub Jul. 20, 2020. Erratum in: Nat Biotechnol. Jan. 2021;39(1):115. doi: 10.1038/s41587-020-0648-3.
Zhao et al., Study on p21 gene knock out in G401 cell line by using CRISPR/Cas9 system. Tianjin Med J. Oct. 2016;44(10):1190-1194.
Zhong et al., Automated Continuous Evolution of Proteins in Vivo. ACS Synth Biol. Jun. 19, 2020;9(6):1270-1276. doi: 10.1021/acssynbio.0c00135. Epub May 12, 2020. Author Manuscript, 14 pages.

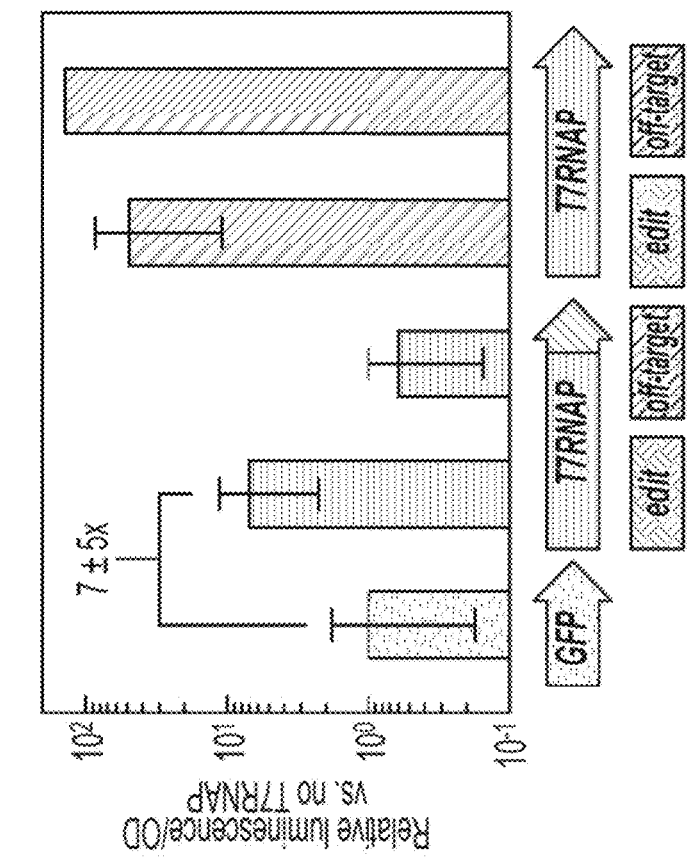
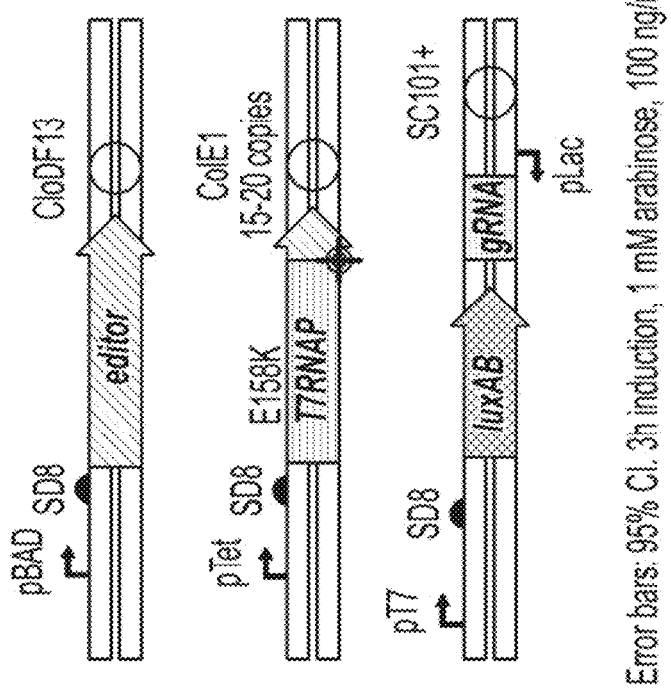
Figure 4

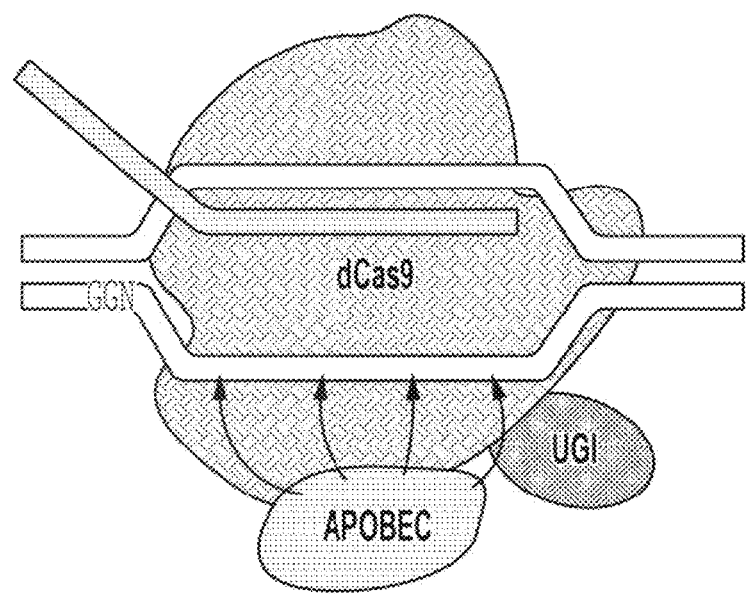
Figure 14
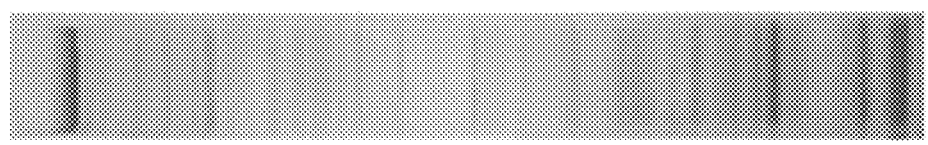
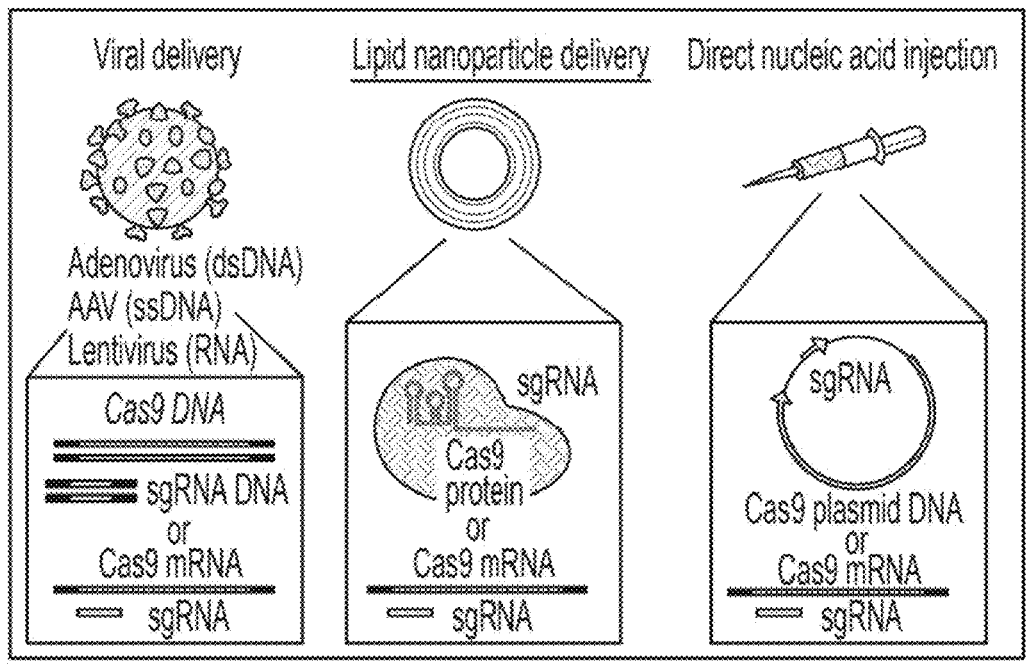
Figure 15

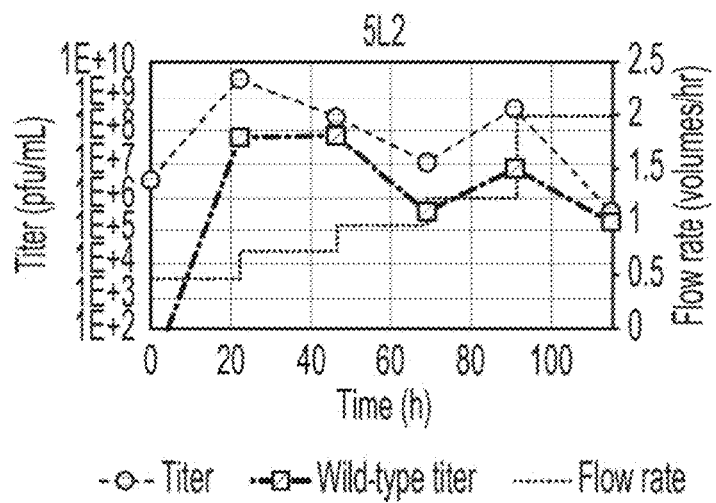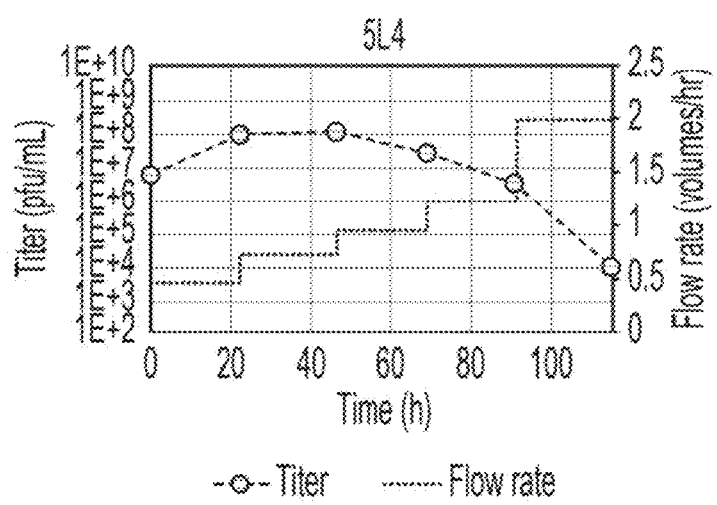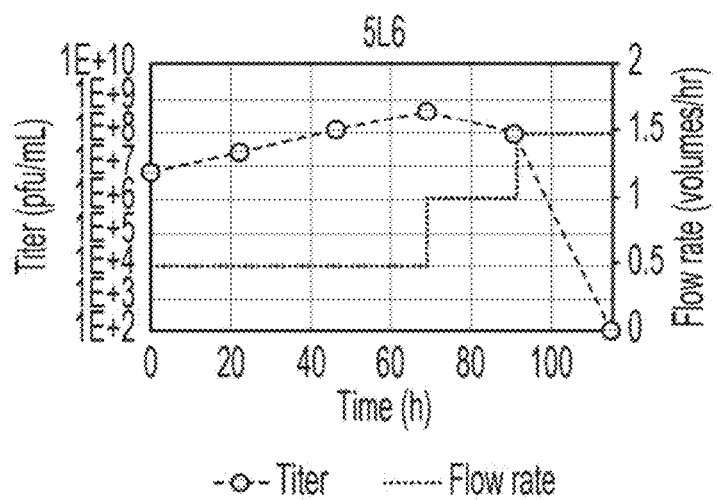
Figure 40 continued

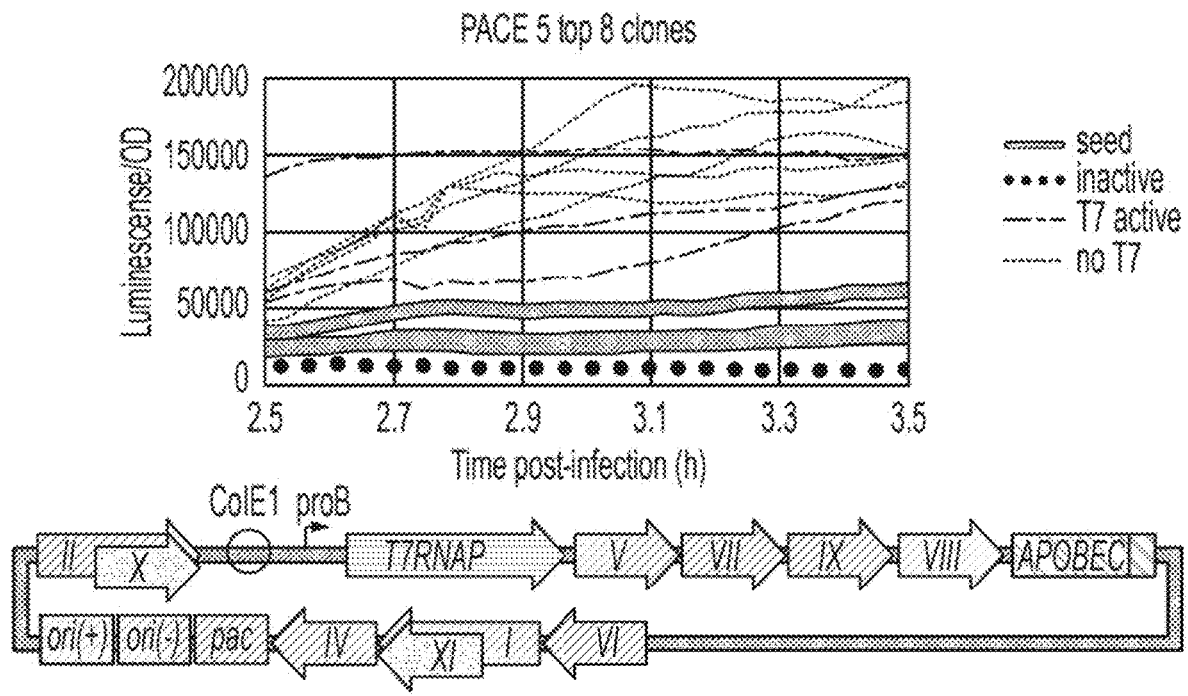
Figure 44
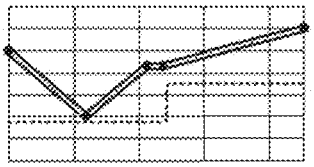
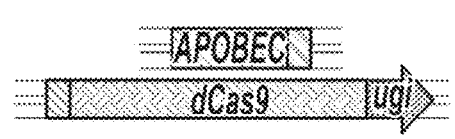
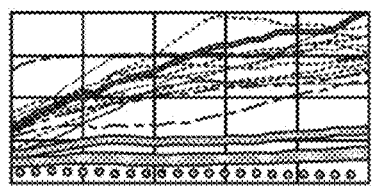
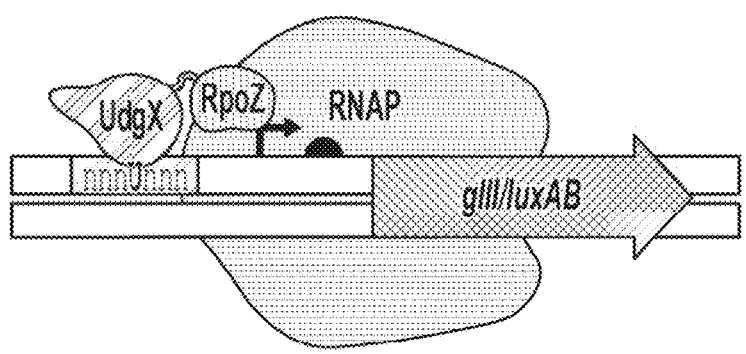
Figure 45

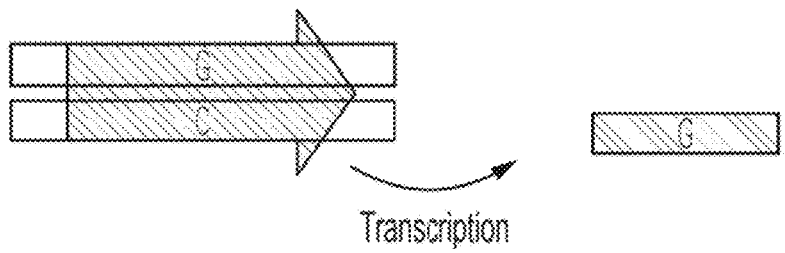
Figure 62
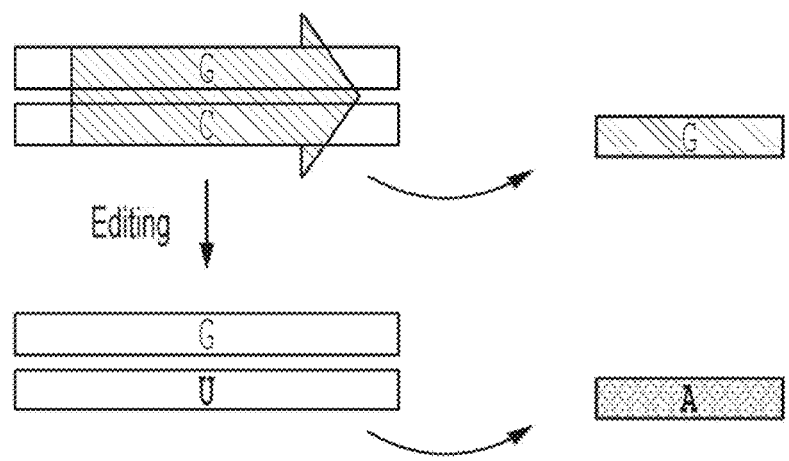
Figure 63
| Non-funtional, G-encoded AA | Arg | Glu | Cys | Ala | Ser | Asp | Arg | Val | Trp |
|---|---|---|---|---|---|---|---|---|---|
| | ↓ | ↓ | ↓ | ↓ | ↓ | ↓ | ↓ | ↓ | ↓ |
| Functional, A-encoded AA | His | Lys | Tyr | Thr | Asn | Asn | Gln | Ile/Met | STOP |
| AAs with an essential coding G (potential off-target changes) | Ala | Asp | Glu | Cys | Gly | Arg | Val | Met |
|---|---|---|---|---|---|---|---|---|
| | ↓ | ↓ | ↓ | ↓ | ↓ | ↓ | ↓ | ↓ |
| | Thr | Asn | Lys | Tyr | Asn Lys Asp Glu | Lys His | Ile | Ile |
Figure 64

| | | target | silent mut. |
|---|---|---|---|
| | | position 8 | position 1 |
| 1 | evo_ancBE4Max (pBT289) | 1.9% | 0.1% |
| 2 | evoCDA (pBT277) | 33.4% | 37.8% |
| 3 | evoAPOBEC (pBT281) | 1.1% | 0.1% |
| 4 | AID-BE4Max mouse opt (AY/AID/JL581) | 1.9% | 1.8% |
| 5 | CDA-BE4Max mouse opt (AY/CDA/JL581) | 8.0% | 16.8% |
| 6 | ancBE4Max (Chris) | 0.2% | 0.1% |
| 7 | evoFERNY (pBT280) | 5.5% | 0.4% |
| 8 | BE4Max (JL581) | 0.1% | 0.0% |
| 9 | GFP (Lonza) | 0.0% | 0.0% |

Figure 139

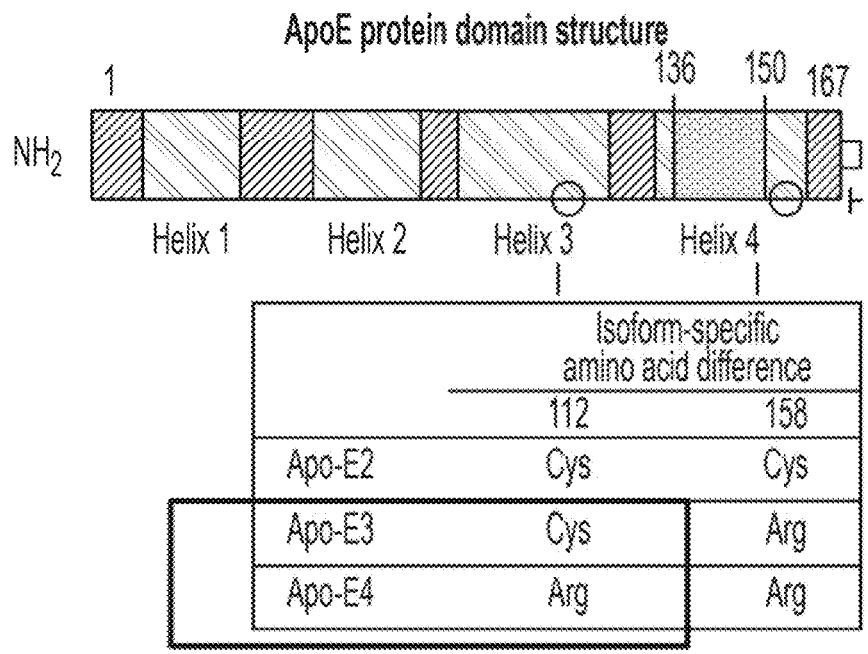
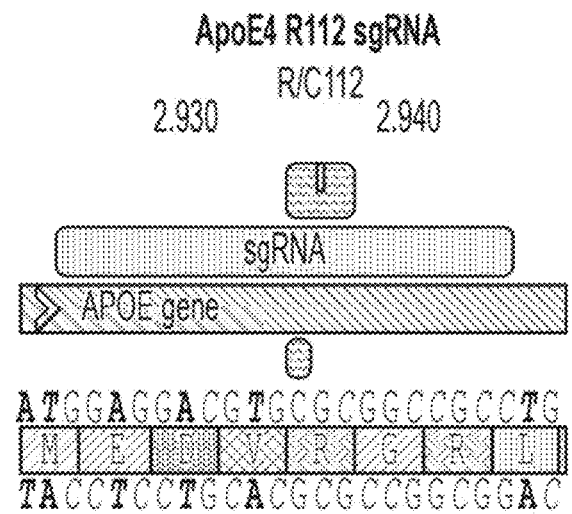
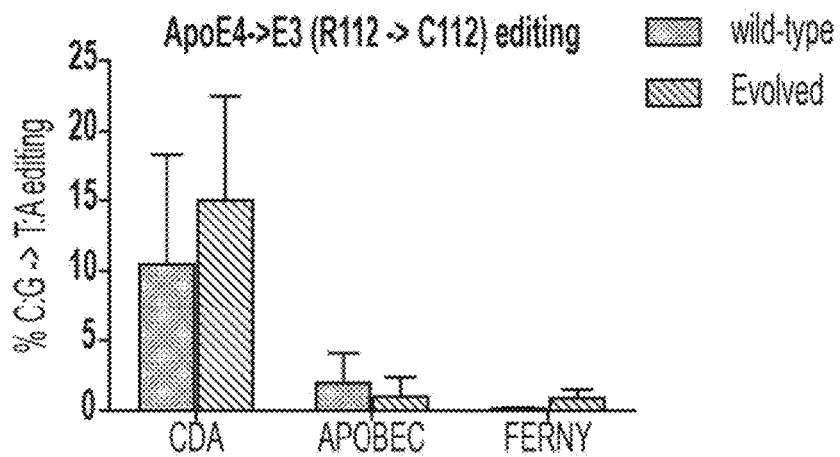
Figure 140

METHODS AND COMPOSITIONS FOR EVOLVING BASE EDITORS USING PHAGE-ASSISTED CONTINUOUS EVOLUTION (PACE)

RELATED APPLICATIONS AND INCORPORATION BY REFERENCE

This application is a continuation of and claims priority under 35 U.S.C. § 120 to U.S. patent application Ser. No. 16/634,405, filed Jan. 27, 2020, which is a national stage filing under 35 U.S.C. § 371 of international PCT application, PCT/US2018/044242, filed Jul. 27, 2018, which claims priority under 35 U.S.C. § 119(e) to U.S. Provisional Patent Application No. 62/538,380, filed Jul. 28, 2017, each of which is incorporated herein by reference.

REFERENCE TO AN ELECTRONIC SEQUENCE LISTING

The contents of the electronic sequence listing (H082470277US02-SEQ-JQM.xml; Size: 247,383 bytes; and Date of Creation: Feb. 27, 2023) is herein incorporated by reference in its entirety.

BACKGROUND OF THE INVENTION

Targeted editing of nucleic acid sequences, for example, the targeted cleavage or the targeted introduction of a specific modification into genomic DNA, is a highly promising approach for the study of gene function and also has the potential to provide new therapies for human genetic diseases, for example, those caused by point mutations. Point mutations represent the majority of known human genetic variants associated with disease (1). Developing robust methods to introduce and correct point mutations is therefore an important challenge to understand and treat diseases with a genetic component.

Engineered base editors have been recently developed (2, 3). Base editors are fusions of catalytically disabled Cas moiety and a nucleobase modification enzyme (e.g., natural or evolved nucleobase deaminases, such as cytidine deaminases that include APOBEC1 ("apolipoprotein B mRNA editing enzyme, catalytic polypeptide 1"), CDA ("cytidine deaminase"), or AID ("activation-induced cytidine deaminase")) domains. In some cases, base editors may also include proteins that alter cellular DNA repair processes to increase the efficiency and stability of the resulting single-nucleotide change, e.g., a UGI domain (2, 3).

Two classes of base editors have been generally described to date: cytidine base editors convert target C•G base pairs to T•A base pairs, and adenine base editors convert A•T base pairs to G•C base pairs. Collectively, these two classes of base editors enable the targeted installation of all four transition mutations (C-to-T, G-to-A, A-to-G, and T-to-C), which collectively account for about 61% of known human pathogenic small nucleotide polymorphisms (SNPs) in the ClinVar database. In particular, C-to-T base editors use a cytidine deaminase to convert cytidine to uridine in the single-stranded DNA loop opened by Cas9. The opposite strand is nicked by Cas9 to stimulate DNA repair mechanisms that use the edited strand as a template, while a fused uracil glycosylase inhibitor (not shown) slows excision of the edited base. Eventually, DNA repair leads to a C•G to T•C base pair conversion.

Base editors can edit many targets with high efficiency, often achieving editing of 30-70% of cells without enrichment following a single treatment. Unfortunately, however, the utility of base editing is limited by several constraints, including the PAM requirement imposed by the particular Cas moiety used (e.g., naturally occurring Cas9 from *S. pyogenes*, or a modified version thereof, or a homolog thereof), off-target base editing of non-target nucleotides nearby the desired editing site, the production of undesired edited genomic byproducts (e.g., indels), and overall low editing efficiencies. For example, current cytidine base editor activity is dependent on the bases surrounding the target nucleotide. C-to-T editors based on the APOBEC1 cytidine deaminase have a preference for editing TC motifs, and disfavor most GC bases. This preference can lead to editing of TC at positions outside the canonical editing window, as well as poor editing of GC targets even when they are optimally positioned. C-to-T editors that use other deaminases such as CDA or AID can provide an effective alternative for certain GC sites, but have overall lower editing efficiency compared to APOBEC1 BEs.

The development of "next-generation" base editors has begun to address some of these limitations, including base editors with different or expanded PAM compatibilities (19-21), high-fidelity base editors with reduced off-target activity (20, 22-25), base editors with narrower editing windows (normally ~5 nucleotides wide) (19), base editors with loosened sequence-context preferences, and a cytidine base editor (BE4) with reduced by-products (6). Nevertheless, despite these recent advances, the efficiency of base editing by base editors varies widely by among other factors, cell type and target locus. Thus, there continues to be a significant need in the art for the development of base editors with improved editing efficiencies with sequence-context agnostic base editing activities. The present describes a phage-assisted continuous evolution system for developing and producing evolved base editors that have high efficiency and are sequence-context agnostic, and thus, addresses the problems in the art.

SUMMARY OF THE INVENTION

The instant specification provides for evolved base editors which overcome deficiencies of those in art (including increased efficiency and/or decreased requirement for specific sequence-context at an editing site) and which are obtained a result of a phage-assisted continuous evolution (PACE) system. In particular, the instant specification provides for evolved cytidine base editors (e.g., based on APOBEC1, CDA, or AID cytidine deaminase domains) which overcome deficiencies of those in art (including increased efficiency and/or decreased requirement for specific sequence-context at an editing site) and which are obtained a result of a phage-assisted continuous evolution (PACE) system. In addition, the instant specification provides for nucleic acid molecules encoding and/or expressing the evolved base editors as described herein, as well as expression vectors or constructs for expressing the evolved base editors described herein, host cells comprising said nucleic acid molecules and expression vectors, and compositions for delivering and/or administering nucleic acid-based embodiments described herein. In addition, the disclosure provides for isolated evolved base editors, as well as compositions comprising said isolated evolved base editors as described herein. Still further, the present disclosure provides for methods of making the evolved base editors, as well as methods of using the evolved base editors or nucleic acid molecules encoding the evolved base editors in applications including editing a nucleic acid molecule, e.g., a genome, with improved efficiency as compared to base editor that forms the state of the art, preferably in a sequence-context agnostic manner (i.e., wherein the desired editing site does not require a specific sequence-context). In embodiments, the method of making provide herein is an improved phage-assisted continuous evolution (PACE) system which may be utilized to evolve one or more components of a base editor (e.g., a Cas9 domain or a cytidine deaminase domain) in a rapid and continuous manner. The specification also provides methods for efficiently editing a target nucleic acid molecule, e.g., a single nucleobase of a genome, with a base editing system described herein (e.g., in the form of an isolated evolved base editor as described herein or a vector or construct encoding same) and conducting based editing, preferably in a sequence-context agnostic manner. Still further, the specification provides therapeutic methods for treating a genetic disease and/or for altering or changing a genetic trait or condition by contacting a target nucleic acid molecule, e.g., a genome, with a base editing system (e.g., in the form of an isolated evolved base editor protein or a vector encoding same) and conducting based editing to treat the genetic disease and/or change the genetic trait (e.g., eye color).

The present inventors have surprisingly discovered improve base editors (e.g., cytindine base editors) by developing an effective continuous evolutionary mutagenesis process (i.e., PACE) that may be used to rapidly improve the function of one or more domains or components of a base editor.

Thus, in one aspect, the specification provides a cytidine deaminase comprising an amino acid sequence that is at least 80%, 85%, 90%, 95%, 98%, 99%, or 99.5% identical to amino acid residues 2-162 of SEQ ID NO: 1, wherein the cytidine deaminase comprises one or more mutations selected from the group consisting of $H102X_1$, $D104X_2$, and $V115X_3$ relative to SEQ ID NO: 1, or a corresponding mutation(s) in another cytidine deaminase, wherein $X_1$ is any amino acid other than H (e.g., H102P), $X_2$ is any amino acid other than D (e.g., D104N), and $X_3$ is any amino acid other than V (e.g., M). In one embodiment, the cytidine deaminase comprises residues 2-162 of SEQ ID NO: 5. The cytidine deaminase can also include an N-terminal methionine (M) amino acid residue.

In another aspect, the specification provides a cytidine deaminase comprising an amino acid sequence that is at least 80%, 85%, 90%, 95%, 98%, 99%, or 99.5% identical to amino acid residues 3-229 of SEQ ID NO: 2, wherein the cytidine deaminase comprises one or more mutations selected from the group consisting of $E4X_1$, $V10X_2$, $E31X_3$, $Y40X_4$, $E95X_5$, $H109X_6$, $H122X_7$, $D124X_8$, $R126X_9$, $R154X_{10}$, $N158X_{11}$, $A165X_{12}$, $P201X_{13}$, $F205X_{14}$, and $I208X_{15}$ relative to SEQ ID NO: 2, or a corresponding mutation(s) in another cytidine deaminase, wherein $X_1$, $X_3$, and $X_5$ are any amino acid other than E, $X_2$ is any amino acid other than V, $X_4$ is any amino acid other than Y, $X_6$ and $X_7$ are any amino acid other than H, $X_8$ is any amino acid other than D, $X_9$ and $X_{10}$ are any amino acid other than R, $X_{11}$ is any amino acid other than N, $X_{12}$ is any amino acid other than A, $X_{13}$ is any amino acid other than P, $X_{14}$ is any amino acid other than F, and $X_{15}$ is any amino acid other than I. In various embodiments: $X_1$ can be K; $X_2$ and $X_5$ can be A; $X_3$ can be V, $X_4$ can be C; $X_6$ and $X_8$ can be N; $X_7$ and $X_{15}$ can be L; $X_9$ and $X_{10}$ can be H; $X_{11}$, $X_{12}$, $X_{13}$; and $X_{14}$ can be S. In various embodiments, the cytidine deaminase may comprise 2, 3, 4, 5, 6, 7, or all 8 mutations that can include E4K, H109N, H122L, D124N, R154H, A165S, P201S, and F205S relative to SEQ ID NO: 2. In one embodiment, the cytidine deaminase comprises the amino acid sequence of SEQ ID NO: 6.

In still another embodiment, the specification provides a cytidine deaminase comprising an amino acid sequence that is at least 80%, 85%, 90%, 95%, 98%, 99%, or 99.5% identical to amino acid residues 2-208 of SEQ ID NO: 3, wherein the cytidine deaminase comprises one or more mutations selected from the group consisting of $H10X_1$, $F23X_2$, $V75X_3$, $K120X_4$, $A123X_5$, $C158X_6$, $I193X_7$, $I195X_8$, and $V197X_9$ relative to SEQ ID NO: 3, or a corresponding mutation(s) in another cytidine deaminase, wherein $X_1$, is any amino acid other than H, $X_2$ is any amino acid other than F, $X_3$ and $X_9$ are any amino acid other than V, $X_4$ is any amino acid other than K, $X_5$ is any amino acid other than A, $X_6$ is any amino acid other than C, and $X_7$ and $X_8$ are any amino acid other than I. In various embodiments: $X_1$ can be Y; $X_2$ can be S; $X_3$ can be I; $X_4$ and $X_6$ can be R; $X_5$ can be V; $X_7$ can be T; $X_8$ can be F or T; and $X_9$ can be A. In one embodiment, the cytidine deaminase comprises the mutations F23S, A123V, and I195F relative to SEQ ID NO: 3. In other embodiments, the cytindine deaminase comprises an N-terminal methionine (M) amino acid residue. In a preferred embodiment, the cytidine deaminase comprises the amino acid sequence of SEQ ID NO: 7.

In still another aspect, the specification provides a cytidine deaminase comprising an amino acid sequence that is at least 80%, 85%, 90%, 95%, 98%, 99%, or 99.5% identical to amino acid residues 3-229 of SEQ ID NO: 4, wherein the cytidine deaminase comprises one or more mutations selected from the group consisting of $E4X_1$, $H122X_2$, $D124X_3$, $R154X_4$, $A165X_5$, $P201X_6$, and $F205X_7$ relative to SEQ ID NO: 4, or a corresponding mutation(s) in another cytidine deaminase, wherein $X_1$ is any amino acid other than E, $X_2$ is any amino acid other than H, $X_3$ is any amino acid other than D, $X_4$ is any amino acid other than R, $X_5$ is any amino acid other than A, $X_6$ is any amino acid other than P, and $X_7$ is any amino acid other than F. In various embodiments, the cytidine deaminase comprises 2, 3, 4, 5, 6, or all 7, mutations selected from the group consisting of $E4X_1$, $H122X_2$, $D124X_3$, $R154X_4$, $A165X_5$, $P201X_6$, and $F205X_7$ relative to SEQ ID NO: 4, wherein $X_1$ is any amino acid other than E, $X_2$ is any amino acid other than H, $X_3$ is any amino acid other than D, $X_4$ is any amino acid other than R, $X_5$ is any amino acid other than A, $X_6$ is any amino acid other than P, and $X_7$ is any amino acid other than F. In certain embodiments: $X_1$ can be K; $X_2$ can be L; $X_3$ can be N; $X_4$ can be H; $X_5$ can be S; $X_6$ can be S; and/or $X_7$ can be S. In other embodiments, the one or more mutations can be selected from the group consisting of E4K, H122L, D124N, R154H, A165S, P201S, and F205S relative to SEQ ID NO: 4. In another embodiment, the deaminase can be SEQ ID NO: 89 or amino acid residues 3-229 of SEQ ID NO: 8 and can comprise an N-terminal methionine (M) amino acid residue, or two N-terminal amino acid residues, which are M and S.

In still another aspect, the specification provides an evolved base editor fusion protein comprising: (i) a nucleic acid programmable DNA binding protein (napDNAbp); (ii) a cytidine deaminase described herein in any of the above aspects; and (iii) a uracil glycosylase inhibitor domain (UGI). The fusion protein can have two, three, four, or five UGI domains. The nucleic acid programmable DNA binding protein (napDNAbp) can be a Cas9 domain. The napDNAbp can also be a CasX, CasY, Cpf1, C2c1, C2c2, C2c3, or Argonaute protein. The Cas9 domain can be a nuclease active Cas9, a nuclease inactive Cas9 (dCas9), or a Cas9 nickase (nCas9).

In various embodiments of the evolved base editor fusion proteins, the nCas9 can have an amino acid sequence that is at least 80%, 85%, 90%, 95%, 98%, 99%, 99.5%, or 99.9% identical to the amino acid sequence

```
                                       (SEQ ID NO: 9)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

FTLTNLGAPAAFKYFDTTIDRKRYTSTKEVLDATLIHQSITGLYETRIDL

SQLGGD.
```

In other embodiments, the UGI domain of the evolved base editor fusion proteins can comprise a domain capable of inhibiting UDG activity. UGI domain comprises an amino acid sequence that is at least 80%, 85%, 90%, 95%, 98%, 99%, 99.5%, or 99.9% identical to the amino acid sequence:

```
                                       (SEQ ID NO: 10)
MTNLSDIIEKETGKQLVIQESILMLPEEVEEVIGNKPESDILVHTAYDES

TDENVMLLTSDAPEYKPWALVIQDSNGENKIKML
```

In various embodiments, the evolved base editor fusion proteins described herein can comprise any of the following structures: NH$_2$-[cytidine deaminase]-[napDNAbp]-[UGI]-COOH; NH$_2$-[cytidine deaminase]-[UGI]-[napDNAbp]-COOH; NH$_2$-[napDNAbp]-[UGI]-[cytidine deaminase]-COOH; NH$_2$-[napDNAbp]-[cytidine deaminase]-[UGI]-COOH; NH$_2$-[UGI]-[cytidine deaminase]-[napDNAbp]-COOH; and NH$_2$-[UGI]-[napDNAbp]-[cytidine deaminase]-COOH; wherein the cytidine deaminase can be an evolved cytidine deaminase described in the above aspects, wherein the UGI is a UGI domain, and wherein each instance of "-" comprises an optional linker.

In other embodiments, the evolved base editor fusion proteins described herein can comprise any of the following structures: NH$_2$-[cytidine deaminase]-[napDNAbp]-[UGI]-[UGI]-COOH; NH$_2$-[cytidine deaminase]-[UGI]-[napDNAbp]-[UGI]-COOH; NH$_2$-[UGI]-[cytidine deaminase]-[napDNAbp]-[UGI]-COOH; NH$_2$-[cytidine deaminase]-[UGI]-[napDNAbp]-[UGI]-COOH; NH$_2$-[cytidine deaminase]-[UGI]-[UGI]-[napDNAbp]-COOH; NH$_2$-[UGI]-[cytidine deaminase]-[UGI]-[napDNAbp]-COOH; NH$_2$-[UGI]-[napDNAbp]-[UGI]-[cytidine deaminase]-COOH; NH$_2$-[napDNAbp]-[UGI]-[UGI]-[cytidine deaminase]-COOH; NH$_2$-[napDNAbp]-[UGI]-[cytidine deaminase]-[UGI]-COOH; NH$_2$-[napDNAbp]-[cytidine deaminase]-[UGI]-[UGI]-COOH; NH$_2$-[napDNAbp]-[UGI]-[cytidine deaminase]-[UGI]-COOH; NH$_2$-[UGI]-[napDNAbp]-[cytidine deaminase]-[UGI]-COOH; NH$_2$-[UGI]-[cytidine deaminase]-[napDNAbp]-[UGI]-COOH; NH$_2$-[UGI]-[cytidine deaminase]-[UGI]-[napDNAbp]-COOH; NH$_2$-[UGI]-[UGI]-[cytidine deaminase]-[napDNAbp]-COOH; NH$_2$-[UGI]-[napDNAbp]-[cytidine deaminase]-[UGI]-COOH; NH$_2$-[UGI]-[napDNAbp]-[UGI]-[cytidine deaminase]-COOH; and NH$_2$-[UGI]-[UGI]-[napDNAbp]-[cytidine deaminase]-COOH; wherein the cytidine deaminase is an evolved cytidine deaminase described in the above aspects, wherein the UGI is a UGI domain, and wherein each instance of "-" comprises an optional linker.

The linkers can comprise any of the following amino acid sequences:

```
                                       (SEQ ID NO: 11)
SGGSSGGSSGSETPGTSESATPESSGGSSGGS;

(SEQ ID NO: 12)
SGGSGGSGGS;

(SEQ ID NO: 14)
SGGS;
or
                                       (SEQ ID NO: 12)
SGGSGGSGGS.
```

In various embodiments, the evolved base editor fusion proteins can further include one or more (e.g., 2, 3, 4, 5, 6, or more) nuclear localization sequences (NLS), such as,

```
                                       (SEQ ID NO: 13)
                   KRTADGSEFEPKKKRKV
```

In various embodiments, the evolved base editor fusion proteins may comprise an amino acid sequence that is at least 80%, 85%, 90%, 95%, 98%, 99%, or 99.5% identical to any one of the amino acid sequence set forth in any one of SEQ ID NOs: 15-20.

In various other embodiments, the specification provides nucleic acid molecules encoding any of the evolved base editor fusion proteins, or domains thereof. The nucleic acid sequences may be codon-optimized for expression in a mammalian cell, e.g., HEK293T.

In still other embodiments, the specification provides vectors with appropriate promoters for driving expression of the nucleic acid sequences encoding the evolved base editors (or one more individual components thereof).

In various embodiment, the continuous evolution/PACE methods of the invention contemplate dividing the expression of the evolved base editor fusion proteins into two or more expression vectors, wherein each expression unit encodes a portion of the evolved base editor fusion protein. The expressed portions include split-intein domains, which drive the autologous formation of the fully formed evolved base editor through the process of protein splicing.

In other aspects, the present specification provides a complex the evolved base editor fusion proteins described herein and an RNA bound to the napDNAbp of the fusion protein, such as a guide RNA (gRNA). The guide RNA can be a single guide RNA or multiple guide RNAs. The RNA can be from 10-100 nucleotides in length, and comprise at least 10 contiguous nucleotides that are complementary to the target sequence, or at least 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides that are complementary to the target sequence.

In some embodiments, that target sequence (the sequence to be edited) is a DNA sequence, including an organism's genome. The organism can be a prokaryote, or a eukaryote, or a vertebrate, a mammal, or a human.

In other embodiments, the specification provides cells that comprise the herein disclosed evolved cytidine deaminases, the evolved base editor fusions, the complexes disclosed herein, the nucleic acid molecules encoding same, or a vector comprising the nucleic acid molecules.

In still other embodiments, the specification provides kits comprising nucleic acid nucleic acid constructs, comprising: a nucleic acid sequence encoding a fusion protein disclosed herein; and a heterologous promoter that drives expression of the fusion protein. The kits can also comprise an expression construct encoding a guide RNA backbone, wherein the construct comprises a cloning site positioned to allow the cloning of a nucleic acid sequence identical or complementary to a target sequence into the guide RNA backbone.

In other embodiments, the specification provides a pharmaceutical composition comprising an evolved base editor fusion protein described herein, and a pharmaceutically acceptable excipient, and optionally a lipid, such as a cationic lipid. The pharmaceutical compostions can also comprise a polymer.

The specification also provides method of using the composition described herein, including the evolved base editors, or nucleic acid molecules encoding same, for editing a target nucleotide sequence (e.g., a genome). The target nucleotide sequence can comprise a target sequence (e.g., a point mutation) associated with a disease or disorder. The target sequence can comprise a T to C point mutation associated with a disease or disorder, and wherein the deamination of the mutant C base results in a sequence that is not associated with a disease or disorder. The target sequence can encode a protein, and where the point mutation is in a codon and results in a change in the amino acid encoded by the mutant codon as compared to a wild-type codon. The target sequence can also be at a splice site, and wherein the point mutation results in a change in the splicing of an mRNA transcript as compared to a wild-type transcript. In addition, the target can be at a promoter of a gene, and wherein the point mutation results in an increased or decreased expression of the gene.

In various embodiments, the evolved base editors results in a deamination of a target site. In some cases, the deamination of the mutant C results in a change of the amino acid encoded by the mutant codon, which in some cases can result in the expression of a wild-type amino acid. The deamination can also result in a change of the mRNA transcript, and even restoring the mRNA transcript to a wild-type state.

The methods described herein involving contacting an evolved base editor with a target nucleotide sequence can occur in vitro or in vivo in a subject. The subject can be someone who has been diagnosed with a disease or disorder, such as a disease or disorder associated with a point mutation in a ApoE gene.

The methods of the invention also relate to RNA polymerases (e.g., T7 RNA polymerases) that are fused to a degron tag.

The methods of the invention also relate to a fusion protein comprising a cytidine deaminase of a base editor fused to an N-intein or a C-intein, and a independently expressed fusion protein comprising the remainder of a base editor that is fused to the complementary N-intein or C-intein domain, such that expression of the cytindine deaminase and the expression of the remainder of the base editor in the same cell results in a complete base editor as a result of the cells's protein splicing machinery acting on the N- and C-intein domains. The cytindine deaminase can be an APOBEC deaminase.

The specification also provides for a first expression vector comprising a nucleic acid molecule that encode a first portion of complete base editor that is fused to a split-intein domain, and a second expression vector comprising a nucleic acid molecule that encodes a second portion of a complete base editor that is fused to the cognate split-intein domain, wherein when expressed in a cell, the cell's protein splicing machinery forms a whole base editor by joining of the split-intein domains and then the subsequent removal of same leaving a residual peptide bond joining the first and second portions.

The specification also provides a vector system for phage-based continuous directed evolution comprising:
  a. a vector comprising a nucleic acid that encodes a base editor protein capable of deaminating a cytosine;
  b. a second vector that encodes the remaining portion of the whole base editor; and
  c. a vector that encodes luxAB and a guide RNA (gRNA).

The specification also provides a method of continuous evolution of nucleic acids comprising: (i) introducing a selection phagemid (SP) comprising a gene of interest to be evolved (e.g., a deaminase) into a flow of bacterial host cells through a lagoon,
  wherein the host cells comprise phage genes required to package the selection phagemid into infectious phage particles, wherein at least one gene required to package the selection phagemid into phage particles is disabled,
  wherein at least one gene required to package the selection phagemid into infectious phage particles is expressed in response to expression of the gene to be evolved in the host cell,
  and wherein the flow rate of the host cells through the lagoon permits replication of the phagemid, but not of the host cells, in the lagoon;
(ii) replicating and mutating the phagemid within the flow of host cells; and (iii) isolating a phagemid comprising a mutated gene to be evolved from the flow of cells.

The host cells can comprise a first accessory plasmid (AP) comprising the gene required to package the selection phagemid into phage particles that is disabled in the host cells, wherein the gene is expressed from the accessory plasmid in response to expression of the fusion protein encoded by the SP.

In certain embodiments, the target is in the genome of an organism. In certain embodiments, the organism is a prokaryote. In certain embodiments, the organism is a eukaryote. In certain embodiments, the organism is a vertebrate. In certain embodiments, the vertebrate is a mammal. In certain embodiments, the mammal is a human.

In one aspect, the specification discloses a cell comprising any one of the presently disclosed evolved base editor fusion proteins.

In one aspect, the specification discloses a cell comprising any one of the presently disclosed nucleic acids.

In one aspect, the specification discloses a cell comprising any one of the presently disclosed vectors.

In one aspect, the specification discloses a cell comprising any one of the presently disclosed complexes.

In one aspect, the specification discloses a method comprising contacting a nucleic acid molecule with any of the presently disclosed complexes. In certain embodiments, the nucleic acid is DNA. In certain embodiments, the nucleic acid is double-stranded DNA. In certain embodiments, the nucleic acid comprises a target sequence associated with a disease or disorder. In certain embodiments, the target sequence comprises a point mutation associated with a disease or disorder.

In certain embodiments, the target sequence comprises a T to C point mutation associated with a disease or disorder, and wherein the deamination of the mutant C base results in a sequence that is not associated with a disease or disorder. In certain embodiments, the target sequence comprises a G to A point mutation associated with a disease or disorder, and wherein the deamination of the mutant C base results in a sequence that is not associated with a disease or disorder.

In certain embodiments, the target sequence in which the desired editing is to occur, is sequence agnostic. That is, the evolved base editors described herein may carrying out efficient and accurate editing without requiring a specific sequence context at the target editing site.

In certain embodiments, the target sequence encodes a protein, and wherein the point mutation is in a codon and results in a change in the amino acid encoded by the mutant codon as compared to a wild-type codon. In certain embodiments, the target sequence is at a splice site, and wherein the point mutation results in a change in the splicing of an mRNA transcript as compared to a wild-type transcript. In certain embodiments, the target sequence is at a promoter of a gene, and wherein the point mutation results in an increased expression of the gene. In certain embodiments, the target sequence is at a promoter of a gene, and wherein the point mutation results in a decreased expression of the gene.

In certain embodiments, the deamination of the mutant C or the mutant A results in a change of the amino acid encoded by the mutant codon. In certain embodiments, the deamination of the mutant C or the mutant A results in the codon encoding a wild-type amino acid. In certain embodiments, the deamination of the mutant C or the mutant A results in a change of the mRNA transcript. In certain embodiments, the deamination of the mutant C or the mutant A results in a wild-type mRNA transcript. In certain embodiments, the deamination of the mutant C or the mutant A results in increased expression of the gene. In certain embodiments, the deamination of the mutant C or the mutant A results in decreased expression of the gene.

In certain embodiments, the contacting is performed in vitro. In certain embodiments, the contacting is performed in vivo in a subject.

In certain embodiments, the subject has been diagnosed with a disease or disorder. In certain embodiments, the disease or disorder is selected from the group consisting of congenital disorder of glycosylation type 1f, familial erythromyalgia, paroxysomal extreme pain disorder, chronic insensitivity to pain, sickle cell anemia, and β-thalassemia. In certain embodiments, the disease or disorder is associated with a point mutation in a MDPU1 gene. In certain embodiments, the disease or disorder is associated with a point mutation in a SCN9a gene. In certain embodiments, the disease or disorder can be treated by increasing the expression of an HBG1 and/or an HBG2 gene.

In one aspect, the specification discloses a kit comprising a nucleic acid construct, comprising (a) a nucleic acid sequence encoding any one of the presently disclosed fusion proteins; and (b) a heterologous promoter that drives expression of the sequence of (a). In certain embodiments, the kit further comprises an expression construct encoding a guide RNA backbone, wherein the construct comprises a cloning site positioned to allow the cloning of a nucleic acid sequence identical or complementary to a target sequence into the guide RNA backbone.

In one aspect, the specification discloses a pharmaceutical composition comprising any one of the presently disclosed fusion proteins.

In one aspect, the specification discloses a pharmaceutical composition comprising any one of the presently disclosed complexes.

In one aspect, the specification discloses a pharmaceutical composition comprising any one of the presently disclosed nucleic acids.

In one aspect, the specification discloses a pharmaceutical composition comprising any one of the presently disclosed vectors. In certain embodiments, the pharmaceutical composition further comprises a pharmaceutically acceptable excipient. In certain embodiments, the pharmaceutical composition further comprises a lipid. In certain embodiments, the lipid is a cationic lipid. In certain embodiments, the pharmaceutical composition further comprises a polymer.

In certain embodiments, the fusion protein comprises the structure: NH2-[any of the presently disclosed cytidine deaminases]-[Cas9 domain]-COOH, and each instance of "-" comprises an optional linker. In certain embodiments, the fusion protein comprises the structure: NH2-[any of the presently disclosed cytidine deaminases]-[Cas9 domain]-[UGI domain]-COOH, and each instance of "-" comprises an optional linker. In certain embodiments, the fusion protein comprises the structure: NH2-[any of the presently disclosed cytidine deaminases]-[Cas9 domain]-[first UGI domain]-[second UGI domain]-COOH, and each instance of "-" comprises an optional linker. In certain embodiments, the fusion protein comprises the structure: NH2-[any of the presently disclosed cytidine deaminases]-[Cas9 domain]-[nuclear localization sequence]-COOH, and each instance of "-" comprises an optional linker. In certain embodiments, the fusion protein comprises the structure: NH2-[first nuclear localization sequence]-[any of the presently disclosed cytidine deaminases]-[Cas9 domain]-[second nuclear localization sequence]-COOH, and each instance of "-" comprises an optional linker. In certain embodiments, the fusion protein comprises the structure: NH2-[first nuclear localization sequence]-[any of the presently disclosed cytidine deaminases]-[Cas9 domain]-[first UGI domain]-[second UGI domain]-[second nuclear localization sequence]-COOH, and each instance of "-" comprises an optional linker.

In one aspect, the specification discloses a nucleic acid that encodes any of the presently disclosed fusion proteins. In certain embodiments, the nucleic acid comprises any of the presently disclosed nucleic acids.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF THE DRAWINGS

FIG. 4 shows T7RNAP expression levels.
FIG. 14 shows a schematic of Pam specificity.
FIG. 15 shows a schematic of expression and activity.
FIG. 44 shows luciferase time-course assay of PACE 5 top 8 clones.
FIG. 45 shows a summary and future directions.
FIG. 62 shows a schematic of template stand editing.
FIG. 63 shows a schematic of template stand editing.
FIG. 64 shows sample coding mutations observed with template strand deamination. Sequences correspond from top to bottom to SEQ ID NOs: 95-98.

FIG. 73 shows the results of reducing T7 RNAP-degron expression, leading to higher turn-on.

FIG. 139 shows evo-deaminase allows base-editing in previously non-editable site; and editing with BE-CDA was increased after evolution (8% to 33%)

FIG. 140 shows schematics of ApoE protein domain structure, ApoE4 R112 sgRNA, and ApoE4→E3 (R112→C112) editing. In the center section, sequences correspond from top to bottom to SEQ ID NOs: 129-131.

DEFINITIONS

Figure 1:
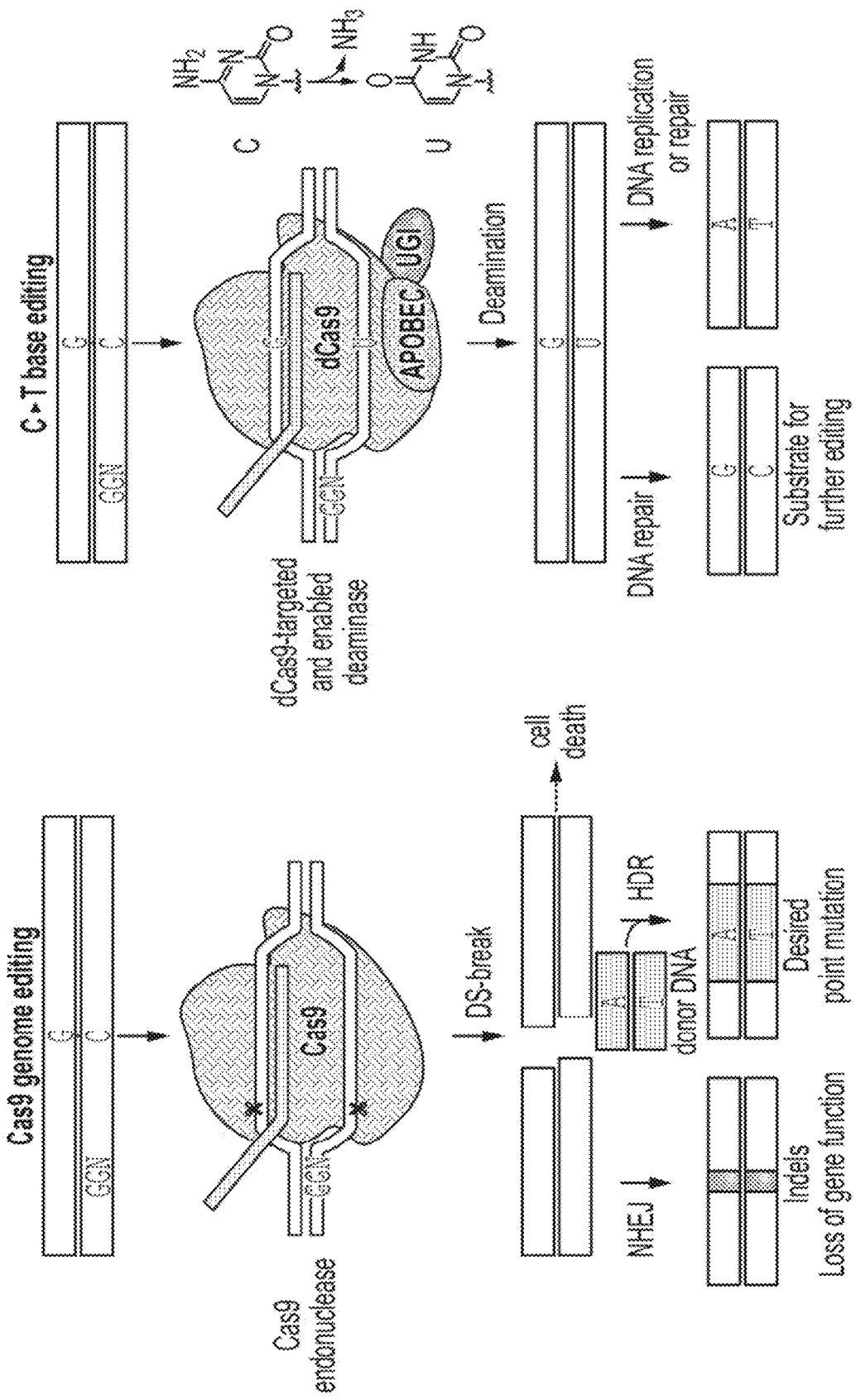
FIG. 1 shows schematics of Cas9 genome editing and C to T base editing.
Figure 2:
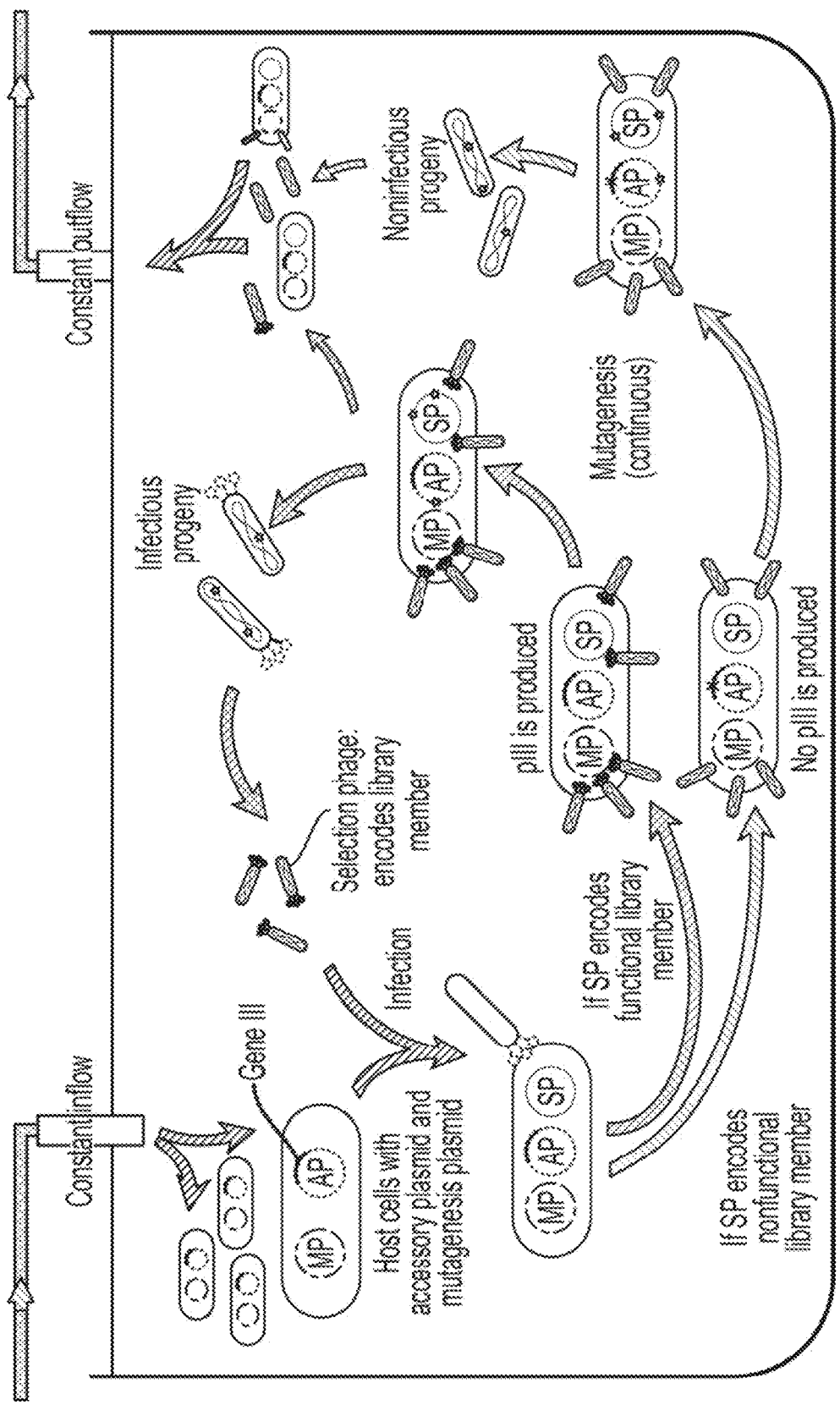
FIG. 2 shows a schematic of PACE.

As used herein and in the claims, the singular forms "a," "an," and "the" include the singular and the plural reference unless the context clearly indicates otherwise. Thus, for example, a reference to "an agent" includes a single agent and a plurality of such agents.

Accessory Plasmid

The term "accessory plasmid," as used herein, refers to a plasmid comprising a gene required for the generation of infectious viral particles under the control of a conditional promoter. In the context of continuous evolution of genes, transcription from the conditional promoter of the accessory plasmid is typically activated, directly or indirectly, by a function of the gene to be evolved. Accordingly, the accessory plasmid serves the function of conveying a competitive advantage to those viral vectors in a given population of viral vectors that carry a version of the gene to be evolved able to activate the conditional promoter or able to activate the conditional promoter more strongly than other versions of the gene to be evolved. In some embodiments, only viral vectors carrying an "activating" version of the gene to be evolved will be able to induce expression of the gene required to generate infectious viral particles in the host cell, and, thus, allow for packaging and propagation of the viral genome in the flow of host cells. Vectors carrying non-activating versions of the gene to be evolved, on the other hand, will not induce expression of the gene required to generate infectious viral vectors, and, thus, will not be packaged into viral particles that can infect fresh host cells.

Ancestral Sequence Reconstruction (ASR)

Ancestral sequence reconstruction (ASR) is the process of analyzing modern sequences within an evolutionary/phylogenetic context to infer the ancestral sequences at particular nodes of a tree using an ASR algorithm. ASR algorithms are known in the art.

Base Editing

Base editing is a genome editing technology that involves the conversion of a specific nucleic acid base into another at a targeted genomic locus. In certain aspects, this can be achieved without requiring double-stranded DNA breaks (DSB). Since many genetic diseases arise from point mutations, this technology has important implications in the study of human health and disease.

To date, other genome editing techniques, including CRISPR-based systems, begin with the introduction of a DSB at a locus of interest. Subsequently, cellular DNA repair enzymes mend the break, commonly resulting in random insertions or deletions (indels) of bases at the site of the DSB. However, when the introduction or correction of a point mutation at a target locus is desired rather than stochastic disruption of the entire gene, these genome editing techniques are unsuitable, as correction rates are low (e.g., typically 0.1% to 5%), with the major genome editing products being indels. In order to increase the efficiency of gene correction without simultaneously introducing random indels, the present inventors previously modified the CRISPR/Cas9 system to directly convert one DNA base into another without DSB formation.

Base Editors

The term "base editors (BEs)" or "nucleobase editors (NBEs)" or as used herein, refers to the improved Cas-fusion proteins described herein. In some embodiments, the fusion protein comprises a nuclease-inactive Cas9 (dCas9) fused to a deaminase which still binds DNA in a guide RNA-programmed manner via the formation of an R-loop, but does not cleave the DNA backbone. For example, the dCas9 of the fusion protein can comprise a D10A and a H840A mutation (which renders Cas9 capable of cleaving only one strand of a nucleic acid duplex) as described in PCT/US2016/058344 (published as WO 2017/070632), which is incorporated herein by reference in its entirety. In some embodiments, the fusion protein comprises a Cas9 nickase fused to a deaminase, e.g., a cytidine deaminase (rAPOBEC1) which converts a DNA base cytosine to uracil. One such base editor is referred to as "BE1" in the literature. In some embodiments, the fusion protein comprises a nuclease-inactive Cas9 fused to a deaminase and further fused to a UGI domain (uracil DNA glycosylase inhibitor, which prevents the subsequent U:G mismatch from being repaired back to a C:G base pair). One such base editor is referred to as "BE2" in the literature. In other embodiments, to improve base editing efficiency, the catalytic His residue at position 840 in the Cas9 HNH domain of BE2 can be restore (resulting in "BE3" as described in the literature), which nicks only the non-edited strand, simulating newly synthesized DNA and leading to the desired U:A product. In other embodiments, the dCas9 is any dCas9 disclosed or described in PCT/US2017/045381 (published as WO 2018/027078), which is incorporated herein by reference in its entirety. The terms "nucleobase editors (NBEs)" and "base editors (BEs)" may be used interchangeably. The term "base editors" encompasses any base editor known or described in the art at the time of this filing, but also the evolved base editors described herein. The base editors known in the state of the art which may be modified by the methods and strategies described herein to improve editing efficiency include, for example, BE1, BE2, BE3, or BE4.

Cas9 or Cas9 Moiety or Cas9 Domain

The term "Cas9" or "Cas9 nuclease" or "Cas9 moiety" or "Cas9 domain" refers to a CRISPR associated protein 9, or functional fragment thereof, and embraces any naturally occurring Cas9 from any organism, any naturally-occurring Cas9 equivalent or functional fragment thereof, any Cas9 homolog, ortholog, or paralog from any organism, and any mutant or variant of a Cas9, naturally-occurring or engineered. More broadly, a Cas9 is a type of "RNA-programmable nuclease" or "RNA-guided nuclease" or more broadly a type of "nucleic acid programmable DNA binding protein (napDNAbp)". The term Cas9 is not meant to be particularly limiting and may be referred to as a "Cas9 or equivalent." Exemplary Cas9 proteins are further described herein and/or are described in the art and are incorporated herein by reference. The present disclosure is unlimited with regard to the particular Cas9 that is employed in the evolved base editors of the invention.

dCas9

As used herein, the term "dCas9" refers to a nuclease-inactive Cas9 or nuclease-dead Cas9, or a functional fragment thereof, and embraces any naturally occurring dCas9 from any organism, any naturally-occurring dCas9 equivalent or functional fragment thereof, any dCas9 homolog, ortholog, or paralog from any organism, and any mutant or variant of a dCas9, naturally-occurring or engineered. The term dCas9 is not meant to be particularly limiting and may be referred to as a "dCas9 or equivalent." Exemplary dCas9 proteins and method for making dCas9 proteins are further described herein and/or are described in the art and are incorporated herein by reference.

Chimeric Protein

The term "chimeric protein" refers to a fusion protein in which the first protein portion and the second protein portion are derived from different species.

Continuous Evolution

The term "continuous evolution," as used herein, refers to an evolution procedure, in which a population of nucleic acids is subjected to multiple rounds of (a) replication, (b) mutation, and (c) selection to produce a desired evolved product, for example, a nucleic acid encoding a protein with a desired activity, wherein the multiple rounds can be performed without investigator interaction and wherein the processes under (a)-(c) can be carried out simultaneously. Typically, the evolution procedure is carried out in vitro, for example, using cells in culture as host cells. In general, a continuous evolution process provided herein relies on a system in which a gene of interest is provided in a nucleic acid vector that undergoes a life-cycle including replication in a host cell and transfer to another host cell, wherein a critical component of the life-cycle is deactivated and reactivation of the component is dependent upon a desired mutation in the gene of interest.

In some embodiments, a gene of interest is transferred from cell to cell in a manner dependent on the activity of the gene of interest. In some embodiments, the transfer vector is a virus infecting cells, for example, a bacteriophage, or a retroviral vector. In some embodiments, the viral vector is a phage vector infecting bacterial host cells. In some embodiments, the transfer vector is a retroviral vector, for example, a lentiviral vector or a vesicular stomatitis virus vector, infecting human or mouse cells. In some embodiments, the transfer vector is a conjugative plasmid transferred from a donor bacterial cell to a recipient bacterial cell.

In some embodiments, the nucleic acid vector comprising the gene of interest is a phage, a viral vector, or naked DNA (e.g., a mobilization plasmid). In some embodiments, transfer of the gene of interest from cell to cell is via infection, transfect ion, transduction, conjugation, or uptake of naked DNA, and efficiency of cell-to-cell transfer (e.g., transfer rate) is dependent on an activity of a product encoded by the gene of interest. For example, in some embodiments, the nucleic acid vector is a phage harboring the gene of interest and the efficiency of phage transfer (via infection) is dependent on an activity of the gene of interest in that a protein required for the generation of phage particles (e.g., pIII for M13 phage) is expressed in the host cells only in the presence of the desired activity of the gene of interest. In another example, the nucleic acid vector is a retroviral vector, for example, a lentiviral or vesicular stomatitis virus vector harboring the gene of interest, and the efficiency of viral transfer from cell to cell is dependent on an activity of the gene of interest in that a protein required for the generation of viral particles (e.g., an envelope protein, such as VSV-g) is expressed in the host cells only in the presence of the desired activity of the gene of interest. In another example, the nucleic acid vector is a DNA vector, for example, in the form of a mobilizable plasmid DNA, comprising the gene of interest, that is transferred between bacterial host cells via conjugation and the efficiency of conjugation-mediated transfer from cell to cell is dependent on an activity of the gene of interest in that a protein required for conjugation-mediated transfer (e.g., traA or traQ) is expressed in the host cells only in the presence of the desired activity of the gene of interest. Host cells contain F plasmid lacking one or both of those genes.

For example, some embodiments provide a continuous evolution system, in which a population of viral vectors comprising a gene of interest to be evolved replicates in a flow of host cells, e.g., a flow through a lagoon, wherein the viral vectors are deficient in a gene encoding a protein that is essential for the generation of infectious viral particles, and wherein that gene is comprised in the host cell under the control of a conditional promoter that can be activated by a gene product encoded by the gene of interest, or a mutated version thereof. In some embodiments, the activity of the conditional promoter depends on a desired function of a gene product encoded by the gene of interest. Viral vectors, in which the gene of interest has not acquired a mutation conferring the desired function, will not activate the conditional promoter, or only achieve minimal activation, while any mutation in the gene of interest that confers the desired mutation will result in activation of the conditional promoter. Since the conditional promoter controls an essential protein for the viral life cycle, activation of this promoter directly corresponds to an advantage in viral spread and replication for those vectors that have acquired an advantageous mutation.

Cytidine Deaminase

As used herein, a "cytidine deaminase" encoded by the CDA gene is an enzyme that catalyzes the removal of an amine group from cytidine (i.e., the base cytosine when attached to a ribose ring) to uridine (C to U) and deoxycytidine to deoxyuridine (C to U). A non-limiting example of a cytidine deaminase is APOBEC1 ("apolipoprotein B mRNA editing enzyme, catalytic polypeptide 1"). Another example is AID ("activation-induced cytidine deaminase"). Under standard Watson-Crick hydrogen bond pairing, a cytosine base hydrogen bonds to a guanine base. When cytidine is converted to uridine (or deoxycytidine is converted to deoxyuridine), the uridine (or the uracil base of uridine) undergoes hydrogen bond pairing with the base adenine. Thus, a conversion of "C" to uridine ("U") by cytidine deaminase will cause the insertion of "A" instead of a "G" during cellular repair and/or replication processes. Since the adenine "A" pairs with thymine "T", the cytidine deaminase in coordination with DNA replication causes the conversion of an C•G pairing to a T•A pairing in the double-stranded DNA molecule.

CRISPR

CRISPR is a family of DNA sequences (i.e., CRISPR clusters) in bacteria and archaea that represent snippets of prior infections by a virus that have invaded the prokaryote. The snippets of DNA are used by the prokaryotic cell to detect and destroy DNA from subsequent attacks by similar viruses and effectively compose, along with an array of CRISPR-associated proteins (including Cas9 and homologs thereof) and CRISPR-associated RNA, a prokaryotic immune defense system. In nature, CRISPR clusters are transcribed and processed into CRISPR RNA (crRNA). In certain types of CRISPR systems (e.g., type II CRISPR systems), correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the RNA. Specifically, the target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species—the guide RNA. See, e.g., Jinek M., Chylinski K., Fonfara I., Hauer M., Doudna J. A., Charpentier E. Science 337:816-821(2012), the entire contents of which is hereby incorporated by reference. Cas9 recognizes a short motif in the CRISPR repeat sequences (the PAM or protospacer adjacent motif) to help distinguish self versus non-self. CRISPR biology, as well as Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference.

Deaminase or Deaminase Domain

As used herein, the term "deaminase" or "deaminase domain" or "deaminase moiety" refers to a protein or enzyme that catalyzes a deamination reaction. In some embodiments, the deaminase is an adenosine deaminase, which catalyzes the hydrolytic deamination of adenine or adenosine (e.g., an engineered adenosine deaminase that deaminates adenosine in DNA). In some embodiments, the deaminase or deaminase domain is a cytidine deaminase, catalyzing the hydrolytic deamination of cytidine or deoxycytidine to uridine or deoxyuridine, respectively. In some embodiments, the deaminase or deaminase domain is a cytidine deaminase domain, catalyzing the hydrolytic deamination of cytosine to uracil. In some embodiments, the deaminase or deaminase domain is a naturally-occurring deaminase from an organism, such as a human, chimpanzee, gorilla, monkey, cow, dog, rat, or mouse. In some embodiments, the deaminase or deaminase domain is a variant of a naturally-occurring deaminase from an organism that does not occur in nature. For example, in some embodiments, the deaminase or deaminase domain is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to a naturally-occurring deaminase from an organism. The term deaminase also embraces any genetically engineered deaminase that may comprise genetic modifications (e.g., one or more mutations) that results in a variant deaminase having an amino acid sequence comprising one or more changes relative to a wildtype counterpart deaminase. Examples of deaminases are given herein, and the term is not meant to be limiting.

Effective Amount

The term "effective amount," as used herein, refers to an amount of a biologically active agent that is sufficient to elicit a desired biological response. For example, in some embodiments, an effective amount of a base editor may refer to the amount of the base editor that is sufficient to edit a target site nucleotide sequence, e.g., a genome. In some embodiments, an effective amount of a base editor provided herein, e.g., of a fusion protein comprising a nuclease-inactive Cas9 domain and a nucleic acid editing domain (e.g., a deaminase domain) may refer to the amount of the fusion protein that is sufficient to induce editing of a target site specifically bound and edited by the fusion protein. As will be appreciated by the skilled artisan, the effective amount of an agent, e.g., a fusion protein, a nuclease, a deaminase, a hybrid protein, a protein dimer, a complex of a protein (or protein dimer) and a polynucleotide, or a polynucleotide, may vary depending on various factors as, for example, on the desired biological response, e.g., on the specific allele, genome, or target site to be edited, on the cell or tissue being targeted, and on the agent being used.

Evolved Base Editor

The term "evolved base editor" or "evolved base editor variant" refers to a base editor formed as a result of mutagenizing a reference or starting-point base editor (or a component or domain thereof) by a continuous evolution method (e.g., PACE), wherein the evolved base editor has one or more amino acid variations introduced into its amino acid sequence relative to the amino acid sequence of the reference or starting-point base editor. Amino acid sequence variations may include one or more mutated residues within the amino acid sequence of the reference base editor, e.g., as a result of a change in the nucleotide sequence encoding the base editor that results in a change in the codon at any particular position in the coding sequence, the deletion of one or more amino acids (e.g., a truncated protein), the insertion of one or more amino acids, or any combination of the foregoing. In some embodiments, an evolved base editor is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to the reference base editor. The evolved base editor may include variants in one or more components or domains of the base editor (e.g., variants introduced into a Cas9 domain, a deaminase domain, or a UGI domain, or variants introduced into combinations of these domains).

Flow

The term "flow", as used herein in the context of host cells, refers to a stream of host cells, wherein fresh host cells are being introduced into a host cell population, for example, a host cell population in a lagoon, remain within the population for a limited time, and are then removed from the host cell population. In a simple form, a host cell flow may be a flow through a tube, or a channel, for example, at a controlled rate. In other embodiments, a flow of host cells is directed through a lagoon that holds a volume of cell culture media and comprises an inflow and an outflow. The introduction of fresh host cells may be continuous or intermittent and removal may be passive, e.g., by overflow, or active, e.g., by active siphoning or pumping. Removal further may be random, for example, if a stirred suspension culture of host cells is provided, removed liquid culture media will contain freshly introduced host cells as well as cells that have been a member of the host cell population within the lagoon for some time. Even though, in theory, a cell could escape removal from the lagoon indefinitely, the average host cell will remain only for a limited period of time within the lagoon, which is determined mainly by the flow rate of the culture media (and suspended cells) through the lagoon.

Since the viral vectors replicate in a flow of host cells, in which fresh, uninfected host cells are provided while infected cells are removed, multiple consecutive viral life cycles can occur without investigator interaction, which allows for the accumulation of multiple advantageous mutations in a single evolution experiment.

Gene of Interest

The term "gene of interest," as used herein, refers to a nucleic acid construct comprising a nucleotide sequence encoding a gene product of interest, for example, a gene product (e.g., a base editor or component/domain thereof) to be evolved in a continuous evolution process as provided herein. The term includes any variations of a gene of interest that are the result of a continuous evolution process according to methods provided herein. For example, in some embodiments, a gene of interest is a nucleic acid construct comprising a nucleotide sequence encoding a protein to be evolved, cloned into a viral vector, for example, a phage genome, so that the expression of the encoding sequence is under the control of one or more promoters in the viral genome. In other embodiments, a gene of interest is a nucleic acid construct comprising a nucleotide sequence encoding a protein to be evolved and a promoter operably linked to the encoding sequence. When cloned into a viral vector, for example, a phage genome, the expression of the encoding sequence of such genes of interest is under the control of the heterologous promoter and, in some embodiments, may also be influenced by one or more promoters comprised in the viral genome.

Function of a Gene of Interest

The term "function of a gene of interest," as interchangeably used with the term "activity of a gene of interest," refers to a function or activity of a gene product, for example, a nucleic acid, or a protein, encoded by the gene of interest. For example, a function of a gene of interest may be an enzymatic activity (e.g., an enzymatic activity resulting in the generation of a reaction product, phosphorylation activity, phosphatase activity, etc.), an ability to activate transcription (e.g., transcriptional activation activity targeted to a specific promoter sequence), a bond-forming activity, (e.g., an enzymatic activity resulting in the formation of a covalent bond), or a binding activity (e.g., a protein, DNA, or RNA binding activity).

Fusion Protein

The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site) and a nucleic acid cleavage domain or a catalytic domain of a nucleic-acid editing protein. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* ($4^{th}$ ed., Cold Spring Harbor Laboratory Press, Cold Spring Harbor, N.Y. (2012)), the entire contents of which are incorporated herein by reference.

Helper Phage

The term "helper phage," as used herein interchangeable with the terms "helper phagemid" and "helper plasmid," refers to a nucleic acid construct comprising a phage gene required for the phage life cycle, or a plurality of such genes, but lacking a structural element required for genome packaging into a phage particle. For example, a helper phage may provide a wild-type phage genome lacking a phage origin of replication. In some embodiments, a helper phage is provided that comprises a gene required for the generation of phage particles, but lacks a gene required for the generation of infectious particles, for example, a full-length pIII gene. In some embodiments, the helper phage provides only some, but not all, genes required for the generation of phage particles. Helper phages are useful to allow modified phages that lack a gene required for the generation of phage particles to complete the phage life cycle in a host cell. Typically, a helper phage will comprise the genes required for the generation of phage particles that are lacking in the phage genome, thus complementing the phage genome. In the continuous evolution context, the helper phage typically complements the selection phage, but both lack a phage gene required for the production of infectious phage particles.

Host Cell

The term "host cell," as used herein, refers to a cell that can host, replicate, and transfer a phage vector useful for a continuous evolution process as provided herein. In embodiments where the vector is a viral vector, a suitable host cell is a cell that can be infected by the viral vector, can replicate it, and can package it into viral particles that can infect fresh host cells. A cell can host a viral vector if it supports expression of genes of viral vector, replication of the viral genome, and/or the generation of viral particles. One criterion to determine whether a cell is a suitable host cell for a given viral vector is to determine whether the cell can support the viral life cycle of a wild-type viral genome that the viral vector is derived from. For example, if the viral vector is a modified M13 phage genome, as provided in some embodiments described herein, then a suitable host cell would be any cell that can support the wild-type M13 phage life cycle. Suitable host cells for viral vectors useful in continuous evolution processes are well known to those of skill in the art, and the disclosure is not limited in this respect. In some embodiments, the viral vector is a phage and the host cell is a bacterial cell. In some embodiments, the host cell is an E. coli cell. Suitable E. coli host strains will be apparent to those of skill in the art, and include, but are not limited to, New England Biolabs (NEB) Turbo, Top10F', DH12S, ER2738, ER2267, and XL1-Blue MRF'. These strain names are art recognized and the genotype of these strains has been well characterized. It should be understood that the above strains are exemplary only and that the invention is not limited in this respect. The term "fresh," as used herein interchangeably with the terms "non-infected" or "uninfected" in the context of host cells, refers to a host cell that has not been infected by a viral vector comprising a gene of interest as used in a continuous evolution process provided herein. A fresh host cell can, however, have been infected by a viral vector unrelated to the vector to be evolved or by a vector of the same or a similar type but not carrying the gene of interest.

In some embodiments, the host cell is a prokaryotic cell, for example, a bacterial cell. In some embodiments, the host cell is an E. coli cell. In some embodiments, the host cell is a eukaryotic cell, for example, a yeast cell, an insect cell, or a mammalian cell. The type of host cell, will, of course, depend on the viral vector employed, and suitable host cell/viral vector combinations will be readily apparent to those of skill in the art.

In some PACE embodiments, for example, in embodiments employing an M13 selection phage, the host cells are E. coli cells expressing the Fertility factor, also commonly referred to as the F factor, sex factor, or F-plasmid. The F-factor is a bacterial DNA sequence that allows a bacterium to produce a sex pilus necessary for conjugation and is essential for the infection of E. coli cells with certain phage, for example, with M13 phage. For example, in some embodiments, the host cells for M13-PACE are of the genotype F'proA+B+Δ(lacIZY) zzf::Tn10(TetR)/endA1 recA1 galE15 galK16 nupG rpsL ΔlacIZYA araD139 Δ(ara, leu)7697 mcrA Δ(mrr-hsdRMS-mcrBC) proBA::pir116λ⁻.

Infectious Viral Particle

The term "infectious viral particle," as used herein, refers to a viral particle able to transport the viral genome it comprises into a suitable host cell. Not all viral particles are able to transfer the viral genome to a suitable host cell. Particles unable to accomplish this are referred to as a non-infectious viral particles. In some embodiments, a viral particle comprises a plurality of different coat proteins, wherein one or some of the coat proteins can be omitted without compromising the structure of the viral particle. In some embodiments, a viral particle is provided in which at least one coat protein cannot be omitted without the loss of infectivity. If a viral particle lacks a protein that confers infectivity, the viral particle is not infectious. For example, an M13 phage particle that comprises a phage genome packaged in a coat of phage proteins (e.g., pVIII) but lacks pIII (protein III) is a non-infectious M13 phage particle because pIII is essential for the infectious properties of M13 phage particles.

Inhibitor of Base Repair

The term "inhibitor of base repair" or "IBR" refers to a protein that is capable of inhibiting the activity of a nucleic acid repair enzyme, for example a base excision repair enzyme. In some embodiments, the IBR is an inhibitor of inosine base excision repair. Exemplary inhibitors of base repair include inhibitors of APE1, Endo III, Endo IV, Endo V, Endo VIII, Fpg, hOGG1, hNEIL1, T7 EndoI, T4PDG, UDG, hSMUG1, and hAAG. In some embodiments, the IBR is an inhibitor of Endo V or hAAG. In some embodiments, the IBR is a catalytically inactive EndoV or a catalytically inactive hAAG.

Inteins

As used herein, the term "intein" refers to auto-processing polypeptide domains found in organisms from all domains of life. An intein (intervening protein) carries out a unique auto-processing event known as protein splicing in which it excises itself out from a larger precursor polypeptide through the cleavage of two peptide bonds and, in the process, ligates the flanking extein (external protein) sequences through the formation of a new peptide bond. This rearrangement occurs post-translationally (or possibly co-translationally), as intein genes are found embedded in frame within other protein-coding genes. Furthermore, intein-mediated protein splicing is spontaneous; it requires no external factor or energy source, only the folding of the intein domain. This process is also known as cis-protein splicing, as opposed to the natural process of trans-protein splicing with "split inteins." Inteins are the protein equivalent of the self-splicing RNA introns (see Perler et al., Nucleic Acids Res. 22:1125-1127 (1994)), which catalyze their own excision from a precursor protein with the concomitant fusion of the flanking protein sequences, known as exteins (reviewed in Perler et al., Curr. Opin. Chem. Biol. 1:292-299 (1997); Perler, F. B. Cell 92(1):1-4 (1998); Xu et al., EMBO J. 15(19):5146-5153 (1996)).

Lagoon, Cellstat, and Turbidostat

The term "lagoon," as used herein, refers to a vessel through which a flow of host cells is directed. When used for a continuous evolution process as provided herein, a lagoon typically holds a population of host cells and a population of viral vectors replicating within the host cell population, wherein the lagoon comprises an outflow through which host cells are removed from the lagoon and an inflow through which fresh host cells are introduced into the lagoon, thus replenishing the host cell population. In some embodiments, the flow of cells through the lagoon is regulated to result in an essentially constant number of host cells within the lagoon. In some embodiments, the flow of cells through the lagoon is regulated to result in an essentially constant number of fresh host cells within the lagoon.

The term "cellstat," as used herein, refers to a culture vessel comprising host cells, in which the number of cells is substantially constant over time.

The term "turbidostat," as used herein, refers to a culture vessel comprising host cells in suspension culture, in which the turbidity of the culture medium is substantially essentially constant over time. In some embodiments, the turbidity of a suspension culture, for example, of bacterial cells, is a measure for the cell density in the culture medium. In some embodiments, a turbidostat comprises an inflow of fresh media and an outflow, and a controller that regulates the flow into and/or out of the turbidostat based on the turbidity of the suspension culture in the turbidostat.

Linker

The term "linker," as used herein, refers to a chemical group or a molecule linking two molecules or moieties, e.g., a binding domain and a cleavage domain of a nuclease. In some embodiments, a linker joins a gRNA binding domain of an RNA-programmable nuclease and the catalytic domain of a recombinase. In some embodiments, a linker joins a dCas9 and base editor moiety (e.g., a cytidine or adenosine deaminase). Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

Mutagen

The term "mutagen," as used herein, refers to an agent that induces mutations or increases the rate of mutation in a given biological system, for example, a host cell, to a level above the naturally-occurring level of mutation in that system. In continuous evolution processes, the mutagen can be a DNA polymerase that lacks a proofreading capability.

Mutagenesis Plasmid

The term "mutagenesis plasmid," as used herein, refers to a plasmid comprising a gene encoding a gene product that acts as a mutagen. In some embodiments, the gene encodes a DNA polymerase lacking a proofreading capability. In some embodiments, the gene is a gene involved in the bacterial SOS stress response, for example, a UmuC, UmuD', or RecA gene. In some embodiments, the gene is a GATC methylase gene, for example, a deoxyadenosine methylase (dam methylase) gene. In some embodiments, the gene is involved in binding of hemimethylated GATC sequences, for example, a seqA gene. In some embodiments, the gene is involved with repression of mutagenic nucleobase export, for example emrR. Mutagenesis plasmids (also referred to as mutagenesis constructs) are described, for example by International Patent Application, PCT/US2016/027795, filed Apr. 16, 2016, published as WO2016/168631 on Oct. 20, 2016, the entire contents of which are incorporated herein by reference.

Mutation

The term "mutation," as used herein, refers to a substitution of a residue within a sequence, e.g., a nucleic acid or amino acid sequence, with another residue, or a deletion or insertion of one or more residues within a sequence. Mutations are typically described herein by identifying the original residue followed by the position of the residue within the sequence and by the identity of the newly substituted residue. Various methods for making the amino acid substitutions (mutations) provided herein are well known in the art, and are provided by, for example, Green and Sambrook, *Molecular Cloning: A Laboratory Manual* (4th ed., Cold Spring Harbor Laboratory Press, Cold Spring Harbor, N.Y. (2012)). Mutations can include a variety of categories, such as single base polymorphisms, microduplication regions, indel, and inversions, and is not meant to be limiting in any way. Mutations can include "loss-of-function" mutations which is the normal result of a mutation that reduces or abolishes a protein activity. Most loss-of-function mutations are recessive, because in a heterozygote the second chromosome copy carries an unmutated version of the gene coding for a fully functional protein whose presence compensates for the effect of the mutation. There are some exceptions where a loss-of-function mutation is dominant, one example being haploinsufficiency, where the organism is unable to tolerate the approximately 50% reduction in protein activity suffered by the heterozygote. This is the explanation for a few genetic diseases in humans, including Marfan syndrome which results from a mutation in the gene for the connective tissue protein called fibrillin. Mutations also embrace "gain-of-function" mutations, which is one which confers an abnormal activity on a protein or cell that is otherwise not present in a normal condition. Many gain-of-function mutations are in regulatory sequences rather than in coding regions, and can therefore have a number of consequences. For example, a mutation might lead to one or more genes being expressed in the wrong tissues, these tissues gaining functions that they normally lack. Alternatively the mutation could lead to overexpression of one or more genes involved in control of the cell cycle, thus leading to uncontrolled cell division and hence to cancer. Because of their nature, gain-of-function mutations are usually dominant.

Non-Naturally Occurring or Engineered

The terms "non-naturally occurring" or "engineered" are used interchangeably and indicate the involvement of the hand of man. The terms, when referring to nucleic acid molecules or polypeptides (e.g., Cas9 or deaminases) mean that the nucleic acid molecule or the polypeptide is at least substantially free from at least one other component with which they are naturally associated in nature and/or as found in nature (e.g., an amino acid sequence not found in nature).

Nucleic Acid/Nucleic Acid Molecule

The term "nucleic acid," as used herein, refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, O(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

Nucleic Acid Programmable R/DNA Binding Protein (napR/DNAbp)

The term "nucleic acid programmable D/RNA binding protein (napR/DNAbp)" refers to any protein that may associate (e.g., form a complex) with one or more nucleic acid molecules (i.e., which may broadly be referred to as a "napR/DNAbp-programming nucleic acid molecule" and includes, for example, guide RNA in the case of Cas systems) which direct or otherwise program the protein to localize to a specific target nucleotide sequence (e.g., a gene locus of a genome) that is complementary to the one or more nucleic acid molecules (or a portion or region thereof) associated with the protein, thereby causing the protein to bind to the nucleotide sequence at the specific target site. This term napR/DNAbp embraces CRISPR Cas 9 proteins, as well as Cas9 equivalents, homologs, orthologs, or paralogs, whether naturally occurring or non-naturally occurring (e.g., engineered or recombinant), and may include a Cas9 equivalent from any type of CRISPR system (e.g., type II, V, VI), including Cpf1 (a type-V CRISPR-Cas systems), C2c1 (a type V CRISPR-Cas system), C2c2 (a type VI CRISPR-Cas system) and C2c3 (a type V CRISPR-Cas system). Further Cas-equivalents are described in Makarova et al., "C2c2 is a single-component programmable RNA-guided RNA-targeting CRISPR effector," Science 2016; 353(6299), the contents of which are incorporated herein by reference. However, the nucleic acid programmable DNA binding protein (napDNAbp) that may be used in connection with this invention are not limited to CRISPR-Cas systems. The invention embraces any such programmable protein, such as the Argonaute protein from *Natronobacterium gregoryi* (NgAgo) which may also be used for DNA-guided genome editing. NgAgo-guide DNA system does not require a PAM sequence or guide RNA molecules, which means genome editing can be performed simply by the expression of generic NgAgo protein and introduction of synthetic oligonucleotides on any genomic sequence. See Gao F, Shen X Z, Jiang F, Wu Y, Han C. DNA-guided genome editing using the *Natronobacterium gregoryi* Argonaute. Nat Biotechnol 2016; 34(7):768-73, which is incorporated herein by reference.

napR/DNAbp-Programming Nucleic Acid Molecule or Guide Sequence

The term "napR/DNAbp-programming nucleic acid molecule" or equivalently "guide sequence" refers the one or more nucleic acid molecules which associate with and direct or otherwise program a napR/DNAbp protein to localize to a specific target nucleotide sequence (e.g., a gene locus of a genome) that is complementary to the one or more nucleic acid molecules (or a portion or region thereof) associated with the protein, thereby causing the napR/DNAbp protein to bind to the nucleotide sequence at the specific target site. A non-limiting example is a guide RNA of a Cas protein of a CRISPR-Cas genome editing system.

Nuclear Localization Signal (NLS)

A nuclear localization signal or sequence (NLS) is an amino acid sequence that tags, designates, or otherwise marks a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal (NES), which targets proteins out of the nucleus. Thus, a single nuclear localization signal can direct the entity with which it is associated to the nucleus of a cell. Such sequences can be of any size and composition, for example more than 25, 25, 15, 12, 10, 8, 7, 6, 5 or 4 amino acids, but will preferably comprise at least a four to eight amino acid sequence known to function as a nuclear localization signal (NLS).

Nucleobase Modification Moiety or Nucleic Acid Effector Domain

The term, as used herein, "nucleobase modification moiety" or equivalently a "nucleic acid effector domain" embraces any protein, enzyme, or polypeptide (or functional fragment thereof) which is capable of modifying a DNA or RNA molecule. Nucleobase modification moieties can be naturally occurring, or can be recombinant. For example, a nucleobase modification moiety can include one or more DNA repair enzymes, for example, and an enzyme or protein involved in base excision repair (BER), nucleotide excision repair (NER), homology-dependent recombinational repair (HR), non-homologous end-joining repair (NHEJ), microhomology end-joining repair (MMEJ), mismatch repair (MMR), direct reversal repair, or other known DNA repair pathway. A nucleobase modification moiety can have one or more types of enzymatic activities, including, but not limited to endonuclease activity, polymerase activity, ligase activity, replication activity, proofreading activity. Nucleobase modification moieties can also include DNA or RNA-modifying enzymes and/or mutagenic enzymes, such as, DNA methylases and deaminating enzymes (i.e., deaminases, including cytidine deaminases and adenosine deaminases, all defined above), which deaminate nucleobases leading in some cases to mutagenic corrections by way of normal cellular DNA repair and replication processes. The "nucleic acid effector domain" (e.g., a DNA effector domain or an RNA effector domain) as used herein may also refer to a protein or enzyme capable of making one or more modifications (e.g., deamination of a cytidine residue) to a nucleic acid (e.g., DNA or RNA). Exemplary nucleic acid editing domains include, but are not limited to a deaminase, a nuclease, a nickase, a recombinase, a methyltransferase, a methylase, an acetylase, an acetyltransferase, a transcriptional activator, or a transcriptional repressor domain. In some embodiments the nucleic acid editing domain is a deaminase (e.g., a cytidine deaminase, such as an APOBEC or an AID deaminase).

Oligonucleotide/Polynucleotide

As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyluridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

PACE (Phage-Assisted Continuous Evolution)

The term "phage-assisted continuous evolution (PACE)," as used herein, refers to continuous evolution that employs phage as viral vectors. The general concept of PACE technology has been described, for example, in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; U.S. Application, U.S. Pat. No. 9,023,594, issued May 5, 2015, International PCT Application, PCT/US2015/012022, filed Jan. 20, 2015, published as WO 2015/134121 on Sep. 11, 2015, and International PCT Application, PCT/US2016/027795, filed Apr. 15, 2016, published as WO 2016/168631 on Oct. 20, 2016, the entire contents of each of which are incorporated herein by reference.

Promoter

The term "promoter" is art-recognized and refers to a nucleic acid molecule with a sequence recognized by the cellular transcription machinery and able to initiate transcription of a downstream gene. A promoter can be constitutively active, meaning that the promoter is always active in a given cellular context, or conditionally active, meaning that the promoter is only active in the presence of a specific condition. For example, a conditional promoter may only be active in the presence of a specific protein that connects a protein associated with a regulatory element in the promoter to the basic transcriptional machinery, or only in the absence of an inhibitory molecule. A subclass of conditionally active promoters are inducible promoters that require the presence of a small molecule "inducer" for activity. Examples of inducible promoters include, but are not limited to, arabinose-inducible promoters, Tet-on promoters, and tamoxifen-inducible promoters. A variety of constitutive, conditional, and inducible promoters are well known to the skilled artisan, and the skilled artisan will be able to ascertain a variety of such promoters useful in carrying out the instant invention, which is not limited in this respect.

Phage

The term "phage," as used herein interchangeably with the term "bacteriophage," refers to a virus that infects bacterial cells. Typically, phages consist of an outer protein capsid enclosing genetic material. The genetic material can be ssRNA, dsRNA, ssDNA, or dsDNA, in either linear or circular form. Phages and phage vectors are well known to those of skill in the art and non-limiting examples of phages that are useful for carrying out the methods provided herein are λ (Lysogen), T2, T4, T7, T12, R17, M13, MS2, G4, P1, P2, P4, Phi X174, N4, Φ6, and Φ29. In certain embodiments, the phage utilized in the present invention is M13. Additional suitable phages and host cells will be apparent to those of skill in the art and the invention is not limited in this aspect. For an exemplary description of additional suitable phages and host cells, see Elizabeth Kutter and Alexander Sulakvelidze: *Bacteriophages: Biology and Applications*. CRC Press; 1$^{st}$ edition (December 2004), ISBN: 0849313368; Martha R. J. Clokie and Andrew M. Kropinski: *Bacteriophages: Methods and Protocols, Volume 1: Isolation, Characterization, and Interactions* (*Methods in Molecular Biology*) Humana Press; 1$^{st}$ edition (December, 2008), ISBN: 1588296822; Martha R. J. Clokie and Andrew M. Kropinski: *Bacteriophages: Methods and Protocols, Volume 2: Molecular and Applied Aspects* (*Methods in Molecular Biology*) Humana Press; 1$^{st}$ edition (December 2008), ISBN: 1603275649; all of which are incorporated herein in their entirety by reference for disclosure of suitable phages and host cells as well as methods and protocols for isolation, culture, and manipulation of such phages).

In some embodiments, the phage is a filamentous phage. In some embodiments, the phage is an M13 phage. M13 phages are well known to those in the art and the biology of M13 phages has extensively been studied. A schematic representation of the wild-type M13 genome is provided in FIG. 16. Wild type M13 phage particles comprise a circular, single-stranded genome of approximately 6.4 kb. The wilttype genome includes ten genes, gI-gX, which, in turn, encode the ten M13 proteins, pI-pX, respectively. gVIII encodes pVIII, also often referred to as the major structural protein of the phage particles, while gIII encodes pIII, also referred to as the minor coat protein, which is required for infectivity of M13 phage particles.

The M13 life cycle includes attachment of the phage to the sex pilus of a suitable bacterial host cell via the pIII protein and insertion of the phage genome into the host cell. The circular, single-stranded phage genome is then converted to a circular, double-stranded DNA, also termed the replicative form (RF), from which phage gene transcription is initiated. The wild type M13 genome comprises nine promoters and two transcriptional terminators as well as an origin of replication. This series of promoters provides a gradient of transcription such that the genes nearest the two transcriptional terminators (gVIII and IV) are transcribed at the highest levels. In wild-type M13 phage, transcription of all 10 genes proceeds in same direction. One of the phage-encode proteins, pII, initiates the generation of linear, single-stranded phage genomes in the host cells, which are subsequently circularized, and bound and stabilized by pV. The circularized, single-stranded M13 genomes are then bound by pVIII, while pV is stripped off the genome, which initiates the packaging process. At the end of the packaging process, multiple copies of pIII are attached to wild-type M13 particles, thus generating infectious phage ready to infect another host cell and concluding the life cycle.

The M13 phage genome can be manipulated, for example, by deleting one or more of the wild type genes, and/or inserting a heterologous nucleic acid construct into the genome. M13 does not have stringent genome size restrictions, and insertions of up to 42 kb have been reported. This allows M13 phage vectors to be used in continuous evolution experiments to evolve genes of interest without imposing a limitation on the length of the gene to be involved.

The M13 phage has been well characterized and the genomic sequence of M13 has been reported. Representative M13 genomic sequences can be retrieved from public databases and an exemplary sequence is provided in entry V00604 of the National Center for Biotechnology Information (NCBI) database (www.ncbi.nlm.nih.gov):

Phage M13 genome:
>gi|56713234|emb|V00604.2| Phage M13 genome (SEQ ID NO: 21)

```
AACGCTACTACTATTAGTAGAATTGATGCCACCTTTTCAGCTCGCGCCC
CAAATGAAAATATAGCTAAACAGGTTATTGACCATTTGCGAAATGTATCTAATGGTC
AAACTAAATCTACTCGTTCGCAGAATTGGGAATCAACTGTTACATGGAATGAAACTT
CCAGACACCGTACTTTAGTTGCATATTTAAAACATGTTGAGCTACAGCACCAGATTC
AGCAATTAAGCTCTAAGCCATCCGCAAAAATGACCTCTTATCAAAAGGAGCAATTA
AAGGTACTCTCTAATCCTGACCTGTTGGAGTTTGCTTCCGGTCTGGTTCGCTTTGAAG
CTCGAATTAAAACGCGATATTTGAAGTCTTTCGGGCTTCCTCTTAATCTTTTTGATGC
AATCCGCTTTGCTTCTGACTATAATAGTCAGGGTAAAGACCTGATTTTTGATTTATGG
TCATTCTCGTTTTCTGAACTGTTTAAAGCATTTGAGGGGGATTCAATGAATATTTATG
ACGATTCCGCAGTATTGGACGCTATCCAGTCTAAACATTTTACTATTACCCCCTCTGG
CAAAACTTCTTTTGCAAAAGCCTCTCGCTATTTTGGTTTTTATCGTCGTCTGGTAAAC
GAGGGTTATGATAGTGTTGCTCTTACTATGCCTCGTAATTCCTTTTGGCGTTATGTAT
CTGCATTAGTTGAATGTGGTATTCCTAAATCTCAACTGATGAATCTTTCTACCTGTAA
TAATGTTGTTCCGTTAGTTCGTTTTATTAACGTAGATTTTTCTTCCCAACGTCCTGACT
GGTATAATGAGCCAGTTCTTAAAATCGCATAAGGTAATTCACAATGATTAAAGTTGA
AATTAAACCATCTCAAGCCCAATTTACTACTCGTTCTGGTGTTTCTCGTCAGGGCAA
GCCTTATTCACTGAATGAGCAGCTTTGTTACGTTGATTTGGGTAATGAATATCCGGTT
CTTGTCAAGATTACTCTTGATGAAGGTCAGCCAGCCTATGCGCCTGGTCTGTACACC
GTTCATCTGTCCTCTTTCAAAGTTGGTCAGTTCGGTTCCCTTATGATTGACCGTCTGC
GCCTCGTTCCGGCTAAGTAACATGGAGCAGGTCGCGGATTTCGACACAATTTATCAG
GCGATGATACAAATCTCCGTTGTACTTTGTTTCGCGCTTGGTATAATCGCTGGGGGTC
AAAGATGAGTGTTTTAGTGTATTCTTTCGCCTCTTTCGTTTTAGGTTGGTGCCTTCGT
AGTGGCATTACGTATTTTACCCGTTTAATGGAAACTTCCTCATGAAAAAGTCTTTAGT
CCTCAAAGCCTCTGTAGCCGTTGCTACCCTCGTTCCGATGCTGTCTTTCGCTGCTGAG
GGTGACGATCCCGCAAAAGCGGCCTTTAACTCCCTGCAAGCCTCAGCGACCGAATA
TATCGGTTATGCGTGGGCGATGGTTGTTGTCATTGTCGGCGCAACTATCGGTATCAA
GCTGTTTAAGAAATTCACCTCGAAAGCAAGCTGATAAACCGATACAATTAAAGGCT
CCTTTTGGAGCCTTTTTTTTGGAGATTTTCAACATGAAAAAATTATTATTCGCAATT
CCTTTAGTTGTTCCTTTCTATTCTCACTCCGCTGAAACTGTTGAAAGTTGTTTAGCAA
AACCCCATACAGAAAATTCATTTACTAACGTCTGGAAAGACGACAAAACTTTAGATC
GTTACGCTAACTATGAGGGTTGTCTGTGGAATGCTACAGGCGTTGTAGTTTGTACTG
GTGACGAAACTCAGTGTTACGGTACATGGGTTCCTATTGGGCTTGCTATCCCTGAAA
ATGAGGGTGGTGGCTCTGAGGGTGGCGGTTCTGAGGGTGGCGGTTCTGAGGGTGGC
GGTACTAAACCTCCTGAGTACGGTGATACACCTATTCCGGGCTATACTTATATCAAC
CCTCTCGACGGCACTTATCCGCCTGGTACTGAGCAAAACCCCGCTAATCCTAATCCT
TCTCTTGAGGAGTCTCAGCCTCTTAATACTTTCATGTTTCAGAATAATAGGTTCCGAA
ATAGGCAGGGGGCATTAACTGTTTATACGGGCACTGTTACTCAAGGCACTGACCCCG
TTAAAACTTATTACCAGTACACTCCTGTATCATCAAAAGCCATGTATGACGCTTACT
GGAACGGTAAATTCAGAGACTGCGCTTTCCATTCTGGCTTTAATGAGGATCCATTCG
TTTGTGAATATCAAGGCCAATCGTCTGACCTGCCTCAACCTCCTGTCAATGCTGGCG
GCGGCTCTGGTGGTGGTTCTGGTGGCGGCTCTGAGGGTGGTGGCTCTGAGGGTGGCG
GTTCTGAGGGTGGCGGCTCTGAGGGAGGCGGTTCCGGTGGTGGCTCTGGTTCCGGTG
ATTTTGATTATGAAAAGATGGCAAACGCTAATAAGGGGGCTATGACCGAAAATGCC
GATGAAAACGCGCTACAGTCTGACGCTAAAGGCAAACTTGATTCTGTCGCTACTGAT
TACGGTGCTGCTATCGATGGTTTCATTGGTGACGTTTCCGGCCTTGCTAATGGTAATG
GTGCTACTGGTGATTTTGCTGGCTCTAATTCCCAAATGGCTCAAGTCGGTGACGGTG
ATAATTCACCTTTAATGAATAATTTCCGTCAATATTTACCTTCCCTCCCTCAATCGGT
TGAATGTCGCCCTTTTGTCTTTAGCGCTGGTAAACCATATGAATTTTCTATTGATTGT
GACAAAATAAACTTATTCCGTGGTGTCTTTGCGTTTCTTTTATATGTTGCCACCTTTA
TGTATGTATTTTCTACGTTTGCTAACATACTGCGTAATAAGGAGTCTTAATCATGCCA
GTTCTTTTGGGTATTCCGTTATTATTGCGTTTCCTCGGTTTCCTTCTGGTAACTTTGTT
CGGCTATCTGCTTACTTTTCTTAAAAAGGGCTTCGGTAAGATAGCTATTGCTATTTCA
TTGTTTCTTGCTCTTATTATTGGGCTTAACTCAATTCTTGTGGGTTATCTCTCTGATAT
TAGCGCTCAATTACCCTCTGACTTTGTTCAGGGTGTTCAGTTAATTCTCCCGTCTAAT
GCGCTTCCCTGTTTTTATGTTATTCTCTCTGTAAAGGCTGCTATTTTCATTTTTGACGT
TAAACAAAAAATCGTTTCTTATTTGGATTGGGATAAATAATATGGCTGTTTATTTTGT
AACTGGCAAATTAGGCTCTGGAAAGACGCTCGTTAGCGTTGGTAAGATTCAGGATA
AAATTGTAGCTGGGTGCAAAATAGCAACTAATCTTGATTTAAGGCTTCAAAACCTCC
CGCAAGTCGGGAGGTTCGCTAAAACGCCTCGCGTTCTTAGAATACCGGATAAGCCTT
CTATATCTGATTTGCTTGCTATTGGGCGCGGTAATGATTCCTACGATGAAAATAAAA
ACGGCTTGCTTGTTCTCGATGAGTGCGGTACTTGGTTTAATACCCGTTCTTGGAATGA
TAAGGAAAGACAGCCGATTATTGATTGGTTTCTACATGCTCGTAAATTAGGATGGGA
TATTATTTTTCTTGTTCAGGACTTATCTATTGTTGATAAACAGGCGCGTTCTGCATTA
GCTGAACATGTTGTTTATTGTCGTCGTCTGGACAGAATTACTTTACCTTTTGTCGGTA
CTTTATATTCTCTTATTACTGGCTCGAAAATGCCTCTGCCTAAATTACATGTTGGCGT
TGTTAAATATGGCGATTCTCAATTAAGCCCTACTGTTGAGCGTTGGCTTTATACTGGT
AAGAATTTGTATAACGCATATGATACTAAACAGGCTTTTTCTAGTAATTATGATTCC
GGTGTTTATTCTTATTTAACGCCTTATTTATCACACGGTCGGTATTTCAAACCATTAA
ATTTAGGTCAGAAGATGAAATTAACTAAAATATATTTGAAAAAGTTTTCTCGCGTTC
TTTGTCTTGCGATTGGATTTGCATCAGCATTTACATATAGTTATATAACCCAACCTAA
GCCGGAGGTTAAAAAGGTAGTCTCTCAGACCTATGATTTTGATAAATTCACTATTGA
CTCTTCTCAGCGTCTTAATCTAAGCTATCGCTATGTTTTCAAGGATTCTAAGGGAAAA
TTAATTAATAGCGACGATTTACAGAAGCAAGGTTATTCACTCACATATATTGATTTA
TGTACTGTTTCCATTAAAAAAGGTAATTCAAATGAAATTGTTAAATGTAATTAATTTT
GTTTTCTTGATGTTTGTTTCATCATCTTCTTTTGCTCAGGTAATTGAAATGAATAATTC
GCCTCTGCGCGATTTTGTAACTTGGTATTCAAAGCAATCAGGCGAATCCGTTATTGTT
TCTCCCGATGTAAAAGGTACTGTTACTGTATATTCATCTGACGTTAAACCTGAAAAT
CTACGCAATTTCTTTATTTCTGTTTTACGTGCTAATAATTTTGATATGGTTGGTTCAAT
```

-continued

```
TCCTTCCATAATTCAGAAGTATAATCCAAACAATCAGGATTATATTGATGAATTGCC
ATCATCTGATAATCAGGAATATGATGATAATTCCGCTCCTTCTGGTGGTTTCTTTGTT
CCGCAAAATGATAATGTTACTCAAACTTTTAAAATTAATAACGTTCGGGCAAAGGAT
TTAATACGAGTTGTCGAATTGTTTGTAAAGTCTAATACTTCTAAATCCTCAAATGTAT
TATCTATTGACGGCTCTAATCTATTAGTGTTAGTGCACCTAAAGATATTTTAGATAA
CCTTCCTCAATTCCTTTCTACTGTTGATTTGCCAACTGACCAGATATTGATTGAGGGT
TTGATATTTGAGGTTCAGCAAGGTGATGCTTTAGATTTTTCATTTGCTGCTGGCTCTC
AGCGTGGCACTGTTGCAGGCGGTGTTAATACTGACCGCCTCACCTCTGTTTTATCTTC
TGCTGGTGGTTCGTTCGGTATTTTTAATGGCGATGTTTTAGGGCTATCAGTTCGCGCA
TTAAAGACTAATAGCCATTCAAAAATATTGTCTGTGCCACGTATTCTTACGCTTTCAG
GTCAGAAGGGTTCTATCTCTGTTGGCCAGAATGTCCCTTTTATTACTGGTCGTGTGAC
TGGTGAATCTGCCAATGTAAATAATCCATTTCAGACGATTGAGCGTCAAAATGTAGG
TATTTCCATGAGCGTTTTTCCTGTTGCAATGGCTGGCGGTAATATTGTTCTGGATATT
ACCAGCAAGGCCGATAGTTTGAGTTCTTCTACTCAGGCAAGTGATGTTATTACTAAT
CAAAGAAGTATTGCTACAACGGTTAATTTGCGTGATGGACAGACTCTTTTACTCGGT
GGCCTCACTGATTATAAAAACACTTCTCAAGATTCTGGCGTACCGTTCCTGTCTAAA
ATCCCTTTAATCGGCCTCCTGTTTAGCTCCCGCTCTGATTCCAACGAGGAAAGCACG
TTATACGTGCTCGTCAAAGCAACCATAGTACGCGCCCTGTAGCGGCGCATTAAGCGC
GGCGGGTGTGGTGGTTACGCGCAGCGTGACCGCTACACTTGCCAGCGCCCTAGCGC
CCGCTCCTTTCGCTTTCTTCCCTTCCTTTCTCGCCACGTTCGCCGGCTTTCCCCGTCAA
GCTCTAAATCGGGGGCTCCCTTTAGGGTTCCGATTTAGTGCTTTACGGCACCTCGAC
CCCAAAAAACTTGATTTGGGTGATGGTTCACGTAGTGGGCCATCGCCCTGATAGACG
GTTTTTCGCCCTTTGACGTTGGAGTCCACGTTCTTTAATAGTGGACTCTTGTTCCAAA
CTGGAACAACACTCAACCCTATCTCGGGCTATTCTTTTGATTTATAAGGGATTTTGCC
GATTTCGGCCTATTGGTTAAAAAATGAGCTGATTTAACAAAAATTTAACGCGAATTT
TAACAAAATATTAACGTTTACAATTTAAATATTTGCTTATACAATCTTCCTGTTTTTG
GGGCTTTTCTGATTATCAACCGGGGTACATATGATTGACATGCTAGTTTTACGATTAC
CGTTCATCGATTCTCTTGTTTGCTCCAGACTCTCAGGCAATGACCTGATAGCCTTTGT
AGACCTCTCAAAAATAGCTACCCTCTCCGGCATGAATTTATCAGCTAGAACGGTTGA
ATATCATATTGATGGTGATTTGACTGTCTCCGGCCTTTCTCACCCTTTTGAATCTTTA
CCTACACATTACTCAGGCATTGCATTTAAAATATATGAGGGTTCTAAAAATTTTTATC
CTTGCGTTGAAATAAAGGCTTCTCCCGCAAAAGTATTACAGGGTCATAATGTTTTTG
GTACAACCGATTTAGCTTTATGCTCTGAGGCTTTATTGCTTAATTTTGCTAATTCTTT
GCCTTGCCTGTATGATTTATTGGATGTT

GENE II: join(6006 . . . 6407, 1 . . . 831)
                                                    (SEQ ID NO: 22)
translation = MIDMLVLRLPFIDSLVCSRLSGNDLIAFVDLSKIATLSGMNLSA
RTVEYHIDGDLTVSGLSHPFESLPTHYSGIAPKIYEGSKNFYPCVEIKASPAKVLQGHNVF
GTTDLALCSEALLLNFANSLPCLYDLLDVNATTISRIDATFSARAPNENIAKQVIDHLRNV
SNGQTKSTRSQNWESTVTWNETSRHRTLVAYLKHVELQHQIQQLSSKPSAKMTSYQKE
QLKVLSNPDLLEFASGLVRFEARIKTRYLKSFGLPLNLFDAIRFASDYNSQGKDLIFDLW
SFSFSELFKAFEGDSMNIYDDSAVLDAIQSKHFTITPSGKTSFAKASRYFGFYRRLVNEGY
DSVALTMPRNSFWRYVSALVECGIPKSQLMNLSTCNNVVPLVRFINVDFSSQRPDWYNE
PVLKIA GENE X: 496 . . . 831
                                                    (SEQ ID NO: 23)
translation = MNIYDDSAVLDAIQSKHFTITPSGKTSFAKASRYFGFYRRLVN
EGYDSVALTMPRNSFWRYVSALVECGIPKSQLMNLSTCNNVVPLVRFINVDFSSQRPDW
YNEPVLKIA GENE V: 843 . . . 1106
                                                    (SEQ ID NO: 24)
translation = MIKVEIKPSQAQFTTRSGVSRQGKPYSLNEQLCYVDLGNEYPV
LVKITLDEGQPAYAPGLYTVHLSSFKVGQFGSLMIDRLRLVPAK GENE VII: 1108 . . . 1209
                                                    (SEQ ID NO: 25)
translation = MEQVADFDTIYQAMIQISVVLCFALGIIAGGQR GENE IX: 1206 . . . 1304
                                                    (SEQ ID NO: 26)
translation = MSVLVYSFASFVLGWCLRSGITYFTRLMETSS GENE VIII: 1301 . . . 1522
                                                    (SEQ ID NO: 27)
translation = MKKSLVLKASVAVATLVPMLSFAAEGDDPAKAAFNSLQASA
TEYIGYAWAMVVVIVGATIGIKLFKKFTSKAS GENE III: 1579 . . . 2853
                                                    (SEQ ID NO: 28)
translation = MKKLLFAIPLVVPFYSHSAETVESCLAKPHTENSFTNVWKDD
KTLDRYANYEGCLWNATGVVVCTGDETQCYGTWVPIGLAIPENEGGGSEGGGSEGGGS
EGGGTKPPEYGDTPIPGYTYINPLDGTYPPGTEQNPANPNPSLEESQPLNTFMFQNNRFR
NRQGALTVYTGTVTQGTDPVKTYYQYTPVSSKAMYDAYWNGKFRDCAFHSGFNEDPF
VCEYQGQSSDLPQPPVNAGGGSGGGSGGGSEGGGSEGGGSEGGGSEGGGSGGGSGSGD
FDYEKMANANKGAMTENADENALQSDAKGKLDSVATDYGAAIDGFIGDVSGLANGNG
ATGDFAGSNSQMAQVGDGDNSPLMNNFRQYLPSLPQSVECRPFVFSAGKPYEFSIDCDK
INLFRGVFAFLLYVATFMYVFSTFANILRNKES
```

```
                             -continued
GENE VI: 2856 . . . 3194
                                                (SEQ ID NO: 29)
translation = MPVLLGIPLLLRFLGFLLVTLFGYLLTFLKKGFGKIAIAISLFLA
LIIGLNSILVGYLSDISAQLPSDFVQGVQLILPSNALPCFYVILSVKAAIFIFDVKQKIVSYL
DWDK GENE I: 3196 . . . 4242
                                                (SEQ ID NO: 30)
translation = MAVYFVTGKLGSGKTLVSVGKIQDKIVAGCKIATNLDLRLQN
LPQVGRFAKTPRVLRIPDKPSISDLLAIGRGNDSYDENKNGLLVLDECGTWFNTRSWND
KERQPIIDWFLHARKLGWDIIFLVQDLSIVDKQARSALAEHVVYCRRLDRITLPFVGTLY
SLITGSKMPLPKLHVGVVKYGDSQLSPTVERWLYTGKNLYNAYDTKQAFSSNYDSGVY
SYLTPYLSHGRYFKPLNLGQKMKLTKIYLKKFSRVLCLAIGFASAFTYSYITQPKPEVKK
VVSQTYDFDKFTIDSSQRLNLSYRYVFKDSKGKLINSDDLQKQGYSLTYIDLCTVSIKKG
NSNEIVKCN GENE IV: 4220 . . . 5500
                                                (SEQ ID NO: 31)
translation = MKLLNVINFVFLMFVSSSSFAQVIEMNNSPLRDFVTWYSKQSG
ESVIVSPDVKGTVTVYSSDVKPENLRNFFISVLRANNFDMVGSIPSIIQKYNPNNQDYIDE
LPSSDNQEYDDNSAPSGGFFVPQNDNVTQTFKINNVRAKDLIRVVELFVKSNTSKSSNVL
SIDGSNLLVVSAPKDILDNLPQFLSTVDLPTDQILIEGLIFEVQQGDALDFSFAAGSQRGT
VAGGVNTDRLTSVLSSAGGSFGIFNGDVLGLSVRALKTNSHSKILSVPRILTLSGQKGSIS
VGQNVPFITGRVTGESANVNNPFQTIERQNVGISMSVFPVAMAGGNIVLDITSKADSLSS
STQASDVITNQRSIATTVNLRDGQTLLLGGLTDYKNTSQDSGVPFLSKIPLIGLLFSSRSDS
NEESTLYVLVKATIVRAL
```

Protein/Peptide/Polypeptide

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. The term "fusion protein" as used herein refers to a hybrid polypeptide which comprises protein domains from at least two different proteins. One protein may be located at the amino-terminal (N-terminal) portion of the fusion protein or at the carboxy-terminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site) and a nucleic acid cleavage domain or a catalytic domain of a recombinase. In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, Molecular Cloning: A Laboratory Manual (4th ed., Cold Spring Harbor Laboratory Press, Cold Spring Harbor, N.Y. (2012)), the entire contents of which are incorporated herein by reference.

Protein Splicing

As used herein, the term "protein splicing" refers to a process in which an interior region of a precursor protein (an intein) is excised and the flanking regions of the protein (exteins) are ligated to form the mature protein. This natural process has been observed in numerous proteins from both prokaryotes and eukaryotes (Perler, F. B., Xu, M. Q., Paulus, H. Current Opinion in Chemical Biology 1997, 1, 292-299; Perler, F. B. Nucleic Acids Research 1999, 27, 346-347). The intein unit contains the necessary components needed to catalyze protein splicing and often contains an endonuclease domain that participates in intein mobility (Perler, F. B., Davis, E. O., Dean, G. E., Gimble, F. S., Jack, W. E., Neff, N., Noren, C. J., Thomer, J., Belfort, M. Nucleic Acids Research 1994, 22, 1127-1127). The resulting proteins are linked, however, not expressed as separate proteins. Protein splicing may also be conducted in trans with split inteins expressed on separate polypeptides spontaneously combine to form a single intein which then undergoes the protein splicing process to join to separate proteins.

Recombinant

The term "recombinant" as used herein in the context of proteins or nucleic acids refers to proteins or nucleic acids that do not occur in nature, but are the product of human engineering. For example, in some embodiments, a recombinant protein or nucleic acid molecule comprises an amino acid or nucleotide sequence that comprises at least one, at least two, at least three, at least four, at least five, at least six, or at least seven mutations as compared to any naturally occurring sequence.

Reference Base Editor

The term "reference base editor," as used herein, refers to the version of a base editor that is used as the starting point for a continuous evolution process, e.g., PACE, to achieve or obtain an evolved base editor. The reference base editor may include naturally-occurring polypeptide sequences. The reference base editor may also include non-naturally-occurring polypeptide sequences, e.g., base editors that have one or more changes in the amino acid sequence (e.g., one or more mutated residues, an insertion of one or more amino acids, or a deletion of one or more amino acids relative to a wildtype or canonical polypeptides). In other words, a reference base editor can comprise base editor components (e.g., deaminases and Cas9) that are naturally occurring (e.g., wildtype human, mouse, rat, horse, or rabbit polypeptide sequences or naturally occurring variants thereof) or they may also include base editors which have already been modified relative to the naturally-occurring sequences, and which are desired to be further evolved and/or changed and/or improved using a continuous evolution process, e.g., PACE, described herein. Analogous definitions will be observed when referring to the individual components of a base editor. For example, a "reference Cas9 domain" or a "reference deaminase" or a "reference UGI" or other such individual components of a base editor refers to the version of a that component or domain that is used as the starting point for a continuous evolution process, e.g., PACE, to achieve or obtain an evolved version or variant of that component or domain.

RNA-Programmable Nuclease/RNA-Guided Nuclease

The term "RNA-programmable nuclease," and "RNA-guided nuclease" are used interchangeably herein and refer to a nuclease that forms a complex with (e.g., binds or associates with) one or more RNA that is not a target for cleavage (e.g., a Cas9 or homolog or variant thereof). In some embodiments, an RNA-programmable nuclease, when in a complex with an RNA, may be referred to as a nuclease:RNA complex. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 (or equivalent) complex to the target); and (2) a domain that binds a Cas9 protein. In some embodiments, domain (2) corresponds to a sequence known as a tracrRNA, and comprises a stem-loop structure. For example, in some embodiments, domain (2) is homologous to a tracrRNA as depicted in FIG. 1E of Jinek et al., *Science* 337:816-821 (2012), the entire contents of which is incorporated herein by reference. Other examples of gRNAs (e.g., those including domain 2) can be found in U.S. Provisional Patent Application, U.S. Ser. No. 61/874,682, filed Sep. 6, 2013, entitled "Switchable Cas9 Nucleases And Uses Thereof," and U.S. Provisional Patent Application, U.S. Ser. No. 61/874,746, filed Sep. 6, 2013, entitled "Delivery System For Functional Nucleases," the entire contents of each are hereby incorporated by reference in their entirety. In some embodiments, a gRNA comprises two or more of domains (1) and (2), and may be referred to as an "extended gRNA." For example, an extended gRNA will, e.g., bind two or more Cas9 proteins and bind a target nucleic acid at two or more distinct regions, as described herein. The gRNA comprises a nucleotide sequence that complements a target site, which mediates binding of the nuclease/RNA complex to said target site, providing the sequence specificity of the nuclease:RNA complex. In some embodiments, the RNA-programmable nuclease is the (CRISPR-associated system) Cas9 endonuclease, for example Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference.

Because RNA-programmable nucleases (e.g., Cas9) use RNA:DNA hybridization to target DNA cleavage sites, these proteins are able to be targeted, in principle, to any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. Science 339, 819-823 (2013); *Mali*, P. et al. RNA-guided human genome engineering via Cas9. Science 339, 823-826 (2013); Hwang, W. Y. et al. Efficient genome editing in zebrafish using a CRISPR-Cas system. *Nature biotechnology* 31, 227-229 (2013); Jinek, M. et al. RNA-programmed genome editing in human cells. eLife 2, e00471 (2013); Dicarlo, J. E. et al. Genome engineering in *Saccharomyces cerevisiae* using CRISPR-Cas systems. *Nucleic acids research* (2013); Jiang, W. et al. RNA-guided editing of bacterial genomes using CRISPR-Cas systems. *Nature biotechnology* 31, 233-239 (2013); the entire contents of each of which are incorporated herein by reference).

Selection Phage

The term "selection phage," as used herein interchangeably with the term "selection plasmid," refers to a modified phage that comprises a nucleic acid sequence encoding a tRNA synthetase to be evolved, and lacks a full-length gene encoding a protein required for the generation of infectious phage particles. For example, some M13 selection phages provided herein comprise a nucleic acid sequence encoding a gene to be evolved, e.g., under the control of an M13 promoter, and lack all or part of a phage gene encoding a protein required for the generation of infectious phage particles, e.g., gI, gII, gIII, gIV, gV, gVI, gVII, gVIII, gIX, or gX, or any combination thereof. For example, some M13 selection phages provided herein comprise a nucleic acid sequence encoding a tRNA synthetase protein to be evolved, e.g., under the control of an M13 promoter, and lack all or part of a gene encoding a protein required for the generation of infective phage particles, e.g., the gIII gene encoding the pIII protein.

Sequence-Context Agnostic

As used herein, the term "sequence-context agnostic" refers to a desired property or characteristic of the evolved base editors described herein in which the sequence proximate (upstream and/or downstream) to the desired target editing site has little or no impact or effect on the efficiency of the evolved base editor to edit the desired target editing site.

Split Inteins

A small fraction (less than 5%) of the identified intein genes encode split inteins.9 Unlike the more common contiguous inteins, these are transcribed and translated as two separate polypeptides, the N-intein and C-intein, each fused to one extein. Upon translation, the intein fragments spontaneously and non-covalently assemble into the canonical intein structure to carry out protein splicing in trans Subject The term "subject," as used herein, refers to an individual organism, for example, an individual mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cattle, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development.

Target Site

The term "target site" refers to a sequence within a nucleic acid molecule that is deaminated by a deaminase or a fusion protein comprising a deaminase (e.g., a dCas9-deaminase fusion protein provided herein).

Vector

The term "vector," as used herein, refers to a nucleic acid that can be modified to encode a gene of interest and that is able to enter into a host cell, mutate and replicate within the host cell, and then transfer a replicated form of the vector into another host cell. Exemplary suitable vectors include viral vectors, such as retroviral vectors or bacteriophages and filamentous phage, and conjugative plasmids. Additional suitable vectors will be apparent to those of skill in the art based on the instant disclosure.

Viral Life Cycle

The term "viral life cycle," as used herein, refers to the viral reproduction cycle comprising insertion of the viral genome into a host cell, replication of the viral genome in the host cell, and packaging of a replication product of the viral genome into a viral particle by the host cell.

Viral Particle

The term "viral particle," as used herein, refers to a viral genome, for example, a DNA or RNA genome, that is associated with a coat of a viral protein or proteins, and, in some cases, with an envelope of lipids. For example, a phage particle comprises a phage genome packaged into a protein encoded by the wild type phage genome.

Viral Vector

The term "viral vector," as used herein, refers to a nucleic acid comprising a viral genome that, when introduced into a suitable host cell, can be replicated and packaged into viral particles able to transfer the viral genome into another host cell. The term viral vector extends to vectors comprising truncated or partial viral genomes. For example, in some embodiments, a viral vector is provided that lacks a gene encoding a protein essential for the generation of infectious viral particles. In suitable host cells, for example, host cells comprising the lacking gene under the control of a conditional promoter, however, such truncated viral vectors can replicate and generate viral particles able to transfer the truncated viral genome into another host cell. In some embodiments, the viral vector is a phage, for example, a filamentous phage (e.g., an M13 phage). In some embodiments, a viral vector, for example, a phage vector, is provided that comprises a gene of interest to be evolved.

Uracil Glycosylase Inhibitor or UGI

The term "uracil glycosylase inhibitor" or "UGI," as used herein, refers to a protein that is capable of inhibiting a uracil-DNA glycosylase base-excision repair enzyme. In some embodiments, a UGI domain comprises a wild-type UGI or a UGI as set forth in SEQ ID NO: 10. In some embodiments, the UGI proteins provided herein include fragments of UGI and proteins homologous to a UGI or a UGI fragment. For example, in some embodiments, a UGI domain comprises a fragment of the amino acid sequence set forth in SEQ ID NO: 10. In some embodiments, a UGI fragment comprises an amino acid sequence that comprises at least 60%, at least 65%, at least 70%, at least 75%, at least 80%, at least 85%, at least 90%, at least 95%, at least 96%, at least 97%, at least 98%, at least 99%, or at least 99.5% of the amino acid sequence as set forth in SEQ ID NO: 10. In some embodiments, a UGI comprises an amino acid sequence homologous to the amino acid sequence set forth in SEQ ID NO: 10, or an amino acid sequence homologous to a fragment of the amino acid sequence set forth in SEQ ID NO: 10. In some embodiments, proteins comprising UGI or fragments of UGI or homologs of UGI or UGI fragments are referred to as "UGI variants." A UGI variant shares homology to UGI, or a fragment thereof. For example a UGI variant is at least 70% identical, at least 75% identical, at least 80% identical, at least 85% identical, at least 90% identical, at least 95% identical, at least 96% identical, at least 97% identical, at least 98% identical, at least 99% identical, at least 99.5% identical, or at least 99.9% identical to a wild type UGI or a UGI as set forth in SEQ ID NO: 10. In some embodiments, the UGI variant comprises a fragment of UGI, such that the fragment is at least 70% identical, at least 80% identical, at least 90% identical, at least 95% identical, at least 96% identical, at least 97% identical, at least 98% identical, at least 99% identical, at least 99.5% identical, or at least 99.9% to the corresponding fragment of wild-type UGI or a UGI as set forth in SEQ ID NO: 10. In some embodiments, the UGI comprises the following amino acid sequence: MTNLSDIIEKETGKQLVIQE-SILMLPEEVEEVIGNKPESDILVHTAYDESTD ENVMLLTSDAPEYKPWALVIQDSNGENKIKML (SEQ ID NO: 10) (P14739|UNGI_BPPB2 Uracil-DNA glycosylase inhibitor).

Treatment

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

Variant

As used herein the term "variant" should be taken to mean the exhibition of qualities that have a pattern that deviates from what occurs in nature, e.g., a variant Cas9 is a Cas9 comprising one or more changes in amino acid residues as compared to a wild type Cas9 amino acid sequence.

Wild Type

As used herein the term "wild type" is a term of the art understood by skilled persons and means the typical form of an organism, strain, gene or characteristic as it occurs in nature as distinguished from mutant or variant forms.

DETAILED DESCRIPTION OF CERTAIN EMBODIMENTS

The present inventors have surprisingly discovered improve base editors (e.g., cytindine base editors) by developing an effective continuous evolutionary mutagenesis process (i.e., PACE) that may be used to rapidly improve the function of one or more domains or components of a base editor.

The instant specification provides for evolved base editors which overcome deficiencies of those in art (including increased efficiency and/or decreased requirement for specific sequence-context at an editing site) and which are obtained a result of a phage-assisted continuous evolution (PACE) system. In particular, the instant specification provides for evolved cytidine base editors (e.g., based on APOBEC1, CDA, or AID cytidine deaminase domains) which overcome deficiencies of those in art (including increased efficiency and/or decreased requirement for specific sequence-context at an editing site) and which are obtained a result of a phage-assisted continuous evolution (PACE) system. In addition, the instant specification provides for nucleic acid molecules encoding and/or expressing the evolved base editors as described herein, as well as expression vectors or constructs for expressing the evolved base editors described herein, host cells comprising said nucleic acid molecules and expression vectors, and compositions for delivering and/or administering nucleic acid-based embodiments described herein. In addition, the disclosure provides for isolated evolved base editors, as well as compositions comprising said isolated evolved base editors as described herein. Still further, the present disclosure provides for methods of making the evolved base editors, as well as methods of using the evolved base editors or nucleic acid molecules encoding the evolved base editors in applications including editing a nucleic acid molecule, e.g., a genome, with improved efficiency as compared to base editor that forms the state of the art, preferably in a sequence-context agnostic manner (i.e., wherein the desired editing site does not require a specific sequence-context). In embodiments, the method of making provide herein is an improved phage-assisted continuous evolution (PACE) system which may be utilized to evolve one or more components of a base editor (e.g., a Cas9 domain or a cytidine deaminase domain) in a rapid and continuous manner. The specification also provides methods for efficiently editing a target nucleic acid molecule, e.g., a single nucleobase of a genome, with a base editing system described herein (e.g., in the form of an isolated evolved base editor as described herein or a vector or construct encoding same) and conducting based editing, preferably in a sequence-context agnostic manner. Still further, the specification provides therapeutic methods for treating a genetic disease and/or for altering or changing a genetic trait or condition by contacting a target nucleic acid molecule, e.g., a genome, with a base editing system (e.g., in the form of an isolated evolved base editor protein or a vector encoding same) and conducting based editing to treat the genetic disease and/or change the genetic trait (e.g., eye color).

I. Evolved Base-Editors

In various aspect, the present disclosure provides evolved base editors as a result of mutagenizing a reference or starting-point base editor (or a component or domain thereof) by a continuous evolution method (e.g., PACE). In various embodiments, the disclosure provides an evolved base editor that has one or more amino acid variations introduced into its amino acid sequence relative to the amino acid sequence of the reference or starting-point base editor. Amino acid sequence variations may include one or more mutated residues within the amino acid sequence of the reference base editor, e.g., as a result of a change in the nucleotide sequence encoding the base editor that results in a change in the codon at any particular position in the coding sequence, the deletion of one or more amino acids (e.g., a truncated protein), the insertion of one or more amino acids, or any combination of the foregoing. In some embodiments, an evolved base editor is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to the reference base editor. The evolved base editor may include variants in one or more components or domains of the base editor (e.g., variants introduced into a Cas9 domain, a deaminase domain, or a UGI domain, or variants introduced into combinations of these domains).

In certain aspects, the methods described herein for evolving base editors begins with a base editor known in the art. The state of the art has described numerous base editors as of this filing. The methods and approaches herein described for improving base editors may be applied to any previously known base editor, or to base editors that may be developed in the further but which lack the beneficial characteristics imparted by the instant methods and modification approaches. Exemplary base editors that may be modified by the methods described herein to achieve the evolved base editors of the invention can include, for example, those described in the following references and/or patent publications, each of which are incorporated by reference in their entireties: (a) PCT/US2014/070038 (published as WO2015/089406, Jun. 18, 2015) and its equivalents in the US or around the world; (b) PCT/US2016/058344 (published as WO2017/070632, Apr. 27, 2017) and its equivalents in the US or around the world; (c) PCT/US2016/058345 (published as WO2017/070633, Apr. 27, 2017) and its equivalent in the US or around the world; (d) PCT/US2017/045381 (published as WO2018/027078, Feb. 8, 2018) and its equivalents in the US or around the world; (e) PCT/US2017/056671 (published as WO2018/071868, Apr. 19, 2018) and its equivalents in the US or around the world; PCT/2017/048390 (WO2017/048390, Mar. 23, 2017) and its equivalents in the US or around the world; (f) PCT/US2017/068114 (not published) and its equivalents in the US or around the world; (g) PCT/US2017/068105 (not published) and its equivalents in the US or around the world; (h) PCT/US2017/046144 (WO2018/031683, Feb. 15, 2018) and its equivalents in the US or around the world; (i) PCT/US2018/024208 (not published) and its equivalents in the US or around the world; (j) PCT/2018/021878 (WO2018/021878, Feb. 1, 2018) and its equivalents in the US and around the world; (k) Komor, A. C., Kim, Y. B., Packer, M. S., Zuris, J. A. & Liu, D. R. Programmable editing of a target base in genomic DNA without double-stranded DNA cleavage. Nature 533, 420-(2016); (l) Gaudelli, N. M. et al. Programmable base editing of A•T to G•C in genomic DNA without DNA cleavage. Nature 551, 464-(2017); (m) any of the references listed in this specification entitled "References" and which reports or describes a base editor known in the art.

In various aspects, the evolved or modified base editors described herein have the following generalized structure: A-B-C, wherein "A" is a Cas moiety or napDNAbp, "B" is nucleic acid effector domain (e.g., a deaminase, such as a cytidine or adenosine deaminase), and "C" represents an optional additional base editor functional domain (e.g., a UGI domain or a NLS domain). In addition, the "-" represents a linker that covalently joins moieties A, B, and C. The linkers can be any suitable type (e.g., amino acid sequences or other biopolymers, or synthetic chemical linkages in the case where the moieties are bioconjugated to one another) or length. In addition, a functional improved base editor of the invention could also include one or more "R" or guide sequences (e.g., guide RNA in the case of a Cas9 or Cas9 equivalent) in order to carry out the R/DNA-programmable functionality of base editors for targeting specific sites to be corrected.

The order of linkage of the moieties is not meant to be particularly limiting so long as the particular arrangement of the elements of moieties produces a functional base editor. That is, the evolved base editors of the invention may also include editors represented by the following structures: B-A-C; B-C-A; C-B-A; C-A-B; and A-C-B. In various embodiments, the evolved base editors may comprise at least one domain of the evolved base editors (e.g., a Cas9 domain or a deaminase domain) that has been evolved by a continuous evolution process (e.g., PACE). Thus, in one embodiment, the specification provides an evolved base editor that comprises an evolved Cas9 domain relative to a reference Cas9 domain, but where the other domains of the base editor have not been evolved. In another embodiment, the specification provides an evolved base editor that comprise an evolved deaminase domain (e.g., an APOBEC1, AID, or CDA domain), but where the other domains of the base editor have not been evolved. In yet another embodiment, the specification provides an evolved base editor that comprise an evolved UGI domain, but where the other domains of the base editor have not been evolved. In still other embodiment, the evolved base editors may comprise combinations of domains which are evolved by the continuous evolution process described herein.

In one embodiment, the evolved base editors may comprise a fusion protein comprising: (i) a nucleic acid programmable DNA binding protein (napDNAbp); (ii) a cytidine deaminase; and (iii) a uracil glycosylase inhibitor domain (UGI), wherein at least one of (i), (ii), or (iii) has be evolved using a continuous evolution process (e.g., PACE) described herein. In various embodiments, the fusion protein can comprise two, three, four, or five, or more UGI domains. In certain embodiments, the nucleic acid programmable DNA binding protein (napDNAbp) is a Cas9 domain. The Cas9 domain in various embodiments can be a nuclease active Cas9, a nuclease inactive Cas9 (dCas9), or a Cas9 nickase (nCas9). In various other embodiments, the napDNAbp is CasX, CasY, Cpf1, C2c1, C2c2, C2c3, or Argonaute protein.

The evolved base editors comprising: (i) a nucleic acid programmable DNA binding protein (napDNAbp); (ii) a cytidine deaminase; and (iii) a uracil glycosylase inhibitor domain (UGI), wherein at least one of (i), (ii), or (iii) has be evolved using a continuous evolution process (e.g., PACE) described herein, can be arranged structurally in a variety of configurations, which include, but are not limited to:

NH$_2$-[cytidine deaminase]-[napDNAbp]-[UGI]-COOH;
NH$_2$-[cytidine deaminase]-[UGI]-[napDNAbp]-COOH;
NH$_2$-[napDNAbp]-[UGI]-[cytidine deaminase]-COOH;
NH$_2$-[napDNAbp]-[cytidine deaminase]-[UGI]-COOH;
NH$_2$-[UGI]-[cytidine deaminase]-[napDNAbp]-COOH; or NH$_2$-[UGI]-[napDNAbp]-[cytidine deaminase]-COOH, wherein each instance of "-" comprises an optional linker.

In other embodiments, the evolved base editors comprising: (i) a nucleic acid programmable DNA binding protein (napDNAbp); (ii) a cytidine deaminase; and (iii) a uracil glycosylase inhibitor domain (UGI), wherein at least one of (i), (ii), or (iii) has be evolved using a continuous evolution process (e.g., PACE) described herein, can be arranged structurally in a variety of configurations, which include, but are not limited to:

NH$_2$-[cytidine deaminase]-[napDNAbp]-[UGI]-[UGI]-COOH;
NH$_2$-[cytidine deaminase]-[UGI]-[napDNAbp]-[UGI]-COOH;
NH$_2$-[UGI]-[cytidine deaminase]-[napDNAbp]-[UGI]-COOH;
NH$_2$-[cytidine deaminase]-[UGI]-[napDNAbp]-[UGI]-COOH;
NH$_2$-[cytidine deaminase]-[UGI]-[UGI]-[napDNAbp]-COOH;
NH$_2$-[UGI]-[cytidine deaminase]-[UGI]-[napDNAbp]-COOH;
NH$_2$-[UGI]-[napDNAbp]-[UGI]-[cytidine deaminase]-COOH;
NH$_2$-[napDNAbp]-[UGI]-[UGI]-[cytidine deaminase]-COOH;
NH$_2$-[napDNAbp]-[UGI]-[cytidine deaminase]-[UGI]-COOH;
NH$_2$-[napDNAbp]-[cytidine deaminase]-[UGI]-[UGI]-COOH;
NH$_2$-[napDNAbp]-[UGI]-[cytidine deaminase]-[UGI]-COOH;
NH$_2$-[UGI]-[napDNAbp]-[cytidine deaminase]-[UGI]-COOH;
NH$_2$-[UGI]-[cytidine deaminase]-[napDNAbp]-[UGI]-COOH;
NH$_2$-[UGI]-[cytidine deaminase]-[UGI]-[napDNAbp]-COOH;
NH$_2$-[UGI]-[UGI]-[cytidine deaminase]-[napDNAbp]-COOH;
NH$_2$-[UGI]-[napDNAbp]-[cytidine deaminase]-[UGI]-COOH;
NH$_2$-[UGI]-[napDNAbp]-[UGI]-[cytidine deaminase]-COOH; and
NH$_2$-[UGI]-[UGI]-[napDNAbp]-[cytidine deaminase]-COOH; wherein each instance of "-" comprises an optional linker.

In some embodiments base editors are evolved using reference base editors, which are summarized below, along with corresponding examples of evolved base editors.

For all sequences below, the text formatting indicates the identity of the base editor components as follows: SV40 BPNLS-deaminase-linker-nCas9-linker-UGI-linker-UGI-SV40 BPNLS The following base editor (SEQ ID NO: 15) includes wild-type rAPOBEC1, which may be used as a reference base editor. This base editor was evolved to generate the evoAPOBEC base editor shown below as (SEQ ID NO: 16).

Full amino acid sequence of wild-type APOBEC BE4Max (SEQ ID NO: 15)
MKRTADGSEFESPKKKRKVSETGPVAVDPTLRRRIEPHEFEVFFDPRELRKETCLLYE

INWGGRHSIWRHTSQNTNKHVEVNFIEKFTTERYFCPNTRCSITWFLSWSPCGECSRAITEFLS

RYPHVTLFIYIARLYHHADPRNRQGLRDLISSGVTIQIMTEQESGYCWRNFVNYSPSNEAHWPR
YPHLWVRLYVLELYCIILGLPPCLNILRRKQPQLTFFTIALQSCHYQRLPPHILWATGLK*SGGS*
*SGGSSGSETPGTSESATPESSGGSSGGS*DKKYSIGLAIGTNSVGWAVITDEYKVPSKKFKVLGN
TDRHSIKKNLIGALLFDSGETAEATRLKRTARRRYTRRKNRICYLQEIFSNEMAKVDDSFFHRL
EESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQL
PGEKKNGLFGNLIALSLGLTPNFKSNFDLAEDAKLQLSKDTYDDDLDNLLAQIGDQYADLFLAA
KNLSDAILLSDILRVNTEITKAPLSASMIKRYDEHHQDLTLLKALVRQQLPEKYKEIFFDQSKN
GYAGYIDGGASQEEFYKFIKPILEKMDGTEELLVKLNREDLLRKQRTFDNGSIPHQIHLGELHA
ILRRQEDFYPFLKDNREKIEKILTFRIPYYVGPLARGNSRFAWMTRKSEETITPWNFEEVVDKG
ASAQSFIERMTNFDKNLPNEKVLPKHSLLYEYFTVYNELTKVKYVTEGMRKPAFLSGEQKKAIV
DLLFKTNRKVTVKQLKEDYFKKIECFDSVEISGVEDRFNASLGTYHDLLKIIKDKDFLDNEENE
DILEDIVLTLTLFEDREMIEERLKTYAHLFDDKVMKQLKRRRYTGWGRLSRKLINGIRDKQSGK
TILDFLKSDGFANRNFMQLIHDDSLTFKEDIQKAQVSGQGDSLHEHIANLAGSPAIKKGILQTV
KVVDELVKVMGRHKPENIVIEMARENQTTQKGQKNSRERMKRIEEGIKELGSQILKEHPVENTQ
LQNEKLYLYYLQNGRDMYVDQELDINRLSDYDVDHIVPQSFLKDDSIDNKVLTRSDKNRGKSDN
VPSEEVVKKMKNYWRQLLNAKLITQRKFDNLTKAERGGLSELDKAGFIKRQLVETRQITKHVAQ
ILDSRMNTKYDENDKLIREVKVITLKSKLVSDFRKDFQFYKVREINNYHHAHDAYLNAVVGTAL
IKKYPKLESEFVYGDYKVYDVRKMIAKSEQEIGKATAKYFFYSNIMNFFKTEITLANGEIRKRP
LIETNGETGEIVWDKGRDFATVRKVLSMPQVNIVKKTEVQTGGFSKESILPKRNSDKLIARKKD
WDPKKYGGFDSPTVAYSVLVVAKVEKGKSKKLKSVKELLGITIMERSSFEKNPIDFLEAKGYKE
VKKDLIIKLPKYSLFELENGRKRMLASAGELQKGNELALPSKYVNFLYLASHYEKLKGSPEDNE
QKQLFVEQHKHYLDEIIEQISEFSKRVILADANLDKVLSAYNKHRDKPIREQAENIIHLFTLTN
LGAPAAFKYFDTTIDRKRYTSTKEVLDATLIHQSITGLYETRIDLSQLGGDSGGSGGSGGS*TNL*
*SDIIEKETGKQLVIQESILMLPEEVEEVIGNKPESDILVHTAYDESTDENVMLLTSDAPEYKPW*
*ALVIQDSNGENKIKMLSGGSGGSGGSTNLSDIIEKETGKQLVIQESILMLPEEVEEVIGNKPES*
*DILVHTAYDESTDENVMLLTSDAPEYKPWALVIQDSNGENKIKMLSGGSKRTADGSEFEPKKKR*
*KV**

The following base editor includes evoAPOBEC, which was evolved based on the base editor provided above (SEQ ID NO: 15).

```
Full amino acid sequence of evoAPOBEC BE4Max
                                              (SEQ ID NO: 16)
```
MKRTADGSEFESPKKKRKVSSKTGPVAVDPTLRRRIEPHEFEVFFDPRELRKETCLLYE
INWGGRHSIWRHTSQNTNKHVEVNFIEKFTTERYFCPNTRCSITWFLSWSPCGECSRAITEFLS
RYPNVTLFIYIARLYHLANPRNRQGLRDLISSGVTIQIMTEQESGYCWHNFVNYSPSNESHWPR
YPHLWVRLYVLELYCIILGLPPCLNILRRKQSQLTSFTIALQSCHYQRLPPHILWATGLK*SGGS*
*SGGSSGSETPGTSESATPESSGGSSGGS*DKKYSIGLAIGTNSVGWAVITDEYKVPSKKFKVLGN
TDRHSIKKNLIGALLFDSGETAEATRLKRTARRRYTRRKNRICYLQEIFSNEMAKVDDSFFHRL
EESFLVEEDKKHERHPIFGNIVDEVAYHEKYPTIYHLRKKLVDSTDKADLRLIYLALAHMIKFR
GHFLIEGDLNPDNSDVDKLFIQLVQTYNQLFEENPINASGVDAKAILSARLSKSRRLENLIAQL -continued

PGEKKNGLFGNLIALSLGLTPNFKSNFDLAEDAKLQLSKDTYDDDLDNLLAQIGDQYADLFLAA

KNLSDAILLSDILRVNTEITKAPLSASMIKRYDEHHQDLTLLLKALVRQQLPEKYKEIFFDQSKN

GYAGYIDGGASQEEFYKFIKPILEKMDGTEELLVKLNREDLLRKQRTFDNGSIPHQIHLGELHA

ILRRQEDFYPFLKDNREKIEKILTFRIPYYVGPLARGNSRFAWMTRKSEETITPWNFEEVVDKG

ASAQSFIERMTNFDKNLPNEKVLPKHSLLYEYFTVYNELTKVKYVTEGMRKPAFLSGEQKKAIV

DLLFKTNRKVTVKQLKEDYFKKIECFDSVEISGVEDRFNASLGTYHDLLKIIKDKDFLDNEENE

DILEDIVLTLTLFEDREMIEERLKTYAHLFDDKVMKQLKRRRYTGWGRLSRKLINGIRDKQSGK

TILDFLKSDGFANRNFMQLIHDDSLTFKEDIQKAQVSGQGDSLHEHIANLAGSPAIKKGILQTV

KVVDELVKVMGRHKPENIVIEMARENQTTQKGQKNSRERMKRIEEGIKELGSQILKEHPVENTA

LQNEKLYLYYLQNGRDMYVDQELDINRLSDYDVDHIVPQSFLKDDSIDNKVLTRSDKNRGKSDN

VPSEEVVKKMKNYWRQLLNAKLITQRKFDNLTKAERGGLSELDKAGFIKRQLVETRQITKHVAQ

ILDSRMNTKYDENDKLIREVKVITLKSKLVSDFRKDFQFYKVREINNYHHAHDAYLNAVVGTAL

IKKYPKLESEFVYGDYKVYDVRKMIAKSEQEIGKATAKYFFYSNIMNFFKTEITLANGEIRKRP

LIETNGETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAKGYKE

VKKDLIIKLPKYSLFELENGRKRMLASAGELQKGNELALPSKYVNFLYLASHYEKLKGSPEDNE

QKQLFVEQHKHYLDEIIEQISEFSKRVILADANLDKVLSAYNKHRDKPIREQAENIIHLFTLTN

LGAPAAFKYFDTTIDRKRYTSTKEVLDATLIHQSITGLYETRIDLSQLGGDSGGSGGSGG*TNL
SDIIEKETGKQLVIQESI LMLPEEVEEVIGNKPESDILVHTAYDESTDENVMLLTSDAPEYKPW
ALVIQDSNGENKIKML* SGGSGGSGGS*TNLSDIIEKETGKQLVIQESILML PEEVEEVIGNKPES
DILVHTAYDESTDEMVMLLTSDAPEYKPWALVIQDSNGENKIKML*SGGS*KRTADGSEFEPKKKR
KV**

The following base editor (SEQ ID NO: 17) includes wild-type pmCDA1, which may be used as a reference base editor. This base editor was evolved to generate the evoCDAbase editor shown below as (SEQ ID NO: 18).

```
Full amino acid sequence of wt-CDA-BE4Max
                                       (SEQ ID NO: 17)
MKRTADGSEFESPKKKRKVSTDAEYVRIHEKLDIYTFKKQFFNNKKSVSH
RCYVLFELKRRGERRACFWGYAVNKPQSGTERGIHAEIFSIRKVEEYLRD
NPGQFTINWYSSWSPCADCAEKILEWYNQELRGNGHTLKIWACKLYYEKN
ARNQIGLWNLRDNGVGLNVMVSEHYQCCRKIFIQSSHNQLNENRWLEKTL
KRAEKRRSELSIMIQVKILHTTKSPAVSGGSSGGSSGSETPGTSESATPE
SSGGSSGGSDKKYSIGLAIGTNSVGWAVITDEYKVPSKKFKVLGNTDRHS
IKKNLIGALLFDSGETAEATRLKRTARRRYTRRKNRICYLQEIFSNEMAK
VDDSFFHRLEESFLVEEDKKHERHPIFGNIVDEVAYHEKYPTIYHLRKKL
VDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLI
ALSLGLTPNFKSNFDLAEDAKLQLSKDTYDDDLDNLLAQIGDQYADLFLA
AKNLSDAILLSDILRVNTEITPILEKMDGTEELLVKLNREDLLRKQRTFD
NGSIPHQIHLGELHAILRRQEDFYPFLKDNREKIEKILTFRIPYYVGPLA
```

-continued

```
RGNSRFAWMTRKSEETITPWNFEEVVDKGASAQSFIERMTNFDKNLPNEK
VLPKHSLLYEYFTVYNELTKVKYVTEGMRKPAFLSGEQKKAIVDLLFKTN
RKVTVKQLKEDYFKKIECFDSVEISGVEDRFNASLGTYHDLLKIIKDKDF
LDNEENEDILEDIVLTLTLFEDREMIEERLKTYAHLFDDKVMKQLKRRRY
TGWGRLSRKLINGIRDKQSGKTILDFLKSDGFANRNFMQLIHDDSLTFKE
DIQKAQVSGQGDSLHEHIANLAGSPAIKKGILQTVKVVDELVKVMGRHKP
ENIVIEMARENQTTQKGQKNSRERMKRIEEGIKELGSQILKEHPVENTQL
QNEKLYLYYLQNGRDMYVDQELDINRLSDYDVDHIVPQSFLKDDSIDNKV
LTRSDKNRGKSDNVPSEEVVKKMKNYWRQLLNAKLITQRKFDNLTKAERG
GLSELDKAGFIKRQLVETRQITKHVAQILDSRMNTKYDENDKLIREVKVI
TLKSKLVSDFRKDFQFYKVREINNYHHAHDAYLNAVVGTALIKKYPKLES
EFVYGDYKVYDVRKMIAKSEQEIGKATAKYFFYSNIMNFFKTEITLANGE
IRKRPLIETNGETGEIVWDKGRDFATVRKVLSMPQVNIVKKTEVQTGGFS
KESILPKRNSDKLIARKKDWDPKKYGGFDSPTVAYSVLVVAKVEKGKSKK
LKSVKELLGITIMERSSFEKNPIDFLEAKGYKEVKKDLIIKLPKYSLFEL
ENGSEFSKRVILADANLDKVLSAYNKHRDKPIREQAENIIHLFTLTNLGA
```

```
-continued
PAAFKYFDTTIDRKRYTSTKEVLDATLIHQSITGLYETRIDLSQLGGDSG

GSGGSGGSTNLSDIIEKETGKQLVIQESILMLPEEVEEVIGNKPESDIL

VHTAYDESTDENVMLLTSDAPEYKPWALVIQDSNGENKIKMLSGGSGGSG

GSTNLSDIIEKETGKQLVIQESILMLPEEVEEVIGNKPESDIL

VHTAYDESTDENVMLLTSDAPEYKPWALVIQDSNGENKIKMLSGGS

KRTADGSEFEPKKKRKV*
```

The following base editor includes evoCDA, which was evolved based on the base editor provided above (SEQ ID NO: 17).

```
Full amino acid sequence of evoCDA-BE4Max
                                    (SEQ ID NO: 18)
MKRTADGSEFESPKKKRKVSTDAEYVRIHEKLDIYTFKKQFSNNKKSVSH

RCYVLFELKRRGERRACFWGYAVNKPQSGTERGIHAEIFSIRKVEEYLRD

NPGQFTINWYSSWSPCADCAEKILEWYNQELRGNGHTLKIWVCKLYYEKN

ARNQIGLWNLRDNGVGLNVMVSEHYQCCRKIFIQSSHNQLNENRWLEKTL

KRAEKRRSELSIMFQVKILHTTKSPAVSGGSSGGGSSGSETPGTSESATPE

SSGGGSSGGSDKKYSIGLAIGTNSVGWAVITDEYKVPSKKFKVLGNTDRHS

IKKNLIGALLFDSGETAEATRLKRTARRRYTRRKNRICYLQEIFSNEMAK

VDDSFFHRLEESFLVEEDKKHERHPIFGNIVDEVAYHEKYPTIYHLRKKL

VDSTDKADLRLIYLALAHMIKFRGHFLIEGDLNPDNSDVDKLFIQLVQTY

NQLFEENPINASGVDAKAILSARLSKSRRLENLIAQLPGEKKNGLFGNLI

ALSLGLTPNFKSNFDLAEDAKLQLSKDTYDDDLDNLLAQIGDQYADLFLA

AKNLSDAILLSDILRVNTEITKAPLSASMIKRYDEHHQDLTLLKALVRQQ

LPEKYKEIFFDQSKNGYAGYIDGGASQEEFYKFIKPILEKMDGTEELLVK

LNREDLLRKQRTFDNGSIPHQIHLGELHAILRRQEDFYPFLKDNREKIEK

ILTFRIPYYVGPLARGNSRFAWMTRKSEETITPWNFEEVVDKGASAQSFI

ERMTNFDKNLPNEKVLPKHSLLYEYFTVYNELTKVKYVTEGMRKPAFLSG

EQKKAIVDLLFKTNRKVTVKQLKEDYFKKIECFDSVEISGVEDRFNASLG

TYHDLLKIIKDKDFLDNEENEDILEDIVLTLTLFEDREMIEERLKTYAHL

FDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVK

VVDELVKVMGRHKPENIVIEMARENQTTKOGKQKNSRERMKRIEEGIKELG

SQILKEHPVENTQLQNEKLYLYYLQNGRDMYVDQELDINRLSDYDVDHIV

PQSFLKDDSIDNKVLTRSDKNRGKSDNVPSEEVVKKMKNYWRQLLNAKLI

TQRKFDNLTKAERGGLSELDKAGFIKRQLVETRQITKHVAQILDSRMNTK

YDENDKLIREVKVITLKSKLVSDFRKDFQFYKVREINNYHHAHDAYLNAV

VGTALIKKYPKLESEFVYGDYKVYDVRKMIAKSEQEIGKATAKYFFYSNI

MNFFKTEITLANGEIRKRPLIETNGETGEIVWDKGRDFATVRKVLSMPQV

NIVKKTEVQTGGFSKESILPKRNSDKLIARKKDWDPKKYGGFDSPTVAYS

VLVVAKVEKGKSKKLKSVKELLGITIMERSSFEKNPIDFLEAKGYKEVKK

DLIIKLPKYSLFELENGRKRMLASAGELQKGNELALPSKYVNFLYLASHY
```

```
-continued
EKLKGSPEDNEQKQLFVEQHKHYLDEIIEQISTKEVLDATLIHQSITGLY

ETRIDLSQLGGDSGGSGGSGGTNLSDIIEKETGKQLVIQESILM

LPEEVEEVIGNKPESDILVHTAYDESTDENVMLLTSDAPEYKPWAL

VIQDSNGENKIKMLSGGSGGSGGSTNLSDIIEKETGKQLVIQESI

LMLPEEVEEVIGNKPESDILVHTAYDESTDENVMLLTSDAPEYKPW

ALVIQDSNGENKIKMLSGGSKRTADGSEFEPKKKRKV*
```

The following base editor (SEQ ID NO: 19) includes wild-type FERNY, which may be used as a reference base editor. This base editor was evolved to generate the evoFERNY base editor shown below as (SEQ ID NO: 20).

```
Full amino acid sequence of FERNY-BE4Max
                                    (SEQ ID NO: 19)
MKRTADGSEFESPKKKRKVSFERNYDPRELRKETYLLYEIKWGKSGKLWR

HWCQNNRTQERNRQGLRDLVNSGVTIRIMDLPDYNYCWKTFVSDQGGDED

YWPGHFAPWIKQYSLKLSGGSSGGSSGSETPGTSESATPESSGGSSGGSD

KKYSIGLAIGTNSVGWAVITDEYKVPSKKFKVLGNTDRHSIKKNLIGALL

FDSGETAEATRLKRTARRRYTRRKNRICYLQEIFSNEMAKVDDSFFHRLE

ESFLVEEDKKHERHPIFGNIVDEVAYHEKYPTIYHLRKKLVDSTDKADLR

LIYLALAHMIKFRGHFLIEGDLNPDNSDVDKLFIQLVQTYNQLFEENPIN

ASGVDAKAILSARLSKSRRLENLIAQLPGEKKNGLFGNLIALSLGLTPNF

KSNFDLAEDAKLQLSKDTYDDDLDNLLAQIGDQYADLFLAAKNLSDAILL

SDILRVNTEITKAPLSASMIKRYDEHHQDLTLLKALVRQQLPEKYKEIFF

DQSKNGYAGYIDGGASQEEFYKFIKPILEKMDGTEELLVKLNREDLLRKQ

RTFDNGSIPHQIHLGELHAILRRQEDFYPFLKDNREKIEKILTFRIPYYV

GPLARGNSRFAWMTRKSEETITPWNFEEVVDKGASAQSFIERMTNFDKNL

PNEKVLPKHSLLYEYFTVYNELTKVKYVTEGMRKPAFLSGEQKKAIVDLL

FKTNRKVTVKQLKEDYFKKIECFDSVEISGVEDRFNASLGTYHDLLKIIK

DKDFLDNEENEDILEDIVLTLTLFEDREMIEERLKTYAHLFDDKVMKQLK

RRRYTGWGRLSRKLINGIRDKQSGKTILDFLKSDGFANRNFMQLIHDDSL

TFKEDIQKAQVSGQGDSLHEHIANLAGSPAIKKGILQTVKVNEKLYLYYL

QNGRDMYVDQELDINRLSDYDVDHIVPQSFLKDDSIDNKVLTRSDKNRGK

SDNVPSEEVVKKMKNYWRQLLNAKLITQRKFDNLTKAERGGLSELDKAGF

IKRQLVETRQITKHVAQILDSRMNTKYDENDKLIREVKVITLKSKLVSDF

RKDFQFYKVREINNYHHAHDAYLNAVVGTALIKKYPKLESEFVYGDYKVY

DVRKMIAKSEQEIGKATAKYFFYSNIMNFFKTEITLANGEIRKRPLIETN

GETGEIVWDKGRDFATVRKVLSMPQVNIVKKTEVQTGGFSKESILPKRNS

DKLIARKKDWDPKKYGGFDSPTVAYSVLVVAKVEKGKSKKLKSVKELLGI

TIMERSSFEKNPIDFLEAKGYKEVKKDLIIKLPKYSLFELENGRKRMLAS

AGELQKGNELALPSKYVNFLYLASHYEKLKGSPEDNEQKQLFVEQHKHYL

DEIIEQISEFSKRVILADANLDKVLSAYNKHRDKPIREQAENIIHLFTLT

NLGAPAAFKYFDTTIDRKRYTSTKEVLDATLIHQSITGLYETRIDLSQLG

GDSGGSGGSGGTNLSDIIEKETGKQLVIQESILMLPEE
```

-continued

VEEVIGNKPESDILVHTAYDESTDENVMLLTSDAPEYKPWAL

VIQDSNGENKIKML SGGSGGSGGTNLSDIIEKETGKQLVIQESI

LMLPEEVEEVIGNKPESDILVHTAYDESTDENVMLLTSDAP

EYKPWALVIQDSNGENKIKML SGGSKRTADGSEFEPKKKRKV*

The following base editor includes evoFERNY, which was evolved based on the base editor provided above (SEQ ID NO: 19).

Full amino acid sequence of evoFERNY-BE4Max
(SEQ ID NO: 20)
MKRTADGSEFESPKKKRKVSFERNYDPRELRKETYLLYEIKWGKSGKLWR

HWCQNNRTQHAEVYFLENIFNARRENPSTHCSITWYLSWSPCAECSQKIV

DFLKEHPNVNLEIYVARLYYPENERNRQGLRDLVNSGVTIRIMDLPDYNY

CWKTFVSDQGGDEDYWPGHFAPWIKQYSLKLSGGSSGGSSGSETPGTSES

ATPESSGGSSGGSDKKYSIGLAIGTNSVGWAVITDEYKVPSKKFKVLGNT

DRHSIKKNLIGALLFDSGETAEATRLKRTARRRYTRRKNRICYLQEIFSN

EMAKVDDSFFHRLEESFLVEEDKKHERHPIFGNIVDEVAYHEKYPTIYHL

RKKLVDSTDKADLRLIYLALAHMIKFRGHFLIEGDLNPDNSDVDKLFIQL

VQTYNQLFEENPINASGVDAKAILSARLSKSRRLENLIAQLPGEKKNGLF

GNLIALSLGLTPNFKSNFDLAEDAKLQLSKDTYDDDLDNLLAQIGDQYAD

LFLAAKNLSDAILLSDILRVNTEITKAPLSASMIKRYDEHHODLTLLKAL

VRQQLPEKYKEIFFDQSKNGYAGYIDGGASQEEFYKFIKPILEKMDGTEE

LLVKLNREDLLRKORTFDNGSIPHQIHLGELHAILRRQEDFYPFLKDNRE

KIEKILTFRIPYYVGPLARGNSRFAWMTRKSEETITPWNFEEVVDKGASA

QSFIERMTNFDKNLPNEKVLPKHSLLYEYFTVYNELTKVKYVTEGMRKPA

FLSGEQKKAIVDLLFKTNRKVTVKQLKEDYFKKIECFDSVEISGVEDRFN

ASLGTYHDLLKIIKDKDFLDNEENEDILEDIVLTLTLFEDREMIEERLKT

YAHLFDDKVMKOLKRRRYTGWGRLSRKLINGIRDKQSGKTILDFLKSDGF

ANRNFMQLIHDDSLTFKEDIQKAQVSGQGDSLHEHIANLAGSPAIKKGIL

QTVKVVDELVKVMGRHKPENIVIEMARENQTTQKGQKNSRERMKRIEEGI

KELGSQILKEHPVENTQLQNEKLYLYYLQNGRDMYVDQELDINRLSDYDV

DHIVPQSFLKDDSIDNKVLTRSDKNRGKSDNVPSEEVVKKMKNYWRQLLN

AKLITQRKFDNLTKAERGGLSELDKAGFIKRQLVETRQITKHVAQILDSR

MNTKYDENDKLIREVKVITLKSKLVSDFRKDFQFYKVREINNYHHAHDAY

LNAVVGTALIKKYPKLESEFVYGDYKVYDVRKMIAKSEQEIGKATAKYFF

YSNIMNFFKTEITLANGEIRKRPLIETNGETGEIVWDKGRDFATVRKVLS

MPQVNIVKKTEVQTGGFSKESILPKRNSDKLIARKKDWDPKKYGGFDSPT

VAYSVLVVAKVEKGKSKKLKSVKELLGITIMERSSFEKNPIDFLEAKGYK

EVKKDLIIKLPKYSLFELENGRKRMLASAGELQKGNELALPSKYVNFLYL

ASHYEKLKGSPEDNEQKQLFVEQHKHYLDEIIEQISEFSKRVILADANLD

KVLSAYNKHRDKPIREQAENIIHLFTLTNLGAPAAFKYFDTTIDRKRYTS

TKEVLDATLIHQSITGLYETRIDLSQLGGDSGGSGGSGGSTNLSD

IIEKETGKQLVIQESILMLPEEVEEVIGNKPSDILVHTA

-continued

YDESTDENVMLLTSDAPEYKPWALVIQDSNGENKIKML SGGSGGSGGS

TNLSDIIEKETGKQLVIQESILMIPEEVEEVIGNKPESDI

LVHTAYDESTDENVMLLTSDAPEYKPWALVIQDSNGENKIKML SGGS

KRTADGSEFEPKKKRKV*

In some embodiments, any of the base editor proteins provided herein may further comprise one or more additional nucleic acid effector moieties, such as, for example, an inhibitor of inosine base excision repair (e.g., a uracil glycosylase inhibitor (UGI) domain or a catalytically inactive inosine-specific nuclease (dISN)). Without wishing to be bound by any particular theory, the UGI domain or dISN may inhibit or prevent base excision repair of a deaminated adenosine residue (e.g., inosine), which may improve the activity or efficiency of the base editor. Additional base editor functionalities are further described herein.

(A) Cas9 Domains

The evolved base editors provided by the instant specification include any suitable Cas9 moiety or equivalent protein, such as a CRISPR associated protein 9, or functional fragment thereof, and embraces any naturally occurring Cas9 from any organism, any naturally-occurring Cas9 equivalent or functional fragment thereof, any Cas9 homolog, ortholog, or paralog from any organism, and any mutant or variant of a Cas9, naturally-occurring or engineered. These Cas9 moieties or equivalent protein may be evolved using a continuous evolution method (e.g., PACE) described herein. The evolved base editors include those in which only the Cas9 moiety is evolved using PACE, or those in which the Cas9 moiety is evolved along with one or more other base editor domains (e.g., a deaminase). The evolved base editors described herein may also include those fusion proteins in which the Cas9 moiety or domain has not been evolved using PACE, but wherein one or more other base editor domains (e.g., deaminase domains) have been evolved using PACE.

More broadly, a Cas9 is a type of "RNA-programmable nuclease" or "RNA-guided nuclease" or "nucleic acid programmable DNA-binding protein." The terms napR/DNAbp or Cas9 are not meant to be particularly limiting. The present disclosure is unlimited with regard to the particular napR/DNAbp, Cas9 or Cas9 equivalent that is employed in the evolved base editors of the invention.

As will be understand in the context of the present disclosure, any Cas9 domain is generally to be regarded as a possible reference polypeptide (i.e., starting point) for processing using the continuous evolution methods (e.g., PACE) described herein. Otherwise, those Cas9 domains which have been evolved using the continuous evolution methods described herein are indicated as such.

In some embodiments, the napR/DNAbp is a Cas moiety.

In various embodiment, the Cas moiety is a S. pyogenes Cas9, which has been mostly widely used as a tool for genome engineering. This Cas9 protein is a large, multi-domain protein containing two distinct nuclease domains. Point mutations can be introduced into Cas9 to abolish nuclease activity, resulting in a dead Cas9 (dCas9) that still retains its ability to bind DNA in a sgRNA-programmed manner. In principle, when fused to another protein or domain, dCas9 can target that protein to virtually any DNA sequence simply by co-expression with an appropriate sgRNA.

In other embodiments, the Cas moiety is a Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisI* (NCBI Ref: NC_018721.1); *Streptococcus thermophilus* (NCBI Ref: YP_820832.1); *Listeria innocua* (NCBI Ref: NP_472073.1); *Campylobacter jejuni* (NCBI Ref: YP_002344900.1); or *Neisseria. meningitidis* (NCBI Ref: YP_002342100.1).

In still other embodiments, the Cas moiety may include any CRISPR associated protein, including but not limited to, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2. Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A.

A Cas moiety may also be referred to as a casn1 nuclease or a CRISPR (clustered regularly interspaced short palindromic repeat)-associated nuclease. As outlined above, CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (mc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. See, e.g., Jinek M., Chylinski K., Fonfara I., Hauer M., Doudna J. A., Charpentier E. Science 337:816-821 (2012), the entire contents of which is hereby incorporated by reference.

Cas9 and equivalents recognizes a short motif in the CRISPR repeat sequences (the PAM or protospacer adjacent motif) to help distinguish self versus non-self. As noted herein, Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607(2011); and "A programmable dual-RNA-guided DNA endonuclease in adaptive bacterial immunity." Jinek M., Chylinski K., Fonfara I., Hauer M., Doudna J. A., Charpentier E. Science 337:816-821(2012), the entire contents of each of which are incorporated herein by reference).

The Cas moiety may include any suitable homologs and/or orthologs. Cas9 homologs and/or orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737; the entire contents of which are incorporated herein by reference. In some embodiments, a Cas9 nuclease has an inactive (e.g., an inactivated) DNA cleavage domain, that is, the Cas9 is a nickase.

In various embodiments, the evolved base editors may comprise a nuclease-inactivated Cas protein may interchangeably be referred to as a "dCas" or "dCas9" protein (for nuclease-"dead" Cas9). Methods for generating a Cas9 protein (or a fragment thereof) having an inactive DNA cleavage domain are known (See, e.g., Jinek et al., *Science*. 337:816-821(2012); Qi et al., "Repurposing CRISPR as an RNA-Guided Platform for Sequence-Specific Control of Gene Expression" (2013) *Cell.* 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H840A completely inactivate the nuclease activity of *S. pyogenes* Cas9 (Jinek et al., *Science*. 337:816-821 (2012); Qi et al., *Cell.* 28; 152(5):1173-83 (2013)). In some embodiments, proteins comprising fragments of Cas9 are provided. For example, in some embodiments, a protein comprises one of two Cas9 domains: (1) the gRNA binding domain of Cas9; or (2) the DNA cleavage domain of Cas9.

In some embodiments, proteins comprising Cas9 or fragments thereof are referred to as "Cas9 variants." A Cas9 variant shares homology to Cas9, or a fragment thereof. For example a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to wild type Cas9. In some embodiments, the Cas9 variant may have 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more amino acid changes compared to a wild type Cas9. In some embodiments, the Cas9 variant comprises a fragment of Cas9 (e.g., a gRNA binding domain or a DNA-cleavage domain), such that the fragment is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% identical to the corresponding fragment of wild type Cas9. In some embodiments, the fragment is at least 30%, at least 35%, at least 40%, at least 45%, at least 50%, at least 55%, at least 60%, at least 65%, at least 70%, at least 75%, at least 80%, at least 85%, at least 90%, at least 95% identical, at least 96%, at least 97%, at least 98%, at least 99%, or at least 99.5% of the amino acid length of a corresponding wild type Cas9.

In some embodiments, the Cas9 fragment is at least 100 amino acids in length. In some embodiments, the fragment is at least 100, 150, 200, 250, 300, 350, 400, 450, 500, 550, 600, 650, 700, 750, 800, 850, 900, 950, 1000, 1050, 1100, 1150, 1200, 1250, or at least 1300 amino acids in length. In some embodiments, wild type Cas9 corresponds to Cas9 from *Streptococcus pyogenes* (NCBI Reference Sequence: NC_017053.1). In other embodiments, wild type Cas9 corresponds to Cas9 from *Streptococcus pyogenes* (NCBI Reference Sequence: NC_002737.2). In still other embodiments, dCas9 corresponds to, or comprises in part or in whole, a Cas9 amino acid sequence having one or more mutations that inactivate the Cas9 nuclease activity.

In some embodiments, the Cas9 domain comprises a D10A mutation, while the residue at position 840 relative to a wild type sequence such as Cas9 from *Streptococcus pyogenes* (NCBI Reference Sequence: NC_017053.1).

Without wishing to be bound by any particular theory, the presence of the catalytic residue H840 restores the activity of the Cas9 to cleave the non-edited (e.g., non-deaminated) strand containing a G opposite the targeted C. Restoration of H840 (e.g., from A840) does not result in the cleavage of the target strand containing the C. Such Cas9 variants are able to generate a single-strand DNA break (nick) at a specific location based on the gRNA-defined target sequence, leading to repair of the non-edited strand, ultimately resulting in a G to A change on the non-edited strand. Briefly, the C of a C-G basepair can be deaminated to a U by a deaminase, e.g., an APOBEC deaminase. Nicking the non-edited strand, having the G, facilitates removal of the G via mismatch repair mechanisms. UGI inhibits UDG, which prevents removal of the U.

In other embodiments, dCas9 variants having mutations other than D10A and H840A are provided, which, e.g., result in nuclease inactivated Cas9 (dCas9). Such mutations, by way of example, include other amino acid substitutions at D10 and H820, or other substitutions within the nuclease domains of Cas9 (e.g., substitutions in the HNH nuclease subdomain and/or the RuvC1 subdomain) with reference to a wild type sequence such as Cas9 from *Streptococcus pyogenes* (NCBI Reference Sequence: NC_017053.1). In some embodiments, variants or homologues of dCas9 (e.g., variants of Cas9 from *Streptococcus pyogenes* (NCBI Reference Sequence: NC_017053.1)) are provided which are at least about 70% identical, at least about 80% identical, at least about 90% identical, at least about 95% identical, at least about 98% identical, at least about 99% identical, at least about 99.5% identical, or at least about 99.9% identical to NCBI Reference Sequence: NC_017053.1. In some embodiments, variants of dCas9 (e.g., variants of NCBI Reference Sequence: NC_017053.1) are provided having amino acid sequences which are shorter, or longer than NC_017053.1 by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids or more.

In some embodiments, the evolved base editors as provided herein comprise the full-length amino acid sequence of a Cas9 protein, e.g., one of the Cas9 sequences provided herein. In other embodiments, however, fusion proteins as provided herein do not comprise a full-length Cas9 sequence, but only a fragment thereof. For example, in some embodiments, a Cas9 fusion protein provided herein comprises a Cas9 fragment, wherein the fragment binds crRNA and tracrRNA or sgRNA, but does not comprise a functional nuclease domain, e.g., in that it comprises only a truncated version of a nuclease domain or no nuclease domain at all. Exemplary amino acid sequences of suitable Cas9 domains and Cas9 fragments are provided herein, and additional suitable sequences of Cas9 domains and fragments will be apparent to those of skill in the art.

It should be appreciated that additional Cas9 proteins (e.g., a nuclease dead Cas9 (dCas9), a Cas9 nickase (nCas9), or a nuclease active Cas9), including variants and homologs thereof, are within the scope of this disclosure. Exemplary Cas9 proteins include, without limitation, those provided below. In some embodiments, the Cas9 protein is a nuclease dead Cas9 (dCas9). In some embodiments, the dCas9 comprises the amino acid sequence (SEQ ID NO: 32). In some embodiments, the Cas9 protein is a Cas9 nickase (nCas9).

In certain embodiments, the evolved base editors of the invention can include a catalytically inactive Cas9 (dCas9) having the following reference sequence:

```
                                           (SEQ ID NO: 32)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII
```

```
KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDAIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD,
``` or an evolved variant thereof that has been evolved using the continuous evolution process (e.g., PACE) described herein.

In other embodiments, the evolved base editors can comprise a Cas9 nickase (nCas9) that comprises an amino acid sequence that is at least 80%, 85%, 90%, 95%, 98%, or 99% identical to the amino acid sequence of:

```
                                            (SEQ ID NO: 9)
DKKYSIGLAIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS

ITGLYETRIDLSQLGGD,
``` and can be an evolved version thereof.

In still other embodiments, the evolved base editors can comprise a catalytically active Cas9 that comprises an amino acid sequence that is at least 80%, 85%, 90%, 95%, 98%, or 99% identical to the amino acid sequence of:

```
                                           (SEQ ID NO: 33)
DKKYSIGLDIGTNSVGWAVITDEYKVPSKKFKVLGNTDRHSIKKNLIGAL

LFDSGETAEATRLKRTARRRYTRRKNRICYLQEIFSNEMAKVDDSFFHRL

EESFLVEEDKKHERHPIFGNIVDEVAYHEKYPTIYHLRKKLVDSTDKADL

RLIYLALAHMIKFRGHFLIEGDLNPDNSDVDKLFIQLVQTYNQLFEENPI

NASGVDAKAILSARLSKSRRLENLIAQLPGEKKNGLFGNLIALSLGLTPN

FKSNFDLAEDAKLQLSKDTYDDDLDNLLAQIGDQYADLFLAAKNLSDAIL

LSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRK

QRTFDNGSIPHQIHLGELHAILRRQEDFYPFLKDNREKIEKILTFRIPYY

VGPLARGNSRFAWMTRKSEETITPWNFEEVVDKGASAQSFIERMTNFDKN

LPNEKVLPKHSLLYEYFTVYNELTKVKYVTEGMRKPAFLSGEQKKAIVDL

LFKTNRKVTVKQLKEDYFKKIECFDSVEISGVEDRFNASLGTYHDLLKII

KDKDFLDNEENEDILEDIVLTLTLFEDREMIEERLKTYAHLFDDKVMKQL

KRRRYTGWGRLSRKLINGIRDKQSGKTILDFLKSDGFANRNFMQLIHDDS

LTFKEDIQKAVSGQGDSLHEHIANLAGSPAIKKGILQTVKVVDELVKVM

GRHKPENIVIEMARENQTTQKGQKNSRERMKRIEEGIKELGSQILKEHPV

ENTQLQNEKLYLYYLQNGRDMYVDQELDINRLSDYDVDHIVPQSFLKDDS

IDNKVLTRSDKNRGKSDNVPSEEVVKKMKNYWRQLLNAKLITQRKFDNLT

KAERGGLSELDKAGFIKRQLVETRQITKHVAQILDSRMNTKYDENDKLIR

EVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEK

GKSKKLKSVKELLGITIMERSSFEKNPIDFLEAKGYKEVKKDLIIKLPKY

SLFELENGRKRMLASAGELQKGNELALPSKYVNFLYLASHYEKLKGSPED

NEQKQLFVEQHKHYLDEIIEQISEFSKRVILADANLDKVLSAYNKHRDKP

IREQAENIIHLFTLTNLGAPAAFKYFDTTIDRKRYTSTKEVLDATLIHQS
```

-continued

ITGLYETRIDLSQLGGD.

In some embodiments, a Cas moiety refers to a Cas9 or Cas9 homolog from archaea (e.g. nanoarchaea), which constitute a domain and kingdom of single-celled prokaryotic microbes. In some embodiments, Cas9 refers to CasX or CasY, which have been described in, for example, Burstein et al., "New CRISPR-Cas systems from uncultivated microbes." Cell Res. 2017 Feb. 21. doi: 10.1038/cr.2017.21, the entire contents of which is hereby incorporated by reference. Using genome-resolved metagenomics, a number of CRISPR-Cas systems were identified, including the first reported Cas9 in the archaeal domain of life. This divergent Cas9 protein was found in little-studied nanoarchaea as part of an active CRISPR-Cas system. In bacteria, two previously unknown systems were discovered, CRISPR-CasX and CRISPR-CasY, which are among the most compact systems yet discovered. In some embodiments, Cas9 refers to CasX, or a variant of CasX. In some embodiments, Cas9 refers to a CasY, or a variant of CasY. It should be appreciated that other RNA-guided DNA binding proteins may be used as a nucleic acid programmable DNA binding protein (napDNAbp), and are within the scope of this disclosure.

In some embodiments, the Cas9 moiety is a nucleic acid programmable DNA binding protein (napDNAbp) of any of the fusion proteins provided herein may be a CasX or CasY protein. In some embodiments, the napDNAbp is a CasX protein. In some embodiments, the napDNAbp is a CasY protein. In some embodiments, the napDNAbp comprises an amino acid sequence that is at least 85%, at least 90%, at least 91%, at least 92%, at least 93%, at least 94%, at least 95%, at least 96%, at least 97%, at least 98%, at least 99%, or at least 99.5% identical to a naturally-occurring CasX or CasY protein. In some embodiments, the napDNAbp is a naturally-occurring CasX or CasY protein. In some embodiments, the napDNAbp comprises an amino acid sequence that is at least 85%, at least 90%, at least 91%, at least 92%, at least 93%, at least 94%, at least 95%, at least 96%, at least 97%, at least 98%, at least 99%, or at least 99.5% identical to a wild-type Cas moiety or any Cas moiety provided herein.

In various embodiments, the nucleic acid programmable DNA binding proteins include, without limitation, Cas9 (e.g., dCas9 and nCas9), CasX, CasY, Cpf1, C2c1, C2c2, C2C3, and Argonaute. One example of a nucleic acid programmable DNA-binding protein that has different PAM specificity than Cas9 is Clustered Regularly Interspaced Short Palindromic Repeats from *Prevotella* and *Francisella* 1 (Cpf1). Similar to Cas9, Cpf1 is also a class 2 CRISPR effector. It has been shown that Cpf1 mediates robust DNA interference with features distinct from Cas9. Cpf1 is a single RNA-guided endonuclease lacking tracrRNA, and it utilizes a T-rich protospacer-adjacent motif (TTN, TTTN, or YTN). Moreover, Cpf1 cleaves DNA via a staggered DNA double-stranded break. Out of 16 Cpf1-family proteins, two enzymes from *Acidaminococcus* and *Lachnospiraceae* are shown to have efficient genome-editing activity in human cells. Cpf1 proteins are known in the art and have been described previously, for example Yamano et al., "Crystal structure of Cpf1 in complex with guide RNA and target DNA." *Cell* (165) 2016, p. 949-962; the entire contents of which is hereby incorporated by reference.

Also useful in the present compositions and methods are nuclease-inactive Cpf1 (dCpf1) variants that may be used as a guide nucleotide sequence-programmable DNA-binding protein domain. The Cpf1 protein has a RuvC-like endonuclease domain that is similar to the RuvC domain of Cas9 but does not have a HNH endonuclease domain, and the N-terminal of Cpf1 does not have the alfa-helical recognition lobe of Cas9. It was shown in Zetsche et al., Cell, 163, 759-771, 2015 (which is incorporated herein by reference) that, the RuvC-like domain of Cpf1 is responsible for cleaving both DNA strands and inactivation of the RuvC-like domain inactivates Cpf1 nuclease activity. For example, mutations corresponding to D917A, E1006A, or D1255A in *Francisella novicida* Cpf1 inactivates Cpf1 nuclease activity. In some embodiments, the dCpf1 of the present disclosure comprises mutations corresponding to D917A, E1006A, D1255A, D917A/E1006A, D917A/D1255A, E1006A/D1255A, or D917A/E1006A/D1255A in SEQ ID NO: 34. It is to be understood that any mutations, e.g., substitution mutations, deletions, or insertions that inactivate the RuvC domain of Cpf1, may be used in accordance with the present disclosure.

In some embodiments, the nucleic acid programmable DNA binding protein (napDNAbp) of any of the fusion proteins provided herein may be a Cpf1 protein. In some embodiments, the Cpf1 protein is a Cpf1 nickase (nCpf1). In some embodiments, the Cpf1 protein is a nuclease inactive Cpf1 (dCpf1). In some embodiments, the Cpf1, the nCpf1, or the dCpf1 comprises an amino acid sequence that is at least 85%, at least 90%, at least 91%, at least 92%, at least 93%, at least 94%, at least 95%, at least 96%, at least 97%, at least 98%, at least 99%, or at least 99.5% identical to any one of SEQ ID NOs: 34-41. In some embodiments, the dCpf1 comprises an amino acid sequence that is at least 85%, at least 90%, at least 91%, at least 92%, at least 93%, at least 94%, at least 95%, at least 96%, at least 97%, at least 98%, at least 99%, or at least 99.5% identical to any one of SEQ ID NOs: 34-41, and comprises mutations corresponding to D917A, E1006A, D1255A, D917A/E1006A, D917A/D1255A, E1006A/D1255A, or D917A/E1006A/D1255A in SEQ ID NO: 34. It should be appreciated that Cpf1 from other bacterial species may also be used in accordance with the present disclosure.

```
Wild type Francisella novicida Cpf1 (SEQ ID NO: 34)
(D917, E1006, and D1255 are bolded and underlined)
                                               (SEQ ID NO: 34)
MSIYQEFVNKYSLSKTLRFELIPQGKTLENIKARGLILDDEKRAKDYKKAKQIIDKYHQFF

IEEILSSVCISEDLLQNYSDVYFKLKKSDDDNLQKDFKSAKDTIKKQISEYIKDSEKFKNL

FNQNLIDAKKGQESDLILWLKQSKDNGIELFKANSDITDIDEALEIIKSFKGWTTYFKGFH

ENRKNVYSSNDIPTSIIYRIVDDNLPKFLENKAKYESLKDKAPEAINYEQIKKDLAEELTF

DIDYKTSEVNQRVFSLDEVFEIANFNNYLNQSGITKFNTIIGGKFVNGENTKRKGINEYIN
```

-continued

LYSQQINDKTLKKYKMSVLFKQILSDTESKSFVIDKLEDDSDVVTTMQSFYEQIAAFKTVE

EKSIKETLSLLFDDLKAQKLDLSKIYFKNDKSLTDLSQQVFDDYSVIGTAVLEYITQQIAP

KNLDNPSKKEQELIAKKTEKAKYLSLETIKLALEEFNKHRDIDKQCRFEEILANFAAIPMI

FDEIAQNKDNLAQISIKYQNQGKKDLLQASAEDDVKAIKDLLDQTNNLLHKLKIFHISQSE

DKANILDKDEHFYLVFEECYFELANIVPLYNKIRNYITQKPYSDEKFKLNFENSTLANGWD

KNKEPDNTAILFIKDDKYYLGVMNKKNNKIFDDKAIKENKGEGYKKIVYKLLPGANKMLPK

VFFSAKSIKFYNPSEDILRIRNHSTHTKNGSPQKGYEKFEFNIEDCRKFIDFYKQSISKHP

EWKDFGFRFSDTQRYNSIDEFYREVENQGYKLTFENISESYIDSVVNQGKLYLFQIYNKDF

SAYSKGRPNLHTLYWKALFDERNLQDVVYKLNGEAELFYRKQSIPKKITHPAKEAIANKNK

DNPKKESVFEYDLIKDKRFTEDKFFFHCPITINFKSSGANKFNDEINLLLKEKANDVHILS

IDRGERHLAYYTLVDGKGNIIKQDTFNIIGNDRMKTNYHDKLAAIEKDRDSARKDWKKINN

IKEMKEGYLSQVVHEIAKLVIEYNAIVVFEDLNFGFKRGRFKVEKQVYQKLEKMLIEKLNY

LVFKDNEFDKTGGVLRAYQLTAPFETFKKMGKQTGIIYYVPAGFTSKICPVTGFVNQLYPK

YESVSKSQEFFSKFDKICYNLDKGYFEFSFDYKNFGDKAAKGKWTIASFGSRLINFRNSDK

NHNWDTREVYPTKELEKLLKDYSIEYGHGECIKAAICGESDKKFFAKLTSVLNTILQMRNS

KTGTELDYLISPVADVNGNFFDSRQAPKNMPQDADANGAYHIGLKGLMLLGRIKNNQEGKK

LNLVIKNEEYFEFVQNRNN

*Francisella novicida* Cpf1 D917A (SEQ ID NO: 35)
(A917, E1006, and D1255 are bolded and underlined)

(SEQ ID NO: 35)

MSIYQEFVNKYSLSKTLRFELIPQGKTLENIKARGLILDDEKRAKDYKKAKKDSEKFKNLF

NQNLIDAKKGQESDLILWLKQSKDNGIELFKANSDITDIDEALEIIKSFKGWTTYFKGFHE

NRKNVYSSNDIPTSIIYRIVDDNLPKFLENKAKYESLKDKAPEAINYEQIKRKGINEYINL

YSQQINDKTLKKYKMSVLFKQILSDTESKSFVIDKLEDDSDVVTTMQSFYEQIAAFKTVEE

KSIKETLSLLFDDLKAQKLDLSKIYFKNDKSLTDLSQQVFDDYSVIGTAVLEYITQQIAPK

NLDNPSKKEQELIAKKTEKAKYLSLETIKLALEEFNKHRDIDKQCRFEEILANFAAIPMIF

DEIAQNKDNLAQISIKYQNQGKKDLLQASAEDDVKAIKDLLDQTNNLLHKLKIFHISQSED

KANILDKDEHFYLVFEECYFELANIVPLYNKIRNYITQKPYSDEKFKLNFENSTLANGWDK

NKEPDNTAILFIKDDKYYLGVMNKKNNKIFDDKAIKENKGEGYKKIVYKLLPGANKMLPKV

FFSAKSIKFYNPSEDILRIRNHSTHTKNGSPQKGYEKFEFNIEDCRKFIDFYKQSISKHPE

WKDFGFRFSDTQRYNSIDEFYREVENQGYKLTFENISESYIDSVVNQGKLYLFQIYNKDFS

AYSKGRPNLHTLYWKALFDERNLQDVVYKLNGEAELFYRKQSIPKKITHPAKEAIANKNKD

NPKKESVFEYDLIKDKRFTEDKFFFHCPITINFKSSGANKFNDEINLLLKEKANDVHILSI

ARGERHLAYYTLVDGKGNIIKQDTFNIIGNDRMKTNYHDKLAAIEKDRDSARKDWKKINNI

KEMKEGYLSQVVHEIAKLVIEYNAIVVFEDLNFGFKRGRFKVEKQVYQKLEKMLIEKLNYL

VFKDNEFDKTGGVLRAYQLTAPFETFKKMGKQTGIIYYVPAGFTSKICPVTGFVNQLYPKY

ESVSKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQMRNSK

TGTELDYLISPVADVNGNFFDSRQAPKNMPQDADANGAYHIGLKGLMLLGRIKNNQEGKKL

NLVIKNEEYFEFVQNRNN

*Francisella novicida* Cpf1 E1006A (SEQ ID NO: 36)
(D917, A1006, and D1255 are bolded and underlined)

(SEQ ID NO: 36)
MSIYQEFVNKYSLSKTLRFELIPQGKTLENIKARGLILDDEKRAKDYKKAKKDSEKFKNLF

NQNLIDAKKGQESDLILWLKQSKDNGIELFKANSDITDIDEALEIIKSFKGWTTYFKGFHE

NRKNVYSSNDIPTSIIYRIVDDNLPKFLENKAKYESLKDKAPEAINYEQIKKDLAEELTFD

IDYKTSEVNQRVFSLDEVFEIANFNNYLNQSGITKFNTIIGGKFVNGENTKRKGINEYINL

YSQQINDKTLKKYKMSVLFKQILSDTESKSFVIDKLEDDSDVVTTMQSFYEQIAAFKTVEE

KSIKETLSLLFDDLKAQKLDLSKIYFKNDKSLTDLSQQVFDDYSVIGTAVLEYITQQIAPK

NLDNPSKKEQELIAKKTEKAKYLSLETIKLALEEFNKHRDIDKQCRFEEILANFAAIPMIF

DEIAQNKDNLAQISIKYQNQGKKDLLQASAEDDVKAIKDLLDQTNNLLHKLKIFHISQSED

KANILDKDEHFYLVFEECYFELANIVPLYNKIRNYITQKPYSDEKFKLNFENSTLANGWDK

NKEPDNTAILFIKDDKYYLGVMNKKNNKIFDDKAIKENKGEGYKKIVYKLLPGANKMLPKV

FFSAKSIKFYNPSEDILRIRNHSTHTKNGSPQKGYEKFEFNIEDCRKFIDFYKQSISKHPE

WKDFGFRFSDTQRYNSIDEFYREVENQGYKLTFENISESYIDSVVNQGKLYLFQIYNKDFS

AYSKGRPNLHTLYWKALFDERNLQDVVYKLNGEAELFYRKQSIPKKITHPAKEAIANKNKD

NPKKESVFEYDLIKDKRFTEDKFFFHCPITINFKSSGANKFNDEINLLLKEKANDVHILSI

DRGERHLAYYTLVDGKGNIIKQDTFNIIGNDRMKTNYHDKLAAIEKDRDSARKDWKKINNI

KEMKEGYLSQVVHEIAKLVIEYNAIVVFADLNFGFKRGRFKVEKQVYQKLEKMLIEKLNYL

VFKDNEFDKTGGVLRAYQLTAPFETFKKMGKQTGIIYYVPAGFTSKICPVTGFVNQLYPKY

ESVSKSQEFFSKFDKICYNLDKGYFEFSFDYKNFGDKAAKGKWTIASFGSRLINFRNSDKN

HNWDTREVYPTKELEKLLKDYSIEYGHGECIKAAICGESDKKFFAKLTSVLNTILQMRNSK

TGTELDYLISPVADVNGNFFDSRQAPKNMPQDADANGAYHIGLKGLMLLGRIKNNQEGKKL

NLVIKNEEYFEFVQNRNN

*Francisella novicida* Cpf1 D1255A (SEQ ID NO: 37)
(D917, E1006, and A1255 are bolded and underlined)

(SEQ ID NO: 37)
MSIYQEFVNKYSLSKTLRFELIPQGKTLENIKARGLILDDEKRAKDYKKAKQIIDKYHQFF

IEEILSSVCISEDLLQNYSDVYFKLKKSDDDNLQKDFKSAKDTIKKQISEYIKDSEKFKNL

FNQNLIDAKKGQESDLILWLKQSKDNGIELFKANSDITDIDEALEIIKSFKGWTTYFKGFH

ENRKNVYSSNDIPTSIIYRIVDDNLPKFLENKAKYESLKDKAPEAINYEQIKKDLAEELTF

DIDYKTSEVNQRVFSLDEVFEIANFNNYLNQSGITKFNTIIGGKFVNGENTKRKGINEYIN

LYSQQINDKTLKKYKMSVLFKQILSDTESKSFVIDKLEDDSDVVTTMQSFYEQIAAFKTVE

EKSIKETLSLLFDDLKAQKLDLSKIYFKNDKSLTDLSQQVFDDYSVIGTAVLEYITQQIAP

KNLDNPSKKEQELIAKKTEKAKYLSLETIKLALEEFNKHRDIDKQCRFEEILANFAAIPMI

FDEIAQNKDNLAQISIKYQNQGKKDLLQASAEDDVKAIKDLLDQTNNLLHKLKIFHISQSE

DKANILDKDEHFYLVFEECYFELANIVPLYNKIRNYITQKPYSDEKFKLNFENSTLANGWD

KNKEPDNTAILFIKDDKYYLGVMNKKNNKIFDDKAIKENKGEGYKKIVYKLLPGANKMLPK

VFFSAKSIKFYNPSEDILRIRNHSTHTKNGSPQKGYEKFEFNIEDCRKFIDFYKQSISKHP

EWKDFGFRFSDTQRYNSIDEFYREVENQGYKLTFENISESYIDSVVNQGKLYLFQIYNKDF

SAYSKGRPNLHTLYWKALFDERNLQDVVYKLNGEAELFYRKQSIPKKITHPAKEAIANKNK

DNPKKESVFEYDLIKDKRFTEDKFFFHCPITINFKSSGANKFNDEINLLLKEKANDVHILS

IDRGERHLAYYTLVDGKGNIIKQDTFNIIGNDRMKTNYHDKLAAIEKDRDSARKDWKKINN

IKEMKEGYLSQVVHEIAKLVIEYNAIVVFEDLNFGFKRGRFKVEKQVYQKLEKMLIEKLNY

-continued

LVFKDNEFDKTGGVLRAYQLTAPFETFKKMGKQTGIIYYVPAGFTSKICPVTGFVNQLYPK

YESVSKSQEFFSKFDKICYNLDKGYFEFSFDYKNFGDKAAKGKWTIASFGSRLINFRNSDK

NHNWDTREVYPTKELEKLLKDYSIEYGHGECIKAAICGESDKKFFAKLTSVLNTILQMRNS

KTGTELDYLISPVADVNGNFFDSRQAPKNMPQDAAANGAYHIGLKGLMLLGRIKNNQEGKK

LNLVIKNEEYFEFVQNRNN

*Francisella novicida* Cpf1 D917A/E1006A (SEQ ID NO: 38)
(A917, A1006, and D1255 are bolded and underlined)
(SEQ ID NO: 38)
MSIYQEFVNKYSLSKTLRFELIPQGKTLENIKARGLILDDEKRAKDYKKAKQIIDKYHQFF

IEEILSSVCISEDLLQNYSDVYFKLKKSDDDNLQKDFKSAKDTIKKQISEYIKDSEKFKNL

FNQNLIDAKKGQESDLILWLKQSKDNGIELFKANSDITDIDEALEIIKSFKGWTTYFKGFH

ENRKNVYSSNDIPTSIIYRIVDDNLPKFLENKAKYESLKDKAPEAINYEQIKKDLAEELTF

DIDYKTSEVNQRVFSLDEVFEIANFNNYLNQSGITKFNTIIGGKFVNGENTKRKGINEYIN

LYSQQINDKTLKKYKMSVLFKQILSDTESKSFVIDKLEDDSDVVTTMQSFYEQIAAFKTVE

EKSIKETLSLLFDDLKAQKLDLSKIYFKNDKSLTDLSQQVFDDYSVIGTAVLEYITQQIAP

KNLDNPSKKEQELIAKKTEKAKYLSLETIKLALEEFNKHRDIDKQCRFEEILANFAAIPMI

FDEIAQNKDNLAQISIKYQNGKKDLLQASAEDDVKAIKDLLDQTNNLLHKLKIFHISQSE

DKANILDKDEHFYLVFEECYFELANIVPLYNKIRNYITQKPYSDEKFKLNFENSTLANGWD

KNKEPDNTAILFIKDDKYYLGVMNKKNNKIFDDKAIKENKGEGYKKIVYKLLPGANKMLPK

VFFSAKSIKFYNPSEDILRIRNHSTHTKNGSPQKGYEKFEFNIEDCRKFIDFYKQSISKHP

EWKDFGFRFSDTQRYNSIDEFYREVENQGYKLTFENISESYIDSVVNQGKLYLFQIYNKDF

SAYSKGRPNLHTLYWKALFDERNLQDVVYKLNGEAELFYRKQSIPKKITHPAKEAIANKNK

DNPKKESVFEYDLIKDKRFTEDKFFFHCPITINFKSSGANKFNDEINLLLKEKANDVHILS

IARGERHLAYYTLVDGKGNIIKQDTFNIIGNDRMKTNYHDKLAAIEKDRDSARKDWKKINN

IKEMKEGYLSQVVHEIAKLVIEYNAIVVFADLNFGFKRGRFKVEKQVYQKLEKMLIEKLNY

LVFKDNEFDKTGGVLRAYQLTAPFETFKKMGKQTGIIYYVPAGFTSKICPVTGFVNQLYPK

YESVSKSQEFFSKFDKICYNLDKGYFEFSFDYKNFGDKAAKGKWTIASFGSRLINFRNSDK

NHNWDTREVYPTKELEKLLKDYSIEYGHGECIKAAICGESDKKFFAKLTSVLNTILQMRNS

KTGTELDYLISPVADVNGNFFDSRQAPKNMPQDADANGAYHIGLKGLMLLGRIKNNQEGKK

LNLVIKNEEYFEFVQNRNN

*Francisella novicida* Cpf1 D917A/D1255A (SEQ ID NO: 39)
(A917, E1006, and A1255 are bolded and underlined)
(SEQ ID NO: 39)
MSIYQEFVNKYSLSKTLRFELIPQGKTLENIKARGLILDDEKRAKDYKKAKQIIDKYHQFF

IEEILSSVCISEDLLQNYSDVYFKLKKSDDDNLQKDFKSAKDTIKKQISEYIKDSEKFKNL

FNQNLIDAKKGQESDLILWLKQSKDNGIELFKANSDITDIDEALEIIKSFKGWTTYFKGFH

ENRKNVYSSNDIPTSIIYRIVDDNLPKFLENKAKYESLKDKAPEAINYEQIKKDLAEELTF

DIDYKTSEVNQRVFSLDEVFEIANFNNYLNQSGITKFNTIIGGKFVNGENTKRKGINEYIN

LYSQQINDKTLKKYKMSVLFKQILSDTESKSFVIDKLEDDSDVVTTMQSFYEQIAAFKTVE

EKSIKETLSLLFDDLKAQKLDLSKIYFKNDKSLTDLSQQVFDDYSVIGTAVLEYITQQIAP

KNLDNPSKKEQELIAKKTEKAKYLSLETIKLALEEFNKHRDIDKQCRFEEILANFAAIPMI

FDEIAQNKDNLAQISIKYQNGKKDLLQASAEDDVKAIKDLLDQTNNLLHKLKIFHISQSE

DKANILDKDEHFYLVFEECYFELANIVPLYNKIRNYITQKPYSDEKFKLNFENSTLANGWD

```
KNKEPDNTAILFIKDDKYYLGVMNKKNNKIFDDKAIKENKGEGYKKIVYKLLPGANKMLPK

VFFSAKSIKFYNPSEDILRIRNHSTHTKNGSPQKGYEKFEFNIEDCRKFIDFYKQSISKHP

EWKDFGFRFSDTQRYNSIDEFYREVENQGYKLTFENISESYIDSVVNQGKLYLFQIYNKDF

SAYSKGRPNLHTLYWKALFDERNLQDVVYKLNGEAELFYRKQSIPKKITHPAKEAIANKNK

DNPKKESVFEYDLIKDKRFTEDKFFFHCPITINFKSSGANKFNDEINLLLKEKANDVHILS

IARGERHLAYYTLVDGKGNIIKQDTFNIIGNDRMKTNYHDKLAAIEKDRDSARKDWKKINN

IKEMKEGYLSQVVHEIAKLVIEYNAIVVFEDLNFGFKRGRFKVEKQVYQKLEKMLIEKLNY

LVFKDNEFDKTGGVLRAYQLTAPFETFKKMGKQTGIIYYVPAGFTSKICPVTGFVNQLYPK

YESVSKSQEFFSKFDKICYNLDKGYFEFSFDYKNFGDKAAKGKWTIASFGSRLINFRNSDK

NHNWDTREVYPTKELEKLLKDYSIEYGHGECIKAAICGESDKKFFAKLTSVLNTILQMRNS

KTGTELDYLISPVADVNGNFFDSRQAPKNMPQDAAANGAYHIGLKGLMLLGRIKNNQEGKK

LNLVIKNEEYFEFVQNRNN
```

*Francisella novicida* +Cpf1 E1006A/D1255A (SEQ ID NO: 40) (D917, A1006, and A1255 are bolded and underlined)

(SEQ ID NO: 40)

MSIYQEFVNKYSLSKTLRFELIPQGKTLENIKARGLILDDEKRAKDYKKAKQIIDKYHQFF

IEEILSSVCISEDLLQNYSDVYFKLKKSDDDNLQKDFKSAKDTIKKQISEYIKDSEKFKNL

FNQNLIDAKKGQESDLILWLKQSKDNGIELFKANSDITDIDEALEIIKSFKGWTTYFKGFH

ENRKNVYSSNDIPTSIIYRIVDDNLPKFLENKAKYESLKDKAPEAINYEQIKKDLAEELTF

DIDYKTSEVNQRVFSLDEVFEIANFNNYLNQSGITKFNTIIGGKFVNGENTKRKGINEYIN

LYSQQINDKTLKKYKMSVLFKQILSDTESKSFVIDKLEDDSDVVTTMQSFYEQIAAFKTVE

EKSIKETLSLLFDDLKAQKLDLSKIYFKNDKSLTDLSQQVFDDYSVIGTAVLEYITQQIAP

KNLDNPSKKEQELIAKKTEKAKYLSLETIKLALEEFNKHRDIDKQCRFEEILANFAAIPMI

FDEIAQNKDNLAQISIKYQNQGKKDLLQASAEDDVKAIKDLLDQTNNLLHKLKIFHISQSE

DKANILDKDEHFYLVFEECYFELANIVPLYNKIRNYITQKPYSDEKFKLNFENSTLANGWD

KNKEPDNTAILFIKDDKYYLGVMNKKNNKIFDDKAIKENKGEGYKKIVYKLLPGANKMLPK

VFFSAKSIKFYNPSEDILRIRNHSTHTKNGSPQKGYEKFEFNIEDCRKFIDFYKQSISKHP

EWKDFGFRFSDTQRYNSIDEFYREVENQGYKLTFENISESYIDSVVNQGKLYLFQIYNKDF

SAYSKGRPNLHTLYWKALFDERNLQDVVYKLNGEAELFYRKQSIPKKITHPAKEAIANKNK

DNPKKESVFEYDLIKDKRFTEDKFFFHCPITINFKSSGANKFNDEINLLLKEKANDVHILS

IDRGERHLAYYTLVDGKGNIIKQDTFNIIGNDRMKTNYHDKLAAIEKDRDSARKDWKKINN

IKEMKEGYLSQVVHEIAKLVIEYNAIVVFADLNFGFKRGRFKVEKQVYQKLEKMLIEKLNY

LVFKDNEFDKTGGVLRAYQLTAPFETFKKMGKQTGIIYYVPAGFTSKICPVTGFVNQLYPK

YESVSKSQEFFSKFDKICYNLDKGYFEFSFDYKNFGDKAAKGKWTIASFGSRLINFRNSDK

NHNWDTREVYPTKELEKLLKDYSIEYGHGECIKAAICGESDKKFFAKLTSVLNTILQMRNS

KTGTELDYLISPVADVNGNFFDSRQAPKNMPQDAAANGAYHIGLKGLMLLGRIKNNQEGKK

LNLVIKNEEYFEFVQNRNN

*Francisella novicida* Cpf1 D917A/E1006A/D1255A (SEQ ID NO: 41) (A917, A1006, and A1255 are bolded and underlined)

(SEQ ID NO: 41)

MSIYQEFVNKYSLSKTLRFELIPQGKTLENIKARGLILDDEKRAKDYKKAKQIIDKYHQFF

IEEILSSVCISEDLLQNYSDVYFKLKKSDDDNLQKDFKSAKDTIKKQISEYIKDSEKFKNL

FNQNLIDAKKGQESDLILWLKQSKDNGIELFKANSDITDIDEALEIIKSFKGWTTYFKGFH

```
-continued
ENRKNVYSSNDIPTSIIYRIVDDNLPKFLENKAKYESLKDKAPEAINYEQIKKDLAEELTF

DIDYKTSEVNQRVFSLDEVFEIANFNNYLNQSGITKFNTIIGGKFVNGENTKRKGINEYIN

LYSQQINDKTLKKYKMSVLFKQILSDTESKSFVIDKLEDDSDVVTTMQSFYEQIAAFKTVE

EKSIKETLSLLFDDLKAQKLDLSKIYFKNDKSLTDLSQQVFDDYSVIGTAVLEYITQQIAP

KNLDNPSKKEQELIAKKTEKAKYLSLETIKLALEEFNKHRDIDKQCRFEEILANFAAIPMI

FDEIAQNKDNLAQISIKYQNQGKKDLLQASAEDDVKAIKDLLDQTNNLLHKLKIFHISQSE

DKANILDKDEHFYLVFEECYFELANIVPLYNKIRNYITQKPYSDEKFKLNFENSTLANGWD

KNKEPDNTAILFIKDDKYYLGVMNKKNNKIFDDKAIKENKGEGYKKIVYKLLPGANKMLPK

VFFSAKSIKFYNPSEDILRIRNHSTHTKNGSPQKGYEKFEFNIEDCRKFIDFYKQSISKHP

EWKDFGFRFSDTQRYNSIDEFYREVENQGYKLTFENISESYIDSVVNQGKLYLFQIYNKDF

SAYSKGRPNLHTLYWKALFDERNLQDVVYKLNGEAELFYRKQSIPKKITHPAKEAIANKNK

DNPKKESVFEYDLIKDKRFTEDKFFFHCPITINFKSSGANKFNDEINLLLKEKANDVHILS

IARGERHLAYYTLVDGKGNIIKQDTFNIIGNDRMKTNYHDKLAAIEKDRDSARKDWKKINN

IKEMKEGYLSQVVHEIAKLVIEYNAIVVFADLNFGFKRGRFKVEKQVYQKLEKMLIEKLNY

LVFKDNEFDKTGGVLRAYQLTAPFETFKKMGKQTGIIYYVPAGFTSKICPVTGFVNQLYPK

YESVSKSQEFFSKFDKICYNLDKGYFEFSFDYKNFGDKAAKGKWTIASFGSRLINFRNSDK

NHNWDTREVYPTKELEKLLKDYSIEYGHGECIKAAICGESDKKFFAKLTSVLNTILQMRNS

KTGTELDYLISPVADVNGNFFDSRQAPKNMPQDAAANGAYHIGLKGLMLLGRIKNNQEGKK

LNLVIKNEEYFEFVQNRNN
```

In some embodiments, the nucleic acid programmable DNA binding protein (napDNAbp) is a nucleic acid programmable DNA binding protein that does not require a canonical (NGG) PAM sequence. In some embodiments, the napDNAbp is an argonaute protein. One example of such a nucleic acid programmable DNA binding protein is an Argonaute protein from *Natronobacterium gregoryi* (NgAgo). NgAgo is a ssDNA-guided endonuclease. NgAgo binds 5' phosphorylated ssDNA of ~24 nucleotides (gDNA) to guide it to its target site and will make DNA double-strand breaks at the gDNA site. In contrast to Cas9, the NgAgo-gDNA system does not require a protospacer-adjacent motif (PAM). Using a nuclease inactive NgAgo (dNgAgo) can greatly expand the bases that may be targeted. The characterization and use of NgAgo have been described in Gao et al., *Nat Biotechnol.*, 2016 July; 34(7):768-73. PubMed PMID: 27136078; Swarts et al., *Nature.* 507(7491) (2014): 258-61; and Swarts et al., *Nucleic Acids Res.* 43(10) (2015): 5120-9, each of which is incorporated herein by reference. The sequence of *Natronobacterium gregoryi* Argonaute is provided in SEQ ID NO: 42.

```
Wild type Natronobacterium gregoryi
Argonaute (SEQ ID NO: 42)
                                        (SEQ ID NO: 42)
MTVIDLDSTTTADELTSGHTYDISVTLTGVYDNTDEQHPRMSLAFEQDNG

ERRYITLWKNTTPKDVFTYDYATGSTYIFTNIDYEVKDGYENLTATYQTT

VENATAQEVGTTDEDETFAGGEPLDHHLDDALNETPDDAETESDSGHVMT

SFASRDQLPEWTLHTYTLTATDGAKTDTEYARRTLAYTVRQELYTDHDAA

PVATDGLMLLTPEPLGETPLDLDCGVRVEADETRTLDYTTAKDRLLAREL
```

```
-continued
VEEGLKRSLWDDYLVRGIDEVLSKEPVLTCDEFDLHERYDLSVEVGHSGR

AYLHINFRHRFVPKLTLADIDDDNIYPGLRVKTTYRPRRGHIVWGLRDEC

ATDSLNTLGNQSVVAYHRNNQTPINTDLLDAIEAADRRVVETRRQGHGDD

AVSFPQELLAVEPNTHQIKQFASDGFHQQARSKTRLSASRCSEKAQAFAE

RLDPVRLNGSTVEFSSEFFTGNNEQQLRLLYENGESVLTFRDGARGAHPD

ETFSKGIVNPPESFEVAVVLPEQQADTCKAQWDTMADLLNQAGAPPTRSE

TVQYDAFSSPESISLNVAGAIDPSEVDAAFVVLPPDQEGFADLASPTETY

DELKKALANMGIYSQMAYFDRFRDAKIFYTRNVALGLLAAAGGVAFTTEH

AMPGDADMFIGIDVSRSYPEDGASGQINIAATATAVYKDGTILGHSSTRP

QLGEKLQSTDVRDIMKNAILGYQQVTGESPTHIVIHRDGFMNEDLDPATE

FLNEQGVEYDIVEIRKQPQTRLLAVSDVQYDTPVKSIAAINQNEPRATVA

TFGAPEYLATRDGGGLPRPIQIERVAGETDIETLTRQVYLLSQSHIQVHN

STARLPITTAYADQASTHATKGYLVQTGAFESNVGFL
```

In some embodiments, the napDNAbp is a prokaryotic homolog of an Argonaute protein. Prokaryotic homologs of Argonaute proteins are known and have been described, for example, in Makarova K., et al., "Prokaryotic homologs of Argonaute proteins are predicted to function as key components of a novel system of defense against mobile genetic elements", *Biol Direct.* 2009 Aug. 25; 4:29. doi: 10.1186/1745-6150-4-29, the entire contents of which is hereby incorporated by reference. In some embodiments, the napDNAbp is a *Marinitoga piezophila* Argunaute (MpAgo) protein. The CRISPR-associated *Marinitoga piezophila* Argunaute (MpAgo) protein cleaves single-stranded target sequences using 5'-phosphorylated guides. The 5' guides are used by all known Argonautes. The crystal structure of an MpAgo-RNA complex shows a guide strand binding site comprising residues that block 5' phosphate interactions. This data suggests the evolution of an Argonaute subclass with noncanonical specificity for a 5'-hydroxylated guide. See, e.g., Kaya et al., "A bacterial Argonaute with noncanonical guide RNA specificity", *Proc Natl Acad Sci USA.* 2016 Apr. 12; 113(15):4057-62, the entire contents of which are hereby incorporated by reference). It should be appreciated that other argonaute proteins may be used, and are within the scope of this disclosure.

In some embodiments, the nucleic acid programmable DNA binding protein (napDNAbp) is a single effector of a microbial CRISPR-Cas system. Single effectors of microbial CRISPR-Cas systems include, without limitation, Cas9, Cpf1, C2c1, C2c2, and C2c3. Typically, microbial CRISPR-Cas systems are divided into Class 1 and Class 2 systems. Class 1 systems have multisubunit effector complexes, while Class 2 systems have a single protein effector. For example, Cas9 and Cpf1 are Class 2 effectors. In addition to Cas9 and Cpf1, three distinct Class 2 CRISPR-Cas systems (C2c1, C2c2, and C2c3) have been described by Shmakov et al., "Discovery and Functional Characterization of Diverse Class 2 CRISPR Cas Systems", *Mol. Cell,* 2015 Nov. 5; 60(3): 385-397, the entire contents of which is hereby incorporated by reference. Effectors of two of the systems, C2c1 and C2c3, contain RuvC-like endonuclease domains related to Cpf1. A third system, C2c2 contains an effector with two predicated HEPN RNase domains. Production of mature CRISPR RNA is tracrRNA-independent, unlike production of CRISPR RNA by C2c1. C2c1 depends on both CRISPR RNA and tracrRNA for DNA cleavage. Bacterial C2c2 has been shown to possess a unique RNase activity for CRISPR RNA maturation distinct from its RNA-activated single-stranded RNA degradation activity. These RNase functions are different from each other and from the CRISPR RNA-processing behavior of Cpf1. See, e.g., East-Seletsky, et al., "Two distinct RNase activities of CRISPR-C2c2 enable guide-RNA processing and RNA detection", *Nature,* 2016 Oct. 13; 538(7624):270-273, the entire contents of which are hereby incorporated by reference. In vitro biochemical analysis of C2c2 in *Leptotrichia shahii* has shown that C2c2 is guided by a single CRISPR RNA and can be programed to cleave ssRNA targets carrying complementary protospacers. Catalytic residues in the two conserved HEPN domains mediate cleavage. Mutations in the catalytic residues generate catalytically inactive RNA-binding proteins. See e.g., Abudayyeh et al., "C2c2 is a single-component programmable RNA-guided RNA-targeting CRISPR effector", *Science,* 2016 Aug. 5; 353(6299), the entire contents of which are hereby incorporated by reference.

The crystal structure of *Alicyclobaccillus acidoterrastris* C2c1 (AacC2c1) has been reported in complex with a chimeric single-molecule guide RNA (sgRNA). See e.g., Liu et al., "C2c1-sgRNA Complex Structure Reveals RNA-Guided DNA Cleavage Mechanism", *Mol. Cell,* 2017 Jan. 19; 65(2):310-322, the entire contents of which are hereby incorporated by reference. The crystal structure has also been reported in *Alicyclobacillus acidoterrastris* C2c1 bound to target DNAs as ternary complexes. See e.g., Yang et al., "PAM-dependent Target DNA Recognition and Cleavage by C2C1 CRISPR-Cas endonuclease", *Cell,* 2016 Dec. 15; 167(7):1814-1828, the entire contents of which are hereby incorporated by reference. Catalytically competent conformations of AacC2c1, both with target and non-target DNA strands, have been captured independently positioned within a single RuvC catalytic pocket, with C2c1-mediated cleavage resulting in a staggered seven-nucleotide break of target DNA. Structural comparisons between C2c1 ternary complexes and previously identified Cas9 and Cpf1 counterparts demonstrate the diversity of mechanisms used by CRISPR-Cas9 systems.

In some embodiments, the nucleic acid programmable DNA binding protein (napDNAbp) of any of the fusion proteins provided herein may be a C2c1, a C2c2, or a C2c3 protein. In some embodiments, the napDNAbp is a C2c1 protein. In some embodiments, the napDNAbp is a C2c2 protein. In some embodiments, the napDNAbp is a C2c3 protein. In some embodiments, the napDNAbp comprises an amino acid sequence that is at least 85%, at least 90%, at least 91%, at least 92%, at least 93%, at least 94%, at least 95%, at least 96%, at least 97%, at least 98%, at least 99%, or at least 99.5% identical to a naturally-occurring C2c1, C2c2, or C2c3 protein. In some embodiments, the napDNAbp is a naturally-occurring C2c1, C2c2, or C2c3 protein. In some embodiments, the napDNAbp comprises an amino acid sequence that is at least 85%, at least 90%, at least 91%, at least 92%, at least 93%, at least 94%, at least 95%, at least 96%, at least 97%, at least 98%, at least 99%, or at least 99.5% identical to any one of SEQ ID NOs: 43 or 44. In some embodiments, the napDNAbp comprises an amino acid sequence of any one SEQ ID NOs: 43 or 44. It should be appreciated that C2c1, C2c2, or C2c3 from other bacterial species may also be used in accordance with the present disclosure.

```
C2c1 (uniprot.org/uniprot/T0D7A2#)
sp|T0D7A2|C2C1_ALIAG CRISPR-associated
endonuclease C2c1 OS = Alicyclobacillus
acidoterrestris (strain ATCC 49025/DSM
3922/CIP 106132/NCIMB 13137/GD3B) GN =
c2c1 PE = 1 SV = 1
```
(SEQ ID NO: 43)

MAVKSIKVKLRLDDMPEIRAGLWKLHKEVNAGVRYYTEWLSLLRQENLYR

RSPNGDGEQECDKTAEECKAELLERLRARQVENGHRGPAGSDDELLQLAR

QLYELLVPQAIGAKGDAQQIARKFLSPLADKDAVGGLGIAKAGNKPRWVR

MREAGEPGWEEEKEKAETRKSADRTADVLRALADFGLKPLMRVYTDSEMS

SVEWKPLRKGQAVRTWDRDMFQQAIERMMSWESWNQRVGQEYAKLVEQKN

RFEQKNFVGQEHLVHLVNQLQQDMKEASPGLESKEQTAHYVTGRALRGSD

KVFEKWGKLAPDAPFDLYDAEIKNVQRRNTRRFGSHDLFAKLAEPEYQAL

WREDASFLTRYAVYNSILRKLNHAKMFATFTLPDATAHPIWTRFDKLGGN

LHQYTFLFNEFGERRHAIRFHKLLKVENGVAREVDDVTVPISMSEQLDNL

LPRDPNEPIALYFRDYGAEQHFTGEFGGAKIQCRRDQLAHMHRRRGARDV

YLNVSVRVQSQSEARGERRPPYAAVFRLVGDNHRAFVHFDKLSDYLAEHP

DDGKLGSEGLLSGLRVMSVDLGLRTSASISVFRVARKDELKPNSKGRVPF

FFPIKGNDNLVAVHERSQLLKLPGETESKDLRAIREERQRTLRQLRTQLA

YLRLLVRCGSEDVGRRERSWAKLIEQPVDAANHMTPDWREAFENELQKLK

SLHGICSDKEWMDAVYESVRRVWRHMGKQVRDWRKDVRSGERPKIRGYAK

DVVGGNSIEQIEYLERQYKFLKSWSFFGKVSGQVIRAEKGSRFAITLREH

IDHAKEDRLKKLADRIIMEALGYVYALDERGKGKWVAKYPPCQLILLEEL

SEYQFNNDRPPSENNQLMQWSHRGVFQELINQAQVHDLLVGTMYAAFSSR

FDARTGAPGIRCRRVPARCTQEHNPEPFPWWLNKFVVEHTLDACPLRADD

```
-continued
LIPTGEGEIFVSPFSAEEGDFHQIHADLNAAQNLQQRLWSDFDISQIRLR

CDWGEVDGELVLIPRLTGKRTADSYSNKVFYTNTGVTYYERERGKKRRKV

FAQEKLSEEEAELLVEADEAREKSVVLMRDPSGIINRGNWTRQKEFWSMV

NQRIEGYLVKQIRSRVPLQDSACENTGDI

C2c2 (uniprot.org/uniprot/P0DOC6)
>sp|P0DOC6|C2C2_LEPSD CRISPR-associated
endoribonuclease C2c2 OS = Leptotrichia
shahii (strain DSM 19757/CCUG 47503/CIP
107916/JCM 16776/LB37) GN = c2c2 PE = 1
SV = 1
                                   (SEQ ID NO: 44)
MGNLFGHKRWYEVRDKKDFKIKRKVKVKRNYDGNKYILNINENNNKEKID

NNKFIRKYINYKKNDNILKEFTRKFHAGNILFKLKGKEGIIRIENNDDFL

ETEEVVLYIEAYGKSEKLKALGITKKKIIDEAIRQGITKDDKKIEIKRQE

NEEEIEIDIRDEYTNKTLNDCSIILRIIENDELETKKSIYEIFKNINMSL

YKIIEKIIENETEKVFENRYYEEHLREKLLKDDKIDVILTNFMEIREKIK

SNLEILGFVKFYLNVGGDKKKSKNKKMLVEKILNINVDLTVEDIADFVIK

ELEFWNITKRIEKVKKVNNEFLEKRRNRTYIKSYVLLDKHEKFKIERENK

KDKIVKFFVENIKNNSIKEKIEKILAEFKIDELIKKLEKELKKGNCDTEI

FGIFKKHYKVNFDSKKFSKKSDEEKELYKIIYRYLKGRIEKILVNEQKVR

LKKMEKIEIEKILNESILSEKILKRVKQYTLEHIMYLGKLRHNDIDMTTV

NTDDFSRLHAKEELDLELITFFASTNMELNKIFSRENINNDENIDFFGGD

REKNYVLDKKILNSKIKIIRDLDFIDNKNNITNNFIRKFTKIGTNERNRI

LHAISKERDLQGTQDDYNKVINIIQNLKISDEEVSKALNLDVVFKDKKNI

ITKINDIKISEENNNDIKYLPSFSKVLPEILNLYRNNPKNEPFDTIETEK

IVLNALIYVNKELYKKLILEDDLEENESKNIFLQELKKTLGNIDEIDENI

IENYYKNAQISASKGNNKAIKKYQKKVIECYIGYLRKNYEELFDFSDFKM

NIQEIKKQIKDINDNKTYERITVKTSDKTIVINDDFEYIISIFALLNSNA

VINKIRNRFFATSVWLNTSEYQNIIDILDEIMQLNTLRNECITENWNLNL

EEFIQKMKEIEKDFDDFKIQTKKEIFNNYYEDIKNNILTEFKDDINGCDV

LEKKLEKIVIFDDETKFEIDKKSNILQDEQRKLSNINKKDLKKKVDQYIK

DKDQEIKSKILCRIIFNSDFLKKYKKEIDNLIEDMESENENKFQEIYYPK

ERKNELYIYKKNLFLNIGNPNFDKIYGLISNDIKMADAKFLFNIDGKNIR

KNKISEIDAILKNLNDKLNGYSKEYKEKYIKKLKENDDFFAKNIQNKNYK

SFEKDYNRVSEYKKIRDLVEFNYLNKIESYLIDINWKLAIQMARFERDMH

YIVNGLRELGIIKLSGYNTGISRAYPKRNGSDGFYTTTAYYKFFDEESYK

KFEKICYGFGIDLSENSEINKPENESIRNYISHFYIVRNPFADYSIAEQI

DRVSNLLSYSTRYNNSTYASVFEVFKKDVNLDYDELKKKFKLIGNNDILE

RLMKPKKVSVLELESYNSDYIKNLIIELLTKIENTNDTL
```

Some aspects of the disclosure provide Cas9 domains that have different PAM specificities. Typically, Cas9 proteins, such as Cas9 from *S. pyogenes* (spCas9), require a canonical NGG PAM sequence to bind a particular nucleic acid region. This may limit the ability to edit desired bases within a genome. In some embodiments, the base editing fusion proteins provided herein may need to be placed at a precise location, for example where a target base is placed within a 4 base region (e.g., a "deamination window"), which is approximately 15 bases upstream of the PAM. See Komor, A. C., et al., "Programmable editing of a target base in genomic DNA without double-stranded DNA cleavage" *Nature* 533, 420-424 (2016), the entire contents of which are hereby incorporated by reference. Accordingly, in some embodiments, any of the fusion proteins provided herein may contain a Cas9 domain that is capable of binding a nucleotide sequence that does not contain a canonical (e.g., NGG) PAM sequence. Cas9 domains that bind to non-canonical PAM sequences have been described in the art and would be apparent to the skilled artisan. For example, Cas9 domains that bind non-canonical PAM sequences have been described in Kleinstiver, B. P., et al., "Engineered CRISPR-Cas9 nucleases with altered PAM specificities" *Nature* 523, 481-485 (2015); and Kleinstiver, B. P., et al., "Broadening the targeting range of *Staphylococcus aureus* CRISPR-Cas9 by modifying PAM recognition" *Nature Biotechnology* 33, 1293-1298 (2015); the entire contents of each are hereby incorporated by reference.

In some embodiments, the Cas9 domain is a Cas9 domain from *Staphylococcus aureus* (SaCas9). In some embodiments, the SaCas9 domain is a nuclease active SaCas9, a nuclease inactive SaCas9 (SaCas9d), or a SaCas9 nickase (SaCas9n). In some embodiments, the SaCas9 comprises the amino acid sequence SEQ ID NO: 45. In some embodiments, the SaCas9 comprises a N579X mutation of SEQ ID NO: 45, wherein X is any amino acid except for N. In some embodiments, the SaCas9 comprises a N579A mutation of SEQ ID NO: 45. In some embodiments, the SaCas9 domain, the SaCas9d domain, or the SaCas9n domain can bind to a nucleic acid sequence having a non-canonical PAM. In some embodiments, the SaCas9 domain, the SaCas9d domain, or the SaCas9n domain can bind to a nucleic acid sequence having a NNGRRT PAM sequence.

In some embodiments, the Cas9 domain of any of the fusion proteins provided herein comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to SEQ ID NO: 45 In some embodiments, the Cas9 domain of any of the fusion proteins provided herein comprises the amino acid sequence of SEQ ID NOs: 45 In some embodiments, the Cas9 domain of any of the fusion proteins provided herein consists of the amino acid sequence of SEQ ID NO: 45.

An exemplary SaCas9 amino acid sequence is:

```
                                   (SEQ ID NO: 45)
KRNYILGLDIGITSVGYGIIDYETRDVIDAGVRLFKEANVENNEGRRSKR

GARRLKRRRRHRIQRVKKLLFDYNLLTDHSELSGINPYEARVKGLSQKLS

EEEFSAALLHLAKRRGVHNVNEVEEDTGNELSTKEQISRNSKALEEKYVA

ELQLERLKKDGEVRGSINRFKTSDYVKEAKQLLKVQKAYHQLDQSFIDTY

IDLLETRRTYYEGPGEGSPFGWKDIKEWYEMLMGHCTYFPEELRSVKYAY

NADLYNALNDLNNLVITRDENEKLEYYEKFQUIENVFKQKKKPTLKQIAK

EILVNEEDIKGYRVTSTGKPEFTNLKVYHDIKDITARKEIIENAELLDQI

AKILTIYQSSEDIQEELTNLNSELTQEEIEQISNLKGYTGTHNLSLKAIN

LILDELWHTNDNQIAIFNRLKLVPKKVDLSQQKEIPTTLVDDFILSPVVK

RSFIQSIKVINAIIKKYGLPNDIIIELAREKNSKDAQKMINEMQKRNRQT

NERIEEIIRTTGKENAKYLIEKIKLHDMQEGKCLYSLEAIPLEDLLNNPF
```

```
NYEVDHIIPRSVSFDNSFNNKVLVKQEENSKKGNRTPFQYLSSSDSKISY

ETFKKHILNLAKGKGRISKTKKEYLLEERDINRFSVQKDFINRNLVDTRY

ATRGLMNLLRSYFRVNNLDVKVKSINGGFTSFLRRKWKFKKERNKGYKHH

AEDALIIANADFIFKEWKKLDKAKKVMENQMFEEKQAESMPEIETEQEYK

EIFITPHQIKHIKDFKDYKYSHRVDKKPNRELINDTLYSTRKDDKGNTLI

VNNLNGLYDKDNDKLKKLINKSPEKLLMYHHDPQTYQKLKLIMEQYGDEK

NPLYKYYEETGNYLTKYSKKDNGPVIKKIKYYGNKLNAHLDITDDYPNSR

NKVVKLSLKPYRFDVYLDNGVYKFVTVKNLDVIKKENYYEVNSKCYEEAK

KLKKISNQAEFIASFYNNDLIKINGELYRVIGVNNDLLNRIEVNMIDITY

REYLENMNDKRPPRIIKTIASKTQSIKKYSTDILGNLYEVKSKKHPQIIK

KG
```

(B) Deaminase Domains

In various embodiments, the evolved base editors provided herein comprise one or more nucleic acid effector domains (e.g., cytidine deaminase), which optionally may be evolved using a continuous evolution process (e.g., PACE) described herein.

In various embodiments, the nucleic acid effector domain may be any protein, enzyme, or polypeptide (or functional fragment thereof) which is capable of modifying a DNA or RNA molecule. Nucleobase modification moieties can be naturally occurring, or can be recombinant. For example, a nucleobase modification moiety can include one or more DNA repair enzymes, for example, and an enzyme or protein involved in base excision repair (BER), nucleotide excision repair (NER), homology-dependent recombinational repair (HR), non-homologous end-joining repair (NHEJ), microhomology end-joining repair (MMEJ), mismatch repair (MMR), direct reversal repair, or other known DNA repair pathway. A nucleobase modification moiety can have one or more types of enzymatic activities, including, but not limited to endonuclease activity, polymerase activity, ligase activity, replication activity, proofreading activity. Nucleobase modification moieties can also include DNA or RNA-modifying enzymes and/or mutagenic enzymes, such as, DNA methylases and deaminating enzymes (i.e., deaminases, including cytidine deaminases and adenosine deaminases, all defined above), which deaminate nucleobases leading in some cases to mutagenic corrections by way of normal cellular DNA repair and replication processes. The "nucleic acid effector domain" (e.g., a DNA effector domain or an RNA effector domain) as used herein may also refer to a protein or enzyme capable of making one or more modifications (e.g., deamination of a cytidine residue) to a nucleic acid (e.g., DNA or RNA). Exemplary nucleic acid editing domains include, but are not limited to a deaminase, a nuclease, a nickase, a recombinase, a methyltransferase, a methylase, an acetylase, an acetyltransferase, a transcriptional activator, or a transcriptional repressor domain. In some embodiments the nucleic acid editing domain is a deaminase (e.g., a cytidine deaminase, such as an APOBEC or an AID deaminase), or an evolved version thereof.

In some embodiments, the nucleic acid editing domain comprises a deaminase. In some embodiments, the deaminase is a cytidine deaminase. In other embodiments, the deaminase is an adenosine deaminase. In some embodiments, the deaminase is an apolipoprotein B mRNA-editing complex (APOBEC) family deaminase. In some embodiments, the deaminase is an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, or an APOBEC4 deaminase. In some embodiments, the deaminase is an activation-induced deaminase (AID). In some embodiments, the deaminase is a Lamprey CDA1 (pmCDA1) deaminase. In some embodiments, the deaminase is from a human, chimpanzee, gorilla, monkey, cow, dog, rat, or mouse. In some embodiments, the deaminase is from a human. In some embodiments the deaminase is from a rat. In some embodiments, the deaminase is a human APOBEC1 deaminase. In some embodiments, the deaminase is pmCDA1. In some embodiments, the deaminase is human APOBEC3G. In some embodiments, the deaminase is a human APOBEC3G variant. In some embodiments, the deaminase is at least 80%, at least 85%, at least 90%, at least 92%, at least 95%, at least 96%, at least 97%, at least 98%, at least 99%, or at least 99.5% identical to any one of the APOBEC amino acid sequences set forth herein.

Some exemplary suitable nucleic-acid editing domains, e.g., deaminases and deaminase domains, that can be fused to Cas9 domains according to aspects of this disclosure are provided below. It should be understood that, in some embodiments, the active domain of the respective sequence can be used, e.g., the domain without a localizing signal (nuclear localization sequence, without nuclear export signal, cytoplasmic localizing signal).

```
Human AID:
                                    (SEQ ID NO: 47)
MDSLLMNRRKFLYQFKNVRWAKGRRETYLCYVVKRRDSATSFSLDFGYLR

NKNGCHVELLFLRYISDWDLDPGRCYRVTWFTSWSPCYDCARHVADFLRG

NPNLSLRIFTARLYFCEDRKAEPEGLRRLHRAGVQIAIMTFKDYFYCWNT

FVENHERTFKAWEGLHENSVRLSRQLRRILLPLYEVDDLRDAFRTLGL (underline: nuclear localization sequence; double underline: nuclear export signal)

Mouse AID:
                                    (SEQ ID NO: 48)
MDSLLMKQKKFLYHFKNVRWAKGRHETYLCYVVKRRDSATSCSLDFGHLR

NKSGCHVELLFLRYISDWDLDPGRCYRVTWFTSWSPCYDCARHVAEFLRW

NPNLSLRIFTARLYFCEDRKAEPEGLRRLHRAGVQIGIMTFKDYFYCWNT

FVENRERTFKAWEGLHENSVRLTRQLRRILLPLYEVDDLRDAFRMLGF (underline: nuclear localization sequence; double underline: nuclear export signal)

Dog AID:
                                    (SEQ ID NO: 49)
MDSLLMKORKFLYHFKNVRWAKGRHETYLCYVVKRRDSATSFSLDFGHLR

NKSGCHVELLFLRYISDWDLDPGRCYRVTWFTSWSPCYDCARHVADFLRG
```

-continued

YPNLSRIFAARLYFCEDRKAEPEGLRRLHRAGVQIAIMTFKDYFYCWNT
FVENREKTFKAWEGLHENSVRLSRQLRRILL<u>PLYEVDDLRDAFRTLGL</u>

(underline: nuclear localization sequence; double
underline: nuclear export signal)

Bovine AID:
(SEQ ID NO: 50)
<u>MDSLLKKQRQFLYQFKNVRWAKGRHETYLCYVVKRRDSPTSFSLDFGHLR</u>
NKAGCHVELLFLRYISDWDLDPGRCYRVTWFTSWSPCYDCARHVADFLRG
YPNLSRIFTARLYFCDKERKAEPEGLRRLHRAGVQIAIMTFKDYFYCWN
TFVENHERTFKAWEGLHENSVRLSRQLRRILL<u>PLYEVDDLRDAFRTLGL</u>

(underline: nuclear localization sequence; double
underline: nuclear export signal)

Rat:AID:
(SEQ ID NO: 51)
<u>MAVGSKPKAALVGPHWERERIWCFLCSTGLGTQQTGQTSRWLRPAATQDP</u>
VSPPRSLLMKQRKFLYHFKNVRWAKGRHETYLCYVVKRRDSATSFSLDFG
YLRNKSGCHVELLFLRYISDWDLDPGRCYRVTWFTSWSPCYDCARHVADF
LRGNPNLSLRIFTARLTGWGALPAGLMSPARPSDYFYCWNTFV<u>ENHERTF
KAWEGLHENSVRLSRRLRRILLPLYEVDDLRDAFRTLGL</u>

(underline: nuclear localization sequence; double
underline: nuclear export signal)

Mouse APOBEC-3:
(SEQ ID NO: 52)
MGPFCLGCSHRKCYSPIRNLISQETFKFHFKNLGYAKGRKDTFLCYEVTR
KDCDSPVSLHHGVFKNKDNI*HAEICFLYWFHDKVLKVLSPREEFKITWYM
SWSPCFEC*AEQIVRFLATHHNLSLDIFSSRLYNVQDPETQQNLCRLVQEG
AQVAAMDLYEFKKCWKKFVDNGGRRFRPWKRLLTNFRYQDSKLQEILRPC
YIPVPSSSSSTLSNICLTKGLPETRFCVEGRRMDPLSEEEFYSQFYNQRV
KHLCYYHRMKPYLCYQLEQFNGQAPLKGCLLSEKGKQ*HAEILFLDKIRSM
ELSQVTITCYLTWSPCPNC*AWQLAAFKRDRPDLILHIYTSRLYFHWKRPF
QKGLCSLWQSGILVDVMDLPQFTDCWTNFVNPKRPFWPWKGLEIISRRTQ
RRLRRIKESWGLQDLVNDFGNLQLGPPMS (italic: nucleic acid editing domain)

Rat APOBEC-3:
(SEQ ID NO: 53)
MGPFCLGCSHRKCYSPIRNLISQETFKFHFKNLRYAIDRKDTFLCYEVTR
KDCDSPVSLHHGVFKNKDNI*HAEICFLYWFHDKVLKVLSPREEFKITWYM
SWSPCFEC*AEQVLRFLATHHNLSLDIFSSRLYNIRDPENQQNLCRLVQEG
AQVAAMDLYEFKKCWKKFVDNGGRRFRPWKKLLTNFRYQDSKLQEILRPC
YIPVPSSSSSTLSNICLTKGLPETRFCVERRRVHLLSEEEFYSQFYNQRV
KHLCYYHGVKPYLCYQLEQFNGQAPLKGCLLSEKGKQ*HAEILFLDKIRSM
ELSQVIITCYLTWSPCPNC*AWQLAAFKRDRPDLILHIYTSRLYFHWKRPF
QKGLCSLWQSGILVDVMDLPQFTDCWTNFVNPKRPFWPWKGLEIISRRTQ
RRLHRIKESWGLQDLVNDFGNLQLGPPMS (italic: nucleic acid editing domain)

Rhesus macaque APOBEC-3G:
(SEQ ID NO: 54)
<u>MVEPMDPRTFVSNFNNRPILSGLNTVWLCCEVKTKDPSGPPLDAKIFQGK
VYSKAKY</u>*HPEMRFLRWFHKWRQLHHDQEYKVTWYVSWSPCTRC*ANSVATF
LAKDPKVTLTIFVARLYYFWKPDYQQALRILCQKRGGPHATMKIMNYNEF
QDCWNKFVDGRGKPFKPRNNLPKHYTLLQATLGELLRHLMDPGTFTSNFN
NKPWVSGQHETYLCYKVERLHNDTWVPLNQHRGFLRNQAPNIHGFPKGR*H
AELCFLDLIPFWKLDGQQYRVTCFTSWSPCFSC*AQEMAKFISNNEHVSLC
IFAARIYDDQGRYQEGLRALHRDGAKIAMMNYSEFEYCWDTFVDRQGRPF
QPWDGLDEHSQALSGRLRAI (italic: nucleic acid editing domain; underline:
cytoplasmic localization signal)

Chimpanzee APOBEC-3G:
(SEQ ID NO: 55)
<u>MKPHFRNPVERMYQDTFSDNFYNRPILSHRNTVWLCYEVKTKGPSRPPLD
AKIFRGQVYSKLKY</u>*HPEMRFFHWFSKWRKLHRDQEYEVTWYISWSPCTKC*
TRDVATFLAEDPKVTLTIFVARLYYFWDPDYQEALRSLCQKRDGPRATMK
IMNYDEFQHCWSKFVYSQRELFEPWNNLPKYYILLHIMLGEILRHSMDPP
TFTSNFNNELWVRGRHETYLCYEVERLHNDTWVLLNQRRGFLCNQAPHKH
GFLEGR*HAELCFLDVIPFWKLDLHQDYRVTCFTSWSPCFSC*AQEMAKFIS
NNKHVSLCIFAARIYDDQGRCQEGLRTLAKAGAKISIMTYSEFKHCWDTF
VDHQGCPFQPWDGLEEHSQALSGRLRAILQNQGN (italic: nucleic acid editing domain; underline:
cytoplasmic localization signal)

Green monkey APOBEC-3G:
(SEQ ID NO: 56)
<u>MNPQIRNMVEQMEPDIFVYYFNNRPILSGRNTVWLCYEVKTKDPSGPPLD
ANIFQGKLYPEAKD</u>*HPEMKFLHWFRKWRQLHRDQEYEVTWYVSWSPCTRC*
ANSVATFLAEDPKVTLTIFVARLYYFWKPDYQQALRILCQERGGPHATMK
IMNYNEFQHCWNEFVDGQGKPFKPRKNLPKHYTLLHATLGELLRHVMDPG
TFTSNFNNKPWVSGQRETYLCYKVERSHNDTWVLLNQHRGFLRNQAPDRH
GFPKGR*HAELCFLDLIPFWKLDDQQYRVTCFTSWSPCFSC*AQKMAKFISN
NKHVSLCIFAARIYDDQGRCQEGLRTLHRDGAKIAVMNYSEFEYCWDTFV
DRQGRPFQPWDGLDEHSQALSGRLRAI (italic: nucleic acid editing domain; underline:
cytoplasmic localization signal)

Human APOBEC-3G:
(SEQ ID NO: 57)
<u>MKPHFRNTVERMYRDTFSYNFYNRPILSRRNTVWLCYEVKTKGPSRPPLD
AKIFRGQVYSELKY</u>*HPEMRFFHWFSKWRKLHRDQEYEVTWYISWSPCTKC*
TRDMATFLAEDPKVTLTIFVARLYYFWDPDYQEALRSLCQKRDGPRATMK
IMNYDEFQHCWSKFVYSQRELFEPWNNLPKYYILLHIMLGEILRHSMDPP
TFTFNFNNEPWVRGRHETYLCYEVERMHNDTWVLLNQRRGFLCNQAPHKH
GFLEGR*HAELCFLDVIPFWKLDLDQDYRVTCFTSWSPCFSC*AQEMAKFIS KNKHVSLCIFTARIYDDQGRCQEGLRTLAEAGAKISIMTYSEFKHCWDTF
VDHQGCPFQPWDGLDEHSQDLSGRLRAILQNQEN (italic: nucleic acid editing domain; underline: cytoplasmic localization signal)

Human APOBEC-3F:
(SEQ ID NO: 58)
MKPHFRNTVERMYRDTFSYNFYNRPILSRRNTVWLCYEVKTKGPSRPRLD
AKIFRGQVYSQPEH*HAEMCFLSWFCGNQLPAYKCFQITWFVSWTPCPDCV*
*AKLAEFLAEHPNVTLTISAARLYYWERDYRRALCRLSQAGARVKIMDDE*
*EFAYCWENFVYSEGQPFMPWYKFDDNYAFLHRTLKEILRNPMEAMYPHIF*
YPHFKNLRKAYGRNESWLCFTMEVVKHHSPVSWKRGVFRNQVDPETH*CHA*
*ERCFLSWFCDDILSPNTNYEVTWYTSWSPCPEC*AGEVAEFLARHSNVNLT
IFTARLYYFWDTDYQEGLRSLSQEGASVEIMGYKDFKYCWENFVYNDDEP
FKPWKGLKYNFLFLDSKLQEILE (italic: nucleic acid editing domain)

Human APOBEC-3B:
(SEQ ID NO: 59)
MNPQIRNPMERMYRDTFYDNFENEPILYGRSYTWLCYEVKIKRGRSNLLW
DTGVFRGQVYFKPQY*HAEMCFLSWFCGNQLPAYKCFQITWFVSWTPCPDC*
*VAKLAEFLSEHPNVTLTISAARLYYWERDYRRALCRLSQAGARVTIMDY*
*EEFAYCWENFVYNEGQQFMPWYKFDENYAFLHRTLKEILRYLMDPDTFTF*
*NFNNDPLVLRRRQTYLCYEVERLDNGTWVLMDQHMGFLCNEAKNLLCGFY*
*GRHAELRFLDLVPSLQLDPAQIYRVTWFISWSPCFSWGCAGEVRAFLQEN*
*THVRLRIFAARIYDYDPLYKEALQMLRDAGAQVSIMTYDEFEYCWDTFVY*
*RQGCPFQPWDGLEEHSQALSGRLRAILQNQGN*

(italic: nucleic acid editing domain)

Rat APOBEC-3B:
(SEQ ID NO: 60)
MQPQGLGPNAGMGPVCLGCSHRRPYSPIRNPLKKLYQQTFYFHFKNVRYA
WGRKNNFLCYEVNGMDCALPVPLRQGVFRKQGHIHAELCFIYWFHDKVLR
VLSPMEEFKVTWYMSWSPCSKCAEQVARFLAAHRNLSLAIFSSRLYYYLR
NPNYQQKLCRLIQEGVHVAAMDLPEFKKCWNKFVDNDGQPFRPWMRLRIN
FSFYDCKLQEIFSRMNLLREDVFYLQFNNSHRVKPVQNRYYRRKSYLCYQ
LERANGQEPLKGYLLYKKGEQHVEILFLEKMRSMELSQVRITCYLTWSPC
PNCARQLAAFKKDHPDLILRIYTSRLYFYWRKKFQKGLCTLWRSGIHVDV
MDLPQFADCWTNFVNPQRPFRPWNELEKNSWRIQRRLRRIKESWGL

Bovine APOBEC-3B:
(SEQ ID NO: 61)
DGWEVAFRSGTVLKAGVLGVSMTEGWAGSGHPGQGACVWTPGTRNTMNLL
REVLFKQQFGNQPRVPAPYYRRKTYLCYQLKQRNDLTLDRGCFRNKKQRH
AEIRFIDKINSLDLNPSQSYKIICYITWSPCPNCANELVNFITRNNHLKL
EIFASRLYFHWIKSFKMGLQDLQNAGISVAVMTHTEFEDCWEQFVDNQSR
PFQPWDKLEQYSASIRRRLQRILTAPI Chimpanzee APOBEC-3B:
(SEQ ID NO: 62)
MNPQIRNPMEWMYQRTFYYNFENEPILYGRSYTWLCYEVKIRRGHSNLLW
DTGVFRGQMYSQPEH*HAEMCFLSWFCGNQLSAYKCFQITWFVSWTPCPDC*
*VAKLAKFLAEHPNVTLTISAARLYYYWERDYRRALCRLSQAGARVKIMDD*
*EEFAYCWENFVYNEGQPFMPWYKFDDNYAFLHRTLKEIIRHLMDPDTFTF*
*NFNNDPLVLRRHQTYLCYEVERLDNGTWVLMDQHMGFLCNEAKNLLCGFY*
*GRHAELRFLDLVPSLQLDPAQIYRVTWFISWSPCFSWGCAGQVRAFLQEN*
*THVRLRIFAARIYDYDPLYKEALQMLRDAGAQVSIMTYDEFEYCWDTFVY*
*RQGCPFQPWDGLEEHSQALSGRLRAILQVRASSLCMVPHRPPPPPQSPGP*
CLPLCSEPPLGSLLPTGRPAPSLPFLLTASFSFPPPASLPPLPSLSLSPG
HLPVPSFHSLTSCSIQPPCSSRIRETEGWASVSKEGRDLG Human APOBEC-3C:
(SEQ ID NO: 63)
MNPQIRNPMKAMYPGTFYFQFKNLWEANDRNETWLCFTVEGIKRRSVVSW
KTGVFRNQVDSETH*CHAERCFLSWFCDDILSPNTKYQVTWYTSWSPCPDC*
AGEVAEFLARHSNVNLTIFTARLYYFQYPCYQEGLRSLSQEGVAVEIMDY
EDFKYCWENFVYNDNEPFKPWKGLKTNFRLLKRRLRESLQ (italic: nucleic acid editing domain)

Gorilla APOBEC3C:
(SEQ ID NO: 64)
MNPQIRNPMKAMYPGTFYFQFKNLWEANDRNETWLCFTVEGIKRRSVVSW
KTGVFRNQVDSETH*CHAERCFLSWFCDDILSPNTNYQVTWYTSWSPCPEC*
AGEVAEFLARHSNVNLTIFTARLYYFQDTDYQEGLRSLSQEGVAVKIMDY
KDFKYCWENFVYNDDEPFKPWKGLKYNFRFLKRRLQEILE (italic: nucleic acid editing domain)

Human APOBEC-3A:
(SEQ ID NO: 65)
MEASPASGPRHLMDPHIFTSNFNNGIGRHKTYLCYEVERLDNGTSVKMDQ
HRGFLHNQAKNLLCGFYGR*HAELRFLDLVPSLQLDPAQIYRVTWFISWSP*
*CFSWGC*AGEVRAFLQENTHVRLRIFAARIYDYDPLYKEALQMLRDAGAQV
SIMTYDEFKHCWDTFVDHQGCPFQPWDGLDEHSQALSGRLRAILQNQGN (italic: nucleic acid editing domain)

Rhesus macaque APOBEC-3A:
(SEQ ID NO: 66)
MDGSPASRPRHLMDPNTFTFNFNNDLSVRGRHQTYLCYEVERLDNGTWVP
MDERRGFLCNKAKNVPCGDYGC*HVELRFLCEVPSWQLDPAQTYRVTWFIS*
*WSPC*FRRGCAGQVRVFLQENKHVRLRIFAARIYDYDPLYQEALRTLRDAG
AQVSIMTYEEFKHCWDTFVDRQGRPFQPWDGLDEHSQALSGRLRAILQNQ
GN (italic: nucleic acid editing domain)

Bovine APOBEC-3A:
(SEQ ID NO: 67)
MDEYTFTENFNNQGWPSKTYLCYEMERLDGDATIPLDEYKGFVRNKGLDQ
PEKPC*HAELYFLGKIHSWNLDRNQHYRLTCFISWSPC*YDCAQKLTTFLKE NHHISLHILASRIYTHNRFGCHQSGLCELQAAGARITIMTFEDFKHCWET
FVDHKGKPFQPWEGLNVKSQALCTELQAILKTQQN
(italic: nucleic acid editing domain)

Human APOBEC-3H:
(SEQ ID NO: 68)
MALLTAETFRLQFNNKRRLRRPYYPRKALLCYQLTPQNGSTPTRGYFENK
KKC*HAEICFINEIKSMGLDETQCYQVTCYLTWSPCSSC*AWELVDFIKAHD
HLNLGIFASRLYYHWCKPQQKGLRLLCGSQVPVEVMGFPKFADCWENFVD
HEKPLSFNPYKMLEELDKNSRAIKRRLERIKIPGVRAQGRYMDILCDAEV
(italic: nucleic acid editing domain)

Rhesus macaque APOBEC-3H:
(SEQ ID NO: 69)
MALLTAKTFSLQFNNKRRVNKPYYPRKALLCYQLTPQNGSTPTRGHLKNK
KKDHAEIRFINKIKSMGLDETQCYQVTCYLTWSPCPSCAGELVDFIKAHR
HLNLRIFASRLYYHWRPNYQEGLLLLCGSQVPVEVMGLPEFTDCWENFVD
HKEPPSFNPSEKLEELDKNSQAIKRRLERIKSRSVDVLENGLRSLQLGPV
TPSSSIRNSR Human APOBEC-3D:
(SEQ ID NO: 70)
MNPQIRNPMERMYRDTFYDNFENEPILYGRSYTWLCYEVKIKRGRSNLLW
DTGVFRGPVLPKRQSNHRQEVYFRFEN*HAEMCFLSWFCGNRLPANRRFQI
TWFVSWNPCLPCV*VKVTKFLAEHPNVTLTISAARLYYYRDRDWRWVLLRL
HKAGARVKIMDYEDFAYCWENFVCNEGQPFMPWYKFDDNYASLHRTLKEI
LRNPMEAMYPHIFYFHFKNLLKACGRNESWLCFTMEVTKHHSAVFRKRGV
FRNQVDPETHC*HAERCFLSWFCDDILSPNTNYEVTWYTSWSPCPEC*AGEV
AEFLARHSNVNLTIFTARLCYFWDTDYQEGLCSLSQEGASVKIMGYKDFV
SCWKNFVYSDDEPFKPWKGLQTNFRLLKRRLREILQ
(italic: nucleic acid editing domain)

Human APOBEC-1:
(SEQ ID NO: 71)
MTSEKGPSTGDPTLRRRIEPWEFDVFYDPRELRKEACLLYEIKWGMSRKI
WRSSGKNTTNHVEVNFIKKFTSERDFHPSMSCSITWFLSWSPCWECSQAI
REFLSRHPGVTLVIYVARLFWHMDQQNRQGLRDLVNSGVTIQIMRASEYY
HCWRNFVNYPPGDEAHWPQYPPLWMMLYALELHCIILSLPPCLKISRRWQ
NHLTFFRLHLQNCHYQTIPPHILLATGLIHPSVAWR Mouse APOBEC-1:
(SEQ ID NO: 72)
MSSETGPVAVDPTLRRRIEPHEFEVFFDPRELRKETCLLYEINWGGRHSV
WRHTSQNTSNHVEVNFLEKFTTERYFRPNTRCSITWFLSWSPCGECSRAI
TEFLSRHPYVTLFIYIARLYHHTDQRNRQGLRDLISSGVTIQIMTEQEYC
YCWRNFVNYPPSNEAYWPRYPHLWVKLYVLELYCIILGLPPCLKILRRKQ
PQLTFFTITLQTCHYQRIPPHLLWATGLK Rat APOBEC-1:
(SEQ ID NO: 73)
MSSETGPVAVDPTLRRRIEPHEFEVFFDPRELRKETCLLYEINWGGRHSI
WRHTSQNTNKHVEVNFIEKFTTERYFCPNTRCSITWFLSWSPCGECSRAI
TEFLSRYPHVTLFIYIARLYHHADPRNRQGLRDLISSGVTIQIMTEQESG
YCWRNFVNYSPSNEAHWPRYPHLWVRLYVLELYCIILGLPPCLNILRRKQ
PQLTFFTIALQSCHYQRLPPHILWATGLK Human APOBEC-2:
(SEQ ID NO: 74)
MAQKEEAAVATEAASQNGEDLENLDDPEKLKELIELPPFEIVTGERLPAN
FFKFQFRNVEYSSGRNKTFLCYVVEAQGKGGQVQASRGYLEDEHAAAHAE
EAFFNTILPAFDPALRYNVTWYVSSSPCAACADRIIKTLSKTKNLRLLIL
VGRLFMWEEPEIQAALKKLKEAGCKLRIMKPQDFEYVWQNFVEQEEGESK
AFQPWEDIQENFLYYEEKLADILK Mouse APOBEC-2:
(SEQ ID NO: 75)
MAQKEEAAEAAAPASQNGDDLENLEDPEKLKELIDLPPFEIVTGVRLPVN
FFKFQFRNVEYSSGRNKTFLCYVVEVQSKGGQAQATQGYLEDEHAGAHAE
EAFFNTILPAFDPALKYNVTWYVSSSPCAACADRILKTLSKTKNLRLLIL
VSRLFMWEEPEVQAALKKLKEAGCKLRIMKPQDFEYIWQNFVEQEEGESK
AFEPWEDIQENFLYYEEKLADILK Rat APOBEC-2:
(SEQ ID NO: 76)
MAQKEEAAEAAAPASQNGDDLENLEDPEKLKELIDLPPFEIVTGVRLPVN
FFKFQFRNVEYSSGRNKTFLCYVVEAQSKGGQVQATQGYLEDEHAGAHAE
EAFFNTILPAFDPALKYNVTWYVSSSPCAACADRILKTLSKTKNLRLLIL
VSRLFMWEEPEVQAALKKLKEAGCKLRIMKPQDFEYLWQNFVEQEEGESK
AFEPWEDIQENFLYYEEKLADILK Bovine APOBEC-2:
(SEQ ID NO: 77)
MAQKEEAAAAAEPASQNGEEVENLEDPEKLKELIELPPFEIVTGERLPAH
YFKFQFRNVEYSSGRNKTFLCYVVEAQSKGGQVQASRGYLEDEHATNHAE
EAFFNSIMPTFDPALRYMVTWYVSSSPCAACADRIVKTLNKTKNLRLLIL
VGRLFMWEEPEIQAALRKLKEAGCRLRIMKPQDFEYIWQNFVEQEEGESK
AFEPWEDIQENFLYYEEKLADILK

*Petromyzon marinus* CDA1 (pmCDA1)
(SEQ ID NO: 78)
MTDAEYVRIHEKLDIYTFKKQFFNNKKSVSHRCYVLFELKRRGERRACFW
GYAVNKPQSGTERGIHAEIFSIRKVEEYLRDNPGQFTINWYSSWSPCADC
AEKILEWYNQELRGNGHTLKIWACKLYYEKNARNQIGLWNLRDNGVGLNV
MVSEHYQCCRKIFIQSSHNQLNENRWLEKTLKRAEKRRSELSIMIQVKIL
HTTKSPAV Human APOBEC3G D316R_D317R
(SEQ ID NO: 79)
MKPHFRNTVERMYRDTFSYNFYNRPILSRRNTVWLCYEVKTKGPSRPPLD
AKIFRGQVYSELKYHPEMRFFHWFSKWRKLHRDQEYEVTWYISWSPCTKC
TRDMATFLAEDPKVTLTIFVARLYYFWDPDYQEALRSLCQKRDGPRATMK
IMNYDEFQHCWSKFVYSQRELFEPWNNLPKYYILLHIMLGEILRHSMDPP
TFTFNFNNEPWVRGRHETYLCYEVERMHNDTWVLLNQRRGFLCNQAPHKH

```
                                  -continued
GFLEGRHAELCFLDVIPFWKLDLDQDYRVTCFTSWSPCFSCAQEMAKFIS

KNKHVSLCIFTARIYRRQGRCQEGLRTLAEAGAKISIMTYSEFKHCWDTF

VDHQGCPFQPWDGLDEHSQDLSGRLRAILQNQEN

Human APOBEC3G chain A
                                           (SEQ ID NO: 80)
MDPPTFTFNFNNEPWVRGRHETYLCYEVERMHNDTWVLLNQRRGFLCNQA

PHKHGFLEGRHAELCFLDVIPFWKLDLDQDYRVTCFTSWSPCFSCAQEMA

KFISKNKHVSLCIFTARIYDDQGRCQEGLRTLAEAGAKISIMTYSEFKHC

WDTFVDHQGCPFQPWDGLDEHSQDLSGRLRAILQ

Human APOBEC3G chain AD120R_D121R
                                           (SEQ ID NO: 81)
MDPPTFTFNFNNEPWVRGRHETYLCYEVERMHNDTWVLLNQRRGFLCNQA

PHKHGFLEGRHAELCFLDVIPFWKLDLDQDYRVTCFTSWSPCFSCAQEMA

KFISKNKHVSLCIFTARIYRRQGRCQEGLRTLAEAGAKISIMTYSEFKHC

WDTFVDHQGCPFQPWDGLDEHSQDLSGRLRAILQ
```

Any of the aforementioned DNA effector domains may be subjected to a continuous evolution process (e.g, PACE) as described herein.

Some aspects of the disclosure provide cytidine deaminases, any of which may be subjected to a continuous evolution process (e.g, PACE) as described herein.

In some embodiments, second protein comprises a nucleic acid editing domain. In some embodiments, the nucleic acid editing domain can catalyze a C to U base change. In some embodiments, the nucleic acid editing domain is a deaminase domain. In some embodiments, the deaminase is a cytidine deaminase or a cytidine deaminase. In some embodiments, the deaminase is an apolipoprotein B mRNA-editing complex (APOBEC) family deaminase. In some embodiments, the deaminase is an APOBEC1 deaminase. In some embodiments, the deaminase is an APOBEC2 deaminase. In some embodiments, the deaminase is an APOBEC3 deaminase. In some embodiments, the deaminase is an APOBEC3A deaminase. In some embodiments, the deaminase is an APOBEC3B deaminase. In some embodiments, the deaminase is an APOBEC3C deaminase. In some embodiments, the deaminase is an APOBEC3D deaminase. In some embodiments, the deaminase is an APOBEC3E deaminase. In some embodiments, the deaminase is an APOBEC3F deaminase. In some embodiments, the deaminase is an APOBEC3G deaminase. In some embodiments, the deaminase is an APOBEC3H deaminase. In some embodiments, the deaminase is an APOBEC4 deaminase. In some embodiments, the deaminase is an activation-induced deaminase (AID). In some embodiments, the deaminase is a vertebrate deaminase. In some embodiments, the deaminase is an invertebrate deaminase. In some embodiments, the deaminase is a human, chimpanzee, gorilla, monkey, cow, dog, rat, or mouse deaminase. In some embodiments, the deaminase is a human deaminase. In some embodiments, the deaminase is a rat deaminase, e.g., rAPOBEC1.

In some embodiments, the nucleic acid editing domain is at least 80%, at least 85%, at least 90%, at least 92%, at least 95%, at least 96%, at least 97%, at least 98%, at least 99%, or at least 99.5% identical to the deaminase domain of any one of the above disclosed deaminase sequences.

Some aspects of the disclosure are based on the recognition that modulating the deaminase domain catalytic activity of any of the fusion proteins provided herein, for example by making point mutations in the deaminase domain, affect the processivity of the fusion proteins (e.g., base editors). For example, mutations that reduce, but do not eliminate, the catalytic activity of a deaminase domain within a base editing fusion protein can make it less likely that the deaminase domain will catalyze the deamination of a residue adjacent to a target residue, thereby narrowing the deamination window. The ability to narrow the deamination window may prevent unwanted deamination of residues adjacent of specific target residues, which may decrease or prevent off-target effects.

In some embodiments, any of the fusion proteins provided herein comprise a deaminase domain (e.g., a cytidine deaminase domain) that has reduced catalytic deaminase activity. In some embodiments, any of the fusion proteins provided herein comprise a deaminase domain (e.g., a cytidine deaminase domain) that has a reduced catalytic deaminase activity as compared to an appropriate control. For example, the appropriate control may be the deaminase activity of the deaminase prior to introducing one or more mutations into the deaminase. In other embodiments, the appropriate control may be a wild-type deaminase. In some embodiments, the appropriate control is a wild-type apolipoprotein B mRNA-editing complex (APOBEC) family deaminase. In some embodiments, the appropriate control is an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, or an APOBEC3H deaminase. In some embodiments, the appropriate control is an activation induced deaminase (AID). In some embodiments, the appropriate control is a cytidine deaminase 1 from *Petromyzon marinus* (pmCDA1). In some embodiments, the deaminse domain may be a deaminase domain that has at least 1%, at least 5%, at least 15%, at least 20%, at least 25%, at least 30%, at least 40%, at least 50%, at least 60%, at least 70%, at least 80%, at least 90%, or at least 95% less catalytic deaminase activity as compared to an appropriate control.

The apolipoprotein B mRNA-editing complex (APOBEC) family of cytidine deaminase enzymes encompasses eleven proteins that serve to initiate mutagenesis in a controlled and beneficial manner. One family member, activation-induced cytidine deaminase (AID), is responsible for the maturation of antibodies by converting cytosines in ssDNA to uracils in a transcription-dependent, strand-biased fashion. The apolipoprotein B editing complex 3 (APOBEC3) enzyme provides protection to human cells against a certain HIV-1 strain via the deamination of cytosines in reverse-transcribed viral ssDNA. These proteins all require a $Zn^{2+}$-coordinating motif (His-X-Glu-$X_{23-26}$-Pro-Cys-$X_{2-4}$-Cys; SEQ ID NO: 82) and bound water molecule for catalytic activity. The Glu residue acts to activate the water molecule to a zinc hydroxide for nucleophilic attack in the deamination reaction. Each family member preferentially deaminates at its own particular "hotspot", ranging from WRC (W is A or T, R is A or G) for hAID, to TTC for hAPOBEC3F. A recent crystal structure of the catalytic domain of APOBEC3G revealed a secondary structure comprised of a five-stranded β-sheet core flanked by six α-helices, which is believed to be conserved across the entire family. The active center loops have been shown to be responsible for both ssDNA binding and in determining "hotspot" identity. Overexpression of these enzymes has been linked to genomic instability and cancer, thus highlighting the importance of sequence-specific targeting.

Some aspects of this disclosure relate to the recognition that the activity of cytidine deaminase enzymes such as APOBEC enzymes can be directed to a specific site in genomic DNA. Without wishing to be bound by any particular theory, advantages of using Cas9 as a recognition agent include (1) the sequence specificity of Cas9 can be easily altered by simply changing the sgRNA sequence; and (2) Cas9 binds to its target sequence by denaturing the dsDNA, resulting in a stretch of DNA that is single-stranded and therefore a viable substrate for the deaminase. It should be understood that other catalytic domains, or catalytic domains from other deaminases, can also be used to generate fusion proteins with Cas9, and that the disclosure is not limited in this regard.

Some aspects of this disclosure are based on the recognition that Cas9:deaminase fusion proteins can efficiently deaminate nucleotides. In view of the results provided herein regarding the nucleotides that can be targeted by Cas9:deaminase fusion proteins, a person of skill in the art will be able to design suitable guide RNAs to target the fusion proteins to a target sequence that comprises a nucleotide to be deaminated.

In certain embodiments, the reference cytidine deaminase domain comprises a "FERNY" polypeptide having an amino acid sequence according to SEQ ID NO: 1 or an amino acid sequence that is at least 60%, 65%, 70%, 75%, 80%, 85%, 90%, 95, 98%, 99%, or 99.5% identical to SEQ ID NO: 1, as follows:

(SEQ ID NO: 1)
MFERNYDPRELRKETYLLYEIKWGKSGKLWRHWCQNNRTQHAEVYFLENI

FNARRFNPSTHCSITWYLSWSPCAECSQKIVDFLKEHPNVNLEIYVARLY

YHEDERNRQGLRDLVNSGVTIRIMDLPDYNYCWKTFVSDQGGDEDYWPGH

FAPWIKQYSLKL

In certain other embodiment, the evolved cytidine deaminase domain (i.e., as a result of the continuous evolution process described herein) comprises a "evoFERNY" polypeptide having an amino acid sequence according to SEQ ID NO: 5 or an amino acid sequence that is at least 60%, 65%, 70%, 75%, 80%, 85%, 90%, 95, 98%, 99%, or 99.5% identical to SEQ ID NO: 5, comprising an H102P and D104N substitutions, as follows:

(SEQ ID NO: 5)
MFERNYDPRELRKETYLLYEIKWGKSGKLWRHWCQNNRTQHAEVYFLENI

FNARRFNPSTHCSITWYLSWSPCAECSQKIVDFLKEHPNVNLEIYVARLY

YPENERNRQGLRDLVNSGVTIRIMDLPDYNYCWKTFVSDQGGDEDYWPGH

FAPWIKQYSLKL

In other embodiment, the reference cytidine deaminase domain comprises a "Rat APOBEC-1" polypeptide having an amino acid sequence according to SEQ ID NO: 2 or an amino acid sequence that is at least 60%, 65%, 70%, 75%, 80%, 85%, 90%, 95, 98%, 99%, or 99.5% identical to SEQ ID NO: 2, as follows:

(SEQ ID NO: 2)
MSSETGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPHVTLFIYIARLYHHADPRNRQGLRDLISSGVTIQIMTEQESG

YCWRNFVNYSPSNEAHWPRYPHLWVRLYVLELYCIILGLPPCLNILRRKQ

PQLTFFTIALQSCHYQRLPPHILWATGLK

In certain other embodiment, the evolved cytidine deaminase domain (i.e., as a result of the continuous evolution process described herein) comprises a "evoAPOBEC" polypeptide having an amino acid sequence according to SEQ ID NO: 6 or an amino acid sequence that is at least 60%, 65%, 70%, 75%, 80%, 85%, 90%, 95, 98%, 99%, or 99.5% identical to SEQ ID NO: 6, and comprising substitutions E4K; H109N; H122L; D124N; R154H; A165S; P201S; F205S as follows:

(SEQ ID NO: 6)
MSSKTGPVAVDPTLRRRIEPHEFEVFFDPRELRKETCLLYEINWGGRHSI

WRHTSQNTNKHVEVNFIEKFTTERYFCPNTRCSITWFLSWSPCGECSRAI

TEFLSRYPNVTLFIYIARLYHLANPRNRQGLRDLISSGVTIQIMTEQESG

YCWHNFVNYSPSNESHWPRYPHLWVRLYVLELYCIILGLPPCLNILRRKQ

SQLTSFTIALQSCHYQRLPPHILWATGLK

In still other embodiments, the reference cytidine deaminase domain comprises a "*Petromyzon marinus* CDA1 (pmCDA1)" polypeptide having an amino acid sequence according to SEQ ID NO: 3 or an amino acid sequence that is at least 60%, 65%, 70%, 75%, 80%, 85%, 90%, 95, 98%, 99%, or 99.5% identical to SEQ ID NO: 3, as follows:

(SEQ ID NO: 3)
MTDAEYVRIHEKLDIYTFKKQFFNNKKSVSHRCYVLFELKRRGERRACFW

GYAVNKPQSGTERGIHAEIFSIRKVEEYLRDNPGQFTINWYSSWSPCADC

AEKILEWYNQELRGNGHTLKIWACKLYYEKNARNQIGLWNLRDNGVGLNV

MVSEHYQCCRKIFIQSSHNQLNENRWLEKTLKRAEKRRSELSIMIQVKIL

HTTKSPAV

In other embodiment, the evolved cytidine deaminase domain (i.e., as a result of the continuous evolution process described herein) comprises a "evoCDA" polypeptide having an amino acid sequence according to SEQ ID NO: 7 or an amino acid sequence that is at least 60%, 65%, 70%, 75%, 80%, 85%, 90%, 95, 98%, 99%, or 99.5% identical to SEQ ID NO: 7 and comprising substitutions F23S; A123V; I195F, as follows:

(SEQ ID NO: 7)
MTDAEYVRIHEKLDIYTFKKQFSNNKKSVSHRCYVLFELKRRGERRACFW

GYAVNKPQSGTERGIHAEIFSIRKVEEYLRDNPGQFTINWYSSWSPCADC

AEKILEWYNQELRGNGHTLKIWVCKLYYEKNARNQIGLWNLRDNGVGLNV

MVSEHYQCCRKIFIQSSHNQLNENRWLEKTLKRAEKRRSELSIMFQVKIL

HTTKSPAV

In yet other embodiments, the reference cytidine deaminase domain comprises a "Anc689 APOBEC" polypeptide having an amino acid sequence according to SEQ ID NO: 4 or an amino acid sequence that is at least 60%, 65%, 70%, 75%, 80%, 85%, 90%, 95, 98%, 99%, or 99.5% identical to SEQ ID NO: 4, as follows:

(SEQ ID NO: 4)
MSSETGPVAVDPTLRRRIEPHEFEVFFDPRELRKETCLLYEIKWGTSHKI

WRHSSKNTTKHVEVNFIEKFTSERHFCPSTSCSITWFLSWSPCGECSKAI

TEFLSQHPNVTLVIYVARLYHHMDQQNRQGLRDLVNSGVTIQIMTAPEYD

YCWRNFVNYPPGKEAHWPRYPPLWMKLYALELHAGILGLPPCLNILRRKQ

PQLTFFTIALQSCHYQRLPPHILWATGLK

In other embodiments, the evolved cytidine deaminase domain (i.e., as a result of the continuous evolution process described herein) comprises a "evoAnc689 APOBEC" polypeptide having an amino acid sequence according to SEQ ID NO: 8 or an amino acid sequence that is at least 60%, 65%, 70%, 75%, 80%, 85%, 90%, 95, 98%, 99%, or 99.5% identical to SEQ ID NO: 8 and comprising substitutions E4K; H122L; D124N; R154H; A165S; P201S; F205S, as follows:

(SEQ ID NO: 8)
MSSKTGPVAVDPTLRRRIEPHEFEVFFDPRELRKETCLLYEIKWGTSHKI

WRHSSKNTTKHVEVNFIEKFTSERHFCPSTSCSITWFLSWSPCGECSKAI

TEFLSQHPNVTLVIYVARLYHLMNQQNRQGLRDLVNSGVTIQIMTAPEYD

YCWHNFVNYPPGKESHWPRYPPLWMKLYALELHAGILGLPPCLNILRRKQ

SQLTSFTIALQSCHYQRLPPHILWATGLK

In some aspects, the specification provides evolved cytidine deaminases which are used to construct base editors that have improved properties. For example, evolved cytidine deaminases, such as those provided herein, are capable of improving base editing efficiency and/or improving the ability of base editors to more efficiently edit bases regardless of the surrounding sequence. For example, in some aspects the disclosure provides evolved APOBEC deaminases (e.g., evolved rAPOBEC1) with improved base editing efficiency in the context of a 5'-G-3' when it is 5' to a target base (e.g., C). In some embodiments, the disclosure provides base editors comprising any of the evolved cytidine deaminases provided herein. It should be appreciated that any of the evolved cydidine deaminases provided herein may be used as a deaminase in a base editor protein, such as any of the base editors provided herein. It should also be appreciated that the disclosure contemplates cytidine deaminases having any of the mutations provided herein, for example any of the mutations described in the Examples section.

(C) UGI Domain

In other embodiments, the base editors described herein may comprise one or more uracil glycosylase inhibitors, which optionally may be evolved using a continuous evolution process (e.g., PACE) described herein.

The term "uracil glycosylase inhibitor" or "UGI," as used herein, refers to a protein that is capable of inhibiting a uracil-DNA glycosylase base-excision repair enzyme. In some embodiments, a UGI domain comprises a wild-type UGI or a UGI as set forth in SEQ ID NO: 10. In some embodiments, the UGI proteins provided herein include fragments of UGI and proteins homologous to a UGI or a UGI fragment. For example, in some embodiments, a UGI domain comprises a fragment of the amino acid sequence set forth in SEQ ID NO: 10. In some embodiments, a UGI fragment comprises an amino acid sequence that comprises at least 60%, at least 65%, at least 70%, at least 75%, at least 80%, at least 85%, at least 90%, at least 95%, at least 96%, at least 97%, at least 98%, at least 99%, or at least 99.5% of the amino acid sequence as set forth in SEQ ID NO: 10. In some embodiments, a UGI comprises an amino acid sequence homologous to the amino acid sequence set forth in SEQ ID NO: 10, or an amino acid sequence homologous to a fragment of the amino acid sequence set forth in SEQ ID NO: 10. In some embodiments, proteins comprising UGI or fragments of UGI or homologs of UGI or UGI fragments are referred to as "UGI variants." A UGI variant shares homology to UGI, or a fragment thereof. For example a UGI variant is at least 70% identical, at least 75% identical, at least 80% identical, at least 85% identical, at least 90% identical, at least 95% identical, at least 96% identical, at least 97% identical, at least 98% identical, at least 99% identical, at least 99.5% identical, or at least 99.9% identical to a wild type UGI or a UGI as set forth in SEQ ID NO: 10. In some embodiments, the UGI variant comprises a fragment of UGI, such that the fragment is at least 70% identical, at least 80% identical, at least 90% identical, at least 95% identical, at least 96% identical, at least 97% identical, at least 98% identical, at least 99% identical, at least 99.5% identical, or at least 99.9% to the corresponding fragment of wild-type UGI or a UGI as set forth in SEQ ID NO: 10. In some embodiments, the UGI comprises the following amino acid sequence:

(SEQ ID NO: 10)
>sp|P14739|UNGI_BPPB2 Uracil-DNA glycosylase
inhibitor
MTNLSDIIEKETGKQLVIQESILMLPEEVEEVIGNKPESDILVHTAYDES

TDENVMLLTSDAPEYKPWALVIQDSNGENKIKML.

The base editors described herein may comprise more than one UGI domain, which may be separated by one or more linkers as described herein.

(D) Split-Intein Domains

In various embodiments described herein, the continuous evolution methods (e.g., PACE) may be used to evolve a first portion of a base editor. A first portion could include a single component or domain, e.g., a Cas9 domain, a deaminase domain, or a UGI domain. The separately evolved component or domain can be then fused to the remaining portions of the base editor within a cell by separately express both the evolved portion and the remaining non-evolved portions with split-intein polypeptide domains. The first portion could more broadly include any first amino acid portion of a base editor that is desired to be evolved using a continuous evolution method described herein. The second portion would in this embodiment refer to the remaining amino acid portion of the base editor that is not evolved using the herein methods. The evolved first portion and the second portion of the base editor could each be expressed with split-intein polypeptide domains in a cell. The natural protein splicing mechanisms of the cell would reassemble the evolved first portion and the non-evolved second portion to form a single fusion protein evolved base editor. The evolved first portion may comprise either the N- or C-terminal part of the single fusion protein. In an analogous manner, use of a second orthogonal trans-splicing intein pair could allow the evolved first portion to comprise an internal part of the single fusion protein.

Thus, any of the evolved and non-evolved components of the base editors herein described may be expressed with split-intein tags in order to facilitate the formation of a complete base editor comprising the evolved and non-evolved component within a cell.

The mechanism of the protein splicing process has been studied in great detail (Chong, et al., J. Biol. Chem. 1996, 271, 22159-22168; Xu, M-Q & Perler, F. B. EMBO Journal, 1996, 15, 5146-5153) and conserved amino acids have been found at the intein and extein splicing points (Xu, et al., EMBO Journal, 1994, 13 5517-522). The constructs described herein contain an intein sequence fused to the 5'-terminus of the first gene (e.g., the evolved portion of the base editor). Suitable intein sequences can be selected from any of the proteins known to contain protein splicing elements. A database containing all known inteins can be found on the World Wide Web (Perler, F. B. Nucleic Acids Research, 1999, 27, 346-347). The intein sequence is fused at the 3' end to the 5' end of a second gene. For targeting of this gene to a certain organelle, a peptide signal can be fused to the coding sequence of the gene. After the second gene, the intein-gene sequence can be repeated as often as desired for expression of multiple proteins in the same cell. For multi-intein containing constructs, it may be useful to use intein elements from different sources. After the sequence of the last gene to be expressed, a transcription termination sequence must be inserted. In one embodiment, a modified intein splicing unit is designed so that it can both catalyze excision of the exteins from the inteins as well as prevent ligation of the exteins. Mutagenesis of the C-terminal extein junction in the *Pyrococcus* species GB-D DNA polymerase was found to produce an altered splicing element that induces cleavage of exteins and inteins but prevents subsequent ligation of the exteins (Xu, M-Q & Perler, F. B. EMBO Journal, 1996, 15, 5146-5153). Mutation of serine 538 to either an alanine or glycine induced cleavage but prevented ligation. Mutation of equivalent residues in other intein splicing units should also prevent extein ligation due to the conservation of amino acids at the C-terminal extein junction to the intein. A preferred intein not containing an endonuclease domain is the *Mycobacterium xenopi* GyrA protein (Telenti, et al. J. Bacteriol. 1997, 179, 6378-6382). Others have been found in nature or have been created artificially by removing the endonuclease domains from endonuclease containing inteins (Chong, et al. J. Biol. Chem. 1997, 272, 15587-15590). In a preferred embodiment, the intein is selected so that it consists of the minimal number of amino acids needed to perform the splicing function, such as the intein from the *Mycobacterium xenopi* GyrA protein (Telenti, A., et al., J. Bacteriol. 1997, 179, 6378-6382). In an alternative embodiment, an intein without endonuclease activity is selected, such as the intein from the *Mycobacterium xenopi* GyrA protein or the *Saccharaomyces cerevisiae* VMA intein that has been modified to remove endonuclease domains (Chong, 1997). Further modification of the intein splicing unit may allow the reaction rate of the cleavage reaction to be altered allowing protein dosage to be controlled by simply modifying the gene sequence of the splicing unit.

Inteins can also exist as two fragments encoded by two separately transcribed and translated genes. These so-called split inteins self-associate and catalyze protein-splicing activity in trans. Split inteins have been identified in diverse cyanobacteria and archaea (Caspi et al, Mol Microbiol. 50: 1569-1577 (2003); Choi J. et al, J Mol Biol. 556: 1093-1106 (2006); Dassa B. et al, Biochemistry. 46:322-330 (2007); Liu X. and Yang J., J Biol Chem. 275:26315-26318 (2003); Wu H. et al.

Proc Natl Acad Sci USA. £5:9226-9231 (1998); and Zettler J. et al, FEBS Letters. 553:909-914 (2009)), but have not been found in eukaryotes thus far. Recently, a bioinformatic analysis of environmental metagenomic data revealed 26 different loci with a novel genomic arrangement. At each locus, a conserved enzyme coding region is interrupted by a split intein, with a freestanding endonuclease gene inserted between the sections coding for intein subdomains. Among them, five loci were completely assembled: DNA helicases (gp41-1, gp41-8); Inosine-5'-monophosphate dehydrogenase (IMPDH-1); and Ribonucleotide reductase catalytic subunits (NrdA-2 and NrdJ-1). This fractured gene organization appears to be present mainly in phages (Dassa et al, Nucleic Acids Research. 57:2560-2573 (2009)).

The split intein Npu DnaE was characterized as having the highest rate reported for the protein trans-splicing reaction. In addition, the Npu DnaE protein splicing reaction is considered robust and high-yielding with respect to different extein sequences, temperatures from 6 to 37° C., and the presence of up to 6M Urea (Zettler J. et al, FEBS Letters. 553:909-914 (2009); Iwai I. et al, FEBS Letters 550: 1853-1858 (2006)). As expected, when the Cys1 Ala mutation at the N-domain of these inteins was introduced, the initial N to S-acyl shift and therefore protein splicing was blocked. Unfortunately, the C-terminal cleavage reaction was also almost completely inhibited. The dependence of the asparagine cyclization at the C-terminal splice junction on the acyl shift at the N-terminal scissile peptide bond seems to be a unique property common to the naturally split DnaE intein alleles (Zettler J. et al. FEBS Letters. 555:909-914 (2009)).

The mechanism of protein splicing typically has four steps [29-30]: 1) an N—S or N—O acyl shift at the intein N-terminus, which breaks the upstream peptide bond and forms an ester bond between the N-extein and the side chain of the intein's first amino acid (Cys or Ser); 2) a transesterification relocating the N-extein to the intein C-terminus, forming a new ester bond linking the N-extein to the side chain of the C-extein's first amino acid (Cys, Ser, or Thr); 3) Asn cyclization breaking the peptide bond between the intein and the C-extein; and 4) a S—N or O—N acyl shift that replaces the ester bond with a peptide bond between the N-extein and C-extein.

Protein trans-splicing, catalyzed by split inteins, provides an entirely enzymatic method for protein ligation [31]. A split-intein is essentially a contiguous intein (e.g. a mini-intein) split into two pieces named N-intein and C-intein, respectively. The N-intein and C-intein of a split intein can associate non-covalently to form an active intein and catalyze the splicing reaction essentially in same way as a contiguous intein does. Split inteins have been found in nature and also engineered in laboratories [31-35]. As used herein, the term "split intein" refers to any intein in which one or more peptide bond breaks exists between the N-terminal and C-terminal amino acid sequences such that the N-terminal and C-terminal sequences become separate molecules that can non-covalently reassociate, or reconstitute, into an intein that is functional for trans-splicing reactions. Any catalytically active intein, or fragment thereof, may be used to derive a split intein for use in the methods of the invention. For example, in one aspect the split intein may be derived from a eukaryotic intein. In another aspect, the split intein may be derived from a bacterial intein. In another aspect, the split intein may be derived from an archaeal intein. Preferably, the split intein so-derived will possess only the amino acid sequences essential for catalyzing trans-splicing reactions.

As used herein, the "N-terminal split intein (In)" refers to any intein sequence that comprises an N-terminal amino acid sequence that is functional for trans-splicing reactions.

An In thus also comprises a sequence that is spliced out when trans-splicing occurs. An In can comprise a sequence that is a modification of the N-terminal portion of a naturally occurring intein sequence. For example, an In can comprise additional amino acid residues and/or mutated residues so long as the inclusion of such additional and/or mutated residues does not render the In non-functional in trans-splicing. Preferably, the inclusion of the additional and/or mutated residues improves or enhances the trans-splicing activity of the In.

As used herein, the "C-terminal split intein (Ic)" refers to any intein sequence that comprises a C-terminal amino acid sequence that is functional for trans-splicing reactions. In one aspect, the Ic comprises 4 to 7 contiguous amino acid residues, at least 4 amino acids of which are from the last β-strand of the intein from which it was derived. An Ic thus also comprises a sequence that is spliced out when trans-splicing occurs. An Ic can comprise a sequence that is a modification of the C-terminal portion of a naturally occurring intein sequence. For example, an Ic can comprise additional amino acid residues and/or mutated residues so long as the inclusion of such additional and/or mutated residues does not render the In non-functional in trans-splicing. Preferably, the inclusion of the additional and/or mutated residues improves or enhances the trans-splicing activity of the Ic.

In some embodiments of the invention, a peptide linked to an Ic or an In can comprise an additional chemical moiety including, among others, fluorescence groups, biotin, polyethylene glycol (PEG), amino acid analogs, unnatural amino acids, phosphate groups, glycosyl groups, radioisotope labels, and pharmaceutical molecules. In other embodiments, a peptide linked to an Ic can comprise one or more chemically reactive groups including, among others, ketone, aldehyde, Cys residues and Lys residues. The N-intein and C-intein of a split intein can associate non-covalently to form an active intein and catalyze the splicing reaction when an "intein-splicing polypeptide (ISP)" is present. As used herein, "intein-splicing polypeptide (ISP)" refers to the portion of the amino acid sequence of a split intein that remains when the Ic, In, or both, are removed from the split intein. In certain embodiments, the In comprises the ISP. In another embodiment, the Ic comprises the ISP. In yet another embodiment, the ISP is a separate peptide that is not covalently linked to In nor to Ic.

Split inteins may be created from contiguous inteins by engineering one or more split sites in the unstructured loop or intervening amino acid sequence between the −12 conserved beta-strands found in the structure of mini-inteins [25-28]. Some flexibility in the position of the split site within regions between the beta-strands may exist, provided that creation of the split will not disrupt the structure of the intein, the structured beta-strands in particular, to a sufficient degree that protein splicing activity is lost.

In protein trans-splicing, one precursor protein consists of an N-extein part followed by the N-intein, another precursor protein consists of the C-intein followed by a C-extein part, and a trans-splicing reaction (catalyzed by the N- and C-inteins together) excises the two intein sequences and links the two extein sequences with a peptide bond. Protein trans-splicing, being an enzymatic reaction, can work with very low (e.g. micromolar) concentrations of proteins and can be carried out under physiological conditions.

(E) Additional Base Editor Functionalities

In various embodiments, the base editors disclosed herein further comprise one or more, preferably at least two nuclear localization signals. In a preferred embodiment, the base editors comprise at least two NLSs. In embodiments with at least two NLSs, the NLSs can be the same NLSs or they can be different NLSs. In addition, the NLSs may be expressed as part of a fusion protein with the remaining portions of the base editors. The location of the NLS fusion can be at the N-terminus, the C-terminus, or within a sequence of a base editor (e.g., inserted between the encoded napR/DNAbp component (e.g., Cas9) and a DNA effector moiety (e.g., a deaminase)).

The NLSs may be any known NLS sequence in the art. The NLSs may also be any future-discovered NLSs for nuclear localization. The NLSs also may be any naturally-occurring NLS, or any non-naturally occurring NLS (e.g., an NLS with one or more desired mutations).

A nuclear localization signal or sequence (NLS) is an amino acid sequence that tags, designates, or otherwise marks a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal (NES), which targets proteins out of the nucleus. A nuclear localization signal can also target the exterior surface of a cell. Thus, a single nuclear localization signal can direct the entity with which it is associated to the exterior of a cell and to the nucleus of a cell. Such sequences can be of any size and composition, for example more than 25, 25, 15, 12, 10, 8, 7, 6, 5 or 4 amino acids, but will preferably comprise at least a four to eight amino acid sequence known to function as a nuclear localization signal (NLS).

The term "nuclear localization sequence" or "NLS" refers to an amino acid sequence that promotes import of a protein into the cell nucleus, for example, by nuclear transport. Nuclear localization sequences are known in the art and would be apparent to the skilled artisan. For example, NLS sequences are described in Plank et al., international PCT application, PCT/EP2000/011690, filed Nov. 23, 2000, published as WO/2001/038547 on May 31, 2001, the contents of which are incorporated herein by reference for their disclosure of exemplary nuclear localization sequences. In some embodiments, a NLS comprises the amino acid sequence

PKKKRKV, (SEQ ID NO: 83)

MDSLLMNRRKFLYQFKNVRWAKGRRETYLC, (SEQ ID NO: 84)

KRTADGSEFESPKKKRKV, (SEQ ID NO: 101)
or

KRTADGSEFEPKKKRKV. (SEQ ID NO: 13)

In one aspect of the invention, a base editor (e.g., a known base editor, such as BE1, BE2, BE3, or BE4) may be modified with one or more nuclear localization signals (NLS), preferably at least two NLSs. In preferred embodiments, the base editors are modified with two or more NLSs. The invention contemplates the use of any nuclear localization signal known in the art at the time of the invention, or any nuclear localization signal that is identified or otherwise made available in the state of the art after the time of the instant filing. A representative nuclear localization signal is a peptide sequence that directs the protein to the nucleus of the cell in which the sequence is expressed. A nuclear localization signal is predominantly basic, can be positioned almost anywhere in a protein's amino acid sequence, generally comprises a short sequence of four amino acids (Autieri & Agrawal, (1998) J. Biol. Chem. 273: 14731-37, incorporated herein by reference) to eight amino acids, and is typically rich in lysine and arginine residues (Magin et al., (2000) Virology 274: 11-16, incorporated herein by reference). Nuclear localization signals often comprise proline residues. A variety of nuclear localization signals have been identified and have been used to effect transport of biological molecules from the cytoplasm to the nucleus of a cell. See, e.g., Tinland et al., (1992) Proc. Natl. Acad. Sci. U.S.A. 89:7442-46; Moede et al., (1999) FEBS Leff. 461:229-34, which is incorporated by reference. Translocation is currently thought to involve nuclear pore proteins.

Most NLSs can be classified in three general groups: (i) a monopartite NLS exemplified by the SV40 large T antigen NLS (PKKKRKV SEQ ID NO: 83); (ii) a bipartite motif consisting of two basic domains separated by a variable number of spacer amino acids and exemplified by the Xenopus nucleoplasmin NLS (KRXXXXXXXXXXXKKKL SEQ ID NO: 102); and (iii) noncanonical sequences such as M9 of the hnRNP A1 protein, the influenza virus nucleoprotein NLS, and the yeast Gal4 protein NLS (Dingwall and Laskey 1991).

Nuclear localization signals appear at various points in the amino acid sequences of proteins. NLS's have been identified at the N-terminus, the C-terminus and in the central region of proteins. Thus, the specification provides base editors that may be modified with one or more NLSs at the C-terminus, the N-terminus, as well as at in internal region of the base editor. The residues of a longer sequence that do not function as component NLS residues should be selected so as not to interfere, for example tonically or sterically, with the nuclear localization signal itself. Therefore, although there are no strict limits on the composition of an NLS-comprising sequence, in practice, such a sequence can be functionally limited in length and composition.

The present disclosure contemplates any suitable means by which to modify a base editor to include one or more NLSs. In one aspect, the base editors can be engineered to express a base editor protein that is translationally fused at its N-terminus or its C-terminus (or both) to one or more NLSs, i.e., to form a base editor-NLS fusion construct. In other embodiments, the base editor-encoding nucleotide sequence can be genetically modified to incorporate a reading frame that encodes one or more NLSs in an internal region of the encoded base editor. In addition, the NLSs may include various amino acid linkers or spacer regions encoded between the base editor and the N-terminally, C-terminally, or internally-attached NLS amino acid sequence, e.g, and in the central region of proteins. Thus, the present disclosure also provides for nucleotide constructs, vectors, and host cells for expressing fusion proteins that comprise a base editor and one or more NLSs.

The evolved base editors described herein may also comprise nuclear localization signals which are linked to a base editor through one or more linkers, e.g., and polymeric, amino acid, nucleic acid, polysaccharide, chemical, or nucleic acid linker element. The linkers within the contemplated scope of the disclosure are not intended to have any limitations and can be any suitable type of molecule (e.g., polymer, amino acid, polysaccharide, nucleic acid, lipid, or any synthetic chemical linker moiety) and be joined to the base editor by any suitable strategy that effectuates forming a bond (e.g., covalent linkage, hydrogen bonding) between the base editor and the one or more NLSs.

The evolved base editors described herein also may include one or more additional functionalities. In certain embodiments, the additional functionalities may include an effector of base repair.

In certain embodiments, the base editors described herein may comprise an inhibitor of base repair. The term "inhibitor of base repair" or "IBR" refers to a protein that is capable in inhibiting the activity of a nucleic acid repair enzyme, for example a base excision repair enzyme. In some embodiments, the IBR is an inhibitor of inosine base excision repair. Exemplary inhibitors of base repair include inhibitors of APE1, Endo III, Endo IV, Endo V, Endo VIII, Fpg, hOGG1, hNEIL1, T7 EndoI, T4PDG, UDG, hSMUG1, and hAAG. In some embodiments, the IBR is an inhibitor of Endo V or hAAG. In some embodiments, the IBR is a catalytically inactive EndoV or a catalytically inactive hAAG.

In some embodiments, the base editor described herein may comprise one or more heterologous protein domains (e.g., about or more than about 1, 2, 3, 4, 5, 6, 7, 8, 9, 10, or more domains in addition to the base editor components). A base editor may comprise any additional protein sequence, and optionally a linker sequence between any two domains. Examples of protein domains that may be fused to a base editor or component thereof (e.g., the napR/DNAbp moiety, the nucleic acid effector moiety, or the NLS moeity) include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A base editor may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a base editor are described in US20110059502, incorporated herein by reference. In some embodiments, a tagged base editor is used to identify the location of a target sequence.

In an aspect of the invention, a reporter gene which includes but is not limited to glutathione-5-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP), may be introduced into a cell to encode a gene product which serves as a marker by which to measure the alteration or modification of expression of the gene product. In a further embodiment of the invention, the DNA molecule encoding the gene product may be introduced into the cell via a vector. In a preferred embodiment of the invention the gene product is luciferase. In a further embodiment of the invention the expression of the gene product is decreased.

Other exemplary features that may be present are localization sequences, such as cytoplasmic localization sequences, export sequences, such as nuclear export sequences, or other localization sequences, as well as sequence tags that are useful for solubilization, purification, or detection of the fusion proteins. Suitable protein tags provided herein include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. Additional suitable sequences will be apparent to those of skill in the art. In some embodiments, the fusion protein comprises one or more His tags.

(F) The Guide Sequence (e.g., a Guide RNA)

In various embodiments, the evolved base editors can be complexed, bound, or otherwise associated with (e.g., via any type of covalent or non-covalent bond) one or more guide sequences, i.e., the sequence which becomes associated or bound to the base editor and directs its localization to a specific target sequence having complementarity to the guide sequence or a portion thereof. The particular design aspects of a guide sequence will depend upon the nucleotide sequence of a genomic target site of interest (i.e., the desired site to be edited) and the type of napR/DNAbp (e.g., type of Cas protein) present in the base editor, among other factors, such as PAM sequence locations, percent G/C content in the target sequence, the degree of microhomology regions, secondary structures, etc.

In general, a guide sequence is any polynucleotide sequence having sufficient complementarity with a target polynucleotide sequence to hybridize with the target sequence and direct sequence-specific binding of a napR/DNAbp (e.g., a Cas9, Cas9 homolog, or Cas9 variant) to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length.

In some embodiments, a guide sequence is less than about 75, 50, 45, 40, 35, 30, 25, 20, 15, 12, or fewer nucleotides in length. The ability of a guide sequence to direct sequence-specific binding of a base editor to a target sequence may be assessed by any suitable assay. For example, the components of a base editor, including the guide sequence to be tested, may be provided to a host cell having the corresponding target sequence, such as by transfection with vectors encoding the components of a base editor disclosed herein, followed by an assessment of preferential cleavage within the target sequence, such as by Surveyor assay as described herein. Similarly, cleavage of a target polynucleotide sequence may be evaluated in a test tube by providing the target sequence, components of a base editor, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNNXGG where NNNNNNNNNNNNXGG (N is A, G, T, or C; and X can be anything) has a single occurrence in the genome. A unique target sequence in a genome may include an S. pyogenes Cas9 target site of the form MMMMMMMMMNNNNNNNNNNNXGG where NNNNNNNNNNNXGG (N is A, G, T, or C; and X can be anything) has a single occurrence in the genome. For the S. thermophilus CRISPR1Cas9, a unique target sequence in a genome may include a Cas9 target site of the form MMMMMMMMNNNNNNNNNNNNXXAGAAW where NNNNNNNNNNNNXXAGAAW (N is A, G, T, or C; X can be anything; and W is A or T) has a single occurrence in the genome. A unique target sequence in a genome may include an S. thermophilus CRISPR 1 Cas9 target site of the form MMMMMMMMMNNNNNNNNNNNXXAGAAW where NNNNNNNNNNNXXAGAAW (N is A, G, T, or C; X can be anything; and W is A or T) has a single occurrence in the genome. For the S. pyogenes Cas9, a unique target sequence in a genome may include a Cas9 target site of the form MMMMMMMMNNNNNNNNNNNNXGGXG where NNNNNNNNNNNNXGGXG (N is A, G, T, or C; and X can be anything) has a single occurrence in the genome. A unique target sequence in a genome may include an S. pyogenes Cas9 target site of the form MMMMMMMMMNNNNNNNNNNNXGGXG where NNNNNNNNNNNXGGXG (N is A, G, T, or C; and X can be anything) has a single occurrence in the genome. In each of these sequences "M" may be A, G, T, or C, and need not be considered in identifying a sequence as unique.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62). Further algorithms may be found in U.S. application Ser. No. 61/836,080; Broad Reference BI-2013/004A); incorporated herein by reference.

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a complex at a target sequence, wherein the complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. Preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In some embodiments, the single transcript further includes a transcription termination sequence; preferably this is a polyT sequence, for example six T nucleotides. Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator:

(1)

(SEQ ID NO: 103)
NNNNNNNNNgttttgtactctcaagatttaGAAAtaaatcttgcagaagc tacaaagataaggcttcatgccgaaatcaacaccctgtcattttatggca gggtgtttcgttatttaaTTTTTT;

(2)

(SEQ ID NO: 104)
NNNNNNNNNNNNNNNNNNNgttttgtactctcaGAAAtgcagaagctaca aagataaggcttcatgccgaaatcaacaccctgtcattttatggcagggt gttttcgttatttaaTTTTTT;

(3)

(SEQ ID NO: 105)
NNNNNNNNNNNNNNNNNNNNgttttgtactctcaGAAAtgcagaagcta caaagataaggcttcatgccgaaatcaacaccctgtcattttatggcagg gtgtTTTTT;

(4)

(SEQ ID NO: 106)
NNNNNNNNNNNNNNNNNNNNNgttttagagctaGAAAtagcaagttaaaat aaggctagtccgttatcaacttgaaaaagtggcaccgagtcggtgcTTTT

TT;

(5)

(SEQ ID NO: 107)
NNNNNNNNNNNNNNNNNNNNNgttttagagctaGAAATAGcaagttaaaat aaggctagtccgttatcaacttgaaaaagtgTTTTTTT;
and (6)

(SEQ ID NO: 108)
NNNNNNNNNNNNNNNNNNNNNgttttagagctagAAATAGcaagttaaaat aaggctagtccgttatcaTTTTTTTT.

In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

It will be apparent to those of skill in the art that in order to target any of the fusion proteins comprising a Cas9 domain and a deaminase, as disclosed herein, to a target site, e.g., a site comprising a point mutation to be edited, it is typically necessary to co-express the fusion protein together with a guide RNA, e.g., an sgRNA. As explained in more detail elsewhere herein, a guide RNA typically comprises a tracrRNA framework allowing for Cas9 binding, and a guide sequence, which confers sequence specificity to the Cas9: nucleic acid editing enzyme/domain fusion protein.

In some embodiments, the guide RNA comprises a structure 5'-[guide sequence]-guuuuagagcua-gaaauagcaaguuaaaauaaaggcuaguccguuaucaac-uugaaaaaguggcaccgagucggugcuuuuu-3' (SEQ ID NO: 109), wherein the guide sequence comprises a sequence that is complementary to the target sequence. The guide sequence is typically 20 nucleotides long. The sequences of suitable guide RNAs for targeting Cas9:nucleic acid editing enzyme/domain fusion proteins to specific genomic target sites will be apparent to those of skill in the art based on the instant disclosure. Such suitable guide RNA sequences typically comprise guide sequences that are complementary to a nucleic sequence within 50 nucleotides upstream or downstream of the target nucleotide to be edited. Some exemplary guide RNA sequences suitable for targeting any of the provided fusion proteins to specific target sequences are provided herein. Additional guide sequences are well known in the art and can be used with the base editors described herein.

(G) Linkers

In certain embodiments, linkers may be used to link any of the peptides or peptide domains or moieties of the invention (e.g., moiety A covalently linked to moiety B which is covalently linked to moiety C).

As defined above, the term "linker," as used herein, refers to a chemical group or a molecule linking two molecules or moieties, e.g., a binding domain and a cleavage domain of a nuclease. In some embodiments, a linker joins a gRNA binding domain of an RNA-programmable nuclease and the catalytic domain of a recombinase. In some embodiments, a linker joins a dCas9 and base editor moiety (e.g., a cytidine or adenosine deaminase). Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The linker may be as simple as a covalent bond, or it may be a polymeric linker many atoms in length. In certain embodiments, the linker is a polypeptide or based on amino acids. In other embodiments, the linker is not peptide-like. In certain embodiments, the linker is a covalent bond (e.g., a carbon-carbon bond, disulfide bond, carbon-heteroatom bond, etc.). In certain embodiments, the linker is a carbon-nitrogen bond of an amide linkage. In certain embodiments, the linker is a cyclic or acyclic, substituted or unsubstituted, branched or unbranched aliphatic or heteroaliphatic linker. In certain embodiments, the linker is polymeric (e.g., polyethylene, polyethylene glycol, polyamide, polyester, etc.). In certain embodiments, the linker comprises a monomer, dimer, or polymer of aminoalkanoic acid. In certain embodiments, the linker comprises an aminoalkanoic acid (e.g., glycine, ethanoic acid, alanine, beta-alanine, 3-aminopropanoic acid, 4-aminobutanoic acid, 5-pentanoic acid, etc.). In certain embodiments, the linker comprises a monomer, dimer, or polymer of aminohexanoic acid (Ahx). In certain embodiments, the linker is based on a carbocyclic moiety (e.g., cyclopentane, cyclohexane). In other embodiments, the linker comprises a polyethylene glycol moiety (PEG). In other embodiments, the linker comprises amino acids. In certain embodiments, the linker comprises a peptide. In certain embodiments, the linker comprises an aryl or heteroaryl moiety. In certain embodiments, the linker is based on a phenyl ring. The linker may included funtionalized moieties to facilitate attachment of a nucleophile (e.g., thiol, amino) from the peptide to the linker. Any electrophile may be used as part of the linker. Exemplary electrophiles include, but are not limited to, activated esters, activated amides, Michael acceptors, alkyl halides, aryl halides, acyl halides, and isothiocyanates.

In some other embodiments, the linker comprises the amino acid sequence (GGGGS)n (SEQ ID NO: 110), (G)n (SEQ ID NO: 111), (EAAAK)n (SEQ ID NO: 112), (GGS)n (SEQ ID NO: 113), (SGGS)n (SEQ ID NO: 114), SGSETPGTSESATPES SEQ ID NO: 115), (XP)n (SEQ ID NO: 116), or any combination thereof, wherein n is independently an integer between 1 and 30, and wherein X is any amino acid. In some embodiments, the linker comprises the amino acid sequence (GGS)n (SEQ ID NO: 117), wherein n is 1, 3, or 7. In some embodiments, the linker comprises the amino acid sequence SGSETPGTSESATPES (SEQ ID NO: 99). In some embodiments, the linker comprises the amino acid sequence SGGSSGGSSGSETPGTSESATPESSGGSSGGS (SEQ ID NO: 11). In some embodiments, the linker comprises the amino acid sequence SGGSGGSGGS (SEQ ID NO:12). In some embodiments, the linker comprises the amino acid sequence SGGS (SEQ ID NO: 14).

In some embodiments, the fusion protein comprises the structure [nucleic acid editing domain]-[optional linker sequence]-[dCas9 or Cas9 nickase]-[optional linker sequence]-[UGI]. In some embodiments, the fusion protein comprises the structure [nucleic acid editing domain]-[optional linker sequence]-[UGI]-[optional linker sequence]-[dCas9 or Cas9 nickase]; [UGI]-[optional linker sequence]-[nucleic acid editing domain]-[optional linker sequence]-[dCas9 or Cas9 nickase]; [UGI]-[optional linker sequence]-[dCas9 or Cas9 nickase]-[optional linker sequence]-[nucleic acid editing domain]; [dCas9 or Cas9 nickase]-[optional linker sequence]-[UGI]-[optional linker sequence]-[nucleic acid editing domain]; or [dCas9 or Cas9 nickase]-[optional linker sequence]-[nucleic acid editing domain]-[optional linker sequence]-[UGI].

Continuous Evolution of Base Editors

Despite recent advances in the design of base editors, the efficiency of base editing varies widely. To increase base editing efficiency, the inventors sought to identify the factors that limit base editing efficiency in cells. It was surprisingly found by the inventors that expression and nuclear localization in human cells imposed key bottlenecks on editing efficiency. The inventors discovered that by optimizing codon usage, using improved nuclear localization sequences (NLSs), and performing ancestral reconstruction of deaminases resulted in base editors with greatly increased editing efficiency, often more than doubling target nucleotide conversion yields as compared to the unmodified counterpart editors. The resulting base editors were shown, as demonstrated in the Examples, to install point mutations relevant to human disease in a variety of mammalian cell types much more efficiently than previously described base editors. These methods can be used to provide evolved base editors that can be used to efficiently edit a nucleic acid molecule in a manner that is dramatically improved as compared to base editors known in the art. The evolved base editors may be used to efficiently edit nucleic acid molecules, e.g., a genome, for example, by correcting a disease-causing point mutation.

Thus, the invention relates in various aspects to methods of making the disclosed evolved base editors by various modes of manipulation that include but are not limited to codon optimization and performance of ancestral reconstruction of components of the base editors (e.g., of a deaminase) to achieve greater expression levels in a cell, and the use of nuclear localization sequences (NLS)s, preferably at least two NLSs to increase the localization of the expressed base editors into a cell nucleus.

Increasing Expression

The base editors contemplated herein can include modifications that result in increased expression through codon optimization and ancestral reconstruction analysis.

In some embodiments, the base editors (or a component thereof) is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In other embodiments, the base editors of the invention have improved expression (as compared to non-modified or state of the art counterpart editors) as a result of ancestral sequence reconstruction analysis. Ancestral sequence reconstruction (ASR) is the process of analyzing modern sequences within an evolutionary/phylogenetic context to infer the ancestral sequences at particular nodes of a tree. These ancient sequences are most often then synthesized, recombinantly expressed in laboratory microorganisms or cell lines, and then characterized to reveal the ancient properties of the extinct biomolecules 2,3,4,5,6. This process has produced tremendous insights into the mechanisms of molecular adaptation and functional divergence7. Despite such insights, a major criticism of ASR is the general inability to benchmark accuracy of the implemented algorithms. It is difficult to benchmark ASR for many reasons. Notably, genetic material is not preserved in fossils on a long enough time scale to satisfy most ASR studies (many millions to billions of years ago), and it is not yet physically possible to travel back in time to collect samples. Reference can be made to Cai et al., "Reconstruction of ancestral protein sequences and its applications," BMC Evolutionary Biology 2004, 4:33 and Zakas et al., "Enhancing the pharmaceutical properties of protein drugs by ancestral sequence reconstruction," Nature Biotechnology, 35, pp. 35-37 (2017), each of which are incorporated herein by reference.

There are many software packages available which can perform ancestral state reconstruction. Generally, these software packages have been developed and maintained through the efforts of scientists in related fields and released under free software licenses. The following list is not meant to be a comprehensive itemization of all available packages, but provides a representative sample of the extensive variety of packages that implement methods of ancestral reconstruction with different strengths and features: PAML (Phylogenetic Analysis by Maximum Likelihood, available at l/abacus.gene.ucl.ac.uk/software/paml.html), BEAST (Bayesian evolutionary analysis by sampling trees, available at //www.beast2.org/wiki/index.php/Main_Page), and Diversitree (FitzJohn RG, 2012. Diversitree: comparative phylogenetic analyses of diversification in R. Methods in Ecology and Evolution), and HyPHy (Hypothesis testing using phylogenies, available at //hyphy.org/w/index.php/Main_Page).

The Examples demonstrate one embodiment for using ASR to increase overall expression of base editors disclosed herein, and to generate functional base editors that have reduced length.

The above description is meant to be non-limiting with regard to making base editors having increased expression, and thereby increase editing efficiencies.

Increasing Nuclear Localization

In one aspect, the specification provides a strategy for improving a base editor by incorporating one or more nuclear localization signals (NLS) therein, e.g., as a N-terminal or C-terminal fusion protein. Preferably, at least two NLSs are incorporated into a base editor. In the Examples, the inventors explored whether sub-optimal nuclear localization could be a basis or poor editing efficiency. The inventors test six combinations of the base editor "BE4" as N- and/or C-terminal fusions to either the SV40 NLS or the bipartite NLS (bpNLS). As shown in the Examples, all the variants using one or two bpNLSs showed improvements in editing efficiency. The presence of a bpNLS at both the N- and C-terminus (referred to hereafter as "bis-bpNLS") performed best, resulting in a 1.3-fold average improvement in BE4-mediated C•G-to-T•A editing efficiency at five exemplary tested genomic loci (48±8.0% average editing compared to 37±5.6% for the C-terminal SV40 NLS used in BE4). These results together suggest that modifying base editors with one or more nuclear localization signals, e.g., a bis-bpNLS, can significantly improve the editing efficiency of previously described for known base editors, such as, BE3 and BE4 (6, 7).

However, the Examples are not intended to be limiting, but only demonstrative of wider strategy for improving base editor efficiency through the modification of the base editor with one or more nuclear localization signals, preferably at least two NLSs. The invention is not intended to be limiting with regard to which NLS is employed, and the manner by which the NLS is attached to or otherwise coupled to a base editor. NLS sequences are known in the art and examples are disclosed herein.

Vectors

Several aspects of the making and using the base editors of the invention relate to vector systems comprising one or more vectors, or vectors as such. Vectors can be designed to clone and/or express the evolved base editors of the disclosure. Vectors can also be designed to transfect the evolved base editors of the disclosure into one or more cells, e.g., a target diseased eukaryotic cell for treatment with the base editor systems and methods disclosed herein.

Vectors can be designed for expression of base editor transcripts (e.g. nucleic acid transcripts, proteins, or enzymes) in prokaryotic or eukaryotic cells. For example, base editor transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press. San Diego, Calif. (1990). Alternatively, expression vectors encoding one or more evolved base editors described herein can be transcribed and translated in vitro, for example using T7 promoter regulatory sequences and T7 polymerase.

Vectors may be introduced and propagated in a prokaryotic cells. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins.

Fusion expression vectors also may be used to express the evolved base editors of the disclosure. Such vectors generally add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89).

In some embodiments, a vector is a yeast expression vector for expressing the evolved base editors described herein. Examples of vectors for expression in yeast *Saccharomyces cerivisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. *Cell*. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter, U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546).

Increasing Base Editor Efficiencies

Some aspects of the disclosure are based on the recognition that any of the base editors provided herein are capable of modifying a specific nucleotide base without generating a significant proportion of indels. An "indel", as used herein, refers to the insertion or deletion of a nucleotide base within a nucleic acid. Such insertions or deletions can lead to frame shift mutations within a coding region of a gene. In some embodiments, it is desirable to generate base editors that efficiently modify (e.g. mutate or deaminate) a specific nucleotide within a nucleic acid, without generating a large number of insertions or deletions (i.e., indels) in the nucleic acid. In certain embodiments, any of the base editors provided herein are capable of generating a greater proportion of intended modifications (e.g., point mutations or deaminations) versus indels. In some embodiments, the base editors provided herein are capable of generating a ratio of intended point mutations to indels that is greater than 1:1. In some embodiments, the base editors provided herein are capable of generating a ratio of intended point mutations to indels that is at least 1.5:1, at least 2:1, at least 2.5:1, at least 3:1, at least 3.5:1, at least 4:1, at least 4.5:1, at least 5:1, at least 5.5:1, at least 6:1, at least 6.5:1, at least 7:1, at least 7.5:1, at least 8:1, at least 10:1, at least 12:1, at least 15:1, at least 20:1, at least 25:1, at least 30:1, at least 40:1, at least 50:1, at least 100:1, at least 200:1, at least 300:1, at least 400:1, at least 500:1, at least 600:1, at least 700:1, at least 800:1, at least 900:1, or at least 1000:1, or more. The number of intended mutations and indels may be determined using any suitable method, for example the methods used in the below Examples. In some embodiments, to calculate indel frequencies, sequencing reads are scanned for exact matches to two 10-bp sequences that flank both sides of a window in which indels might occur. If no exact matches are located, the read is excluded from analysis. If the length of this indel window exactly matches the reference sequence the read is classified as not containing an indel. If the indel window is two or more bases longer or shorter than the reference sequence, then the sequencing read is classified as an insertion or deletion, respectively.

In some embodiments, the base editors provided herein are capable of limiting formation of indels in a region of a nucleic acid. In some embodiments, the region is at a nucleotide targeted by a base editor or a region within 2, 3, 4, 5, 6, 7, 8, 9, or 10 nucleotides of a nucleotide targeted by a base editor. In some embodiments, any of the base editors provided herein are capable of limiting the formation of indels at a region of a nucleic acid to less than 1%, less than 1.5%, less than 2%, less than 2.5%, less than 3%, less than 3.5%, less than 4%, less than 4.5%, less than 5%, less than 6%, less than 7%, less than 8%, less than 9%, less than 10%, less than 12%, less than 15%, or less than 20%. The number of indels formed at a nucleic acid region may depend on the amount of time a nucleic acid (e.g., a nucleic acid within the genome of a cell) is exposed to a base editor. In some embodiments, an number or proportion of indels is determined after at least 1 hour, at least 2 hours, at least 6 hours, at least 12 hours, at least 24 hours, at least 36 hours, at least 48 hours, at least 3 days, at least 4 days, at least 5 days, at least 7 days, at least 10 days, or at least 14 days of exposing a nucleic acid (e.g., a nucleic acid within the genome of a cell) to a base editor.

Some aspects of the disclosure are based on the recognition that any of the base editors provided herein are capable of efficiently generating an intended mutation, such as a point mutation, in a nucleic acid (e.g. a nucleic acid within a genome of a subject) without generating a significant number of unintended mutations, such as unintended point mutations. In some embodiments, a intended mutation is a mutation that is generated by a specific base editor bound to a gRNA, specifically designed to generate the intended mutation. In some embodiments, the intended mutation is a mutation associated with a disease or disorder. In some embodiments, the intended mutation is a adenine (A) to guanine (G) point mutation associated with a disease or disorder. In some embodiments, the intended mutation is a thymine (T) to cytosine (C) point mutation associated with a disease or disorder. In some embodiments, the intended mutation is a adenine (A) to guanine (G) point mutation within the coding region of a gene. In some embodiments, the intended mutation is a thymine (T) to cytosine (C) point mutation within the coding region of a gene. In some embodiments, the intended mutation is a point mutation that generates a stop codon, for example, a premature stop codon within the coding region of a gene. In some embodiments, the intended mutation is a mutation that eliminates a stop codon. In some embodiments, the intended mutation is a mutation that alters the splicing of a gene. In some embodiments, the intended mutation is a mutation that alters the regulatory sequence of a gene (e.g., a gene promotor or gene repressor). In some embodiments, any of the base editors provided herein are capable of generating a ratio of intended mutations to unintended mutations (e.g., intended point mutations:unintended point mutations) that is greater than 1:1. In some embodiments, any of the base editors provided herein are capable of generating a ratio of intended mutations to unintended mutations (e.g., intended point mutations:unintended point mutations) that is at least 1.5:1, at least 2:1, at least 2.5:1, at least 3:1, at least 3.5:1, at least 4:1, at least 4.5:1, at least 5:1, at least 5.5:1, at least 6:1, at least 6.5:1, at least 7:1, at least 7.5:1, at least 8:1, at least 10:1, at least 12:1, at least 15:1, at least 20:1, at least 25:1, at least 30:1, at least 40:1, at least 50:1, at least 100:1, at least 150:1, at least 200:1, at least 250:1, at least 500:1, or at least 1000:1, or more. It should be appreciated that the characteristics of the base editors described in the "Base Editor Efficiency" section, herein, may be applied to any of the fusion proteins, or methods of using the fusion proteins provided herein.

II. Methods of Making and Using Evolved Base-Editors

Some aspects of this disclosure provide methods of making the evolved base editors disclosed herein, or base editor complexes comprising one or more napR/DNAbp-programming nucleic acid molecules (e.g., Cas9 guide RNAs) and a nucleobase editor provided herein. In addition, some aspects of the disclosure provide methods of using the evolved base editors for editing a target nucleotide sequence (e.g., a genome).

Continuous Evolution Methods

Various aspects of the disclosure relate to providing continuous evolution methods and systems (e.g., appropriate vectors, cells, phage, flow vessels, etc.).

The continuous evolution methods provided herein allow for a gene of interest (e.g., a base editor gene) in a viral vector to be evolved over multiple generations of viral life cycles in a flow of host cells to acquire a desired function or activity.

Some aspects of this invention provide a method of continuous evolution of a gene of interest, comprising (a) contacting a population of host cells with a population of viral vectors comprising the gene of interest, wherein (1) the host cell is amenable to infection by the viral vector; (2) the host cell expresses viral genes required for the generation of viral particles; (3) the expression of at least one viral gene required for the production of an infectious viral particle is dependent on a function of the gene of interest; and (4) the viral vector allows for expression of the protein in the host cell, and can be replicated and packaged into a viral particle by the host cell. In some embodiments, the method comprises (b) contacting the host cells with a mutagen. In some embodiments, the method further comprises (c) incubating the population of host cells under conditions allowing for viral replication and the production of viral particles, wherein host cells are removed from the host cell population, and fresh, uninfected host cells are introduced into the population of host cells, thus replenishing the population of host cells and creating a flow of host cells. The cells are incubated in all embodiments under conditions allowing for the gene of interest to acquire a mutation. In some embodiments, the method further comprises (d) isolating a mutated version of the viral vector, encoding an evolved gene product (e.g., protein), from the population of host cells.

In some embodiments, a method of phage-assisted continuous evolution is provided comprising (a) contacting a population of bacterial host cells with a population of phages that comprise a gene of interest to be evolved and that are deficient in a gene required for the generation of infectious phage, wherein (1) the phage allows for expression of the gene of interest in the host cells; (2) the host cells are suitable host cells for phage infection, replication, and packaging; and (3) the host cells comprise an expression construct encoding the gene required for the generation of infectious phage, wherein expression of the gene is dependent on a function of a gene product of the gene of interest. In some embodiments the method further comprises (b) incubating the population of host cells under conditions allowing for the mutation of the gene of interest, the production of infectious phage, and the infection of host cells with phage, wherein infected cells are removed from the population of host cells, and wherein the population of host cells is replenished with fresh host cells that have not been infected by the phage. In some embodiments, the method further comprises (c) isolating a mutated phage replication product encoding an evolved protein from the population of host cells.

In some embodiments, the viral vector or the phage is a filamentous phage, for example, an M13 phage, such as an M13 selection phage as described in more detail elsewhere herein. In some such embodiments, the gene required for the production of infectious viral particles is the M13 gene III (gIII).

In some embodiments, the viral vector infects mammalian cells. In some embodiments, the viral vector is a retroviral vector. In some embodiments, the viral vector is a vesicular stomatitis virus (VSV) vector. As a dsRNA virus, VSV has a high mutation rate, and can carry cargo, including a gene of interest, of up to 4.5 kb in length. The generation of infectious VSV particles requires the envelope protein VSV-G, a viral glycoprotein that mediates phosphatidylserine attachment and cell entry. VSV can infect a broad spectrum of host cells, including mammalian and insect cells. VSV is therefore a highly suitable vector for continuous evolution in human, mouse, or insect host cells. Similarly, other retroviral vectors that can be pseudotyped with VSV-G envelope protein are equally suitable for continuous evolution processes as described herein.

It is known to those of skill in the art that many retroviral vectors, for example, Murine Leukemia Virus vectors, or Lentiviral vectors can efficiently be packaged with VSV-G envelope protein as a substitute for the virus's native envelope protein. In some embodiments, such VSV-G packagable vectors are adapted for use in a continuous evolution system in that the native envelope (env) protein (e.g., VSV-G in VSVS vectors, or env in MLV vectors) is deleted from the viral genome, and a gene of interest is inserted into the viral genome under the control of a promoter that is active in the desired host cells. The host cells, in turn, express the VSV-G protein, another env protein suitable for vector pseudotyping, or the viral vector's native env protein, under the control of a promoter the activity of which is dependent on an activity of a product encoded by the gene of interest, so that a viral vector with a mutation leading to an increased activity of the gene of interest will be packaged with higher efficiency than a vector with baseline or a loss-of-function mutation.

In some embodiments, mammalian host cells are subjected to infection by a continuously evolving population of viral vectors, for example, VSV vectors comprising a gene of interest and lacking the VSV-G encoding gene, wherein the host cells comprise a gene encoding the VSV-G protein under the control of a conditional promoter. Such retrovirus-bases system could be a two-vector system (the viral vector and an expression construct comprising a gene encoding the envelope protein), or, alternatively, a helper virus can be employed, for example, a VSV helper virus. A helper virus typically comprises a truncated viral genome deficient of structural elements required to package the genome into viral particles, but including viral genes encoding proteins required for viral genome processing in the host cell, and for the generation of viral particles. In such embodiments, the viral vector-based system could be a three-vector system (the viral vector, the expression construct comprising the envelope protein driven by a conditional promoter, and the helper virus comprising viral functions required for viral genome propagation but not the envelope protein). In some embodiments, expression of the five genes of the VSV genome from a helper virus or expression construct in the host cells, allows for production of infectious viral particles carrying a gene of interest, indicating that unbalanced gene expression permits viral replication at a reduced rate, suggesting that reduced expression of VSV-G would indeed serve as a limiting step in efficient viral production.

One advantage of using a helper virus is that the viral vector can be deficient in genes encoding proteins or other functions provided by the helper virus, and can, accordingly, carry a longer gene of interest. In some embodiments, the helper virus does not express an envelope protein, because expression of a viral envelope protein is known to reduce the infectability of host cells by some viral vectors via receptor interference. Viral vectors, for example retroviral vectors, suitable for continuous evolution processes, their respective envelope proteins, and helper viruses for such vectors, are well known to those of skill in the art. For an overview of some exemplary viral genomes, helper viruses, host cells, and envelope proteins suitable for continuous evolution procedures as described herein, see Coffin et al., Retroviruses, CSHL Press 1997, ISBNO-87969-571-4, incorporated herein in its entirety.

In some embodiments, the incubating of the host cells is for a time sufficient for at least 10, at least 20, at least 30, at least 40, at least 50, at least 100, at least 200, at least 300, at least 400, at least, 500, at least 600, at least 700, at least 800, at least 900, at least 1000, at least 1250, at least 1500, at least 1750, at least 2000, at least 2500, at least 3000, at least 4000, at least 5000, at least 7500, at least 10000, or more consecutive viral life cycles. In certain embodiments, the viral vector is an M13 phage, and the length of a single viral life cycle is about 10-20 minutes.

In some embodiments, the cells are contacted and/or incubated in suspension culture. For example, in some embodiments, bacterial cells are incubated in suspension culture in liquid culture media. Suitable culture media for bacterial suspension culture will be apparent to those of skill in the art, and the invention is not limited in this regard. See, for example, Molecular Cloning: A Laboratory Manual, 2nd Ed., ed. by Sambrook, Fritsch, and Maniatis (Cold Spring Harbor Laboratory Press: 1989); Elizabeth Kutter and Alexander Sulakvelidze: Bacteriophages: Biology and Applications. CRC Press; 1st edition (December 2004), ISBN: 0849313368; Martha R. J. Clokie and Andrew M. Kropinski: Bacteriophages: Methods and Protocols, Volume 1: Isolation, Characterization, and Interactions (Methods in Molecular Biology) Humana Press; 1st edition (December, 2008), ISBN: 1588296822; Martha R. J. Clokie and Andrew M. Kropinski: Bacteriophages: Methods and Protocols, Volume 2: Molecular and Applied Aspects (Methods in Molecular Biology) Humana Press; 1st edition (December 2008), ISBN: 1603275649; all of which are incorporated herein in their entirety by reference for disclosure of suitable culture media for bacterial host cell culture). Suspension culture typically requires the culture media to be agitated, either continuously or intermittently. This is achieved, in some embodiments, by agitating or stirring the vessel comprising the host cell population. In some embodiments, the outflow of host cells and the inflow of fresh host cells is sufficient to maintain the host cells in suspension. This in particular, if the flow rate of cells into and/or out of the lagoon is high.

In some embodiments, a viral vector/host cell combination is chosen in which the life cycle of the viral vector is significantly shorter than the average time between cell divisions of the host cell. Average cell division times and viral vector life cycle times are well known in the art for many cell types and vectors, allowing those of skill in the art to ascertain such host cell/vector combinations. In certain embodiments, host cells are being removed from the population of host cells contacted with the viral vector at a rate that results in the average time of a host cell remaining in the host cell population before being removed to be shorter than the average time between cell divisions of the host cells, but to be longer than the average life cycle of the viral vector employed. The result of this is that the host cells, on average, do not have sufficient time to proliferate during their time in the host cell population while the viral vectors do have sufficient time to infect a host cell, replicate in the host cell, and generate new viral particles during the time a host cell remains in the cell population. This assures that the only replicating nucleic acid in the host cell population is the viral vector, and that the host cell genome, the accessory plasmid, or any other nucleic acid constructs cannot acquire mutations allowing for escape from the selective pressure imposed.

For example, in some embodiments, the average time a host cell remains in the host cell population is about 10, about 11, about 12, about 13, about 14, about 15, about 16, about 17, about 18, about 19, about 20, about 21, about 22, about 23, about 24, about 25, about 30, about 35, about 40, about 45, about 50, about 55, about 60, about 70, about 80, about 90, about 100, about 120, about 150, or about 180 minutes.

In some embodiments, the average time a host cell remains in the host cell population depends on how fast the host cells divide and how long infection (or conjugation) requires. In general, the flow rate should be faster than the average time required for cell division, but slow enough to allow viral (or conjugative) propagation. The former will vary, for example, with the media type, and can be delayed by adding cell division inhibitor antibiotics (FtsZ inhibitors in E. coli, etc.). Since the limiting step in continuous evolution is production of the protein required for gene transfer from cell to cell, the flow rate at which the vector washes out will depend on the current activity of the gene(s) of interest. In some embodiments, titratable production of the protein required for the generation of infectious particles, as described herein, can mitigate this problem. In some embodiments, an indicator of phage infection allows computer-controlled optimization of the flow rate for the current activity level in real-time.

In some embodiments, the host cell population is continuously replenished with fresh, uninfected host cells. In some embodiments, this is accomplished by a steady stream of fresh host cells into the population of host cells. In other embodiments, however, the inflow of fresh host cells into the lagoon is semi-continuous or intermittent (e.g., batch-fed). In some embodiments, the rate of fresh host cell inflow into the cell population is such that the rate of removal of cells from the host cell population is compensated. In some embodiments, the result of this cell flow compensation is that the number of cells in the cell population is substantially constant over the time of the continuous evolution procedure. In some embodiments, the portion of fresh, uninfected cells in the cell population is substantially constant over the time of the continuous evolution procedure. For example, in some embodiments, about 10%, about 15%, about 20%, about 25%, about 30%, about 40%, about 50%, about 60%, about 70%, about 75%, about 80%, or about 90% of the cells in the host cell population are not infected by virus. In general, the faster the flow rate of host cells is, the smaller the portion of cells in the host cell population that are infected will be. However, faster flow rates allow for more transfer cycles, e.g., viral life cycles, and, thus, for more generations of evolved vectors in a given period of time, while slower flow rates result in a larger portion of infected host cells in the host cell population and therefore a larger library size at the cost of slower evolution. In some embodiments, the range of effective flow rates is invariably bounded by the cell division time on the slow end and vector washout on the high end In some embodiments, the viral load, for example, as measured in infectious viral particles per volume of cell culture media is substantially constant over the time of the continuous evolution procedure.

In some embodiments, the fresh host cells comprise the accessory plasmid required for selection of viral vectors, for example, the accessory plasmid comprising the gene required for the generation of infectious phage particles that is lacking from the phages being evolved. In some embodiments, the host cells are generated by contacting an uninfected host cell with the relevant vectors, for example, the accessory plasmid and, optionally, a mutagenesis plasmid, and growing an amount of host cells sufficient for the replenishment of the host cell population in a continuous evolution experiment. Methods for the introduction of plasmids and other gene constructs into host cells are well known to those of skill in the art and the invention is not limited in this respect. For bacterial host cells, such methods include, but are not limited to electroporation and heat-shock of competent cells. In some embodiments, the accessory plasmid comprises a selection marker, for example, an antibiotic resistance marker, and the fresh host cells are grown in the presence of the respective antibiotic to ensure the presence of the plasmid in the host cells. Where multiple plasmids are present, different markers are typically used. Such selection markers and their use in cell culture are known to those of skill in the art, and the invention is not limited in this respect.

In some embodiments, the host cell population in a continuous evolution experiment is replenished with fresh host cells growing in a parallel, continuous culture. In some embodiments, the cell density of the host cells in the host cell population contacted with the viral vector and the density of the fresh host cell population is substantially the same.

Typically, the cells being removed from the cell population contacted with the viral vector comprise cells that are infected with the viral vector and uninfected cells. In some embodiments, cells are being removed from the cell populations continuously, for example, by effecting a continuous outflow of the cells from the population. In other embodiments, cells are removed semi-continuously or intermittently from the population. In some embodiments, the replenishment of fresh cells will match the mode of removal of cells from the cell population, for example, if cells are continuously removed, fresh cells will be continuously introduced. However, in some embodiments, the modes of replenishment and removal may be mismatched, for example, a cell population may be continuously replenished with fresh cells, and cells may be removed semi-continuously or in batches.

In some embodiments, the rate of fresh host cell replenishment and/or the rate of host cell removal is adjusted based on quantifying the host cells in the cell population. For example, in some embodiments, the turbidity of culture media comprising the host cell population is monitored and, if the turbidity falls below a threshold level, the ratio of host cell inflow to host cell outflow is adjusted to effect an increase in the number of host cells in the population, as manifested by increased cell culture turbidity. In other embodiments, if the turbidity rises above a threshold level, the ratio of host cell inflow to host cell outflow is adjusted to effect a decrease in the number of host cells in the population, as manifested by decreased cell culture turbidity. Maintaining the density of host cells in the host cell population within a specific density range ensures that enough host cells are available as hosts for the evolving viral vector population, and avoids the depletion of nutrients at the cost of viral packaging and the accumulation of cell-originated toxins from overcrowding the culture.

In some embodiments, the cell density in the host cell population and/or the fresh host cell density in the inflow is about 102 cells/ml to about 1012 cells/ml. In some embodiments, the host cell density is about 102 cells/ml, about 103 cells/ml, about 104 cells/ml, about 105 cells/ml, about 5·105 cells/ml, about 106 cells/ml, about 5·106 cells/ml, about 107 cells/ml, about 5·10⁷ cells/ml, about 10⁸ cells/ml, about 5·10⁸ cells/ml, about 10⁹ cells/ml, about 5·10⁹ cells/ml, about 10¹⁰ cells/ml, or about 5·10¹⁰ cells/ml. In some embodiments, the host cell density is more than about 10¹⁰ cells/ml.

In some embodiments, the host cell population is contacted with a mutagen. In some embodiments, the cell population contacted with the viral vector (e.g., the phage), is continuously exposed to the mutagen at a concentration that allows for an increased mutation rate of the gene of interest, but is not significantly toxic for the host cells during their exposure to the mutagen while in the host cell population. In other embodiments, the host cell population is contacted with the mutagen intermittently, creating phases of increased mutagenesis, and accordingly, of increased viral vector diversification. For example, in some embodiments, the host cells are exposed to a concentration of mutagen sufficient to generate an increased rate of mutagenesis in the gene of interest for about 10%, about 20%, about 50%, or about 75% of the time.

In some embodiments, the host cells comprise a mutagenesis expression construct, for example, in the case of bacterial host cells, a mutagenesis plasmid. In some embodiments, the mutagenesis plasmid comprises a gene expression cassette encoding a mutagenesis-promoting gene product, for example, a proofreading-impaired DNA polymerase. In other embodiments, the mutagenesis plasmid, including a gene involved in the SOS stress response, (e.g., UmuC, UmuD', and/or RecA). In some embodiments, the mutagenesis-promoting gene is under the control of an inducible promoter. Suitable inducible promoters are well known to those of skill in the art and include, for example, arabinose-inducible promoters, tetracycline or doxycyclin-inducible promoters, and tamoxifen-inducible promoters. In some embodiments, the host cell population is contacted with an inducer of the inducible promoter in an amount sufficient to effect an increased rate of mutagenesis. For example, in some embodiments, a bacterial host cell population is provided in which the host cells comprise a mutagenesis plasmid in which a dnaQ926, UmuC, UmuD', and RecA expression cassette is controlled by an arabinose-inducible promoter. In some such embodiments, the population of host cells is contacted with the inducer, for example, arabinose in an amount sufficient to induce an increased rate of mutation.

The use of an inducible mutagenesis plasmid allows one to generate a population of fresh, uninfected host cells in the absence of the inducer, thus avoiding an increased rate of mutation in the fresh host cells before they are introduced into the population of cells contacted with the viral vector. Once introduced into this population, however, these cells can then be induced to support an increased rate of mutation, which is particularly useful in some embodiments of continuous evolution. For example, in some embodiments, the host cell comprise a mutagenesis plasmid as described herein, comprising an arabinose-inducible promoter driving expression of dnaQ926, UmuC, UmuD', and RecA730 from a pBAD promoter (see, e.g., Khlebnikov A, Skaug T, Keasling J D. Modulation of gene expression from the arabinose-inducible araBAD promoter. J Ind Microbiol Biotechnol. 2002 July; 29(1):34-7; incorporated herein by reference for disclosure of a pBAD promoter). In some embodiments, the fresh host cells are not exposed to arabinose, which activates expression of the above identified genes and, thus, increases the rate of mutations in the arabinose-exposed cells, until the host cells reach the lagoon in which the population of selection phage replicates. Accordingly, in some embodiments, the mutation rate in the host cells is normal until they become part of the host cell population in the lagoon, where they are exposed to the inducer (e.g., arabinose) and, thus, to increased mutagenesis. In some embodiments, a method of continuous evolution is provided that includes a phase of diversifying the population of viral vectors by mutagenesis, in which the cells are incubated under conditions suitable for mutagenesis of the viral vector in the absence of stringent selection for the mutated replication product of the viral vector encoding the evolved protein. This is particularly useful in embodiments in which a desired function to be evolved is not merely an increase in an already present function, for example, an increase in the transcriptional activation rate of a transcription factor, but the acquisition of a function not present in the gene of interest at the outset of the evolution procedure. A step of diversifying the pool of mutated versions of the gene of interest within the population of viral vectors, for example, of phage, allows for an increase in the chance to find a mutation that conveys the desired function.

In some embodiments, diversifying the viral vector population is achieved by providing a flow of host cells that does not select for gain-of-function mutations in the gene of interest for replication, mutagenesis, and propagation of the population of viral vectors. In some embodiments, the host cells are host cells that express all genes required for the generation of infectious viral particles, for example, bacterial cells that express a complete helper phage, and, thus, do not impose selective pressure on the gene of interest. In other embodiments, the host cells comprise an accessory plasmid comprising a conditional promoter with a baseline activity sufficient to support viral vector propagation even in the absence of significant gain-of-function mutations of the gene of interest. This can be achieved by using a "leaky" conditional promoter, by using a high-copy number accessory plasmid, thus amplifying baseline leakiness, and/or by using a conditional promoter on which the initial version of the gene of interest effects a low level of activity while a desired gain-of-function mutation effects a significantly higher activity.

For example, as described in more detail in the Example section, in some embodiments, a population of host cells comprising a high-copy accessory plasmid with a gene required for the generation of infectious phage particles is contacted with a selection phage comprising a gene of interest, wherein the accessory plasmid comprises a conditional promoter driving expression of the gene required for the generation from a conditional promoter, the activity of which is dependent on the activity of a gene product encoded by the gene of interest. In some such embodiments, a low stringency selection phase can be achieved by designing the conditional promoter in a way that the initial gene of interest exhibits some activity on that promoter. For example, if a transcriptional activator, such as a T7RNAP or a transcription factor is to be evolved to recognize a non-native target DNA sequence (e.g., a T3RNAP promoter sequence, on which T7RNAP has no activity), a low-stringency accessory plasmid can be designed to comprise a conditional promoter in which the target sequence comprises a desired characteristic, but also retains a feature of the native recognition sequence that allows the transcriptional activator to recognize the target sequence, albeit with less efficiency than its native target sequence. Initial exposure to such a low-stringency accessory plasmid comprising a hybrid target sequence (e.g., a T7/T3 hybrid promoter, with some features of the ultimately desired target sequence and some of the native target sequence) allows the population of phage vectors to diversify by acquiring a plurality of mutations that are not immediately selected against based on the permissive character of the accessory plasmid. Such a diversified population of phage vectors can then be exposed to a stringent selection accessory plasmid, for example, a plasmid comprising in its conditional promoter the ultimately desired target sequence that does not retain a feature of the native target sequence, thus generating a strong negative selective pressure against phage vectors that have not acquired a mutation allowing for recognition of the desired target sequence.

In some embodiments, an initial host cell population contacted with a population of evolving viral vectors is replenished with fresh host cells that are different from the host cells in the initial population. For example, in some embodiments, the initial host cell population is made of host cells comprising a low-stringency accessory plasmid, or no such plasmid at all, or are permissible for viral infection and propagation. In some embodiments, after diversifying the population of viral vectors in the low-stringency or no-selection host cell population, fresh host cells are introduced into the host cell population that impose a more stringent selective pressure for the desired function of the gene of interest. For example, in some embodiments, the secondary fresh host cells are not permissible for viral replication and propagation anymore. In some embodiments, the stringently selective host cells comprise an accessory plasmid in which the conditional promoter exhibits none or only minimal baseline activity, and/or which is only present in low or very low copy numbers in the host cells.

Such methods involving host cells of varying selective stringency allow for harnessing the power of continuous evolution methods as provided herein for the evolution of functions that are completely absent in the initial version of the gene of interest, for example, for the evolution of a transcription factor recognizing a foreign target sequence that a native transcription factor, used as the initial gene of interest, does not recognize at all. Or, for another example, the recognition of a desired target sequence by a DNA-binding protein, a recombinase, a nuclease, a zinc-finger protein, or an RNA-polymerase, that does not bind to or does not exhibit any activity directed towards the desired target sequence.

In some embodiments, negative selection is applied during a continuous evolution method as described herein, by penalizing undesired activities. In some embodiments, this is achieved by causing the undesired activity to interfere with pIII production. For example, expression of an antisense RNA complementary to the gIII RBS and/or start codon is one way of applying negative selection, while expressing a protease (e.g., TEV) and engineering the protease recognition sites into pIII is another.

In some embodiments, negative selection is applied during a continuous evolution method as described herein, by penalizing the undesired activities of evolved products. This is useful, for example, if the desired evolved product is an enzyme with high specificity, for example, a transcription factor or protease with altered, but not broadened, specificity. In some embodiments, negative selection of an undesired activity is achieved by causing the undesired activity to interfere with pIII production, thus inhibiting the propagation of phage genomes encoding gene products with an undesired activity. In some embodiments, expression of a dominant-negative version of pIII or expression of an anti-sense RNA complementary to the gIII RBS and/or gIII start codon is linked to the presence of an undesired activity. In some embodiments, a nuclease or protease cleavage site, the recognition or cleavage of which is undesired, is inserted into a pIII transcript sequence or a pIII amino acid sequence, respectively. In some embodiments, a transcriptional or translational repressor is used that represses expression of a dominant negative variant of pIII and comprises a protease cleavage site the recognition or cleaveage of which is undesired.

In some embodiments, counter-selection against activity on non-target substrates is achieved by linking undesired evolved product activities to the inhibition of phage propagation. For example, in some embodiments, in which a transcription factor is evolved to recognize a specific target sequence, but not an undesired off-target sequence, a negative selection cassette is employed, comprising a nucleic acid sequence encoding a dominant-negative version of pIII (pIII-neg) under the control of a promoter comprising the off-target sequence. If an evolution product recognizes the off-target sequence, the resulting phage particles will incorporate pIII-neg, which results in an inhibition of phage infective potency and phage propagation, thus constituting a selective disadvantage for any phage genomes encoding an evolution product exhibiting the undesired, off-target activity, as compared to evolved products not exhibiting such an activity. In some embodiments, a dual selection strategy is applied during a continuous evolution experiment, in which both positive selection and negative selection constructs are present in the host cells. In some such embodiments, the positive and negative selection constructs are situated on the same plasmid, also referred to as a dual selection accessory plasmid.

For example, in some embodiments, a dual selection accessory plasmid is employed comprising a positive selection cassette, comprising a pIII-encoding sequence under the control of a promoter comprising a target nucleic acid sequence, and a negative selection cassette, comprising a pIII-neg encoding cassette under the control of a promoter comprising an off-target nucleic acid sequence. One advantage of using a simultaneous dual selection strategy is that the selection stringency can be fine-tuned based on the activity or expression level of the negative selection construct as compared to the positive selection construct. Another advantage of a dual selection strategy is the selection is not dependent on the presence or the absence of a desired or an undesired activity, but on the ratio of desired and undesired activities, and, thus, the resulting ratio of pIII and pIII-neg that is incorporated into the respective phage particle.

Some aspects of this invention provide or utilize a dominant negative variant of pIII (pIII-neg). These aspects are based on the surprising discovery that a pIII variant that comprises the two N-terminal domains of pIII and a truncated, termination-incompetent C-terminal domain is not only inactive but is a dominant-negative variant of pIII. A pIII variant comprising the two N-terminal domains of pIII and a truncated, termination-incompetent C-terminal domain was described in Bennett, N. J.; Rakonjac, J., Unlocking of the filamentous bacteriophage virion during infection is mediated by the C domain of pII. Journal of Molecular Biology 2006, 356 (2), 266-73; the entire contents of which are incorporated herein by reference. However, the dominant negative property of such pIII variants has not been previously described. Some aspects of this invention are based on the surprising discovery that a pIII-neg variant as provided herein is efficiently incorporated into phage particles, but it does not catalyze the unlocking of the particle for entry during infection, rendering the respective phage noninfectious even if wild type pIII is present in the same phage particle. Accordingly, such pIII-neg variants are useful for devising a negative selection strategy in the context of PACE, for example, by providing an expression construct comprising a nucleic acid sequence encoding a pIII-neg variant under the control of a promoter comprising a recognition motif, the recognition of which is undesired. In other embodiments, pIII-neg is used in a positive selection strategy, for example, by providing an expression construct in which a pIII-neg encoding sequence is controlled by a promoter comprising a nuclease target site or a repressor recognition site, the recognition of either one is desired.

Positive and negative selection strategies can further be designed to link non-DNA directed activities to phage propagation efficiency. For example, protease activity towards a desired target protease cleavage site can be linked to pIII expression by devising a repressor of gene expression that can be inactivated by a protease recognizing the target site. In some embodiments, pIII expression is driven by a promoter comprising a binding site for such a repressor. Suitable transcriptional repressors are known to those in the art, and one exemplary repressor is the lambda repressor protein, that efficiently represses the lambda promoter pR and can be modified to include a desired protease cleavage site (see, e.g., Sices, H. J.; Kristie, T. M., A genetic screen for the isolation and characterization of site-specific proteases. Proc Natl Acad Sci USA 1998, 95 (6), 2828-33; and Sices, H. J.; Leusink, M. D.; Pacheco, A.; Kristie, T. M., Rapid genetic selection of inhibitor-resistant protease mutants: clinically relevant and novel mutants of the HIV protease. AIDS Res Hum Retroviruses 2001, 17 (13), 1249-55, the entire contents of each of which are incorporated herein by reference). The lambda repressor (cI) contains an N-terminal DNA binding domain and a C-terminal dimerization domain. These two domains are connected by a flexible linker. Efficient transcriptional repression requires the dimerization of cI, and, thus, cleavage of the linker connecting dimerization and binding domains results in abolishing the repressor activity of cI.

Some embodiments provide a pIII expression construct that comprises a pR promoter (containing cI binding sites) driving expression of pIII. When expressed together with a modified cI comprising a desired protease cleavage site in the linker sequence connecting dimerization and binding domains, the cI molecules will repress pIII transcription in the absence of the desired protease activity, and this repression will be abolished in the presence of such activity, thus providing a linkage between protease cleavage activity and an increase in pIII expression that is useful for positive PACE protease selection. Some embodiments provide a negative selection strategy against undesired protease activity in PACE evolution products. In some embodiments, the negative selection is conferred by an expression cassette comprising a pIII-neg encoding nucleic acid under the control of a cI-repressed promoter. When co-expressed with a cI repressor protein comprising an undesired protease cleavage site, expression of pIII-neg will occur in cell harboring phage expressing a protease exhibiting protease activity towards the undesired target site, thus negatively selecting against phage encoding such undesired evolved products. A dual selection for protease target specificity can be achieved by co-expressing cI-repressible pIII and pIII-neg encoding expression constructs with orthogonal cI variants recognizing different DNA target sequences, and thus allowing for simultaneous expression without interfering with each other. Orthogonal cI variants in both dimerization specificity and DNA-binding specificity are known to those of skill in the art (see, e.g., Wharton, R. P.; Ptashne, M., Changing the binding specificity of a repressor by redesigning an alphahelix. Nature 1985, 316 (6029), 601-5; and Wharton, R. P.; Ptashne, M., A new-specificity mutant of 434 repressor that defines an amino acid-base pair contact. Nature 1987, 326 (6116), 888-91, the entire contents of each of which are incorporated herein by reference).

Other selection schemes for gene products having a desired activity are well known to those of skill in the art or will be apparent from the instant disclosure. Selection strategies that can be used in continuous evolution processes and methods as provided herein include, but are not limited to, selection strategies useful in two-hybrid screens. For example, the T7 RNAP selection strategy described in more detail elsewhere herein is an example of a promoter recognition selection strategy. Two-hybrid accessory plasmid set-ups further permit the evolution of protein-protein interactions, and accessory plasmids requiring site-specific recombinase activity for production of the protein required for the generation of infectious viral particles, for example, pIII, allow recombinases to be evolved to recognize any desired target site. A two-hybrid setup or a related one-hybrid setup can further be used to evolve DNA-binding proteins, while a three-hybrid setup can evolve RNA-protein interactions.

Biosynthetic pathways producing small molecules can also be evolved with a promoter or riboswitch (e.g., controlling gene III expression/translation) that is responsive to the presence of the desired small molecule. For example, a promoter that is transcribed only in the presence of butanol could be placed on the accessory plasmid upstream of gene III to optimize a biosynthetic pathway encoding the enzymes for butanol synthesis. A phage vector carrying a gene of interest that has acquired an activity boosting butanol synthesis would have a selective advantage over other phages in an evolving phage population that have not acquired such a gain-of-function. Alternatively, a chemical complementation system, for example, as described in Baker and Cornish, PNAS, 2002, incorporated herein by reference, can be used to evolve individual proteins or enzymes capable of bond formation reactions ( ). In other embodiments, a trans-splicing intron designed to splice itself into a particular target sequence can be evolved by expressing only the latter half of gene III from the accessory plasmid, preceded by the target sequence, and placing the other half (fused to the trans-splicing intron) on the selection phage. Successful splicing would reconstitute full-length pIII-encoding mRNA. Protease specificity and activity can be evolved by expressing pIII fused to a large protein from the accessory plasmid, separated by a linker containing the desired protease recognition site. Cleavage of the linker by active protease encoded by the selection phage would result in infectious pIII, while uncleaved pIII would be unable to bind due to the blocking protein. Further, As described, for example, by Malmborg and Borrebaeck 1997, a target antigen can be fused to the F pilus of a bacteria, blocking wild-type pIII from binding. Phage displaying antibodies specific to the antigen could bind and infect, yielding enrichments of >1000-fold in phage display. In some embodiments, this system can be adapted for continuous evolution, in that the accessory plasmid is designed to produce wild-type pIII to contact the tolA receptor and perform the actual infection (as the antibody-pIII fusion binds well but infects with low efficiency), while the selection phage encodes the pIII-antibody fusion protein. Progeny phage containing both types of pIII tightly adsorb to the F pilus through the antibody-antigen interaction, with the wild-type pIII contacting tolA and mediating high-efficiency infection. To allow propagation when the initial antibody-antigen interaction is weak, a mixture of host cells could flow into the lagoon: a small fraction expressing wild-type pili and serving as a reservoir of infected cells capable of propagating any selection phage regardless of activity, while the majority of cells requires a successful interaction, serving as the "reward" for any mutants that improve their binding affinity. This last system, in some embodiments, can evolve new antibodies that are effective against a target pathogen faster than the pathogen itself can evolve, since the evolution rates of PACE and other systems described herein are higher than those of human-specific pathogens, for example, those of human viruses.

Figure 3:
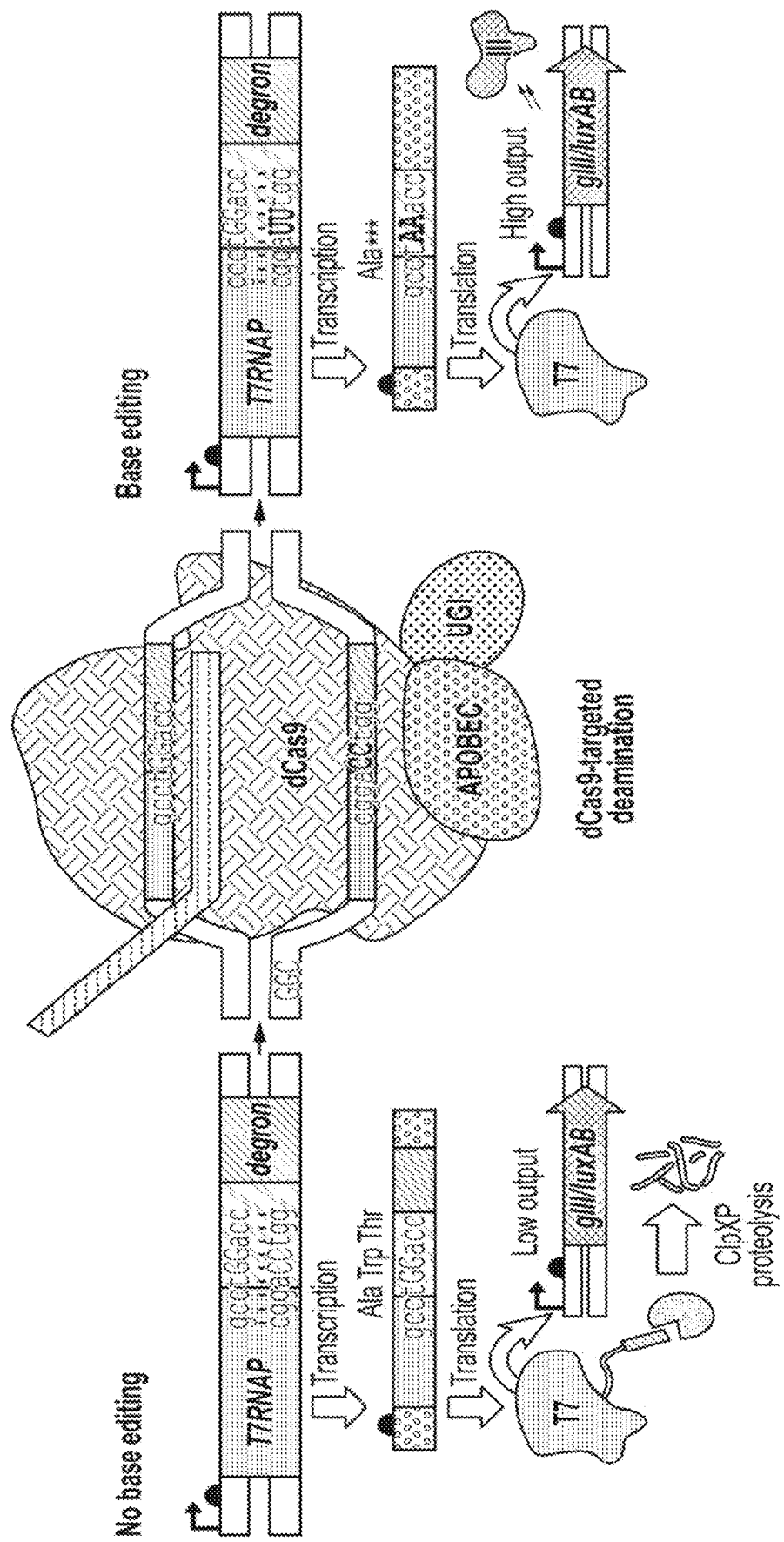
FIG. 3 shows a schematic of no base editing versus base editing.
Figure 5:
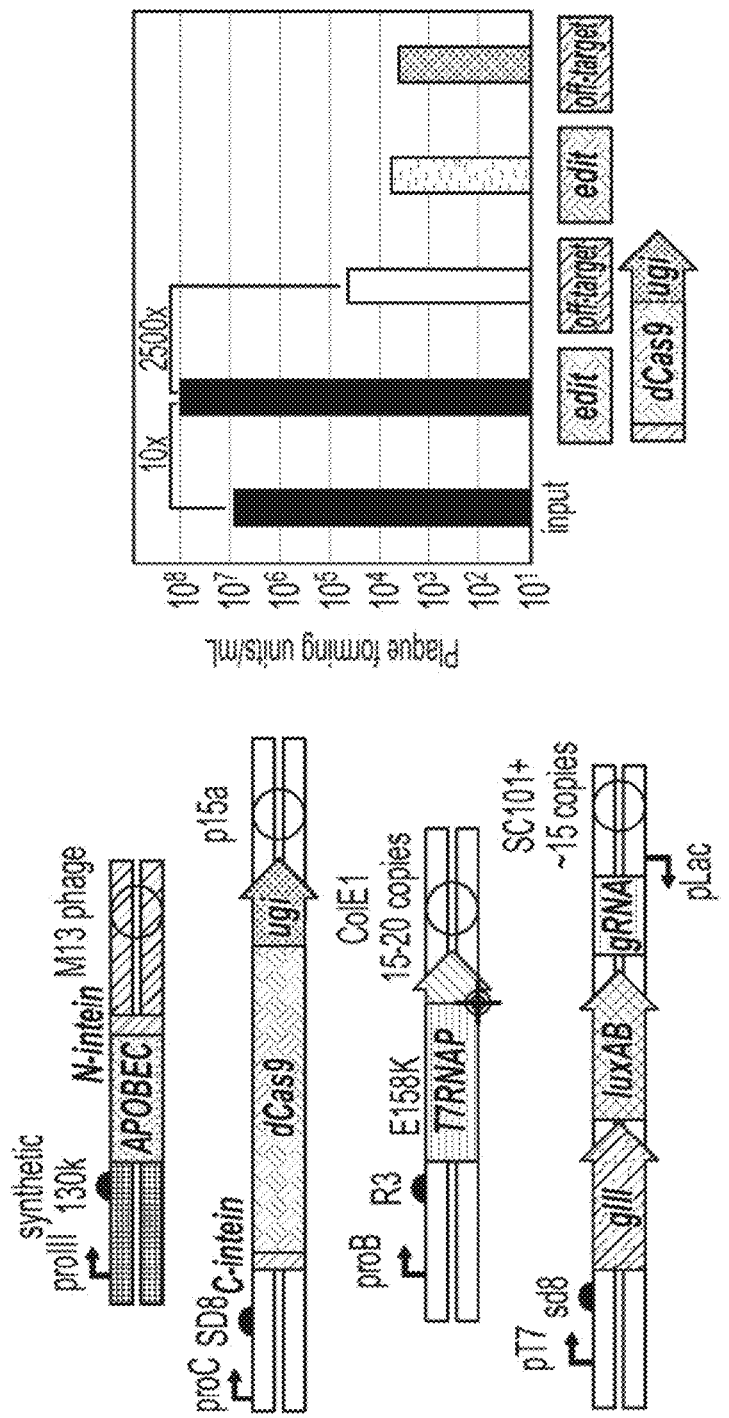
FIG. 5 shows T7RNAP expression with modified phage backbone using a split intein.
Figure 6:
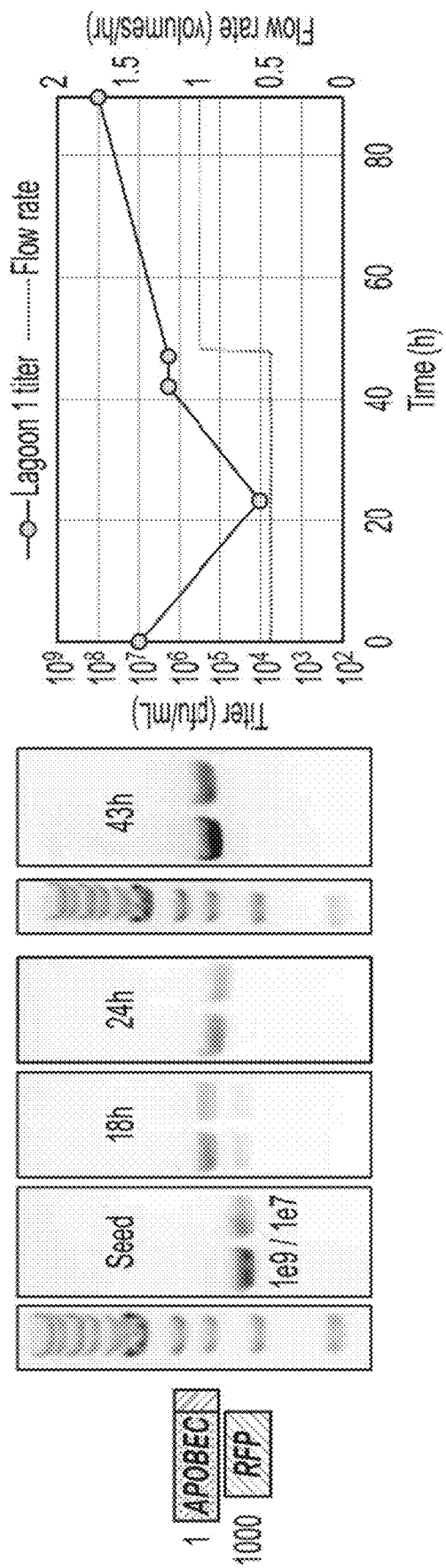
FIG. 6 shows APOBEC phage growth takes over within 24 hours.

Methods and strategies to design conditional promoters suitable for carrying out the selections strategies described herein are well known to those of skill in the art. Some exemplary design strategies are summarized in FIG. 3B. For an overview over exemplary suitable selection strategies and methods for designing conditional promoters driving the expression of a gene required for cell-cell gene transfer, e.g. gIII, see Vidal and Legrain, Yeast n-hybrid review, Nucleic Acid Research 27, 919 (1999), incorporated herein in its entirety.

Apparatus for Continued Evolution

The invention also provides apparatuses for continuous evolution of a nucleic acid. The core element of such an apparatus is a lagoon allowing for the generation of a flow of host cells in which a population of viral vectors can replicate and propagate. In some embodiments, the lagoon comprises a cell culture vessel comprising an actively replicating population of viral vectors, for example, phage vectors comprising a gene of interest, and a population of host cells, for example, bacterial host cells. In some embodiments, the lagoon comprises an inflow for the introduction of fresh host cells into the lagoon and an outflow for the removal of host cells from the lagoon. In some embodiments, the inflow is connected to a turbidostat comprising a culture of fresh host cells. In some embodiments, the outflow is connected to a waste vessel, or a sink. In some embodiments, the lagoon further comprises an inflow for the introduction of a mutagen into the lagoon. In some embodiments that inflow is connected to a vessel holding a solution of the mutagen. In some embodiments, the lagoon comprises an inflow for the introduction of an inducer of gene expression into the lagoon, for example, of an inducer activating an inducible promoter within the host cells that drives expression of a gene promoting mutagenesis (e.g., as part of a mutagenesis plasmid), as described in more detail elsewhere herein. In some embodiments, that inflow is connected to a vessel comprising a solution of the inducer, for example, a solution of arabinose.

In some embodiments, the lagoon comprises a population of viral vectors. In some embodiments, the lagoon comprises a population of viral vectors. In some embodiments, the viral vectors are phage, for example, M13 phages deficient in a gene required for the generation of infectious viral particles as described herein. In some such embodiments, the host cells are prokaryotic cells amenable to phage infection, replication, and propagation of phage, for example, host cells comprising an accessory plasmid comprising a gene required for the generation of infectious viral particles under the control of a conditional promoter as described herein.

In some embodiments, the lagoon comprises a controller for regulation of the inflow and outflow rates of the host cells, the inflow of the mutagen, and/or the inflow of the inducer. In some embodiments, a visual indicator of phage presence, for example, a fluorescent marker, is tracked and used to govern the flow rate, keeping the total infected population constant. In some embodiments, the visual marker is a fluorescent protein encoded by the phage genome, or an enzyme encoded by the phage genome that, once expressed in the host cells, results in a visually detectable change in the host cells. In some embodiments, the visual tracking of infected cells is used to adjust a flow rate to keep the system flowing as fast as possible without risk of vector washout.

In some embodiments, the expression of the gene required for the generation of infectious particles is titratable. In some embodiments, this is accomplished with an accessory plasmid producing pIII proportional to the amount of anhydrotetracycline added to the lagoon. Other In some embodiments, such a titrable expression construct can be combined with another accessory plasmid as described herein, allowing simultaneous selection for activity and titratable control of pIII. This permits the evolution of activities too weak to otherwise survive in the lagoon, as well as allowing neutral drift to escape local fitness peak traps. In some embodiments, negative selection is applied during a continuous evolution method as described herein, by penalizing undesired activities. In some embodiments, this is achieved by causing the undesired activity to interfere with pIII production. For example, expression of an antisense RNA complementary to the gIII RBS and/or start codon is one way of applying negative selection, while expressing a protease (e.g., TEV) and engineering the protease recognition sites into pIII is another.

In some embodiments, the apparatus comprises a turbidostat. In some embodiments, the turbidostat comprises a cell culture vessel in which the population of fresh host cells is situated, for example, in liquid suspension culture. In some embodiments, the turbidostat comprises an outflow that is connected to an inflow of the lagoon, allowing the introduction of fresh cells from the turbidostat into the lagoon. In some embodiments, the turbidostat comprises an inflow for the introduction of fresh culture media into the turbidostat. In some embodiments, the inflow is connected to a vessel comprising sterile culture media. In some embodiments, the turbidostat further comprises an outflow for the removal of host cells from the turbidostat. In some embodiments, that outflow is connected to a waste vessel or drain.

In some embodiments, the turbidostat comprises a turbidity meter for measuring the turbidity of the culture of fresh host cells in the turbidostat. In some embodiments, the turbidostat comprises a controller that regulated the inflow of sterile liquid media and the outflow into the waste vessel based on the turbidity of the culture liquid in the turbidostat.

In some embodiments, the lagoon and/or the turbidostat comprises a shaker or agitator for constant or intermittent agitation, for example, a shaker, mixer, stirrer, or bubbler, allowing for the population of host cells to be continuously or intermittently agitated and oxygenated.

In some embodiments, the controller regulates the rate of inflow of fresh host cells into the lagoon to be substantially the same (volume/volume) as the rate of outflow from the lagoon. In some embodiments, the rate of inflow of fresh host cells into and/or the rate of outflow of host cells from the lagoon is regulated to be substantially constant over the time of a continuous evolution experiment. In some embodiments, the rate of inflow and/or the rate of outflow is from about 0.1 lagoon volumes per hour to about 25 lagoon volumes per hour. In some embodiments, the rate of inflow and/or the rate of outflow is approximately 0.1 lagoon volumes per hour (lv/h), approximately 0.2 lv/h, approximately 0.25 lv/h, approximately 0.3 lv/h, approximately 0.4 lv/h, approximately 0.5 lv/h, approximately 0.6 lv/h, approximately 0.7 lv/h, approximately 0.75 lv/h, approximately 0.8 lv/h, approximately 0.9 lv/h, approximately 1 lv/h, approximately 2 lv/h, approximately 2.5 lv/h, approximately 3 lv/h, approximately 4 lv/h, approximately 5 lv/h, approximately 7.5 lv/h, approximately 10 lv/h, or more than 10 lv/h.

In some embodiments, the inflow and outflow rates are controlled based on a quantitative assessment of the population of host cells in the lagoon, for example, by measuring the cell number, cell density, wet biomass weight per volume, turbidity, or cell growth rate. In some embodiments, the lagoon inflow and/or outflow rate is controlled to maintain a host cell density of from about $10^2$ cells/ml to about $10^{12}$ cells/ml in the lagoon. In some embodiments, the inflow and/or outflow rate is controlled to maintain a host cell density of about $10^2$ cells/ml, about $10^3$ cells/ml, about $10^4$ cells/ml, about $10^5$ cells/ml, about $5 \times 10^5$ cells/ml, about $10^6$ cells/ml, about $5 \times 10^6$ cells/ml, about $10^7$ cells/ml, about $5 \times 10^7$ cells/ml, about $10^8$ cells/ml, about $5 \times 10^8$ cells/ml, about $10^9$ cells/ml, about $5 \times 10^9$ cells/ml, about $10^{10}$ cells/ml, about $5 \times 10^{10}$ cells/ml, or more than $5 \times 10^{10}$ cells/ml, in the lagoon. In some embodiments, the density of fresh host cells in the turbidostat and the density of host cells in the lagoon are substantially identical.

In some embodiments, the lagoon inflow and outflow rates are controlled to maintain a substantially constant number of host cells in the lagoon. In some embodiments, the inflow and outflow rates are controlled to maintain a substantially constant frequency of fresh host cells in the lagoon. In some embodiments, the population of host cells is continuously replenished with fresh host cells that are not infected by the phage. In some embodiments, the replenishment is semi-continuous or by batch-feeding fresh cells into the cell population.

In some embodiments, the lagoon volume is from approximately 1 ml to approximately 100 l, for example, the lagoon volume is approximately 1 ml, approximately 10 ml, approximately 50 ml, approximately 100 ml, approximately 200 ml, approximately 250 ml, approximately 500 ml, approximately 750 ml, approximately 1 l, approximately 2 ml, approximately 2.5 l, approximately 3 l, approximately 4 l, approximately 5 l, approximately 10 l, approximately 1 ml-10 ml, approximately 10 ml-50 ml, approximately 50 ml-100, approximately 100 ml-250 ml, approximately 250 ml-500 ml, approximately 500 ml-1 l, approximately 1 l-2 l, approximately 2 l-5 l, approximately 5 l-10 l, approximately 10-50 l, approximately 50-100 l, or more than 100 l.

In some embodiments, the lagoon and/or the turbidostat further comprises a heater and a thermostat controlling the temperature. In some embodiments, the temperature in the lagoon and/or the turbidostat is controlled to be from about 4° C. to about 55° C., preferably from about 25° C. to about 39° C., for example, about 37° C.

In some embodiments, the inflow rate and/or the outflow rate is controlled to allow for the incubation and replenishment of the population of host cells for a time sufficient for at least 10, at least 20, at least 30, at least 40, at least 50, at least 100, at least 200, at least 300, at least 400, at least, 500, at least 600, at least 700, at least 800, at least 900, at least 1000, at least 1250, at least 1500, at least 1750, at least 2000, at least 2500, at least 3000, at least 4000, at least 5000, at least 7500, at least 10000, or more consecutive viral vector or phage life cycles. In some embodiments, the time sufficient for one phage life cycle is about 10 minutes.

Therefore, in some embodiments, the time of the entire evolution procedure is about 12 hours, about 18 hours, about 24 hours, about 36 hours, about 48 hours, about 50 hours, about 3 days, about 4 days, about 5 days, about 6 days, about 7 days, about 10 days, about two weeks, about 3 weeks, about 4 weeks, or about 5 weeks.

For example, in some embodiments, a PACE apparatus is provided, comprising a lagoon of about 100 ml, or about 1 l volume, wherein the lagoon is connected to a turbidostat of about 0.5 l, 1 l, or 3 l volume, and to a vessel comprising an inducer for a mutagenesis plasmid, for example, arabinose, wherein the lagoon and the turbidostat comprise a suspension culture of $E.\ coli$ cells at a concentration of about $5 \times 10^8$ cells/ml. In some embodiments, the flow of cells through the lagoon is regulated to about 3 lagoon volumes per hour. In some embodiments, cells are removed from the lagoon by continuous pumping, for example, by using a waste needle set at a height of the lagoon vessel that corresponds to a desired volume of fluid (e.g., about 100 ml, in the lagoon. In some embodiments, the host cells are $E.\ coli$ cells comprising the F' plasmid, for example, cells of the genotype F'proA+B+$\Delta$(lacIZY) zzf::Tn10(TetR)/endA1 recA1 galE15 galK16 nupG rpsL $\Delta$lacIZYA araD139 $\Delta$(ara,leu)7697 mcrA $\Delta$(mrr-hsdRMS-mcrBC) proBA::pir116$\lambda$–. In some embodiments, the selection phage comprises an M13 genome, in which the pIII-encoding region, or a part thereof, has been replaced with a gene of interest, for example, a coding region that is driven by a wild-type phage promoter. In some embodiments, the host cells comprise an accessory plasmid in which a gene encoding a protein required for the generation of infectious phage particles, for example, M13 pIII, is expressed from a conditional promoter as described in more detail elsewhere herein. In some embodiments, the host cells further comprise a mutagenesis plasmid, for example, a mutagenesis plasmid expressing a mutagenesis-promoting protein from an inducible promoter, such as an arabinose-inducible promoter. In some embodiments the apparatus is set up to provide fresh media to the turbidostat for the generation of a flow of cells of about 2-4 lagoon volumes per hour for about 3-7 days.

Vectors and Reagents

The invention provides viral vectors for the inventive continuous evolution processes. In some embodiments, phage vectors for phage-assisted continuous evolution are provided. In some embodiments, a selection phage is provided that comprises a phage genome deficient in at least one gene required for the generation of infectious phage particles and a gene of interest to be evolved.

For example, in some embodiments, the selection phage comprises an M13 phage genome deficient in a gene required for the generation of infectious M13 phage particles, for example, a full-length gIII. In some embodiments, the selection phage comprises a phage genome providing all other phage functions required for the phage life cycle except the gene required for generation of infectious phage particles. In some such embodiments, an M13 selection phage is provided that comprises a gI, gII, gIV, gV, gVI, gVII, gVIII, gIX, and a gX gene, but not a full-length gIII. In some embodiments, the selection phage comprises a 3'-fragment of gIII, but no full-length gIII. The 3'-end of gIII comprises a promoter (see FIG. 16) and retaining this promoter activity is beneficial, in some embodiments, for an increased expression of gVI, which is immediately downstream of the gIII 3'-promoter, or a more balanced (wild-type phage-like) ratio of expression levels of the phage genes in the host cell, which, in turn, can lead to more efficient phage production. In some embodiments, the 3'-fragment of gIII gene comprises the 3'-gIII promoter sequence. In some embodiments, the 3'-fragment of gIII comprises the last 180 bp, the last 150 bp, the last 125 bp, the last 100 bp, the last 50 bp, or the last 25 bp of gIII. In some embodiments, the 3'-fragment of gIII comprises the last 180 bp of gIII.

M13 selection phage is provided that comprises a gene of interest in the phage genome, for example, inserted downstream of the gVIII 3'-terminator and upstream of the gIII-3'-promoter. In some embodiments, an M13 selection phage is provided that comprises a multiple cloning site for cloning a gene of interest into the phage genome, for example, a multiple cloning site (MCS) inserted downstream of the gVIII 3'-terminator and upstream of the gIII-3'-promoter.

Some aspects of this invention provide a vector system for continuous evolution procedures, comprising of a viral vector, for example, a selection phage, and a matching accessory plasmid. In some embodiments, a vector system for phage-based continuous directed evolution is provided that comprises (a) a selection phage comprising a gene of interest to be evolved, wherein the phage genome is deficient in a gene required to generate infectious phage; and (b) an accessory plasmid comprising the gene required to generate infectious phage particle under the control of a conditional promoter, wherein the conditional promoter is activated by a function of a gene product encoded by the gene of interest.

In some embodiments, the selection phage is an M13 phage as described herein. For example, in some embodiments, the selection phage comprises an M13 genome including all genes required for the generation of phage particles, for example, gI, gII, gIV, gV, gVI, gVII, gVIII, gIX, and gX gene, but not a full-length gIII gene. In some embodiments, the selection phage genome comprises an F1 or an M13 origin of replication. In some embodiments, the selection phage genome comprises a 3'-fragment of gIII gene. In some embodiments, the selection phage comprises a multiple cloning site upstream of the gIII 3'-promoter and downstream of the gVIII 3'-terminator.

In some embodiments, the selection phage does not comprise a full length gVI. GVI is similarly required for infection as gIII and, thus, can be used in a similar fashion for selection as described for gIII herein. However, it was found that continuous expression of pIII renders some host cells resistant to infection by M13. Accordingly, it is desirable that pIII is produced only after infection. This can be achieved by providing a gene encoding pIII under the control of an inducible promoter, for example, an arabinose-inducible promoter as described herein, and providing the inducer in the lagoon, where infection takes place, but not in the turbidostat, or otherwise before infection takes place. In some embodiments, multiple genes required for the generation of infectious phage are removed from the selection phage genome, for example, gIII and gVI, and provided by the host cell, for example, in an accessory plasmid as described herein.

The vector system may further comprise a helper phage, wherein the selection phage does not comprise all genes required for the generation of phage particles, and wherein the helper phage complements the genome of the selection phage, so that the helper phage genome and the selection phage genome together comprise at least one functional copy of all genes required for the generation of phage particles, but are deficient in at least one gene required for the generation of infectious phage particles.

In some embodiments, the accessory plasmid of the vector system comprises an expression cassette comprising the gene required for the generation of infectious phage under the control of a conditional promoter. In some embodiments, the accessory plasmid of the vector system comprises a gene encoding pIII under the control of a conditional promoter the activity of which is dependent on a function of a product of the gene of interest.

In some embodiments, the vector system further comprises a mutagenesis plasmid, for example, an arabinose-inducible mutagenesis plasmid as described herein.

In some embodiments, the vector system further comprises a helper plasmid providing expression constructs of any phage gene not comprised in the phage genome of the selection phage or in the accessory plasmid.

In various embodiments of the vectors used herein in the continuous evolution processes may include the following components in any combination:

(SEQ ID NO: 132)
gttttagagctagaaatagcaagttaaaataaggetagtccgttatcaacttgaaaaag tggcaccgagtcggtgcttttttt T7 RNA Polymerase
(SEQ ID NO: 133)
MNTINIAKNDFSDIELAAIPFNTLADHYGERLAREQLALEHESYEMGEARF

RKMFERQLKAGEVADNAAAKPLITTLLPKMIARINDWFEEVKAKRGKRPTAFQFLQEIK

PEAVAYITIKTTLACLTSADNTTVQAVASAIGRAIEDEARFGRIRDLKAKHFKKNVEEQL

NKRVGHVYKKAFMQVVEADMLSKGLLGGEAWSSWHKEDSIHVGVRCIEMLIESTGMV

SLHRQNAGVVGQDSETIELAPEYAEAIATRAGALAGISPMFQPCVVPPKPWTGITGGGY

WANGRRPLALVRTHSKKALMRYEDVYMPEVYKAINIAQNTAWKINKKVLAVANVITK

WKHCPVEDIPAIEREELPMKPEDIDMNPEALTAWKRAAAAVYRKDKARKSRRISLEFML

EQANKFANHKAIWFPYNMDWRGRVYAVSMFNPQGNDMTKGLLTLAKGKPIGKEGYY

WLKIHGANCAGVDKVPFPERIKFIEENHENIMACAKSPLENTWWAEQDSPFCFLAFCFE

YAGVQHHGLSYNCSLPLAFDGSCSGIQHFSAMLRDEVGGRAVNLLPSETVQDIYGIVAK

KVNEILQADAINGTDNEVVTVTDENTGEISEKVKLGTKALAGQWLAYGVTRSVTKRSV

MTLAYGSKEFGFRQQVLEDTIQPAIDSGKGLMFTQPNQAAGYMAKLIWESVSVTVVAA

-continued

```
VEAMNWLKSAAKLLAAEVKDKKTGEILRKRCAVHWVTPDGFPVWQEYKKPIQTRLNL

MFLGQFRLQPTINTNKDSEIDAHKQESGIAPNFVHSQDGSHLRKTVVWAHEKYGIESFA

LIHDSFGTIPADAANLFKAVRETMVDTYESCDVLADFYDQFADQLHESQLDKMPALPA

KGNLNLRDILESDFAFA*
```

Degron tag (SEQ ID NO: 134)
```
AANDENYNYALAA
```

Fusion sequence is (SEQ ID NO: 135)
```
MNTINIAKNDFSDIELAAIPFNTLADHYGERLAREQLALEHESYEMGEARF

RKMFERQLKAGEVADNAAAKPLITTLLPKMIARINDWFEEVKAKRGKRPTAFQFLQEIK

PEAVAYITIKTTLACLTSADNTTVQAVASAIGRAIEDEARFGRIRDLKAKHFKKNVEEQL

NKRVGHVYKKAFMQVVEADMLSKGLLGGEAWSSWHKEDSIHVGVRCIEMLIESTGMV

SLHRQNAGVVGQDSETIELAPEYAEAIATRAGALAGISPMFQPCVVPPKPWTGITGGGY

WANGRRPLALVRTHSKKALMRYEDVYMPEVYKAINIAQNTAWKINKKVLAVANVITK

WKHCPVEDIPAIEREELPMKPEDIDMNPEALTAWKRAAAAVYRKDKARKSRRISLEFML

EQANKFANHKAIWFPYNMDWRGRVYAVSMFNPQGNDMTKGLLTLAKGKPIGKEGYY

WLKIHGANCAGVDKVPFPERIKFIEENHENIMACAKSPLENTWWAEQDSPFCFLAFCFE

YAGVQHHGLSYNCSLPLAFDGSCSGIQHFSAMLRDEVGGRAVNLLPSETVQDIYGIVAK

KVNEILQADAINGTDNEVVTVTDENTGEISEKVKLGTKALAGQWLAYGVTRSVTKRSV

MTLAYGSKEFGFRQQVLEDTIQPAIDSGKGLMFTQPNQAAGYMAKLIWESVSVTVVAA

VEAMNWLKSAAKLLAAEVKDKKTGEILRKRCAVHWVTPDGFPVWQEYKKPIQTRLNL

MFLGQFRLQPTINTNKDSEIDAHKQESGIAPNFVHSQDGSHLRKTVVWAHEKYGIESFA

LIHDSFGTIPADAANLFKAVRETMVDTYESCDVLADFYDQFADQLHESQLDKMPALPA

KGNLNLRDILESDFAFAWTRAANDENYNYALAA*
```

DnaE intein (fusion to deaminases via the XTEN linker)

(SEQ ID NO: 136)
```
CLSYETEILTVEYGLLPIGKIVEKRIECTVYSVDNNGNIYTQPVAQWHDRG

EQEVFEYCLEDGSLIRATKDHKFMTVDGQMLPIDEIFERELDLMRVDNLPN*
```

Fusion to APOBEC (SEQ ID NO: 137)
```
MSSETGPVAVDPTLRRRIEPHEFEVFFDPRELRKETCLLYEINWGGRHSIW

RHTSQNTNKHVEVNFIEKFTTERYFCPNTRCSITWFLSWSPCGECSRAITEFLSRYPHVTL

FIYIARLYHHADPRNRQGLRDLISSGVTIQIMTEQESGYCWRNFVNYSPSNEAHWPRYPH

LWVRLYVLELYCIILGLPPCLNILRRKQPQLTFFTIALQSCHYQRLPPHILWATGLKSGSE

TPGTSESATPECLSYETEILTVEYGLLPIGKIVEKRIECTVYSVDNNGNIYTQPVAQWHDR

GEQEVFEYCLEDGSLIRATKDHKFMTVDGQMLPIDEIFERELDLMRVDNLPN*
```

C-intein fused to cas9

(SEQ ID NO: 138)
```
MIKIATRKYLGKQNVYDIGVERDHNFALKNGFIASNC
```

Fusion to cas9

(SEQ ID NO: 139)
```
MIKIATRKYLGKQNVYDIGVERDHNFALKNGFIASNCFNKYSIGLAIGTNS

VGWAVITDEYKVPSKKFKVLGNTDRHSIKKNLIGALLFDSGETAEATRLKRTARRRYTR

RKNRICYLQEIFSNEMAKVDDSFFHRLEESFLVEEDKKHERHPIFGNIVDEVAYHEKYPTI

YHLRKKLVDSTDKADLRLIYLALAHMIKFRGHFLIEGDLNPDNSDVDKLFIQLVQTYNQ
```

-continued

```
LFEENPINASGVDAKAILSARLSKSRRLENLIAQLPGEKKNGLFGNLIALSLGLTPNFKSN

FDLAEDAKLQLSKDTYDDDLDNLLAQIGDQYADLFLAAKNLSDAILLSDILRVNTEITKA

PLSASMIKRYDEHHQDLTLLKALVRQQLPEKYKEIFFDQSKNGYAGYIDGGASQEEFYK

FIKPILEKMDGTEELLVKLNREDLLRKQRTFDNGSIPHQIHLGELHAILRRQEDFYPFLKD

NREKIEKILTFRIPYYVGPLARGNSRFAWMTRKSEETITPWNFEEVVDKGASAQSFIERM

TNFDKNLPNEKVLPKHSLLYEYFTVYNELTKVKYVTEGMRKPAFLSGEQKKAIVDLLFK

TNRKVTVKQLKEDYFKKIECFDSVEISGVEDRFNASLGTYHDLLKIIKDKDFLDNEENED

ILEDIVLTLTLFEDREMIEERLKTYAHLFDDKVMKQLKRRRYTGWGRLSRKLINGIRDKQ

SGKTILDFLKSDGFANRNFMQLIHDDSLTFKEDIQKAQVSGQGDSLHEHIANLAGSPAIK

KGILQTVKVVDELVKVMGRHKPENIVIEMARENQTTQKGQKNSRERMKRIEEGIKELGS

QILKEHPVENTQLQNEKLYLYYLQNGRDMYVDQELDINRLSDYDVDAIVPQSFLKDDSI

DNKVLTRSDKNRGKSDNVPSEEVVKKMKNYWRQLLNAKLITQRKFDNLTKAERGGLS

ELDKAGFIKRQLVETRQITKHVAQILDSRMNTKYDENDKLIREVKVITLKSKLVSDFRKD

FQFYKVREINNYHHAHDAYLNAVVGTALIKKYPKLESEFVYGDYKVYDVRKMIAKSEQ

EIGKATAKYFFYSNIMNFFKTEITLANGEIRKRPLIETNGETGEIVWDKGRDFATVRKVLS

MPQVNIVKKTEVQTGGFSKESILPKRNSDKLIARKKDWDPKKYGGFDSPTVAYSVLVV

AKVEKGKSKKLKSVKELLGITIMERSSFEKNPIDFLEAKGYKEVKKDLIIKLPKYSLFELE

NGRKRMLASAGELQKGNELALPSKYVNFLYLASHYEKLKGSPEDNEQKQLFVEQHKH

YLDEIIEQISEFSKRVILADANLDKVLSAYNKHRDKPIREQAENIIHLFTLTNLGAPAAFKY

FDTTIDRKRYTSTKEVLDATLIHQSITGLYETRIDLSQLGGDSGGSMTNLSDIIEKETGKQ

LVIQESILMLPEEVEEVIGNKPESDILVHTAYDESTDENVMLLTSDAPEYKPWALVIQDS

NGENKIKML*
```

Editing DNA or RNA

Some aspects of the disclosure provide methods for editing a nucleic acid using the base editors described herein. In some embodiments, the method is a method for editing a nucleobase of a nucleic acid (e.g., a base pair of a double-stranded DNA sequence). In some embodiments, the method comprises the steps of: a) contacting a target region of a nucleic acid (e.g., a double-stranded DNA sequence) with a complex comprising a base editor (e.g., a Cas9 domain fused to an adenosine deaminase) and a guide nucleic acid (e.g., gRNA), wherein the target region comprises a targeted nucleobase pair, b) inducing strand separation of said target region, c) converting a first nucleobase of said target nucleobase pair in a single strand of the target region to a second nucleobase, and d) cutting no more than one strand of said target region, where a third nucleobase complementary to the first nucleobase base is replaced by a fourth nucleobase complementary to the second nucleobase. In some embodiments, the method results in less than 20% indel formation in the nucleic acid. It should be appreciated that in some embodiments, step b is omitted. In some embodiments, the first nucleobase is an adenine. In some embodiments, the second nucleobase is a deaminated adenine, or inosine. In some embodiments, the third nucleobase is a thymine. In some embodiments, the fourth nucleobase is a cytosine. In some embodiments, the method results in less than 19%, 18%, 16%, 14%, 12%, 10%, 8%, 6%, 4%, 2%, 1%, 0.5%, 0.2%, or less than 0.1% indel formation. In some embodiments, the method further comprises replacing the second nucleobase with a fifth nucleobase that is complementary to the fourth nucleobase, thereby generating an intended edited base pair (e.g., A:T to G:C). In some embodiments, the fifth nucleobase is a guanine. In some embodiments, at least 5% of the intended base pairs are edited. In some embodiments, at least 10%, 15%, 20%, 25%, 30%, 35%, 40%, 45%, or 50% of the intended base paires are edited.

In some embodiments, the ratio of intended products to unintended products in the target nucleotide is at least 2:1, 5:1, 10:1, 20:1, 30:1, 40:1, 50:1, 60:1, 70:1, 80:1, 90:1, 100:1, or 200:1, or more. In some embodiments, the ratio of intended point mutation to indel formation is greater than 1:1, 10:1, 50:1, 100:1, 500:1, or 1000:1, or more. In some embodiments, the cut single strand (nicked strand) is hybridized to the guide nucleic acid. In some embodiments, the cut single strand is opposite to the strand comprising the first nucleobase. In some embodiments, the base editor comprises a Cas9 domain. In some embodiments, the first base is adenine, and the second base is not a G, C, A, or T. In some embodiments, the second base is inosine. In some embodiments, the first base is adenine. In some embodiments, the second base is not a G, C, A, or T. In some embodiments, the second base is inosine. In some embodiments, the base editor inhibits base excision repair of the edited strand. In some embodiments, the base editor protects or binds the non-edited strand. In some embodiments, the base editor comprises UGI activity. In some embodiments, the base editor comprises a catalytically inactive inosine-specific nuclease. In some embodiments, the base editor comprises nickase activity. In some embodiments, the intended edited base pair is upstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides upstream of the PAM site. In some embodiments, the intended edited basepair is downstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides downstream stream of the PAM site. In some embodiments, the method does not require a canonical (e.g., NGG) PAM site. In some embodiments, the nucleobase editor comprises a linker. In some embodiments, the linker is 1-25 amino acids in length. In some embodiments, the linker is 5-20 amino acids in length. In some embodiments, linker is 10, 11, 12, 13, 14, 15, 16, 17, 18, 19, or 20 amino acids in length. In some embodiments, the target region comprises a target window, wherein the target window comprises the target nucleobase pair. In some embodiments, the target window comprises 1-10 nucleotides. In some embodiments, the target window is 1-9, 1-8, 1-7, 1-6, 1-5, 1-4, 1-3, 1-2, or 1 nucleotides in length. In some embodiments, the target window is 1, 2, 3, 4, 5, 6, 7, 8, 9, 10, 11, 12, 13, 14, 15, 16, 17, 18, 19, or 20 nucleotides in length. In some embodiments, the intended edited base pair is within the target window. In some embodiments, the target window comprises the intended edited base pair. In some embodiments, the method is performed using any of the base editors provided herein. In some embodiments, a target window is a deamination window.

In some embodiments, the disclosure provides methods for editing a nucleotide. In some embodiments, the disclosure provides a method for editing a nucleobase pair of a double-stranded DNA sequence. In some embodiments, the method comprises a) contacting a target region of the double-stranded DNA sequence with a complex comprising a base editor and a guide nucleic acid (e.g., gRNA), where the target region comprises a target nucleobase pair, b) inducing strand separation of said target region, c) converting a first nucleobase of said target nucleobase pair in a single strand of the target region to a second nucleobase, d) cutting no more than one strand of said target region, wherein a third nucleobase complementary to the first nucleobase base is replaced by a fourth nucleobase complementary to the second nucleobase, and the second nucleobase is replaced with a fifth nucleobase that is complementary to the fourth nucleobase, thereby generating an intended edited base pair, wherein the efficiency of generating the intended edited base pair is at least 5%. It should be appreciated that in some embodiments, step b is omitted. In some embodiments, at least 5% of the intended base pairs are edited. In some embodiments, at least 10%, 15%, 20%, 25%, 30%, 35%, 40%, 45%, or 50% of the intended base pairs are edited. In some embodiments, the method causes less than 19%, 18%, 16%, 14%, 12%, 10%, 8%, 6%, 4%, 2%, 1%, 0.5%, 0.2%, or less than 0.1% indel formation. In some embodiments, the ratio of intended product to unintended products at the target nucleotide is at least 2:1, 5:1, 10:1, 20:1, 30:1, 40:1, 50:1, 60:1, 70:1, 80:1, 90:1, 100:1, or 200:1, or more. In some embodiments, the ratio of intended point mutation to indel formation is greater than 1:1, 10:1, 50:1, 100:1, 500:1, or 1000:1, or more. In some embodiments, the cut single strand is hybridized to the guide nucleic acid. In some embodiments, the cut single strand is opposite to the strand comprising the first nucleobase. In some embodiments, the first base is adenine. In some embodiments, the second nucleobase is not G, C, A, or T. In some embodiments, the second base is inosine. In some embodiments, the base editor inhibits base excision repair of the edited strand. In some embodiments, the base editor protects (e.g., form base excision repair) or binds the non-edited strand. In some embodiments, the nucleobase editor comprises UGI activity. In some embodiments, the base editor comprises a catalytically inactive inosine-specific nuclease. In some embodiments, the nucleobase editor comprises nickase activity. In some embodiments, the intended edited base pair is upstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides upstream of the PAM site. In some embodiments, the intended edited basepair is downstream of a PAM site. In some embodiments, the intended edited base pair is 1, 2, 3, 4, 5, 6, 7, 8, 9, 10, 11, 12, 13, 14, 15, 16, 17, 18, 19, or 20 nucleotides downstream stream of the PAM site. In some embodiments, the method does not require a canonical (e.g., NGG) PAM site. In some embodiments, the nucleobase editor comprises a linker. In some embodiments, the linker is 1-25 amino acids in length. In some embodiments, the linker is 5-20 amino acids in length. In some embodiments, the linker is 10, 11, 12, 13, 14, 15, 16, 17, 18, 19, or 20 amino acids in length. In some embodiments, the target region comprises a target window, wherein the target window comprises the target nucleobase pair. In some embodiments, the target window comprises 1-10 nucleotides. In some embodiments, the target window is 1-9, 1-8, 1-7, 1-6, 1-5, 1-4, 1-3, 1-2, or 1 nucleotides in length. In some embodiments, the target window is 1, 2, 3, 4, 5, 6, 7, 8, 9, 10, 11, 12, 13, 14, 15, 16, 17, 18, 19, or 20 nucleotides in length. In some embodiments, the intended edited base pair occurs within the target window. In some embodiments, the target window comprises the intended edited base pair. In some embodiments, the nucleobase editor is any one of the base editors provided herein.

In another embodiment, the disclosure provides editing methods comprising contacting a DNA, or RNA molecule with any of the base editors provided herein, and with at least one guide nucleic acid (e.g., guide RNA), wherein the guide nucleic acid, (e.g., guide RNA) is about 15-100 nucleotides long and comprises a sequence of at least 10 contiguous nucleotides that is complementary to a target sequence. In some embodiments, the 3' end of the target sequence is immediately adjacent to a canonical PAM sequence (NGG). In some embodiments, the 3' end of the target sequence is not immediately adjacent to a canonical PAM sequence (NGG). In some embodiments, the 3' end of the target sequence is immediately adjacent to an AGC, GAG, TTT, GTG, or CAA sequence.

In some embodiments, the target DNA sequence comprises a sequence associated with a disease or disorder. In some embodiments, the target DNA sequence comprises a point mutation associated with a disease or disorder. In some embodiments, the activity of the fusion protein (e.g., comprising an adenosine deaminase and a Cas9 domain), or the complex, results in a correction of the point mutation. In some embodiments, the target DNA sequence comprises a G→A point mutation associated with a disease or disorder, and wherein the deamination of the mutant A base results in a sequence that is not associated with a disease or disorder. In some embodiments, the target DNA sequence encodes a protein, and the point mutation is in a codon and results in a change in the amino acid encoded by the mutant codon as compared to the wild-type codon. In some embodiments, the deamination of the mutant A results in a change of the amino acid encoded by the mutant codon. In some embodiments, the deamination of the mutant A results in the codon encoding the wild-type amino acid. In some embodiments, the contacting is in vivo in a subject. In some embodiments, the subject has or has been diagnosed with a disease or disorder. In some embodiments, the disease or disorder is phenylketonuria, von Willebrand disease (vWD), a neoplastic disease associated with a mutant PTEN or BRCA1, or Li-Fraumeni syndrome. A list of exemplary diseases and disorders that may be treated using the base editors described herein is shown in Table 1. Table 1 includes the target gene, the mutation to be corrected, the related disease and the nucleotide sequence of the associated protospacer and PAM.

proteins provided herein, e.g., the fusion proteins comprising a nucleic acid programmable DNA binding protein (e.g., Cas9) and an adenosine deaminase domain can be used to correct any single point G to A or C to T mutation. In the first case, deamination of the mutant A to I corrects the mutation, and in the latter case, deamination of the A that is base-paired with the mutant T, followed by a round of replication, corrects the mutation. Exemplary point mutations that can be corrected are listed in Tables 1.

The successful correction of point mutations in disease-associated genes and alleles opens up new strategies for

TABLE 1

List of exemplary diseases that may be treated using the base editors described herein. The A to be edited in the protospacer is indicated by underlining and the PAM is indicated in bold.

| Target Gene | Mutation | ATCC Cell Line | Disease | Protospacer and PAM |
|---|---|---|---|---|
| PTEN | Cys136Tyr | HTB-128 | Cancer Predisposition | TATATGCATATTTATTACATCGG (SEQ ID NO: 85) |
| PTEN | Arg233Ter | HTB-13 | Cancer Predisposition | CCGTCATGTGGGTCCTGAATGG (SEQ ID NO: 86) |
| TP53 | Glu258Lys | HTB-65 | Cancer Predisposition | ACACTGAAAGACTCCAGGTCAGG (SEQ ID NO: 87) |
| BRCA1 | Gly1738Arg | NA | Cancer Predisposition | GTCAGAAGAGATGTGGTCAATGG (SEQ ID NO: 8S) |
| BRCA1 | 4097-1G>A | NA | Cancer Predisposition | TTTAAAGTGAAGCAGCATCTGGG (SEQ ID NO: 89)<br>ATTTAAAGTGAAGCAGCATCTGG (SEQ ID NO: 90) |
| PAH | Thr380Met | NA | Phenylketonuria | ACTCCATGACAGTGTAATTTGG (SEQ ID NO: 91) |
| VWF | Sær1285Phe | NA | von Willebrand (Hemophilia) | GCCTGGAGAAGCCATCCAGCAGG (SEQ ID NO: 92) |
| VWF | Arg2535Ter | NA | von Willebrand (Hemophilia} | CTCAGACACACTCATTGATGAGG (SEQ ID NO: 93) |
| TP53 | Arg175His | HCC1395 | Li-Fraumeni syndrome | GAGGCACTGCCCCCACCATGAGCG (SEQ ID NO: 94) |

Some embodiments provide methods for using the evolved base editors provided herein. In some embodiments, the base editors are used to introduce a point mutation into a nucleic acid by deaminating a target nucleobase, e.g., a C residue. In some embodiments, the deamination of the target nucleobase results in the correction of a genetic defect, e.g., in the correction of a point mutation that leads to a loss of function in a gene product. In some embodiments, the genetic defect is associated with a disease or disorder, e.g., a lysosomal storage disorder or a metabolic disease, such as, for example, type I diabetes. In some embodiments, the methods provided herein are used to introduce a deactivating point mutation into a gene or allele that encodes a gene product that is associated with a disease or disorder. For example, in some embodiments, methods are provided herein that employ a DNA editing fusion protein to introduce a deactivating point mutation into an oncogene (e.g., in the treatment of a proliferative disease). A deactivating mutation may, in some embodiments, generate a premature stop codon in a coding sequence, which results in the expression of a truncated gene product, e.g., a truncated protein lacking the function of the full-length protein.

In some embodiments, the purpose of the methods provided herein is to restore the function of a dysfunctional gene via genome editing. The nucleobase editing proteins provided herein can be validated for gene editing-based human therapeutics in vitro, e.g., by correcting a disease-associated mutation in human cell culture. It will be understood by the skilled artisan that the nucleobase editing gene correction with applications in therapeutics and basic research. Site-specific single-base modification systems like the disclosed fusions of a nucleic acid programmable DNA binding protein and an adenosine deaminase domain also have applications in "reverse" gene therapy, where certain gene functions are purposely suppressed or abolished. In these cases, site-specifically mutating residues that lead to inactivating mutations in a protein, or mutations that inhibit function of the protein can be used to abolish or inhibit protein function Methods of Treatment The instant disclosure provides methods for the treatment of a subject diagnosed with a disease associated with or caused by a point mutation that can be corrected by a DNA editing fusion protein provided herein. For example, in some embodiments, a method is provided that comprises administering to a subject having such a disease, e.g., a cancer associated with a point mutation as described above, an effective amount of an adenosine deaminase fusion protein that corrects the point mutation or introduces a deactivating mutation into a disease-associated gene. In some embodiments, the disease is a proliferative disease. In some embodiments, the disease is a genetic disease. In some embodiments, the disease is a neoplastic disease. In some embodiments, the disease is a metabolic disease. In some embodiments, the disease is a lysosomal storage disease. Other diseases that can be treated by correcting a point mutation or introducing a deactivating mutation into a disease-associated gene will be known to those of skill in the art, and the disclosure is not limited in this respect.

The instant disclosure provides methods for the treatment of additional diseases or disorders, e.g., diseases or disorders that are associated or caused by a point mutation that can be corrected by deaminase-mediated gene editing. Some such diseases are described herein, and additional suitable diseases that can be treated with the strategies and fusion proteins provided herein will be apparent to those of skill in the art based on the instant disclosure. Exemplary suitable diseases and disorders are listed below. It will be understood that the numbering of the specific positions or residues in the respective sequences depends on the particular protein and numbering scheme used. Numbering might be different, e.g., in precursors of a mature protein and the mature protein itself, and differences in sequences from species to species may affect numbering. One of skill in the art will be able to identify the respective residue in any homologous protein and in the respective encoding nucleic acid by methods well known in the art, e.g., by sequence alignment and determination of homologous residues. Exemplary suitable diseases and disorders include, without limitation: 2-methyl-3-hydroxybutyric aciduria; 3 beta-Hydroxysteroid dehydrogenase deficiency; 3-Methylglutaconic aciduria; 3-Oxo-5 alpha-steroid delta 4-dehydrogenase deficiency; 46,XY sex reversal, type 1, 3, and 5; 5-Oxoprolinase deficiency; 6-pyruvoyl-tetrahydropterin synthase deficiency; Aarskog syndrome; Aase syndrome; Achondrogenesis type 2; Achromatopsia 2 and 7; Acquired long QT syndrome; Acrocallosal syndrome, Schinzel type; Acrocapitofemoral dysplasia; Acrodysostosis 2, with or without hormone resistance; Acroerythrokeratoderma; Acromicric dysplasia; Acth-independent macronodular adrenal hyperplasia 2; Activated PI3K-delta syndrome; Acute intermittent porphyria; deficiency of Acyl-CoA dehydrogenase family, member 9; Adams-Oliver syndrome 5 and 6; Adenine phosphoribosyltransferase deficiency; Adenylate kinase deficiency; hemolytic anemia due to Adenylosuccinate lyase deficiency; Adolescent nephronophthisis; Renal-hepatic-pancreatic dysplasia; Meckel syndrome type 7; Adrenoleukodystrophy; Adult junctional epidermolysis bullosa; Epidermolysis bullosa, junctional, localisata variant; Adult neuronal ceroid lipofuscinosis; Adult neuronal ceroid lipofuscinosis; Adult onset ataxia with oculomotor apraxia; ADULT syndrome; Afibrinogenemia and congenital Afibrinogenemia; autosomal recessive Agammaglobulinemia 2; Age-related macular degeneration 3, 6, 11, and 12; Aicardi Goutieres syndromes 1, 4, and 5; Chilbain lupus 1; Alagille syndromes 1 and 2; Alexander disease; Alkaptonuria; Allan-Herndon-Dudley syndrome; Alopecia universalis congenital; Alpers encephalopathy; Alpha-1-antitrypsin deficiency; autosomal dominant, autosomal recessive, and X-linked recessive Alport syndromes; Alzheimer disease, familial, 3, with spastic paraparesis and apraxia; Alzheimer disease, types, 1, 3, and 4; hypocalcification type and hypomaturation type, IIA1 Amelogenesis imperfecta; Aminoacylase 1 deficiency; Amish infantile epilepsy syndrome; Amyloidogenic transthyretin amyloidosis; Amyloid Cardiomyopathy, Transthyretin-related; Cardiomyopathy; Amyotrophic lateral sclerosis types 1, 6, 15 (with or without frontotemporal dementia), 22 (with or without frontotemporal dementia), and 10; Frontotemporal dementia with TDP43 inclusions, TARDBP-related; Andermann syndrome; Andersen Tawil syndrome; Congenital long QT syndrome; Anemia, nonspherocytic hemolytic, due to G6PD deficiency; Angelman syndrome; Severe neonatal-onset encephalopathy with microcephaly; susceptibility to Autism, X-linked 3; Angiopathy, hereditary, with nephropathy, aneurysms, and muscle cramps; Angiotensin i-converting enzyme, benign serum increase; Aniridia, cerebellar ataxia, and mental retardation; Anonychia; Antithrombin III deficiency; Antley-Bixler syndrome with genital anomalies and disordered steroidogenesis; Aortic aneurysm, familial thoracic 4, 6, and 9; Thoracic aortic aneurysms and aortic dissections; Multisystemic smooth muscle dysfunction syndrome; Moyamoya disease 5; Aplastic anemia; Apparent mineralocorticoid excess; Arginase deficiency; Argininosuccinate lyase deficiency; Aromatase deficiency; Arrhythmogenic right ventricular cardiomyopathy types 5, 8, and 10; Primary familial hypertrophic cardiomyopathy; Arthrogryposis multiplex congenita, distal, X-linked; Arthrogryposis renal dysfunction cholestasis syndrome; Arthrogryposis, renal dysfunction, and cholestasis 2; Asparagine synthetase deficiency; Abnormality of neuronal migration; Ataxia with vitamin E deficiency; Ataxia, sensory, autosomal dominant; Ataxia-telangiectasia syndrome; Hereditary cancer-predisposing syndrome; Atransferrinemia; Atrial fibrillation, familial, 11, 12, 13, and 16; Atrial septal defects 2, 4, and 7 (with or without atrioventricular conduction defects); Atrial standstill 2; Atrioventricular septal defect 4; Atrophia bulborum hereditaria; ATR-X syndrome; Auriculocondylar syndrome 2; Autoimmune disease, multisystem, infantile-onset; Autoimmune lymphoproliferative syndrome, type 1a; Autosomal dominant hypohidrotic ectodermal dysplasia; Autosomal dominant progressive external ophthalmoplegia with mitochondrial DNA deletions 1 and 3; Autosomal dominant torsion dystonia 4; Autosomal recessive centronuclear myopathy; Autosomal recessive congenital ichthyosis 1, 2, 3, 4A, and 4B; Autosomal recessive cutis laxa type IA and 1B; Autosomal recessive hypohidrotic ectodermal dysplasia syndrome; Ectodermal dysplasia 11b; hypohidrotic/hair/tooth type, autosomal recessive; Autosomal recessive hypophosphatemic bone disease; Axenfeld-Rieger syndrome type 3; Bainbridge-Ropers syndrome; Bannayan-Riley-Ruvalcaba syndrome; PTEN hamartoma tumor syndrome; Baraitser-Winter syndromes 1 and 2; Barakat syndrome; Bardet-Biedl syndromes 1, 11, 16, and 19; Bare lymphocyte syndrome type 2, complementation group E; Bartter syndrome antenatal type 2; Bartter syndrome types 3, 3 with hypocalciuria, and 4; Basal ganglia calcification, idiopathic, 4; Beaded hair; Benign familial hematuria; Benign familial neonatal seizures 1 and 2; Seizures, benign familial neonatal, 1, and/or myokymia; Seizures, Early infantile epileptic encephalopathy 7; Benign familial neonatal-infantile seizures; Benign hereditary chorea; Benign scapuloperoneal muscular dystrophy with cardiomyopathy; Bernard-Soulier syndrome, types A1 and A2 (autosomal dominant); Bestrophinopathy, autosomal recessive; beta Thalassemia; Bethlem myopathy and Bethlem myopathy 2; Bietti crystalline corneoretinal dystrophy; Bile acid synthesis defect, congenital, 2; Biotinidase deficiency; Birk Barel mental retardation dysmorphism syndrome; Blepharophimosis, ptosis, and epicanthus inversus; Bloom syndrome; Borjeson-Forssman-Lehmann syndrome; Boucher Neuhauser syndrome; Brachydactyly types A1 and A2; Brachydactyly with hypertension; Brain small vessel disease with hemorrhage; Branched-chain ketoacid dehydrogenase kinase deficiency; Branchiootic syndromes 2 and 3; Breast cancer, early-onset; Breast-ovarian cancer, familial 1, 2, and 4; Brittle cornea syndrome 2; Brody myopathy; Bronchiectasis with or without elevated sweat chloride 3; Brown-Vialetto-Van laere syndrome and Brown-Vialetto-Van Laere syndrome 2; Brugada syndrome; Brugada syndrome 1; Ventricular fibrillation; Paroxysmal familial ventricular fibrillation; Brugada syndrome and Brugada syndrome 4; Long QT syndrome; Sudden cardiac death; Bull eye macular dystrophy; Stargardt disease 4; Cone-rod dystrophy 12; Bullous ichthyosiform erythroderma; Burn-Mckeown syndrome; Candidiasis, familial, 2, 5, 6, and 8; Carbohydrate-deficient glycoprotein syndrome type I and II; Carbonic anhydrase VA deficiency, hyperammonemia due to; Carcinoma of colon; Cardiac arrhythmia; Long QT syndrome, LQT1 subtype; Cardioencephalomyopathy, fatal infantile, due to cytochrome c oxidase deficiency; Cardiofaciocutaneous syndrome; Cardiomyopathy; Danon disease; Hypertrophic cardiomyopathy; Left ventricular noncompaction cardiomyopathy; Carnevale syndrome; Carney complex, type 1; Carnitine acylcarnitine translocase deficiency; Carnitine palmitoyltransferase I, II, II (late onset), and II (infantile) deficiency; Cataract 1, 4, autosomal dominant, autosomal dominant, multiple types, with microcornea, coppock-like, juvenile, with microcornea and glucosuria, and nuclear diffuse nonprogressive; Catecholaminergic polymorphic ventricular tachycardia; Caudal regression syndrome; Cd8 deficiency, familial; Central core disease; Centromeric instability of chromosomes 1, 9 and 16 and immunodeficiency; Cerebellar ataxia infantile with progressive external ophthalmoplegi and Cerebellar ataxia, mental retardation, and dysequilibrium syndrome 2; Cerebral amyloid angiopathy, APP-related; Cerebral autosomal dominant and recessive arteriopathy with subcortical infarcts and leukoencephalopathy; Cerebral cavernous malformations 2; Cerebrooculofacioskeletal syndrome 2; Cerebro-oculo-facioskeletal syndrome; Cerebroretinal microangiopathy with calcifications and cysts; Ceroid lipofuscinosis neuronal 2, 6, 7, and 10; Ch\xc3\xa9diak-Higashi syndrome, Chediak-Higashi syndrome, adult type; Charcot-Marie-Tooth disease types 1B, 2B2, 2C, 2F, 2I, 2U (axonal), 1C (demyelinating), dominant intermediate C, recessive intermediate A, 2A2, 4C, 4D, 4H, IF, IVF, and X; Scapuloperoneal spinal muscular atrophy; Distal spinal muscular atrophy, congenital nonprogressive; Spinal muscular atrophy, distal, autosomal recessive, 5; CHARGE association; Childhood hypophosphatasia; Adult hypophosphatasia; Cholecystitis; Progressive familial intrahepatic cholestasis 3; Cholestasis, intrahepatic, of pregnancy 3; Cholestanol storage disease; Cholesterol monooxygenase (side-chain cleaving) deficiency; Chondrodysplasia Blomstrand type; Chondrodysplasia punctata 1, X-linked recessive and 2 X-linked dominant; CHOPS syndrome; Chronic granulomatous disease, autosomal recessive cytochrome b-positive, types 1 and 2; Chudley-McCullough syndrome; Ciliary dyskinesia, primary, 7, 11, 15, 20 and 22; Citrullinemia type I; Citrullinemia type I and II; Cleidocranial dysostosis; C-like syndrome; Cockayne syndrome type A; Coenzyme Q10 deficiency, primary 1, 4, and 7; Coffin Siris/Intellectual Disability; Coffin-Lowry syndrome; Cohen syndrome; Cold-induced sweating syndrome 1; COLE-CARPENTER SYNDROME 2; Combined cellular and humoral immune defects with granulomas; Combined d-2- and 1-2-hydroxyglutaric aciduria; Combined malonic and methylmalonic aciduria; Combined oxidative phosphorylation deficiencies 1, 3, 4, 12, 15, and 25; Combined partial and complete 17-alpha-hydroxylase/17,20-lyase deficiency; Common variable immunodeficiency 9; Complement component 4, partial deficiency of, due to dysfunctional c1 inhibitor; Complement factor B deficiency; Cone monochromatism; Cone-rod dystrophy 2 and 6; Cone-rod dystrophy amelogenesis imperfecta; Congenital adrenal hyperplasia and Congenital adrenal hypoplasia, X-linked; Congenital amegakaryocytic thrombocytopenia; Congenital aniridia; Congenital central hypoventilation; Hirschsprung disease 3; Congenital contractural arachnodactyly; Congenital contractures of the limbs and face, hypotonia, and developmental delay; Congenital disorder of glycosylation types 1B, 1D, 1G, 1H, 1J, 1K, 1N, 1P, 2C, 2J, 2K, IIm; Congenital dyserythropoietic anemia, type I and II; Congenital ectodermal dysplasia of face; Congenital erythropoietic porphyria; Congenital generalized lipodystrophy type 2; Congenital heart disease, multiple types, 2; Congenital heart disease; Interrupted aortic arch; Congenital lipomatous overgrowth, vascular malformations, and epidermal nevi; Non-small cell lung cancer; Neoplasm of ovary; Cardiac conduction defect, nonspecific; Congenital microvillous atrophy; Congenital muscular dystrophy; Congenital muscular dystrophy due to partial LAMA2 deficiency; Congenital muscular dystrophy-dystroglycanopathy with brain and eye anomalies, types A2, A7, A8, All, and A14; Congenital muscular dystrophy-dystroglycanopathy with mental retardation, types B2, B3, B5, and B15; Congenital muscular dystrophy-dystroglycanopathy without mental retardation, type B5; Congenital muscular hypertrophy-cerebral syndrome; Congenital myasthenic syndrome, acetazolamide-responsive; Congenital myopathy with fiber type disproportion; Congenital ocular coloboma; Congenital stationary night blindness, type 1A, 1B, 1C, 1E, 1F, and 2A; Coproporphyria; Cornea plana 2; Corneal dystrophy, Fuchs endothelial, 4; Corneal endothelial dystrophy type 2; Corneal fragility keratoglobus, blue sclerae and joint hypermobility; Cornelia de Lange syndromes 1 and 5; Coronary artery disease, autosomal dominant 2; Coronary heart disease; Hyperalphalipoproteinemia 2; Cortical dysplasia, complex, with other brain malformations 5 and 6; Cortical malformations, occipital; Corticosteroid-binding globulin deficiency; Corticosterone methyloxidase type 2 deficiency; Costello syndrome; Cowden syndrome 1; Coxa plana; Craniodiaphyseal dysplasia, autosomal dominant; Craniosynostosis 1 and 4; Craniosynostosis and dental anomalies; Creatine deficiency, X-linked; Crouzon syndrome; Cryptophthalmos syndrome; Cryptorchidism, unilateral or bilateral; Cushing symphalangism; Cutaneous malignant melanoma 1; Cutis laxa with osteodystrophy and with severe pulmonary, gastrointestinal, and urinary abnormalities; Cyanosis, transient neonatal and atypical nephropathic; Cystic fibrosis; Cystinuria; Cytochrome c oxidase i deficiency; Cytochrome-c oxidase deficiency; D-2-hydroxyglutaric aciduria 2; Darier disease, segmental; Deafness with labyrinthine aplasia microtia and microdontia (LAMM); Deafness, autosomal dominant 3a, 4, 12, 13, 15, autosomal dominant nonsyndromic sensorineural 17, 20, and 65; Deafness, autosomal recessive 1A, 2, 3, 6, 8, 9, 12, 15, 16, 18b, 22, 28, 31, 44, 49, 63, 77, 86, and 89; Deafness, cochlear, with myopia and intellectual impairment, without vestibular involvement, autosomal dominant, X-linked 2; Deficiency of 2-methylbutyryl-CoA dehydrogenase; Deficiency of 3-hydroxyacyl-CoA dehydrogenase; Deficiency of alpha-mannosidase; Deficiency of aromatic-L-amino-acid decarboxylase; Deficiency of bisphosphoglycerate mutase; Deficiency of butyryl-CoA dehydrogenase; Deficiency of ferroxidase; Deficiency of galactokinase; Deficiency of guanidinoacetate methyltransferase; Deficiency of hyaluronoglucosaminidase; Deficiency of ribose-5-phosphate isomerase; Deficiency of steroid 11-beta-monooxygenase; Deficiency of UDPglucose-hexose-1-phosphate uridylyltransferase; Deficiency of xanthine oxidase; Dejerine-Sottas disease; Charcot-Marie-Tooth disease, types ID and IVF; Dejerine-Sottas syndrome, autosomal dominant; Dendritic cell, monocyte, B lymphocyte, and natural killer lymphocyte deficiency; Desbuquois dysplasia 2; Desbuquois syndrome; DFNA 2 Nonsyndromic Hearing Loss; Diabetes mellitus and insipidus with optic atrophy and deafness; Diabetes mellitus, type 2, and insulin-dependent, 20; Diamond-Blackfan anemia 1, 5, 8, and 10; Diarrhea 3 (secretory sodium, congenital, syndromic) and 5 (with tufting enteropathy, congenital); Dicarboxylic amino-aciduria; Diffuse palmoplantar keratoderma, Bothnian type; Digitorenocerebral syndrome; Dihydropteridine reductase deficiency; Dilated cardiomyopathy 1A, 1AA, 1C, 1G, 1BB, 1DD, 1FF, 1HH, 1I, 1KK, 1N, 1S, 1Y, and 3B; Left ventricular noncompaction 3; Disordered steroidogenesis due to cytochrome p450 oxidoreductase deficiency; Distal arthrogryposis type 2B; Distal hereditary motor neuronopathy type 2B; Distal myopathy Markesbery-Griggs type; Distal spinal muscular atrophy, X-linked 3; Distichiasis-lymphedema syndrome; Dominant dystrophic epidermolysis bullosa with absence of skin; Dominant hereditary optic atrophy; Donnai Barrow syndrome; Dopamine beta hydroxylase deficiency; Dopamine receptor d2, reduced brain density of; Dowling-degos disease 4; Doyne honeycomb retinal dystrophy; Malattia leventinese; Duane syndrome type 2; Dubin-Johnson syndrome; Duchenne muscular dystrophy; Becker muscular dystrophy; Dysfibrinogenemia; Dyskeratosis congenita autosomal dominant and autosomal dominant, 3; Dyskeratosis congenita, autosomal recessive, 1, 3, 4, and 5; Dyskeratosis congenita X-linked; Dyskinesia, familial, with facial myokymia; Dysplasminogenemia; Dystonia 2 (torsion, autosomal recessive), 3 (torsion, X-linked), 5 (Dopa-responsive type), 10, 12, 16, 25, 26 (Myoclonic); Seizures, benign familial infantile, 2; Early infantile epileptic encephalopathy 2, 4, 7, 9, 10, 11, 13, and 14; Atypical Rett syndrome; Early T cell progenitor acute lymphoblastic leukemia; Ectodermal dysplasia skin fragility syndrome; Ectodermal dysplasia-syndactyly syndrome 1; Ectopia lentis, isolated autosomal recessive and dominant; Ectrodactyly, ectodermal dysplasia, and cleft lip/palate syndrome 3; Ehlers-Danlos syndrome type 7 (autosomal recessive), classic type, type 2 (progeroid), hydroxylysine-deficient, type 4, type 4 variant, and due to tenascin-X deficiency; Eichsfeld type congenital muscular dystrophy; Endocrine-cerebroosteodysplasia; Enhanced s-cone syndrome; Enlarged vestibular aqueduct syndrome; Enterokinase deficiency; Epidermodysplasia verruciformis; Epidermolysa bullosa simplex and limb girdle muscular dystrophy, simplex with mottled pigmentation, simplex with pyloric atresia, simplex, autosomal recessive, and with pyloric atresia; Epidermolytic palmoplantar keratoderma; Familial febrile seizures 8; Epilepsy, childhood absence 2, 12 (idiopathic generalized, susceptibility to) 5 (nocturnal frontal lobe), nocturnal frontal lobe type 1, partial, with variable foci, progressive myoclonic 3, and X-linked, with variable learning disabilities and behavior disorders; Epileptic encephalopathy, childhood-onset, early infantile, 1, 19, 23, 25, 30, and 32; Epiphyseal dysplasia, multiple, with myopia and conductive deafness; Episodic ataxia type 2; Episodic pain syndrome, familial, 3; Epstein syndrome; Fechtner syndrome; Erythropoietic protoporphyria; Estrogen resistance; Exudative vitreoretinopathy 6; Fabry disease and Fabry disease, cardiac variant; Factor H, VII, X, v and factor viii, combined deficiency of 2, xiii, a subunit, deficiency; Familial adenomatous polyposis 1 and 3; Familial amyloid nephropathy with urticaria and deafness; Familial cold urticarial; Familial aplasia of the vermis; Familial benign pemphigus; Familial cancer of breast; Breast cancer, susceptibility to; Osteosarcoma; Pancreatic cancer 3; Familial cardiomyopathy; Familial cold autoinflammatory syndrome 2; Familial colorectal cancer; Familial exudative vitreoretinopathy, X-linked; Familial hemiplegic migraine types 1 and 2; Familial hypercholesterolemia; Familial hypertrophic cardiomyopathy 1, 2, 3, 4, 7, 10, 23 and 24; Familial hypokalemia-hypomagnesemia; Familial hypoplastic, glomerulocystic kidney; Familial infantile myasthenia; Familial juvenile gout; Familial Mediterranean fever and Familial mediterranean fever, autosomal dominant; Familial porencephaly; Familial *Porphyria cutanea tarda*; Familial pulmonary capillary hemangiomatosis; Familial renal glucosuria; Familial renal hypouricemia; Familial restrictive cardiomyopathy 1; Familial type 1 and 3 hyperlipoproteinemia; Fanconi anemia, complementation group E, I, N, and O; Fanconi-Bickel syndrome; Favism, susceptibility to; Febrile seizures, familial, 11; Feingold syndrome 1; Fetal hemoglobin quantitative trait locus 1; FG syndrome and FG syndrome 4; Fibrosis of extraocular muscles, congenital, 1, 2, 3a (with or without extraocular involvement), 3b; Fish-eye disease; Fleck corneal dystrophy; Floating-Harbor syndrome; Focal epilepsy with speech disorder with or without mental retardation; Focal segmental glomerulosclerosis 5; Forebrain defects; Frank Ter Haar syndrome; Borrone Di Rocco Crovato syndrome; Frasier syndrome; Wilms tumor 1; Freeman-Sheldon syndrome; Frontometaphyseal dysplasia 1and 3; Frontotemporal dementia; Frontotemporal dementia and/or amyotrophic lateral sclerosis 3 and 4; Frontotemporal Dementia Chromosome 3-Linked and Frontotemporal dementia ubiquitin-positive; Fructose-biphosphatase deficiency; Fuhrmann syndrome; Gamma-aminobutyric acid transaminase deficiency; Gamstorp-Wohlfart syndrome; Gaucher disease type 1 and Subacute neuronopathic; Gaze palsy, familial horizontal, with progressive scoliosis; Generalized dominant dystrophic epidermolysis bullosa; Generalized epilepsy with febrile seizures plus 3, type 1, type 2; Epileptic encephalopathy Lennox-Gastaut type; Giant axonal neuropathy; Glanzmann thrombasthenia; Glaucoma 1, open angle, e, F, and G; Glaucoma 3, primary congenital, d; Glaucoma, congenital and Glaucoma, congenital, Coloboma; Glaucoma, primary open angle, juvenile-onset; Glioma susceptibility 1; Glucose transporter type 1 deficiency syndrome; Glucose-6-phosphate transport defect; GLUT1 deficiency syndrome 2; Epilepsy, idiopathic generalized, susceptibility to, 12; Glutamate formiminotransferase deficiency; Glutaric acidemia IIA and IIB; Glutaric aciduria, type 1; Glutathione synthetase deficiency; Glycogen storage disease 0 (muscle), II (adult form), IXa2, IXc, type 1A; type II, type IV, IV (combined hepatic and myopathic), type V, and type VI; Goldmann-Favre syndrome; Gordon syndrome; Gorlin syndrome; Holoprosencephaly sequence; Holoprosencephaly 7; Granulomatous disease, chronic, X-linked, variant; Granulosa cell tumor of the ovary; Gray platelet syndrome; Griscelli syndrome type 3; Groenouw corneal dystrophy type I; Growth and mental retardation, mandibulofacial dysostosis, microcephaly, and cleft palate; Growth hormone deficiency with pituitary anomalies; Growth hormone insensitivity with immunodeficiency; GTP cyclohydrolase I deficiency; Hajdu-Cheney syndrome; Hand foot uterus syndrome; Hearing impairment; Hemangioma, capillary infantile; Hematologic neoplasm; Hemochromatosis type 1, 2B, and 3; Microvascular complications of diabetes 7; Transferrin serum level quantitative trait locus 2; Hemoglobin H disease, nondeletional; Hemolytic anemia, nonspherocytic, due to glucose phosphate isomerase deficiency; Hemophagocytic lymphohistiocytosis, familial, 2; Hemophagocytic lymphohistiocytosis, familial, 3; Heparin cofactor II deficiency; Hereditary acrodermatitis enteropathica; Hereditary breast and ovarian cancer syndrome; Ataxia-telangiectasia-like disorder; Hereditary diffuse gastric cancer; Hereditary diffuse leukoencephalopathy with spheroids; Hereditary factors II, IX, VIII deficiency disease; Hereditary hemorrhagic telangiectasia type 2; Hereditary insensitivity to pain with anhidrosis; Hereditary lymphedema type I; Hereditary motor and sensory neuropathy with optic atrophy; Hereditary myopathy with early respiratory failure; Hereditary neuralgic amyotrophy; Hereditary Nonpolyposis Colorectal Neoplasms; Lynch syndrome I and II; Hereditary pancreatitis; Pancreatitis, chronic, susceptibility to; Hereditary sensory and autonomic neuropathy type IIB amd IIA; Hereditary sideroblastic anemia; Hermansky-Pudlak syndrome 1, 3, 4, and 6; Heterotaxy, visceral, 2, 4, and 6, autosomal; Heterotaxy, visceral, X-linked; Heterotopia; Histiocytic medullary reticulosis; Histiocytosis-lymphadenopathy plus syndrome; Holocarboxylase synthetase deficiency; Holoprosencephaly 2, 3, 7, and 9; Holt-Oram syndrome; Homocysteinemia due to MTHFR deficiency, CBS deficiency, and Homocystinuria, pyridoxine-responsive; Homocystinuria-Megaloblastic anemia due to defect in cobalamin metabolism, cblE complementation type; Howel-Evans syndrome; Hurler syndrome; Hutchinson-Gilford syndrome; Hydrocephalus; Hyperammonemia, type III; Hypercholesterolaemia and Hypercholesterolemia, autosomal recessive; Hyperekplexia 2 and Hyperekplexia hereditary; Hyperferritinemia cataract syndrome; Hyperglycinuria; Hyperimmunoglobulin D with periodic fever; Mevalonic aciduria; Hyperimmunoglobulin E syndrome; Hyperinsulinemic hypoglycemia familial 3, 4, and 5; Hyperinsulinism-hyperammonemia syndrome; Hyperlysinemia; Hypermanganesemia with dystonia, polycythemia and cirrhosis; Hyperornithinemia-hyperammonemia-homocitrullinuria syndrome; Hyperparathyroidism 1 and 2; Hyperparathyroidism, neonatal severe; Hyperphenylalaninemia, bh4-deficient, a, due to partial pts deficiency, BH4-deficient, D, and non-pku; Hyperphosphatasia with mental retardation syndrome 2, 3, and 4; Hypertrichotic osteochondrodysplasia; Hypobetalipoproteinemia, familial, associated with apob32; Hypocalcemia, autosomal dominant 1; Hypocalciuric hypercalcemia, familial, types 1 and 3; Hypochondrogenesis; Hypochromic microcytic anemia with iron overload; Hypoglycemia with deficiency of glycogen synthetase in the liver; Hypogonadotropic hypogonadism 11 with or without anosmia; Hypohidrotic ectodermal dysplasia with immune deficiency; Hypohidrotic X-linked ectodermal dysplasia; Hypokalemic periodic paralysis 1 and 2; Hypomagnesemia 1, intestinal; Hypomagnesemia, seizures, and mental retardation; Hypomyelinating leukodystrophy 7; Hypoplastic left heart syndrome; Atrioventricular septal defect and common atrioventricular junction; Hypospadias 1 and 2, X-linked; Hypothyroidism, congenital, nongoitrous, 1; Hypotrichosis 8 and 12; Hypotrichosis-lymphedema-telangiectasia syndrome; I blood group system; Ichthyosis bullosa of Siemens; Ichthyosis exfoliativa; Ichthyosis prematurity syndrome; Idiopathic basal ganglia calcification 5; Idiopathic fibrosing alveolitis, chronic form; Dyskeratosis congenita, autosomal dominant, 2 and 5; Idiopathic hypercalcemia of infancy; Immune dysfunction with T-cell inactivation due to calcium entry defect 2; Immunodeficiency 15, 16, 19, 30, 31C, 38, 40, 8, due to defect in cd3-zeta, with hyper IgM type 1 and 2, and X-Linked, with magnesium defect, Epstein-Barr virus infection, and neoplasia; Immunodeficiency-centromeric instability-facial anomalies syndrome 2; Inclusion body myopathy 2 and 3; Nonaka myopathy; Infantile convulsions and paroxysmal choreoathetosis, familial; Infantile cortical hyperostosis; Infantile GM1 gangliosidosis; Infantile hypophosphatasia; Infantile nephronophthisis; Infantile nystagmus, X-linked; Infantile Parkinsonism-dystonia; Infertility associated with multi-tailed spermatozoa and excessive DNA; Insulin resistance; Insulin-resistant diabetes mellitus and acanthosis nigricans; Insulin-dependent diabetes mellitus secretory diarrhea syndrome; Interstitial nephritis, karyomegalic; Intrauterine growth retardation, metaphyseal dysplasia, adrenal hypoplasia congenita, and genital anomalies; Iodotyrosyl coupling defect; IRAK4 deficiency; Iridogoniodysgenesis dominant type and type 1; Iron accumulation in brain; Ischiopatellar dysplasia; Islet cell hyperplasia; Isolated 17,20-lyase deficiency; Isolated lutropin deficiency; Isovaleryl-CoA dehydrogenase deficiency; Jankovic Rivera syndrome; Jervell and Lange-Nielsen syndrome 2; Joubert syndrome 1, 6, 7, 9/15 (digenic), 14, 16, and 17, and Orofaciodigital syndrome xiv; Junctional epidermolysis bullosa gravis of Herlitz; Juvenile GM>1<gangliosidosis; Juvenile polyposis syndrome; Juvenile polyposis/hereditary hemorrhagic telangiectasia syndrome; Juvenile retinoschisis; Kabuki make-up syndrome; Kallmann syndrome 1, 2, and 6; Delayed puberty; Kanzaki disease; Karak syndrome; Kartagener syndrome; Kenny-Caffey syndrome type 2; Keppen-Lubinsky syndrome; Keratoconus 1; Keratosis follicularis; Keratosis palmoplantaris striata 1; Kindler syndrome; L-2-hydroxyglutaric aciduria; Larsen syndrome, dominant type; Lattice corneal dystrophy Type III; Leber amaurosis; Zellweger syndrome; Peroxisome biogenesis disorders; Zellweger syndrome spectrum; Leber congenital amaurosis 11, 12, 13, 16, 4, 7, and 9; Leber optic atrophy; Aminoglycoside-induced deafness; Deafness, nonsyndromic sensorineural, mitochondrial; Left ventricular noncompaction 5; Left-right axis malformations; Leigh disease; Mitochondrial short-chain Enoyl-CoA Hydratase 1 deficiency; Leigh syndrome due to mitochondrial complex I deficiency; Leiner disease; Leri Weill dyschondrosteosis; Lethal congenital contracture syndrome 6; Leukocyte adhesion deficiency type I and III; Leukodystrophy, Hypomyelinating, 11 and 6; Leukoencephalopathy with ataxia, with Brainstem and Spinal Cord Involvement and Lactate Elevation, with vanishing white matter, and progressive, with ovarian failure; Leukonychia totalis; Lewy body dementia; Lichtenstein-Knorr Syndrome; Li-Fraumeni syndrome 1; Lig4 syndrome; Limb-girdle muscular dystrophy, type 1B, 2A, 2B, 2D, C1, C5, C9, C14; Congenital muscular dystrophy-dystroglycanopathy with brain and eye anomalies, type A14 and B14; Lipase deficiency combined; Lipid proteinosis; Lipodystrophy, familial partial, type 2 and 3; Lissencephaly 1, 2 (X-linked), 3, 6 (with microcephaly), X-linked; Subcortical laminar heterotopia, X-linked; Liver failure acute infantile; Loeys-Dietz syndrome 1, 2, 3; Long QT syndrome 1, 2, 2/9, 2/5, (digenic), 3, 5 and 5, acquired, susceptibility to; Lung cancer; Lymphedema, hereditary, id; Lymphedema, primary, with myelodysplasia; Lymphoproliferative syndrome 1, 1 (X-linked), and 2; Lysosomal acid lipase deficiency; Macrocephaly, macrosomia, facial dysmorphism syndrome; Macular dystrophy, vitelliform, adult-onset; Malignant hyperthermia susceptibility type 1; Malignant lymphoma, non-Hodgkin; Malignant melanoma; Malignant tumor of prostate; Mandibuloacral dysostosis; Mandibuloacral dysplasia with type A or B lipodystrophy, atypical; Mandibulofacial dysostosis, Treacher Collins type, autosomal recessive; Mannose-binding protein deficiency; Maple syrup urine disease type 1A and type 3; Marden Walker like syndrome; Marfan syndrome; Marinesco-Sj\xc3\xb6gren syndrome; Martsolf syndrome; Maturity-onset diabetes of the young, type 1, type 2, type 11, type 3, and type 9; May-Hegglin anomaly; MYH9 related disorders; Sebastian syndrome; McCune-Albright syndrome; Somatotroph adenoma; Sex cord-stromal tumor; Cushing syndrome;

McKusick Kaufman syndrome; McLeod neuroacanthocytosis syndrome; Meckel-Gruber syndrome; Medium-chain acyl-coenzyme A dehydrogenase deficiency; Medulloblastoma; Megalencephalic leukoencephalopathy with subcortical cysts 1and 2a; Megalencephaly cutis marmorata telangiectatica congenital; PIK3CA Related Overgrowth Spectrum; Megalencephaly-polymicrogyria-polydactyly-hydrocephalus syndrome 2; Megaloblastic anemia, thiamine-responsive, with diabetes mellitus and sensorineural deafness; Meier-Gorlin syndromes 1and 4; Melnick-Needles syndrome; Meningioma; Mental retardation, X-linked, 3, 21, 30, and 72; Mental retardation and microcephaly with pontine and cerebellar hypoplasia; Mental retardation X-linked syndromic 5; Mental retardation, anterior maxillary protrusion, and strabismus; Mental retardation, autosomal dominant 12, 13, 15, 24, 3, 30, 4, 5, 6, and 9; Mental retardation, autosomal recessive 15, 44, 46, and 5; Mental retardation, stereotypic movements, epilepsy, and/or cerebral malformations; Mental retardation, syndromic, Claes-Jensen type, X-linked; Mental retardation, X-linked, nonspecific, syndromic, Hedera type, and syndromic, wu type; Merosin deficient congenital muscular dystrophy; Metachromatic leukodystrophy juvenile, late infantile, and adult types; Metachromatic leukodystrophy; Metatrophic dysplasia; Methemoglobinemia types I and 2; Methionine adenosyltransferase deficiency, autosomal dominant; Methylmalonic acidemia with homocystinuria; Methylmalonic aciduria cblB type; Methylmalonic aciduria due to methylmalonyl-CoA mutase deficiency; METHYLMALONIC ACIDURIA, mut(0) TYPE; Microcephalic osteodysplastic primordial dwarfism type 2; Microcephaly with or without chorioretinopathy, lymphedema, or mental retardation; Microcephaly, hiatal hernia and nephrotic syndrome; Microcephaly; Hypoplasia of the corpus callosum; Spastic paraplegia 50, autosomal recessive; Global developmental delay; CNS hypomyelination; Brain atrophy; Microcephaly, normal intelligence and immunodeficiency; Microcephaly-capillary malformation syndrome; Microcytic anemia; Microphthalmia syndromic 5, 7, and 9; Microphthalmia, isolated 3, 5, 6, 8, and with coloboma 6; Microspherophakia; Migraine, familial basilar; Miller syndrome; Minicore myopathy with external ophthalmoplegia; Myopathy, congenital with cores; Mitchell-Riley syndrome; mitochondrial 3-hydroxy-3-methylglutaryl-CoA synthase deficiency; Mitochondrial complex I, II, III, III (nuclear type 2, 4, or 8) deficiency; Mitochondrial DNA depletion syndrome 11, 12 (cardiomyopathic type), 2, 4B (MNGIE type), 8B (MNGIE type); Mitochondrial DNA-depletion syndrome 3 and 7, hepatocerebral types, and 13 (encephalomyopathic type); Mitochondrial phosphate carrier and pyruvate carrier deficiency; Mitochondrial trifunctional protein deficiency; Long-chain 3-hydroxyacyl-CoA dehydrogenase deficiency; Miyoshi muscular dystrophy 1; Myopathy, distal, with anterior tibial onset; Mohr-Tranebjaerg syndrome; Molybdenum cofactor deficiency, complementation group A; Mowat-Wilson syndrome; Mucolipidosis III Gamma; Mucopolysaccharidosis type VI, type VI (severe), and type VII; Mucopolysaccharidosis, MPS-I-H/S, MPS-II, MPS-III-A, MPS-III-B, MPS-III-C, MPS-IV-A, MPS-IV-B; Retinitis Pigmentosa 73; Gangliosidosis GM1 type1 (with cardiac involvement) 3; Multicentric osteolysis nephropathy; Multicentric osteolysis, nodulosis and arthropathy; Multiple congenital anomalies; Atrial septal defect 2; Multiple congenital anomalies-hypotonia-seizures syndrome 3; Multiple Cutaneous and Mucosal Venous Malformations; Multiple endocrine neoplasia, types 1and 4; Multiple epiphyseal dysplasia 5 or Dominant; Multiple gastrointestinal atresias; Multiple pterygium syndrome Escobar type; Multiple sulfatase deficiency; Multiple synostoses syndrome 3; Muscle AMP deaminase deficiency; Muscle eye brain disease; Muscular dystrophy, congenital, megaconial type; Myasthenia, familial infantile, 1; Myasthenic Syndrome, Congenital, 11, associated with acetylcholine receptor deficiency; Myasthenic Syndrome, Congenital, 17, 2A (slow-channel), 4B (fast-channel), and without tubular aggregates; Myeloperoxidase deficiency; MYH-associated polyposis; Endometrial carcinoma; Myocardial infarction 1; Myoclonic dystonia; Myoclonic-Atonic Epilepsy; Myoclonus with epilepsy with ragged red fibers; Myofibrillar myopathy 1 and ZASP-related; Myoglobinuria, acute recurrent, autosomal recessive; Myoneural gastrointestinal encephalopathy syndrome; Cerebellar ataxia infantile with progressive external ophthalmoplegia; Mitochondrial DNA depletion syndrome 4B, MNGIE type; Myopathy, centronuclear, 1, congenital, with excess of muscle spindles, distal, 1, lactic acidosis, and sideroblastic anemia 1, mitochondrial progressive with congenital cataract, hearing loss, and developmental delay, and tubular aggregate, 2; Myopia 6; Myosclerosis, autosomal recessive; Myotonia congenital; Congenital myotonia, autosomal dominant and recessive forms; Nail-patella syndrome; Nance-Horan syndrome; Nanophthalmos 2; Navajo neurohepatopathy; Nemaline myopathy 3 and 9; Neonatal hypotonia; Intellectual disability; Seizures; Delayed speech and language development; Mental retardation, autosomal dominant 31; Neonatal intrahepatic cholestasis caused by citrin deficiency; Nephrogenic diabetes insipidus, Nephrogenic diabetes insipidus, X-linked; Nephrolithiasis/osteoporosis, hypophosphatemic, 2; Nephronophthisis 13, 15 and 4; Infertility; Cerebello-oculo-renal syndrome (nephronophthisis, oculomotor apraxia and cerebellar abnormalities); Nephrotic syndrome, type 3, type 5, with or without ocular abnormalities, type 7, and type 9; Nestor-Guillermo progeria syndrome; Neu-Laxova syndrome 1; Neurodegeneration with brain iron accumulation 4 and 6; Neuroferritinopathy; Neurofibromatosis, type 1and type 2; Neurofibrosarcoma; Neurohypophyseal diabetes insipidus; Neuropathy, Hereditary Sensory, Type IC; Neutral 1 amino acid transport defect; Neutral lipid storage disease with myopathy; Neutrophil immunodeficiency syndrome; Nicolaides-Baraitser syndrome; Niemann-Pick disease type C1, C2, type A, and type C1, adult form; Non-ketotic hyperglycinemia; Noonan syndrome 1 and 4, LEOPARD syndrome 1; Noonan syndrome-like disorder with or without juvenile myelomonocytic leukemia; Normokalemic periodic paralysis, potassium-sensitive; Norum disease; Epilepsy, Hearing Loss, And Mental Retardation Syndrome; Mental Retardation, X-Linked 102 and syndromic 13; Obesity; Ocular albinism, type I; Oculocutaneous albinism type 1B, type 3, and type 4; Oculodentodigital dysplasia; Odontohypophosphatasia; Odontotrichomelic syndrome; Oguchi disease; Oligodontia-colorectal cancer syndrome; Opitz G/BBB syndrome; Optic atrophy 9; Oral-facial-digital syndrome; Ornithine aminotransferase deficiency; Orofacial cleft 11 and 7, Cleft lip/palate-ectodermal dysplasia syndrome; Orstavik Lindemann Solberg syndrome; Osteoarthritis with mild chondrodysplasia; Osteochondritis dissecans; Osteogenesis imperfecta type 12, type 5, type 7, type 8, type I, type III, with normal sclerae, dominant form, recessive perinatal lethal; Osteopathia striata with cranial sclerosis; Osteopetrosis autosomal dominant type 1 and 2, recessive 4, recessive 1, recessive 6; Osteoporosis with pseudoglioma; Oto-palato-digital syndrome, types I and II; Ovarian dysgenesis 1; Ovarioleukodystrophy; Pachyonychia congenita 4 and type 2; Paget disease of bone, familial; Pallister-Hall syndrome;

Palmoplantar keratoderma, nonepidermolytic, focal or diffuse; Pancreatic agenesis and congenital heart disease; Papillon-Lef\xc3\xa8vre syndrome; Paragangliomas 3; Paramyotonia congenita of von Eulenburg; Parathyroid carcinoma; Parkinson disease 14, 15, 19 (juvenile-onset), 2, 20 (early-onset), 6, (autosomal recessive early-onset, and 9; Partial albinism; Partial hypoxanthine-guanine phosphoribosyltransferase deficiency; Patterned dystrophy of retinal pigment epithelium; PC-K6a; Pelizaeus-Merzbacher disease; Pendred syndrome; Peripheral demyelinating neuropathy, central dysmyelination; Hirschsprung disease; Permanent neonatal diabetes mellitus; Diabetes mellitus, permanent neonatal, with neurologic features; Neonatal insulin-dependent diabetes mellitus; Maturity-onset diabetes of the young, type 2; Peroxisome biogenesis disorder 14B, 2A, 4A, 5B, 6A, 7A, and 7B; Perrault syndrome 4; Perry syndrome; Persistent hyperinsulinemic hypoglycemia of infancy; familial hyperinsulinism; Phenotypes; Phenylketonuria; Pheochromocytoma; Hereditary Paraganglioma-Pheochromocytoma Syndromes; Paragangliomas 1; Carcinoid tumor of intestine; Cowden syndrome 3; Phosphoglycerate dehydrogenase deficiency; Phosphoglycerate kinase 1 deficiency; Photosensitive trichothiodystrophy; Phytanic acid storage disease; Pick disease; Pierson syndrome; Pigmentary retinal dystrophy; Pigmented nodular adrenocortical disease, primary, 1; Pilomatrixoma; Pitt-Hopkins syndrome; Pituitary dependent hypercortisolism; Pituitary hormone deficiency, combined 1, 2, 3, and 4; Plasminogen activator inhibitor type 1 deficiency; Plasminogen deficiency, type I; Platelet-type bleeding disorder 15 and 8; Poikiloderma, hereditary fibrosing, with tendon contractures, myopathy, and pulmonary fibrosis; Polycystic kidney disease 2, adult type, and infantile type; Polycystic lipomembranous osteodysplasia with sclerosing leukoencephalopathy; Polyglucosan body myopathy 1 with or without immunodeficiency; Polymicrogyria, asymmetric, bilateral frontoparietal; Polyneuropathy, hearing loss, ataxia, retinitis pigmentosa, and cataract; Pontocerebellar hypoplasia type 4; Popliteal pterygium syndrome; Porencephaly 2; Porokeratosis 8, disseminated superficial actinic type; Porphobilinogen synthase deficiency; *Porphyria cutanea* tarda; Posterior column ataxia with retinitis pigmentosa; Posterior polar cataract type 2; Prader-Willi-like syndrome; Premature ovarian failure 4, 5, 7, and 9; Primary autosomal recessive microcephaly 10, 2, 3, and 5; Primary ciliary dyskinesia 24; Primary dilated cardiomyopathy; Left ventricular noncompaction 6; 4, Left ventricular noncompaction 10; Paroxysmal atrial fibrillation; Primary hyperoxaluria, type I, type, and type III; Primary hypertrophic osteoarthropathy, autosomal recessive 2; Primary hypomagnesemia; Primary open angle glaucoma juvenile onset 1; Primary pulmonary hypertension; Primrose syndrome; Progressive familial heart block type 1B; Progressive familial intrahepatic cholestasis 2 and 3; Progressive intrahepatic cholestasis; Progressive myoclonus epilepsy with ataxia; Progressive pseudorheumatoid dysplasia; Progressive sclerosing poliodystrophy; Prolidase deficiency; Proline dehydrogenase deficiency; Schizophrenia 4; Properdin deficiency, X-linked; Propionic academia; Proprotein convertase 1/3 deficiency; Prostate cancer, hereditary, 2; Protan defect; Proteinuria; Finnish congenital nephrotic syndrome; *Proteus* syndrome; Breast adenocarcinoma; Pseudoachondroplastic spondyloepiphyseal dysplasia syndrome; Pseudohypoaldosteronism type 1 autosomal dominant and recessive and type 2; Pseudohypoparathyroidism type 1A, Pseudopseudohypoparathyroidism; Pseudoneonatal adrenoleukodystrophy; Pseudoprimary hyperaldosteronism; Pseudoxanthoma elasticum; Generalized arterial calcification of infancy 2; Pseudoxanthoma elasticum-like disorder with multiple coagulation factor deficiency; Psoriasis susceptibility 2; PTEN hamartoma tumor syndrome; Pulmonary arterial hypertension related to hereditary hemorrhagic telangiectasia; Pulmonary Fibrosis And/Or Bone Marrow Failure, Telomere-Related, 1 and 3; Pulmonary hypertension, primary, 1, with hereditary hemorrhagic telangiectasia; Purine-nucleoside phosphorylase deficiency; Pyruvate carboxylase deficiency; Pyruvate dehydrogenase E1-alpha deficiency; Pyruvate kinase deficiency of red cells; Raine syndrome; Rasopathy; Recessive dystrophic epidermolysis bullosa; Nail disorder, nonsyndromic congenital, 8; Reifenstein syndrome; Renal adysplasia; Renal carnitine transport defect; Renal coloboma syndrome; Renal dysplasia; Renal dysplasia, retinal pigmentary dystrophy, cerebellar ataxia and skeletal dysplasia; Renal tubular acidosis, distal, autosomal recessive, with late-onset sensorineural hearing loss, or with hemolytic anemia; Renal tubular acidosis, proximal, with ocular abnormalities and mental retardation; Retinal cone dystrophy 3B; Retinitis pigmentosa; Retinitis pigmentosa 10, 11, 12, 14, 15, 17, and 19; Retinitis pigmentosa 2, 20, 25, 35, 36, 38, 39, 4, 40, 43, 45, 48, 66, 7, 70, 72; Retinoblastoma; Rett disorder; Rhabdoid tumor predisposition syndrome 2; Rhegmatogenous retinal detachment, autosomal dominant; Rhizomelic chondrodysplasia punctata type 2 and type 3; Roberts-SC phocomelia syndrome; Robinow Sorauf syndrome; Robinow syndrome, autosomal recessive, autosomal recessive, with brachy-syn-polydactyly; Rothmund-Thomson syndrome; Rapadilino syndrome; RRM2B-related mitochondrial disease; Rubinstein-Taybi syndrome; Salla disease; Sandhoff disease, adult and infantil types; Sarcoidosis, early-onset; Blau syndrome; Schindler disease, type 1; Schizencephaly; Schizophrenia 15; Schneckenbecken dysplasia; Schwannomatosis 2; Schwartz Jampel syndrome type 1; Sclerocornea, autosomal recessive; Sclerosteosis; Secondary hypothyroidism; Segawa syndrome, autosomal recessive; Senior-Loken syndrome 4 and 5; Sensory ataxic neuropathy, dysarthria, and ophthalmoparesis; Sepiapterin reductase deficiency; SeSAME syndrome; Severe combined immunodeficiency due to ADA deficiency, with microcephaly, growth retardation, and sensitivity to ionizing radiation, atypical, autosomal recessive, T cell-negative, B cell-positive, NK cell-negative of NK-positive; Partial adenosine deaminase deficiency; Severe congenital neutropenia; Severe congenital neutropenia 3, autosomal recessive or dominant; Severe congenital neutropenia and 6, autosomal recessive; Severe myoclonic epilepsy in infancy; Generalized epilepsy with febrile seizures plus, types 1 and 2; Severe X-linked myotubular myopathy; Short QT syndrome 3; Short stature with nonspecific skeletal abnormalities; Short stature, auditory canal atresia, mandibular hypoplasia, skeletal abnormalities; Short stature, onychodysplasia, facial dysmorphism, and hypotrichosis; Primordial dwarfism; Short-rib thoracic dysplasia 11 or 3 with or without polydactyly; Sialidosis type I and II; Silver spastic paraplegia syndrome; Slowed nerve conduction velocity, autosomal dominant; Smith-Lemli-Opitz syndrome; Snyder Robinson syndrome; Somatotroph adenoma; Prolactinoma; familial, Pituitary adenoma predisposition; Sotos syndrome 1 or 2; Spastic ataxia 5, autosomal recessive, Charlevoix-Saguenay type, 1, 10, or 11, autosomal recessive; Amyotrophic lateral sclerosis type 5; Spastic paraplegia 15, 2, 3, 35, 39, 4, autosomal dominant, 55, autosomal recessive, and 5A; Bile acid synthesis defect, congenital, 3; Spermatogenic failure 11, 3, and 8; Spherocytosis types 4 and 5; Spheroid body myopathy; Spinal muscular atrophy, lower extremity predominant 2, autosomal dominant; Spinal muscular atrophy, type II; Spinocerebellar ataxia 14, 21, 35, 40, and 6; Spinocerebellar ataxia autosomal recessive 1 and 16; Splenic hypoplasia; Spondylocarpotarsal synostosis syndrome; Spondylocheirodysplasia, Ehlers-Danlos syndrome-like, with immune dysregulation, Aggrecan type, with congenital joint dislocations, short limb-hand type, Sedaghatian type, with cone-rod dystrophy, and Kozlowski type; Parastremmatic dwarfism; Stargardt disease 1; Cone-rod dystrophy 3; Stickler syndrome type 1; Kniest dysplasia; Stickler syndrome, types 1(nonsyndromic ocular) and 4; Sting-associated vasculopathy, infantile-onset; Stormorken syndrome; Sturge-Weber syndrome, Capillary malformations, congenital, 1; Succinyl-CoA acetoacetate transferase deficiency; Sucrase-isomaltase deficiency; Sudden infant death syndrome; Sulfite oxidase deficiency, isolated; Supravalvar aortic stenosis; Surfactant metabolism dysfunction, pulmonary, 2 and 3; Symphalangism, proximal, 1b; Syndactyly Cenani Lenz type; Syndactyly type 3; Syndromic X-linked mental retardation 16; Talipes equinovarus; Tangier disease; TARP syndrome; Tay-Sachs disease, B1 variant, Gm2-gangliosidosis (adult), Gm2-gangliosidosis (adult-onset); Temtamy syndrome; Tenorio Syndrome; Terminal osseous dysplasia; Testosterone 17-beta-dehydrogenase deficiency; Tetraamelia, autosomal recessive; Tetralogy of Fallot; Hypoplastic left heart syndrome 2; Truncus arteriosus; Malformation of the heart and great vessels; Ventricular septal defect 1; Thiel-Behnke corneal dystrophy; Thoracic aortic aneurysms and aortic dissections; Marfanoid habitus; Three M syndrome 2; Thrombocytopenia, platelet dysfunction, hemolysis, and imbalanced globin synthesis; Thrombocytopenia, X-linked; Thrombophilia, hereditary, due to protein C deficiency, autosomal dominant and recessive; Thyroid agenesis; Thyroid cancer, follicular; Thyroid hormone metabolism, abnormal; Thyroid hormone resistance, generalized, autosomal dominant; Thyrotoxic periodic paralysis and Thyrotoxic periodic paralysis 2; Thyrotropin-releasing hormone resistance, generalized; Timothy syndrome; TNF receptor-associated periodic fever syndrome (TRAPS); Tooth agenesis, selective, 3 and 4; Torsades de pointes; Townes-Brocks-branchiootorenal-like syndrome; Transient bullous dermolysis of the newborn; Treacher collins syndrome 1; Trichomegaly with mental retardation, dwarfism and pigmentary degeneration of retina; Trichorhinophalangeal dysplasia type I; Trichorhinophalangeal syndrome type 3; Trimethylaminuria; Tuberous sclerosis syndrome; Lymphangiomyomatosis; Tuberous sclerosis 1 and 2; Tyrosinase-negative oculocutaneous albinism; Tyrosinase-positive oculocutaneous albinism; Tyrosinemia type I; UDPglucose-4-epimerase deficiency; Ullrich congenital muscular dystrophy; Ulna and fibula absence of with severe limb deficiency; Upshaw-Schulman syndrome; Urocanate hydratase deficiency; Usher syndrome, types 1, 1B, 1D, 1G, 2A, 2C, and 2D; Retinitis pigmentosa 39; UV-sensitive syndrome; Van der Woude syndrome; Van Maldergem syndrome 2; Hennekam lymphangiectasia-lymphedema syndrome 2; Variegate porphyria; Ventriculomegaly with cystic kidney disease; Verheij syndrome; Very long chain acyl-CoA dehydrogenase deficiency; Vesicoureteral reflux 8; Visceral heterotaxy 5, autosomal; Visceral myopathy; Vitamin D-dependent rickets, types l and 2; Vitelliform dystrophy; von Willebrand disease type 2M and type 3; Waardenburg syndrome type 1, 4C, and 2E (with neurologic involvement); Klein-Waardenberg syndrome; Walker-Warburg congenital muscular dystrophy; Warburg micro syndrome 2 and 4; Warts, hypogammaglobulinemia, infections, and myelokathexis; Weaver syndrome; Weill-Marchesani syndrome 1 and 3; Weill-Marchesani-like syndrome; Weissenbacher-Zweymuller syndrome; Werdnig-Hoffmann disease; Charcot-Marie-Tooth disease; Werner syndrome; WFS1-Related Disorders; Wiedemann-Steiner syndrome; Wilson disease; Wolfram-like syndrome, autosomal dominant; Worth disease; Van Buchem disease type 2; Xeroderma pigmentosum, complementation group b, group D, group E, and group G; X-linked agammaglobulinemia; X-linked hereditary motor and sensory neuropathy; X-linked ichthyosis with steryl-sulfatase deficiency; X-linked periventricular heterotopia; Oto-palato-digital syndrome, type I; X-linked severe combined immunodeficiency; Zimmermann-Laband syndrome and Zimmermann-Laband syndrome 2; and Zonular pulverulent cataract 3.

The instant disclosure provides lists of genes comprising pathogenic G to A or C to T mutations. Such pathogenic G to A or C to T mutations may be corrected using the methods and compositions provided herein, for example by mutating the A to a G, and/or the T to a C, thereby restoring gene function. Table 2 includes exemplary mutations that can be corrected using base editors described herein. Table 2 includes the gene symbol, the associated phenotype, the mutation to be corrected and exemplary gRNA sequences which may be used to correct the mutations. The gRNA sequences provided in Table 2 are sequences that encode RNA that can direct Cas9, or any of the base editors provided herein, to a target site. For example, the gRNA sequences provided in Table 2 may be cloned into a gRNA expression vector, such as pFYF to encode a gRNA that targets Cas9, or any of the base editors provided herein, to a target site in order to correct a disease-related mutation. It should be appreciated, however, that additional mutations may be corrected to treat additional diseases associated with a G to A or C to T mutation. Furthermore, additional gRNAs may be designed based on the disclosure and the knowledge in the art, which would be appreciated by the skilled artisan.

Pharmaceutical Compositions

Other aspects of the present disclosure relate to pharmaceutical compositions comprising any of the adenosine deaminases, fusion proteins, or the fusion protein-gRNA complexes described herein. The term "pharmaceutical composition", as used herein, refers to a composition formulated for pharmaceutical use. In some embodiments, the pharmaceutical composition further comprises a pharmaceutically acceptable carrier. In some embodiments, the pharmaceutical composition comprises additional agents (e.g. for specific delivery, increasing half-life, or other therapeutic compounds).

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the compound from one site (e.g., the delivery site) of the body, to another site (e.g., organ, tissue or portion of the body). A pharmaceutically acceptable carrier is "acceptable" in the sense of being compatible with the other ingredients of the formulation and not injurious to the tissue of the subject (e.g., physiologically compatible, sterile, physiologic pH, etc.). Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

In some embodiments, the pharmaceutical composition is formulated for delivery to a subject, e.g., for gene editing. Suitable routes of administrating the pharmaceutical composition described herein include, without limitation: topical, subcutaneous, transdermal, intradermal, intralesional, intraarticular, intraperitoneal, intravesical, transmucosal, gingival, intradental, intracochlear, transtympanic, intraorgan, epidural, intrathecal, intramuscular, intravenous, intravascular, intraosseus, periocular, intratumoral, intracerebral, and intracerebroventricular administration.

In some embodiments, the pharmaceutical composition described herein is administered locally to a diseased site (e.g., tumor site). In some embodiments, the pharmaceutical composition described herein is administered to a subject by injection, by means of a catheter, by means of a suppository, or by means of an implant, the implant being of a porous, non-porous, or gelatinous material, including a membrane, such as a sialastic membrane, or a fiber.

In other embodiments, the pharmaceutical composition described herein is delivered in a controlled release system. In one embodiment, a pump may be used (see, e.g., Langer, 1990, Science 249:1527-1533; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used. (See, e.g., Medical Applications of Controlled Release (Langer and Wise eds., CRC Press, Boca Raton, Fla., 1974); Controlled Drug Bioavailability, Drug Product Design and Performance (Smolen and Ball eds., Wiley, New York, 1984); Ranger and Peppas, 1983, Macromol. Sci. Rev. Macromol. Chem. 23:61. See also Levy et al., 1985, Science 228:190; During et al., 1989, Ann. Neurol. 25:351; Howard et al., 1989, J. Neurosurg. 71:105.) Other controlled release systems are discussed, for example, in Langer, supra.

In some embodiments, the pharmaceutical composition is formulated in accordance with routine procedures as a composition adapted for intravenous or subcutaneous administration to a subject, e.g., a human. In some embodiments, pharmaceutical composition for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical composition is administered by injection, an ampoule of sterile water for injection or saline can be provided so that the ingredients can be mixed prior to administration.

A pharmaceutical composition for systemic administration may be a liquid, e.g., sterile saline, lactated Ringer's or Hank's solution. In addition, the pharmaceutical composition can be in solid forms and re-dissolved or suspended immediately prior to use. Lyophilized forms are also contemplated.

The pharmaceutical composition can be contained within a lipid particle or vesicle, such as a liposome or microcrystal, which is also suitable for parenteral administration. The particles can be of any suitable structure, such as unilamellar or plurilamellar, so long as compositions are contained therein. Compounds can be entrapped in "stabilized plasmid-lipid particles" (SPLP) containing the fusogenic lipid dioleoylphosphatidylethanolamine (DOPE), low levels (5-10 mol %) of cationic lipid, and stabilized by a polyethyleneglycol (PEG) coating (Zhang Y. P. et al., *Gene Ther.* 1999, 6:1438-47). Positively charged lipids such as N-[1-(2,3-dioleoyloxi)propyl]-N,N,N-trimethyl-amoniummethylsulfate, or "DOTAP," are particularly preferred for such particles and vesicles. The preparation of such lipid particles is well known. See, e.g., U.S. Pat. Nos. 4,880,635; 4,906,477; 4,911,928; 4,917,951; 4,920,016; and 4,921,757; each of which is incorporated herein by reference.

The pharmaceutical composition described herein may be administered or packaged as a unit dose, for example. The term "unit dose" when used in reference to a pharmaceutical composition of the present disclosure refers to physically discrete units suitable as unitary dosage for the subject, each unit containing a predetermined quantity of active material calculated to produce the desired therapeutic effect in association with the required diluent; i.e., carrier, or vehicle.

Further, the pharmaceutical composition can be provided as a pharmaceutical kit comprising (a) a container containing a compound of the invention in lyophilized form and (b) a second container containing a pharmaceutically acceptable diluent (e.g., sterile water) for injection. The pharmaceutically acceptable diluent can be used for reconstitution or dilution of the lyophilized compound of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

In another aspect, an article of manufacture containing materials useful for the treatment of the diseases described above is included. In some embodiments, the article of manufacture comprises a container and a label. Suitable containers include, for example, bottles, vials, syringes, and test tubes. The containers may be formed from a variety of materials such as glass or plastic. In some embodiments, the container holds a composition that is effective for treating a disease described herein and may have a sterile access port. For example, the container may be an intravenous solution bag or a vial having a stopper pierceable by a hypodermic injection needle. The active agent in the composition is a compound of the invention. In some embodiments, the label on or associated with the container indicates that the composition is used for treating the disease of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use.

Delivery Methods

In some aspects, the invention provides methods comprising delivering one or more polynucleotides, such as or one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a base editor as described herein in combination with (and optionally complexed with) a guide sequence is delivered to a cell. Conventional viral and non-viral based gene transfer methods can be used to introduce nucleic acids in mammalian cells or target tissues. Such methods can be used to administer nucleic acids encoding components of a base editor to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology Doerfler and Bihm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a viruses can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by, reference.

Kits, Vectors, Cells

Some aspects of this disclosure provide kits comprising a nucleic acid construct comprising a nucleotide sequence encoding an adenosine deaminase capable of deaminating an adenosine in a deoxyribonucleic acid (DNA) molecule. In some embodiments, the nucleotide sequence encodes any of the adenosine deaminases provided herein. In some embodiments, the nucleotide sequence comprises a heterologous promoter that drives expression of the adenosine deaminase.

Some aspects of this disclosure provide kits comprising a nucleic acid construct, comprising (a) a nucleotide sequence encoding a napDNAbp (e.g., a Cas9 domain) fused to an adenosine deaminase, or a fusion protein comprising a napDNAbp (e.g., Cas9 domain) and an adenosine deaminase as provided herein; and (b) a heterologous promoter that drives expression of the sequence of (a). In some embodiments, the kit further comprises an expression construct encoding a guide nucleic acid backbone, (e.g., a guide RNA backbone), wherein the construct comprises a cloning site positioned to allow the cloning of a nucleic acid sequence identical or complementary to a target sequence into the guide nucleic acid (e.g., guide RNA backbone).

Some aspects of this disclosure provide cells comprising any of the adenosine deaminases, fusion proteins, or complexes provided herein. In some embodiments, the cells comprise a nucleotide that encodes any of the adenosine deaminases or fusion proteins provided herein. In some embodiments, the cells comprise any of the nucleotides or vectors provided herein.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A 172, A20, A253, A431, A-549, ALC, B16, B35, BCP-1 cells, BEAS-2B, bEnd.3, BHK-21, BR 293. BxPC3. C3H-10T1/2, C6/36, Cal-27, CHO, CHO-7, CHO-IR, CHO-K1, CHO-K2, CHO-T, CHO Dhfr-/-, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK 11, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

EXAMPLES

Example 1: Continuous Evolution of Base Editor or Component Thereof Using PACE CRISPR-Cas9 genome editing has greatly expanded the scope of synthetic biology and genetic medicine, and its versatility is a major asset since it allows sequences to be deleted or replaced. However, many genetic targets of interest for human medicine are single-base point mutations. To make these small changes, CRISPR-Cas9 approaches must still introduce genome-destabilizing double-strand breaks and rely on homologous recombination with added template DNA to repair them.

Base editing is an alternative approach which modifies DNA bases in place without double-strand breaks. Cas9 is used to target the editing site and provide single-stranded DNA substrate to a tethered deaminase, which converts cytidine to uracil. Normal DNA repair can then lead to replacing a G-C pair with A-T, as shown below.

Existing base editing methods need improvement to be more versatile tools and especially to be viable as therapeutics, since safety and efficacy requirements are high and in vivo delivery is challenging. A rapid biomolecule evolution method, phage-assisted continuous evolution (PACE), is being used to develop more effective base editors with high activity and sequence generality and precise base targeting.

In PACE, the gene under selection is encoded on the M13 bacteriophage genome. Its activity is linked to M13 propagation by controlling expression of gene III so that only active variants produce infectious progeny phage. Phage are continuously propagated and mutagenized, but mutations accumulate only in the phage genome, not the host or its selection circuit, because fresh host cells are continually flowed into (and out of) the growth vessel, effectively resetting the selection background. Only phage that pass the selection can reproduce and survive the continuous dilution process.

The key to a new PACE selection is linking gene III expression to the activity of interest. A low stringency selection was designed in which base editing activates T7 RNA polymerase, which transcribes gIII. A single editing event can lead to high output amplification immediately upon transcription of the edited DNA.

Selection Optimization and Validation

The proof-of-concept circuit outlined herein showed guide-RNA dependent activation of T7 RNA polymerase, but turn-on was not optimal. The expression level of T7RNAP was optimized through promoter/RBS scanning. Although plasmid-encoded editor expression gave high fold activation using optimized constructs (>200× in 3 h), phage-encoded editor gave no turn-on and editor phage did not propagate on the circuit more strongly than empty control phage.

Unusually for a PACE selection, selective propagation was achieved by optimizing the phage, rather than using a higher-activity gene variant or lowering the selection stringency. The phage backbone was replaced with one that had been propagated in PACE for hundreds of generations. The DNA size burden of the editor was also reduced by using a split intein, where an N-intein and a C-intein, which are expressed separately, join to form a fusion protein. In this scheme, only the N-terminal deaminase is encoded on the phage, along with a linker and the N-terminal part of a trans-splicing intein. The full base editor is reconstituted upon phage infection by splicing with the host-encoded, constitutively expressed C-terminal dCas9 and UGI. This restricts mutations to the deaminase and linker, which limits accessible targets. Improvements in phage backbone and deaminase activity during evolution now allow may allow the full base editor to be encoded on the phage (Table 1 below).

The selection was validated by propagating a mixture of active (APOBEC-N-intein) and inactive (RFP) phage on the circuit under continuous flow. Even with a 1000× excess of RFP phage, APOBEC phage took over within 24 h, regardless of their initial titer.

Figure 7:
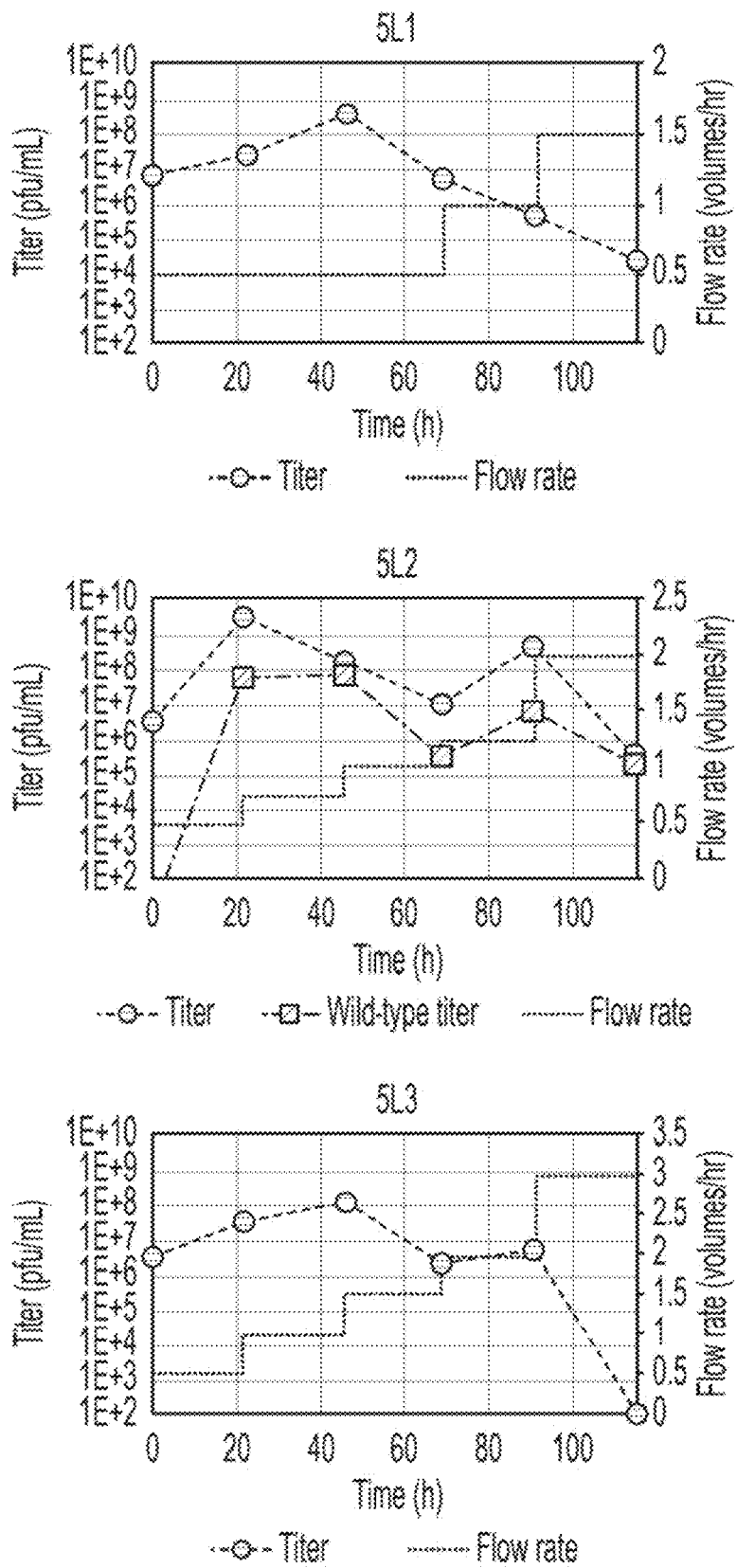
FIG. 7 shows propagation in PACE on the low-stringency circuit.
Figure 7:
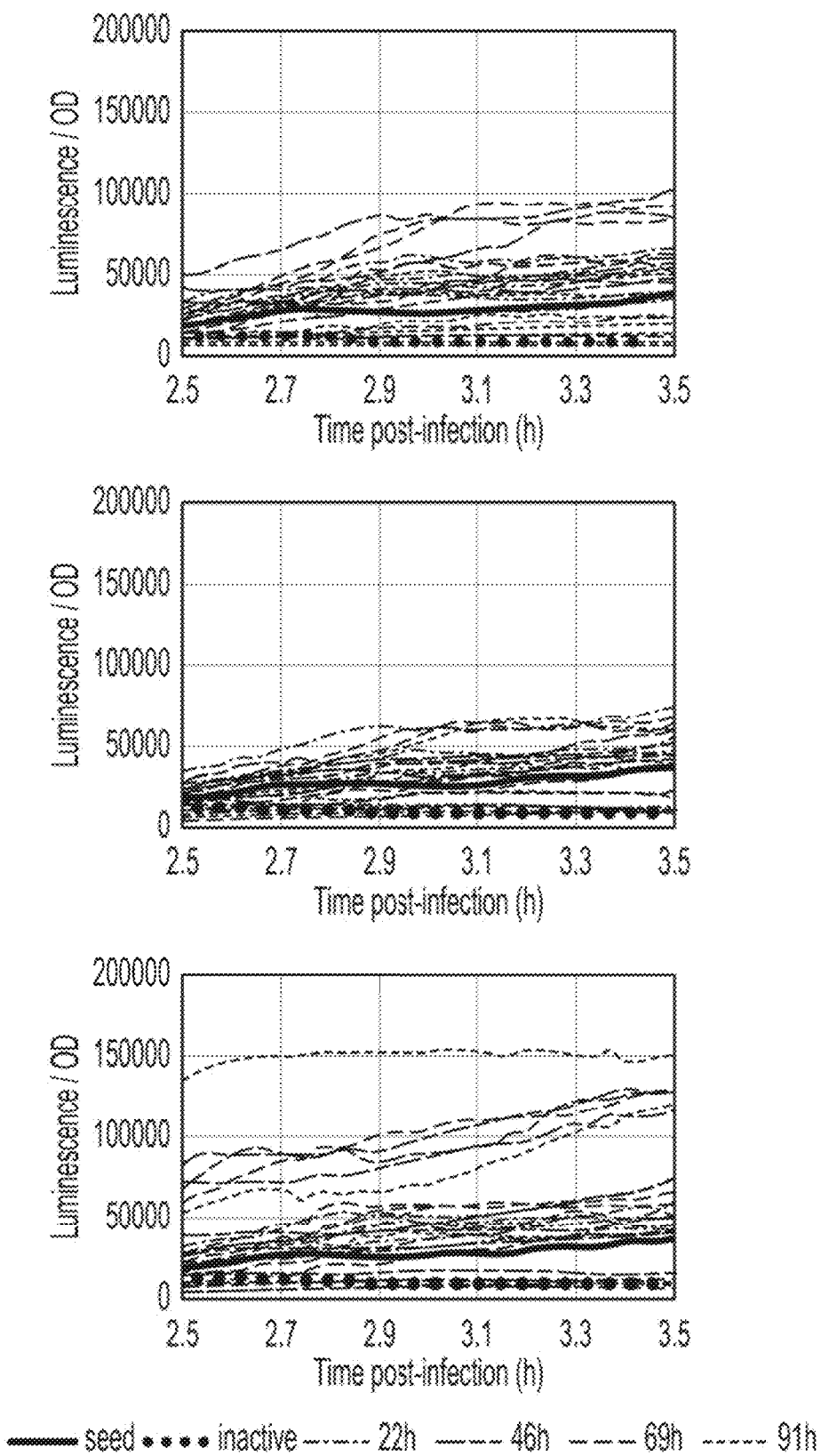
Figure 8:
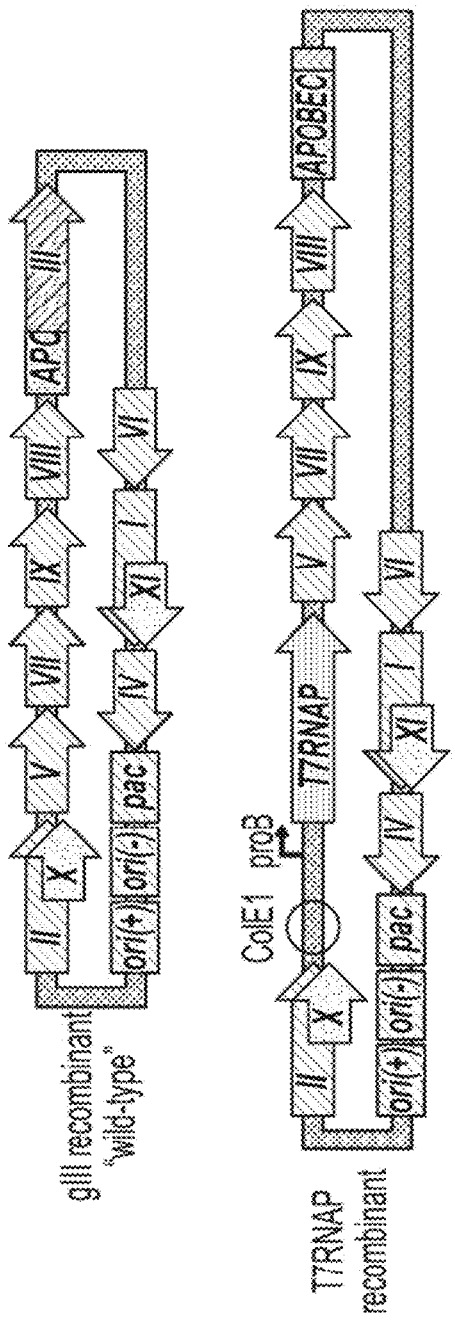
FIG. 8 shows a schematic of gIII recombinant wild-type versus T7RNAP recombinant.
Figure 9:
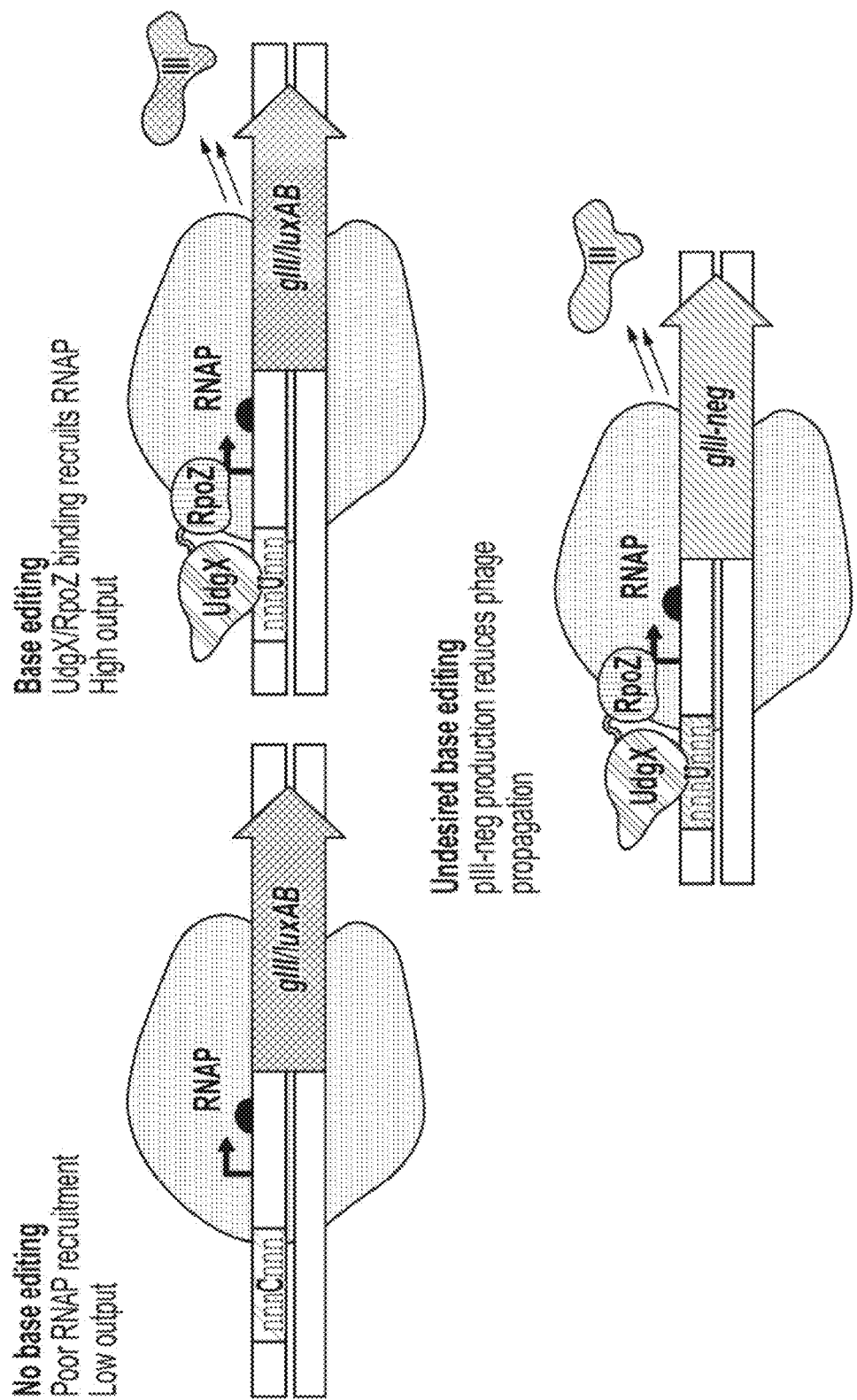
FIG. 9 shows a schematic of base editing.

Propagation in PACE on the low-stringency circuit is robust (shown in FIG. 7, 3 flow rate schedules for the same input phage and circuit). Luciferase assays for circuit activation by individual clones (24 per lagoon, 8 per time-point) show improvement over the starting genotype, but this is so far largely due to backbone optimization.

Recombination of gene III or activated T7 RNA polymerase onto the phage allows base editing independent propagation on the circuit. Recoding to reduce homology, negative selection rounds to remove T7 activity on phage and improved base editor clones reduced or eliminated these problems.

Alternative Selection: Uracil Binding "One-Hybrid"

The low-stringency T7 RNAP activation selection has limited potential for adapting to different targets and/or negative selection, because the editing site is within a functionally sensitive coding sequence. An alternative scheme was designed based on a one-hybrid DNA binding domain selection used for TALEN and Cas9 evolutions in PACE. Base editing (not shown) installs a uracil upstream of a weak promoter, which is bound by uracil-DNA binding protein UdgX fused to a transcriptional activator. This architecture would allow arbitrary target sequence specification and a symmetric dual selection for unwanted base editing activity.

Transcriptional activation is sensitive to the spatial organization of RpoZ, RNAP and the promoter. A series of UdgX-RpoZ fusions were screened with editing targeted to various upstream positions. Some sites and activator fusions show very modest but reproducible guide-RNA-dependent transcriptional activation. However, the most active phage clones from PACE can so far produce only 1.6× activation on the optimized circuit, which is not enough to support propagation.

Phage-Assisted Continuous Evolution of Nucleobase Editors (Base Editors)

The invention outlined herein describes base editing as a method for precision genome modification, phage-assisted continuous evolution, development of a low-stringency selection for base editing, selection tuning and validation, and the first steps of directed evolution.

Figure 10:
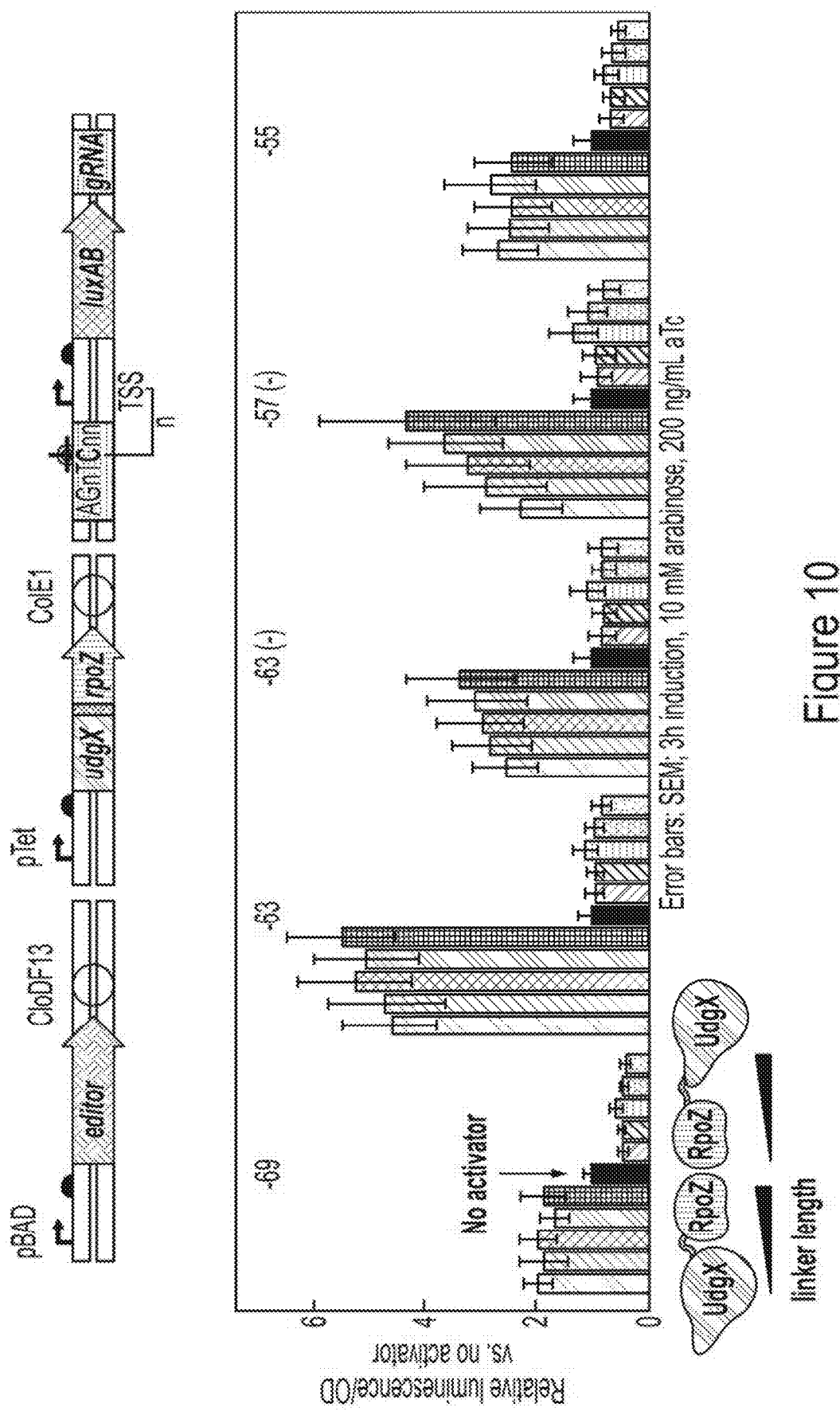
FIG. 10 shows screening with EdgX-RpoZ fusions.
Figures 10, 11:
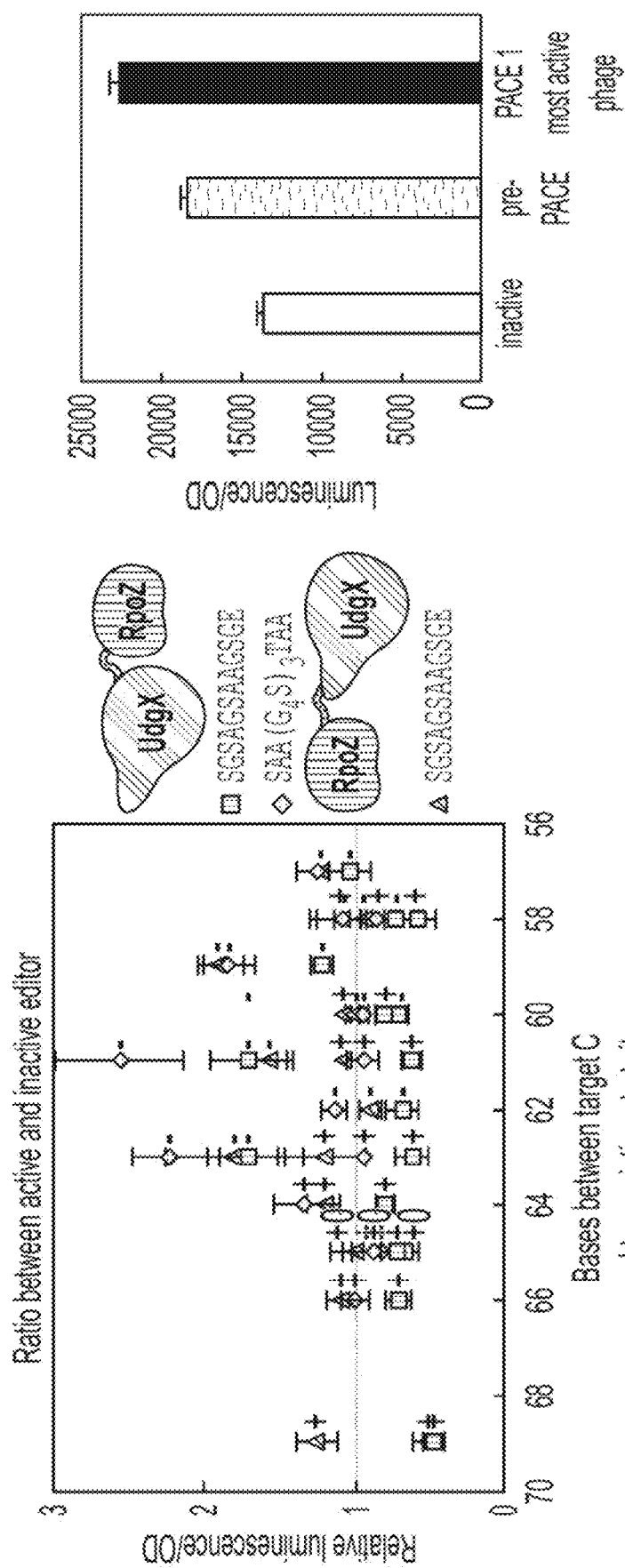
FIG. 11 shows ClinVAR database pathogenic variations.

Point mutations are an important genome editing target. Single nucleotide polymorphisms account for ~90% of human genetic variation. Single base changes could address many human diseases. Introducing stop codons instead of indels gives more uniform knockouts and reduced cell death. FIG. 11 shows the ClinVAR database pathogenic variations.

Figure 12:
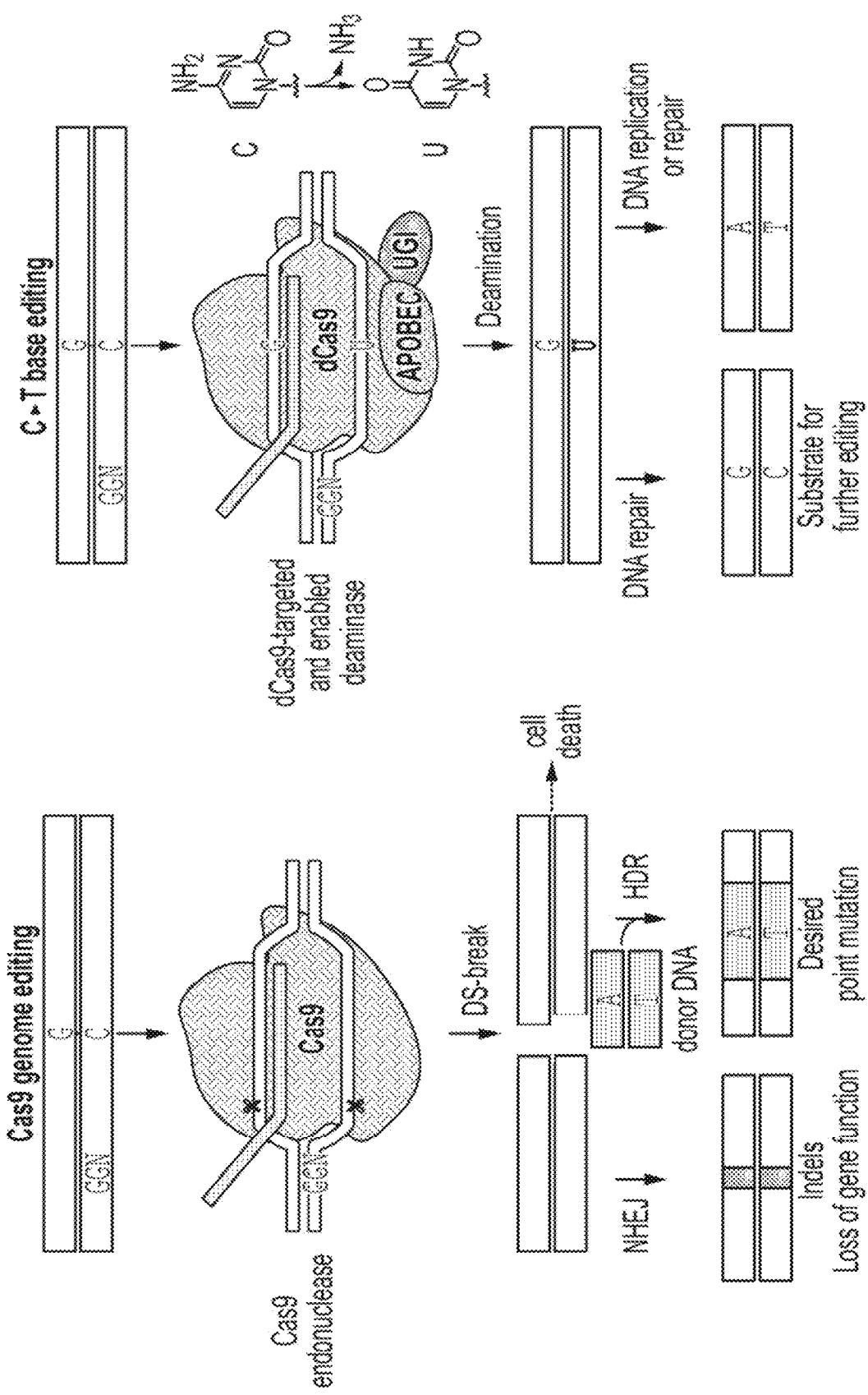
FIG. 12 shows a schematic of Cas9 genome editing and C to T base editing.

Base editing introduces a point mutation without double-strand breaks as illustrated in FIG. 12.

Figure 13:
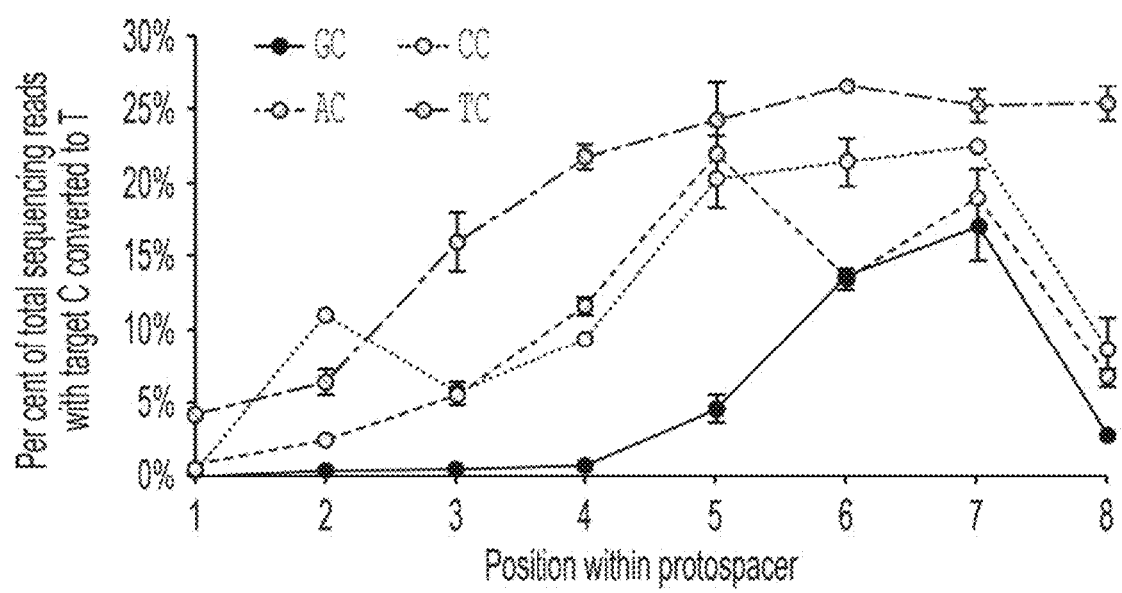
FIG. 13 shows the base editing results.

Base editing can be improved. Multiple Cs within the "window" may be edited. Sequence context affects editing efficiency (FIG. 13). PAM specificity and window control sites that can be edited precisely or at all (FIG. 14). Expression and activity (on specific sites) are critical when delivery is limiting (FIG. 15).

Figure 16:
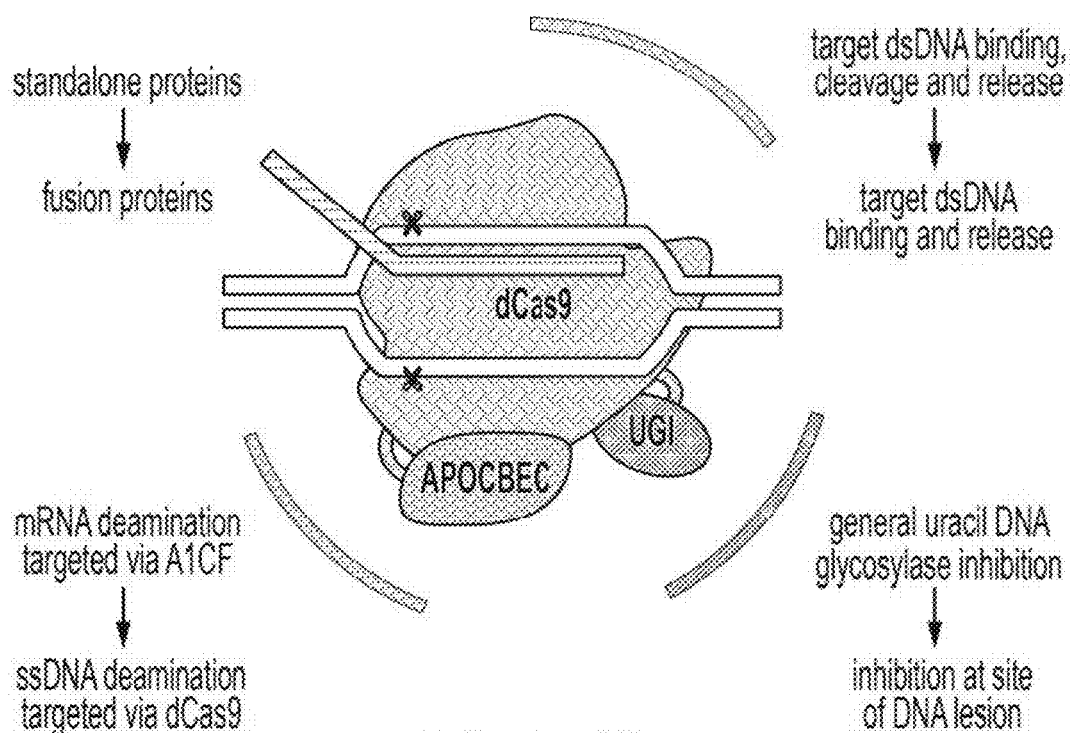
FIG. 16 shows a schematic of the proposed base evolution method.
Figure 17:
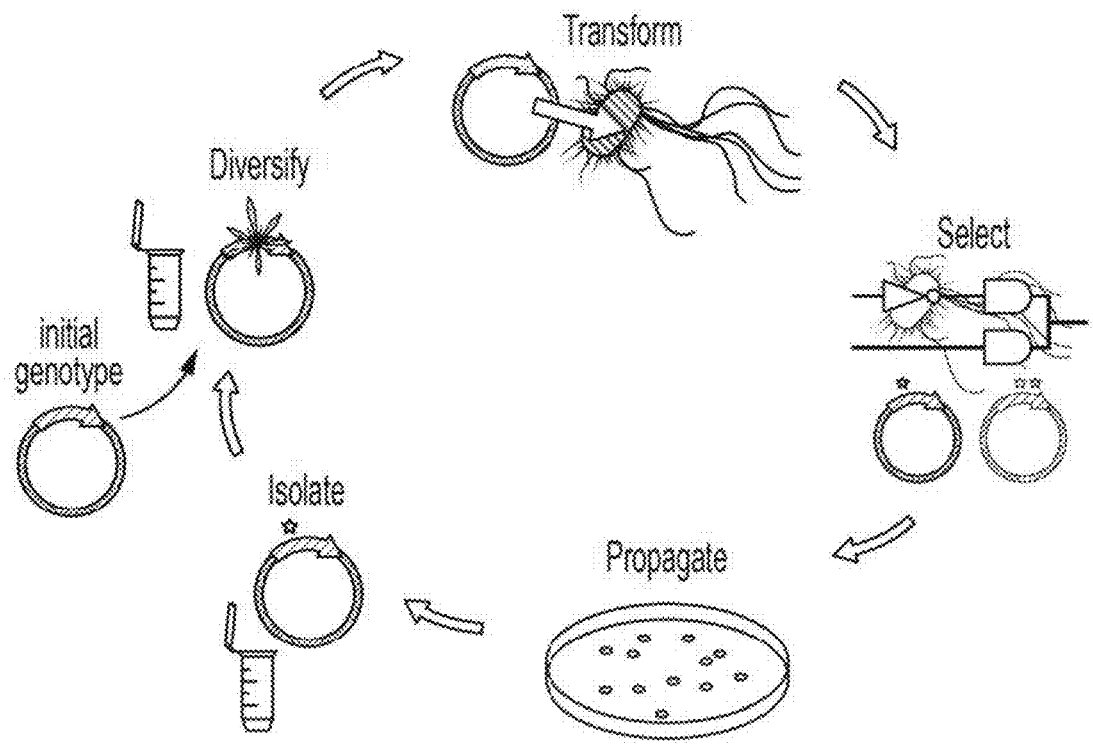
FIG. 17 shows a schematic of the evolution process.
Figure 18:
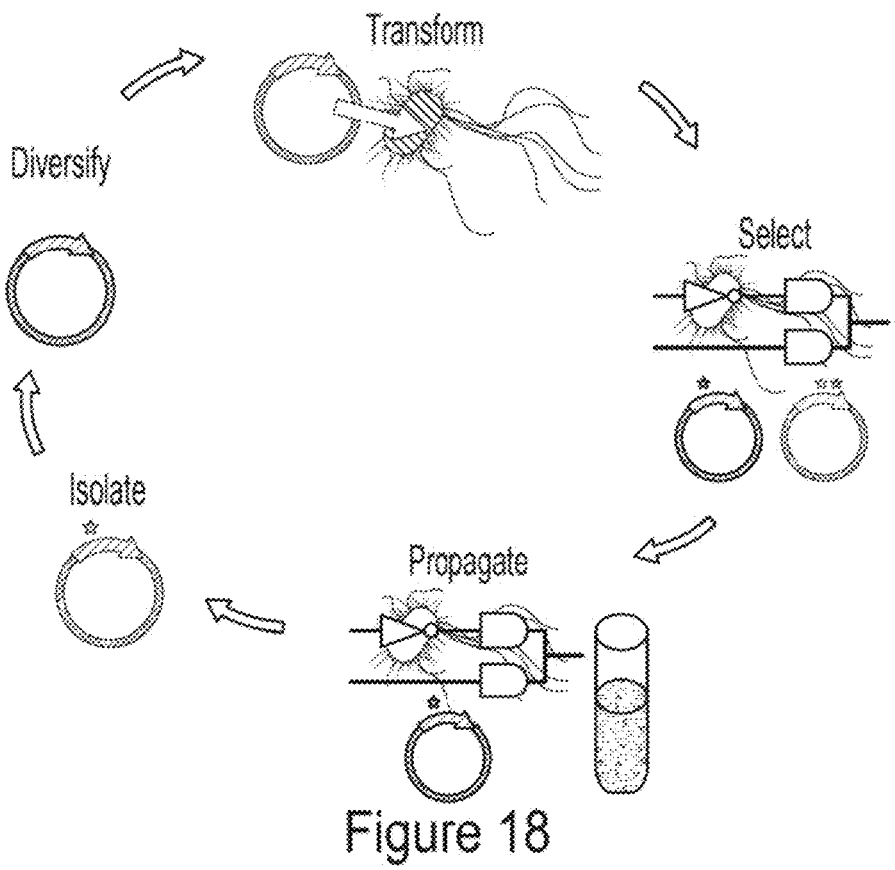
FIG. 18 shows a schematic of continuous directed evolution in vivo.
Figure 19:
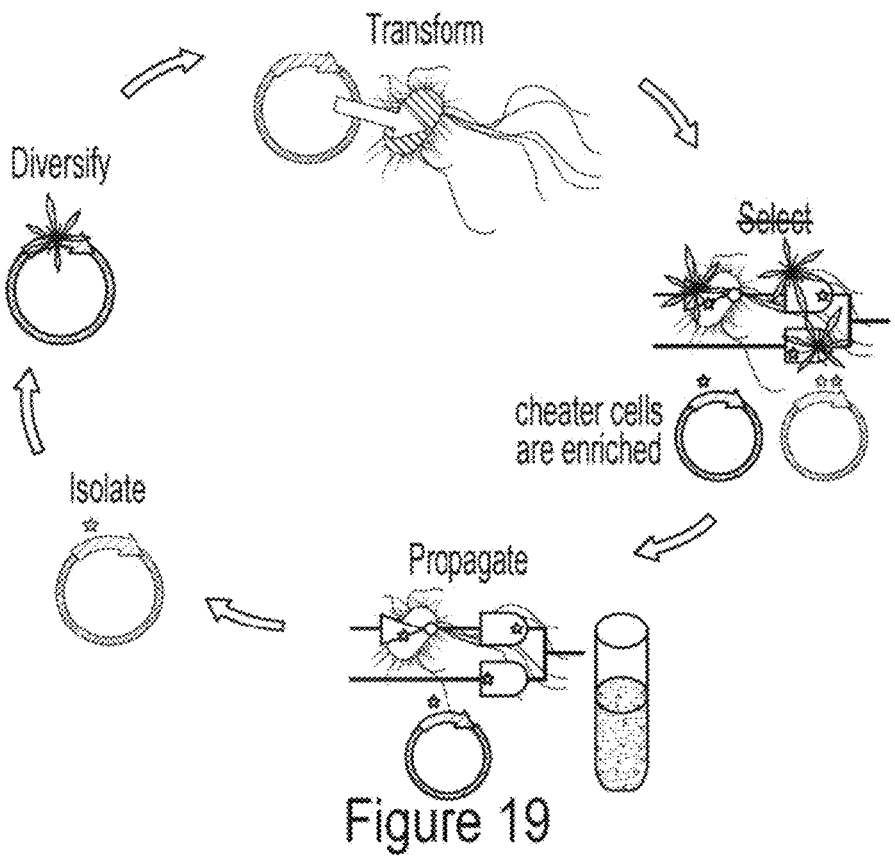
FIG. 19 shows a schematic of continuous directed evolution in vivo.

Base editing could benefit from an unbiased evolution method as shown in FIG. 16. Further, discrete rounds of directed evolution take time as illustrated in FIG. 17. As described herein continuous directed evolution combines all steps in vivo (see FIGS. 18 and 19).

Figure 20:
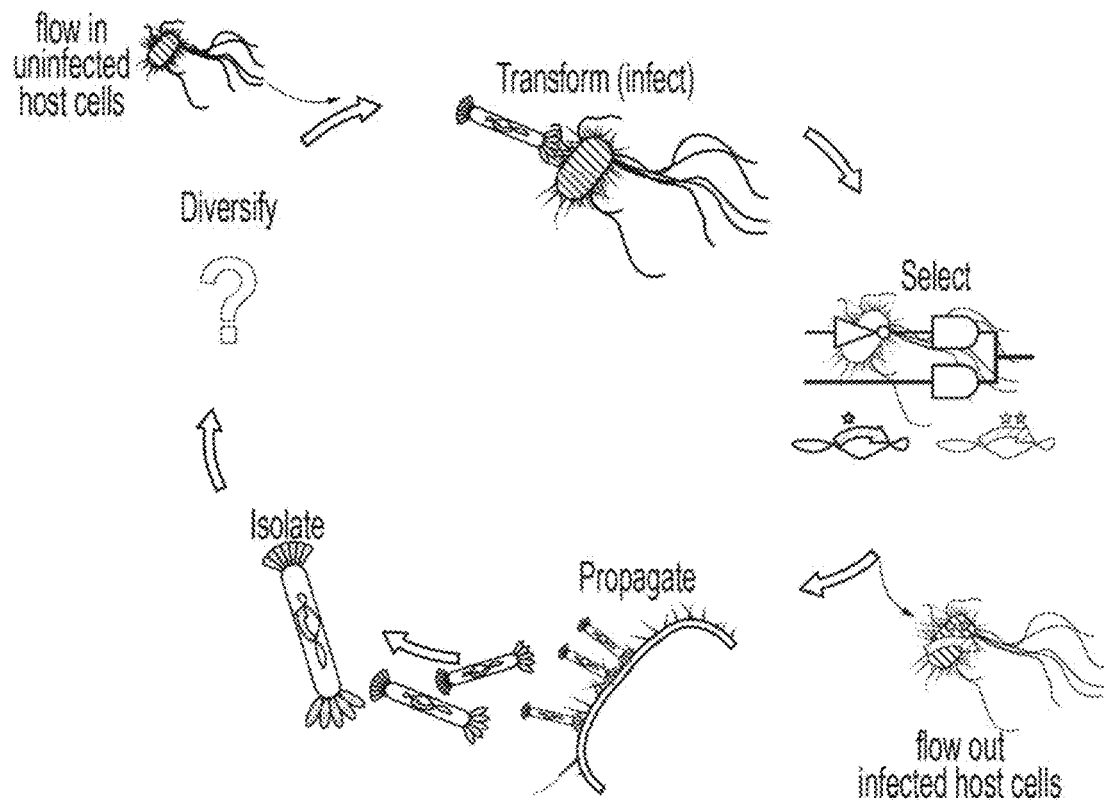
FIG. 20 shows a schematic of phage-assisted continuous evolution.
Figure 21:
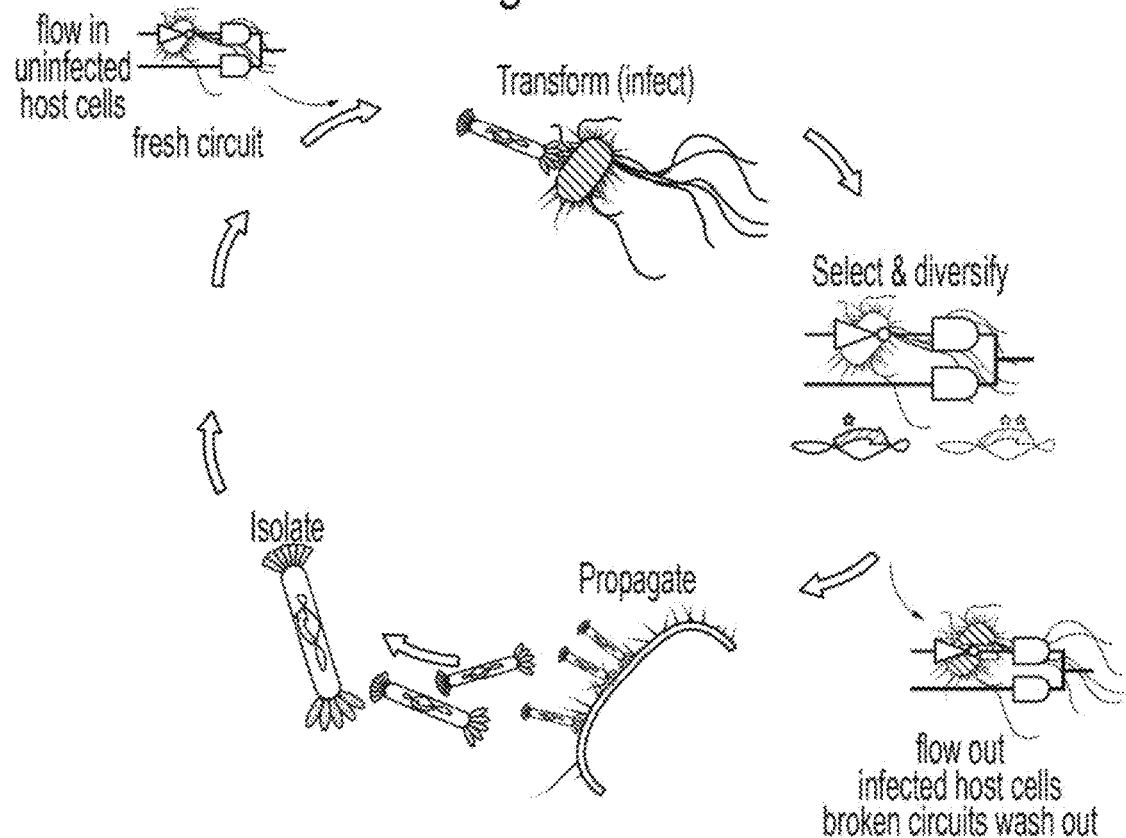
FIG. 21 shows a schematic of phage-assisted continuous evolution.

Phage-assisted continuous evolution limits mutations to the evolving gene (FIGS. 20 and 21).

PACE on Base Editors

Base editors are large and poorly expressed. First, protein expression level and maturation time prove to be problematic. Second, phage genome size impairs fitness and incentivizes cheating. Editing happens slowly. In mammalian cells editing occurs at 3-5 days for maximal levels. In bacteria editing occurs at 40-60 generations for maximal levels. Thus, if DNA repair or replication is required >1 generation is needed. Finally, editor binding may interfere with editing readout (CRISPRi). Cas9 residence times are long and editing a protein coding sequence can lead to CRISPRi.

Figure 22:
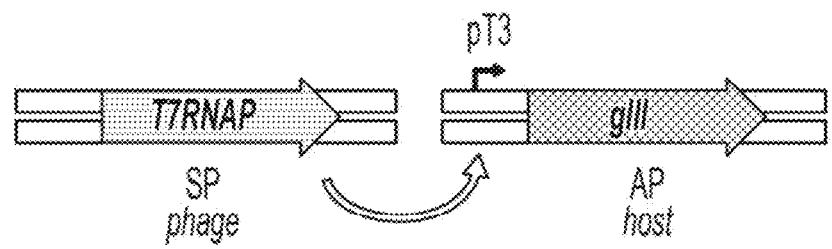
FIG. 22 shows a schematic of PACE selection for use in base editing.
Figure 23:
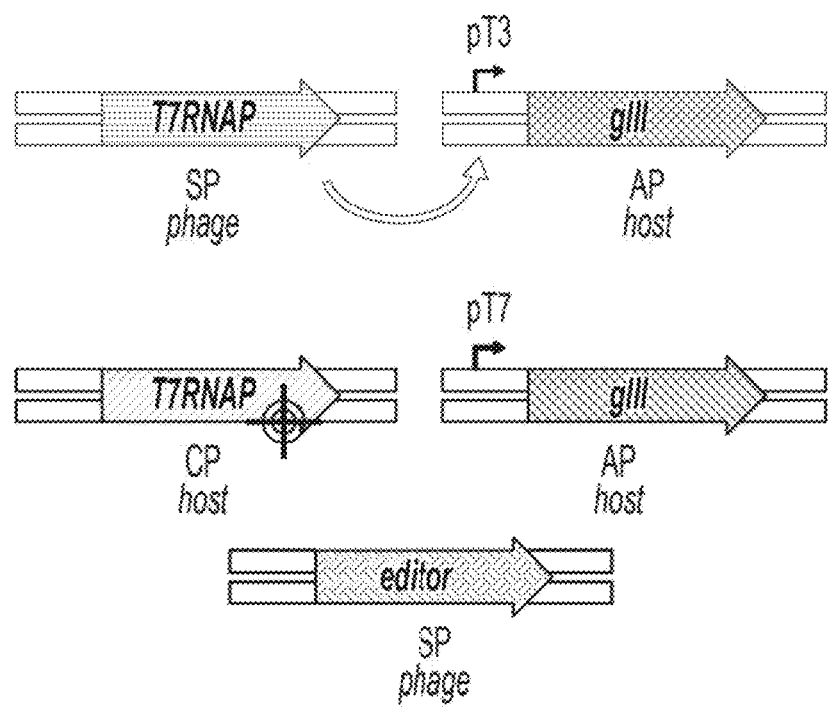
FIG. 23 shows a schematic of PACE selection for use in base editing.
Figure 24:
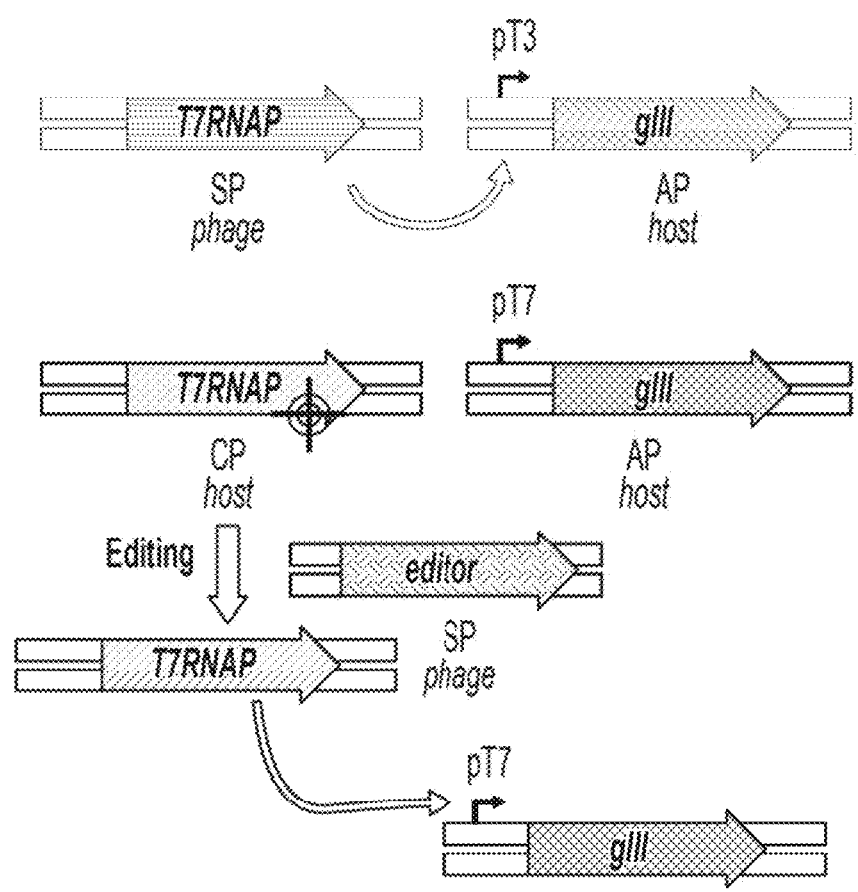
FIG. 24 shows a schematic of PACE selection for use in base editing.

The PACE selection can be adapted for base editing as shown in FIGS. 22, 23, and 24. This provides the benefits of huge amplification with low stringency and it is tunable.

Any PACE circuit can in principle be adapted for base editing by 1) moving the phage component that is normally under selection to the host cell and 2) inactivating that component, or any part of the circuit, in a way that can be corrected by a base edit. In FIG. 24, T7 RNA polymerase is activated by base editing. Other analogous examples include 1) catalytically activating a protease or converting a non-cleavable substrate to a cleavable one by base editing, or 2) catalytically activating a recombinase by base editing, etc.

Figure 25:
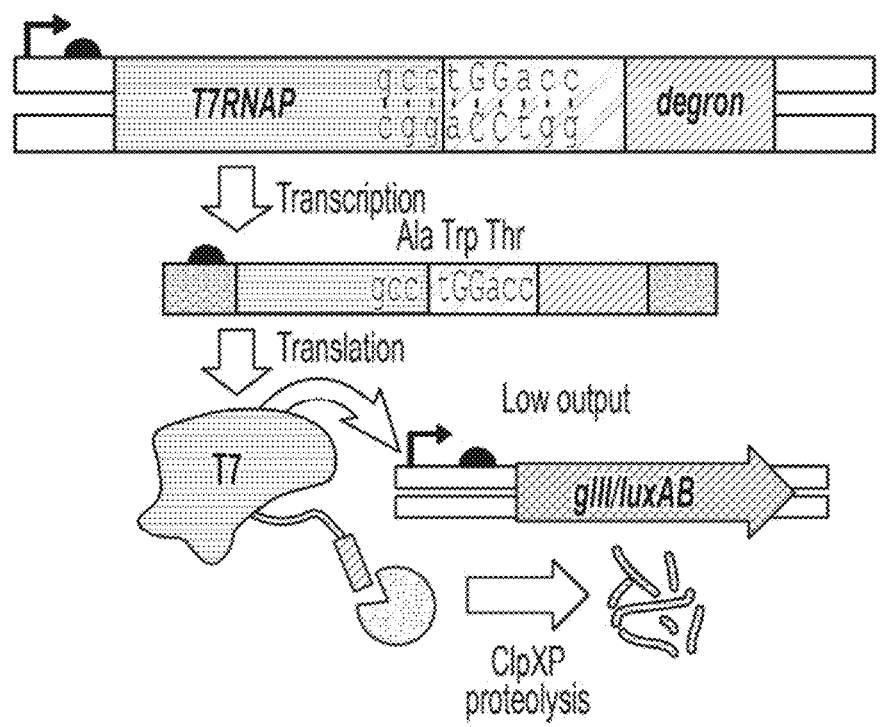
FIG. 25 shows a schematic of C-terminal degron tag cuts on T7 RNAP activity.
Figure 26:
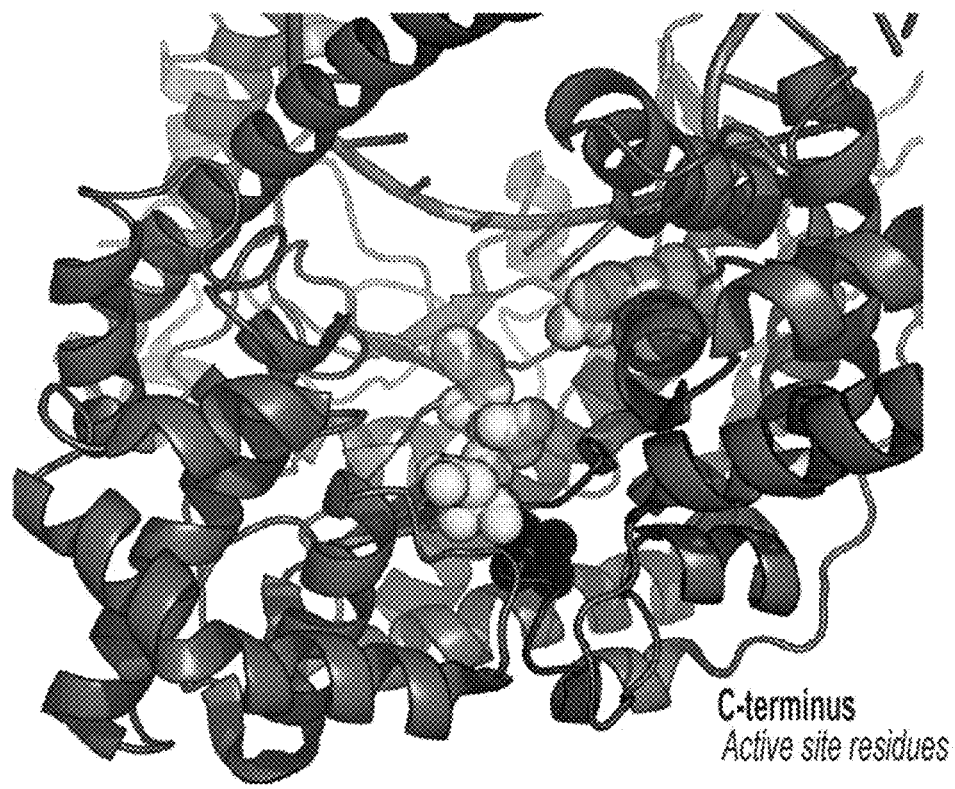
FIG. 26 shows a protein model of the C-terminus of T7 RNAP.
Figure 27:
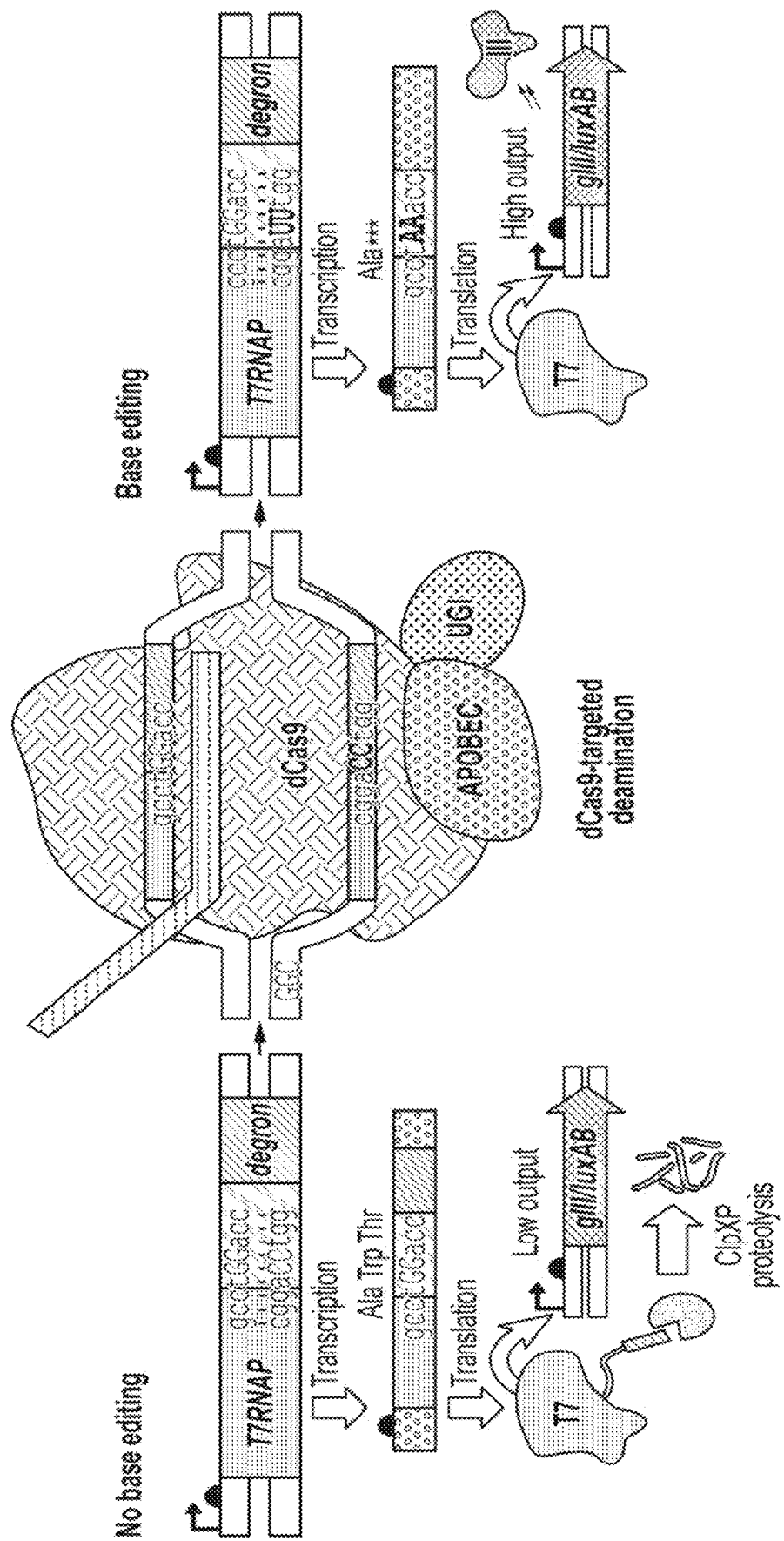
FIG. 27 shows a schematic of a C-terminal degron tag in both no base editing and base editing.

A C-terminal degron tag cuts T7 RNAP activity as shown in FIG. 25. In some embodiments, a degron tag is an amino acid sequence that targets a protein for degradation. In some embodiments, the degron tag is ubiquitin-dependent. In some embodiments, the degron tag is ubiquitin-independent. Further, the C-terminus of T7 RNA Polymerase participates in catalysis. A model of the T7 RNA polymerase C-terminus is shown in FIG. 26. FIG. 27 illustrates the effect of a C-terminal degron tag on T7 RNAP activity for both base editing and no base editing. T7 RNAP is inactivated by fusion of a C-terminal degron tag that targets it for proteolysis and blocks its C-terminal carboxylate (which participates in catalysis). Editing of the Trp codon on the template strand converts it to a stop in mRNA (TAA, TGA or TAG depending on the position and number of base edits) and restores wild-type T7 RNAP.

Figure 28:
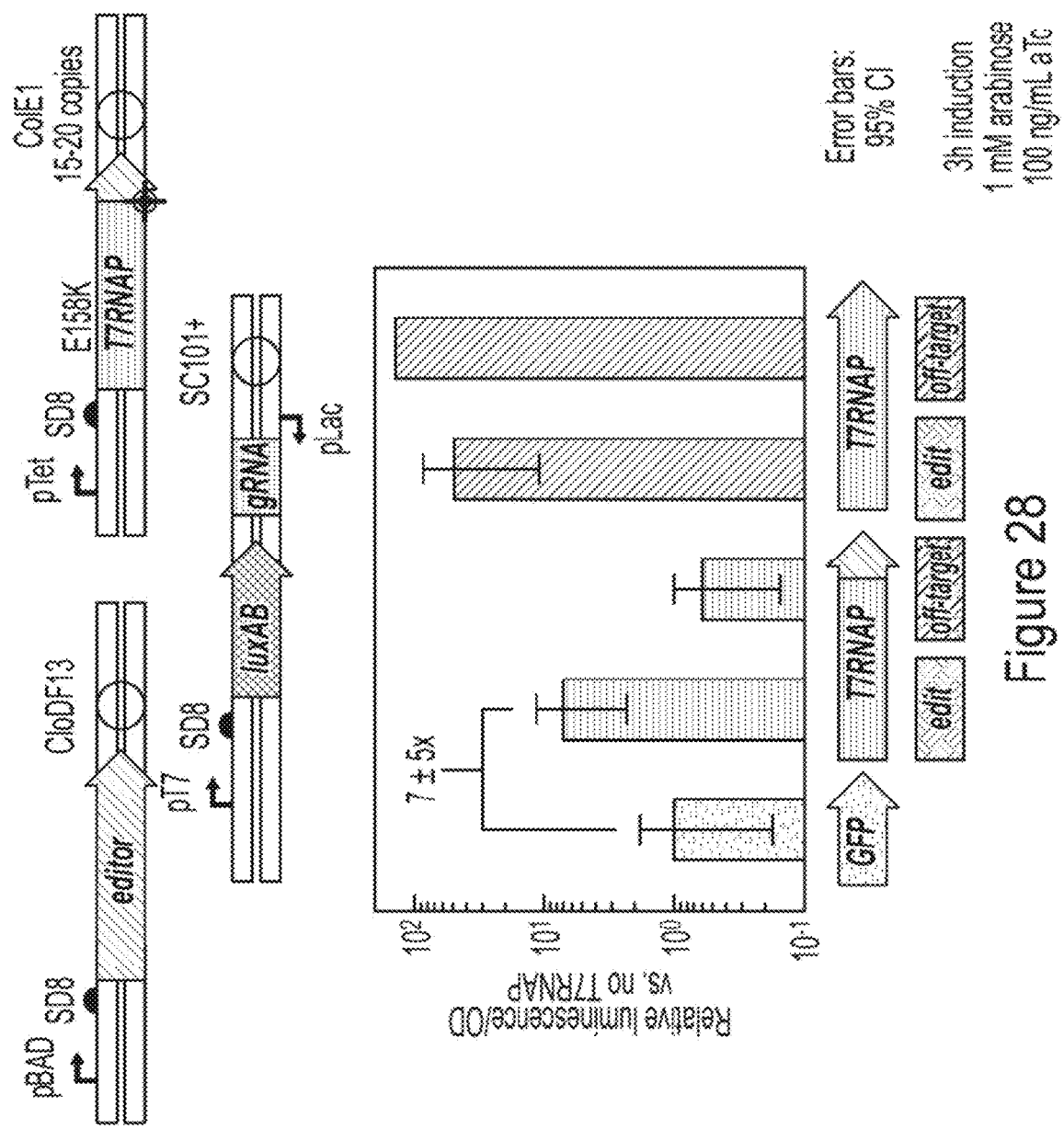
FIG. 28 shows a schematic of the activation of T7RNAP and base editing results.
Figure 29:
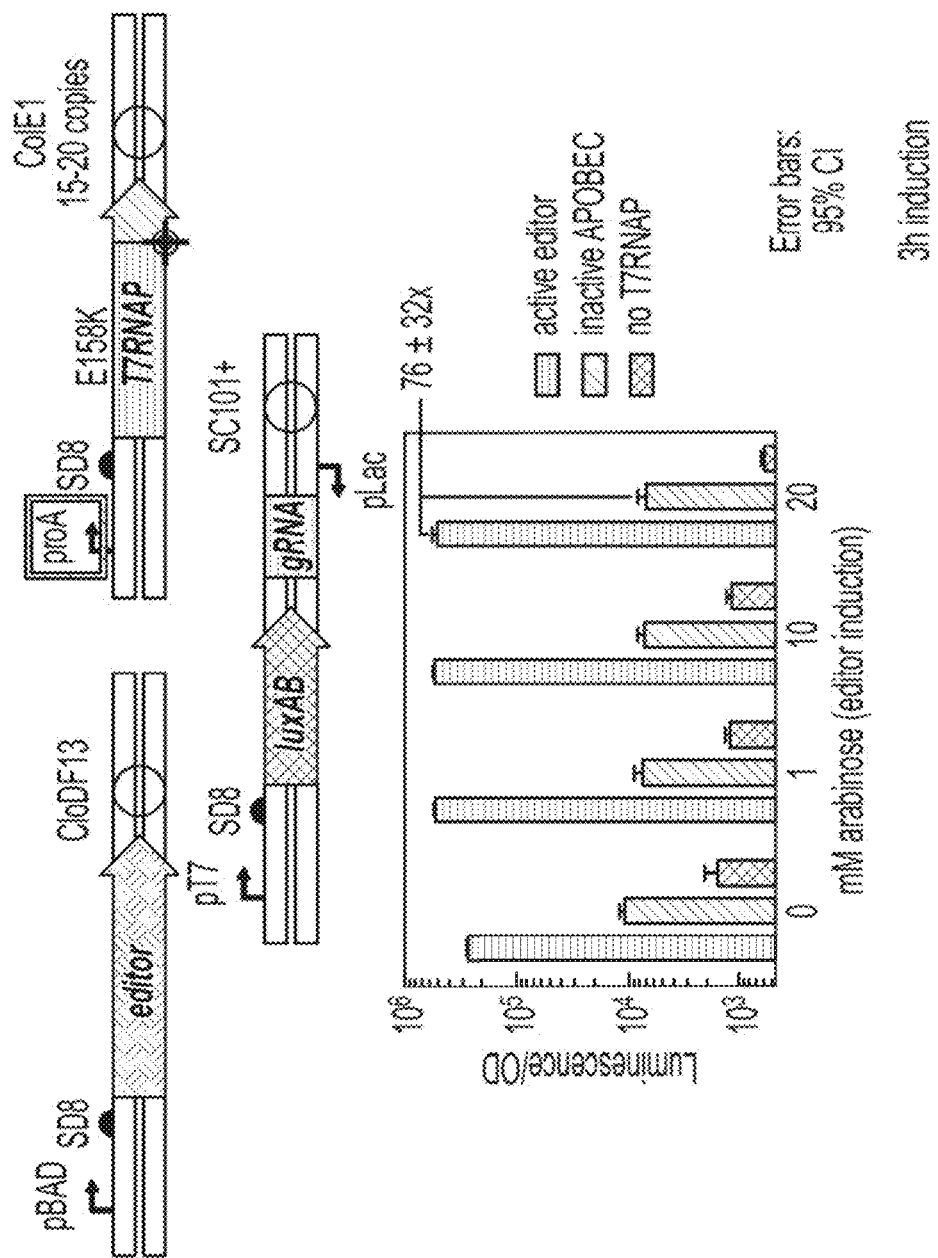
FIG. 29 shows a schematic of constitutive T7RNAP expression and base editing results.

Base editing activates T7RNAP. A schematic for the activation of T7RNAP and the base editing results are given in FIG. 28. Plasmid-based expression of editor shows 1) guide RNA dependent activation of the circuit via a luciferase reporter, columns 2 and 3 and 2) minimal impact of base editor targeting to wild-type T7 RNAP on circuit output. However, constitutive T7RNAP expression works better as shown in FIG. 29. Use of a constitutive promoter for T7 RNAP improves circuit turn-on by >10-fold.

Figure 30:
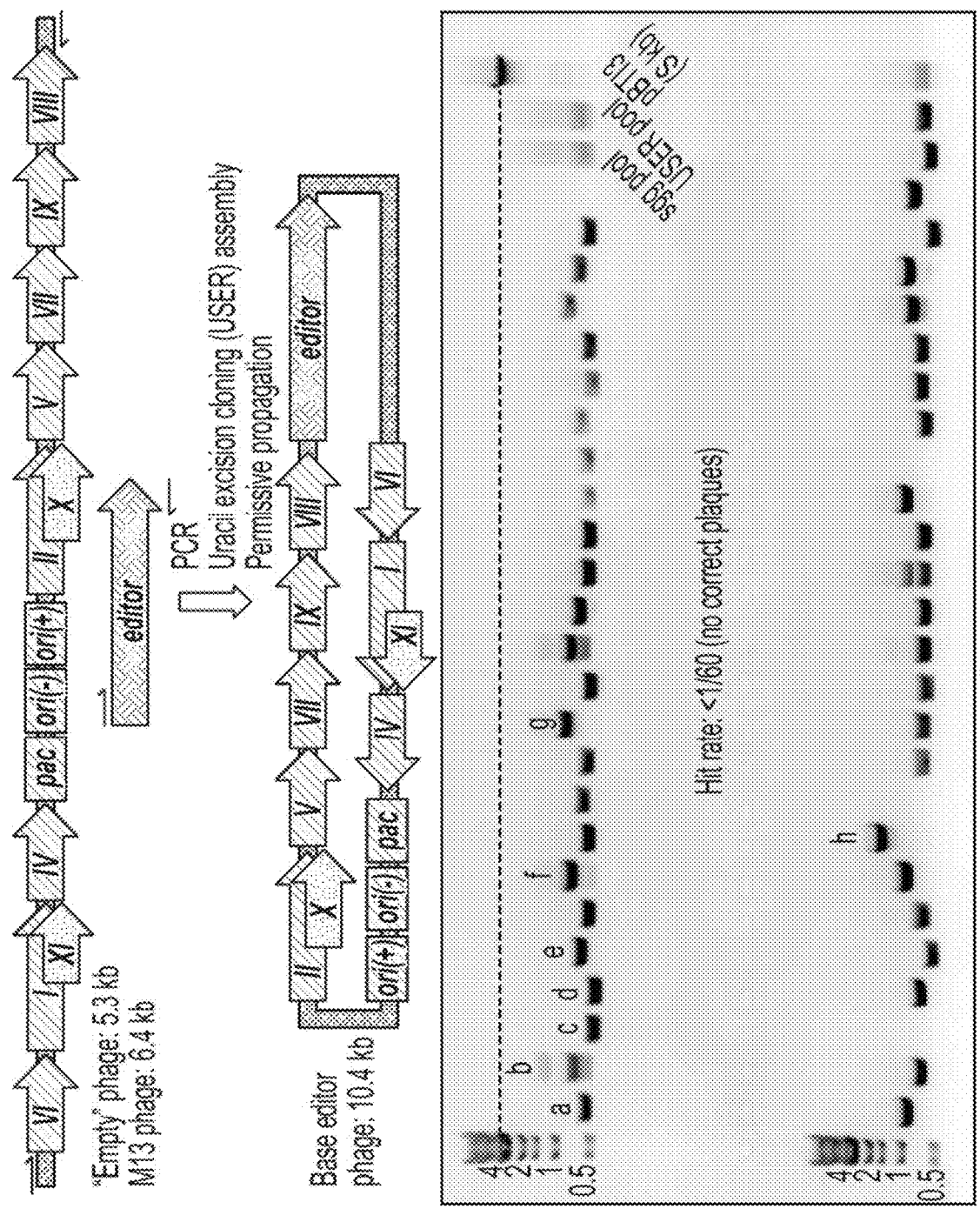
FIG. 30 shows a schematic of base editor phages.
Figure 31:
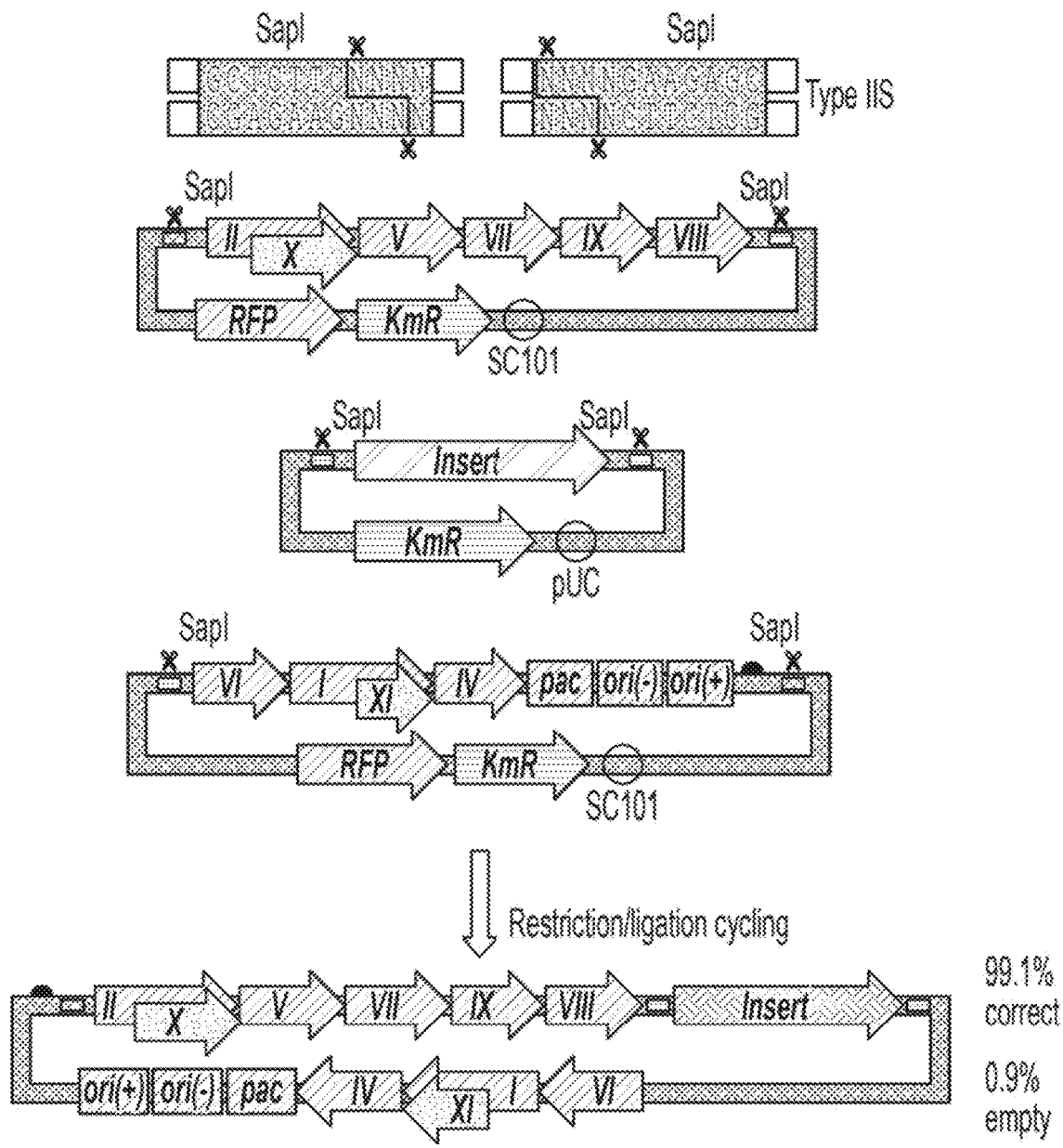
FIG. 31 shows a schematic of base editor phage assembly using Golden Gate cloning.

Base editor phage are very large as shown in FIG. 30. Golden Gate cloning allows clonal phage assembly without PCR. This is illustrated in FIG. 31.

Figure 32:
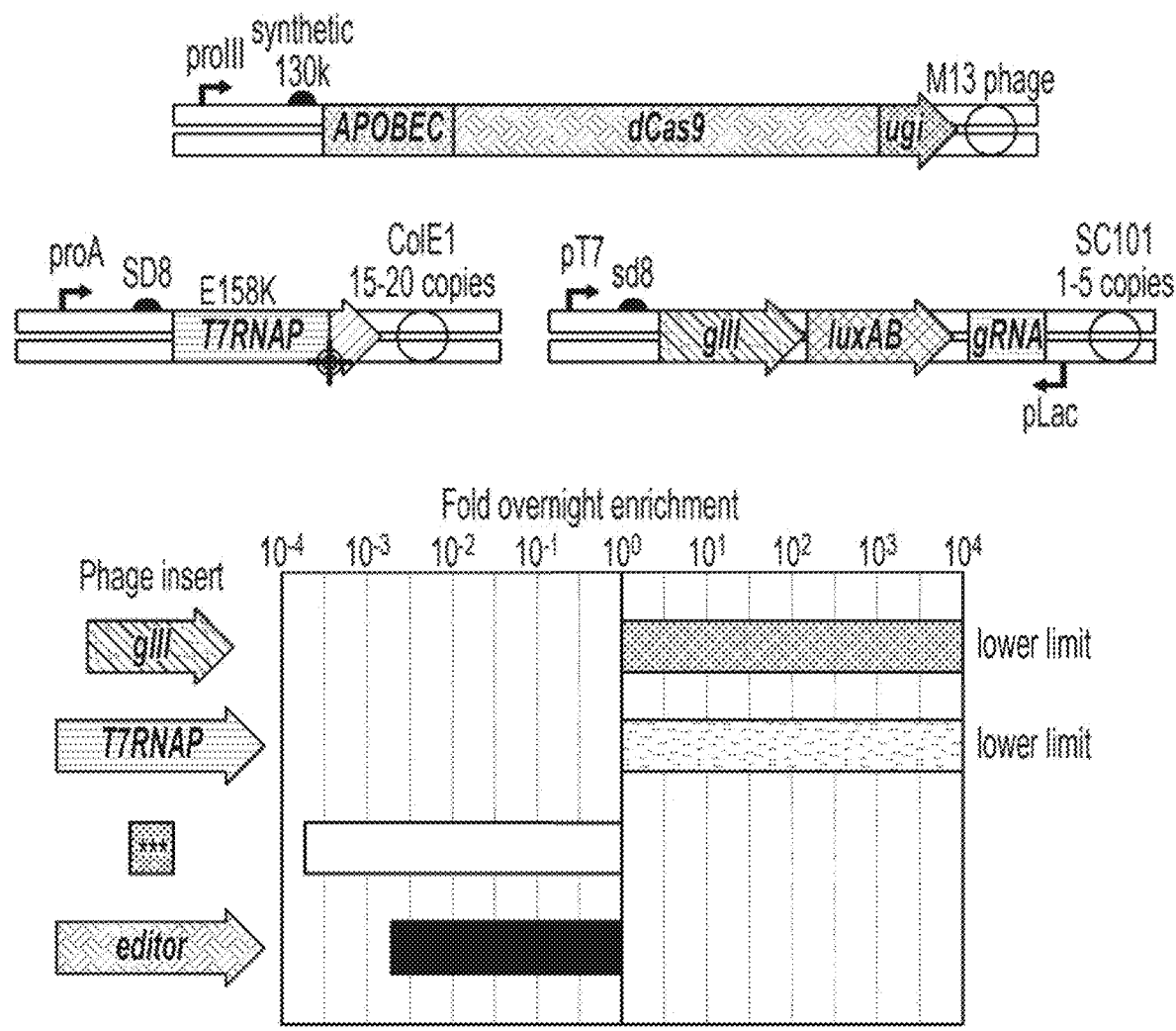
FIG. 32 shows first-generation SP.
Figure 33:
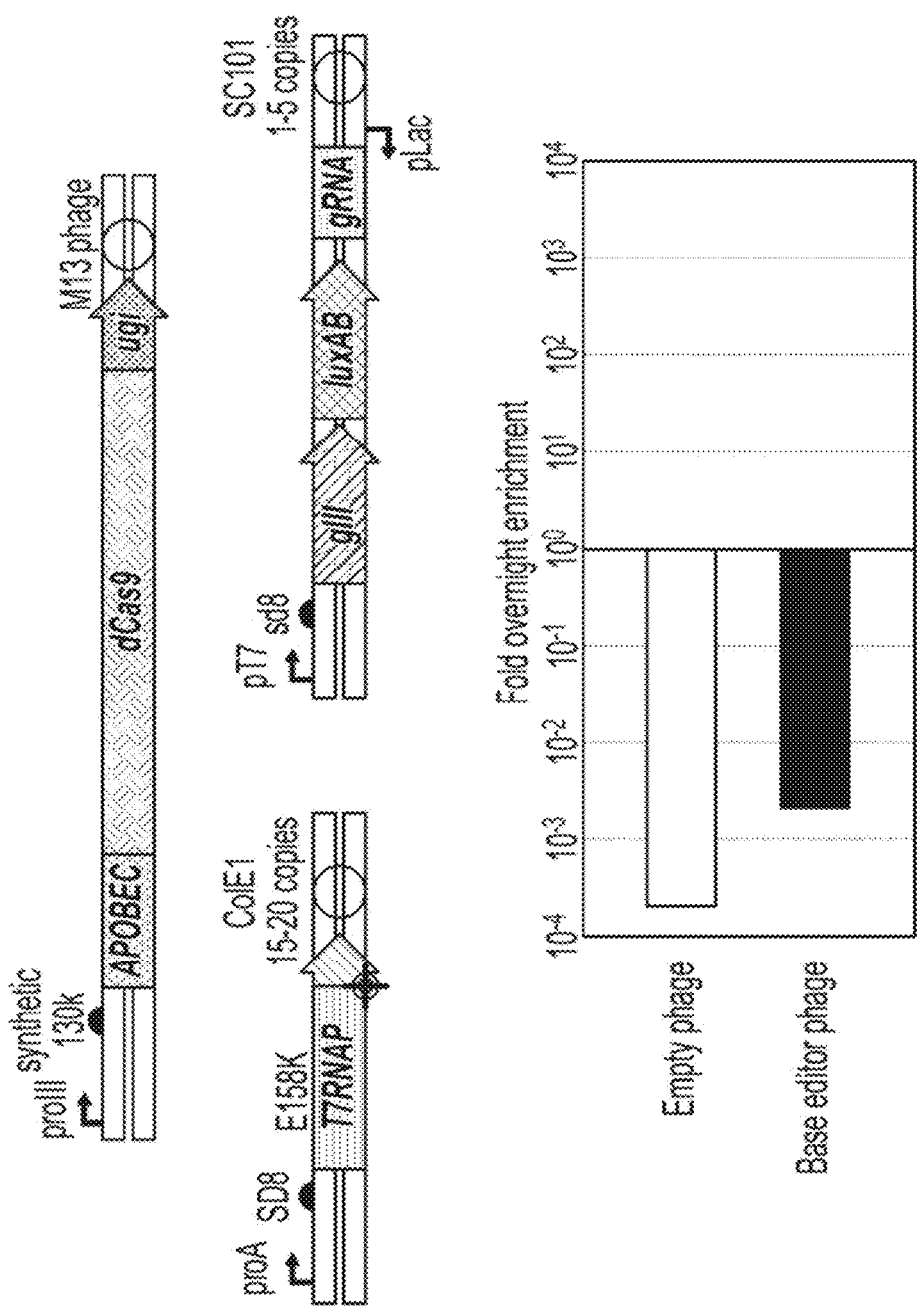
FIG. 33 shows a schematic of selection and optimization.

The first-generation SP does not enrich on the C-terminal degron circuit. The results of the first-generation SP are shown in FIG. 32. Unevolved full-length base editor on phage does not propagate on the base editing circuit, even though positive (gIII phage which propagate on any infectable host cell, or T7 RNAP phage which short-circuit the selection) and negative (empty/stop codon phage, which have no base editing activity) controls behave as expected. However, base editor phage propagate more efficiently than empty phage, suggesting that editing-dependent propagation is occurring. One benefit of this method is that different selections can be used to achieve optimization as shown in FIG. 33. The steps are as follows: 1) Clone the editor into a PACE-optimized phage backbone, 2) Reduce the expression of T7RNAP, 3) Increase the copy number of the gIII plasmid, and 4) Split the editor with an intein and put dCas9.ugi on a host plasmid.

Figure 34:
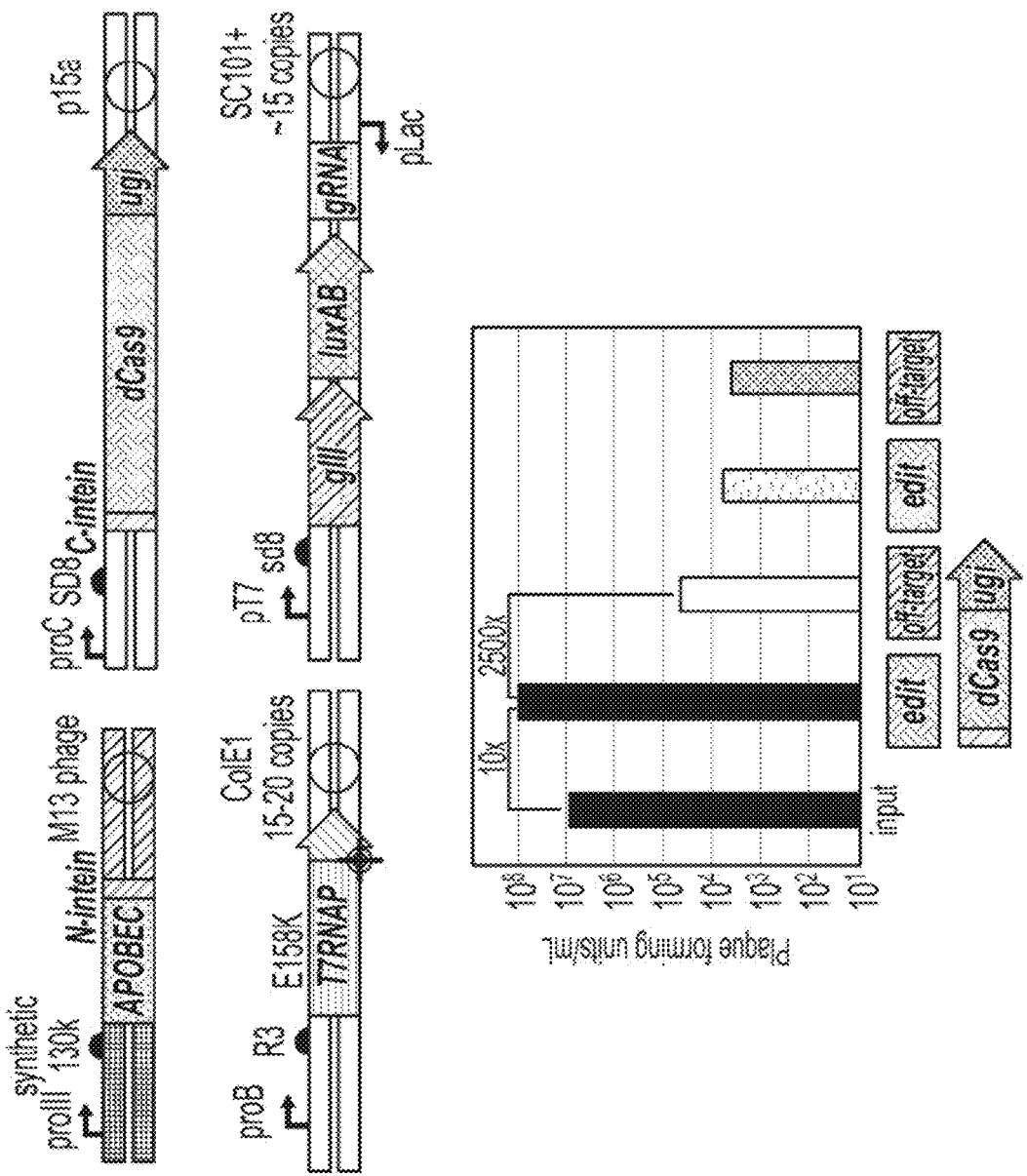
FIG. 34 shows a schematic of Intein-split base editor and gRNA-dependent propagation.
Figure 35:
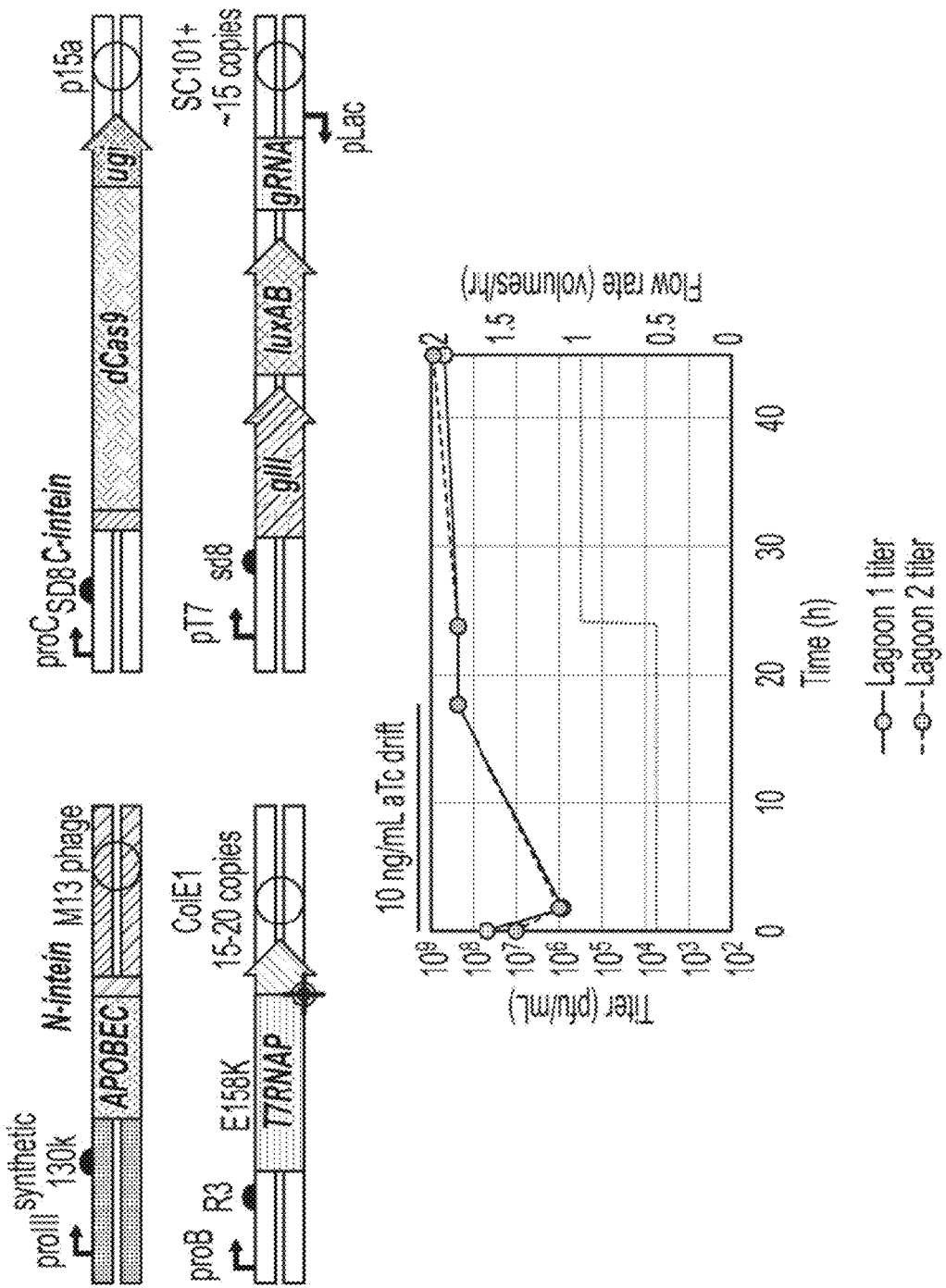
FIG. 35 shows a schematic of Intein-split base editor in PACE.

Intein-split base editor shows gRNA-dependent propagation as shown in FIG. 34. Two key changes allow guide-RNA-dependent enrichment (10-fold overnight) of base editor. 1) Use of a phage backbone with ~30 accumulated mutations from other PACE projects improves propagation. 2) Splitting the base editor using a trans-splicing split intein allows the phage cargo to be limited to the deaminase and N-intein, while the C-intein, Cas9 and UGI are expressed by the host cell. This reduces the phage genome size substantially and speeds up replication and packaging. It also limits evolution to the phage-encoded deaminase, which allows PACE to uncover deaminase-driven base editor changes more efficiently. Intein-split base editor further propagates in PACE as shown in FIG. 35. The optimized split base editor can persist in continuous flow PACE (titers increase over time).

Figure 36:
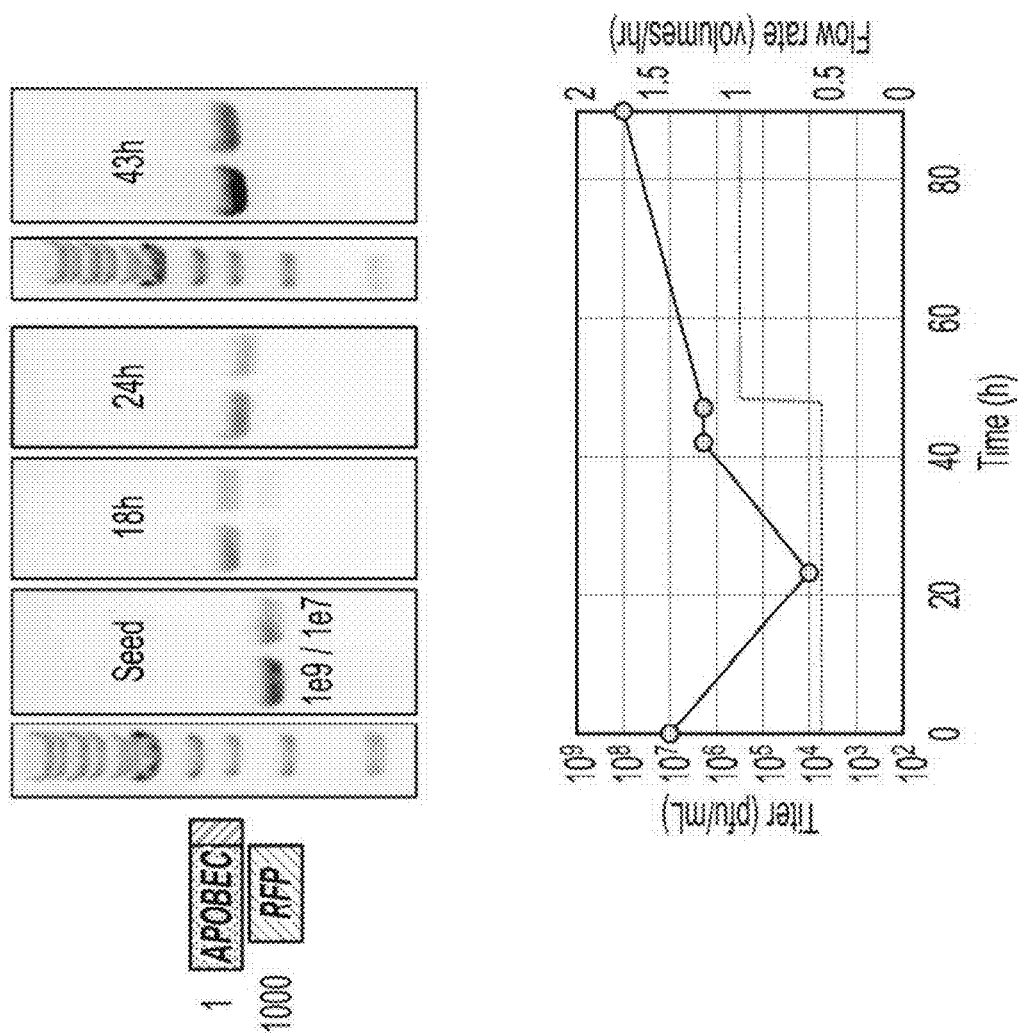
FIG. 36 shows results for an active editor.

An active editor can take over a lagoon as shown in FIG. 36. Active split BE phage take over a lagoon seeded with a vast excess of inactive (RFP) phage, even at low titer of active phage (1e7 pfu/mL RFP phage, 1e4 pfu/mL active phage).

Figure 37:
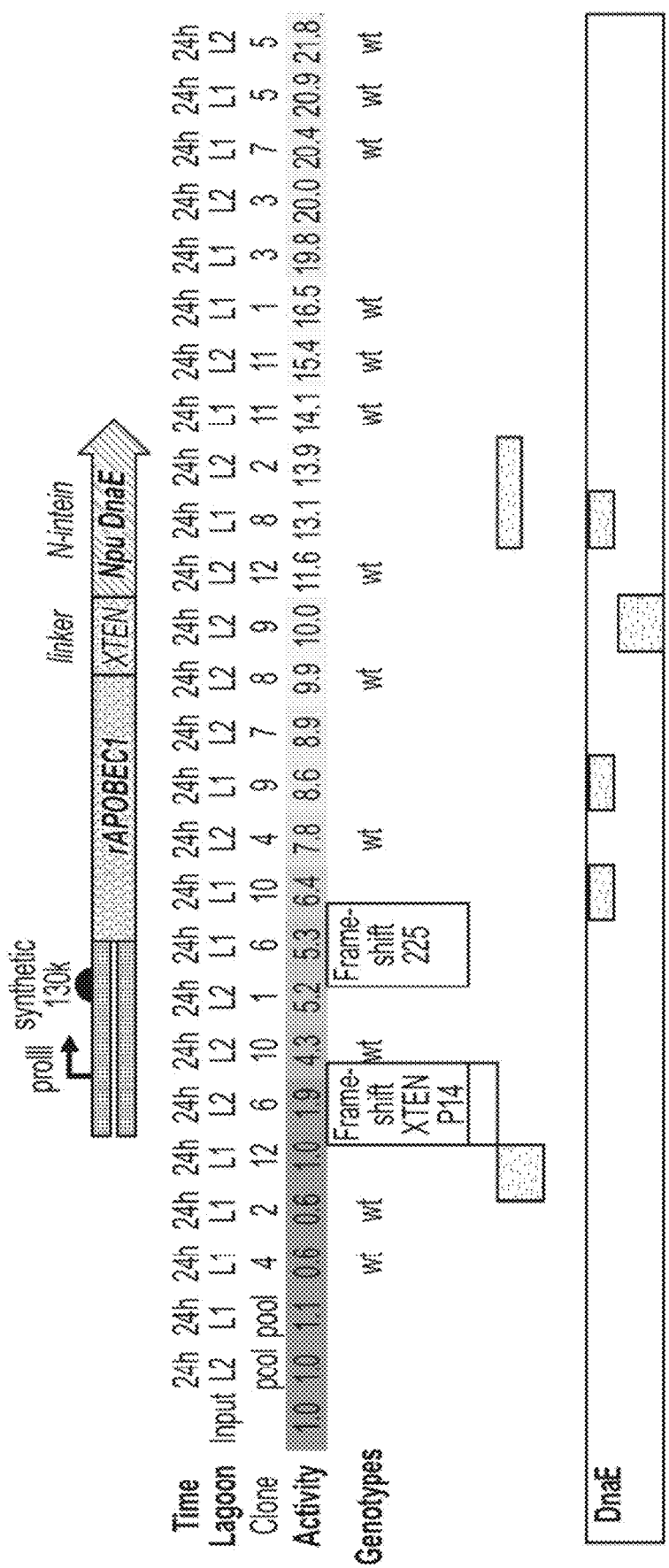
FIG. 37 shows mutations observed in intein-split base editor.
Figure 37:
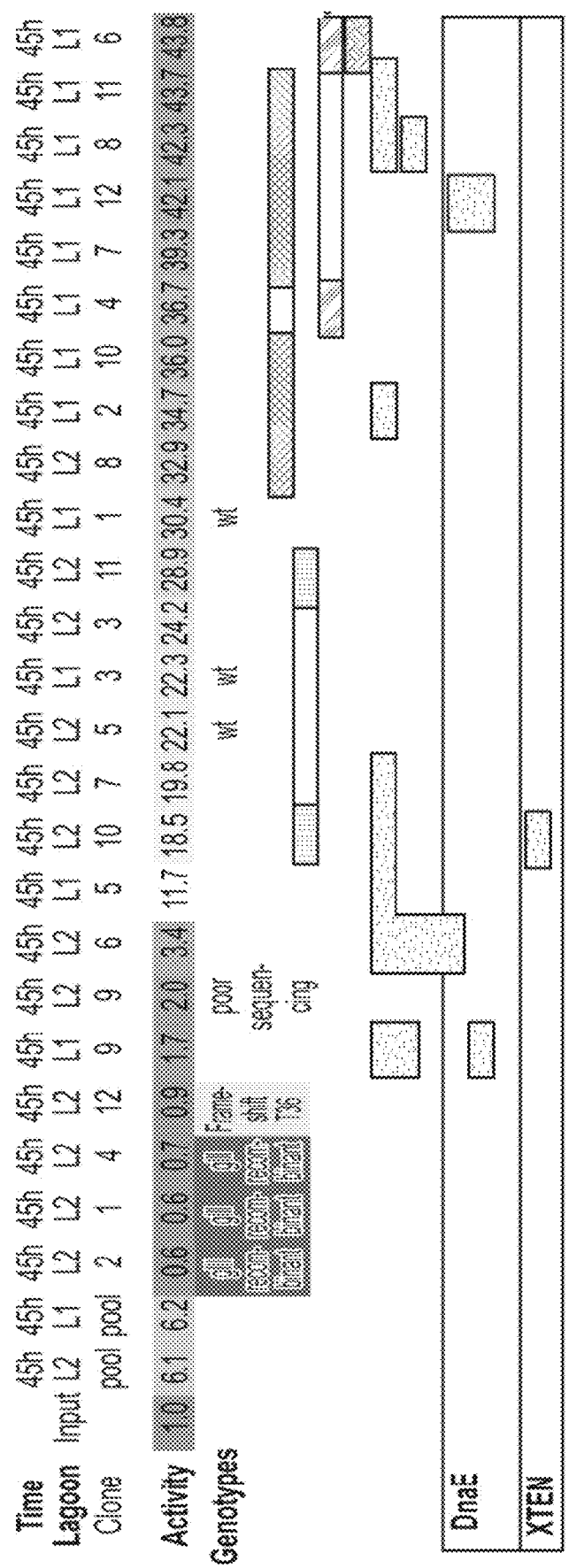

Intein-split base editor accumulates mutations as shown in FIG. 37.

Figure 38:
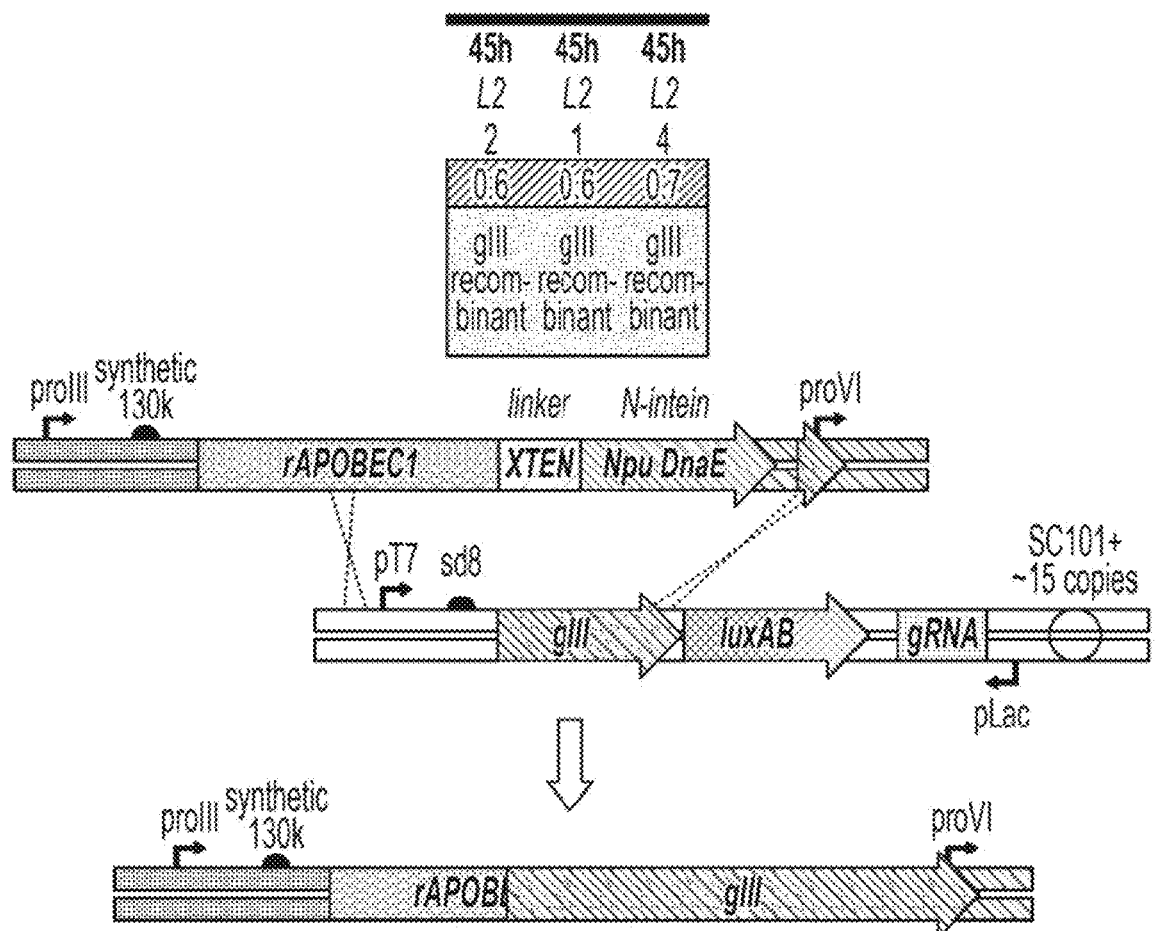
FIG. 38 shows a schematic of cheaters developed with recombination.
Figure 39:
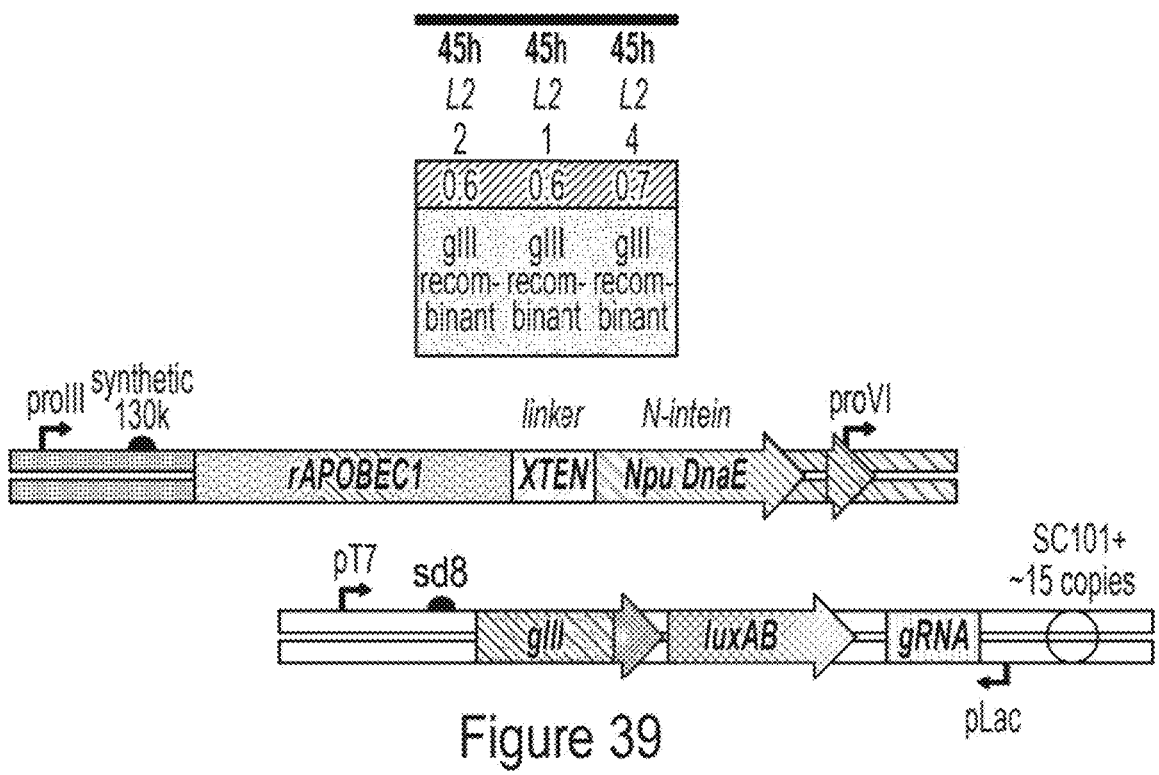
FIG. 39 shows a schematic of cheaters developed with recombination.

Recombination generates cheaters with wild-type propagation as shown in FIGS. 38 and 39.

Figure 40:
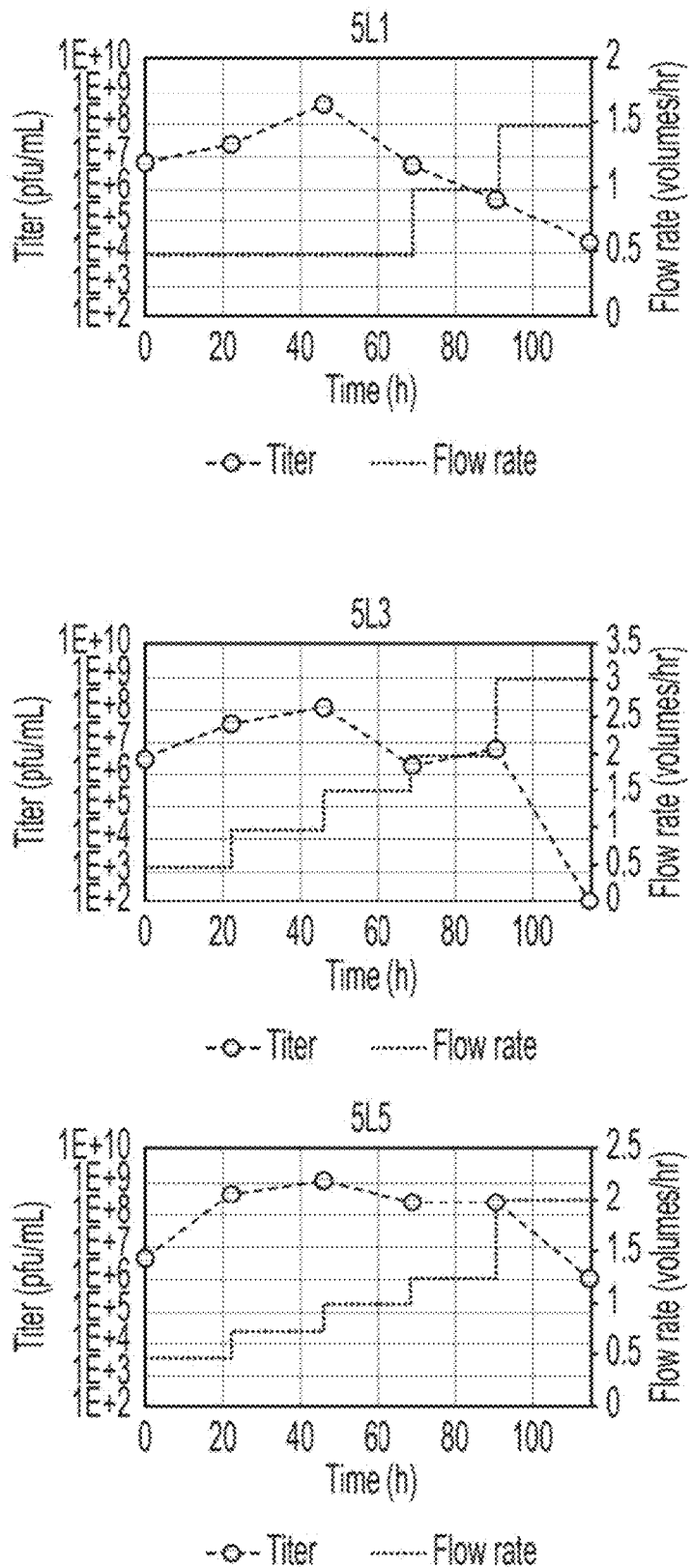
FIG. 40 shows PACE data.

Further PACE shows reduced gIII recombination. PACE data is shown in FIG. 40.

Figure 41:
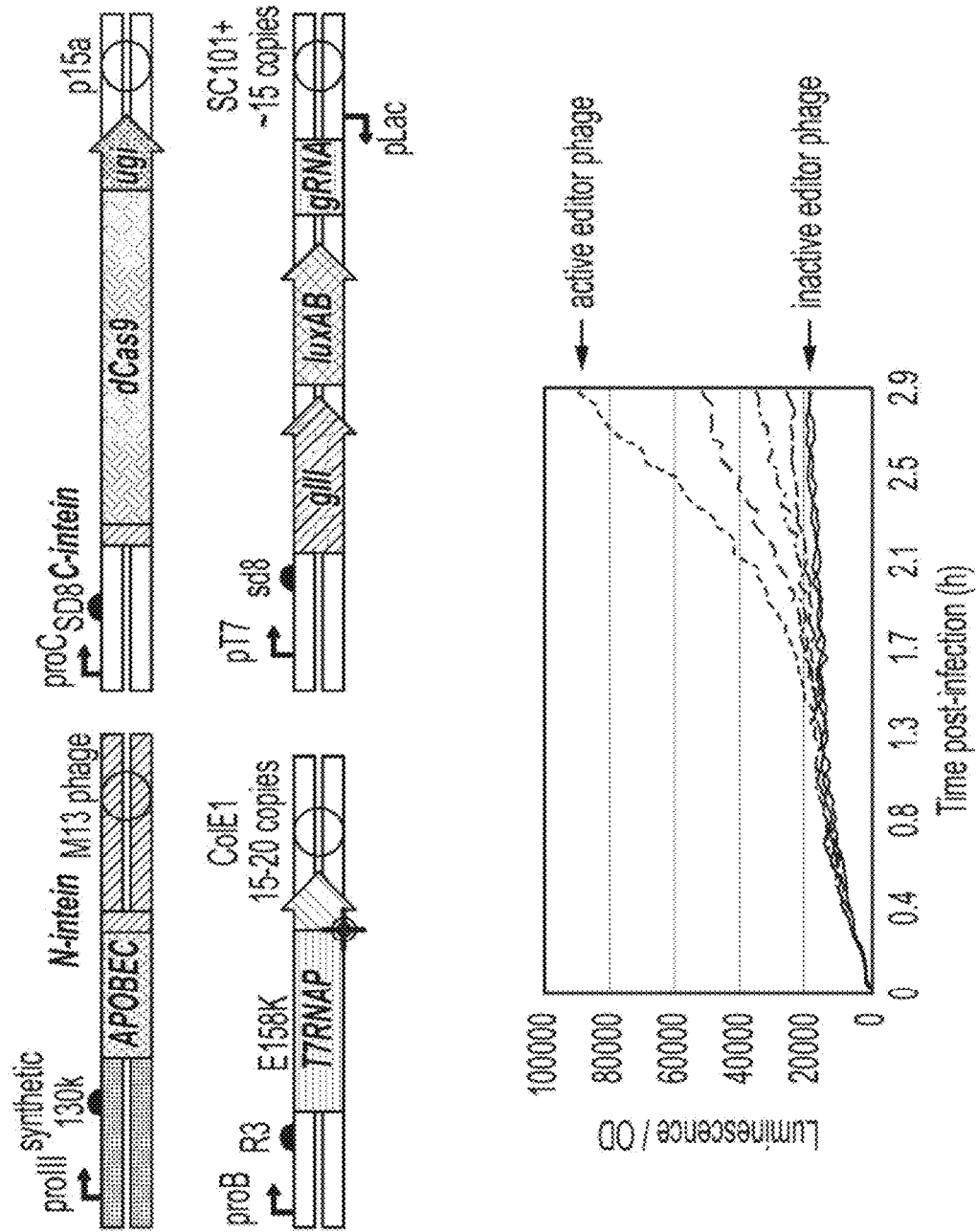
FIG. 41 shows phage base editing activity assayed with a luciferase readout.
Figure 42:
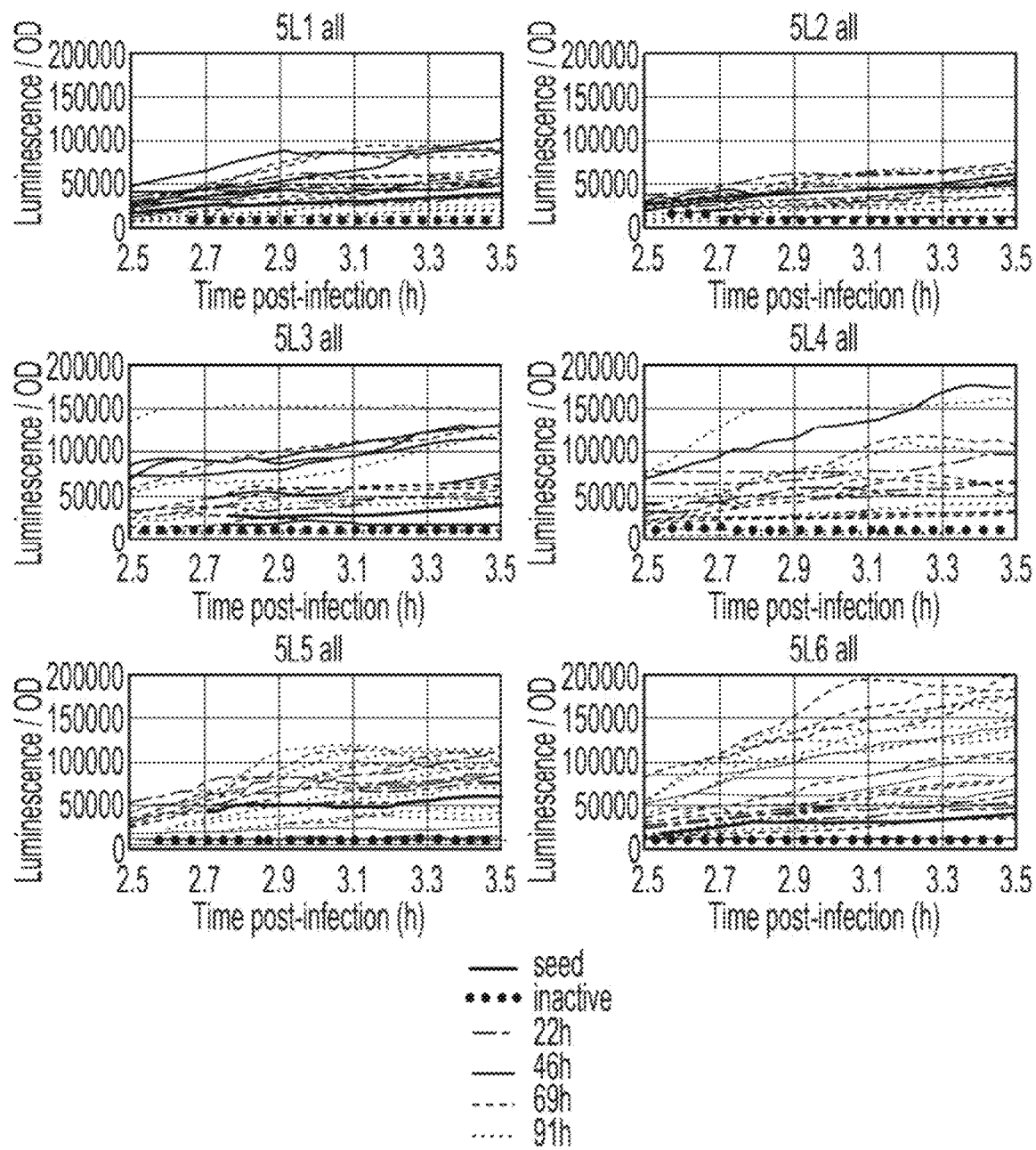
FIG. 42 shows luciferase time-course assays.

Phage base editing activity can be assayed with a luciferase readout as shown in FIG. 41. Luciferase assay time-courses allow BE phage activity to be estimated. Between 2 and 3 h post-infection of host cells, a linear phase of luminescence/OD/time is observed whose slope is taken as a measure or circuit activation rate. Luciferase time-course assays show improved phage fitness as shown in FIG. 42.

Figure 43:
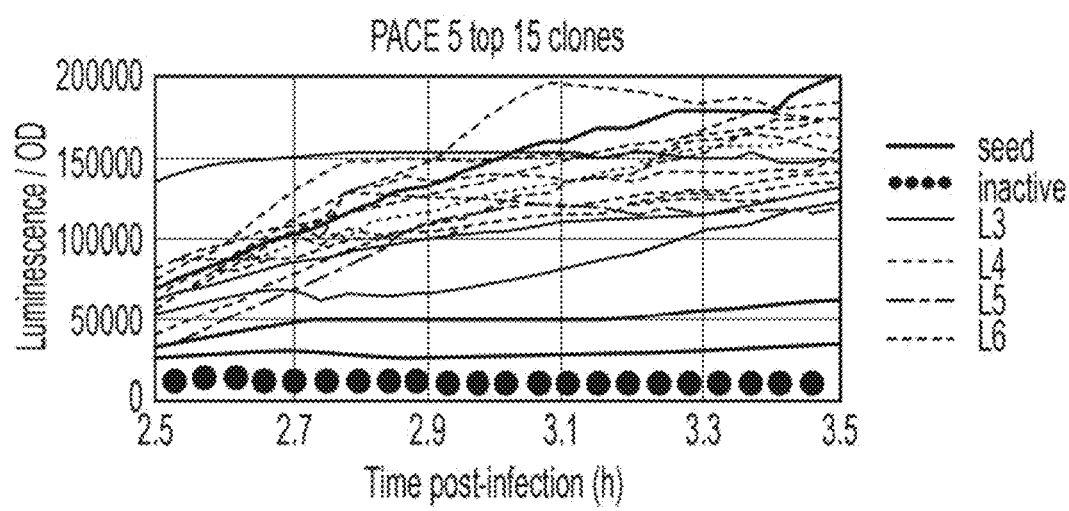
FIG. 43 shows luciferase time-course assay of PACE 5 top 15 clones.

Further PACE experiments produce phage progeny (assayed individually from different lagoons and time-points, colored lines) that have faster circuit activation rates than the parent genotypes (thick black lines). The PACE 5 top 15 clones are shown in FIG. 43. Recombination of T7RNAP onto the phage creates cheaters. The PACE 5 top 8 clones are shown in FIG. 44 with cheaters highlighted.

In summary, T7RNAP activation selects for active base editors, base editors can propagate in PACE, and optimized inputs can make a selection work. In future developments, cheating will be made less effective than improvements and full-length base editor PACE will be enabled. Additionally, an alternative selection will be booted up. This is illustrated in FIG. 45.

Figure 46:
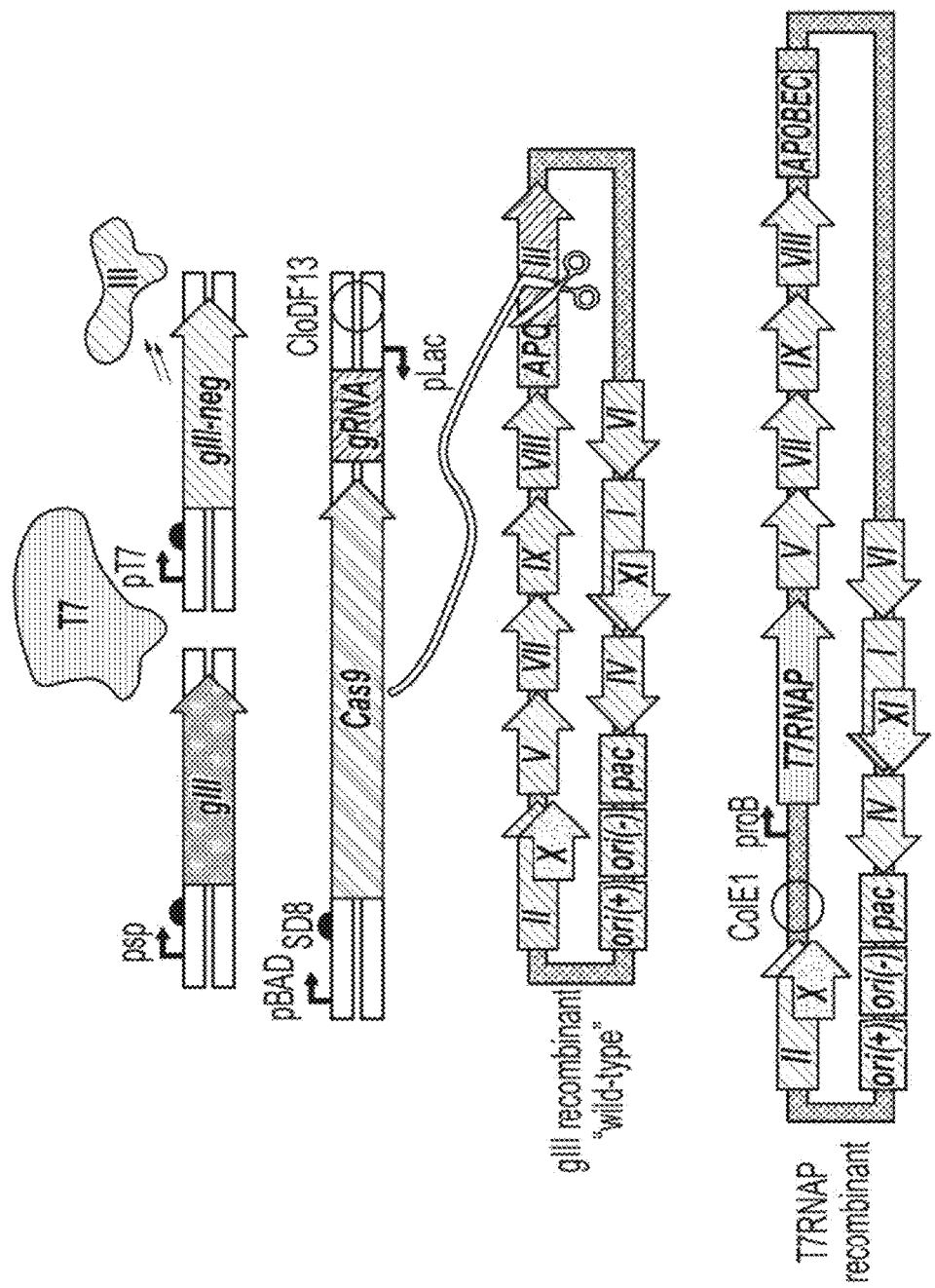
FIG. 46 shows a schematic of "cleaning" the PACE output.

The PACE output may be "cleaned" as shown in FIG. 46.

Figure 47:
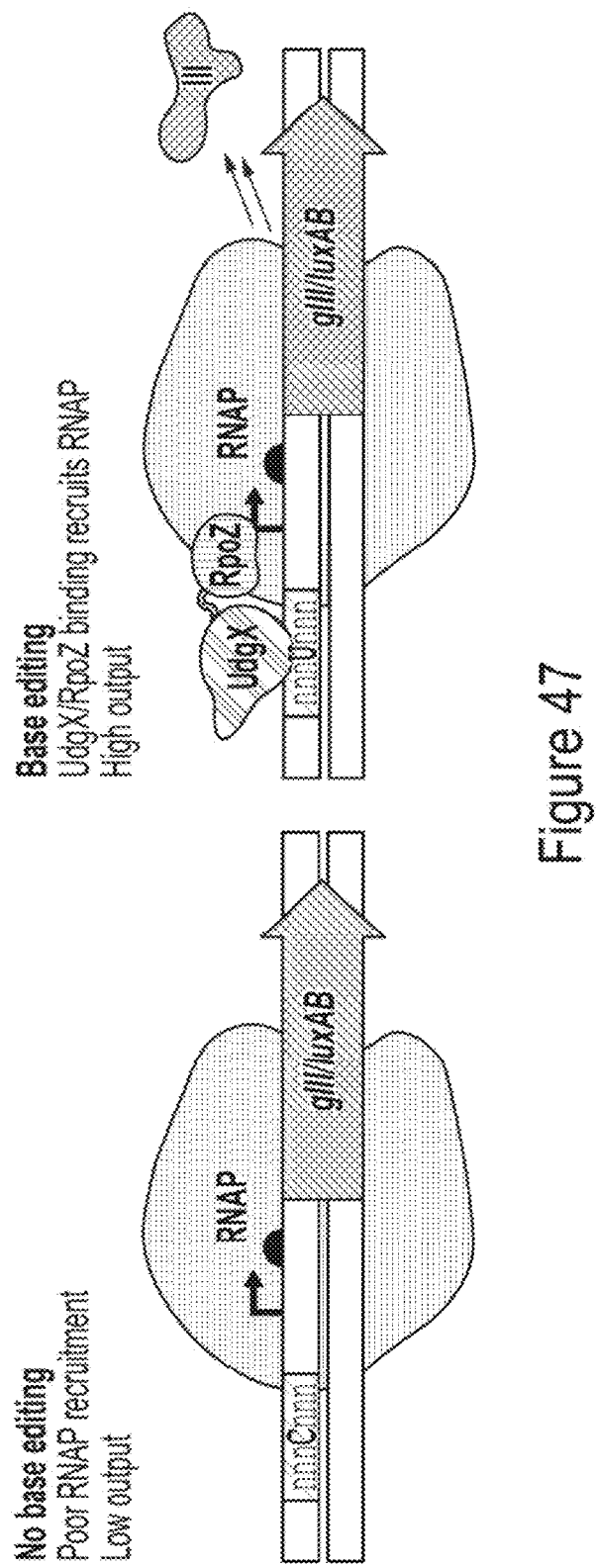
FIG. 47 shows a schematic of "1.5-hybrid" selection.
Figure 48:
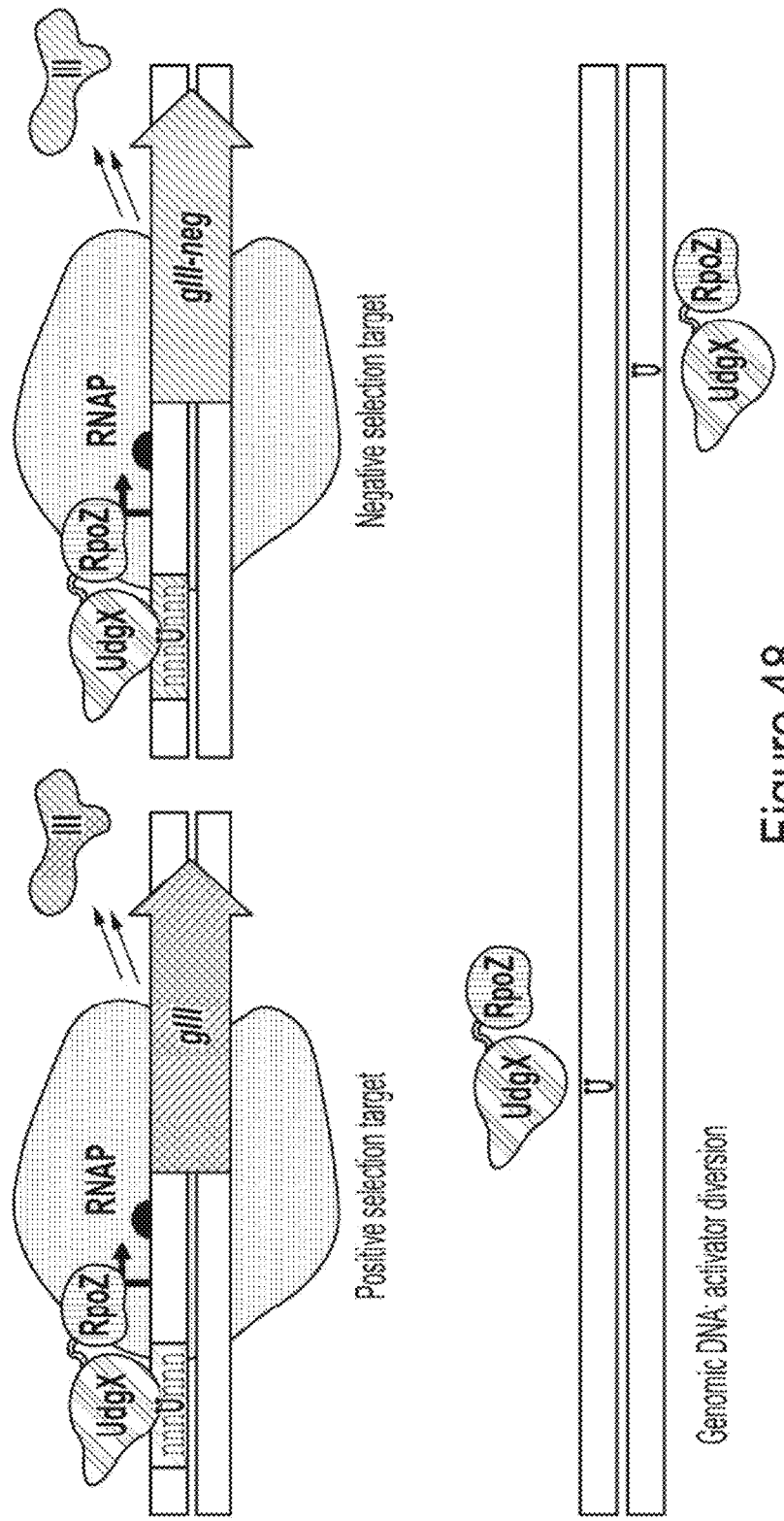
FIG. 48 shows a schematic of "1.5-hybrid" selection.

A uracil-DNA binding protein could enable a "1.5-hybrid" selection. This is illustrated in FIGS. 47 and 48.

Figure 49:
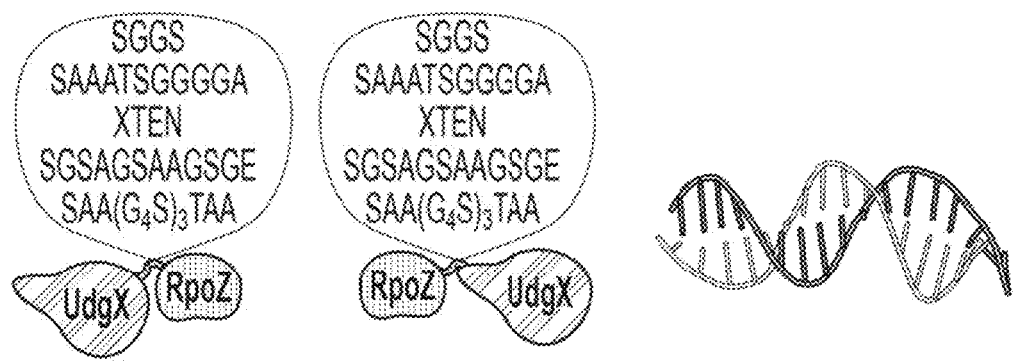
FIG. 49 shows a schematic of transcriptional activator recruitment. The protein sequences correspond to SEQ ID NO: 46.
Figure 50:
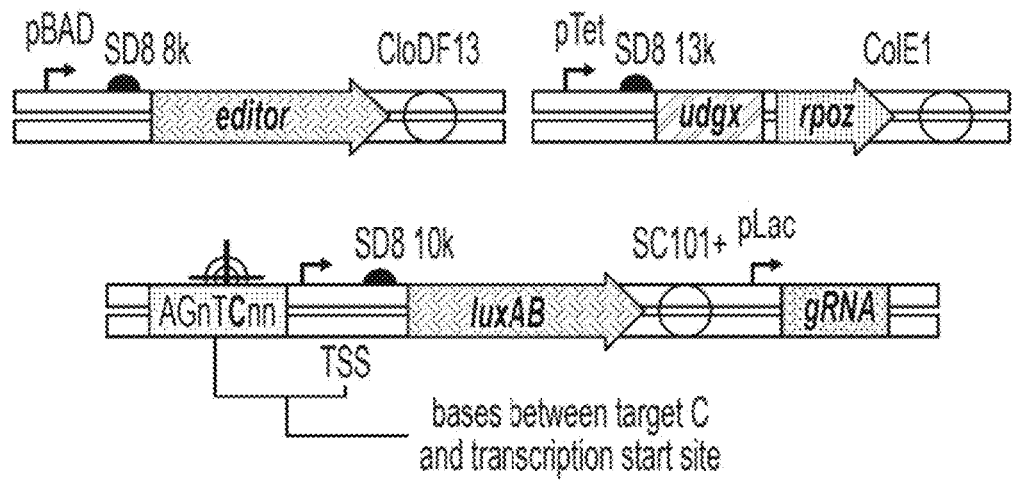
FIG. 50 shows a schematic of transcriptional activator recruitment.
Figure 51:
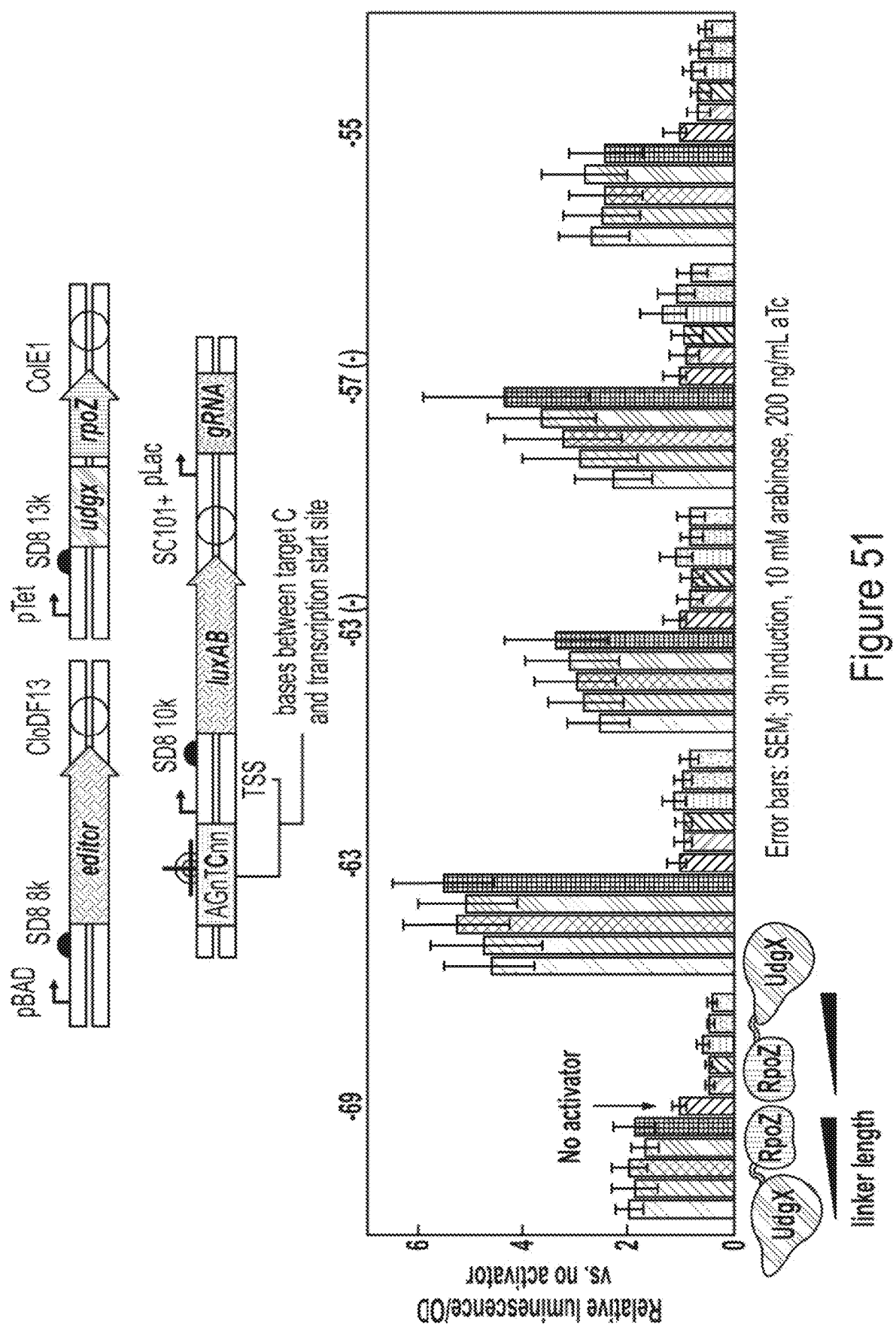
FIG. 51 shows a schematic of transcriptional activator recruitment.
Figure 52:
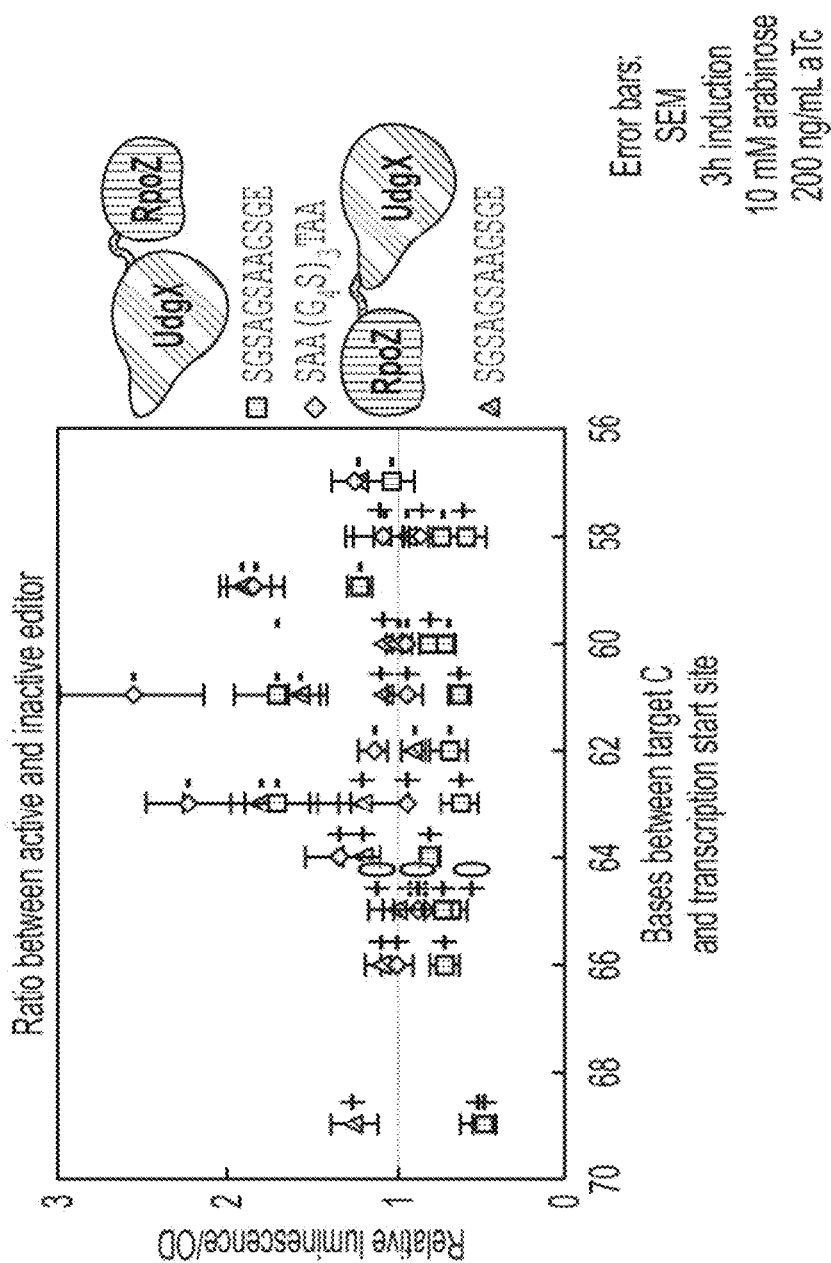
FIG. 52 shows responsive bases to editing. The protein sequences in the key correspond from top to bottom to SEQ ID NOs: 99, 100, and 99.
Figure 53:
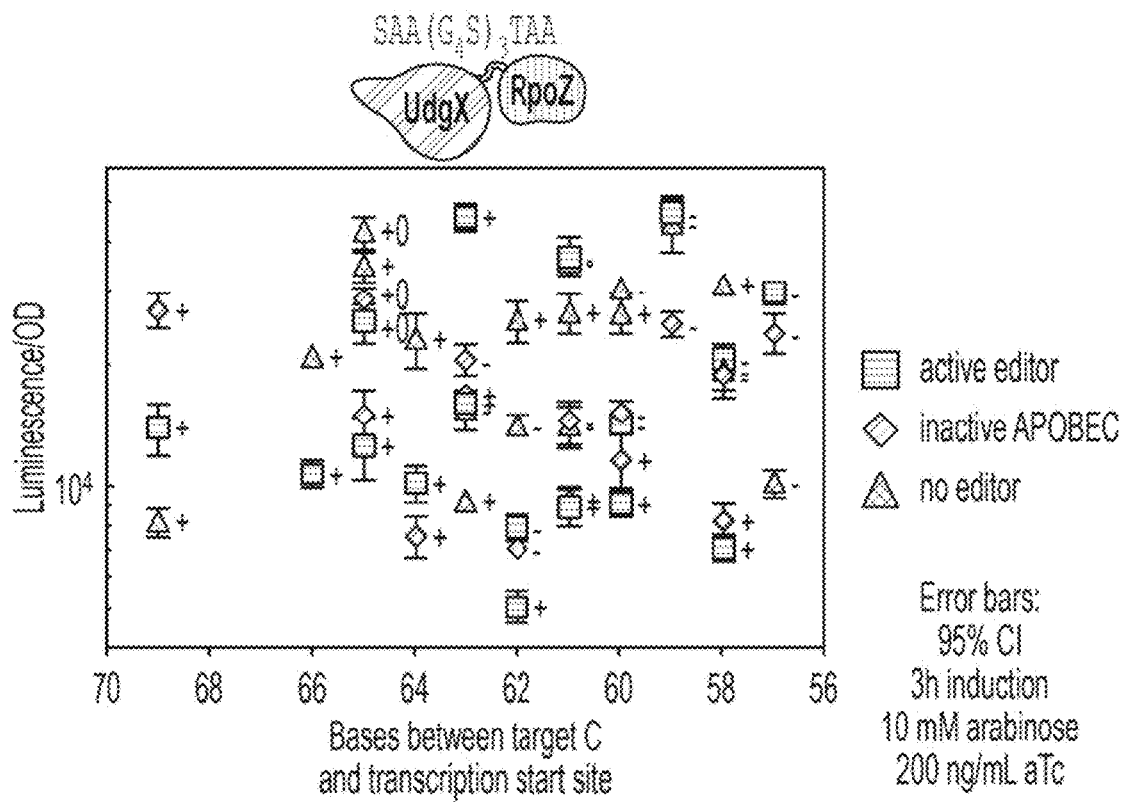
FIG. 53 shows responsive bases to editing. The protein sequence corresponds to SEQ ID NO: 100.
Figure 54:
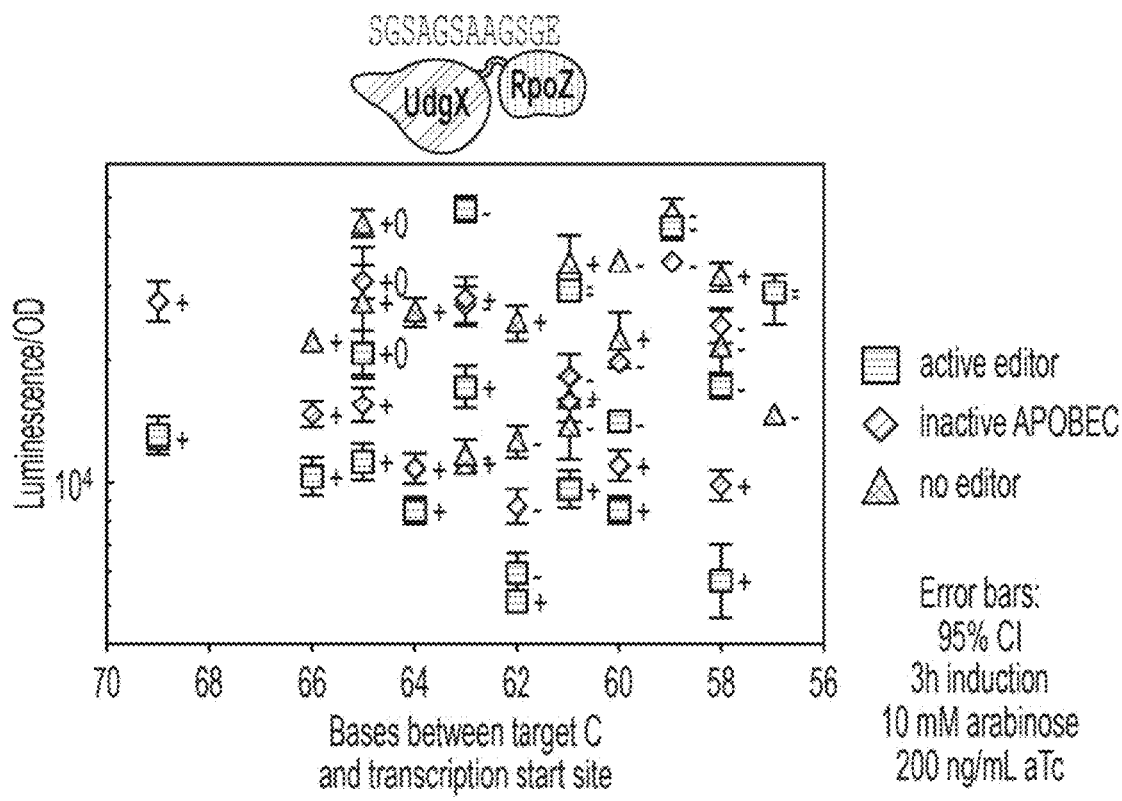
FIG. 54 shows responsive bases to editing. The protein sequence corresponds to SEQ ID NO: 99.
Figure 55:
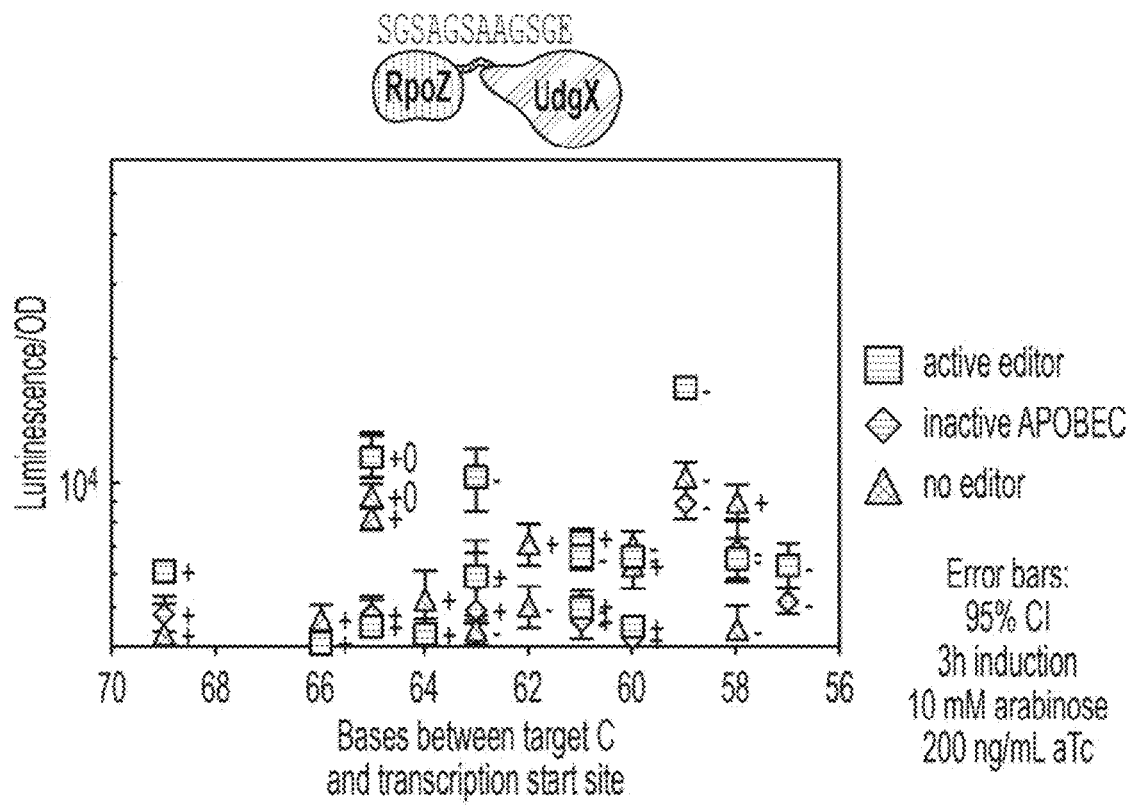
FIG. 55 shows responsive bases to editing. The protein sequence corresponds to SEQ ID NO: 99.
Figure 56:
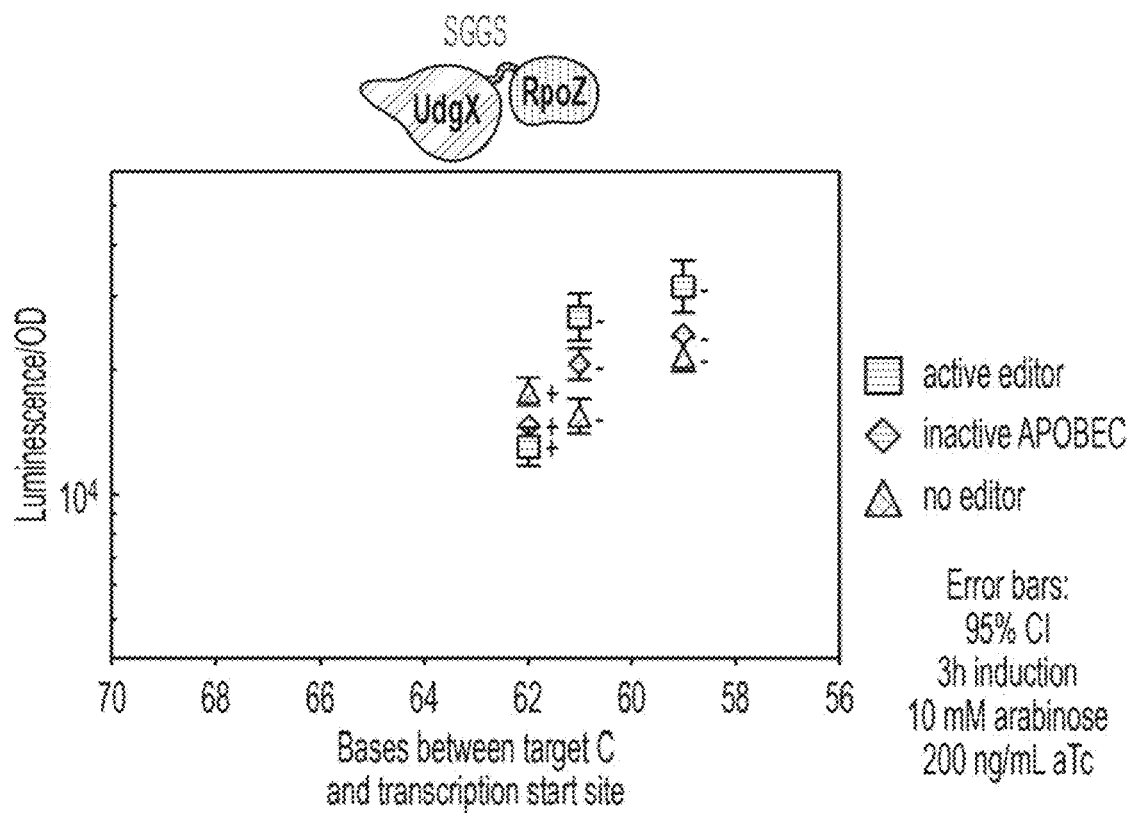
FIG. 56 shows responsive bases to editing. The protein sequence corresponds to SEQ ID NO: 14.

Transcriptional activator recruitment is sensitive to spatial organization as illustrated in FIGS. 49, 50, and 51.

Further screening shows that some positions are responsive to editing as shown in FIGS. 52, 53, 54, 55, and 56.

Figure 57:
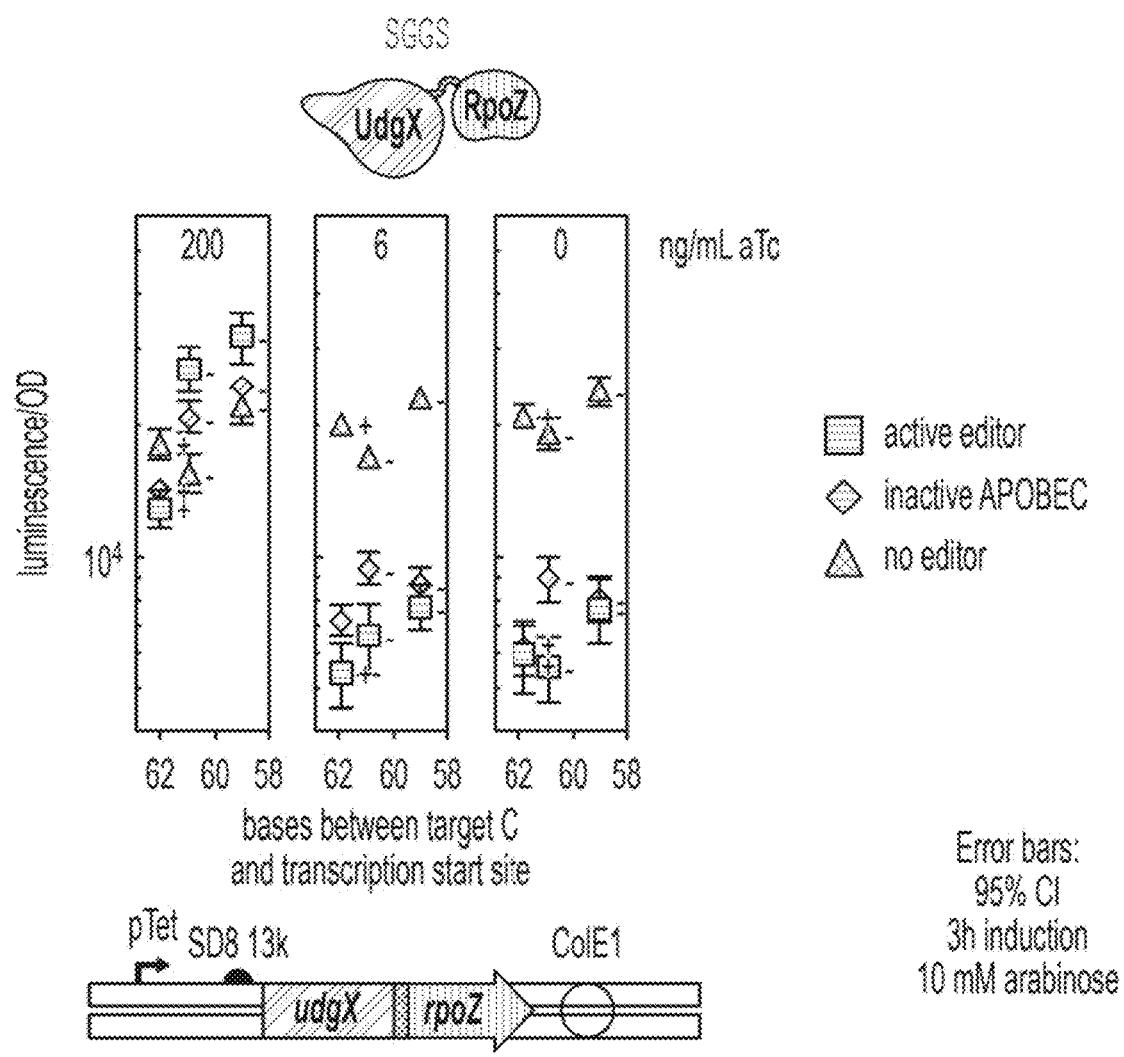
FIG. 57 shows maximal response with high activator expression. The protein sequence corresponds to SEQ ID NO: 14.

The response is maximal with high activator expression as shown in FIG. 57.

Figure 58:
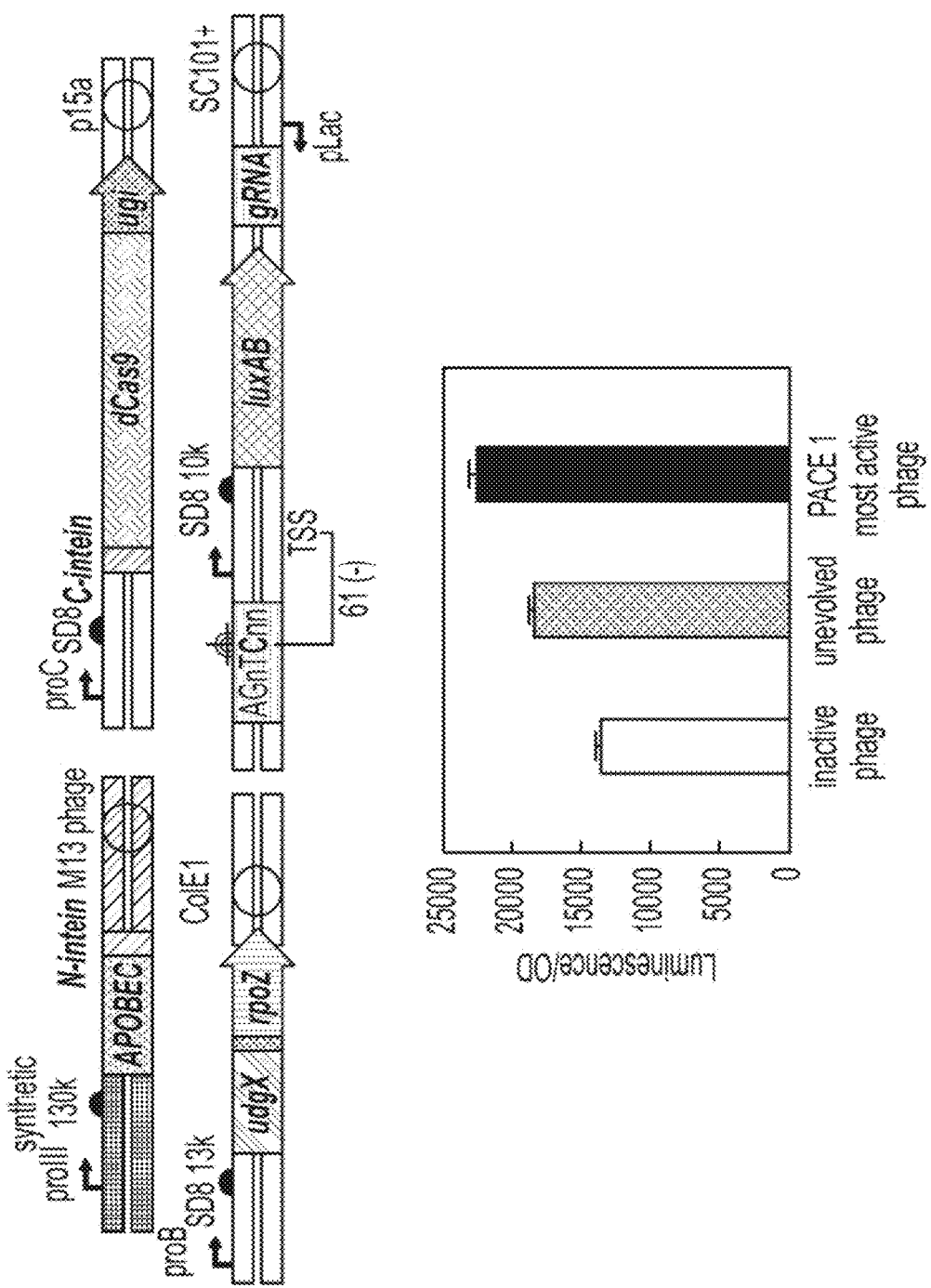
FIG. 58 shows PACE-evolved phage circuit optimization.
Figure 59:
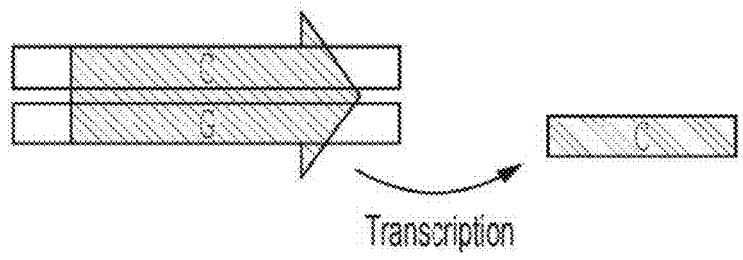
FIG. 59 shows a schematic of template stand editing.
Figure 60:
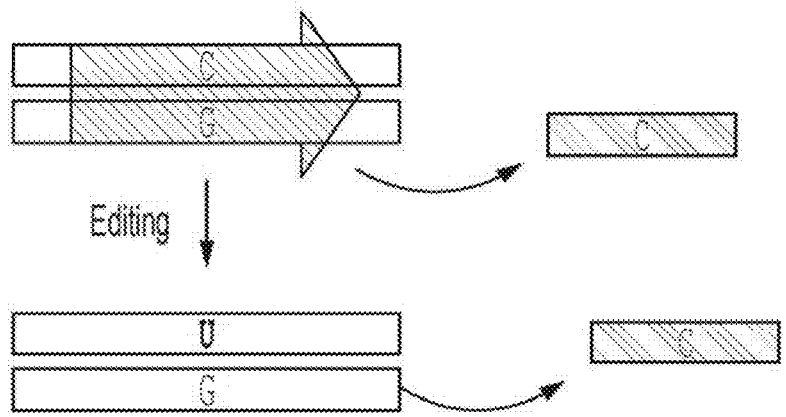
FIG. 60 shows a schematic of template stand editing.
Figure 61:
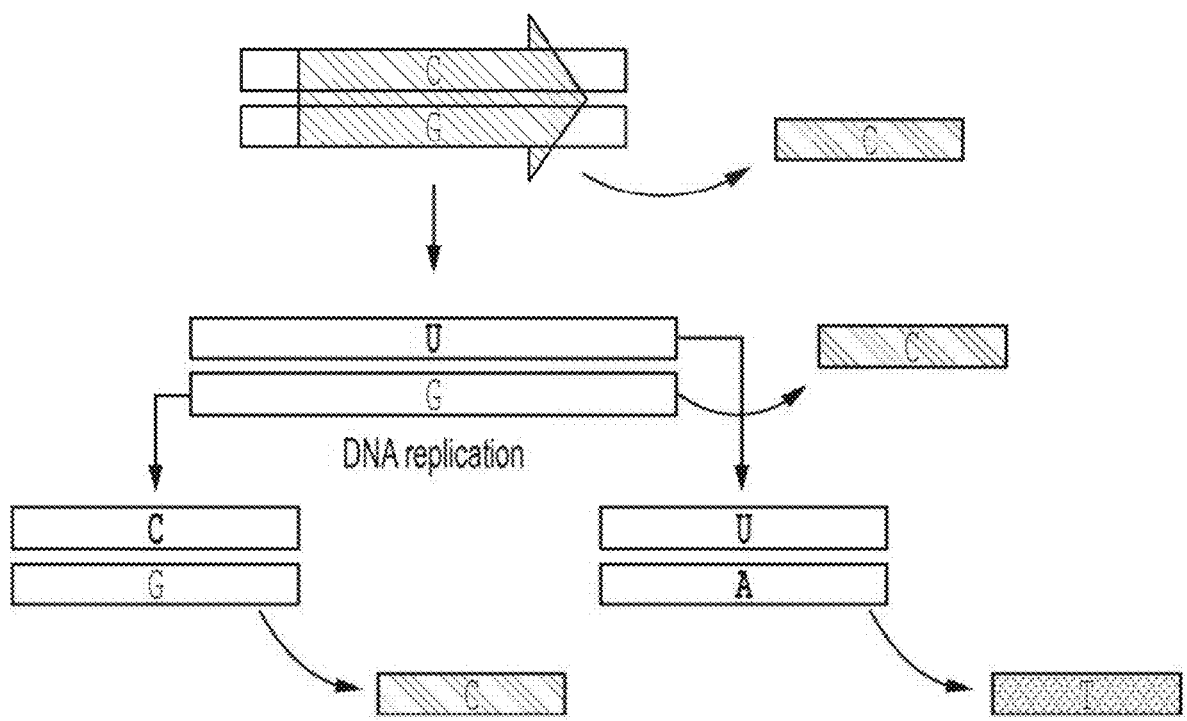
FIG. 61 shows a schematic of template stand editing.

PACE-evolved phage show activation of the optimized circuit as illustrated in FIG. 58.

Template strand editing leads to faster expression-level response as shown in FIGS. 59, 60, 61, 62, and 63.

Template strand deamination leads to a limited set of coding mutations as shown in FIG. 64.

Figure 65:
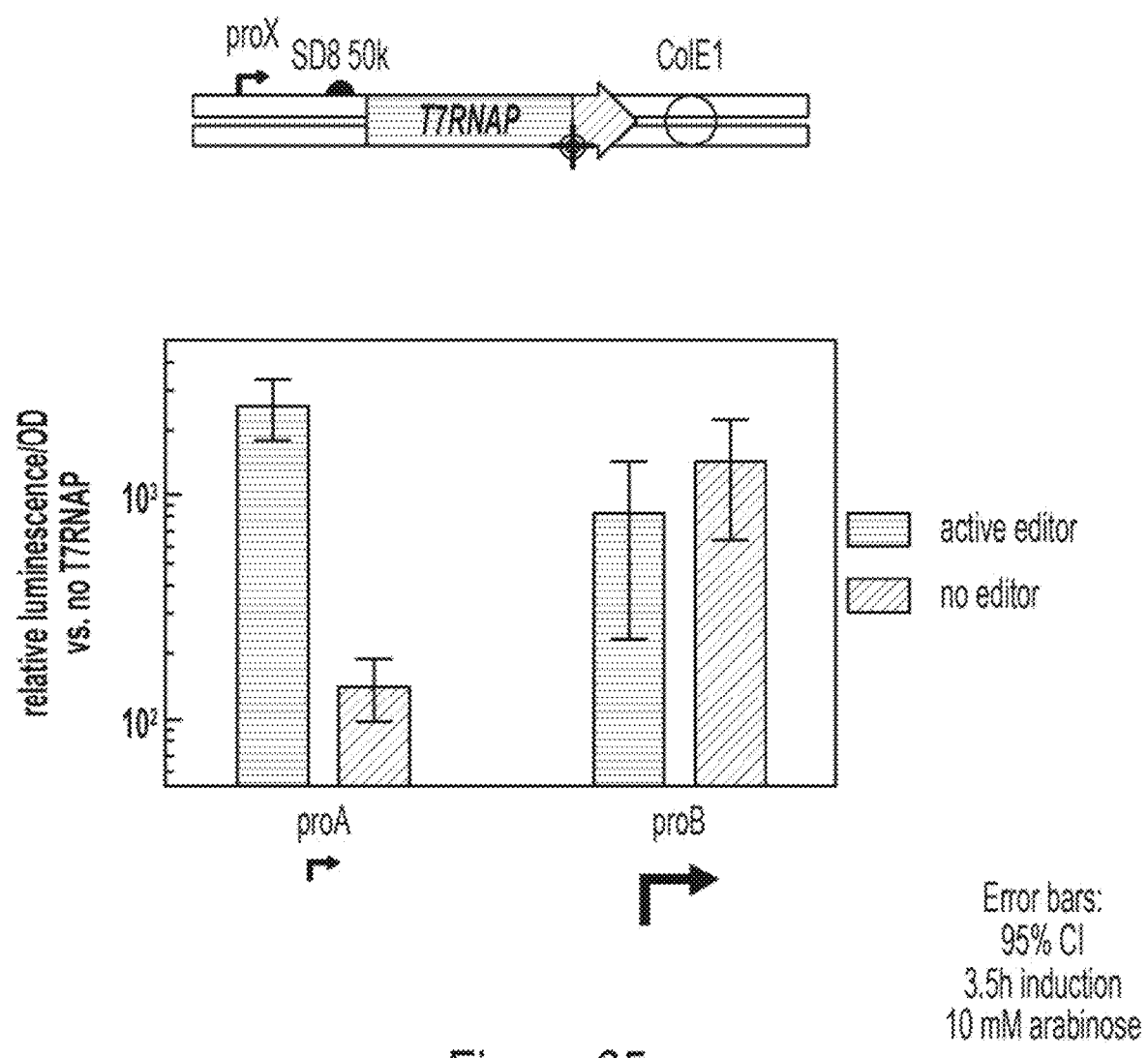
FIG. 65 shows results of stronger T7RNAP expression.

Stronger T7RNAP expression reduces turn-on and is toxic as shown in FIG. 65.

Figure 66:
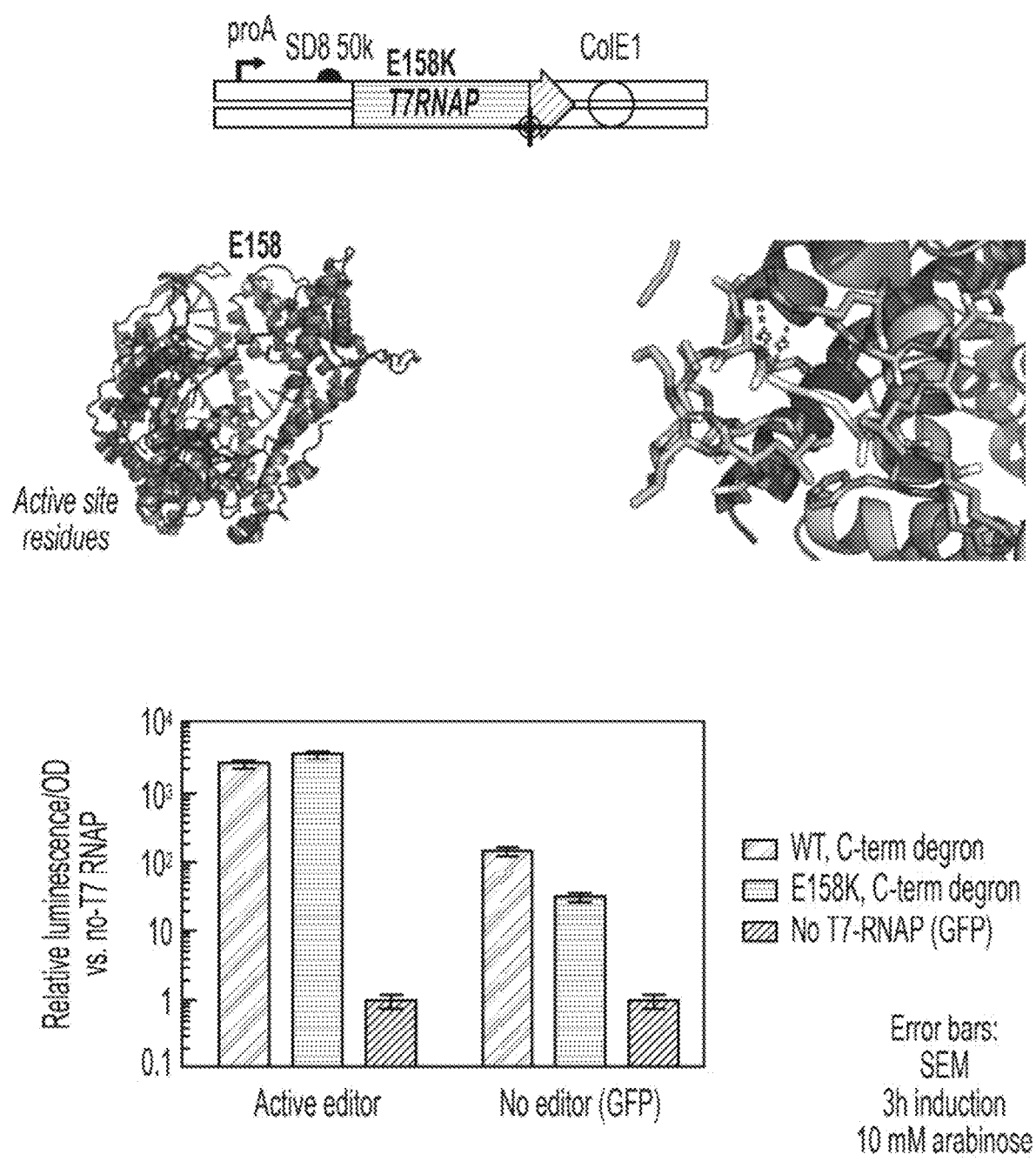
FIG. 66 shows a schematic of the E158K mutation.

A spontaneous E158K mutation reduces background as illustrated in FIG. 66.

Figure 67:
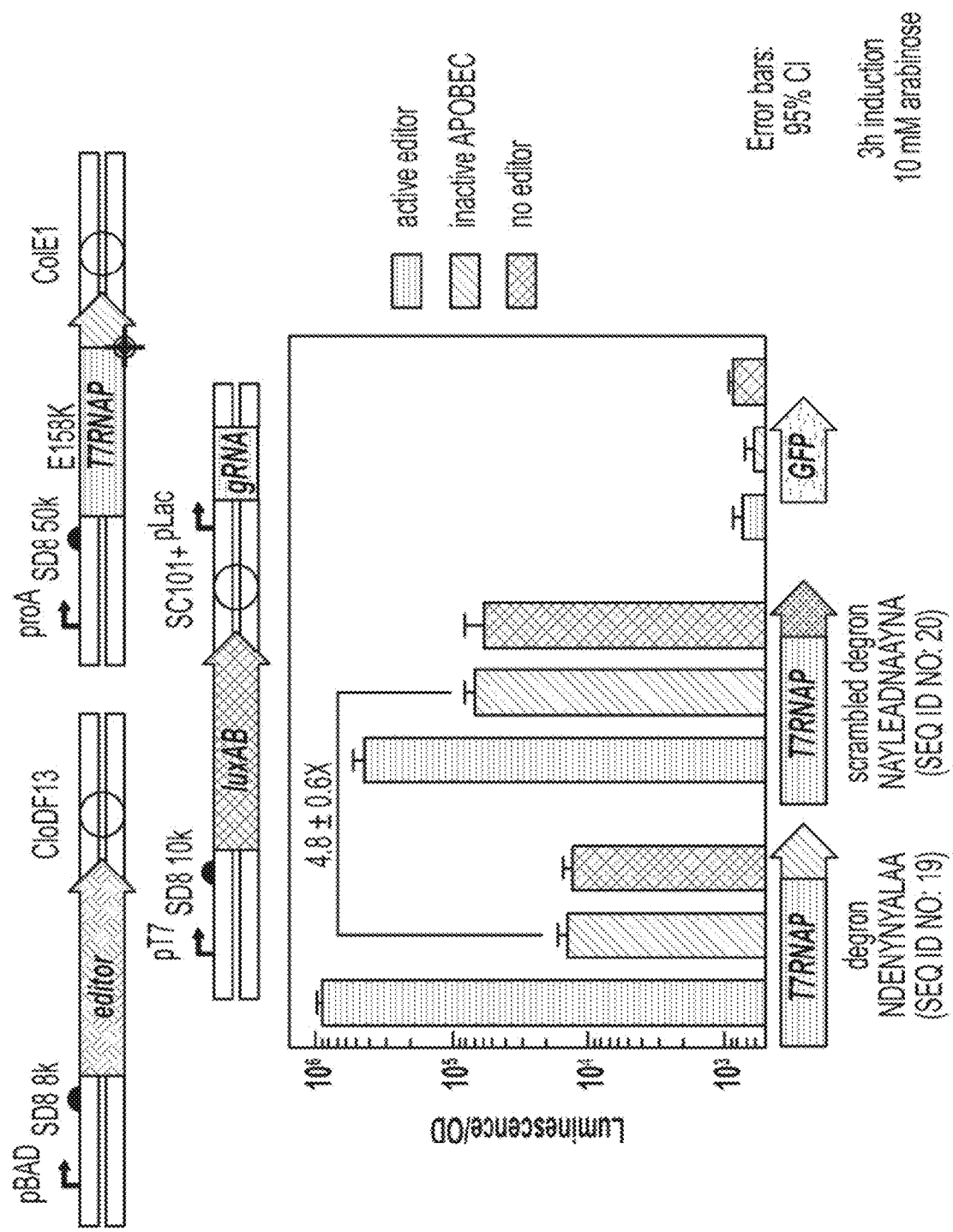
FIG. 67 shows a schematic of the E158K mutation.

The degron is critical to reducing toxicity but not to reducing activity as shown in FIG. 67.

Figure 68:
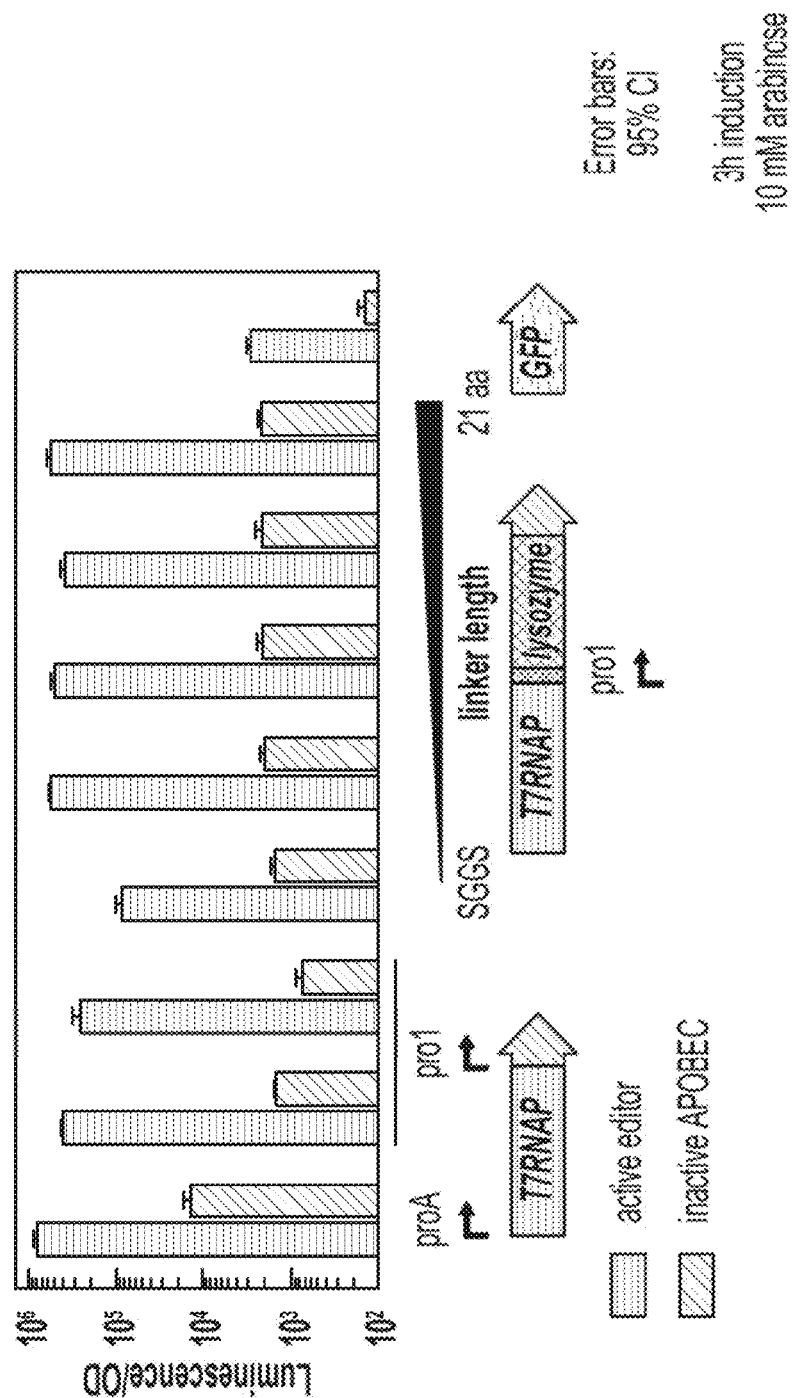
FIG. 68 shows C-terminal T7 lysozyme-degron fusions.

C-terminal T7 lysozyme-degron fusions do not have reduced background as shown in FIG. 68.

Figure 69:
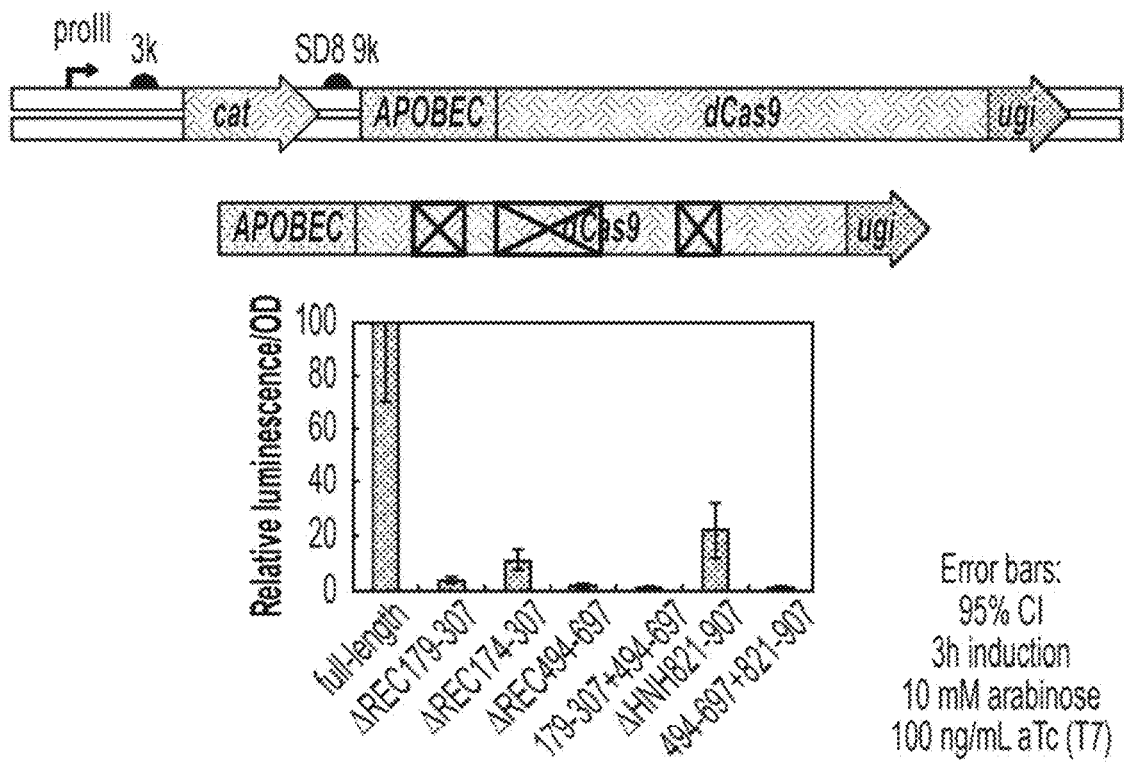
FIG. 69 shows a schematic and results with smaller editor variants.

Smaller or better expressed editor variants might help as illustrated in FIG. 69.

Figure 70:
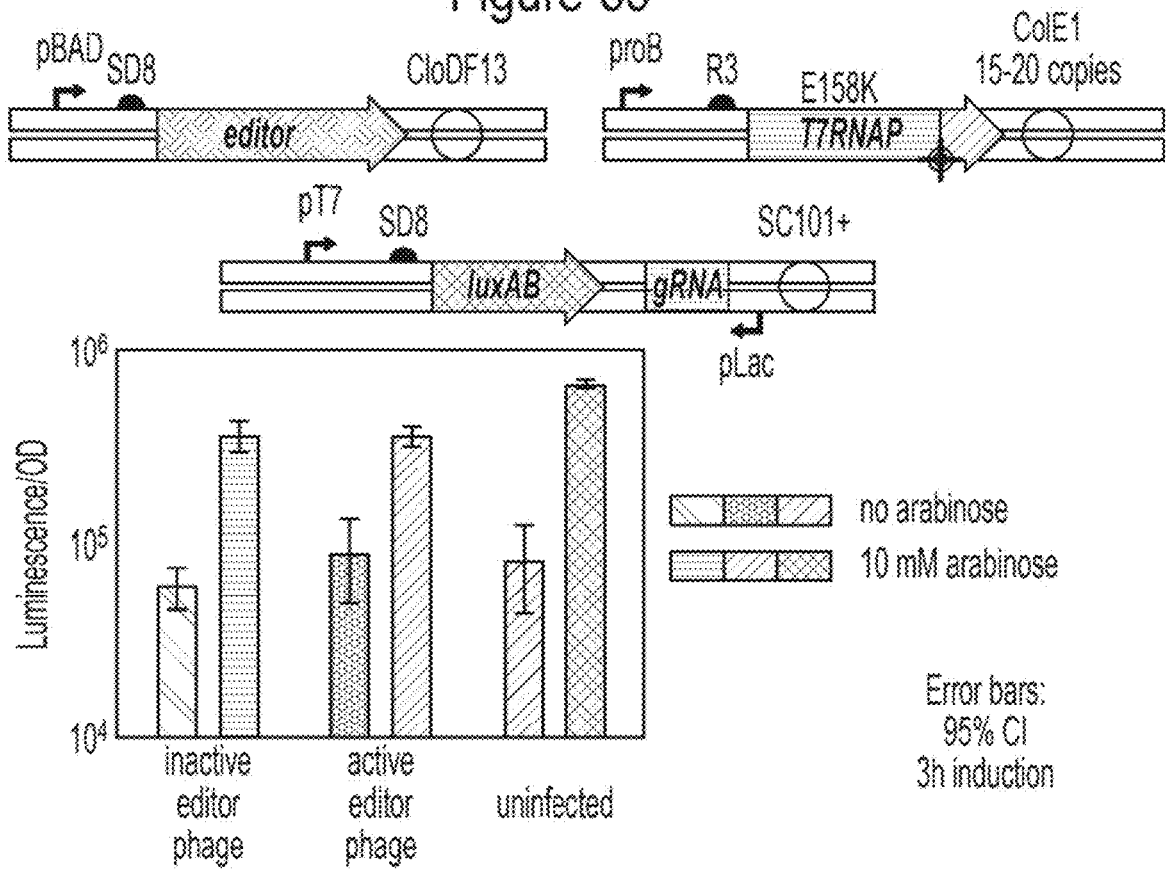
FIG. 70 shows a schematic and results of the plasmid-encoded editor.

Plasmid-encoded editor is functional in phage-infected cells as shown in FIG. 70.

Figure 71:
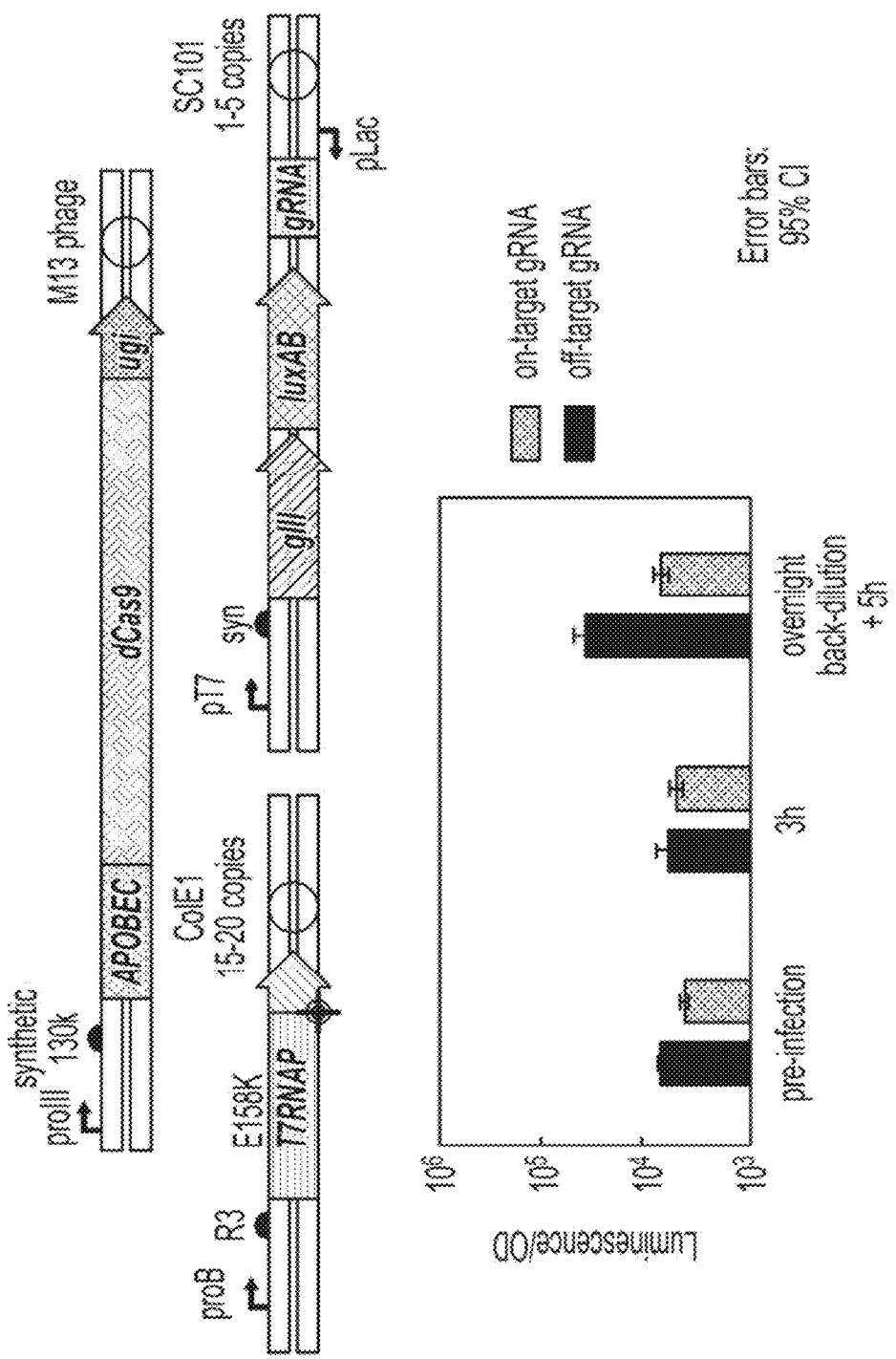
FIG. 71 shows a schematic of the phage-encoded editor.
Figure 72:
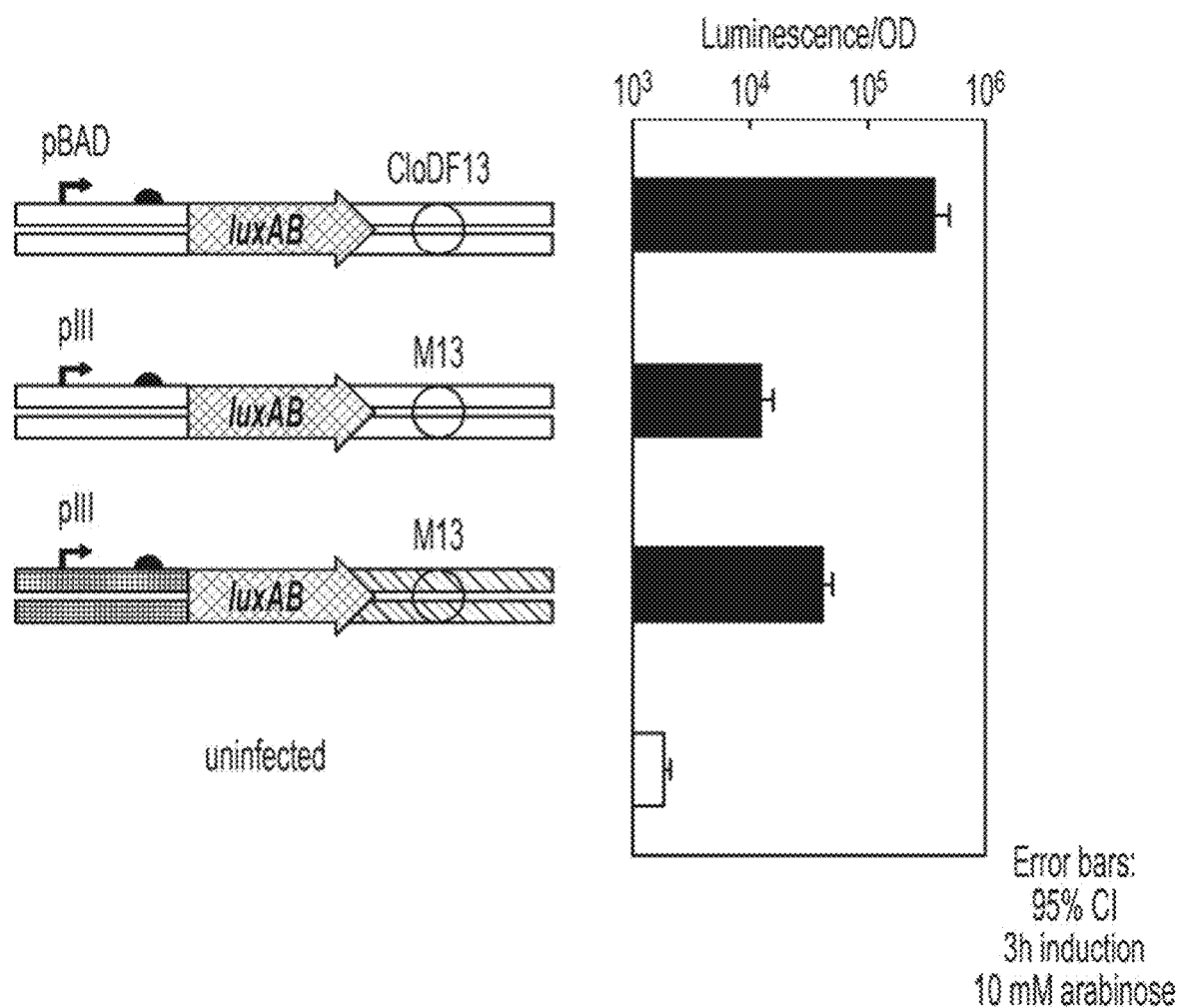
FIG. 72 shows a comparison of expression from the phage genome versus the plasmid.

The phage-encoded editor is active as shown in FIG. 71.

Expression from the phage genome is lower than from plasmid.

Figure 73:
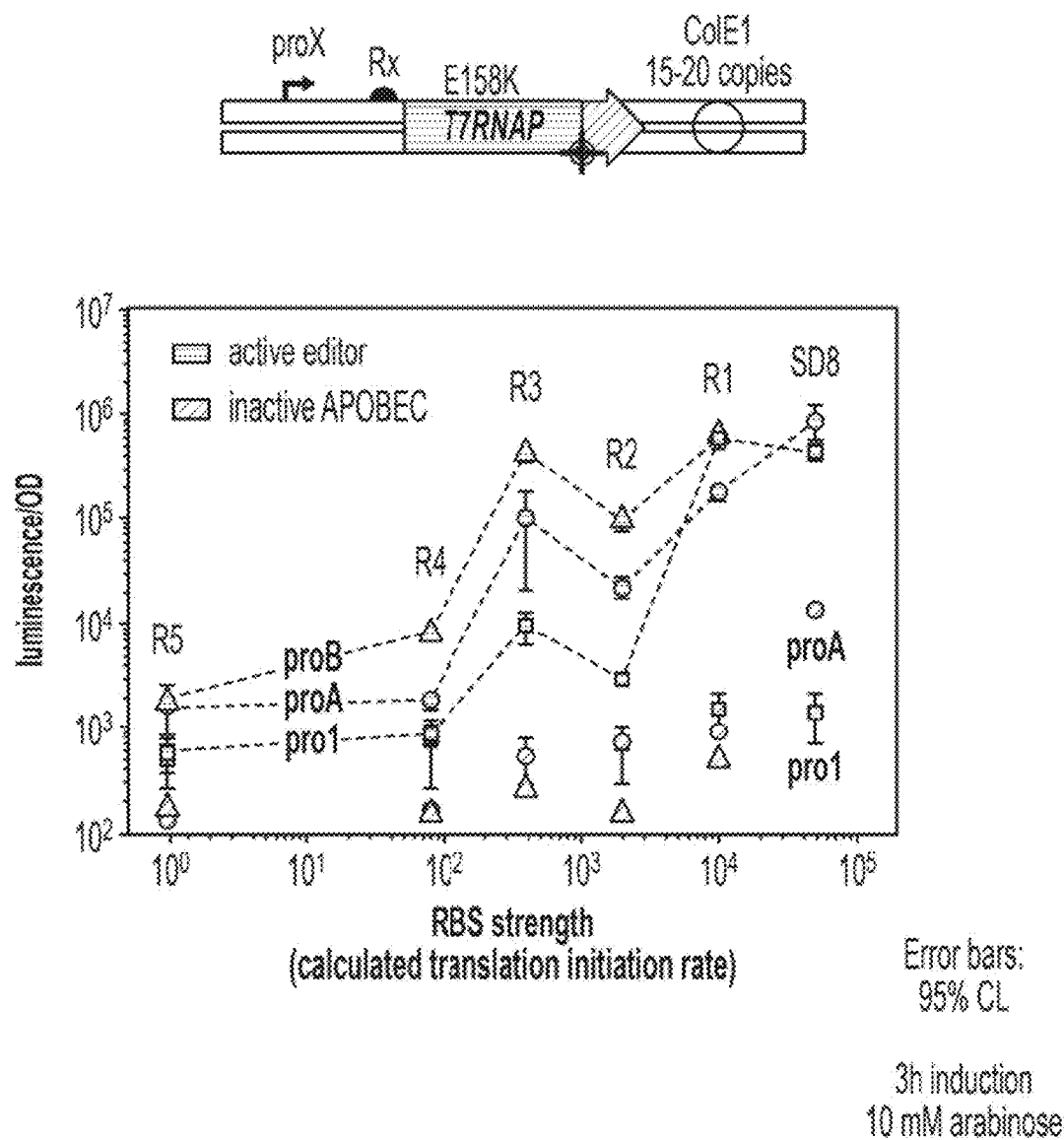

Scanning promoter and RBS strength for T7 RNAP expression allows optimization of circuit activation (as-sessed by luciferase output change when expressing active vs. inactive base editor on a plasmid). The original circuit, SD8 proA, has much lower fold activation and higher background than the optimized circuit (R3 proB). This is shown in FIG. 73.

Figure 74:
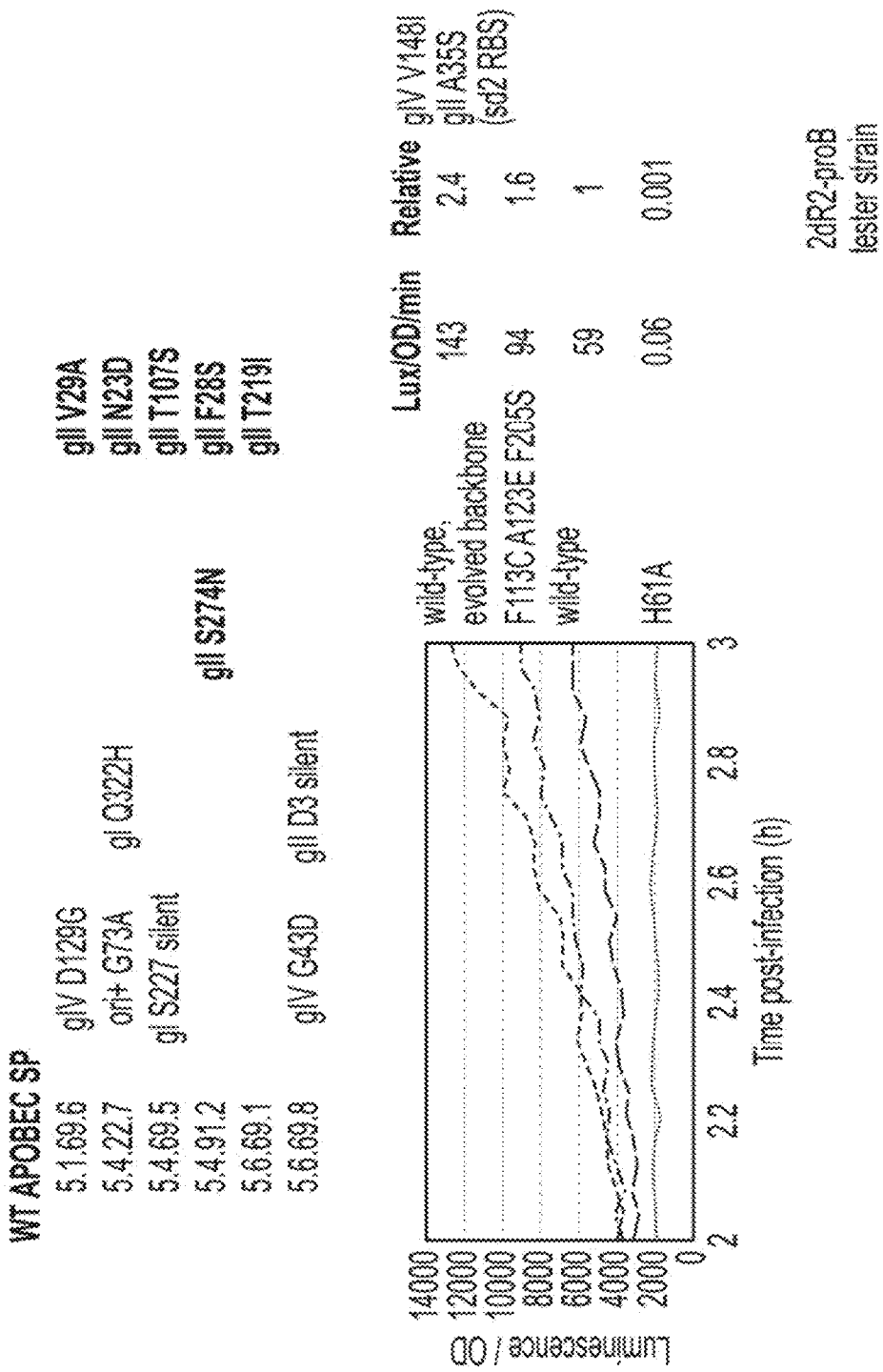
FIG. 74 shows that phage backbone mutations play a significant role.

Mutations in the phage backbone, rather than exclusively in the deaminase-intein fusion insert, can lead to substantial changes in phage activity (FIG. 74).

Figure 75:
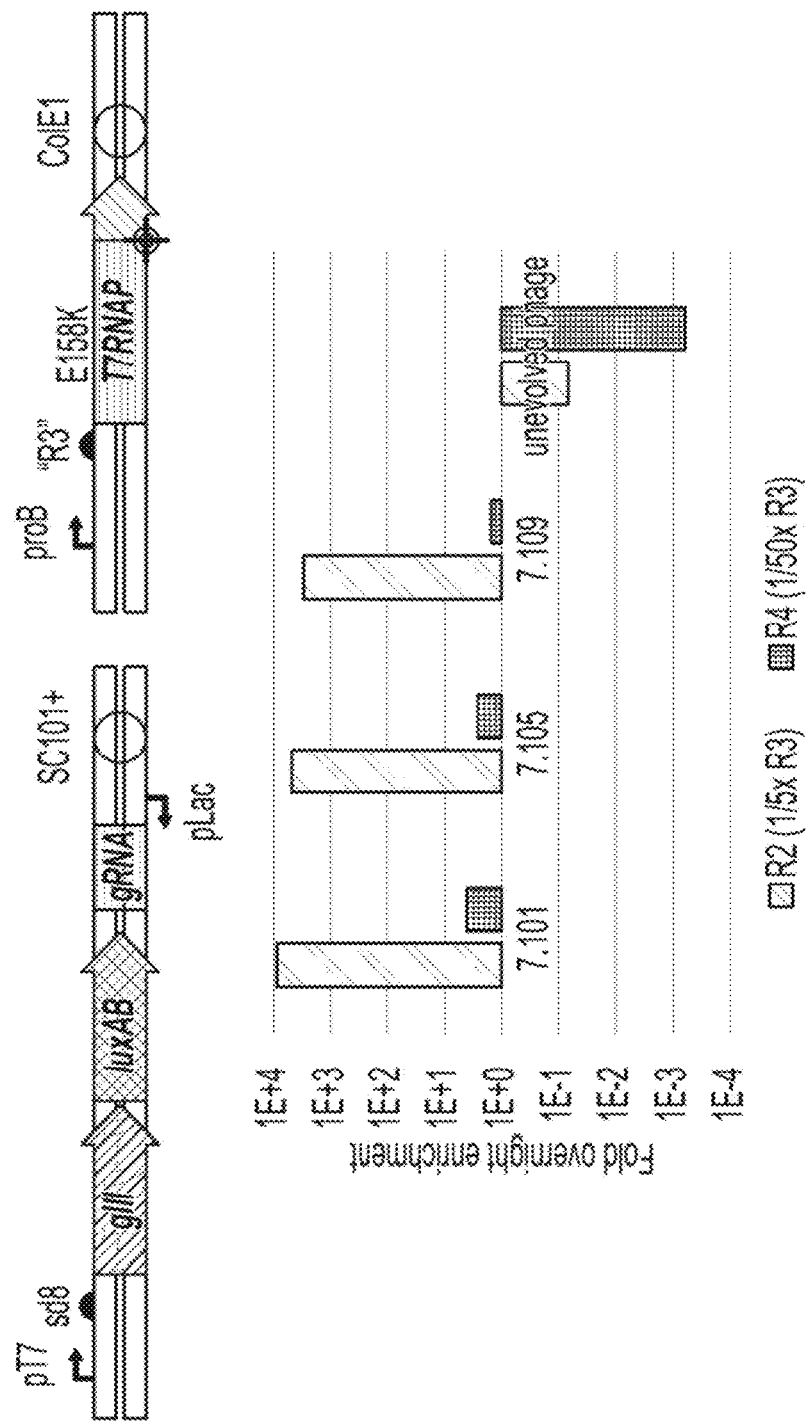
FIG. 75 shows that the evolved phage propagate better.

PACE-evolved phage not only activate the circuit faster in the luciferase assay, they can also propagate more efficiently than unevolved phage (right) on more stringent circuits (R2 and R4 RBSs lead to lower T7 RNAP expression levels, and therefore require more editing events for circuit activation, than R3). These more stringent circuits allow continued PACE on phage that strongly enrich on the R3 circuit (not shown), FIG. 75.

Figure 76:
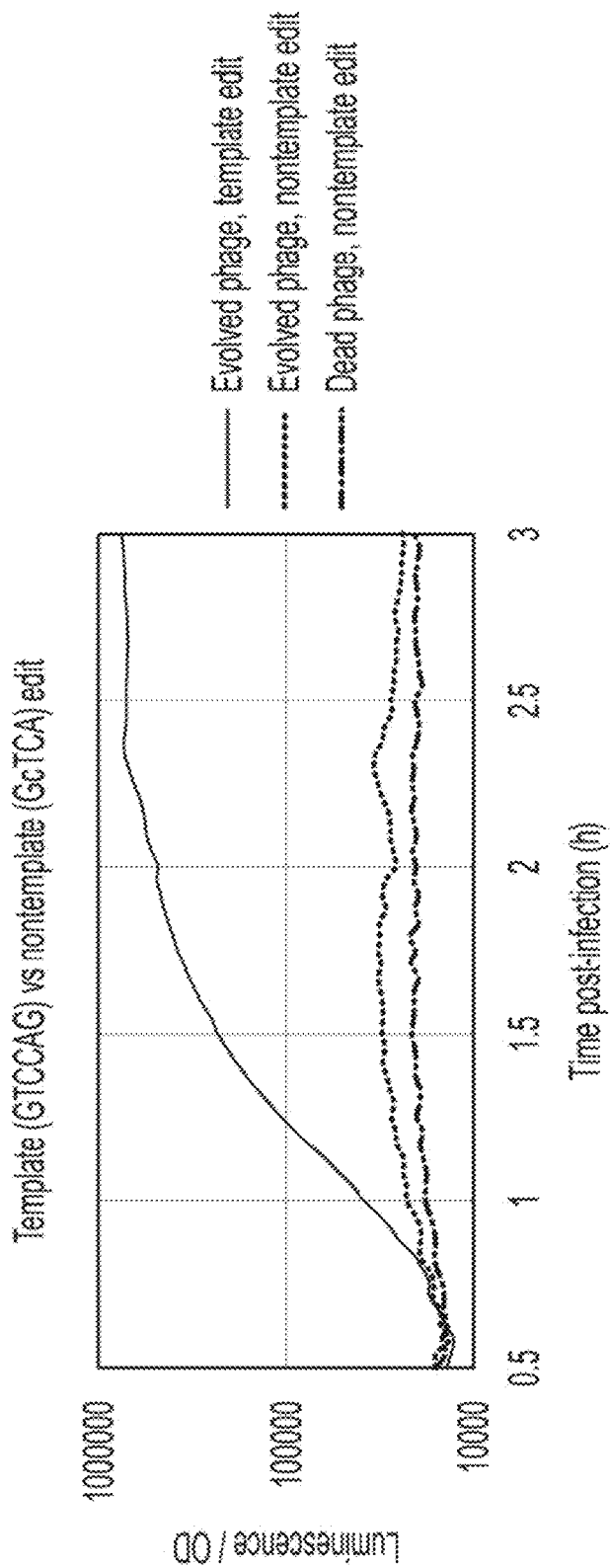
FIG. 76 shows that non-template strand editing may not activate the circuit.

Editing of the template strand for RNA polymerization, as designed into the T7 RNAP activation circuit, is required for activation on PACE-compatible time-scales (FIG. 76). Non-template editing, which requires plasmid replication and possibly DNA repair to lead to an mRNA-level phenotype, does not show activation even by evolved phage within 3 h, while the analogous template strand edit leads to strong activation.

The full-length BE2 PACE now looks practical. Propagation of >10-fold is required for successful PACE. Although full-length wild-type base editors fail to propagate even with an evolved phage backbone, adding deaminase mutations from split BE PACE leads to up to 1000× propagation. PACE on full-length BEs will allow evolution of all BE components including dCas9.

TABLE 2

Evolved phage backbones (backbone #) and deaminase mutations (insert) allow full-length base editors to propagate on the BE circuit, suggesting that the entire BE can be evolved.

| Backbone | Insert | Propagation on stringency 1 5'TCC (preliminary) |
|---|---|---|
| 137 (PACE7) | empty | ↓4000× |
| 137 | dCas9.ugi | ↓50× |
| 13 | BE2 | ↓2000× |
| 29 | BE2 | ↓100× |
| 137 | BE2 | ↑2× |
| 137 | BE2 A165S F205S | ↑80× |
| 137 | BE2 H109N A165S P201S F205S | ↑1000× |

Several deaminases are active enough for PACE. BE3 and BE4 are based on rat APOBEC1. They have high overall activity, severely compromised activity editing GC targets, and high editing on TC targets. Alternative deaminases have been demonstrated as base editors. AID and CDA both work well on GC targets but have lower activity than APOBEC1 generally. APOBEC3G works less well than all of these (Komor, A. C. et al. Improved base excision repair inhibition and bacteriophage Mu Gan protein yields C:G-to-T:A base editors with higher efficiency and product purity. Sci Adv 3, eaao4774 (2017)). The TARGET-AID base editing implementation uses CDA (Nishida, K. et al. Targeted nucleotide editing using hybrid prokaryotic and vertebrate adaptive immune systems. Science 353, aaf8729-aaf8729 (2016)). "FERNY" is an N- and C-terminally truncated ancestral sequence reconstruction based on an APOBEC family phylogenetic tree. rAPOBEC1: 229 aa; FERNY: 161 aa. The sequence similarity to rAPOBEC1 is 55%. The ancestral reconstruction technique is described in a submitted paper (Koblan et al., Nature Biotechnol submitted) but the FERNY sequence is not described there.

Figure 77:
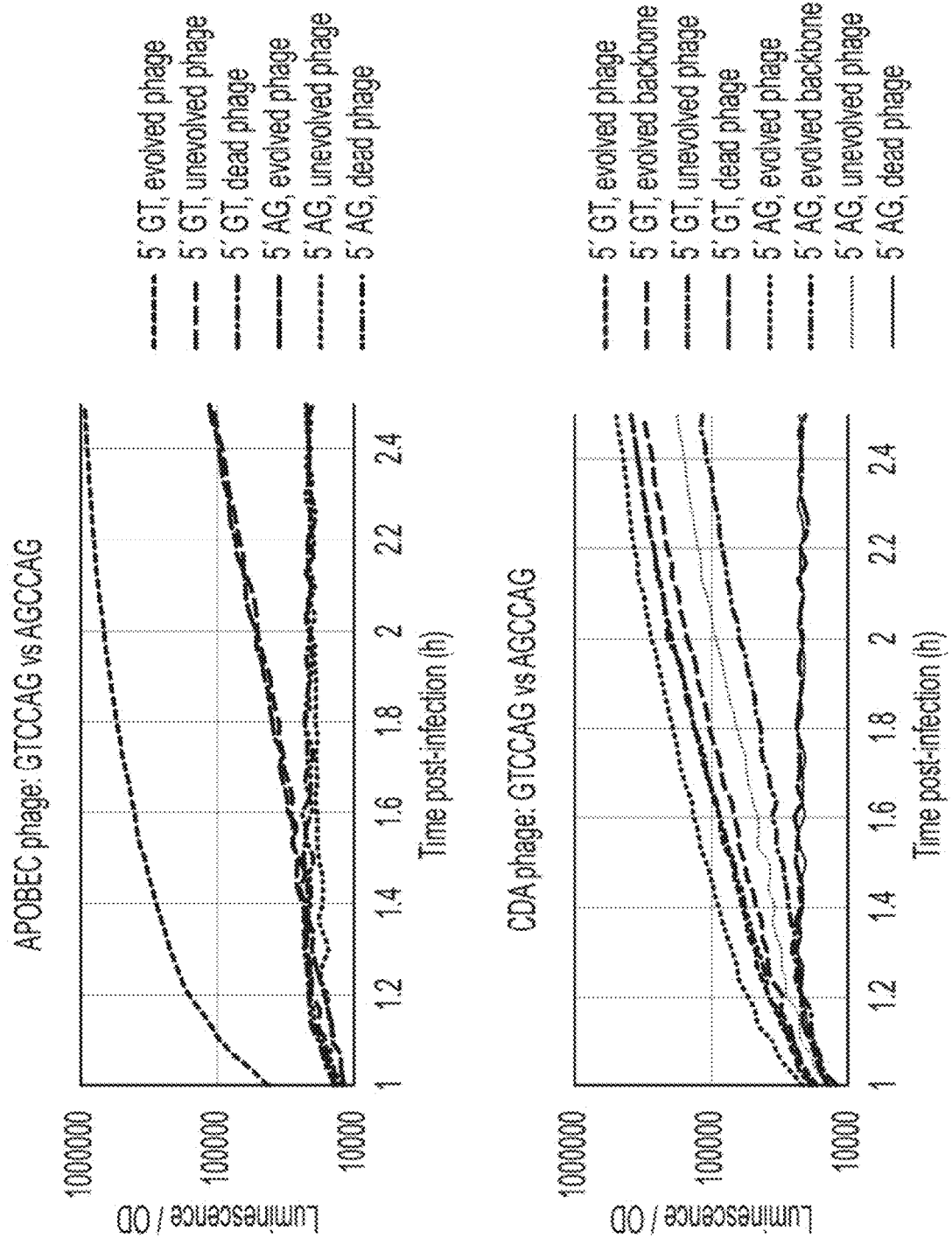
FIG. 77 shows that 5' AG reduces APOBEC but not CDA editing.
Figure 78:
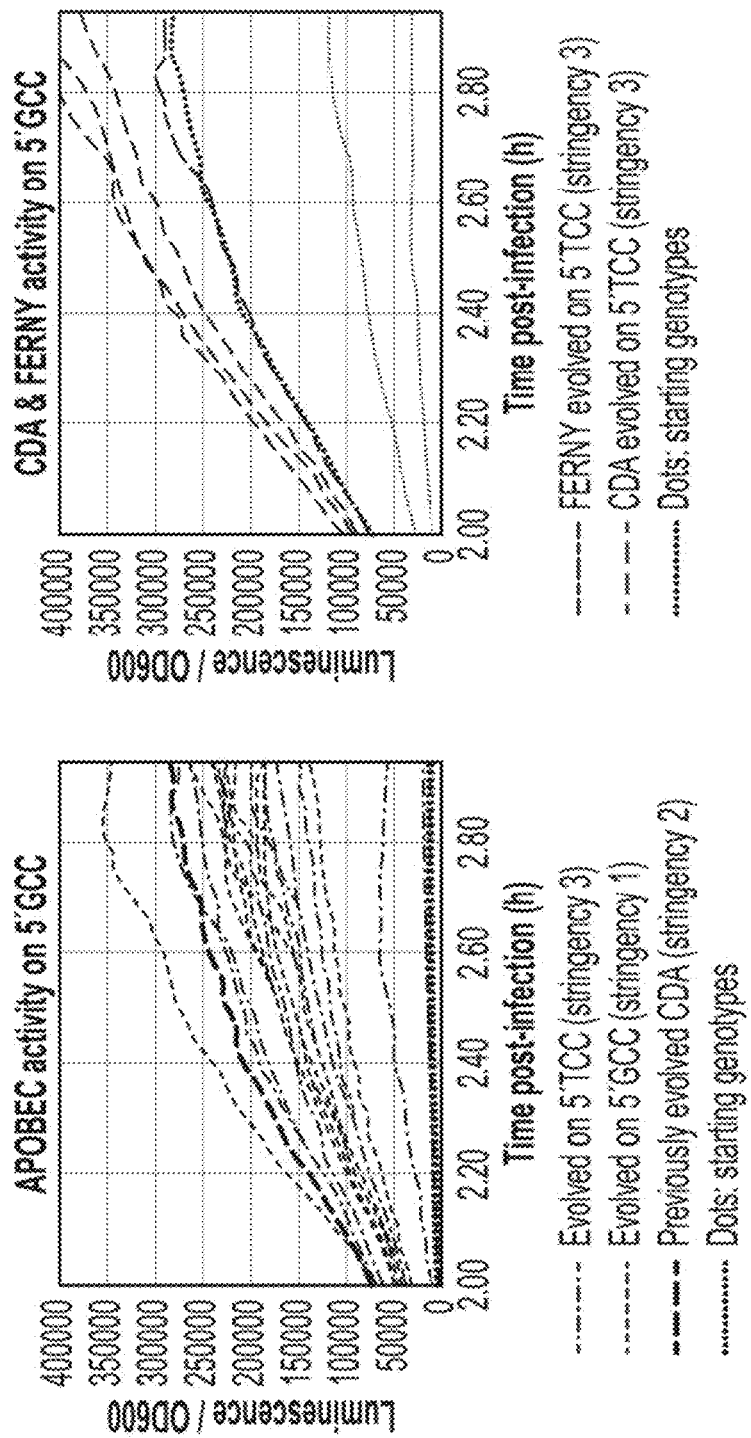
FIG. 78 shows PCE 12 evolving a 5'-base agnostic APOBEC.
Figure 79:
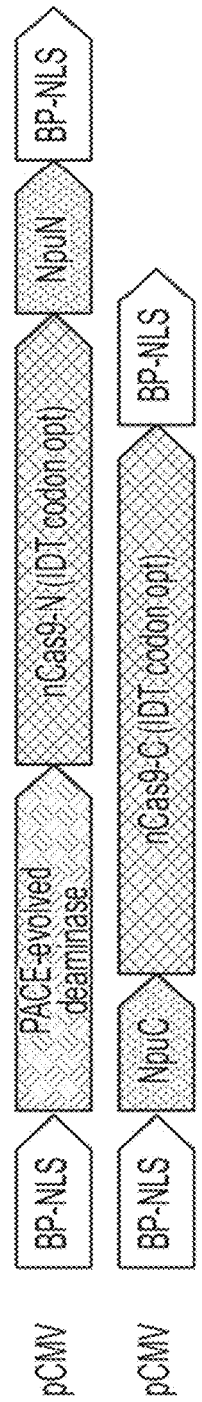
FIG. 79 shows HEK cell editing of early PACE evolved deaminases using split BE constructs, showing improvements over wild-type BE.
Figure 80:
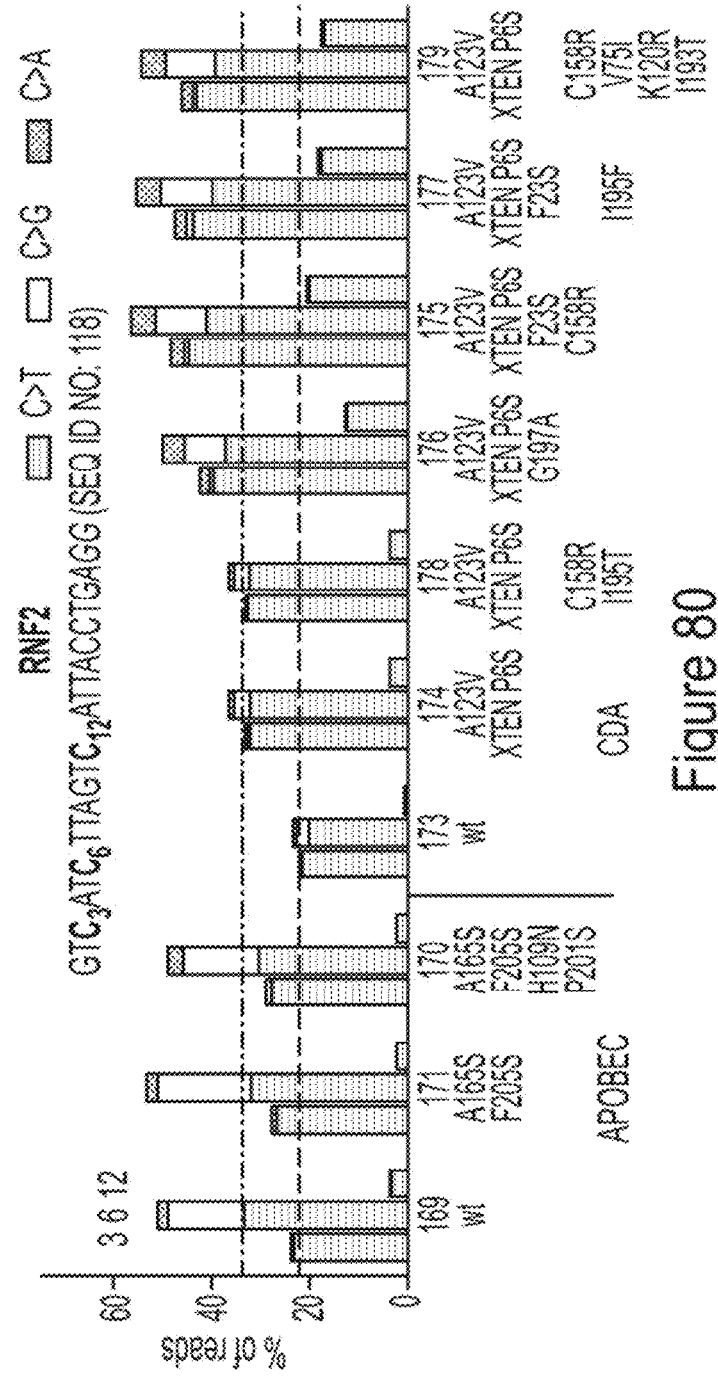
FIG. 80 shows HEK cell editing of early PACE evolved deaminases using split BE constructs, showing improvements over wild-type BE.
Figure 81:
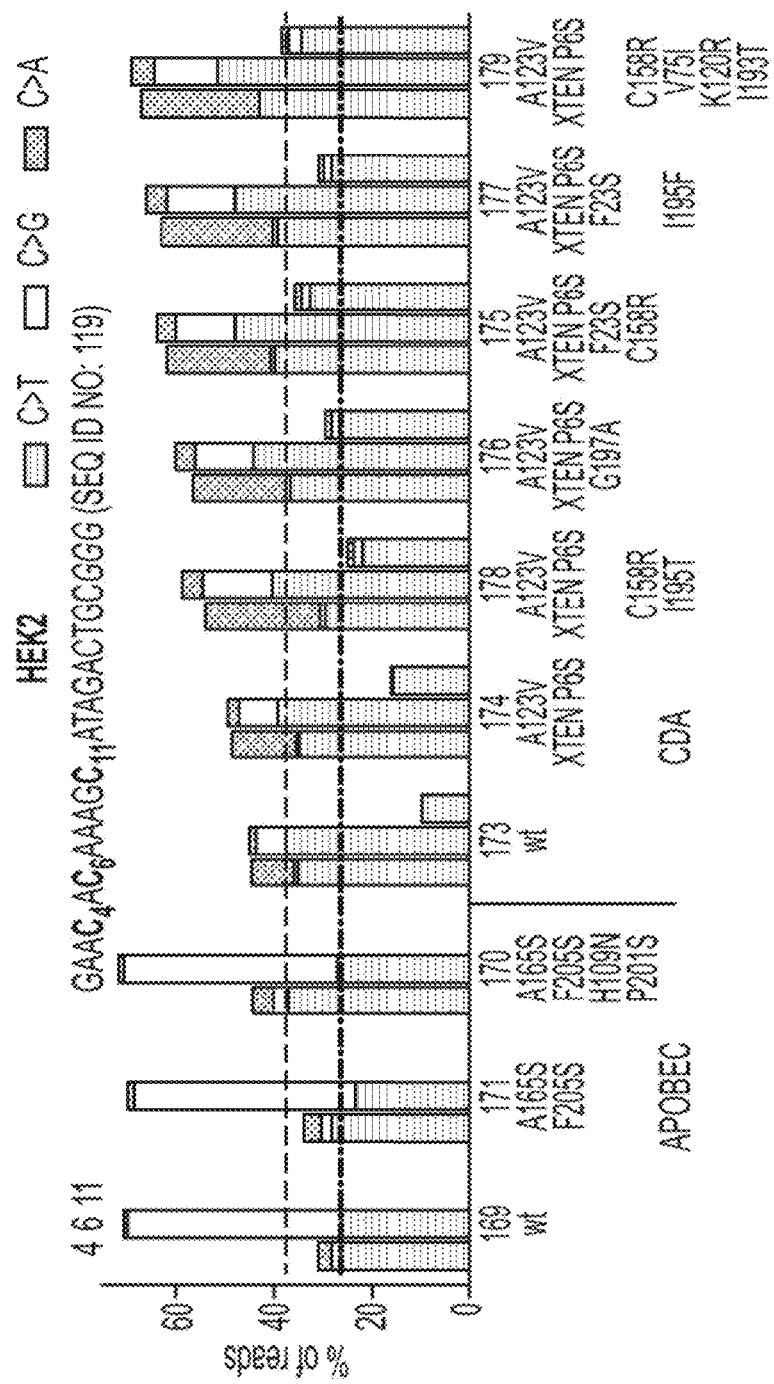
FIG. 81 shows HEK cell editing of early PACE evolved deaminases using split BE constructs, showing improvements over wild-type BE.
Figure 82:
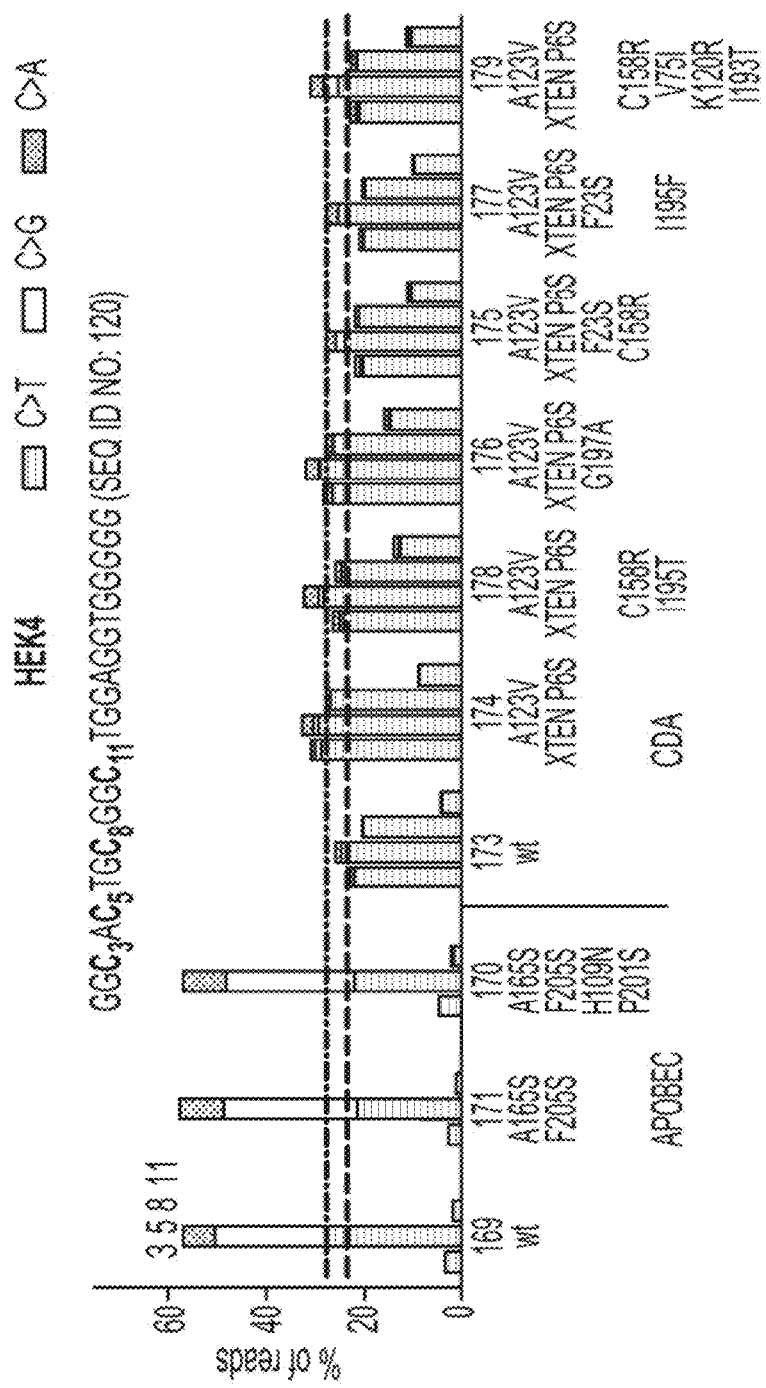
FIG. 82 shows HEK cell editing of early PACE evolved deaminases using split BE constructs, showing improvements over wild-type BE.
Figure 83:
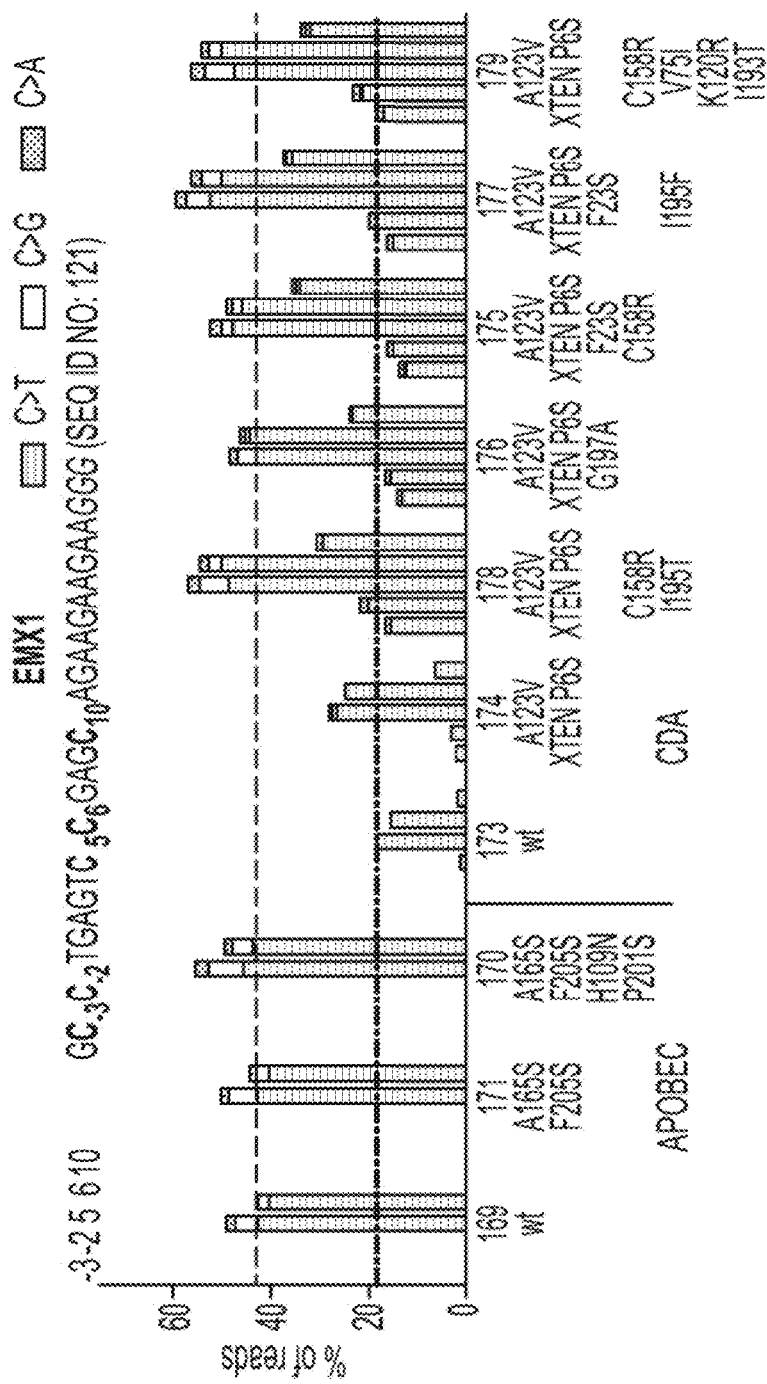
FIG. 83 shows HEK cell editing of early PACE evolved deaminases using split BE constructs, showing improvements over wild-type BE.

Luciferase assays show that an AGCC target dramatically cuts activation rate by rAPOBEC1 compared to an ATCC target, butpmCDA1 can activate both (FIG. 77). PACE evolution can produce rAPOBEC1 genotypes and phage that can activate the GCC circuit as strongly as the TCC circuit, and CDA and FERNY phage that have comparable activation rates to APOBEC1 (FIG. 78). HEK cell editing of early PACE evolved deaminases using split BE constructs shows improvements over wild-type BE (FIGS. 79-83, Table 3).

TABLE 3

Genotypes of evolved base editors in preliminary HEK assay.

| Plasmid | Deaminase | Origin | Evolved on | Genotype |
|---|---|---|---|---|
| pBT169 | rAPOBEC1 | wild-type | 5'TCC | |
| pBT170 | rAPOBEC1 | PACE7 top clone | 5'TCC | H109N A165S P201S F205S |
| pBT171 | rAPOBEC1 | PACE7 top clone | 5'TCC | A165S F205S |
| pBT173 | pmCDA1 | wild-type | 5'TCC | |
| pBT174 | pmCDA1 | PACE 5 top clone | 5'TCC | A123V, XTEN P6S |
| pBT175 | pmCDA1 | PACE10 top clone | 5'TCC | F23S A123V C158R, XTEN P6S |
| pBT176 | pmCDA1 | PACE10 top clone | 5'TCC | A123V G197A, XTEN P6S |
| pBT177 | pmCDA1 | PACE10 top clone | 5'TCC | F23S A123V I195F, XTEN P6S |
| pBT178 | pmCDA1 | PACE10 top clone | 5'TCC | A123V C158R I195T, XTEN P6S |
| pBT179 | pmCDA1 | PACE10 top clone | 5'TCC | V75I K120R A123V C158R I193T, XTEN P6S |

Testing of a large set of PACE-derived APOBEC, CDA and FERNY genotypes as full-length base editors in HEK cells shows that they have improved editing characteristics compared to wild-type deaminases (Table 4).

TABLE 4

PACE12 produced improved deaminase genotypes. Regular text is PACE5-PACE10 and italic text is PACE12.

| Plasmid | Deaminase | Evolved on | Deaminase genotype |
|---|---|---|---|
| pBT209 | rAPOBEC1 | | wt |
| pBT210 | pmCDA1 | | wt |
| pBT211 | FERNY | | "wt" |
| pBT212 | hsAID | | wt |

TABLE 4-continued

PACE12 produced improved deaminase genotypes. Regular text is
PACE5-PACE10 and italic text is PACE12.

| Plasmid | Deaminase | Evolved on | Deaminase genotype |
|---|---|---|---|
| pBT213 | pmCDA1 | TCC | *A123V* |
| pBT214 | rAPOBEC1 | TCC | H109N A165S P201S F205S |
| pBT215 | rAPOBEC1 | TCC | E4K H109N A165S P201S F205S |
| pBT216 | rAPOBEC1 | TCC | A165S F205S |
| pBT217 | pmCDA1 | TCC | F23S *A123V* C158R |
| pBT218 | FERNY | TCC | V115M |
| pBT219 | pmCDA1 | TCC | *A123V* V197A |
| pBT220 | pmCDA1 | TCC | A123V C158R I195T |
| pBT221 | pmCDA1 | TCC | V75I K120R *A123V C158R* I193T |
| pBT222 | pmCDA1 | *TCC* | *F23S A123V I195F* |
| pBT223 | rAPOBEC1 | *GCC* | *E4K H109N H122L D124N R154H A165S P201S F205S* |
| pBT224 | FERNY | *TCC* | *H102P D104N* |
| pBT226 | rAPOBEC1 | *TCC* | *E4K V10A E95A H109N H122L D124N A165S P201S F205S* |
| pBT227 | pmCDA1 | *TCC* | *A123V D143N N149D I162V T202 -1 frameshift* |
| pBT229 | rAPOBEC1 | *GCC* | *E4K H109N H122L D124N A165S P201S F205S* |
| pBT232 | rAPOBEC1 | *TCC* | *E4K H109N D124N A165S P201S F205S* |
| pBT233 | rAPOBEC1 | *TCC* | *E4K Y40C H109N H122L D124N A165S P201S F205S* |
| pBT234 | rAPOBEC1 | *GCC* | *E4K H109N H122L D124N N158S A165S P201S F205S* |
| pBT235 | rAPOBEC1 | *GCC* | *H109N H122L R126H A165S P201S F205S* |
| pBT236 | rAPOBEC1 | *GCC* | *E4K H109N H122L R126H A165S P201S F205S* |
| pBT237 | rAPOBEC1 | *TCC* | *E4K E95A H109N H122L D124N A165S P201S F205S* |

Figure 84:
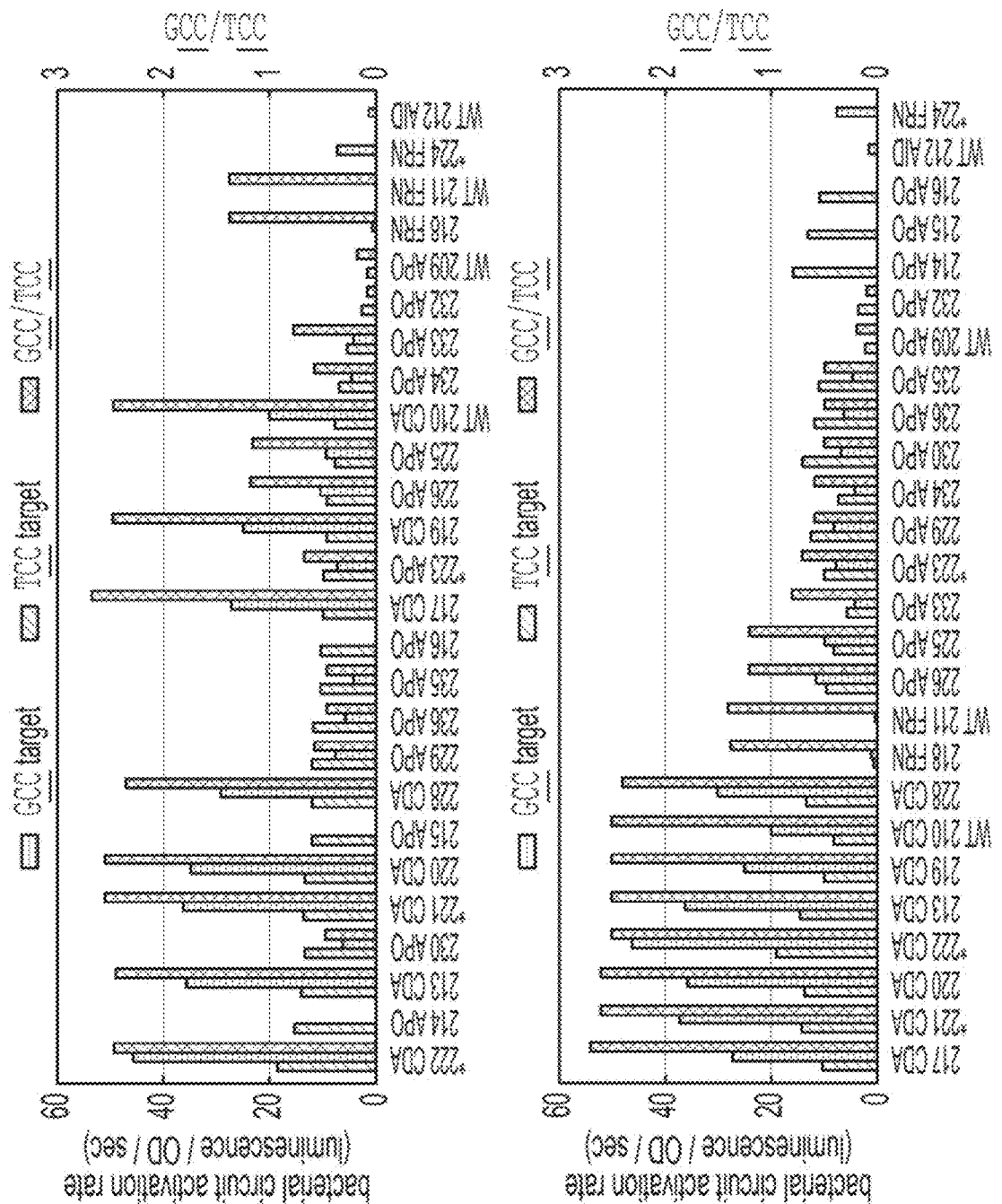
FIG. 84 shows that bacterial circuit activation shows improved GCC editing.

FIG. 84 shows that deaminases can be assayed in bacteria by BE circuit activation rate if they are cloned into isogenic phage backbones. Only the deaminase genotypes differ so they determine the activation rates. In FIG. 84, the data were collected by subcloning evolved deaminases into a standardized phage backbone, so they should primarily reflect the characteristics of the deaminases.

Figure 85:
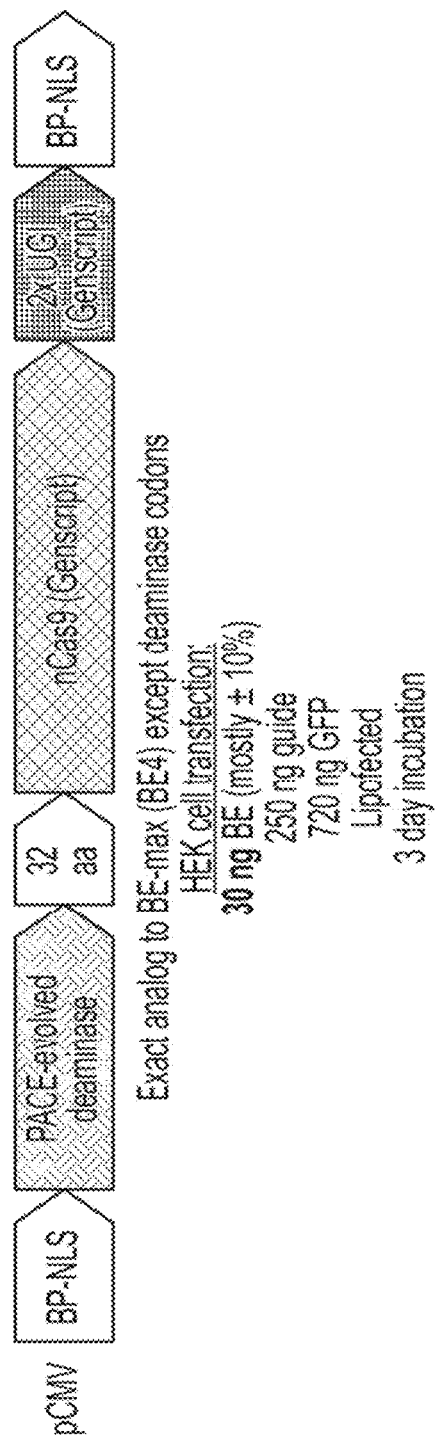
FIG. 85 shows experimental details for PACE evolved deaminases. These show improvements in HEK cell editing.
Figure 86:
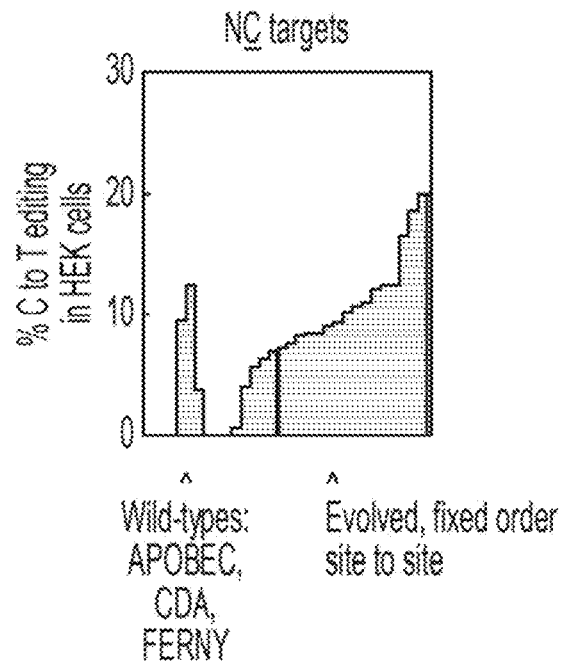
FIG. 86 shows NC targets.
Figure 87:
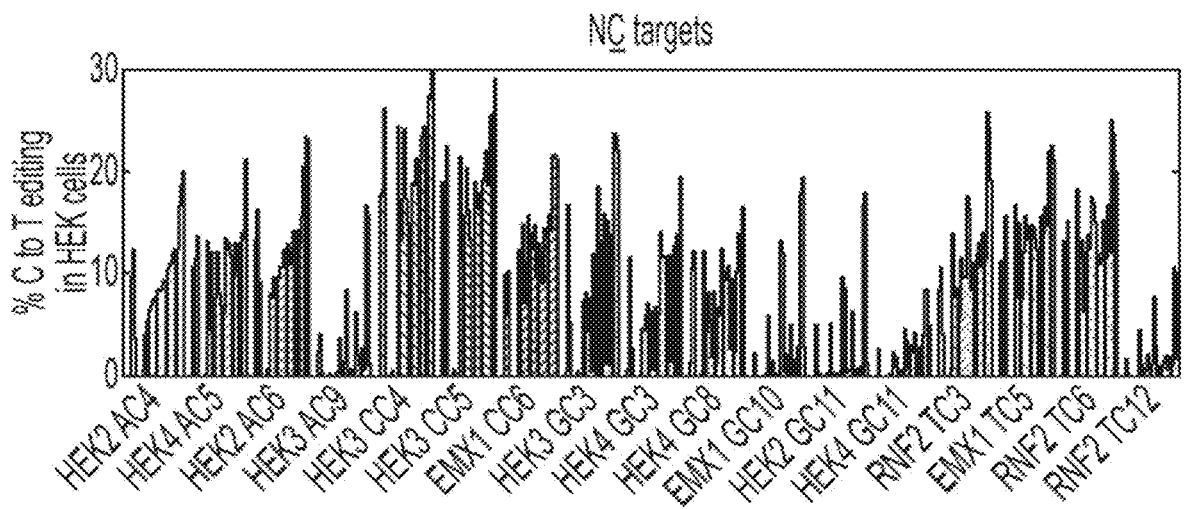
FIG. 87 shows NC targets.
Figure 88:
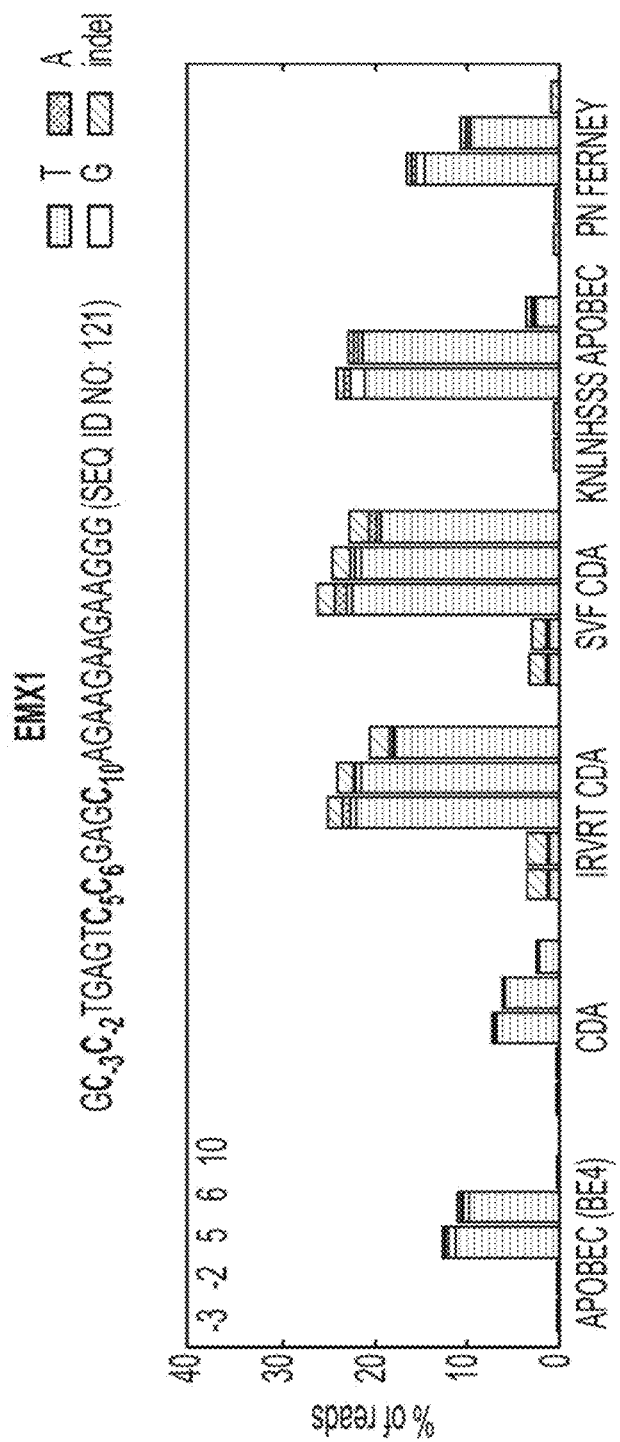
FIG. 88 shows EMX1 data showing improved activity of evolved vs wild-type deaminases in HEK cells at a low transfection dose (30 ng).
Figure 89:
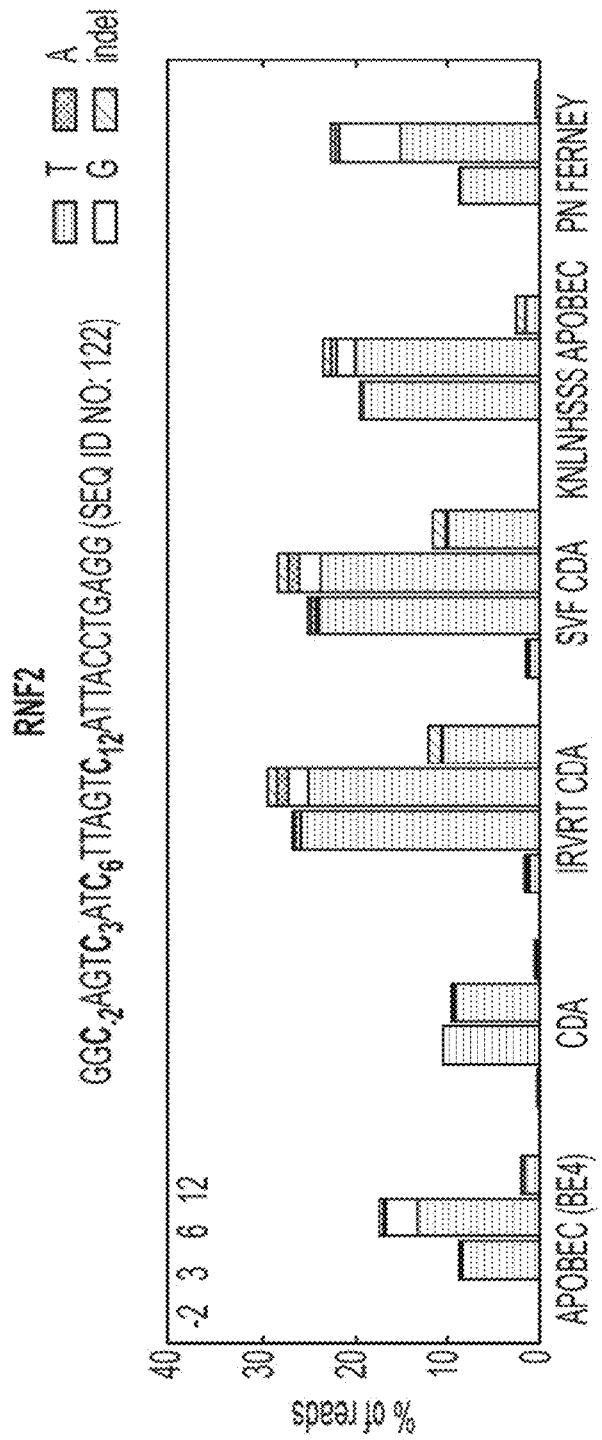
FIG. 89 shows RNF2 data showing improved activity of evolved vs wild-type deaminases in HEK cells at a low transfection dose (30 ng).
Figure 90:
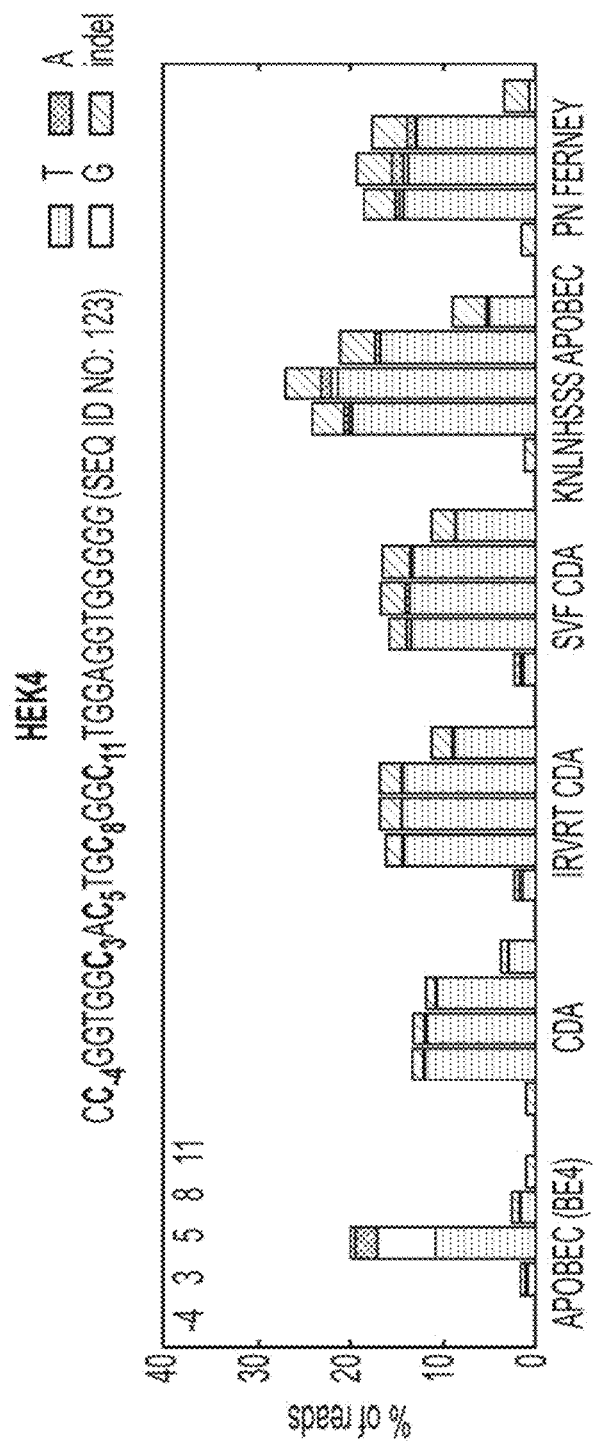
FIG. 90 shows HEK4 data showing improved activity of evolved vs wild-type deaminases in HEK cells at a low transfection dose (30 ng).
Figure 91:
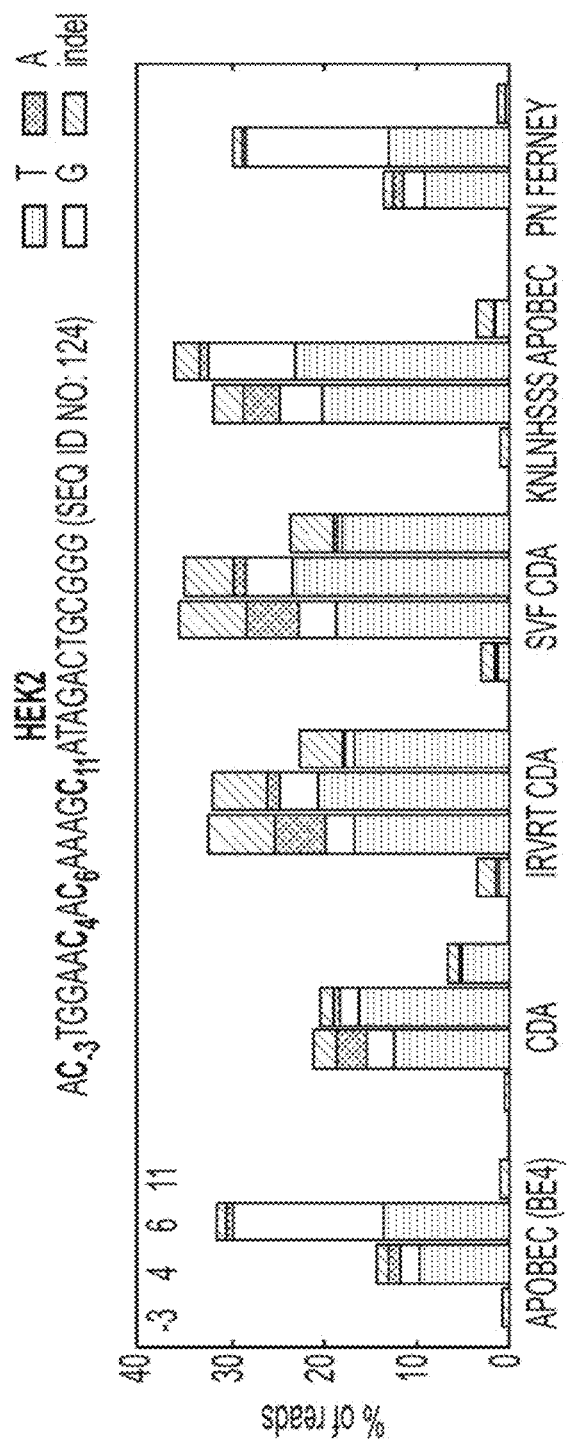
FIG. 91 shows HEK2 data showing improved activity of evolved vs wild-type deaminases in HEK cells at a low transfection dose (30 ng).
Figure 92:
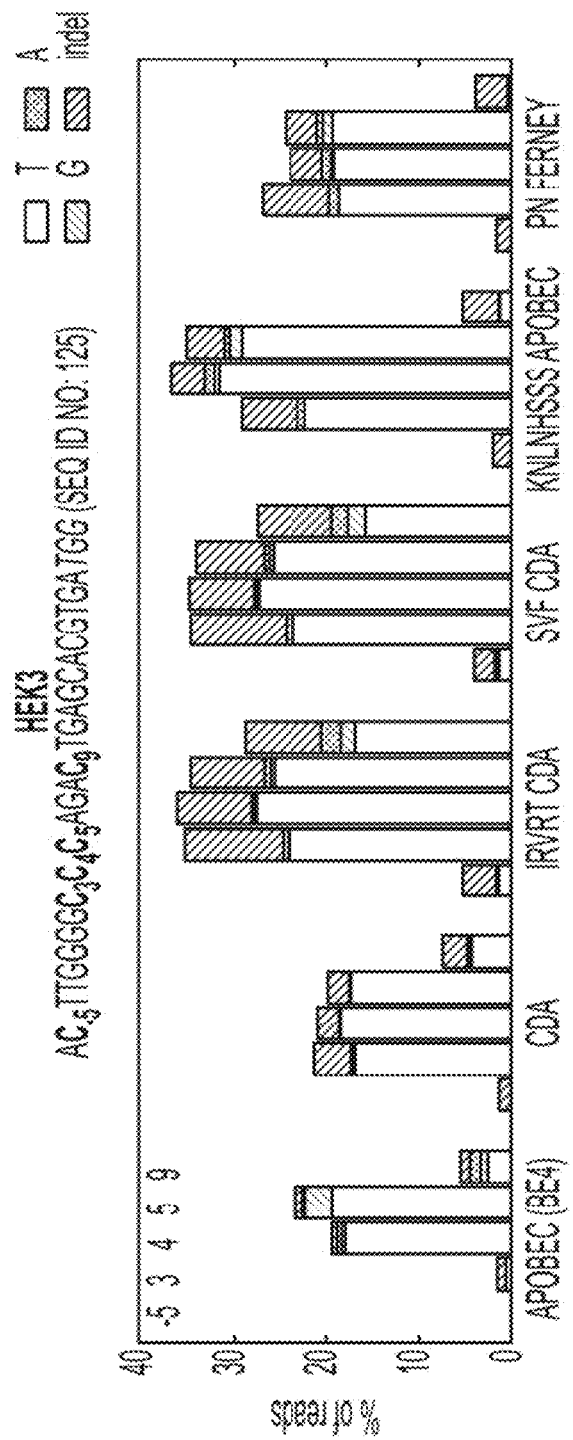
FIG. 92 shows HEK3 data showing improved activity of evolved vs wild-type deaminases in HEK cells at a low transfection dose (30 ng).
Figure 93:
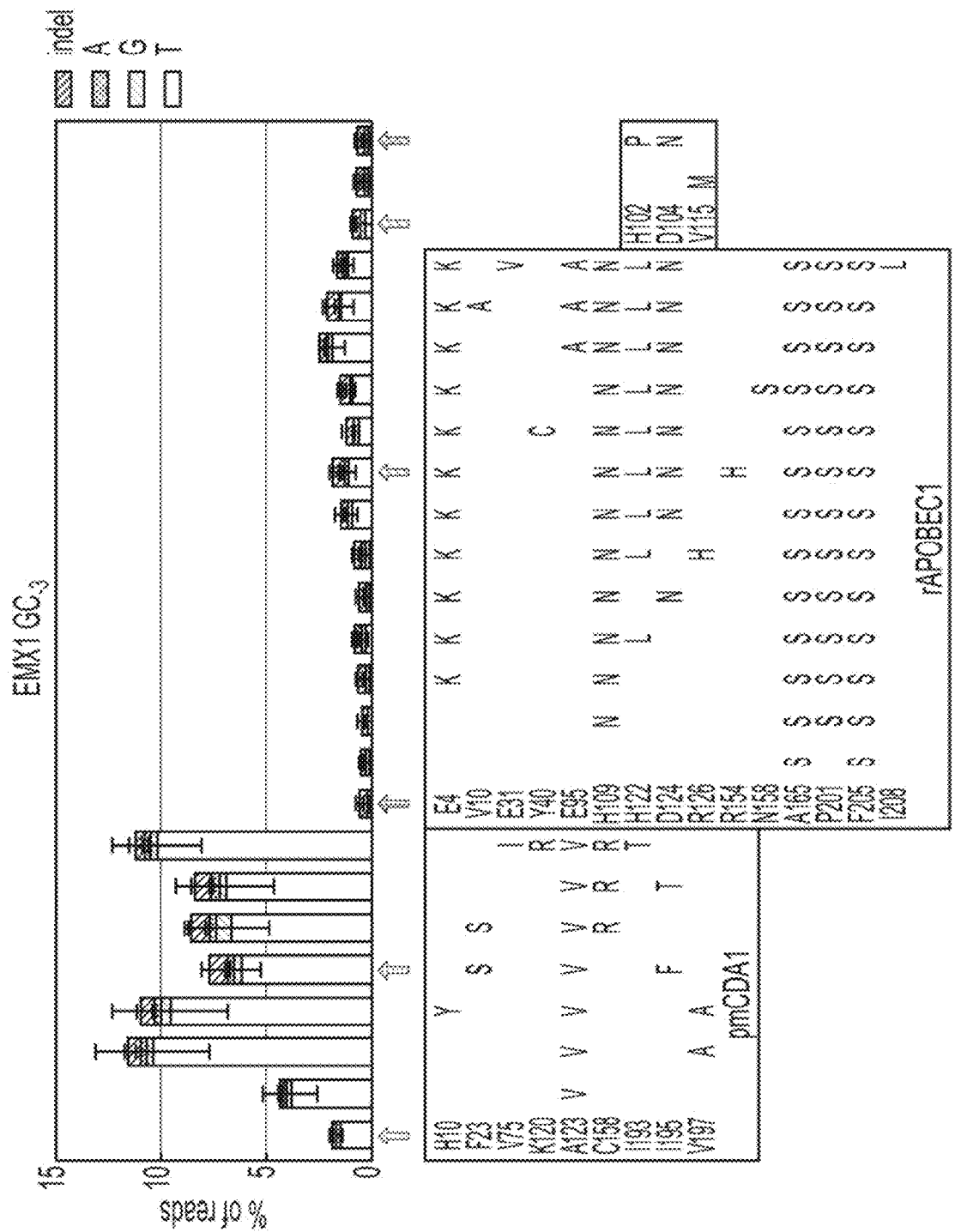
FIG. 93 shows 750 ng transfection HEK cell editing for EMX1 $GC_{-3}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 94:
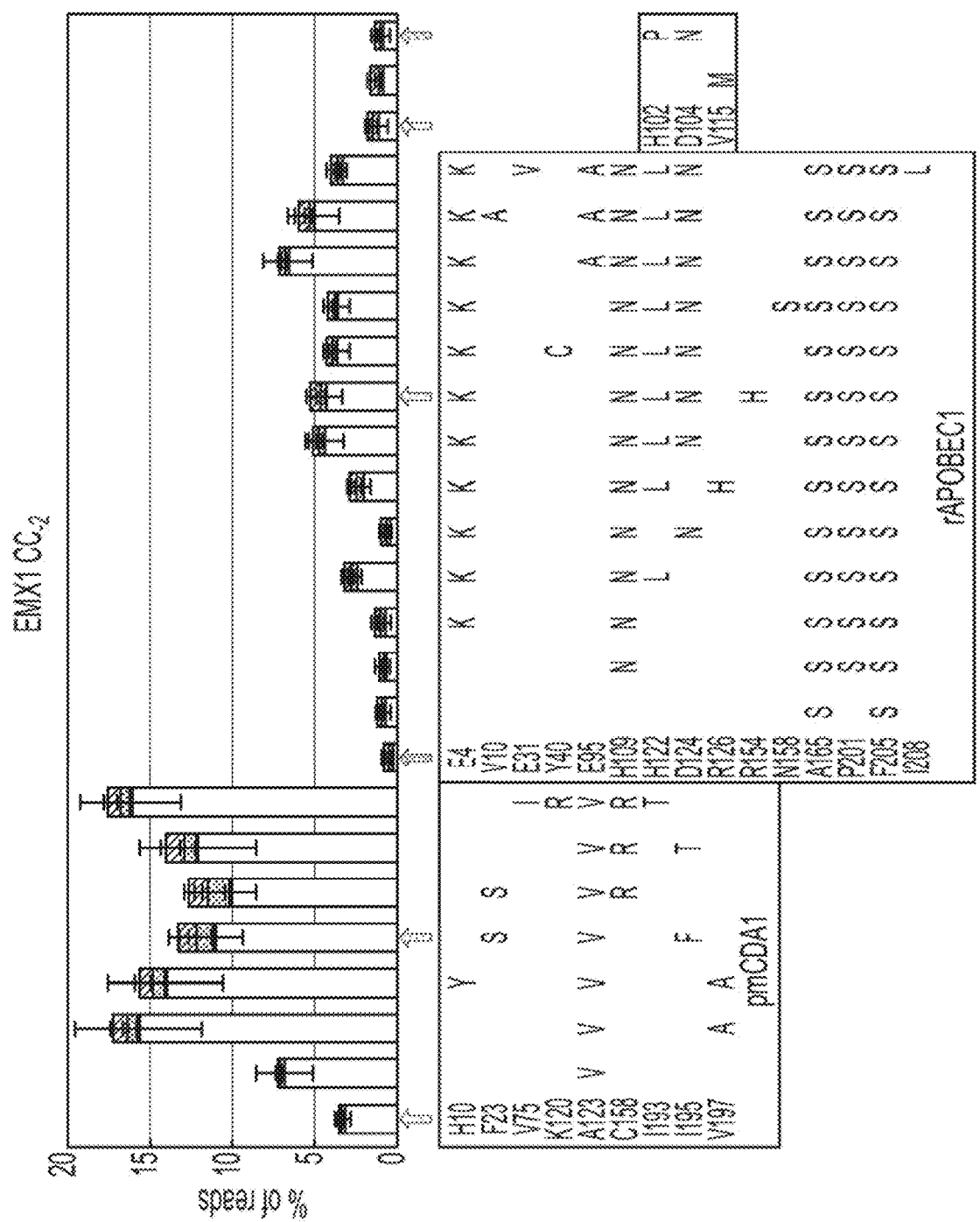
FIG. 94 shows 750 ng transfection HEK cell editing for EMX1 $CC_{-2}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 95:
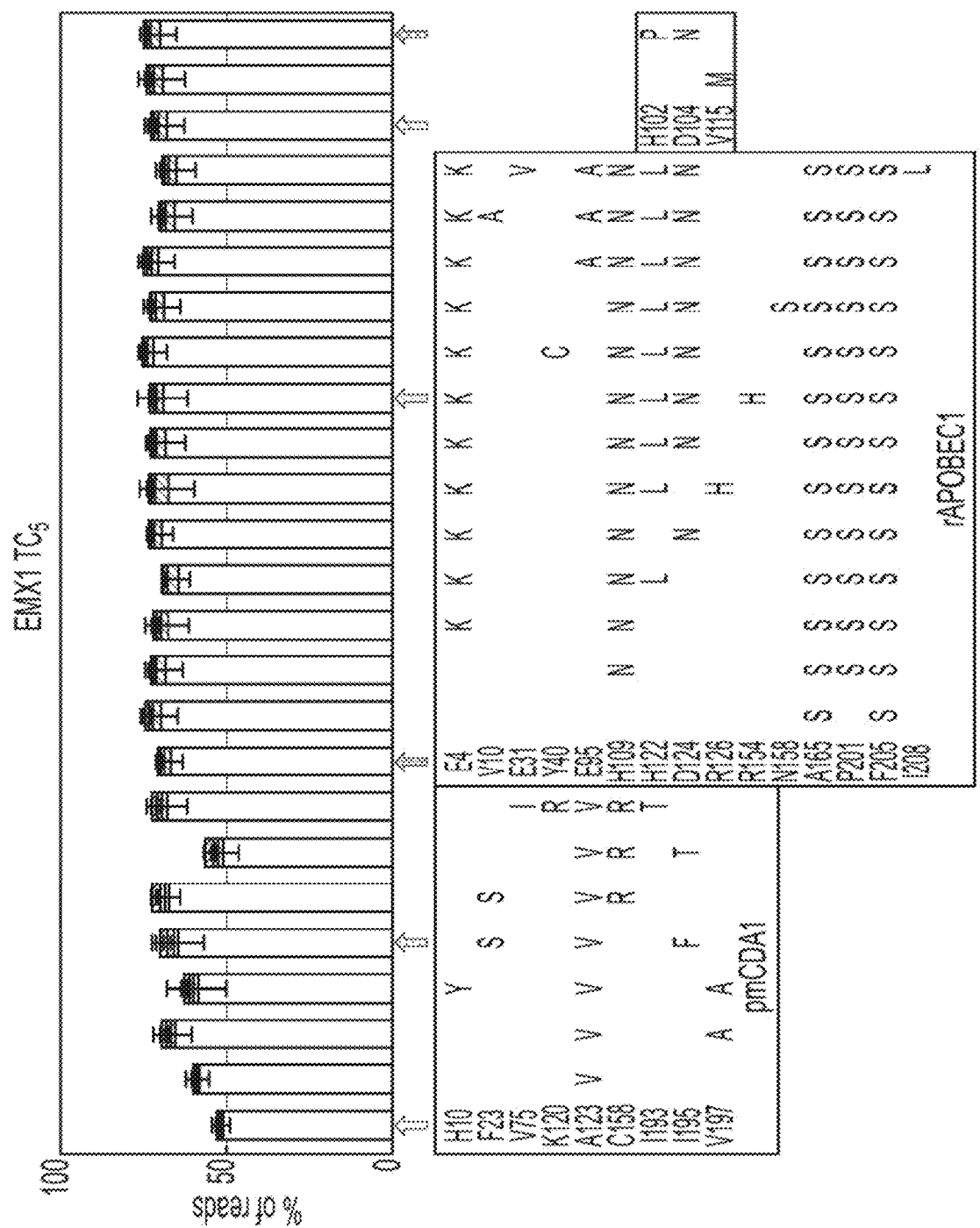
FIG. 95 shows 750 ng transfection HEK cell editing for EMX1 $TC_5$. HEK cell editing: 750 ng base editor, 250 ng guide RNA; lipofected; 3 day incubation. N=3 except where indicated; error bars=SD. Arrows show wild-type and "evo" genotypes selected for further study.
Figure 96:
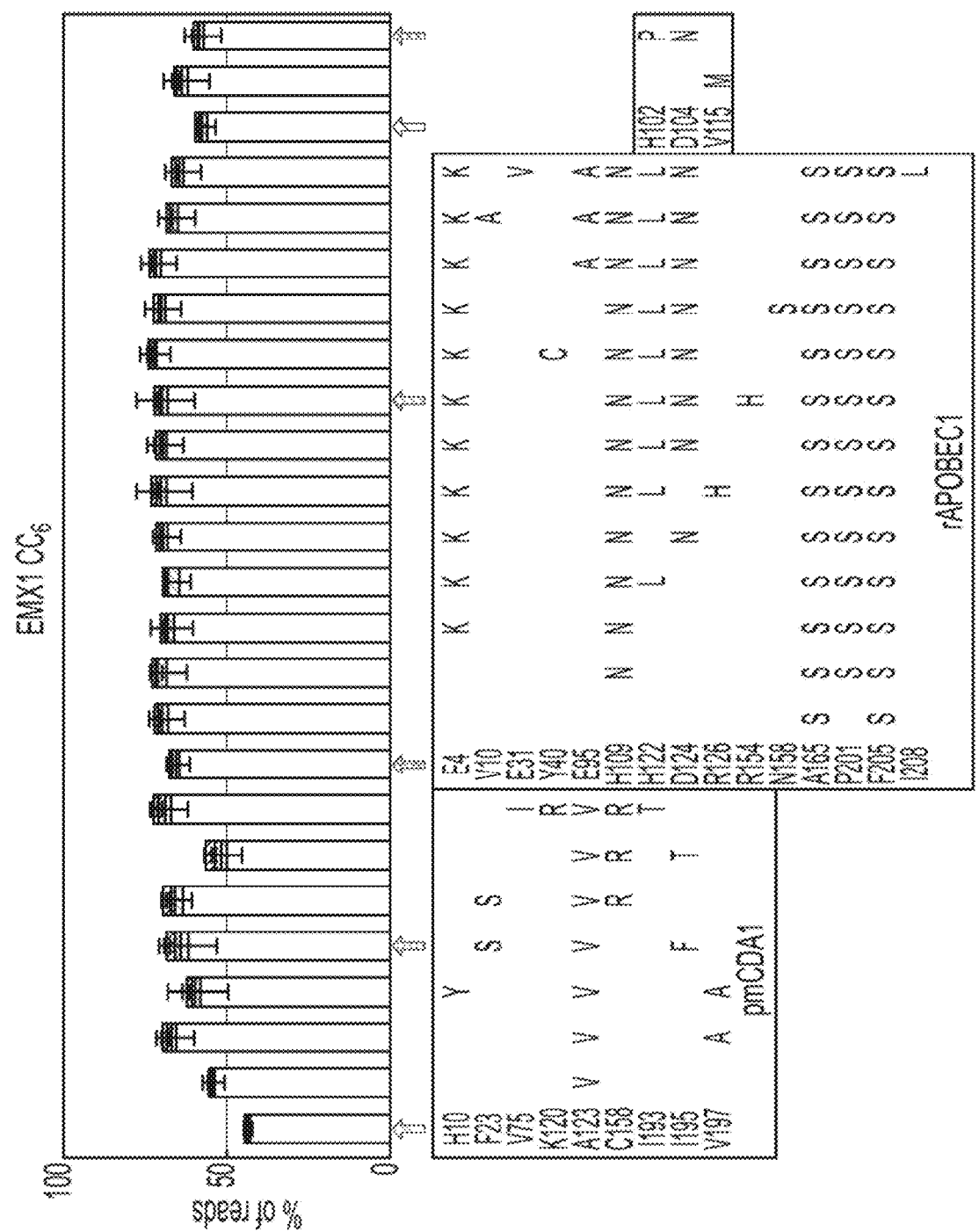
FIG. 96 shows 750 ng transfection HEK cell editing for EMX1 $CC_6$. HEK cell editing: 750 ng base editor, 250 ng guide RNA; lipofected; 3 day incubation. N=3 except where indicated; error bars=SD. Arrows show wild-type and "evo" genotypes selected for further study.
Figure 97:
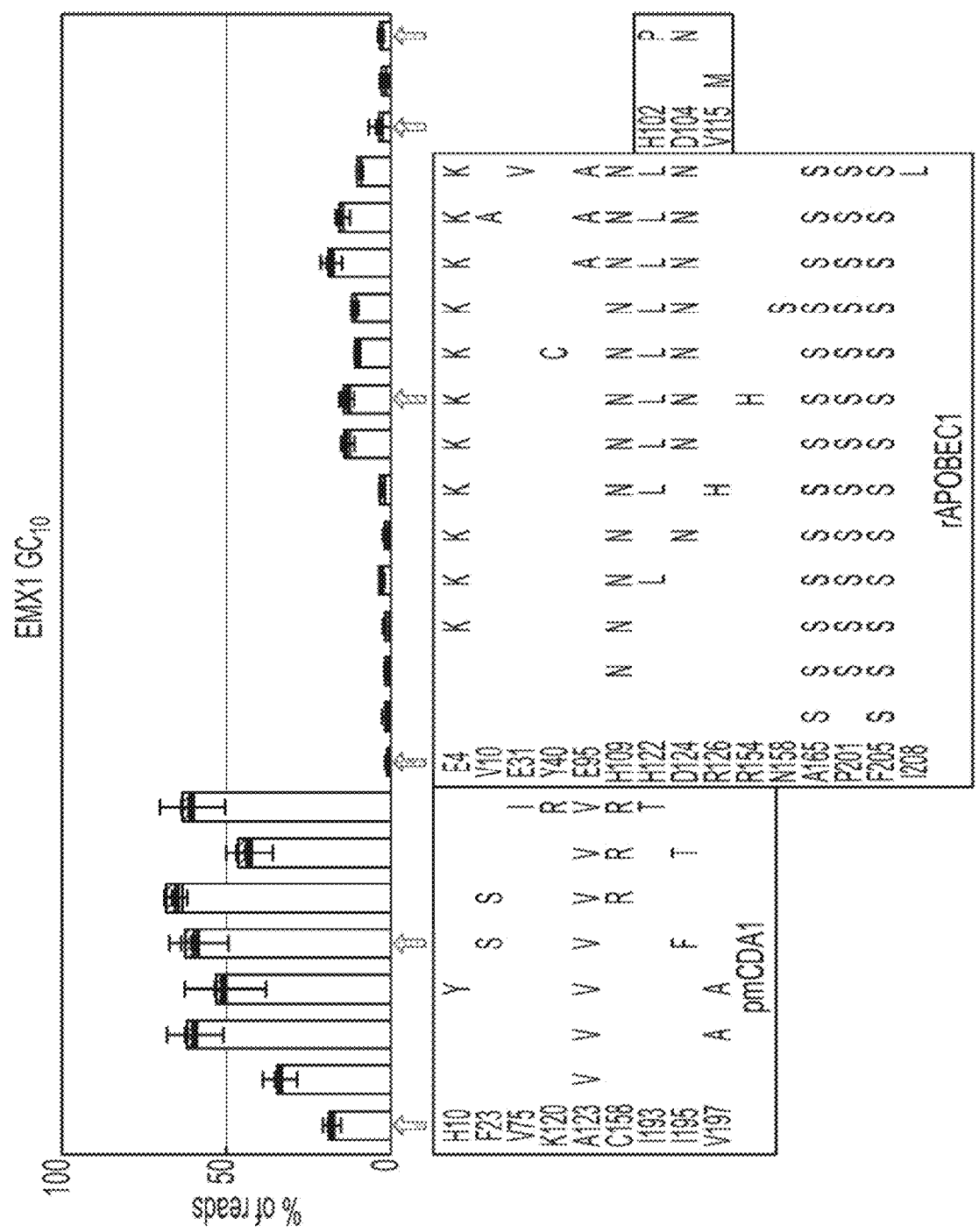
FIG. 97 shows 750 ng transfection HEK cell editing for EMX1 $GC_{10}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 98:
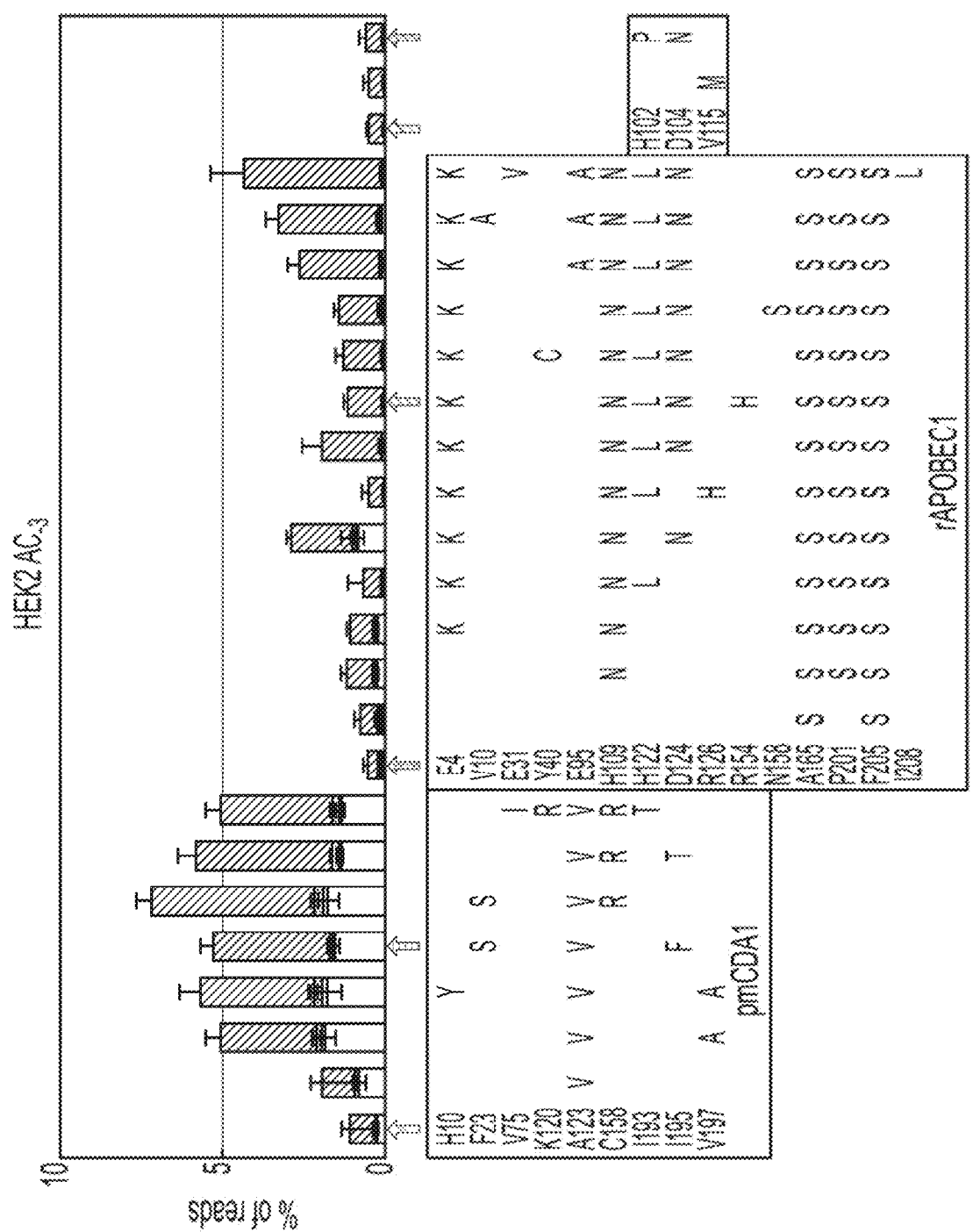
FIG. 98 shows 750 ng transfection HEK cell editing for HEK2 $AC_{-3}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 99:
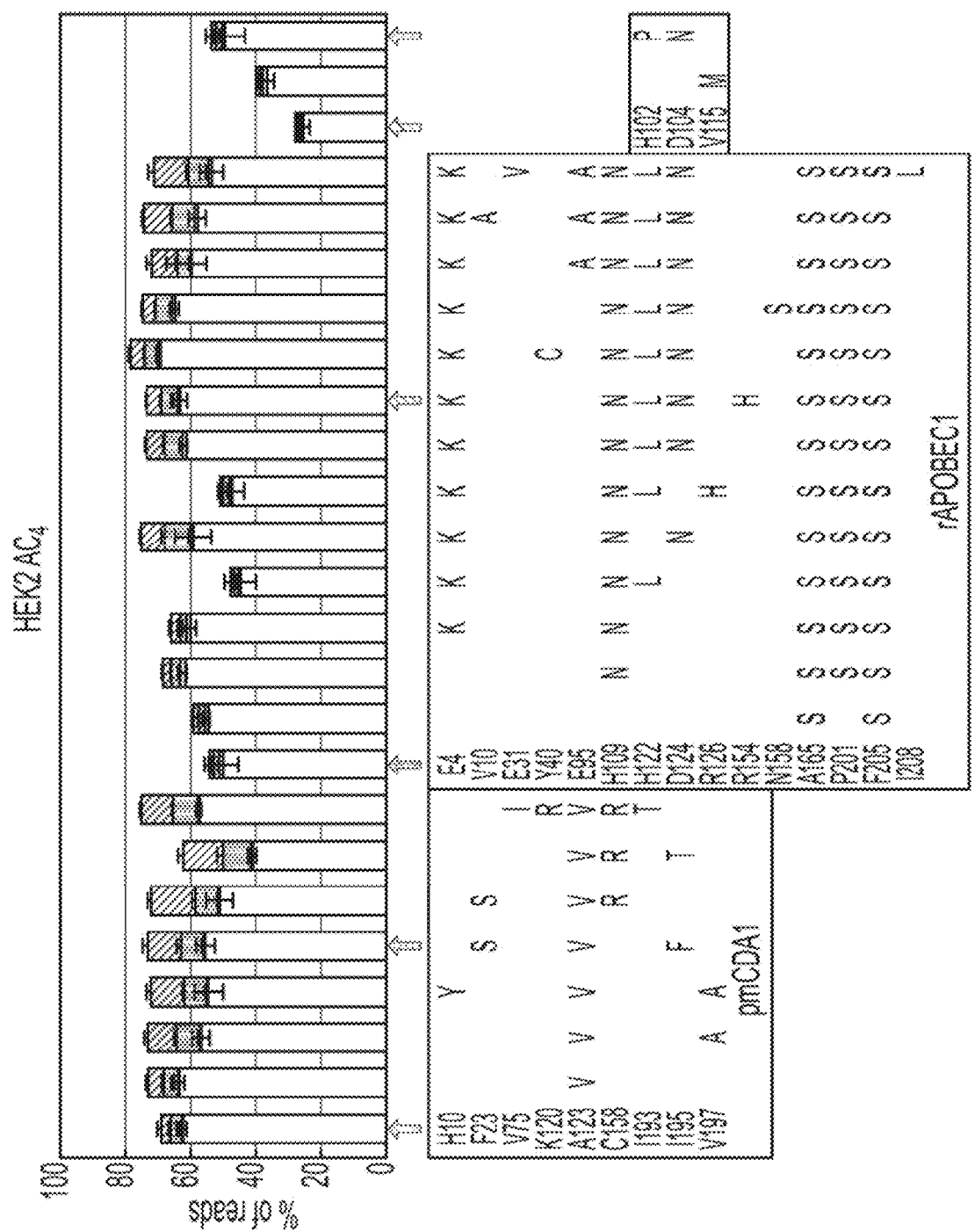
FIG. 99 shows 750 ng transfection HEK cell editing for HEK2 $AC_4$. HEK cell editing: 750 ng base editor, 250 ng guide RNA; lipofected; 3 day incubation. N=3 except where indicated; error bars=SD. Arrows show wild-type and "evo" genotypes selected for further study.
Figure 100:
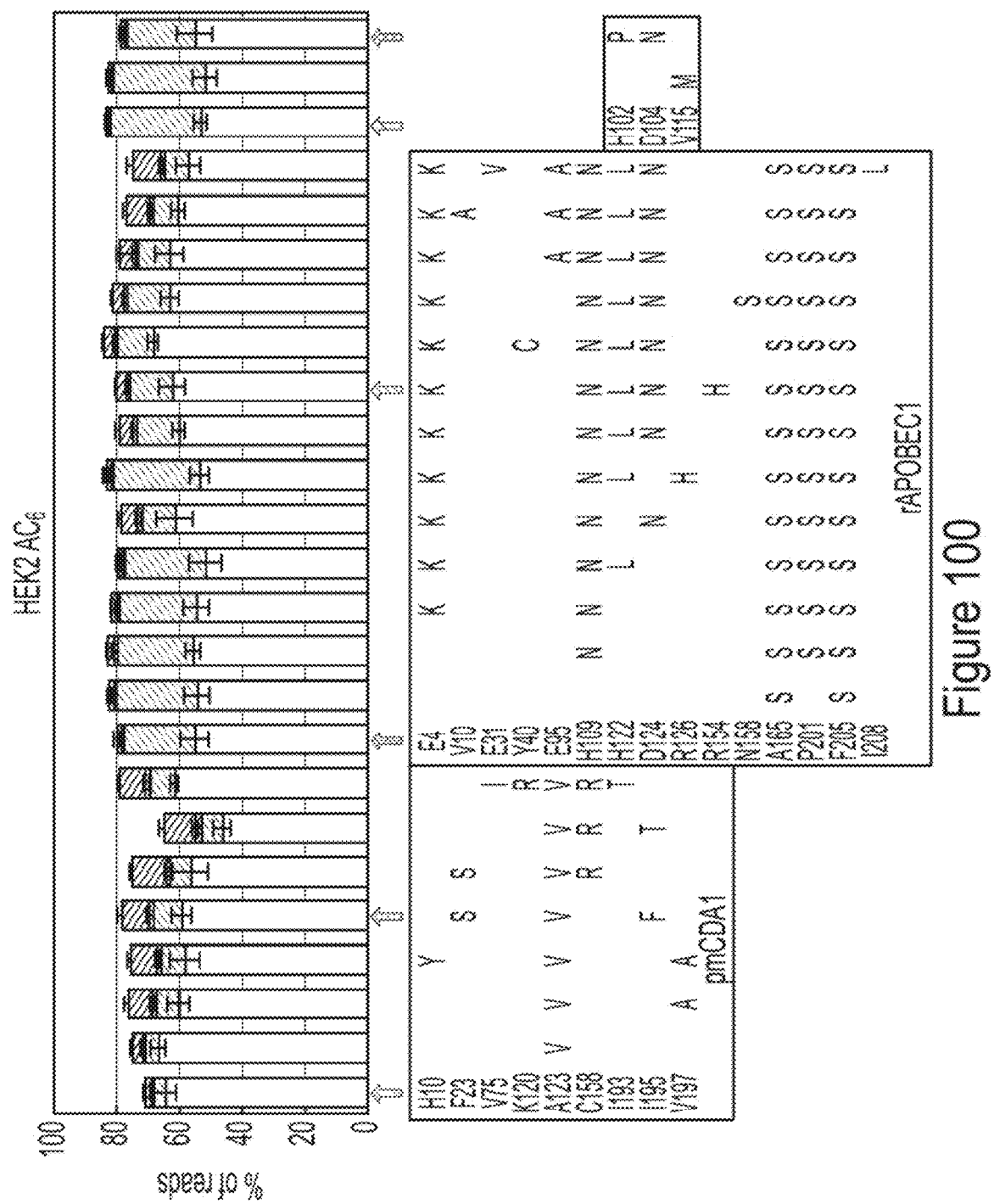
FIG. 100 shows 750 ng transfection HEK cell editing for HEK2 $AC_6$. HEK cell editing: 750 ng base editor, 250 ng guide RNA; lipofected; 3 day incubation. N=3 except where indicated; error bars=SD. Arrows show wild-type and "evo" genotypes selected for further study.
Figure 101:
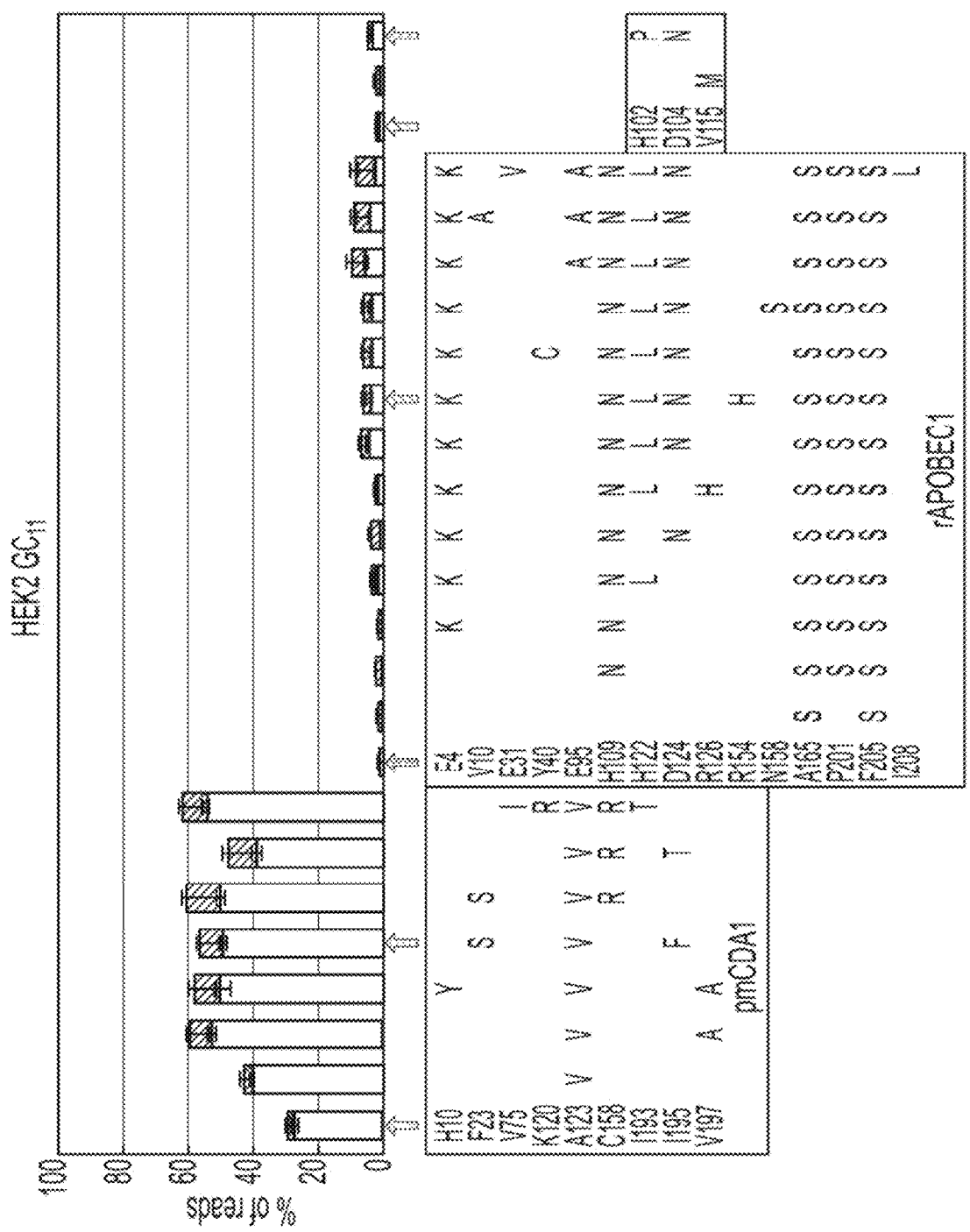
FIG. 101 shows 750 ng transfection HEK cell editing for HEK2 $GC_{11}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 102:
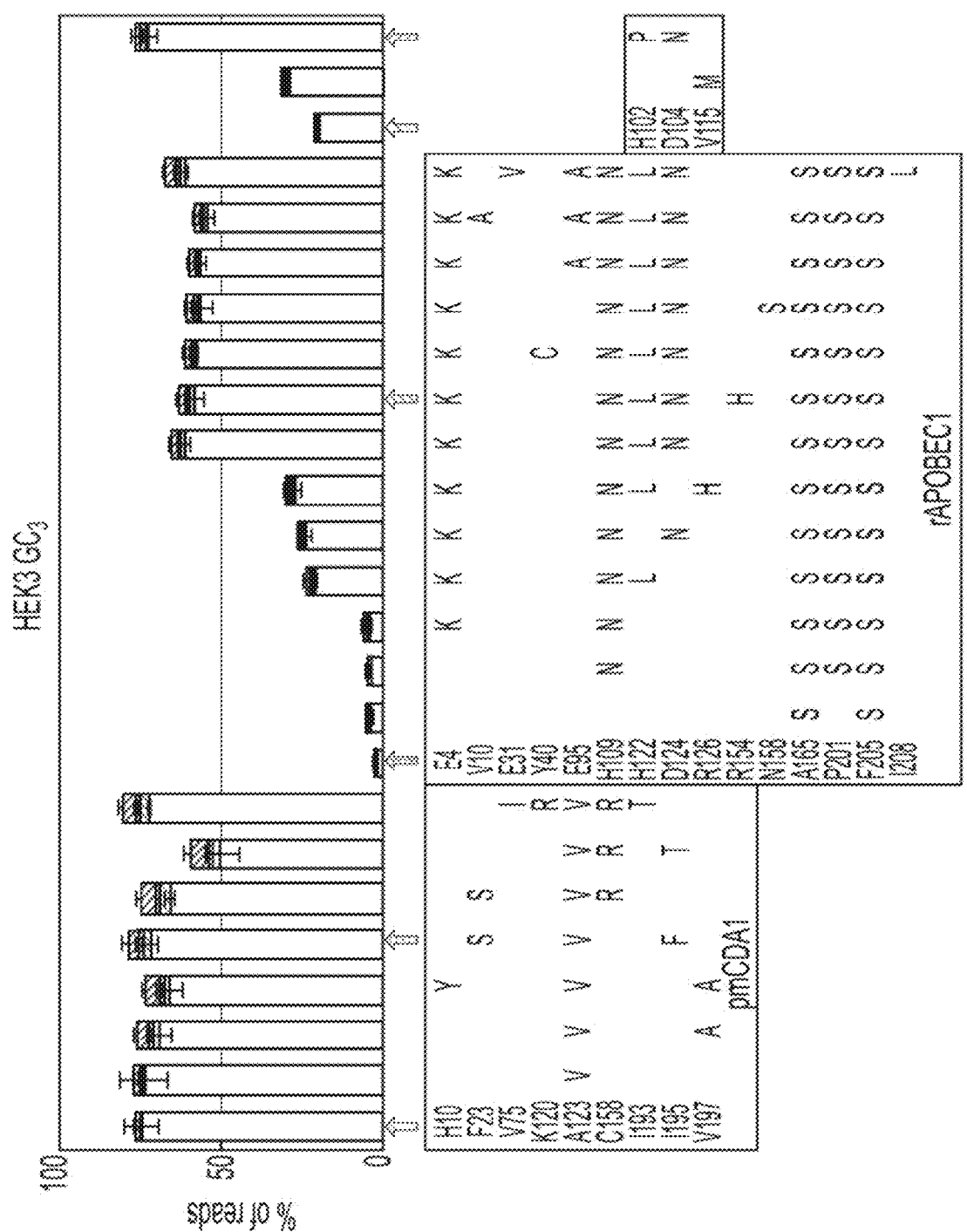
FIG. 102 shows 750 ng transfection HEK cell editing for HEK3 $GC_3$. HEK cell editing: 750 ng base editor, 250 ng guide RNA; lipofected; 3 day incubation. N=3 except where indicated; error bars=SD. Arrows show wild-type and "evo" genotypes selected for further study.
Figure 103:
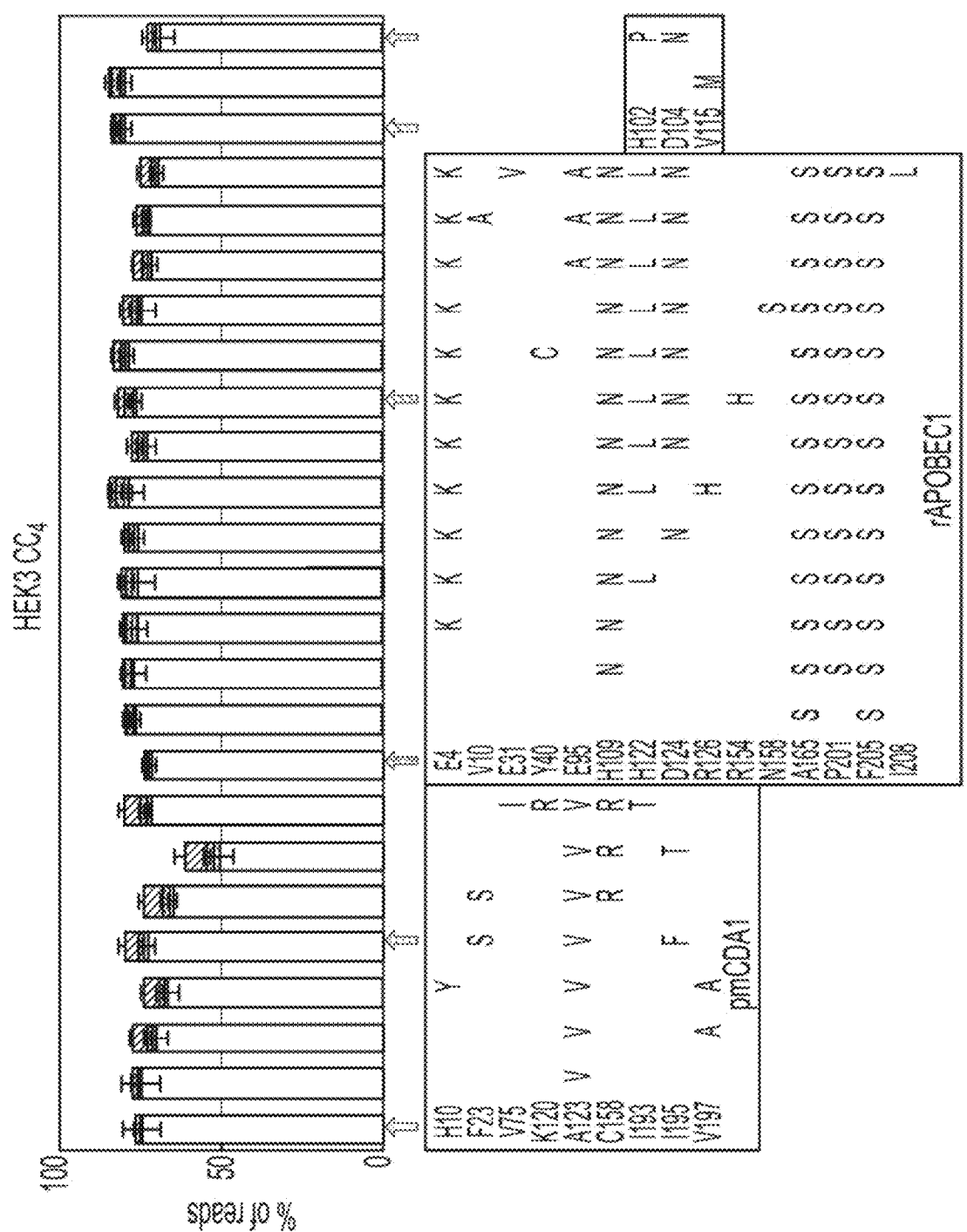
FIG. 103 shows 750 ng transfection HEK cell editing for HEK3 $CC_4$. HEK cell editing: 750 ng base editor, 250 ng guide RNA; lipofected; 3 day incubation. N=3 except where indicated; error bars=SD. Arrows show wild-type and "evo" genotypes selected for further study.
Figure 104:
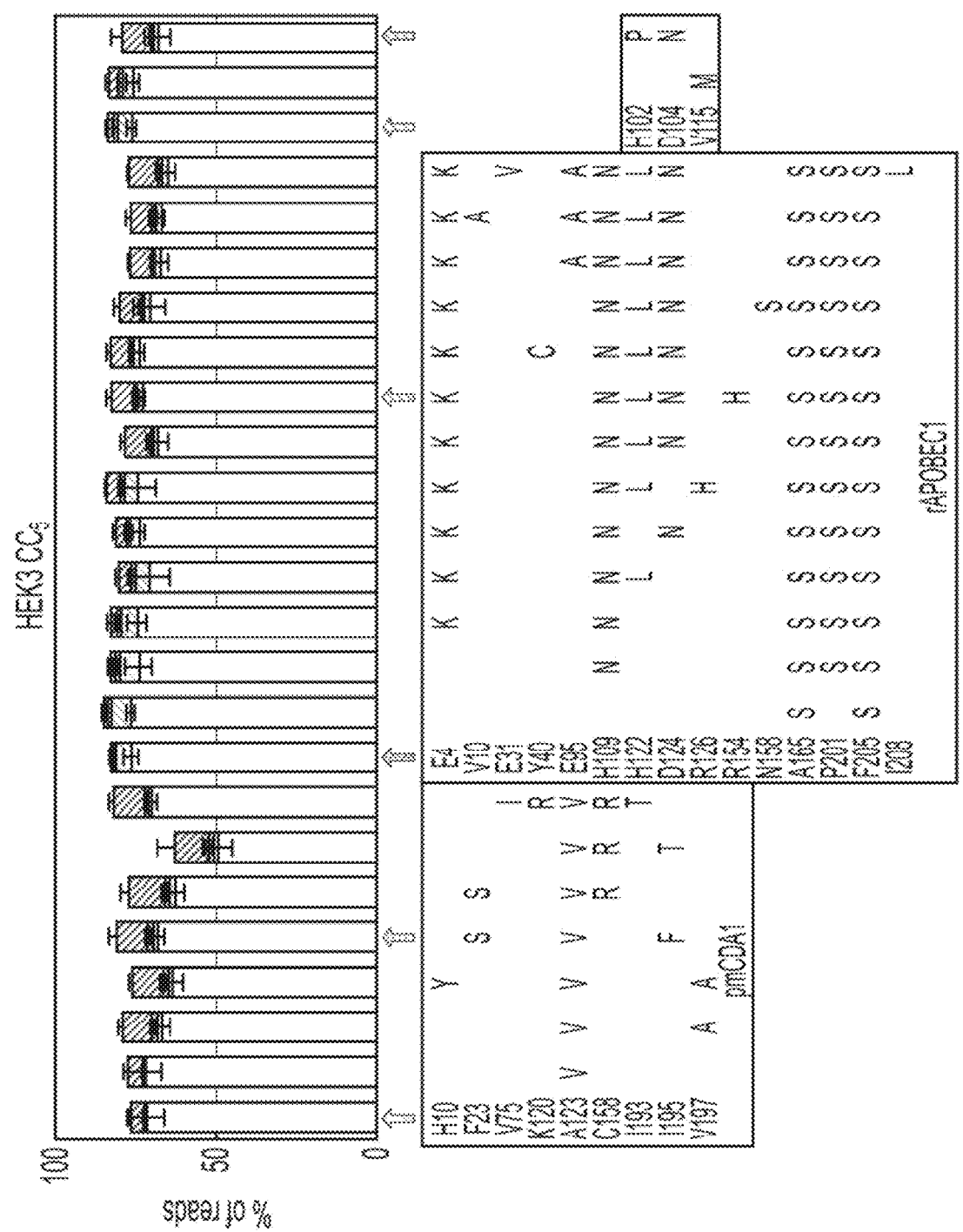
FIG. 104 shows 750 ng transfection HEK cell editing for HEK3 $CC_5$. HEK cell editing: 750 ng base editor, 250 ng guide RNA; lipofected; 3 day incubation. N=3 except where indicated; error bars=SD. Arrows show wild-type and "evo" genotypes selected for further study.
Figure 105:
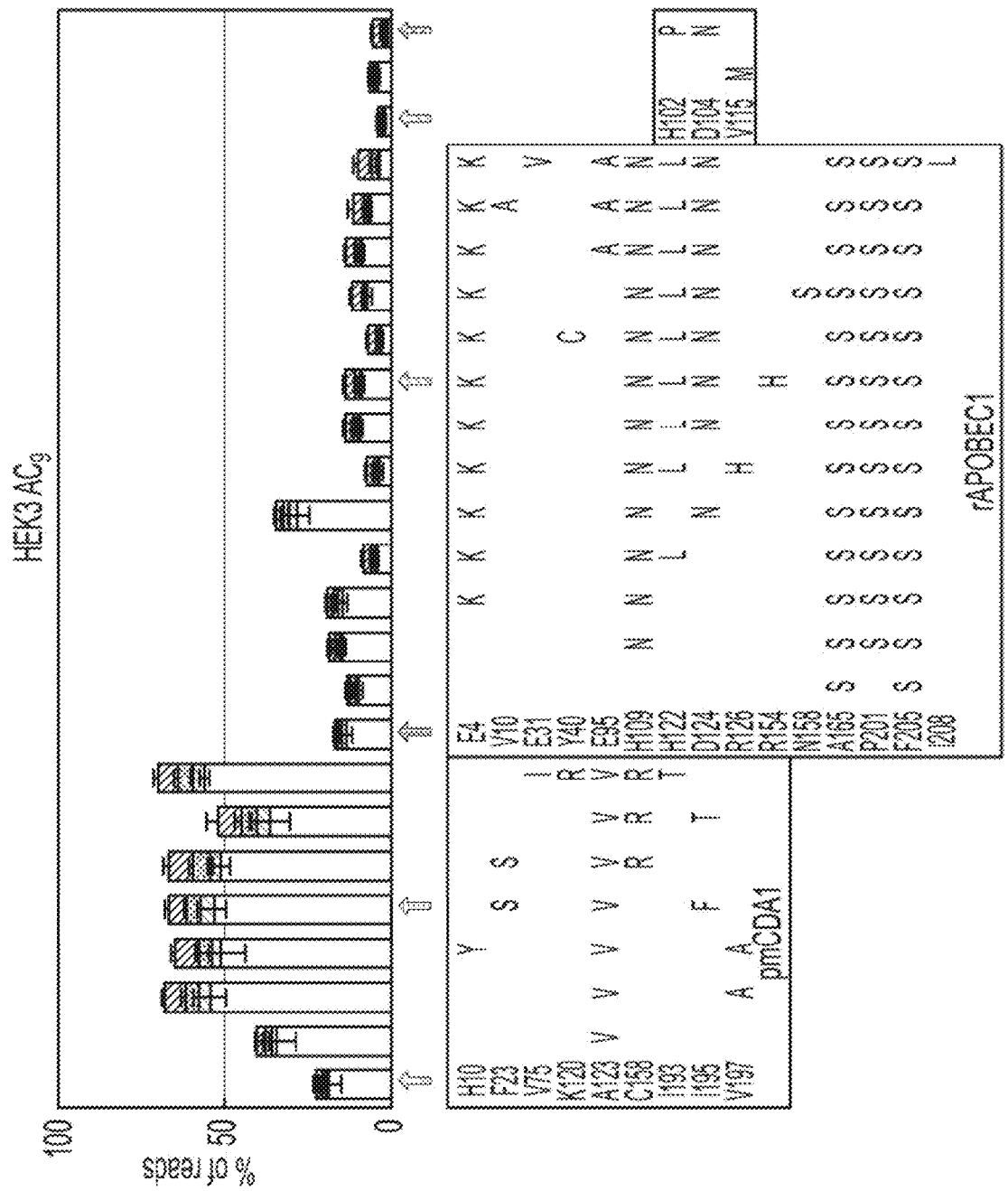
FIG. 105 shows 750 ng transfection HEK cell editing for HEK3 $AC_9$. HEK cell editing: 750 ng base editor, 250 ng guide RNA; lipofected; 3 day incubation. N=3 except where indicated; error bars=SD. Arrows show wild-type and "evo" genotypes selected for further study.
Figure 106:
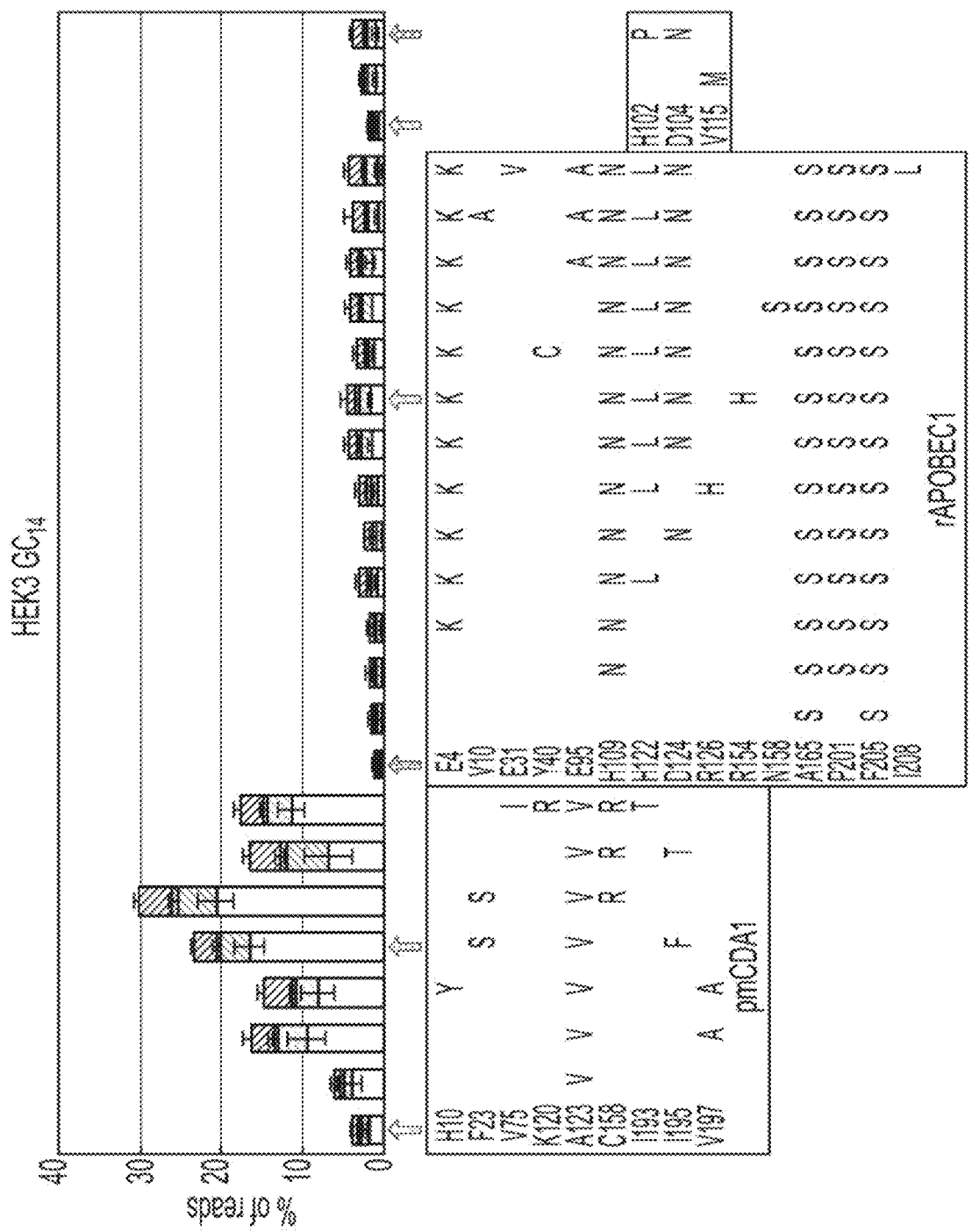
FIG. 106 shows 750 ng transfection HEK cell editing for HEK3 $GC_{14}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 107:
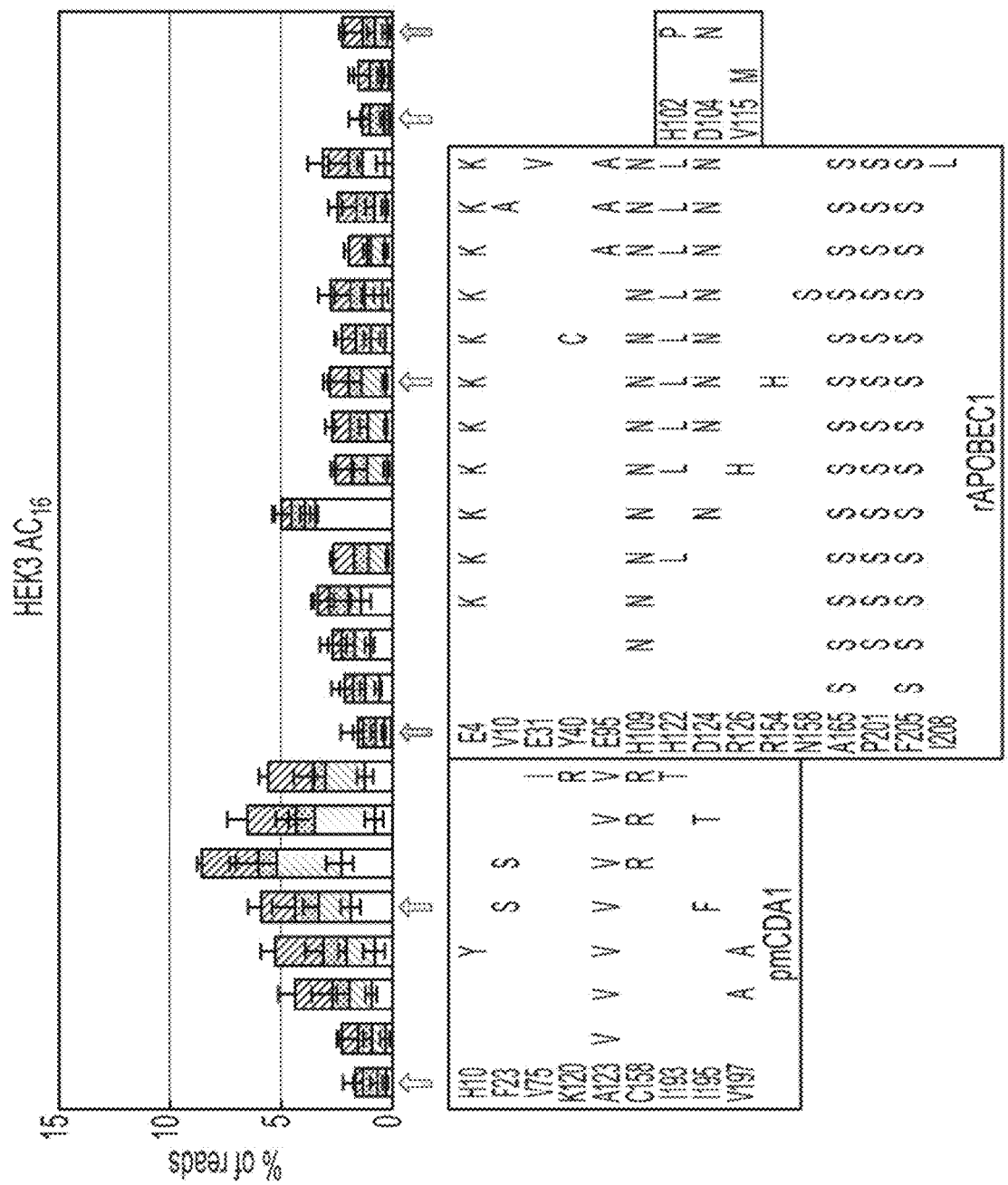
FIG. 107 shows 750 ng transfection HEK cell editing for HEK3 $AC_{16}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 108:
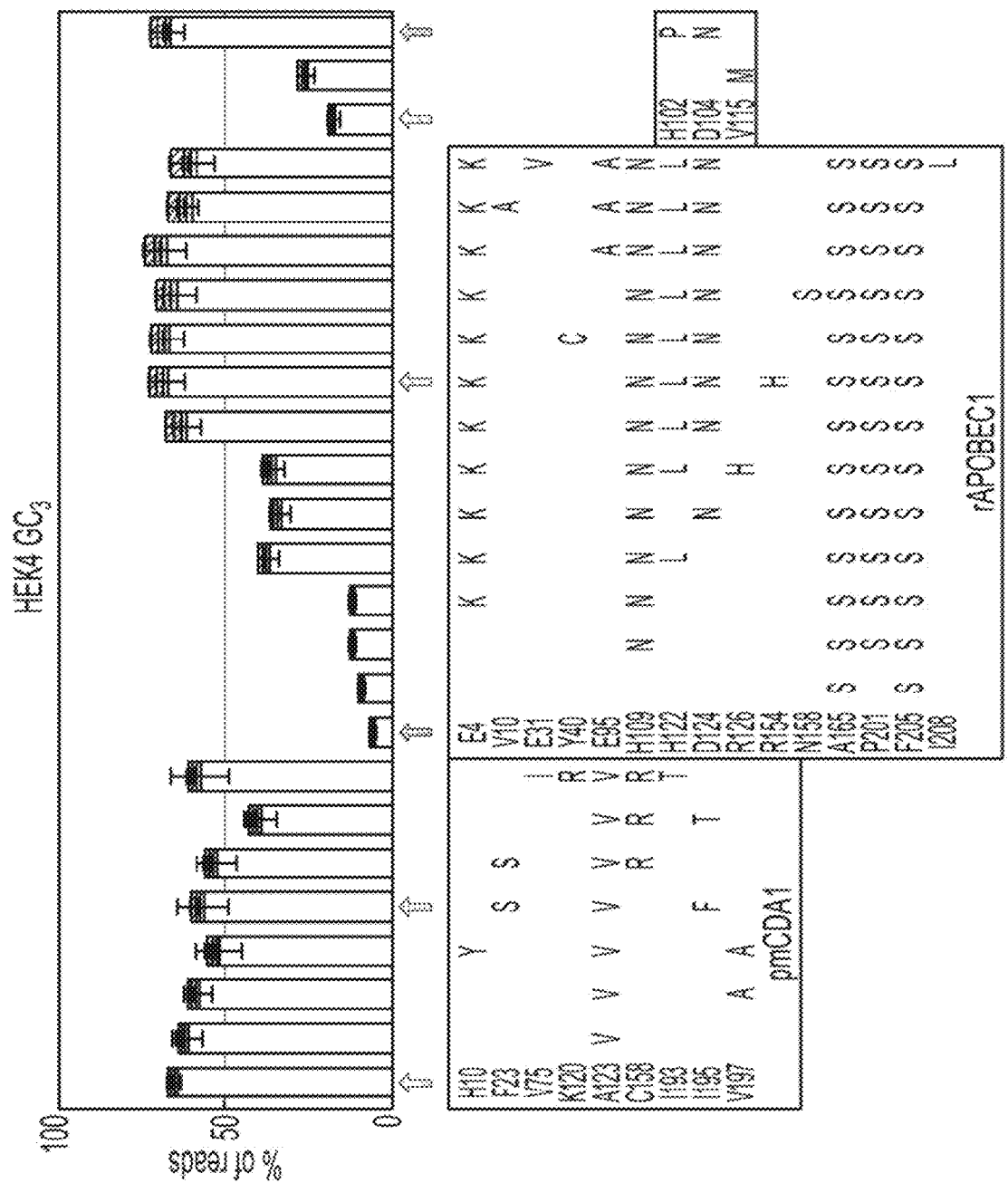
FIG. 108 shows 750 ng transfection HEK cell editing for HEK4 $GC_3$. HEK cell editing: 750 ng base editor, 250 ng guide RNA; lipofected; 3 day incubation. N=3 except where indicated; error bars=SD. Arrows show wild-type and "evo" genotypes selected for further study.
Figure 109:
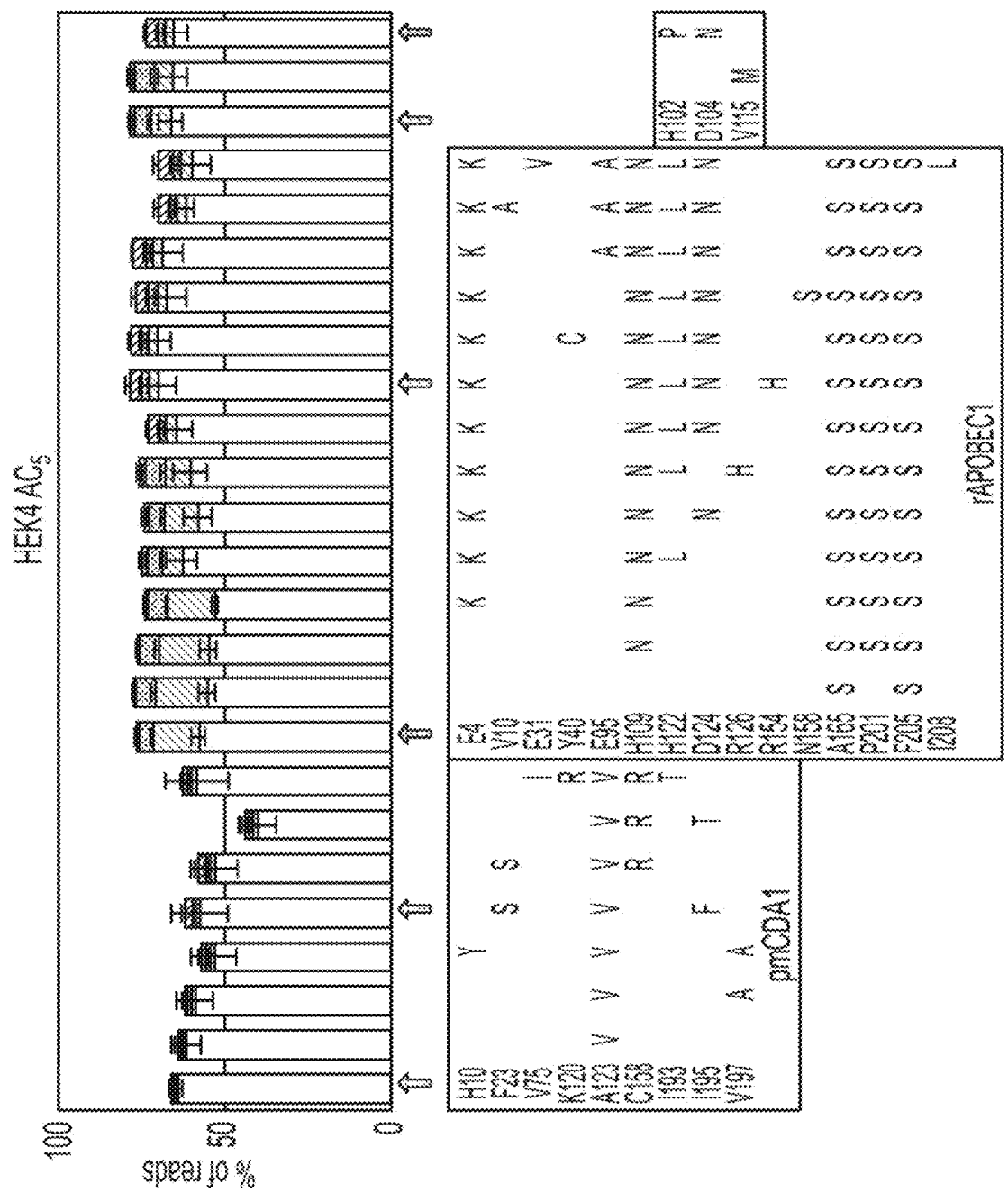
FIG. 109 shows 750 ng transfection HEK cell editing for HEK4 $AC_5$. HEK cell editing: 750 ng base editor, 250 ng guide RNA; lipofected; 3 day incubation. N=3 except where indicated; error bars=SD. Arrows show wild-type and "evo" genotypes selected for further study.
Figure 110:
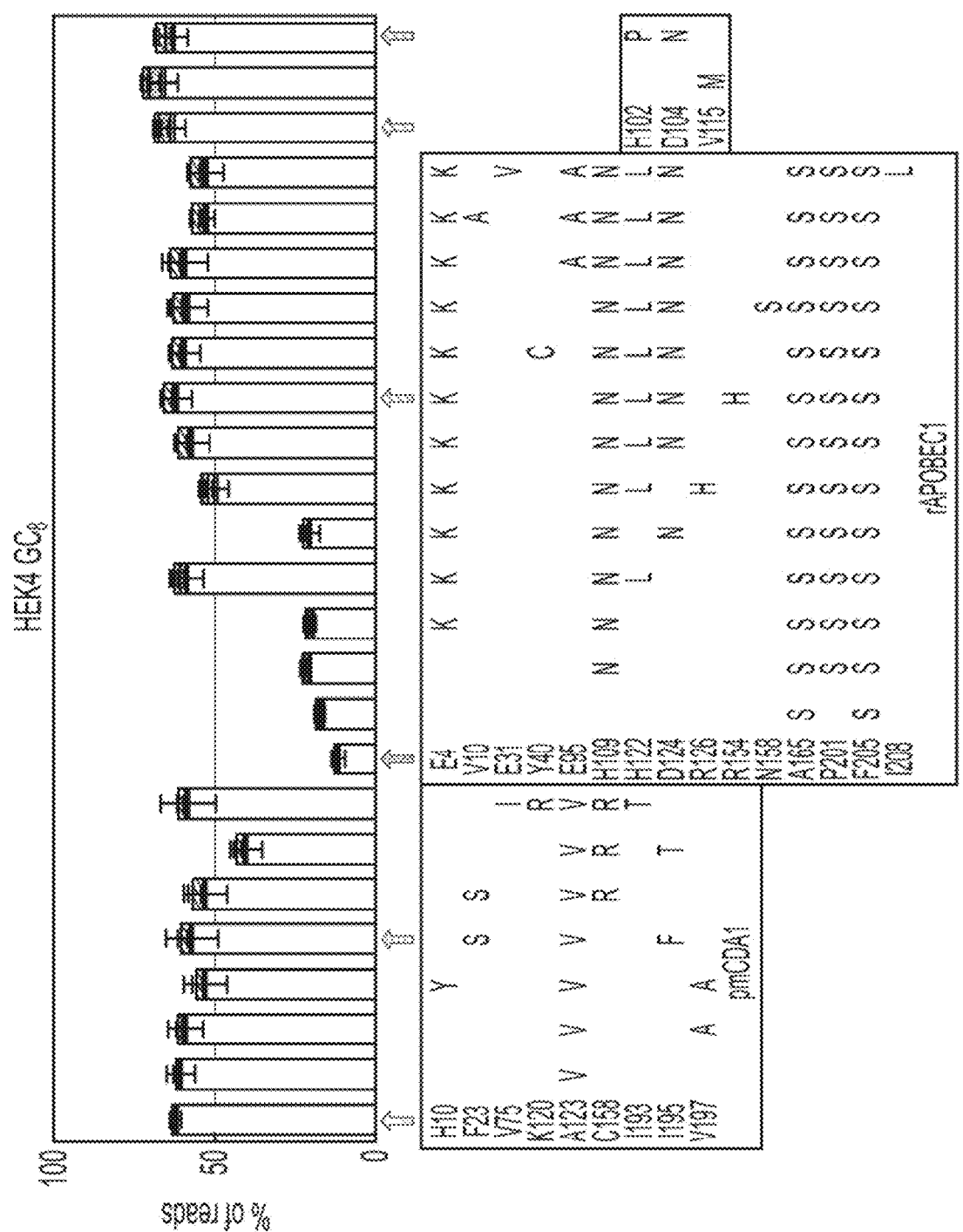
FIG. 110 shows 750 ng transfection HEK cell editing for HEK4 $GC_5$. HEK cell editing: 750 ng base editor, 250 ng guide RNA; lipofected; 3 day incubation. N=3 except where indicated; error bars=SD. Arrows show wild-type and "evo" genotypes selected for further study.
Figure 111:
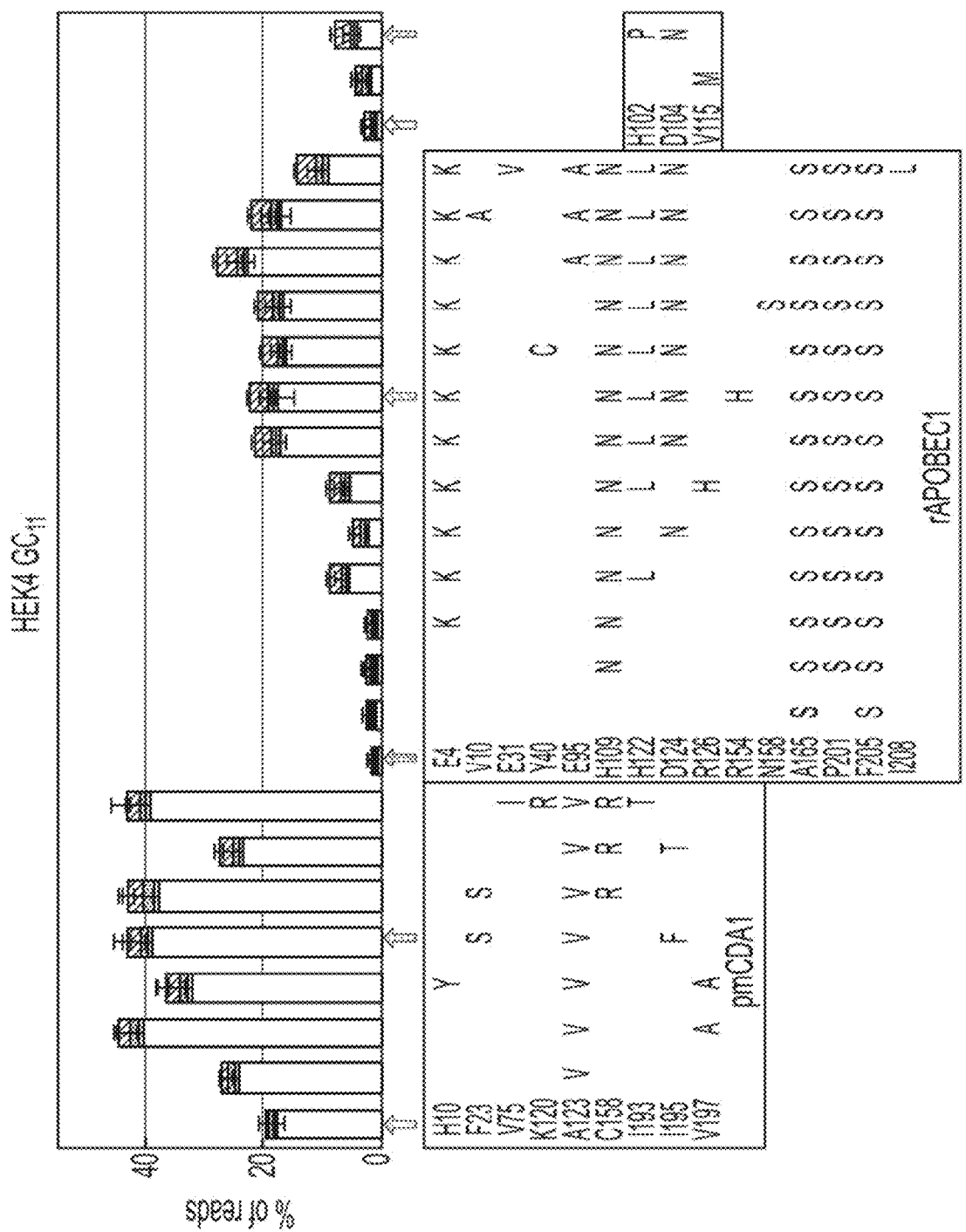
FIG. 111 shows 750 ng transfection HEK cell editing for HEK4 $GC_{11}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 112:
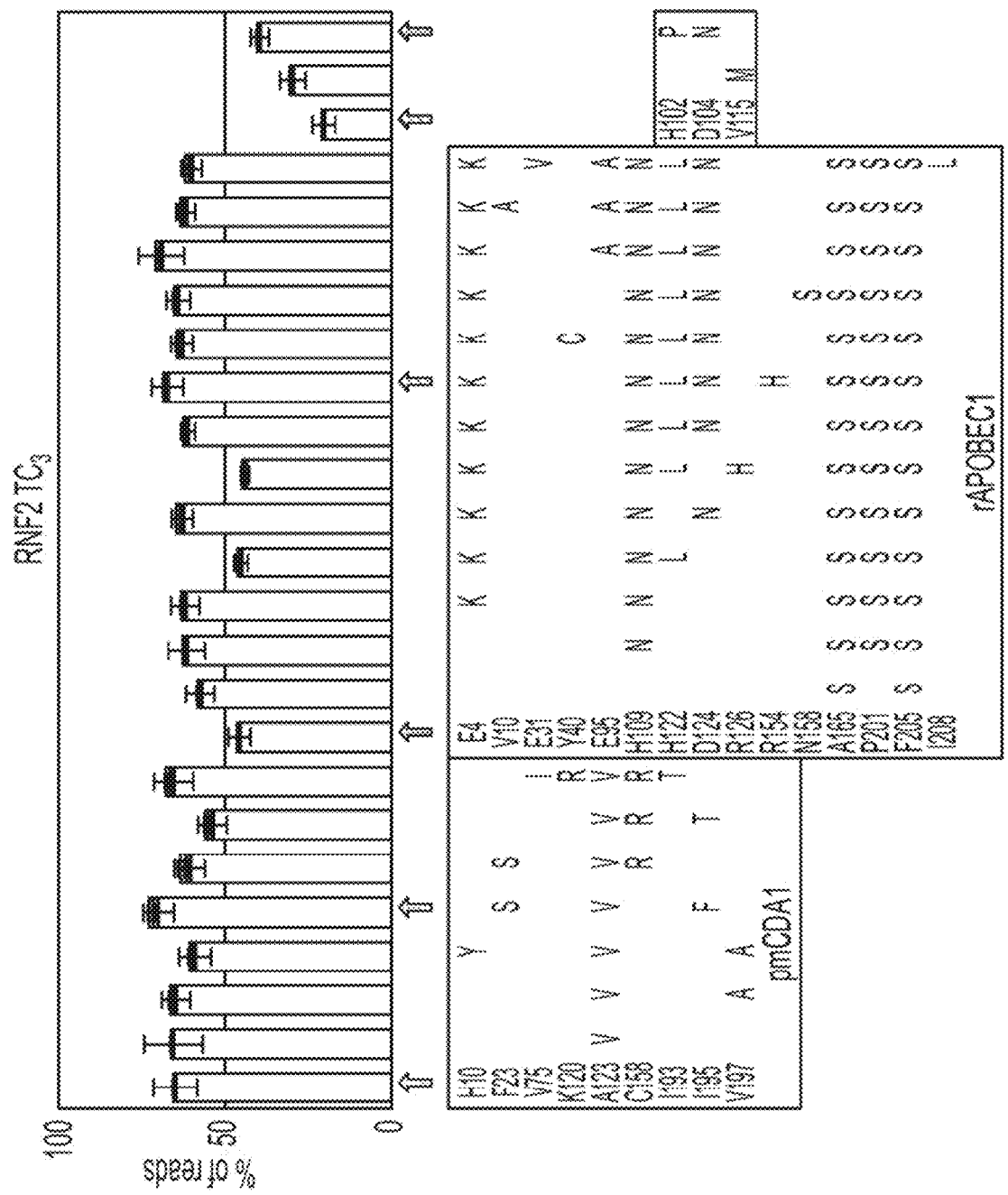
FIG. 112 shows 750 ng transfection HEK cell editing for RNF2 $TC_3$. HEK cell editing: 750 ng base editor, 250 ng guide RNA; lipofected; 3 day incubation. N=3 except where indicated; error bars=SD. Arrows show wild-type and "evo" genotypes selected for further study.
Figure 113:
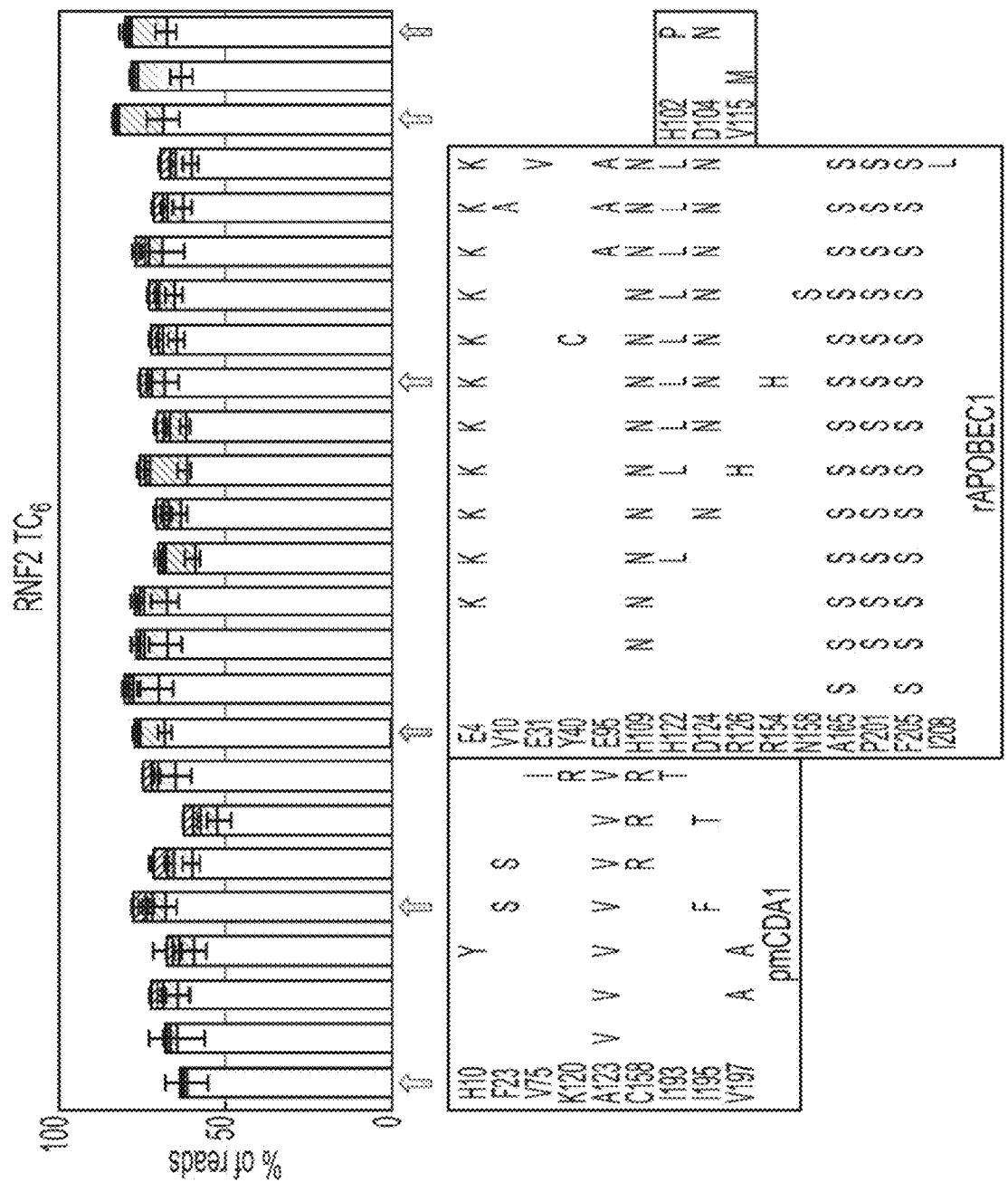
FIG. 113 shows 750 ng transfection HEK cell editing for RNF2 $TC_6$. HEK cell editing: 750 ng base editor, 250 ng guide RNA; lipofected; 3 day incubation. N=3 except where indicated; error bars=SD. Arrows show wild-type and "evo" genotypes selected for further study.
Figure 114:
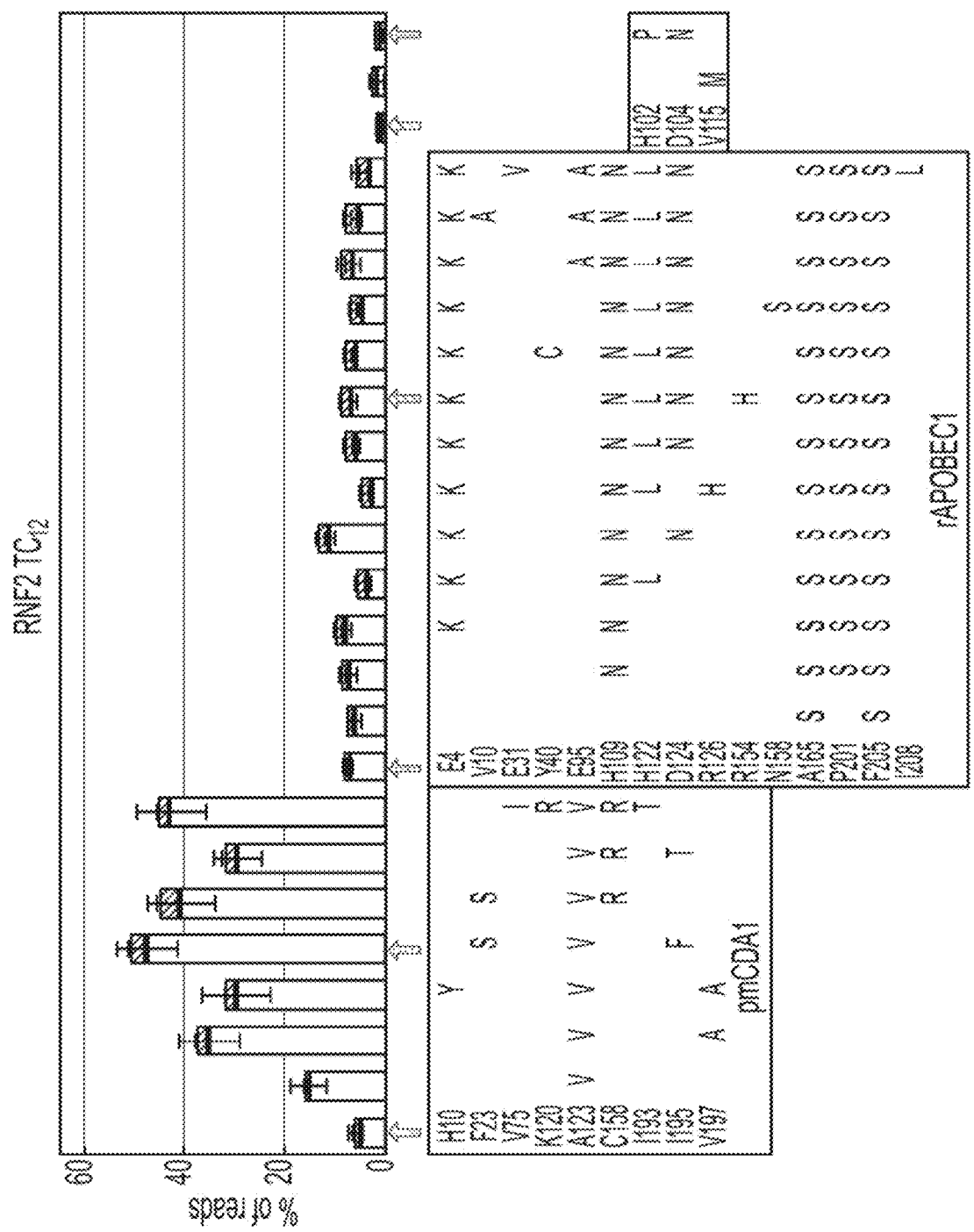
FIG. 114 shows 750 ng transfection HEK cell editing for RNF2 $TC_{12}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 115:
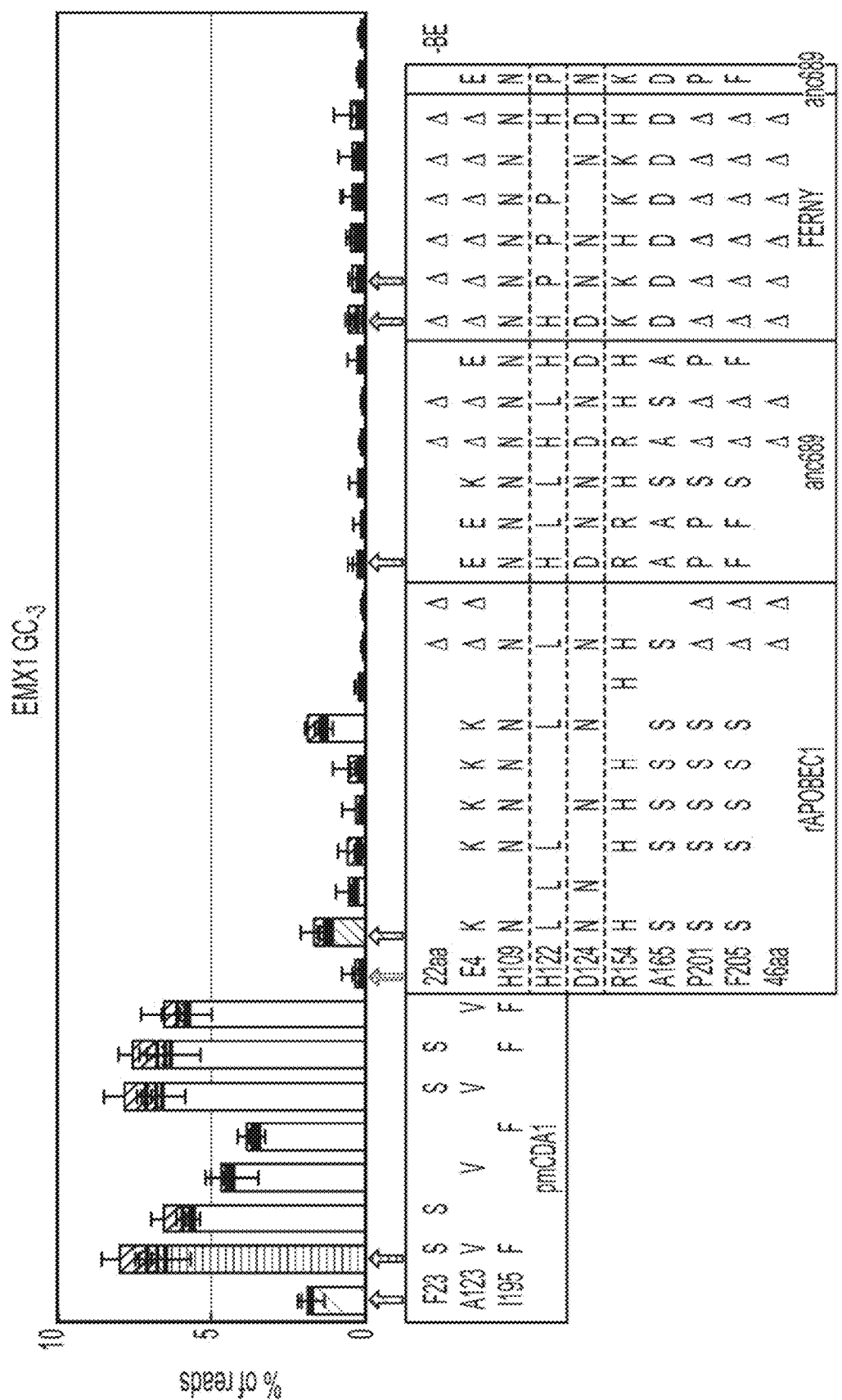
FIG. 115 shows 750 ng transfection HEK cell editing for EMX1 $GC_{-3}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 116:
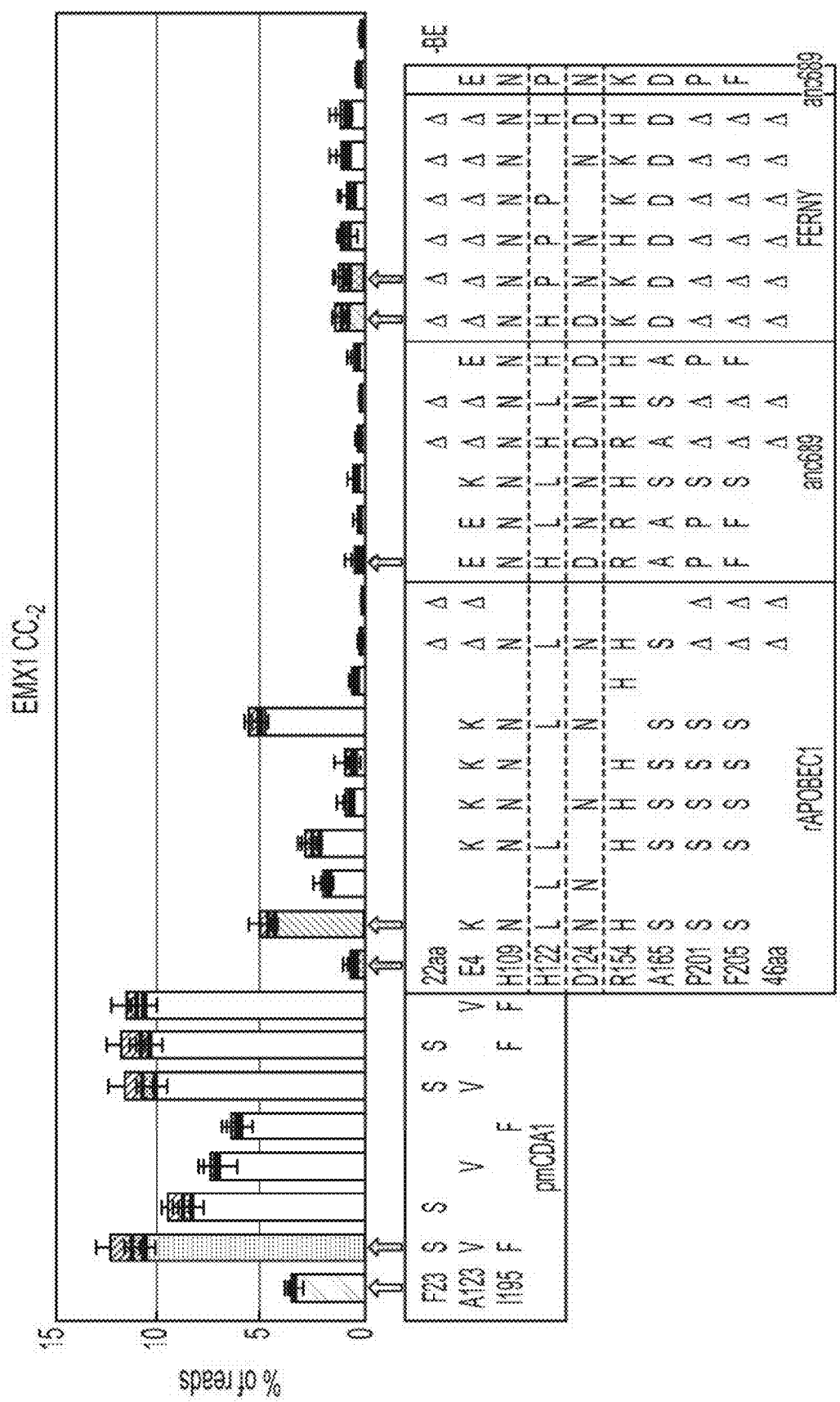
FIG. 116 shows 750 ng transfection HEK cell editing for EMX1 $CC_{-2}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 117:
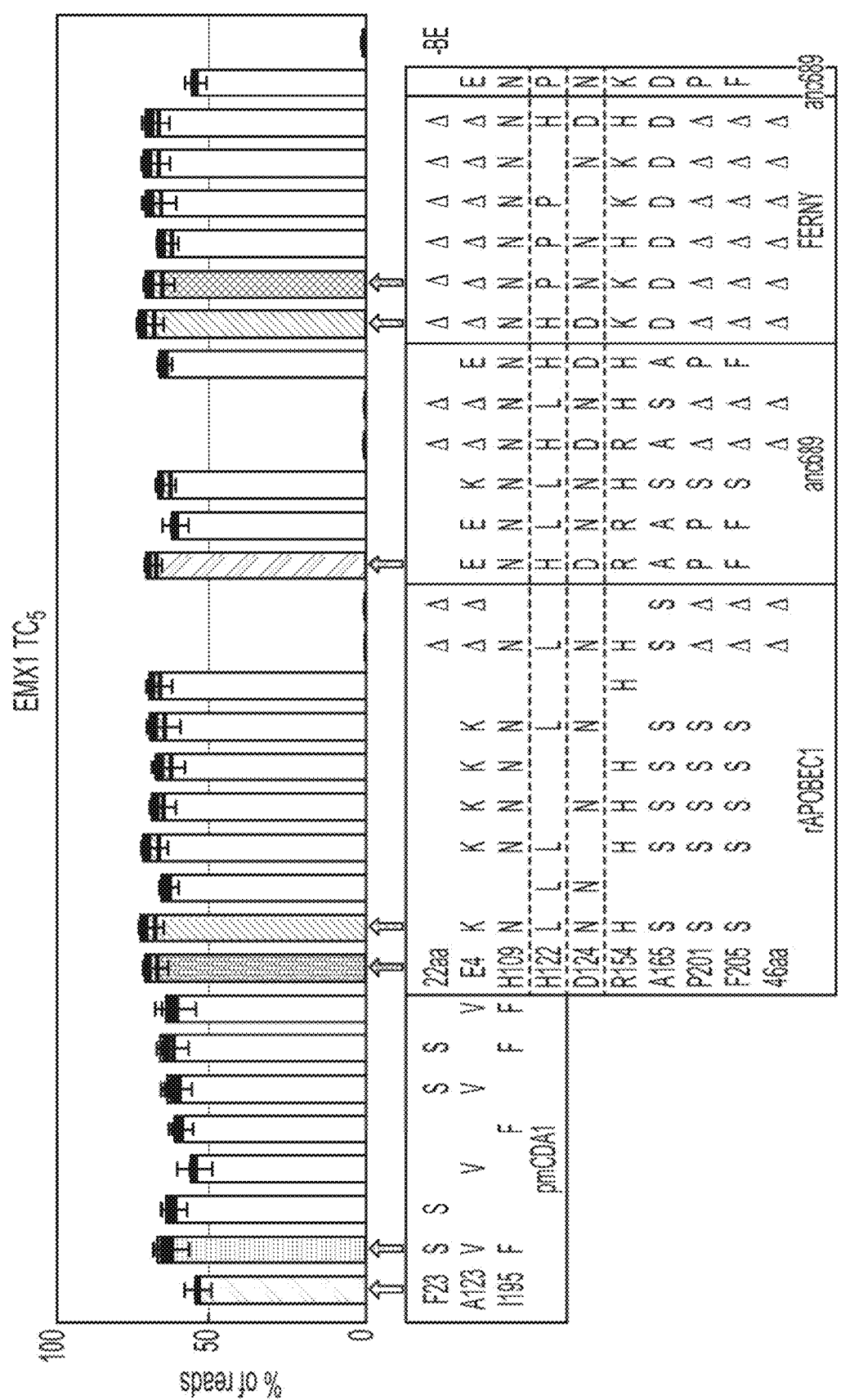
FIG. 117 shows 750 ng transfection HEK cell editing for EMX1 $TC_5$. HEK cell editing: 750 ng base editor, 250 ng guide RNA; lipofected; 3 day incubation. N=3 except where indicated; error bars=SD. Arrows show wild-type and "evo" genotypes selected for further study.
Figure 118:
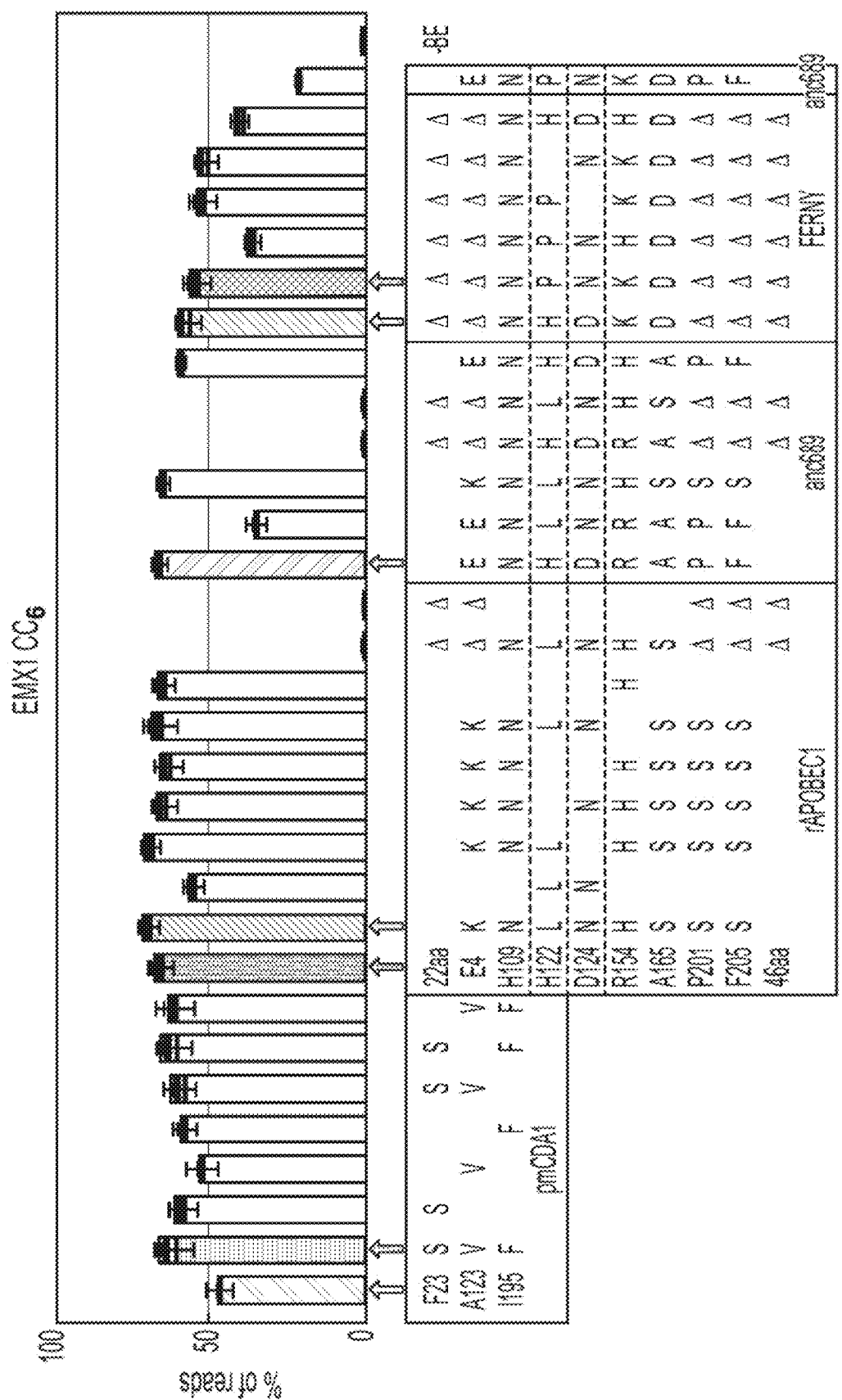
FIG. 118 shows 750 ng transfection HEK cell editing for EMX1 $CC_6$. HEK cell editing: 750 ng base editor, 250 ng guide RNA; lipofected; 3 day incubation. N=3 except where indicated; error bars=SD. Arrows show wild-type and "evo" genotypes selected for further study.
Figure 119:
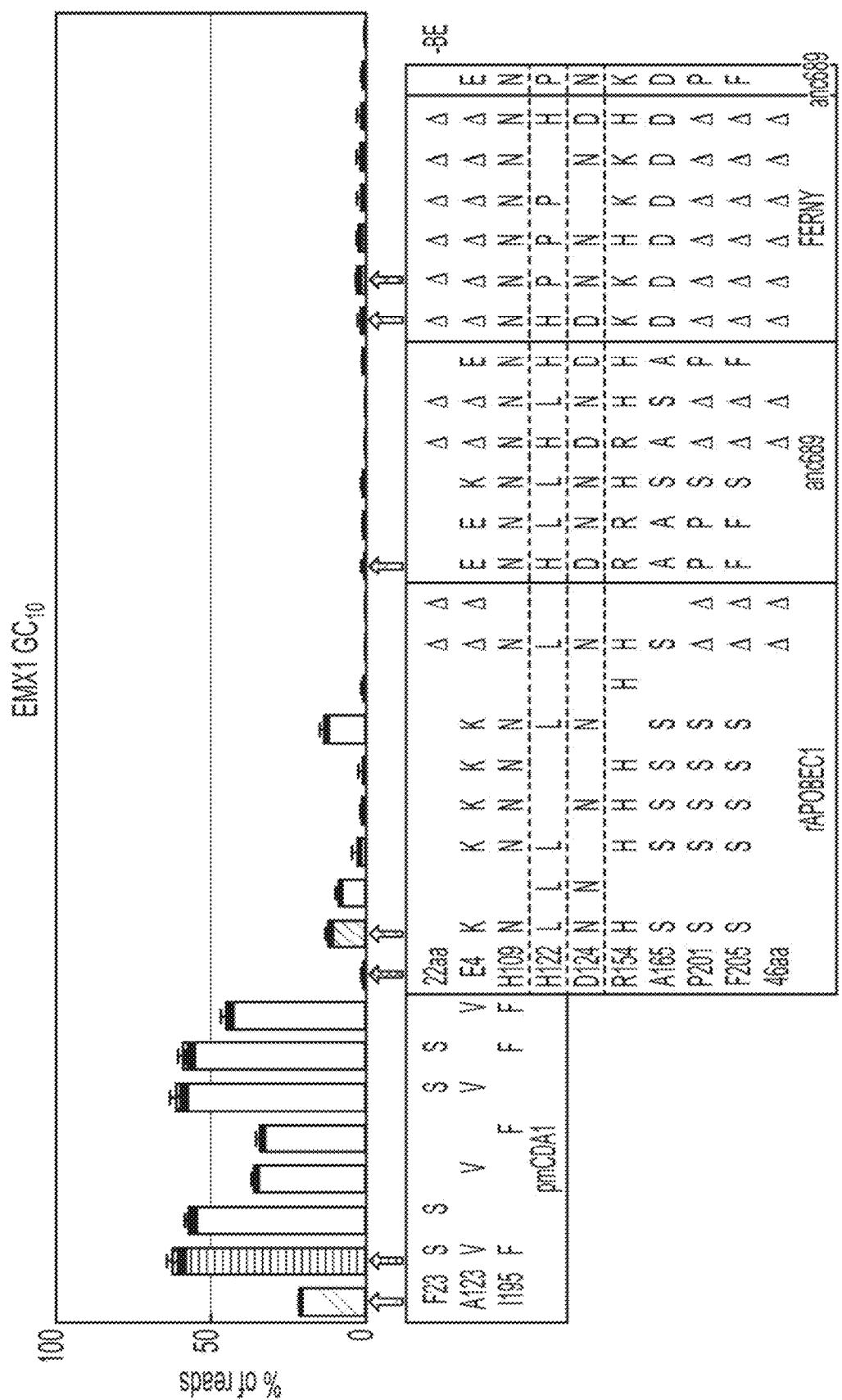
FIG. 119 shows 750 ng transfection HEK cell editing for EMX1 $GC_{10}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 120:
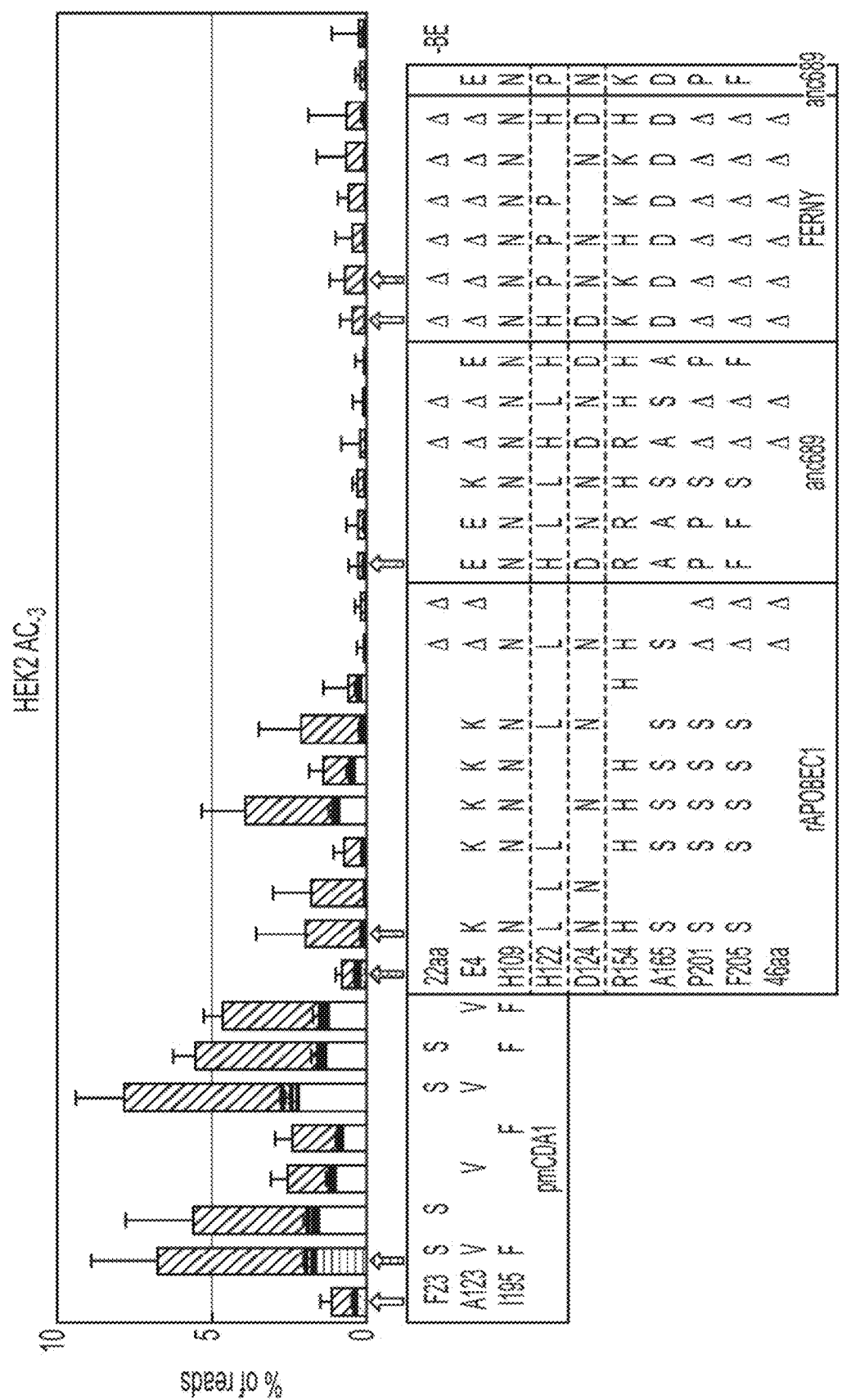
FIG. 120 shows 750 ng transfection HEK cell editing for HEK2 $AC_{-3}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 121:
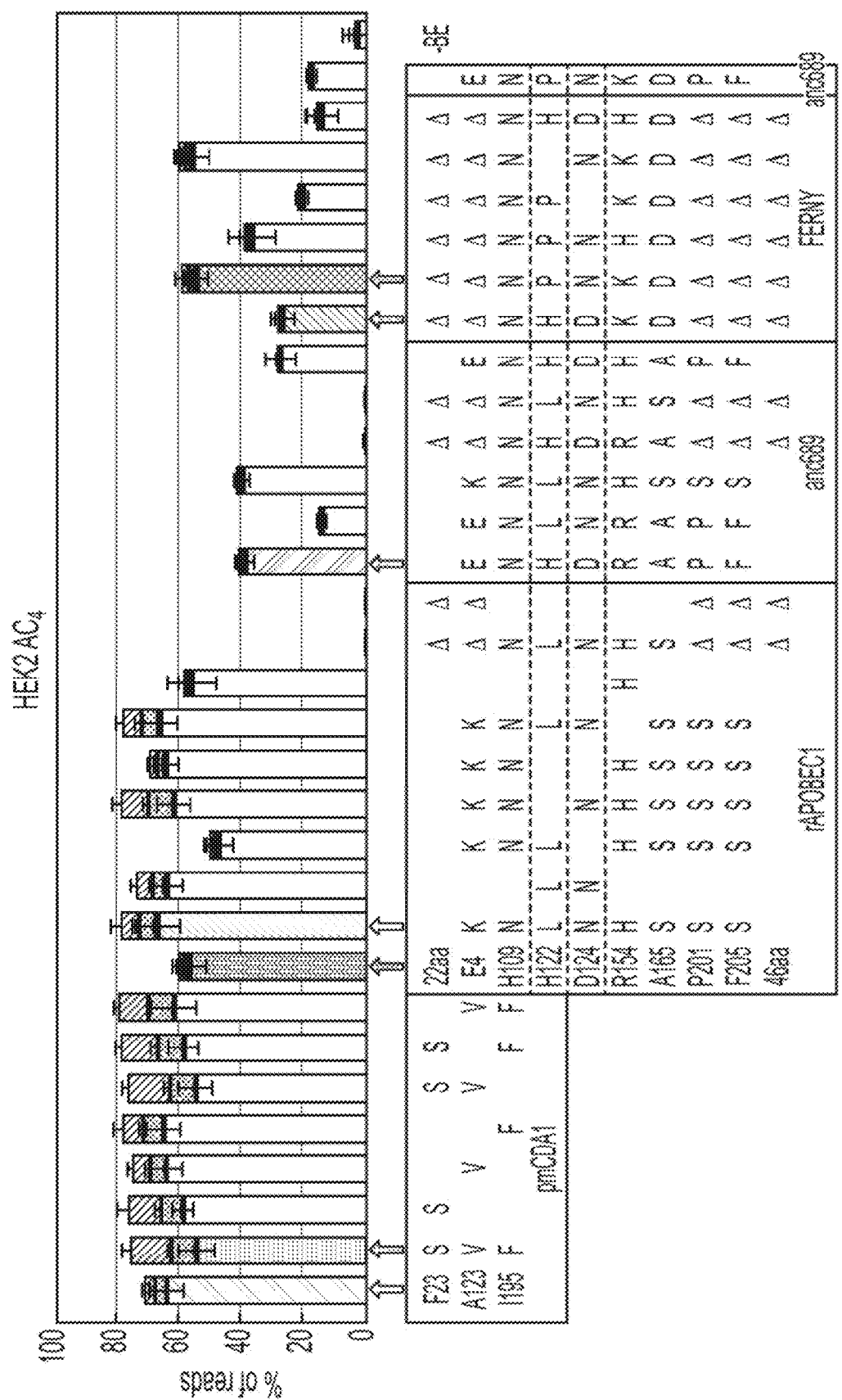
FIG. 121 shows 750 ng transfection HEK cell editing for HEK2 $AC_4$. HEK cell editing: 750 ng base editor, 250 ng guide RNA; lipofected; 3 day incubation. N=3 except where indicated; error bars=SD. Arrows show wild-type and "evo" genotypes selected for further study.
Figure 122:
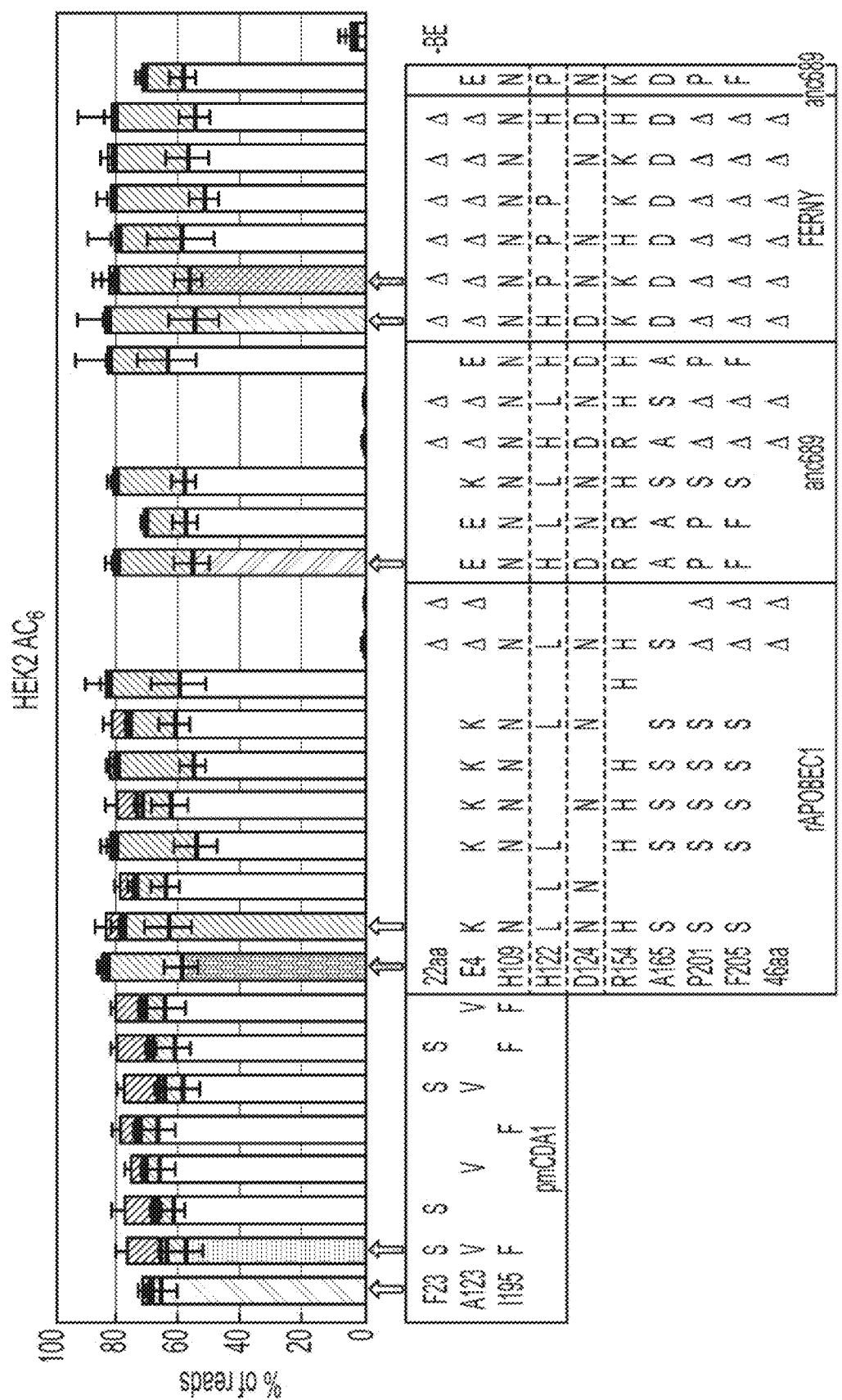
FIG. 122 shows 750 ng transfection HEK cell editing for HEK2 $AC_6$. HEK cell editing: 750 ng base editor, 250 ng guide RNA; lipofected; 3 day incubation. N=3 except where indicated; error bars=SD. Arrows show wild-type and "evo" genotypes selected for further study.
Figure 123:
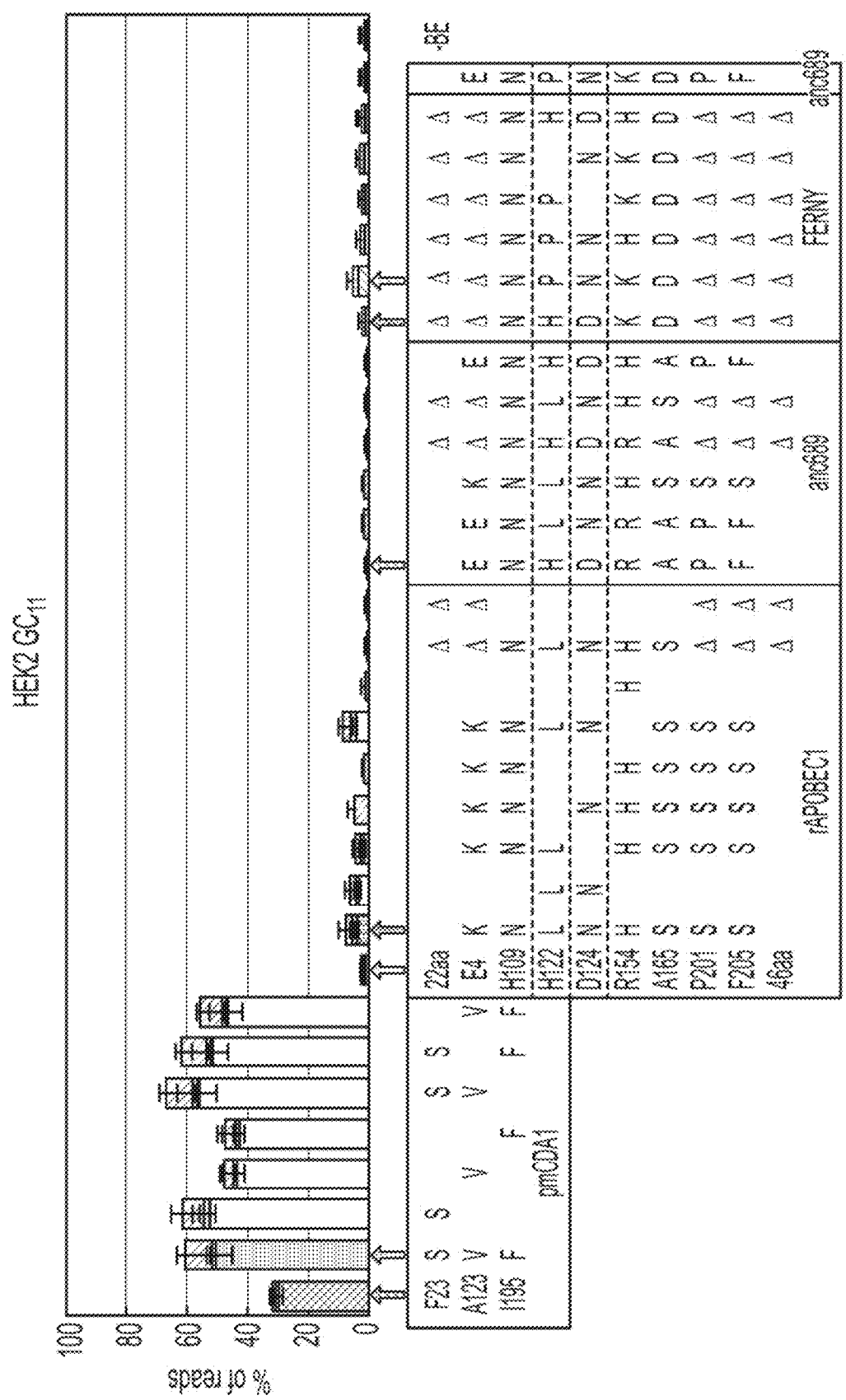
FIG. 123 shows 750 ng transfection HEK cell editing for HEK2 $GC_{11}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 124:
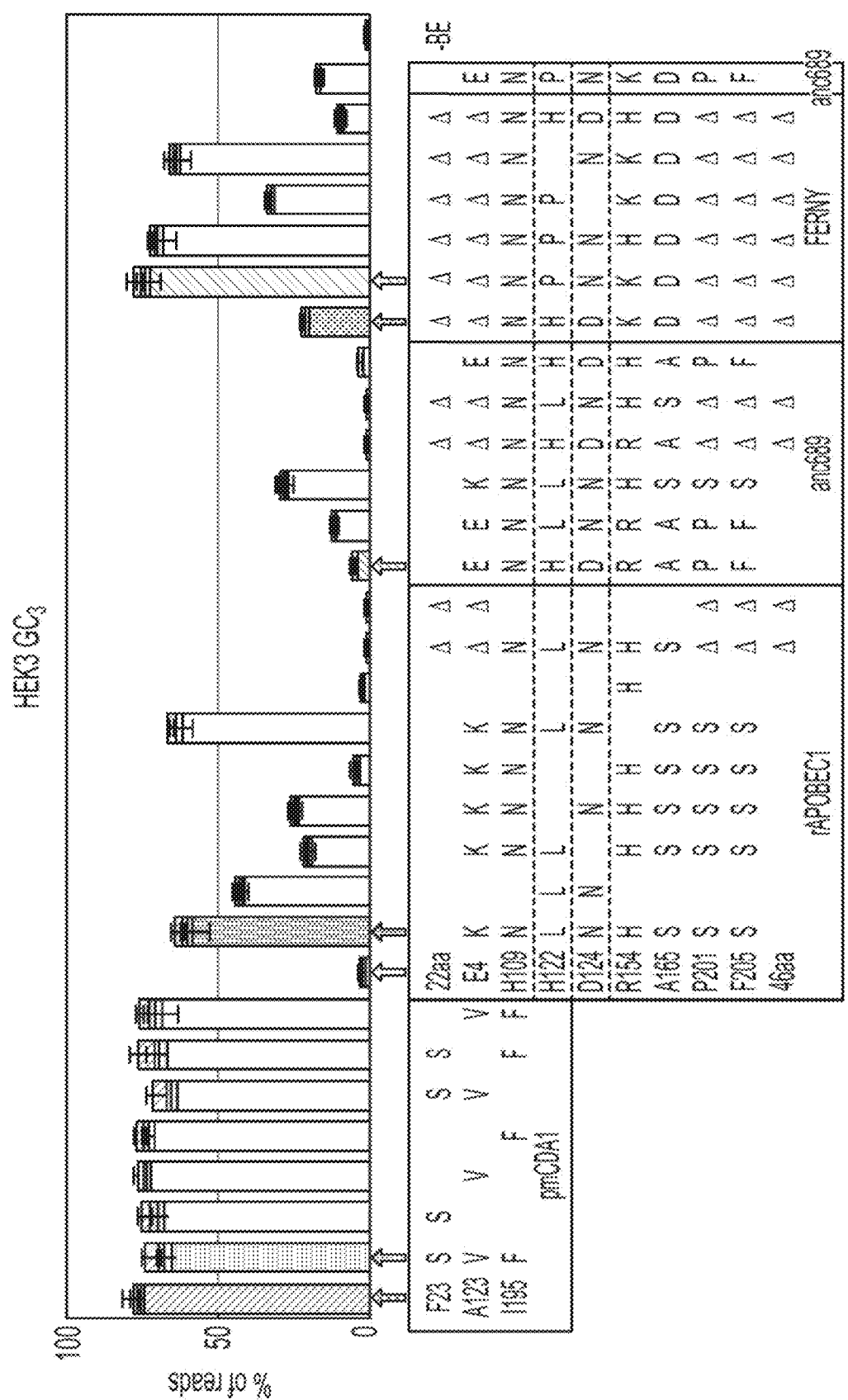
FIG. 124 shows 750 ng transfection HEK cell editing for HEK3 $GC_3$. HEK cell editing: 750 ng base editor, 250 ng guide RNA; lipofected; 3 day incubation. N=3 except where indicated; error bars=SD. Arrows show wild-type and "evo" genotypes selected for further study.
Figure 125:
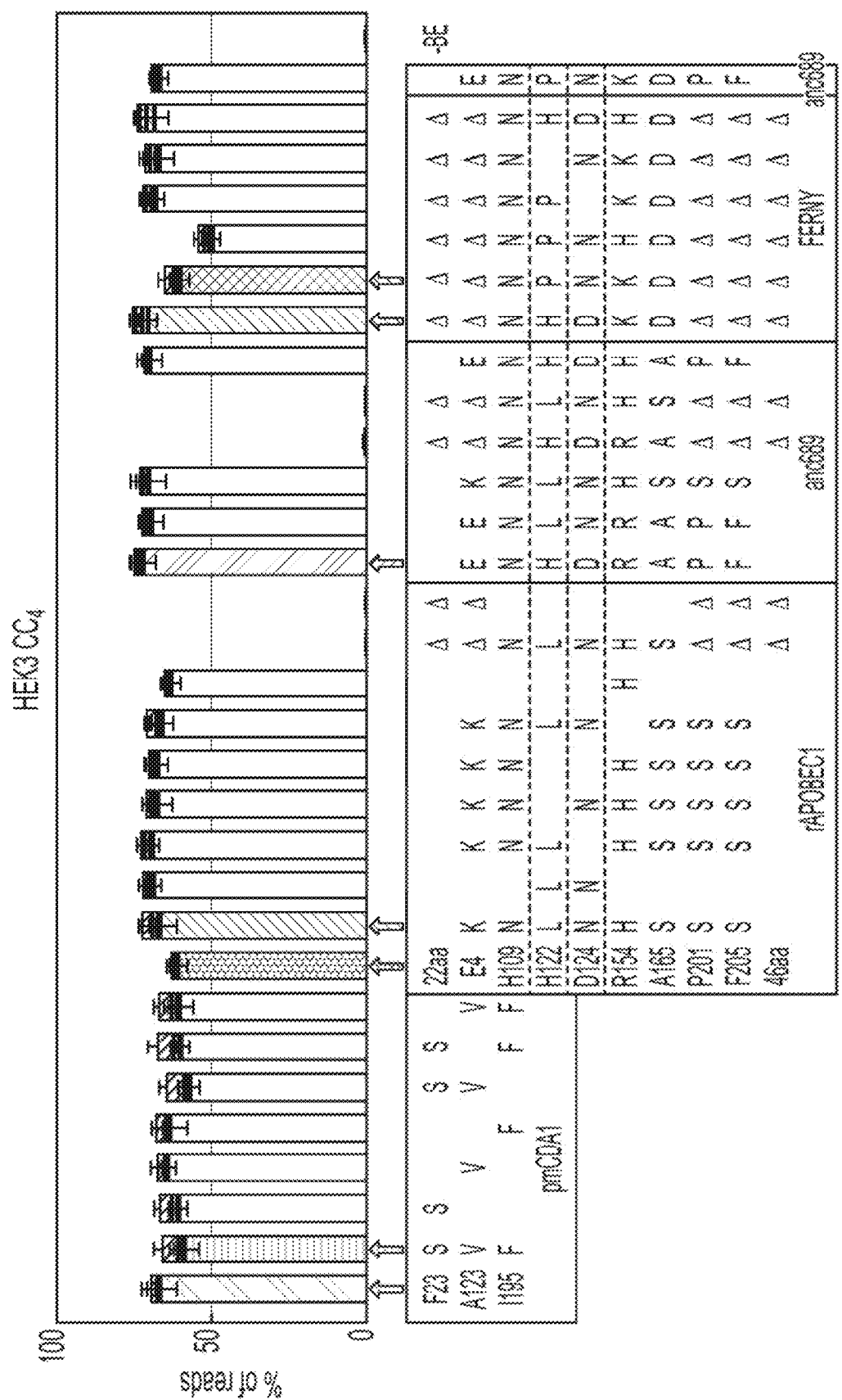
FIG. 125 shows 750 ng transfection HEK cell editing for HEK3 $CC_4$. HEK cell editing: 750 ng base editor, 250 ng guide RNA; lipofected; 3 day incubation. N=3 except where indicated; error bars=SD. Arrows show wild-type and "evo" genotypes selected for further study.
Figure 126:
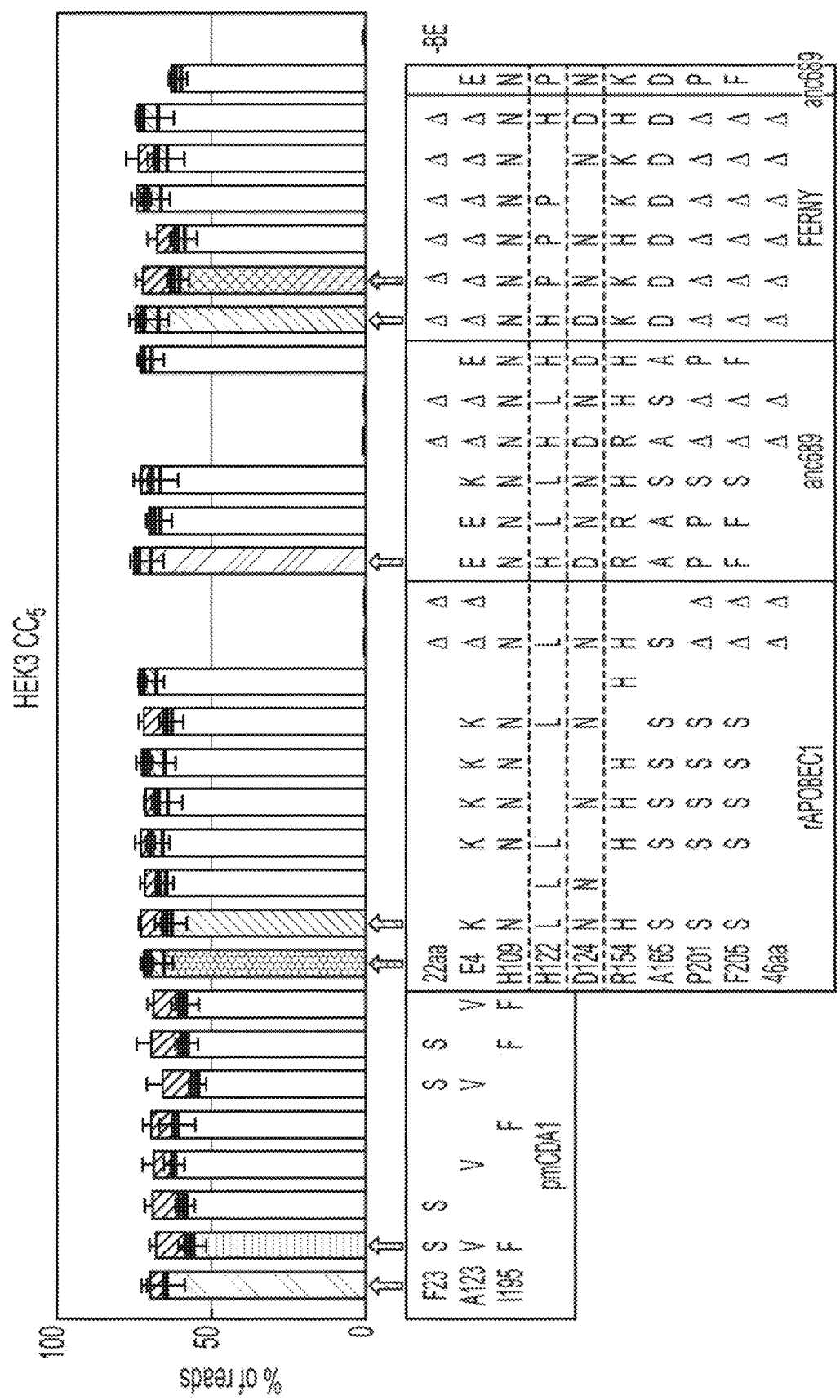
FIG. 126 shows 750 ng transfection HEK cell editing for HEK3 $CC_5$. HEK cell editing: 750 ng base editor, 250 ng guide RNA; lipofected; 3 day incubation. N=3 except where indicated; error bars=SD. Arrows show wild-type and "evo" genotypes selected for further study.
Figure 127:
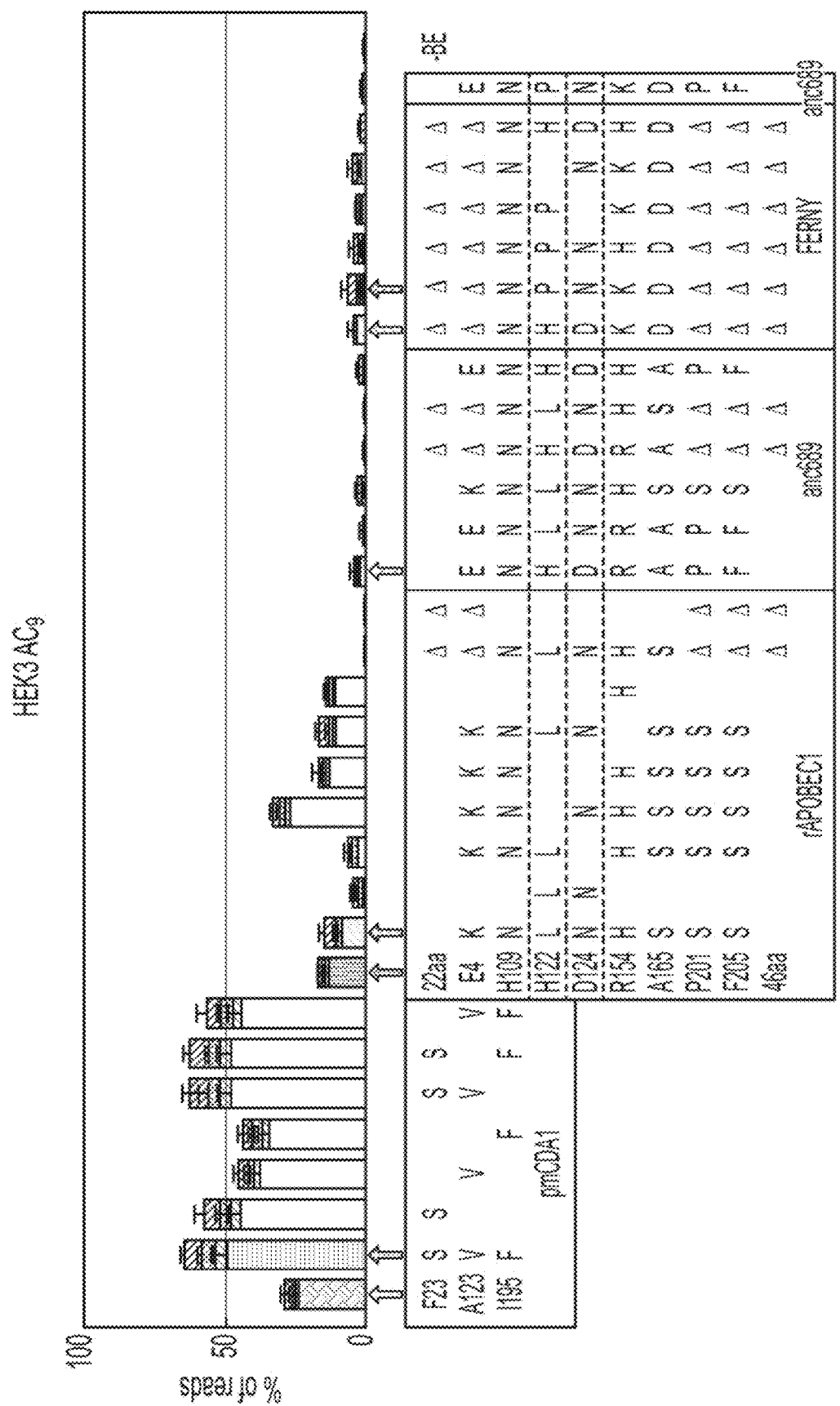
FIG. 127 shows 750 ng transfection HEK cell editing for HEK3 $AC_9$. HEK cell editing: 750 ng base editor, 250 ng guide RNA; lipofected; 3 day incubation. N=3 except where indicated; error bars=SD. Arrows show wild-type and "evo" genotypes selected for further study.
Figure 128:
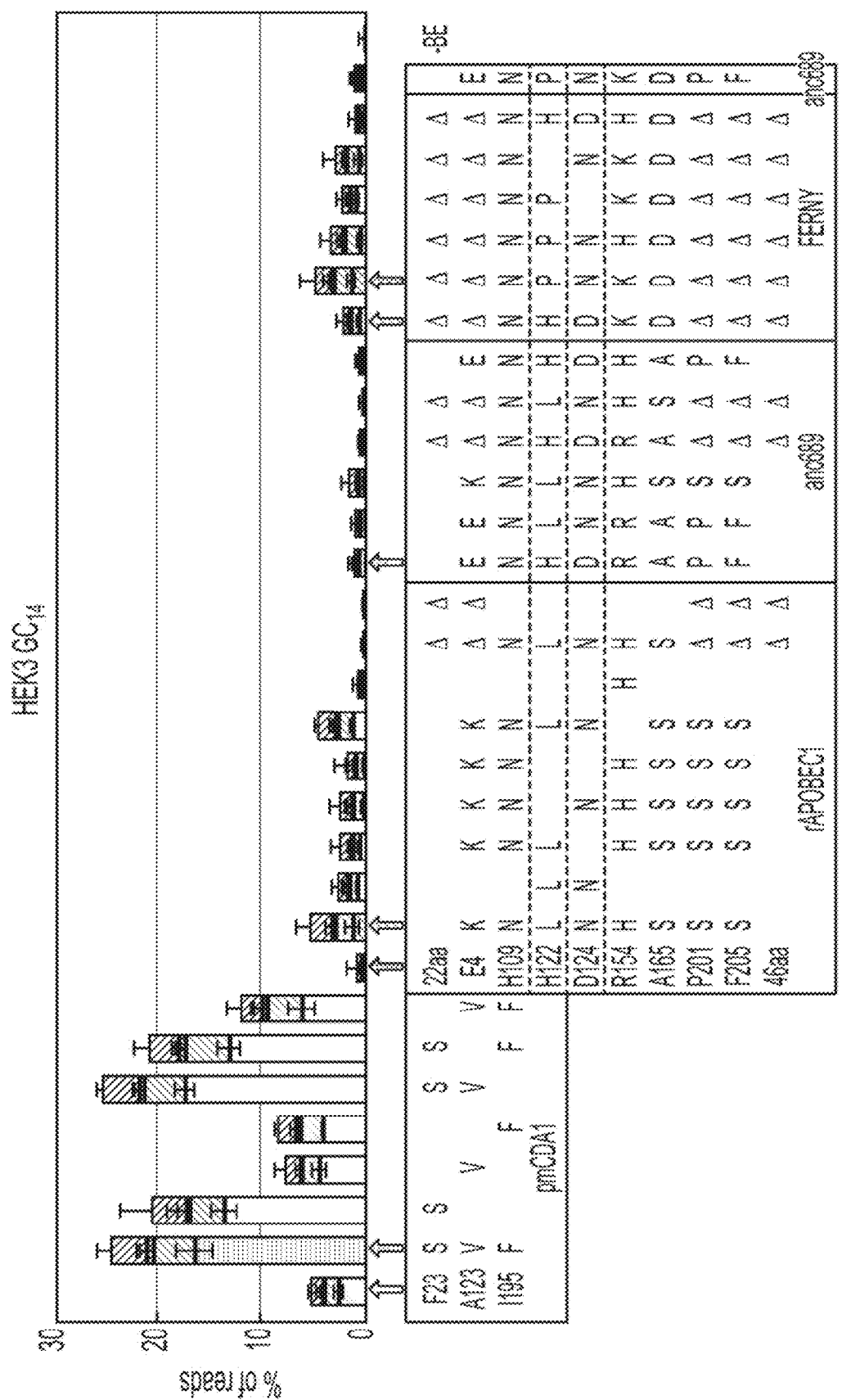
FIG. 128 shows 750 ng transfection HEK cell editing for HEK3 $GC_{14}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 129:
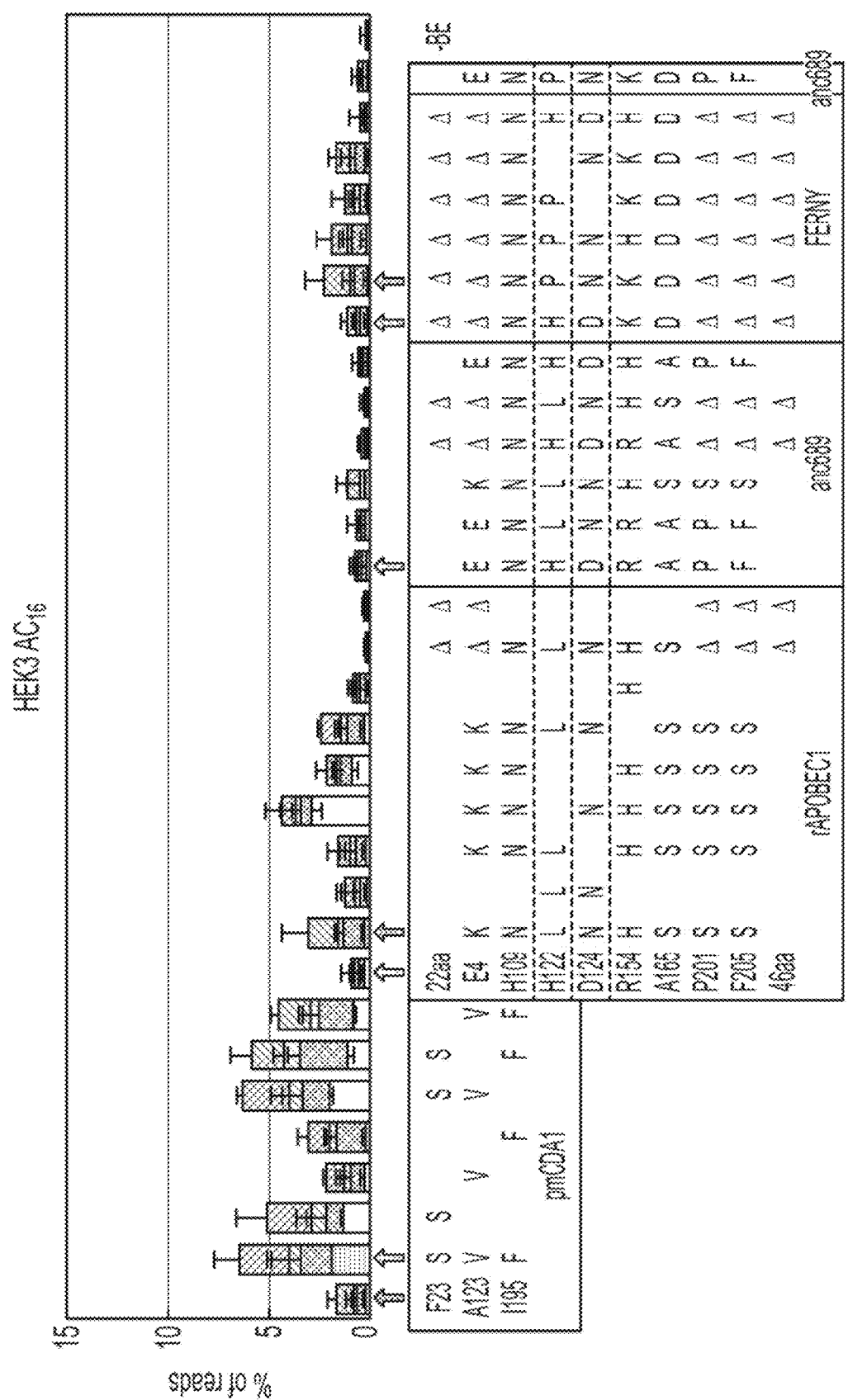
FIG. 129 shows 750 ng transfection HEK cell editing for HEK3 $AC_{16}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 130:
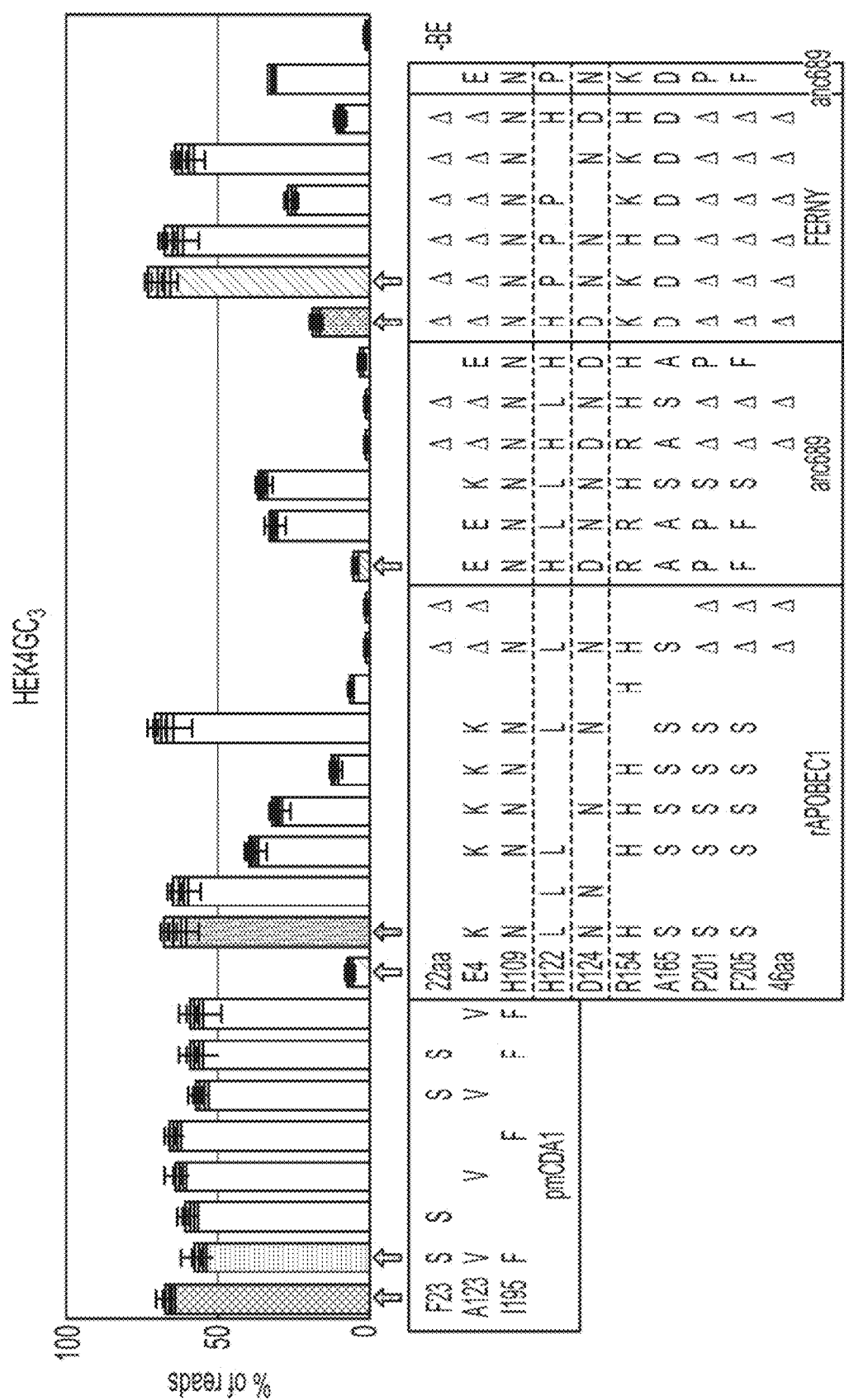
FIG. 130 shows 750 ng transfection HEK cell editing for HEK4 $GC_3$. HEK cell editing: 750 ng base editor, 250 ng guide RNA; lipofected; 3 day incubation. N=3 except where indicated; error bars=SD. Arrows show wild-type and "evo" genotypes selected for further study.
Figure 131:
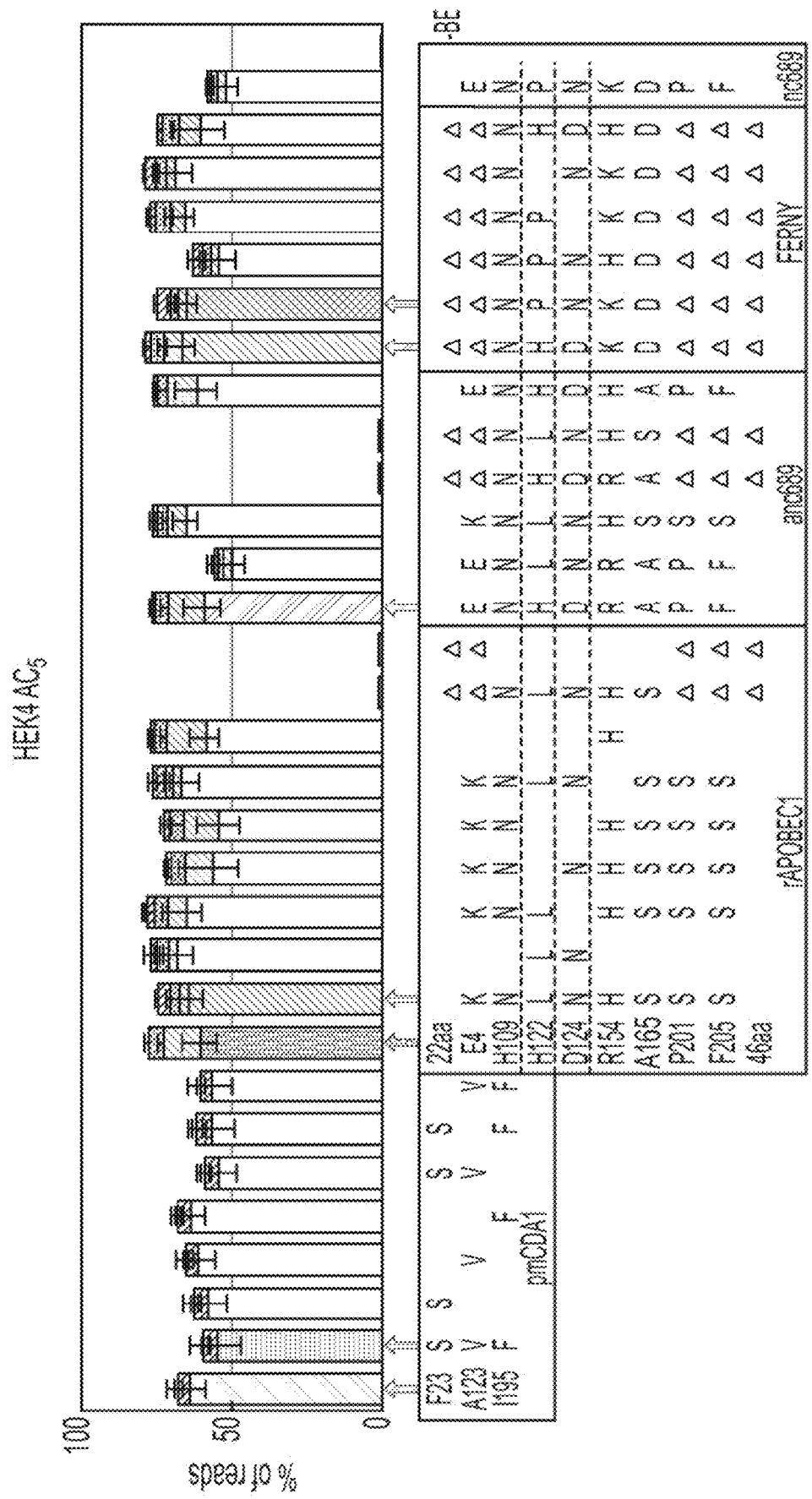
FIG. 131 shows 750 ng transfection HEK cell editing for HEK4 $AC_5$. HEK cell editing: 750 ng base editor, 250 ng guide RNA; lipofected; 3 day incubation. N=3 except where indicated; error bars=SD. Arrows show wild-type and "evo" genotypes selected for further study.
Figure 132:
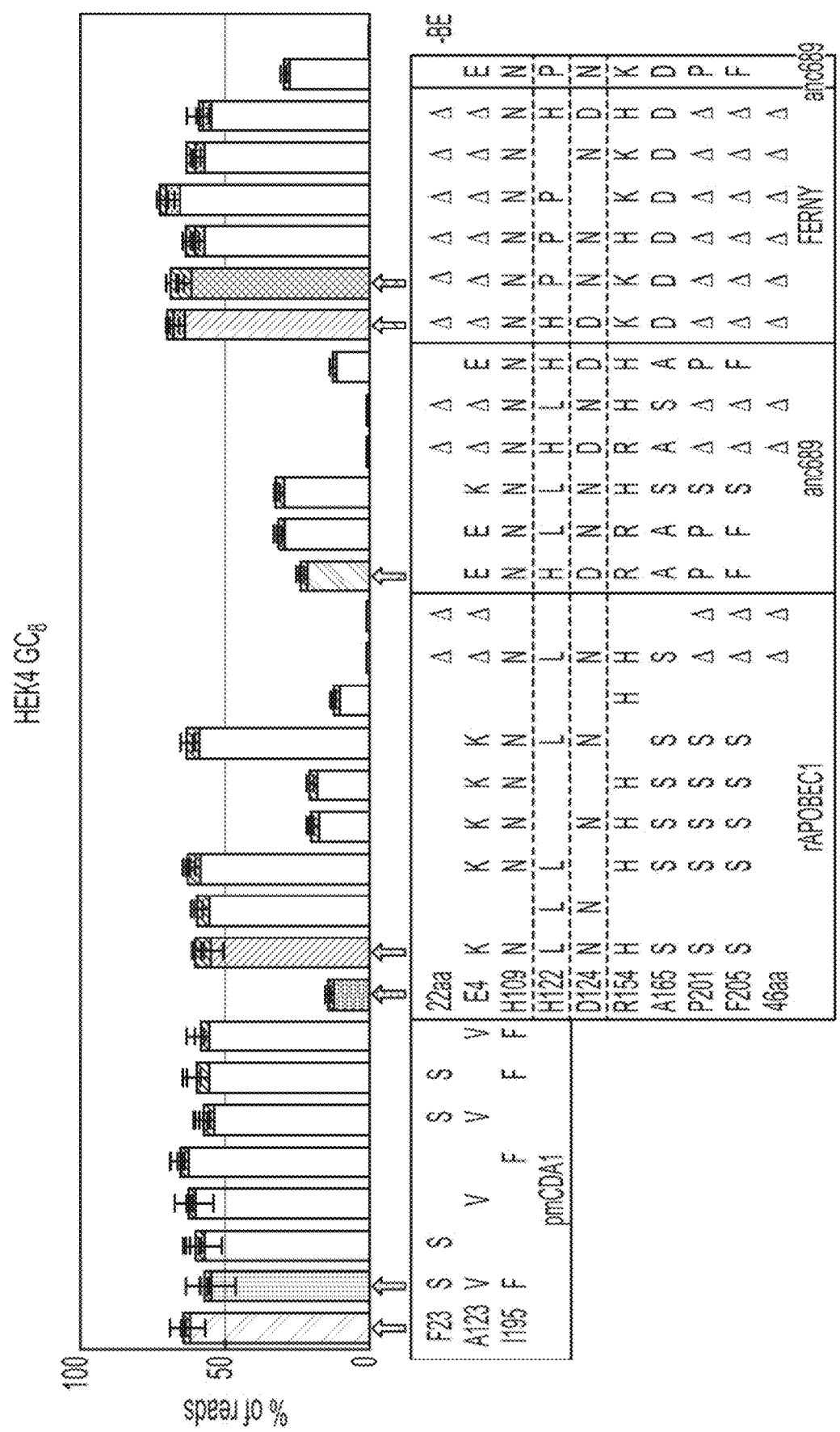
FIG. 132 shows 750 ng transfection HEK cell editing for HEK4 $GC_5$. HEK cell editing: 750 ng base editor, 250 ng guide RNA; lipofected; 3 day incubation. N=3 except where indicated; error bars=SD. Arrows show wild-type and "evo" genotypes selected for further study.
Figure 133:
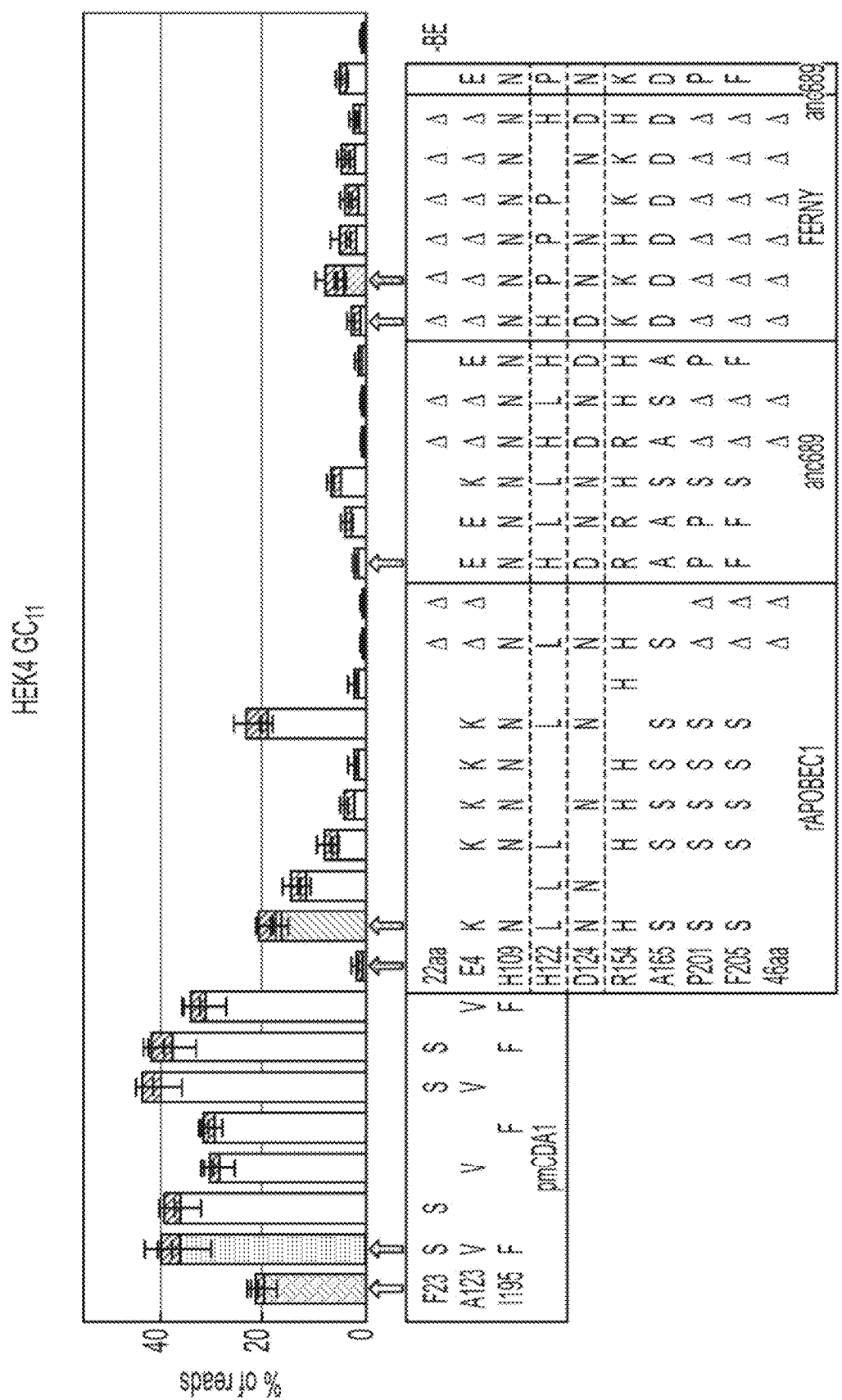
FIG. 133 shows 750 ng transfection HEK cell editing for HEK4 $GC_{11}$. HEK cell editing: 750 ng base editor, 250 ng guide RNA; lipofected; 3 day incubation. N=3 except where indicated; error bars=SD. Arrows show wild-type and "evo" genotypes selected for further study.
Figure 134:
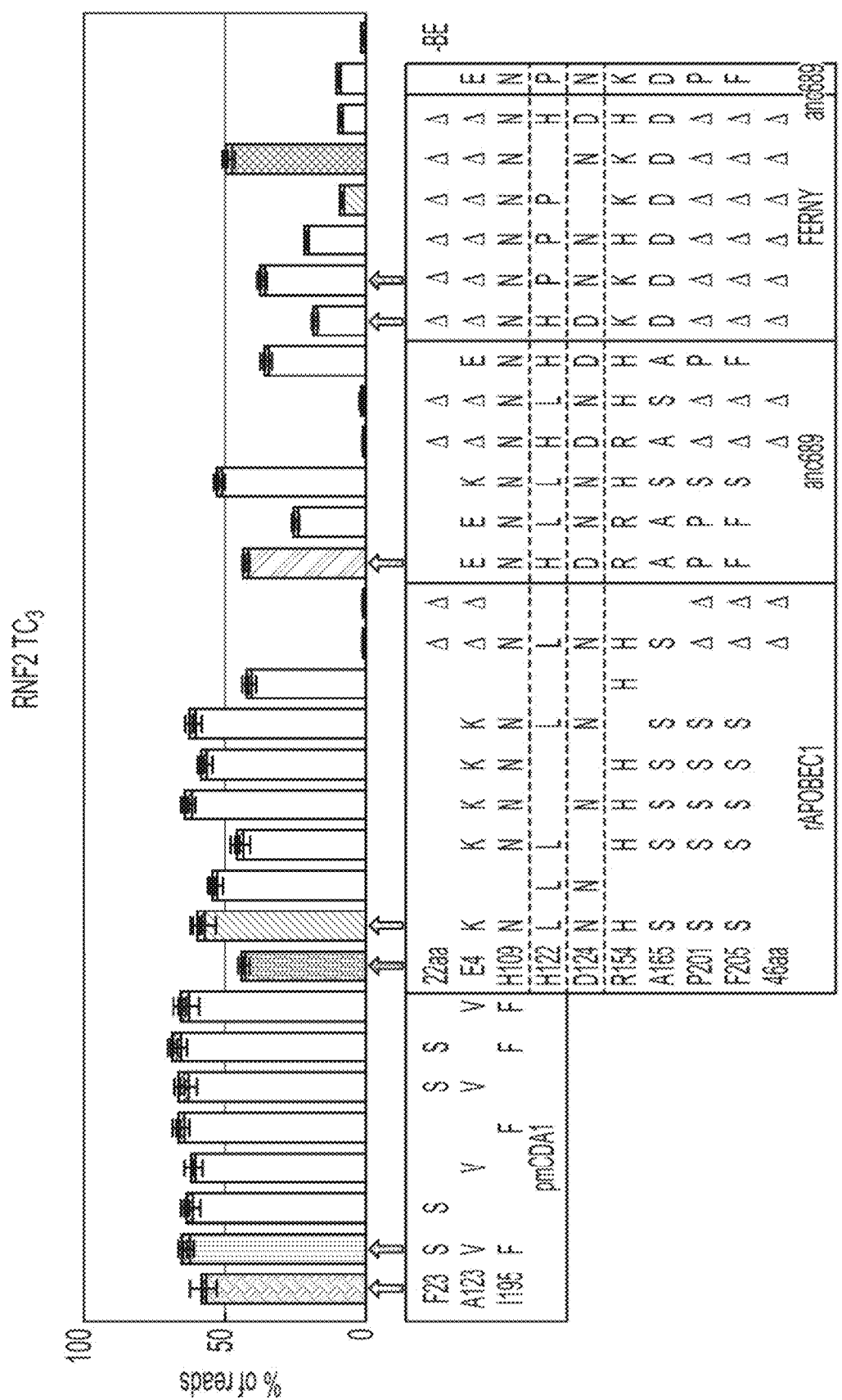
FIG. 134 shows 750 ng transfection HEK cell editing for RNF2 $TC_3$. HEK cell editing: 750 ng base editor, 250 ng guide RNA; lipofected; 3 day incubation. N=3 except where indicated; error bars=SD. Arrows show wild-type and "evo" genotypes selected for further study.
Figure 135:
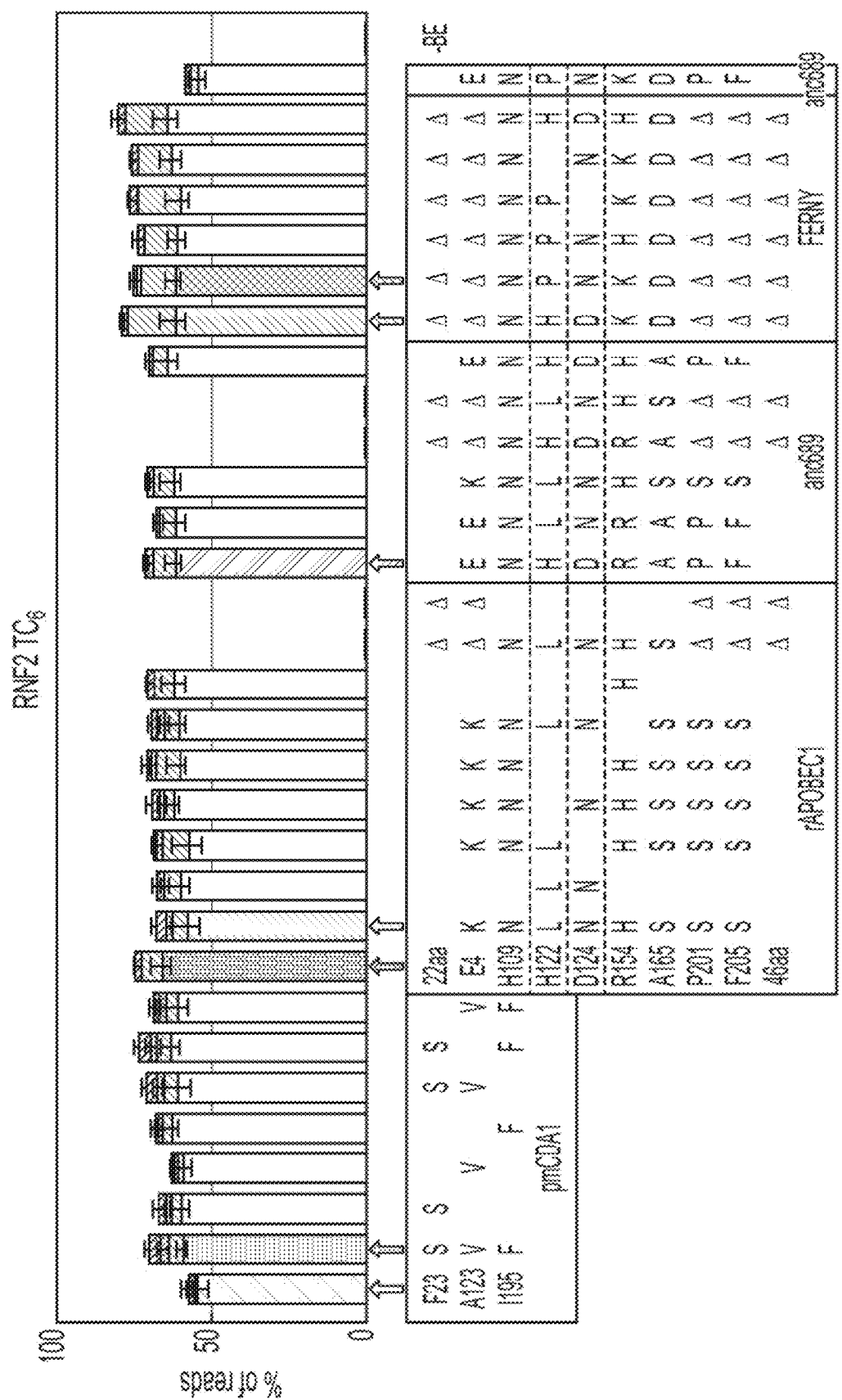
FIG. 135 shows 750 ng transfection HEK cell editing for RNF2 $TC_6$. HEK cell editing: 750 ng base editor, 250 ng guide RNA; lipofected; 3 day incubation. N=3 except where indicated; error bars=SD. Arrows show wild-type and "evo" genotypes selected for further study.
Figure 136:
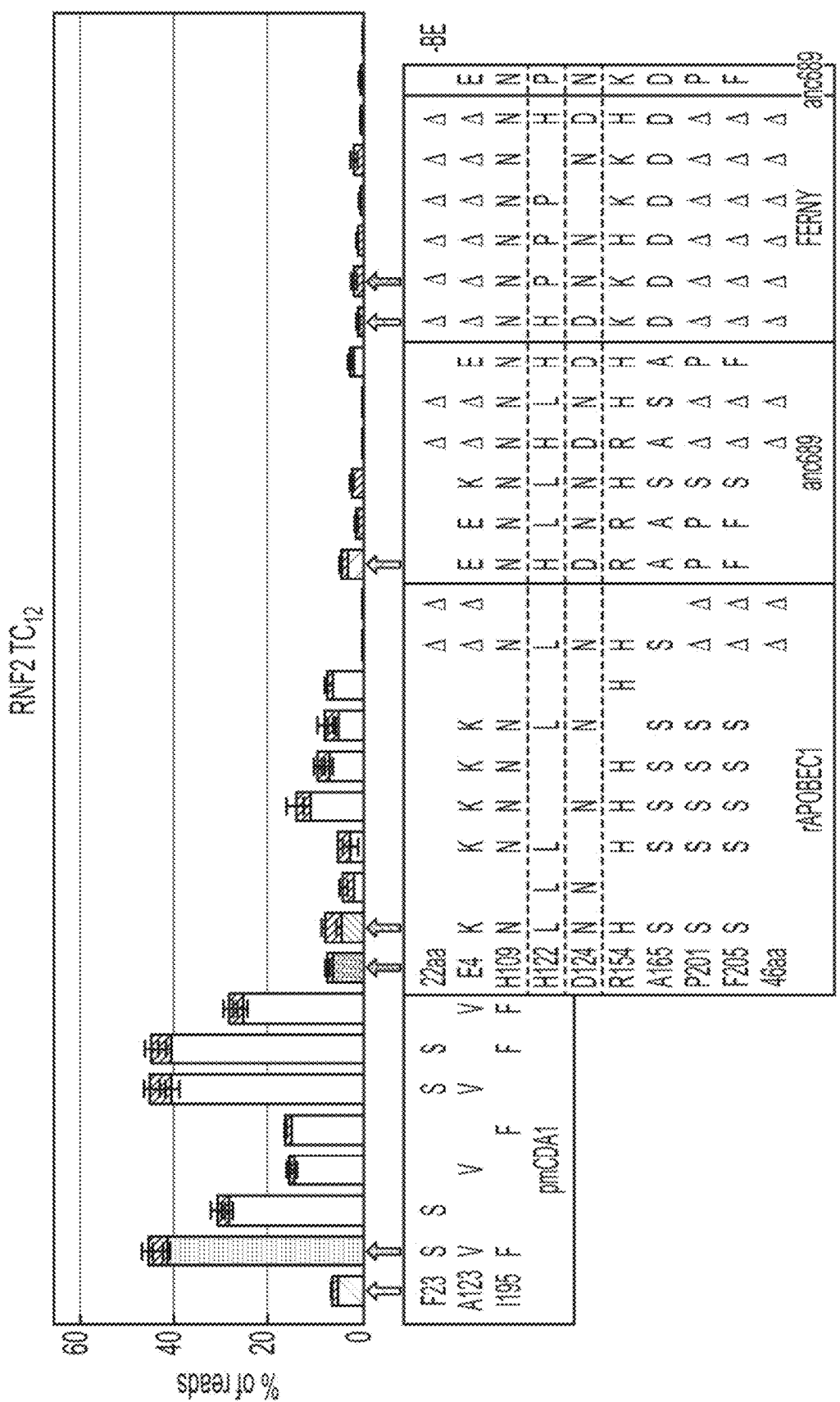
FIG. 136 shows 750 ng transfection HEK cell editing for RNF2 TC$_{12}$. HEK cell editing: 750 ng base editor, 250 ng guide RNA; lipofected; 3 day incubation. N=3 except where indicated; error bars=SD. Arrows show wild-type and "evo" genotypes selected for further study.

PACE evolved deaminases show improvements in HEK cell editing (FIGS. 85-87). For each C in a target site, editing % is shown in the same order for wild-type and evolved deaminases.

Four genotypes stand out (Table 5, FIGS. 88-92). Two CDA variants have essentially equivalent activity, and have higher editing than wild-type CDA and a slightly broadened window. The evolved APOBEC genotype has activity on GC targets, whereas wild-type APOBEC has very low activity on GC. The evolved FERNY genotype also has high GC activity and is comparably active to APOBEC despite being a shorter protein.

be carried out on ABE to improve/alter deaminase activity, window or context specificity. Full-length base editor PACE will allow mutations in Cas9 that affect PAM specificity, editing window, target site residence etc. Negative selection can be implemented by supplying a second copy of T7 RNAP with orthogonal promoter specificity (T3) and a recoded C-terminus. Undesired edits activate the T3 variant (by removing the C-terminal degron in the same manner as the positive selection) and drive production of pIII-neg, which reduces phage propagation. Negative selection can be carried out on targets with a specific 5' base or a specific window position. Positive and negative selection can occur simultaneously in the same host cell. One example use case for this tandem dual selection would be to select for editing at position 1 and against editing at position 5, forcing the editing window to shift away from the PAM. Window shifting for BEs that use a given deaminase has never been reliably achieved.

TABLE 5

Four genotypes stand out.

| Plasmid | Deaminase | Evolved on | PACE | Deaminase genotype | Abbr. | Actual transfection |
|---|---|---|---|---|---|---|
| pBT221 | pmCDA1 | TCC | 10 | V75I K120R A123V C158R I193T | IRVRT | 38.5 ng |
| pBT222 | pmCDA1 | TCC | 12 | F23S A123V I195F | SVF | 33.2 ng |
| pBT223 | rAPOBEC1 | GCC | 12 | E4K H109N H122L D124N R154H A165S P201S F205S | KNLNHSSS | 30.0 ng |
| pBT224 | FERNY | TCC | 12 | H102P D104N | PN | n.d. |
| pBT209 | rAPOBEC1 | | | wt | | 27.6 ng |
| pBT210 | CDA | | | wt | | 28.6 ng |

The PACE selection can be adapted to other evolutionary targets. These extensions have not been validated experimentally yet. The bases 5' to the CCA edit site can be varied freely, allowing selection for editing at specific 5' sequence contexts. Editing at most positions within the window can be selected for (e.g. editing at +1). ABE (A to G base editor) activity can be selected for by reverting stop codons to Q or R in T7 RNAP via editing. Analogous positive selections can The following data (Table 6, FIGS. 93-114) use deaminase genotypes derived directly from PACE, without codon optimization, in the context of codon-optimized BE4Max. They show that at a high transfection dose (750 ng editor plasmid), several evolved genotypes have superior or equal performance to wild-type deaminases. The evolved CDA ("evoCDA", pBT222), APOBEC ("evoAPOBEC", pBT223) and FERNY (pBT224) genotypes outperform wild-type at almost all sites. Performance at the margins of the editing window at this high, saturating dose of editor is particularly illustrative of activity differences between wild-type and evolved deaminases.

were selected based on the n=1 30 ng transfection data shown earlier in this deck. These genotypes were 1) Genscript codon optimized, 2) subjected to limited reversion analysis and 3) mutations were transferred to the context of wild-type deaminase or anc689 (ancBE4Max, Koblan, L. W. et al. Improving cytidine and adenine base editors by expression optimization and ancestral reconstruction. Nature Publishing Group 1-9 (2018). doi:10.1038/nbt.4172).

FIGS. 115-136 show editing from Genscript codon-optimized deaminases, equivalent in composition to BE4Max (state-of-the-art rAPOBEC1-based base editor) and ancBE4Max (reconstructed ancestor anc689 that outperforms BE4Max on some sites) except for the evolved mutations. The dose is high (750 ng) and therefore editing at the center of the window is saturated as in the previous data.

TABLE 6

Deaminase genotypes derived directly from PACE.

| Plasmid | Deaminase | | | | | | | |
|---|---|---|---|---|---|---|---|---|
| pBT210 | wt-pmCDA1 | H10 | F23 | V75 | K120 | A123 | C158 | I193 | I195 |
| pBT213 | pmCDA1 | | | | | V | | | |
| pBT219 | pmCDA1 | | | | | V | | | |
| pBT228 | pmCDA1 | Y | | | | V | | | |
| pBT222 | evo-pmCDA1 | | S | | | V | | | F |
| pBT217 | pmCDA1 | | S | | | V | R | | |
| pBT220 | pmCDA | | | | | V | R | | T |
| pBT221 | pmCDA1 | | | I | R | V | R | T | |
| pBT209 | wt-rAPOBEC1 | E4 | V10 | E31 | Y40 | E95 | H109 | H122 | D124 |
| pBT216 | rAPOBEC1 | | | | | | | | |
| pBT214 | rAPOBEC1 | | | | | | N | | |
| pBT215 | rAPOBEC1 | K | | | | | N | | |
| pBT230 | rAPOBEC1 | K | | | | | N | L | |
| pBT232 | rAPOBEC1 | K | | | | | N | | N |
| pBT236 | rAPOBEC1 | K | | | | | N | L | |
| pBT229 | rAPOBEC1 | K | | | | | N | L | N |
| pBT223 | evo-rAPOBEC1 | K | | | | | N | L | N |
| pBT233 | rAPOBEC1 | K | | | C | | N | L | N |
| pBT234 | rAPOBEC1 | K | | | | | N | | N |
| pBT237 | rAPOBEC1 | K | | | | A | N | L | N |
| pBT226 | rAPOBEC1 | K | A | | | A | N | L | N |
| pBT225 | rAPOBEC1 | K | | V | | A | N | L | N |
| pBT211 | wt-FERNY | | | | | | | H102 | D104 |
| pBT218 | FERNY | | | | | | | | |
| pBT224 | evo-FERNY | | | | | | | P | N |

| Plasmid | | | | | | | | Evolved on | PACE analog |
|---|---|---|---|---|---|---|---|---|---|
| pBT210 | V197 | | | | | | | n/a | 149 |
| pBT213 | | | | | | | | TCC | P5.107 |
| pBT219 | A | | | | | | | TCC | P10.4.64C4 |
| pBT228 | A | | | | | | | TCC | P12.107 |
| pBT222 | | | | | | | | TCC | P10.493G10 |
| pBT217 | | | | | | | | TCC | P10.4.64A4 |
| pBT220 | | | | | | | | TCC | P10.4.64F4 |
| pBT221 | | | | | | | | TCC | P10.4.93B10 |
| pBT209 | R126 | R154 | N158 | A165 | P201 | F205 | I208 | n/a | 106b |
| pBT216 | | | S | | | S | | TCC | P7.103 |
| pBT214 | | | S | S | S | | | TCC | P7.101 |
| pBT215 | | | S | S | S | | | TCC | P7.102 |
| pBT230 | | | S | S | S | | | TCC | P12.110 |
| pBT232 | | | S | S | S | | | TCC | P12.115E4K |
| pBT236 | H | | S | S | S | | | GCC | P12.122E4K |
| pBT229 | | | S | S | S | | | GCC | P12.108 |
| pBT223 | | H | S | S | S | | | GCC | P12.101 |
| pBT233 | | | S | S | S | | | TCC | P12.118 |
| pBT234 | | S | S | S | S | | | GCC | P12.121 |
| pBT237 | | | S | S | S | | | TCC | P12.123 |
| pBT226 | | | S | S | S | | | TCC | P12.104 |
| pBT225 | | | S | S | S | | L | TCC | P12.103 |
| pBT211 | V115 | | | | | | | n/a | 136c |
| pBT218 | M | | | | | | | TCC | P10.2.44B2 |
| pBT224 | | | | | | | | TCC | P12.102 |

Transfecting 750 ng base editor saturates editing at positions near the middle of the editing window, obscuring differences between genotypes. Evolved deaminases are equivalent within error or superior to wild-type deaminases at almost every site and position. Editing at the margins of the window shows the strongest differences between editor activity (e.g. HEK4 GC11, RNF2 TC12). Approximately 5 evolved CDA genotypes have equivalent high editing activity and expanded window size. Approximately 7 evolved APOBEC genotypes have equivalent high editing activity and edit GC targets (e.g. HEK3 GC3 and HEK4 GC3) efficiently. The single evoCDA and evoAPOBEC genotypes Two mutations in the specificity loop (dotted lines in mutant table) of APOBEC/FERNY are critical for GC activity. These mutations are specific to the deaminase context they evolved in; neither set ports to the anc689 background. This loop region is known to influence the −1 and −2 base preferences for various cytidine deaminases (e.g. Kohli, R. M. et al. A portable hot spot recognition loop transfers sequence preferences from APOBEC family members to activation-induced cytidine deaminase. Journal of Biological Chemistry 284, 22898-22904 (2009)). Truncating APOBEC or anc689 to FERNY's size completely inactivates them. All three of the evoCDA mutations seem to be functional, but the F23S mutation appears most important. evoCDA has a half-maximal-activity window of ~1-13 (vs CDA~1-9). evoAPOBEC has a similar window to APOBEC, expanded by about 0.5 bases to either side. evoAPOBEC and evoFERNY are superior to anc689 (current state of the art BE) at all sites tested. evoAPOBEC has higher editing than evoFERNY on only a few targets. evoFERNY is ~161 aa long compared to ~227 aa for APOBEC/anc689, making it a better choice for delivery methods where DNA size is constrained.

Genscript codon optimization improves activity but only marginally (compare PACE genotype and Genscript codon optimized transfection data) so the protein sequence is the primary determinant of performance.

Figure 137:
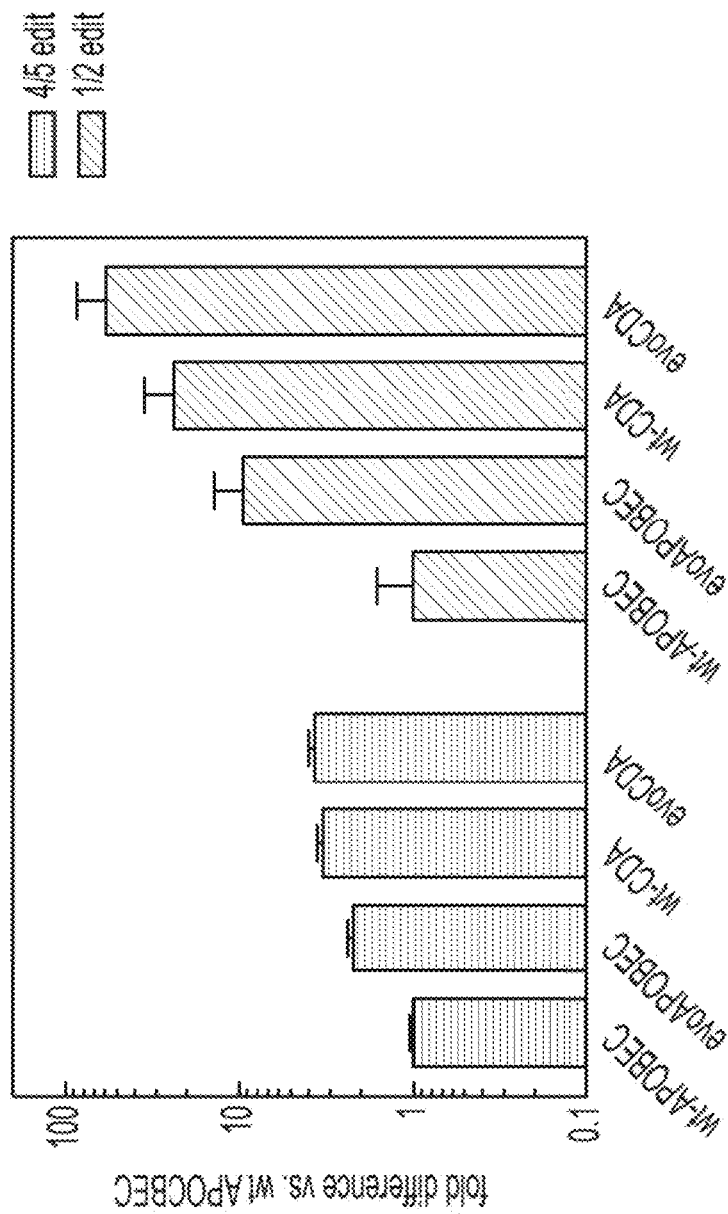
FIG. 137 shows extension of the PACE selection to shift or widen the editing window. N=6 independent host cell cultures were infected with backbone-isogenic phage containing deaminase-intein fusions. The rate of circuit activation in the linear phase between 2-3 hours post-infection (luminescence per OD600 per minute) is normalized to wt-APOBEC for each circuit. Error bars show SEM.

What follows is proof of concept data for using BE PACE to shift or widen the editing window of a deaminase (FIG. 137). CDA has a wider window than APOBEC1 (and each evo version has a wider window than the wild-type). PACE circuits were constructed where the guide RNA places the GTCC editing target at positions 4 and 5 or at positions 1 and 2. The circuits were otherwise identical. Deaminases with a wider window outperform wild-type APOBEC1 much more strongly when the target is at ½ than at ⅘. Therefore evolution on the ½ circuit is expected to enrich deaminases with a wider window, or a window shifted away from the PAM.

Brief Methods:

Plasmids were constructed by USER and Golden Gate cloning using standard molecular biology techniques. All DNA amplified by PCR was sequence-verified prior to use.

Luciferase Reporter Assays:

For a typical assay, S1030 or S2060 cells [Carlson, J. C., Badran, A. H., Guggiana-Nilo, D. A. & Liu, D. R. Negative selection and stringency modulation in phage-assisted continuous evolution. Nature Chemical Biology 10, 216-222 (2014)] containing the appropriate plasmids were inoculated in 1 mL DRM media containing carbenicillin (50 µg/mL), kanamycin (30 µg/mL), chloramphenicol (40 µg/mL) and/or spectinomycin (100 µg/mL) as appropriate and grown overnight at 37 degrees C. in deep 96-well plates, capacity 2 mL (Eppendorf), fitted with breathable top film seals. Independent biological replicates were either separate colonies from a fresh transformation of one or more plasmids, or independent overnight outgrowths of a −80 glycerol stock. Overnight cultures were back-diluted 50-fold into fresh DRM with antibiotics, then grown for ~1.5 h (for phage-expressed base editor) or 2 h (for plasmid-expressed base editor) in deep-well plates. For phage assays, 135 µL of host cell culture was mixed with 15 µL of high-titer phage stock (>1e10 pfu/mL) in a clear-bottom black 96-well assay plate (Costar). For plasmid-expressed base editor assays, cultures were induced with arabinose (10 mM or as shown) and grown for a further 3 h, then transferred to assay plates (150-200 µL per well). OD600 and luminescence were monitored using an Infinite M1000 Pro microplate reader (Tecan) with temperature set to 37 degrees C. For kinetic assays, readings were made every 3.5 minutes during the monitoring period and the plate was shaken for 30 s between reads.

Propagation Assays (Slides 11, 13, 19):

Log-phase host cells in DRM prepared as described for luciferase assays were mixed with titered phage stocks to a final concentration of ~1e6 pfu/mL and a volume of 1 mL and grown overnight in deep-well plates with breathable top film seals. The cultures were centrifuged (3,600×g, 10 minutes) to remove cells and the supernatants titered as previously described [Badran, A. H. et al. Continuous evolution of *Bacillus thuringiensis* toxins overcomes insect resistance. Nature 533, 1-19 (2016)]. Fold enrichment was calculated by dividing the titer of phage propagated on host cells by the titer of phage at the same input concentration shaken overnight without cells.

PACE experiments were performed essentially as described [Badran, A. H. et al. Continuous evolution of *Bacillus thuringiensis* toxins overcomes insect resistance. Nature 533, 1-19 (2016)].

Mammalian cell experiments: Base editor plasmids were prepared by Golden Gate cloning and midiprepped using ZymoPure Midi Kits (Zymo Research). HEK cell transfections, HTS library preparation and sequencing were performed essentially as described (Komor, A. C. et al. Improved base excision repair inhibition and bacteriophage Mu Gam protein yields C:G-to-T:A base editors with higher efficiency and product purity. Sci Adv 3, eaao4774 (2017).

Summary of Editing in Baringo Mouse: A Hearing Deafness Model

Figure 138:
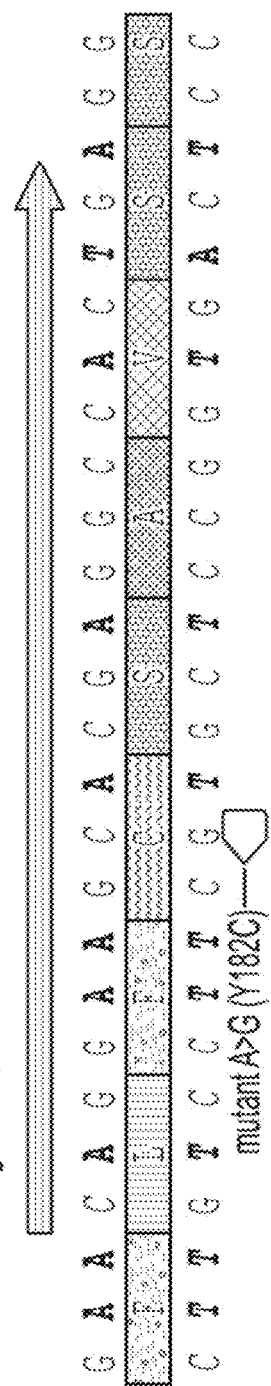
FIG. 138 shows a schematic of the combination of the selected evolution deaminases and constructs in embryonic cells. From top to bottom, sequences correspond to SEQ ID NOs: 126-128.
Figure 141:
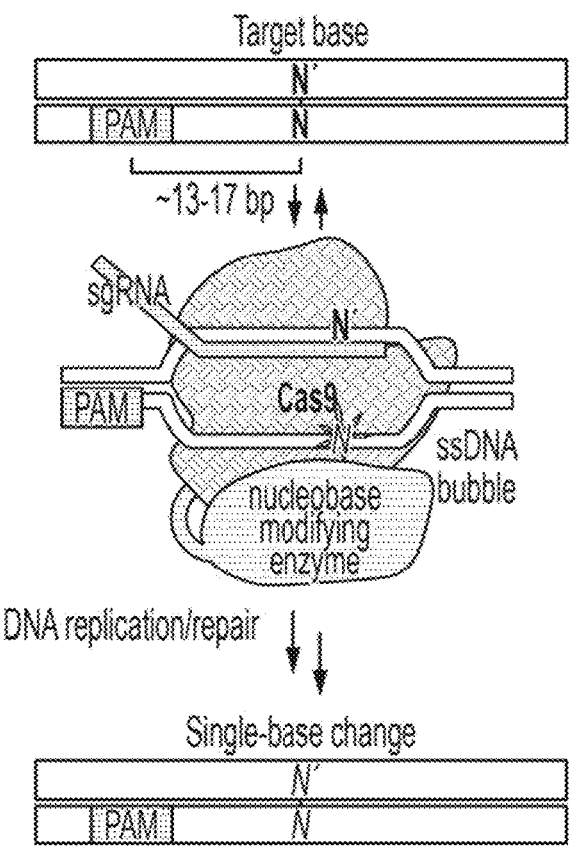
FIG. 141 shows a schematic of single base change by the nucleobase modifying enzyme.
Figure 142:
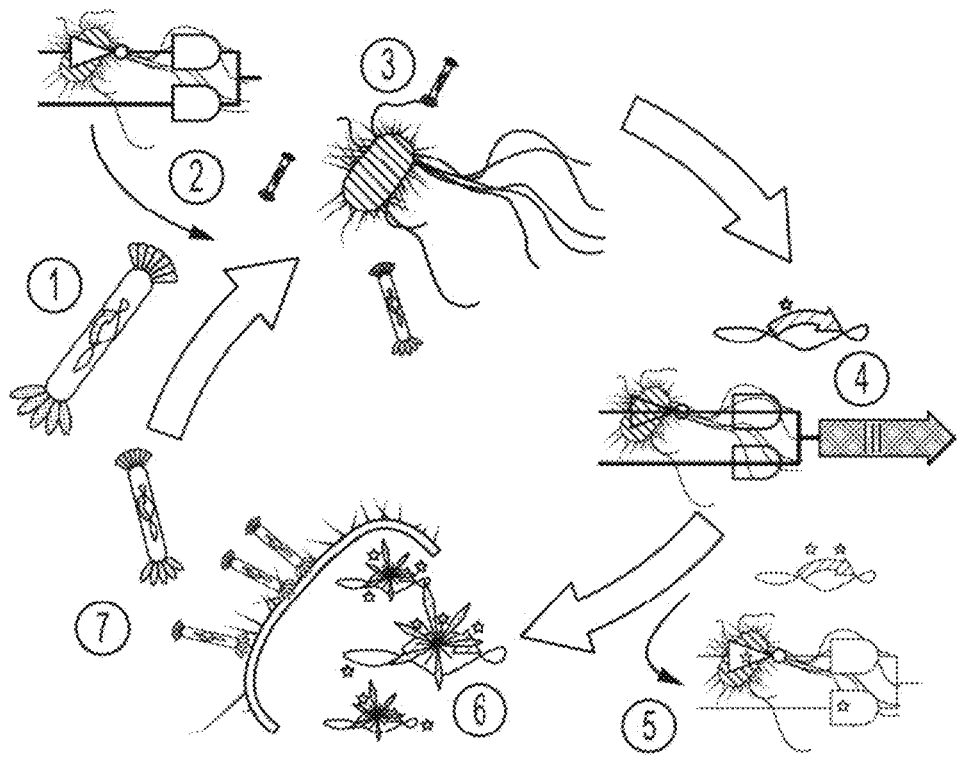
FIG. 142: During PACE, an activity of interest is coupled to the propagation of bacteriophage that encode that activity in their genome (1). This coupling is accomplished by a genetic circuit encoded by *E. coli* host cells (2) that are pumped continuously into a fixed-volume vessel where they are infected by phage (3). Phage encoding genes that activate the circuit lead to expression of phage gene III (4), which allows them to reproduce, while phage with inactive genes do not. Infected host cells and phage continually flow out of the vessel (5), diluting out inactive genes. Active phage genomes are replicated with strong artificial mutagenesis (6), then released as infective particles into the culture medium (7) so that they can infect new host cells. Only phage that encode the activity under selection can propagate fast enough to overcome the dilution rate.
Figure 143:
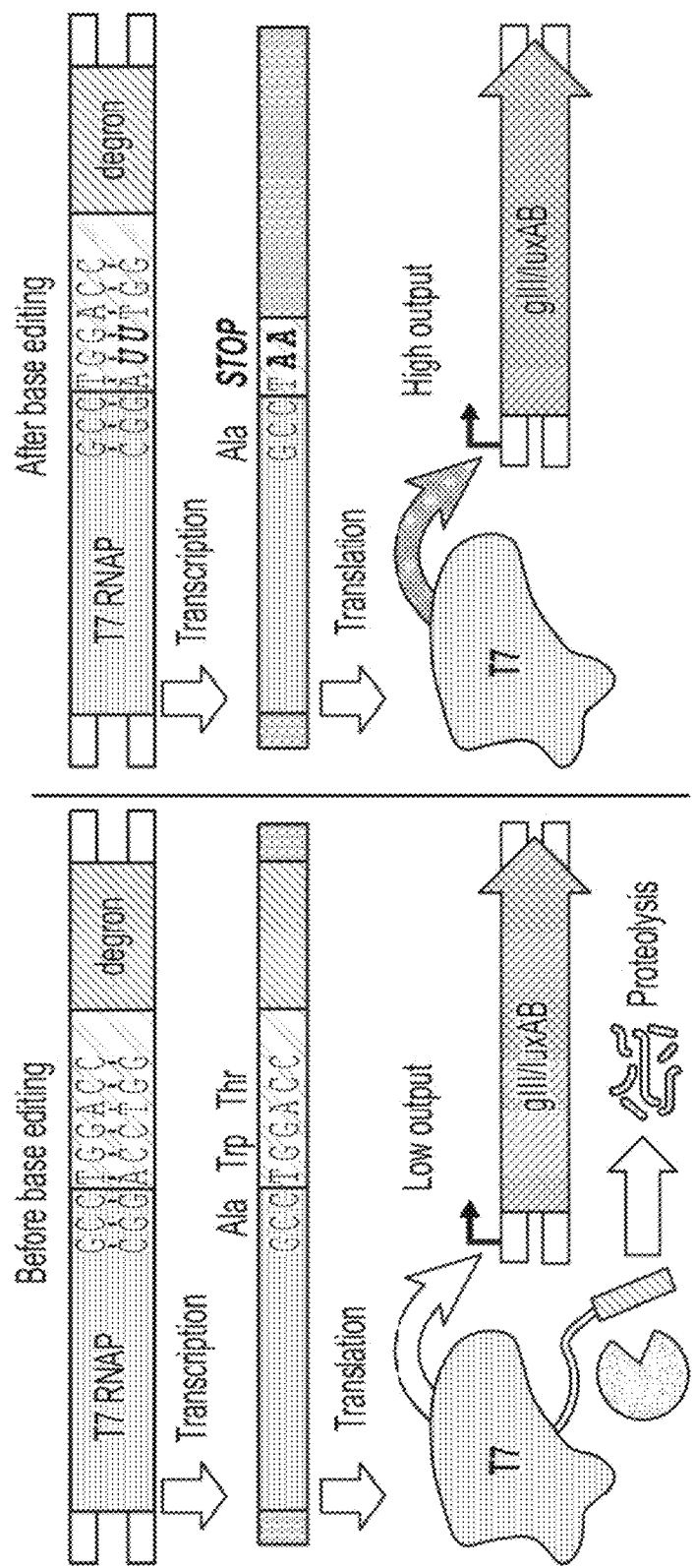
FIG. 143 shows that activation of the base editing selection circuit is dependent on all circuit components and the presence of a full-length base editor protein and on-target guide RNA.
Figure 143:
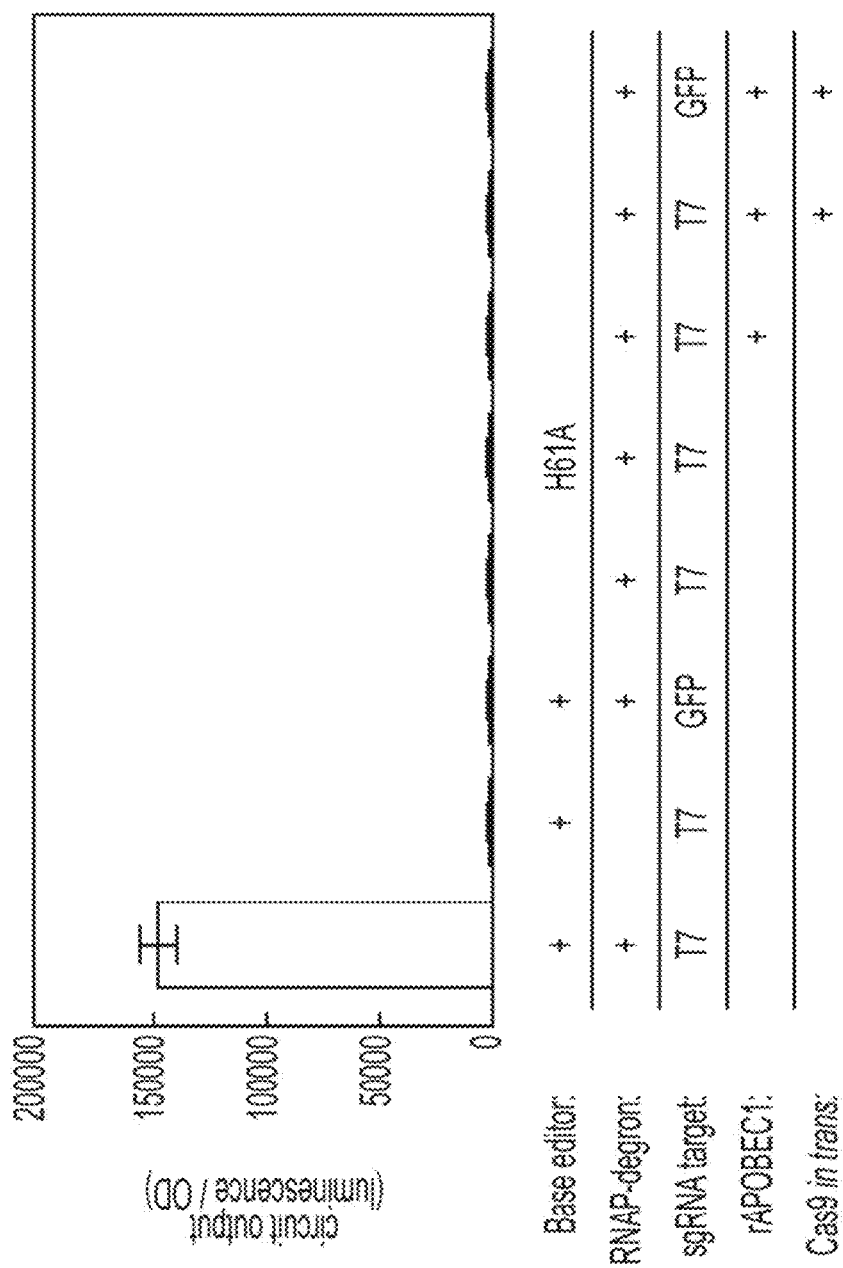
Figure 144:
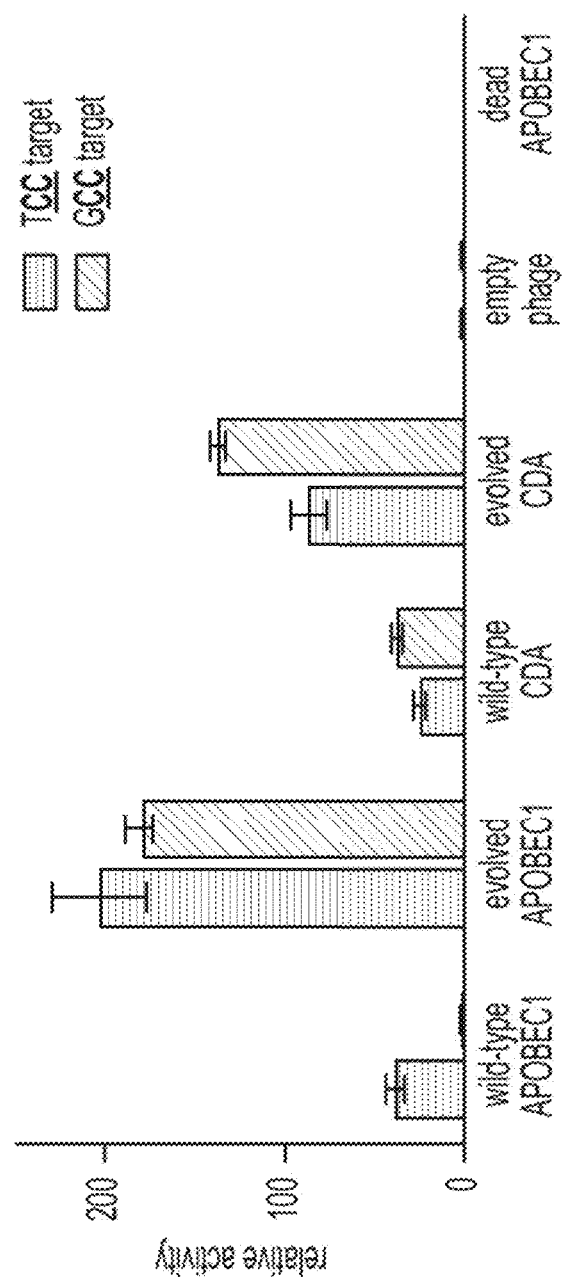
FIG. 144 shows relative activity of evolved deaminase phage with a TCC and GCC target on the selection circuit.

To overcome APOBEC1 sequence specificity issues and efficiently edit the Baringo site, it was shown that BE4 variants with activation-induced (cytidine) deaminase (AID) or cytidine deaminase (CDA) worked well at targeting Baringo mutation. In FIG. 138, the evolution deaminases were combined and the constructs were nucleofected in Baringo embryonic cells. Evo-deaminase allows base-editing in previously non-editable site, and editing with BE-CDA was increased after evolution (8% to 33%) (FIG. 139).

Summary: Continuous Directed Evolution of Base Editors

Genome editing has revolutionized the life sciences and offers the potential to cure genetic diseases. Base editing, a new strategy for genome editing that enables the direct, irreversible conversion of one target base into another in a programmable manner, without requiring a double-strand break in DNA or a donor template, has recently been developed.1-4 Since the majority of disease-relevant mutations are single-base changes, base editors are applicable to the study and treatment of many diseases with a genetic component.

C-to-T base editors use a cytidine deaminase to convert cytidine to uridine in the single-stranded DNA loop opened by Cas9. The opposite strand is nicked by Cas9 to stimulate DNA repair mechanisms that use the edited strand as a template, while a fused uracil glycosylase inhibitor (not shown) slows excision of the edited base. Eventually, DNA repair leads to a C•G to T•C base pair conversion.

Base editors can edit many targets with high efficiency, often achieving editing of 30-70% of cells without enrichment following a single treatment. Current cytidine base editor activity, however, is dependent on the bases surrounding the target nucleotide. C-to-T editors based on the APOBEC1 cytidine deaminase have a preference for editing TC motifs, and disfavor most GC bases. This preference can lead to editing of TC at positions outside the canonical editing window, 3 as well as poor editing of GC targets even when they are optimally positioned. C-to-T editors that use other deaminases such as CDA or AID can provide an effective alternative for certain GC sites, but have overall lower editing efficiency compared to APOBEC1 BEs.3,5 The goal is to use directed evolution to generate a highly active, sequence-context-agnostic base editor.

The C-to-T base editor is an engineered enzyme fusion with >1800 amino acids that uses three protein components in tandem to perform non-native functions, and there is very limited structural and mechanistic information about it. All of these features make unbiased directed evolution an attractive platform for improving base editor function. PACE, phage-assisted continuous evolution, is used herein, which can carry out hundreds of rounds of mutation and selection in each experiment. The aim was to adapt this powerful system to select for base editing.

Coupling base editing to phage replication requires a circuit that can be strongly activated by a single base conversion. A PACE selection was designed and validated in which base editing leads to expression of T7 RNA polymerase, which than transcribes gene III (or a luciferase reporter) from a T7 promoter. Base editing of the transcription template strand converts a Trp codon to a stop codon in mRNA, removing a proteolytic degradation tag from the translated enzyme. This architecture has a wide dynamic range, is tuneable by altering T7 RNA polymerase transcription, and it decouples editing efficiency from downstream DNA repair steps that differ between E. coli and mammalian cells.

To begin PACE using the circuit, evolution was chosen to be restricted to the deaminase portion of base editors. This reduces the size of the phage genome, speeding up propagation, and creates a more densely functional mutational target compared to including Cas9. This was accomplished by encoding the deaminase on the phage fused to a trans-splicing split intein. The remainder of the editor (nuclease-dead Cas9 and uracil glycosylase inhibitor) is then expressed in the host cell, also as a split intein fusion, and the full-length editor is reconstituted by protein splicing after phage infection.

The present selection can be used to improve base editing activity or to select for 5' sequence context compatibility by varying the identify of the base 5' of the target CCA. This PACE base editing selection was applied to improve C-to-T editing of a GCC target that is poorly edited by APOBEC1-based editors such as BE3 and BE4.1,3 APOBEC1 phage was subjected to PACE first on a TCC target to optimize activity, then on the GCC target. One APOBEC1 variant emerging from PACE displayed an activity increase of 180-fold over wild-type APOBEC1 on the GCC target in a bacterial luciferase reporter assay. The same circuits were used to evolve a higher-activity variant of CDA, which has high native GC activity but lower overall efficiency.3 The apparent activity of CDA was improved 3- to 4-fold in the bacterial luciferase assay. Testing of these evolved deaminases in mammalian cells to edit diverse genomic targets is underway and a manuscript is in preparation.

The availability of a PACE selection for base editing opens up many possibilities for improving base editor function. The next goal is to shift and narrow the editing window, which will allow precise modification of a target C without editing of nearby 'bystander' Cs and lead to clean conversion to a single allele. This will require implementing a tandem dual selection, with positive selection in the desired window and negative selection outside it (with Christine Zheng, Harvard class of 2018). A similar approach can be used to select for context-specific editors that modify only Cs within a given sequence context, again reducing bystander C modification. Finally, the BE PACE selection can be applied to A-to-G base editors11 and to new base editor variants that use engineered Cas9 or its homologs to improve their performance.

REFERENCES

1 Komor, A. C., Kim, Y. B., Packer, M. S., Zuris, J. A. & Liu, D. R. Programmable editing of a target base in genomic DNA without double-stranded DNA cleavage. *Nature* 533, 420-424, doi:10.1038/nature17946 (2016).

2 Kim, Y. B. et al. Increasing the genome-targeting scope and precision of base editing with engineered Cas9-cytidine deaminase fusions. *Nat. Biotech.* 35, 371-376, doi:10.1038/nbt.3803 (2017).

3 Komor, A. C. et al. Improved base excision repair inhibition and bacteriophage Mu Gam protein yields C:G-to-T:A base editors with higher efficiency and product purity. *Sci Adv* 3, eaao4774, doi:10.1126/sciadv.aao4774 (2017).

4 Rees, H. A. et al. Improving the DNA specificity and applicability of base editing through protein engineering and protein delivery. *Nat Commun* 8, 15790, doi:10.1038/ncomms15790 (2017).

5 Nishida, K. et al. Targeted nucleotide editing using hybrid prokaryotic and vertebrate adaptive immune systems. *Science* 353, doi:10.1126/science.aaf8729 (2016).

6 Esvelt, K. M., Carlson, J. C. & Liu, D. R. A system for the continuous directed evolution of biomolecules. *Nature* 472, 499-503, doi:10.1038/nature09929 (2011).

7 Carlson, J. C., Badran, A. H., Guggiana-Nilo, D. A. & Liu, D. R. Negative selection and stringency modulation in phage-assisted continuous evolution. *Nat Chem Biol* 10, 216-222, doi:10.1038/nchembio.1453 (2014).

8 Leconte, A. M. et al. A population-based experimental model for protein evolution: effects of mutation rate and selection stringency on evolutionary outcomes. *Biochemistry* 52, 1490-1499, doi:10.1021/bi3016185 (2013).

9 Hubbard, B. P. et al. Continuous directed evolution of DNA-binding proteins to improve TALEN specificity. *Nat Methods* 12, 939-942, doi:10.1038/nmeth.3515 (2015).

10 Bryson, D. I. et al. Continuous directed evolution of aminoacyl-tRNA synthetases. *Nat Chem Biol*, doi: 10.1038/nchembio.2474 (2017).

11 Gaudelli, N. M. et al. Programmable base editing of A*T to G*C in genomic DNA without DNA cleavage. *Nature* 551, 464-471, doi:10.1038/nature24644 (2017).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A cytidine deaminase comprising an amino acid sequence that is at least 80% identical to amino acid residues 2-208 of SEQ ID NO: 3, wherein the cytidine deaminase comprises one or more mutations selected from the group consisting of H10X$_1$, F23X$_2$, V75X$_3$, K120X$_4$, A123X$_5$, C158X$_6$, I193X$_7$, I195X$_8$, and V197X$_9$ relative to SEQ ID NO: 3, or a corresponding mutation(s) in another cytidine deaminase, wherein X$_1$, is any amino acid other than H, X$_2$ is any amino acid other than F, X$_3$ and X$_9$ are any amino acid other than V, X$_4$ is any amino acid other than K, X$_5$ is any amino acid other than A, X$_6$ is any amino acid other than C, and X$_7$ and X8 are any amino acid other than I.

2. The cytidine deaminase of claim 1 comprising amino acid residues 2-208 of SEQ ID NO: 3, wherein the cytidine deaminase comprises one or more mutations selected from the group consisting of H10X$_1$, F23X$_2$, V75X$_3$, K120X$_4$, A123X$_5$, C158X$_6$, I193X$_7$, I195X$_8$, and V197X$_9$ relative to SEQ ID NO: 3, wherein X$_1$, is any amino acid other than H, X$_2$ is any amino acid other than F, X$_3$ and X$_9$ are any amino acid other than V, X$_4$ is any amino acid other than K, X$_5$ is any amino acid other than A, X$_6$ is any amino acid other than C, and X$_7$ and X$_8$ are any amino acid other than I.

3. The cytidine deaminase of claim 1, wherein the cytidine deaminase comprises amino acid residues 2-208 of SEQ ID NO: 7.

4. A fusion protein comprising:
  (i) a nucleic acid programmable DNA binding protein (napDNAbp) and
  (ii) the cytidine deaminase of claim 1.

5. A complex comprising the fusion protein of claim 4 and an RNA bound to the napDNAbp of the fusion protein.

6. A method comprising contacting a nucleic acid molecule with the complex of claim 5.

7. A pharmaceutical composition comprising the fusion protein of claim 4 and a pharmaceutically acceptable excipient.

8. The fusion protein of claim 4 further comprising a uracil glycosylase inhibitor domain (UGI).

9. The fusion protein of claim 4, wherein the amino acid sequence of said fusion protein is the amino acid sequence as set forth in SEQ ID NO: 18.

\* \* \* \* \*

```
                            SEQUENCE LISTING

Sequence total quantity: 139
SEQ ID NO: 1            moltype = AA   length = 162
FEATURE                 Location/Qualifiers
REGION                  1..162
                        note = Synthetic Polypeptide
source                  1..162
                        mol_type = protein
                        organism = synthetic construct
SEQUENCE: 1
MFERNYDPRE LRKETYLLYE IKWGKSGKLW RHWCQNNRTQ HAEVYFLENI FNARRFNPST    60
HCSITWYLSW SPCAECSQKI VDFLKEHPNV NLEIYVARLY YHEDERNRQG LRDLVNSGVT   120
IRIMDLPDYN YCWKTFVSDQ GGDEDYWPGH FAPWIKQYSL KL                     162

SEQ ID NO: 2            moltype = AA   length = 229
FEATURE                 Location/Qualifiers
REGION                  1..229
                        note = Synthetic Polypeptide
source                  1..229
                        mol_type = protein
                        organism = synthetic construct
SEQUENCE: 2
MSSETGPVAV DPTLRRRIEP HEFEVFFDPR ELRKETCLLY EINWGGRHSI WRHTSQNTNK    60
HVEVNFIEKF TTERYFCPNT RCSITWFLSW SPCGECSRAI TEFLSRYPHV TLFIYIARLY   120
HHADPRNRQG LRDLISSGVT IQIMTEQESG YCWRNFVNYS PSNEAHWPRY PHLWVRLYVL   180
ELYCIILGLP PCLNILRRKQ PQLTFFTIAL QSCHYQRLPP HILWATGLK              229

SEQ ID NO: 3            moltype = AA   length = 208
FEATURE                 Location/Qualifiers
REGION                  1..208
                        note = Synthetic Polypeptide
source                  1..208
                        mol_type = protein
                        organism = synthetic construct
SEQUENCE: 3
MTDAEYVRIH EKLDIYTFKK QFFNNKKSVS HRCYVLFELK RRGERRACFW GYAVNKPQSG    60
TERGIHAEIF SIRKVEEYLR DNPGQFTINW YSSWSPCADC AEKILEWYNQ ELRGNGHTLK   120
IWACKLYYEK NARNQIGLWN LRDNGVGLNV MVSEHYQCCR KIFIQSSHNQ LNENRWLEKT   180
LKRAEKRRSE LSIMIQVKIL HTTKSPAV                                     208

SEQ ID NO: 4            moltype = AA   length = 229
FEATURE                 Location/Qualifiers
REGION                  1..229
                        note = Synthetic Polypeptide
source                  1..229
                        mol_type = protein
                        organism = synthetic construct
SEQUENCE: 4
```

```
MSSETGPVAV DPTLRRRIEP HEFEVFFDPR ELRKETCLLY EIKWGTSHKI WRHSSKNTTK    60
HVEVNFIEKF TSERHFCPST SCSITWFLSW SPCGECSKAI TEFLSQHPNV TLVIYVARLY   120
HHMDQQNRQG LRDLVNSGVT IQIMTAPEYD YCWRNFVNYP PGKEAHWPRY PPLWMKLYAL   180
ELHAGILGLP PCLNILRRKQ PQLTFFTIAL QSCHYQRLPP HILWATGLK              229

SEQ ID NO: 5             moltype = AA   length = 162
FEATURE                  Location/Qualifiers
REGION                   1..162
                         note = Synthetic Polypeptide
source                   1..162
                         mol_type = protein
                         organism = synthetic construct
SEQUENCE: 5
MFERNYDPRE LRKETYLLYE IKWGKSGKLW RHWCQNNRTQ HAEVYFLENI FNARRFNPST    60
HCSITWYLSW SPCAECSQKI VDFLKEHPNV NLEIYVARLY YPENERNRQG LRDLVNSGVT   120
IRIMDLPDYN YCWKTFVSDQ GGDEDYWPGH FAPWIKQYSL KL                     162

SEQ ID NO: 6             moltype = AA   length = 229
FEATURE                  Location/Qualifiers
REGION                   1..229
                         note = Synthetic Polypeptide
source                   1..229
                         mol_type = protein
                         organism = synthetic construct
SEQUENCE: 6
MSSKTGPVAV DPTLRRRIEP HEFEVFFDPR ELRKETCLLY EINWGGRHSI WRHTSQNTNK    60
HVEVNFIEKF TTERYFCPNT RCSITWFLSW SPCGECSRAI TEFLSRYPNV TLFIYIARLY   120
HLANPRNRQG LRDLISSGVT IQIMTEQESG YCWHNFVNYS PSNESHWPRY PHLWVRLYVL   180
ELYCIILGLP PCLNILRRKQ SQLTSFTIAL QSCHYQRLPP HILWATGLK              229

SEQ ID NO: 7             moltype = AA   length = 208
FEATURE                  Location/Qualifiers
REGION                   1..208
                         note = Synthetic Polypeptide
source                   1..208
                         mol_type = protein
                         organism = synthetic construct
SEQUENCE: 7
MTDAEYVRIH EKLDIYTFKK QFSNNKKSVS HRCYVLFELK RRGERRACFW GYAVNKPQSG    60
TERGIHAEIF SIRKVEEYLR DNPGQFTINW YSSWSPCADC AEKILEWYNQ ELRGNGHTLK   120
IWVCKLYYEK NARNQIGLWN LRDNGVGLNV MVSEHYQCCR KIFIQSSHNQ LNENRWLEKT   180
LKRAEKRRSE LSIMFQVKIL HTTKSPAV                                     208

SEQ ID NO: 8             moltype = AA   length = 229
FEATURE                  Location/Qualifiers
REGION                   1..229
                         note = Synthetic Polypeptide
source                   1..229
                         mol_type = protein
                         organism = synthetic construct
SEQUENCE: 8
MSSKTGPVAV DPTLRRRIEP HEFEVFFDPR ELRKETCLLY EIKWGTSHKI WRHSSKNTTK    60
HVEVNFIEKF TSERHFCPST SCSITWFLSW SPCGECSKAI TEFLSQHPNV TLVIYVARLY   120
HLMNQQNRQG LRDLVNSGVT IQIMTAPEYD YCWHNFVNYP PGKESHWPRY PPLWMKLYAL   180
ELHAGILGLP PCLNILRRKQ SQLTSFTIAL QSCHYQRLPP HILWATGLK              229

SEQ ID NO: 9             moltype = AA   length = 1367
FEATURE                  Location/Qualifiers
REGION                   1..1367
                         note = Synthetic Polypeptide
source                   1..1367
                         mol_type = protein
                         organism = synthetic construct
SEQUENCE: 9
DKKYSIGLAI GTNSVGWAVI TDEYKVPSKK FKVLGNTDRH SIKKNLIGAL LFDSGETAEA    60
TRLKRTARRR YTRRKNRICY LQEIFSNEMA KVDDSFFHRL EESFLVEEDK KHERHPIFGN   120
IVDEVAYHEK YPTIYHLRKK LVDSTDKADL RLIYLALAHM IKFRGHFLIE GDLNPDNSDV   180
DKLFIQLVQT YNQLFEENPI NASGVDAKAI LSARLSKSRR LENLIAQLPG EKKNGLFGNL   240
IALSLGLTPN FKSNFDLAED AKLQLSKDTY DDDLDNLLAQ IGDQYADLFL AAKNLSDAIL   300
LSDILRVNTE ITKAPLSASM IKRYDEHHQD LTLLKALVRQ QLPEKYKEIF FDQSKNGYAG   360
YIDGGASQEE FYKFIKPILE KMDGTEELLV KLNREDLLRK QRTFDNGSIP HQIHLGELHA   420
ILRRQEDFYP FLKDNREKIE KILTFRIPYY VGPLARGNSR FAWMTRKSEE TITPWNFEEV   480
VDKGASAQSF IERMTNFDKN LPNEKVLPKH SLLYEYFTVY NELTKVKYVT EGMRKPAFLS   540
GEQKKAIVDL LFKTNRKVTV KQLKEDYFKK IECFDSVEIS GVEDRFNASL GTYHDLLKII   600
KDKDFLDNEE NEDILEDIVL TLTLFEDREM IEERLKTYAH LFDDKVMKQL KRRRYTGWGR   660
LSRKLINGIR DKQSGKTILD FLKSDGFANR NFMQLIHDDS LTFKEDIQKA QVSGQGDSLH   720
EHIANLAGSP AIKKGILQTV KVVDELVKVM GRHKPENIVI EMARENQTTQ KGQKNSRERM   780
KRIEEGIKEL GSQILKEHPV ENTQLQNEKL YLYYLQNGRD MYVDQELDIN RLSDYDVDHI   840
VPQSFLKDDS IDNKVLTRSD KNRGKSDNVP SEEVVKKMKN YWRQLLNAKL ITQRKFDNLT   900
```

```
KAERGGLSEL DKAGFIKRQL VETRQITKHV AQILDSRMNT KYDENDKLIR EVKVITLKSK  960
LVSDFRKDFQ FYKVREINNY HHAHDAYLNA VVGTALIKKY PKLESEFVYG DYKVYDVRKM 1020
IAKSEQEIGK ATAKYFFYSN IMNFFKTEIT LANGEIRKRP LIETNGETGE IVWDKGRDFA 1080
TVRKVLSMPQ VNIVKKTEVQ TGGFSKESIL PKRNSDKLIA RKKDWDPKKY GGFDSPTVAY 1140
SVLVVAKVEK GKSKKLKSVK ELLGITIMER SSFEKNPIDF LEAKGYKEVK KDLIIKLPKY 1200
SLFELENGRK RMLASAGELQ KGNELALPSK YVNFLYLASH YEKLKGSPED NEQKQLFVEQ 1260
HKHYLDEIIE QISEFSKRVI LADANLDKVL SAYNKHRDKP IREQAENIIH LFTLTNLGAP 1320
AAFKYFDTTI DRKRYTSTKE VLDATLIHQS ITGLYETRID LSQLGGD                1367

SEQ ID NO: 10         moltype = AA  length = 84
FEATURE               Location/Qualifiers
REGION                1..84
                      note = Synthetic Polypeptide
source                1..84
                      mol_type = protein
                      organism = synthetic construct
SEQUENCE: 10
MTNLSDIIEK ETGKQLVIQE SILMLPEEVE EVIGNKPESD ILVHTAYDES TDENVMLLTS  60
DAPEYKPWAL VIQDSNGENK IKML                                         84

SEQ ID NO: 11         moltype = AA  length = 32
FEATURE               Location/Qualifiers
REGION                1..32
                      note = Synthetic Polypeptide
source                1..32
                      mol_type = protein
                      organism = synthetic construct
SEQUENCE: 11
SGGSSGGSSG SETPGTSESA TPESSGGSSG GS                                32

SEQ ID NO: 12         moltype = AA  length = 10
FEATURE               Location/Qualifiers
REGION                1..10
                      note = Synthetic Polypeptide
source                1..10
                      mol_type = protein
                      organism = synthetic construct
SEQUENCE: 12
SGGSGGSGGS                                                         10

SEQ ID NO: 13         moltype = AA  length = 17
FEATURE               Location/Qualifiers
REGION                1..17
                      note = Synthetic Polypeptide
source                1..17
                      mol_type = protein
                      organism = synthetic construct
SEQUENCE: 13
KRTADGSEFE PKKKRKV                                                 17

SEQ ID NO: 14         moltype = AA  length = 4
FEATURE               Location/Qualifiers
REGION                1..4
                      note = Synthetic Polypeptide
source                1..4
                      mol_type = protein
                      organism = synthetic construct
SEQUENCE: 14
SGGS                                                               4

SEQ ID NO: 15         moltype = AA  length = 1853
FEATURE               Location/Qualifiers
REGION                1..1853
                      note = Synthetic Polypeptide
source                1..1853
                      mol_type = protein
                      organism = synthetic construct
SEQUENCE: 15
MKRTADGSEF ESPKKKRKVS SETGPVAVDP TLRRRIEPHE FEVFFDPREL RKETCLLYEI   60
NWGGRHSIWR HTSQNTNKHV EVNFIEKFTT ERYFCPNTRC SITWFLSWSP CGECSRAITE  120
FLSRYPHVTL FIYIARLYHH ADPRNRQGLR DLISSGVTIQ IMTEQESGYC WRNFVNYSPS  180
NEAHWPRYPH LWVRLYVLEL YCIILGLPPC LNILRRKQPQ LTFFTIALQS CHYQRLPPHI  240
LWATGLKSGG SSGGSSGSET PGTSESATPE SSGGSSGGSD KKYSIGLAIG TNSVGWAVIT  300
DEYKVPSKKF KVLGNTDRHS IKKNLIGALL FDSGETAEAT RLKRTARRRY TRRKNRICYL  360
QEIFSNEMAK VDDSFFHRLE ESFLVEEDKK HERHPIFGNI VDEVAYHEKY PTIYHLRKKL  420
VDSTDKADLR LIYLALAHMI KFRGHFLIEG DLNPDNSDVD KLFIQLVQTY NQLFEENPIN  480
ASGVDAKAIL SARLSKSRRL ENLIAQLPGE KKNGLFGNLI ALSLGLTPNF KSNFDLAEDA  540
KLQLSKDTYD DDLDNLLAQI GDQYADLFLA AKNLSDAILL SDILRVNTEI TKAPLSASMI  600
KRYDEHHQDL TLLKALVRQQ LPEKYKEIFF DQSKNGYAGY IDGGASQEEF YKFIKPILEK  660
```

```
MDGTEELLVK LNREDLLRKQ RTFDNGSIPH QIHLGELHAI LRRQEDFYPF LKDNREKIEK    720
ILTFRIPYYV GPLARGNSRF AWMTRKSEET ITPWNFEEVV DKGASAQSFI ERMTNFDKNL    780
PNEKVLPKHS LLYEYFTVYN ELTKVKYVTE GMRKPAFLSG EQKKAIVDLL FKTNRKVTVK    840
QLKEDYFKKI ECFDSVEISG VEDRFNASLG TYHDLLKIIK DKDFLDNEEN EDILEDIVLT    900
LTLFEDREMI EERLKTYAHL FDDKVMKQLK RRRYTGWGRL SRKLINGIRD KQSGKTILDF    960
LKSDGFANRN FMQLIHDDSL TFKEDIQKAQ VSGQGDSLHE HIANLAGSPA IKKGILQTVK   1020
VVDELVKVMG RHKPENIVIE MARENQTTQK GQKNSRERMK RIEEGIKELG SQILKEHPVE   1080
NTQLQNEKLY LYYLQNGRDM YVDQELDINR LSDYDVDHIV PQSFLKDDSI DNKVLTRSDK   1140
NRGKSDNVPS EEVVKKMKNY WRQLLNAKLI TQRKFDNLTK AERGGLSELD KAGFIKRQLV   1200
ETRQITKHVA QILDSRMNTK YDENDKLIRE VKVITLKSKL VSDFRKDFQF YKVREINNYH   1260
HAHDAYLNAV VGTALIKKYP KLESEFVYGD YKVYDVRKMI AKSEQEIGKA TAKYFFYSNI   1320
MNFFKTEITL ANGEIRKRPL IETNGETGEI VWDKGRDFAT VRKVLSMPQV NIVKKTEVQT   1380
GGFSKESILP KRNSDKLIAR KKDWDPKKYG GFDSPTVAYS VLVVAKVEKG KSKKLKSVKE   1440
LLGITIMERS SFEKNPIDFL EAKGYKEVKK DLIIKLPKYS LFELENGRKR MLASAGELQK   1500
GNELALPSKY VNFLYLASHY EKLKGSPEDN EQKQLFVEQH KHYLDEIIEQ ISEFSKRVIL   1560
ADANLDKVLS AYNKHRDKPI REQAENIIHL FTLTNLGAPA AFKYFDTTID RKRYTSTKEV   1620
LDATLIHQSI TGLYETRIDL SQLGGDSGGS GGSGGSTNLS DIIEKETGKQ LVIQESILML   1680
PEEVEEVIGN KPESDILVHT AYDESTDENV MLLTSDAPEY KPWALVIQDS NGENKIKMLS   1740
GGSGGSGGST NLSDIIEKET GKQLVIQESI LMLPEEVEEV IGNKPESDIL VHTAYDESTD   1800
ENVMLLTSDA PEYKPWALVI QDSNGENKIK MLSGGSKRTA DGSEFEPKKK RKV          1853

SEQ ID NO: 16           moltype = AA  length = 1853
FEATURE                 Location/Qualifiers
REGION                  1..1853
                        note = Synthetic Polypeptide
source                  1..1853
                        mol_type = protein
                        organism = synthetic construct
SEQUENCE: 16
MKRTADGSEF ESPKKKRKVS SKTGPVAVDP TLRRRIEPHE FEVFFDPREL RKETCLLYEI     60
NWGGRHSIWR HTSQNTNKHV EVNFIEKFTT ERYFCPNTRC SITWFLSWSP CGECSRAITE    120
FLSRYPNVTL FIYIARLYHL ANPRNRQGLR DLISSGVTIQ IMTEQESGYC WHNFVNYSPS    180
NESHWPRYPH LWVRLYVLEL YCIILGLPPC LNILRRKQSQ LTSFTIALQS CHYQRLPPHI    240
LWATGLKSGG SSGGSSGSET PGTSESATPE SSGGSSGGSD KKYSIGLAIG TNSVGWAVIT    300
DEYKVPSKKF KVLGNTDRHS IKKNLIGALL FDSGETAEAT RLKRTARRRY TRRKNRICYL    360
QEIFSNEMAK VDDSFFHRLE ESFLVEEDKK HERHPIFGNI VDEVAYHEKY PTIYHLRKKL    420
VDSTDKADLR LIYLALAHMI KFRGHFLIEG DLNPDNSDVD KLFIQLVQTY NQLFEENPIN    480
ASGVDAKAIL SARLSKSRRL ENLIAQLPGE KKNGLFGNLI ALSLGLTPNF KSNFDLAEDA    540
KLQLSKDTYD DDLDNLLAQI GDQYADLFLA AKNLSDAILL SDILRVNTEI TKAPLSASMI    600
KRYDEHHQDL TLLKALVRQQ LPEKYKEIFF DQSKNGYAGY IDGGASQEEF YKFIKPILEK    660
MDGTEELLVK LNREDLLRKQ RTFDNGSIPH QIHLGELHAI LRRQEDFYPF LKDNREKIEK    720
ILTFRIPYYV GPLARGNSRF AWMTRKSEET ITPWNFEEVV DKGASAQSFI ERMTNFDKNL    780
PNEKVLPKHS LLYEYFTVYN ELTKVKYVTE GMRKPAFLSG EQKKAIVDLL FKTNRKVTVK    840
QLKEDYFKKI ECFDSVEISG VEDRFNASLG TYHDLLKIIK DKDFLDNEEN EDILEDIVLT    900
LTLFEDREMI EERLKTYAHL FDDKVMKQLK RRRYTGWGRL SRKLINGIRD KQSGKTILDF    960
LKSDGFANRN FMQLIHDDSL TFKEDIQKAQ VSGQGDSLHE HIANLAGSPA IKKGILQTVK   1020
VVDELVKVMG RHKPENIVIE MARENQTTQK GQKNSRERMK RIEEGIKELG SQILKEHPVE   1080
NTQLQNEKLY LYYLQNGRDM YVDQELDINR LSDYDVDHIV PQSFLKDDSI DNKVLTRSDK   1140
NRGKSDNVPS EEVVKKMKNY WRQLLNAKLI TQRKFDNLTK AERGGLSELD KAGFIKRQLV   1200
ETRQITKHVA QILDSRMNTK YDENDKLIRE VKVITLKSKL VSDFRKDFQF YKVREINNYH   1260
HAHDAYLNAV VGTALIKKYP KLESEFVYGD YKVYDVRKMI AKSEQEIGKA TAKYFFYSNI   1320
MNFFKTEITL ANGEIRKRPL IETNGETGEI VWDKGRDFAT VRKVLSMPQV NIVKKTEVQT   1380
GGFSKESILP KRNSDKLIAR KKDWDPKKYG GFDSPTVAYS VLVVAKVEKG KSKKLKSVKE   1440
LLGITIMERS SFEKNPIDFL EAKGYKEVKK DLIIKLPKYS LFELENGRKR MLASAGELQK   1500
GNELALPSKY VNFLYLASHY EKLKGSPEDN EQKQLFVEQH KHYLDEIIEQ ISEFSKRVIL   1560
ADANLDKVLS AYNKHRDKPI REQAENIIHL FTLTNLGAPA AFKYFDTTID RKRYTSTKEV   1620
LDATLIHQSI TGLYETRIDL SQLGGDSGGS GGSGGSTNLS DIIEKETGKQ LVIQESILML   1680
PEEVEEVIGN KPESDILVHT AYDESTDENV MLLTSDAPEY KPWALVIQDS NGENKIKMLS   1740
GGSGGSGGST NLSDIIEKET GKQLVIQESI LMLPEEVEEV IGNKPESDIL VHTAYDESTD   1800
ENVMLLTSDA PEYKPWALVI QDSNGENKIK MLSGGSKRTA DGSEFEPKKK RKV          1853

SEQ ID NO: 17           moltype = AA  length = 1833
FEATURE                 Location/Qualifiers
REGION                  1..1833
                        note = Synthetic Polypeptide
source                  1..1833
                        mol_type = protein
                        organism = synthetic construct
SEQUENCE: 17
MKRTADGSEF ESPKKKRKVS TDAEYVRIHE KLDIYTFKKQ FFNNKKSVSH RCYVLFELKR     60
RGERRACFWG YAVNKPQSGT ERGIHAEIFS IRKVEEYLRD NPGQFTINWY SSWSPCADCA    120
EKILEWYNQE LRGNGHTLKI WACKLYYEKN ARNQIGLWNL RDNGVGLNVM VSEHYQCCRK    180
IPIQSSHNQL NENRWLEKTL KRAEKRRSEL SIMIQVKILH TTKSPAVSGG SSGGSSGSET    240
PGTSESATPE SSGGSSGGSD KKYSIGLAIG TNSVGWAVIT DEYKVPSKKF KVLGNTDRHS    300
IKKNLIGALL FDSGETAEAT RLKRTARRRY TRRKNRICYL QEIFSNEMAK VDDSFFHRLE    360
ESFLVEEDKK HERHPIFGNI VDEVAYHEKY PTIYHLRKKL VDSTDKADLR LIYLALAHMI    420
KFRGHFLIEG DLNPDNSDVD KLFIQLVQTY NQLFEENPIN ASGVDAKAIL SARLSKSRRL    480
ENLIAQLPGE KKNGLFGNLI ALSLGLTPNF KSNFDLAEDA KLQLSKDTYD DDLDNLLAQI    540
GDQYADLFLA AKNLSDAILL SDILRVNTEI TKAPLSASMI KRYDEHHQDL TLLKALVRQQ    600
```

```
LPEKYKEIFF DQSKNGYAGY IDGGASQEEF YKFIKPILEK MDGTEELLVK LNREDLLRKQ    660
RTFDNGSIPH QIHLGELHAI LRRQEDFYPF LKDNREKIEK ILTFRIPYYV GPLARGNSRF    720
AWMTRKSEET ITPWNFEEVV DKGASAQSFI ERMTNFDKNL PNEKVLPKHS LLYEYFTVYN    780
ELTKVKVYTE GMRKPAFLSG EQKKAIVDLL FKTNRKVTVK QLKEDYFKKI ECFDSVEISG    840
VEDRFNASLG TYHDLLKIIK DKDFLDNEEN EDILEDIVLT LTLFEDREMI EERLKTYAHL    900
FDDKVMKQLK RRRYTGWGRL SRKLINGIRD KQSGKTILDF LKSDGFANRN FMQLIHDDSL    960
TFKEDIQKAQ VSGQGDSLHE HIANLAGSPA IKKGILQTVK VVDELVKVMG RHKPENIVIE   1020
MARENQTTQK GQKNSRERMK RIEEGIKELG SQILKEHPVE NTQLQNEKLY LYYLQNGRDM   1080
YVDQELDINR LSDYDVDHIV PQSFLKDDSI DNKVLTRSDK NRGKSDNVPS EEVVKKMKNY   1140
WRQLLNAKLI TQRKFDNLTK AERGGLSELD KAGFIKRQLV ETRQITKHVA QILDSRMNTK   1200
YDENDKLIRE VKVITLKSKL VSDFRKDFQF YKVREINNYH HAHDAYLNAV VGTALIKKYP   1260
KLESEFVYGD YKVYDVRKMI AKSEQEIGKA TAKYFFYSNI MNFFKTEITL ANGEIRKRPL   1320
IETNGETGEI VWDKGRDFAT VRKVLSMPQV NIVKKTEVQT GGFSKESILP KRNSDKLIAR   1380
KKDWDPKKYG GFDSPTVAYS VLVVAKVEKG KSKKLKSVKE LLGITIMERS SFEKNPIDFL   1440
EAKGYKEVKK DLIIKLPKYS LFELENGRKR MLASAGELQK GNELALPSKY VNFLYLASHY   1500
EKLKGSPEDN EQKQLFVEQH KHYLDEIIEQ ISEFSKRVIL ADANLDKVLS AYNKHRDKPI   1560
REQAENIIHL FTLTNLGAPA AFKYFDTTID RKRYTSTKEV LDATLIHQSI TGLYETRIDL   1620
SQLGGDSGGS GGSGGSTNLS DIIEKETGKQ LVIQESILML PEEVEEVIGN KPESDILHVT   1680
AYDESTDENV MLLTSDAPEY KPWALVIQDS NGENKIKMLS GGSGGSGGST NLSDIIEKET   1740
GKQLVIQESI LMLPEEVEEV IGNKPESDIL VHTAYDESTD ENVMLLTSDA PEYKPWALVI   1800
QDSNGENKIK MLSGGSKRTA DGSEFEPKKK RKV                                1833

SEQ ID NO: 18            moltype = AA   length = 1833
FEATURE                  Location/Qualifiers
REGION                   1..1833
                         note = Synthetic Polypeptide
source                   1..1833
                         mol_type = protein
                         organism = synthetic construct
SEQUENCE: 18
MKRTADGSEF ESPKKKRKVS TDAEYVRIHE KLDIYTFKKQ FSNNKKSVSH RCYVLFELKR     60
RGERRACFWG YAVNKPQSGT ERGIHAEIFS IRKVEEYLRD NPGQFTINWY SSWSPCADCA    120
EKILEWYNQE LRGNGHTLKI WVCKLYYEKN ARNQIGLWNL RDNGVGLNVM VSEHYQCCRK    180
IFIQSSHNQL NENRWKILH KRAEKRRSEL SIMFQVKILH TTKSPAVSGG SSGGSSGSET    240
PGTSESATPE SSGGSSGGSD KKYSIGLAIG TNSVGWAVIT DEYKVPSKKF KVLGNTDRHS    300
IKKNLIGALL FDSGETAEAT RLKRTARRRY TRRKNRICYL QEIFSNEMAK VDDSFFHRLE    360
ESFLVEEDKK HERHPIFGNI VDEVAYHEKY PTIYHLRKKL VDSTDKADLR LIYLALAHMI    420
KFRGHFLIEG DLNPDNSDVD KLFIQLVQTY NQLFEENPIN ASGVDAKAIL SARLSKSRRL    480
ENLIAQLPGE KKNGLFGNLI ALSLGLTPNF KSNFDLAEDA KLQLSKDTYD DDLDNLLAQI    540
GDQYADLFLA AKNLSDAILL SDILRVNTEI TKAPLSASMI KRYDEHHQDL TLLKALVRQQ    600
LPEKYKEIFF DQSKNGYAGY IDGGASQEEF YKFIKPILEK MDGTEELLVK LNREDLLRKQ    660
RTFDNGSIPH QIHLGELHAI LRRQEDFYPF LKDNREKIEK ILTFRIPYYV GPLARGNSRF    720
AWMTRKSEET ITPWNFEEVV DKGASAQSFI ERMTNFDKNL PNEKVLPKHS LLYEYFTVYN    780
ELTKVKVYTE GMRKPAFLSG EQKKAIVDLL FKTNRKVTVK QLKEDYFKKI ECFDSVEISG    840
VEDRFNASLG TYHDLLKIIK DKDFLDNEEN EDILEDIVLT LTLFEDREMI EERLKTYAHL    900
FDDKVMKQLK RRRYTGWGRL SRKLINGIRD KQSGKTILDF LKSDGFANRN FMQLIHDDSL    960
TFKEDIQKAQ VSGQGDSLHE HIANLAGSPA IKKGILQTVK VVDELVKVMG RHKPENIVIE   1020
MARENQTTQK GQKNSRERMK RIEEGIKELG SQILKEHPVE NTQLQNEKLY LYYLQNGRDM   1080
YVDQELDINR LSDYDVDHIV PQSFLKDDSI DNKVLTRSDK NRGKSDNVPS EEVVKKMKNY   1140
WRQLLNAKLI TQRKFDNLTK AERGGLSELD KAGFIKRQLV ETRQITKHVA QILDSRMNTK   1200
YDENDKLIRE VKVITLKSKL VSDFRKDFQF YKVREINNYH HAHDAYLNAV VGTALIKKYP   1260
KLESEFVYGD YKVYDVRKMI AKSEQEIGKA TAKYFFYSNI MNFFKTEITL ANGEIRKRPL   1320
IETNGETGEI VWDKGRDFAT VRKVLSMPQV NIVKKTEVQT GGFSKESILP KRNSDKLIAR   1380
KKDWDPKKYG GFDSPTVAYS VLVVAKVEKG KSKKLKSVKE LLGITIMERS SFEKNPIDFL   1440
EAKGYKEVKK DLIIKLPKYS LFELENGRKR MLASAGELQK GNELALPSKY VNFLYLASHY   1500
EKLKGSPEDN EQKQLFVEQH KHYLDEIIEQ ISEFSKRVIL ADANLDKVLS AYNKHRDKPI   1560
REQAENIIHL FTLTNLGAPA AFKYFDTTID RKRYTSTKEV LDATLIHQSI TGLYETRIDL   1620
SQLGGDSGGS GGSGGSTNLS DIIEKETGKQ LVIQESILML PEEVEEVIGN KPESDILVHT   1680
AYDESTDENV MLLTSDAPEY KPWALVIQDS NGENKIKMLS GGSGGSGGST NLSDIIEKET   1740
GKQLVIQESI LMLPEEVEEV IGNKPESDIL VHTAYDESTD ENVMLLTSDA PEYKPWALVI   1800
QDSNGENKIK MLSGGSKRTA DGSEFEPKKK RKV                                1833

SEQ ID NO: 19            moltype = AA   length = 1787
FEATURE                  Location/Qualifiers
REGION                   1..1787
                         note = Synthetic Polypeptide
source                   1..1787
                         mol_type = protein
                         organism = synthetic construct
SEQUENCE: 19
MKRTADGSEF ESPKKKRKVS FERNYDPREL RKETYLLYEI KWGKSGKLWR HWCQNNRTQH     60
AEVYFLENIF NARRFNPSTH CSITWYLSWS PCAECSQKIV DFLKEHPNVN LEIYVARLYY    120
HEDERNRQGL RDLVNSGVTI RIMDLPDYNY CWKTFVSDQG GDEDYWPGHF APWIKQYSLK    180
LSGGSSGGSS GSETPGTSES ATPESSGGSS GGSDKKYSIG LAIGTNSVGW AVITDEYKVP    240
SKKFKVLGNT DRHSIKKNLI GALLFDSGET AEATRLKRTA RRRYTRRKNR ICYLQEIFSN    300
EMAKVDDSFF HRLEESFLVE EDKKHERHPI FGNIVDEVAY HEKYPTIYHL RKKLVDSTDK    360
ADLRLIYLAL AHMIKFRGHF LIEGDLNPDN SDVDKLFIQL VQTYNQLFEE NPINASGVDA    420
KAILSARLSK SRRLENLIAQ LPGEKKNGLF GNLIALSLGL TPNFKSNFDL AEDAKLQLSK    480
DTYDDDLDNL LAQIGDQYAD LFLAAKNLSD AILLSDILRV NTEITKAPLS ASMIKRYDEH    540
```

```
HQDLTLLKAL VRQQLPEKYK EIFFDQSKNG YAGYIDGGAS QEEFYKFIKP ILEKMDGTEE    600
LLVKLNREDL LRKQRTFDNG SIPHQIHLGE LHAILRRQED FYPFLKDNRE KIEKILTFRI    660
PYYVGPLARG NSRFAWMTRK SEETITPWNF EEVVDKGASA QSFIERMTNF DKNLPNEKVL    720
PKHSLLYEYF TVYNELTKVK YVTEGMRKPA FLSGEQKKAI VDLLFKTNRK VTVKQLKEDY    780
FKKIECFDSV EISGVEDRFN ASLGTYHDLL KIIKDKDFLD NEENEDILED IVLTLTLFED    840
REMIEERLKT YAHLFDDKVM KQLKRRRYTG WGRLSRKLIN GIRDKQSGKT ILDFLKSDGF    900
ANRNFMQLIH DDSLTFKEDI QKAQVSGQGD SLHEHIANLA GSPAIKKGIL QTVKVVDELV    960
KVMGRHKPEN IVIEMARENQ TTQKGQKNSR ERMKRIEEGI KELGSQILKE HPVENTQLQN   1020
EKLYLYYLQN GRDMYVDQEL DINRLSDYDV DHIVPQSFLK DDSIDNKVLT RSDKNRGKSD   1080
NVPSEEVVKK MKNYWRQLLN AKLITQRKFD NLTKAERGGL SELDKAGFIK RQLVETRQIT   1140
KHVAQILDSR MNTKYDENDK LIREVKVITL KSKLVSDFRK DFQFYKVREI NNYHHAHDAY   1200
LNAVVGTALI KKYPKLESEF VYGDYKVYDV RKMIAKSEQE IGKATAKYFF YSNIMNFFKT   1260
EITLANGEIR KRPLIETNGE TGEIVWDKGR DFATVRKVLS MPQVNIVKKT EVQTGGFSKE   1320
SILPKRNSDK LIARKKDWDP KKYGGFDSPT VAYSVLVVAK VEKGKSKKLK SVKELLGITI   1380
MERSSFEKNP IDFLEAKGYK EVKKDLIIKL PKYSLFELEN GRKRMLASAG ELQKGNELAL   1440
PSKYVNFLYL ASHYEKLKGS PEDNEQKQLF VEQHKHYLDE IIEQISEFSK RVILADANLD   1500
KVLSAYNKHR DKPIREQAEN IIHLFTLTNL GAPAAFKYFD TTIDRKRYTS TKEVLDATLI   1560
HQSITGLYET RIDLSQLGGD SGSGGSGGS TNLSDIIEKE TGKQLVIQES ILMLPEEVEE    1620
VIGNKPESDI LVHTAYDEST DENVMLLTSD APEYKPWALV IQDSNGENKI KMLSGGSGGS   1680
GGSTNLSDII EKETGKQLVI QESILMLPEE VEEVIGNKPE SDILVHTAYD ESTDENVMLL   1740
TSDAPEYKPW ALVIQDSNGE NKIKMLSGGS KRTADGSEFE PKKKRKV                 1787

SEQ ID NO: 20           moltype = AA   length = 1787
FEATURE                 Location/Qualifiers
REGION                  1..1787
                        note = Synthetic Polypeptide
source                  1..1787
                        mol_type = protein
                        organism = synthetic construct
SEQUENCE: 20
MKRTADGSEF ESPKKKRKVS FERNYDPREL RKETYLLYEI KWGKSGKLWR HWCQNNRTQH     60
AEVYFLENIF NARRFNPSTH CSITWYLSWS PCAECSQKIV DFLKEHPNVN LEIYVARLYY    120
PENERNRQGL RDLVNSGVTI RIMDLPDYNY CWKTFVSDQG GDEDYWPGHF APWIKQYSLK    180
LSGGSGGSS GSETPGTSES ATPESSGGSS GGSDKKYSIG LAIGTNSVGW AVITDEYKVP    240
SKKFKVLGNT DRHSIKKNLI GALLFDSGET AEATRLKRTA RRRYTRRKNR ICYLQEIFSN    300
EMAKVDDSFF HRLEESFLVE EDKKHERHPI FGNIVDEVAY HEKYPTIYHL RKKLVDSTDK    360
ADLRLIYLAL AHMIKFRGHF LIEGDLNPDN SDVDKLFIQL VQTYNQLFEE NPINASGVDA    420
KAILSARLSK SRRLENLIAQ LPGEKKNGLF GNLIALSLGL TPNFKSNFDL AEDAKLQLSK    480
DTYDDDLDNL LAQIGDQYAD LFLAAKNLSD AILLSDILRV NTEITKAPLS ASMIKRYDEH    540
HQDLTLLKAL VRQQLPEKYK EIFFDQSKNG YAGYIDGGAS QEEFYKFIKP ILEKMDGTEE    600
LLVKLNREDL LRKQRTFDNG SIPHQIHLGE LHAILRRQED FYPFLKDNRE KIEKILTFRI    660
PYYVGPLARG NSRFAWMTRK SEETITPWNF EEVVDKGASA QSFIERMTNF DKNLPNEKVL    720
PKHSLLYEYF TVYNELTKVK YVTEGMRKPA FLSGEQKKAI VDLLFKTNRK VTVKQLKEDY    780
FKKIECFDSV EISGVEDRFN ASLGTYHDLL KIIKDKDFLD NEENEDILED IVLTLTLFED    840
REMIEERLKT YAHLFDDKVM KQLKRRRYTG WGRLSRKLIN GIRDKQSGKT ILDFLKSDGF    900
ANRNFMQLIH DDSLTFKEDI QKAQVSGQGD SLHEHIANLA GSPAIKKGIL QTVKVVDELV    960
KVMGRHKPEN IVIEMARENQ TTQKGQKNSR ERMKRIEEGI KELGSQILKE HPVENTQLQN   1020
EKLYLYYLQN GRDMYVDQEL DINRLSDYDV DHIVPQSFLK DDSIDNKVLT RSDKNRGKSD   1080
NVPSEEVVKK MKNYWRQLLN AKLITQRKFD NLTKAERGGL SELDKAGFIK RQLVETRQIT   1140
KHVAQILDSR MNTKYDENDK LIREVKVITL KSKLVSDFRK DFQFYKVREI NNYHHAHDAY   1200
LNAVVGTALI KKYPKLESEF VYGDYKVYDV RKMIAKSEQE IGKATAKYFF YSNIMNFFKT   1260
EITLANGEIR KRPLIETNGE TGEIVWDKGR DFATVRKVLS MPQVNIVKKT EVQTGGFSKE   1320
SILPKRNSDK LIARKKDWDP KKYGGFDSPT VAYSVLVVAK VEKGKSKKLK SVKELLGITI   1380
MERSSFEKNP IDFLEAKGYK EVKKDLIIKL PKYSLFELEN GRKRMLASAG ELQKGNELAL   1440
PSKYVNFLYL ASHYEKLKGS PEDNEQKQLF VEQHKHYLDE IIEQISEFSK RVILADANLD   1500
KVLSAYNKHR DKPIREQAEN IIHLFTLTNL GAPAAFKYFD TTIDRKRYTS TKEVLDATLI   1560
HQSITGLYET RIDLSQLGGD SGSGGSGGS TNLSDIIEKE TGKQLVIQES ILMLPEEVEE    1620
VIGNKPESDI LVHTAYDEST DENVMLLTSD APEYKPWALV IQDSNGENKI KMLSGGSGGS   1680
GGSTNLSDII EKETGKQLVI QESILMLPEE VEEVIGNKPE SDILVHTAYD ESTDENVMLL   1740
TSDAPEYKPW ALVIQDSNGE NKIKMLSGGS KRTADGSEFE PKKKRKV                 1787

SEQ ID NO: 21           moltype = DNA   length = 6407
FEATURE                 Location/Qualifiers
source                  1..6407
                        mol_type = genomic DNA
                        note = Bacteriophage
                        organism = unidentified
SEQUENCE: 21
aacgctacta ctattagtag aattgatgcc acctttttcag ctcgcgcccc aaatgaaaat     60
atagctaaac aggttattga ccatttgcga aatgtatcta atggtcaaac taaatctact    120
cgttcgcaga attgggaatc aactgttaca tggaatgaaa cttccagaca ccgtacttta    180
gttgcatatt taaaacatgt tgagctacag caccagattc agcaattaag ctctaagcca    240
tccgcaaaaa tgacctctta tcaaaaggag caattaaagg tactctctaa tcctgacctg    300
ttggagtttg cttccggtct ggttcgcttt gaagctcgaa ttaaaacgcg atatttgaag    360
tctttcgggc ttcctcttaa tctttttgat gcaatccgct ttgcttctga ctataatagt    420
cagggtaaag acctgatttt tgatttatgg tcattctcgt tttctgaact gtttaaagca    480
tttgaggggg attcaatgaa tatttatgac gattccgcag tattggacgc tatccagtct    540
aaacatttta ctattacccc ctctggcaaa acttcttttg caaagcctc tcgctatttt    600
ggttttttatc gtcgtctggt aaacgagggt tatgatagtg ttgctcttac tatgcctcgt    660
```

```
aattccttttt ggcgttatgt atctgcatta gttgaatgtg gtattcctaa atctcaactg    720
atgaatcttt ctacctgtaa taatgttgtt ccgttagttc gttttattaa cgtagatttt    780
tcttcccaac gtcctgactg gtataatgag ccagttctta aaatcgcata aggtaattca    840
caatgattaa agttgaaatt aaaccatctc aagcccaatt tactactcgt tctggtgttt    900
ctcgtcaggg caagccttat tcactgaatg agcagctttc ttacgttgat ttgggtaatg    960
aatatccggt tcttgtcaag attactcttg atgaaggtca gccagcctat gcgcctggtc   1020
tgtacaccgt tcatctgtcc tcttttcaaag ttggtcagtt cggttccctt atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctgggggt   1200
caaagatgag tgttttagtg tattctttcg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctccttt ggagcctttt   1560
tttttggaga ttttcaacat gaaaaaatta ttattcgcaa ttcctttagt tgttcctttc   1620
tattctcact ccgctgaaac tgttgaaagt tgtttagcaa aaccccatac agaaaattca   1680
tttactaacg tctggaaaga cgacaaaact ttagatcgtt acgctaacta tgaggggttgt   1740
ctgtggaatg ctacaggcgt tgtagtttgt actggtgacg aaactcagtg ttacggtaca   1800
tgggttccta ttgggcttgc tatccctgaa aatgagggtg gtggctctga gggtggcggt   1860
tctgagggtg gcggttctga gggtggcggt actaaacctc ctgagtacgg tgatacacct   1920
attccgggct atacttatat caaccctctc gacggcactt atccgcctgg tactgagcaa   1980
aaccccgcta atcctaatcc ttctcttgag gagtctcagc ctcttaatac tttcatgttt   2040
cagaataata ggttccgaaa taggcagggg gcattaactg tttatacggg cactgttact   2100
caaggcactg acccgttaa aacttattac cagtacactc ctgtatcatc aaaagccatg   2160
tatgacgctt actggaacgg taaattcaga gactgcgctt tccattctgg ctttaatgag   2220
gatccattcg tttgtgaata tcaaggccaa tcgtctgacc tgcctcaacc tcctgtcaat   2280
gctggcggcg gctctggtgg tggttctggt ggcggctctg agggtggtgg ctctgagggt   2340
ggcggttctg agggtggcgg ctctgaggga ggcggttccg gtggtggctc tggttccggt   2400
gattttgatt atgaaaagat ggcaaacgct aataagggct ctatgaccga aaatgccgat   2460
gaaaacgcgc tacagtctga cgctaaaggc aaacttgatt ctgtcgctac tgattacggt   2520
gctgctatcg atggtttcat tggtgacgtt tccggccttg ctaatggtaa tggtgctact   2580
ggtgattttg ctggctctaa ttcccaaatg gctcaagtcg gtgacggtga taattcacct   2640
ttaatgaata atttccgtca atatttacct tccctccctc aatcggttga atgtcgccct   2700
tttgtcttta gcgctgtaa accatatgaa ttttctattg attgtgacaa aataaactta   2760
ttccgtggtg tctttgcgtt tcttttatat gttgccacct ttatgtatgt attttctacg   2820
tttgctaaca tactgcgtaa taaggagtct taatcatgcc agttcttttg ggtattccgt   2880
tattattgcg tttcctcggt ttccttctgg taactttgtt cggctatctg cttacttttc   2940
ttaaaagggg cttcggtaag atagcttattg ctattttcatt gtttcttgct cttattattg   3000
ggcttaactc aattcttgtg ggttatctct ctgatattag cgctcaatta ccctctgact   3060
ttgttcaggg tgttcagtta attctcccgt ctaatgcgct tccctgtttt tatgttattc   3120
tctctgtaaa ggctgctatt ttcattttt gacgttaaaca aaaaatcgtt tcttatttgg   3180
attgggataa ataatatggc tgtttatttt gtaactggca aattaggctc tggaaagacg   3240
ctcgttagcg ttggtaagat tcaggataaa attgtagctg ggtgcaaaat agcaactaat   3300
cttgatttaa ggcttcaaaa cctcccgcaa gtcgggaggt tcgctaaaac gcctcgcgtt   3360
cttagaatac cggataagcc ttctatatct gatttgcttg ctattgggcg cggtaatgat   3420
tcctacgatg aaaataaaaa cggcttgctt gttctcgatg agtgcggtac ttggtttaat   3480
acccgttctt ggaatgataa ggaaagacag ccgattattg attggtttct acatgctcgt   3540
aaattaggat gggatattat ttttcttgtt caggacttat ctattgttga taaacaggcg   3600
cgttctgcat tagctgaaca tgttgtttat tgtcgtcgtc tggacagaat tactttacct   3660
tttgtcgata cttttatattc tcttattact ggctcgaaaa tgcctctgcc taaattacat   3720
gttggcgttg ttaaatatgg cgattctcaa ttaagcccta ctgttgagcg ttggctttat   3780
actggtaaga atttgtataa cgcatatgat actaaacagg cttttttctag taattatgat   3840
tccggtgttt attcttattt aacgccttat ttatcacacg gtcggtattt caaaccatta   3900
aatttaggtc agaagatgaa attaactaaa atatatttga aaaagttttc tcgcgttctt   3960
tgtcttgcga ttggatttgc atcagcattt acatatagtt atataaccca acctaagccg   4020
gaggttaaaa aggtagtctc tcagacctat gattttgata aattcactat tgactcttct   4080
cagcgtctta atctaagcta tcgctatgtt ttcaaggatt ctaagggaaa attaattaat   4140
agcgacgatt tacagaagca aggttattca ctcacatata ttgatttatg tactgtttcc   4200
attaaaaaag gtaattcaaa tgaaattgtt aaatgtaatt aattttgttt tcttgatgtt   4260
tgtttcatca tcttcttttg ctcaggtaat tgaaatgaat aattcgcctc tgcgcgattt   4320
tgtaacttgg tattcaaagc aatcaggcga atccgttatt gtttctcccg atgtaaaagg   4380
tactgttact gtatattcat ctgacgttaa acctgaaaat ctacgcaatt tctttatttc   4440
tgttttacgt gctaataatt ttgatatggt tggttcaatt ccttccataa ttcagaagta   4500
taatccaaac aatcaggatt atattgatga attgccatca tctgataatc aggaatatga   4560
tgataattcc gctccttctg gtggtttctt tgttccgcaa aatgataatg ttactcaaac   4620
ttttaaaatt aataacgttc gggcaaagga tttaatacga gttgtcgaat tgtttgtaaa   4680
gtctaatact tctaaatcct caaatgtatt atctattgac ggctctaatc tattagttgt   4740
tagtgcacct aaagatattt tagataacct tcctcaattc ctttctactg ttgatttgcc   4800
aactgaccag atattgattg agggtttgat atttgaggtt cagcaaggtg atgctttaga   4860
ttttttcattt gctgctggct ctcagcgtgg cactgttgca ggcggtgtta atactgaccg   4920
cctcacctct gttttatctt ctgctggtgg ttcgttcggt attttaatg gcgatgtttt   4980
agggctatca gttcgcgcat taaagactaa tagccattca aaaatattgt ctgtgccacg   5040
tattcttacg ctttctggta gaagggttc atctccagaatg tcccttttca   5100
tactggtcgt gtgactggtg aatctgccaa tgtaaataat ccatttcaga cgattgagcg   5160
tcaaaatgta ggtattttcca tgagcgtttt tcctgttgca atggctggcg gtaatattgt   5220
tctggatatt accagcaagg ccgatagttt gagttcttct actcaggcaa gtgatgttat   5280
tactaatcaa agaagtattg ctacaacggt taatttgcgt gatggacaga ctcttttact   5340
cggtggcctc actgattata aaaacacttc tcaagattct ggcgtaccgt tcctgtctaa   5400
```

```
aatcccttta atcggcctcc tgtttagctc ccgctctgat tccaacgagg aaagcacgtt   5460
atacgtgctc gtcaaagcaa ccatagtacg cgccctgtag cggcgcatta agcgcggcgg   5520
gtgtggtggt tacgcgcagc gtgaccgcta cacttgccag cgccctagcg cccgctcctt   5580
tcgctttctt cccttcCttt ctcgccacgt tcgccggctt tccccgtcaa gctctaaatc   5640
ggggggctccc tttagggttc cgattTagtg ctttacggcg cctcgacccc aaaaaacttg   5700
atttgggtga tggttcacgt agtgggccat cgccctgata gacggttttt cgcccctttga   5760
cgttggagtc cacgttcttt aatagtggac tcttgttcca aactggaaca acactcaacc   5820
ctatctcggg ctattctttt gatttataag ggattttgcc gatttcggcc tattggtaa    5880
aaaatgagct gatttaacaa aaatttaacg cgaattttaa caaaatatta acgtttacaa   5940
tttaaatatt tgcttataca atcttcctgt ttttggggct tttctgatta tcaaccgggg   6000
tacatatgat tgacatgcta gttttacgat taccgttcat cgattctctt gtttgctcca   6060
gactctcagg caatgacctg atagcctttg tagacctctc aaaaatagct accctctccg   6120
gcatgaattt atcagctaga acggttgaat atcatattga tggtgatttg actgtctccg   6180
gccttctca cccttttgaa tctttaccta cacattactc aggcattgca tttaaaatat   6240
atgagggttc taaaaatttt tatccttgcg ttgaaataaa ggcttctccc gcaaaagtat   6300
tacagggtca taatgttttt ggtacaaccg atttagcttt atgctctgag gctttattgc   6360
ttaattttgc taattcttTg ccttgcctgt atgatttatt ggatgtt                6407

SEQ ID NO: 22        moltype = AA   length = 410
FEATURE              Location/Qualifiers
source               1..410
                     mol_type = protein
                     note = Bacteriophage
                     organism = unidentified
SEQUENCE: 22
MIDMLVLRLP FIDSLVCSRL SGNDLIAFVD LSKIATLSGM NLSARTVEYH IDGDLTVSGL    60
SHPFESLPTH YSGIAFKIYE GSKNFYPCVE IKASPAKVLQ GHNVFGTTDL ALCSEALLLN   120
FANSLPCLYD LLDVNATTIS RIDATFSARA PNENIAKQVI DHLRNVSNGQ TKSTRSQNWE   180
STVTWNETSR HRTLVAYLKH VELQHQIQQL SSKPSAKMTS YQKEQLKVLS NPDLLEFASG   240
LVRFEARIKT RYLKSFGLPL NLFDAIRFAS DYNSQGKDLI FDLWSFSFSE LFKAFEGDSM   300
NIYDDSAVLD AIQSKHFTIT PSGKTSFAKA SRYFGFYRRL VNEGYDSVAL TMPRNSFWRY   360
VSALVECGIP KSQLMNLSTC NNVVPLVRFI NVDFSSQRPD WYNEPVLKIA              410

SEQ ID NO: 23        moltype = AA   length = 111
FEATURE              Location/Qualifiers
source               1..111
                     mol_type = protein
                     note = Bacteriophage
                     organism = unidentified
SEQUENCE: 23
MNIYDDSAVL DAIQSKHFTI TPSGKTSFAK ASRYFGFYRR LVNEGYDSVA LTMPRNSFWR    60
YVSALVECGI PKSQLMNLST CNNVVPLVRF INVDFSSQRP DWYNEPVLKI A            111

SEQ ID NO: 24        moltype = AA   length = 87
FEATURE              Location/Qualifiers
source               1..87
                     mol_type = protein
                     note = Bacteriophage
                     organism = unidentified
SEQUENCE: 24
MIKVEIKPSQ AQFTTRSGVS RQGKPYSLNE QLCYVDLGNE YPVLVKITLD EGQPAYAPGL    60
YTVHLSSFKV GQFGSLMIDR LRLVPAK                                        87

SEQ ID NO: 25        moltype = AA   length = 33
FEATURE              Location/Qualifiers
source               1..33
                     mol_type = protein
                     note = Bacteriophage
                     organism = unidentified
SEQUENCE: 25
MEQVADFDTI YQAMIQISVV LCFALGIIAG GQR                                 33

SEQ ID NO: 26        moltype = AA   length = 32
FEATURE              Location/Qualifiers
source               1..32
                     mol_type = protein
                     note = Bacteriophage
                     organism = unidentified
SEQUENCE: 26
MSVLVYSFAS FVLGWCLRSG ITYFTRLMET SS                                  32

SEQ ID NO: 27        moltype = AA   length = 73
FEATURE              Location/Qualifiers
source               1..73
                     mol_type = protein
                     note = Bacteriophage
                     organism = unidentified
SEQUENCE: 27
MKKSLVLKAS VAVATLVPML SFAAEGDDPA KAAFNSLQAS ATEYIGYAWA MVVVIVGATI    60
```

```
GIKLFKKFTS KAS                                                          73

SEQ ID NO: 28             moltype = AA  length = 424
FEATURE                   Location/Qualifiers
source                    1..424
                          mol_type = protein
                          note = Bacteriophage
                          organism = unidentified
SEQUENCE: 28
MKKLLFAIPL VVPFYSHSAE TVESCLAKPH TENSFTNVWK DDKTLDRYAN YEGCLWNATG        60
VVVCTGDETQ CYGTWVPIGL AIPENEGGGS EGGGSEGGGS EGGGTKPPEY GDTPIPGYTY       120
INPLDGTYPP GTEQNPANPN PSLEESQPLN TFMFQNNRFR NRQGALTVYT GTVTQGTDPV       180
KTYYQYTPVS SKAMYDAYWN GKFRDCAFHS GFNEDPFVCE YQGQSSDLPQ PPVNAGGGSG       240
GGSGGGSEGG GSEGGGSEGG GSEGGGSGGG SGSGDFDYEK MANANKGAMT ENADENALQS       300
DAKGKLDSVA TDYGAAIDGF IGDVSGLANG NGATGDFAGS NSQMAQVGDG DNSPLMNNFR       360
QYLPSLPQSV ECRPFVFSAG KPYEFSIDCD KINLFRGVFA FLLYVATFMY VFSTFANILR       420
NKES                                                                   424

SEQ ID NO: 29             moltype = AA  length = 112
FEATURE                   Location/Qualifiers
source                    1..112
                          mol_type = protein
                          note = Bacteriophage
                          organism = unidentified
SEQUENCE: 29
MPVLLGIPLL LRFLGFLLVT LFGYLLTFLK KGFGKIAIAI SLFLALIIGL NSILVGYLSD        60
ISAQLPSDFV QGVQLILPSN ALPCFYVILS VKAAIFIFDV KQKIVSYLDW DK               112

SEQ ID NO: 30             moltype = AA  length = 348
FEATURE                   Location/Qualifiers
source                    1..348
                          mol_type = protein
                          note = Bacteriophage
                          organism = unidentified
SEQUENCE: 30
MAVYFVTGKL GSGKTLVSVG KIQDKIVAGC KIATNLDLRL QNLPQVGRFA KTPRVLRIPD        60
KPSISDLLAI GRGNDSYDEN KNGLLVLDEC GTWFNTRSWN DKERQPIIDW FLHARKLGWD       120
IIFLVQDLSI VDKQARSALA EHVVYCRRLD RITLPFVGTL YSLITGSKMP LPKLHVGVVK       180
YGDSQLSPTV ERWLYTGKNL YNAYDTKQAF SSNYDSGVYS YLTPYLSHGR YFKPLNLGQK       240
MKLTKIYLKK FSRVLCLAIG FASAFTYSYI TQPKPEVKKV VSQTYDFDKF TIDSSQRLNL       300
SYRYVFKDSK GKLINSDDLQ KQGYSLTYID LCTVSIKKGN SNEIVKCN                   348

SEQ ID NO: 31             moltype = AA  length = 426
FEATURE                   Location/Qualifiers
source                    1..426
                          mol_type = protein
                          note = Bacteriophage
                          organism = unidentified
SEQUENCE: 31
MKLLNVINFV FLMFVSSSSF AQVIEMNNSP LRDFVTWYSK QSGESVIVSP DVKGTVTVYS        60
SDVKPENLRN FFISVLRANN FDMVGSIPSI IQKYNPNNQD YIDELPSSDN QEYDDNSAPS       120
GGFFVPQNDN VTQTFKINNV RAKDLIRVVE LFVKSNTSKS SNVLSIDGSN LLVVSAPKDI       180
LDNLPQFLST VDLPTDQILI EGLIFEVQQG DALDFSFAAG SQRGTVAGGV NTDRLTSVLS       240
SAGGSFGIFN GDVLGLSVRA LKTNSHSKIL SVPRILTLSG QKGSISVGQN VPFITGRVTG       300
ESANVNNPFQ TIERQNVGIS MSVFPVAMAG GNIVLDITSK ADSLSSSTQA SDVITNQRSI       360
ATTVNLRDGQ TLLLGGLTDY KNTSQDSGVP FLSKIPLIGL LFSSRSDSNE ESTLYVLVKA       420
TIVRAL                                                                 426

SEQ ID NO: 32             moltype = AA  length = 1367
FEATURE                   Location/Qualifiers
REGION                    1..1367
                          note = Synthetic Polypeptide
source                    1..1367
                          mol_type = protein
                          organism = synthetic construct
SEQUENCE: 32
DKKYSIGLAI GTNSVGWAVI TDEYKVPSKK FKVLGNTDRH SIKKNLIGAL LFDSGETAEA        60
TRLKRTARRR YTRRKNRICY LQEIFSNEMA KVDDSFFHRL EESFLVEEDK KHERHPIFGN       120
IVDEVAYHEK YPTIYHLRKK LVDSTDKADL RLIYLALAHM IKFRGHFLIE GDLNPDNSDV       180
DKLFIQLVQT YNQLFEENPI NASGVDAKAI LSARLSKSRR LENLIAQLPG EKKNGLFGNL       240
IALSLGLTPN FKSNFDLAED AKLQLSKDTY DDDLDNLLAQ IGDQYADLFL AAKNLSDAIL       300
LSDILRVNTE ITKAPLSASM IKRYDEHHQD LTLLKALVRQ QLPEKYKEIF FDQSKNGYAG       360
YIDGGASQEE FYKFIKPILE KMDGTEELLV KLNREDLLRK QRTFDNGSIP HQIHLGELHA       420
ILRRQEDFYP FLKDNREKIE KILTFRIPYY VGPLARGNSR FAWMTRKSEE TITPWNFEEV       480
VDKGASAQSF IERMTNFDKN LPNEKVLPKH SLLYEYFTVY NELTKVKYVT EGMRKPAFLS       540
GEQKKAIVDL LFKTNRKVTV KQLKEDYFKK IECFDSVEIS GVEDRFNASL GTYHDLLKII       600
KDKDFLDNEE NEDILEDIVL TLTLFEDREM IEERLKTYAH LFDDKVMKQL KRRRYTGWGR       660
LSRKLINGIR DKQSGKTILD FLKSDGFANR NFMQLIHDDS LTFKEDIQKA QVSGQGDSLH       720
EHIANLAGSP AIKKGILQTV KVVDELVKVM GRHKPENIVI EMARENQTTQ KGQKNSRERM       780
```

```
KRIEEGIKEL GSQILKEHPV ENTQLQNEKL YLYYLQNGRD MYVDQELDIN RLSDYDVDAI    840
VPQSFLKDDS IDNKVLTRSD KNRGKSDNVP SEEVVKKMKN YWRQLLNAKL ITQRKFDNLT    900
KAERGGLSEL DKAGFIKRQL VETRQITKHV AQILDSRMNT KYDENDKLIR EVKVITLKSK    960
LVSDFRKDFQ FYKVREINNY HHAHDAYLNA VVGTALIKKY PKLESEFVYG DYKVYDVRKM   1020
IAKSEQEIGK ATAKYFFYSN IMNFFKTEIT LANGEIRKRP LIETNGETGE IVWDKGRDFA   1080
TVRKVLSMPQ VNIVKKTEVQ TGGFSKESIL PKRNSDKLIA RKKDWDPKKY GGFDSPTVAY   1140
SVLVVAKVEK GKSKKLKSVK ELLGITIMER SSFEKNPIDF LEAKGYKEVK KDLIIKLPKY   1200
SLFELENGRK RMLASAGELQ KGNELALPSK YVNFLYLASH YEKLKGSPED NEQKQLFVEQ   1260
HKHYLDEIIE QISEFSKRVI LADANLDKVL SAYNKHRDKP IREQAENIIH LFTLTNLGAP   1320
AAFKYFDTTI DRKRYTSTKE VLDATLIHQS ITGLYETRID LSQLGGD                1367

SEQ ID NO: 33         moltype = AA  length = 1367
FEATURE               Location/Qualifiers
REGION                1..1367
                      note = Synthetic Polypeptide
source                1..1367
                      mol_type = protein
                      organism = synthetic construct
SEQUENCE: 33
DKKYSIGLDI GTNSVGWAVI TDEYKVPSKK FKVLGNTDRH SIKKNLIGAL LFDSGETAEA     60
TRLKRTARRR YTRRKNRICY LQEIFSNEMA KVDDSFFHRL EESFLVEEDK KHERHPIFGN    120
IVDEVAYHEK YPTIYHLRKK LVDSTDKADL RLIYLALAHM IKFRGHFLIE GDLNPDNSDV    180
DKLFIQLVQT YNQLFEENPI NASGVDAKAI LSARLSKSRR LENLIAQLPG EKKNGLFGNL    240
IALSLGLTPN FKSNFDLAED AKLQLSKDTY DDDLDNLLAQ IGDQYADLFL AAKNLSDAIL    300
LSDILRVNTE ITKAPLSASM IKRYDEHHQD LTLLKALVRQ QLPEKYKEIF FDQSKNGYAG    360
YIDGGASQEE FYKFIKPILE KMDGTEELLV KLNREDLLRK QRTFDNGSIP KQIHLGELHA    420
ILRRQEDFYP FLKDNREKIE KILTFRIPYY VGPLARGNSR FAWMTRKSEE TITPWNFEEV    480
VDKGASAQSF IERMTNFDKN LPNEKVLPKH SLLYEYFTVY NELTKVKYVT EGMRKPAFLS    540
GEQKKAIVDL LFKTNRKVTV KQLKEDYFKK IECFDSVEIS GVEDRFNASL GTYHDLLKII    600
KDKDFLDNEE NEDILEDIVL TLTLFEDREM IEERLKTYAH LFDDKVMKQL KRRRYTGWGR    660
LSRKLINGIR DKQSGKTILD FLKSDGFANR NFMQLIHDDS LTFKEDIQKA QVSGQGDSLH    720
EHIANLAGSP AIKKGILQTV KVVDELVKVM GRHKPENIVI EMARENQTTQ KGQKNSRERM    780
KRIEEGIKEL GSQILKEHPV ENTQLQNEKL YLYYLQNGRD MYVDQELDIN RLSDYDVDHI    840
VPQSFLKDDS IDNKVLTRSD KNRGKSDNVP SEEVVKKMKN YWRQLLNAKL ITQRKFDNLT    900
KAERGGLSEL DKAGFIKRQL VETRQITKHV AQILDSRMNT KYDENDKLIR EVKVITLKSK    960
LVSDFRKDFQ FYKVREINNY HHAHDAYLNA VVGTALIKKY PKLESEFVYG DYKVYDVRKM   1020
IAKSEQEIGK ATAKYFFYSN IMNFFKTEIT LANGEIRKRP LIETNGETGE IVWDKGRDFA   1080
TVRKVLSMPQ VNIVKKTEVQ TGGFSKESIL PKRNSDKLIA RKKDWDPKKY GGFDSPTVAY   1140
SVLVVAKVEK GKSKKLKSVK ELLGITIMER SSFEKNPIDF LEAKGYKEVK KDLIIKLPKY   1200
SLFELENGRK RMLASAGELQ KGNELALPSK YVNFLYLASH YEKLKGSPED NEQKQLFVEQ   1260
HKHYLDEIIE QISEFSKRVI LADANLDKVL SAYNKHRDKP IREQAENIIH LFTLTNLGAP   1320
AAFKYFDTTI DRKRYTSTKE VLDATLIHQS ITGLYETRID LSQLGGD                1367

SEQ ID NO: 34         moltype = AA  length = 1300
FEATURE               Location/Qualifiers
source                1..1300
                      mol_type = protein
                      note = Francisella novicida
                      organism = unidentified
SEQUENCE: 34
MSIYQEFVNK YSLSKTLRFE LIPQGKTLEN IKARGLILDD EKRAKDYKKA KQIIDKYHQF     60
FIEEILSSVC ISEDLLQNYS DVYFKLKKSD DDNLQKDFKS AKDTIKKQIS EYIKDSEKFK    120
NLFNQNLIDA KKGQESDLIL WLKQSKDNGI ELFKANSDIT DIDEALEIIK SFKGWTTYFK    180
GFHENRKNVY SSNDIPTSII YRIVDDNLPK FLENKAKYES LKDKAPEAIN YEQIKKDLAE    240
ELTFDIDYKT SEVNQRVFSL DEVFEIANFN NYLNQSGITK FNTIIGGKFV NGENTKRKGI    300
NEYINLYSQQ INDKTLKKYK MSVLFKQILS DTESKSFVID KLEDDSDVVT TMQSFYEQIA    360
APKTVEEKSI KETLSLLFDD LKAQKLDLSK IYFKNDKSLT DLSQQVFDDY SVIGTAVLEY    420
ITQQIAPKNL DNPSKKEQEL IAKKTEKAKY LSLETIKLAL EEFNKHRDID KQCRFEEILA    480
NFAAIPMIFD EIAQNKDNLA QISIKYQNQG KKDLLQASAE DDVKAIKDLL DQTNNLLHKL    540
KIFHISQSED KANILDKDEH FYLVFEECYF ELANIVPLYN KIRNYITQKP YSDEKFKLNF    600
ENSTLANGWD KNKEPDNTAI LFIKDDKYYL GVMNKKNNKI FDDKAIKENK GEGYKKIVYK    660
LLPGANKMLP KVFFSAKSIK FYNPSEDILR IRNHSTHTKN GSPQKGYEKF EFNIEDCRKF    720
IDFYKQSISK HPEWKDFGFR FSDTQRYNSI DEFYREVENQ GYKLTFENIS ESYIDSVVNQ    780
GKLYLFQIYN KDFSAYSKGR PNLHTLYWKA LFDERNLQDV VYKLNGEAEL FYRKQSIPKK    840
ITHPAKEAIA NKNKDNPKKE SVFEYDLIKD KRFTEDKFFF HCPITINFKS SGANKFNDEI    900
NLLLKEKAND VHILSIDRGE RHLAYYTLVD GKGNIIKQDT FNIIGNDRMK TNYHDKLAAI    960
EKDRDSARKD WKKINNIKEM KEGYLSQVVH EIAKLVIEYN AIVVFEDLNF GFKRGRFKVE   1020
KQVYQKLEKM LIEKLNYLVF KDNEFDKTGG VLRAYQLTAP FETFKKMGKQ TGIIYYVPAG   1080
FTSKICPVTG FVNQLYPKYE SVSKSQEFFS KFDKICYNLD KGYFEFSFDY KNFGDKAAKG   1140
KWTIASFGSR LINFRNSDKN HNWDTREVYP TKELEKLLKD YSIEYGHGEC IKAAICGESD   1200
KKFFAKLTSV LNTILQMRNS KTGTELDYLI SPVADVNGNF FDSRQAPKNM PQDADANGAY   1260
HIGLKGLMLL GRIKNNQEGK KLNLVIKNEE YFEFVQNRNN                         1300

SEQ ID NO: 35         moltype = AA  length = 1300
FEATURE               Location/Qualifiers
REGION                1..1300
                      note = Synthetic Polypeptide
source                1..1300
                      mol_type = protein
```

```
                        organism = synthetic construct
SEQUENCE: 35
MSIYQEFVNK YSLSKTLRFE LIPQGKTLEN IKARGLILDD EKRAKDYKKA KQIIDKYHQF   60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
APKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK SFEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIARGE RHLAYYTLVD GKGNIIKQDT FNIIGNDRMK TNYHDKLAAI  960
EKDRDSARKD WKKINNIKEM KEGYLSQVVH EIAKLVIEYN AIVVFEDLNF GFKRGRFKVE 1020
KQVYQKLEKM LIEKLNYLVF KDNEFDKTGG VLRAYQLTAP FETFKKMGKQ TGIIYYVPAG 1080
FTSKICPVTG FVNQLYPKYE SVSKSQEFFS KFDKICYNLD KGYFEFSFDY KNFGDKAAKG 1140
KWTIASFGSR LINFRNSDKN HNWDTREVYP TKELEKLLKD YSIEYGHGEC IKAAICGESD 1200
KKFFAKLTSV LNTILQMRNS KTGTELDYLI SPVADVNGNF FDSRQAPKNM PQDADANGAY 1260
HIGLKGLMLL GRIKNNQEGK KLNLVIKNEE YFEFVQNRNN                       1300

SEQ ID NO: 36           moltype = AA  length = 1300
FEATURE                 Location/Qualifiers
REGION                  1..1300
                        note = Synthetic Polypeptide
source                  1..1300
                        mol_type = protein
                        organism = synthetic construct
SEQUENCE: 36
MSIYQEFVNK YSLSKTLRFE LIPQGKTLEN IKARGLILDD EKRAKDYKKA KQIIDKYHQF   60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
APKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
NLLLKEKAND VHILSIDRGE RHLAYYTLVD GKGNIIKQDT FNIIGNDRMK TNYHDKLAAI  960
EKDRDSARKD WKKINNIKEM KEGYLSQVVH EIAKLVIEYN AIVVFADLNF GFKRGRFKVE 1020
KQVYQKLEKM LIEKLNYLVF KDNEFDKTGG VLRAYQLTAP FETFKKMGKQ TGIIYYVPAG 1080
FTSKICPVTG FVNQLYPKYE SVSKSQEFFS KFDKICYNLD KGYFEFSFDY KNFGDKAAKG 1140
KWTIASFGSR LINFRNSDKN HNWDTREVYP TKELEKLLKD YSIEYGHGEC IKAAICGESD 1200
KKFFAKLTSV LNTILQMRNS KTGTELDYLI SPVADVNGNF FDSRQAPKNM PQDADANGAY 1260
HIGLKGLMLL GRIKNNQEGK KLNLVIKNEE YFEFVQNRNN                       1300

SEQ ID NO: 37           moltype = AA  length = 1300
FEATURE                 Location/Qualifiers
REGION                  1..1300
                        note = Synthetic Polypeptide
source                  1..1300
                        mol_type = protein
                        organism = synthetic construct
SEQUENCE: 37
MSIYQEFVNK YSLSKTLRFE LIPQGKTLEN IKARGLILDD EKRAKDYKKA KQIIDKYHQF   60
FIEEILSSVC ISEDLLQNYS DVYFKLKKSD DDNLQKDFKS AKDTIKKQIS EYIKDSEKFK  120
NLFNQNLIDA KKGQESDLIL WLKQSKDNGI ELFKANSDIT DIDEALEIIK SFKGWTTYFK  180
GFHENRKNVY SSNDIPTSII YRIVDDNLPK FLENKAKYES LKDKAPEAIN YEQIKKDLAE  240
ELTFDIDYKT SEVNQRVFSL DEVFEIANFN NYLNQSGITK FNTIIGGKFV NGENTKRKGI  300
NEYINLYSQQ INDKTLKKYK MSVLFKQILS DTESKSFVID KLEDDSDVVT TMQSFYEQIA  360
APKTVEEKSI KETLSLLFDD LKAQKLDLSK IYFKNDKSLT DLSQQVFDDY SVIGTAVLEY  420
ITQQIAPKNL DNPSKKEQEL IAKKTEKAKY LSLETIKLAL EEFNKHRDID KQCRFEEILA  480
NFAAIPMIFD EIAQNKDNLA QISIKYQNQG KKDLLQASAE DDVKAIKDLL DQTNNLLHKL  540
KIFHISQSED KANILDKDEH FYLVFEECYF ELANIVPLYN KIRNYITQKP YSDEKFKLNF  600
ENSTLANGWD KNKEPDNTAI LFIKDDKYYL GVMNKKNNKI FDDKAIKENK GEGYKKIVYK  660
LLPGANKMLP KVFFSAKSIK FYNPSEDILR IRNHSTHTKN GSPQKGYEKF EFNIEDCRKF  720
IDFYKQSISK HPEWKDFGFR FSDTQRYNSI DEFYREVENQ GYKLTFENIS ESYIDSVVNQ  780
GKLYLFQIYN KDFSAYSKGR PNLHTLYWKA LFDERNLQDV VYKLNGEAEL FYRKQSIPKK  840
ITHPAKEAIA NKNKDNPKKE SVFEYDLIKD KRFTEDKFFF HCPITINFKS SGANKFNDEI  900
```

```
NLLLKEKAND VHILSIDRGE RHLAYYTLVD GKGNIIKQDT FNIIGNDRMK TNYHDKLAAI    960
EKDRDSARKD WKKINNIKEM KEGYLSQVVH EIAKLVIEYN AIVVFEDLNF GFKRGRFKVE   1020
KQVYQKLEKM LIEKLNYLVF KDNEFDKTGG VLRAYQLTAP FETFKKMGKQ TGIIYYVPAG   1080
FTSKICPVTG FVNQLYPKYE SVSKSQEFFS KFDKICYNLD KGYFEFSFDY KNFGDKAAKG   1140
KWTIASFGSR LINFRNSDKN HNWDTREVYP TKELEKLLKD YSIEYGHGEC IKAAICGESD   1200
KKFFAKLTSV LNTILQMRNS KTGTELDYLI SPVADVNGNF FDSRQAPKNM PQDAAANGAY   1260
HIGLKGLMLL GRIKNNQEGK KLNLVIKNEE YFEFVQNRNN                         1300

SEQ ID NO: 38            moltype = AA   length = 1300
FEATURE                  Location/Qualifiers
REGION                   1..1300
                         note = Synthetic Polypeptide
source                   1..1300
                         mol_type = protein
                         organism = synthetic construct
SEQUENCE: 38
MSIYQEFVNK YSLSKTLRFE LIPQGKTLEN IKARGLILDD EKRAKDYKKA KQIIDKYHQF     60
FIEEILSSVC ISEDLLQNYS DVYFKLKKSD DDNLQKDFKS AKDTIKKQIS EYIKDSEKFK    120
NLFNQNLIDA KKGQESDLIL WLKQSKDNGI ELFKANSDIT DIDEALEIIK SFKGWTTYFK    180
GFHENRKNVY SSNDIPTSII YRIVDDNLPK FLENKAKYES LKDKAPEAIN YEQIKKDLAE    240
ELTFDIDYKT SEVNQRVFSL DEVFEIANFN NYLNQSGITK FNTIIGGKFV NGENTKRKGI    300
NEYINLYSQQ INDKTLKKYK MSVLFKQILS DTESKSFVID KLEDDSDVVT TMQSFYEQIA    360
AFKTVEEKSI KETLSLLFDD LKAQKLDLSK IYFKNDKSLT DLSQQVFDDY SVIGTAVLEY    420
ITQQIAPKNL DNPSKKEQEL IAKKTEKAKY LSLETIKLAL EEFNKHRDID KQCRFEEILA    480
NFAAIPMIFD EIAQNKDNLA QISIKYQNQG KKDLLQASAE DDVKAIKDLL DQTNNLLHKL    540
KIFHISQSED KANILDKDEH FYLVFEECYF ELANIVPLYN KIRNYITQKP YSDEKFKLNF    600
ENSTLANGWD KNKEPDNTAI LFIKDDKYYL GVMNKKNNKI FDDKAIKENK GEGYKKIVYK    660
LLPGANKMLP KVFFSAKSIK FYNPSEDILR IRNHSTHTKN GSPQKGYEKF EFNIEDCRKF    720
IDFYKQSISK HPEWKDFGFR FSDTQRYNSI DEFYREVENQ GYKLTFENIS ESYIDSVVNQ    780
GKLYLFQIYN KDFSAYSKGR PNLHTLYWKA LFDERNLQDV VYKLNGEAEL FYRKQSIPKK    840
ITHPAKEAIA NKNKDNPKKE SVFEYDLIKD KRFTEDKFFF HCPITINFKS SGANKFNDEI    900
NLLLKEKAND VHILSIARGE RHLAYYTLVD GKGNIIKQDT FNIIGNDRMK TNYHDKLAAI    960
EKDRDSARKD WKKINNIKEM KEGYLSQVVH EIAKLVIEYN AIVVFADLNF GFKRGRFKVE   1020
KQVYQKLEKM LIEKLNYLVF KDNEFDKTGG VLRAYQLTAP FETFKKMGKQ TGIIYYVPAG   1080
FTSKICPVTG FVNQLYPKYE SVSKSQEFFS KFDKICYNLD KGYFEFSFDY KNFGDKAAKG   1140
KWTIASFGSR LINFRNSDKN HNWDTREVYP TKELEKLLKD YSIEYGHGEC IKAAICGESD   1200
KKFFAKLTSV LNTILQMRNS KTGTELDYLI SPVADVNGNF FDSRQAPKNM PQDADANGAY   1260
HIGLKGLMLL GRIKNNQEGK KLNLVIKNEE YFEFVQNRNN                         1300

SEQ ID NO: 39            moltype = AA   length = 1300
FEATURE                  Location/Qualifiers
REGION                   1..1300
                         note = Synthetic Polypeptide
source                   1..1300
                         mol_type = protein
                         organism = synthetic construct
SEQUENCE: 39
MSIYQEFVNK YSLSKTLRFE LIPQGKTLEN IKARGLILDD EKRAKDYKKA KQIIDKYHQF     60
FIEEILSSVC ISEDLLQNYS DVYFKLKKSD DDNLQKDFKS AKDTIKKQIS EYIKDSEKFK    120
NLFNQNLIDA KKGQESDLIL WLKQSKDNGI ELFKANSDIT DIDEALEIIK SFKGWTTYFK    180
GFHENRKNVY SSNDIPTSII YRIVDDNLPK FLENKAKYES LKDKAPEAIN YEQIKKDLAE    240
ELTFDIDYKT SEVNQRVFSL DEVFEIANFN NYLNQSGITK FNTIIGGKFV NGENTKRKGI    300
NEYINLYSQQ INDKTLKKYK MSVLFKQILS DTESKSFVID KLEDDSDVVT TMQSFYEQIA    360
AFKTVEEKSI KETLSLLFDD LKAQKLDLSK IYFKNDKSLT DLSQQVFDDY SVIGTAVLEY    420
ITQQIAPKNL DNPSKKEQEL IAKKTEKAKY LSLETIKLAL EEFNKHRDID KQCRFEEILA    480
NFAAIPMIFD EIAQNKDNLA QISIKYQNQG KKDLLQASAE DDVKAIKDLL DQTNNLLHKL    540
KIFHISQSED KANILDKDEH FYLVFEECYF ELANIVPLYN KIRNYITQKP YSDEKFKLNF    600
ENSTLANGWD KNKEPDNTAI LFIKDDKYYL GVMNKKNNKI FDDKAIKENK GEGYKKIVYK    660
LLPGANKMLP KVFFSAKSIK FYNPSEDILR IRNHSTHTKN GSPQKGYEKF EFNIEDCRKF    720
IDFYKQSISK HPEWKDFGFR FSDTQRYNSI DEFYREVENQ GYKLTFENIS ESYIDSVVNQ    780
GKLYLFQIYN KDFSAYSKGR PNLHTLYWKA LFDERNLQDV VYKLNGEAEL FYRKQSIPKK    840
ITHPAKEAIA NKNKDNPKKE SVFEYDLIKD KRFTEDKFFF HCPITINFKS SGANKFNDEI    900
NLLLKEKAND VHILSIARGE RHLAYYTLVD GKGNIIKQDT FNIIGNDRMK TNYHDKLAAI    960
EKDRDSARKD WKKINNIKEM KEGYLSQVVH EIAKLVIEYN AIVVFEDLNF GFKRGRFKVE   1020
KQVYQKLEKM LIEKLNYLVF KDNEFDKTGG VLRAYQLTAP FETFKKMGKQ TGIIYYVPAG   1080
FTSKICPVTG FVNQLYPKYE SVSKSQEFFS KFDKICYNLD KGYFEFSFDY KNFGDKAAKG   1140
KWTIASFGSR LINFRNSDKN HNWDTREVYP TKELEKLLKD YSIEYGHGEC IKAAICGESD   1200
KKFFAKLTSV LNTILQMRNS KTGTELDYLI SPVADVNGNF FDSRQAPKNM PQDAAANGAY   1260
HIGLKGLMLL GRIKNNQEGK KLNLVIKNEE YFEFVQNRNN                         1300

SEQ ID NO: 40            moltype = AA   length = 1300
FEATURE                  Location/Qualifiers
REGION                   1..1300
                         note = Synthetic Polypeptide
source                   1..1300
                         mol_type = protein
                         organism = synthetic construct
SEQUENCE: 40
MSIYQEFVNK YSLSKTLRFE LIPQGKTLEN IKARGLILDD EKRAKDYKKA KQIIDKYHQF     60
```

```
FIEEILSSVC ISEDLLQNYS DVYFKLKKSD DDNLQKDFKS AKDTIKKQIS EYIKDSEKFK    120
NLFNQNLIDA KKGQESDLIL WLKQSKDNGI ELFKANSDIT DIDEALEIIK SFKGWTTYFK    180
GFHENRKNVY SSNDIPTSII YRIVDDNLPK FLENKAKYES LKDKAPEAIN YEQIKKDLAE    240
ELTFDIDYKT SEVNQRVFSL DEVFEIANFN NYLNQSGITK FNTIIGGKFV NGENTKRKGI    300
NEYINLYSQQ INDKTLKKYK MSVLFKQILS DTESKSFVID KLEDDSDVVT TMQSFYEQIA    360
AFKTVEEKSI KETLSLLFDD LKAQKLDLSK IYFKNDKSLT DLSQQVFDDY SVIGTAVLEY    420
ITQQIAPKNL DNPSKKEQEL IAKKTEKAKY LSLETIKLAL EEFNKHRDID KQCRFEEILA    480
NFAAIPMIFD EIAQNKDNLA QISIKYQNQG KKDLLQASAE DDVKAIKDLL DQTNNLLHKL    540
KIFHISQSED KANILDKDEH FYLVFEECYF ELANIVPLYN KIRNYITQKP YSDEKFKLNF    600
ENSTLANGWD KNKEPDNTAI LFIKDDKYYL GVMNKKNNKI FDDKAIKENK GEGYKKIVYK    660
LLPGANKMLP KVFFSAKSIK FYNPSEDILR IRNHSTHTKN GSPQKGYEKF EFNIEDCRKF    720
IDFYKQSISK HPEWKDFGFR FSDTQRYNSI DEFYREVENQ GYKLTFENIS ESYIDSVVNQ    780
GKLYLFQIYN KDFSAYSKGR PNLHTLYWKA LFDERNLQDV VYKLNGEAEL FYRKQSIPKK    840
ITHPAKEAIA NKNKDNPKKE SVFEYDLIKD KRFTEDKFFF HCPITINFKS SGANKFNDEI    900
NLLLLEKAND VHILSIDRGE RHLAYYTLVD GKGNIIKQDT FNIIGNDRMK TNYHDKLAAI    960
EKDRDSARKD WKKINNIKEM KEGYLSQVVH EIAKLVIEYN AIVVFADLNF GFKRGRFKVE   1020
KQVYQKLEKM LIEKLNYLVF KDNEFDKTGG VLRAYQLTAP FETFKKMGKQ TGIIYYVPAG   1080
FTSKICPVTG FVNQLYPKYE SVSKSQEFFS KFDKICYNLD KGYFEFSFDY KNFGDKAAKG   1140
KWTIASFGSR LINFRNSDKN HNWDTREVYP TKELEKLLKD YSIEYGHGEC IKAAICGESD   1200
KKFFAKLTSV LNTILQMRNS KTGTELDYLI SPVADVNGNF FDSRQAPKNM PQDAAANGAY   1260
HIGLKGLMLL GRIKNNQEGK KLNLVIKNEE YFEFVQNRNN                         1300

SEQ ID NO: 41           moltype = AA   length = 1300
FEATURE                 Location/Qualifiers
REGION                  1..1300
                        note = Synthetic Polypeptide
source                  1..1300
                        mol_type = protein
                        organism = synthetic construct
SEQUENCE: 41
MSIYQEFVNK YSLSKTLRFE LIPQGKTLEN IKARGLILDD EKRAKDYKKA KQIIDKYHQF     60
FIEEILSSVC ISEDLLQNYS DVYFKLKKSD DDNLQKDFKS AKDTIKKQIS EYIKDSEKFK    120
NLFNQNLIDA KKGQESDLIL WLKQSKDNGI ELFKANSDIT DIDEALEIIK SFKGWTTYFK    180
GFHENRKNVY SSNDIPTSII YRIVDDNLPK FLENKAKYES LKDKAPEAIN YEQIKKDLAE    240
ELTFDIDYKT SEVNQRVFSL DEVFEIANFN NYLNQSGITK FNTIIGGKFV NGENTKRKGI    300
NEYINLYSQQ INDKTLKKYK MSVLFKQILS DTESKSFVID KLEDDSDVVT TMQSFYEQIA    360
AFKTVEEKSI KETLSLLFDD LKAQKLDLSK IYFKNDKSLT DLSQQVFDDY SVIGTAVLEY    420
ITQQIAPKNL DNPSKKEQEL IAKKTEKAKY LSLETIKLAL EEFNKHRDID KQCRFEEILA    480
NFAAIPMIFD EIAQNKDNLA QISIKYQNQG KKDLLQASAE DDVKAIKDLL DQTNNLLHKL    540
KIFHISQSED KANILDKDEH FYLVFEECYF ELANIVPLYN KIRNYITQKP YSDEKFKLNF    600
ENSTLANGWD KNKEPDNTAI LFIKDDKYYL GVMNKKNNKI FDDKAIKENK GEGYKKIVYK    660
LLPGANKMLP KVFFSAKSIK FYNPSEDILR IRNHSTHTKN GSPQKGYEKF EFNIEDCRKF    720
IDFYKQSISK HPEWKDFGFR FSDTQRYNSI DEFYREVENQ GYKLTFENIS ESYIDSVVNQ    780
GKLYLFQIYN KDFSAYSKGR PNLHTLYWKA LFDERNLQDV VYKLNGEAEL FYRKQSIPKK    840
ITHPAKEAIA NKNKDNPKKE SVFEYDLIKD KRFTEDKFFF HCPITINFKS SGANKFNDEI    900
NLLLLEKAND VHILSIDRGE RHLAYYTLVD GKGNIIKQDT FNIIGNDRMK TNYHDKLAAI    960
EKDRDSARKD WKKINNIKEM KEGYLSQVVH EIAKLVIEYN AIVVFADLNF GFKRGRFKVE   1020
KQVYQKLEKM LIEKLNYLVF KDNEFDKTGG VLRAYQLTAP FETFKKMGKQ TGIIYYVPAG   1080
FTSKICPVTG FVNQLYPKYE SVSKSQEFFS KFDKICYNLD KGYFEFSFDY KNFGDKAAKG   1140
KWTIASFGSR LINFRNSDKN HNWDTREVYP TKELEKLLKD YSIEYGHGEC IKAAICGESD   1200
KKFFAKLTSV LNTILQMRNS KTGTELDYLI SPVADVNGNF FDSRQAPKNM PQDAAANGAY   1260
HIGLKGLMLL GRIKNNQEGK KLNLVIKNEE YFEFVQNRNN                         1300

SEQ ID NO: 42           moltype = AA   length = 887
FEATURE                 Location/Qualifiers
source                  1..887
                        mol_type = protein
                        organism = Natronobacterium gregoryi
SEQUENCE: 42
MTVIDLDSTT TADELTSGHT YDISVTLTGV YDNTDEQHPR MSLAFEQDNG ERRYITLWKN     60
TTPKDVFTYD YATGSTYIFT NIDYEVKDGY ENLTATYQTT VENATAQEVG TTDEDETFAG    120
GEPLDHHLDD ALNETPDDAE TESDSGHVMT SFASRDQLPE WTLHTYTLTA TDGAKTDTEY    180
ARRTLAYTVR QELYTDHDAA PVATDGLMLL TPEPLGETPL DLDCGVRVEA DETRTLDYTT    240
AKDRLLAREL VEEGLKRSLW DDYLVRGIDE VLSKEPVLTC DEFDLHERYD LSVEVGHSGR    300
AYLHINFRHR FVPKLTLADI DDDNIYPGLR VKTTYRPRRG HIVWGLRDEC ATDSLNTLGN    360
QSVVAYHRNN QTPINTDLLD AIEAADRRVV ETRRQGHGDD AVSFPQELLA VEPNTHQIKQ    420
FASDGFHQQA RSKTRLSASR CSEKAQAFAE RLDPVRLNGS TVEFSSEFFT GNNEQQLRLL    480
YENGESVLTF RDGARGAHPD ETFSKGIVNP PESFEVAVVL PEQQADTCKA QWDTMADLLN    540
QAGAPPTRSE TVQYDAFSSP ESISLNVAGA IDPSEVDAAF VVLPPDQEGF ADLASPTETY    600
DELKKALANM GIYSQMAYFD RFRDAKIFYT RNVALGLLAA AGGVAFTTEH AMPGDADMFI    660
GIDVSRSYPE DGASGQINIA ATATAVYKDG TILGHSSTRP QLGEKLQSTD VRDIMKNAIL    720
GYQQVTGESP THIVIHRDGF MNEDLDPATE FLNEQGVEYD IVEIRKQPQT RLLAVSDVQY    780
DTPVKSIAAI NQNEPRATVA TFGAPEYLAT RDGGGLPRPI QIERVAGETD IETLTRQVYL    840
LSQSHIQVHN STARLPITTA YADQASTHAT KGYLVQTGAF ESNVGFL                  887

SEQ ID NO: 43           moltype = AA   length = 1129
FEATURE                 Location/Qualifiers
source                  1..1129
                        mol_type = protein
```

```
                        organism = Alicyclobacillus acidoterrestris
SEQUENCE: 43
MAVKSIKVKL RLDDMPEIRA GLWKLHKEVN AGVRYYTEWL SLLRQENLYR RSPNGDGEQE    60
CDKTAEECKA ELLERLRARQ VENGHRGPAG SDDELLQLAR QLYELLVPQA IGAKGDAQQI   120
ARKFLSPLAD KDAVGGLGIA KAGNKPRWVR MREAGEPGWE EEKEKAETRK SADRTADVLR   180
ALADFGLKPL MRVYTDSEMS SVEWKPLRKG QAVRTWDRDM FQQAIERMMS WESWNQRVGQ   240
EYAKLVEQKN RFEQKNFVGQ EHLVHLVNQL QQDMKEASPG LESKEQTAHY VTGRALRGSD   300
KVFEKWGKLA PDAPFDLYDA EIKNVQRRNT RRFGSHDLFA KLAEPEYQAL WREDASFLTR   360
YAVYNSILRK LNHAKMFATF TLPDATAHPI WTRFDKLGGN LHQYTFLFNE FGERRHAIRF   420
HKLLKVENGV AREVDDVTVP ISMSEQLDNL LPRDPNEPIA LYFRDYGAEQ HFTGEFGGAK   480
IQCRRDQLAH MHRRRGARDV YLNVSVRVQS QSEARGERRP PYAAVFRLVG DNHRAFVHFD   540
KLSDYLAEHP DDGKLGSEGL LSGLRVMSVD LGLRTSASIS VFRVARKDEL KPNSKGRVPF   600
FFPIKGNDNL VAVHERSQLL KLPGETESKD LRAIREERQR TLRQLRTQLA YLRLLVRCGS   660
EDVGRRERSW AKLIEQPVDA ANHMTPDWRE AFENELQKLK SLHGICSDKE WMDAVYESVR   720
RVWRHMGKQV RDWRKDVRSG ERPKIRGYAK DVVGGNSIEQ IEYLERQYKF LKSWSFFGKV   780
SGQVIRAEKG SRFAITLREH IDHAKEDRLK KLADRIIMEA LGYVYALDER GKGKWVAKYP   840
PCQLILLEEL SEYQFNNDRP PSENNQLMQW SHRGVFQELI NQAQVHDLLV GTMYAAFSSR   900
FDARTGAPGI RCRRVPARCT QEHNPEPFPW WLNKFVVEHT LDACPLRADD LIPTGEGEIF   960
VSPFSAEEGD FHQIHADLNA AQNLQQRLWS DFDISQIRLR CDWGEVDGEL VLIPRLTGKR  1020
TADSYSNKVF YTNTGVTYYE RERGKKRRKV FAQEKLSEEE AELLVEADEA REKSVVLMRD  1080
PSGIINRGNW TRQKEFWSMV NQRIEGYLVK QIRSRVPLQD SACENTGDI             1129

SEQ ID NO: 44         moltype = AA   length = 1389
FEATURE               Location/Qualifiers
source                1..1389
                      mol_type = protein
                      organism = Leptotrichia shahii
SEQUENCE: 44
MGNLFGHKRW YEVRDKKDFK IKRKVKVKRN YDGNKYILNI NENNNKEKID NNKFIRKYIN    60
YKKNDNILKE FTRKFHAGNI LFKLKGKEGI IRIENNDDPL ETEEVVLYIE AYGKSEKLKA   120
LGITKKKIID EAIRQGITKD DKKIEIKRQE NEEEIEIDIR DEYTNKTLND CSIILRIIEN   180
DELETKKSIY EIFKNINMSL YKIIEKIIEN ETEKVFENRY YEEHLREKLL KDDKIDVILT   240
NFMEIREKIK SNLEILGFVK FYLNVGGDKK KSKNKKMLVE KILNINVDLT VEDIADFVIK   300
ELEFWNITKR IEKVKKVNNE FLEKRRNRTY IKSYVLLDKH EKFKIERENK KDKIVKFFVE   360
NIKNNSIKEK IEKILAEFKI DELIKKLEKE LKKGNCDTEI FGIFKKHYKV NFDSKKFSKK   420
SDEEKELYKI IYRYLKGRIE KILVNEQKVR LKKMEKIEIE KILNESILSE KILKRVKQYT   480
LEHIMYLGKL RHNDIDMTTV NTDDFSRLHA KEELDLELIT FFASTNMELN KIFSRENINN   540
DENIDFFGGD REKNYVLDKK ILNSKIKIIR DLDPIDNKNN ITNNFIRKFT KIGTNERNRI   600
LHAISKERDL QGTQDDYNKV INIIQNLKIS DEEVSKALNL DVVFKDKKNI ITKINDIKIS   660
EENNNDIKYL PSFSKVLPEI LNLYRNNPKN EPFDTIETEK IVLNALIYVN KELYKKLILE   720
DDLEENESKN IFLQELKKTL GNIDEIDENI IENYYKNAQI SASKGNNKAI KKYQKKVIEC   780
YIGYLRKNYE ELFDFSDFKM NIQEIKKQIK DINDNKTYER ITVKTSDKTI VINDDFEYII   840
SIFALLNSNA VINKIRNRFF ATSVWLNTSE YQNIIDILDE IMQLNTLRNE CITENWNLNL   900
EEFIQKMKEI EKDFDDDFKIQ TKKEIFNNYY EDIKNNILTE FKDDINGCDV LEKKLEKIVI   960
FDDETKFEID KKSNILQDEQ RKLSNINKKD LKKKVDQYIK DKDQEIKSKI LCRIIFNSDF  1020
LKKYKKEIDN LIEDMESENE NKFQEIYYPK ERKNELYIYK KNLFLNIGNP NFDKIYGLIS  1080
NDIKMADAKF LFNIDKLNG KNKISEIDAI LKNLNDKLNG YSKEYKEKYI KKLKENDDFF  1140
AKNIQNKNYK SFEKDYNRVS EYKKIRDLVE FNYLNKIESY LIDINWKLAI QMARFERDMH  1200
YIVNGLRELG IIKLSGYNTG ISRAYPKRNG SDGFYTTTAY YKFFDEESYK KFEKICYGFG  1260
IDLSENSEIN KPENESIRNY ISHFYIVRNP FADYSIAEQI DRVSNLLSYS TRYNNSTYAS  1320
VPFEVFKKDVN LDYDELKKKF KLIGNNDILE RLMKPKKVSV LELESYNSDY IKNLIIELLT  1380
KIENTNDTL                                                         1389

SEQ ID NO: 45         moltype = AA   length = 1052
FEATURE               Location/Qualifiers
REGION                1..1052
                      note = Synthetic Polypeptide
source                1..1052
                      mol_type = protein
                      organism = synthetic construct
SEQUENCE: 45
KRNYILGLDI GITSVGYGII DYETRDVIDA GVRLFKEANV ENNEGRRSKR GARRLKRRRR    60
HRIQRVKKLL FDYNLLTDHS ELSGINPYEA RVKGLSQKLS EEEFSAALLH LAKRRGVHNV   120
NEVEEDTGNE LSTKEQISRN SKALEEKYVA ELQLERLKKD GEVRGSINRF KTSDYVKEAK   180
QLLKVQKAYH QLDQSFIDTY IDLLETRRTY YEGPGEGSPF GWKDIKEWYE MLMGHCTYFP   240
EELRSVKYAY NADLYNALND LNNLVITRDE NEKLEYYEKF QIIENVFKQK KKPTLKQIAK   300
EILVNEEDIK GYRVTSTGKP EFTNLKVYHD IKDITARKEI IENAELLDQI AKILTIYQSS   360
EDIQEELTNL NSELTQEEIE QISNLKGYTG THNLSLKAIN LILDELWHTN DNQIAIFNRL   420
KLVPKKVDLS QQKEIPTTLV DDFILSPVVK RSFIQSIKVI NAIIKKYGLP NDIIIELARE   480
KNSKDAQKMI NEMQKRNRQT NERIEEIIRT TGKENAKYLI EKIKLHDMQE GKCLYSLEAI   540
PLEDDLLNNPF NYEVDHIIPR SVSFDNSFNN KVLVKQEENS KKGNRTPFQY LSSSDSKISY   600
ETFKKHILNL AKGKGRISKT KKEYLLEERD INRFSVQKDF INRNLVDTRY ATRGLMNLLR   660
SYFRVNNLDV KVKSINGGFT SFLRRKWKFK KERNKGYKHH AEDALIIANA DFIFKEWKKL   720
DKAKKVMENQ MFEEKQAESM PEIETEQEYK EIFITPHQIK HIKDFKDYKY SHRVDKKPNR   780
ELINDTLYST RKDDKGNTLI VNNLNGLYDK DNDKLKKLIN KSPEKLLMYH HDPQTYQKLK   840
LIMEQYGDEK NPLYKYYEET GNYLTKYSKK DNGPVIKKIK YYGNKLNAHL DITDDYPNSR   900
NKVVKLSLKP YRFDVYLDNG VYKFVTVKNL DVIKKENYYE VNSKCYEEAK KLKKISNQAE   960
FIASFYNNDL IKINGELYRV IGVNNDLLNR IEVNMIDITY REYLENMNDK RPPRIIKTIA  1020
SKTQSIKKYS TDILGNLYEV KSKKHPQIIK KG                               1052
```

```
SEQ ID NO: 46           moltype = AA   length = 52
FEATURE                 Location/Qualifiers
REGION                  1..52
                        note = Synthetic Polypeptide
SITE                    16
                        note = misc_feature - Xaa can be any naturally occurring
                        amino acid
source                  1..52
                        mol_type = protein
                        organism = synthetic construct
SEQUENCE: 46
SGGSSAAATS GGGGAXTENS GSAGSAAGSG ESAAGGGGSG GGGSGGGGST AA         52

SEQ ID NO: 47           moltype = AA   length = 198
FEATURE                 Location/Qualifiers
REGION                  1..198
                        note = Synthetic Polypeptide
source                  1..198
                        mol_type = protein
                        organism = synthetic construct
SEQUENCE: 47
MDSLLMNRRK FLYQFKNVRW AKGRRETYLC YVVKRRDSAT SFSLDFGYLR NKNGCHVELL   60
FLRYISDWDL DPGRCYRVTW FTSWSPCYDC ARHVADFLRG NPNLSLRIFT ARLYFCEDRK  120
AEPEGLRRLH RAGVQIAIMT FKDYFYCWNT FVENHERTFK AWEGLHENSV RLSRQLRRIL  180
LPLYEVDDLR DAFRTLGL                                                198

SEQ ID NO: 48           moltype = AA   length = 198
FEATURE                 Location/Qualifiers
REGION                  1..198
                        note = Synthetic Polypeptide
source                  1..198
                        mol_type = protein
                        organism = synthetic construct
SEQUENCE: 48
MDSLLMQKK FLYHFKNVRW AKGRHETYLC YVVKRRDSAT SCSLDFGHLR NKSGCHVELL    60
FLRYISDWDL DPGRCYRVTW FTSWSPCYDC ARHVAEFLRW NPNLSLRIFT ARLYFCEDRK  120
AEPEGLRRLH RAGVQIGIMT FKDYFYCWNT FVENRERTFK AWEGLHENSV RLTRQLRRIL  180
LPLYEVDDLR DAFRMLGF                                                198

SEQ ID NO: 49           moltype = AA   length = 198
FEATURE                 Location/Qualifiers
REGION                  1..198
                        note = Synthetic Polypeptide
source                  1..198
                        mol_type = protein
                        organism = synthetic construct
SEQUENCE: 49
MDSLLMQRK FLYHFKNVRW AKGRHETYLC YVVKRRDSAT SFSLDFGHLR NKSGCHVELL    60
FLRYISDWDL DPGRCYRVTW FTSWSPCYDC ARHVADFLRG YPNLSLRIFA ARLYFCEDRK  120
AEPEGLRRLH RAGVQIAIMT FKDYFYCWNT FVENREKTFK AWEGLHENSV RLSRQLRRIL  180
LPLYEVDDLR DAFRTLGL                                                198

SEQ ID NO: 50           moltype = AA   length = 199
FEATURE                 Location/Qualifiers
REGION                  1..199
                        note = Synthetic Polypeptide
source                  1..199
                        mol_type = protein
                        organism = synthetic construct
SEQUENCE: 50
MDSLLKKQRQ FLYQFKNVRW AKGRHETYLC YVVKRRDSPT SFSLDFGHLR NKAGCHVELL   60
FLRYISDWDL DPGRCYRVTW FTSWSPCYDC ARHVADFLRG YPNLSLRIFT ARLYFCDKER  120
KAEPEGLRRL HRAGVQIAIM TFKDYFYCWN TFVENHERTF KAWEGLHENS VRLSRQLRRI  180
LLPLYEVDDL RDAFRTLGL                                               199

SEQ ID NO: 51           moltype = AA   length = 239
FEATURE                 Location/Qualifiers
REGION                  1..239
                        note = Synthetic Polypeptide
source                  1..239
                        mol_type = protein
                        organism = synthetic construct
SEQUENCE: 51
MAVGSKPKAA LVGPHWERER IWCFLCSTGL GTQQTGQTSR WLRPAATQDP VSPPRSLLMK   60
QRKFLYHFKN VRWAKGRHET YLCYVVKRRD SATSFSLDPG YLRNKSGCHV ELLFLRYISD  120
WDLDPGRCYR VTWFTSWSPC YDCARHVADF LRGNPNLSLR IFTARLTGWG ALPAGLMSPA  180
RPSDYFYCWN TFVENHERTF KAWEGLHENS VRLSRRLRRI LLPLYEVDDL RDAFRTLGL   239
```

```
SEQ ID NO: 52                  moltype = AA   length = 429
FEATURE                        Location/Qualifiers
REGION                         1..429
                               note = Synthetic Polypeptide
source                         1..429
                               mol_type = protein
                               organism = synthetic construct
SEQUENCE: 52
MGPFCLGCSH RKCYSPIRNL ISQETFKFHF KNLGYAKGRK DTFLCYEVTR KDCDSPVSLH   60
HGVFKNKDNI HAEICFLYWF HDKVLKVLSP REEFKITWYM SWSPCFECAE QIVRFLATHH  120
NLSLDIFSSR LYNVQDPETQ QNLCRLVQEG AQVAAMDLYE FKKCWKKFVD NGGRRFRPWK  180
RLLTNFRYQD SKLQEILRPC YIPVPSSSSS TLSNICLTKG LPETRFCVEG RRMDPLSEEE  240
FYSQFYNQRV KHLCYYHRMK PYLCYQLEQF NGQAPLKGCL LSEKGKQHAE ILFLDKIRSM  300
ELSQVTITCY LTWSPCPNCA WQLAAFKRDR PDLILHIYTS RLYFHWKRPF QKGLCSLWQS  360
GILVDVMDLP QFTDCWTNFV NPKRPFWPWK GLEIISRRTQ RRLRRIKESW GLQDLVNDFG  420
NLQLGPPMS                                                          429

SEQ ID NO: 53                  moltype = AA   length = 429
FEATURE                        Location/Qualifiers
REGION                         1..429
                               note = Synthetic Polypeptide
source                         1..429
                               mol_type = protein
                               organism = synthetic construct
SEQUENCE: 53
MGPFCLGCSH RKCYSPIRNL ISQETFKFHF KNLRYAIDRK DTFLCYEVTR KDCDSPVSLH   60
HGVFKNKDNI HAEICFLYWF HDKVLKVLSP REEFKITWYM SWSPCFECAE QVLRFLATHH  120
NLSLDIFSSR LYNIRDPENQ QNLCRLVQEG AQVAAMDLYE FKKCWKKFVD NGGRRFRPWK  180
KLLTNFRYQD SKLQEILRPC YIPVPSSSSS TLSNICLTKG LPETRFCVER RRVHLLSEEE  240
FYSQFYNQRV KHLCYYHGVK PYLCYQLEQF NGQAPLKGCL LSEKGKQHAE ILFLDKIRSM  300
ELSQVIITCY LTWSPCPNCA WQLAAFKRDR PDLILHIYTS RLYFHWKRPF QKGLCSLWQS  360
GILVDVMDLP QFTDCWTNFV NPKRPFWPWK GLEIISRRTQ RRLHRIKESW GLQDLVNDFG  420
NLQLGPPMS                                                          429

SEQ ID NO: 54                  moltype = AA   length = 370
FEATURE                        Location/Qualifiers
REGION                         1..370
                               note = Synthetic Polypeptide
source                         1..370
                               mol_type = protein
                               organism = synthetic construct
SEQUENCE: 54
MVEPMDPRTF VSNFNNRPIL SGLNTVWLCC EVKTKDPSGP PLDAKIFQGK VYSKAKYHPE   60
MRFLRWFPHKW RQLHHDQEYK VTWYVSWSPC TRCANSVATF LAKDPKVTLT IFVARLYYFW 120
KPDYQQALRI LCQKRGGPHA TMKIMNYNEF QDCWNKFVDG RGKPFKPRNN LPKHYTLLQA  180
TLGELLRHLM DPGTFTSNFN NKPWVSGQHE TYLCYKVERL HNDTWVPLNQ HRGFLRNQAP  240
NIHGFPKGRH AELCFLDLIP FWKLDGQQYR VTCFTSWSPC FSCAQEMAKF ISNNEHVSLC  300
IFAARIYDDQ GRYQEGLRAL HRDGAKIAMM NYSEFEYCWD TFVDRQGRPF QPWDGLDEHS  360
QALSGRLRAI                                                         370

SEQ ID NO: 55                  moltype = AA   length = 384
FEATURE                        Location/Qualifiers
REGION                         1..384
                               note = Synthetic Polypeptide
source                         1..384
                               mol_type = protein
                               organism = synthetic construct
SEQUENCE: 55
MKPHFRNPVE RMYQDTFSDN FYNRPILSHR NTVWLCYEVK TKGPSRPPLD AKIFRGQVYS   60
KLKYHPEMRF FHWFSKWRKL HRDQEYEVTW YISWSPCTKC TRDVATFLAE DPKVTLTIFV  120
ARLYYFWDPD YQEALRSLCQ KRDGPRATMK IMNYDEFQHC WSKFVYSQRE LFEPWNNLPK  180
YYILLHIMLG EILRHSMDPP TFTSNFNNEL WVRGRHETYL CYEVERLHND TWVLLNQRRG  240
FLCNQAPHKH GFLEGRHAEL CFLDVIPFWK LDLHQDYRVT CFTSWSPCFS CAQEMAKFIS  300
NNKHVSLCIF AARIYDDQGR CQEGLRTLAK AGAKISIMTY SEFKHCWDTF VDHQGCPFQP  360
WDGLEEHSQA LSGRLRAILQ NQGN                                         384

SEQ ID NO: 56                  moltype = AA   length = 377
FEATURE                        Location/Qualifiers
REGION                         1..377
                               note = Synthetic Polypeptide
source                         1..377
                               mol_type = protein
                               organism = synthetic construct
SEQUENCE: 56
MNPQIRNMVE QMEPDIFVYY FNNRPILSGR NTVWLCYEVK TKDPSGPPLD ANIFQGKLYP   60
EAKDHPEMKF LHWFRKWRQL HRDQEYEVTW YVSWSPCTRC ANSVATFLAE DPKVTLTIFV  120
ARLYYFWKPD YQQALRILCQ ERGGPHATMK IMNYNEFQHC WNEFVDGQGK PFKPRKNLPK  180
HYTLLHATLG ELLRHVMDPG TFTSNFNNKP WVSGQRETYL CYKVERSHND TWVLLNQHRG  240
FLRNQAPDRH GFPKGRHAEL CFLDLIPFWK LDDQQYRVTC FTSWSPCFSC AQKMAKFISN  300
```

```
NKHVSLCIFA ARIYDDQGRC QEGLRTLHRD GAKIAVMNYS EFEYCWDTFV DRQGRPFQPW    360
DGLDEHSQAL SGRLRAI                                                  377

SEQ ID NO: 57           moltype = AA  length = 384
FEATURE                 Location/Qualifiers
REGION                  1..384
                        note = Synthetic Polypeptide
source                  1..384
                        mol_type = protein
                        organism = synthetic construct
SEQUENCE: 57
MKPHFRNTVE RMYRDTFSYN FYNRPILSRR NTVWLCYEVK TKGPSRPPLD AKIFRGQVYS    60
ELKYHPEMRF FHWFSKWRKL HRDQEYEVTW YISWSPCTKC TRDMATFLAE DPKVTLTIFV    120
ARLYYFWDPD YQEALRSLCQ KRDGPRATMK IMNYDEFQHC WSKFVYSQRE LFEPWNNLPK    180
YYILLHIMLG EILRHSMDPP TFTFNFNNEP WVRGRHETYL CYEVERMHND TWVLLNQRRG    240
FLCNQAPHKH GFLEGRHAEL CFLDVIPFWK LDLDQDYRVT CFTSWSPCFS CAQEMAKFIS    300
KNKHVSLCIF TARIYDDQGR CQEGLRTLAE AGAKISIMTY SEFKHCWDTF VDHQGCPFQP    360
WDGLDEHSQD LSGRLRAILQ NQEN                                          384

SEQ ID NO: 58           moltype = AA  length = 373
FEATURE                 Location/Qualifiers
REGION                  1..373
                        note = Synthetic Polypeptide
source                  1..373
                        mol_type = protein
                        organism = synthetic construct
SEQUENCE: 58
MKPHFRNTVE RMYRDTFSYN FYNRPILSRR NTVWLCYEVK TKGPSRPRLD AKIFRGQVYS    60
QPEHHAEMCF LSWFCGNQLP AYKCFQITWF VSWTPCPDCV AKLAEFLAEH PNVTLTISAA    120
RLYYYWDPD RRALCRLSQA GARVKIMDDE EFAYCWENFV YSEGQPFMPW YKFDDNYAFL     180
HRTLKEILRN PMEAMYPHIF YFHFKNLRKA YGRNESWLCF TMEVVKHHSP VSWKRGVFRN    240
QVDPETHCHA ERCFLSWFCD DILSPNTNYE VTWYTSWSPC PECAGEVAEF LARHSNVNLT    300
IFTARLYYFW DTDYQEGLRS LSQEGASVEI MGYKDFKYCW ENFVYNDDEP FKPWKGLKYN    360
FLFLDSKLQE ILE                                                      373

SEQ ID NO: 59           moltype = AA  length = 382
FEATURE                 Location/Qualifiers
REGION                  1..382
                        note = Synthetic Polypeptide
source                  1..382
                        mol_type = protein
                        organism = synthetic construct
SEQUENCE: 59
MNPQIRNPME RMYRDTFYDN FENEPILYGR SYTWLCYEVK IKRGRSNLLW DTGVFRGQVY    60
FKPQYHAEMC FLSWFCGNQL PAYKCFQITW FVSWTPCPDC VAKLAEFLSE HPNVTLTISA    120
ARLYYYWERD YRRALCRLSQ AGARVTIMDY EEFAYCWENF VYNEGQQFMP WYKFDENYAF    180
LHRTLKEILR YLMDPDTFTF NFNNDPLVLR RRQTYLCYEV ERLDNGTWVL MDQHMGFLCN    240
EAKNLLCGFY GRHAELRFLD LVPSLQLDPA QIYRVTWFIS WSPCFSWGCA GEVRAFLQEN    300
THVRLRIFAA RIYDYDPLYK EALQMLRDAG AQVSIMTYDE FEYCWDTFVY RQGCPFQPWD    360
GLEEHSQALS GRLRAILQNQ GN                                            382

SEQ ID NO: 60           moltype = AA  length = 396
FEATURE                 Location/Qualifiers
REGION                  1..396
                        note = Synthetic Polypeptide
source                  1..396
                        mol_type = protein
                        organism = synthetic construct
SEQUENCE: 60
MQPQGLGPNA GMGPVCLGCS HRRPYSPIRN PLKKLYQQTF YFHFKNVRYA WGRKNNFLCY    60
EVNGMDCALP VPLRQGVFRK QGHIHAELCF IYWFHDKVLR VLSPMEEFKV TWYMSWSPCS    120
KCAEQVARFL AAHRNLSLAI FSSRLYYYLR NPNYQQKLCR LIQEGVHVAA MDLPEFKKCW    180
NKFVDNDGQP FRPWMRLRIN FSFYDCKLQE IFSRMNLLRE DVFYLQFNNS HRVKPVQNFY    240
YRRKSYLCYQ LERANGQEPL KGYLLYKKGE QHVEILFLEK MRSMELSQVR ITCYLTWSPC    300
PNCARQLAAF KKDHPDLILR IYTSRLYFYW RKKFQKGLCT LWRSGIHVDV MDLPQFADCW    360
TNFVNPQRPF RPWNELEKNS WRIQRRLRRI KESWGL                             396

SEQ ID NO: 61           moltype = AA  length = 227
FEATURE                 Location/Qualifiers
REGION                  1..227
                        note = Synthetic Polypeptide
source                  1..227
                        mol_type = protein
                        organism = synthetic construct
SEQUENCE: 61
DGWEVAFRSG TVLKAGVLGV SMTEGWAGSG HPGQGACVWT PGTRNTMNLL REVLFKQQFG    60
NQPRVPAPYY RRKTYLCYQL KQRNDLTLDR GCFRNKKQRH AEIRFIDKIN SLDLNPSQSY    120
KIICYITWSP CPNCANELVN FITRNNHLKL EIFASRLYH WIKSFKMGLQ DLQNAGISVA     180
VMTHTEFEDC WEQFVDNQSR PFQPWDKLEQ YSASIRRRLQ RILTAPI                 227
```

```
SEQ ID NO: 62            moltype = AA  length = 490
FEATURE                  Location/Qualifiers
REGION                   1..490
                         note = Synthetic Polypeptide
source                   1..490
                         mol_type = protein
                         organism = synthetic construct
SEQUENCE: 62
MNPQIRNPME WMYQRTFYYN FENEPILYGR SYTWLCYEVK IRRGHSNLLW DTGVFRGQMY     60
SQPEHHAEMC FLSWFCGNQL SAYKCFQITW FVSWTPCPDC VAKLAKFLAE HPNVTLTISA    120
ARLYYYWERD YRRALCRLSQ AGARVKIMDD EEFAYCWENF VYNEGQPFMP WYKFDDNYAF    180
LHRTLKEIIR HLMDPDTFTF NFNNDPLVLR RHQTYLCYEV ERLDNGTWVL MDQHMGFLCN    240
EAKNLLCGFY GRHAELRFLD LVPSLQLDPA QIYRVTWFIS WSPCFSWGCA GQVRAFLQEN    300
THVRLRIFAA RIYDYDPLYK EALQMLRDAG AQVSIMTYDE FEYCWDTFVY RQGCPFQPWD    360
GLEEHSQALS GRLRAILQVR ASSLCMVPHR PPPPPQSPGP CLPLCSEPPL GSLLPTGRPA    420
PSLPFLLTAS FSFPPPASLP PLPSLSLSPG HLPVPSFHSL TSCSIQPPCS SRIRETEGWA    480
SVSKEGRDLG                                                          490

SEQ ID NO: 63            moltype = AA  length = 190
FEATURE                  Location/Qualifiers
REGION                   1..190
                         note = Synthetic Polypeptide
source                   1..190
                         mol_type = protein
                         organism = synthetic construct
SEQUENCE: 63
MNPQIRNPMK AMYPGTFYFQ FKNLWEANDR NETWLCFTVE GIKRRSVVSW KTGVFRNQVD     60
SETHCHAERC FLSWFCDDIL SPNTKYQVTW YTSWSPCPDC AGEVAEFLAR HSNVNLTIFT    120
ARLYYFQYPC YQEGLRSLSQ EGVAVEIMDY EDFKYCWENF VYNDNEPFKP WKGLKTNFRL    180
LKRRLRESLQ                                                          190

SEQ ID NO: 64            moltype = AA  length = 190
FEATURE                  Location/Qualifiers
REGION                   1..190
                         note = Synthetic Polypeptide
source                   1..190
                         mol_type = protein
                         organism = synthetic construct
SEQUENCE: 64
MNPQIRNPMK AMYPGTFYFQ FKNLWEANDR NETWLCFTVE GIKRRSVVSW KTGVFRNQVD     60
SETHCHAERC FLSWFCDDIL SPNTNYQVTW YTSWSPCPEC AGEVAEFLAR HSNVNLTIFT    120
ARLYYFQDTD YQEGLRSLSQ EGVAVKIMDY KDFKYCWENF VYNDDEPFKP WKGLKYNFRF    180
LKRRLQEILE                                                          190

SEQ ID NO: 65            moltype = AA  length = 199
FEATURE                  Location/Qualifiers
REGION                   1..199
                         note = Synthetic Polypeptide
source                   1..199
                         mol_type = protein
                         organism = synthetic construct
SEQUENCE: 65
MEASPASGPR HLMDPHIFTS NFNNGIGRHK TYLCYEVERL DNGTSVKMDQ HRGFLHNQAK     60
NLLCGFYGRH AELRFLDLVP SLQLDPAQIY RVTWFISWSP CFSWGCAGEV RAFLQENTHV    120
RLRIFAARIY DYDPLYKEAL QMLRDAGAQV SIMTYDEFKH CWDTFVDHQG CPFQPWDGLD    180
EHSQALSGRL RAILQNQGN                                                199

SEQ ID NO: 66            moltype = AA  length = 202
FEATURE                  Location/Qualifiers
REGION                   1..202
                         note = Synthetic Polypeptide
source                   1..202
                         mol_type = protein
                         organism = synthetic construct
SEQUENCE: 66
MDGSPASRPR HLMDPNTFTF NFNNDLSVRG RHQTYLCYEV ERLDNGTWVP MDERRGFLCN     60
KAKNVPCGDY GCHVELRFLC EVPSWQLDPA QTYRVTWFIS WSPCFRRGCA GQVRVFLQEN    120
KHVRLRIFAA RIYDYDPLYQ EALRTLRDAG AQVSIMTYEE FKHCWDTFVD RQGRPFQPWD    180
GLDEHSQALS GRLRAILQNQ GN                                            202

SEQ ID NO: 67            moltype = AA  length = 185
FEATURE                  Location/Qualifiers
REGION                   1..185
                         note = Synthetic Polypeptide
source                   1..185
                         mol_type = protein
                         organism = synthetic construct
SEQUENCE: 67
```

```
MDEYTFTENF NNQGWPSKTY LCYEMERLDG DATIPLDEYK GFVRNKGLDQ PEKPCHAELY    60
FLGKIHSWNL DRNQHYRLTC FISWSPCYDC AQKLTTFLKE NHHISLHILA SRIYTHNRFG   120
CHQSGLCELQ AAGARITIMT FEDFKHCWET FVDHKGKPFQ PWEGLNVKSQ ALCTELQAIL   180
KTQQN                                                               185

SEQ ID NO: 68           moltype = AA  length = 200
FEATURE                 Location/Qualifiers
REGION                  1..200
                        note = Synthetic Polypeptide
source                  1..200
                        mol_type = protein
                        organism = synthetic construct
SEQUENCE: 68
MALLTAETFR LQFNNKRRLR RPYYPRKALL CYQLTPQNGS TPTRGYFENK KKCHAEICFI    60
NEIKSMGLDE TQCYQVTCYL TWSPCSSCAW ELVDFIKAHD HLNLGIFASR LYYHWCKPQQ   120
KGLRLLCGSQ VPVEVMGFPK FADCWENFVD HEKPLSFNPY KMLEELDKNS RAIKRRLERI   180
KIPGVRAQGR YMDILCDAEV                                               200

SEQ ID NO: 69           moltype = AA  length = 210
FEATURE                 Location/Qualifiers
REGION                  1..210
                        note = Synthetic Polypeptide
source                  1..210
                        mol_type = protein
                        organism = synthetic construct
SEQUENCE: 69
MALLTAKTFS LQFNNKRRVN KPYYPRKALL CYQLTPQNGS TPTRGHLKNK KKDHAEIRFI    60
NKIKSMGLDE TQCYQVTCYL TWSPCPSCAG ELVDFIKAHR HLNRIFASR  LYYHWRPNYQ   120
EGLLLLCGSQ VPVEVMGLPE FTDCWENFVD HKEPPSFNPS EKLEELDKNS QAIKRRLERI   180
KSRSVDVLEN GLRSLQLGPV TPSSSIRNSR                                    210

SEQ ID NO: 70           moltype = AA  length = 386
FEATURE                 Location/Qualifiers
REGION                  1..386
                        note = Synthetic Polypeptide
source                  1..386
                        mol_type = protein
                        organism = synthetic construct
SEQUENCE: 70
MNPQIRNPME RMYRDTFYDN FENEPILYGR SYTWLCYEVK IKRGRSNLLW DTGVFRGPVL    60
PKRQSNHRQE VYFRFENHAE MCFLSWFCGN RLPANRRFQI TWFVSWNPCL PCVVKVTKFL   120
AEHPNVTLTI SAARLYYYRD RDWRWVLLRL HKAGARVKIM DYEDFAYCWE NFVCNEGQPF   180
MPWYKFDDNY ASLHRTLKEI LRNPMEAMYP HIFYFHFKNL LKACGRNESW LCFTMEVTKH   240
HSAVFRKRGV FRNQVDPETH CHAERCFLSW FCDDILSPNT NYEVTWYTSW SPCPECAGEV   300
AEFLARHSNV NLTIFTARLC YFWDTDYQEG LCSLSQEGAS VKIMGYKDFV SCWKNFVYSD   360
DEPFKPWKGL QTNFRLLKRR LREILQ                                        386

SEQ ID NO: 71           moltype = AA  length = 236
FEATURE                 Location/Qualifiers
REGION                  1..236
                        note = Synthetic Polypeptide
source                  1..236
                        mol_type = protein
                        organism = synthetic construct
SEQUENCE: 71
MTSEKGPSTG DPTLRRRIEP WEFDVFYDPR ELRKEACLLY EIKWGMSRKI WRSSGKNTTN    60
HVEVNFIKKF TSERDFHPSM SCSITWFLSW SPCWECSQAI REFLSRHPGV TLVIYVARLF   120
WHMDQQNRQG LRDLVNSGVT IQIMRASEYY HCWRNFVNYP PGDEAHWPQY PPLWMMLYAL   180
ELHCIILSLP PCLKISRRWQ NHLTFFRLHL QNCHYQTIPP HILLATGLIH PSVAWR       236

SEQ ID NO: 72           moltype = AA  length = 229
FEATURE                 Location/Qualifiers
REGION                  1..229
                        note = Synthetic Polypeptide
source                  1..229
                        mol_type = protein
                        organism = synthetic construct
SEQUENCE: 72
MSSETGPVAV DPTLRRRIEP HEFEVFFDPR ELRKETCLLY EINWGGRHSV WRHTSQNTSN    60
HVEVNFLEKF TTERYFRPNT RCSITWFLSW SPCGECSRAI TEFLSRHPYV TLFIYIARLY   120
HHTDQRNRQG LRDLISSGVT IQIMTEQEYC YCWRNFVNYP PSNEAYWPRY PHLWVKLYVL   180
ELYCIILGLP PCLKILRRKQ PQLTFFTITL QTCHYQRIPP HLLWATGLK               229

SEQ ID NO: 73           moltype = AA  length = 229
FEATURE                 Location/Qualifiers
REGION                  1..229
                        note = Synthetic Polypeptide
source                  1..229
                        mol_type = protein
```

```
                         organism = synthetic construct
SEQUENCE: 73
MSSETGPVAV DPTLRRRIEP HEFEVFFDPR ELRKETCLLY EINWGGRHSI WRHTSQNTNK    60
HVEVNFIEKF TTERYFCPNT RCSITWFLSW SPCGECSRAI TEFLSRYPHV TLFIYIARLY   120
HHADPRNRQG LRDLISSGVT IQIMTEQESG YCWRNFVNYS PSNEAHWPRY PHLWVRLYVL   180
ELYCIILGLP PCLNILRRKQ PQLTFFTIAL QSCHYQRLPP HILWATGLK              229

SEQ ID NO: 74            moltype = AA  length = 224
FEATURE                  Location/Qualifiers
REGION                   1..224
                         note = Synthetic Polypeptide
source                   1..224
                         mol_type = protein
                         organism = synthetic construct
SEQUENCE: 74
MAQKEEAAVA TEAASQNGED LENLDDPEKL KELIELPPFE IVTGERLPAN FFKFQFRNVE    60
YSSGRNKTFL CYVVEAQGKG GQVQASRGYL EDEHAAAHAE EAFFNTILPA FDPALRYNVT   120
WYVSSSPCAA CADRIIKTLS KTKNLRLLIL VGRLFMWEEP EIQAALKKLK EAGCKLRIMK   180
PQDFEYVWQN FVEQEEGESK AFQPWEDIQE NFLYYEEKLA DILK                   224

SEQ ID NO: 75            moltype = AA  length = 224
FEATURE                  Location/Qualifiers
REGION                   1..224
                         note = Synthetic Polypeptide
source                   1..224
                         mol_type = protein
                         organism = synthetic construct
SEQUENCE: 75
MAQKEEAAEA AAPASQNGDD LENLEDPEKL KELIDLPPFE IVTGVRLPVN FFKFQFRNVE    60
YSSGRNKTFL CYVVEVQSKG GQAQATQGYL EDEHAGAHAE EAFFNTILPA FDPALKYNVT   120
WYVSSSPCAA CADRILKTLS KTKNLRLLIL VSRLFMWEEP EVQAALKKLK EAGCKLRIMK   180
PQDFEYIWQN FVEQEEGESK AFEPWEDIQE NFLYYEEKLA DILK                   224

SEQ ID NO: 76            moltype = AA  length = 224
FEATURE                  Location/Qualifiers
REGION                   1..224
                         note = Synthetic Polypeptide
source                   1..224
                         mol_type = protein
                         organism = synthetic construct
SEQUENCE: 76
MAQKEEAAEA AAPASQNGDD LENLEDPEKL KELIDLPPFE IVTGVRLPVN FFKFQFRNVE    60
YSSGRNKTFL CYVVEAQSKG GQVQATQGYL EDEHAGAHAE EAFFNTILPA FDPALKYNVT   120
WYVSSSPCAA CADRILKTLS KTKNLRLLIL VSRLFMWEEP EVQAALKKLK EAGCKLRIMK   180
PQDFEYLWQN FVEQEEGESK AFEPWEDIQE NFLYYEEKLA DILK                   224

SEQ ID NO: 77            moltype = AA  length = 224
FEATURE                  Location/Qualifiers
REGION                   1..224
                         note = Synthetic Polypeptide
source                   1..224
                         mol_type = protein
                         organism = synthetic construct
SEQUENCE: 77
MAQKEEAAAA AEPASQNGEE VENLEDPEKL KELIELPPFE IVTGERLPAH YFKFQFRNVE    60
YSSGRNKTFL CYVVEAQSKG GQVQASRGYL EDEHATNHAE EAFFNSIMPT FDPALRYMVT   120
WYVSSSPCAA CADRIVKTLN KTKNLRLLIL VGRLFMWEEP EIQAALRKLK EAGCRLRIMK   180
PQDFEYIWQN FVEQEEGESK AFEPWEDIQE NFLYYEEKLA DILK                   224

SEQ ID NO: 78            moltype = AA  length = 208
FEATURE                  Location/Qualifiers
REGION                   1..208
                         note = Synthetic Polypeptide
source                   1..208
                         mol_type = protein
                         organism = synthetic construct
SEQUENCE: 78
MTDAEYVRIH EKLDIYTFKK QFFNNKKSVS HRCYVLFELK RRGERRACFW GYAVNKPQSG    60
TERGIHAEIF SIRKVEEYLR DNPGQFTINW YSSWSPCADC AEKILEWYNQ ELRGNGHTLK   120
IWACKLYYEK NARNQIGLWN LRDNGVGLNV MVSEHYQCCR KIFIQSSHNQ LNENRWLEKT   180
LKRAEKRRSE LSIMIQVKIL HTTKSPAV                                     208

SEQ ID NO: 79            moltype = AA  length = 384
FEATURE                  Location/Qualifiers
REGION                   1..384
                         note = Synthetic Polypeptide
source                   1..384
                         mol_type = protein
                         organism = synthetic construct
```

```
SEQUENCE: 79
MKPHFRNTVE  RMYRDTFSYN  FYNRPILSRR  NTVWLCYEVK  TKGPSRPPLD  AKIFRGQVYS   60
ELKYHPEMRF  FHWFSKWRKL  HRDQEYEVTW  YISWSPCTKC  TRDMATFLAE  DPKVTLTIFV  120
ARLYYFWDPD  YQEALRSLCQ  KRDGPRATMK  IMNYDEFQHC  WSKFVYSQRE  LFEPWNNLPK  180
YYILLHIMLG  EILRHSMDPP  TFTFNFNNEP  WVRGRHETYL  CYEVERMHND  TWVLLNQRRG  240
FLCNQAPHKH  GFLEGRHAEL  CFLDVIPFWK  LDLDQDYRVT  CFTSWSPCFS  CAQEMAKFIS  300
KNKHVSLCIF  TARIYRRQGR  CQEGLRTLAE  AGAKISIMTY  SEFKHCWDTF  VDHQGCPFQP  360
WDGLDEHSQD  LSGRLRAILQ  NQEN                                            384

SEQ ID NO: 80           moltype = AA  length = 184
FEATURE                 Location/Qualifiers
REGION                  1..184
                        note = Synthetic Polypeptide
source                  1..184
                        mol_type = protein
                        organism = synthetic construct
SEQUENCE: 80
MDPPTFTFNF  NNEPWVRGRH  ETYLCYEVER  MHNDTWVLLN  QRRGFLCNQA  PHKHGFLEGR   60
HAELCFLDVI  PFWKLDLDQD  YRVTCFTSWS  PCFSCAQEMA  KFISKNKHVS  LCIFTARIYD  120
DQGRCQEGLR  TLAEAGAKIS  IMTYSEFKHC  WDTFVDHQGC  PFQPWDGLDE  HSQDLSGRLR  180
AILQ                                                                    184

SEQ ID NO: 81           moltype = AA  length = 184
FEATURE                 Location/Qualifiers
REGION                  1..184
                        note = Synthetic Polypeptide
source                  1..184
                        mol_type = protein
                        organism = synthetic construct
SEQUENCE: 81
MDPPTFTFNF  NNEPWVRGRH  ETYLCYEVER  MHNDTWVLLN  QRRGFLCNQA  PHKHGFLEGR   60
HAELCFLDVI  PFWKLDLDQD  YRVTCFTSWS  PCFSCAQEMA  KFISKNKHVS  LCIFTARIYR  120
RQGRCQEGLR  TLAEAGAKIS  IMTYSEFKHC  WDTFVDHQGC  PFQPWDGLDE  HSQDLSGRLR  180
AILQ                                                                    184

SEQ ID NO: 82           moltype = AA  length = 36
FEATURE                 Location/Qualifiers
REGION                  1..36
                        note = Synthetic Polypeptide
SITE                    2
                        note = misc_feature - Xaa can be any naturally occurring
                         amino acid
REGION                  4..29
                        note = misc_feature - Xaa can be any naturally occurring
                         amino acid
REGION                  27..29
                        note = misc_feature - May be absent
REGION                  32..35
                        note = misc_feature - Xaa can be any naturally occurring
                         amino acid
REGION                  34..35
                        note = misc_feature - May be absent
source                  1..36
                        mol_type = protein
                        organism = synthetic construct
SEQUENCE: 82
HXEXXXXXXX  XXXXXXXXXX  XXXXXXXXXP  CXXXXC                               36

SEQ ID NO: 83           moltype = AA  length = 7
FEATURE                 Location/Qualifiers
REGION                  1..7
                        note = Synthetic Polypeptide
source                  1..7
                        mol_type = protein
                        organism = synthetic construct
SEQUENCE: 83
PKKKRKV                                                                   7

SEQ ID NO: 84           moltype = AA  length = 30
FEATURE                 Location/Qualifiers
REGION                  1..30
                        note = Synthetic Polypeptide
source                  1..30
                        mol_type = protein
                        organism = synthetic construct
SEQUENCE: 84
MDSLLMNRRK  FLYQFKNVRW  AKGRRETYLC                                       30

SEQ ID NO: 85           moltype = DNA  length = 23
```

```
FEATURE                 Location/Qualifiers
misc_feature            1..23
                        note = Synthetic Polypeptide
source                  1..23
                        mol_type = other DNA
                        organism = synthetic construct
SEQUENCE: 85
tatatgcata tttattacat cgg                                              23

SEQ ID NO: 86           moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 86
ccgtcatgtg ggtcctgaat tgg                                              23

SEQ ID NO: 87           moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 87
acactgaaag actccaggtc agg                                              23

SEQ ID NO: 88           moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 88
gtcagaagag atgtggtcaa tgg                                              23

SEQ ID NO: 89           moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 89
tttaaagtga agcagcatct ggg                                              23

SEQ ID NO: 90           moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 90
atttaaagtg aagcagcatc tgg                                              23

SEQ ID NO: 91           moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 91
actccatgac agtgtaattt tgg                                              23

SEQ ID NO: 92           moltype = DNA   length = 23
FEATURE                 Location/Qualifiers
misc_feature            1..23
                        note = Synthetic Polynucleotide
source                  1..23
                        mol_type = other DNA
                        organism = synthetic construct
SEQUENCE: 92
gcctggagaa gccatccagc agg                                              23
```

```
SEQ ID NO: 93             moltype = DNA  length = 23
FEATURE                   Location/Qualifiers
misc_feature              1..23
                          note = Synthetic Polynucleotide
source                    1..23
                          mol_type = other DNA
                          organism = synthetic construct
SEQUENCE: 93
ctcagacaca ctcattgatg agg                                         23

SEQ ID NO: 94             moltype = DNA  length = 24
FEATURE                   Location/Qualifiers
misc_feature              1..24
                          note = Synthetic Polynucleotide
source                    1..24
                          mol_type = other DNA
                          organism = synthetic construct
SEQUENCE: 94
gaggcactgc ccccaccatg agcg                                        24

SEQ ID NO: 95             moltype = AA  length = 9
FEATURE                   Location/Qualifiers
REGION                    1..9
                          note = Synthetic Polypeptide
source                    1..9
                          mol_type = protein
                          organism = synthetic construct
SEQUENCE: 95
RECASDRVW                                                         9

SEQ ID NO: 96             moltype = AA  length = 8
FEATURE                   Location/Qualifiers
REGION                    1..8
                          note = Synthetic Polypeptide
SITE                      8
                          note = misc_feature - Xaa is Ile or Met
source                    1..8
                          mol_type = protein
                          organism = synthetic construct
SEQUENCE: 96
HKYTNNQX                                                          8

SEQ ID NO: 97             moltype = AA  length = 8
FEATURE                   Location/Qualifiers
REGION                    1..8
                          note = Synthetic Polypeptide
source                    1..8
                          mol_type = protein
                          organism = synthetic construct
SEQUENCE: 97
ADECGRVM                                                          8

SEQ ID NO: 98             moltype = AA  length = 8
FEATURE                   Location/Qualifiers
REGION                    1..8
                          note = Synthetic Polypeptide
SITE                      5
                          note = misc_feature - Xaa is Asn, Lys, Asp, or Glu
SITE                      6
                          note = misc_feature - Xaa is Lys or His
source                    1..8
                          mol_type = protein
                          organism = synthetic construct
SEQUENCE: 98
TNKYXXII                                                          8

SEQ ID NO: 99             moltype = AA  length = 12
FEATURE                   Location/Qualifiers
REGION                    1..12
                          note = Synthetic Polypeptide
source                    1..12
                          mol_type = protein
                          organism = synthetic construct
SEQUENCE: 99
SGSAGSAAGS GE                                                     12

SEQ ID NO: 100            moltype = AA  length = 21
FEATURE                   Location/Qualifiers
REGION                    1..21
```

```
                        note = Synthetic Polypeptide
source                  1..21
                        mol_type = protein
                        organism = synthetic construct
SEQUENCE: 100
SAAGGGGSGG GGSGGGGSTA A                                           21

SEQ ID NO: 101          moltype = AA  length = 18
FEATURE                 Location/Qualifiers
REGION                  1..18
                        note = Synthetic Polypeptide
source                  1..18
                        mol_type = protein
                        organism = synthetic construct
SEQUENCE: 101
KRTADGSEFE SPKKKRKV                                               18

SEQ ID NO: 102          moltype = AA  length = 16
FEATURE                 Location/Qualifiers
REGION                  1..16
                        note = Synthetic Polypeptide
REGION                  3..12
                        note = misc_feature - Xaa can be any naturally occurring
                         amino acid
source                  1..16
                        mol_type = protein
                        organism = synthetic construct
SEQUENCE: 102
KRXXXXXXXX XXKKKL                                                 16

SEQ ID NO: 103          moltype = DNA  length = 125
FEATURE                 Location/Qualifiers
misc_feature            1..125
                        note = Synthetic Polynucleotide
misc_feature            1..8
                        note = n is a, c, g, or t
source                  1..125
                        mol_type = other DNA
                        organism = synthetic construct
SEQUENCE: 103
nnnnnnnngt ttttgtactc tcaagattta gaaataaatc ttgcagaagc tacaaagata  60
aggcttcatg ccgaaatcaa caccctgtca ttttatggca gggtgttttc gttatttaat 120
ttttt                                                            125

SEQ ID NO: 104          moltype = DNA  length = 121
FEATURE                 Location/Qualifiers
misc_feature            1..121
                        note = Synthetic Polynucleotide
misc_feature            1..18
                        note = n is a, c, g, or t
source                  1..121
                        mol_type = other DNA
                        organism = synthetic construct
SEQUENCE: 104
nnnnnnnnnn nnnnnnnngt ttttgtactc tcagaaatgc agaagctaca aagataaggc  60
ttcatgccga aatcaacacc ctgtcatttt atggcagggt gttttcgtta tttaatttttt 120
t                                                                121

SEQ ID NO: 105          moltype = DNA  length = 109
FEATURE                 Location/Qualifiers
misc_feature            1..109
                        note = Synthetic Polynucleotide
misc_feature            1..20
                        note = n is a, c, g, or t
source                  1..109
                        mol_type = other DNA
                        organism = synthetic construct
SEQUENCE: 105
nnnnnnnnnn nnnnnnnnnn gttttgtac tctcagaaat gcagaagcta caaagataag  60
gcttcatgcc gaaatcaaca ccctgtcatt ttatggcagg gtgttttt             109

SEQ ID NO: 106          moltype = DNA  length = 102
FEATURE                 Location/Qualifiers
misc_feature            1..102
                        note = Synthetic Polynucleotide
misc_feature            1..20
                        note = n is a, c, g, or t
source                  1..102
                        mol_type = other DNA
```

```
                            organism = synthetic construct
SEQUENCE: 106
nnnnnnnnnn nnnnnnnnnn gttttagagc tagaaatagc aagttaaaat aaggctagtc    60
cgttatcaac ttgaaaaagt ggcaccgagt cggtgctttt tt                      102

SEQ ID NO: 107          moltype = DNA   length = 88
FEATURE                 Location/Qualifiers
misc_feature            1..88
                        note = Synthetic Polynucleotide
misc_feature            1..20
                        note = n is a, c, g, or t
source                  1..88
                        mol_type = other DNA
                        organism = synthetic construct
SEQUENCE: 107
nnnnnnnnnn nnnnnnnnnn gttttagagc tagaaatagc aagttaaaat aaggctagtc    60
cgttatcaac ttgaaaaagt gttttttt                                       88

SEQ ID NO: 108          moltype = DNA   length = 76
FEATURE                 Location/Qualifiers
misc_feature            1..76
                        note = Synthetic Polynucleotide
misc_feature            1..20
                        note = n is a, c, g, or t
source                  1..76
                        mol_type = other DNA
                        organism = synthetic construct
SEQUENCE: 108
nnnnnnnnnn nnnnnnnnnn gttttagagc tagaaatagc aagttaaaat aaggctagtc    60
cgttatcatt tttttt                                                    76

SEQ ID NO: 109          moltype = RNA   length = 82
FEATURE                 Location/Qualifiers
misc_feature            1..82
                        note = Synthetic Polynucleotide
source                  1..82
                        mol_type = other RNA
                        organism = synthetic construct
SEQUENCE: 109
gttttagagc tagaaatagc aagttaaaat aaaggctagt ccgttatcaa cttgaaaaag    60
tggcaccgag tcggtgcttt tt                                             82

SEQ ID NO: 110          moltype = AA   length = 150
FEATURE                 Location/Qualifiers
REGION                  1..150
                        note = Synthetic Polypeptide
REGION                  6..150
                        note = misc_feature - May be absent
source                  1..150
                        mol_type = protein
                        organism = synthetic construct
SEQUENCE: 110
GGGGSGGGGS GGGSGGGGS GGGGSGGGGS GGGGSGGGGS GGGGSGGGGS GGGGSGGGGS     60
GGGGSGGGGS GGGGSGGGGS GGGGSGGGGS GGGGSGGGGS GGGGSGGGGS GGGGSGGGGS   120
GGGGSGGGGS GGGGSGGGGS GGGGSGGGGS                                    150

SEQ ID NO: 111          moltype = AA   length = 30
FEATURE                 Location/Qualifiers
REGION                  1..30
                        note = Synthetic Polypeptide
REGION                  2..30
                        note = misc_feature - May be absent
source                  1..30
                        mol_type = protein
                        organism = synthetic construct
SEQUENCE: 111
GGGGGGGGGG GGGGGGGGGG GGGGGGGGGG                                     30

SEQ ID NO: 112          moltype = AA   length = 150
FEATURE                 Location/Qualifiers
REGION                  1..150
                        note = Synthetic Polypeptide
REGION                  6..150
                        note = misc_feature - May be absent
source                  1..150
                        mol_type = protein
                        organism = synthetic construct
SEQUENCE: 112
EAAAKEAAAK EAAAKEAAAK EAAAKEAAAK EAAAKEAAAK EAAAKEAAAK EAAAKEAAAK     60
```

```
EAAAKEAAAK EAAAKEAAAK EAAAKEAAAK EAAAKEAAAK EAAAKEAAAK EAAAKEAAAK    120
EAAAKEAAAK EAAAKEAAAK EAAAKEAAAK                                     150

SEQ ID NO: 113          moltype = AA  length = 90
FEATURE                 Location/Qualifiers
REGION                  1..90
                        note = Synthetic Polypeptide
REGION                  4..90
                        note = misc_feature - May be absent
source                  1..90
                        mol_type = protein
                        organism = synthetic construct
SEQUENCE: 113
GGSGGSGGSG GSGGSGGSGG SGGSGGSGGS GGSGGSGGSG GSGGSGGSGG SGGSGGSGGS    60
GGSGGSGGSG GSGGSGGSGG SGGSGGSGGS                                     90

SEQ ID NO: 114          moltype = AA  length = 120
FEATURE                 Location/Qualifiers
REGION                  1..120
                        note = Synthetic Polypeptide
REGION                  5..120
                        note = misc_feature - May be absent
source                  1..120
                        mol_type = protein
                        organism = synthetic construct
SEQUENCE: 114
SGGSSGGSSG GSSGGSSGGS SGGSSGGSSG GSSGGSSGGS SGGSSGGSSG GSSGGSSGGS    60
SGGSSGGSSG GSSGGSSGGS SGGSSGGSSG GSSGGSSGGS SGGSSGGSSG GSSGGSSGGS    120

SEQ ID NO: 115          moltype = AA  length = 16
FEATURE                 Location/Qualifiers
REGION                  1..16
                        note = Synthetic Polypeptide
source                  1..16
                        mol_type = protein
                        organism = synthetic construct
SEQUENCE: 115
SGSETPGTSE SATPES                                                    16

SEQ ID NO: 116          moltype = AA  length = 60
FEATURE                 Location/Qualifiers
REGION                  1..60
                        note = Synthetic Polypeptide
SITE                    1
                        note = misc_feature - Xaa can be any naturally occurring
                         amino acid
SITE                    3
                        note = misc_feature - Xaa can be any naturally occurring
                         amino acid
REGION                  3..60
                        note = misc_feature - May be absent
SITE                    5
                        note = misc_feature - Xaa can be any naturally occurring
                         amino acid
SITE                    7
                        note = misc_feature - Xaa can be any naturally occurring
                         amino acid
SITE                    9
                        note = misc_feature - Xaa can be any naturally occurring
                         amino acid
SITE                    11
                        note = misc_feature - Xaa can be any naturally occurring
                         amino acid
SITE                    13
                        note = misc_feature - Xaa can be any naturally occurring
                         amino acid
SITE                    15
                        note = misc_feature - Xaa can be any naturally occurring
                         amino acid
SITE                    17
                        note = misc_feature - Xaa can be any naturally occurring
                         amino acid
SITE                    19
                        note = misc_feature - Xaa can be any naturally occurring
                         amino acid
SITE                    21
                        note = misc_feature - Xaa can be any naturally occurring
                         amino acid
SITE                    23
```

```
SITE            25
                note = misc_feature - Xaa can be any naturally occurring
                  amino acid
SITE            27
                note = misc_feature - Xaa can be any naturally occurring
                  amino acid
SITE            29
                note = misc_feature - Xaa can be any naturally occurring
                  amino acid
SITE            31
                note = misc_feature - Xaa can be any naturally occurring
                  amino acid
SITE            33
                note = misc_feature - Xaa can be any naturally occurring
                  amino acid
SITE            35
                note = misc_feature - Xaa can be any naturally occurring
                  amino acid
SITE            37
                note = misc_feature - Xaa can be any naturally occurring
                  amino acid
SITE            39
                note = misc_feature - Xaa can be any naturally occurring
                  amino acid
SITE            41
                note = misc_feature - Xaa can be any naturally occurring
                  amino acid
SITE            43
                note = misc_feature - Xaa can be any naturally occurring
                  amino acid
SITE            45
                note = misc_feature - Xaa can be any naturally occurring
                  amino acid
SITE            47
                note = misc_feature - Xaa can be any naturally occurring
                  amino acid
SITE            49
                note = misc_feature - Xaa can be any naturally occurring
                  amino acid
SITE            51
                note = misc_feature - Xaa can be any naturally occurring
                  amino acid
SITE            53
                note = misc_feature - Xaa can be any naturally occurring
                  amino acid
SITE            55
                note = misc_feature - Xaa can be any naturally occurring
                  amino acid
SITE            57
                note = misc_feature - Xaa can be any naturally occurring
                  amino acid
SITE            59
                note = misc_feature - Xaa can be any naturally occurring
                  amino acid
source          1..60
                mol_type = protein
                organism = synthetic construct
SEQUENCE: 116
XPXPXPXPXP XPXPXPXPXP XPXPXPXPXP XPXPXPXPXP XPXPXPXPXP XPXPXPXPXP    60

SEQ ID NO: 117          moltype = AA  length = 21
FEATURE                 Location/Qualifiers
REGION                  1..21
                        note = Synthetic Polypeptide
REGION                  4..21
                        note = misc_feature - May be absent
source                  1..21
                        mol_type = protein
                        organism = synthetic construct
SEQUENCE: 117
GGSGGSGGSG GSGGSGGSGG S                                              21

SEQ ID NO: 118          moltype = DNA  length = 23
FEATURE                 Location/Qualifiers
misc_feature            1..23
                        note = Synthetic Polynucleotide
source                  1..23
```

```
                        mol_type = other DNA
                        organism = synthetic construct
SEQUENCE: 118
gtcatcttag tcattacctg agg                                              23

SEQ ID NO: 119          moltype = DNA  length = 23
FEATURE                 Location/Qualifiers
misc_feature            1..23
                        note = Synthetic Polynucleotide
source                  1..23
                        mol_type = other DNA
                        organism = synthetic construct
SEQUENCE: 119
gaacacaaag catagactgc ggg                                              23

SEQ ID NO: 120          moltype = DNA  length = 22
FEATURE                 Location/Qualifiers
misc_feature            1..22
                        note = Synthetic Polynucleotide
source                  1..22
                        mol_type = other DNA
                        organism = synthetic construct
SEQUENCE: 120
ggcactgcgg ctggaggtgg gg                                               22

SEQ ID NO: 121          moltype = DNA  length = 27
FEATURE                 Location/Qualifiers
misc_feature            1..27
                        note = Synthetic Polynucleotide
source                  1..27
                        mol_type = other DNA
                        organism = synthetic construct
SEQUENCE: 121
gcctgagtcc gagcagaaga agaaggg                                          27

SEQ ID NO: 122          moltype = DNA  length = 25
FEATURE                 Location/Qualifiers
misc_feature            1..25
                        note = Synthetic Polynucleotide
source                  1..25
                        mol_type = other DNA
                        organism = synthetic construct
SEQUENCE: 122
ggcagtcatc ttagtcatta cctga                                            25

SEQ ID NO: 123          moltype = DNA  length = 26
FEATURE                 Location/Qualifiers
misc_feature            1..26
                        note = Synthetic Polynucleotide
source                  1..26
                        mol_type = other DNA
                        organism = synthetic construct
SEQUENCE: 123
ccggtggcac tgcggctgga ggtggg                                           26

SEQ ID NO: 124          moltype = DNA  length = 25
FEATURE                 Location/Qualifiers
misc_feature            1..25
                        note = Synthetic Polynucleotide
source                  1..25
                        mol_type = other DNA
                        organism = synthetic construct
SEQUENCE: 124
actggaacac aaagcataga ctgcg                                            25

SEQ ID NO: 125          moltype = DNA  length = 27
FEATURE                 Location/Qualifiers
misc_feature            1..27
                        note = Synthetic Polynucleotide
source                  1..27
                        mol_type = other DNA
                        organism = synthetic construct
SEQUENCE: 125
acttggggcc cagactgagc acgtgat                                          27

SEQ ID NO: 126          moltype = DNA  length = 26
FEATURE                 Location/Qualifiers
misc_feature            1..26
                        note = Synthetic Polynucleotide
```

```
source                  1..26
                        mol_type = other DNA
                        organism = synthetic construct
SEQUENCE: 126
gaacaggaag cacgaggcca ctgagg                                            26

SEQ ID NO: 127          moltype = AA   length = 9
FEATURE                 Location/Qualifiers
REGION                  1..9
                        note = Synthetic Polypeptide
source                  1..9
                        mol_type = protein
                        organism = synthetic construct
SEQUENCE: 127
FLFCSAVSS                                                               9

SEQ ID NO: 128          moltype = DNA   length = 26
FEATURE                 Location/Qualifiers
misc_feature            1..26
                        note = Synthetic Polynucleotide
source                  1..26
                        mol_type = other DNA
                        organism = synthetic construct
SEQUENCE: 128
cttgtccttc gtgctccggt gactcc                                            26

SEQ ID NO: 129          moltype = DNA   length = 24
FEATURE                 Location/Qualifiers
misc_feature            1..24
                        note = Synthetic Polynucleotide
source                  1..24
                        mol_type = other DNA
                        organism = synthetic construct
SEQUENCE: 129
atggaggacg tgcgcggccg cctg                                              24

SEQ ID NO: 130          moltype = AA   length = 8
FEATURE                 Location/Qualifiers
REGION                  1..8
                        note = Synthetic Polypeptide
source                  1..8
                        mol_type = protein
                        organism = synthetic construct
SEQUENCE: 130
MEDVRGRL                                                                8

SEQ ID NO: 131          moltype = DNA   length = 24
FEATURE                 Location/Qualifiers
misc_feature            1..24
                        note = Synthetic Polynucleotide
source                  1..24
                        mol_type = other DNA
                        organism = synthetic construct
SEQUENCE: 131
tacctcctgc acgcgccggc ggac                                              24

SEQ ID NO: 132          moltype = DNA   length = 83
FEATURE                 Location/Qualifiers
misc_feature            1..83
                        note = Synthetic Polynucleotide
source                  1..83
                        mol_type = other DNA
                        organism = synthetic construct
SEQUENCE: 132
gttttagagc tagaaatagc aagttaaaat aaggctagtc cgttatcaac ttgaaaaagt       60
ggcaccgagt cggtgctttt ttt                                               83

SEQ ID NO: 133          moltype = AA   length = 883
FEATURE                 Location/Qualifiers
REGION                  1..883
                        note = Synthetic Polypeptide
source                  1..883
                        mol_type = protein
                        organism = synthetic construct
SEQUENCE: 133
MNTINIAKND FSDIELAAIP FNTLADHYGE RLAREQLALE HESYEMGEAR FRKMFERQLK       60
AGEVADNAAA KPLITTLLPK MIARINDWFE EVKAKRGKRP TAFQFLQEIK PEAVAYITIK      120
TTLACLTSAD NTTVQAVASA IGRAIEDEAR FGRIRDLKAK HFKKNVEEQL NKRVGHVYKK      180
AFMQVVEADM LSKGLLGGEA WSSWHKEDSI HVGVRCIEML IESTGMVSLH RQNAGVVGQD      240
```

```
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFA                     883

SEQ ID NO: 134          moltype = AA   length = 13
FEATURE                 Location/Qualifiers
REGION                  1..13
                        note = Synthetic Polypeptide
source                  1..13
                        mol_type = protein
                        organism = synthetic construct
SEQUENCE: 134
AANDENYNYA LAA                                                       13

SEQ ID NO: 135          moltype = AA   length = 899
FEATURE                 Location/Qualifiers
REGION                  1..899
                        note = Synthetic Polypeptide
source                  1..899
                        mol_type = protein
                        organism = synthetic construct
SEQUENCE: 135
MNTINIAKND FSDIELAAIP FNTLADHYGE RLAREQLALE HESYEMGEAR FRKMFERQLK     60
AGEVADNAAA KPLITTLLPK MIARINDWFE EVKAKRGKRP TAFQFLQEIK PEAVAYITIK    120
TTLACLTSAD NTTVQAVASA IGRAIEDEAR FGRIRDLKAK HFKKNVEEQL NKRVGHVYKK    180
APMQVVEADM LSKGLLGGEA WSSWHKEDSI HVGVRCIEML IESTGMVSLH RQNAGVVGQD    240
SETIELAPEY AEAIATRAGA LAGISPMFQP CVVPPKPWTG ITGGGYWANG RRPLALVRTH    300
SKKALMRYED VYMPEVYKAI NIAQNTAWKI NKKVLAVANV ITKWKHCPVE DIPAIEREEL    360
PMKPEDIDMN PEALTAWKRA AAAVYRKDKA RKSRRISLEF MLEQANKFAN HKAIWFPYNM    420
DWRGRVYAVS MFNPQGNDMT KGLLTLAKGK PIGKEGYYWL KIHGANCAGV DKVPFPERIK    480
FIEENHENIM ACAKSPLENT WWAEQDSPFC FLAFCFEYAG VQHHGLSYNC SLPLAFDGSC    540
SGIQHFSAML RDEVGGRAVN LLPSETVQDI YGIVAKKVNE ILQADAINGT DNEVVTVTDE    600
NTGEISEKVK LGTKALAGQW LAYGVTRSVT KRSVMTLAYG SKEFGFRQQV LEDTIQPAID    660
SGKGLMFTQP NQAAGYMAKL IWESVSVTVV AAVEAMNWLK SAAKLLAAEV KDKKTGEILR    720
KRCAVHWVTP DGFPVWQEYK KPIQTRLNLM FLGQFRLQPT INTNKDSEID AHKQESGIAP    780
NFVHSQDGSH LRKTVVWAHE KYGIESFALI HDSFGTIPAD AANLFKAVRE TMVDTYESCD    840
VLADFYDQFA DQLHESQLDK MPALPAKGNL NLRDILESDF AFAWTRAAND ENYNYALAA    899

SEQ ID NO: 136          moltype = AA   length = 102
FEATURE                 Location/Qualifiers
REGION                  1..102
                        note = Synthetic Polypeptide
source                  1..102
                        mol_type = protein
                        organism = synthetic construct
SEQUENCE: 136
CLSYETEILT VEYGLLPIGK IVEKRIECTV YSVDNNGNIY TQPVAQWHDR GEQEVFEYCL     60
EDGSLIRATK DHKFMTVDGQ MLPIDEIFER ELDLMRVDNL PN                      102

SEQ ID NO: 137          moltype = AA   length = 346
FEATURE                 Location/Qualifiers
REGION                  1..346
                        note = Synthetic Polypeptide
source                  1..346
                        mol_type = protein
                        organism = synthetic construct
SEQUENCE: 137
MSSETGPVAV DPTLRRRIEP HEFEVFFDPR ELRKETCLLY EINWGGRHSI WRHTSQNTNK     60
HVEVNFIEKF TTERYFCPNT RCSITWFLSW SPCGECSRAI TEFLSRYPHV TLFIYIARLY    120
HHADPRNRQG LRDLISSGVT IQIMTEQESG YCWRNFVNYS PSNEAHWPRY PHLWVRLYVL    180
ELYCIILGLP PCLNILRRKQ PQLTFFTIAL QSCHYQRLPP HILWATGLKS GSETPGTSES    240
ATPECLSYET EILTVEYGLL PIGKIVEKRI ECTVYSVDNN GNIYTQPVAQ WHDRGEQEVF    300
EYCLEDGSLI RATKDHKFMT VDGQMLPIDE IFERELDLMR VDNLPN                   346

SEQ ID NO: 138          moltype = AA   length = 37
FEATURE                 Location/Qualifiers
REGION                  1..37
                        note = Synthetic Polypeptide
source                  1..37
                        mol_type = protein
                        organism = synthetic construct
```

```
SEQUENCE: 138
MIKIATRKYL GKQNVYDIGV ERDHNFALKN GFIASNC                              37

SEQ ID NO: 139          moltype = AA  length = 1492
FEATURE                 Location/Qualifiers
REGION                  1..1492
                        note = Synthetic Polypeptide
source                  1..1492
                        mol_type = protein
                        organism = synthetic construct
SEQUENCE: 139
MIKIATRKYL GKQNVYDIGV ERDHNFALKN GFIASNCFNK YSIGLAIGTN SVGWAVITDE    60
YKVPSKKFKV LGNTDRHSIK KNLIGALLFD SGETAEATRL KRTARRRYTR RKNRICYLQE   120
IFSNEMAKVD DSFFHRLEES FLVEEDKKHE RHPIFGNIVD EVAYHEKYPT IYHLRKKLVD   180
STDKADLRLI YLALAHMIKF RGHFLIEGDL NPDNSDVDKL FIQLVQTYNQ LFEENPINAS   240
GVDAKAILSA RLSKSRRLEN LIAQLPGEKK NGLFGNLIAL SLGLTPNFKS NFDLAEDAKL   300
QLSKDTYDDD LDNLLAQIGD QYADLFLAAK NLSDAILLSD ILRVNTEITK APLSASMIKR   360
YDEHHQDLTL LKALVRQQLP EKYKEIFFDQ SKNGYAGYID GGASQEEFYK FIKPILEKMD   420
GTEELLVKLN REDLLRKQRT FDNGSIPHQI HLGELHAILR RQEDFYPFLK DNREKIEKIL   480
TFRIPYYVGP LARGNSRFAW MTRKSEETIT PWNFEEVVDK GASAQSFIER MTNFDKNLPN   540
EKVLPKHSLL YEYFTVYNEL TKVKYVTEGM RKPAFLSGEQ KKAIVDLLFK TNRKVTVKQL   600
KEDYFKKIEC FDSVEISGVE DRFNASLGTY HDLLKIIKDK DFLDNEENED ILEDIVLTLT   660
LFEDREMIEE RLKTYAHLFD DKVMKQLKRR RYTGWGRLSR KLINGIRDKQ SGKTILDFLK   720
SDGFANRNFM QLIHDDSLTF KEDIQKAQVS GQGDSLHEHI ANLAGSPAIK KGILQTVKVV   780
DELVKVMGRH KPENIVIEMA RENQTTQKGQ KNSRERMKRI EEGIKELGSQ ILKEHPVENT   840
QLQNEKLYLY YLQNGRDMYV DQELDINRLS DYDVDAIVPQ SFLKDDSIDN KVLTRSDKNR   900
GKSDNVPSEE VVKKMKNYWR QLLNAKLITQ RKFDNLTKAE RGGLSELDKA GFIKRQLVET   960
RQITKHVAQI LDSRMNTKYD ENDKLIREVK VITLKSKLVS DFRKDFQFYK VREINNYHHA  1020
HDAYLNAVVG TALIKKYPKL ESEFVYGDYK VYDVRKMIAK SEQEIGKATA KYFFYSNIMN  1080
FFKTEITLAN GEIRKRPLIE TNGETGEIVW DKGRDFATVR KVLSMPQVNI VKKTEVQTGG  1140
FSKESILPKR NSDKLIARKK DWDPKKYGGF DSPTVAYSVL VVAKVEKGKS KKLKSVKELL  1200
GITIMERSSF EKNPIDFLEA KGYKEVKKDL IIKLPKYSLF ELENGRKRML ASAGELQKGN  1260
ELALPSKYVN FLYLASHYEK LKGSPEDNEQ KQLFVEQHKH YLDEIIEQIS EFSKRVILAD  1320
ANLDKVLSAY NKHRDKPIRE QAENIIHLFT LTNLGAPAAF KYFDTTIDRK RYTSTKEVLD  1380
ATLIHQSITG LYETRIDLSQ LGGDSGGSMT NLSDIIEKET GKQLVIQESI LMLPEEVEEV  1440
IGNKPESDIL VHTAYDESTD ENVMLLTSDA PEYKPWALVI QDSNGENKIK ML          1492
```